US011299493B2

(12) United States Patent
Chakravarty et al.

(10) Patent No.: US 11,299,493 B2
(45) Date of Patent: Apr. 12, 2022

(54) HETEROCYCLIC COMPOUNDS AND USES THEREOF

(71) Applicant: NUVATION BIO INC., New York, NY (US)

(72) Inventors: Sarvajit Chakravarty, Edmond, OK (US); Son Minh Pham, San Francisco, CA (US); Jayakanth Kankanala, St. Paul, MN (US); Anil Kumar Agarwal, Noida (IN); Brahmam Pujala, Greater Noida (IN); Sanjeev Soni, Greater Noida (IN); Satish K. Arya, Noida (IN); Deepak Palve, Noida (IN); Ashu Gupta, Noida (IN); Varun Kumar, Noida (IN)

(73) Assignee: Nuvation Bio Inc., New York, NY (US)

( * ) Notice: Subject to any disclaimer, the term of this patent is extended or adjusted under 35 U.S.C. 154(b) by 0 days.

(21) Appl. No.: 16/155,838

(22) Filed: Oct. 9, 2018

(65) Prior Publication Data

US 2019/0106427 A1    Apr. 11, 2019

Related U.S. Application Data

(60) Provisional application No. 62/570,043, filed on Oct. 9, 2017.

(51) Int. Cl.
*C07D 487/04* (2006.01)
*C07D 471/04* (2006.01)
*A61P 35/00* (2006.01)

(52) U.S. Cl.
CPC ............ *C07D 487/04* (2013.01); *A61P 35/00* (2018.01); *C07D 471/04* (2013.01)

(58) Field of Classification Search
CPC ...... C07D 471/04; C07D 487/04; A61P 35/00
See application file for complete search history.

(56) References Cited

U.S. PATENT DOCUMENTS

| 6,995,153 | B2 | 2/2006 | Seto et al. |
|---|---|---|---|
| 7,834,019 | B2 | 11/2010 | Sagara et al. |
| 8,329,711 | B2 | 12/2012 | Furuyama et al. |
| 8,703,779 | B2 | 4/2014 | Petrova et al. |
| 8,791,125 | B2 | 7/2014 | Sagara et al. |
| 9,655,899 | B2 | 5/2017 | Shumway |
| 9,850,247 | B2 | 12/2017 | Harrison et al. |
| 2006/0069093 | A1 | 3/2006 | Scarborough et al. |
| 2006/0258651 | A1 | 11/2006 | Linschoten |
| 2007/0254892 | A1 | 11/2007 | Sagara et al. |
| 2010/0221211 | A1 | 9/2010 | Furuyama et al. |
| 2013/0102590 | A1 | 4/2013 | Mastracchio et al. |
| 2016/0008361 | A1 | 1/2016 | Shumway |
| 2019/0084985 | A1 | 3/2019 | Reigan et al. |
| 2019/0106436 | A1 | 4/2019 | Chakravarty et al. |
| 2019/0248795 | A1 | 8/2019 | Burkamp et al. |
| 2020/0325142 | A1 | 10/2020 | Chakravarty et al. |

FOREIGN PATENT DOCUMENTS

| EP | 2168966 A1 | 3/2010 |
|---|---|---|
| WO | WO-2009/054332 A1 | 4/2009 |
| WO | WO-2010/067888 A1 | 6/2010 |
| WO | WO-2013/013031 A1 | 1/2013 |
| WO | WO-2013/059485 A1 | 4/2013 |
| WO | WO-2013/126656 A1 | 8/2013 |
| WO | WO-2014/167347 A1 | 10/2014 |
| WO | WO-2015/019037 A1 | 2/2015 |
| WO | WO-2015/092431 A1 | 6/2015 |
| WO | WO-2017/075629 A2 | 5/2017 |
| WO | WO-2018/011569 A1 | 1/2018 |
| WO | WO-2018/011570 A1 | 1/2018 |
| WO | WO-2018/0526621 A1 | 3/2018 |
| WO | WO-2018/090939 A1 | 5/2018 |
| WO | WO-2018/133829 A1 | 7/2018 |
| WO | WO-2018/162932 A1 | 9/2018 |
| WO | WO-2018/171633 A1 | 9/2018 |
| WO | WO-2018/183891 A1 | 10/2018 |
| WO | WO-2019/011228 A1 | 1/2019 |
| WO | WO-2019/028008 A1 | 2/2019 |
| WO | WO-2019/037678 A1 | 2/2019 |
| WO | WO-2019/096322 A1 | 5/2019 |
| WO | WO-2019/134539 A1 | 7/2019 |
| WO | WO-2019/165204 A1 | 8/2019 |
| WO | WO-2019/169065 A2 | 9/2019 |
| WO | WO-2019-173082 A1 | 9/2019 |

OTHER PUBLICATIONS

English translation of WO2019037678, publ. Feb. 28, 2019, priority date Sep. 20, 2017, pp. 1-34 (Year: 2019).*
Rodriguez, "Know the Most Common Types of Cancer", publ online Feb. 8, 2010, Everyday Health, pp. 1-13 (Year: 2010).*
Wistuba et al., Nature Rev. Clin. Oncol., 2011, vol. 8, pp. 135-141 (Year: 2011).*
Bhatia et al., Nature Biotechnology, 2012, vol. 30(7), pp. 604-610 (Year: 2012).*
Kaiser, Science, 2012, vol. 337, pp. 282-284 (Year: 2012).*
Barbosa, R.S.S. et al. (2019). "Sequential Combination of Bortezomid and WEE1 Inhibitor, MK-1775, Induced Apoptosis in Multiple Myeloma Cell Lines," *Biochemical and Biophysical Research Communications* 8 pgs.
Bridges, K.A. et al. (Sep. 1, 2011; e-pub. Jul. 28, 2011). "MK-1775, a Novel Wee1 Kinase Inhibitor, Radiosensitizes p53-Defective Human Tumor Cells," Clinical Cancer Research 17(17):5638-5648.
Brown, J.S. et al. (Feb. 6, 2018; e-pub. Nov. 9, 2017). "Combining DNA Damaging Therapeutics with Immunotherapy: More Haste, Less Speed," British Journal of Cancer 118(3):312-324.
Bukhari, A.B. et al. (Mar. 2019). "Inhibiting Wee1 and ATR Kinases Produces Tumor-Selective Synthetic Lethality and Suppresses Metastasis," The Journal of Clinical Investigation 129(3):1329-1344.
Chang, Q. et al. (2016; e-pub. Feb. 18, 2016). "Cytokinetic Effects of Wee1 Disruption in Pancreatic Cancer," Cell Cycle 15(4):593-604.

(Continued)

*Primary Examiner* — Sarah Pihonak
(74) *Attorney, Agent, or Firm* — Morrison & Foerster LLP

(57) ABSTRACT

Heterocyclic compounds as Wee1 inhibitors are provided. The compounds may find use as therapeutic agents for the treatment of diseases and may find particular use in oncology.

34 Claims, No Drawings

(56) References Cited

OTHER PUBLICATIONS

Chen, X. et al. (Dec. 2018; e-pub. Sep. 4, 2018). "Cyclin E Overexpression Sensitizes Triple-Negative Breast Cancer to Wee1 Kinase Inhibition," Clinical Cancer Research 24(24):6594-6610, (pre-published version is provided).
Chou, T.C. (Jan. 15, 2010; e-pub. Jan. 12, 2010). "Drug Combination Studies and Their Synergy Quantification Using the Chou-Talalay Method," Cancer Research 70(2):440-446.
Coyne, G.O.S. et al. (Jan. 2018). "Abstract B079: Single Agent AZD 1775, a Wee1 Inhibitor, Shows Activity in BRCA Deficient Patients," Molecular Cancer Therapeutics 17(1 Suppl):BO79, 4 pages.
Cuneo, K.C. et al. (Aug. 9, 2019). "Dose Escalation Trial of the Wee1 Inhibitor Adavosertib (AZD1775) in Combination With Gemcitabine and Radiation for Patients With Locally Advanced Pancreatic Cancer," *Journal of Clinical Oncology* 9 pages.
De Gooijer, M.C. et al. (Jun. 2018; e-pub. Nov. 17, 2017). "ATP-binding Cassette Transporters Limit the Brain Penetration of Wee1 Inhibitors," Invest New Drugs 36(3):380-387.
Do, K. et al. (2013; e-pub. Aug. 26, 2013). "Wee1 Kinase as a Target for Cancer Therapy," Cell Cycle 12(19):3159-3164.
Do, K. et al. (Oct. 20, 2015; e-pub. May 11, 2015). "Phase I Study of Single-Agent AZD1775 (MK-1775), a Wee1 Kinase Inhibitor, in Patients With Refractory Solid Tumors," Journal of Clinical Oncology 33(30):3409-3415.
Fang, Y. et al. (Jun. 10, 2019). "Sequential Therapy with PARP and WEE1 Inhibitors Minimizes Toxicity while Maintaining Efficacy," Cancer Cell 35:851-867.
Francis, A.M. et al. (Sep. 2017; e-pub. Jun. 15, 2017). "CDK4/6 Inhibitors Sensitize Rb-Positive Sarcoma Cells to Wee1 Kinase Inhibition Through Reversible Cell Cycle Arrest," Molecular Cancer Therapeutics 16(9):1751-1764.
Friedman, J. et al. (2018). "Inhibition of WEE1 Kinase and Cell Cycle Checkpoint Activation Sensitizes Head and Neck Cancers to Natural Killer Cell Therapies," Journal for ImmunoTherapy of Cancer 6:59, 12 pages.
Fu, S. et al. (Sep. 2018; e-pub. Aug. 13, 2018). "Strategic Development of AZD1775, a Wee1 Kinase Inhibitor, for Cancer Therapy," Expert Opinion on Investigational Drugs 27(9):741-751.
Garcia, T.B. et al. (2018; e-pub. Nov. 11, 2017). "Increased Activity of Both CDK1 and CDK2 is Necessary for the Combinatorial Activity of WEE1 Inhibition and Cytarabine," Leukemia Research 64:30-33.
Garcia, T.B. et al. (Oct. 2017; e-pub. Jun. 27, 2017). "A Small Molecule Inhibitor of WEE1, AZD1775, Synergies with Olaparib by Impairing Homologous Recombination and Enhancing DNA Damaga and Apoptosis in Acute Leukemia," Molecular Cancer Therapeutics 16(10):2058-2068.
Garimella, S.V. et al. (Jan. 2012; e-pub. Nov. 23, 2011). "WEE1 Inhibition Sensitizes Basal Breast Cancer Cells to TRAIL-Induced Apoptosis," Molecular Cancer Research 10(1):75-85.
Gavory, G. et al. (Jul. 2016). "Novel, Potent & Selective Inhibitors of Wee1 with Robust Antitumor Activity in Various Cancer Xenograft Models," *Poster presented at* Proceedings: AACR 107th Annual Meeting 2016; Apr. 16-20, 2016; New Orleans, LA, 76(14):LB-159, 1 page.
Geenen, J.J.J. et al. (Aug. 15, 2017; e-pub. Apr. 25, 2017). "Molecular Pathways: Targeting the Protein Kinase Wee1 in Cancer," Clinical Cancer Research 23(16):OF1-OF5.
Guertin, A.D. et al. (2012). "Unique Functions of CHK1 and WEE1 Underlie Synergistic Anti-Tumor Activity Upon Pharmacologic Inhibition," Cancer Cell International 12:45, 12 pages.
Guertin, A.D. et al. (Aug. 2013; e-pub. May 22, 2013). "Preclinical Evaluation of the WEE1 Inhibitor MK-1775 as Single-Agent Anticancer Therapy," Molecular Cancer Therapeutics 12(8):1442-1452.
Hai, J. et al. (Nov. 15, 2017; e-pub. Aug. 18, 2017). "Synergy of WEE1 and mTOR Inhibition in Mutant KRAS-driven Lung Cancers," Clin Cancer Res 23(22):6993-7005.

Hamilton, D.H. et al. (May 1, 2014; e-pub. Mar. 13, 2014). "WEE1 Inhibition Alleviates Resistance to Immune Attack of Tumor Cells Undergoing Epithelial-Mesenchymal Transition," Cancer Research 74(9):2510-2519.
Hauge, S. et al. (Apr. 2019; e-pub. Apr. 3, 2019). "p21 Limits S Phase DNA Damage Caused by the Wee1 Inhibitor MK1775," Cell Cycle 18(8):834-847.
Hirai, H. et al. (Nov. 2009; e-pub. Nov. 3, 2009). "Small-Molecule Inhibition of Wee1 Kinase by MK-1775 Selectively Sensitizes P53-Deficient Tumor Cells to DNA-Damaging Agents," Molecular Cancer Therapeutics 8(11):2992-3000.
Hsieh, H.-J. et al. (2018). "Systems Biology Approach Reveals a Link Between mTORCI and G2/M DNA Damage Checkpoint Recovery," Nature Communications 9:3982, 14 pages.
Hu, Y. et al. (2018, e-pub. Dec. 24, 2018). "Pharmacophore Modeling, Multiple Docking, and Molecular Dynamics Studies on Wee1 Kinase Inhibitors," *Journal of Biomolecular Structure and Dynamics* 14 pages.
International Search Report and Written Opinion dated Jan. 28, 2019 for PCT Application No. PCT/US2018/055091 filed on Oct. 9, 2018, 10 pages.
Invitation to Pay Additional Fees and, Where Applicable, Protest Fee dated Nov. 19, 2018 for PCT Application No. PCT/US2018/055091 filed on Oct. 9, 2018, 2 pages.
Iwai, A. et al. (Oct. 1, 2012; e-pub. Aug. 30, 2012). "Combined Inhibition of Wee1 and Hsp90 Activates Intrinsic Apoptosis in Cancer Cells," Cell Cycle 11(19):3649-3655.
Jin, J. et al. (May 2018). "Combined Inhibition of ATR and WEE1 as a Novel Therapeutic Strategy in Triple-Negative Breast Cancer," Neoplasia 20(5):478-488.
Jin, M.H. et al. (2019). "Therapeutic Co-Targeting of WEE1 and ATM Downregulates PD-L1 Expression in Pancreatic Cancer," *Cancer Research and Treatment*, 40 pages.
Karakashev, S. et al. (Dec. 19, 2017). "BET Bromodomain Inhibition Synergizes with PARP Inhibitor in Epithelial Ovarian Cancer," Cell Reports 21:3398-3405.
Karnak, D. et al. (Oct. 1, 2014; e-pub. Aug. 12, 2014). "Combined Inhibition of Wee1 and PARP1/2 for Radiosensitization in Pancreatic Cancer," Clinical Cancer Research 20(19):5085-5096.
Kausar, T. et al. (Oct. 2015). "Sensitization of Pancreatic Cancers to Gemcitabine Chemoradiation by WEE1 Kinase Inhibition Depends on Homologous Recombination Repair," Neoplasia 17(10):757-766.
Kaye, S.B. (2016). "DNA Repair Inhibitors in Ovarian Cancer: Current Status and Future Strategies," *Presented at* Progress and Controversies in Gynecologic Oncology Conference, 37 pages.
Kim, H.-Y et al. (Jun. 23, 2016). "Targeting the WEE1 Kinase as a Molecular Targeted Therapy for Gastric Cancer," Oncotarget 7(31):49902-49916.
Kreahling, J.M. et al. (Jan. 2012). "MK1775, A Selective Wee1 Inhibitor, Shows Single-Agent Antitumor Activity against Sarcoma Cells," Molecular Cancer Therapeutics 11(1):174-182, 15 pages.
Kreahling, J.M. et al. (Mar. 8, 2013). "Wee1 Inhibition by MK-1775 Leads to Tumor Inhibition and Enhances Efficacy of Gemcitabine in Human Sarcomas," PLOS One 8(3):e57523, 8 pages.
Kuzu, O.F. et al. (Sep. 28, 2017; e-pub. Jul. 13, 2017). "Improving Pharmacological Targeting of AKT in Melanoma," Cancer Letters 404:29-36.
Lallo, A. et al. (Oct. 15, 2018 e-pub. Jun. 25, 2018). "The Combination of the PARP Inhibitor Olaparib and the Wee1 Inhibitor AZD1775 as a New Therapeutic Option for Small Cell Lung Cancer," Clinical Cancer Research 24(20):5153-5164, 33 pages.
Lee, J.W. et al. (pre-published on Feb. 12, 2019). "Combined Aurora Kinase A (AURKA) and WEE1 Inhibition Demonstrates Synergistic Antitumor Effect in Squamous Cell Carcinoma of the Head and Neck," Clinical Cancer Research, 42 pages.
Leijen, S. et al. (Dec. 20, 2016; e-pub. Oct. 31, 2016). "Phase II Study of WEE1 Inhibitor AZD1775 Plus Carboplatin in Patients With TP53-Mutated Ovarian Cancer Refractory or Resistant to First-Line Therapy Within 3 Months," Journal of Clinical Oncology 34(36):4354-4361.
Leijen, S. et al. (Dec. 20, 2016; e-pub. Sep. 6, 2016). "Phase I Study Evaluating WEE1 Inhibitor AZD1775 as Monotherapy and in

(56) References Cited

OTHER PUBLICATIONS

Combination With Gemcitabine, Cisplatin, or Carboplatin in Patients With Advanced Solid Tumors," Journal of Clinical Oncology 34(36):4371-4380.

Lescarbeau, R.S. et al. (Jun. 2016; e-pub. Mar. 23, 2016). "Quantitative Phosphoproteomics Reveals Wee1 Kinase as a Therapeutic Target in a Model of Proneural Glioblastoma," Molecular Cancer Therapeutics 15(6):1332-1343.

Lewis, C.W. et al. (May 13, 2017). "Prolonged mitotic arrest induced by Wee1 inhibition sensitizes breast cancer cells to paclitaxel," Oncotarget 8(43):73705-73722.

Li, J. et al. (Dec. 15, 2017; e-pub. Sep. 19, 2017). "Quantitative and Mechanistic Understanding of AZD1775 Penetration across Human Blood-Brain Barrier in Glioblastoma Patients Using an IVIVE-PBPK Modeling Approach," Clinical Cancer Research 23(24):7454-7466.

Liang, J. et al. (2019, e-pub. Sep. 24, 2019). "Genome-Wide CRISPR-Cas9 Screen Reveals Selective Vulnerability of ATRX-Mutant Cancers to WEE1 Inhibition," *AACR Journals*, 42 pages.

LIU, W. et al. (2019, e-pub. June 13, 2019). "Targeting the WEE1 Kinase Strengthens The Antitumor Activity of Imatinib Via Promoting KIT Autophagic Degradation in Gastrointestingal Stromal Tumors," *Gastric Cancer*, 13 pages.

Liu, D. et al. (2019). "Enhancement of Chemosensitivity by WEE1 Inhibition in EGFR-TKIs Resistant Non-Small Cell Lung Cancer," *Biomedicine & Pharmacotherapy* 117:109185, 8 pages.

Lübbehüsen, C. et al. (2019; e-pub. Apr. 23, 2019). "Characterization of Three Novel H3F3A-mutated Giant Cell Tumor Cell Lines and Targeting of Their Wee1 Pathway," Scientific Reports 9:6458, 10 pages.

Mastracchio, A. et al. (e-pub. Apr. 9, 2019). "Investigation of Biaryl Heterocycles as Inhibitors of Wee1 Kinase," Bioorganic & Medicinal Chemistry Letters 29(12):1481-1486.

Matheson, C.J. et al. (Apr. 15, 2016; e-pub. Jan. 8, 2016). "A WEE1 Inhibitor Analog of AZD1775 Maintains Synergy with Cisplatin and Demonstrates Reduced Single-Agent Cytotoxicity in Medulloblastoma Cells," ACS Chem. Biol. 11(4):921-930.

Matheson, C.J. et al. (Oct. 2016). "Targeting WEE1 Kinase in Cancer," Trends in Pharmacological Sciences 37(10):872-881.

Mendez, E. et al. (Jun. 15, 2018; e-pub. Mar. 13, 2018). "A Phase I Clinical Trial of AZD1775 in Combination with Neoadjuvant Weekly Docetaxel and Cisplatin Before Definitive Therapy in Head and Neck Squamous Cell Carcinoma," Clinical Cancer Research 24(12):2740-2748.

Mokyr, M.B. et al. (Dec. 1, 1998). "Realization of the Therapeutic Potential of CTLA-4 Blockade in Low-Dose Chemotherapy-treated Tumor-bearing Mice," Cancer Research 58:5301-5304.

Mueller, S. et al. (2014; e-pub. Dec. 4, 2013). "Targeting Wee1 for the Treatment of Pediatric High-Grade Gliomas," Neuro-Oncology 16(3):352-360.

Mueller, S. et al. (Oct. 20, 2015). "WEE1 Kinase As a Target for Cancer Therapy," Journal of Clinical Oncology 33(30):3485-3487.

Music, D. et al. (Apr. 2016; e-pub. Jan. 6, 2016). "Expression and Prognostic Value of the WEE1 Kinase in Gliomas," J Neurooncol 127(2):381-399, 9 pages.

O'Dowd, C. et al. (2019). "Antitumor Activity of the Novel Oral Highly Selective Wee1 Inhibitor Debio0123," Abstract #4423, *Poster presented at* AACR 2019, Atlanta, GA, US,1 page.

O'Neil, J. et al. (Jun. 2016; e-pub. Mar. 16, 2016). "An Unbiased Oncology Compound Screen to Identify Novel Combination Strategies," Molecular Cancer Therapeutics 15(6):1155-1162.

Palmer, B.D. et al. (2006; e-pub. Jul. 15, 2006). "4-Phenylpyrrolo[3,4-c]carbazole-1,3(2H,6H)-dione Inhibitors of the Checkpoint Kinase Wee1. Structure-Activity Relationships for Chromophore Modification and Phenyl Ring Substitution," J. Med. Chem. 49(16):4896-4911.

Peer, C.J. et al. (Dec. 15, 2017; e-pub. Oct. 10, 2017). "Jumping the Barrier Modeling Drug Penetration across the Blood-Brain Barrier," Clinical Cancer Research 23(24):7437-7439.

Pfister, S.X. et al. (Nov. 9, 2015). "Inhibiting WEE1 Selectively Kills Histone H3K36me3-Deficient Cancers by dNTP Starvation," Cancer Cell 28:557-568.

Pokorny, J.L. et al. (Apr. 15, 2015; e-pub. Jan. 21, 2015). "The Efficacy of the Wee1 Inhibitor MK-1775 Combined with Temozolomide Is Limited by Heterogeneous Distribution across the Blood-Brain Barrier in Glioblastoma," Clinical Cancer Research 21(8):1916-1924.

Rajeshkumar, N.V. et al. (May 1, 2011; e-pub. Mar. 9, 2011). "MK-1775, a Potent Wee1 Inhibitor, Synergizes with Gemcitabine to Achieve Tumor Regressions, Selectively in p53-Deficient Pancreatic Cancer Xenografts," Clinical Cancer Research 17(9):2799-2806.

Restelli, V. et al. (pre-published May 7, 2019). "DNA Damage Response Inhibitor Combinations Exert Synergistic Antitumor Activity in Aggressive B Cell Lymphomas," Molecular Cancer Therapeutics, 25 pages, (Pre-published Copy provided).

Richer, A.L. et al. (Sep. 1, 2017; e-pub. Jun. 26, 2017). "WEE1 Kinase Inhibitor AZD1775 has Pre-Clinical Efficacy in LKB1-Deficient Non-small Cell Lung Cancer," The Journal of Cancer Research 77(17):4663-4672.

Sanai, N. et al. (Aug. 15, 2018; e-pub. May 24, 2018). "Phase 0 Trial of AZD1775 in First-Recurrence Glioblastoma Patients," Clinical Cancer Research 24(16):3820-3828.

Schmidt, M. et al. (Nov. 23, 2017). "Regulation of G2/M Transition by Inhibition of WEE1 and PKMYT1 Kinases," Molecules 22:2045, pp. 1-17.

Serpigo, A.F. et al. (Jun. 13, 2019). "Wee1 Rather Than Plk1 is Inhibited by AZD1775 at Therapeutically Relevant Concentrations," Cancers 11(819), 10 pages.

Steino, A. et al. (Jul. 2018). "Dianhydrogalactitol (VAL-083) has the Potential to Overcome Major Challenges in the Treatment of Diffuse Intrinsic Pontine Glioma (DIPG)," *Poster presented at* AACR Annual Meeting 2018; Apr. 14-18, 2018; Chicago, IL, 78(13Supplement), 1 page.

Sun, A. et al. (Apr. 2010). "A Phase Ib Study to Evaluate Induction of pCDC2 in Skin Biopsies from Patients with Solid Tumors Treated with DNA-damaging Chemotherapy," *Poster presented at* AACR 101st Annual Meeting 2010, Apr. 17-21, 2010, Washington D.C, Merck & Co., Inc., 70(8 Supplement), 1 page.

Sun, L. et al. (2018; e-pub. Jul. 23, 2018). "WEE1 Kinase Inhibition Reverses G2/M Cell Cycle Checkpoint Activation to Sensitize Cancer Cells to Immunotherapy," OncoImmunology 7(10):e1488359-1-e1488359-14.

Takashima, Y. et al. (e-pub. ahead of print—Jun. 14, 2019). "Bromodomain and Extraterminal Domain Inhibition Synergizes with WEE1WEE1-Inhibitor AZD1775 Effect by Impairing Non Non-Homologous End Joining and Enhancing DNA Damage in Non Non-Small Cell Lung Cancer," Int J Cancer, 34 pages.

Toledo, C.M. et al. (Dec. 22, 2015). "Genome-Wide CRISPR-Cas9 Screens Reveal Loss of Redundancy Between PKMYT1 and WEE1 in Glioblastoma Stem-like Cells," Cell Reports 13:2425-2439.

Tong, Y. et al. (2015). "Pyrimidine-Based Tricyclic Molecules as Potent and Orally Efficacious Inhibitors of Wee1 Kinase," ACS Med. Chem. Lett. 6:58-62.

Touat, M. et al. (2017; e-pub. Jun. 12, 2017). "Glioblastoma Targeted Therapy: Updated Approaches from Recent Biological Insights," Annals of Oncology 28:1457-1472.

Wang, Y. et al. (Mar. 2004). "Knockdown of Chk1, Wee1 and Myt1 by RNA Interference Abrogates G2 Checkpoint and Induces Apoptosis," Cancer Biology & Therapy 3(3):305-313.

Wichapong, K. et al. (2009; e-pub. Sep. 30, 2008). "Receptor-based 3D-QSAR Studies of Checkpoint Wee1 Kinase Inhibitors," European Journal of Medicinal Chemistry 44:1383-1395.

Wright, G. et al. (Jul. 21, 2017; e-pub. May 30, 2017). "Dual Targeting of WEE1 and PLK1 by AZD1775 Elicits Single Agent Cellular Anticancer Activity," ACS Chemical Biology 12(7):1883-1892., 18 pages.

Wu, S. et al. (2018; e-pub. Jul. 7, 2017). "Activation of WEE1 Confers Resistance to PI3K Inhibition in Glioblastoma," Neuro-Oncology 20(1):78-91.

(56) References Cited

OTHER PUBLICATIONS

Wu, M. et al. (2019). "miR-526b-3p Serves as a Prognostic Factor abd Regulates the Proliferation, Invasion, and Migration of Giloma through Targeting WEE1," Cancer Management and Research 11:3099-3110.

Zhang, M. et al. (2017). "WEE1 inhibition By MK1775 as a Single-Agent Therapy Inhibits Ovarian Cancer Viability," Oncology Letters 14:3580-3586.

Zhang, P. et al. (Jul. 21, 2019). "BRD4 Inhibitor AZD5153 Suppresses the Proliferation of Colorectal Cancer Cells and Sensitizes the Anticancer Effect of PARP Inhibitor," *International Journal of Biological Sciences* 15(9):1942-1954.

Zhao, W. et al. (2015). "The Role and Mechanism of WEE1 on the Cisplatin Resistance Reversal of the HepG2/DDP Human Hepatic Cancer Cell Line," Oncology Letters 10:3081-3086.

Zhou, L. et al. (Apr. 2015). "A Regimen Combining the Wee1 Inhibitor AZD1775 With HDAC Inhibitors Targets Human Acute Myeloid Leukemia Cells Harboring Various Genetic Mutations," Leukemia 29(4):807-818, 24 pages.

Zhu, J.-Y. et al. (Aug. 9, 2017). "Structural Basis of Wee Kinases Functionality and Inactivation by Diverse Small Molecule Inhibitors," Journal of Medicinal Chemistry 60:7863-7875.

Zupkovitz, G. et al. (Mar. 2010; e-pub. Dec. 22, 2009). "The Cyclin-Dependent Kinase Inhibitor p21 Is a Crucial Target for Histone Deacetylase 1 as a Regulator of Cellular Proliferation," Molecular and Cellular Biology 30(5):1171-1181.

International Preliminary Report on Patentability, dated Apr. 14, 2020, for PCT Application No. PCT/US2018/055091 filed on Oct. 9, 2018, 6 pages.

U.S. Appl. No. 17/594,293, filed Oct. 8, 2021, for Chakravarty et al. (Copy not submitted herewith pursuant to the waiver of 37 C.F.R. § 1.98(a)(2)(iii) issued by the Office on Sep. 21, 2004).

U.S. Appl. No. 17/594,296, filed Oct. 8, 2021, for Chakravarty et al. (Copy not submitted herewith pursuant to the waiver of 37 C.F.R. § 1.98(a)(2)(iii) issued by the Office on Sep. 21, 2004).

U.S. Appl. No. 17/594,298, filed Oct. 8, 2021, for Chakravarty et al. (Copy not submitted herewith pursuant to the waiver of 37 C.F.R. § 1.98(a)(2)(iii) issued by the Office on Sep. 21, 2004).

U.S. Appl. No. 17/594,299, filed Oct. 8, 2021, for Chakravarty et al. (Copy not submitted herewith pursuant to the waiver of 37 C.F.R. § 1.98(a)(2)(iii) issued by the Office on Sep. 21, 2004).

\* cited by examiner

HETEROCYCLIC COMPOUNDS AND USES THEREOF

CROSS-REFERENCE TO RELATED APPLICATIONS

This application claims priority to U.S. Provisional Application No. 62/570,043, filed Oct. 9, 2017, the contents of which are incorporated herein by reference in their entirety.

FIELD OF THE INVENTION

This disclosure relates generally to therapeutics engaged in inhibition of the DNA damage checkpoint kinase, Wee1, which potentiates genotoxic chemotherapies by abrogating cell-cycle arrest and proper DNA repair. The invention also provides pharmaceutically acceptable compositions comprising compounds of the present invention and methods of using said compositions in the treatment of diseases associated with this pathway.

BACKGROUND OF THE INVENTION

Wee1 is a tyrosine kinase that phosphorylates and inactivates Cdc2 and is involved in G checkpoint signaling. More particularly, Wee1 is involved in $G_2$-M checkpoint signaling. Because p53 is a key regulator in the G checkpoint, p53-deficient tumors rely only on the G checkpoint after DNA damage. More particularly, because p53 is a key regulator in the $G_1$-S checkpoint, p53-deficient tumors rely only on the $G_2$-M checkpoint after DNA damage. Hence, such tumors are selectively sensitized to DNA-damaging agents by Wee1 inhibition.

Wee1 belongs to a family of protein kinases involved in the terminal phosphorylation and inactivation of cyclin-dependent kinase 1-bound cyclin B, resulting in G cell cycle arrest in response to DNA damage. Wee1 was first identified in fission yeast, where Wee1 deficiency resulted in premature mitotic entry and replication of smaller-sized yeast. It is the major kinase responsible for the inhibitory phosphorylation of the tyrosine.

Before cells undergo mitosis, they progress through a tightly controlled cascade of $G_1$-S, intra-S, and $G_2$-M checkpoints. Wee1 kinase has emerged as a key $G_2$-M checkpoint regulator. This tyrosine kinase negatively regulates entry into mitosis by catalyzing an inhibitory phosphorylation of Cdc2 (the human homolog of cyclin-dependent kinase 1 (CDK1) on tyrosine-15 (Y15). This results in inactivation of the Cdc2/cyclin B complex, which arrests cells in $G_2$-M, allowing for DNA repair. Such inhibition also occurs through Chk1-mediated inhibition of Cdc25 phosphatases, which remove the inhibitory phosphorylation on Cdc2. Thus, entry into mitosis rests on a balance between the opposing activities of Wee1 and Chk1/Cdc25. Wee1 inhibition is thus expected to abrogate $G_2$-M arrest and propel cells into premature mitosis, a hypothesis confirmed by studies documenting that Wee1 inhibition by either small molecule inhibitors or small interference RNA leads to premature entry into mitosis and consequent cell death through mitotic catastrophe or apoptosis. (S. Muller, *J. Clinical. Oncology*, 2015).

Recently, a few classes of Wee1 inhibitors have been disclosed. Among them is a selective inhibitor, AZD-1775 (1,2-allyl-1-(6-(2-hydroxypropan-2-yl)pyridin-2-yl)-6-((4-(4methylpiperazin-1-yl)phenyl)amino)-1H-pyrazolo[3,4-d]pyrimidin-3 (2H)-one). AZD-1775 exhibited antitumor activity in various preclinical studies as a monotherapy or in potentiating chemo- and radiotherapy, and is currently in phase I/II clinical trials.

Wee1 is highly expressed in several cancer types, including hepatocellular carcinoma, breast cancers, cervical cancers, lung cancers, squamous cell carcinoma, diffuse intrinsic pontine glioma (DIPG), glioblastoma, medulloblastoma, leukemia, melanoma, and ovarian cancers. (P. Reigan et al., *Trends in Pharmacol. Sci.*, 2016).

There are few Wee1 inhibitors in clinical development. There is scope to improve Wee1 inhibitor selectivity and the properties of the inhibitors to permit targeting of specific cancer types.

BRIEF SUMMARY OF THE INVENTION

In one aspect, provided is a compound of Formula (I):

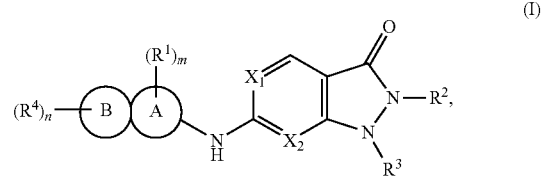

(I)

or a tautomer or isomer thereof, or a pharmaceutically acceptable salt of any of the foregoing, wherein m, n, $X_1$, $X_2$, A, B, $R^1$, $R^2$, $R^3$ and $R^4$ are as detailed herein.

In some embodiments, provided is a compound of Formula (Ia):

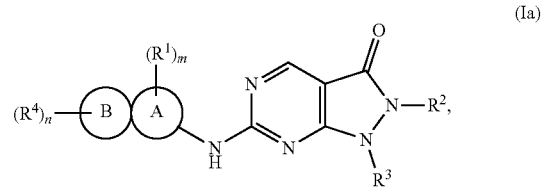

(Ia)

or a salt thereof, wherein A, B, $R^1$, $R^2$, $R^3$ and $R^4$ are as detailed herein. In some embodiments, provided is a compound of Formula (Ia), or a tautomer or isomer thereof, or a pharmaceutically acceptable salt of any of the foregoing.

In some embodiments, the compound of Formula (I) or a salt thereof, is of the Formula (Ia), (Ia-1 to Ia-12), (Ib), (Ib-1 to Ib-9), (Ic) or (Ic-1 to Ic-9), or a tautomer or isomer thereof, or a pharmaceutically acceptable salt of any of the foregoing, as detailed herein. In some embodiments, the compound of Formula (I) or a salt thereof, is of Formula (Ia), (Ia-1), (Ia-2), (Ia-3), (Ia-4), (Ia-5), or (Ia-6) as detailed herein.

In another aspect, provided is a method of treating cancer in an individual in need thereof comprising administering to the individual a therapeutically effective amount of a compound as detailed herein, such as a compound of Formula (I), (Ia), (Ia-1), (Ia-2), (Ia-3), (Ia-4), (Ia-5), or (Ia-6) or a pharmaceutically acceptable salt thereof. In some embodiments, provided is a method of treating cancer in an individual in need thereof comprising administering to the individual a therapeutically effective amount of a compound as detailed herein, such as a compound of Formula (I), (Ia), (Ia-1 to Ia-12), (Ib), (Ib-1 to Ib-9), (Ic) or (Ic-1 to Ic-9), or a tautomer or isomer thereof, or a pharmaceutically acceptable salt of any of the foregoing. Also provided is a method of inhibiting Wee1 in a cell, comprising administering a compound detailed herein, or a salt thereof, to the cell. Also provided is a method of inhibiting Wee1 in a cell, comprising administering a compound detailed herein, or a tautomer or isomer thereof, or a pharmaceutically acceptable salt of any of the foregoing, to the cell.

In another aspect, provided are pharmaceutical compositions comprising a compound detailed herein and a pharmaceutically acceptable carrier or excipient. In another aspect, provided are pharmaceutical compositions comprising a compound, or a tautomer or isomer thereof, or a pharmaceutically acceptable salt of any of the foregoing, detailed herein and a pharmaceutically acceptable carrier or excipient. Kits comprising a compound detailed herein or a salt thereof are also provided. Kits comprising a compound, or a tautomer or isomer thereof, or a pharmaceutically acceptable salt of any of the foregoing, detailed herein are also provided. A compound as detailed herein, or a salt thereof, is also provided for the manufacture of a medicament for the treatment of cancer. A compound, or a tautomer or isomer thereof, or a pharmaceutically acceptable salt of any of the foregoing, as detailed herein is also provided for the manufacture of a medicament for the treatment of cancer.

DETAILED DESCRIPTION OF THE INVENTION

Definitions

"Alkyl" refers to and includes saturated linear and branched univalent hydrocarbon structures and combination thereof, having the number of carbon atoms designated (i.e., $C_1$-$C_{10}$ means one to ten carbons). Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"), 3 to 8 carbon atoms (a "$C_3$-$C_8$ alkyl"), 1 to 6 carbon atoms (a "$C_1$-$C_6$ alkyl"), 1 to 5 carbon atoms (a "$C_1$-$C_5$ alkyl"), or 1 to 4 carbon atoms (a "$C_1$-$C_4$ alkyl"). Examples of alkyl include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkenyl" as used herein refers to an unsaturated linear or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). The alkenyl group may be in "cis" or "trans" configurations, or alternatively in "E" or "Z" configurations. Particular alkenyl groups are those having 2 to 20 carbon atoms (a "$C_2$-$C_{20}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

"Alkylene" as used herein refers to the same residues as alkyl, but having bivalency. Particular alkylene groups are those having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—CH$_2$—), ethylene (—CH$_2$CH$_2$—), propylene (—CH$_2$CH$_2$CH$_2$—), butylene (—CH$_2$CH$_2$CH$_2$CH$_2$—), and the like.

"Alkynyl" as used herein refers to an unsaturated linear or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Aryl" refers to and includes polyunsaturated aromatic hydrocarbon groups. Aryl may contain additional fused rings (e.g., from 1 to 3 rings), including additionally fused aryl, heteroaryl, cycloalkyl, and/or heterocyclyl rings. In one variation, the aryl group contains from 6 to 14 annular carbon atoms. Examples of aryl groups include, but are not limited to, phenyl, naphthyl, biphenyl, and the like.

"Carbonyl" refers to the group C=O.

"Cycloalkyl" refers to and includes cyclic univalent hydrocarbon structures, which may be fully saturated, mono- or polyunsaturated, but which are non-aromatic, having the number of carbon atoms designated (e.g., $C_1$-$C_{10}$ means one to ten carbons). Cycloalkyl can consist of one ring, such as cyclohexyl, or multiple rings, such as adamantly, but excludes aryl groups. A cycloalkyl comprising more than one ring may be fused, spiro or bridged, or combinations thereof. A preferred cycloalkyl is a cyclic hydrocarbon having from 3 to 13 annular carbon atoms. A more preferred cycloalkyl is a cyclic hydrocarbon having from 3 to 8 annular carbon atoms (a "$C_3$-$C_8$ cycloalkyl"). Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like.

"Halo" or "halogen" refers to elements of the Group 17 series having atomic number 9 to 85. Preferred halo groups include fluoro, chloro, bromo and iodo. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halo; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl (—CF$_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—OCF$_3$).

"Heteroaryl" refers to and includes unsaturated aromatic cyclic groups having from 1 to 10 annular carbon atoms and at least one annular heteroatom, including but not limited to heteroatoms such as nitrogen, oxygen and sulfur, wherein the nitrogen and sulfur atoms are optionally oxidized, and the nitrogen atom(s) are optionally quaternized. A heteroaryl group can be attached to the remainder of the molecule at an annular carbon or at an annular heteroatom. Heteroaryl may contain additional fused rings (e.g., from 1 to 3 rings), including additionally fused aryl, heteroaryl, cycloalkyl, and/or heterocyclyl rings. Examples of heteroaryl groups include, but are not limited to, pyridyl, pyrimidyl, thiophenyl, furanyl, thiazolyl, and the like.

"Heterocycle" or "heterocyclyl" refers to a saturated or an unsaturated non-aromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. A heterocyclyl group may have a single ring or multiple condensed rings, but excludes heteroaryl groups. A heterocycle comprising more than one ring may be fused, spiro or bridged, or any combination thereof. In fused ring systems, one or more of the fused rings can be aryl or heteroaryl. Examples of heterocyclyl groups include, but are not limited to, tetrahydropyranyl, dihydropyranyl, piperidinyl, piperazinyl, pyrrolidinyl, thiazolinyl, thiazolidinyl, tetrahydrofuranyl, tetrahydrothiophenyl, 2,3-dihydrobenzo[b]thiophen-2-yl, 4-amino-2-oxopyrimidin-1(2H)-yl, and the like.

"Oxo" refers to the moiety =O.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 2 to 5, 3 to 5, 2 to 3, 2 to 4, 3 to 4, 1 to 3, 1 to 4 or 1 to 5 substituents.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" or "treating" is an approach for obtaining beneficial or desired results including clinical results. For example, beneficial or desired results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals. In reference to cancers or other unwanted cell proliferation, beneficial or desired results include shrinking a tumor (reducing tumor size); decreasing the growth rate of the tumor (such as to suppress tumor growth); reducing the number of cancer cells; inhibiting, retarding or slowing to some extent and preferably stopping cancer cell infiltration into peripheral organs; inhibiting (slowing to some extent and preferably stopping) tumor metastasis; inhibiting tumor growth; preventing or delaying occurrence and/or recurrence of tumor; and/or relieving to some extent one or more of the symptoms associated with the cancer. In some embodiments, beneficial or desired results include preventing or delaying occurrence and/or recurrence, such as of unwanted cell proliferation.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

As used herein, an "effective dosage" or "effective amount" of compound or salt thereof or pharmaceutical composition is an amount sufficient to effect beneficial or desired results. For prophylactic use, beneficial or desired results include results such as eliminating or reducing the risk, lessening the severity of, or delaying the onset of the disease, including biochemical, histological and/or behavioral symptoms of the disease, its complications and intermediate pathological phenotypes presenting during development of the disease. For therapeutic use, beneficial or desired results include ameliorating, palliating, lessening, delaying or decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more administrations, in the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. An effective dosage can be administered in one or more administrations. For purposes of this disclosure, an effective dosage of compound or a salt thereof, or pharmaceutical composition is an amount sufficient to accomplish prophylactic or therapeutic treatment either directly or indirectly. It is intended and understood that an effective dosage of a compound or salt thereof, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, the term "individual" is a mammal, including humans. An individual includes, but is not limited to, human, bovine, horse, feline, canine, rodent, or primate. In some embodiments, the individual is human. The individual (such as a human) may have advanced disease or lesser extent of disease, such as low tumor burden. In some embodiments, the individual is at an early stage of a proliferative disease (such as cancer). In some embodiments, the individual is at an advanced stage of a proliferative disease (such as an advanced cancer).

Reference to "about" a value or parameter herein includes (and describes) embodiments that are directed to that value or parameter per se. For example, description referring to "about X" includes description of "X".

It is understood that aspects and variations described herein also include "consisting" and/or "consisting essentially of" aspects and variations.

Compounds

In one aspect, provided is a compound of Formula (I):

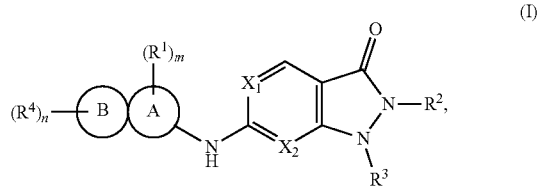
(I)

or a tautomer or isomer thereof, or a pharmaceutically acceptable salt of any of the foregoing, wherein:

$X_1$ is N or CR;

$X_2$ is N or CR, wherein at least one of $X_1$ and $X_2$ is N;

each R is independently hydrogen, $C_1$-$C_6$ alkyl, halogen or CN;

A is phenyl or 5- to 6-membered heteroaryl, each of which is optionally substituted by $R^1$;

B is $C_6$-$C_{14}$ aryl, 5- to 10-membered heteroaryl, $C_3$-$C_8$ cycloalkyl, or 3- to 12-membered heterocyclyl, each of which is optionally substituted by $R^4$, wherein A is fused to B;

m is 0, 1, 2, 3, or 4;

n is 0, 1, 2, 3, or 4;

$R^1$ is independently halogen, —CN, $C_1$-$C_6$ alkyl, $C_2$-$C_6$ alkenyl, $C_2$-$C_6$ alkynyl, —C(O)$R^{17}$, —C(O)O$R^{17}$, —N$R^{17}R^{18}$ or —C(O)N$R^{17}R^{18}$;

$R^2$ is independently hydrogen, $C_1$-$C_6$ alkyl, $C_2$-$C_6$ alkenyl, $C_2$-$C_6$ alkynyl, $C_3$-$C_6$ cycloalkyl, —($C_1$-$C_3$ alkylene)CN, —($C_1$-$C_3$ alkylene)O$R^{10}$, —($C_1$-$C_3$ alkylene)N$R^{11}R^{12}$, —($C_1$-$C_3$ alkylene)CF$_3$, —($C_1$-$C_3$ alkylene)C(O)$R^{10}$, —($C_1$-$C_3$ alkylene)C(O)N$R^{11}R^{12}$, —($C_2$-$C_3$ alkylene)N$R^{10}$C(O)$R^{11}$, —($C_1$-$C_3$ alkylene)S(O)$_2R^{10}$, —($C_2$-$C_3$ alkylene)N$R^{10}$S(O)$_2R^{11}$, —($C_1$-$C_3$ alkylene)S(O)$_2$N$R^{11}R^{12}$, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl), or —($C_1$-$C_3$ alkylene)($C_6$-$C_{14}$ aryl), wherein each $R^2$ is independently optionally substituted by halogen, oxo, —O$R^{13}$, $C_1$-$C_6$ alkyl, or —N$R^{13}R^{14}$;

$R^3$ is independently hydrogen, $C_1$-$C_6$ alkyl, —C(O)$R^{10}$, —S(O)$R^{10}$, —S(O)$_2R^{10}$, $C_3$-$C_6$ cycloalkyl, 3- to 12-membered heterocyclyl, 5- to 10-membered heteroaryl, $C_6$-$C_{14}$ aryl, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl), or —($C_1$-$C_3$ alkylene)($C_6$-$C_{14}$ aryl), wherein each $R^3$ is independently optionally substituted by halogen, oxo, —O$R^{13}$, —N$R^{13}R^{14}$, —C(O)$R^{13}$, —C(O)O$R^{13}$, —C(O)N$R^{13}R^{14}$, —N$R^{13}$C(O)$R^{14}$, —CN, —S$R^{13}$, —S(O)$R^{13}$, —S(O)$_2R^{13}$, —Si($C_1$-$C_6$ alkyl)$_3$, —P(O)$R^{13}R^{14}$, —N$R^{13}$S(O)$_2R^{14}$, —($C_1$-$C_3$ alkylene)O$R^{13}$, —($C_1$-$C_3$ alkylene)N$R^{13}R^{14}$, —($C_1$-$C_3$ alkylene)C(O)$R^{13}$, $C_3$-$C_8$ cycloalkyl optionally substituted by $C_1$-$C_6$ alkyl, CN, CF$_3$, oxo, —OH, —N$R^{15}R^{16}$, —O$R^{15}$ or halogen, 3- to 12-membered heterocyclyl optionally substituted by oxo, —OH, —N$R^{15}R^{16}$, —C(O)O$R^{15}$, —O$R^{15}$ or halogen, or $C_1$-$C_6$ alkyl optionally substituted by oxo, —OH, —N$R^{15}R^{16}$, —C(O)O$R^{15}$, —O$R^{15}$ or halogen, with the proviso that the 5- to 10-membered heteroaryl and $C_6$-$C_{14}$ aryl of $R^3$ is not substituted by

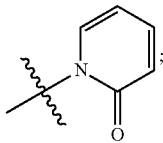

each $R^4$ is independently oxo, $C_1$-$C_6$ alkyl, $C_2$-$C_6$ alkenyl, $C_2$-$C_6$ alkynyl, halogen, —C(O)$R^{17}$, —C(O)O$R^{17}$, —C(O)N$R^{17}R^{18}$, —CN, —Si($C_1$-$C_6$ alkyl)$_3$, —O$R^{17}$, —N$R^{17}R^{18}$, —OC(O)N$R^{17}R^{18}$, —N$R^{17}$C(O)$R^{18}$, —S(O)$_2R^{17}$, —N$R^{17}$S(O)$_2R^{18}$, —S(O)$_2$N$R^{17}R^{18}$, $C_3$-$C_6$ cycloalkyl, 3- to 6-membered heterocyclyl, —($C_1$-$C_3$ alkylene)CN, —($C_1$-$C_3$ alkylene)O$R^{17}$, —($C_1$-$C_3$ alkylene)N$R^{17}R^{18}$, —($C_1$-$C_3$ alkylene)CF$_3$, —($C_1$-$C_3$ alkylene)C(O)$R^{17}$, —($C_1$-$C_3$ alkylene)C(O)N$R^{17}R^{18}$, —($C_1$-$C_3$ alkylene)N$R^{17}$C(O)$R^{18}$, —($C_1$-$C_3$ alkylene)S(O)$_2R^{17}$, —($C_1$-$C_3$ alkylene)N$R^{17}$S(O)$_2R^{18}$, —($C_1$-$C_3$ alkylene)S(O)$_2$N$R^{17}R^{18}$, —($C_1$-$C_3$ alkylene)($C_3$-$C_6$ cycloalkyl) or —($C_1$-$C_3$ alkylene)(3- to 6-membered heterocyclyl), wherein each $R^4$ is independently optionally substituted by halogen, oxo, —O$R^{19}$, —N$R^{19}R^{20}$, or —C(O)$R^{19}$, or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$;

$R^{10}$ is independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl, or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl are independently optionally substituted by halogen, oxo, —CN, —O$R^{15}$, —N$R^{15}R^{16}$, —P(O)(O$R^{15}$)(O$R^{16}$), phenyl optionally substituted by halogen, or $C_1$-$C_6$ alkyl optionally substituted by halogen, —OH or oxo;

$R^{11}$ and $R^{12}$ are each independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl, or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl are independently optionally substituted by halogen, oxo, —CN, —O$R^{15}$, —N$R^{15}R^{16}$, or $C_1$-$C_6$ alkyl optionally substituted by halogen, —OH or oxo, or $R^{11}$ and $R^{12}$ are taken together with the atom to which they attached to form a 3- to 6-membered heterocyclyl optionally substituted by halogen, oxo, —O$R^{15}$, —N$R^{15}R^{16}$ or $C_1$-$C_6$ alkyl optionally substituted by halogen, oxo or —OH;

$R^{13}$ and $R^{14}$ are each independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl, 3- to 6-membered heterocyclyl, —C(O)O$R^{15}$, —($C_1$-$C_3$ alkylene)O$R^{15}$ or —C(O)N$R^{15}R^{16}$, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl are independently optionally substituted by halogen, oxo, —CN, —O$R^{15}$, —N$R^{15}R^{16}$, or $C_1$-$C_6$ alkyl optionally substituted by halogen, —OH or oxo, or $R^{13}$ and $R^{14}$ are taken together with the atom to which they attached to form a 3-6 membered heterocyclyl optionally substituted by halogen or $C_1$-$C_6$ alkyl optionally substituted by halogen or oxo;

$R^{15}$ and $R^{16}$ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo, or $R^{15}$ and $R^{16}$ are taken together with the atom to which they attached to form a 3-6 membered heterocyclyl optionally substituted by halogen, oxo or $C_1$-$C_6$ alkyl optionally substituted by oxo or halogen; and each $R^{17}$, $R^{18}$, $R^{19}$, and $R^{20}$ is independently hydrogen, $C_3$-$C_6$ cycloalkyl, 3-6 membered heterocyclyl or $C_1$-$C_6$ alkyl, each of which is optionally substituted by halogen, oxo or —OH, or $R^{17}$ and $R^{18}$ are taken together with the atom to which they attached to form a 3-6 membered heterocyclyl optionally substituted by halogen, oxo or —OH.

In some embodiments of a compound of Formula (I), B is $C_6$ aryl, 5- to 7-membered heteroaryl, $C_3$-$C_8$ cycloalkyl, or 3- to 8-membered heterocyclyl, each of which is optionally substituted by $R^4$, wherein B is fused to A.

In some embodiments, provided is a compound of Formula (Ia):

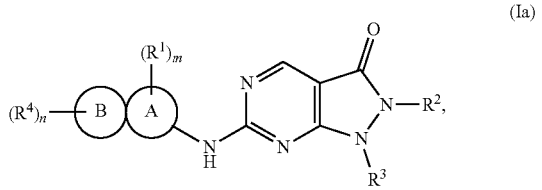

(Ia)

or a salt thereof, wherein:

A is phenyl or 6-membered heteroaryl, each of which is optionally substituted by $R^1$;

B is $C_6$ aryl, 5- to 6-membered heteroaryl, $C_3$-$C_8$ cycloalkyl, or 3- to 8-membered heterocyclyl, each of which is optionally substituted by $R^4$, wherein A is fused to B;

m is 0, 1, 2, 3, or 4;

n is 0, 1, 2, 3, or 4;

$R^1$ is independently halogen, —CN, $C_1$-$C_6$ alkyl, $C_2$-$C_6$ alkenyl, $C_2$-$C_6$ alkynyl, —C(O)$R^{17}$, —C(O)O$R^{17}$, or —C(O)N$R^{17}R^{18}$;

$R^2$ is independently hydrogen, $C_1$-$C_6$ alkyl, $C_2$-$C_6$ alkenyl, $C_2$-$C_6$ alkynyl, $C_3$-$C_6$ cycloalkyl, —($C_1$-$C_3$ alkylene)CN, —($C_1$-$C_3$ alkylene)O$R^{10}$, —($C_1$-$C_3$ alkylene)N$R^{11}R^{12}$, —($C_1$-$C_3$ alkylene)CF$_3$, —($C_1$-$C_3$ alkylene)C(O)$R^{10}$, —($C_1$-$C_3$ alkylene)C(O)N$R^{11}R^{12}$, —($C_2$-$C_3$ alkylene)N$R^{10}$C(O)$R^{11}$, —($C_1$-$C_3$ alkylene)S(O)$_2R^{10}$, —($C_2$-$C_3$ alkylene)N$R^{10}$S(O)$_2R^{11}$, —($C_1$-$C_3$ alkylene)S(O)$_2$N$R^{11}R^{12}$, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl), or —($C_1$-$C_3$ alkylene)($C_6$-$C_{14}$ aryl), wherein each $R^2$ is independently optionally substituted by halogen, oxo, —O$R^{13}$, $C_1$-$C_6$ alkyl, or —N$R^{13}R^{14}$;

$R^3$ is independently hydrogen, $C_1$-$C_6$ alkyl, —C(O)$R^{10}$, —S(O)$R^{10}$, —S(O)$_2R^{10}$, $C_3$-$C_6$ cycloalkyl, 3- to 12-membered heterocyclyl, 5- to 10-membered heteroaryl, $C_6$-$C_{14}$ aryl, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl), or —($C_1$-$C_3$ alkylene)($C_6$-$C_{14}$ aryl), wherein each $R^3$ is independently optionally substituted by halogen, oxo, —O$R^{13}$, —N$R^{13}R^{14}$, —C(O)$R^{13}$, —C(O)N$R^{13}R^{14}$, —N$R^{13}$C(O)$R^{14}$, —CN, —S(O)$R^{13}$, —S(O)$_2R^{13}$, —($C_1$-$C_3$ alkylene)O$R^{13}$, —($C_1$-$C_3$ alkylene)N$R^{13}R^{14}$, —($C_1$-$C_3$ alkylene)C(O)$R^{13}$, $C_3$-$C_8$ cycloalkyl, 3- to 12-membered heterocyclyl optionally substituted by oxo, —OH or halogen, or $C_1$-$C_6$ alkyl optionally substituted by oxo, —OH or halogen;

each $R^4$ is independently oxo, $C_1$-$C_6$ alkyl, $C_2$-$C_6$ alkenyl, $C_2$-$C_6$ alkynyl, —C(O)$R^{17}$, —C(O)O$R^{17}$, or —C(O)N$R^{17}R^{18}$, wherein each $R^4$ is independently optionally substituted by halogen, oxo, —O$R^{19}$, —N$R^{19}R^{20}$, or —C(O)$R^{19}$, or two $R^4$ are taken together with the carbon to which they attach to form a $C_3$-$C_6$ cycloalkyl;

$R^{10}$ is independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl, or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl are independently optionally substituted by halogen, oxo, —CN, —O$R^{15}$, —N$R^{15}R^{16}$, —P(O)(O$R^{15}$)(O$R^{16}$), phenyl optionally substituted by halogen, or $C_1$-$C_6$ alkyl optionally substituted by halogen, —OH or oxo;

$R^{11}$ and $R^{12}$ are each independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl, or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl are independently optionally substituted by halogen, oxo, —CN, —O$R^{15}$, —N$R^{15}R^{16}$, or $C_1$-$C_6$ alkyl optionally substituted by halogen, —OH or oxo, or $R^{11}$ and $R^{12}$ are taken together with the atom to which they attached to form a 3- to 6-membered heterocyclyl optionally substituted by halogen, oxo, —O$R^{15}$, —N$R^{15}R^{16}$ or $C_1$-$C_6$ alkyl optionally substituted by halogen, oxo or —OH;

$R^{13}$ and $R^{14}$ are each independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl, or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl are independently optionally substituted by halogen, oxo, —CN, —O$R^{15}$, —N$R^{15}R^{16}$, or $C_1$-$C_6$ alkyl optionally substituted by halogen, —OH or oxo, or $R^{13}$ and $R^{14}$ are taken together with the atom to which they attached to form a 3-6 membered heterocyclyl optionally substituted by halogen or $C_1$-$C_6$ alkyl optionally substituted by halogen or oxo;

$R^{15}$ and $R^{16}$ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;

or $R^{15}$ and $R^{16}$ are taken together with the atom to which they attached to form a 3-6 membered heterocyclyl optionally substituted by halogen, oxo or $C_1$-$C_6$ alkyl optionally substituted by oxo or halogen; and each $R^{17}$, $R^{18}$, $R^{19}$, and $R^{20}$ is independently hydrogen or $C_1$-$C_6$ alkyl.

In some embodiments, provided is a compound of Formula (Ia), or a tautomer or isomer thereof, or a pharmaceutically acceptable salt of any of the foregoing.

In some embodiments of a compound of Formula (Ia), the the 5- to 10-membered heteroaryl and $C_6$-$C_{14}$ aryl of $R^3$ is not substituted by

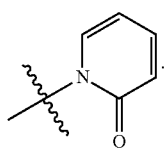 [SMILES: *n1ccccc1=O]

In some embodiments, the compound of Formula (I) is of Formula (Ib):

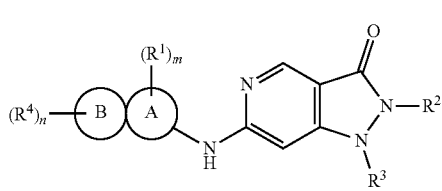

or a tautomer or isomer thereof, or a pharmaceutically acceptable salt of any of the foregoing, wherein m, n, A, B, $R^1$, $R^2$, $R^3$ and $R^4$ are as detailed herein. In some embodiments of a compound of Formula (Ib), B is $C_6$ aryl, 5- to 7-membered heteroaryl, $C_3$-$C_8$ cycloalkyl, or 3- to 8-membered heterocyclyl, each of which is optionally substituted by $R^4$, wherein B is fused to A.

In some embodiments, the compound of Formula (I) is of Formula (Ic):

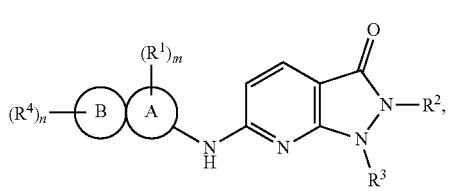

or a tautomer or isomer thereof, or a pharmaceutically acceptable salt of any of the foregoing, wherein m, n, A, B, $R^1$, $R^2$, $R^3$ and $R^4$ are as detailed herein. In some embodiments of a compound of Formula (I), $X_1$ is N. In some embodiments of a compound of Formula (Ic), B is $C_6$ aryl, 5- to 7-membered heteroaryl, $C_3$-$C_8$ cycloalkyl, or 3- to 8-membered heterocyclyl, each of which is optionally substituted by $R^4$, wherein B is fused to A.

In some embodiments of a compound of Formula (I), $X_1$ is CR. In some embodiments of a compound of Formula (I), $X_1$ is CH. In some embodiments, $X_1$ is N. In some embodiments of a compound of Formula (I), $X_2$ is N. In some embodiments of a compound of Formula (I), $X_2$ is CR. In some embodiments of a compound of Formula (I), $X_2$ is CH.

In some embodiments of a compound of Formula (I), $X_1$ is N and $X_2$ is CR. In some embodiments of a compound of Formula (I), $X_1$ is N and $X_2$ is CH. In some embodiments of a compound of Formula (I), $X_1$ is CR and $X_2$ is N. In some embodiments of a compound of Formula (I), $X_1$ is CH and $X_2$ is N. In some embodiments of a compound of Formula (I), $X_1$ and $X_2$ both are N.

In some embodiments of a compound of Formula (I), R is hydrogen, $C_1$-$C_6$ alkyl, halogen or CN. In some embodiments of a compound of Formula (I), R is hydrogen. In some embodiments of a compound of Formula (I), R is $C_1$-$C_6$ alkyl. In some embodiments of a compound of Formula (I), R is methyl. In some embodiments of a compound of Formula (I), R is halogen. In some embodiments of a compound of Formula (I), R is CN.

In some embodiments of a compound of Formula (I), A is phenyl optionally substituted by $R^1$. In some embodiments of a compound of Formula (I), A is unsubstituted phenyl. In some embodiments of a compound of Formula (I), A is phenyl substituted by $R^1$.

In some embodiments of a compound of Formula (I), A is 5- to 6-membered heteroaryl optionally substituted by $R^1$. In some embodiments of a compound of Formula (I), A is 6-membered heteroaryl optionally substituted by $R^1$. In some embodiments of a compound of Formula (I), A is unsubstituted 6-membered heteroaryl. In some embodiments of a compound of Formula (I), A is 6-membered heteroaryl substituted by $R^1$. In some embodiments of a compound of Formula (I), A is unsubstituted 5-membered heteroaryl. In some embodiments of a compound of Formula (I), A is 5-membered heteroaryl substituted by $R^1$.

In some embodiments of a compound of Formula (I), A is selected from the group consisting of:

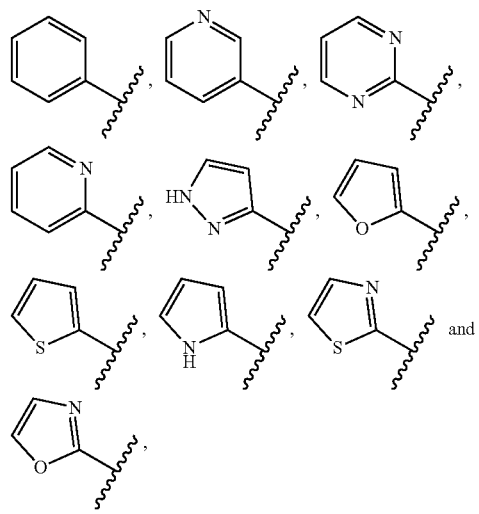

wherein the wavy lines denote attachment points to the parent molecule and each is fused with B and is optionally substituted by $R^1$.

In some embodiments of a compound of Formula (I), A is selected from the group consisting of:

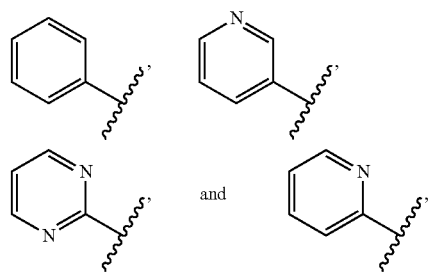

wherein the wavy lines denote attachment points to the parent molecule and each is fused with B and is optionally substituted by $R^1$.

In some embodiments of a compound of Formula (I), $R^1$ is independently halogen, —CN, oxo, $C_1$-$C_6$ alkyl, $C_2$-$C_6$ alkenyl, $C_2$-$C_6$ alkynyl, —C(O)$R^{17}$, —C(O)O$R^{17}$, —N$R^{17}R^{18}$ or —C(O)N$R^{17}R^{18}$. In some embodiments of a compound of Formula (I), $R^1$ is independently halogen, —CN, oxo, $C_1$-$C_6$ alkyl, $C_2$-$C_6$ alkenyl, $C_2$-$C_6$ alkynyl, —C(O)$R^{17}$, —C(O)O$R^{17}$, or —C(O)N$R^{17}R^{18}$. In some embodiments of a compound of Formula (I), $R^1$ is independently —CN, $C_1$-$C_6$ alkyl, or halogen. In some embodiments of a compound of Formula (I), $R^1$ is —CN. In some embodiments of a compound of Formula (I), $R^1$ is $C_1$-$C_6$ alkyl. In some embodiments of a compound of Formula (I), $R^1$ is halogen.

In some embodiments of a compound of Formula (I), A is phenyl optionally substituted by $R^1$, and $R^1$ is independently —CN, $C_1$-$C_6$ alkyl, or halogen. In some embodiments of a compound of Formula (I), A is 6-membered heteroaryl optionally substituted by $R^1$, and $R^1$ is independently —CN, $C_1$-$C_6$ alkyl, or halogen.

In some embodiments of a compound of Formula (I), A is selected from the group consisting of:

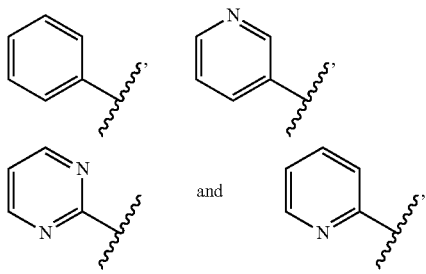

and wherein the wavy lines denote attachment points to the parent molecule and each is fused with B and optionally substituted by $R^1$, wherein $R^1$ is independently —CN, $C_1$-$C_6$ alkyl, or halogen.

In some embodiments of a compound of Formula (I), B is $C_6$ aryl, 5- to 7-membered heteroaryl, $C_3$-$C_8$ cycloalkyl, or 3- to 8-membered heterocyclyl, each of which is unsubstituted. In some embodiments of a compound of Formula (I), B is $C_6$ aryl, 5- to 7-membered heteroaryl, $C_3$-$C_8$ cycloalkyl, or 3- to 8-membered heterocyclyl, each of which is substituted with $R^4$. In some embodiments of a compound of Formula (I), B is $C_6$ aryl or 3- to 8-membered heterocyclyl, each of which is unsubstituted. In some embodiments of a compound of Formula (I), B is $C_6$ aryl or 3- to 8-membered heterocyclyl, each of which is optionally substituted with $R^4$.

In some embodiments of a compound of Formula (I), B is $C_6$ aryl which is optionally substituted by $R^4$. In some embodiments of a compound of Formula (I), B is $C_6$ aryl which is unsubstituted. In some embodiments of a compound of Formula (I), B is 5- to 7-membered heteroaryl which is optionally substituted by $R^4$. In some embodiments of a compound of Formula (I), B is 5- to 7-membered heteroaryl which is unsubstituted. In some embodiments of a compound of Formula (I), B is $C_3$-$C_8$ cycloalkyl which is optionally substituted by $R^4$. In some embodiments of a compound of Formula (I), B is $C_3$-$C_8$ cycloalkyl which is unsubstituted. In some embodiments of a compound of Formula (I), B is 3- to 7-membered heterocyclyl which is optionally substituted by $R^4$. In some embodiments of a compound of Formula (I), B is 3- to 8-membered heterocyclyl which is optionally substituted by $R^4$. In some embodiments of a compound of Formula (I), B is 3- to 8-membered heterocyclyl which is unsubstituted.

In some embodiments of a compound of Formula (I), B is $C_6$ aryl, 5- to 7-membered heteroaryl, $C_3$-$C_8$ cycloalkyl, or 3- to 8-membered heterocyclyl, each of which is substituted with $R^4$ and each $R^4$ is independently oxo, $C_1$-$C_6$ alkyl, $C_2$-$C_6$ alkenyl, $C_2$-$C_6$ alkynyl, halogen, —C(O)$R^{17}$, —C(O)O$R^{17}$, —C(O)N$R^{17}R^{18}$, —CN, —Si($C_1$-$C_6$ alkyl)$_3$, —O$R^{17}$, —N$R^{17}R^{18}$, —OC(O)N$R^{17}R^{18}$, —N$R^{17}$C(O)$R^{18}$, —S(O)$_2R^{17}$, —N$R^{17}$S(O)$_2R^{18}$, —S(O)$_2$N$R^{17}R^{18}$, $C_3$-$C_6$ cycloalkyl, 3- to 6-membered heterocyclyl, —($C_1$-$C_3$ alkylene)CN, —($C_1$-$C_3$ alkylene)O$R^{17}$, —($C_1$-$C_3$ alkylene)N$R^{17}R^{18}$, —($C_1$-$C_3$ alkylene)CF$_3$, —($C_1$-$C_3$ alkylene)C(O)$R^{17}$, —($C_1$-$C_3$ alkylene)C(O)N$R^{17}R^{18}$, —($C_1$-$C_3$ alkylene)N$R^{17}$C(O)$R^{18}$, —($C_1$-$C_3$ alkylene)S(O)$_2R^{17}$, —($C_1$-$C_3$ alkylene)N$R^{17}$S(O)$_2R^{18}$, —($C_1$-$C_3$ alkylene)S(O)$_2$N$R^{17}R^{18}$, —($C_1$-$C_3$ alkylene)($C_3$-$C_6$ cycloalkyl) or —($C_1$-$C_3$ alkylene)(3- to 6-membered heterocyclyl), wherein each $R^4$ is independently optionally substituted by halogen, oxo, —O$R^{19}$, —N$R^{19}R^{20}$, or —C(O)$R^{19}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments of a compound of Formula (I), B is $C_6$ aryl, 5- to 7-membered heteroaryl, $C_3$-$C_8$ cycloalkyl, or 3- to 8-membered heterocyclyl, each of which is substituted with $R^4$, wherein $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments of a compound of Formula (I), B is $C_6$ aryl optionally substituted with $R^4$, wherein $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments of a compound of Formula (I), B is 5- to 7-membered heteroaryl optionally substituted with $R^4$, wherein $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments of a compound of Formula (I), B is $C_3$-$C_8$ cycloalkyl optionally substituted with $R^4$, wherein $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments of a compound of Formula (I), B is 3- to 8-membered heterocyclyl optionally substituted with $R^4$, wherein $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments of a compound of Formula (I), B is 6-membered heterocyclyl optionally substituted by $R^4$, wherein $R^4$ is independently $C_1$-$C_6$ alkyl. In some embodiments of a compound of Formula (I), B is 6-membered heterocyclyl having one nitrogen atom, wherein the 6-membered heterocyclyl is optionally substituted by $R^4$ and $R^4$ is independently $C_1$-$C_6$ alkyl.

In some embodiments of a compound of Formula (I), B is $C_6$ aryl, 5- to 7-membered heteroaryl, $C_3$-$C_8$ cycloalkyl, or 3- to 8-membered heterocyclyl, each of which is substituted with $R^4$ and each $R^4$ is independently oxo, $C_1$-$C_6$ alkyl, $C_2$-$C_6$ alkenyl, $C_2$-$C_6$ alkynyl, —C(O)$R^{17}$, —C(O)O$R^{17}$, or —C(O)N$R^{17}R^{18}$, wherein each $R^4$ is independently optionally substituted by halogen, oxo, —O$R^{19}$, —N$R^{19}R^{20}$, or —C(O)$R^{19}$; or two $R^4$ are taken together with the carbon to which they attach to form a $C_3$-$C_6$ cycloalkyl. In some embodiments of a compound of Formula (I), B is $C_6$ aryl, 5- to 7-membered heteroaryl, $C_3$-$C_8$ cycloalkyl, or 3- to 8-membered heterocyclyl, each of which is substituted with $R^4$, wherein $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$ are taken together with the carbon to which they attach to form a $C_3$-$C_6$ cycloalkyl. In some embodiments of a compound of Formula (I), B is $C_6$ aryl optionally substituted with $R^4$, wherein $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$ are taken together with the carbon to which they attach to form a $C_3$-$C_6$ cycloalkyl. In some embodiments of a compound of Formula (I), B is 5- to 7-membered heteroaryl optionally substituted with $R^4$, wherein $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$ are taken together with the carbon to which they attach to form a $C_3$-$C_6$ cycloalkyl. In some embodiments of a compound of Formula (I), B is $C_3$-$C_8$ cycloalkyl optionally substituted with $R^4$, wherein $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$ are taken together with the carbon to which they attach to form a $C_3$-$C_6$ cycloalkyl. In some embodiments of a compound of Formula (I), B is 3- to 8-membered heterocyclyl optionally substituted with $R^4$, wherein $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$ are taken together with the carbon to which they attach to form a $C_3$-$C_6$ cycloalkyl. In some embodiments of a compound of Formula (I), B is 6-membered heterocyclyl optionally substituted by $R^4$, wherein $R^4$ is independently $C_1$-$C_6$ alkyl. In some embodiments of a compound of Formula (I), B is 6-membered heterocyclyl having one nitrogen atom, wherein the 6-membered heterocyclyl is optionally substituted by $R^4$ and $R^4$ is independently $C_1$-$C_6$ alkyl.

In some embodiments of a compound of Formula (I), A is unsubstituted phenyl fused with B, wherein B is $C_6$ aryl, 5- to 7-membered heteroaryl, $C_3$-$C_8$ cycloalkyl, or 3- to 8-membered heterocyclyl, each of which is substituted with $R^4$; $R^4$ is independently oxo, $C_1$-$C_6$ alkyl, $C_2$-$C_6$ alkenyl, $C_2$-$C_6$ alkynyl, —C(O)$R^{17}$, —C(O)O$R^{17}$, or —C(O)NR$^{17}R^{18}$, wherein each $R^4$ is independently optionally substituted by halogen, oxo, —O$R^{19}$, —N$R^{19}R^{20}$, or —C(O)$R^{19}$; or two $R^4$ are taken together with the carbon to which they attach to form a $C_3$-$C_6$ cycloalkyl. In some embodiments of a compound of Formula (I), A is unsubstituted phenyl fused with B, wherein B is 3- to 8-membered heterocyclyl optionally substituted with $R^4$; $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$, when bound to the same carbon or two different carbon atoms, are taken together with the carbon to which they are attached to form a $C_3$-$C_6$ cycloalkyl or 3- to 7-membered heterocyclyl, each is optionally substituted by $R^{19}$. In some embodiments of a compound of Formula (I), A is unsubstituted phenyl fused with B, wherein B is 3- to 8-membered heterocyclyl optionally substituted with $R^4$; $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$ are taken together with the carbon to which they attach to form a $C_3$-$C_6$ cycloalkyl. In some embodiments of a compound of Formula (I), A is unsubstituted phenyl fused with B, wherein B is 6-membered heterocyclyl having one nitrogen atom, wherein the 6-membered heterocyclyl is optionally substituted by $R^4$; $R^4$ is independently $C_1$-$C_6$ alkyl.

In some embodiments of a compound of Formula (I), A is phenyl optionally substituted by $R^1$ and fused with B, wherein $R^1$ is independently —CN, $C_1$-$C_6$ alkyl, or halogen; B is $C_6$ aryl, 5- to 7-membered heteroaryl, $C_3$-$C_8$ cycloalkyl, or 3- to 8-membered heterocyclyl, each of which is substituted with $R^4$; $R^4$ is independently oxo, $C_1$-$C_6$ alkyl, $C_2$-$C_6$ alkenyl, $C_2$-$C_6$ alkynyl, halogen, —C(O)$R^{17}$, —C(O)O$R^{17}$, —C(O)N$R^{17}R^{18}$, —CN, —Si($C_1$-$C_6$ alkyl)$_3$, —O$R^{17}$, —N$R^{17}R^{18}$, —OC(O)N$R^{17}R^{18}$, —N$R^{17}$C(O)$R^{18}$, —S(O)$_2R^{17}$, —N$R^{17}$S(O)$_2R^{18}$, —S(O)$_2$N$R^{17}R^{18}$, $C_3$-$C_6$ cycloalkyl, 3- to 6-membered heterocyclyl, —($C_1$-$C_3$ alkylene)CN, —($C_1$-$C_3$ alkylene)O$R^{17}$, —($C_1$-$C_3$ alkylene)N$R^{17}R^{18}$, —($C_1$-$C_3$ alkylene)CF$_3$, —($C_1$-$C_3$ alkylene)C(O)$R^{17}$, —($C_1$-$C_3$ alkylene)C(O)N$R^{17}R^{18}$, —($C_1$-$C_3$ alkylene)N$R^{17}$C(O)$R^{18}$, —($C_1$-$C_3$ alkylene)S(O)$_2R^{17}$, —($C_1$-$C_3$ alkylene)N$R^{17}$S(O)$_2R^{18}$, —($C_1$-$C_3$ alkylene)S(O)$_2$N$R^{17}R^{18}$, —($C_1$-$C_3$ alkylene)($C_3$-$C_6$ cycloalkyl) or —($C_1$-$C_3$ alkylene) (3- to 6-membered heterocyclyl), wherein each $R^4$ is independently optionally substituted by halogen, oxo, —O$R^{19}$, —N$R^{19}R^{20}$, or —C(O)$R^{19}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments of a compound of Formula (I), A is phenyl optionally substituted by $R^1$ and fused with B, wherein $R^1$ is independently —CN, $C_1$-$C_6$ alkyl, or halogen; B is 3- to 8-membered heterocyclyl optionally substituted with $R^4$; $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$.

In some embodiments of a compound of Formula (I), A is phenyl optionally substituted by $R^1$ and fused with B, wherein $R^1$ is independently —CN, $C_1$-$C_6$ alkyl, or halogen; B is $C_6$ aryl, 5- to 7-membered heteroaryl, $C_3$-$C_8$ cycloalkyl, or 3- to 8-membered heterocyclyl, each of which is substituted with $R^4$; $R^4$ is independently oxo, $C_1$-$C_6$ alkyl, $C_2$-$C_6$ alkenyl, $C_2$-$C_6$ alkynyl, —C(O)$R^{17}$, —C(O)O$R^{17}$, or —C(O)N$R^{17}R^{18}$, wherein each $R^4$ is independently optionally substituted by halogen, oxo, —O$R^{19}$, —N$R^{19}R^{20}$, or —C(O)$R^{19}$; or two $R^4$ are taken together with the carbon to which they attach to form a $C_3$-$C_6$ cycloalkyl. In some embodiments of a compound of Formula (I), A is phenyl optionally substituted by $R^1$ and fused with B, wherein $R^1$ is independently —CN, $C_1$-$C_6$ alkyl, or halogen; B is 3- to 8-membered heterocyclyl optionally substituted with $R^4$; $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$ are taken together with the carbon to which they attach to form a $C_3$-$C_6$ cycloalkyl.

In some embodiments of a compound of Formula (I), A is unsubstituted 6-membered heteroaryl fused with B, wherein B is $C_6$ aryl, 5- to 7-membered heteroaryl, $C_3$-$C_8$ cycloalkyl, or 3- to 8-membered heterocyclyl, each of which is substituted with $R^4$; $R^4$ is independently oxo, $C_1$-$C_6$ alkyl, $C_2$-$C_6$ alkenyl, $C_2$-$C_6$ alkynyl, halogen, —C(O)$R^{17}$, —C(O)O$R^{17}$, —C(O)N$R^{17}R^{18}$, —CN, —Si($C_1$-$C_6$ alkyl)$_3$, —O$R^{17}$, —N$R^{17}R^{18}$, —OC(O)N$R^{17}R^{18}$, —N$R^{17}$C(O)$R^{18}$, —S(O)$_2R^{17}$, —N$R^{17}$S(O)$_2R^{18}$, —S(O)$_2$N$R^{17}R^{18}$, $C_3$-$C_6$ cycloalkyl, 3- to 6-membered heterocyclyl, —($C_1$-$C_3$ alkylene)CN, —($C_1$-$C_3$ alkylene)O$R^{17}$, —($C_1$-$C_3$ alkylene)N$R^{17}R^{18}$, —($C_1$-$C_3$ alkylene)CF$_3$, —($C_1$-$C_3$ alkylene)C(O)$R^{17}$, —($C_1$-$C_3$ alkylene)C(O)N$R^{17}R^{18}$, —($C_1$-$C_3$ alkylene)N$R^{17}$C(O)$R^{18}$, —($C_1$-$C_3$ alkylene)S(O)$_2R^{17}$, —($C_1$-$C_3$ alkylene)N$R^{17}$S(O)$_2R^{18}$, —($C_1$-$C_3$ alkylene)S(O)$_2$N$R^{17}R^{18}$, —($C_1$-$C_3$ alkylene)($C_3$-$C_6$ cycloalkyl), or —($C_1$-$C_3$ alkylene)(3- to 6-membered heterocyclyl), wherein each $R^4$ is independently optionally substituted by halogen, oxo, —O$R^{19}$, —N$R^{19}R^{20}$, or —C(O)$R^{19}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments of a compound of Formula (I), A is unsubstituted 6-membered heteroaryl fused with B, wherein B is 3- to 8-membered heterocyclyl optionally substituted with $R^4$; $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments of a compound of Formula (I), A is unsubstituted 6-membered heteroaryl fused with B, wherein B is 6-membered heterocyclyl having one nitrogen atom, wherein the 6-membered heterocyclyl is optionally substituted by $R^4$; $R^4$ is independently $C_1$-$C_6$ alkyl.

In some embodiments of a compound of Formula (I), A is unsubstituted 6-membered heteroaryl fused with B, wherein B is $C_6$ aryl, 5- to 7-membered heteroaryl, $C_3$-$C_8$ cycloalkyl, or 3- to 8-membered heterocyclyl, each of which is substituted with $R^4$; $R^4$ is independently oxo, $C_1$-$C_6$ alkyl, $C_2$-$C_6$ alkenyl, $C_2$-$C_6$ alkynyl, —C(O)$R^{17}$, —C(O)O$R^{17}$, or —C(O)N$R^{17}R^{18}$, wherein each $R^4$ is independently optionally substituted by halogen, oxo, —O$R^{19}$, —N$R^{19}R^{20}$, or —C(O)$R^{19}$; or two $R^4$ are taken together with the carbon to which they attach to form a $C_3$-$C_6$ cycloalkyl. In some embodiments of a compound of Formula (I), A is unsubstituted 6-membered heteroaryl fused with B, wherein B is 3- to 8-membered heterocyclyl optionally substituted with $R^4$; $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$ are taken together with the carbon to which they attach to form a $C_3$-$C_6$ cycloalkyl. In some embodiments of a compound of Formula (I), A is unsubstituted 6-membered heteroaryl fused with B, wherein B is 6-membered heterocyclyl having one nitrogen atom, wherein the 6-membered heterocyclyl is optionally substituted by $R^4$; $R^4$ is independently $C_1$-$C_6$ alkyl.

In some embodiments, provided is a compound of Formula (Ia-1):

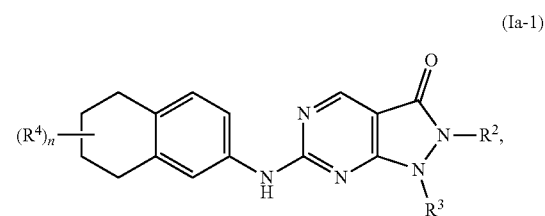

(Ia-1)

or a tautomer or isomer thereof, or a pharmaceutically acceptable salt of any of the foregoing, wherein n is 0, 1, 2, 3, or 4, each $R^4$ is independently oxo, $C_1$-$C_6$ alkyl, $C_2$-$C_6$ alkenyl, $C_2$-$C_6$ alkynyl, halogen, —C(O)$R^{17}$, —C(O)O$R^{17}$, —C(O)N$R^{17}R^{18}$, —CN, —Si($C_1$-$C_6$ alkyl)$_3$, —O$R^{17}$, —N$R^{17}R^{18}$, —OC(O)N$R^{17}R^{18}$, —N$R^{17}$C(O)$R^{18}$, —S(O)$_2R^{17}$, —N$R^{17}$S(O)$_2R^{18}$, —S(O)$_2$N$R^{17}R^{18}$, $C_3$-$C_6$ cycloalkyl, 3- to 6-membered heterocyclyl, —($C_1$-$C_3$ alkylene)CN, —($C_1$-$C_3$ alkylene)O$R^{17}$, —($C_1$-$C_3$ alkylene)N$R^{17}R^{18}$, —($C_1$-$C_3$ alkylene)CF$_3$, —($C_1$-$C_3$ alkylene)C(O)$R^{17}$, —($C_1$-$C_3$ alkylene)C(O)N$R^{17}R^{18}$, —($C_1$-$C_3$ alkylene)N$R^{17}$C(O)$R^{18}$, —($C_1$-$C_3$ alkylene)S(O)$_2R^{17}$, —($C_1$-$C_3$ alkylene)N$R^{17}$S(O)$_2R^{18}$, —($C_1$-$C_3$ alkylene)S(O)$_2$N$R^{17}R^{18}$, —($C_1$-$C_3$ alkylene)($C_3$-$C_6$ cycloalkyl) or —($C_1$-$C_3$ alkylene) (3- to 6-membered heterocyclyl), wherein each $R^4$ is independently optionally substituted by halogen, oxo, —O$R^{19}$, —N$R^{19}R^{20}$, or —C(O)$R^{19}$, or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments, $R^4$ is independently oxo, $C_1$-$C_6$ alkyl or —C(O)$R^{17}$, wherein the $C_1$-$C_6$ alkyl or —C(O)$R^{17}$ is optionally substituted by —O$R^{19}$; or two $R^4$, when bound to the same carbon or two different carbon atoms, are taken together with the carbon carbons to which they are attached to form a $C_3$-$C_6$ cycloalkyl or 3- to 7-membered heterocyclyl, each is optionally substituted by $R^{19}$. In some embodiments, $R^4$ is independently $C_1$-$C_6$ alkyl or —C(O)$R^{17}$. In some embodiments, $R^4$ is independently $C_1$-$C_6$ alkyl or —C(O)$R^{17}$, wherein $R^{17}$ is $C_1$-$C_6$ alkyl optionally substituted with —OH.

In some embodiments, provided is a compound of Formula (Ia-1):

19

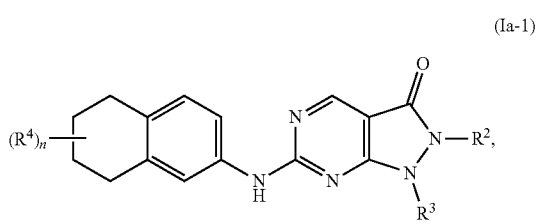

(Ia-1)

or a salt thereof, wherein n is 0, 1, 2, 3, or 4, each $R^4$ is independently oxo, $C_1$-$C_6$ alkyl, $C_2$-$C_6$ alkenyl, $C_2$-$C_6$ alkynyl, —C(O)$R^{17}$, —C(O)O$R^{17}$, or —C(O)N$R^{17}R^{18}$, wherein each $R^4$ is independently optionally substituted by halogen, oxo, —O$R^{19}$, —N$R^{19}R^{20}$, or —C(O)$R^{19}$, or two $R^4$ are taken together with the carbon to which they attach to form a $C_3$-$C_6$ cycloalkyl. In some embodiments, $R^4$ is independently oxo, $C_1$-$C_6$ alkyl or —C(O)$R^{17}$, wherein the $C_1$-$C_6$ alkyl or —C(O)$R^{17}$ is optionally substituted by —O$R^{19}$; or two $R^4$ are taken together with the carbon to which they attach to form a $C_3$-$C_6$ cycloalkyl. In some embodiments, $R^4$ is independently $C_1$-$C_6$ alkyl or —C(O)$R^{17}$. In some embodiments, $R^4$ is independently $C_1$-$C_6$ alkyl or —C(O)$R^{17}$, wherein $R^{17}$ is $C_1$-$C_6$ alkyl optionally substituted with —OH.

In some embodiments, provided is a compound of Formula (Ia-2):

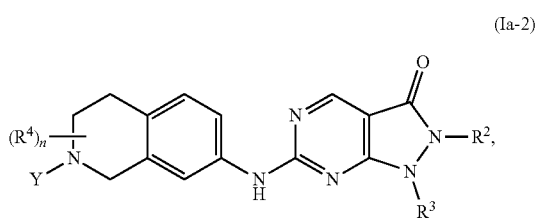

(Ia-2)

or salt thereof, wherein Y is hydrogen or $R^4$, and n is 0, 1, 2, 3, or 4. In some embodiments of a compound of Formula (Ia-2), Y is hydrogen. In some embodiments of a compound of Formula (Ia-2), Y is $R^4$. In some embodiments, each $R^4$ is independently oxo, $C_1$-$C_6$ alkyl, $C_2$-$C_6$ alkenyl, $C_2$-$C_6$ alkynyl, halogen, —C(O)$R^{17}$, —C(O)O$R^{17}$, —C(O)N$R^{17}R^{18}$, —CN, —Si($C_1$-$C_6$ alkyl)$_3$, —O$R^{17}$, —N$R^{17}R^{18}$, —OC(O)N$R^{17}R^{18}$, —N$R^{17}$C(O)$R^{18}$, —S(O)$_2R^{17}$, —N$R^{17}$S(O)$_2R^{18}$, —S(O)$_2$N$R^{17}R^{18}$, $C_3$-$C_6$ cycloalkyl, 3- to 6-membered heterocyclyl, —($C_1$-$C_3$ alkylene)CN, —($C_1$-$C_3$ alkylene)O$R^{17}$, —($C_1$-$C_3$ alkylene)N$R^{17}R^{18}$, —($C_1$-$C_3$ alkylene)CF$_3$, —($C_1$-$C_3$ alkylene)C(O)$R^{17}$, —($C_1$-$C_3$ alkylene)C(O)N$R^{17}R^{18}$, —($C_1$-$C_3$ alkylene)N$R^{17}$C(O)$R^{18}$, —($C_1$-$C_3$ alkylene)S(O)$_2R^{17}$, —($C_1$-$C_3$ alkylene)N$R^{17}$S(O)$_2R^{18}$, —($C_1$-$C_3$ alkylene)S(O)$_2$N$R^{17}R^{18}$, —($C_1$-$C_3$ alkylene)($C_3$-$C_6$ cycloalkyl), or —($C_1$-$C_3$ alkylene)(3- to 6-membered heterocyclyl), wherein each $R^4$ is independently optionally substituted by halogen, oxo, —O$R^{19}$, —N$R^{19}R^{20}$, or —C(O)$R^{19}$, or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments, $R^4$ is independently oxo, $C_1$-$C_6$ alkyl or —C(O)$R^{17}$, wherein the $C_1$-$C_6$ alkyl or —C(O)$R^{17}$ is optionally substituted by —O$R^{19}$; or two $R^4$, when bound to the same carbon or two different carbon atoms, are taken together with the carbon to which they are attached to form

20 a $C_3$-$C_6$ cycloalkyl or 3- to 7-membered heterocyclyl, each is optionally substituted by $R^{19}$. In some embodiments, $R^4$ is independently $C_1$-$C_6$ alkyl or —C(O)$R^{17}$, wherein $R^{17}$ is $C_1$-$C_6$ alkyl optionally substituted with —OH. In some embodiments, Y is hydrogen, $R^4$ is independently $C_1$-$C_6$ alkyl and n is 2. In some embodiments, Y is hydrogen, $R^4$ is methyl and n is 2.

In some embodiments, provided is a compound of Formula (Ia-2):

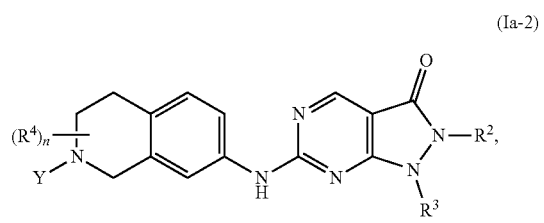

(Ia-2)

or salt thereof, wherein Y is hydrogen or $R^4$, and n is 0, 1, 2, 3, or 4. In some embodiments, Y is hydrogen. In some embodiments, Y is $R^4$. In some embodiments, each $R^4$ is independently oxo, $C_1$-$C_6$ alkyl, $C_2$-$C_6$ alkenyl, $C_2$-$C_6$ alkynyl, —C(O)$R^{17}$, —C(O)O$R^{17}$, or —C(O)N$R^{17}R^{18}$, wherein each $R^4$ is independently optionally substituted by halogen, oxo, —O$R^{19}$, —N$R^{19}R^{20}$, or —C(O)$R^{19}$, or two $R^4$ are taken together with the carbon to which they attach to form a $C_3$-$C_6$ cycloalkyl. In some embodiments, $R^4$ is independently oxo, $C_1$-$C_6$ alkyl or —C(O)$R^{17}$, wherein the $C_1$-$C_6$ alkyl or —C(O)$R^{17}$ is optionally substituted by —O$R^{19}$; or two $R^4$ are taken together with the carbon to which they attach to form a $C_3$-$C_6$ cycloalkyl. In some embodiments, $R^4$ is independently $C_1$-$C_6$ alkyl or —C(O)$R^{17}$, wherein $R^{17}$ is $C_1$-$C_6$ alkyl optionally substituted with —OH. In some embodiments, Y is hydrogen, $R^4$ is independently $C_1$-$C_6$ alkyl and n is 2. In some embodiments, Y is hydrogen, $R^4$ is methyl and n is 2.

In some embodiments, provided is a compound of Formula (Ia-3):

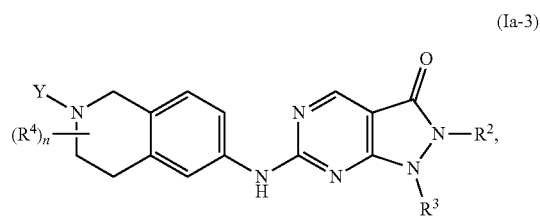

(Ia-3)

or a tautomer or isomer thereof, or a pharmaceutically acceptable salt of any of the foregoing, wherein Y is hydrogen or $R^4$, and n is 0, 1, 2, 3, or 4. In some embodiments of a compound of Formula (Ia-3), Y is hydrogen. In some embodiments of a compound of Formula (Ia-3), Y is $R^4$. In some embodiments, each $R^4$ is independently oxo, $C_1$-$C_6$ alkyl, $C_2$-$C_6$ alkenyl, $C_2$-$C_6$ alkynyl, halogen, —C(O)$R^{17}$, —C(O)O$R^{17}$, —C(O)N$R^{17}R^{18}$, —CN, —Si($C_1$-$C_6$ alkyl)$_3$, —O$R^{17}$, —N$R^{17}R^{18}$, —OC(O)N$R^{17}R^{18}$, —N$R^{17}$C(O)$R^{18}$, —S(O)$_2R^{17}$, —N$R^{17}$S(O)$_2R^{18}$, —S(O)$_2$N$R^{17}R^{18}$, $C_3$-$C_6$ cycloalkyl, 3- to 6-membered heterocyclyl, —($C_1$-$C_3$ alkylene)CN, —($C_1$-$C_3$ alkylene)O$R^{17}$, —($C_1$-$C_3$ alkylene)N$R^{17}R^{18}$, —($C_1$-$C_3$ alkylene)CF$_3$, —($C_1$-$C_3$ alkylene)C(O)$R^{17}$, —($C_1$-$C_3$ alkylene)C(O)N$R^{17}R^{18}$, —($C_1$-$C_3$ alkylene)N$R^{17}$C(O)$R^{18}$, —($C_1$-$C_3$ alkylene)S(O)$_2R^{17}$, —($C_1$-$C_3$ alkylene)N$R^{17}$S(O)$_2R^{18}$, —($C_1$-$C_3$ alkylene)S(O)$_2$N$R^{17}R^{18}$, —(C₁-C₃ alkylene)(C₃-C₆ cycloalkyl) or —(C₁-C₃ alkylene) (3- to 6-membered heterocyclyl), wherein each $R^4$ is independently optionally substituted by halogen, oxo, —OR¹⁹, —NR¹⁹R²⁰, or —C(O)R¹⁹, or two $R^4$, when bound to the same carbon or two different carbon atoms, are taken together with the carbon or carbons to which they are attached to form a C₃-C₆ cycloalkyl or 3- to 7-membered heterocyclyl, each is optionally substituted by R¹⁹. In some embodiments, $R^4$ is independently oxo, C₁-C₆ alkyl or —C(O)R¹⁷, wherein the C₁-C₆ alkyl or —C(O)R¹⁷ is optionally substituted by —OR¹⁹; or two $R^4$, when bound to the same carbon or two different carbon atoms, are taken together with the carbon or carbons to which they are attached to form a C₃-C₆ cycloalkyl or 3- to 7-membered heterocyclyl, each is optionally substituted by R¹⁹. In some embodiments, $R^4$ is independently C₁-C₆ alkyl or —C(O) R¹⁷. In some embodiments, $R^4$ is independently C₁-C₆ alkyl or —C(O)R¹⁷, wherein R¹⁷ is C₁-C₆ alkyl optionally substituted with —OH. In some embodiments, Y is hydrogen and n is 0.

In some embodiments, provided is a compound of Formula (Ia-3):

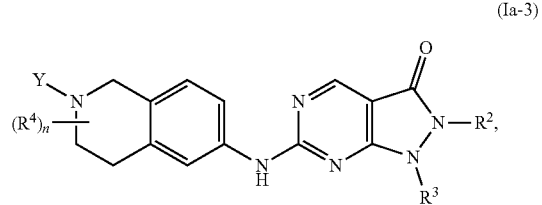

(Ia-3)

or a salt thereof, wherein Y is hydrogen or $R^4$, and n is 0, 1, 2, 3, or 4. In some embodiments, Y is hydrogen. In some embodiments, Y is $R^4$. In some embodiments, each $R^4$ is independently oxo, C₁-C₆ alkyl, C₂-C₆ alkenyl, C₂-C₆ alkynyl, —C(O)R¹⁷, —C(O)OR¹⁷, or —C(O)NR¹⁷R¹⁸, wherein each $R^4$ is independently optionally substituted by halogen, oxo, —OR¹⁹, —NR¹⁹R²⁰, or —C(O)R¹⁹, or two $R^4$ are taken together with the carbon to which they attach to form a C₃-C₆ cycloalkyl. In some embodiments, $R^4$ is independently oxo, C₁-C₆ alkyl or —C(O)R¹⁷, wherein the C₁-C₆ alkyl or —C(O)R¹⁷ is optionally substituted by —OR¹⁹; or two $R^4$ are taken together with the carbon to which they attach to form a C₃-C₆ cycloalkyl. In some embodiments, $R^4$ is independently C₁-C₆ alkyl or —C(O)R¹⁷. In some embodiments, $R^4$ is independently C₁-C₆ alkyl or —C(O) R¹⁷, wherein R¹⁷ is C₁-C₆ alkyl optionally substituted with —OH. In some embodiments, Y is hydrogen and n is 0.

In some embodiments, provided is a compound of Formula (Ia-4):

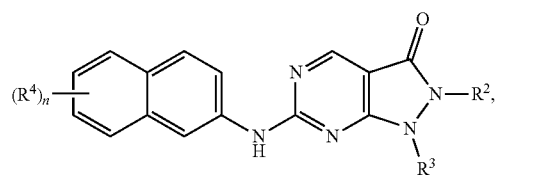

(Ia-4)

or a tautomer or isomer thereof, or a pharmaceutically acceptable salt of any of the foregoing, wherein n is 0, 1, 2, 3, or 4, each $R^4$ is independently oxo, C₁-C₆ alkyl, C₂-C₆ alkenyl, C₂-C₆ alkynyl, halogen, —C(O)R¹⁷, —C(O)OR¹⁷, —C(O)NR¹⁷R¹⁸, —CN, —Si(C₁-C₆ alkyl)₃, —OR¹⁷, —NR¹⁷R¹⁸, —OC(O)NR¹⁷R¹⁸, —NR¹⁷C(O)R¹⁸, —S(O)₂R¹⁷, —NR¹⁷S(O)₂R¹⁸, —S(O)₂NR¹⁷R¹⁸, C₃-C₆ cycloalkyl, 3- to 6-membered heterocyclyl, —(C₁-C₃ alkylene)CN, —(C₁-C₃ alkylene)OR¹⁷, —(C₁-C₃ alkylene) NR¹⁷R¹⁸, —(C₁-C₃ alkylene)CF₃, —(C₁-C₃ alkylene)C(O) R¹⁷, —(C₁-C₃ alkylene)C(O)NR¹⁷R¹⁸, —(C₁-C₃ alkylene) NR¹⁷C(O)R¹⁸, —(C₁-C₃ alkylene)S(O)₂R¹⁷, —(C₁-C₃ alkylene)NR¹⁷S(O)₂R¹⁸, —(C₁-C₃ alkylene)S(O)₂NR¹⁷R¹⁸, —(C₁-C₃ alkylene)(C₃-C₆ cycloalkyl), or —(C₁-C₃ alkylene)(3- to 6-membered heterocyclyl), wherein each $R^4$ is independently optionally substituted by halogen, oxo, —OR¹⁹, —NR¹⁹R²⁰, or —C(O)R¹⁹, or two $R^4$, when bound to the same carbon or two different carbon atoms, are taken together with the carbon or carbons to which they are attached to form a C₃-C₆ cycloalkyl or 3- to 7-membered heterocyclyl, each is optionally substituted by R¹⁹. In some embodiments, $R^4$ is independently oxo, C₁-C₆ alkyl or —C(O)R¹⁷, wherein the C₁-C₆ alkyl or —C(O)R¹⁷ is optionally substituted by —OR¹⁹; or two $R^4$, when bound to the same carbon or two different carbon atoms, are taken together with the carbon or carbons to which they are attached to form a C₃-C₆ cycloalkyl or 3- to 7-membered heterocyclyl, each is optionally substituted by R¹⁹. In some embodiments, $R^4$ is independently C₁-C₆ alkyl or —C(O) R¹⁷. In some embodiments, $R^4$ is independently C₁-C₆ alkyl or —C(O)R¹⁷, wherein R¹⁷ is C₁-C₆ alkyl optionally substituted with —OH.

In some embodiments, provided is a compound of Formula (Ia-4):

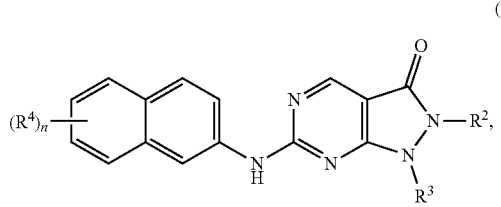

(Ia-4)

or a salt thereof, wherein n is 0, 1, 2, 3, or 4, each $R^4$ is independently oxo, C₁-C₆ alkyl, C₂-C₆ alkenyl, C₂-C₆ alkynyl, —C(O)R¹⁷, —C(O)OR¹⁷, or —C(O)NR¹⁷R¹⁸, wherein each $R^4$ is independently optionally substituted by halogen, oxo, —OR¹⁹, —NR¹⁹R²⁰, or —C(O)R¹⁹, or two $R^4$ are taken together with the carbon to which they attach to form a C₃-C₆ cycloalkyl. In some embodiments, $R^4$ is independently oxo, C₁-C₆ alkyl or —C(O)R¹⁷, wherein the C₁-C₆ alkyl or —C(O)R¹⁷ is optionally substituted by —OR¹⁹; or two $R^4$ are taken together with the carbon to which they attach to form a C₃-C₆ cycloalkyl. In some embodiments, $R^4$ is independently C₁-C₆ alkyl or —C(O)R¹⁷. In some embodiments, $R^4$ is independently C₁-C₆ alkyl or —C(O) R¹⁷, wherein R¹⁷ is C₁-C₆ alkyl optionally substituted with —OH.

In some embodiments, provided is a compound of Formula (Ia-5):

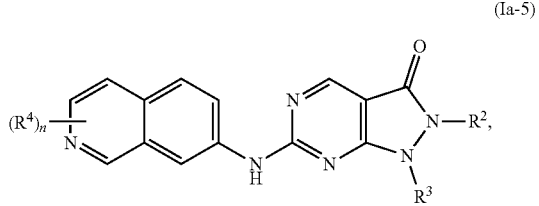

(Ia-5)

or a tautomer or isomer thereof, or a pharmaceutically acceptable salt of any of the foregoing, wherein n is 0, 1, 2, 3, or 4, each $R^4$ is independently oxo, $C_1$-$C_6$ alkyl, $C_2$-$C_6$ alkenyl, $C_2$-$C_6$ alkynyl, halogen, —C(O)$R^{17}$, —C(O)O$R^{17}$, —C(O)N$R^{17}R^{18}$, —CN, —Si($C_1$-$C_6$ alkyl)$_3$, —O$R^{17}$, —N$R^{17}R^{18}$, —OC(O)N$R^{17}R^{18}$, —N$R^{17}$C(O)$R^{18}$, —S(O)$_2R^{17}$, —N$R^{17}$S(O)$_2R^{18}$, —S(O)$_2$N$R^{17}R^{18}$, $C_3$-$C_6$ cycloalkyl, 3- to 6-membered heterocyclyl, —($C_1$-$C_3$ alkylene)CN, —($C_1$-$C_3$ alkylene)O$R^{17}$, —($C_1$-$C_3$ alkylene)N$R^{17}R^{18}$, —($C_1$-$C_3$ alkylene)CF$_3$, —($C_1$-$C_3$ alkylene)C(O)$R^{17}$, —($C_1$-$C_3$ alkylene)C(O)N$R^{17}R^{18}$, —($C_1$-$C_3$ alkylene)N$R^{17}$C(O)$R^{18}$, —($C_1$-$C_3$ alkylene)S(O)$_2R^{17}$, —($C_1$-$C_3$ alkylene)N$R^{17}$S(O)$_2R^{18}$, —($C_1$-$C_3$ alkylene)S(O)$_2$N$R^{17}R^{18}$, —($C_1$-$C_3$ alkylene)($C_3$-$C_6$ cycloalkyl) or —($C_1$-$C_3$ alkylene) (3- to 6-membered heterocyclyl), wherein each $R^4$ is independently optionally substituted by halogen, oxo, —O$R^{19}$, —N$R^{19}R^{20}$, or —C(O)$R^{19}$, or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments, $R^4$ is independently oxo, $C_1$-$C_6$ alkyl or —C(O)$R^{17}$, wherein the $C_1$-$C_6$ alkyl or —C(O)$R^{17}$ is optionally substituted by —O$R^{19}$; or two $R^4$, when bound to the same carbon or two different carbon atoms, are taken together with the carbon or carbons to which they are attached to form a $C_3$-$C_6$ cycloalkyl or 3- to 7-membered heterocyclyl each is optionally substituted by $R^{19}$. In some embodiments, $R^4$ is independently $C_1$-$C_6$ alkyl or —C(O)$R^{17}$. In some embodiments, $R^4$ is independently $C_1$-$C_6$ alkyl or —C(O)$R^{17}$, wherein $R^{17}$ is $C_1$-$C_6$ alkyl optionally substituted with —OH.

In some embodiments, provided is a compound of Formula (Ia-5):

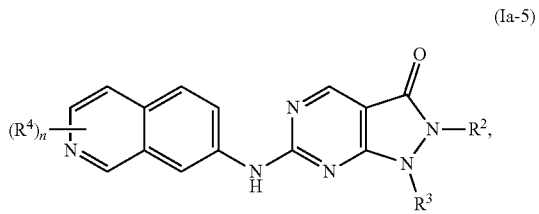

(Ia-5)

or a salt thereof, wherein n is 0, 1, 2, 3, or 4, each $R^4$ is independently oxo, $C_1$-$C_6$ alkyl, $C_2$-$C_6$ alkenyl, $C_2$-$C_6$ alkynyl, —C(O)$R^{17}$, —C(O)O$R^{17}$, or —C(O)N$R^{17}R^{18}$, wherein each $R^4$ is independently optionally substituted by halogen, oxo, —O$R^{19}$, —N$R^{19}R^{20}$, or —C(O)$R^{19}$, or two $R^4$ are taken together with the carbon to which they attach to form a $C_3$-$C_6$ cycloalkyl. In some embodiments, $R^4$ is independently oxo, $C_1$-$C_6$ alkyl or —C(O)$R^{17}$, wherein the $C_1$-$C_6$ alkyl or —C(O)$R^{17}$ is optionally substituted by —O$R^{19}$; or two $R^4$ are taken together with the carbon to which they attach to form a $C_3$-$C_6$ cycloalkyl. In some embodiments, $R^4$ is independently $C_1$-$C_6$ alkyl or —C(O)$R^{17}$. In some embodiments, $R^4$ is independently $C_1$-$C_6$ alkyl or —C(O)$R^{17}$, wherein $R^{17}$ is $C_1$-$C_6$ alkyl optionally substituted with —OH.

In some embodiments, provided is a compound of Formula (Ia-6):

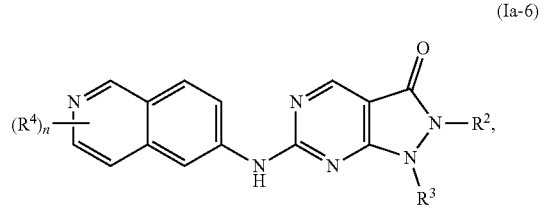

(Ia-6)

or a tautomer or isomer thereof, or a pharmaceutically acceptable salt of any of the foregoing, wherein n is 0, 1, 2, 3, or 4, each $R^4$ is independently oxo, $C_1$-$C_6$ alkyl, $C_2$-$C_6$ alkenyl, $C_2$-$C_6$ alkynyl, halogen, —C(O)$R^{17}$, —C(O)O$R^{17}$, —C(O)N$R^{17}R^{18}$, —CN, —Si($C_1$-$C_6$ alkyl)$_3$, —O$R^{17}$, —N$R^{17}R^{18}$, —OC(O)N$R^{17}R^{18}$, —N$R^{17}$C(O)$R^{18}$, —S(O)$_2R^{17}$, —N$R^{17}$S(O)$_2R^{18}$, —S(O)$_2$N$R^{17}R^{18}$, $C_3$-$C_6$ cycloalkyl, 3- to 6-membered heterocyclyl, —($C_1$-$C_3$ alkylene)CN, —($C_1$-$C_3$ alkylene)O$R^{17}$, —($C_1$-$C_3$ alkylene)N$R^{17}R^{18}$, —($C_1$-$C_3$ alkylene)CF$_3$, —($C_1$-$C_3$ alkylene)C(O)$R^{17}$, —($C_1$-$C_3$ alkylene)C(O)N$R^{17}R^{18}$, —($C_1$-$C_3$ alkylene)N$R^{17}$C(O)$R^{18}$, —($C_1$-$C_3$ alkylene)S(O)$_2R^{17}$, —($C_1$-$C_3$ alkylene)N$R^{17}$S(O)$_2R^{18}$, —($C_1$-$C_3$ alkylene)S(O)$_2$N$R^{17}R^{18}$, —($C_1$-$C_3$ alkylene)($C_3$-$C_6$ cycloalkyl) or —($C_1$-$C_3$ alkylene) (3- to 6-membered heterocyclyl), wherein each $R^4$ is independently optionally substituted by halogen, oxo, —O$R^{19}$, —N$R^{19}R^{20}$, or —C(O)$R^{19}$, or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments, $R^4$ is independently oxo, $C_1$-$C_6$ alkyl or —C(O)$R^{17}$, wherein the $C_1$-$C_6$ alkyl or —C(O)$R^{17}$ is optionally substituted by —O$R^{19}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments, $R^4$ is independently $C_1$-$C_6$ alkyl or —C(O)$R^{17}$. In some embodiments, $R^4$ is independently $C_1$-$C_6$ alkyl or —C(O)$R^{17}$, wherein $R^{17}$ is $C_1$-$C_6$ alkyl optionally substituted with —OH.

In some embodiments, provided is a compound of Formula (Ia-6):

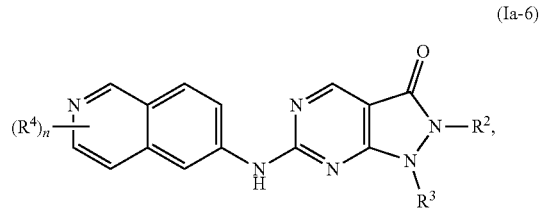

(Ia-6)

or a salt thereof, wherein n is 0, 1, 2, 3, or 4, each $R^4$ is independently oxo, $C_1$-$C_6$ alkyl, $C_2$-$C_6$ alkenyl, $C_2$-$C_6$ alkynyl, —C(O)$R^{17}$, —C(O)O$R^{17}$, or —C(O)N$R^{17}R^{18}$, wherein each $R^4$ is independently optionally substituted by halogen, oxo, —OR$^{19}$, —NR$^{19}$R$^{20}$, or —C(O)R$^{19}$, or two R$^4$ are taken together with the carbon to which they attach to form a C$_3$-C$_6$ cycloalkyl. In some embodiments, R$^4$ is independently oxo, C$_1$-C$_6$ alkyl or —C(O)R$^{17}$, wherein the C$_1$-C$_6$ alkyl or —C(O)R$^{17}$ is optionally substituted by —OR$^{19}$; or two R$^4$ are taken together with the carbon to which they attach to form a C$_3$-C$_6$ cycloalkyl. In some embodiments, R$^4$ is independently C$_1$-C$_6$ alkyl or —C(O)R$^{17}$. In some embodiments, R$^4$ is independently C$_1$-C$_6$ alkyl or —C(O)R$^{17}$, wherein R$^{17}$ is C$_1$-C$_6$ alkyl optionally substituted with —OH.

In some embodiments, provided is a compound of Formula (Ia-7):

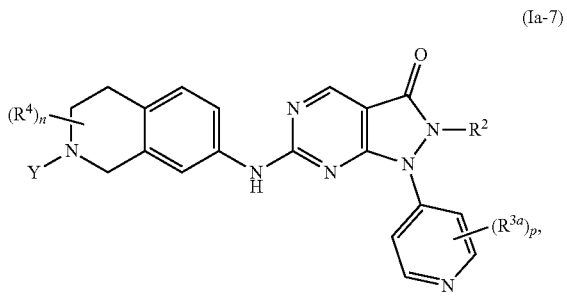

(Ia-7)

or a tautomer or isomer thereof, or a pharmaceutically acceptable salt of any of the foregoing, wherein Y is hydrogen or R$^4$, n and p are independently 0, 1, 2, 3, or 4; R$^{3a}$ is independently hydrogen, halogen, oxo, —OR$^{13}$, —NR$^{13}$R$^{14}$, —C(O)R$^{13}$, —C(O)OR$^{13}$, —C(O)NR$^{13}$R$^{14}$, —NR$^{13}$C(O)R$^{14}$, —CN, —SR$^{13}$, —S(O)R$^{13}$, —S(O)$_2$R$^{13}$, —Si(C$_1$-C$_6$ alkyl)$_3$, —P(O)R$^{13}$R$^{14}$, —NR$^{13}$S(O)$_2$R$^{14}$, —(C$_1$-C$_3$ alkylene)OR$^{13}$, —(C$_1$-C$_3$ alkylene)NR$^{13}$R$^{14}$, —(C$_1$-C$_3$ alkylene)C(O)R$^{13}$, C$_3$-C$_8$ cycloalkyl optionally substituted by C$_1$-C$_6$ alkyl, CN, CF$_3$, oxo, —OH, —NR$^{15}$R$^{16}$, —OR$^{15}$ or halogen, 3- to 12-membered heterocyclyl optionally substituted by oxo, —OH, —NR$^{15}$R$^{16}$, —C(O)OR$^{15}$, —OR$^{15}$ or halogen, or C$_1$-C$_6$ alkyl optionally substituted by oxo, —OH, —NR$^{15}$R$^{16}$, —C(O)OR$^{15}$, —OR$^{15}$ or halogen, with the proviso that R$^{3a}$ is not

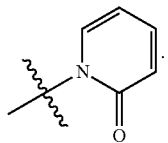

In some embodiments of a compound of Formula (Ia-7), Y is hydrogen. In some embodiments of a compound of Formula (Ia-7), Y is R$^4$. In some embodiments, each R$^4$ is independently oxo, C$_1$-C$_6$ alkyl, C$_2$-C$_6$ alkenyl, C$_2$-C$_6$ alkynyl, halogen, —C(O)R$^{17}$, —C(O)OR$^{17}$, —C(O)NR$^{17}$R$^{18}$, —Si(C$_1$-C$_6$ alkyl)$_3$, —CN, —OR$^{17}$, —NR$^{17}$R$^{18}$, —OC(O)NR$^{17}$R$^{18}$, —NR$^{17}$C(O)R$^{18}$, —S(O)$_2$R$^{17}$, —NR$^{17}$S(O)$_2$R$^{18}$, —S(O)$_2$NR$^{17}$R$^{18}$, C$_3$-C$_6$ cycloalkyl, 3- to 6-membered heterocyclyl, —(C$_1$-C$_3$ alkylene)CN, —(C$_1$-C$_3$ alkylene)OR$^{17}$, —(C$_1$-C$_3$ alkylene)NR$^{17}$R$^{18}$, —(C$_1$-C$_3$ alkylene)CF$_3$, —(C$_1$-C$_3$ alkylene)C(O)R$^{17}$, —(C$_1$-C$_3$ alkylene)C(O)NR$^{17}$R$^{18}$, —(C$_1$-C$_3$ alkylene)NR$^{17}$C(O)R$^{18}$, —(C$_1$-C$_3$ alkylene)S(O)$_2$R$^{17}$, —(C$_1$-C$_3$ alkylene)NR$^{17}$S(O)$_2$R$^{18}$, —(C$_1$-C$_3$ alkylene)S(O)$_2$NR$^{17}$R$^{18}$, —(C$_1$-C$_3$ alkylene)(C$_3$-C$_6$ cycloalkyl), or —(C$_1$-C$_3$ alkylene)(3- to 6-membered heterocyclyl), wherein each R$^4$ is independently optionally substituted by halogen, oxo, —OR$^{19}$, —NR$^{19}$R$^{20}$, or —C(O)R$^{19}$, or two R$^4$ when bound to the same carbon or two different carbon atoms, are taken together with the carbon or carbons to which they are attached to form a C$_3$-C$_6$ cycloalkyl or 3- to 7-membered heterocyclyl, each is optionally substituted by R$^{19}$. In some embodiments, R$^{3a}$ is C$_3$-C$_8$ cycloalkyl optionally substituted by C$_1$-C$_6$ alkyl, CN, CF$_3$, oxo, —OH, —NR$^{15}$R$^{16}$, —OR$^{15}$ or halogen, 3- to 12-membered heterocyclyl optionally substituted by oxo, —OH, —NR$^{15}$R$^{16}$, —C(O)OR$^{15}$, —OR$^{15}$ or halogen, or C$_1$-C$_6$ alkyl optionally substituted by oxo, —OH, —NR$^{15}$R$^{16}$, —C(O)OR$^{15}$, —OR$^{15}$ or halogen, with the proviso that R$^{3a}$ is not

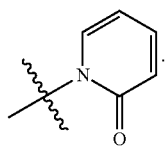 [SMILES: *n1ccccc1=O]

In some embodiments, R$^{3a}$ is C$_1$-C$_6$ alkyl optionally substituted by oxo, —OH, —NR$^{15}$R$^{16}$, —C(O)OR$^{15}$, —OR$^{15}$ or halogen.

In some embodiments, provided is a compound of Formula (Ia-8):

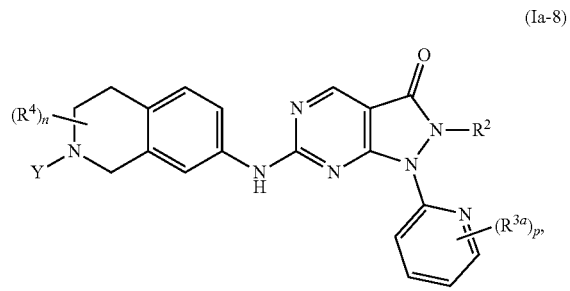

(Ia-8)

or a tautomer or isomer thereof, or a pharmaceutically acceptable salt of any of the foregoing, wherein Y is hydrogen or R$^4$, n and p are independently 0, 1, 2, 3, or 4; R$^{3a}$ is independently hydrogen, halogen, oxo, —OR$^{13}$, —NR$^{13}$R$^{14}$, —C(O)R$^{13}$, —C(O)OR$^{13}$, —C(O)NR$^{13}$R$^{14}$, —NR$^{13}$C(O)R$^{14}$, —CN, —SR$^{13}$, —S(O)R$^{13}$, —S(O)$_2$R$^{13}$, —Si(C$_1$-C$_6$ alkyl)$_3$, —P(O)R$^{13}$R$^{14}$, —NR$^{13}$S(O)$_2$R$^{14}$, —(C$_1$-C$_3$ alkylene)OR$^{13}$, —(C$_1$-C$_3$ alkylene)NR$^{13}$R$^{14}$, —(C$_1$-C$_3$ alkylene)C(O)R$^{13}$, C$_3$-C$_8$ cycloalkyl optionally substituted by C$_1$-C$_6$ alkyl, CN, CF$_3$, oxo, —OH, —NR$^{15}$R$^{16}$, —OR$^{15}$ or halogen, 3- to 12-membered heterocyclyl optionally substituted by oxo, —OH, —NR$^{15}$R$^{16}$, —C(O)OR$^{15}$, —OR$^{15}$ or halogen, or C$_1$-C$_6$ alkyl optionally substituted by oxo, —OH, —NR$^{15}$R$^{16}$, —C(O)OR$^{15}$, —OR$^{15}$ or halogen, with the proviso that R$^{3a}$ is not

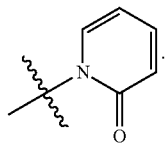

In some embodiments of a compound of Formula (Ia-8), Y is hydrogen. In some embodiments of a compound of Formula (Ia-8), Y is $R^4$. In some embodiments, each $R^4$ is independently oxo, $C_1$-$C_6$ alkyl, $C_2$-$C_6$ alkenyl, $C_2$-$C_6$ alkynyl, halogen, —C(O)$R^{17}$, —C(O)O$R^{17}$, —C(O)N$R^{17}R^{18}$, —CN, —Si($C_1$-$C_6$ alkyl)$_3$, —O$R^{17}$, —N$R^{17}R^{18}$, —OC(O)N$R^{17}R^{18}$, —N$R^{17}$C(O)$R^{18}$, —S(O)$_2$$R^{17}$, —N$R^{17}$S(O)$_2$$R^{18}$, —S(O)$_2$N$R^{17}R^{18}$, $C_3$-$C_6$ cycloalkyl, 3- to 6-membered heterocyclyl, —($C_1$-$C_3$ alkylene)CN, —($C_1$-$C_3$ alkylene)O$R^{17}$, —($C_1$-$C_3$ alkylene)N$R^{17}R^{18}$, —($C_1$-$C_3$ alkylene)CF$_3$, —($C_1$-$C_3$ alkylene)C(O)$R^{17}$, —($C_1$-$C_3$ alkylene)C(O)N$R^{17}R^{18}$, —($C_1$-$C_3$ alkylene)N$R^{17}$C(O)$R^{18}$, —($C_1$-$C_3$ alkylene)S(O)$_2$$R^{17}$, —($C_1$-$C_3$ alkylene)N$R^{17}$S(O)$_2$$R^{18}$, —($C_1$-$C_3$ alkylene)S(O)$_2$N$R^{17}R^{18}$, —($C_1$-$C_3$ alkylene)($C_3$-$C_6$ cycloalkyl), or —($C_1$-$C_3$ alkylene)(3- to 6-membered heterocyclyl), wherein each $R^4$ is independently optionally substituted by halogen, oxo, —O$R^{19}$, —N$R^{19}R^{20}$, or —C(O)$R^{19}$, or two $R^4$ when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments, $R^{3a}$ is $C_3$-$C_8$ cycloalkyl optionally substituted by $C_1$-$C_6$ alkyl, CN, CF$_3$, oxo, —OH, —N$R^{15}R^{16}$, —O$R^{15}$ or halogen, 3- to 12-membered heterocyclyl optionally substituted by oxo, —OH, —N$R^{15}R^{16}$, —C(O)O$R^{15}$, —O$R^{15}$ or halogen, or $C_1$-$C_6$ alkyl optionally substituted by oxo, —OH, —N$R^{15}R^{16}$, —C(O)O$R^{15}$, —O$R^{15}$ or halogen, with the proviso that $R^{3a}$ is not

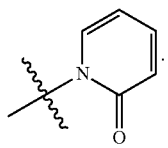 [SMILES: *n1ccccc1=O]

In some embodiments, $R^{3a}$ is $C_1$-$C_6$ alkyl optionally substituted by oxo, —OH, —N$R^{15}R^{16}$, —C(O)O$R^{15}$, —O$R^{15}$ or halogen.

In some embodiments, provided is a compound of Formula (Ia-9):

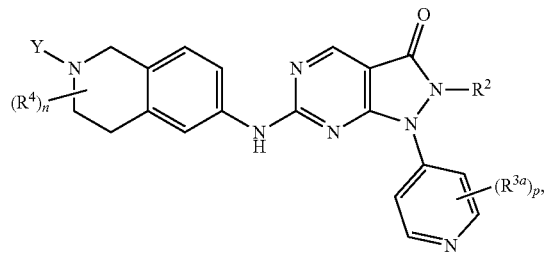

(Ia-9)

or a tautomer or isomer thereof, or a pharmaceutically acceptable salt of any of the foregoing, wherein Y is hydrogen or $R^4$, n and p are independently 0, 1, 2, 3, or 4; $R^{3a}$ is independently hydrogen, halogen, oxo, —O$R^{13}$, —N$R^{13}R^{14}$, —C(O)$R^{13}$, —C(O)O$R^{13}$, —C(O)N$R^{13}R^{14}$, —N$R^{13}$C(O)$R^{14}$, —CN, —S$R^{13}$, —S(O)$R^{13}$, —S(O)$_2$$R^{13}$, —Si($C_1$-$C_6$ alkyl)$_3$, —P(O)$R^{13}R^{14}$, —N$R^{13}$S(O)$_2$$R^{14}$, —($C_1$-$C_3$ alkylene)O$R^{13}$, —($C_1$-$C_3$ alkylene)N$R^{13}R^{14}$, —($C_1$-$C_3$ alkylene)C(O)$R^{13}$, $C_3$-$C_8$ cycloalkyl optionally substituted by $C_1$-$C_6$ alkyl, CN, CF$_3$, oxo, —OH, —N$R^{15}R^{16}$, —O$R^{15}$ or halogen, 3- to 12-membered heterocyclyl optionally substituted by oxo, —OH, —N$R^{15}R^{16}$, —C(O)O$R^{15}$, —O$R^{15}$ or halogen, or $C_1$-$C_6$ alkyl optionally substituted by oxo, —OH, —N$R^{15}R^{16}$, —C(O)O$R^{15}$, —O$R^{15}$ or halogen, with the proviso that $R^{3a}$ is not

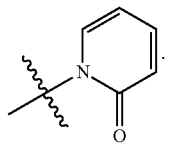 [SMILES: *n1ccccc1=O]

In some embodiments of a compound of Formula (Ia-9), Y is hydrogen. In some embodiments of a compound of Formula (Ia-9), Y is $R^4$. In some embodiments, each $R^4$ is independently oxo, $C_1$-$C_6$ alkyl, $C_2$-$C_6$ alkenyl, $C_2$-$C_6$ alkynyl, halogen, —C(O)$R^{17}$, —C(O)O$R^{17}$, —C(O)N$R^{17}R^{18}$, —CN, —Si($C_1$-$C_6$ alkyl)$_3$, —O$R^{17}$, —N$R^{17}R^{18}$, —OC(O)N$R^{17}R^{18}$, —N$R^{17}$C(O)$R^{18}$, —S(O)$_2$$R^{17}$, —N$R^{17}$S(O)$_2$$R^{18}$, —S(O)$_2$N$R^{17}R^{18}$, $C_3$-$C_6$ cycloalkyl, 3- to 6-membered heterocyclyl, —($C_1$-$C_3$ alkylene)CN, —($C_1$-$C_3$ alkylene)O$R^{17}$, —($C_1$-$C_3$ alkylene)N$R^{17}R^{18}$, —($C_1$-$C_3$ alkylene)CF$_3$, —($C_1$-$C_3$ alkylene)C(O)$R^{17}$, —($C_1$-$C_3$ alkylene)C(O)N$R^{17}R^{18}$, —($C_1$-$C_3$ alkylene)N$R^{17}$C(O)$R^{18}$, —($C_1$-$C_3$ alkylene)S(O)$_2$$R^{17}$, —($C_1$-$C_3$ alkylene)N$R^{17}$S(O)$_2$$R^{18}$, —($C_1$-$C_3$ alkylene)S(O)$_2$N$R^{17}R^{18}$, —($C_1$-$C_3$ alkylene)($C_3$-$C_6$ cycloalkyl), or —($C_1$-$C_3$ alkylene)(3- to 6-membered heterocyclyl), wherein each $R^4$ is independently optionally substituted by halogen, oxo, —O$R^{19}$, —N$R^{19}R^{20}$, or —C(O)$R^{19}$, or two $R^4$ when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments, $R^{3a}$ is $C_3$-$C_8$ cycloalkyl optionally substituted by $C_1$-$C_6$ alkyl, CN, CF$_3$, oxo, —OH, —N$R^{15}R^{16}$, —O$R^{15}$ or halogen, 3- to 12-membered heterocyclyl optionally substituted by oxo, —OH, —N$R^{15}R^{16}$, —C(O)O$R^{15}$, —O$R^{15}$ or halogen, or $C_1$-$C_6$ alkyl optionally substituted by oxo, —OH, —N$R^{15}R^{16}$, —C(O)O$R^{15}$, —O$R^{15}$ or halogen, with the proviso that $R^{3a}$ is not

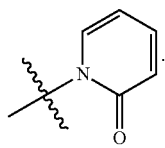 [SMILES: *n1ccccc1=O]

In some embodiments, $R^{3a}$ is $C_1$-$C_6$ alkyl optionally substituted by oxo, —OH, —N$R^{15}R^{16}$, —C(O)O$R^{15}$, —O$R^{15}$ or halogen.

In some embodiments, provided is a compound of Formula (Ia-10):

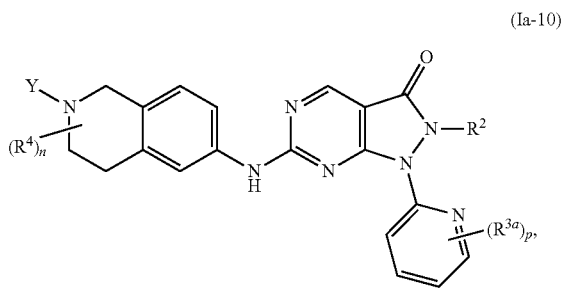

(Ia-10)

or a tautomer or isomer thereof, or a pharmaceutically acceptable salt of any of the foregoing, wherein Y is hydrogen or $R^4$, n and p are independently 0, 1, 2, 3, or 4; $R^{3a}$ is independently hydrogen, halogen, oxo, $-OR^{13}$, $-NR^{13}R^{14}$, $-C(O)R^{13}$, $-C(O)OR^{13}$, $-C(O)NR^{13}R^{14}$, $-NR^{13}C(O)R^{14}$, $-CN$, $-SR^{13}$, $-S(O)R^{13}$, $-S(O)_2R^{13}$, $-Si(C_1-C_6$ alkyl$)_3$, $-P(O)R^{13}R^{14}$, $-NR^{13}S(O)_2R^{14}$, $-(C_1-C_3$ alkylene$)OR^{13}$, $-(C_1-C_3$ alkylene$)NR^{13}R^{14}$, $-(C_1-C_3$ alkylene$)C(O)R^{13}$, $C_3-C_8$ cycloalkyl optionally substituted by $C_1-C_6$ alkyl, CN, $CF_3$, oxo, $-OH$, $-NR^{15}R^{16}$, $-OR^{15}$ or halogen, 3- to 12-membered heterocyclyl optionally substituted by oxo, $-OH$, $-NR^{15}R^{16}$, $-C(O)OR^{15}$, $-OR^{15}$ or halogen, or $C_1-C_6$ alkyl optionally substituted by oxo, $-OH$, $-NR^{15}R^{16}$, $-C(O)OR^{15}$, $-OR^{15}$ or halogen, with the proviso that $R^{3a}$ is not

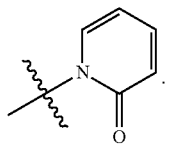

In some embodiments of a compound of Formula (Ia-10), Y is hydrogen. In some embodiments of a compound of Formula (Ia-10), Y is $R^4$. In some embodiments, each $R^4$ is independently oxo, $C_1-C_6$ alkyl, $C_2-C_6$ alkenyl, $C_2-C_6$ alkynyl, halogen, $-C(O)R^{17}$, $-C(O)OR^{17}$, $-C(O)NR^{17}R^{18}$, $-CN$, $-Si(C_1-C_6$ alkyl$)_3$, $-OR^{17}$, $-NR^{17}R^{18}$, $-OC(O)NR^{17}R^{18}$, $-NR^{17}C(O)R^{18}$, $-S(O)_2R^{17}$, $-NR^{17}S(O)_2R^{18}$, $-S(O)_2NR^{17}R^{18}$, $C_3-C_6$ cycloalkyl, 3- to 6-membered heterocyclyl, $-(C_1-C_3$ alkylene$)CN$, $-(C_1-C_3$ alkylene$)OR^{17}$, $-(C_1-C_3$ alkylene$)NR^{17}R^{18}$, $-(C_1-C_3$ alkylene$)CF_3$, $-(C_1-C_3$ alkylene$)C(O)R^{17}$, $-(C_1-C_3$ alkylene$)C(O)NR^{17}R^{18}$, $-(C_1-C_3$ alkylene$)NR^{17}C(O)R^{18}$, $-(C_1-C_3$ alkylene$)S(O)_2R^{17}$, $-(C_1-C_3$ alkylene$)NR^{17}S(O)_2R^{18}$, $-(C_1-C_3$ alkylene$)S(O)_2NR^{17}R^{18}$, $-(C_1-C_3$ alkylene$)(C_3-C_6$ cycloalkyl$)$, or $-(C_1-C_3$ alkylene$)(3$- to 6-membered heterocyclyl$)$, wherein each $R^4$ is independently optionally substituted by halogen, oxo, $-OR^{19}$, $-NR^{19}R^{20}$, or $-C(O)R^{19}$, or two $R^4$ when bound to the same carbon or two different carbon atoms, are taken together with the carbon or carbons to which they are attached to form a $C_3-C_6$ cycloalkyl or 3- to 7-membered heterocyclyl, each is optionally substituted by $R^{19}$. In some embodiments, $R^{3a}$ is $C_3-C_8$ cycloalkyl optionally substituted by $C_1-C_6$ alkyl, CN, $CF_3$, oxo, $-OH$, $-NR^{15}R^{16}$, $-OR^{15}$ or halogen, 3- to 12-membered heterocyclyl optionally substituted by oxo, $-OH$, $-NR^{15}R^{16}$, $-C(O)OR^{15}$, $-OR^{15}$ or halogen, or $C_1-C_6$ alkyl optionally substituted by oxo, $-OH$, $-NR^{15}R^{16}$, $-C(O)OR^{15}$, $-OR^{15}$ or halogen, with the proviso that $R^{3a}$ is not

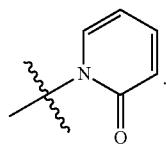

In some embodiments, $R^{3a}$ is $C_1-C_6$ alkyl optionally substituted by oxo, $-OH$, $-NR^{15}R^{16}$, $-C(O)OR^{15}$, $-OR^{15}$ or halogen.

In some embodiments, provided is a compound of Formula (Ia-11):

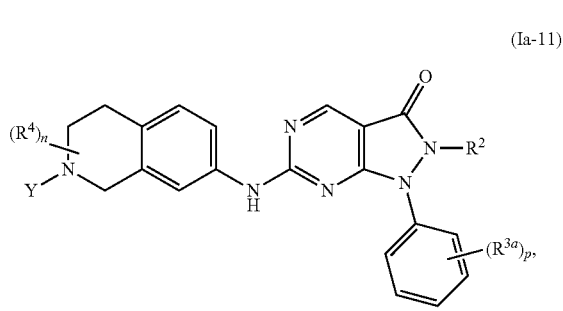

(Ia-11)

or a tautomer or isomer thereof, or a pharmaceutically acceptable salt of any of the foregoing, wherein Y is hydrogen or $R^4$, n and p are independently 0, 1, 2, 3, or 4; $R^{3a}$ is independently hydrogen, halogen, oxo, $-OR^{13}$, $-NR^{13}R^{14}$, $-C(O)R^{13}$, $-C(O)OR^{13}$, $-C(O)NR^{13}R^{14}$, $-NR^{13}C(O)R^{14}$, $-CN$, $-SR^{13}$, $-S(O)R^{13}$, $-S(O)_2R^{13}$, $-Si(C_1-C_6$ alkyl$)_3$, $-P(O)R^{13}R^{14}$, $-NR^{13}S(O)_2R^{14}$, $-(C_1-C_3$ alkylene$)OR^{13}$, $-(C_1-C_3$ alkylene$)NR^{13}R^{14}$, $-(C_1-C_3$ alkylene$)C(O)R^{13}$, $C_3-C_8$ cycloalkyl optionally substituted by $C_1-C_6$ alkyl, CN, $CF_3$, oxo, $-OH$, $-NR^{15}R^{16}$, $-OR^{15}$ or halogen, 3- to 12-membered heterocyclyl optionally substituted by oxo, $-OH$, $-NR^{15}R^{16}$, $-C(O)OR^{15}$, $-OR^{15}$ or halogen, or $C_1-C_6$ alkyl optionally substituted by oxo, $-OH$, $-NR^{15}R^{16}$, $-C(O)OR^{15}$, $-OR^{15}$ or halogen, with the proviso that $R^{3a}$ is not

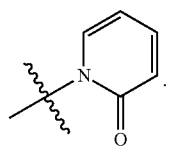

In some embodiments of a compound of Formula (Ia-11), Y is hydrogen. In some embodiments of a compound of Formula (Ia-11), Y is $R^4$. In some embodiments, each $R^4$ is independently oxo, $C_1-C_6$ alkyl, $C_2-C_6$ alkenyl, $C_2-C_6$ alkynyl, halogen, $-C(O)R^{17}$, $-C(O)OR^{17}$, $-C(O)NR^{17}R^{18}$, $-CN$, $-Si(C_1-C_6$ alkyl$)_3$, $-OR^{17}$, $-NR^{17}R^{18}$, $-OC(O)NR^{17}R^{18}$, $-NR^{17}C(O)R^{18}$, $-S(O)_2R^{17}$, $-NR^{17}S(O)_2R^{18}$, $-S(O)_2NR^{17}R^{18}$, $C_3-C_6$ cycloalkyl, 3- to 6-membered heterocyclyl, $-(C_1-C_3$ alkylene$)CN$, $-(C_1-C_3$ alkylene$)OR^{17}$, $-(C_1-C_3$ alkylene$)NR^{17}R^{18}$, $-(C_1-C_3$ alkylene$)CF_3$, $-(C_1-C_3$ alkylene$)C(O)R^{17}$, $-(C_1-C_3$ alkylene$)C(O)NR^{17}R^{18}$, $-(C_1-C_3$ alkylene$)NR^{17}C(O)R^{18}$, $-(C_1-C_3$ alkylene$)S(O)_2R^{17}$, $-(C_1-C_3$ alkylene$)NR^{17}S(O)_2R^{18}$, $-(C_1-C_3$ alkylene$)S(O)_2NR^{17}R^{18}$, $-(C_1-C_3$ alkylene$)(C_3-C_6$ cycloalkyl$)$, or $-(C_1-C_3$ alkylene$)(3$- to 6-membered heterocyclyl$)$, wherein each $R^4$ is independently optionally substituted by halogen, oxo, —OR$^{19}$, —NR$^{19}$R$^{20}$, or —C(O)R$^{19}$, or two R$^4$ when bound to the same carbon or two different carbon atoms, are taken together with the carbon to which they are attached to form a C$_3$-C$_6$ cycloalkyl or 3- to 7-membered heterocyclyl, each is optionally substituted by R$^{19}$. In some embodiments, R$^{3a}$ is halogen, C$_3$-C$_8$ cycloalkyl optionally substituted by C$_1$-C$_6$ alkyl, CN, CF$_3$, oxo, —OH, —NR$^{15}$R$^{16}$, —OR$^{15}$ or halogen, 3- to 12-membered heterocyclyl optionally substituted by oxo, —OH, —NR$^{15}$R$^{16}$, —C(O)OR$^{15}$, —OR$^{15}$ or halogen, or C$_1$-C$_6$ alkyl optionally substituted by oxo, —OH, —NR$^{15}$R$^{16}$, —C(O)OR$^{15}$, —OR$^{15}$ or halogen, with the proviso that R$^{3a}$ is not

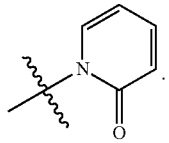

In some embodiments, R$^{3a}$ is halogen. In some embodiments, R$^{3a}$ is C$_1$-C$_6$ alkyl optionally substituted by oxo, —OH, —NR$^{15}$R$^{16}$, —C(O)OR$^{15}$, —OR$^{15}$ or halogen.

In some embodiments, provided is a compound of Formula (Ia-12):

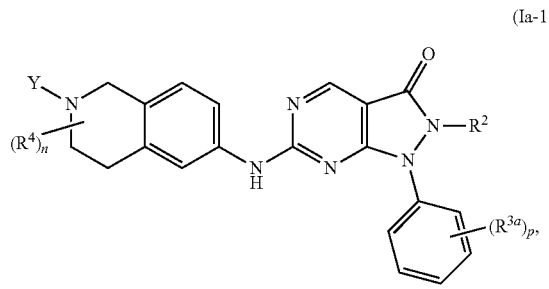

(Ia-12)

or a tautomer or isomer thereof, or a pharmaceutically acceptable salt of any of the foregoing, wherein Y is hydrogen or R$^4$, n and p are independently 0, 1, 2, 3, or 4; R$^{3a}$ is independently hydrogen, halogen, oxo, —OR$^{13}$, —NR$^{13}$R$^{14}$, —C(O)R$^{13}$, —C(O)OR$^{13}$, —C(O)NR$^{13}$R$^{14}$, —NR$^{13}$C(O)R$^{14}$, —CN, —SR$^{13}$, —S(O)R$^{13}$, —S(O)$_2$R$^{13}$, —Si(C$_1$-C$_6$ alkyl)$_3$, —P(O)R$^{13}$R$^{14}$, —NR$^{13}$S(O)$_2$R$^{14}$, —(C$_1$-C$_3$ alkylene)OR$^{13}$, —(C$_1$-C$_3$ alkylene)NR$^{13}$R$^{14}$, —(C$_1$-C$_3$ alkylene)C(O)R$^{13}$, C$_3$-C$_8$ cycloalkyl optionally substituted by C$_1$-C$_6$ alkyl, CN, CF$_3$, oxo, —OH, —NR$^{15}$R$^{16}$, —OR$^{15}$ or halogen, 3- to 12-membered heterocyclyl optionally substituted by oxo, —OH, —NR$^{15}$R$^{16}$, —C(O)OR$^{15}$, —OR$^{15}$ or halogen, or C$_1$-C$_6$ alkyl optionally substituted by oxo, —OH, —NR$^{15}$R$^{16}$, —C(O)OR$^{15}$, —OR$^{15}$ or halogen, with the proviso that R$^{3a}$ is not

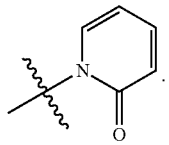

In some embodiments of a compound of Formula (Ia-12), Y is hydrogen. In some embodiments of a compound of Formula (Ia-12), Y is R$^4$. In some embodiments, each R$^4$ is independently oxo, C$_1$-C$_6$ alkyl, C$_2$-C$_6$ alkenyl, C$_2$-C$_6$ alkynyl, halogen, —C(O)R$^{17}$, —C(O)OR$^{17}$, —C(O)NR$^{17}$R$^{18}$, —CN, —Si(C$_1$-C$_6$ alkyl)$_3$, —OR$^{17}$, —NR$^{17}$R$^{18}$, —OC(O)NR$^{17}$R$^{18}$, —NR$^{17}$C(O)R$^{18}$, —S(O)$_2$R$^{17}$, —NR$^{17}$S(O)$_2$R$^{18}$, —S(O)$_2$NR$^{17}$R$^{18}$, C$_3$-C$_6$ cycloalkyl, 3- to 6-membered heterocyclyl, —(C$_1$-C$_3$ alkylene)CN, —(C$_1$-C$_3$ alkylene)OR$^{17}$, —(C$_1$-C$_3$ alkylene)NR$^{17}$R$^{18}$, —(C$_1$-C$_3$ alkylene)CF$_3$, —(C$_1$-C$_3$ alkylene)C(O)R$^{17}$, —(C$_1$-C$_3$ alkylene)C(O)NR$^{17}$R$^{18}$, —(C$_1$-C$_3$ alkylene)NR$^{17}$C(O)R$^{18}$, —(C$_1$-C$_3$ alkylene)S(O)$_2$R$^{17}$, —(C$_1$-C$_3$ alkylene)NR$^{17}$S(O)$_2$R$^{18}$, —(C$_1$-C$_3$ alkylene)S(O)$_2$NR$^{17}$R$^{18}$, —(C$_1$-C$_3$ alkylene)(C$_3$-C$_6$ cycloalkyl), or —(C$_1$-C$_3$ alkylene)(3- to 6-membered heterocyclyl), wherein each R$^4$ is independently optionally substituted by halogen, oxo, —OR$^{19}$, —NR$^{19}$R$^{20}$, or —C(O)R$^{19}$, or two R$^4$ when bound to the same carbon or two different carbon atoms, are taken together with the carbon or carbons to which they are attached to form a C$_3$-C$_6$ cycloalkyl or 3- to 7-membered heterocyclyl, each is optionally substituted by R$^{19}$. In some embodiments, R$^{3a}$ is halogen, C$_3$-C$_8$ cycloalkyl optionally substituted by C$_1$-C$_6$ alkyl, CN, CF$_3$, oxo, —OH, —NR$^{15}$R$^{16}$, —OR$^{15}$ or halogen, 3- to 12-membered heterocyclyl optionally substituted by oxo, —OH, —NR$^{15}$R$^{16}$, —C(O)OR$^{15}$, —OR$^{15}$ or halogen, or C$_1$-C$_6$ alkyl optionally substituted by oxo, —OH, —NR$^{15}$R$^{16}$, —OR$^{15}$ or halogen, with the proviso that R$^{3a}$ is not

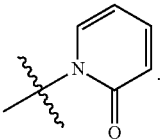

In some embodiments, R$^{3a}$ is halogen; In some embodiments, R$^{3a}$ is C$_1$-C$_6$ alkyl optionally substituted by oxo, —OH, —NR$^{15}$R$^{16}$, —C(O)OR$^{15}$, —OR$^{15}$ or halogen.

In some embodiments, provided is a compound of Formula (Ib-1):

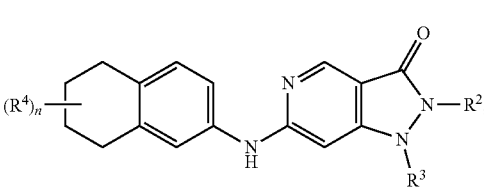

(Ib-1)

or a tautomer or isomer thereof, or a pharmaceutically acceptable salt of any of the foregoing, wherein n is 0, 1, 2, 3, or 4, each R$^4$ is independently oxo, C$_1$-C$_6$ alkyl, C$_2$-C$_6$ alkenyl, C$_2$-C$_6$ alkynyl, halogen, —C(O)R$^{17}$, —C(O)OR$^{17}$, —C(O)NR$^{17}$R$^{18}$, —CN, —Si(C$_1$-C$_6$ alkyl)$_3$, —OR$^{17}$, —NR$^{17}$R$^{18}$, —OC(O)NR$^{17}$R$^{18}$, —NR$^{17}$C(O)R$^{18}$, —S(O)$_2$R$^{17}$, —NR$^{17}$S(O)$_2$R$^{18}$, —S(O)$_2$NR$^{17}$R$^{18}$, C$_3$-C$_6$ cycloalkyl, 3- to 6-membered heterocyclyl, —(C$_1$-C$_3$ alkylene)CN, —(C$_1$-C$_3$ alkylene)OR$^{17}$, —(C$_1$-C$_3$ alkylene)NR$^{17}$R$^{18}$, —(C$_1$-C$_3$ alkylene)CF$_3$, —(C$_1$-C$_3$ alkylene)C(O)R$^{17}$, —(C$_1$-C$_3$ alkylene)C(O)NR$^{17}$R$^{18}$, —(C$_1$-C$_3$ alkylene)NR$^{17}$C(O)R$^{18}$, —(C$_1$-C$_3$ alkylene)S(O)$_2$R$^{17}$, —(C$_1$-C$_3$ alkylene)NR$^{17}$S(O)$_2$R$^{18}$, —(C$_1$-C$_3$ alkylene)S(O)$_2$NR$^{17}$R$^{18}$, —(C$_1$-C$_3$ alkylene)(C$_3$-C$_6$ cycloalkyl) or —(C$_1$-C$_3$ alkylene)(3- to 6-membered heterocyclyl), wherein each R$^4$ is independently optionally substituted by halogen, oxo, —OR$^{19}$, —NR$^{19}$R$^{20}$, or —C(O)R$^{19}$, or two R$^4$, when bound to the same carbon or two different carbon atoms, are taken together with the carbon or carbons to which they are attached to form a C$_3$-C$_6$ cycloalkyl or 3- to 7-membered heterocyclyl, each is optionally substituted by R$^{19}$. In some embodiments, R$^4$ is independently oxo, C$_1$-C$_6$ alkyl or —C(O)R$^{17}$, wherein the C$_1$-C$_6$ alkyl or —C(O)R$^{17}$ is optionally substituted by —OR$^{19}$; or two R$^4$, when bound to the same carbon or two different carbon atoms, are taken together with the carbon or carbons to which they are attached to form a C$_3$-C$_6$ cycloalkyl or 3- to 7-membered heterocyclyl, each is optionally substituted by R$^{19}$. In some embodiments, R$^4$ is independently C$_1$-C$_6$ alkyl or —C(O)R$^{17}$. In some embodiments, R$^4$ is independently C$_1$-C$_6$ alkyl or —C(O)R$^{17}$, wherein R$^{17}$ is C$_1$-C$_6$ alkyl optionally substituted with —OH.

In some embodiments, provided is a compound of Formula (Ib-2):

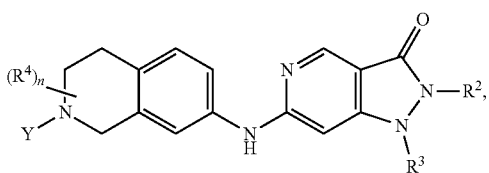

(Ib-2)

or a tautomer or isomer thereof, or a pharmaceutically acceptable salt of any of the foregoing, wherein Y is hydrogen or R$^4$, and n is 0, 1, 2, 3, or 4. In some embodiments of a compound of Formula (Ib-2), Y is hydrogen. In some embodiments of a compound of Formula (Ib-2), Y is R$^4$. In some embodiments, each R$^4$ is independently oxo, C$_1$-C$_6$ alkyl, C$_2$-C$_6$ alkenyl, C$_2$-C$_6$ alkynyl, halogen, —C(O)R$^{17}$, —C(O)OR$^{17}$, —C(O)NR$^{17}$R$^{18}$, —CN, —Si(C$_1$-C$_6$ alkyl)$_3$, —OR$^{17}$, —NR$^{17}$R$^{18}$, —OC(O)NR$^{17}$R$^{18}$, —NR$^{17}$C(O)R$^{18}$, —S(O)$_2$R$^{17}$, —NR$^{17}$S(O)$_2$R$^{18}$, —S(O)$_2$NR$^{17}$R$^{18}$, C$_3$-C$_6$ cycloalkyl, 3- to 6-membered heterocyclyl, —(C$_1$-C$_3$ alkylene)CN, —(C$_1$-C$_3$ alkylene)OR$^{17}$, —(C$_1$-C$_3$ alkylene)NR$^{17}$R$^{18}$, —(C$_1$-C$_3$ alkylene)CF$_3$, —(C$_1$-C$_3$ alkylene)C(O)R$^{17}$, —(C$_1$-C$_3$ alkylene)C(O)NR$^{17}$R$^{18}$, —(C$_1$-C$_3$ alkylene)NR$^{17}$C(O)R$^{18}$, —(C$_1$-C$_3$ alkylene)S(O)$_2$R$^{17}$, —(C$_1$-C$_3$ alkylene)NR$^{17}$S(O)$_2$R$^{18}$, —(C$_1$-C$_3$ alkylene)S(O)$_2$NR$^{17}$R$^{18}$, —(C$_1$-C$_3$ alkylene)(C$_3$-C$_6$ cycloalkyl), or —(C$_1$-C$_3$ alkylene)(3- to 6-membered heterocyclyl), wherein each R$^4$ is independently optionally substituted by halogen, oxo, —OR$^{19}$, —NR$^{19}$R$^{20}$, or —C(O)R$^{19}$, or two R$^4$, when bound to the same carbon or two different carbon atoms, are taken together with the carbon or carbons to which they are attached to form a C$_3$-C$_6$ cycloalkyl or 3- to 7-membered heterocyclyl, each is optionally substituted by R$^{19}$. In some embodiments, R$^4$ is independently oxo, C$_1$-C$_6$ alkyl or —C(O)R$^{17}$, wherein the C$_1$-C$_6$ alkyl or —C(O)R$^{17}$ is optionally substituted by —OR$^{19}$; or two R$^4$, when bound to the same carbon or two different carbon atoms, are taken together with the carbon to which they are attached to form a C$_3$-C$_6$ cycloalkyl or 3- to 7-membered heterocyclyl, each is optionally substituted by R$^{19}$. In some embodiments, R$^4$ is independently C$_1$-C$_6$ alkyl or —C(O)R$^{17}$, wherein R$^{17}$ is C$_1$-C$_6$ alkyl optionally substituted with —OH. In some embodiments, Y is hydrogen, R$^4$ is independently C$_1$-C$_6$ alkyl and n is 2. In some embodiments, Y is hydrogen, R$^4$ is methyl and n is 2.

In some embodiments, provided is a compound of Formula (Ib-3):

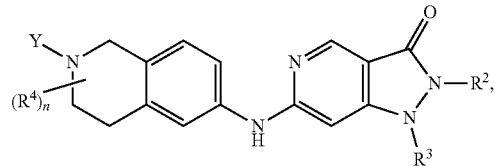

(Ib-3)

or a tautomer or isomer thereof, or a pharmaceutically acceptable salt of any of the foregoing, wherein Y is hydrogen or R$^4$, and n is 0, 1, 2, 3, or 4. In some embodiments of a compound of Formula (Ib-3), Y is hydrogen. In some embodiments of a compound of Formula (Ib-3), Y is R$^4$. In some embodiments, each R$^4$ is independently oxo, C$_1$-C$_6$ alkyl, C$_2$-C$_6$ alkenyl, C$_2$-C$_6$ alkynyl, halogen, —C(O)R$^{17}$, —C(O)OR$^{17}$, —C(O)NR$^{17}$R$^{18}$, —CN, —Si(C$_1$-C$_6$ alkyl)$_3$, —OR$^{17}$, —NR$^{17}$R$^{18}$, —OC(O)NR$^{17}$R$^{18}$, —NR$^{17}$C(O)R$^{18}$, —S(O)$_2$R$^{17}$, —NR$^{17}$S(O)$_2$R$^{18}$, —S(O)$_2$NR$^{17}$R$^{18}$, C$_3$-C$_6$ cycloalkyl, 3- to 6-membered heterocyclyl, —(C$_1$-C$_3$ alkylene)CN, —(C$_1$-C$_3$ alkylene)OR$^{17}$, —(C$_1$-C$_3$ alkylene)NR$^{17}$R$^{18}$, —(C$_1$-C$_3$ alkylene)CF$_3$, —(C$_1$-C$_3$ alkylene)C(O)R$^{17}$, —(C$_1$-C$_3$ alkylene)C(O)NR$^{17}$R$^{18}$, —(C$_1$-C$_3$ alkylene)NR$^{17}$C(O)R$^{18}$, —(C$_1$-C$_3$ alkylene)S(O)$_2$R$^{17}$, —(C$_1$-C$_3$ alkylene)NR$^{17}$S(O)$_2$R$^{18}$, —(C$_1$-C$_3$ alkylene)S(O)$_2$NR$^{17}$R$^{18}$, —(C$_1$-C$_3$ alkylene)(C$_3$-C$_6$ cycloalkyl) or —(C$_1$-C$_3$ alkylene)(3- to 6-membered heterocyclyl), wherein each R$^4$ is independently optionally substituted by halogen, oxo, —OR$^{19}$, —NR$^{19}$R$^{20}$, or —C(O)R$^{19}$, or two R$^4$, when bound to the same carbon or two different carbon atoms, are taken together with the carbon or carbons to which they are attached to form a C$_3$-C$_6$ cycloalkyl or 3- to 7-membered heterocyclyl, each is optionally substituted by R$^{19}$. In some embodiments, R$^4$ is independently oxo, C$_1$-C$_6$ alkyl or —C(O)R$^{17}$, wherein the C$_1$-C$_6$ alkyl or —C(O)R$^{17}$ is optionally substituted by —OR$^{19}$; or two R$^4$, when bound to the same carbon or two different carbon atoms, are taken together with the carbon or carbons to which they are attached to form a C$_3$-C$_6$ cycloalkyl or 3- to 7-membered heterocyclyl, each is optionally substituted by R$^{19}$. In some embodiments, R$^4$ is independently C$_1$-C$_6$ alkyl or —C(O)R$^{17}$. In some embodiments, R$^4$ is independently C$_1$-C$_6$ alkyl or —C(O)R$^{17}$, wherein R$^{17}$ is C$_1$-C$_6$ alkyl optionally substituted with —OH. In some embodiments, Y is hydrogen and n is 0.

In some embodiments, provided is a compound of Formula (Ib-4):

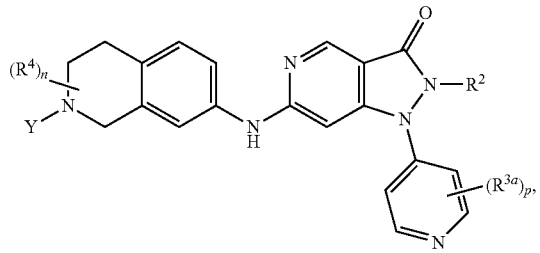

(Ib-4)

or a tautomer or isomer thereof, or a pharmaceutically acceptable salt of any of the foregoing, wherein Y is hydrogen or $R^4$, n and p are independently 0, 1, 2, 3, or 4; $R^{3a}$ is independently hydrogen, halogen, oxo, —$OR^{13}$, —$NR^{13}R^{14}$, —$C(O)R^{13}$, —$C(O)OR^{13}$, —$C(O)NR^{13}R^{14}$, —$NR^{13}C(O)R^{14}$, —CN, —$SR^{13}$, —$S(O)R^{13}$, —$S(O)_2R^{13}$, —$Si(C_1-C_6$ alkyl$)_3$, —$P(O)R^{13}R^{14}$, —$NR^{13}S(O)_2R^{14}$, —$(C_1-C_3$ alkylene$)OR^{13}$, —$(C_1-C_3$ alkylene$)NR^{13}R^{14}$, —$(C_1-C_3$ alkylene$)C(O)R^{13}$, $C_3-C_8$ cycloalkyl optionally substituted by $C_1-C_6$ alkyl, CN, $CF_3$, oxo, —OH, —$NR^{15}R^{16}$, —$OR^{15}$ or halogen, 3- to 12-membered heterocyclyl optionally substituted by oxo, —OH, —$NR^{15}R^{16}$, —$C(O)OR^{15}$, —$OR^{15}$ or halogen, or $C_1-C_6$ alkyl optionally substituted by oxo, —OH, —$NR^{15}R^{16}$, —$C(O)OR^{15}$, —$OR^{15}$ or halogen, with the proviso that $R^{3a}$ is not

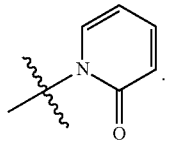

In some embodiments of a compound of Formula (Ib-4), Y is hydrogen. In some embodiments of a compound of Formula (Ib-4), Y is $R^4$. In some embodiments, each $R^4$ is independently oxo, $C_1-C_6$ alkyl, $C_2-C_6$ alkenyl, $C_2-C_6$ alkynyl, halogen, —$C(O)R^{17}$, —$C(O)OR^{17}$, —$C(O)NR^{17}R^{18}$, —$Si(C_1-C_6$ alkyl$)_3$, —CN, —$OR^{17}$, —$NR^{17}R^{18}$, —$OC(O)NR^{17}R^{18}$, —$NR^{17}C(O)R^{18}$, —$S(O)_2R^{17}$, —$NR^{17}S(O)_2R^{18}$, —$S(O)_2NR^{17}R^{18}$, $C_3-C_6$ cycloalkyl, 3- to 6-membered heterocyclyl, —$(C_1-C_3$ alkylene$)CN$, —$(C_1-C_3$ alkylene$)OR^{17}$, —$(C_1-C_3$ alkylene$)NR^{17}R^{18}$, —$(C_1-C_3$ alkylene$)CF_3$, —$(C_1-C_3$ alkylene$)C(O)R^{17}$, —$(C_1-C_3$ alkylene$)C(O)NR^{17}R^{18}$, —$(C_1-C_3$ alkylene$)NR^{17}C(O)R^{18}$, —$(C_1-C_3$ alkylene$)S(O)_2R^{17}$, —$(C_1-C_3$ alkylene$)NR^{17}S(O)_2R^{18}$, —$(C_1-C_3$ alkylene$)S(O)_2NR^{17}R^{18}$, —$(C_1-C_3$ alkylene$)(C_3-C_6$ cycloalkyl), or —$(C_1-C_3$ alkylene)(3- to 6-membered heterocyclyl), wherein each $R^4$ is independently optionally substituted by halogen, oxo, —$OR^{19}$, —$NR^{19}R^{20}$, or —$C(O)R^{19}$, or two $R^4$ when bound to the same carbon or two different carbon atoms, are taken together with the carbon or carbons to which they are attached to form a $C_3-C_6$ cycloalkyl or 3- to 7-membered heterocyclyl, each is optionally substituted by $R^{19}$. In some embodiments, $R^{3a}$ is $C_3-C_8$ cycloalkyl optionally substituted by $C_1-C_6$ alkyl, CN, $CF_3$, oxo, —OH, —$NR^{15}R^{16}$, —$OR^{15}$ or halogen, 3- to 12-membered heterocyclyl optionally substituted by oxo, —OH, —$NR^{15}R^{16}$, —$C(O)OR^{15}$, —$OR^{15}$ or halogen, or $C_1-C_6$ alkyl optionally substituted by oxo, —OH, —$NR^{15}R^{16}$, —$C(O)OR^{15}$, —$OR^{15}$ or halogen, with the proviso that $R^{3a}$ is not

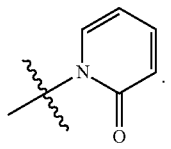

In some embodiments, $R^{3a}$ is $C_1-C_6$ alkyl optionally substituted by oxo, —OH, —$NR^{15}R^{16}$, —$C(O)OR^{15}$, —$OR^{15}$ or halogen.

In some embodiments, provided is a compound of Formula (Ib-5):

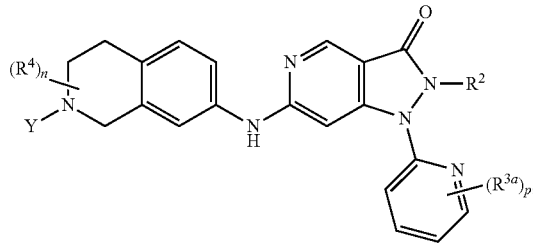

(Ib-5)

or a tautomer or isomer thereof, or a pharmaceutically acceptable salt of any of the foregoing, wherein Y is hydrogen or $R^4$, n and p are independently 0, 1, 2, 3, or 4; $R^{3a}$ is independently hydrogen, halogen, oxo, —$OR^{13}$, —$NR^{13}R^{14}$, —$C(O)R^{13}$, —$C(O)OR^{13}$, —$C(O)NR^{13}R^{14}$, —$NR^{13}C(O)R^{14}$, —CN, —$SR^{13}$, —$S(O)R^{13}$, —$S(O)_2R^{13}$, —$Si(C_1-C_6$ alkyl$)_3$, —$P(O)R^{13}R^{14}$, —$NR^{13}S(O)_2R^{14}$, —$(C_1-C_3$ alkylene$)OR^{13}$, —$(C_1-C_3$ alkylene$)NR^{13}R^{14}$, —$(C_1-C_3$ alkylene$)C(O)R^{13}$, $C_3-C_8$ cycloalkyl optionally substituted by $C_1-C_6$ alkyl, CN, $CF_3$, oxo, —OH, —$NR^{15}R^{16}$, —$OR^{15}$ or halogen, 3- to 12-membered heterocyclyl optionally substituted by oxo, —OH, —$NR^{15}R^{16}$, —$C(O)OR^{15}$, —$OR^{15}$ or halogen, or $C_1-C_6$ alkyl optionally substituted by oxo, —OH, —$NR^{15}R^{16}$, —$C(O)OR^{15}$, —$OR^{15}$ or halogen, with the proviso that $R^{3a}$ is not

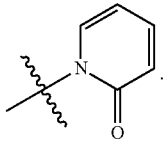

In some embodiments of a compound of Formula (Ib-5), Y is hydrogen. In some embodiments of a compound of Formula (Ib-5), Y is $R^4$. In some embodiments, each $R^4$ is independently oxo, $C_1-C_6$ alkyl, $C_2-C_6$ alkenyl, $C_2-C_6$ alkynyl, halogen, —$C(O)R^{17}$, —$C(O)OR^{17}$, —$C(O)NR^{17}R^{18}$, —CN, —$Si(C_1-C_6$ alkyl$)_3$, —$OR^{17}$, —$NR^{17}R^{18}$, —$OC(O)NR^{17}R^{18}$, —$NR^{17}C(O)R^{18}$, —$S(O)_2R^{17}$, —$NR^{17}S(O)_2R^{18}$, —$S(O)_2NR^{17}R^{18}$, $C_3-C_6$ cycloalkyl, 3- to 6-membered heterocyclyl, —$(C_1-C_3$ alkylene$)CN$, —$(C_1-C_3$ alkylene$)OR^{17}$, —$(C_1-C_3$ alkylene$)NR^{17}R^{18}$, —$(C_1-C_3$ alkylene$)CF_3$, —$(C_1-C_3$ alkylene$)C(O)R^{17}$, —$(C_1-C_3$ alkylene$)C(O)NR^{17}R^{18}$, —$(C_1-C_3$ alkylene$)NR^{17}C(O)R^{18}$, —$(C_1-C_3$ alkylene$)S(O)_2R^{17}$, —$(C_1-C_3$ alkylene$)NR^{17}S(O)_2R^{18}$, —$(C_1-C_3$ alkylene$)S(O)_2NR^{17}R^{18}$, —$(C_1-C_3$ alkylene$)(C_3-C_6$ cycloalkyl), or —$(C_1-C_3$ alkylene)(3- to 6-membered heterocyclyl), wherein each $R^4$ is independently optionally substituted by halogen, oxo, —$OR^{19}$, —$NR^{19}R^{20}$, or —$C(O)R^{19}$, or two $R^4$ when bound to the same carbon or two different carbon atoms, are taken together with the carbon or carbons to which they are attached to form a $C_3-C_6$ cycloalkyl or 3- to 7-membered heterocyclyl, each is optionally substituted by $R^{19}$. In some embodiments, $R^{3a}$ is $C_3-C_8$ cycloalkyl optionally substituted by $C_1-C_6$ alkyl, CN, $CF_3$, oxo, —OH, —$NR^{15}R^{16}$, —$OR^{15}$ or halogen, 3- to 12-membered heterocyclyl optionally substituted by oxo, —OH, —$NR^{15}R^{16}$, —$C(O)OR^{15}$, —$OR^{15}$ or halogen, or $C_1-C_6$ alkyl optionally substituted by oxo, —OH, —$NR^{15}R^{16}$, —$C(O)OR^{15}$, —$OR^{15}$ or halogen, with the proviso that $R^{3a}$ is not

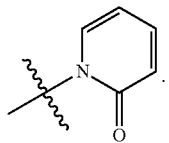

In some embodiments, $R^{3a}$ is $C_1$-$C_6$ alkyl optionally substituted by oxo, —OH, —NR$^{15}$R$^{16}$, —C(O)OR$^{15}$, —OR$^{15}$ or halogen.

In some embodiments, provided is a compound of Formula (Ib-6):

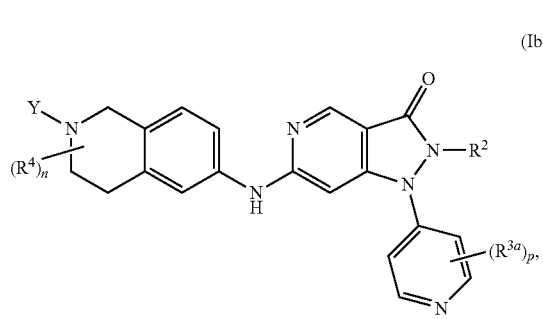

(Ib-6)

or a tautomer or isomer thereof, or a pharmaceutically acceptable salt of any of the foregoing, wherein Y is hydrogen or $R^4$, n and p are independently 0, 1, 2, 3, or 4; $R^{3a}$ is independently hydrogen, halogen, oxo, —OR$^{13}$, —NR$^{13}$R$^{14}$, —C(O)R$^{13}$, —C(O)OR$^{13}$, —C(O)NR$^{13}$R$^{14}$, —NR$^{13}$C(O)R$^{14}$, —CN, —SR$^{13}$, —S(O)R$^{13}$, —S(O)$_2$R$^{13}$, —Si($C_1$-$C_6$ alkyl)$_3$, —P(O)R$^{13}$R$^{14}$, —NR$^{13}$S(O)$_2$R$^{14}$, —($C_1$-$C_3$ alkylene)OR$^{13}$, —($C_1$-$C_3$ alkylene)NR$^{13}$R$^{14}$, —($C_1$-$C_3$ alkylene)C(O)R$^{13}$, $C_3$-$C_8$ cycloalkyl optionally substituted by $C_1$-$C_6$ alkyl, CN, CF$_3$, oxo, —OH, —NR$^{15}$R$^{16}$, —OR$^{15}$ or halogen, 3- to 12-membered heterocyclyl optionally substituted by oxo, —OH, —NR$^{15}$R$^{16}$, —C(O)OR$^{15}$, —OR$^{15}$ or halogen, or $C_1$-$C_6$ alkyl optionally substituted by oxo, —OH, —NR$^{15}$R$^{16}$, —C(O)OR$^{15}$, —OR$^{15}$ or halogen, with the proviso that $R^{3a}$ is not

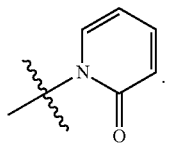

In some embodiments of a compound of Formula (Ib-6), Y is hydrogen. In some embodiments of a compound of Formula (Ib-6), Y is $R^4$. In some embodiments, each $R^4$ is independently oxo, $C_1$-$C_6$ alkyl, $C_2$-$C_6$ alkenyl, $C_2$-$C_6$ alkynyl, halogen, —C(O)R$^{17}$, —C(O)OR$^{17}$, —C(O)NR$^{17}$R$^{18}$, —CN, —Si($C_1$-$C_6$ alkyl)$_3$, —OR$^{17}$, —NR$^{17}$R$^{18}$, —OC(O)NR$^{17}$R$^{18}$, —NR$^{17}$C(O)R$^{18}$, —S(O)$_2$R$^{17}$, —NR$^{17}$S(O)$_2$R$^{18}$, —S(O)$_2$NR$^{17}$R$^{18}$, $C_3$-$C_6$ cycloalkyl, 3- to 6-membered heterocyclyl, —($C_1$-$C_3$ alkylene)CN, —($C_1$-$C_3$ alkylene)OR$^{17}$, —($C_1$-$C_3$ alkylene)NR$^{17}$R$^{18}$, —($C_1$-$C_3$ alkylene)CF$_3$, —($C_1$-$C_3$ alkylene)C(O)R$^{17}$, —($C_1$-$C_3$ alkylene)C(O)NR$^{17}$R$^{18}$, —($C_1$-$C_3$ alkylene)NR$^{17}$C(O)R$^{18}$, —($C_1$-$C_3$ alkylene)S(O)$_2$R$^{17}$, —($C_1$-$C_3$ alkylene)NR$^{17}$S(O)$_2$R$^{18}$, —($C_1$-$C_3$ alkylene)S(O)$_2$NR$^{17}$R$^{18}$, —($C_1$-$C_3$ alkylene)($C_3$-$C_6$ cycloalkyl), or —($C_1$-$C_3$ alkylene)(3- to 6-membered heterocyclyl), wherein each $R^4$ is independently optionally substituted by halogen, oxo, —OR$^{19}$, —NR$^{19}$R$^{20}$, or —C(O)R$^{19}$, or two $R^4$ when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments, $R^{3a}$ is $C_3$-$C_8$ cycloalkyl optionally substituted by $C_1$-$C_6$ alkyl, CN, CF$_3$, oxo, —OH, —NR$^{15}$R$^{16}$, —OR$^{15}$ or halogen, 3- to 12-membered heterocyclyl optionally substituted by oxo, —OH, —NR$^{15}$R$^{16}$, —C(O)OR$^{15}$, —OR$^{15}$ or halogen, or $C_1$-$C_6$ alkyl optionally substituted by oxo, —OH, —NR$^{15}$R$^{16}$, —C(O)OR$^{15}$, —OR$^{15}$ or halogen, with the proviso that $R^{3a}$ is not

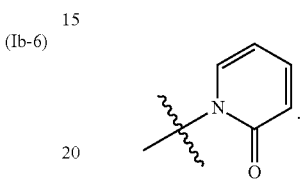

In some embodiments, $R^{3a}$ is $C_1$-$C_6$ alkyl optionally substituted by oxo, —OH, —NR$^{15}$R$^{16}$, —C(O)OR$^{15}$, —OR$^{15}$ or halogen.

In some embodiments, provided is a compound of Formula (Ib-7):

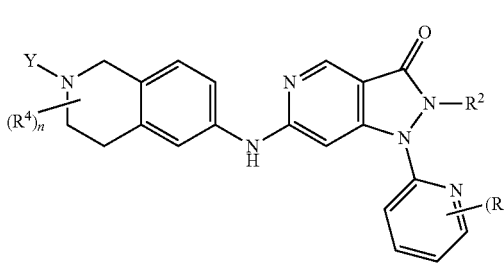

(Ib-7)

or a tautomer or isomer thereof, or a pharmaceutically acceptable salt of any of the foregoing, wherein Y is hydrogen or $R^4$, n and p are independently 0, 1, 2, 3, or 4; $R^{3a}$ is independently hydrogen, halogen, oxo, —OR$^{13}$, —NR$^{13}$R$^{14}$, —C(O)R$^{13}$, —C(O)OR$^{13}$, —C(O)NR$^{13}$R$^{14}$, —NR$^{13}$C(O)R$^{14}$, —CN, —SR$^{13}$, —S(O)R$^{13}$, —S(O)$_2$R$^{13}$, —Si($C_1$-$C_6$ alkyl)$_3$, —P(O)R$^{13}$R$^{14}$, —NR$^{13}$S(O)$_2$R$^{14}$, —($C_1$-$C_3$ alkylene)OR$^{13}$, —($C_1$-$C_3$ alkylene)NR$^{13}$R$^{14}$, —($C_1$-$C_3$ alkylene)C(O)R$^{13}$, $C_3$-$C_8$ cycloalkyl optionally substituted by $C_1$-$C_6$ alkyl, CN, CF$_3$, oxo, —OH, —NR$^{15}$R$^{16}$, —OR$^{15}$ or halogen, 3- to 12-membered heterocyclyl optionally substituted by oxo, —OH, —NR$^{15}$R$^{16}$, —C(O)OR$^{15}$, —OR$^{15}$ or halogen, or $C_1$-$C_6$ alkyl optionally substituted by oxo, —OH, —NR$^{15}$R$^{16}$, —C(O)OR$^{15}$, —OR$^{15}$ or halogen, with the proviso that $R^{3a}$ is not

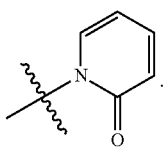

In some embodiments of a compound of Formula (Ib-7), Y is hydrogen. In some embodiments of a compound of Formula (Ib-7), Y is R⁴. In some embodiments, each R⁴ is independently oxo, $C_1$-$C_6$ alkyl, $C_2$-$C_6$ alkenyl, $C_2$-$C_6$ alkynyl, halogen, —C(O)R¹⁷, —C(O)OR¹⁷, —C(O)NR¹⁷R¹⁸, —CN, —Si($C_1$-$C_6$ alkyl)₃, —OR¹⁷, —NR¹⁷R¹⁸, —OC(O)NR¹⁷R¹⁸, —NR¹⁷C(O)R¹⁸, —S(O)₂R¹⁷, —NR¹⁷S(O)₂R¹⁸, —S(O)₂NR¹⁷R¹⁸, $C_3$-$C_6$ cycloalkyl, 3- to 6-membered heterocyclyl, —($C_1$-$C_3$ alkylene)CN, —($C_1$-$C_3$ alkylene)OR¹⁷, —($C_1$-$C_3$ alkylene)NR¹⁷R¹⁸, —($C_1$-$C_3$ alkylene)CF₃, —($C_1$-$C_3$ alkylene)C(O)R¹⁷, —($C_1$-$C_3$ alkylene)C(O)NR¹⁷R¹⁸, —($C_1$-$C_3$ alkylene)NR¹⁷C(O)R¹⁸, —($C_1$-$C_3$ alkylene)S(O)₂R¹⁷, —($C_1$-$C_3$ alkylene)NR¹⁷S(O)₂R¹⁸, —($C_1$-$C_3$ alkylene)S(O)₂NR¹⁷R¹⁸, —($C_1$-$C_3$ alkylene)($C_3$-$C_6$ cycloalkyl), or —($C_1$-$C_3$ alkylene)(3- to 6-membered heterocyclyl), wherein each R⁴ is independently optionally substituted by halogen, oxo, —OR¹⁹, —NR¹⁹R²⁰, or —C(O)R¹⁹, or two R⁴ when bound to the same carbon or two different carbon atoms, are taken together with the carbon or carbons to which they are attached to form a $C_3$-$C_6$ cycloalkyl or 3- to 7-membered heterocyclyl, each is optionally substituted by R¹⁹. In some embodiments, R³ᵃ is $C_3$-$C_8$ cycloalkyl optionally substituted by $C_1$-$C_6$ alkyl, CN, CF₃, oxo, —OH, —NR¹⁵R¹⁶, —OR¹⁵ or halogen, 3- to 12-membered heterocyclyl optionally substituted by oxo, —OH, —NR¹⁵R¹⁶, —C(O)OR¹⁵, —OR¹⁵ or halogen, or $C_1$-$C_6$ alkyl optionally substituted by oxo, —OH, —NR¹⁵R¹⁶, —C(O)OR¹⁵, —OR¹⁵ or halogen, with the proviso that R³ᵃ is not

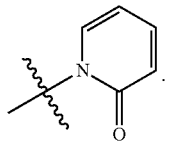

In some embodiments, R³ᵃ is $C_1$-$C_6$ alkyl optionally substituted by oxo, —OH, —NR¹⁵R¹⁶, —C(O)OR¹⁵, —OR¹⁵ or halogen.

In some embodiments, provided is a compound of Formula (Ib-8):

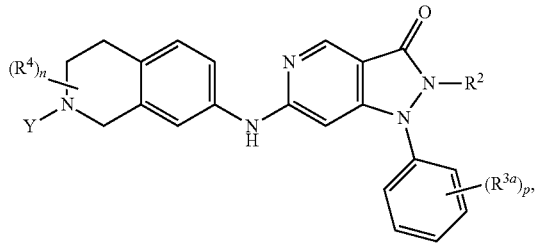

(Ib-8)

or a tautomer or isomer thereof, or a pharmaceutically acceptable salt of any of the foregoing, wherein Y is hydrogen or R⁴, n and p are independently 0, 1, 2, 3, or 4; R³ᵃ is independently hydrogen, halogen, —OR¹³, —NR¹³R¹⁴, —C(O)R¹³, —C(O)OR¹³, —C(O)NR¹³R¹⁴, —NR¹³C(O)R¹⁴, —CN, —SR¹³, —S(O)R¹³, —S(O)₂R¹³, —Si($C_1$-$C_6$ alkyl)₃, —P(O)R¹³R¹⁴, —NR¹³S(O)₂R¹⁴, —($C_1$-$C_3$ alkylene)OR¹³, —($C_1$-$C_3$ alkylene)NR¹³R¹⁴, —($C_1$-$C_3$ alkylene)C(O)R¹³, $C_3$-$C_8$ cycloalkyl optionally substituted by $C_1$-$C_6$ alkyl, CN, CF₃, oxo, —OH, —NR¹⁵R¹⁶, —OR¹⁵ or halogen, 3- to 12-membered heterocyclyl optionally substituted by oxo, —OH, —NR¹⁵R¹⁶, —C(O)OR¹⁵, —OR¹⁵ or halogen, or $C_1$-$C_6$ alkyl optionally substituted by oxo, —OH, —NR¹⁵R¹⁶, —C(O)OR¹⁵, —OR¹⁵ or halogen, with the proviso that R³ᵃ is not

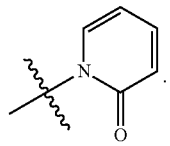

In some embodiments of a compound of Formula (Ib-8), Y is hydrogen. In some embodiments of a compound of Formula (Ib-8), Y is R⁴. In some embodiments, each R⁴ is independently oxo, $C_1$-$C_6$ alkyl, $C_2$-$C_6$ alkenyl, $C_2$-$C_6$ alkynyl, halogen, —C(O)R¹⁷, —C(O)OR¹⁷, —C(O)NR¹⁷R¹⁸, —CN, —Si($C_1$-$C_6$ alkyl)₃, —OR¹⁷, —NR¹⁷R¹⁸, —OC(O)NR¹⁷R¹⁸, —NR¹⁷C(O)R¹⁸, —S(O)₂R¹⁷, —NR¹⁷S(O)₂R¹⁸, —S(O)₂NR¹⁷R¹⁸, $C_3$-$C_6$ cycloalkyl, 3- to 6-membered heterocyclyl, —($C_1$-$C_3$ alkylene)CN, —($C_1$-$C_3$ alkylene)OR¹⁷, —($C_1$-$C_3$ alkylene)NR¹⁷R¹⁸, —($C_1$-$C_3$ alkylene)CF₃, —($C_1$-$C_3$ alkylene)C(O)R¹⁷, —($C_1$-$C_3$ alkylene)C(O)NR¹⁷R¹⁸, —($C_1$-$C_3$ alkylene)NR¹⁷C(O)R¹⁸, —($C_1$-$C_3$ alkylene)S(O)₂R¹⁷, —($C_1$-$C_3$ alkylene)NR¹⁷S(O)₂R¹⁸, —($C_1$-$C_3$ alkylene)S(O)₂NR¹⁷R¹⁸, —($C_1$-$C_3$ alkylene)($C_3$-$C_6$ cycloalkyl), or —($C_1$-$C_3$ alkylene)(3- to 6-membered heterocyclyl), wherein each R⁴ is independently optionally substituted by halogen, oxo, —OR¹⁹, —NR¹⁹R²⁰, or —C(O)R¹⁹, or two R⁴ when bound to the same carbon or two different carbon atoms, are taken together with the carbon or carbons to which they are attached to form a $C_3$-$C_6$ cycloalkyl or 3- to 7-membered heterocyclyl, each is optionally substituted by R¹⁹. In some embodiments, R³ᵃ is halogen, $C_3$-$C_8$ cycloalkyl optionally substituted by $C_1$-$C_6$ alkyl, CN, CF₃, oxo, —OH, —NR¹⁵R¹⁶, —OR¹⁵ or halogen, 3- to 12-membered heterocyclyl optionally substituted by oxo, —OH, —NR¹⁵R¹⁶, —C(O)OR¹⁵, —OR¹⁵ or halogen, or $C_1$-$C_6$ alkyl optionally substituted by oxo, —OH, —NR¹⁵R¹⁶, —C(O)OR¹⁵, —OR¹⁵ or halogen, with the proviso that R³ᵃ is not

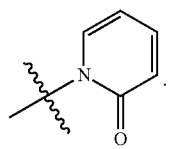

In some embodiments, R³ᵃ is halogen; In some embodiments, R³ᵃ is $C_1$-$C_6$ alkyl optionally substituted by oxo, —OH, —NR¹⁵R¹⁶, —C(O)OR¹⁵, —OR¹⁵ or halogen.

In some embodiments, provided is a compound of Formula (Ib-9):

(Ib-9)

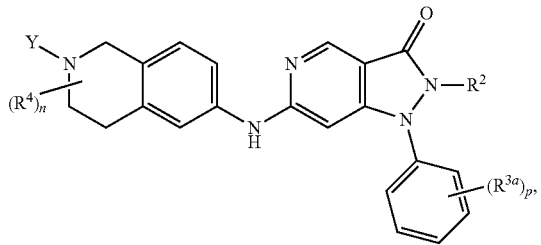

or a tautomer or isomer thereof, or a pharmaceutically acceptable salt of any of the foregoing, wherein Y is hydrogen or $R^4$, n and p are independently 0, 1, 2, 3, or 4; $R^{3a}$ is independently hydrogen, halogen, oxo, $-OR^{13}$, $-NR^{13}R^{14}$, $-C(O)R^{13}$, $-C(O)OR^{13}$, $-C(O)NR^{13}R^{14}$, $-NR^{13}C(O)R^{14}$, $-CN$, $-SR^{13}$, $-S(O)R^{13}$, $-S(O)_2R^{13}$, $-Si(C_1-C_6$ alkyl$)_3$, $-P(O)R^{13}R^{14}$, $-NR^{13}S(O)_2R^{14}$, $-(C_1-C_3$ alkylene$)OR^{13}$, $-(C_1-C_3$ alkylene$)NR^{13}R^{14}$, $-(C_1-C_3$ alkylene$)C(O)R^{13}$, $C_3-C_8$ cycloalkyl optionally substituted by $C_1-C_6$ alkyl, CN, $CF_3$, oxo, $-OH$, $-NR^{15}R^{16}$, $-OR^{15}$ or halogen, 3- to 12-membered heterocyclyl optionally substituted by oxo, $-OH$, $-NR^{15}R^{16}$, $-C(O)OR^{15}$, $-OR^{15}$ or halogen, or $C_1-C_6$ alkyl optionally substituted by oxo, $-OH$, $-NR^{15}R^{16}$, $-C(O)OR^{15}$, $-OR^{15}$ or halogen, with the proviso that $R^{3a}$ is not

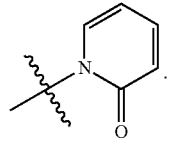

In some embodiments of a compound of Formula (Ib-9), Y is hydrogen. In some embodiments of a compound of Formula (Ib-9), Y is $R^4$. In some embodiments, each $R^4$ is independently oxo, $C_1-C_6$ alkyl, $C_2-C_6$ alkenyl, $C_2-C_6$ alkynyl, halogen, $-C(O)R^{17}$, $-C(O)OR^{17}$, $-C(O)NR^{17}R^{18}$, $-CN$, $-Si(C_1-C_6$ alkyl$)_3$, $-OR^{17}$, $-NR^{17}R^{18}$, $-OC(O)NR^{17}R^{18}$, $-NR^{17}C(O)R^{18}$, $-S(O)_2R^{17}$, $-NR^{17}S(O)_2R^{18}$, $-S(O)_2NR^{17}R^{18}$, $C_3-C_6$ cycloalkyl, 3- to 6-membered heterocyclyl, $-(C_1-C_3$ alkylene$)CN$, $-(C_1-C_3$ alkylene$)OR^{17}$, $-(C_1-C_3$ alkylene$)NR^{17}R^{18}$, $-(C_1-C_3$ alkylene$)CF_3$, $-(C_1-C_3$ alkylene$)C(O)R^{17}$, $-(C_1-C_3$ alkylene$)C(O)NR^{17}R^{18}$, $-(C_1-C_3$ alkylene$)NR^{17}C(O)R^{18}$, $-(C_1-C_3$ alkylene$)S(O)_2R^{17}$, $-(C_1-C_3$ alkylene$)NR^{17}S(O)_2R^{18}$, $-(C_1-C_3$ alkylene$)S(O)_2NR^{17}R^{18}$, $-(C_1-C_3$ alkylene$)(C_3-C_6$ cycloalkyl$)$, or $-(C_1-C_3$ alkylene$)(3$- to 6-membered heterocyclyl$)$, wherein each $R^4$ is independently optionally substituted by halogen, oxo, $-OR^{19}$, $-NR^{19}R^{20}$, or $-C(O)R^{19}$, or two $R^4$ when bound to the same carbon or two different carbon atoms, are taken together with the carbon or carbons to which they are attached to form a $C_3-C_6$ cycloalkyl or 3- to 7-membered heterocyclyl, each is optionally substituted by $R^{19}$. In some embodiments, $R^{3a}$ is halogen, $C_3-C_8$ cycloalkyl optionally substituted by $C_1-C_6$ alkyl, CN, $CF_3$, oxo, $-OH$, $-NR^{15}R^{16}$, $-OR^{15}$ or halogen, 3- to 12-membered heterocyclyl optionally substituted by oxo, $-OH$, $-NR^{15}R^{16}$, $-C(O)OR^{15}$, $-OR^{15}$ or halogen, or $C_1-C_6$ alkyl optionally substituted by oxo, $-OH$, $-NR^{15}R^{16}$, $-OR^{15}$ or halogen, with the proviso that $R^{3a}$ is not

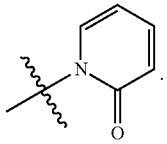

In some embodiments, $R^{3a}$ is halogen. In some embodiments, $R^{3a}$ is $C_1-C_6$ alkyl optionally substituted by oxo, $-OH$, $-NR^{15}R^{16}$, $-C(O)OR^{15}$, $-OR^{15}$ or halogen.

In some embodiments, provided is a compound of Formula (Ic-1):

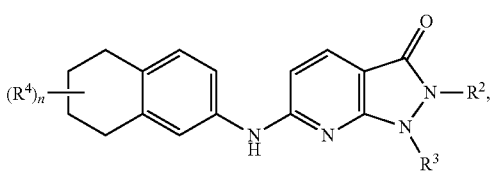

(Ic-1)

or a tautomer or isomer thereof, or a pharmaceutically acceptable salt of any of the foregoing, wherein n is 0, 1, 2, 3, or 4; each $R^4$ is independently oxo, $C_1-C_6$ alkyl, $C_2-C_6$ alkenyl, $C_2-C_6$ alkynyl, halogen, $-C(O)R^{17}$, $-C(O)OR^{17}$, $-C(O)NR^{17}R^{18}$, $-CN$, $-Si(C_1-C_6$ alkyl$)_3$, $-OR^{17}$, $-NR^{17}R^{18}$, $-OC(O)NR^{17}R^{18}$, $-NR^{17}C(O)R^{18}$, $-S(O)_2R^{17}$, $-NR^{17}S(O)_2R^{18}$, $-S(O)_2NR^{17}R^{18}$, $C_3-C_6$ cycloalkyl, 3- to 6-membered heterocyclyl, $-(C_1-C_3$ alkylene$)CN$, $-(C_1-C_3$ alkylene$)OR^{17}$, $-(C_1-C_3$ alkylene$)NR^{17}R^{18}$, $-(C_1-C_3$ alkylene$)CF_3$, $-(C_1-C_3$ alkylene$)C(O)R^{17}$, $-(C_1-C_3$ alkylene$)C(O)NR^{17}R^{18}$, $-(C_1-C_3$ alkylene$)NR^{17}C(O)R^{18}$, $-(C_1-C_3$ alkylene$)S(O)_2R^{17}$, $-(C_1-C_3$ alkylene$)NR^{17}S(O)_2R^{18}$, $-(C_1-C_3$ alkylene$)S(O)_2NR^{17}R^{18}$, $-(C_1-C_3$ alkylene$)(C_3-C_6$ cycloalkyl$)$ or $-(C_1-C_3$ alkylene$)$ (3- to 6-membered heterocyclyl), wherein each $R^4$ is independently optionally substituted by halogen, oxo, $-OR^{19}$, $-NR^{19}R^{20}$, or $-C(O)R^{19}$, or two $R^4$, when bound to the same carbon or two different carbon atoms, are taken together with the carbon or carbons to which they are attached to form a $C_3-C_6$ cycloalkyl or 3- to 7-membered heterocyclyl, each is optionally substituted by $R^{19}$. In some embodiments, $R^4$ is independently oxo, $C_1-C_6$ alkyl or $-C(O)R^{17}$, wherein the $C_1-C_6$ alkyl or $-C(O)R^{17}$ is optionally substituted by $-OR^{19}$; or two $R^4$, when bound to the same carbon or two different carbon atoms, are taken together with the carbon or carbons to which they are attached to form a $C_3-C_6$ cycloalkyl or 3- to 7-membered heterocyclyl, each is optionally substituted by $R^{19}$. In some embodiments, $R^4$ is independently $C_1-C_6$ alkyl or $-C(O)R^{17}$. In some embodiments, $R^4$ is independently $C_1-C_6$ alkyl or $-C(O)R^{17}$, wherein $R^{17}$ is $C_1-C_6$ alkyl optionally substituted with $-OH$.

In some embodiments, provided is a compound of Formula (Ic-2):

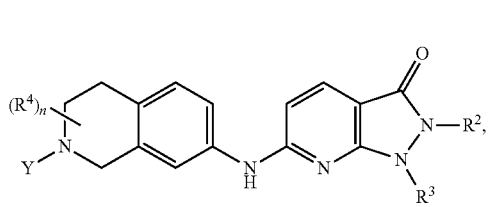

(Ic-2)

or a tautomer or isomer thereof, or a pharmaceutically acceptable salt of any of the foregoing, wherein Y is hydrogen or $R^4$, and n is 0, 1, 2, 3, or 4. In some embodiments of a compound of Formula (Ic-2), Y is hydrogen. In some embodiments of a compound of Formula (Ic-2), Y is $R^4$. In some embodiments, each $R^4$ is independently oxo, $C_1$-$C_6$ alkyl, $C_2$-$C_6$ alkenyl, $C_2$-$C_6$ alkynyl, halogen, —C(O)$R^{17}$, —C(O)O$R^{17}$, —C(O)N$R^{17}R^{18}$, —CN, —Si($C_1$-$C_6$ alkyl)$_3$, —O$R^{17}$, —N$R^{17}R^{18}$, —OC(O)N$R^{17}R^{18}$, —N$R^{17}$C(O)$R^{18}$, —S(O)$_2R^{17}$, —N$R^{17}$S(O)$_2R^{18}$, —S(O)$_2$N$R^{17}R^{18}$, $C_3$-$C_6$ cycloalkyl, 3- to 6-membered heterocyclyl, —($C_1$-$C_3$ alkylene)CN, —($C_1$-$C_3$ alkylene)O$R^{17}$, —($C_1$-$C_3$ alkylene)N$R^{17}R^{18}$, —($C_1$-$C_3$ alkylene)CF$_3$, —($C_1$-$C_3$ alkylene)C(O)$R^{17}$, —($C_1$-$C_3$ alkylene)C(O)N$R^{17}R^{18}$, —($C_1$-$C_3$ alkylene)N$R^{17}$C(O)$R^{18}$, —($C_1$-$C_3$ alkylene)S(O)$_2R^{17}$, —($C_1$-$C_3$ alkylene)N$R^{17}$S(O)$_2R^{18}$, —($C_1$-$C_3$ alkylene)S(O)$_2$N$R^{17}R^{18}$, —($C_1$-$C_3$ alkylene)($C_3$-$C_6$ cycloalkyl), or —($C_1$-$C_3$ alkylene)(3- to 6-membered heterocyclyl), wherein each $R^4$ is independently optionally substituted by halogen, oxo, —O$R^{19}$, —N$R^{19}R^{20}$, or —C(O)$R^{19}$, or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments, $R^4$ is independently oxo, $C_1$-$C_6$ alkyl or —C(O)$R^{17}$, wherein the $C_1$-$C_6$ alkyl or —C(O)$R^{17}$ is optionally substituted by —O$R^{19}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments, $R^4$ is independently $C_1$-$C_6$ alkyl or —C(O)$R^{17}$, wherein $R^{17}$ is $C_1$-$C_6$ alkyl optionally substituted with —OH. In some embodiments, Y is hydrogen, $R^4$ is independently $C_1$-$C_6$ alkyl and n is 2. In some embodiments, Y is hydrogen, $R^4$ is methyl and n is 2.

In some embodiments, provided is a compound of Formula (Ic-3):

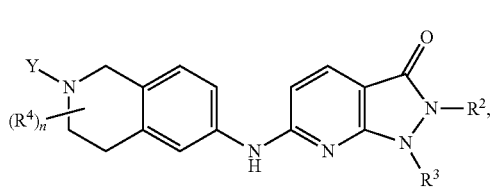

(Ic-3)

or a tautomer or isomer thereof, or a pharmaceutically acceptable salt of any of the foregoing, wherein Y is hydrogen or $R^4$, and n is 0, 1, 2, 3, or 4. In some embodiments of a compound of Formula (Ic-3), Y is hydrogen. In some embodiments of a compound of Formula (Ic-3), Y is $R^4$. In some embodiments, each $R^4$ is independently oxo, $C_1$-$C_6$ alkyl, $C_2$-$C_6$ alkenyl, $C_2$-$C_6$ alkynyl, halogen, —C(O)$R^{17}$, —C(O)O$R^{17}$, —C(O)N$R^{17}R^{18}$, —CN, —Si($C_1$-$C_6$ alkyl)$_3$, —O$R^{17}$, —N$R^{17}R^{18}$, —OC(O)N$R^{17}R^{18}$, —N$R^{17}$C(O)$R^{18}$, —S(O)$_2R^{17}$, —N$R^{17}$S(O)$_2R^{18}$, —S(O)$_2$N$R^{17}R^{18}$, $C_3$-$C_6$ cycloalkyl, 3- to 6-membered heterocyclyl, —($C_1$-$C_3$ alkylene)CN, —($C_1$-$C_3$ alkylene)O$R^{17}$, —($C_1$-$C_3$ alkylene)N$R^{17}R^{18}$, —($C_1$-$C_3$ alkylene)CF$_3$, —($C_1$-$C_3$ alkylene)C(O)$R^{17}$, —($C_1$-$C_3$ alkylene)C(O)N$R^{17}R^{18}$, —($C_1$-$C_3$ alkylene)N$R^{17}$C(O)$R^{18}$, —($C_1$-$C_3$ alkylene)S(O)$_2R^{17}$, —($C_1$-$C_3$ alkylene)N$R^{17}$S(O)$_2R^{18}$, —($C_1$-$C_3$ alkylene)S(O)$_2$N$R^{17}R^{18}$, —($C_1$-$C_3$ alkylene)($C_3$-$C_6$ cycloalkyl) or —($C_1$-$C_3$ alkylene)(3- to 6-membered heterocyclyl), wherein each $R^4$ is independently optionally substituted by halogen, oxo, —O$R^{19}$, —N$R^{19}R^{20}$, or —C(O)$R^{19}$, or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments, $R^4$ is independently oxo, $C_1$-$C_6$ alkyl or —C(O)$R^{17}$, wherein the $C_1$-$C_6$ alkyl or —C(O)$R^{17}$ is optionally substituted by —O$R^{19}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments, $R^4$ is independently $C_1$-$C_6$ alkyl or —C(O)$R^{17}$. In some embodiments, $R^4$ is independently $C_1$-$C_6$ alkyl or —C(O)$R^{17}$, wherein $R^{17}$ is $C_1$-$C_6$ alkyl optionally substituted with —OH. In some embodiments, Y is hydrogen and n is 0.

In some embodiments, provided is a compound of Formula (Ic-4):

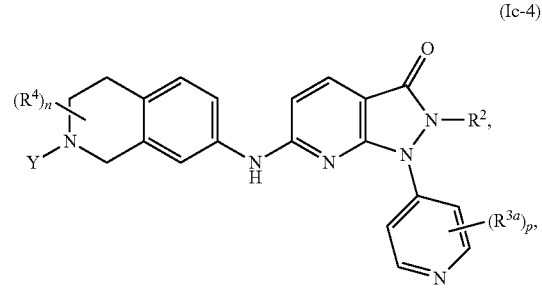

(Ic-4)

or a tautomer or isomer thereof, or a pharmaceutically acceptable salt of any of the foregoing, wherein Y is hydrogen or $R^4$, n and p are independently 0, 1, 2, 3, or 4; $R^{3a}$ is independently hydrogen, halogen, oxo, —O$R^{13}$, —N$R^{13}R^{14}$, —C(O)$R^{13}$, —C(O)O$R^{13}$, —C(O)N$R^{13}R^{14}$, —N$R^{13}$C(O)$R^{14}$, —CN, —S$R^{13}$, —S(O)$R^{13}$, —S(O)$_2R^{13}$, —Si($C_1$-$C_6$ alkyl)$_3$, —P(O)$R^{13}R^{14}$, —N$R^{13}$S(O)$_2R^{14}$, —($C_1$-$C_3$ alkylene)O$R^{13}$, —($C_1$-$C_3$ alkylene)N$R^{13}R^{14}$, —($C_1$-$C_3$ alkylene)C(O)$R^{13}$, $C_3$-$C_8$ cycloalkyl optionally substituted by $C_1$-$C_6$ alkyl, CN, CF$_3$, oxo, —OH, —N$R^{15}R^{16}$, —O$R^{15}$ or halogen, 3- to 12-membered heterocyclyl optionally substituted by oxo, —OH, —N$R^{15}R^{16}$, —C(O)O$R^{15}$, —O$R^{15}$ or halogen, or $C_1$-$C_6$ alkyl optionally substituted by oxo, —OH, —N$R^{15}R^{16}$, —C(O)O$R^{15}$, —O$R^{15}$ or halogen, with the proviso that $R^{3a}$ is not

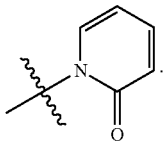

In some embodiments of a compound of Formula (Ic-4), Y is hydrogen. In some embodiments of a compound of Formula (Ic-4), Y is $R^4$. In some embodiments, each $R^4$ is independently oxo, $C_1$-$C_6$ alkyl, $C_2$-$C_6$ alkenyl, $C_2$-$C_6$ alkynyl, halogen, —C(O)$R^{17}$, —C(O)O$R^{17}$, —C(O)N$R^{17}R^{18}$, —Si($C_1$-$C_6$ alkyl)$_3$, —CN, —O$R^{17}$, —N$R^{17}R^{18}$, —OC(O)N$R^{17}R^{18}$, —N$R^{17}$C(O)$R^{18}$, —S(O)$_2R^{17}$, —N$R^{17}$S(O)$_2R^{18}$, —S(O)$_2$N$R^{17}R^{18}$, $C_3$-$C_6$ cycloalkyl, 3- to 6-membered heterocyclyl, —($C_1$-$C_3$ alkylene)CN, —($C_1$-$C_3$ alkylene)O$R^{17}$, —($C_1$-$C_3$ alkylene)N$R^{17}R^{18}$, —($C_1$-$C_3$ alkylene)CF$_3$, —($C_1$-$C_3$ alkylene)C(O)$R^{17}$, —($C_1$-$C_3$ alkylene)C(O)N$R^{17}R^{18}$, —($C_1$-$C_3$ alkylene)N$R^{17}$C(O)$R^{18}$, —($C_1$-$C_3$ alkylene)S(O)$_2R^{17}$, —($C_1$-$C_3$ alkylene)N$R^{17}$S(O)$_2R^{18}$, —($C_1$-$C_3$ alkylene)S(O)$_2$N$R^{17}R^{18}$, —($C_1$-$C_3$ alkylene)($C_3$-$C_6$ cycloalkyl), or —($C_1$-$C_3$ alkylene)(3- to 6-membered heterocyclyl), wherein each $R^4$ is independently optionally substituted by halogen, oxo, —O$R^{19}$, —N$R^{19}R^{20}$, or —C(O)$R^{19}$, or two $R^4$ when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments, $R^{3a}$ is $C_3$-$C_8$ cycloalkyl optionally substituted by $C_1$-$C_6$ alkyl, CN, CF$_3$, oxo, —OH, —N$R^{15}R^{16}$, —O$R^{15}$ or halogen, 3- to 12-membered heterocyclyl optionally substituted by oxo, —OH, —N$R^{15}R^{16}$, —C(O)O$R^{15}$, —O$R^{15}$ or halogen, or $C_1$-$C_6$ alkyl optionally substituted by oxo, —OH, —N$R^{15}R^{16}$, —C(O)O$R^{15}$, —O$R^{15}$ or halogen, with the proviso that $R^{3a}$ is not

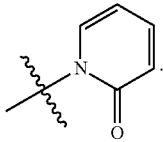

In some embodiments, $R^{3a}$ is $C_1$-$C_6$ alkyl optionally substituted by oxo, —OH, —N$R^{15}R^{16}$, —C(O)O$R^{15}$, —O$R^{15}$ or halogen.

In some embodiments, provided is a compound of Formula (Ic-5):

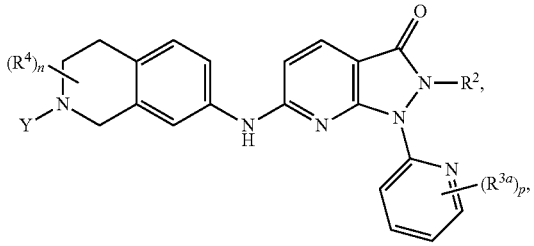

(Ic-5)

or a tautomer or isomer thereof, or a pharmaceutically acceptable salt of any of the foregoing, wherein Y is hydrogen or $R^4$, n and p are independently 0, 1, 2, 3, or 4; $R^{3a}$ is independently hydrogen, halogen, oxo, —O$R^{13}$, —N$R^{13}R^{14}$, —C(O)$R^{13}$, —C(O)O$R^{13}$, —C(O)N$R^{13}R^{14}$, —N$R^{13}$C(O)$R^{14}$, —CN, —S$R^{13}$, —S(O)$R^{13}$, —S(O)$_2R^{13}$, —Si($C_1$-$C_6$ alkyl)$_3$, —P(O)$R^{13}R^{14}$, —N$R^{13}$S(O)$_2R^{14}$, —($C_1$-$C_3$ alkylene)O$R^{13}$, —($C_1$-$C_3$ alkylene)N$R^{13}R^{14}$, —($C_1$-$C_3$ alkylene)C(O)$R^{13}$, $C_3$-$C_8$ cycloalkyl optionally substituted by $C_1$-$C_6$ alkyl, CN, CF$_3$, oxo, —OH, —N$R^{15}R^{16}$, —O$R^{15}$ or halogen, 3- to 12-membered heterocyclyl optionally substituted by oxo, —OH, —N$R^{15}R^{16}$, —C(O)O$R^{15}$, —O$R^{15}$ or halogen, or $C_1$-$C_6$ alkyl optionally substituted by oxo, —OH, —N$R^{15}R^{16}$, —C(O)O$R^{15}$, —O$R^{15}$ or halogen, with the proviso that $R^{3a}$ is not

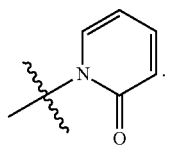

In some embodiments of a compound of Formula (Ic-5), Y is hydrogen. In some embodiments of a compound of Formula (Ic-5), Y is $R^4$. In some embodiments, each $R^4$ is independently oxo, $C_1$-$C_6$ alkyl, $C_2$-$C_6$ alkenyl, $C_2$-$C_6$ alkynyl, halogen, —C(O)$R^{17}$, —C(O)O$R^{17}$, —C(O)N$R^{17}R^{18}$, —CN, —Si($C_1$-$C_6$ alkyl)$_3$, —O$R^{17}$, —N$R^{17}R^{18}$, —OC(O)N$R^{17}R^{18}$, —N$R^{17}$C(O)$R^{18}$, —S(O)$_2R^{17}$, —N$R^{17}$S(O)$_2R^{18}$, —S(O)$_2$N$R^{17}R^{18}$, $C_3$-$C_6$ cycloalkyl, 3- to 6-membered heterocyclyl, —($C_1$-$C_3$ alkylene)CN, —($C_1$-$C_3$ alkylene)O$R^{17}$, —($C_1$-$C_3$ alkylene)N$R^{17}R^{18}$, —($C_1$-$C_3$ alkylene)CF$_3$, —($C_1$-$C_3$ alkylene)C(O)$R^{17}$, —($C_1$-$C_3$ alkylene)C(O)N$R^{17}R^{18}$, —($C_1$-$C_3$ alkylene)N$R^{17}$C(O)$R^{18}$, —($C_1$-$C_3$ alkylene)S(O)$_2R^{17}$, —($C_1$-$C_3$ alkylene)N$R^{17}$S(O)$_2R^{18}$, —($C_1$-$C_3$ alkylene)S(O)$_2$N$R^{17}R^{18}$, —($C_1$-$C_3$ alkylene)($C_3$-$C_6$ cycloalkyl), or —($C_1$-$C_3$ alkylene)(3- to 6-membered heterocyclyl), wherein each $R^4$ is independently optionally substituted by halogen, oxo, —O$R^{19}$, —N$R^{19}R^{20}$, or —C(O)$R^{19}$, or two $R^4$ when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments, $R^{3a}$ is $C_3$-$C_8$ cycloalkyl optionally substituted by $C_1$-$C_6$ alkyl, CN, CF$_3$, oxo, —OH, —N$R^{15}R^{16}$, —O$R^{15}$ or halogen, 3- to 12-membered heterocyclyl optionally substituted by oxo, —OH, —N$R^{15}R^{16}$, —C(O)O$R^{15}$, —O$R^{15}$ or halogen, or $C_1$-$C_6$ alkyl optionally substituted by oxo, —OH, —N$R^{15}R^{16}$, —C(O)O$R^{15}$, —O$R^{15}$ or halogen, with the proviso that $R^{3a}$ is not

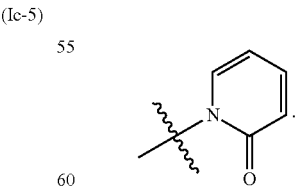

In some embodiments, $R^{3a}$ is $C_1$-$C_6$ alkyl optionally substituted by oxo, —OH, —N$R^{15}R^{16}$, —C(O)O$R^{15}$, —O$R^{15}$ or halogen.

In some embodiments, provided is a compound of Formula (Ic-6):

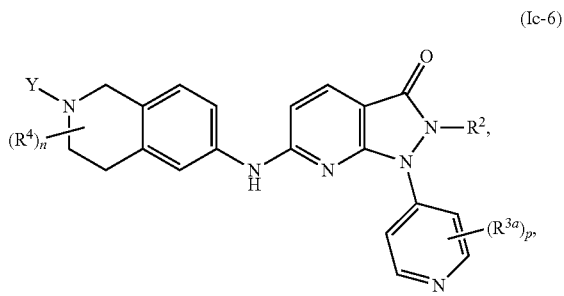

(Ic-6)

or a tautomer or isomer thereof, or a pharmaceutically acceptable salt of any of the foregoing, wherein Y is hydrogen or $R^4$, n and p are independently 0, 1, 2, 3, or 4; $R^{3a}$ is independently hydrogen, halogen, oxo, —$OR^{13}$, —$NR^{13}R^{14}$, —$C(O)R^{13}$, —$C(O)OR^{13}$, —$C(O)NR^{13}R^{14}$, —$NR^{13}C(O)R^{14}$, —CN, —$SR^{13}$, —$S(O)R^{13}$, —$S(O)_2R^{13}$, —$Si(C_1$-$C_6$ alkyl$)_3$, —$P(O)R^{13}R^{14}$, —$NR^{13}S(O)_2R^{14}$, —$(C_1$-$C_3$ alkylene)$OR^{13}$, —$(C_1$-$C_3$ alkylene)$NR^{13}R^{14}$, —$(C_1$-$C_3$ alkylene)$C(O)R^{13}$, $C_3$-$C_8$ cycloalkyl optionally substituted by $C_1$-$C_6$ alkyl, CN, $CF_3$, oxo, —OH, —$NR^{15}R^{16}$, —$OR^{15}$ or halogen, 3- to 12-membered heterocyclyl optionally substituted by oxo, —OH, —$NR^{15}R^{16}$, —$C(O)OR^{15}$, —$OR^{15}$ or halogen, or $C_1$-$C_6$ alkyl optionally substituted by oxo, —OH, —$NR^{15}R^{16}$, —$C(O)OR^{15}$, —$OR^{15}$ or halogen, with the proviso that $R^{3a}$ is not

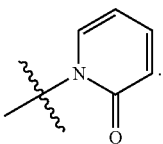

In some embodiments of a compound of Formula (Ic-6), Y is hydrogen. In some embodiments of a compound of Formula (Ic-6), Y is $R^4$. In some embodiments, each $R^4$ is independently oxo, $C_1$-$C_6$ alkyl, $C_2$-$C_6$ alkenyl, $C_2$-$C_6$ alkynyl, halogen, —$C(O)R^{17}$, —$C(O)OR^{17}$, —$C(O)NR^{17}R^{18}$, —CN, —$Si(C_1$-$C_6$ alkyl$)_3$, —$OR^{17}$, —$NR^{17}R^{18}$, —$OC(O)NR^{17}R^{18}$, —$NR^{17}C(O)R^{18}$, —$S(O)_2R^{17}$, —$NR^{17}S(O)_2R^{18}$, —$S(O)_2NR^{17}R^{18}$, $C_3$-$C_6$ cycloalkyl, 3- to 6-membered heterocyclyl, —$(C_1$-$C_3$ alkylene)CN, —$(C_1$-$C_3$ alkylene)$OR^{17}$, —$(C_1$-$C_3$ alkylene)$NR^{17}R^{18}$, —$(C_1$-$C_3$ alkylene)$CF_3$, —$(C_1$-$C_3$ alkylene)$C(O)R^{17}$, —$(C_1$-$C_3$ alkylene)$C(O)NR^{17}R^{18}$, —$(C_1$-$C_3$ alkylene)$NR^{17}C(O)R^{18}$, —$(C_1$-$C_3$ alkylene)$S(O)_2R^{17}$, —$(C_1$-$C_3$ alkylene)$NR^{17}S(O)_2R^{18}$, —$(C_1$-$C_3$ alkylene)$S(O)_2NR^{17}R^{18}$, —$(C_1$-$C_3$ alkylene)($C_3$-$C_6$ cycloalkyl), or —$(C_1$-$C_3$ alkylene)(3- to 6-membered heterocyclyl), wherein each $R^4$ is independently optionally substituted by halogen, oxo, —$OR^{19}$, —$NR^{19}R^{20}$, or —$C(O)R^{19}$, or two $R^4$ when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$. In some embodiments, $R^{3a}$ is $C_3$-$C_8$ cycloalkyl optionally substituted by $C_1$-$C_6$ alkyl, CN, $CF_3$, oxo, —OH, —$NR^{15}R^{16}$, —$OR^{15}$ or halogen, 3- to 12-membered heterocyclyl optionally substituted by oxo, —OH, —$NR^{15}R^{16}$, —$C(O)OR^{15}$, —$OR^{15}$ or halogen, or $C_1$-$C_6$ alkyl optionally substituted by oxo, —OH, —$NR^{15}R^{16}$, —$C(O)OR^{15}$, —$OR^{15}$ or halogen, with the proviso that $R^{3a}$ is not

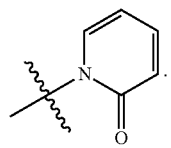

In some embodiments, $R^{3a}$ is $C_1$-$C_6$ alkyl optionally substituted by oxo, —OH, —$NR^{15}R^{16}$, —$C(O)OR^{15}$, —$OR^{15}$ or halogen.

In some embodiments, provided is a compound of Formula (Ic-7):

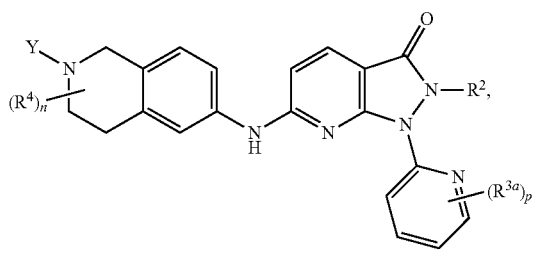

(Ic-7)

or a tautomer or isomer thereof, or a pharmaceutically acceptable salt of any of the foregoing, wherein Y is hydrogen or $R^4$, n and p are independently 0, 1, 2, 3, or 4; $R^{3a}$ is independently hydrogen, halogen, oxo, —$OR^{13}$, —$NR^{13}R^{14}$, —$C(O)R^{13}$, —$C(O)OR^{13}$, —$C(O)NR^{13}R^{14}$, —$NR^{13}C(O)R^{14}$, —CN, —$SR^{13}$, —$S(O)R^{13}$, —$S(O)_2R^{13}$, —$Si(C_1$-$C_6$ alkyl$)_3$, —$P(O)R^{13}R^{14}$, —$NR^{13}S(O)_2R^{14}$, —$(C_1$-$C_3$ alkylene)$OR^{13}$, —$(C_1$-$C_3$ alkylene)$NR^{13}R^{14}$, —$(C_1$-$C_3$ alkylene)$C(O)R^{13}$, $C_3$-$C_8$ cycloalkyl optionally substituted by $C_1$-$C_6$ alkyl, CN, $CF_3$, oxo, —OH, —$NR^{15}R^{16}$, —$OR^{15}$ or halogen, 3- to 12-membered heterocyclyl optionally substituted by oxo, —OH, —$NR^{15}R^{16}$, —$C(O)OR^{15}$, —$OR^{15}$ or halogen, or $C_1$-$C_6$ alkyl optionally substituted by oxo, —OH, —$NR^{15}R^{16}$, —$C(O)OR^{15}$, —$OR^{15}$ or halogen, with the proviso that $R^{3a}$ is not

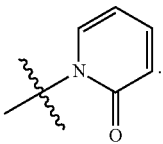

In some embodiments of a compound of Formula (Ic-7), Y is hydrogen. In some embodiments of a compound of Formula (Ic-7), Y is $R^4$. In some embodiments, each $R^4$ is independently oxo, $C_1$-$C_6$ alkyl, $C_2$-$C_6$ alkenyl, $C_2$-$C_6$ alkynyl, halogen, —$C(O)R^{17}$, —$C(O)OR^{17}$, —$C(O)NR^{17}R^{18}$, —CN, —$Si(C_1$-$C_6$ alkyl$)_3$, —$OR^{17}$, —$NR^{17}R^{18}$, —$OC(O)NR^{17}R^{18}$, —$NR^{17}C(O)R^{18}$, —$S(O)_2R^{17}$, —$NR^{17}S(O)_2R^{18}$, —$S(O)_2NR^{17}R^{18}$, $C_3$-$C_6$ cycloalkyl, 3- to 6-membered heterocyclyl, —$(C_1$-$C_3$ alkylene)CN, —$(C_1$-$C_3$ alkylene)$OR^{17}$, —$(C_1$-$C_3$ alkylene)$NR^{17}R^{18}$, —$(C_1$-$C_3$ alkylene)$CF_3$, —$(C_1$-$C_3$ alkylene)$C(O)R^{17}$, —$(C_1$-$C_3$ alkylene)$C(O)NR^{17}R^{18}$, —$(C_1$-$C_3$ alkylene)$NR^{17}C(O)R^{18}$, —$(C_1$-$C_3$ alkylene)$S(O)_2R^{17}$, —$(C_1$-$C_3$ alkylene)$NR^{17}S(O)_2R^{18}$, —$(C_1$-$C_3$ alkylene)$S(O)_2NR^{17}R^{18}$, —$(C_1$-$C_3$ alkylene)($C_3$-$C_6$ cycloalkyl), or —$(C_1$-$C_3$ alkylene)(3- to 6-membered heterocyclyl), wherein each $R^4$ is independently optionally substituted by halogen, oxo, —OR$^{19}$, —NR$^{19}$R$^{20}$, or —C(O)R$^{19}$, or two R$^4$ when bound to the same carbon or two different carbon atoms, are taken together with the carbon or carbons to which they are attached to form a C$_3$-C$_6$ cycloalkyl or 3- to 7-membered heterocyclyl, each is optionally substituted by R$^{19}$. In some embodiments, R$^{3a}$ is C$_3$-C$_8$ cycloalkyl optionally substituted by C$_1$-C$_6$ alkyl, CN, CF$_3$, oxo, —OH, —NR$^{15}$R$^{16}$, —OR$^{15}$ or halogen, 3- to 12-membered heterocyclyl optionally substituted by —OH, —NR$^{15}$R$^{16}$, —C(O)OR$^{15}$, —OR$^{15}$ or halogen, or C$_1$-C$_6$ alkyl optionally substituted by oxo, —OH, —NR$^{15}$R$^{16}$, —C(O)OR$^{15}$, —OR$^{15}$ or halogen, with the proviso that R$^{3a}$ is not

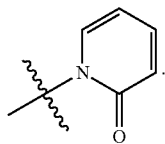

In some embodiments, R$^{3a}$ is C$_1$-C$_6$ alkyl optionally substituted by oxo, —OH, —NR$^{15}$R$^{16}$, —C(O)OR$^{15}$, —OR$^{15}$ or halogen.

In some embodiments, provided is a compound of Formula (Ic-8):

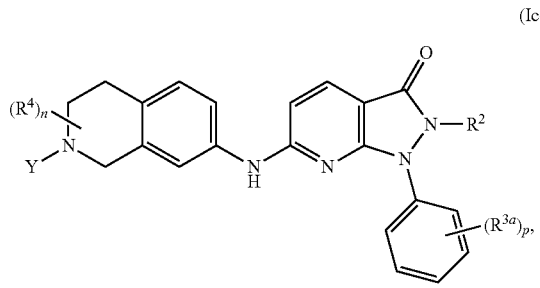

(Ic-8)

or a tautomer or isomer thereof, or a pharmaceutically acceptable salt of any of the foregoing, wherein Y is hydrogen or R$^4$, n and p are independently 0, 1, 2, 3, or 4; R$^{3a}$ is independently hydrogen, halogen, oxo, —OR$^{13}$, —NR$^{13}$R$^{14}$, —C(O)R$^{13}$, —C(O)OR$^{13}$, —C(O)NR$^{13}$R$^{14}$, —NR$^{13}$C(O)R$^{14}$, —CN, —SR$^{13}$, —S(O)R$^{13}$, —S(O)$_2$R$^{13}$, —Si(C$_1$-C$_6$ alkyl)$_3$, —P(O)R$^{13}$R$^{14}$, —NR$^{13}$S(O)$_2$R$^{14}$, —(C$_1$-C$_3$ alkylene)OR$^{13}$, —(C$_1$-C$_3$ alkylene)NR$^{13}$R$^{14}$, —(C$_1$-C$_3$ alkylene)C(O)R$^{13}$, C$_3$-C$_8$ cycloalkyl optionally substituted by C$_1$-C$_6$ alkyl, CN, CF$_3$, oxo, —OH, —NR$^{15}$R$^{16}$, —OR$^{15}$ or halogen, 3- to 12-membered heterocyclyl optionally substituted by oxo, —OH, —NR$^{15}$R$^{16}$, —C(O)OR$^{15}$, —OR$^{15}$ or halogen, or C$_1$-C$_6$ alkyl optionally substituted by oxo, —OH, —NR$^{15}$R$^{16}$, —C(O)OR$^{15}$, —OR$^{15}$ or halogen, with the proviso that R$^{3a}$ is not

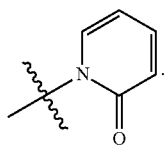 [SMILES: *n1ccccc1=O]

In some embodiments of a compound of Formula (Ic-8), Y is hydrogen. In some embodiments of a compound of Formula (Ic-8), Y is R$^4$. In some embodiments, each R$^4$ is independently oxo, C$_1$-C$_6$ alkyl, C$_2$-C$_6$ alkenyl, C$_2$-C$_6$ alkynyl, halogen, —C(O)R$^{17}$, —C(O)OR$^{17}$, —C(O)NR$^{17}$R$^{18}$, —CN, —Si(C$_1$-C$_6$ alkyl)$_3$, —OR$^{17}$, —NR$^{17}$R$^{18}$, —OC(O)NR$^{17}$R$^{18}$, —NR$^{17}$C(O)R$^{18}$, —S(O)$_2$R$^{17}$, —NR$^{17}$S(O)$_2$R$^{18}$, —S(O)$_2$NR$^{17}$R$^{18}$, C$_3$-C$_6$ cycloalkyl, 3- to 6-membered heterocyclyl, —(C$_1$-C$_3$ alkylene)CN, —(C$_1$-C$_3$ alkylene)OR$^{17}$, —(C$_1$-C$_3$ alkylene)NR$^{17}$R$^{18}$, —(C$_1$-C$_3$ alkylene)CF$_3$, —(C$_1$-C$_3$ alkylene)C(O)R$^{17}$, —(C$_1$-C$_3$ alkylene)C(O)NR$^{17}$R$^{18}$, —(C$_1$-C$_3$ alkylene)NR$^{17}$C(O)R$^{18}$, —(C$_1$-C$_3$ alkylene)S(O)$_2$R$^{17}$, —(C$_1$-C$_3$ alkylene)NR$^{17}$S(O)$_2$R$^{18}$, —(C$_1$-C$_3$ alkylene)S(O)$_2$NR$^{17}$R$^{18}$, —(C$_1$-C$_3$ alkylene)(C$_3$-C$_6$ cycloalkyl), or —(C$_1$-C$_3$ alkylene)(3- to 6-membered heterocyclyl), wherein each R$^4$ is independently optionally substituted by halogen, oxo, —OR$^{19}$, —NR$^{19}$R$^{20}$, or —C(O)R$^{19}$, or two R$^4$ when bound to the same carbon or two different carbon atoms, are taken together with the carbon or carbons to which they are attached to form a C$_3$-C$_6$ cycloalkyl or 3- to 7-membered heterocyclyl, each is optionally substituted by R$^{19}$. In some embodiments, R$^{3a}$ is halogen, C$_3$-C$_8$ cycloalkyl optionally substituted by C$_1$-C$_6$ alkyl, CN, CF$_3$, oxo, —OH, —NR$^{15}$R$^{16}$, —OR$^{15}$ or halogen, 3- to 12-membered heterocyclyl optionally substituted by oxo, —OH, —NR$^{15}$R$^{16}$, —C(O)OR$^{15}$, —OR$^{15}$ or halogen, or C$_1$-C$_6$ alkyl optionally substituted by oxo, —OH, —NR$^{15}$R$^{16}$, —C(O)OR$^{15}$, —OR$^{15}$ or halogen, with the proviso that R$^{3a}$ is not

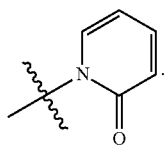 [SMILES: *n1ccccc1=O]

In some embodiments, R$^{3a}$ is halogen; In some embodiments, R$^{3a}$ is C$_1$-C$_6$ alkyl optionally substituted by oxo, —OH, —NR$^{15}$R$^{16}$, —C(O)OR$^{15}$, —OR$^{15}$ or halogen.

In some embodiments, provided is a compound of Formula (Ic-9):

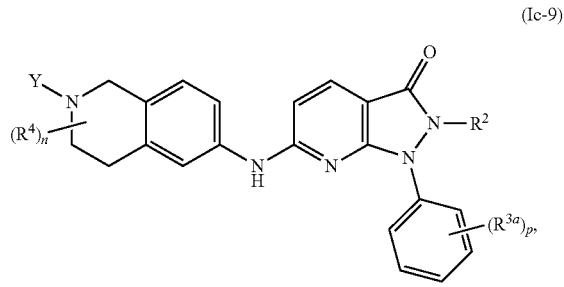

(Ic-9)

or a tautomer or isomer thereof, or a pharmaceutically acceptable salt of any of the foregoing, wherein Y is hydrogen or R$^4$, n and p are independently 0, 1, 2, 3, or 4; R$^{3a}$ is independently hydrogen, halogen, oxo, —OR$^{13}$, —NR$^{13}$R$^{14}$, —C(O)R$^{13}$, —C(O)OR$^{13}$, —C(O)NR$^{13}$R$^{14}$, —NR$^{13}$C(O)R$^{14}$, —CN, —SR$^{13}$, —S(O)R$^{13}$, —S(O)$_2$R$^{13}$, —Si(C$_1$-C$_6$ alkyl)$_3$, —P(O)R$^{13}$R$^{14}$, —NR$^{13}$S(O)$_2$R$^{14}$, —(C$_1$-C$_3$ alkylene)OR$^{13}$, —(C$_1$-C$_3$ alkylene)NR$^{13}$R$^{14}$, —(C$_1$-C$_3$ alkylene)C(O)R$^{13}$, C$_3$-C$_8$ cycloalkyl optionally substituted by C$_1$-C$_6$ alkyl, CN, CF$_3$, oxo, —OH, —NR$^{15}$R$^{16}$, —OR$^{15}$ or halogen, 3- to 12-membered heterocyclyl optionally substituted by oxo, —OH, —NR$^{15}$R$^{16}$, —C(O)OR$^{15}$, —OR$^{15}$ or halogen, or C$_1$-C$_6$ alkyl optionally substituted by oxo, —OH, —NR$^{15}$R$^{16}$, —C(O)OR$^{15}$, —OR$^{15}$ or halogen, with the proviso that R$^{3a}$ is not

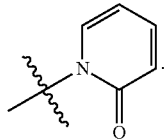 [SMILES: *n1ccccc1=O]

In some embodiments of a compound of Formula (Ic-9), Y is hydrogen. In some embodiments of a compound of Formula (Ic-9), Y is R$^4$. In some embodiments, each R$^4$ is independently oxo, C$_1$-C$_6$ alkyl, C$_2$-C$_6$ alkenyl, C$_2$-C$_6$ alkynyl, halogen, —C(O)R$^{17}$, —C(O)OR$^{17}$, —C(O)NR$^{17}$R$^{18}$, —CN, —Si(C$_1$-C$_6$ alkyl)$_3$, —OR$^{17}$, —NR$^{17}$R$^{18}$, —OC(O)NR$^{17}$R$^{18}$, —NR$^{17}$C(O)R$^{18}$, —S(O)$_2$R$^{17}$, —NR$^{17}$S(O)$_2$R$^{18}$, —S(O)$_2$NR$^{17}$R$^{18}$, C$_3$-C$_6$ cycloalkyl, 3- to 6-membered heterocyclyl, —(C$_1$-C$_3$ alkylene)CN, —(C$_1$-C$_3$ alkylene)OR$^{17}$, —(C$_1$-C$_3$ alkylene)NR$^{17}$R$^{18}$, —(C$_1$-C$_3$ alkylene)CF$_3$, —(C$_1$-C$_3$ alkylene)C(O)R$^{17}$, —(C$_1$-C$_3$ alkylene)C(O)NR$^{17}$R$^{18}$, —(C$_1$-C$_3$ alkylene)NR$^{17}$C(O)R$^{18}$, —(C$_1$-C$_3$ alkylene)S(O)$_2$R$^{17}$, —(C$_1$-C$_3$ alkylene)NR$^{17}$S(O)$_2$R$^{18}$, —(C$_1$-C$_3$ alkylene)S(O)$_2$NR$^{17}$R$^{18}$, —(C$_1$-C$_3$ alkylene)(C$_3$-C$_6$ cycloalkyl), or —(C$_1$-C$_3$ alkylene)(3- to 6-membered heterocyclyl), wherein each R$^4$ is independently optionally substituted by halogen, oxo, —OR$^{19}$, —NR$^{19}$R$^{20}$, or —C(O)R$^{19}$, or two R$^4$ when bound to the same carbon or two different carbon atoms, are taken together with the carbon or carbons to which they are attached to form a C$_3$-C$_6$ cycloalkyl or 3- to 7-membered heterocyclyl, each is optionally substituted by R$^{19}$. In some embodiments, R$^{3a}$ is halogen, C$_3$-C$_8$ cycloalkyl optionally substituted by C$_1$-C$_6$ alkyl, CN, CF$_3$, oxo, —OH, —NR$^{15}$R$^{16}$, —OR$^{15}$ or halogen, 3- to 12-membered heterocyclyl optionally substituted by oxo, —OH, —NR$^{15}$R$^{16}$, —C(O)OR$^{15}$, —OR$^{15}$ or halogen, or C$_1$-C$_6$ alkyl optionally substituted by oxo, —OH, —NR$^{15}$R$^{16}$, —OR$^{15}$ or halogen, with the proviso that R$^{3a}$ is not

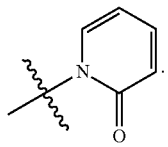 [SMILES: *n1ccccc1=O]

In some embodiments, R$^{3a}$ is halogen. In some embodiments, R$^{3a}$ is C$_1$-C$_6$ alkyl optionally substituted by oxo, —OH, —NR$^{15}$R$^{16}$, —C(O)OR$^{15}$, —OR$^{15}$ or halogen.

It is understood that for compounds of formula (Ia), (Ia-1 to Ia-12), (Ib), (Ib-1 to Ib-9), (Ic) and (IC-1 to Ic-9), the variables R$^2$ and R$^3$ are as defined in formula (I) or in any variation thereof. It is also understood that any combination of R$^2$ and R$^3$ described for formula (I) in one aspect applies to any of formulae (Ia), (Ia-1 to Ia-12), (Ib), (Ib-1 to Ib-9), (Ic) and (IC-1 to Ic-9). It is understood that for compounds of formula (Ia), (Ia-1), (Ia-2), (Ia-3), (Ia-4), (Ia-5) or (Ia-6), the variables R$^2$ and R$^3$ are as defined in formula (I) or in any variation thereof. It is also understood that any combination of R$^2$ and R$^3$ described for formula (I) in one aspect applies to any of formulae (Ia), (Ia-1), (Ia-2), (Ia-3), (Ia-4), (Ia-5) and (Ia-6).

In some embodiments of a compound of Formula (I), A, B, R$^1$ and R$^4$ together are selected from the group consisting of:

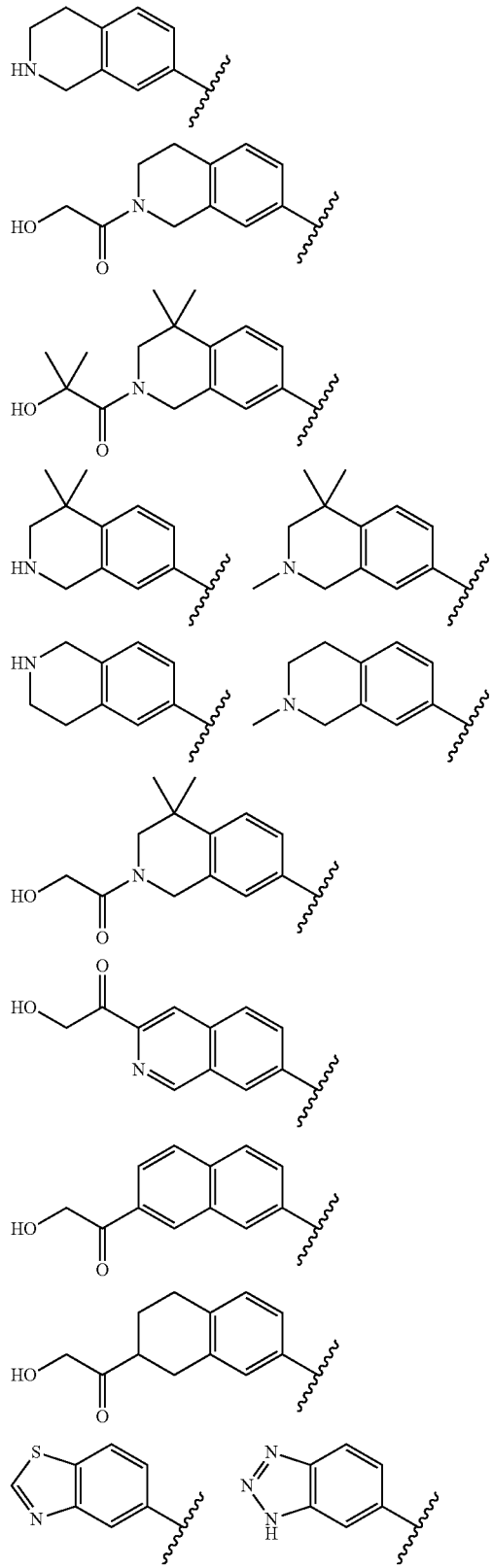

-continued
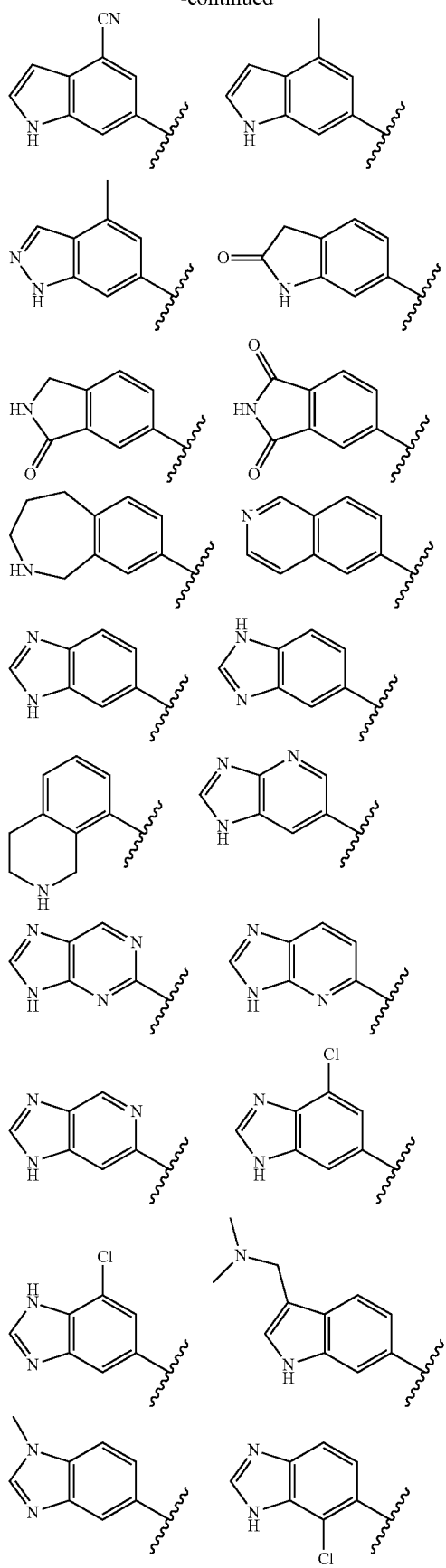
-continued
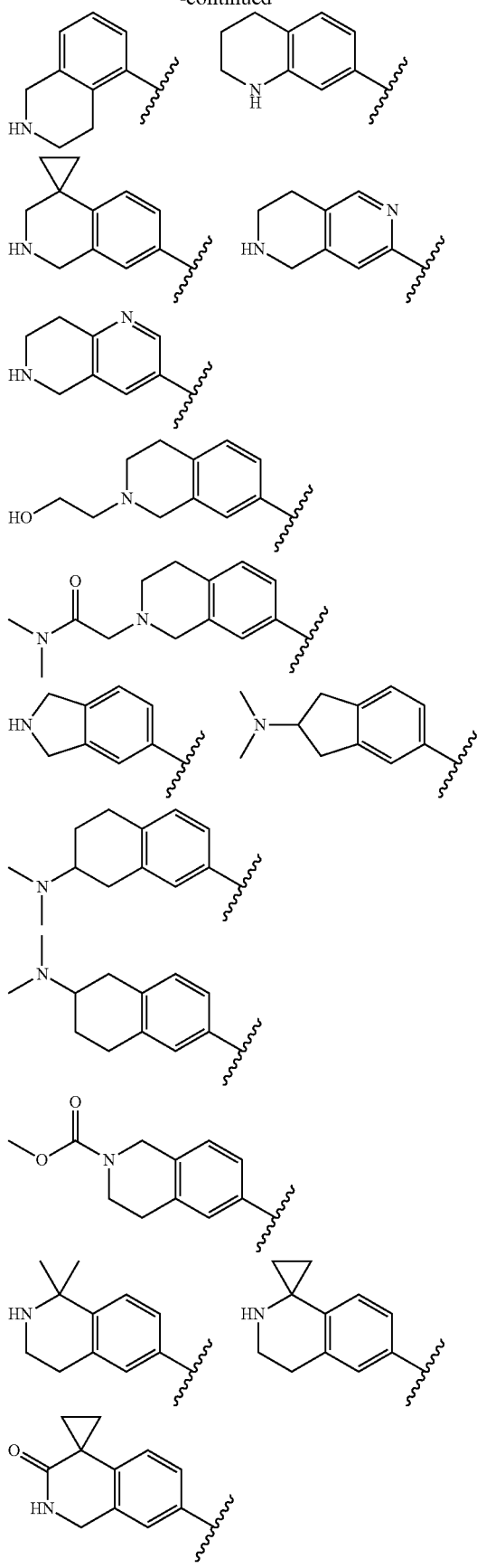

55
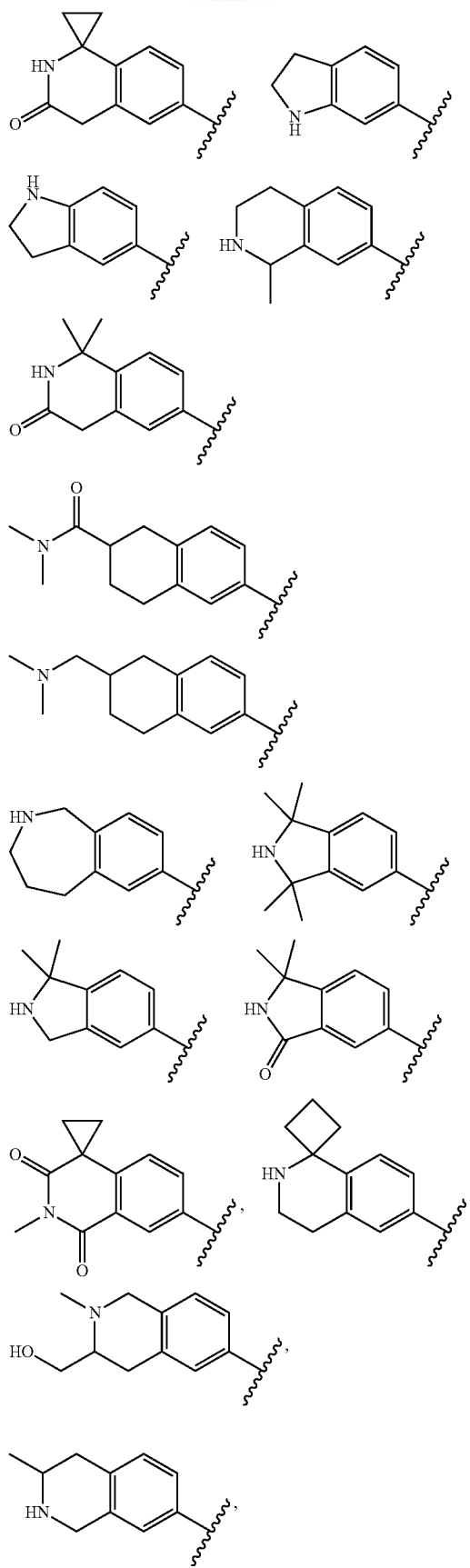
56
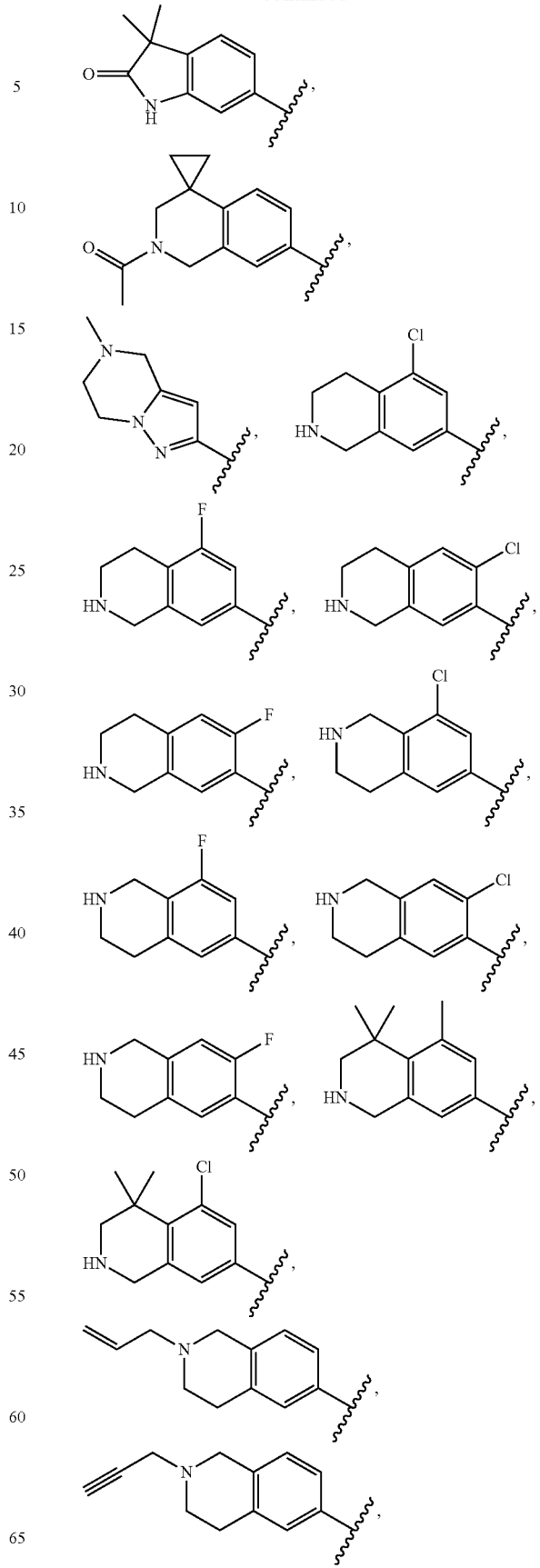

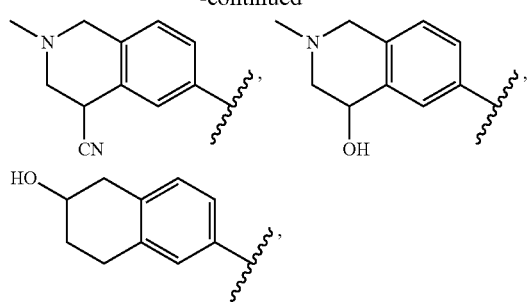
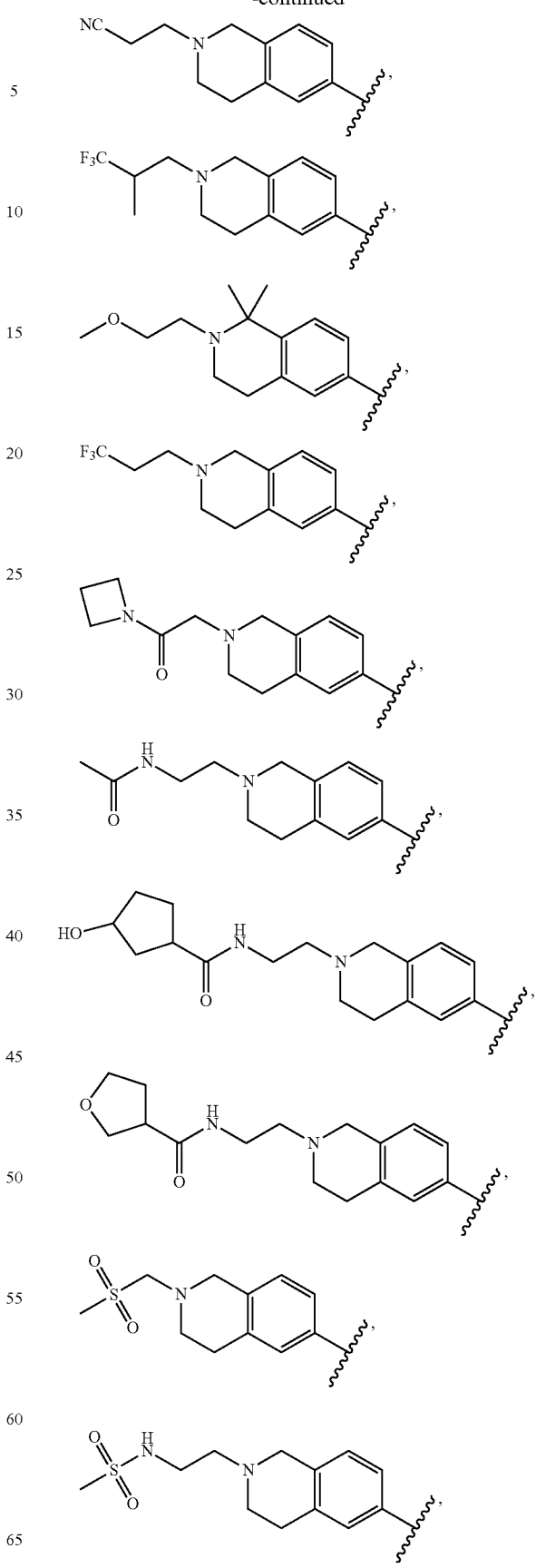

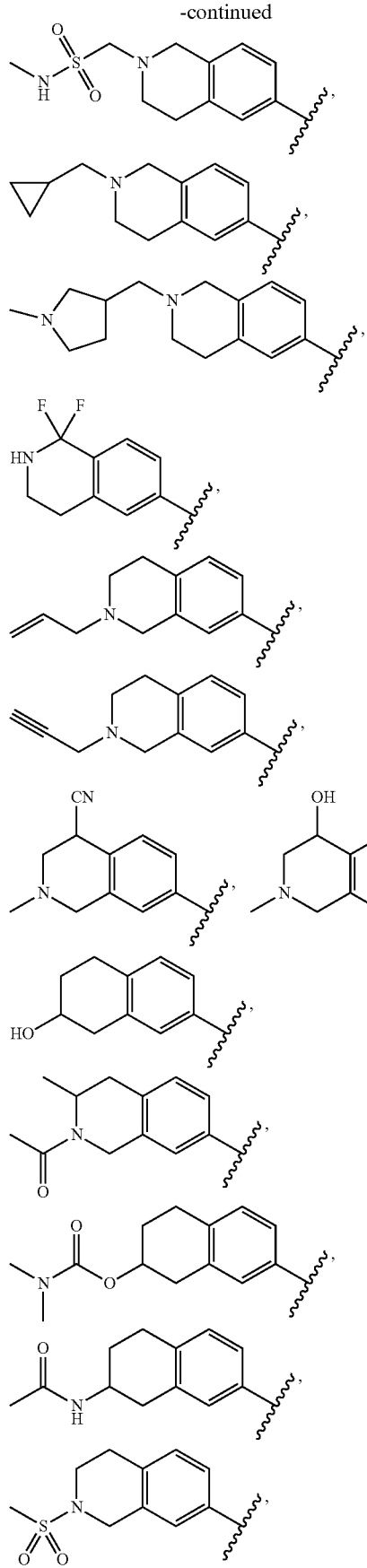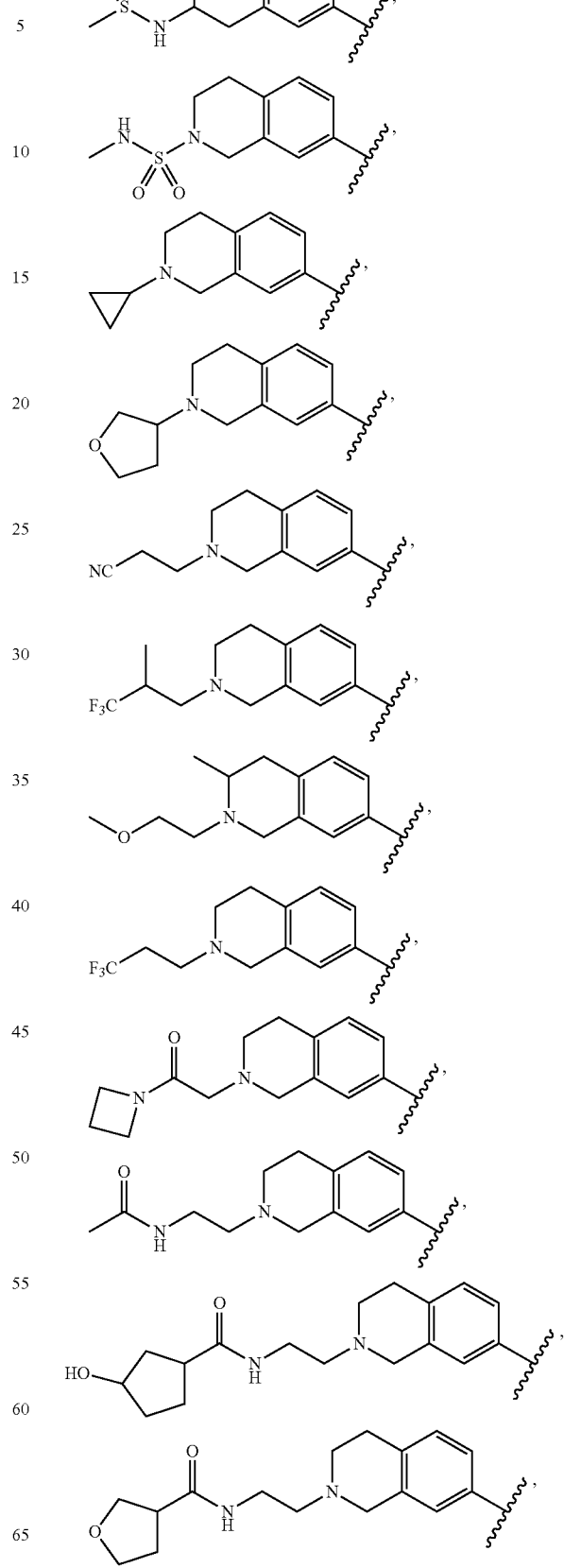

-continued
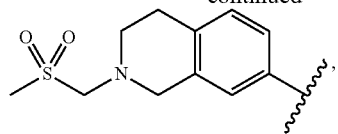
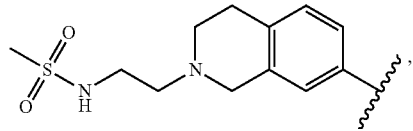
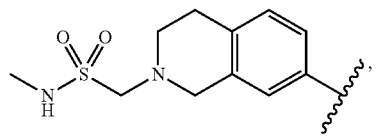
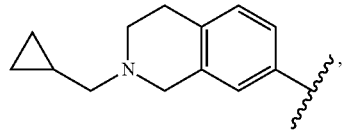
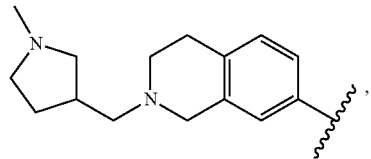
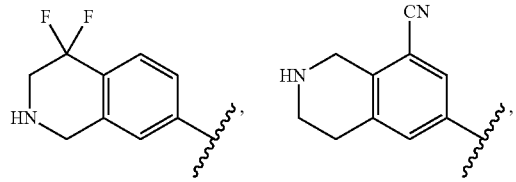
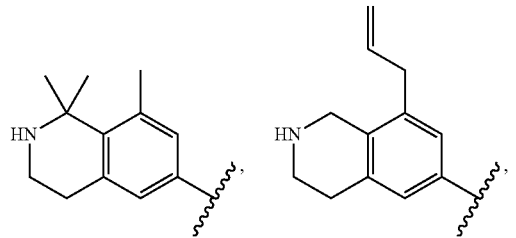
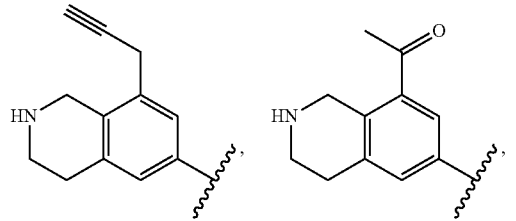
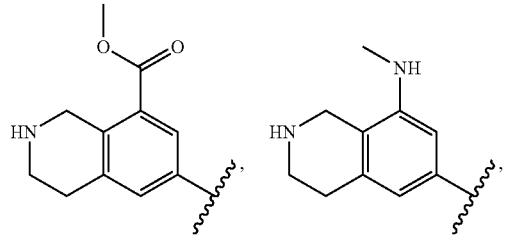
-continued
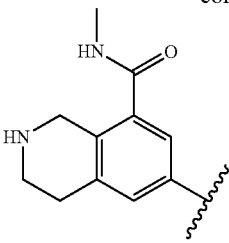
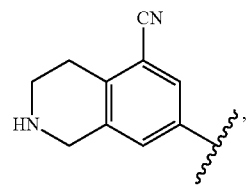
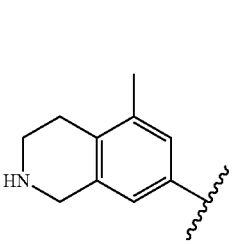
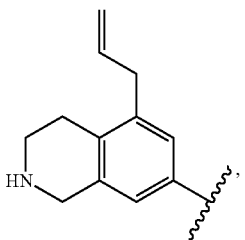
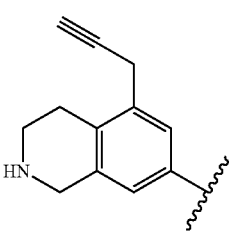
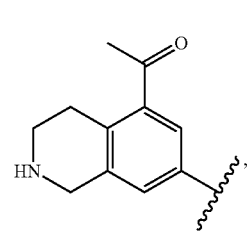
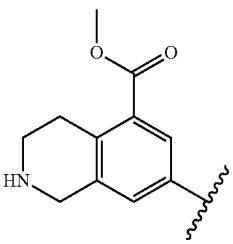
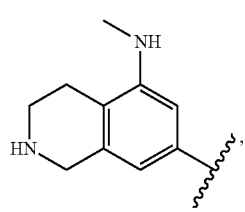
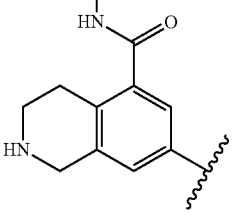
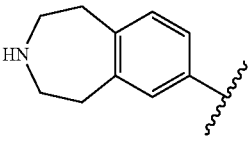
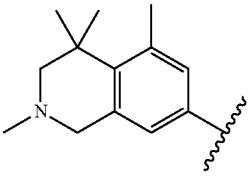
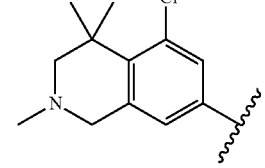
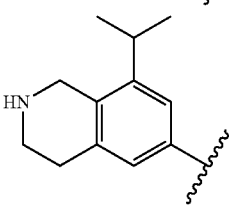
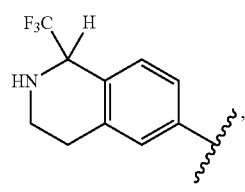

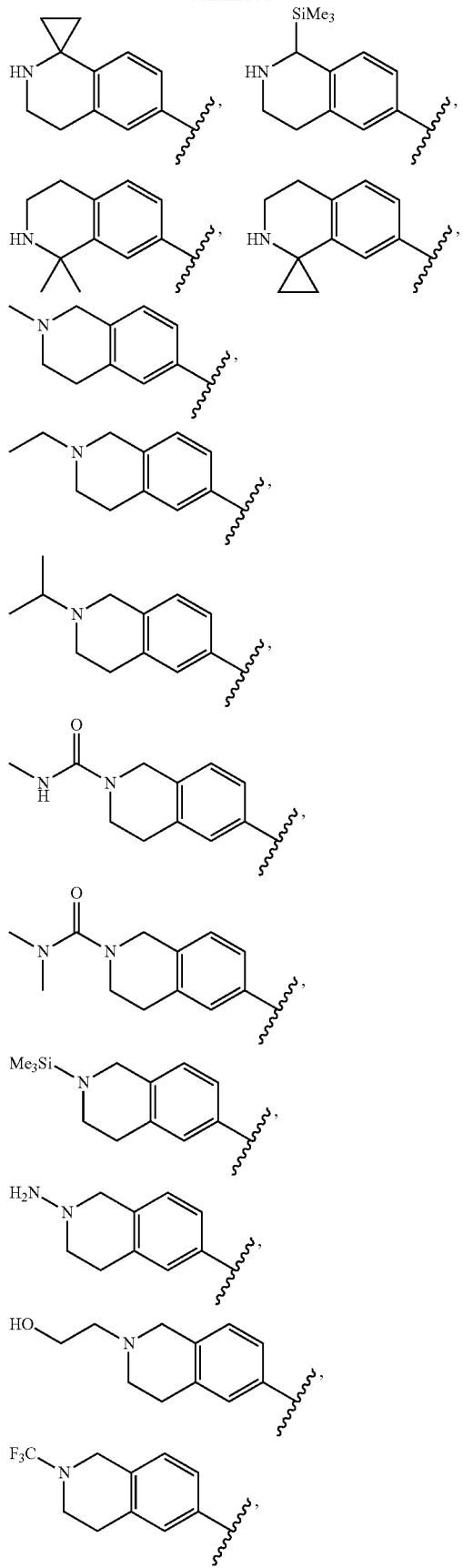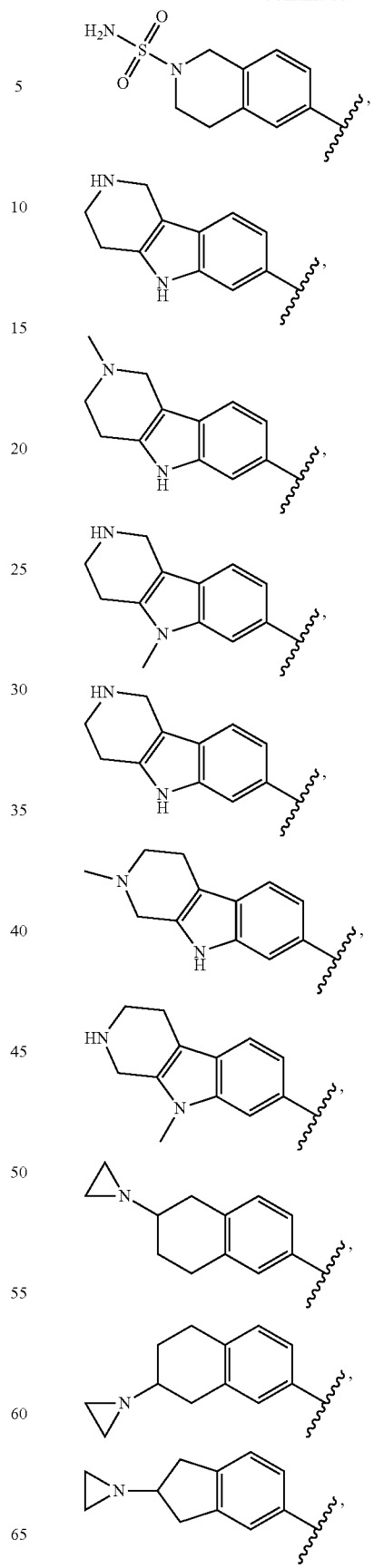

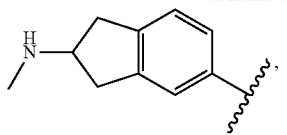
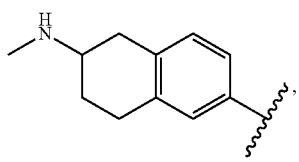
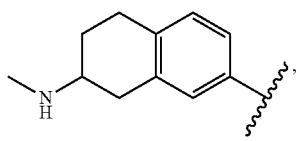
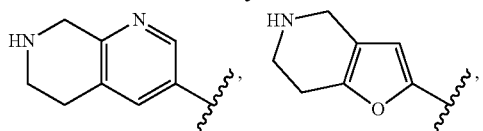
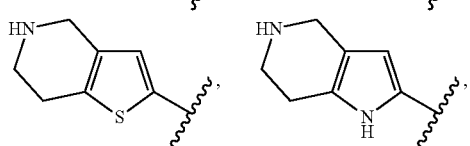
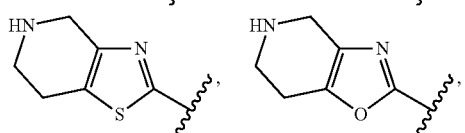
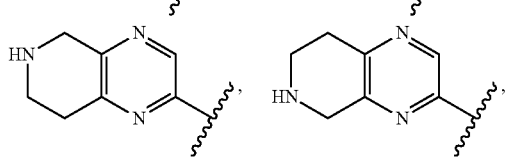
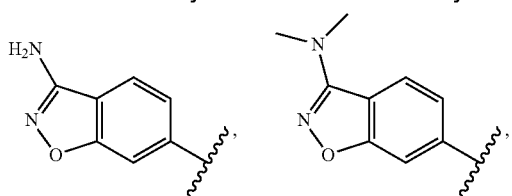
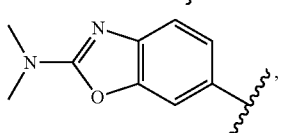
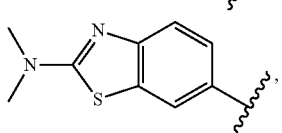
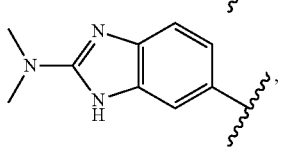
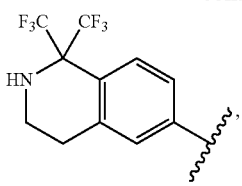
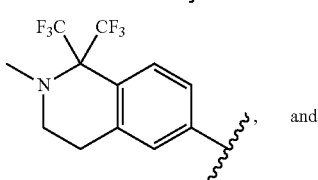
and
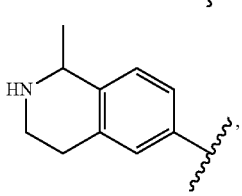
wherein the wavy lines denote attachment points to the parent molecule.
In some embodiments of a compound of Formula (I), A, B, $R^1$ and $R^4$ together are selected from the group consisting of:
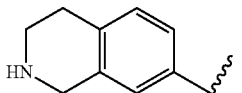
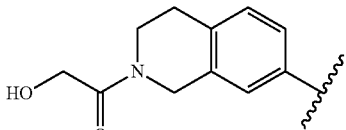
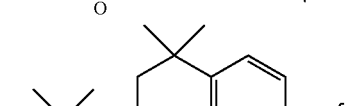
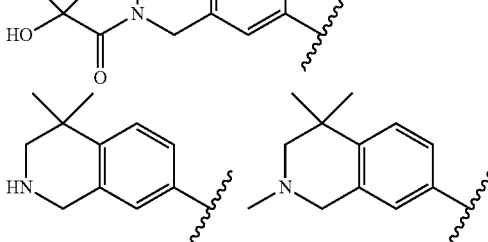
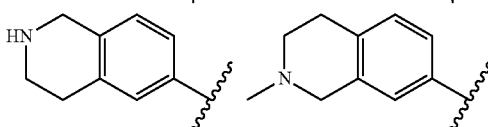
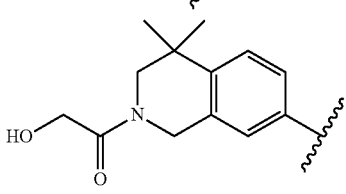

-continued

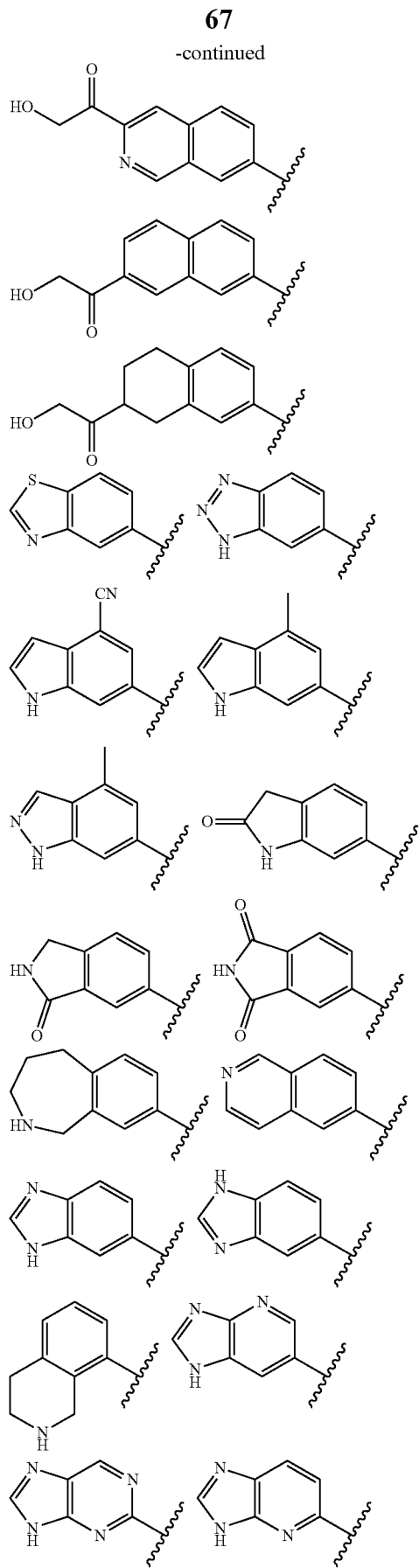

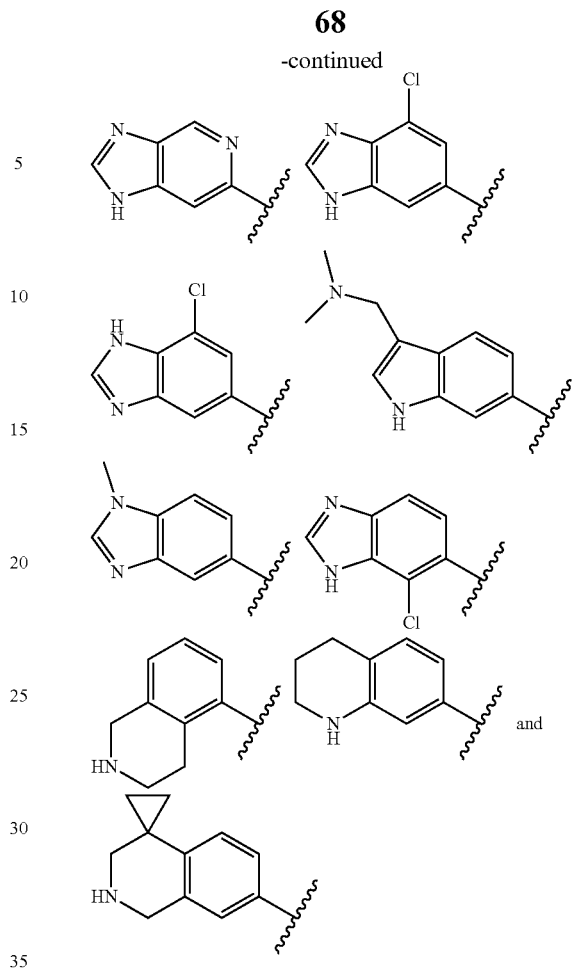

wherein the wavy lines denote attachment points to the parent molecule.

In some embodiments of a compound of Formula (I), (Ia), (Ia-1 to Ia-12), (Ib), (Ib-1 to Ib-9), (Ic) or (Ic-1 to Ic-9), $R^2$ is hydrogen, $C_1$-$C_6$ alkyl, $C_2$-$C_6$ alkenyl, $C_3$-$C_6$ cycloalkyl, —($C_1$-$C_3$ alkylene)CN, —($C_1$-$C_3$ alkylene)$OR^{10}$, —($C_1$-$C_3$ alkylene)$S(O)_2R^{10}$, —($C_1$-$C_3$ alkylene)(5- to 10-membered heteroaryl), —($C_1$-$C_3$ alkylene)($C_6$-$C_{14}$ aryl), or —($C_1$-$C_3$ alkylene)($C_3$-$C_6$ cycloalkyl), each of which is optionally substituted by halogen or $C_1$-$C_6$ alkyl. In some embodiments of a compound of Formula (I), (Ia), (Ia-1 to Ia-12), (Ib), (Ib-1 to Ib-9), (Ic) or (Ic-1 to Ic-9), $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl). In some embodiments of a compound of Formula (I), (Ia), (Ia-1 to Ia-12), (Ib), (Ib-1 to Ib-9), (Ic) or (Ic-1 to Ic-9), $R^2$ is $C_1$-$C_6$ alkyl or —($C_1$-$C_3$ alkylene)($C_3$-$C_6$ cycloalkyl). In some embodiments of a compound of Formula (I), (Ia), (Ia-1 to Ia-12), (Ib), (Ib-1 to Ib-9), (Ic) or (Ic-1 to Ic-9), $R^2$ is $C_1$-$C_6$ alkyl or $C_2$-$C_6$ alkenyl. In some embodiments of a compound of Formula (I), (Ia), (Ia-1 to Ia-12), (Ib), (Ib-1 to Ib-9), (Ic) or (Ic-1 to Ic-9), $R^2$ is —($C_1$-$C_3$ alkylene)($C_3$-$C_6$ cycloalkyl) or $C_2$-$C_6$ alkenyl. In some embodiments of a compound of Formula (I), (Ia), (Ia-1 to Ia-12), (Ib), (Ib-1 to Ib-9), (Ic) or (Ic-1 to Ic-9), $R^2$ is $C_1$-$C_6$ alkyl. In some embodiments of a compound of Formula (I), (Ia), (Ia-1 to Ia-12), (Ib), (Ib-1 to Ib-9), (Ic) or (Ic-1 to Ic-9), $R^2$ is $C_2$-$C_6$ alkenyl. In some embodiments of a compound of Formula (I), (Ia), (Ia-1 to Ia-12), (Ib), (Ib-1 to Ib-9), (Ic) or (Ic-1 to Ic-9), $R^2$ is —($C_1$-$C_3$ alkylene)($C_3$-$C_6$ cycloalkyl). In some embodiments of a compound of Formula (I), (Ia), (Ia-1 to Ia-12), (Ib), (Ib-1 to Ib-9), (Ic) or (Ic-1 to Ic-9), $R^2$ is $C_3$-$C_6$ cycloalkyl.

In some embodiments of a compound of Formula (I), (Ia), (Ia-1), (Ia-2), (Ia-3), (Ia-4), (Ia-5) or (Ia-6), $R^2$ is hydrogen, $C_1$-$C_6$ alkyl, $C_2$-$C_6$ alkenyl, $C_3$-$C_6$ cycloalkyl, —($C_1$-$C_3$ alkylene)CN, —($C_1$-$C_3$ alkylene)OR$^{10}$, —($C_1$-$C_3$ alkylene)S(O)$_2$R$^{10}$, —($C_1$-$C_3$ alkylene)(5- to 10-membered heteroaryl), —($C_1$-$C_3$ alkylene)($C_6$-$C_{14}$ aryl), or —($C_1$-$C_3$ alkylene)($C_3$-$C_6$ cycloalkyl), each of which is optionally substituted by halogen or $C_1$-$C_6$ alkyl. In some embodiments of a compound of Formula (I), (Ia), (Ia-1), (Ia-2), (Ia-3), (Ia-4), (Ia-5) or (Ia-6), $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl). In some embodiments of a compound of Formula (I), (Ia), (Ia-1), (Ia-2), (Ia-3), (Ia-4), (Ia-5) or (Ia-6), $R^2$ is $C_1$-$C_6$ alkyl or —($C_1$-$C_3$ alkylene)($C_3$-$C_6$ cycloalkyl). In some embodiments of a compound of Formula (I), (Ia), (Ia-1), (Ia-2), (Ia-3), (Ia-4), (Ia-5) or (Ia-6), or (If), $R^2$ is $C_1$-$C_6$ alkyl or $C_2$-$C_6$ alkenyl. In some embodiments of a compound of Formula (I), (Ia), (Ia-1), (Ia-2), (Ia-3), (Ia-4), (Ia-5) or (Ia-6), $R^2$ is —($C_1$-$C_3$ alkylene)($C_3$-$C_6$ cycloalkyl) or $C_2$-$C_6$ alkenyl. In some embodiments of a compound of Formula (I), (Ia), (Ia-1), (Ia-2), (Ia-3), (Ia-4), (Ia-5) or (Ia-6), $R^2$ is $C_1$-$C_6$ alkyl. In some embodiments of a compound of Formula (I), (Ia), (Ia-1), (Ia-2), (Ia-3), (Ia-4), (Ia-5) or (Ia-6), $R^2$ is $C_2$-$C_6$ alkenyl. In some embodiments of a compound of Formula (I), (Ia), (Ia-1), (Ia-2), (Ia-3), (Ia-4), (Ia-5) or (Ia-6), $R^2$ is —($C_1$-$C_3$ alkylene)($C_3$-$C_6$ cycloalkyl). In some embodiments of a compound of Formula (I), (Ia), (Ia-1), (Ia-2), (Ia-3), (Ia-4), (Ia-5) or (Ia-6), $R^2$ is $C_3$-$C_6$ cycloalkyl.

In some embodiments of a compound of Formula (I), (Ia), (Ia-1 to Ia-12), (Ib), (Ib-1 to Ib-9), (Ic) or (Ic-1 to Ic-9), $R^2$ is selected from the group consisting of:
methyl, ethyl, isopropyl, cyclopropyl, cyclobutyl,

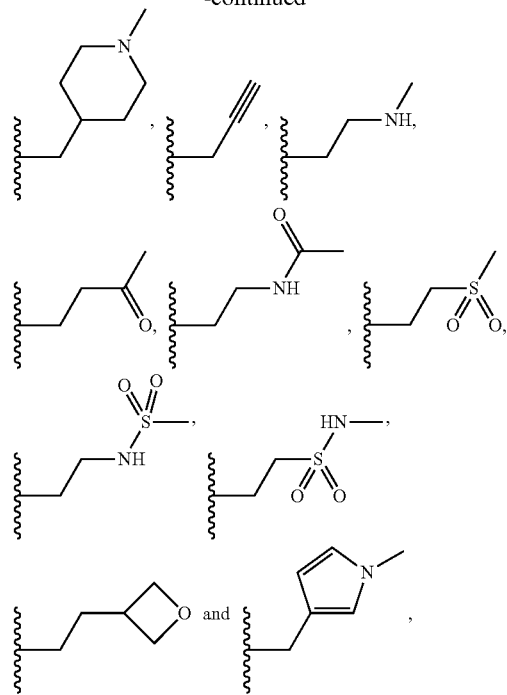

wherein the wavy lines denote attachment points to the parent molecule.

In some embodiments of a compound of Formula (I), (Ia), (Ia-1), (Ia-2), (Ia-3), (Ia-4), (Ia-5) or (Ia-6), $R^2$ is selected from the group consisting of:
methyl, ethyl, isopropyl, cyclopropyl,

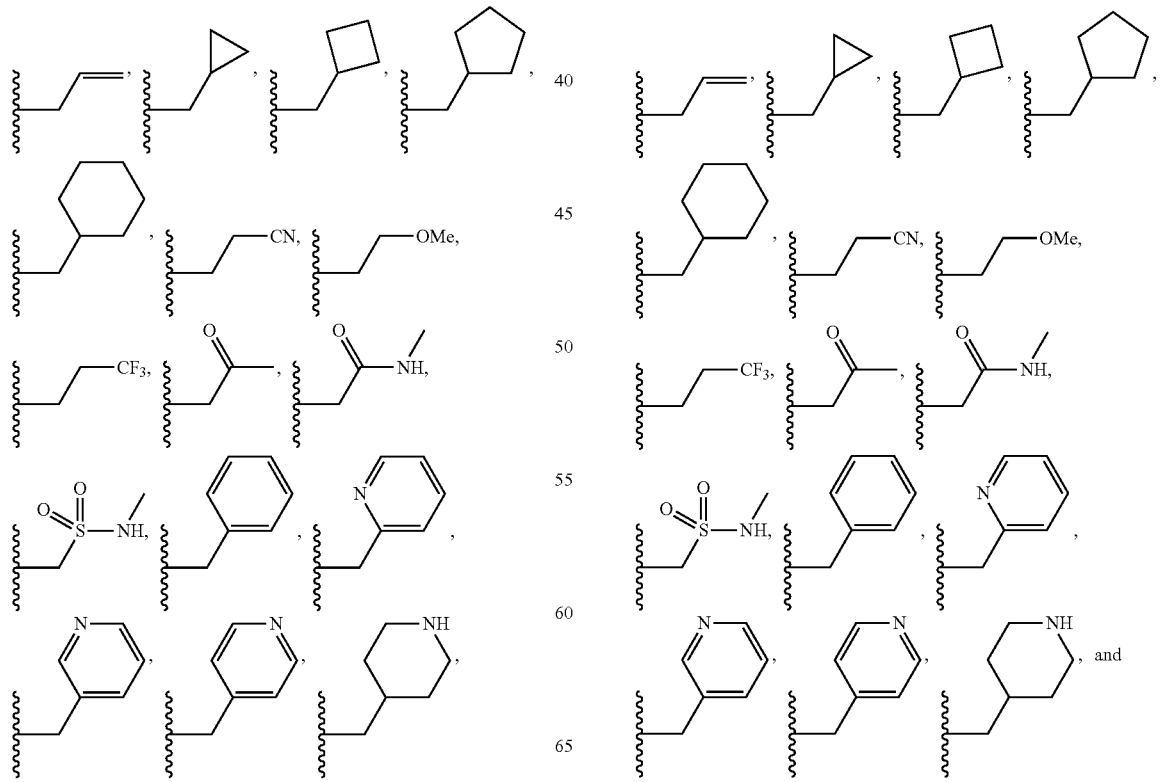

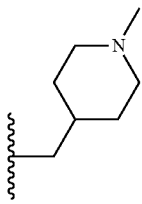

wherein the wavy lines denote attachment points to the parent molecule.

In some embodiments of a compound of Formula (I), A is unsubstituted phenyl fused with B, wherein B is $C_6$ aryl, 5- to 7-membered heteroaryl, $C_3$-$C_8$ cycloalkyl, or 3- to 8-membered heterocyclyl, each of which is substituted with $R^4$; $R^4$ is independently oxo, $C_1$-$C_6$ alkyl, $C_2$-$C_6$ alkenyl, $C_2$-$C_6$ alkynyl, halogen, —$C(O)R^{17}$, —$C(O)OR^{17}$, —$C(O)NR^{17}R^{18}$, —CN, —$Si(C_1$-$C_6$ alkyl$)_3$, —$OR^{17}$, —$NR^{17}R^{18}$, —$OC(O)NR^{17}R^{18}$, —$NR^{17}C(O)R^{18}$, —$S(O)_2R^{17}$, —$NR^{17}S(O)_2R^{18}$, —$S(O)_2NR^{17}R^{18}$, $C_3$-$C_6$ cycloalkyl, 3- to 6-membered heterocyclyl, —($C_1$-$C_3$ alkylene)CN, —($C_1$-$C_3$ alkylene)$OR^{17}$, —($C_1$-$C_3$ alkylene)$NR^{17}R^{18}$, —($C_1$-$C_3$ alkylene)$CF_3$, —($C_1$-$C_3$ alkylene)$C(O)R^{17}$, —($C_1$-$C_3$ alkylene)$C(O)NR^{17}R^{18}$, —($C_1$-$C_3$ alkylene)$NR^{17}C(O)R^{18}$, —($C_1$-$C_3$ alkylene)$S(O)_2R^{17}$, —($C_1$-$C_3$ alkylene)$NR^{17}S(O)_2R^{18}$, —($C_1$-$C_3$ alkylene)$S(O)_2NR^{17}R^{18}$, —($C_1$-$C_3$ alkylene)($C_3$-$C_6$ cycloalkyl) or —($C_1$-$C_3$ alkylene)(3- to 6-membered heterocyclyl), wherein each $R^4$ is independently optionally substituted by halogen, oxo, —$OR^{19}$, —$NR^{19}R^{20}$, or —$C(O)R^{19}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$; $R^2$ is hydrogen, $C_1$-$C_6$ alkyl, $C_2$-$C_6$ alkenyl, $C_3$-$C_6$ cycloalkyl, —($C_1$-$C_3$ alkylene)CN, —($C_1$-$C_3$ alkylene)$OR^{10}$, —($C_1$-$C_3$ alkylene)$S(O)_2R^{10}$, —($C_1$-$C_3$ alkylene)(5- to 10-membered heteroaryl), —($C_1$-$C_3$ alkylene)($C_6$-$C_{14}$ aryl), or —($C_1$-$C_3$ alkylene)($C_3$-$C_6$ cycloalkyl), each of which is optionally substituted by halogen or $C_1$-$C_6$ alkyl. In some embodiments of a compound of Formula (I), A is unsubstituted phenyl fused with B, wherein B is $C_6$ aryl, 5- to 7-membered heteroaryl, $C_3$-$C_8$ cycloalkyl, or 3- to 8-membered heterocyclyl, each of which is substituted with $R^4$; $R^4$ is independently oxo, $C_1$-$C_6$ alkyl, $C_2$-$C_6$ alkenyl, $C_2$-$C_6$ alkynyl, —$C(O)R^{17}$, —$C(O)OR^{17}$, or —$C(O)NR^{17}R^{18}$, wherein each $R^4$ is independently optionally substituted by halogen, oxo, —$OR^{19}$, —$NR^{19}R^{20}$, or —$C(O)R^{19}$; or two $R^4$ are taken together with the carbon to which they attach to form a $C_3$-$C_6$ cycloalkyl; $R^2$ is hydrogen, $C_1$-$C_6$ alkyl, $C_2$-$C_6$ alkenyl, $C_3$-$C_6$ cycloalkyl, —($C_1$-$C_3$ alkylene)CN, —($C_1$-$C_3$ alkylene)$OR^{10}$, —($C_1$-$C_3$ alkylene)$S(O)_2R^{10}$, —($C_1$-$C_3$ alkylene)(5- to 10-membered heteroaryl), —($C_1$-$C_3$ alkylene)($C_6$-$C_{14}$ aryl), or —($C_1$-$C_3$ alkylene)($C_3$-$C_6$ cycloalkyl), each of which is optionally substituted by halogen or $C_1$-$C_6$ alkyl. In some embodiments of a compound of Formula (I), A is unsubstituted phenyl fused with B, wherein B is 3- to 8-membered heterocyclyl optionally substituted with $R^4$; $R^4$ is independently oxo, $C_1$-$C_6$ alkyl, or —$C(O)R^{17}$, wherein the $C_1$-$C_6$ alkyl or —$C(O)R^{17}$ is optionally substituted by —$OR^{19}$ or —$NR^{19}R^{20}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$; $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl). In some embodiments of a compound of Formula (I), A is unsubstituted phenyl fused with B, wherein B is 3- to 8-membered heterocyclyl optionally substituted with $R^4$; $R^4$ is independently oxo, $C_1$-$C_6$ alkyl, or —$C(O)R^{17}$, wherein the $C_1$-$C_6$ alkyl or —$C(O)R^{17}$ is optionally substituted by —$OR^{19}$ or —$NR^{19}R^{20}$; or two $R^4$ are taken together with the carbon to which they attach to form a $C_3$-$C_6$ cycloalkyl; $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl). In some embodiments of a compound of Formula (I), A is unsubstituted phenyl fused with B, wherein B is 6-membered heterocyclyl having one nitrogen atom, wherein the 6-membered heterocyclyl is optionally substituted by $R^4$; $R^4$ is independently $C_1$-$C_6$ alkyl; $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl). In some embodiments of a compound of Formula (I), A is unsubstituted phenyl fused with B, wherein B is 6-membered heterocyclyl having one nitrogen atom, wherein the 6-membered heterocyclyl is optionally substituted by $R^4$; $R^4$ is independently $C_1$-$C_6$ alkyl; $R^2$ is selected from the group consisting of: allyl, cyclopropylmethyl, isopropyl, cyclopropyl, ethyl, and propyl.

In some embodiments of a compound of Formula (I), A is phenyl optionally substituted by $R^1$ and fused with B, wherein $R^1$ is independently —CN, $C_1$-$C_6$ alkyl, or halogen; B is $C_6$ aryl, 5- to 7-membered heteroaryl, $C_3$-$C_8$ cycloalkyl, or 3- to 8-membered heterocyclyl, each of which is substituted with $R^4$; $R^4$ is independently oxo, $C_1$-$C_6$ alkyl, $C_2$-$C_6$ alkenyl, $C_2$-$C_6$ alkynyl, halogen, —$C(O)R^{17}$, —$C(O)OR^{17}$, —$C(O)NR^{17}R^{18}$, —CN, —$Si(C_1$-$C_6$ alkyl$)_3$, —$OR^{17}$, —$NR^{17}R^{18}$, —$OC(O)NR^{17}R^{18}$, —$NR^{17}C(O)R^{18}$, —$S(O)_2R^{17}$, —$NR^{17}S(O)_2R^{18}$, —$S(O)_2NR^{17}R^{18}$, $C_3$-$C_6$ cycloalkyl, 3- to 6-membered heterocyclyl, —($C_1$-$C_3$ alkylene)CN, —($C_1$-$C_3$ alkylene)$OR^{17}$, —($C_1$-$C_3$ alkylene)$NR^{17}R^{18}$, —($C_1$-$C_3$ alkylene)$CF_3$, —($C_1$-$C_3$ alkylene)$C(O)R^{17}$, —($C_1$-$C_3$ alkylene)$C(O)NR^{17}R^{18}$, —($C_1$-$C_3$ alkylene)$NR^{17}C(O)R^{18}$, —($C_1$-$C_3$ alkylene)$S(O)_2R^{17}$, —($C_1$-$C_3$ alkylene)$NR^{17}S(O)_2R^{18}$, —($C_1$-$C_3$ alkylene)$S(O)_2NR^{17}R^{18}$, —($C_1$-$C_3$ alkylene)($C_3$-$C_6$ cycloalkyl) or —($C_1$-$C_3$ alkylene)(3- to 6-membered heterocyclyl), wherein each $R^4$ is independently optionally substituted by halogen, oxo, —$OR^{19}$, —$NR^{19}R^{20}$, or —$C(O)R^{19}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$; $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl). In some embodiments of a compound of Formula (I), A is phenyl optionally substituted by $R^1$ and fused with B, wherein $R^1$ is independently —CN, $C_1$-$C_6$ alkyl, or halogen; B is 3- to 8-membered heterocyclyl optionally substituted with $R^4$; $R^4$ is independently oxo, $C_1$-$C_6$ alkyl, or —$C(O)R^{17}$, wherein the $C_1$-$C_6$ alkyl or —$C(O)R^{17}$ is optionally substituted by —$OR^{19}$ or —$NR^{19}R^{20}$; or two $R^4$ are, when bound to the same carbon or two different carbon atoms, are taken together with the carbon to which they are attached to form a $C_3$-$C_6$ cycloalkyl or 3- to 7-membered heterocyclyl, each is optionally substituted by $R^{19}$; $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl). In some embodiments of a compound of Formula (I), A is phenyl optionally substituted by $R^1$ and fused with B, wherein $R^1$ is independently —CN, $C_1$-$C_6$ alkyl, or halogen; B is 3- to 8-membered heterocyclyl optionally substituted with $R^4$; $R^4$ is independently oxo, $C_1$-$C_6$ alkyl, or —$C(O)R^{17}$, wherein the $C_1$-$C_6$ alkyl or —$C(O)R^{17}$ is optionally substituted by —$OR^{19}$ or —$NR^{19}R^{20}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$; $R^2$ is selected from the group consisting of: allyl, cyclopropylmethyl, isopropyl, cyclopropyl, ethyl, and propyl.

In some embodiments of a compound of Formula (I), A is phenyl optionally substituted by $R^1$ and fused with B, wherein $R^1$ is independently —CN, $C_1$-$C_6$ alkyl, or halogen; B is $C_6$ aryl, 5- to 7-membered heteroaryl, $C_3$-$C_8$ cycloalkyl, or 3- to 8-membered heterocyclyl, each of which is substituted with $R^4$; $R^4$ is independently oxo, $C_1$-$C_6$ alkyl, $C_2$-$C_6$ alkenyl, $C_2$-$C_6$ alkynyl, —C(O)$R^{17}$, —C(O)O$R^{17}$, or —C(O)N$R^{17}R^{18}$, wherein each $R^4$ is independently optionally substituted by halogen, oxo, —O$R^{19}$, —N$R^{19}R^{20}$, or —C(O)$R^{19}$; or two $R^4$ are taken together with the carbon to which they attach to form a $C_3$-$C_6$ cycloalkyl; $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl). In some embodiments of a compound of Formula (I), A is phenyl optionally substituted by $R^1$ and fused with B, wherein $R^1$ is independently —CN, $C_1$-$C_6$ alkyl, or halogen; B is 3- to 8-membered heterocyclyl optionally substituted with $R^4$; $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$ are taken together with the carbon to which they attach to form a $C_3$-$C_6$ cycloalkyl; $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl). In some embodiments of a compound of Formula (I), A is phenyl optionally substituted by $R^1$ and fused with B, wherein $R^1$ is independently —CN, $C_1$-$C_6$ alkyl, or halogen; B is 3- to 8-membered heterocyclyl optionally substituted with $R^4$; $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$ are taken together with the carbon to which they attach to form a $C_3$-$C_6$ cycloalkyl; $R^2$ is selected from the group consisting of: allyl, cyclopropylmethyl, isopropyl, cyclopropyl, ethyl, and propyl.

In some embodiments of a compound of Formula (I), A is unsubstituted 6-membered heteroaryl fused with B, wherein B is $C_6$ aryl, 5- to 7-membered heteroaryl, $C_3$-$C_8$ cycloalkyl, or 3- to 8-membered heterocyclyl, each of which is substituted with $R^4$; $R^4$ is independently oxo, $C_1$-$C_6$ alkyl, $C_2$-$C_6$ alkenyl, $C_2$-$C_6$ alkynyl, halogen, —C(O)$R^{17}$, —C(O)O$R^{17}$, —C(O)N$R^{17}R^{18}$, —CN, —Si($C_1$-$C_6$ alkyl)$_3$, —O$R^{17}$, —N$R^{17}R^{18}$, —OC(O)N$R^{17}R^{18}$, —N$R^{17}$C(O)$R^{18}$, —S(O)$_2R^{17}$, —N$R^{17}$S(O)$_2R^{18}$, —S(O)$_2$N$R^{17}R^{18}$, $C_3$-$C_6$ cycloalkyl, 3- to 6-membered heterocyclyl, —($C_1$-$C_3$ alkylene)CN, —($C_1$-$C_3$ alkylene)O$R^{17}$, —($C_1$-$C_3$ alkylene)N$R^{17}R^{18}$, —($C_1$-$C_3$ alkylene)CF$_3$, —($C_1$-$C_3$ alkylene)C(O)$R^{17}$, —($C_1$-$C_3$ alkylene)C(O)N$R^{17}R^{18}$, —($C_1$-$C_3$ alkylene)N$R^{17}$C(O)$R^{18}$, —($C_1$-$C_3$ alkylene)S(O)$_2R^{17}$, —($C_1$-$C_3$ alkylene)N$R^{17}$S(O)$_2R^{18}$, —($C_1$-$C_3$ alkylene)S(O)$_2$N$R^{17}R^{18}$, —($C_1$-$C_3$ alkylene)($C_3$-$C_6$ cycloalkyl) or —($C_1$-$C_3$ alkylene)(3- to 6-membered heterocyclyl), wherein each $R^4$ is independently optionally substituted by halogen, oxo, —O$R^{19}$, —N$R^{19}R^{20}$, or —C(O)$R^{19}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$; $R^2$ is hydrogen, $C_1$-$C_6$ alkyl, $C_2$-$C_6$ alkenyl, $C_3$-$C_6$ cycloalkyl, —($C_1$-$C_3$ alkylene)CN, —($C_1$-$C_3$ alkylene)O$R^{10}$, —($C_1$-$C_3$ alkylene)S(O)$_2R^{10}$, —($C_1$-$C_3$ alkylene)(5- to 10-membered heteroaryl), —($C_1$-$C_3$ alkylene)($C_6$-$C_{14}$ aryl), or —($C_1$-$C_3$ alkylene)($C_3$-$C_6$ cycloalkyl), each of which is optionally substituted by halogen or $C_1$-$C_6$ alkyl. In some embodiments of a compound of Formula (I), A is unsubstituted 6-membered heteroaryl fused with B, wherein B is 3- to 8-membered heterocyclyl optionally substituted with $R^4$; $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$, when bound to the same carbon or two different carbon atoms, are taken together with the carbon to which they are attached to form a $C_3$-$C_6$ cycloalkyl or 3- to 7-membered heterocyclyl, each is optionally substituted by $R^{19}$; $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl). In some embodiments of a compound of Formula (I), A is unsubstituted 6-membered heteroaryl fused with B, wherein B is 6-membered heterocyclyl having one nitrogen atom, wherein the 6-membered heterocyclyl is optionally substituted by $R^4$; $R^4$ is independently $C_1$-$C_6$ alkyl; $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl). In some embodiments of a compound of Formula (I), A is unsubstituted 6-membered heteroaryl fused with B, wherein B is 6-membered heterocyclyl having one nitrogen atom, wherein the 6-membered heterocyclyl is optionally substituted by $R^4$; $R^4$ is independently $C_1$-$C_6$ alkyl; $R^2$ is selected from the group consisting of: allyl, cyclopropylmethyl, isopropyl, cyclopropyl, ethyl, and propyl.

In some embodiments of a compound of Formula (I), A is unsubstituted 6-membered heteroaryl fused with B, wherein B is $C_6$ aryl, 5- to 7-membered heteroaryl, $C_3$-$C_8$ cycloalkyl, or 3- to 8-membered heterocyclyl, each of which is substituted with $R^4$; $R^4$ is independently oxo, $C_1$-$C_6$ alkyl, $C_2$-$C_6$ alkenyl, $C_2$-$C_6$ alkynyl, —C(O)$R^{17}$, —C(O)O$R^{17}$, or —C(O)N$R^{17}R^{18}$, wherein each $R^4$ is independently optionally substituted by halogen, oxo, —O$R^{19}$, —N$R^{19}R^{20}$, or —C(O)$R^{19}$; or two $R^4$ are taken together with the carbon to which they attach to form a $C_3$-$C_6$ cycloalkyl; $R^2$ is hydrogen, $C_1$-$C_6$ alkyl, $C_2$-$C_6$ alkenyl, $C_3$-$C_6$ cycloalkyl, —($C_1$-$C_3$ alkylene)CN, —($C_1$-$C_3$ alkylene)O$R^{10}$, —($C_1$-$C_3$ alkylene)S(O)$_2R^{10}$, —($C_1$-$C_3$ alkylene)(5- to 10-membered heteroaryl), —($C_1$-$C_3$ alkylene)($C_6$-$C_{14}$ aryl), or —($C_1$-$C_3$ alkylene)($C_3$-$C_6$ cycloalkyl), each of which is optionally substituted by halogen or $C_1$-$C_6$ alkyl. In some embodiments of a compound of Formula (I), A is unsubstituted 6-membered heteroaryl fused with B, wherein B is 3- to 8-membered heterocyclyl optionally substituted with $R^4$; $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$ are taken together with the carbon to which they attach to form a $C_3$-$C_6$ cycloalkyl; $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl). In some embodiments of a compound of Formula (I), A is unsubstituted 6-membered heteroaryl fused with B, wherein B is 6-membered heterocyclyl having one nitrogen atom, wherein the 6-membered heterocyclyl is optionally substituted by $R^4$; $R^4$ is independently $C_1$-$C_6$ alkyl; $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl). In some embodiments of a compound of Formula (I), A is unsubstituted 6-membered heteroaryl fused with B, wherein B is 6-membered heterocyclyl having one nitrogen atom, wherein the 6-membered heterocyclyl is optionally substituted by $R^4$; $R^4$ is independently $C_1$-$C_6$ alkyl; $R^2$ is selected from the group consisting of: allyl, cyclopropylmethyl, isopropyl, cyclopropyl, ethyl, and propyl.

In some embodiments of a compound of Formula (I), A, B, $R^1$ and $R^4$ together are selected from the group consisting of:

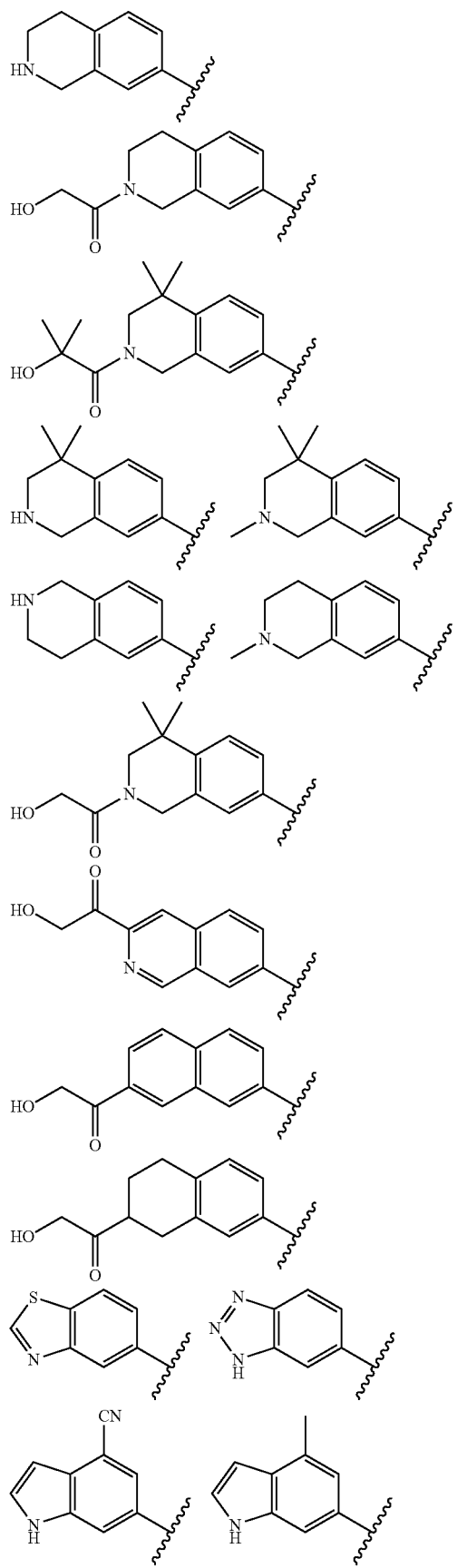
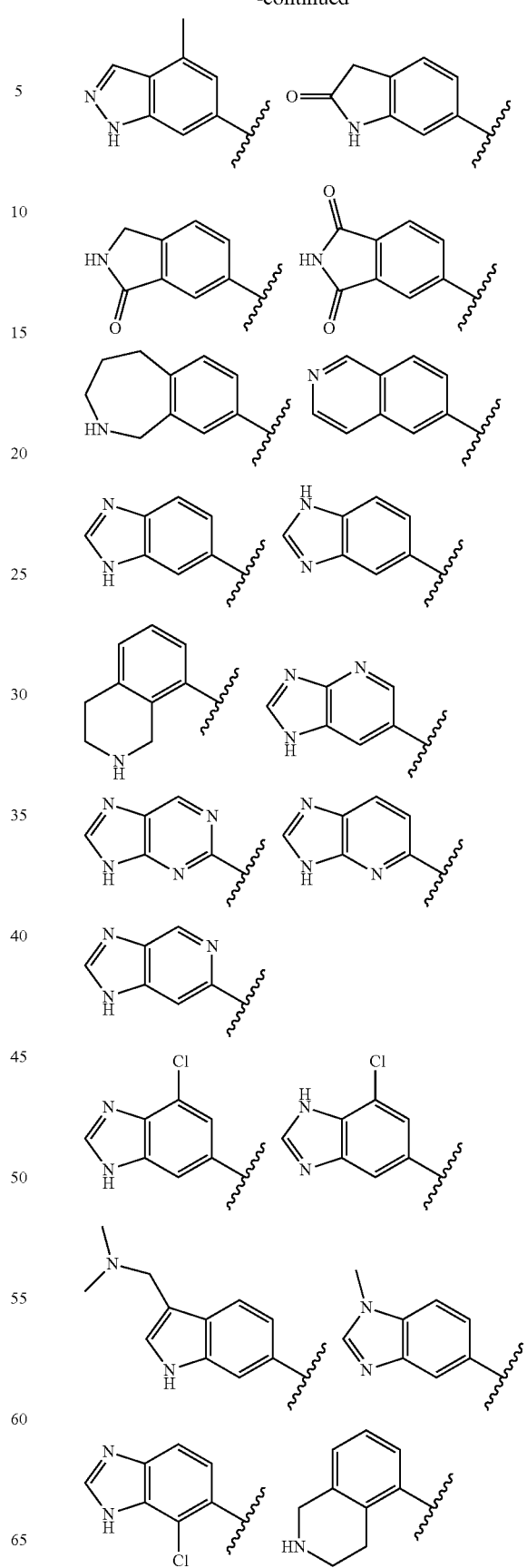

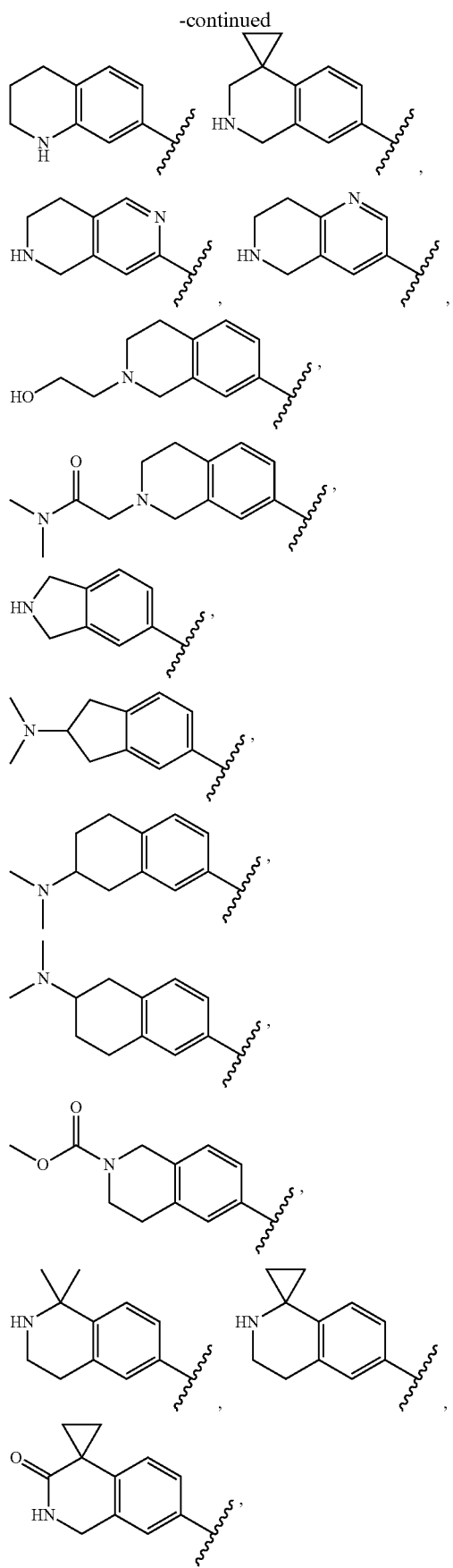
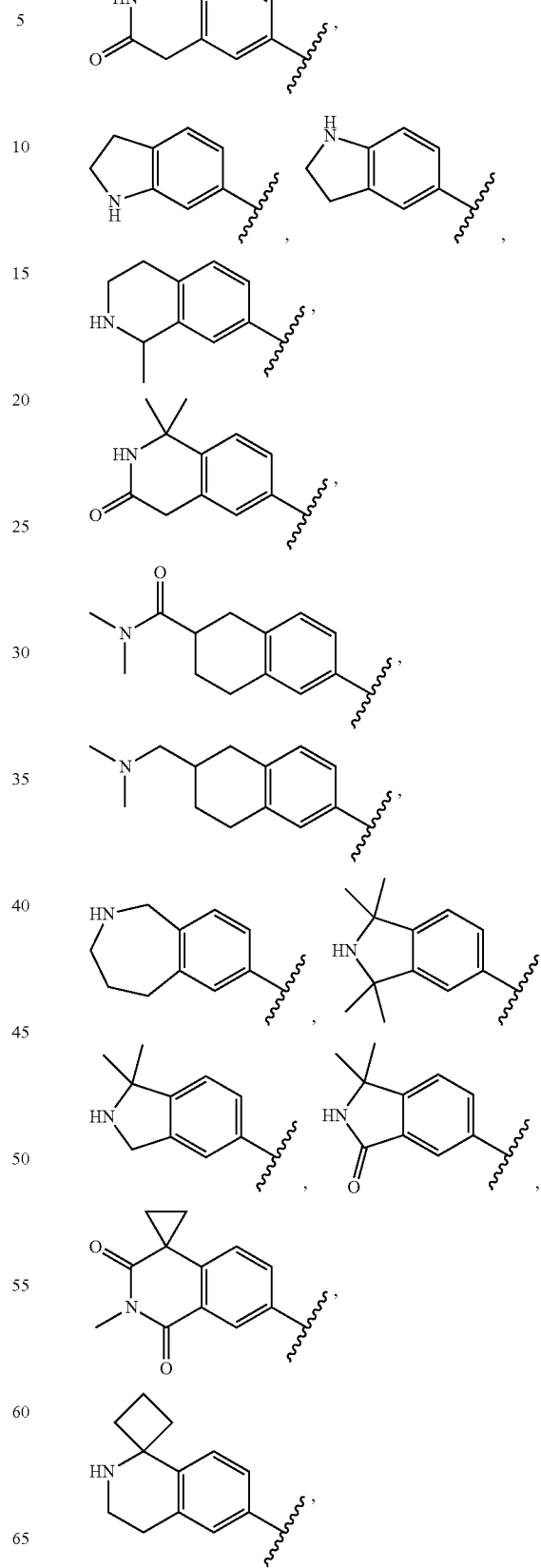

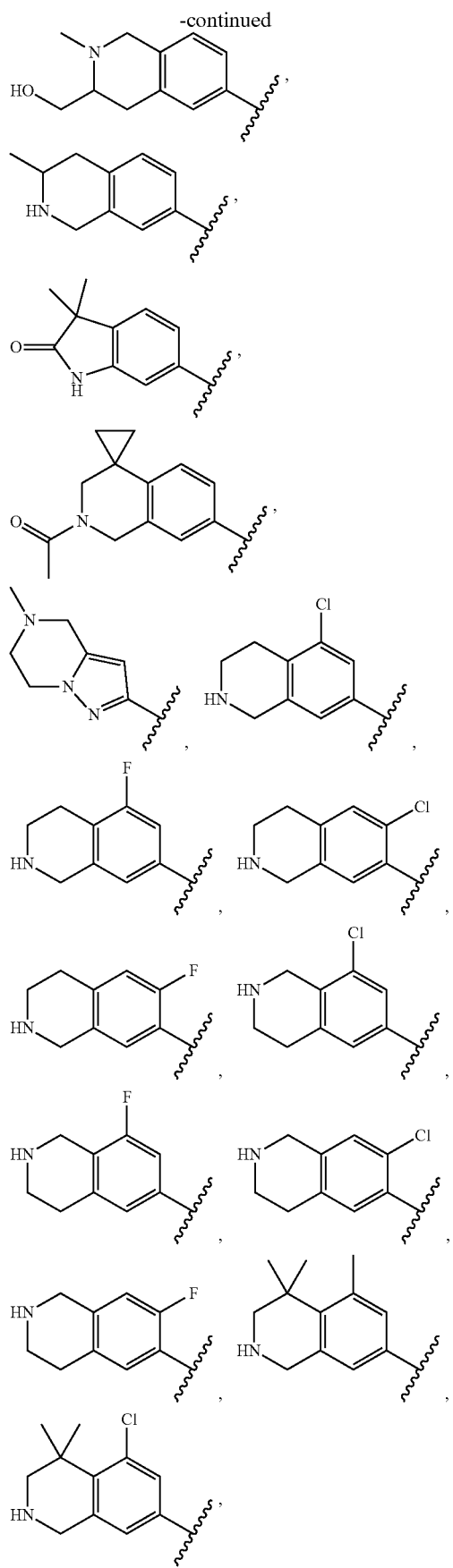
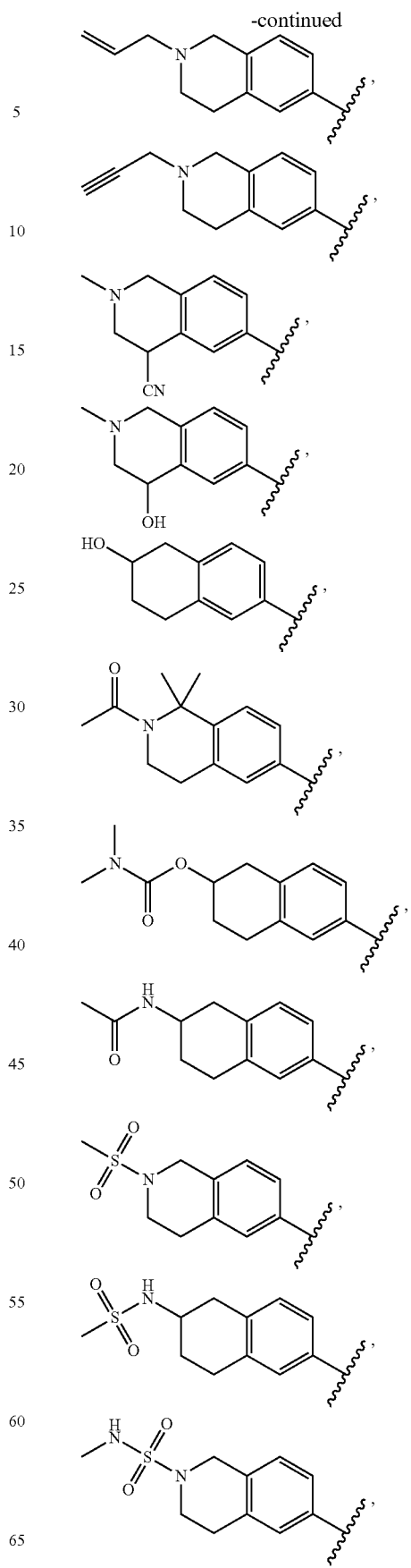

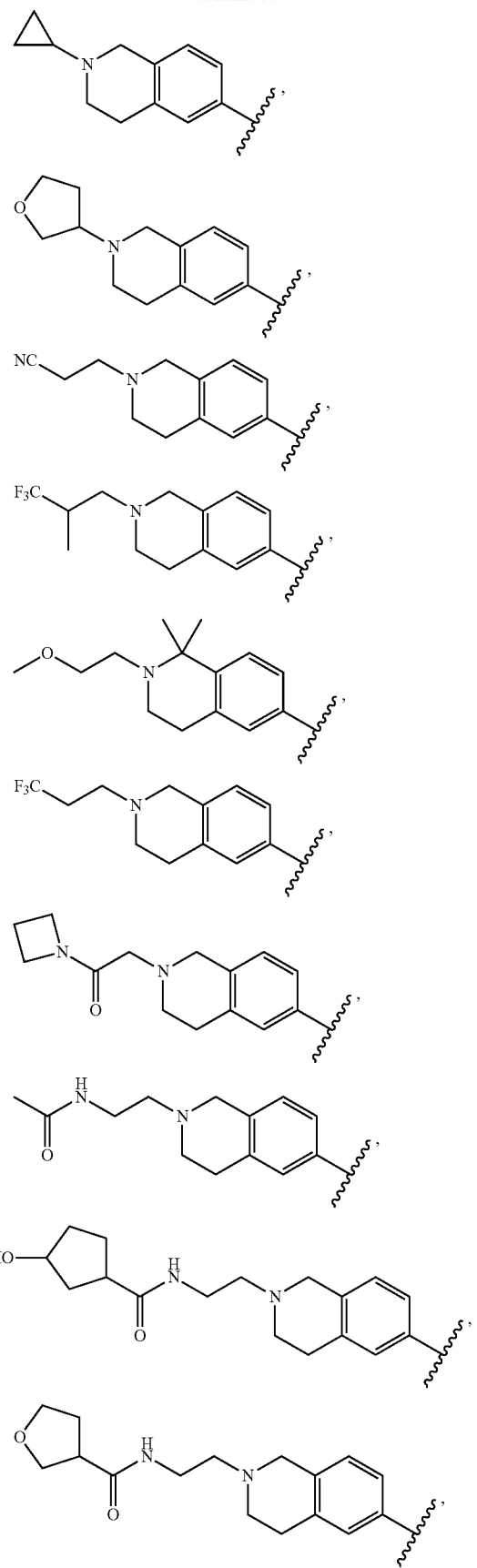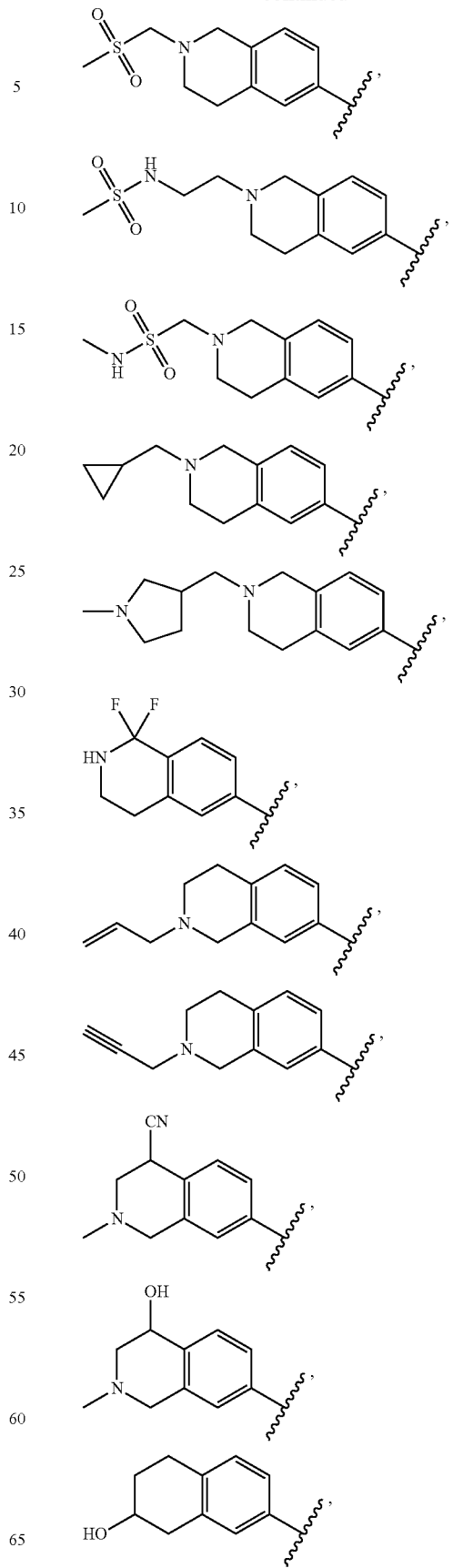

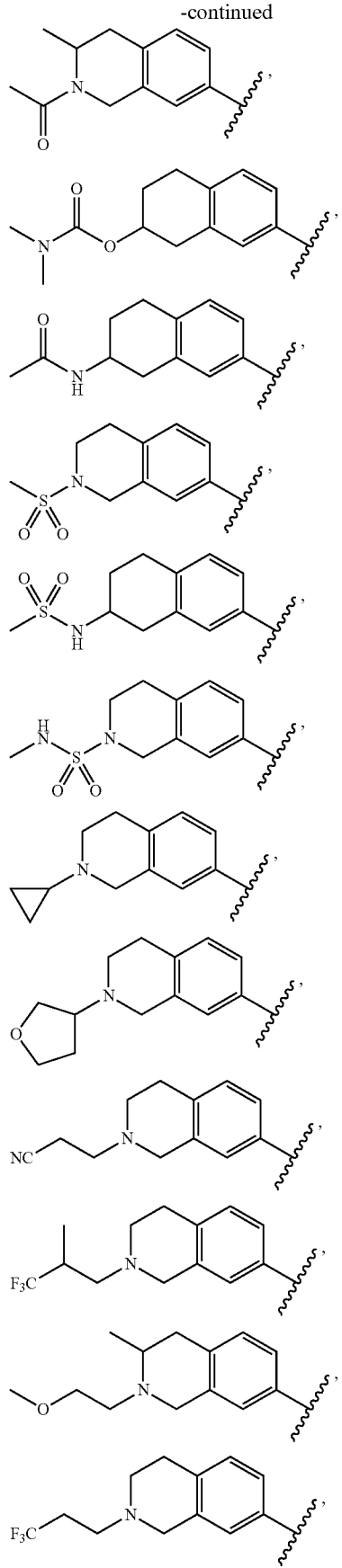
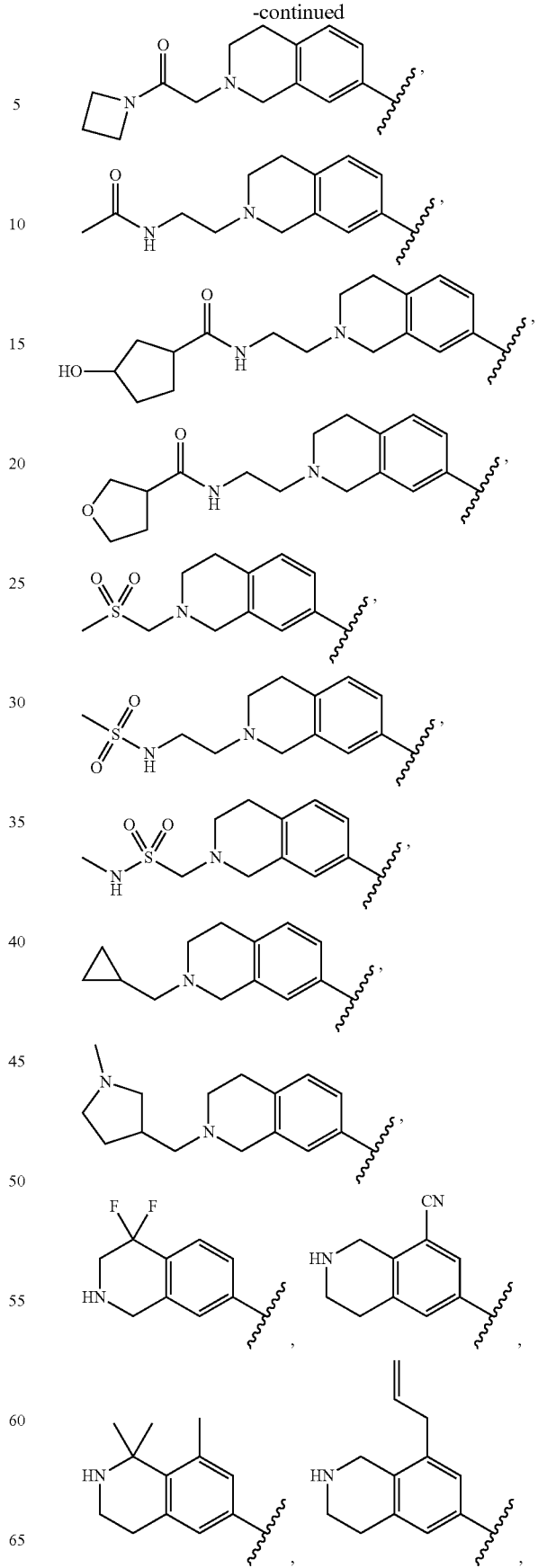

85
-continued
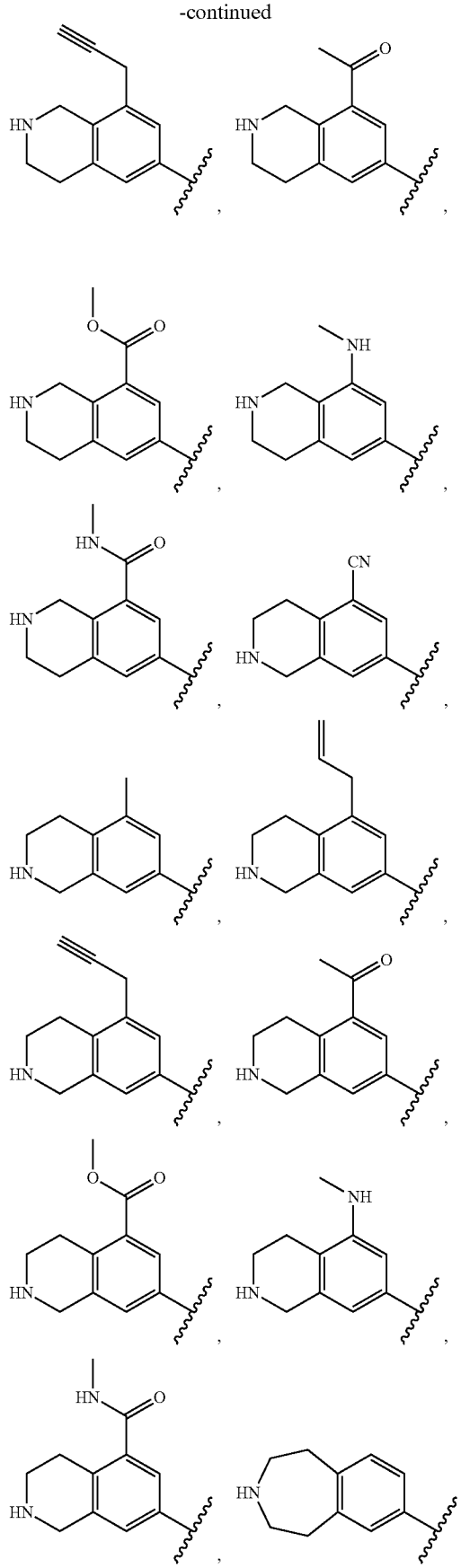
86
-continued
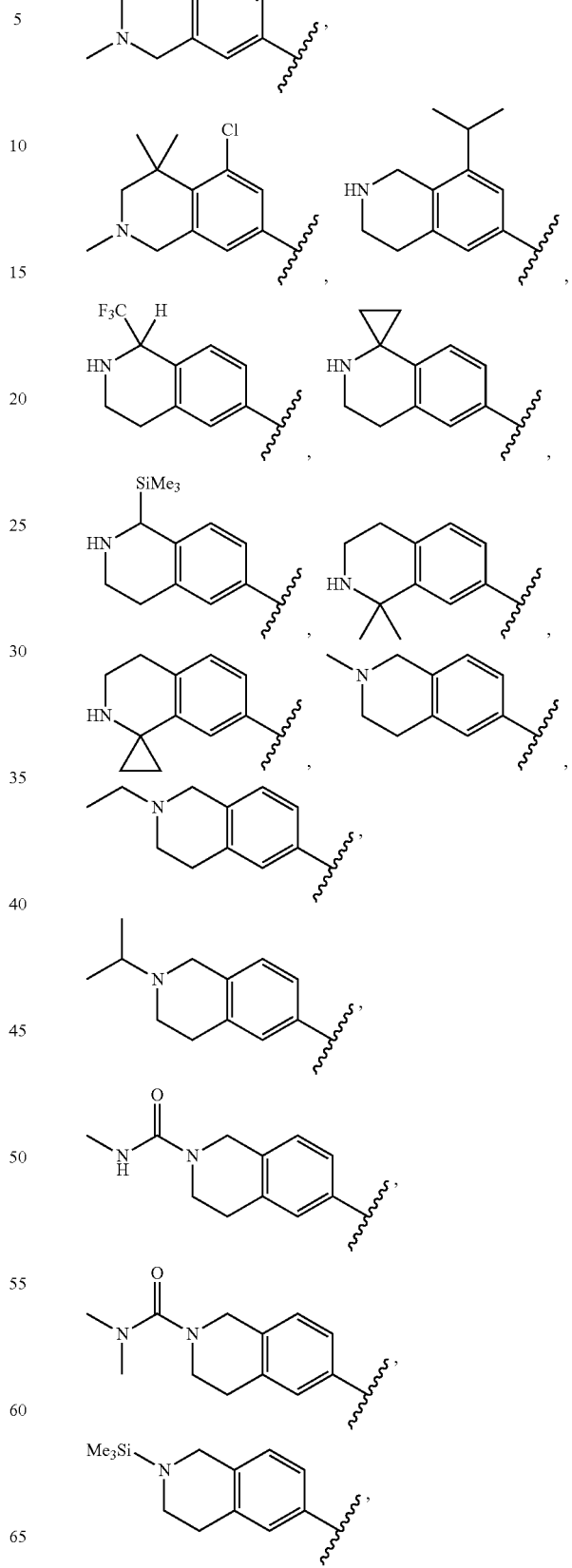

87
-continued
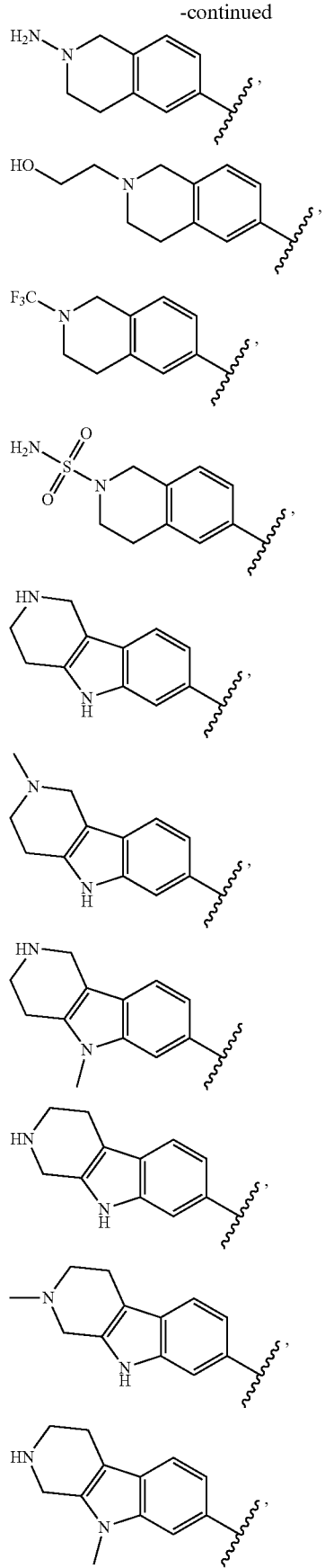
88
-continued
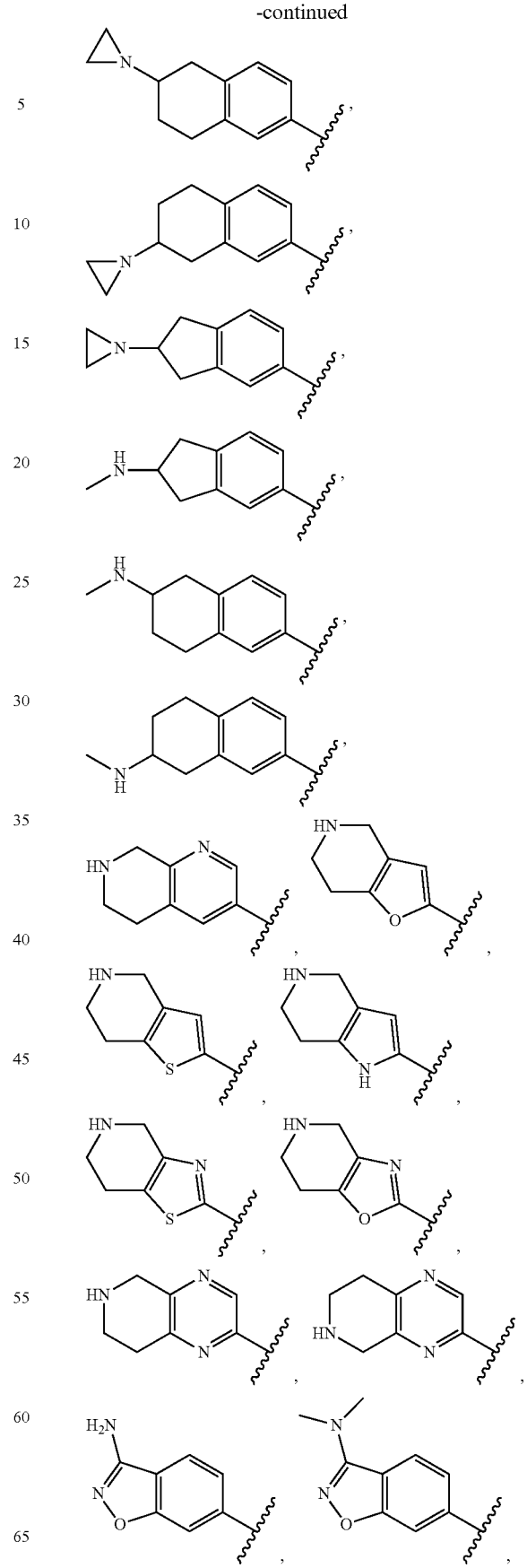

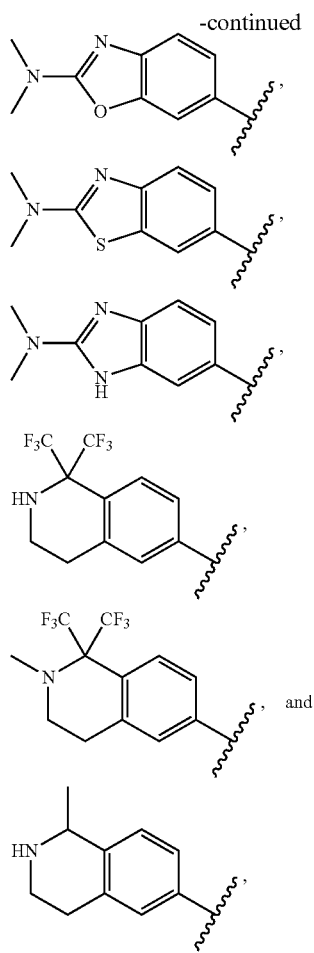
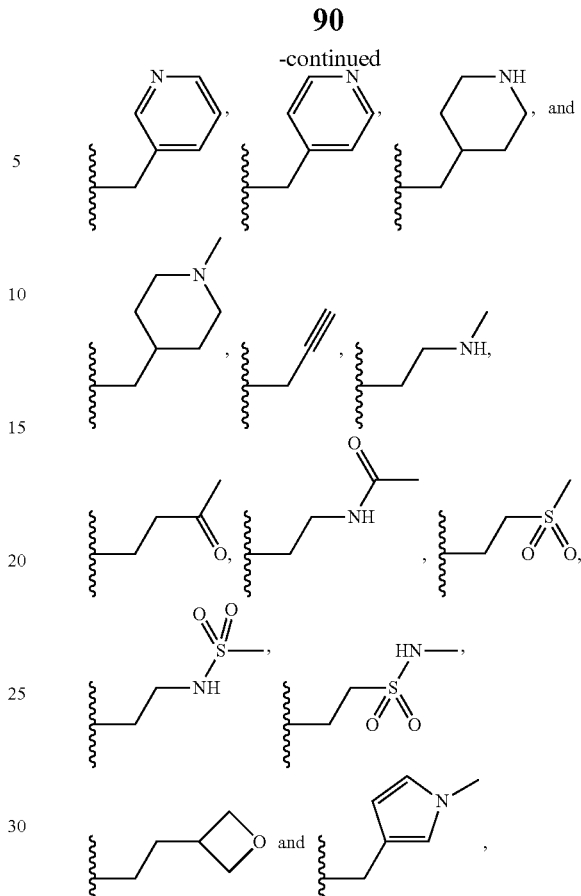
wherein the wavy lines denote attachment points to the parent molecule; R² is selected from the group consisting of: methyl, ethyl, isopropyl, cyclopropyl, cyclobutyl,
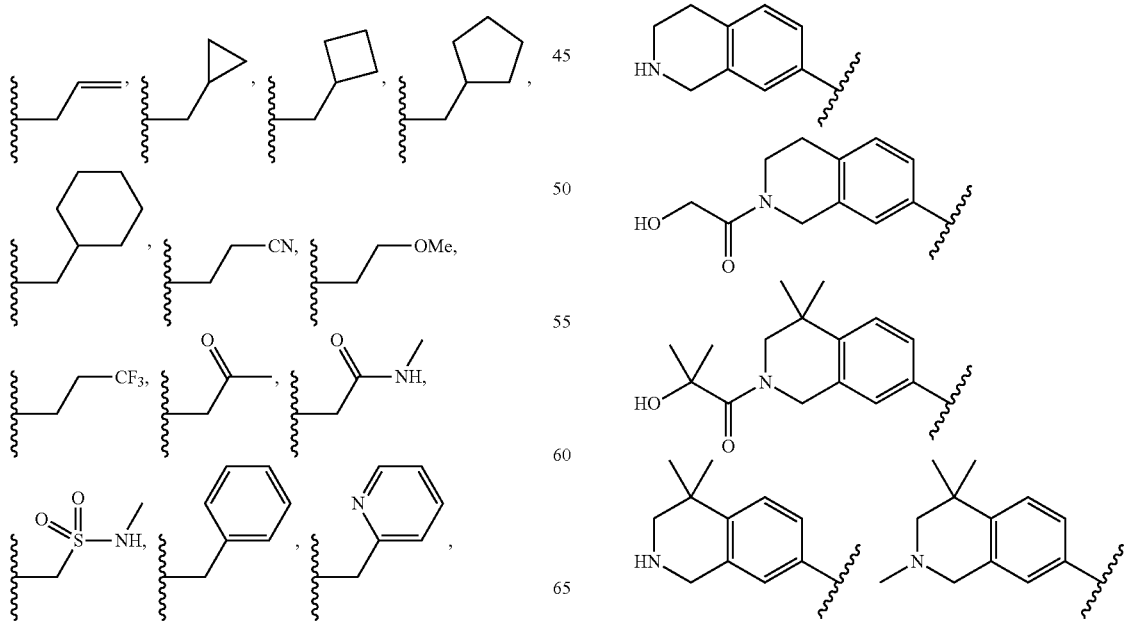
wherein the wavy lines denote attachment points to the parent molecule.
In some embodiments of a compound of Formula (I), A, B, R¹ and R⁴ together are selected from the group consisting of:

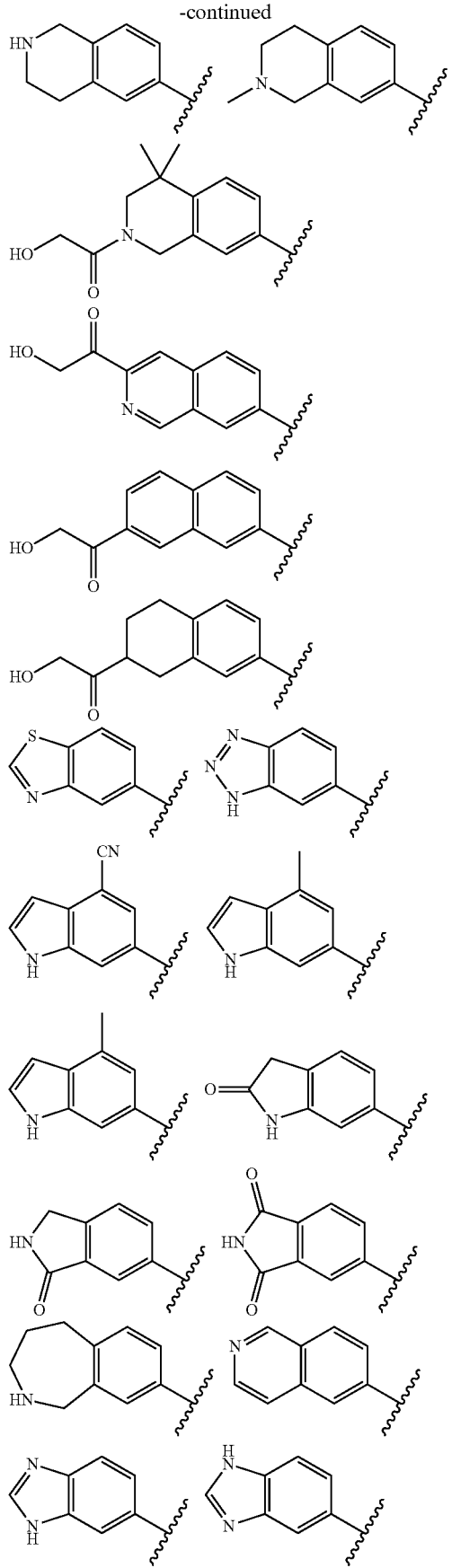
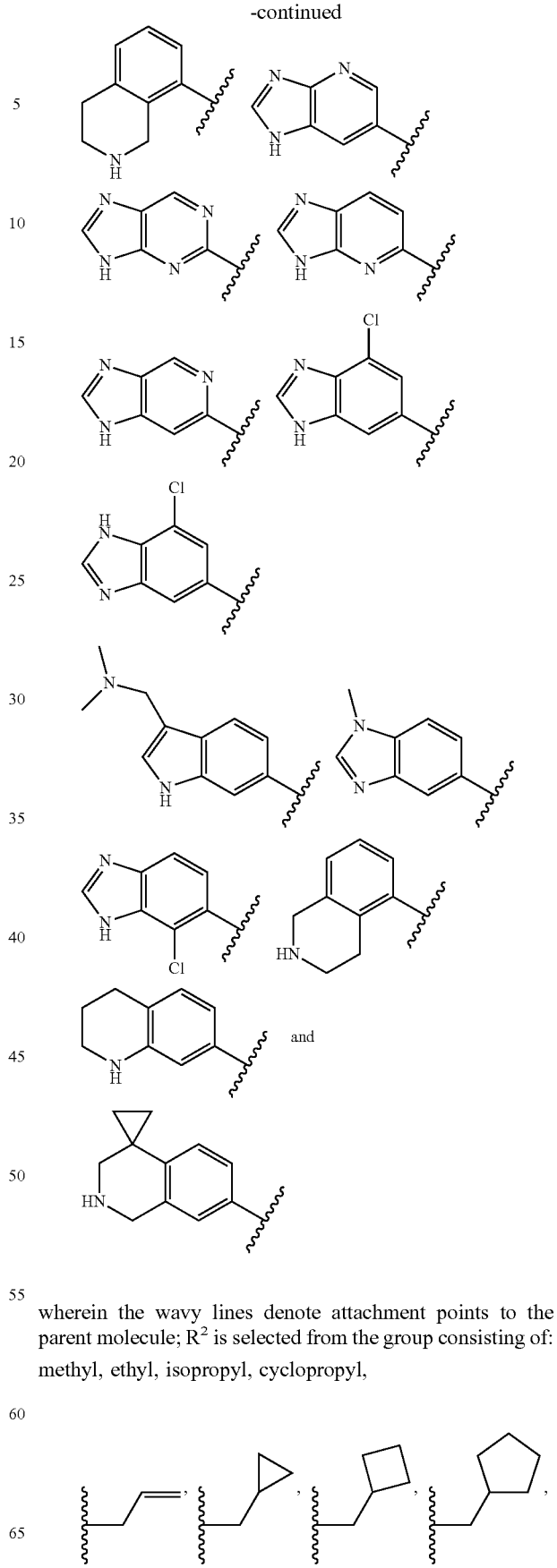
wherein the wavy lines denote attachment points to the parent molecule; R² is selected from the group consisting of: methyl, ethyl, isopropyl, cyclopropyl,

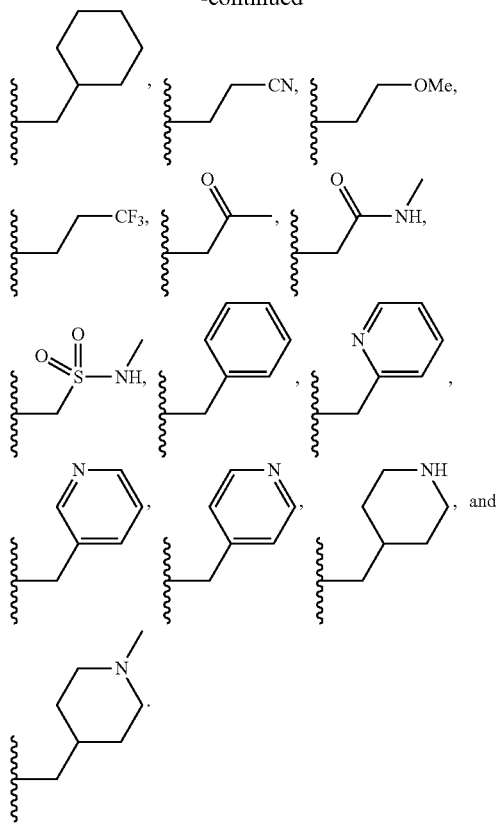

In some embodiments of a compound of Formula (I), (Ia), (Ia-1 to Ia-6), (Ib), (Ib-1 to Ib-3), (Ic) or (Ic-1 to Ic-3), $R^3$ is hydrogen, $C_1$-$C_6$ alkyl, —C(O)$R^{10}$, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl), —S(O)$R^{10}$, —S(O)$_2$$R^{10}$, or 5- to 10-membered heteroaryl, each of which is optionally substituted by halogen, oxo, —OR$^{13}$, —NR$^{13}$R$^{14}$, —C(O)R$^{13}$, —C(O)OR$^{13}$, —C(O)NR$^{13}$R$^{14}$, —NR$^{13}$C(O)R$^{14}$, —CN, —SR$^{13}$, —S(O)R$^{13}$, —S(O)$_2$R$^{13}$, —Si($C_1$-$C_6$ alkyl)$_3$, —P(O)R$^{13}$R$^{14}$, —NR$^{13}$S(O)$_2$R$^{14}$, —($C_1$-$C_3$ alkylene)OR$^{13}$, —($C_1$-$C_3$ alkylene)NR$^{13}$R$^{14}$, —($C_1$-$C_3$ alkylene)C(O)R$^{13}$, $C_3$-$C_8$ cycloalkyl optionally substituted by $C_1$-$C_6$ alkyl, CN, CF$_3$, oxo, —OH, —NR$^{15}$R$^{16}$, —OR$^{15}$ or halogen, 3- to 12-membered heterocyclyl optionally substituted by oxo, —OH, —NR$^{15}$R$^{16}$, —C(O)OR$^{15}$, —OR$^{15}$ or halogen, or $C_1$-$C_6$ alkyl optionally substituted by oxo, —OH, —NR$^{15}$R$^{16}$, —C(O)OR$^{15}$, —OR$^{15}$ or halogen, with the proviso that the 5- to 10-membered heteroaryl of $R^3$ is not substituted by

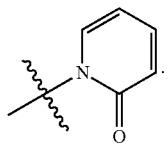 [SMILES: *n1ccccc1=O]

In some embodiments of a compound of Formula (I), (Ia), (Ia-1 to Ia-6), (Ib), (Ib-1 to Ib-3), (Ic) or (Ic-1 to Ic-3), $R^3$ is —C(O)R$^{10}$ or 5- to 10-membered heteroaryl which is unsubstituted. In some embodiments of a compound of Formula (I), (Ia), (Ia-1 to Ia-6), (Ib), (Ib-1 to Ib-3), (Ic) or (Ic-1 to Ic-3), $R^3$ is —C(O)R$^{10}$ or 5- to 10-membered heteroaryl optionally substituted by halogen, oxo, —OR$^{13}$, —NR$^{13}$R$^{14}$, —C(O)R$^{13}$, —C(O)NR$^{13}$R$^{14}$, —NR$^{13}$C(O)R$^{14}$, —CN, —S(O)R$^{13}$, —SR$^{13}$, —S(O)$_2$R$^{13}$, —($C_1$-$C_3$ alkylene)OR$^{13}$, —($C_1$-$C_3$ alkylene)NR$^{13}$R$^{14}$, —($C_1$-$C_3$ alkylene)C(O)R$^{13}$, $C_3$-$C_8$ cycloalkyl optionally substituted by $C_1$-$C_6$ alkyl, CN, CF$_3$, oxo, —OH, —NR$^{15}$R$^{16}$, —OR$^{15}$ or halogen, 3- to 12-membered heterocyclyl optionally substituted by oxo, —OH, or halogen, or $C_1$-$C_6$ alkyl optionally substituted by oxo, —OH, or halogen, with the proviso that the 5- to 10-membered heteroaryl of $R^3$ is not substituted by

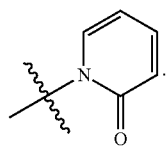

In some embodiments of a compound of Formula (I), (Ia), (Ia-1 to Ia-6), (Ib), (Ib-1 to Ib-3), (Ic) or (Ic-1 to Ic-3), $R^3$ is —C(O)R$^{10}$ or 5- to 10-membered heteroaryl substituted by 3- to 12-membered heterocyclyl optionally substituted by oxo, —OH, —NR$^{15}$R$^{16}$, —C(O)OR$^{15}$, —OR$^{15}$ or halogen, —CN, —($C_1$-$C_3$ alkylene)NR$^{13}$R$^{14}$, $C_3$-$C_8$ cycloalkyl optionally substituted by $C_1$-$C_6$ alkyl, CN, CF$_3$, oxo, —OH, —NR$^{15}$R$^{16}$, —OR$^{15}$ or halogen, —C(O)R$^{13}$, —NR$^{13}$R$^{14}$, —OR$^{13}$, or $C_1$-$C_6$ alkyl optionally substituted by —OH or halogen, with the proviso that the 5- to 10-membered heteroaryl of $R^3$ is not substituted by

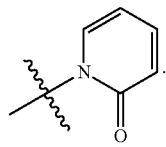 [SMILES: *n1ccccc1=O]

In some embodiments of a compound of Formula (I), (Ia), (Ia-1 to Ia-6), (Ib), (Ib-1 to Ib-3), (Ic) or (Ic-1 to Ic-3), $R^3$ is 5- to 10-membered heteroaryl substituted by 3- to 12-membered heterocyclyl optionally substituted by oxo, —OH, —NR$^{15}$R$^{16}$, —C(O)OR$^{15}$, —OR$^{15}$ or halogen, —CN, —($C_1$-$C_3$ alkylene)NR$^{13}$R$^{14}$, $C_3$-$C_8$ cycloalkyl optionally substituted by $C_1$-$C_6$ alkyl, CN, CF$_3$, oxo, —OH, —NR$^{15}$R$^{16}$, —OR$^{15}$ or halogen, —C(O)R$^{13}$, —NR$^{13}$R$^{14}$, —OR$^{13}$, or $C_1$-$C_6$ alkyl optionally substituted by —OH or halogen, with the proviso that the 5- to 10-membered heteroaryl of $R^3$ is not substituted by

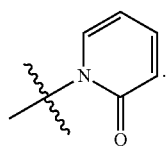 [SMILES: *n1ccccc1=O]

In some embodiments of a compound of Formula (I), (Ia), (Ia-1 to Ia-6), (Ib), (Ib-1 to Ib-3), (Ic) or (Ic-1 to Ic-3), $R^3$ is 5- to 10-membered heteroaryl substituted by —OR$^{13}$ or $C_1$-$C_6$ alkyl, wherein the $C_1$-$C_6$ alkyl is optionally substituted by —OH or halogen. In some embodiments of a compound of Formula (I), (Ia), (Ia-1 to Ia-6), (Ib), (Ib-1 to Ib-3), (Ic) or (Ic-1 to Ic-3), $R^3$ is 5- to 10-membered heteroaryl substituted by —$OR^{13}$ or $C_1$-$C_6$ alkyl, wherein the $C_1$-$C_6$ alkyl is unsubstituted.

In some embodiments of a compound of Formula (I), (Ia), (Ia-1), (Ia-2), (Ia-3), (Ia-4), (Ia-5) or (Ia-6), $R^3$ is hydrogen, $C_1$-$C_6$ alkyl, —$C(O)R^{10}$, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl), —S(O) $R^{10}$, —$S(O)_2R^{10}$, or 5- to 10-membered heteroaryl, each of which is optionally substituted by halogen, oxo, —$OR^{13}$, —$NR^{13}R^{14}$, —$C(O)R^{13}$, —CN, —$S(O)R^{13}$, —$S(O)_2R^{13}$, —($C_1$-$C_3$ alkylene)$OR^{13}$, —($C_1$-$C_3$ alkylene)$NR^{13}R^{14}$, —($C_1$-$C_3$ alkylene)$C(O)R^{13}$, $C_3$-$C_8$ cycloalkyl, 3- to 12-membered heterocyclyl optionally substituted by oxo, —OH, or halogen, or $C_1$-$C_6$ alkyl optionally substituted by oxo, —OH, or halogen. In some embodiments of a compound of Formula (I), (Ia), (Ia-1), (Ia-2), (Ia-3), (Ia-4), (Ia-5) or (Ia-6), or (If), $R^3$ is —$C(O)R^{10}$ or 5- to 10-membered heteroaryl which is unsubstituted. In some embodiments of a compound of Formula (I), (Ia), (Ia-1), (Ia-2), (Ia-3), (Ia-4), (Ia-5) or (Ia-6), $R^3$ is —$C(O)R^{10}$ or 5- to 10-membered heteroaryl optionally substituted by halogen, oxo, —$OR^{13}$, —$NR^{13}R^{14}$, —$C(O)R^{13}$, —$C(O)NR^{13}R^{14}$, —$NR^{13}C(O)R^{14}$, —CN, —$S(O)R^{13}$, —$S(O)_2R^{13}$, —($C_1$-$C_3$ alkylene)$OR^{13}$, —($C_1$-$C_3$ alkylene)$NR^{13}R^{14}$, —($C_1$-$C_3$ alkylene)$C(O)R^{13}$, $C_3$-$C_8$ cycloalkyl, 3- to 12-membered heterocyclyl optionally substituted by oxo, —OH, or halogen, or $C_1$-$C_6$ alkyl optionally substituted by oxo, —OH, or halogen. In some embodiments of a compound of Formula (I), (Ia), (Ia-1), (Ia-2), (Ia-3), (Ia-4), (Ia-5) or (Ia-6), $R^3$ is —$C(O)R^{10}$ or 5- to 10-membered heteroaryl substituted by 3- to 12-membered heterocyclyl optionally substituted by oxo, —OH, or halogen, —CN, —($C_1$-$C_3$ alkylene)$NR^{13}R^{14}$, $C_3$-$C_8$ cycloalkyl, —$C(O)R^{13}$, —$NR^{13}R^{14}$, —$OR^{13}$, or $C_1$-$C_6$ alkyl optionally substituted by —OH or halogen. In some embodiments of a compound of Formula (I), (Ia), (Ia-1), (Ia-2), (Ia-3), (Ia-4), (Ia-5) or (Ia-6), $R^3$ is 5- to 10-membered heteroaryl substituted by 3- to 12-membered heterocyclyl optionally substituted by oxo, —OH, or halogen, —CN, —($C_1$-$C_3$ alkylene)$NR^{13}R^{14}$, $C_3$-$C_8$ cycloalkyl, —$C(O)R^{13}$, —$NR^{13}R^{14}$, —$OR^{13}$, or $C_1$-$C_6$ alkyl optionally substituted by —OH or halogen. In some embodiments of a compound of Formula (I), (Ia), (Ia-1), (Ia-2), (Ia-3), (Ia-4), (Ia-5) or (Ia-6), $R^3$ is 5- to 10-membered heteroaryl substituted by —$OR^{13}$ or $C_1$-$C_6$ alkyl, wherein the $C_1$-$C_6$ alkyl is optionally substituted by —OH.

In some embodiments of a compound of Formula (I), (Ia), (Ia-1 to Ia-6), (Ib), (Ib-1 to Ib-3), (Ic) or (Ic-1 to Ic-3), $R^3$ is —$C(O)R^{10}$ or 6-membered heteroaryl optionally substituted by halogen, oxo, —$OR^{13}$, —$NR^{13}R^{14}$, —$C(O)R^{13}$, —$C(O)OR^{13}$, —$C(O)N^{13}R^{14}$, —$NR^{13}C(O)R^{14}$, —CN, —$SR^{13}$, —$S(O)R^{13}$, —$S(O)_2R^{13}$, —$Si(C_1$-$C_6$ alkyl$)_3$, —$P(O)R^{13}R^{14}$, —$NR^{13}S(O)_2R^{14}$, —($C_1$-$C_3$ alkylene)$OR^{13}$, —($C_1$-$C_3$ alkylene)$NR^{13}R^{14}$, —($C_1$-$C_3$ alkylene)$C(O)R^{13}$, $C_3$-$C_8$ cycloalkyl optionally substituted by $C_1$-$C_6$ alkyl, CN, $CF_3$, oxo, —OH, —$NR^{15}R^{16}$, —$OR^{15}$ or halogen, 3- to 12-membered heterocyclyl optionally substituted by oxo, —OH, —$NR^{15}R^{16}$, —$C(O)OR^{15}$, —$OR^{15}$ or halogen, or $C_1$-$C_6$ alkyl optionally substituted by oxo, —OH, —$NR^{15}R^{16}$, —$C(O)OR^{15}$, —$OR^{15}$ or halogen, with the proviso that the 6-membered heteroaryl of $R^3$ is not substituted by

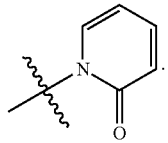

In some embodiments of a compound of Formula (I), (Ia), (Ia-1 to Ia-6), (Ib), (Ib-1 to Ib-3), (Ic) or (Ic-1 to Ic-3), $R^3$ is 6-membered heteroaryl optionally substituted by 3- to 12-membered heterocyclyl optionally substituted by oxo, —OH, —$NR^{15}R^{16}$, —$C(O)OR^{15}$, —$OR^{15}$ or halogen, —CN, —($C_1$-$C_3$ alkylene)$NR^{13}R^{14}$, $C_3$-$C_8$ cycloalkyl optionally substituted by $C_1$-$C_6$ alkyl, CN, $CF_3$, oxo, —OH, —$NR^{15}R^{16}$, —$OR^{15}$ or halogen, —$C(O)R^{13}$, —$NR^{13}R^{14}$, —$OR^{13}$, or $C_1$-$C_6$ alkyl optionally substituted by —OH, —$NR^{15}R^{16}$, —$OR^{15}$ or halogen, with the proviso that the 6-membered heteroaryl of $R^3$ is not substituted by

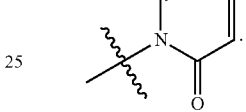

In some embodiments of a compound of Formula (I), (Ia), (Ia-1 to Ia-6), (Ib), (Ib-1 to Ib-3), (Ic) or (Ic-1 to Ic-3), $R^3$ is 6-membered heteroaryl optionally substituted by —$OR^{13}$ or $C_1$-$C_6$ alkyl, wherein the $C_1$-$C_6$ alkyl is optionally substituted by —OH or halogen.

In some embodiments of a compound of Formula (I), (Ia), (Ia-1), (Ia-2), (Ia-3), (Ia-4), (Ia-5) or (Ia-6), $R^3$ is —$C(O)R^{10}$ or 6-membered heteroaryl optionally substituted by halogen, oxo, —$OR^{13}$, —$NR^{13}R^{14}$, —$C(O)R^{13}$, —$C(O)NR^{13}R^{14}$, —$NR^{13}C(O)R^{14}$, —CN, —$S(O)R^{13}$, —$S(O)_2R^{13}$, —($C_1$-$C_3$ alkylene)$OR^{13}$, —($C_1$-$C_3$ alkylene)$NR^{13}R^{14}$, —($C_1$-$C_3$ alkylene)$C(O)R^{13}$, $C_3$-$C_8$ cycloalkyl, 3- to 12-membered heterocyclyl optionally substituted by oxo, —OH, or halogen, or $C_1$-$C_6$ alkyl optionally substituted by oxo, —OH, or halogen. In some embodiments of a compound of Formula (I), (Ia), (Ia-1), (Ia-2), (Ia-3), (Ia-4), (Ia-5) or (Ia-6), $R^3$ is 6-membered heteroaryl optionally substituted by 3- to 12-membered heterocyclyl optionally substituted by oxo, —OH, or halogen, —CN, —($C_1$-$C_3$ alkylene)$NR^{13}R^{14}$, $C_3$-$C_8$ cycloalkyl, —$C(O)R^{13}$, —$NR^{13}R^{14}$, —$OR^{13}$, or $C_1$-$C_6$ alkyl optionally substituted by —OH or halogen. In some embodiments of a compound of Formula (I), (Ia), (Ia-1), (Ia-2), (Ia-3), (Ia-4), (Ia-5) or (Ia-6), $R^3$ is 6-membered heteroaryl optionally substituted by —$OR^{13}$ or $C_1$-$C_6$ alkyl, wherein the $C_1$-$C_6$ alkyl is optionally substituted by —OH.

In some embodiments of a compound of Formula (I), (Ia), (Ia-1 to Ia-6), (Ib), (Ib-1 to Ib-3), (Ic) or (Ic-1 to Ic-3), $R^3$ is pyridinyl optionally substituted by halogen, oxo, —$OR^{13}$, —$NR^{13}R^{14}$, —$C(O)R^{13}$, —$C(O)NR^{13}R^{14}$, —$NR^{13}C(O)R^{14}$, —CN, —$S(O)R^{13}$, —$SR^{13}$, —$S(O)_2R^{13}$, —($C_1$-$C_3$ alkylene)$OR^{13}$, —($C_1$-$C_3$ alkylene)$NR^{13}R^{14}$, —($C_1$-$C_3$ alkylene)$C(O)R^{13}$, $C_3$-$C_8$ cycloalkyl optionally substituted by $C_1$-$C_6$ alkyl, CN, $CF_3$, oxo, —OH, —$NR^{15}R^{16}$, —$OR^{15}$ or halogen, 3- to 12-membered heterocyclyl optionally substituted by oxo, —$NR^{15}R^{16}$, —$C(O)OR^{15}$, —$OR^{15}$, —OH, or halogen, or $C_1$-$C_6$ alkyl optionally substituted by oxo, —OH, —$NR^{15}R^{16}$, —$C(O)OR^{15}$, —$OR^{15}$ or halogen.

In some embodiments of a compound of Formula (I), (Ia), (Ia-1 to Ia-6), (Ib), (Ib-1 to Ib-3), (Ic) or (Ic-1 to Ic-3), $R^3$ is pyridinyl optionally substituted by 3- to 12-membered heterocyclyl optionally substituted by oxo, —OH, or halogen, —CN, —($C_1$-$C_3$ alkylene)$NR^{13}R^{14}$, $C_3$-$C_8$ cycloalkyl optionally substituted by —OH or halogen, —C(O)$R^{13}$, —$NR^{13}R^{14}$, —$OR^{13}$, or $C_1$-$C_6$ alkyl optionally substituted by —OH or halogen, with the proviso that the pyridinyl of $R^3$ is not substituted by

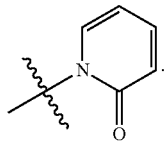 [SMILES: *n1ccccc1=O]

In some embodiments of a compound of Formula (I), (Ia), (Ia-1 to Ia-6), (Ib), (Ib-1 to Ib-3), (Ic) or (Ic-1 to Ic-3), $R^3$ is pyridinyl optionally substituted by —$OR^{13}$ or $C_1$-$C_6$ alkyl, wherein the $C_1$-$C_6$ alkyl is optionally substituted by —OH. In some embodiments of a compound of Formula (I), (Ia), (Ia-1 to Ia-6), (Ib), (Ib-1 to Ib-3), (Ic) or (Ic-1 to Ic-3), $R^3$ is pyridinyl substituted by $C_1$-$C_6$ alkyl, wherein the $C_1$-$C_6$ alkyl is optionally substituted by —OH. In some embodiments of a compound of Formula (I), (Ia), (Ia-1 to Ia-6), (Ib), (Ib-1 to Ib-3), (Ic) or (Ic-1 to Ic-3), $R^3$ is pyridinyl substituted by $C_1$-$C_6$ alkyl, wherein the $C_1$-$C_6$ alkyl is optionally substituted by halogen. In some embodiments of a compound of Formula (I), (Ia), (Ia-1 to Ia-6), (Ib), (Ib-1 to Ib-3), (Ic) or (Ic-1 to Ic-3), $R^3$ is pyridinyl substituted by $C_1$-$C_6$ alkyl, wherein the $C_1$-$C_6$ alkyl is tertiary butyl.

In some embodiments of a compound of Formula (I), (Ia), (Ia-1), (Ia-2), (Ia-3), (Ia-4), (Ia-5) or (Ia-6), $R^3$ is pyridinyl optionally substituted by halogen, oxo, —$OR^{13}$, —$NR^{13}R^{14}$, —C(O)$R^{13}$, —C(O)$NR^{13}R^{14}$, —$NR^{13}$C(O)$R^{14}$, —CN, —S(O)$R^{13}$, —S(O)$_2R^{13}$, —($C_1$-$C_3$ alkylene)$OR^{13}$, —($C_1$-$C_3$ alkylene)$NR^{13}R^{14}$, —($C_1$-$C_3$ alkylene)C(O)$R^{13}$, $C_3$-$C_8$ cycloalkyl, 3- to 12-membered heterocyclyl optionally substituted by oxo, —OH, or halogen, or $C_1$-$C_6$ alkyl optionally substituted by oxo, —OH, or halogen. In some embodiments of a compound of Formula (I), (Ia), (Ia-1), (Ia-2), (Ia-3), (Ia-4), (Ia-5) or (Ia-6), $R^3$ is pyridinyl optionally substituted by 3- to 12-membered heterocyclyl optionally substituted by oxo, —OH, or halogen, —CN, —($C_1$-$C_3$ alkylene)$NR^{13}R^{14}$, $C_3$-$C_8$ cycloalkyl, —C(O)$R^{13}$, —$NR^{13}R^{14}$, —$OR^{13}$, or $C_1$-$C_6$ alkyl optionally substituted by —OH or halogen. In some embodiments of a compound of Formula (I), (Ia), (Ia-1), (Ia-2), (Ia-3), (Ia-4), (Ia-5) or (Ia-6), $R^3$ is pyridinyl optionally substituted by —$OR^{13}$ or $C_1$-$C_6$ alkyl, wherein the $C_1$-$C_6$ alkyl is optionally substituted by —OH.

In some embodiments of a compound of Formula (I), (Ia), (Ia-1 to Ia-12), (Ib), (Ib-1 to Ib-9), (Ic) or (Ic-1 to Ic-9), $R^2$ is selected from the group consisting of:

methyl, ethyl, isopropyl, cyclopropyl, cyclobutyl,

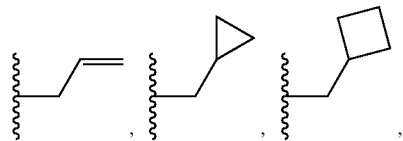

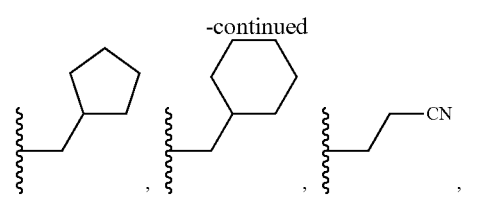

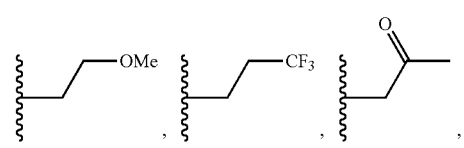

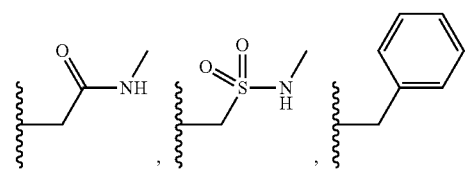

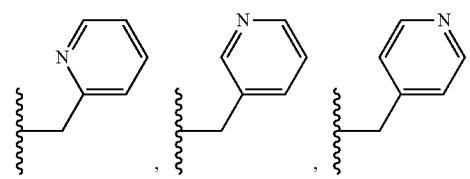

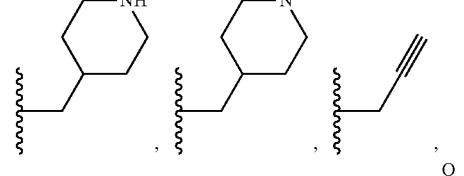

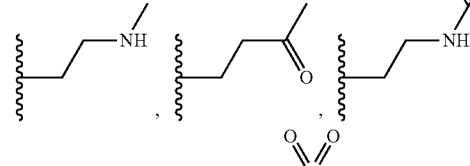

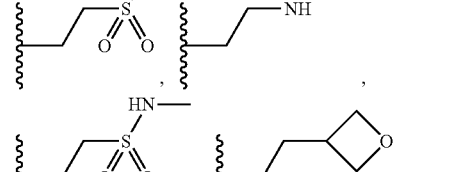

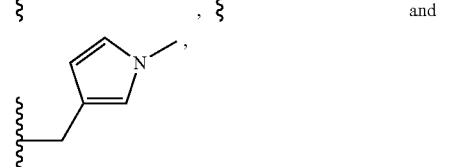

and

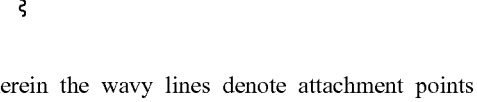

wherein the wavy lines denote attachment points to the parent molecule.

In some embodiments of a compound of Formula (I), (Ia), (Ia-1), (Ia-2), (Ia-3), (Ia-4), (Ia-5) or (Ia-6), R² is selected from the group consisting of:
methyl, ethyl, isopropyl, cyclopropyl,
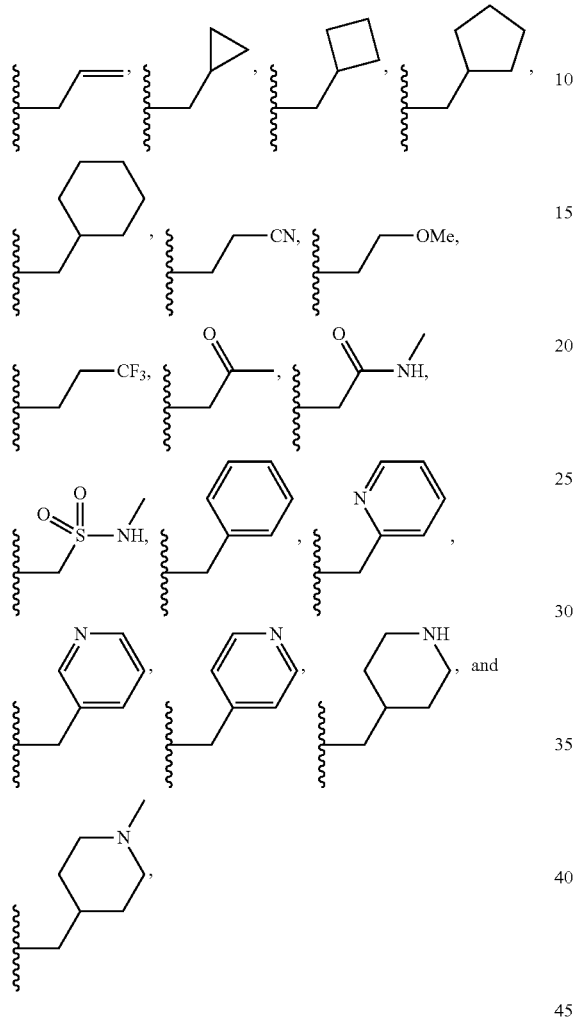
wherein the wavy lines denote attachment points to the parent molecule.
In some embodiments of a compound of Formula (I), (Ia), (Ia-1 to Ia-6), (Ib), (Ib-1 to Ib-3), (Ic) or (Ic-1 to Ic-3), R³ is selected from the group consisting of:
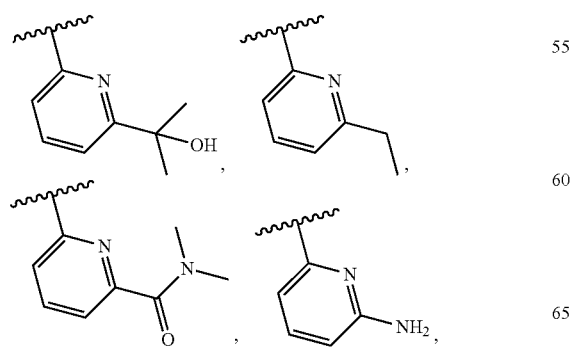
-continued
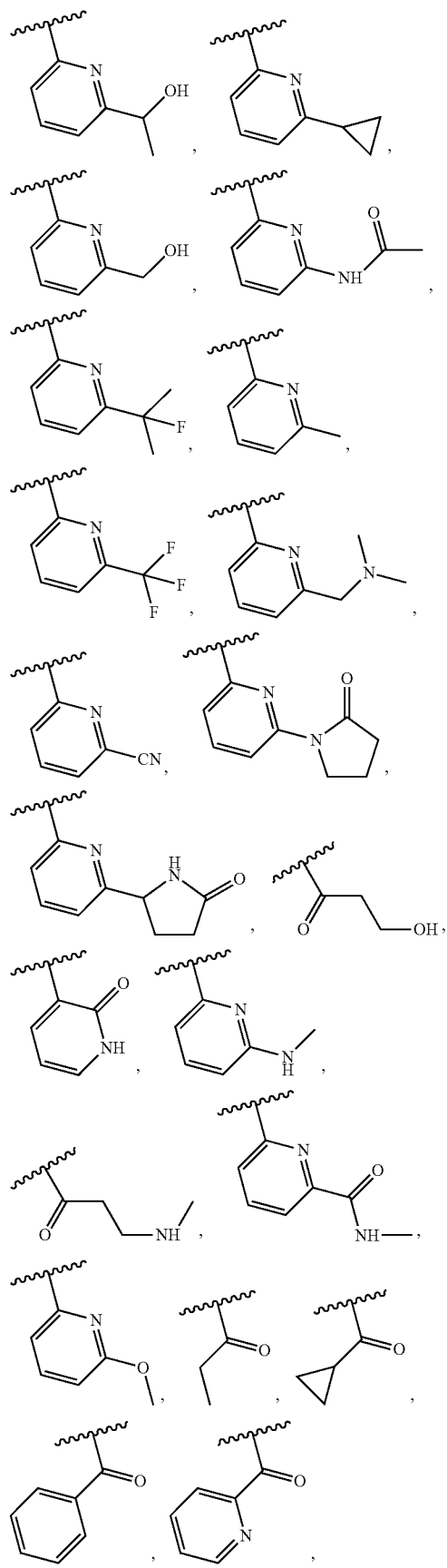

101
-continued
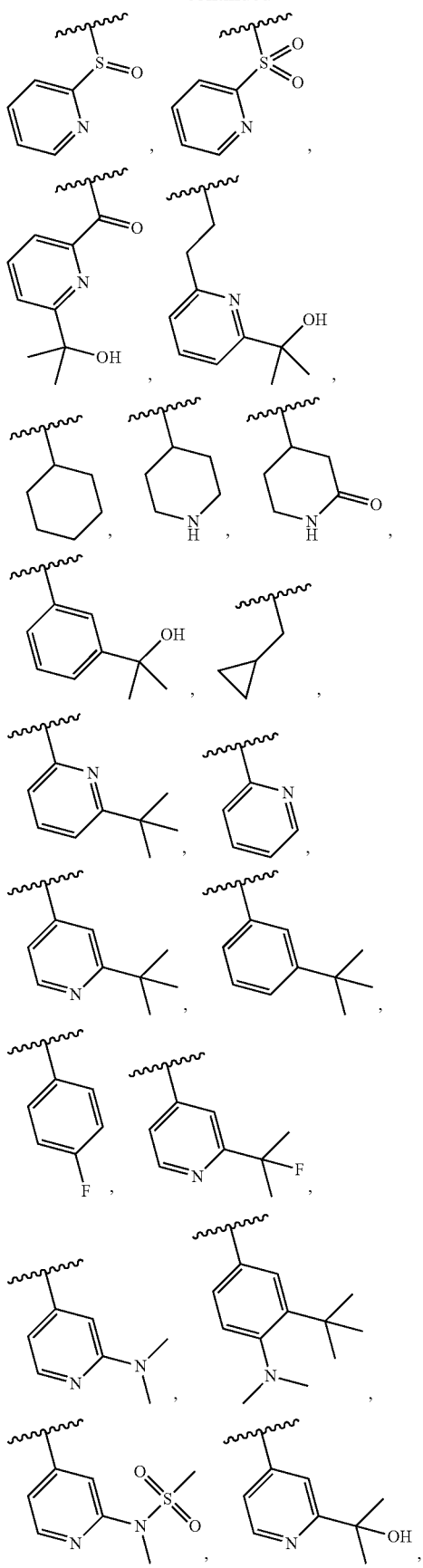
102
-continued
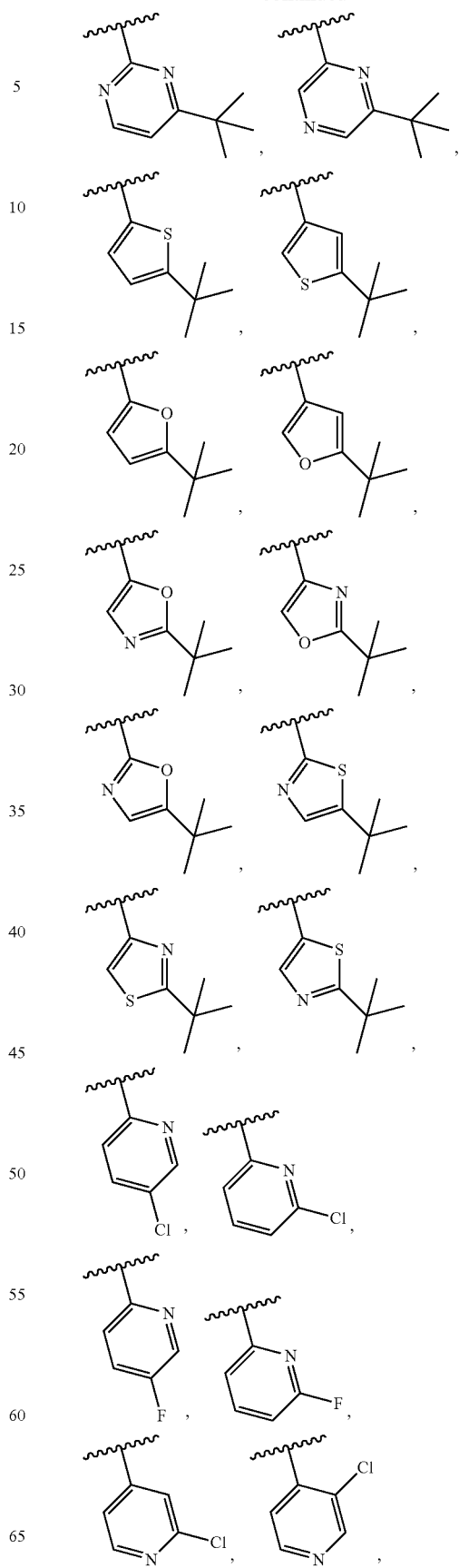

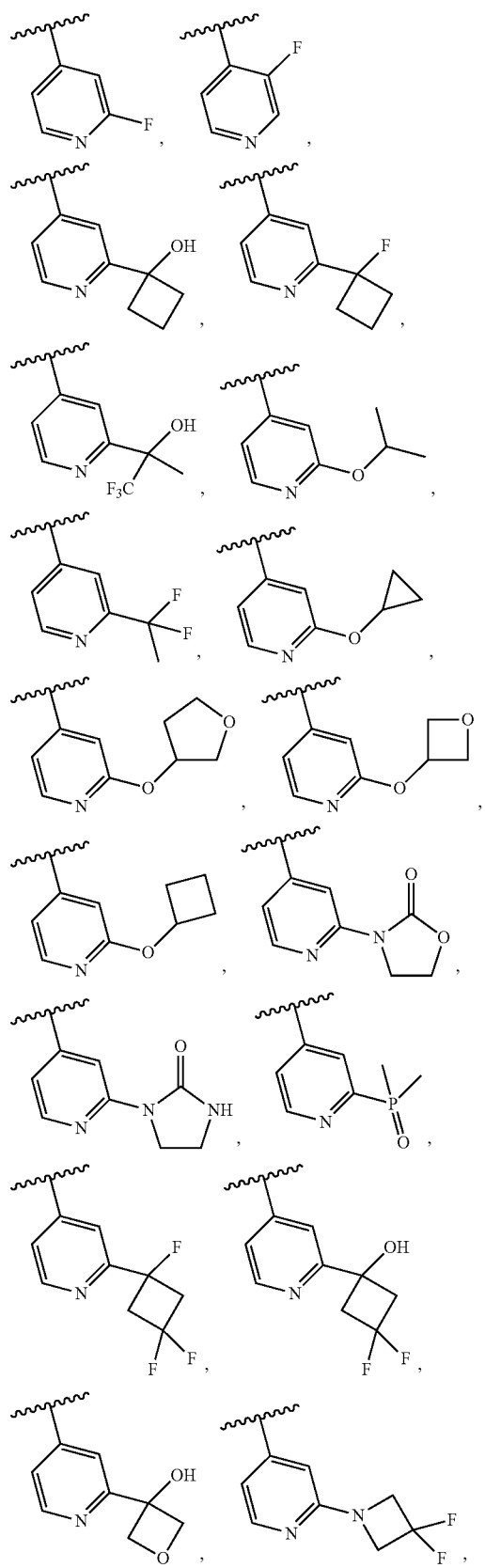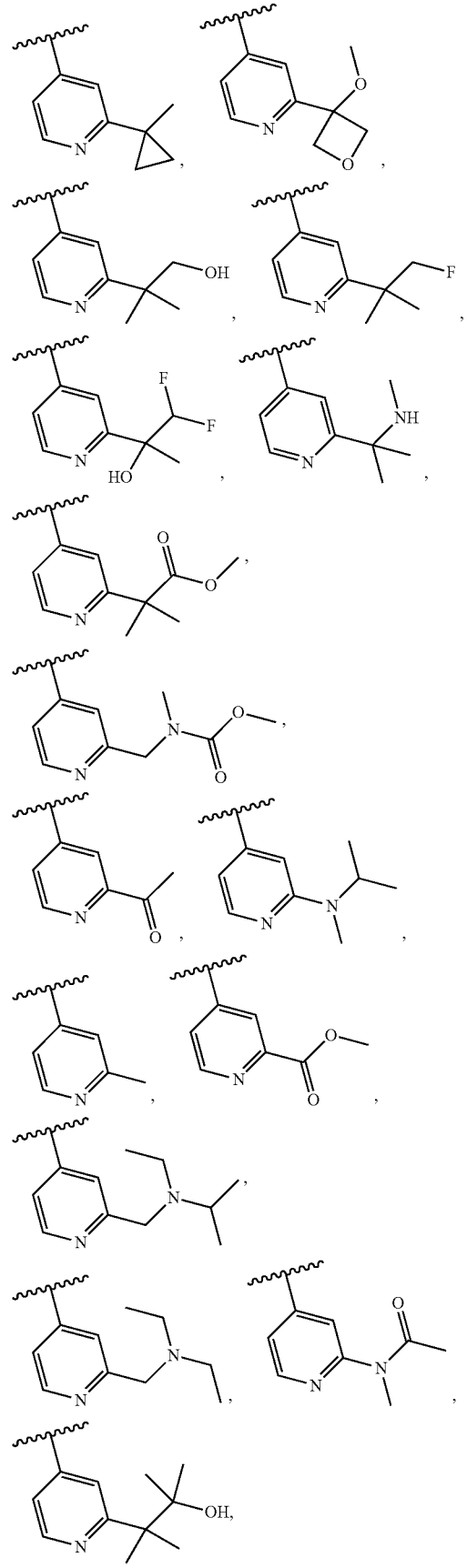

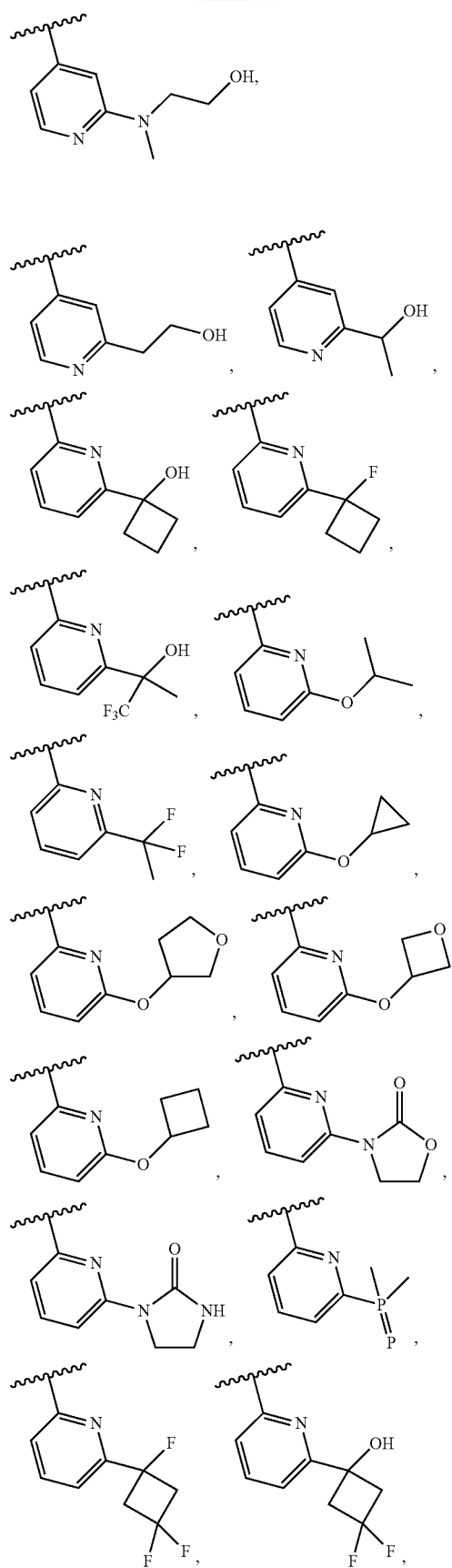
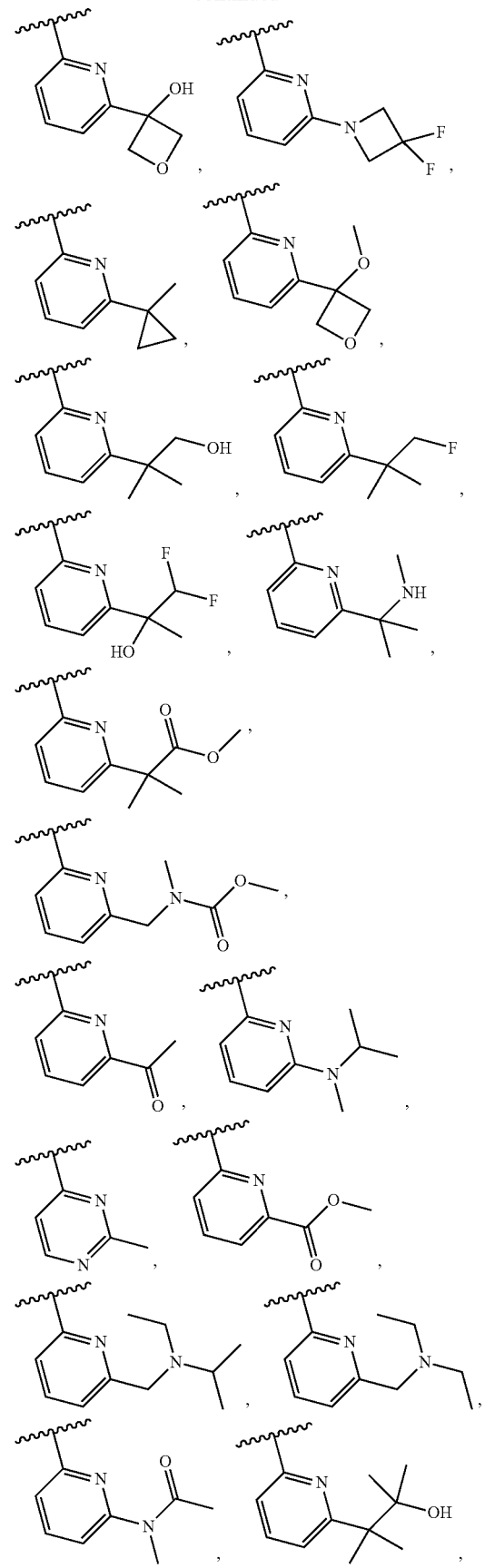

-continued
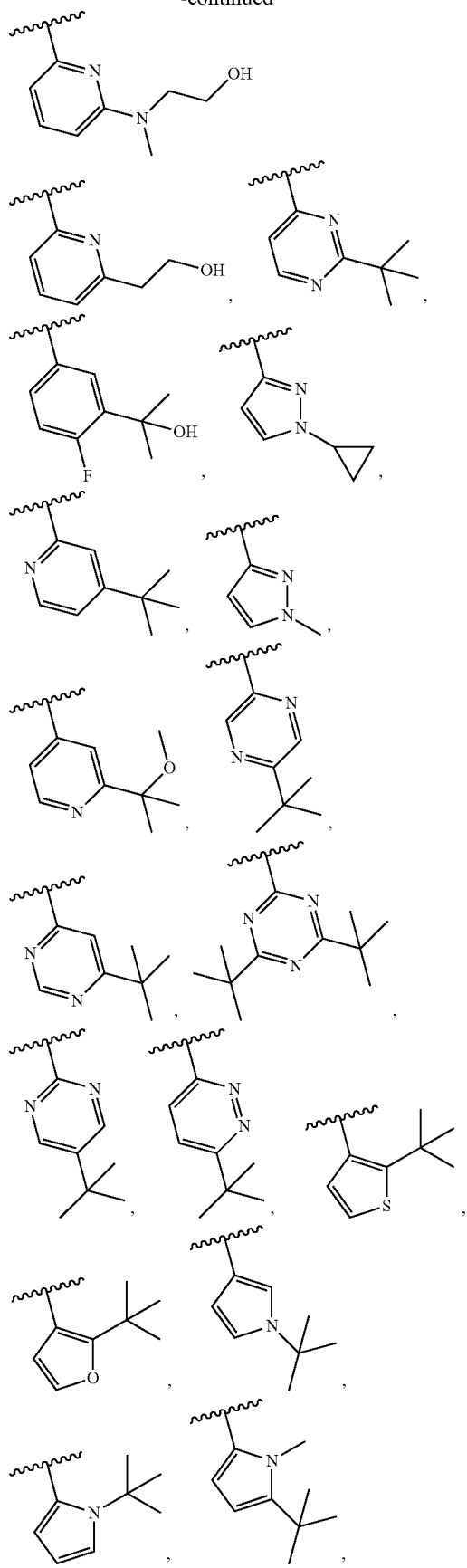
-continued
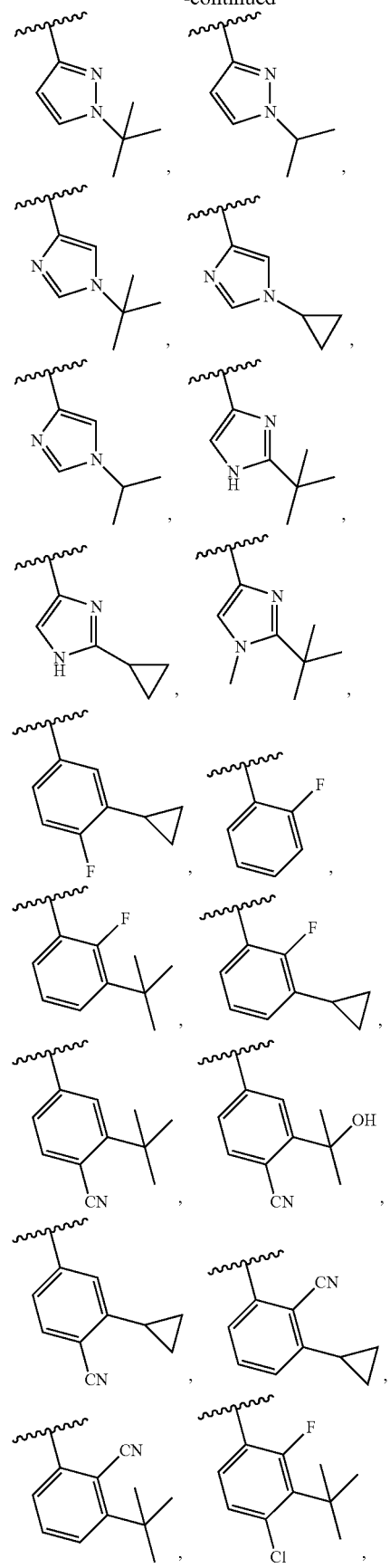

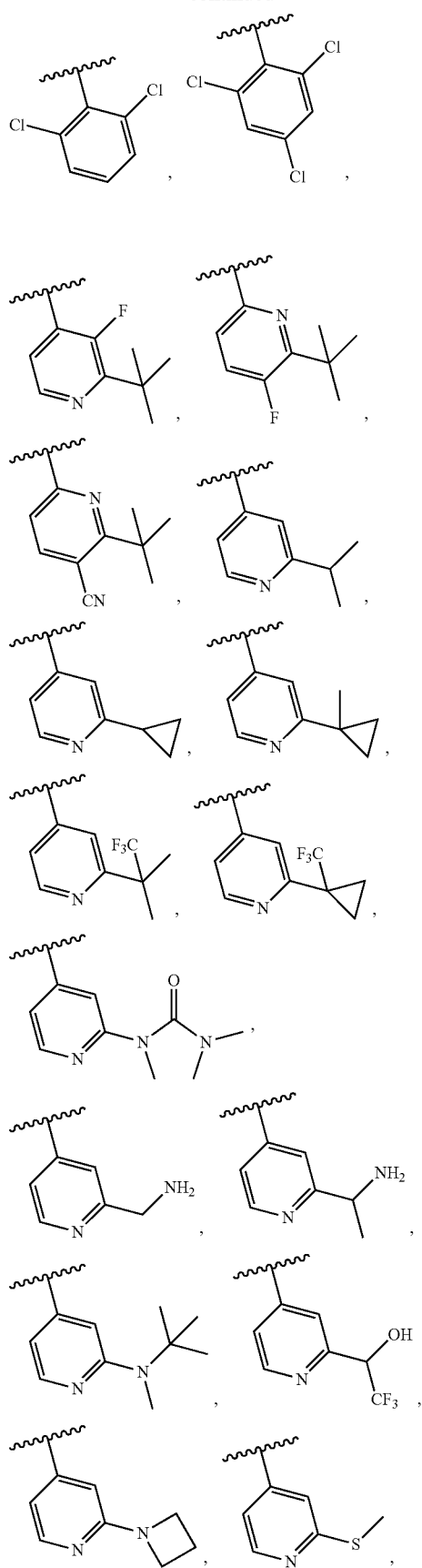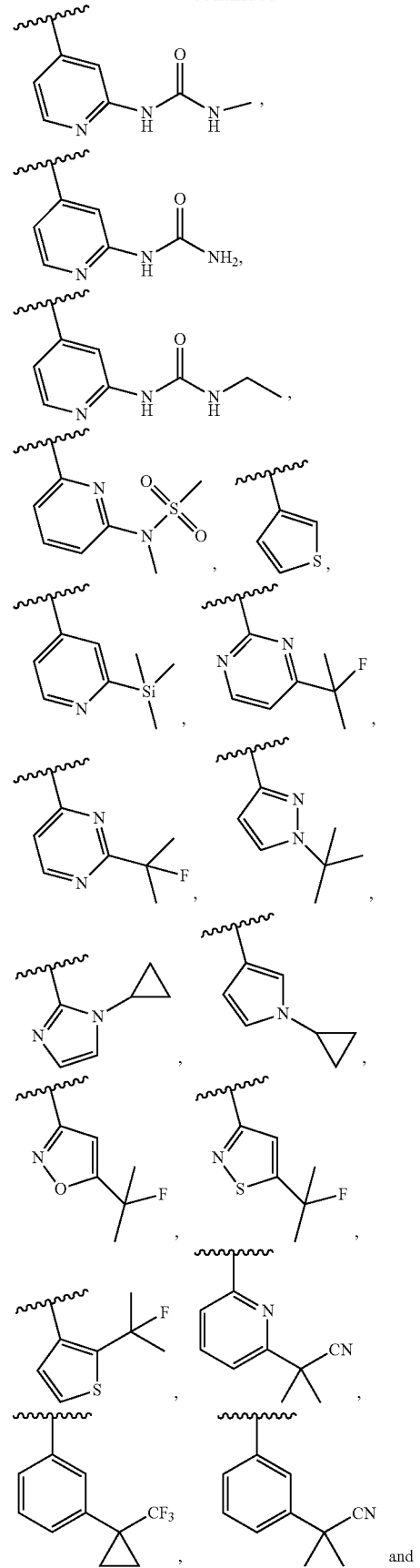

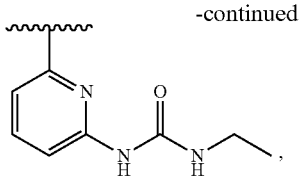

wherein the wavy lines denote attachment points to the parent molecule.

In some embodiments of a compound of Formula (I), (Ia), (Ia-1), (Ia-2), (Ia-3), (Ia-4), (Ia-5) or (Ia-6), $R^3$ is selected from the group consisting of:

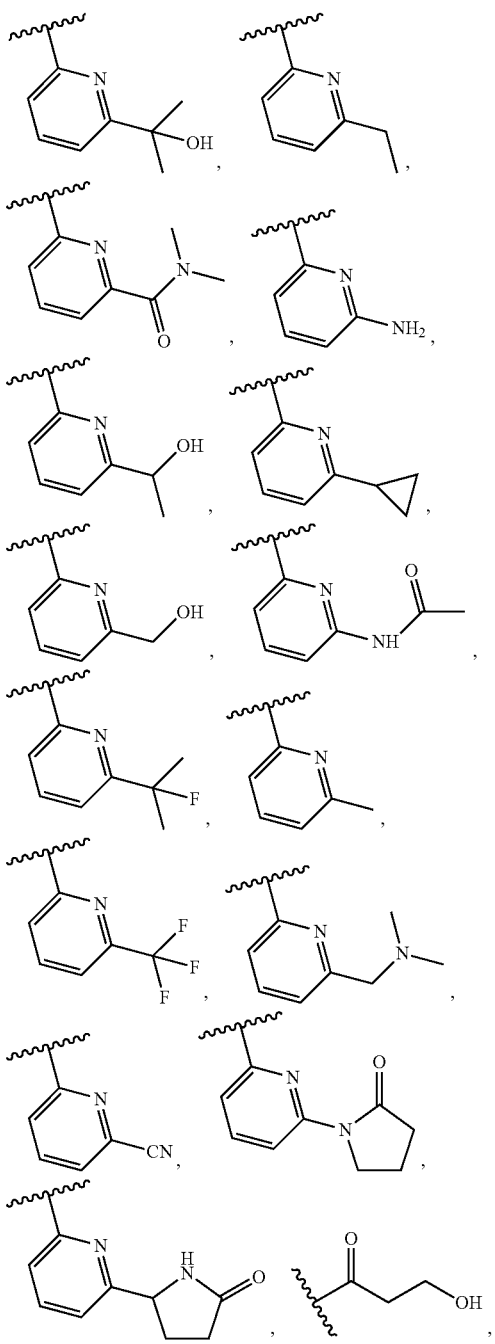

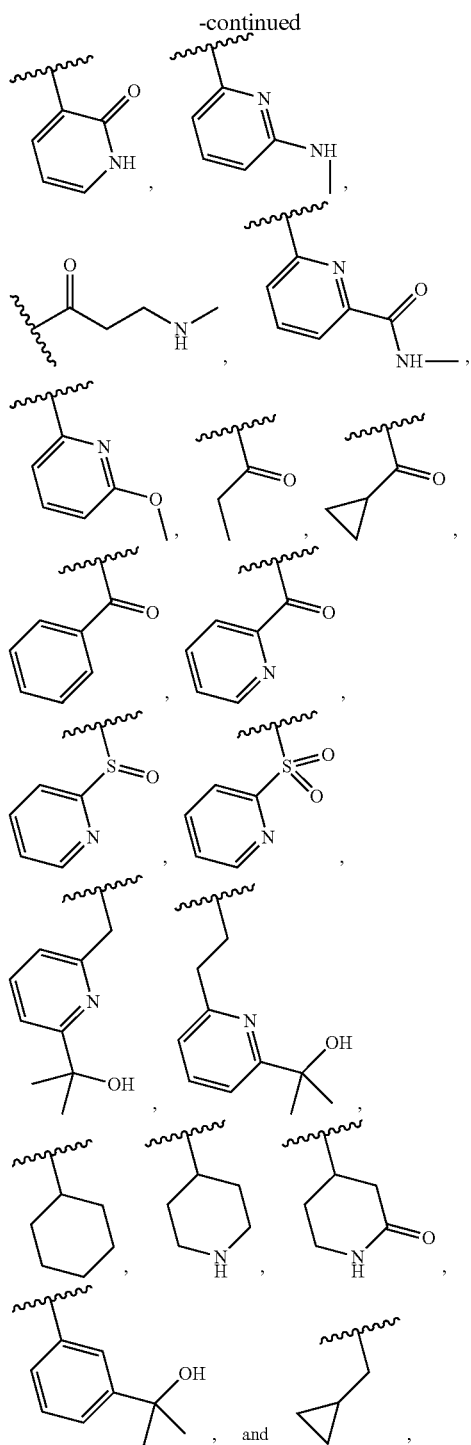

wherein the wavy lines denote attachment points to the parent molecule.

In some embodiments of a compound of Formula (I), A is unsubstituted phenyl fused with B, wherein B is $C_6$ aryl, 5- to 7-membered heteroaryl, $C_3$-$C_8$ cycloalkyl, or 3- to 8-membered heterocyclyl, each of which is substituted with $R^4$; $R^4$ is independently oxo, $C_1$-$C_6$ alkyl, $C_2$-$C_6$ alkenyl, $C_2$-$C_6$ alkynyl, halogen, —C(O)$R^{17}$, —C(O)O$R^{17}$, —C(O)N$R^{17}R^{18}$, —CN, —Si($C_1$-$C_6$ alkyl)$_3$, —O$R^{17}$, —N$R^{17}R^{18}$, —OC(O)N$R^{17}R^{18}$, —N$R^{17}$C(O)$R^{18}$, —S(O)$_2R^{17}$, —N$R^{17}$S(O)$_2R^{18}$, —S(O)$_2$N$R^{17}R^{18}$, $C_3$-$C_6$ cycloalkyl, 3- to 6-membered heterocyclyl, —(C$_1$-C$_3$ alkylene)CN, —(C$_1$-C$_3$ alkylene)OR$^{17}$, —(C$_1$-C$_3$ alkylene)NR$^{17}$R$^{18}$, —(C$_1$-C$_3$ alkylene)CF$_3$, —(C$_1$-C$_3$ alkylene)C(O)R$^{17}$, —(C$_1$-C$_3$ alkylene)C(O)NR$^{17}$R$^{18}$, —(C$_1$-C$_3$ alkylene)NR$^{17}$C(O)R$^{18}$, —(C$_1$-C$_3$ alkylene)S(O)$_2$R$^{17}$, —(C$_1$-C$_3$ alkylene)NR$^{17}$S(O)$_2$R$^{18}$, —(C$_1$-C$_3$ alkylene)S(O)$_2$NR$^{17}$R$^{18}$, —(C$_1$-C$_3$ alkylene)(C$_3$-C$_6$ cycloalkyl) or —(C$_1$-C$_3$ alkylene)(3- to 6-membered heterocyclyl), wherein each R$^4$ is independently optionally substituted by halogen, oxo, —OR$^{19}$, —NR$^{19}$R$^{20}$, or —C(O)R$^{19}$; or two R$^4$, when bound to the same carbon or two different carbon atoms, are taken together with the carbon or carbons to which they are attached to form a C$_3$-C$_6$ cycloalkyl or 3- to 7-membered heterocyclyl, each is optionally substituted by R$^{19}$; R$^2$ is C$_1$-C$_6$ alkyl, C$_3$-C$_6$ cycloalkyl, C$_2$-C$_6$ alkenyl, or —(C$_1$-C$_3$ alkylene)(C$_3$-C$_6$ cycloalkyl); R$^3$ is hydrogen, C$_1$-C$_6$ alkyl, —C(O)R$^{10}$, —(C$_1$-C$_3$ alkylene)(C$_3$-C$_6$ cycloalkyl), —(C$_1$-C$_3$ alkylene)(3- to 12-membered heterocyclyl), —(C$_1$-C$_3$ alkylene)(5- to 10-membered heteroaryl), —S(O)R$^{10}$, —S(O)$_2$R$^{10}$, or 5- to 10-membered heteroaryl, each of which is optionally substituted by halogen, oxo, —OR$^{13}$, —NR$^{13}$R$^{14}$, —C(O)R$^{13}$, —C(O)OR$^{13}$, —CN, —SR$^{13}$, —S(O)R$^{13}$, —S(O)$_2$R$^{13}$, —Si(C$_1$-C$_6$ alkyl)$_3$, —P(O)R$^{13}$R$^{14}$, —NR$^{13}$S(O)$_2$R$^{14}$, —(C$_1$-C$_3$ alkylene)OR$^{13}$, —(C$_1$-C$_3$ alkylene)NR$^{13}$R$^{14}$, —(C$_1$-C$_3$ alkylene)C(O)R$^{13}$, C$_3$-C$_8$ cycloalkyl optionally substituted by C$_1$-C$_6$ alkyl, CN, CF$_3$, oxo, —OH, —NR$^{15}$R$^{16}$, —OR$^{15}$ or halogen, 3- to 12-membered heterocyclyl optionally substituted by oxo, —OH, —NR$^{15}$R$^{16}$, —C(O)OR$^{15}$, —OR$^{15}$ or halogen, or C$_1$-C$_6$ alkyl optionally substituted by oxo, —OH, —NR$^{15}$R$^{16}$, —C(O)OR$^{15}$, —OR$^{15}$, or halogen, with the proviso that the 5- to 10-membered heteroaryl of R$^3$ is not substituted by

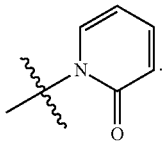 [SMILES: *n1ccccc1=O]

In some embodiments of a compound of Formula (I), A is unsubstituted phenyl fused with B, wherein B is C$_6$ aryl, 3- to 7-membered heteroaryl, C$_3$-C$_8$ cycloalkyl, or 3- to 8-membered heterocyclyl, each of which is substituted with R$^4$; R$^4$ is independently oxo, C$_1$-C$_6$ alkyl, C$_2$-C$_6$ alkenyl, C$_2$-C$_6$ alkynyl, —C(O)R$^{17}$, —C(O)OR$^{17}$, or —C(O)NR$^{17}$R$^{18}$, wherein each R$^4$ is independently optionally substituted by halogen, oxo, —OR$^{19}$, —NR$^{19}$R$^{20}$, or —C(O)R$^{19}$; or two R$^4$, when bound to the same carbon or two different carbon atoms, are taken together with the carbon or carbons to which they are attached to form a C$_3$-C$_6$ cycloalkyl or 3- to 7-membered heterocyclyl, each is optionally substituted by R$^{19}$; R$^2$ is C$_1$-C$_6$ alkyl, C$_3$-C$_6$ cycloalkyl, C$_2$-C$_6$ alkenyl, or —(C$_1$-C$_3$ alkylene)(C$_3$-C$_6$ cycloalkyl); R$^3$ is —C(O)R$^{10}$ or 5- to 10-membered heteroaryl optionally substituted by halogen, oxo, —OR$^{13}$, —NR$^{13}$R$^{14}$, —C(O)R$^{13}$, —C(O)NR$^{13}$R$^{14}$, —NR$^{13}$C(O)R$^{14}$, —CN, —SR$^{13}$, —S(O)R$^{13}$, —S(O)$_2$R$^{13}$, —(C$_1$-C$_3$ alkylene)OR$^{13}$, —(C$_1$-C$_3$ alkylene)NR$^{13}$R$^{14}$, —(C$_1$-C$_3$ alkylene)C(O)R$^{13}$, C$_3$-C$_8$ cycloalkyl optionally substituted by oxo, —OH or halogen, 3- to 12-membered heterocyclyl optionally substituted by oxo, —OH, or halogen, or C$_1$-C$_6$ alkyl optionally substituted by oxo, —OH, or halogen, with the proviso that the 5- to 10-membered heteroaryl of R$^3$ is not substituted by

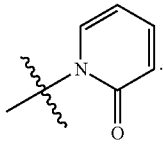

In some embodiments of a compound of Formula (I), A is unsubstituted phenyl fused with B, wherein B is 3- to 8-membered heterocyclyl optionally substituted with R$^4$; R$^4$ is independently oxo, C$_1$-C$_6$ alkyl, or —C(O)R$^{17}$, wherein the C$_1$-C$_6$ alkyl or —C(O)R$^{17}$ is optionally substituted by —OR$^{19}$ or —NR$^{19}$R$^{20}$; or two R$^4$, when bound to the same carbon or two different carbon atoms, are taken together with the carbon to which they are attached to form a C$_3$-C$_6$ cycloalkyl or 3- to 7-membered heterocyclyl, each is optionally substituted by R$^{19}$; R$^2$ is C$_1$-C$_6$ alkyl, C$_3$-C$_6$ cycloalkyl, C$_2$-C$_6$ alkenyl, or —(C$_1$-C$_3$ alkylene)(C$_3$-C$_6$ cycloalkyl); R$^3$ is 5- to 10-membered heteroaryl substituted by 3- to 12-membered heterocyclyl optionally substituted by oxo, —OH, or halogen, —CN, —(C$_1$-C$_3$ alkylene)NR$^{13}$R$^{14}$, C$_3$-C$_8$ cycloalkyl optionally substituted by oxo, —OH or halogen, —C(O)R$^{13}$, —NR$^{13}$R$^{14}$, —OR$^{13}$, or C$_1$-C$_6$ alkyl optionally substituted by —OH or halogen, with the proviso that the 5- to 10-membered heteroaryl of R$^3$ is not substituted by

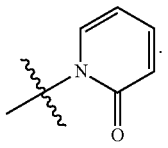

In some embodiments of a compound of Formula (I), A is unsubstituted phenyl fused with B, wherein B is 6-membered heterocyclyl having one nitrogen atom, wherein the 6-membered heterocyclyl is optionally substituted by R$^4$; R$^4$ is independently C$_1$-C$_6$ alkyl; R$^2$ is C$_1$-C$_6$ alkyl, C$_3$-C$_6$ cycloalkyl, C$_2$-C$_6$ alkenyl, or —(C$_1$-C$_3$ alkylene)(C$_3$-C$_6$ cycloalkyl); R$^3$ is 5- to 10-membered heteroaryl substituted by 3- to 12-membered heterocyclyl optionally substituted by oxo, —OH, or halogen, —CN, —(C$_1$-C$_3$ alkylene)NR$^{13}$R$^{14}$, C$_3$-C$_8$ cycloalkyl optionally substituted by oxo, —OH or halogen, —C(O)R$^{13}$, —NR$^{13}$R$^{14}$, —OR$^{13}$, or C$_1$-C$_6$ alkyl optionally substituted by —OH or halogen, with the proviso that the 5- to 10-membered heteroaryl of R$^3$ is not substituted by

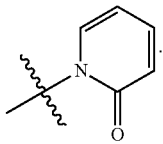 [SMILES: *n1ccccc1=O]

In some embodiments of a compound of Formula (I), A is unsubstituted phenyl fused with B, wherein B is 6-membered heterocyclyl having one nitrogen atom, wherein the 6-membered heterocyclyl is optionally substituted by R$^4$; R$^4$ is independently C$_1$-C$_6$ alkyl; R$^2$ is selected from the group consisting of: allyl, cyclopropylmethyl, isopropyl, cyclopropyl, ethyl, and propyl; R$^3$ is 5- to 10-membered heteroaryl substituted by —OR$^{13}$ or C$_1$-C$_6$ alkyl, wherein the C$_1$-C$_6$ alkyl is optionally substituted by —OH or halogen.

In some embodiments of a compound of Formula (I), A is unsubstituted phenyl fused with B, wherein B is C$_6$-C$_{14}$ aryl, 5- to 10-membered heteroaryl, C$_3$-C$_8$ cycloalkyl, or 3- to 12-membered heterocyclyl, each of which is substituted with R$^4$; R$^4$ is independently oxo, C$_1$-C$_6$ alkyl, C$_2$-C$_6$ alkenyl, C$_2$-C$_6$ alkynyl, —C(O)R$^{17}$, —C(O)OR$^{17}$, or —C(O)NR$^{17}$R$^{18}$, wherein each R$^4$ is independently optionally substituted by halogen, oxo, —OR$^{19}$, —NR$^{19}$R$^{20}$, or —C(O)R$^{19}$; or two R$^4$ are taken together with the carbon to which they attach to form a C$_3$-C$_6$ cycloalkyl; R$^2$ is C$_1$-C$_6$ alkyl, C$_3$-C$_6$ cycloalkyl, C$_2$-C$_6$ alkenyl, or —(C$_1$-C$_3$ alkylene)(C$_3$-C$_6$ cycloalkyl); R$^3$ is hydrogen, C$_1$-C$_6$ alkyl, —C(O)R$^{10}$, —(C$_1$-C$_3$ alkylene)(C$_3$-C$_6$ cycloalkyl), —(C$_1$-C$_3$ alkylene)(3- to 12-membered heterocyclyl), —(C$_1$-C$_3$ alkylene)(5- to 10-membered heteroaryl), —S(O)R$^{10}$, —S(O)$_2$R$^{10}$, or 5- to 10-membered heteroaryl, each of which is optionally substituted by halogen, oxo, —OR$^{13}$, —NR$^{13}$R$^{14}$, —C(O)R$^{13}$, —CN, —S(O)R$^{13}$, —S(O)$_2$R$^{13}$, —(C$_1$-C$_3$ alkylene)OR$^{13}$, —(C$_1$-C$_3$ alkylene)NR$^{13}$R$^{14}$, —(C$_1$-C$_3$ alkylene)C(O)R$^{13}$, C$_3$-C$_8$ cycloalkyl, 3- to 12-membered heterocyclyl optionally substituted by oxo, —OH, or halogen, or C$_1$-C$_6$ alkyl optionally substituted by oxo, —OH, or halogen. In some embodiments of a compound of Formula (I), A is unsubstituted phenyl fused with B, wherein B is C$_6$-C$_{14}$ aryl, 5- to 10-membered heteroaryl, C$_3$-C$_8$ cycloalkyl, or 3- to 12-membered heterocyclyl, each of which is substituted with R$^4$; R$^4$ is independently oxo, C$_1$-C$_6$ alkyl, C$_2$-C$_6$ alkenyl, C$_2$-C$_6$ alkynyl, —C(O)R$^{17}$, —C(O)OR$^{17}$, or —C(O)NR$^{17}$R$^{18}$, wherein each R$^4$ is independently optionally substituted by halogen, oxo, —OR$^{19}$, —NR$^{19}$R$^{20}$, or —C(O)R$^{19}$; or two R$^4$ are taken together with the carbon to which they attach to form a C$_3$-C$_6$ cycloalkyl; R$^2$ is C$_1$-C$_6$ alkyl, C$_3$-C$_6$ cycloalkyl, C$_2$-C$_6$ alkenyl, or —(C$_1$-C$_3$ alkylene)(C$_3$-C$_6$ cycloalkyl); R$^3$ is —C(O)R$^{10}$ or 5- to 10-membered heteroaryl optionally substituted by halogen, oxo, —OR$^{13}$, —NR$^{13}$R$^{14}$, —C(O)R$^{13}$, —C(O)NR$^{13}$R$^{14}$, —NR$^{13}$C(O)R$^{14}$, —CN, —S(O)R$^{13}$, —S(O)$_2$R$^{13}$, —(C$_1$-C$_3$ alkylene)OR$^{13}$, —(C$_1$-C$_3$ alkylene)NR$^{13}$R$^{14}$, —(C$_1$-C$_3$ alkylene)C(O)R$^{13}$, C$_3$-C$_8$ cycloalkyl, 3- to 12-membered heterocyclyl optionally substituted by oxo, —OH, or halogen, or C$_1$-C$_6$ alkyl optionally substituted by oxo, —OH, or halogen. In some embodiments of a compound of Formula (I), A is unsubstituted phenyl fused with B, wherein B is 3- to 12-membered heterocyclyl optionally substituted with R$^4$; R$^4$ is independently oxo, C$_1$-C$_6$ alkyl, or —C(O)R$^{17}$, wherein the C$_1$-C$_6$ alkyl or —C(O)R$^{17}$ is optionally substituted by —OR$^{19}$ or —NR$^{19}$R$^{20}$; or two R$^4$ are taken together with the carbon to which they attach to form a C$_3$-C$_6$ cycloalkyl; R$^2$ is C$_1$-C$_6$ alkyl, C$_3$-C$_6$ cycloalkyl, C$_2$-C$_6$ alkenyl, or —(C$_1$-C$_3$ alkylene)(C$_3$-C$_6$ cycloalkyl); R$^3$ is 5- to 10-membered heteroaryl substituted by 3- to 12-membered heterocyclyl optionally substituted by oxo, —OH, or halogen, —CN, —(C$_1$-C$_3$ alkylene)NR$^{13}$R$^{14}$, C$_3$-C$_8$ cycloalkyl, —C(O)R$^{13}$, —NR$^{13}$R$^{14}$, —OR$^{13}$, or C$_1$-C$_6$ alkyl optionally substituted by —OH or halogen. In some embodiments of a compound of Formula (I), A is unsubstituted phenyl fused with B, wherein B is 6-membered heterocyclyl having one nitrogen atom, wherein the 6-membered heterocyclyl is optionally substituted by R$^4$; R$^4$ is independently C$_1$-C$_6$ alkyl; R$^2$ is C$_1$-C$_6$ alkyl, C$_3$-C$_6$ cycloalkyl, C$_2$-C$_6$ alkenyl, or —(C$_1$-C$_3$ alkylene)(C$_3$-C$_6$ cycloalkyl); R$^3$ is 5- to 10-membered heteroaryl substituted by 3- to 12-membered heterocyclyl optionally substituted by oxo, —OH, or halogen, —CN, —(C$_1$-C$_3$ alkylene)NR$^{13}$R$^{14}$, C$_3$-C$_8$ cycloalkyl, —C(O)R$^{13}$, —NR$^{13}$R$^{14}$, —OR$^{13}$, or C$_1$-C$_6$ alkyl optionally substituted by —OH or halogen. In some embodiments of a compound of Formula (I), A is unsubstituted phenyl fused with B, wherein B is 6-membered heterocyclyl having one nitrogen atom, wherein the 6-membered heterocyclyl is optionally substituted by R$^4$; R$^4$ is independently C$_1$-C$_6$ alkyl; R$^2$ is selected from the group consisting of: allyl, cyclopropylmethyl, isopropyl, cyclopropyl, ethyl, and propyl; R$^3$ is 5- to 10-membered heteroaryl substituted by —OR$^{13}$ or C$_1$-C$_6$ alkyl, wherein the C$_1$-C$_6$ alkyl is optionally substituted by —OH.

In some embodiments of a compound of Formula (I), A is phenyl optionally substituted by R$^1$ and fused with B, wherein R$^1$ is independently —CN, C$_1$-C$_6$ alkyl, or halogen; B is C$_6$ aryl, 5- to 7-membered heteroaryl, C$_3$-C$_8$ cycloalkyl, or 3- to 8-membered heterocyclyl, each of which is substituted with R$^4$; R$^4$ is independently oxo, C$_1$-C$_6$ alkyl, C$_2$-C$_6$ alkenyl, C$_2$-C$_6$ alkynyl, halogen, —C(O)R$^{17}$, —C(O)OR$^{17}$, —C(O)NR$^{17}$R$^{18}$, —CN, —Si(C$_1$-C$_6$ alkyl)$_3$, —OR$^{17}$, —NR$^{17}$R$^{18}$, —OC(O)NR$^{17}$R$^{18}$, —NR$^{17}$C(O)R$^{18}$, —S(O)$_2$R$^{17}$, —NR$^{17}$S(O)$_2$R$^{18}$, —S(O)$_2$NR$^{17}$R$^{18}$, C$_3$-C$_6$ cycloalkyl, 3- to 6-membered heterocyclyl, —(C$_1$-C$_3$ alkylene)CN, —(C$_1$-C$_3$ alkylene)OR$^{17}$, —(C$_1$-C$_3$ alkylene)NR$^{17}$R$^{18}$, —(C$_1$-C$_3$ alkylene)CF$_3$, —(C$_1$-C$_3$ alkylene)C(O)R$^{17}$, —(C$_1$-C$_3$ alkylene)C(O)NR$^{17}$R$^{18}$, —(C$_1$-C$_3$ alkylene)NR$^{17}$C(O)R$^{18}$, —(C$_1$-C$_3$ alkylene)S(O)$_2$R$^{17}$, —(C$_1$-C$_3$ alkylene)NR$^{17}$S(O)$_2$R$^{18}$, —(C$_1$-C$_3$ alkylene)S(O)$_2$NR$^{17}$R$^{18}$, —(C$_1$-C$_3$ alkylene)(C$_3$-C$_6$ cycloalkyl) or —(C$_1$-C$_3$ alkylene)(3- to 6-membered heterocyclyl), wherein each R$^4$ is independently optionally substituted by halogen, oxo, —OR$^{19}$, —NR$^{19}$R$^{20}$, or —C(O)R$^{19}$; or two R$^4$, when bound to the same carbon or two different carbon atoms, are taken together with the carbon or carbons to which they are attached to form a C$_3$-C$_6$ cycloalkyl or 3- to 7-membered heterocyclyl, each is optionally substituted by R$^{19}$; R$^2$ is C$_1$-C$_6$ alkyl, C$_3$-C$_6$ cycloalkyl, C$_2$-C$_6$ alkenyl, or —(C$_1$-C$_3$ alkylene)(C$_3$-C$_6$ cycloalkyl); R$^3$ is hydrogen, C$_1$-C$_6$ alkyl, —C(O)R$^{10}$, —(C$_1$-C$_3$ alkylene)(C$_3$-C$_6$ cycloalkyl), —(C$_1$-C$_3$ alkylene)(3- to 12-membered heterocyclyl), —(C$_1$-C$_3$ alkylene)(5- to 10-membered heteroaryl), —S(O)R$^{10}$, —S(O)$_2$R$^{10}$, or 5- to 10-membered heteroaryl, each of which is optionally substituted by halogen, oxo, —OR$^{13}$, —NR$^{13}$R$^{14}$, —C(O)R$^{13}$, —C(O)OR$^{13}$, —CN, —SR$^{13}$, —S(O)R$^{13}$, —S(O)$_2$R$^{13}$, —Si(C$_1$-C$_6$ alkyl)$_3$, —P(O)R$^{13}$R$^{14}$, —NR$^{13}$S(O)$_2$R$^{14}$, —(C$_1$-C$_3$ alkylene)OR$^{13}$, —(C$_1$-C$_3$ alkylene)NR$^{13}$R$^{14}$, —(C$_1$-C$_3$ alkylene)C(O)R$^{13}$, C$_3$-C$_8$ cycloalkyl optionally substituted by C$_1$-C$_6$ alkyl, CN, CF$_3$, oxo, —OH, —NR$^{15}$R$^{16}$, —OR$^{15}$ or halogen, 3- to 12-membered heterocyclyl optionally substituted by oxo, —OH, —NR$^{15}$R$^{16}$, —C(O)OR$^{15}$, —OR$^{15}$ or halogen, or C$_1$-C$_6$ alkyl optionally substituted by oxo, —OH, —NR$^{15}$R$^{16}$, —C(O)OR$^{15}$, —OR$^{15}$, or halogen, with the proviso that the 5- to 10-membered heteroaryl of R$^3$ is not substituted by

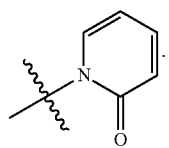

In some embodiments of a compound of Formula (I), A is phenyl optionally substituted by R$^1$ and fused with B, wherein R$^1$ is independently —CN, C$_1$-C$_6$ alkyl, or halogen; B is C$_6$ aryl, 5- to 7-membered heteroaryl, C$_3$-C$_8$ cycloalkyl, or 3- to 8-membered heterocyclyl, each of which is substituted with R$^4$; R$^4$ is independently oxo, C$_1$-C$_6$ alkyl, C$_2$-C$_6$ alkenyl, $C_2$-$C_6$ alkynyl, —C(O)$R^{17}$, —C(O)O$R^{17}$, or —C(O)N$R^{17}R^{18}$, wherein each $R^4$ is independently optionally substituted by halogen, oxo, —O$R^{19}$, —N$R^{19}R^{20}$, or —C(O)$R^{19}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$; $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl); $R^3$ is —C(O)$R^{10}$ or 5- to 10-membered heteroaryl optionally substituted by halogen, oxo, —O$R^{13}$, —N$R^{13}R^{14}$, —C(O)$R^{13}$, —C(O)N$R^{13}R^{14}$, —N$R^{13}$C(O)$R^{14}$, —CN, —S$R^{13}$, —S(O)$R^{13}$, —S(O)$_2R^{13}$, —($C_1$-$C_3$ alkylene)O$R^{13}$, —($C_1$-$C_3$ alkylene)N$R^{13}R^{14}$, —($C_1$-$C_3$ alkylene)C(O)$R^{13}$, $C_3$-$C_8$ cycloalkyl optionally substituted by oxo, —OH or halogen, 3- to 12-membered heterocyclyl optionally substituted by oxo, —OH, or halogen, or $C_1$-$C_6$ alkyl optionally substituted by oxo, —OH, or halogen, with the proviso that the 5- to 10-membered heteroaryl of $R^3$ is not substituted by

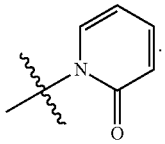

In some embodiments of a compound of Formula (I), A is phenyl optionally substituted by $R^1$ and fused with B, wherein $R^1$ is independently —CN, $C_1$-$C_6$ alkyl, or halogen; B is 3- to 8-membered heterocyclyl optionally substituted with $R^4$; $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$; $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl); $R^3$ is 5- to 10-membered heteroaryl substituted by 3- to 12-membered heterocyclyl optionally substituted by oxo, —OH, or halogen, —CN, —($C_1$-$C_3$ alkylene)N$R^{13}R^{14}$, $C_3$-$C_8$ cycloalkyl optionally substituted by oxo, —OH or halogen, —C(O)$R^{13}$, —N$R^{13}R^{14}$, —O$R^{13}$, or $C_1$-$C_6$ alkyl optionally substituted by —OH or halogen, with the proviso that the 5- to 10-membered heteroaryl of $R^3$ is not substituted by

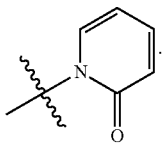 [SMILES: *n1ccccc1=O]

In some embodiments of a compound of Formula (I), A is phenyl optionally substituted by $R^1$ and fused with B, wherein $R^1$ is independently —CN, $C_1$-$C_6$ alkyl, or halogen; B is 3- to 8-membered heterocyclyl optionally substituted with $R^4$; $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$; $R^2$ is selected from the group consisting of: allyl, cyclopropylmethyl, isopropyl, cyclopropyl, ethyl, and propyl; $R^3$ is 5- to 10-membered heteroaryl substituted by —O$R^{13}$ or $C_1$-$C_6$ alkyl, wherein the $C_1$-$C_6$ alkyl is optionally substituted by —OH or halogen.

In some embodiments of a compound of Formula (I), A is phenyl optionally substituted by $R^1$ and fused with B, wherein $R^1$ is independently —CN, $C_1$-$C_6$ alkyl, or halogen; B is $C_6$-$C_{14}$ aryl, 5- to 10-membered heteroaryl, $C_3$-$C_8$ cycloalkyl, or 3- to 12-membered heterocyclyl, each of which is substituted with $R^4$; $R^4$ is independently oxo, $C_1$-$C_6$ alkyl, $C_2$-$C_6$ alkenyl, $C_2$-$C_6$ alkynyl, —C(O)$R^{17}$, —C(O)O$R^{17}$, or —C(O)N$R^{17}R^{18}$, wherein each $R^4$ is independently optionally substituted by halogen, oxo, —O$R^{19}$, —N$R^{19}R^{20}$, or —C(O)$R^{19}$; or two $R^4$ are taken together with the carbon to which they attach to form a $C_3$-$C_6$ cycloalkyl; $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl); $R^3$ is hydrogen, $C_1$-$C_6$ alkyl, —C(O)$R^{10}$, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl), —S(O)$R^{10}$, —S(O)$_2R^{10}$, or 5- to 10-membered heteroaryl, each of which is optionally substituted by halogen, oxo, —O$R^{13}$, —N$R^{13}R^{14}$, —C(O)$R^{13}$, —CN, —S(O)$R^{13}$, —S(O)$_2R^{13}$, —($C_1$-$C_3$ alkylene)O$R^{13}$, —($C_1$-$C_3$ alkylene)N$R^{13}R^{14}$, —($C_1$-$C_3$ alkylene)C(O)$R^{13}$, $C_3$-$C_8$ cycloalkyl, 3- to 12-membered heterocyclyl optionally substituted by oxo, —OH, or halogen, or $C_1$-$C_6$ alkyl optionally substituted by oxo, —OH, or halogen. In some embodiments of a compound of Formula (I), A is phenyl optionally substituted by $R^1$ and fused with B, wherein $R^1$ is independently —CN, $C_1$-$C_6$ alkyl, or halogen; B is $C_6$-$C_{14}$ aryl, 5- to 10-membered heteroaryl, $C_3$-$C_8$ cycloalkyl, or 3- to 12-membered heterocyclyl, each of which is substituted with $R^4$; $R^4$ is independently oxo, $C_1$-$C_6$ alkyl, $C_2$-$C_6$ alkenyl, $C_2$-$C_6$ alkynyl, —C(O)$R^{17}$, —C(O)O$R^{17}$, or —C(O)N$R^{17}R^{18}$, wherein each $R^4$ is independently optionally substituted by halogen, oxo, —O$R^{19}$, —N$R^{19}R^{20}$, or —C(O)$R^{19}$; or two $R^4$ are taken together with the carbon to which they attach to form a $C_3$-$C_6$ cycloalkyl; $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl); $R^3$ is —C(O)$R^{10}$ or 5- to 10-membered heteroaryl optionally substituted by halogen, oxo, —O$R^{13}$, —N$R^{13}R^{14}$, —C(O)$R^{13}$, —C(O)N$R^{13}R^{14}$, —N$R^{13}$C(O)$R^{14}$, —CN, —S(O)$R^{13}$, —S(O)$_2R^{13}$, —($C_1$-$C_3$ alkylene)O$R^{13}$, —($C_1$-$C_3$ alkylene)N$R^{13}R^{14}$, —($C_1$-$C_3$ alkylene)C(O)$R^{13}$, $C_3$-$C_8$ cycloalkyl, 3- to 12-membered heterocyclyl optionally substituted by oxo, —OH, or halogen, or $C_1$-$C_6$ alkyl optionally substituted by oxo, —OH, or halogen. In some embodiments of a compound of Formula (I), A is phenyl optionally substituted by $R^1$ and fused with B, wherein $R^1$ is independently —CN, $C_1$-$C_6$ alkyl, or halogen; B is 3- to 12-membered heterocyclyl optionally substituted with $R^4$; $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$ are taken together with the carbon to which they attach to form a $C_3$-$C_6$ cycloalkyl; $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl); $R^3$ is 5- to 10-membered heteroaryl substituted by 3- to 12-membered heterocyclyl optionally substituted by oxo, —OH, or halogen, —CN, —($C_1$-$C_3$ alkylene)N$R^{13}R^{14}$, $C_3$-$C_8$ cycloalkyl, —C(O)$R^{13}$, —N$R^{13}R^{14}$, —O$R^{13}$, or $C_1$-$C_6$ alkyl optionally substituted by —OH or halogen. In some embodiments of a compound of Formula (I), A is phenyl optionally substituted by $R^1$ and fused with B, wherein $R^1$ is independently —CN, $C_1$-$C_6$ alkyl, or halogen; B is 3- to 12-membered heterocyclyl optionally substituted with $R^4$; $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$ are taken together with the carbon to which they attach to form a $C_3$-$C_6$ cycloalkyl; $R^2$ is selected from the group consisting of: allyl, cyclopropylmethyl, isopropyl, cyclopropyl, ethyl, and propyl; $R^3$ is 5- to 10-membered heteroaryl substituted by —O$R^{13}$ or $C_1$-$C_6$ alkyl, wherein the $C_1$-$C_6$ alkyl is optionally substituted by —OH.

In some embodiments of a compound of Formula (I), A is unsubstituted 6-membered heteroaryl fused with B, wherein B is $C_6$ aryl, 5- to 7-membered heteroaryl, $C_3$-$C_8$ cycloalkyl, or 3- to 8-membered heterocyclyl, each of which is substituted with $R^4$; $R^4$ is independently oxo, $C_1$-$C_6$ alkyl, $C_2$-$C_6$ alkenyl, $C_2$-$C_6$ alkynyl, halogen, —C(O)$R^{17}$, —C(O)O$R^{17}$, —C(O)N$R^{17}R^{18}$, —CN, —Si($C_1$-$C_6$ alkyl)$_3$, —O$R^{17}$, —N$R^{17}R^{18}$, —OC(O)N$R^{17}R^{18}$, —N$R^{17}$C(O)$R^{18}$, —S(O)$_2R^{17}$, —N$R^{17}$S(O)$_2R^{18}$, —S(O)$_2$N$R^{17}R^{18}$, $C_3$-$C_6$ cycloalkyl, 3- to 6-membered heterocyclyl, —($C_1$-$C_3$ alkylene)CN, —($C_1$-$C_3$ alkylene)O$R^{17}$, —($C_1$-$C_3$ alkylene)N$R^{17}R^{18}$, —($C_1$-$C_3$ alkylene)CF$_3$, —($C_1$-$C_3$ alkylene)C(O)$R^{17}$, —($C_1$-$C_3$ alkylene)C(O)N$R^{17}R^{18}$, —($C_1$-$C_3$ alkylene)N$R^{17}$C(O)$R^{18}$, —($C_1$-$C_3$ alkylene)S(O)$_2R^{17}$, —($C_1$-$C_3$ alkylene)N$R^{17}$S(O)$_2R^{18}$, —($C_1$-$C_3$ alkylene)S(O)$_2$N$R^{17}R^{18}$, —($C_1$-$C_3$ alkylene)($C_3$-$C_6$ cycloalkyl) or —($C_1$-$C_3$ alkylene) (3- to 6-membered heterocyclyl), wherein each $R^4$ is independently optionally substituted by halogen, oxo, —O$R^{19}$, —N$R^{19}R^{20}$, or —C(O)$R^{19}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$; $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl); $R^3$ is hydrogen, $C_1$-$C_6$ alkyl, —C(O)$R^{10}$, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl), —S(O)$R^{10}$, —S(O)$_2R^{10}$, or 5- to 10-membered heteroaryl, each of which is optionally substituted by halogen, oxo, —O$R^{13}$, —N$R^{13}R^{14}$, —C(O)$R^{13}$, —C(O)O$R^{13}$, —CN, —S$R^{13}$, —S(O)$R^{13}$, —S(O)$_2R^{13}$, —Si($C_1$-$C_6$ alkyl)$_3$, —P(O)$R^{13}R^{14}$, —N$R^{13}$S(O)$_2R^{14}$, —($C_1$-$C_3$ alkylene)O$R^{13}$, —($C_1$-$C_3$ alkylene)N$R^{13}R^{14}$, —($C_1$-$C_3$ alkylene)C(O)$R^{13}$, $C_3$-$C_8$ cycloalkyl optionally substituted by $C_1$-$C_6$ alkyl, CN, CF$_3$, oxo, —OH, —N$R^{15}R^{16}$, —O$R^{15}$ or halogen, 3- to 12-membered heterocyclyl optionally substituted by oxo, —OH, —N$R^{15}R^{16}$, —C(O)O$R^{15}$, —O$R^{15}$, or halogen, or $C_1$-$C_6$ alkyl optionally substituted by oxo, —OH, —N$R^{15}R^{16}$, —C(O)O$R^{15}$, —O$R^{15}$ or halogen, with the proviso that the 5- to 10-membered heteroaryl of $R^3$ is not substituted by

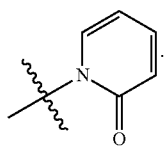 [SMILES: *n1ccccc1=O]

In some embodiments of a compound of Formula (I), A is unsubstituted 6-membered heteroaryl fused with B, wherein B is $C_6$ aryl, 5- to 7-membered heteroaryl, $C_3$-$C_8$ cycloalkyl, or 3- to 8-membered heterocyclyl, each of which is substituted with $R^4$; $R^4$ is independently oxo, $C_1$-$C_6$ alkyl, $C_2$-$C_6$ alkenyl, $C_2$-$C_6$ alkynyl, —C(O)$R^{17}$, —C(O)O$R^{17}$, or —C(O)N$R^{17}R^{18}$, wherein each $R^4$ is independently optionally substituted by halogen, oxo, —O$R^{19}$, —N$R^{19}R^{20}$, or —C(O)$R^{19}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$; $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl); $R^3$ is —C(O)$R^{10}$ or 5- to 10-membered heteroaryl optionally substituted by halogen, oxo, —O$R^{13}$, —N$R^{13}R^{14}$, —C(O)$R^{13}$, —C(O)N$R^{13}R^{14}$, —N$R^{13}$C(O)$R^{14}$, —CN, —S$R^{13}$, —S(O)$R^{13}$, —S(O)$_2R^{13}$, —($C_1$-$C_3$ alkylene)O$R^{13}$, —($C_1$-$C_3$ alkylene)N$R^{13}R^{14}$, —($C_1$-$C_3$ alkylene)C(O)$R^{13}$, $C_3$-$C_8$ cycloalkyl optionally substituted by oxo, —OH or halogen, 3- to 12-membered heterocyclyl optionally substituted by oxo, —OH, or halogen, or $C_1$-$C_6$ alkyl optionally substituted by oxo, —OH, or halogen, with the proviso that the 5- to 10-membered heteroaryl of $R^3$ is not substituted by

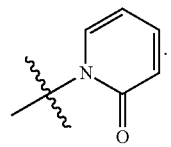

In some embodiments of a compound of Formula (I), A is unsubstituted 6-membered heteroaryl fused with B, wherein B is 3- to 12-membered heterocyclyl optionally substituted with $R^4$; $R^4$ is independently oxo, $C_1$-$C_6$ alkyl, or —C(O)$R^{17}$, wherein the $C_1$-$C_6$ alkyl or —C(O)$R^{17}$ is optionally substituted by —O$R^{19}$ or —N$R^{19}R^{20}$; or two $R^4$, when bound to the same carbon or two different carbon atoms, are taken together with the carbon or carbons to which they are attached to form a $C_3$-$C_6$ cycloalkyl or 3- to 7-membered heterocyclyl, each is optionally substituted by $R^{19}$; $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl); $R^3$ is 5- to 10-membered heteroaryl substituted by 3- to 12-membered heterocyclyl optionally substituted by oxo, —OH, or halogen, —CN, —($C_1$-$C_3$ alkylene)N$R^{13}R^{14}$, $C_3$-$C_8$ cycloalkyl optionally substituted by oxo, —OH or halogen, —C(O)$R^{13}$, —N$R^{13}R^{14}$, —O$R^{13}$, or $C_1$-$C_6$ alkyl optionally substituted by —OH or halogen, with the proviso that the 5- to 10-membered heteroaryl of $R^3$ is not substituted by

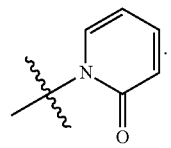

In some embodiments of a compound of Formula (I), A is unsubstituted 6-membered heteroaryl fused with B, wherein B is 6-membered heterocyclyl having one nitrogen atom, wherein the 6-membered heterocyclyl is optionally substituted by $R^4$; $R^4$ is independently $C_1$-$C_6$ alkyl; $R^2$ is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl); $R^3$ is 5- to 10-membered heteroaryl substituted by 3- to 12-membered heterocyclyl optionally substituted by oxo, —OH, or halogen, —CN, —($C_1$-$C_3$ alkylene)N$R^{13}R^{14}$, $C_3$-$C_8$ cycloalkyl optionally substituted by oxo, —OH or halogen, —C(O)$R^{13}$, —N$R^{13}R^{14}$, —O$R^{13}$, or $C_1$-$C_6$ alkyl optionally substituted by —OH or halogen, with the proviso that the 5- to 10-membered heteroaryl of R³ is not substituted by

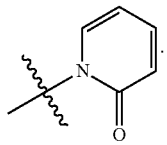

In some embodiments of a compound of Formula (I), A is unsubstituted 6-membered heteroaryl fused with B, wherein B is 6-membered heterocyclyl having one nitrogen atom, wherein the 6-membered heterocyclyl is optionally substituted by R⁴; R⁴ is independently $C_1$-$C_6$ alkyl; R² is selected from the group consisting of: allyl, cyclopropylmethyl, isopropyl, cyclopropyl, ethyl, and propyl; R³ is 5- to 10-membered heteroaryl substituted by —OR¹³ or $C_1$-$C_6$ alkyl, wherein the $C_1$-$C_6$ alkyl is optionally substituted by —OH or halogen.

In some embodiments of a compound of Formula (I), A is unsubstituted 6-membered heteroaryl fused with B, wherein B is $C_6$-$C_{14}$ aryl, 5- to 10-membered heteroaryl, $C_3$-$C_8$ cycloalkyl, or 3- to 12-membered heterocyclyl, each of which is substituted with R⁴; R⁴ is independently oxo, $C_1$-$C_6$ alkyl, $C_2$-$C_6$ alkenyl, $C_2$-$C_6$ alkynyl, —C(O)R¹⁷, —C(O)OR¹⁷, or —C(O)NR¹⁷R¹⁸, wherein each R⁴ is independently optionally substituted by halogen, oxo, —OR¹⁹, —NR¹⁹R²⁰, or —C(O)R¹⁹; or two R⁴ are taken together with the carbon to which they attach to form a $C_3$-$C_6$ cycloalkyl; R² is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl); R³ is hydrogen, $C_1$-$C_6$ alkyl, —C(O)R¹⁰, —($C_1$-$C_3$ alkylene)($C_3$-$C_6$ cycloalkyl), —($C_1$-$C_3$ alkylene)(3- to 12-membered heterocyclyl), —($C_1$-$C_3$ alkylene)(5- to 10-membered heteroaryl), —S(O)R¹⁰, —S(O)₂R¹⁰, or 5- to 10-membered heteroaryl, each of which is optionally substituted by halogen, oxo, —OR¹³, —NR¹³R¹⁴, —C(O)R¹³, —CN, —S(O)R¹³, —S(O)₂R¹³, —($C_1$-$C_3$ alkylene)OR¹³, —($C_1$-$C_3$ alkylene)NR¹³R¹⁴, —($C_1$-$C_3$ alkylene)C(O)R¹³, $C_3$-$C_8$ cycloalkyl, 3- to 12-membered heterocyclyl optionally substituted by oxo, —OH, or halogen, or $C_1$-$C_6$ alkyl optionally substituted by oxo, —OH, or halogen. In some embodiments of a compound of Formula (I), A is unsubstituted 6-membered heteroaryl fused with B, wherein B is $C_6$-$C_{14}$ aryl, 5- to 10-membered heteroaryl, $C_3$-$C_8$ cycloalkyl, or 3- to 12-membered heterocyclyl, each of which is substituted with R⁴; R⁴ is independently oxo, $C_1$-$C_6$ alkyl, $C_2$-$C_6$ alkenyl, $C_2$-$C_6$ alkynyl, —C(O)R¹⁷, —C(O)OR¹⁷, or —C(O)NR¹⁷R¹⁸, wherein each R⁴ is independently optionally substituted by halogen, oxo, —OR¹⁹, —NR¹⁹R²⁰, or —C(O)R¹⁹; or two R⁴ are taken together with the carbon to which they attach to form a $C_3$-$C_6$ cycloalkyl; R² is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl); R³ is —C(O)R¹⁰ or 5- to 10-membered heteroaryl optionally substituted by halogen, oxo, —OR¹³, —NR¹³R¹⁴, —C(O)R¹³, —C(O)NR¹³R¹⁴, —NR¹³C(O)R¹⁴, —CN, —S(O)R¹³, —S(O)₂R¹³, —($C_1$-$C_3$ alkylene)OR¹³, —($C_1$-$C_3$ alkylene)NR¹³R¹⁴, —($C_1$-$C_3$ alkylene)C(O)R¹³, $C_3$-$C_8$ cycloalkyl, 3- to 12-membered heterocyclyl optionally substituted by oxo, —OH, or halogen, or $C_1$-$C_6$ alkyl optionally substituted by oxo, —OH, or halogen. In some embodiments of a compound of Formula (I), A is unsubstituted 6-membered heteroaryl fused with B, wherein B is 3- to 12-membered heterocyclyl optionally substituted with R⁴; R⁴ is independently oxo, $C_1$-$C_6$ alkyl, or —C(O)R¹⁷, wherein the $C_1$-$C_6$ alkyl or —C(O)R¹⁷ is optionally substituted by —OR¹⁹ or —NR¹⁹R²⁰; or two R⁴ are taken together with the carbon to which they attach to form a $C_3$-$C_6$ cycloalkyl; R² is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl); R³ is 5- to 10-membered heteroaryl substituted by 3- to 12-membered heterocyclyl optionally substituted by oxo, —OH, or halogen, —CN, —($C_1$-$C_3$ alkylene)NR¹³R¹⁴, $C_3$-$C_8$ cycloalkyl, —C(O)R¹³, —NR¹³R¹⁴, —OR¹³, or $C_1$-$C_6$ alkyl optionally substituted by —OH or halogen. In some embodiments of a compound of Formula (I), A is unsubstituted 6-membered heteroaryl fused with B, wherein B is 6-membered heterocyclyl having one nitrogen atom, wherein the 6-membered heterocyclyl is optionally substituted by R⁴; R⁴ is independently $C_1$-$C_6$ alkyl; R² is $C_1$-$C_6$ alkyl, $C_3$-$C_6$ cycloalkyl, $C_2$-$C_6$ alkenyl, or —($C_1$-$C_3$ alkylene)($C_3$-$C_6$ cycloalkyl); R³ is 5- to 10-membered heteroaryl substituted by 3- to 12-membered heterocyclyl optionally substituted by oxo, —OH, or halogen, —CN, —($C_1$-$C_3$ alkylene)NR¹³R¹⁴, $C_3$-$C_8$ cycloalkyl, —C(O)R¹³, —NR¹³R¹⁴, —OR¹³, or $C_1$-$C_6$ alkyl optionally substituted by —OH or halogen. In some embodiments of a compound of Formula (I), A is unsubstituted 6-membered heteroaryl fused with B, wherein B is 6-membered heterocyclyl having one nitrogen atom, wherein the 6-membered heterocyclyl is optionally substituted by R⁴; R⁴ is independently $C_1$-$C_6$ alkyl; R² is selected from the group consisting of: allyl, cyclopropylmethyl, isopropyl, cyclopropyl, ethyl, and propyl; R³ is 5- to 10-membered heteroaryl substituted by —OR¹³ or $C_1$-$C_6$ alkyl, wherein the $C_1$-$C_6$ alkyl is optionally substituted by —OH.

It is understood that each description of A and B may be combined with each description of R² and/or R³ the same as if each and every combination were specifically and individually listed. For example, in one aspect, it is understood that each description of A and B may be combined in one aspect with a variation in which R² is allyl and R³ is

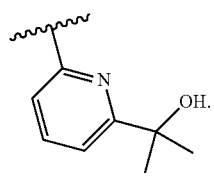 [SMILES: *c1cccc(C(C)(C)O)n1]

In some embodiments, it is understood that each description of A and B may be combined in one aspect with a variation in which R² is allyl and R³ is

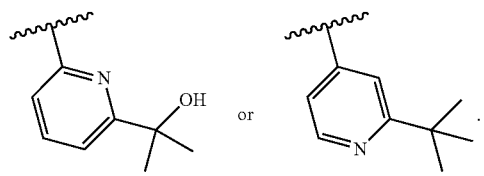 [SMILES: *c1cccc(C(C)(C)O)n1 ; *c1ccnc(C(C)(C)C)c1]

In some embodiments, provided is a compound of Formula (I), wherein A, B, R¹ and R⁴ together are selected from the group consisting of:

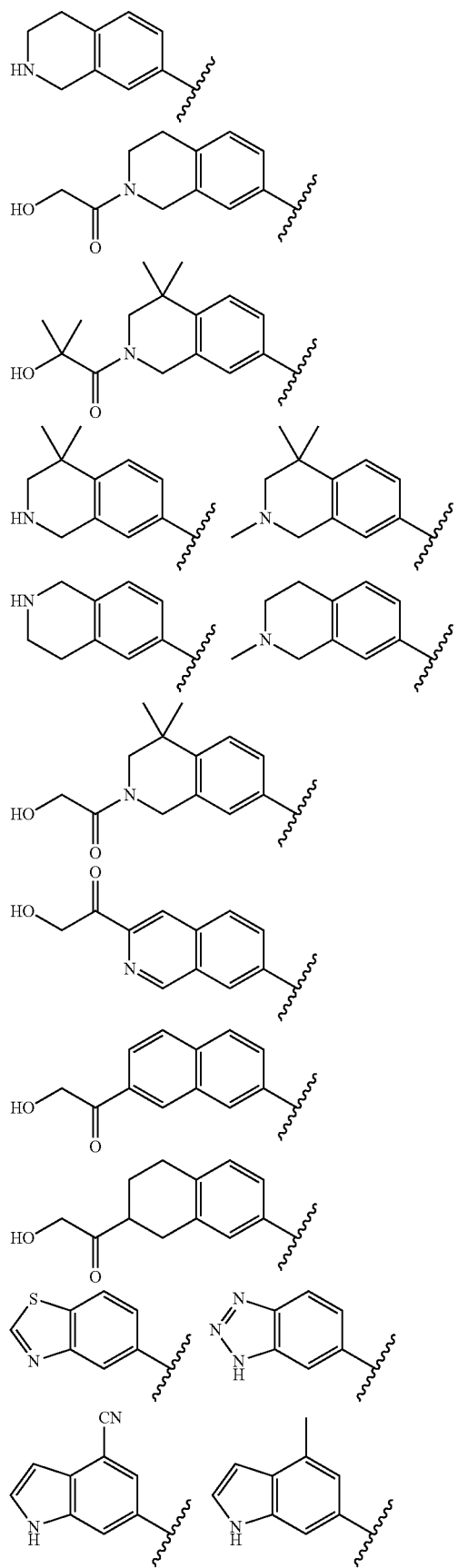
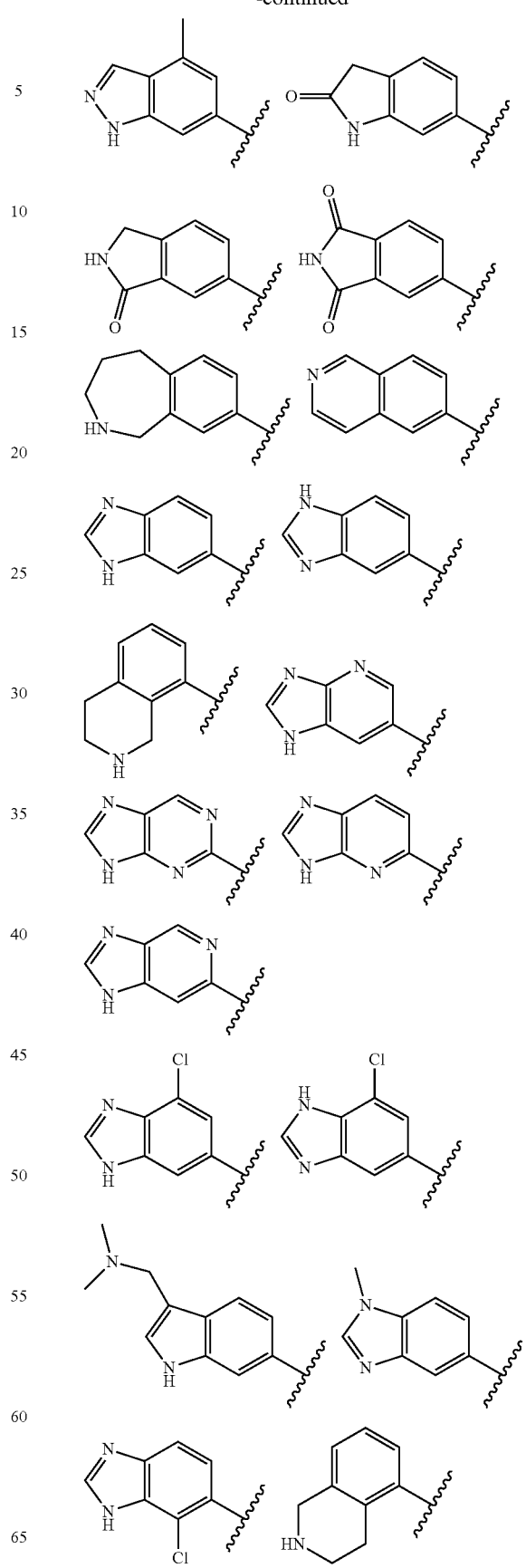

-continued
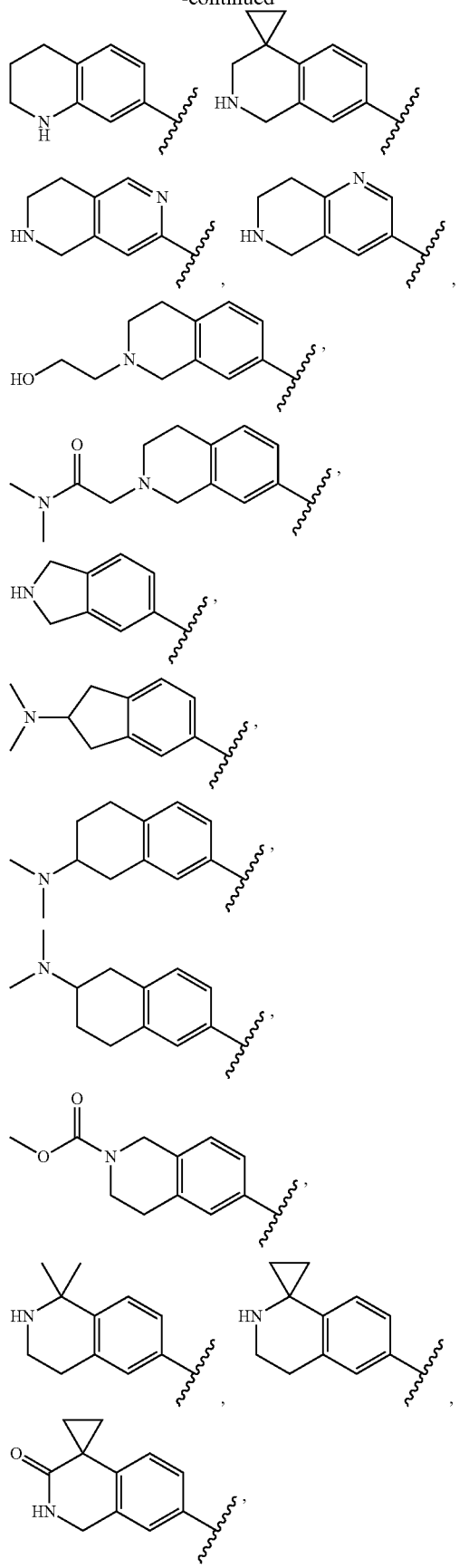
-continued
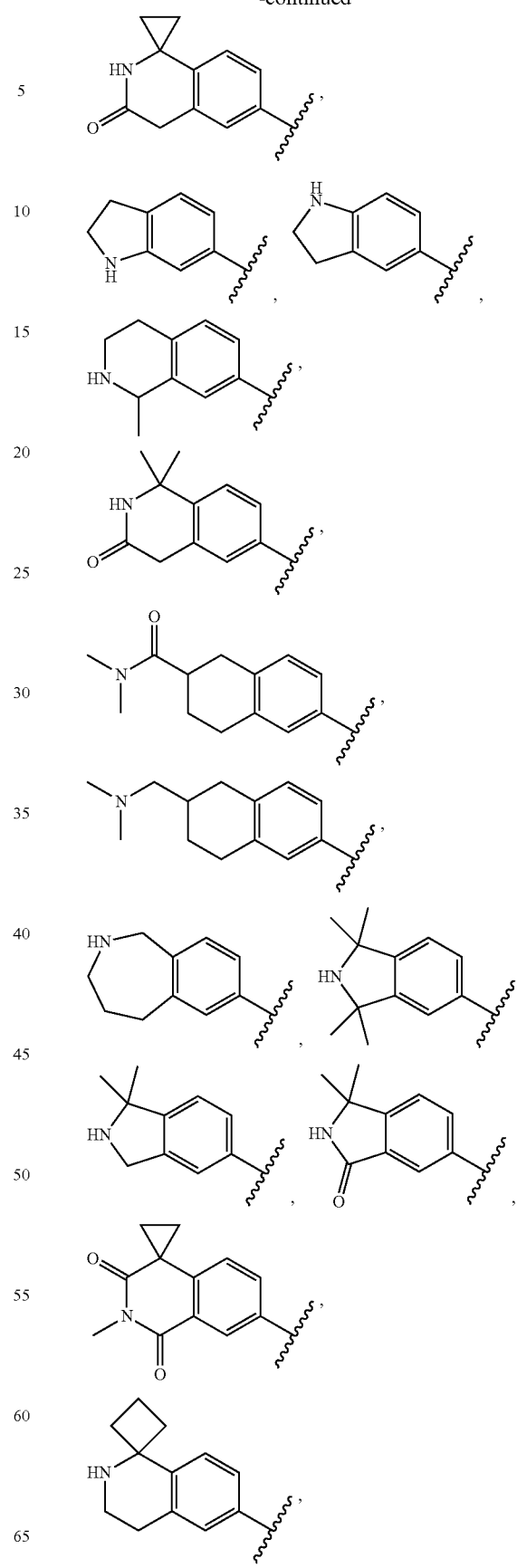

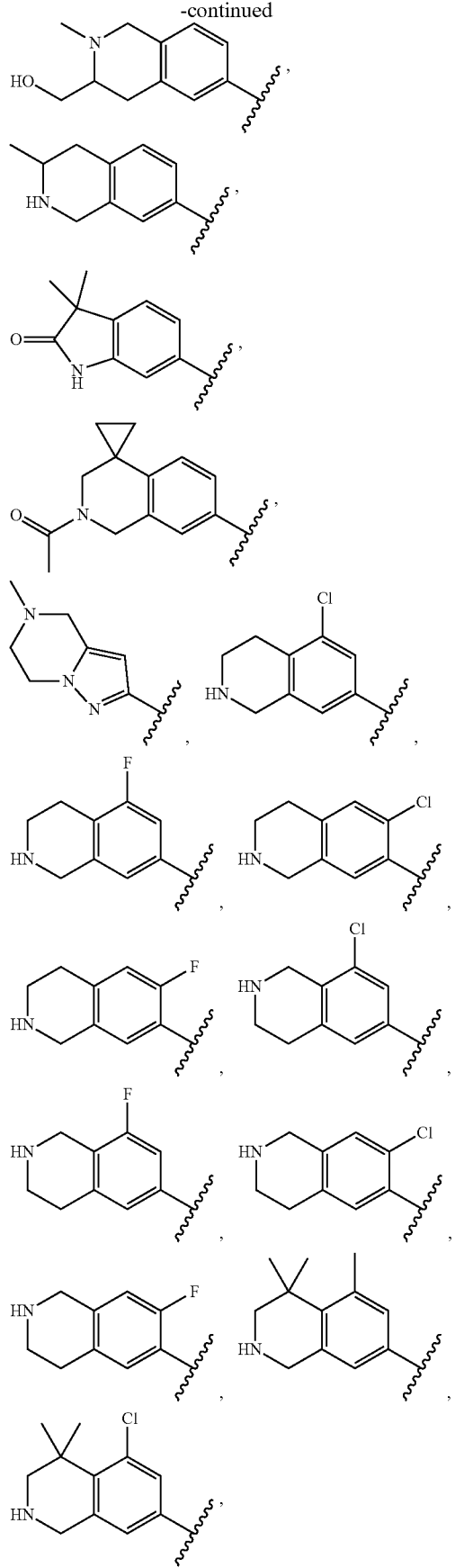
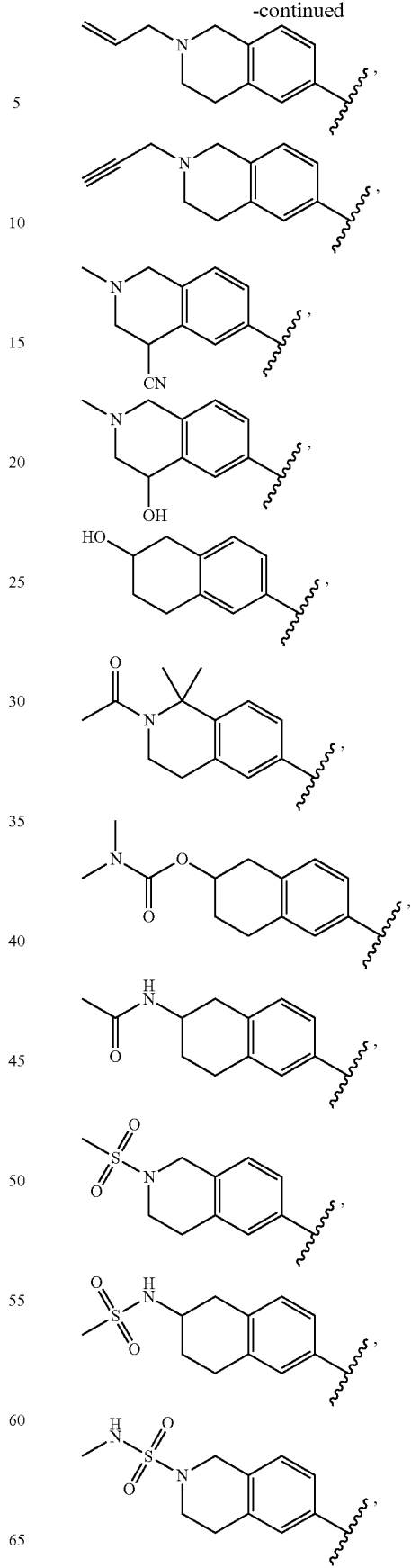

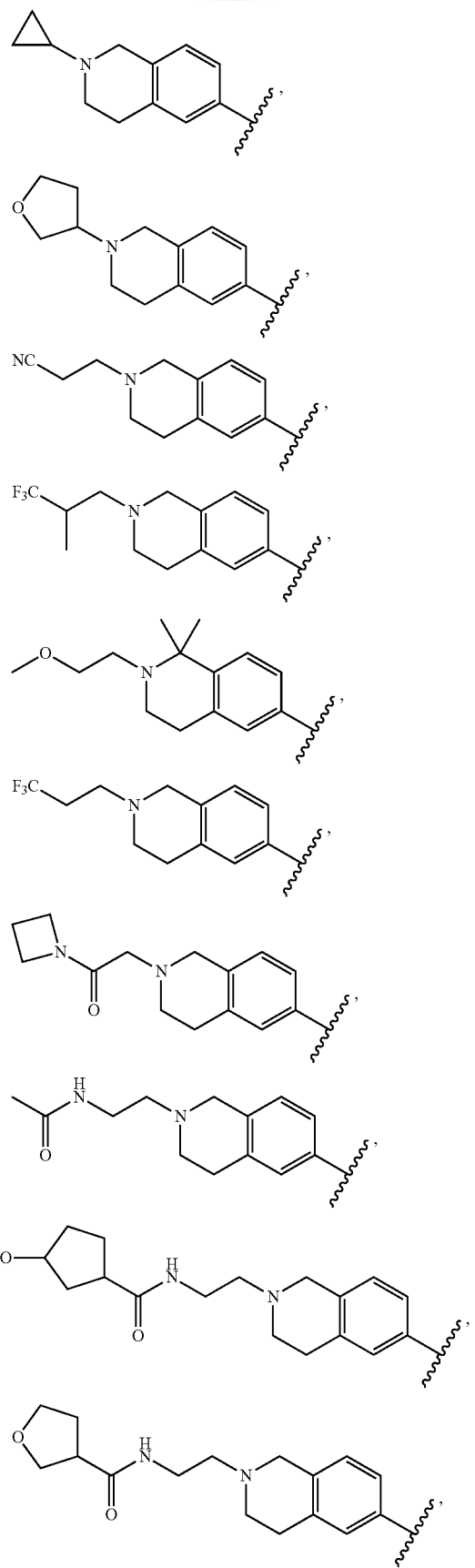
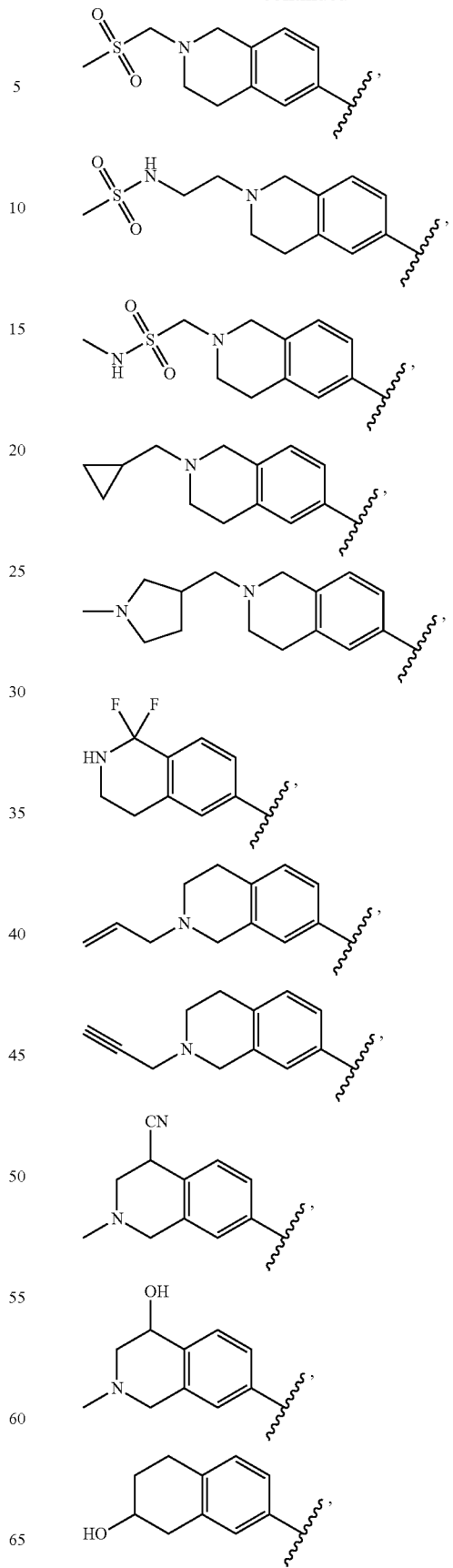

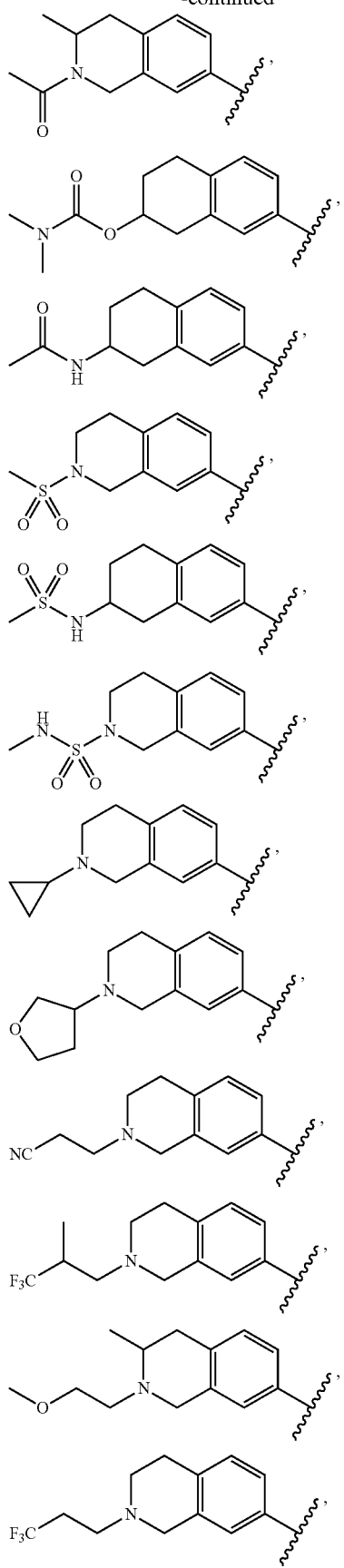
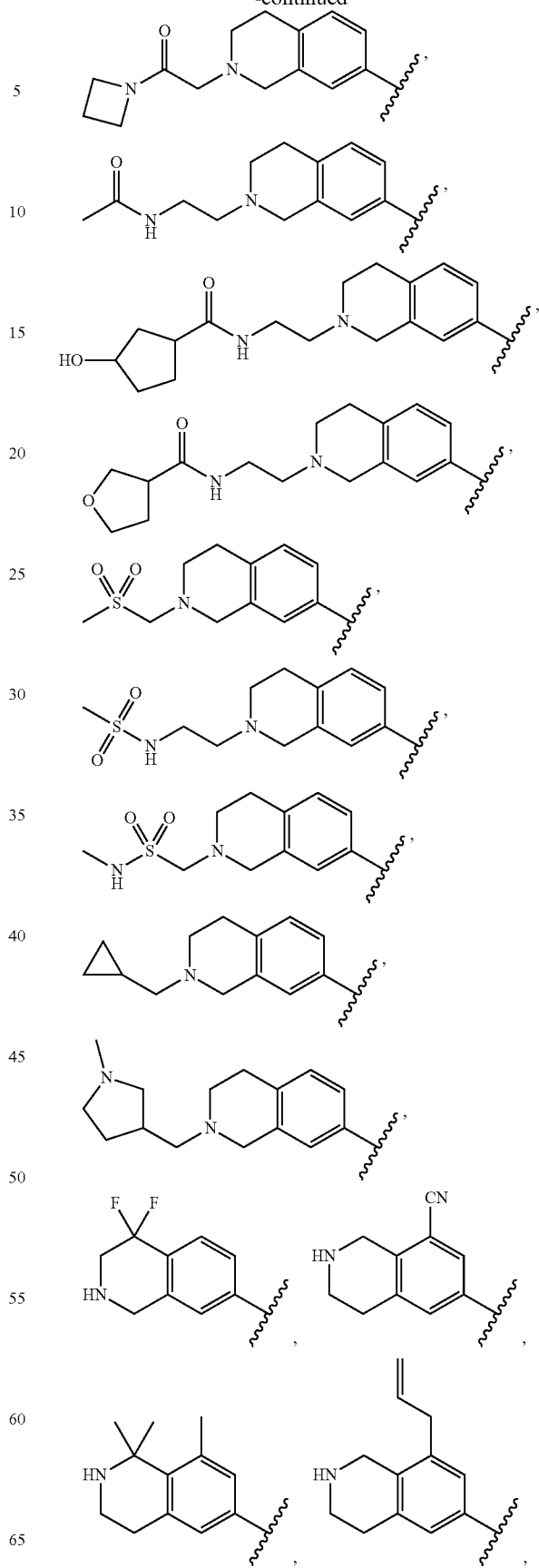

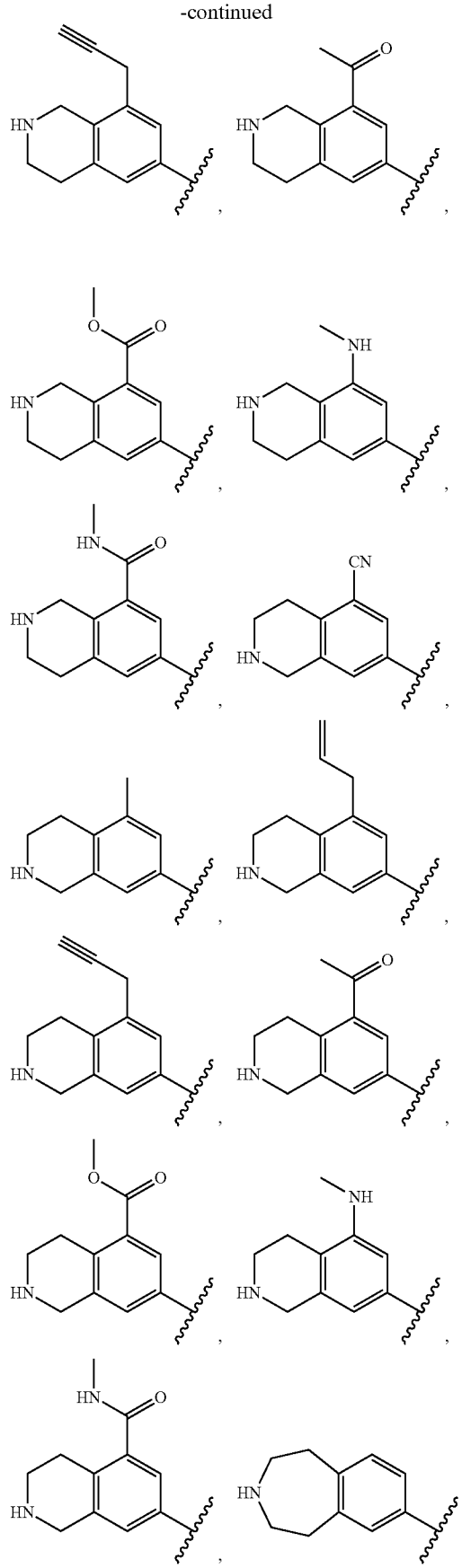
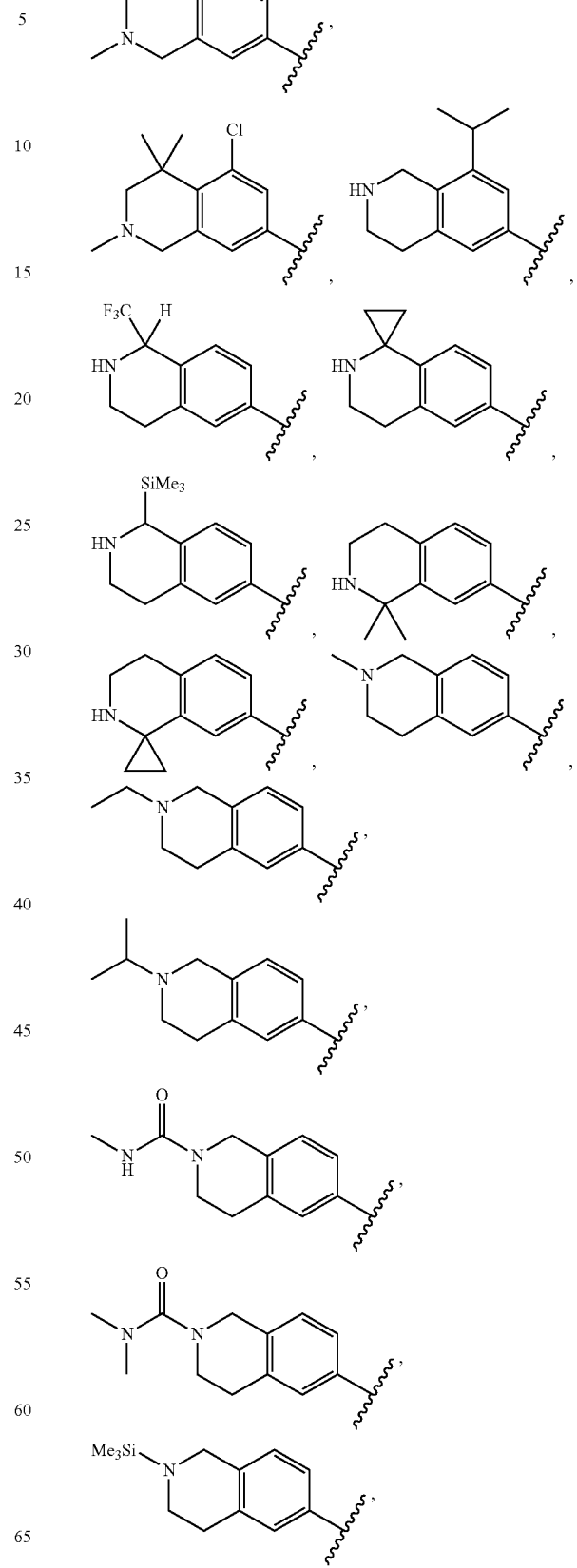

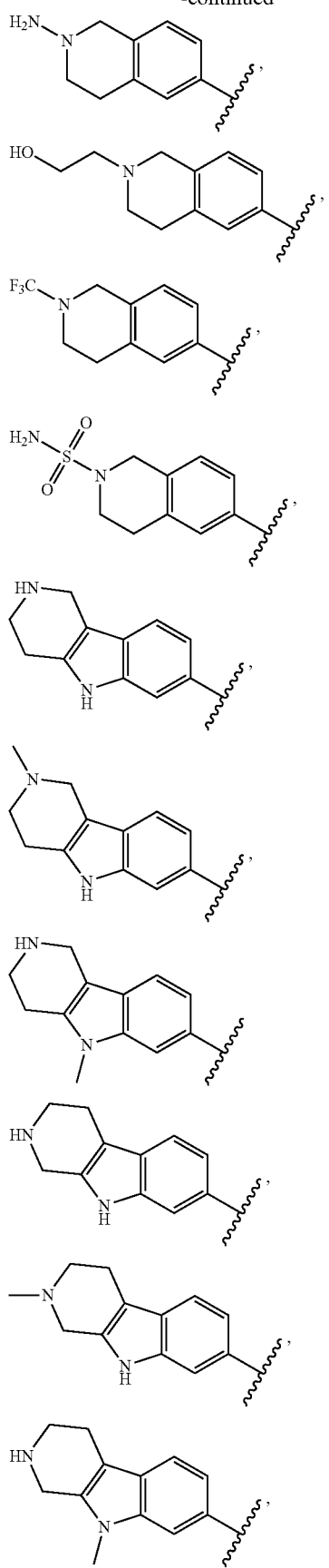
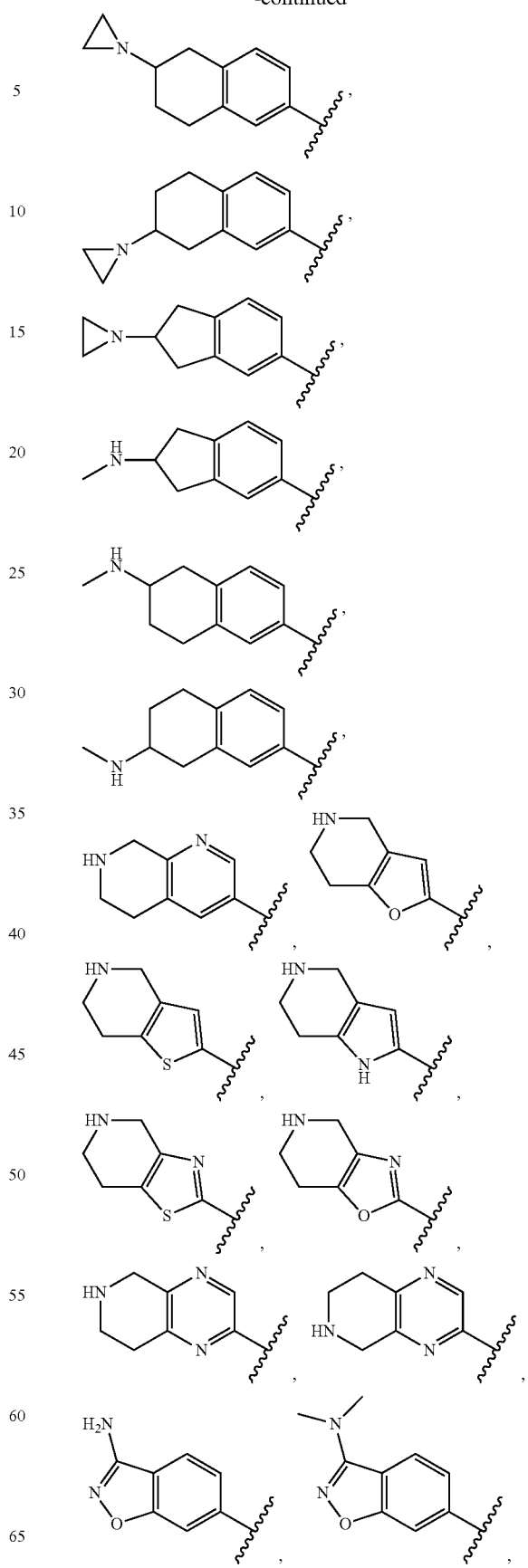

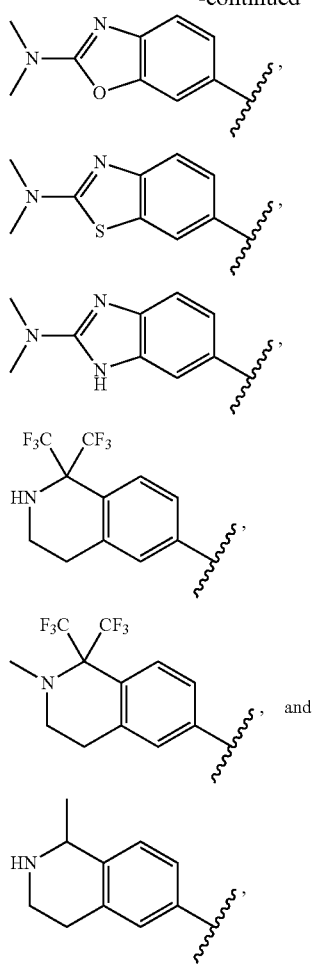
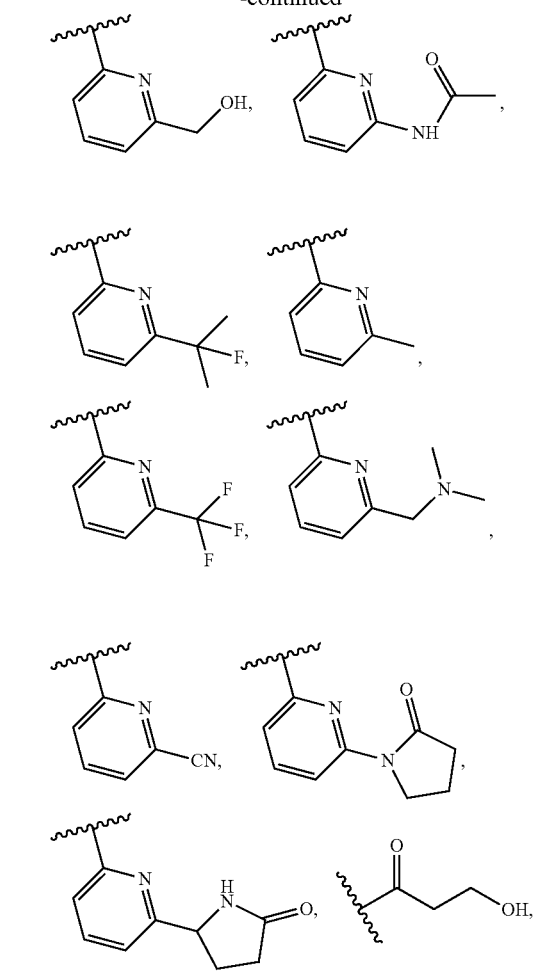
wherein the wavy lines denote attachment points to the parent molecule;
R[2] is selected from the group consisting of: allyl, cyclopropylmethyl, isopropyl, cyclopropyl, ethyl, and propyl; and
R[3] is selected from the group consisting of:
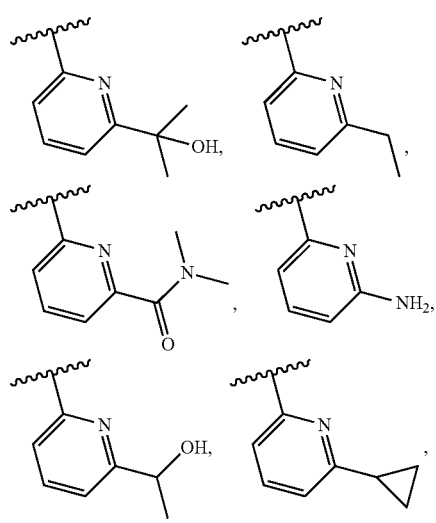
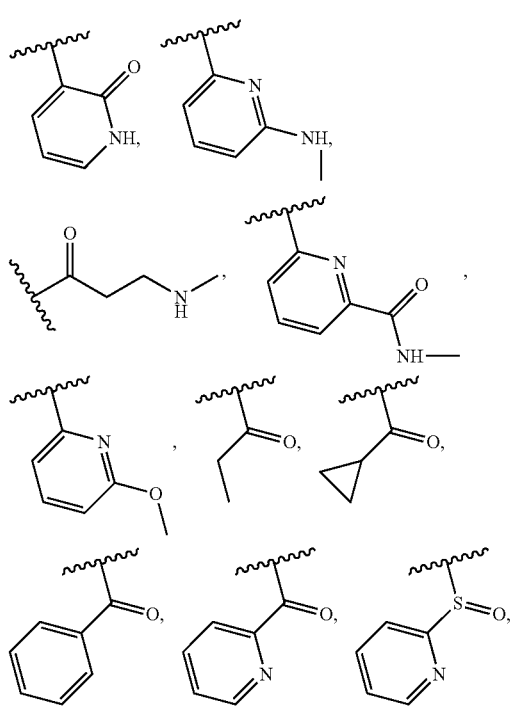

US 11,299,493 B2

139
-continued

140
-continued

-continued
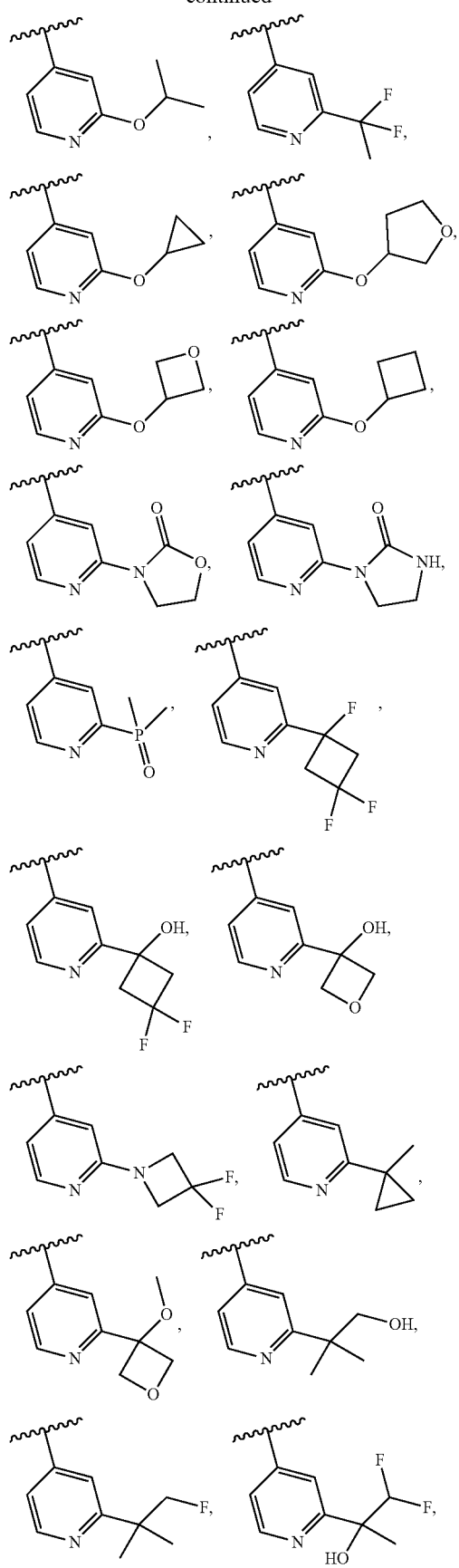
-continued
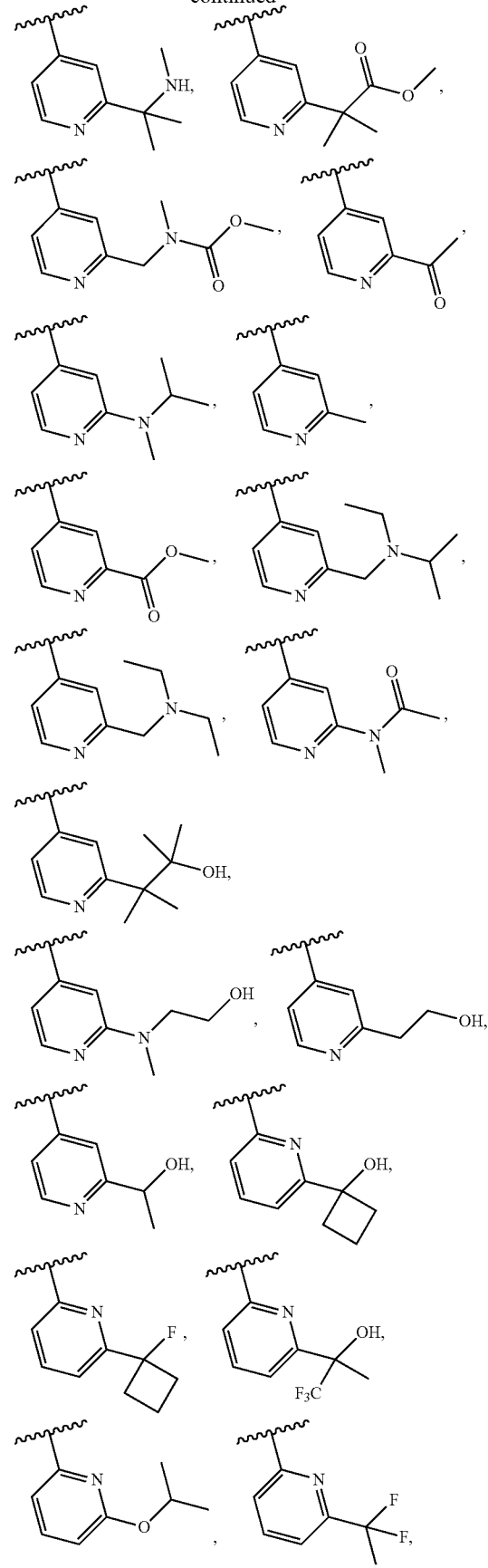

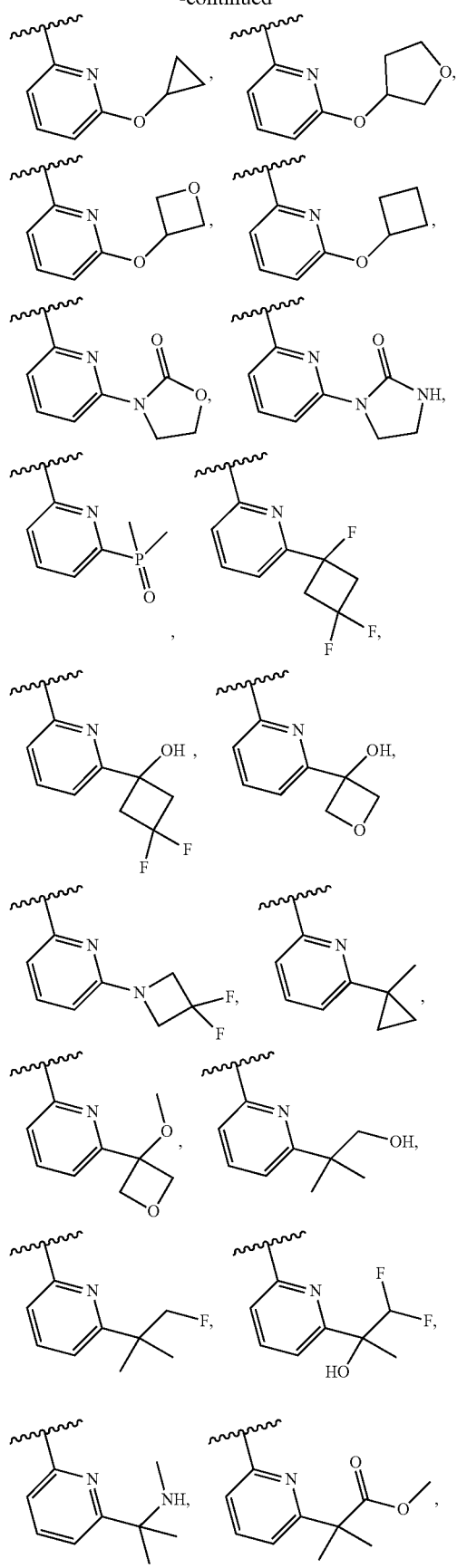
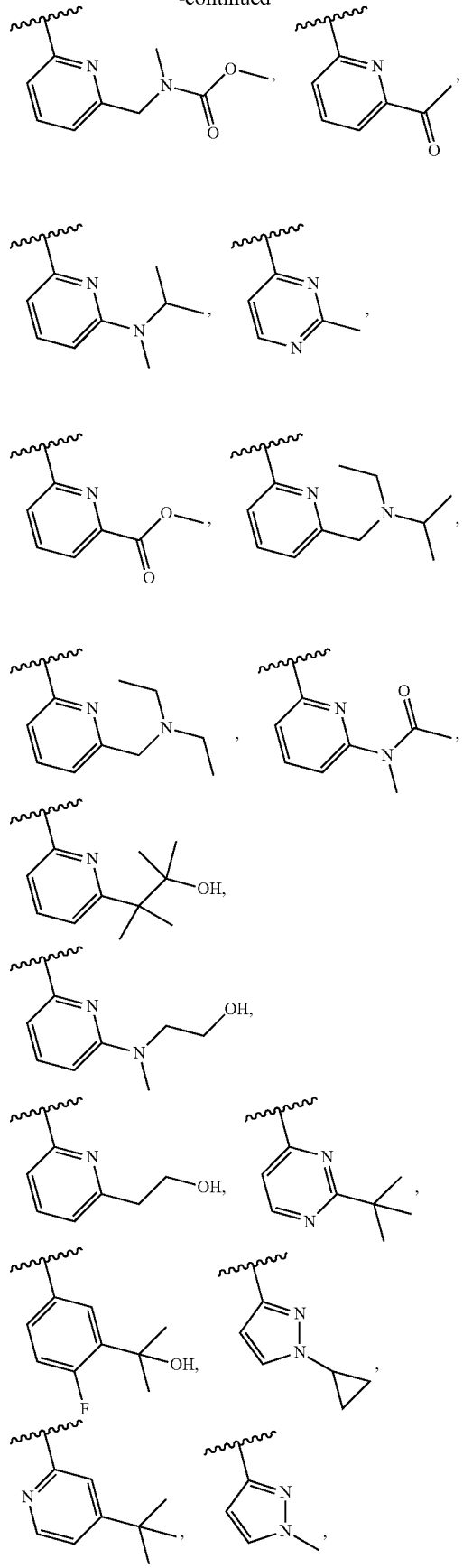

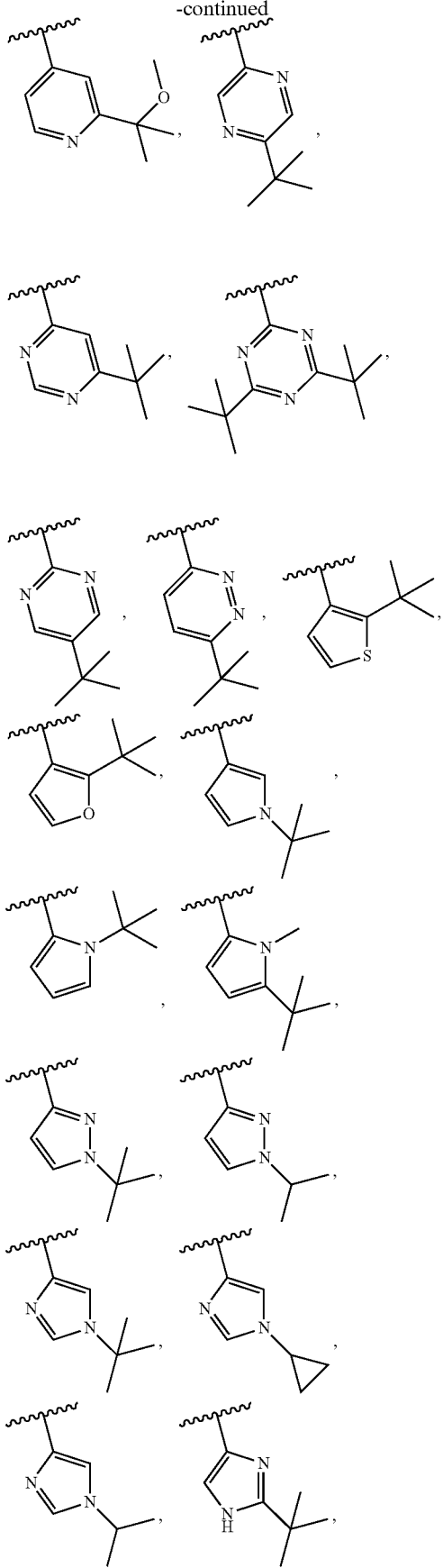
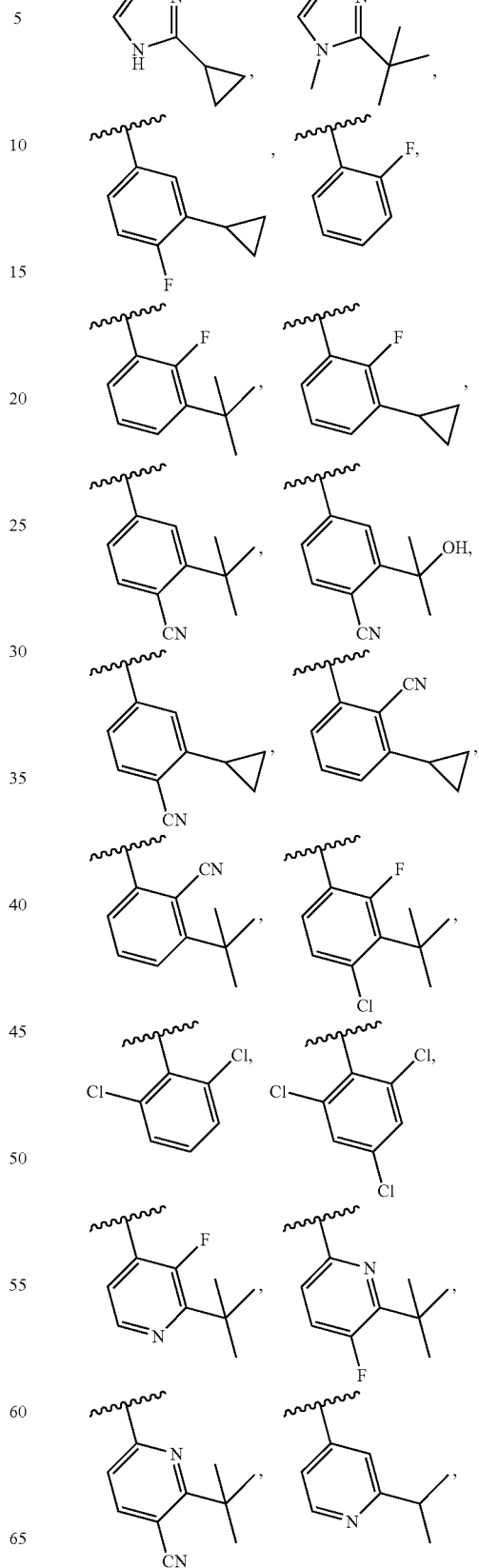

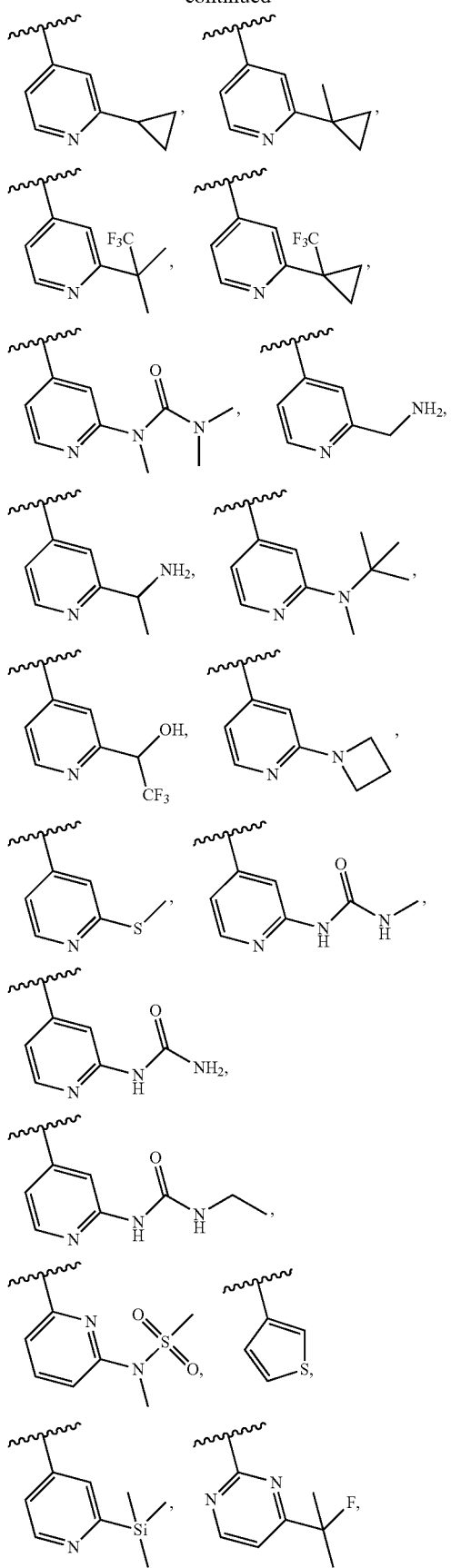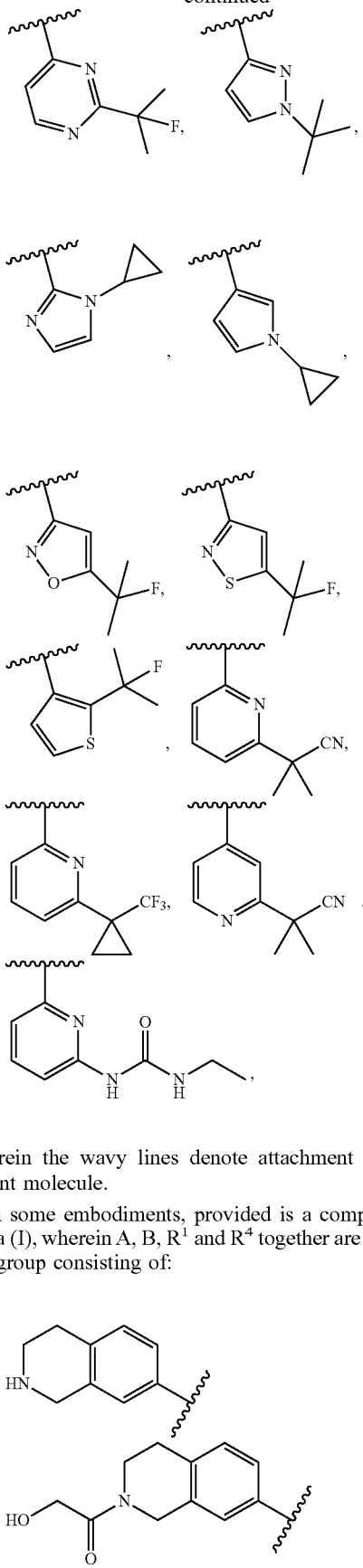
wherein the wavy lines denote attachment points to the parent molecule.
In some embodiments, provided is a compound of Formula (I), wherein A, B, R¹ and R⁴ together are selected from the group consisting of:
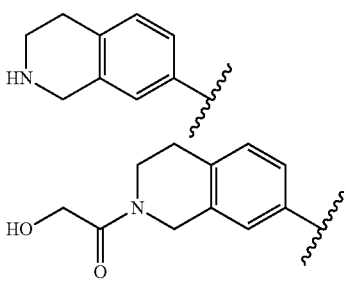

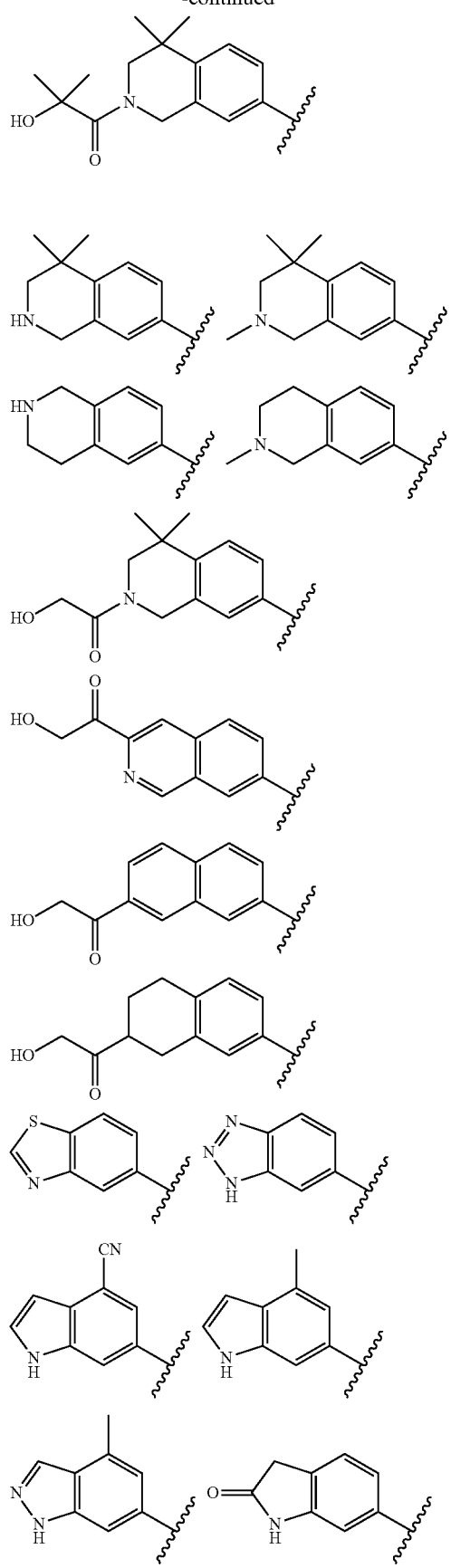
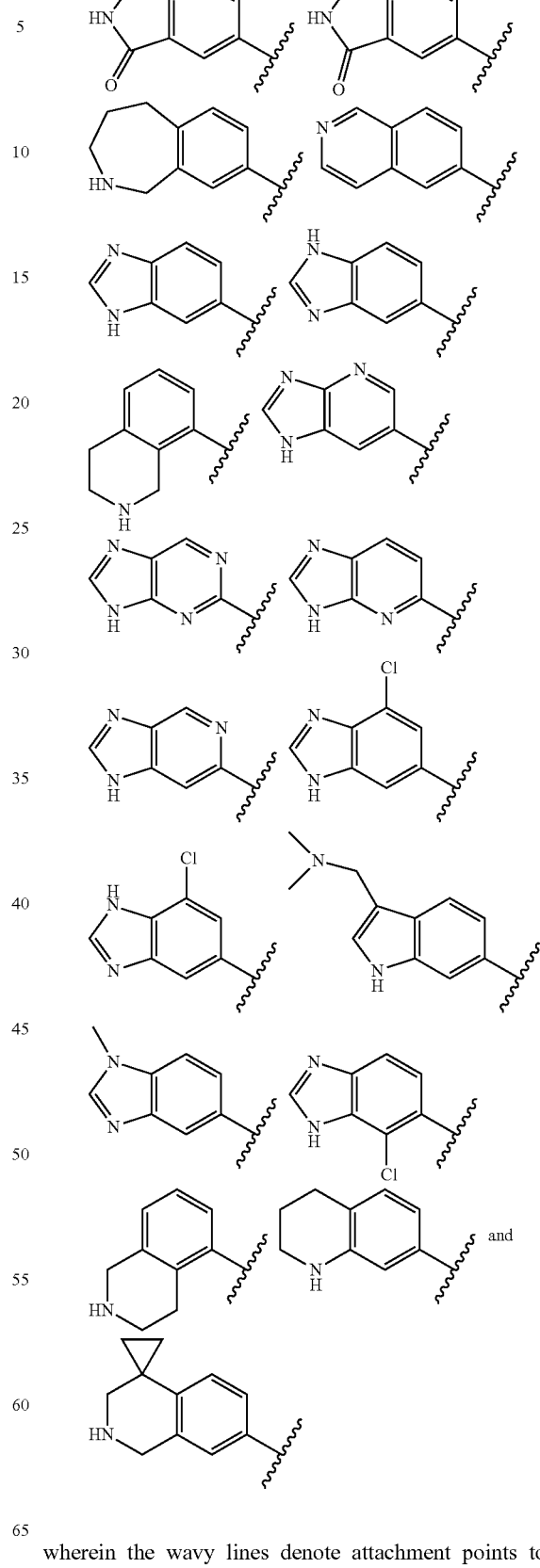
wherein the wavy lines denote attachment points to the parent molecule;

$R^2$ is selected from the group consisting of: allyl, cyclopropylmethyl, isopropyl, cyclopropyl, ethyl, and propyl; and $R^3$ is selected from the group consisting of:

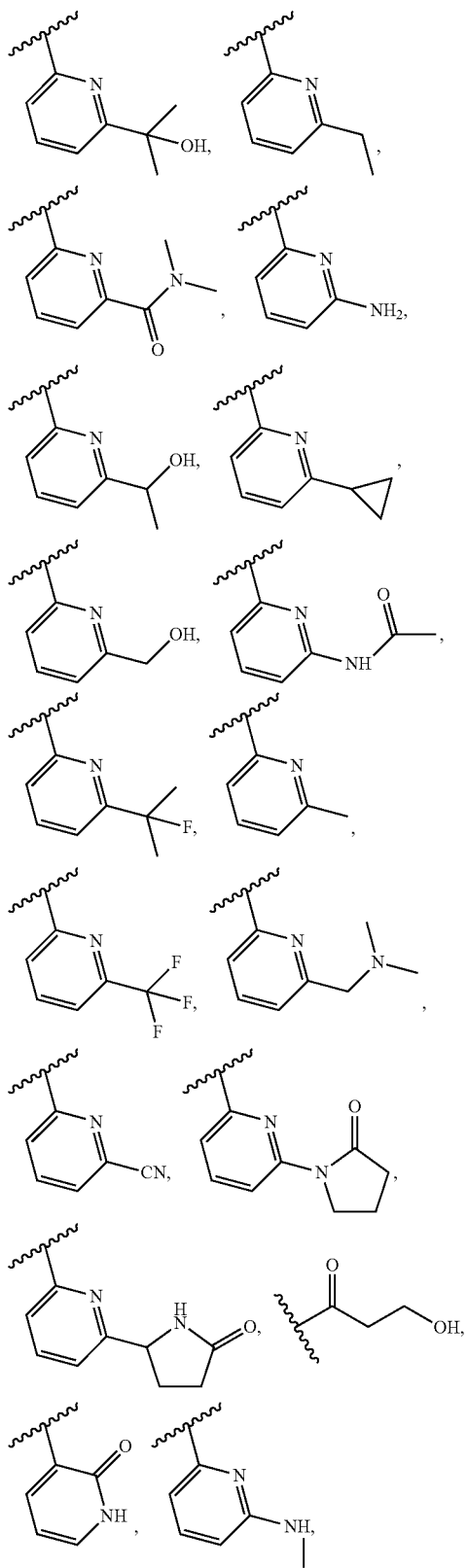

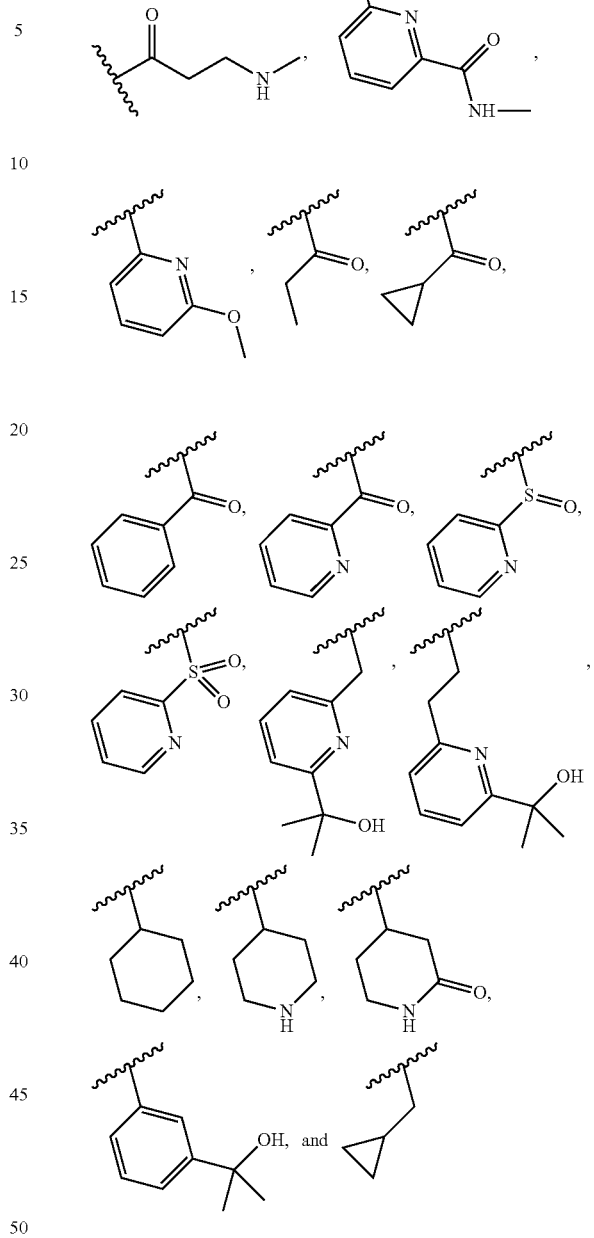

wherein the wavy lines denote attachment points to the parent molecule.

In some embodiments, provided is a compound of Formula (Ia-2), wherein Y is hydrogen; $R^4$ is independently $C_1$-$C_6$ alkyl and n is 2; $R^2$ is $C_1$-$C_6$ alkyl; and $R^3$ is 6-membered heteroaryl optionally substituted by $C_1$-$C_6$ alkyl, wherein the $C_1$-$C_6$ alkyl is optionally substituted by —OH or halogen. In some embodiments, provided is a compound of Formula (Ia-2), wherein Y is hydrogen; $R^4$ is methyl and n is 2; $R^2$ is $C_1$-$C_6$ alkyl; and $R^3$ is 6-membered heteroaryl optionally substituted by $C_1$-$C_6$ alkyl, wherein the $C_1$-$C_6$ alkyl is optionally substituted by —OH or halogen. In some embodiments, provided is a compound of Formula (Ia-2), wherein Y is hydrogen; $R^4$ is methyl and n is 2; $R^2$ is ethyl or isopropyl; and $R^3$ is

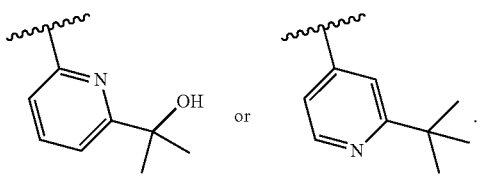 [SMILES: *c1cccc(C(C)(C)O)n1 ; *c1ccnc(C(C)(C)C)c1]

In some embodiments, provided is a compound of Formula (Ia-3), wherein Y is hydrogen and n is 0; $R^2$ is $C_1$-$C_6$ alkyl; and $R^3$ is 6-membered heteroaryl optionally substituted by $C_1$-$C_6$ alkyl, wherein the $C_1$-$C_6$ alkyl is optionally substituted by —OH or halogen. In some embodiments, provided is a compound of Formula (Ia-3), Y is hydrogen and n is 0; $R^2$ is ethyl or isopropyl; and $R^3$ is

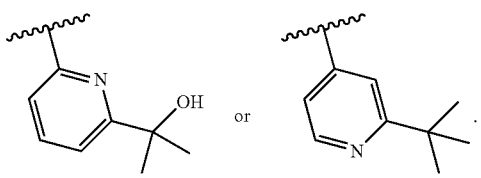 [SMILES: *c1cccc(C(C)(C)O)n1 ; *c1ccnc(C(C)(C)C)c1]

In some embodiments, provided is a compound of Formula (Ia-2), wherein Y is hydrogen; $R^4$ is independently $C_1$-$C_6$ alkyl and n is 2; $R^2$ is $C_1$-$C_6$ alkyl; and $R^3$ is 6-membered heteroaryl optionally substituted by $C_1$-$C_6$ alkyl, wherein the $C_1$-$C_6$ alkyl is optionally substituted by —OH. In some embodiments, provided is a compound of Formula (Ia-2), wherein Y is hydrogen; $R^4$ is methyl and n is 2; $R^2$ is $C_1$-$C_6$ alkyl; and $R^3$ is 6-membered heteroaryl optionally substituted by $C_1$-$C_6$ alkyl, wherein the $C_1$-$C_6$ alkyl is optionally substituted by —OH. In some embodiments, provided is a compound of Formula (Ia-2), wherein Y is hydrogen; $R^4$ is methyl and n is 2; $R^2$ is ethyl; and $R^3$ is

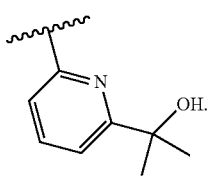 [SMILES: *c1cccc(C(C)(C)O)n1]

In some embodiments, provided is a compound of Formula (Ia-3), wherein Y is hydrogen and n is 0; $R^2$ is $C_1$-$C_6$ alkyl; and $R^3$ is 6-membered heteroaryl optionally substituted by $C_1$-$C_6$ alkyl, wherein the $C_1$-$C_6$ alkyl is optionally substituted by —OH. In some embodiments, provided is a compound of Formula (Ia-3), Y is hydrogen and n is 0; $R^2$ is ethyl; and $R^3$ is

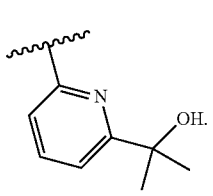 [SMILES: *c1cccc(C(C)(C)O)n1]

In some embodiments, provided is a compound of Formula (I), wherein: A, B, $R^1$ and $R^4$ together are

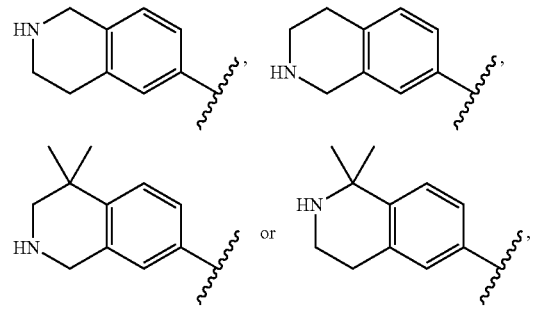

wherein the wavy lines denote attachment points to the parent molecule;

$R^2$ is selected from the group consisting of: allyl, cyclopropylmethyl, isopropyl, cyclopropyl, ethyl, and propyl;

and $R^3$ is selected from the group consisting of

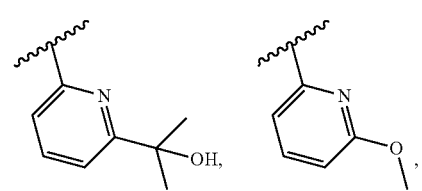

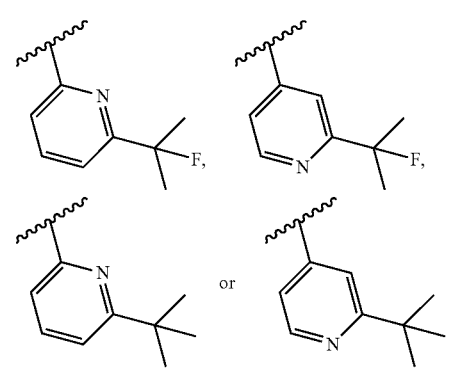

In some embodiments, provided is a compound of Formula (I), wherein:

A, B, $R^1$ and $R^4$ together are

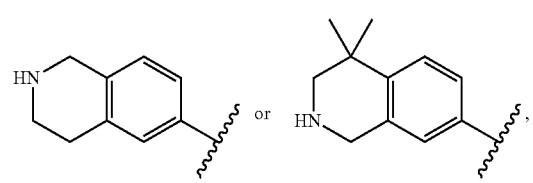 [SMILES: *c1ccc2c(c1)CCNC2 ; *c1ccc2c(c1)CNCC2(C)C]

wherein the wavy lines denote attachment points to the parent molecule;

$R^2$ is selected from the group consisting of: allyl, cyclopropylmethyl, isopropyl, cyclopropyl, ethyl, and propyl;

and R³ is

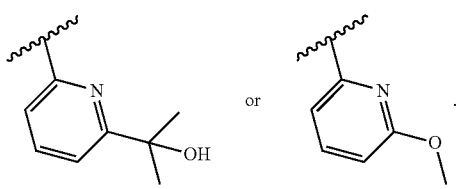

Also provided are salts of compounds referred to herein, such as pharmaceutically acceptable salts. The invention also includes any or all of the stereochemical forms, including any enantiomeric or diastereomeric forms, and any tautomers or other forms of the compounds described. In some embodiments, an isomer of a compound detained herein is a stereoisomer.

A compound as detailed herein may in one aspect be in a purified form and compositions comprising a compound in purified forms are detailed herein. Compositions comprising a compound as detailed herein or a salt thereof are provided, such as compositions of substantially pure compounds. Compositions comprising a compound as detailed herein or a tautomer or isomer thereof, or a pharmaceutically acceptable salt of any of the foregoing are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. In some embodiments, a composition of substantially pure compound or a salt thereof is provided wherein the composition contains no more than 25%, 20%, 15%, 10%, or 5% impurity. In some embodiments, a composition of substantially pure compound or a salt thereof is provided wherein the composition contains or no more than 3%, 2%, 1% or 0.5% impurity.

Representative compounds are listed in Table 1A and Table 1B.

TABLE 1A

| Compound No. | Structure |
| --- | --- |
| 1.1 | 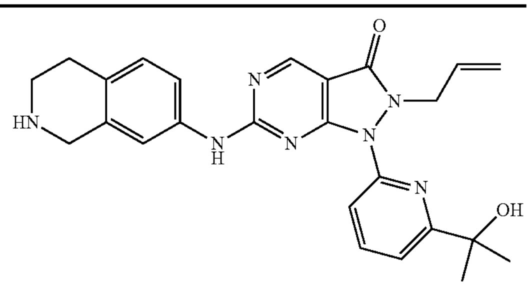 |
| 1.2 | 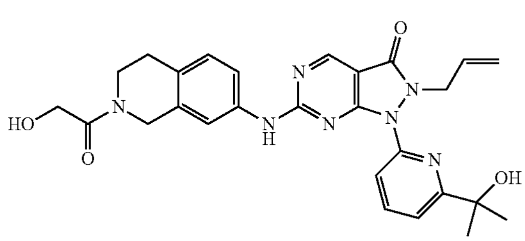 [SMILES: C=CCn1c(=O)c2cnc(Nc3ccc4c(c3)CN(C(=O)CO)CC4)nc2n1-c1cccc(C(C)(C)O)n1] |

TABLE 1A-continued

| Compound No. | Structure |
| --- | --- |
| 1.3 | 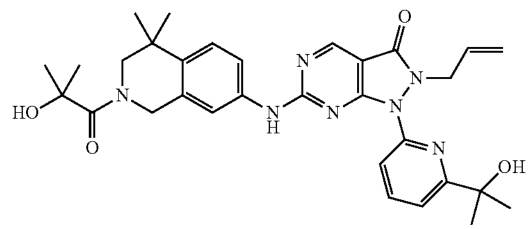 [SMILES: C=CCn1c(=O)c2cnc(Nc3ccc4c(c3)CN(C(=O)C(C)(C)O)CC4(C)C)nc2n1-c1cccc(C(C)(C)O)n1] |
| 1.4 | 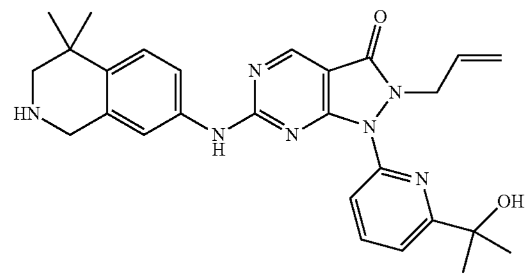 [SMILES: C=CCn1c(=O)c2cnc(Nc3ccc4c(c3)CNCC4(C)C)nc2n1-c1cccc(C(C)(C)O)n1] |
| 1.5 | 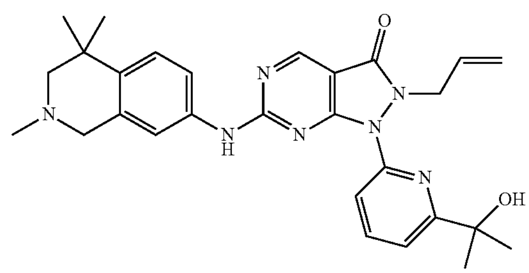 [SMILES: C=CCn1c(=O)c2cnc(Nc3ccc4c(c3)CN(C)CC4(C)C)nc2n1-c1cccc(C(C)(C)O)n1] |
| 1.6 | 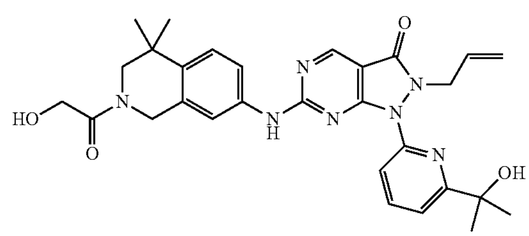 [SMILES: C=CCn1c(=O)c2cnc(Nc3ccc4c(c3)CN(C(=O)CO)CC4(C)C)nc2n1-c1cccc(C(C)(C)O)n1] |
| 1.7 | 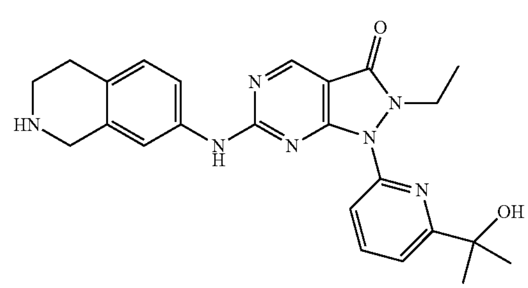 [SMILES: CCn1c(=O)c2cnc(Nc3ccc4c(c3)CNCC4)nc2n1-c1cccc(C(C)(C)O)n1] |

TABLE 1A-continued

| Compound No. | Structure |
|---|---|
| 1.8 | 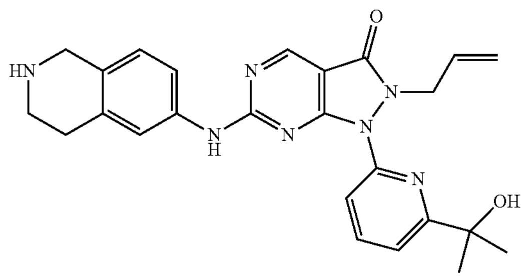 [SMILES: C=CCn1c(=O)c2cnc(Nc3ccc4c(c3)CCNC4)nc2n1-c1cccc(C(C)(C)O)n1] |
| 1.9 | 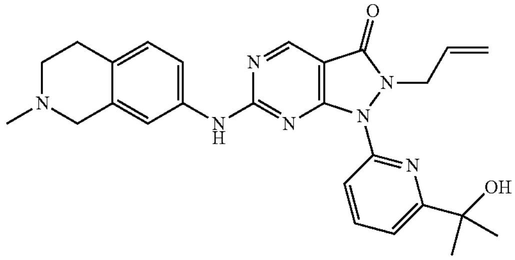 [SMILES: C=CCn1c(=O)c2cnc(Nc3ccc4c(c3)CN(C)CC4)nc2n1-c1cccc(C(C)(C)O)n1] |
| 1.10 | 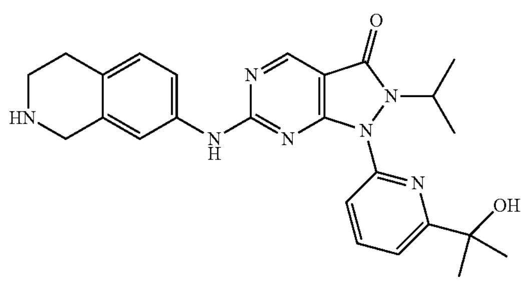 [SMILES: CC(C)n1c(=O)c2cnc(Nc3ccc4c(c3)CNCC4)nc2n1-c1cccc(C(C)(C)O)n1] |
| 1.11 | 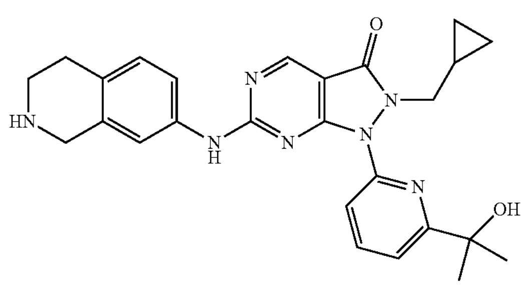 [SMILES: CC(C)(O)c1cccc(-n2c3nc(Nc4ccc5c(c4)CNCC5)ncc3c(=O)n2CC2CC2)n1] |
| 1.12 | 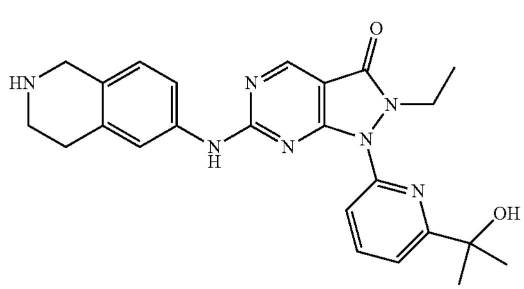 [SMILES: CCn1c(=O)c2cnc(Nc3ccc4c(c3)CCNC4)nc2n1-c1cccc(C(C)(C)O)n1] |
| 1.13 | 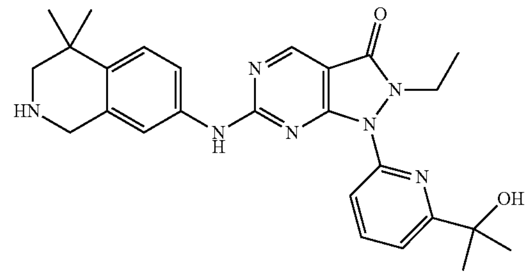 [SMILES: CCn1c(=O)c2cnc(Nc3ccc4c(c3)CNCC4(C)C)nc2n1-c1cccc(C(C)(C)O)n1] |
| 1.14 | 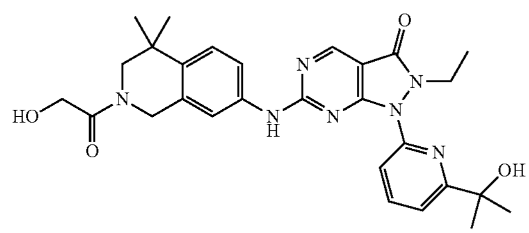 [SMILES: CCn1c(=O)c2cnc(Nc3ccc4c(c3)CN(C(=O)CO)CC4(C)C)nc2n1-c1cccc(C(C)(C)O)n1] |
| 1.15 | 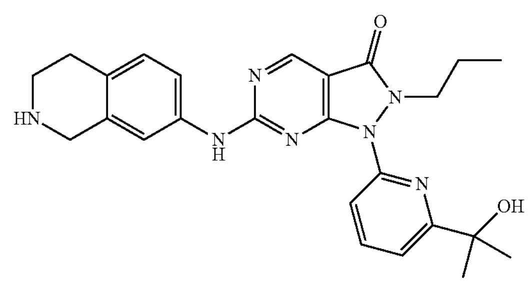 [SMILES: CCCn1c(=O)c2cnc(Nc3ccc4c(c3)CNCC4)nc2n1-c1cccc(C(C)(C)O)n1] |
| 1.16 | 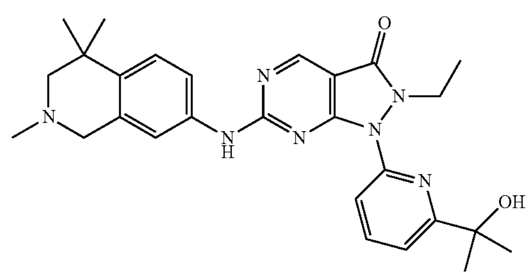 [SMILES: CCn1c(=O)c2cnc(Nc3ccc4c(c3)CN(C)CC4(C)C)nc2n1-c1cccc(C(C)(C)O)n1] |
| 1.17 | 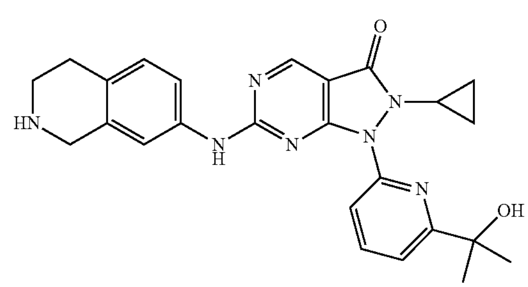 [SMILES: CC(C)(O)c1cccc(-n2c3nc(Nc4ccc5c(c4)CNCC5)ncc3c(=O)n2C2CC2)n1] |

TABLE 1A-continued

| Compound No. | Structure |
|---|---|
| 1.18 | 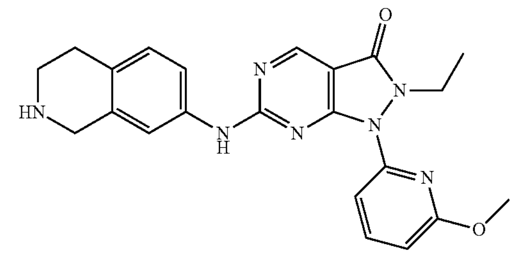 [SMILES: CCn1c(=O)c2cnc(Nc3ccc4c(c3)CNCC4)nc2n1-c1cccc(OC)n1] |
| 1.19 | 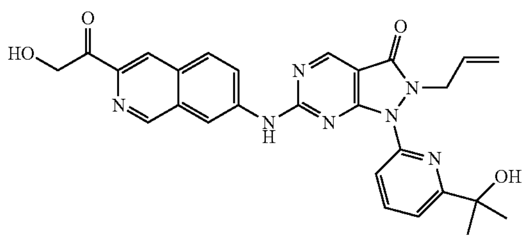 [SMILES: C=CCn1c(=O)c2cnc(Nc3ccc4cc(C(=O)CO)ncc4c3)nc2n1-c1cccc(C(C)(C)O)n1] |
| 1.20 | 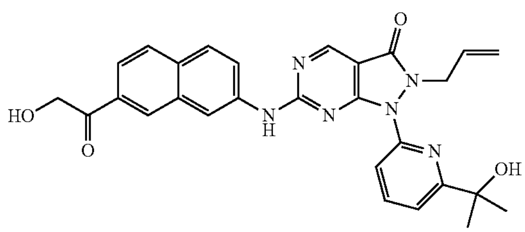 [SMILES: C=CCn1c(=O)c2cnc(Nc3ccc4ccc(C(=O)CO)cc4c3)nc2n1-c1cccc(C(C)(C)O)n1] |
| 1.21 | 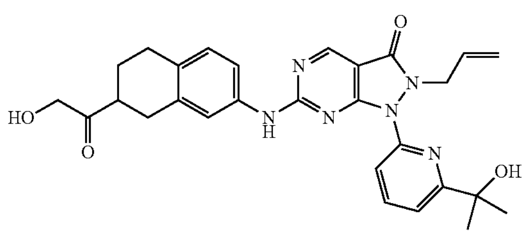 |
| 1.22 | 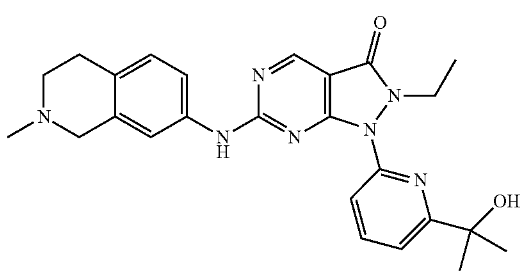 [SMILES: CCn1c(=O)c2cnc(Nc3ccc4c(c3)CN(C)CC4)nc2n1-c1cccc(C(C)(C)O)n1] |
| 1.23 | 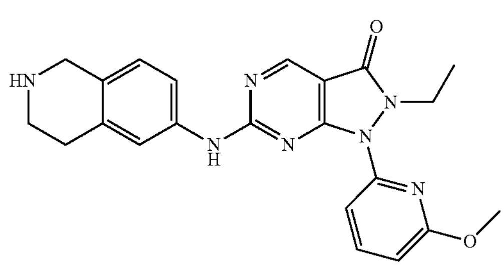 [SMILES: CCn1c(=O)c2cnc(Nc3ccc4c(c3)CCNC4)nc2n1-c1cccc(OC)n1] |
| 1.24 | |
| 1.25 | |
| 1.26 | |
| 1.27 | |
| 1.28 | |

TABLE 1A-continued

| Compound No. | Structure |
|---|---|
| 1.29 | 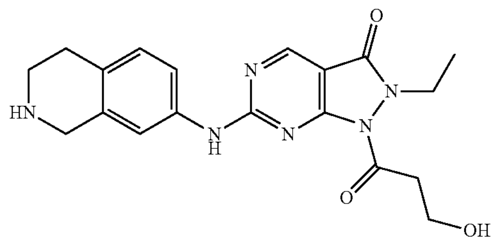 [SMILES: CCn1c(=O)c2cnc(Nc3ccc4c(c3)CNCC4)nc2n1C(=O)CCO] |
| 1.30 | 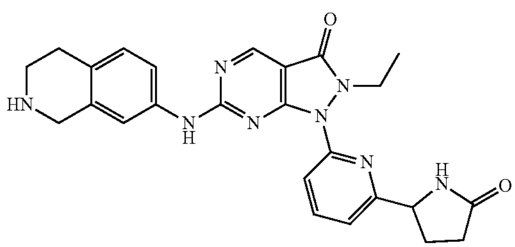 [SMILES: CCn1c(=O)c2cnc(Nc3ccc4c(c3)CNCC4)nc2n1-c1cccc(C2CCC(=O)N2)n1] |
| 1.31 | 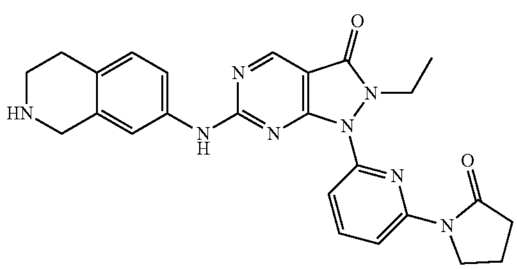 [SMILES: CCn1c(=O)c2cnc(Nc3ccc4c(c3)CNCC4)nc2n1-c1cccc(N2CCCC2=O)n1] |
| 1.32 | 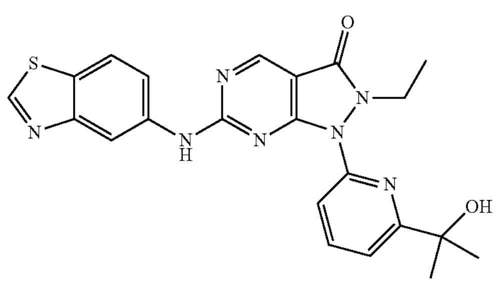 [SMILES: CCn1c(=O)c2cnc(Nc3ccc4scnc4c3)nc2n1-c1cccc(C(C)(C)O)n1] |
| 1.33 | 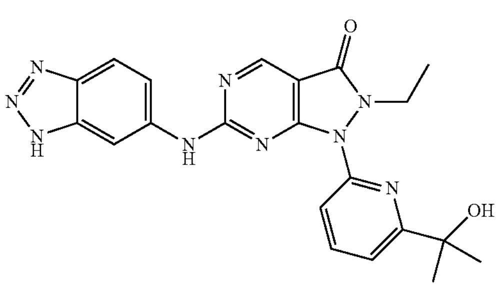 [SMILES: CCn1c(=O)c2cnc(Nc3ccc4nn[nH]c4c3)nc2n1-c1cccc(C(C)(C)O)n1] |
| 1.34 | |
| 1.35 | |
| 1.36 | |
| 1.37 | |
| 1.38 | |

TABLE 1A-continued

| Compound No. | Structure |
|---|---|
| 1.39 | 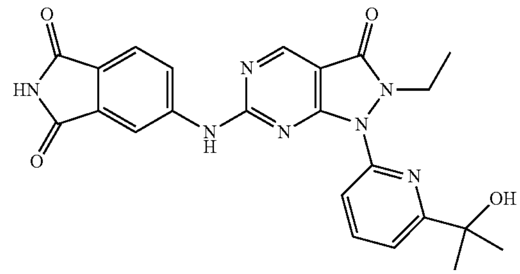 [SMILES: CCn1c(=O)c2cnc(Nc3ccc4c(c3)C(=O)NC4=O)nc2n1-c1cccc(C(C)(C)O)n1] |
| 1.40 | 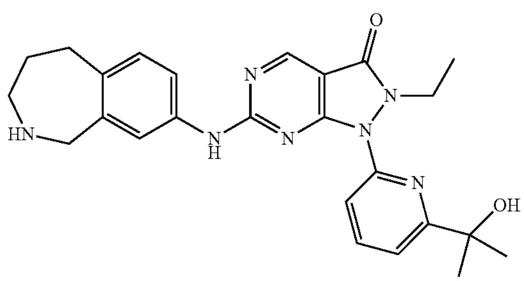 [SMILES: CCn1c(=O)c2cnc(Nc3ccc4c(c3)CNCCC4)nc2n1-c1cccc(C(C)(C)O)n1] |
| 1.41 | 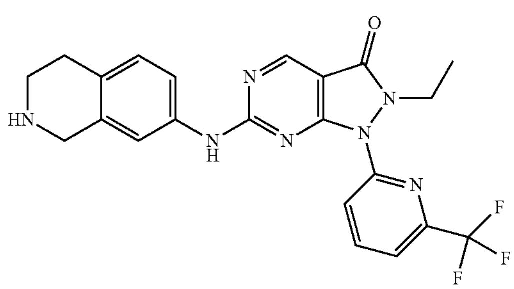 [SMILES: CCn1c(=O)c2cnc(Nc3ccc4c(c3)CNCC4)nc2n1-c1cccc(C(F)(F)F)n1] |
| 1.42 | 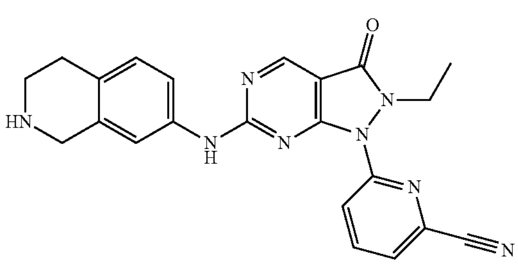 [SMILES: CCn1c(=O)c2cnc(Nc3ccc4c(c3)CNCC4)nc2n1-c1cccc(C#N)n1] |
| 1.43 | 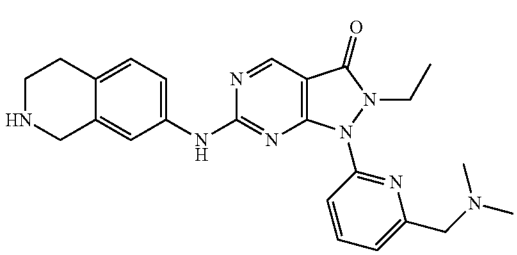 [SMILES: CCn1c(=O)c2cnc(Nc3ccc4c(c3)CNCC4)nc2n1-c1cccc(CN(C)C)n1] |
| 1.44 | |
| 1.45 | |
| 1.46 | |
| 1.47 | |
| 1.48 | |

TABLE 1A-continued

| Compound No. | Structure |
|---|---|
| 1.49 | 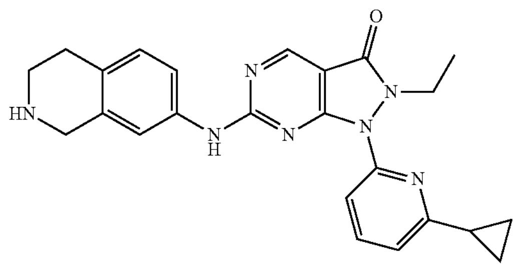 [SMILES: CCn1c(=O)c2cnc(Nc3ccc4c(c3)CNCC4)nc2n1-c1cccc(C2CC2)n1] |
| 1.50 | 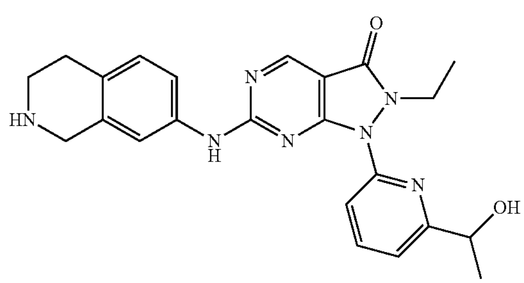 [SMILES: CCn1c(=O)c2cnc(Nc3ccc4c(c3)CNCC4)nc2n1-c1cccc(C(C)O)n1] |
| 1.51 | 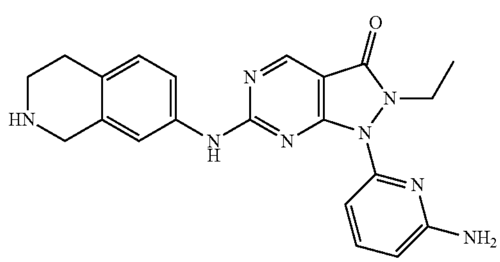 [SMILES: CCn1c(=O)c2cnc(Nc3ccc4c(c3)CNCC4)nc2n1-c1cccc(N)n1] |
| 1.52 | 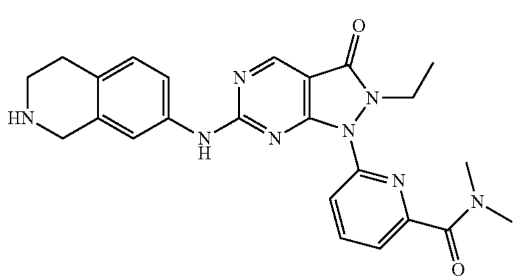 [SMILES: CCn1c(=O)c2cnc(Nc3ccc4c(c3)CNCC4)nc2n1-c1cccc(C(=O)N(C)C)n1] |
| 1.53 | 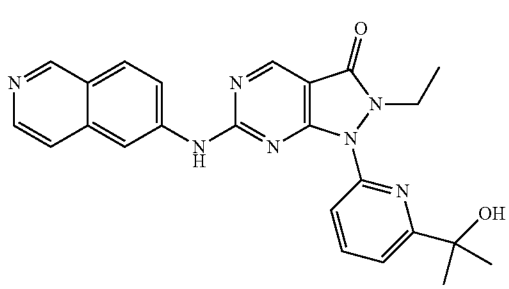 [SMILES: CCn1c(=O)c2cnc(Nc3ccc4cnccc4c3)nc2n1-c1cccc(C(C)(C)O)n1] |
| 1.54 | |
| 1.55 | |
| 1.56 | |
| 1.57 | |
| 1.58 | |

TABLE 1A-continued

| Compound No. | Structure |
|---|---|
| 1.59 | 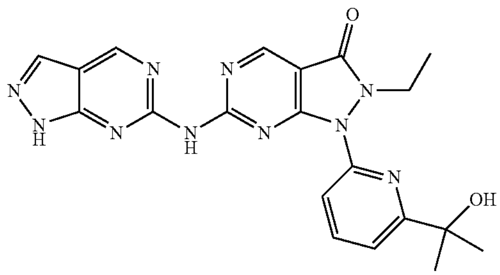 [SMILES: CCn1c(=O)c2cnc(Nc3ncc4cn[nH]c4n3)nc2n1-c1cccc(C(C)(C)O)n1] |
| 1.60 | 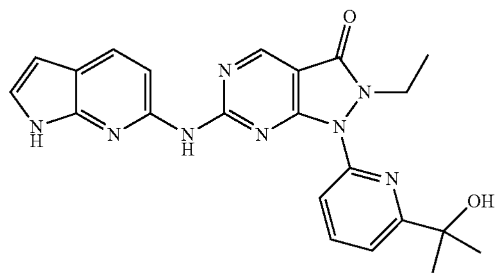 [SMILES: CCn1c(=O)c2cnc(Nc3ccc4cc[nH]c4n3)nc2n1-c1cccc(C(C)(C)O)n1] |
| 1.61 | 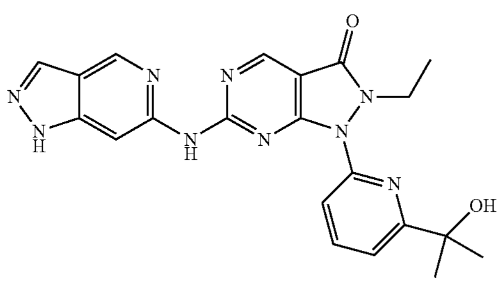 [SMILES: CCn1c(=O)c2cnc(Nc3cc4[nH]ncc4cn3)nc2n1-c1cccc(C(C)(C)O)n1] |
| 1.62 | 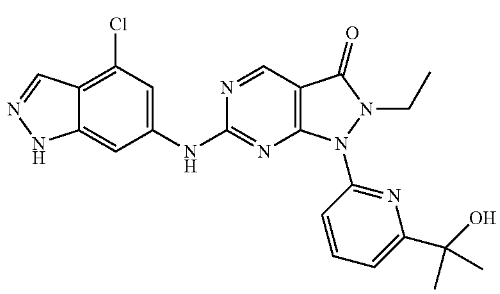 [SMILES: CCn1c(=O)c2cnc(Nc3cc(Cl)c4cn[nH]c4c3)nc2n1-c1cccc(C(C)(C)O)n1] |
| 1.63 | 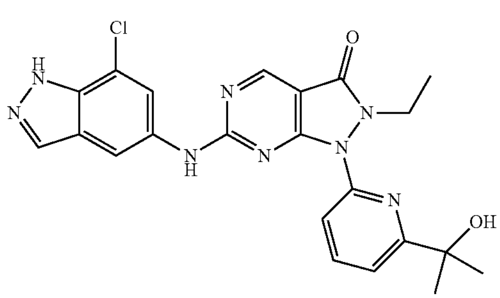 [SMILES: CCn1c(=O)c2cnc(Nc3cc(Cl)c4[nH]ncc4c3)nc2n1-c1cccc(C(C)(C)O)n1] |

TABLE 1A-continued

| Compound No. | Structure |
|---|---|
| 1.64 | 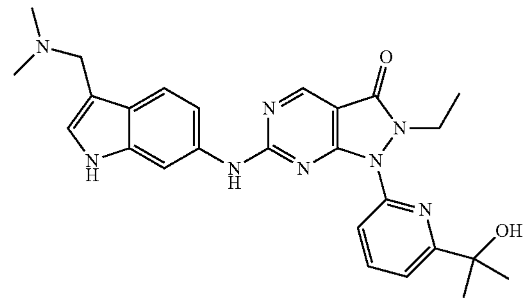 [SMILES: CCn1c(=O)c2cnc(Nc3ccc4c(CN(C)C)c[nH]c4c3)nc2n1-c1cccc(C(C)(C)O)n1] |
| 1.65 | 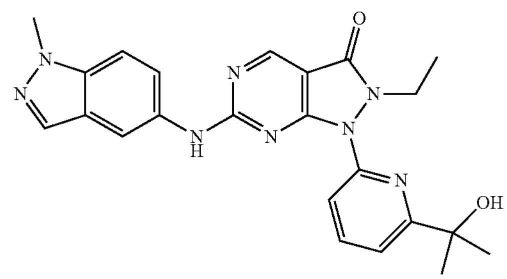 [SMILES: CCn1c(=O)c2cnc(Nc3ccc4c(cnn4C)c3)nc2n1-c1cccc(C(C)(C)O)n1] |
| 1.66 | 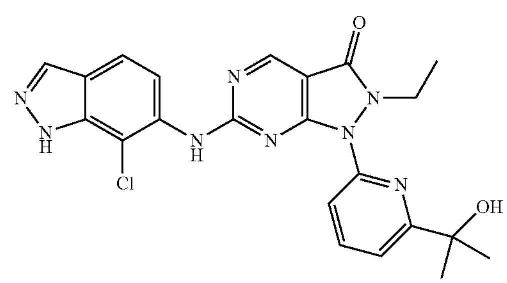 [SMILES: CCn1c(=O)c2cnc(Nc3ccc4cn[nH]c4c3Cl)nc2n1-c1cccc(C(C)(C)O)n1] |
| 1.67 | 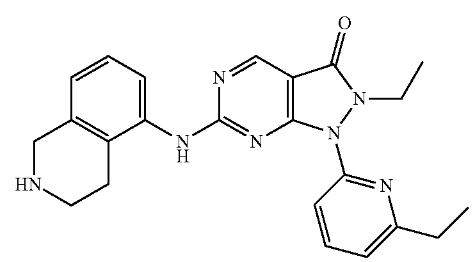 [SMILES: CCc1cccc(-n2c3nc(Nc4cccc5c4CCNC5)ncc3c(=O)n2CC)n1] |
| 1.68 | 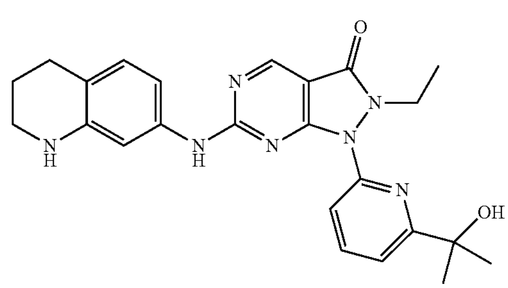 [SMILES: CCn1c(=O)c2cnc(Nc3ccc4c(c3)NCCC4)nc2n1-c1cccc(C(C)(C)O)n1] |

TABLE 1A-continued

| Compound No. | Structure |
|---|---|
| 1.69 | 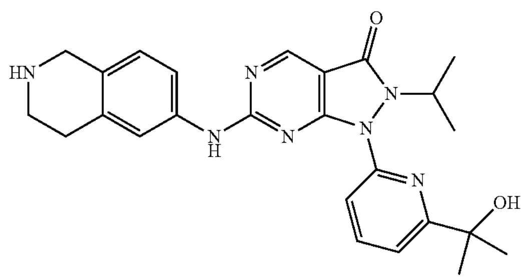 [SMILES: CC(C)n1c(=O)c2cnc(Nc3ccc4c(c3)CCNC4)nc2n1-c1cccc(C(C)(C)O)n1] |
| 1.70 | 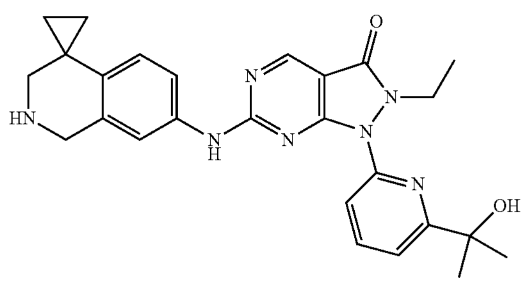 [SMILES: CCn1c(=O)c2cnc(Nc3ccc4c(c3)CNCC43CC3)nc2n1-c1cccc(C(C)(C)O)n1] |
| 1.71 | 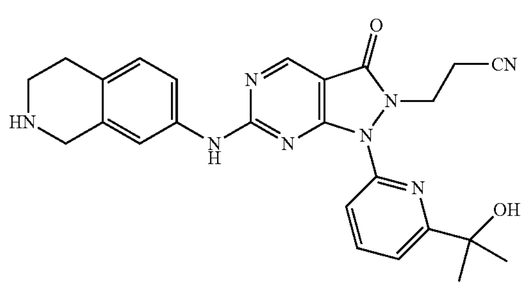 [SMILES: CC(C)(O)c1cccc(-n2c3nc(Nc4ccc5c(c4)CNCC5)ncc3c(=O)n2CCC#N)n1] |
| 1.72 | 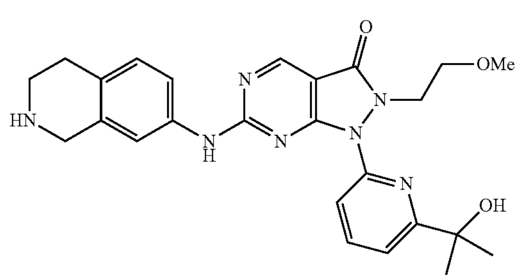 [SMILES: COCCn1c(=O)c2cnc(Nc3ccc4c(c3)CNCC4)nc2n1-c1cccc(C(C)(C)O)n1] |
| 1.73 | 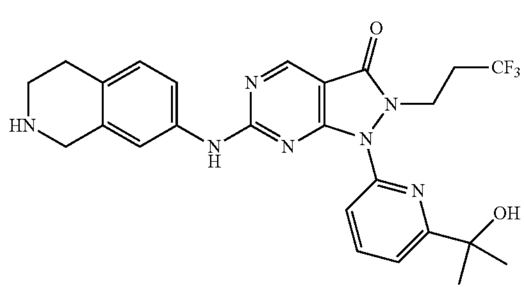 |
| 1.74 | |
| 1.75 | |
| 1.76 | |
| 1.77 | |
| 1.78 | |

TABLE 1A-continued

| Compound No. | Structure |
|---|---|
| 1.79 | (tetrahydroisoquinolin-6-ylamino)-pyrazolo[3,4-d]pyrimidin-3(2H)-one with N-(pyridin-3-ylmethyl) and N-[6-(2-hydroxypropan-2-yl)pyridin-2-yl] substituents |
| 1.80 | (tetrahydroisoquinolin-6-ylamino)-pyrazolo[3,4-d]pyrimidin-3(2H)-one with N-(pyridin-4-ylmethyl) and N-[6-(2-hydroxypropan-2-yl)pyridin-2-yl] substituents |
| 1.81 | (tetrahydroisoquinolin-6-ylamino)-pyrazolo[3,4-d]pyrimidin-3(2H)-one with N-(cyclobutylmethyl) and N-[6-(2-hydroxypropan-2-yl)pyridin-2-yl] substituents |
| 1.82 | (tetrahydroisoquinolin-6-ylamino)-pyrazolo[3,4-d]pyrimidin-3(2H)-one with N-(cyclopentylmethyl) and N-[6-(2-hydroxypropan-2-yl)pyridin-2-yl] substituents |
| 1.83 | (tetrahydroisoquinolin-6-ylamino)-pyrazolo[3,4-d]pyrimidin-3(2H)-one with N-(cyclohexylmethyl) and N-[6-(2-hydroxypropan-2-yl)pyridin-2-yl] substituents |
| 1.84 | (tetrahydroisoquinolin-6-ylamino)-pyrazolo[3,4-d]pyrimidin-3(2H)-one with N-[(1-methylpiperidin-4-yl)methyl] and N-[6-(2-hydroxypropan-2-yl)pyridin-2-yl] substituents |
| 1.85 | (tetrahydroisoquinolin-6-ylamino)-pyrazolo[3,4-d]pyrimidin-3(2H)-one with N-(2-cyanoethyl) and N-[6-(2-hydroxypropan-2-yl)pyridin-2-yl] substituents |
| 1.86 | (tetrahydroisoquinolin-6-ylamino)-pyrazolo[3,4-d]pyrimidin-3(2H)-one with N-(2-methoxyethyl) and N-[6-(2-hydroxypropan-2-yl)pyridin-2-yl] substituents |
| 1.87 | (tetrahydroisoquinolin-6-ylamino)-pyrazolo[3,4-d]pyrimidin-3(2H)-one with N-(3,3,3-trifluoropropyl) and N-[6-(2-hydroxypropan-2-yl)pyridin-2-yl] substituents |
| 1.88 | (tetrahydroisoquinolin-6-ylamino)-pyrazolo[3,4-d]pyrimidin-3(2H)-one with N-(2-oxopropyl) and N-[6-(2-hydroxypropan-2-yl)pyridin-2-yl] substituents |

TABLE 1A-continued
| Compound No. | Structure |
|---|---|
| 1.89 | 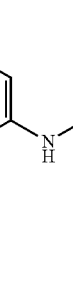 |
| 1.90 | 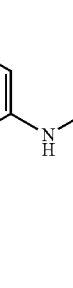 |
| 1.91 | 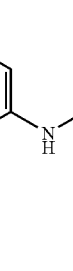 |
| 1.92 | 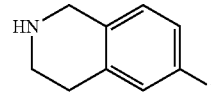 |
| 1.93 | 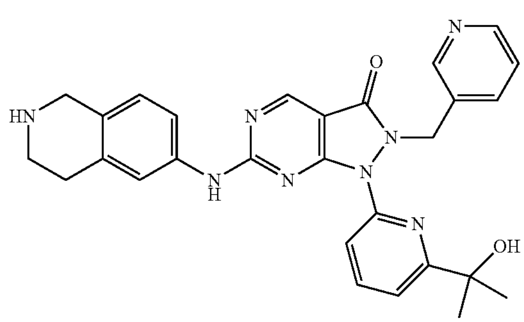 [SMILES: CC(C)(O)c1cccc(-n2c3nc(Nc4ccc5c(c4)CCNC5)ncc3c(=O)n2Cc2cccnc2)n1] |
| 1.94 |  |
| 1.95 | 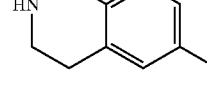 |
| 1.96 | 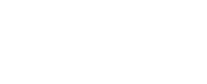 |
| 1.97 |  |
| 1.98 | 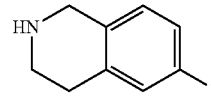 |

TABLE 1A-continued

| Compound No. | Structure |
|---|---|
| 1.99 | 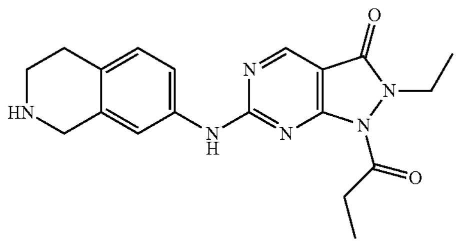 [SMILES: CCC(=O)n1c2nc(Nc3ccc4c(c3)CNCC4)ncc2c(=O)n1CC] |
| 1.100 | 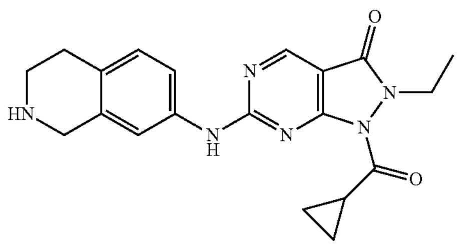 [SMILES: CCn1c(=O)c2cnc(Nc3ccc4c(c3)CNCC4)nc2n1C(=O)C1CC1] |
| 1.101 | 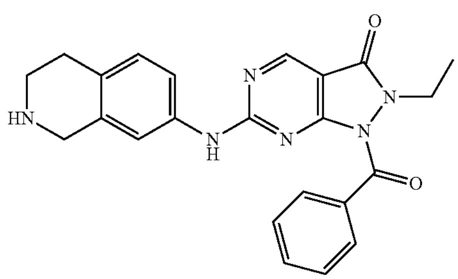 [SMILES: CCn1c(=O)c2cnc(Nc3ccc4c(c3)CNCC4)nc2n1C(=O)c1ccccc1] |
| 1.102 | 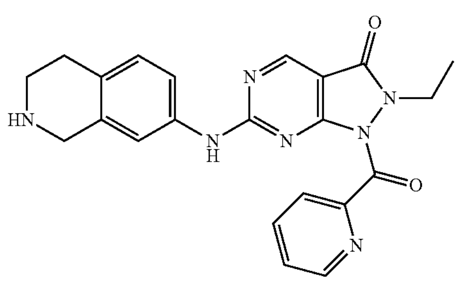 [SMILES: CCn1c(=O)c2cnc(Nc3ccc4c(c3)CNCC4)nc2n1C(=O)c1ccccn1] |
| 1.103 | 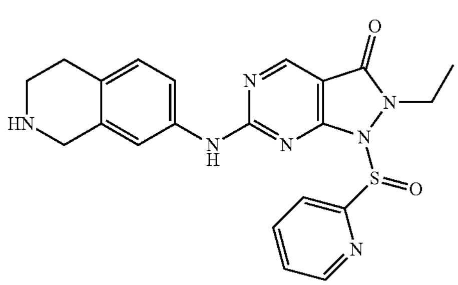 [SMILES: CCn1c(=O)c2cnc(Nc3ccc4c(c3)CNCC4)nc2n1S(=O)c1ccccn1] |
| 1.104 | |
| 1.105 | |
| 1.106 | |
| 1.107 | |
| 1.108 | |

TABLE 1A-continued

| Compound No. | Structure |
|---|---|
| 1.109 | 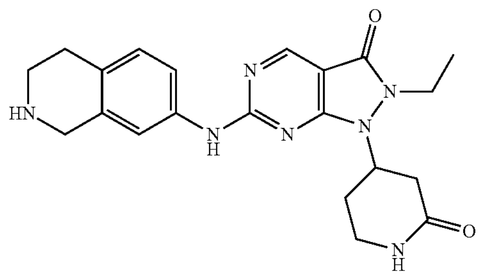 [SMILES: CCn1c(=O)c2cnc(Nc3ccc4c(c3)CNCC4)nc2n1C1CCNC(=O)C1] |
| 1.110 | 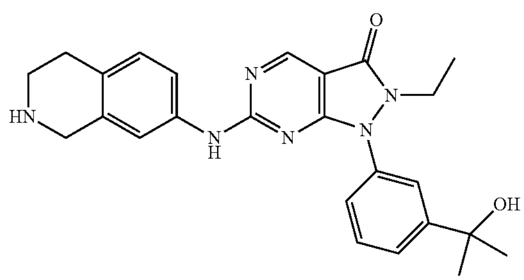 |
| 1.111 | 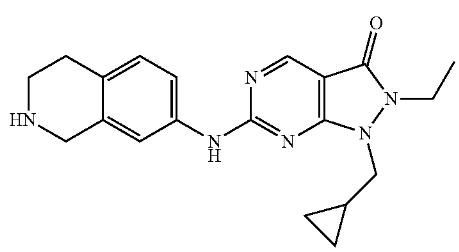 [SMILES: CCn1c(=O)c2cnc(Nc3ccc4c(c3)CNCC4)nc2n1CC1CC1] |
| 1.112 | 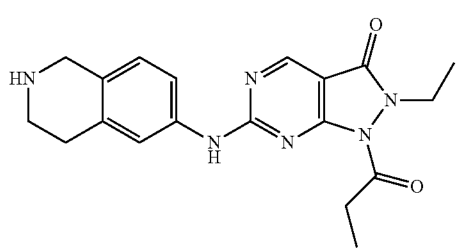 [SMILES: CCC(=O)n1c2nc(Nc3ccc4c(c3)CCNC4)ncc2c(=O)n1CC] |
| 1.113 | 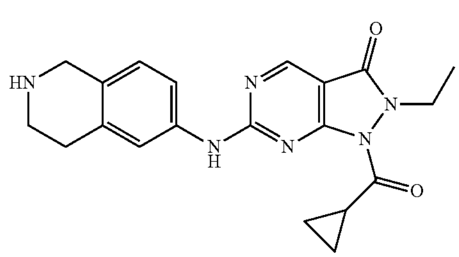 [SMILES: CCn1c(=O)c2cnc(Nc3ccc4c(c3)CCNC4)nc2n1C(=O)C1CC1] |
| 1.114 | |
| 1.115 | |
| 1.116 | |
| 1.117 | |
| 1.118 | |

TABLE 1A-continued
| Compound No. | Structure |
|---|---|
| 1.119 | 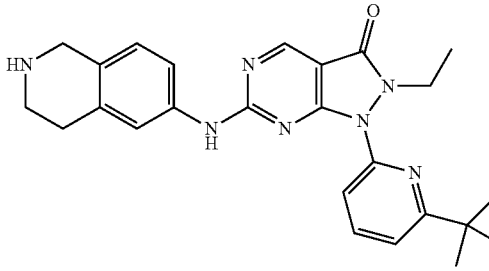 |
| 1.120 | 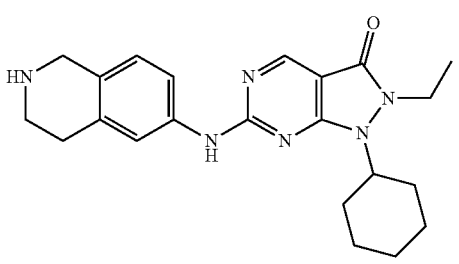 [SMILES: CCn1c(=O)c2cnc(Nc3ccc4c(c3)CCNC4)nc2n1C1CCCCC1] |
| 1.121 | 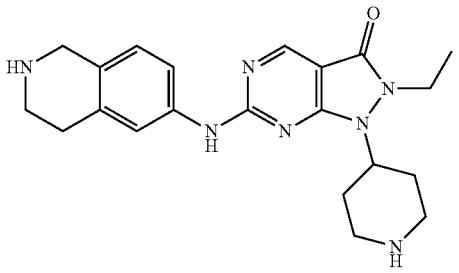 [SMILES: CCn1c(=O)c2cnc(Nc3ccc4c(c3)CCNC4)nc2n1C1CCNCC1] |
| 1.122 | 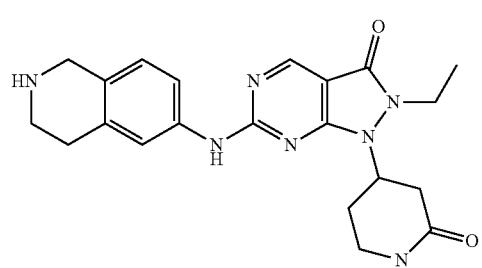 |
| 1.123 | 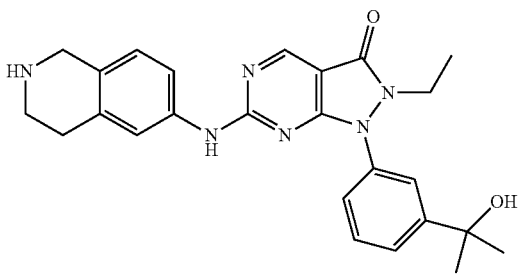 [SMILES: CCn1c(=O)c2cnc(Nc3ccc4c(c3)CCNC4)nc2n1-c1cccc(C(C)(C)O)c1] |
| 1.124 | 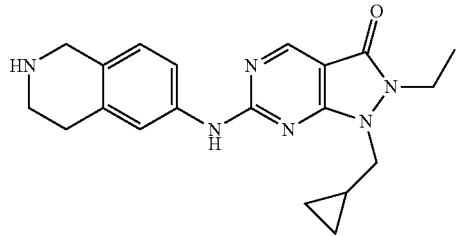 [SMILES: CCn1c(=O)c2cnc(Nc3ccc4c(c3)CCNC4)nc2n1CC1CC1] |
| 1.125 | 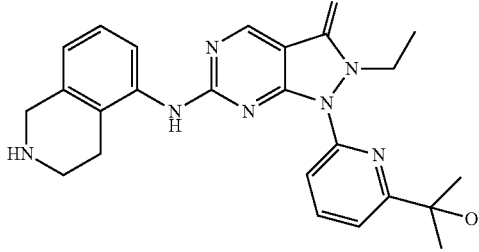 |
| 1.126 | 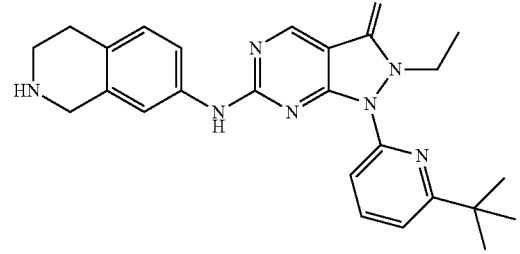 |
| 1.127 | 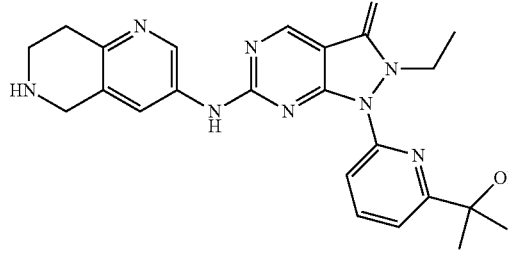 |
| 1.128 | 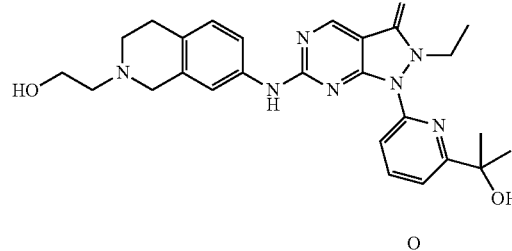 |
| 1.129 | 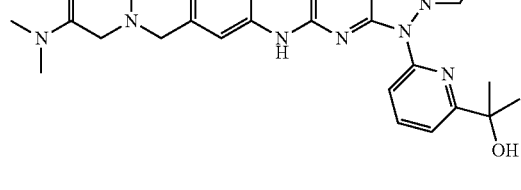 |

TABLE 1A-continued

| Compound No. | Structure |
|---|---|
| 1.130 | 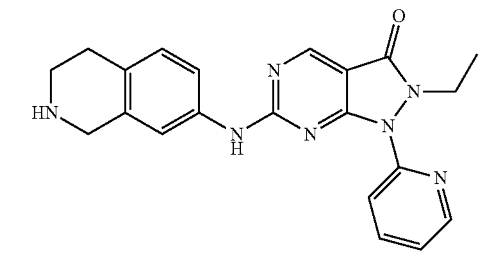 [SMILES: CCn1c(=O)c2cnc(Nc3ccc4c(c3)CNCC4)nc2n1-c1ccccn1] |
| 1.131 | 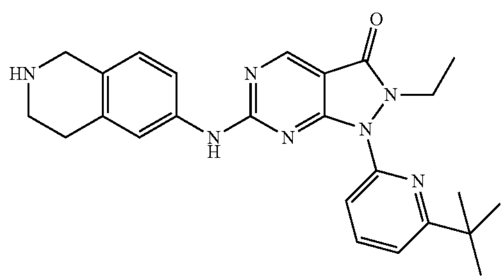 [SMILES: CCn1c(=O)c2cnc(Nc3ccc4c(c3)CCNC4)nc2n1-c1cccc(C(C)(C)C)n1] |
| 1.132 | 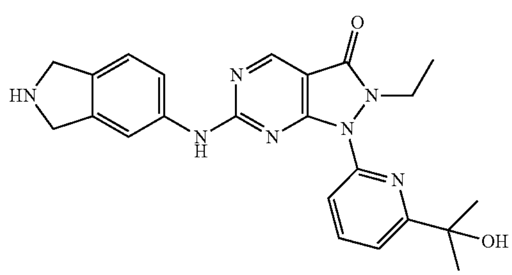 [SMILES: CCn1c(=O)c2cnc(Nc3ccc4c(c3)CNC4)nc2n1-c1cccc(C(C)(C)O)n1] |
| 1.133 | 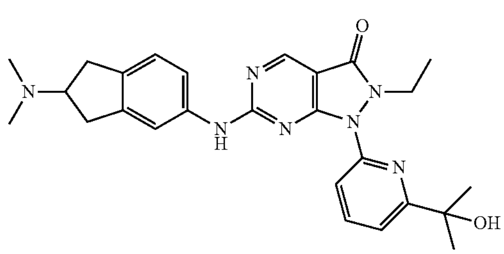 [SMILES: CCn1c(=O)c2cnc(Nc3ccc4c(c3)CC(N(C)C)C4)nc2n1-c1cccc(C(C)(C)O)n1] |
| 1.134 | 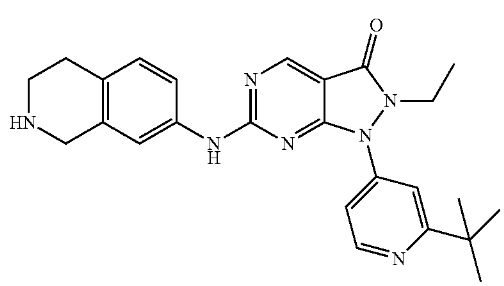 [SMILES: CCn1c(=O)c2cnc(Nc3ccc4c(c3)CNCC4)nc2n1-c1ccnc(C(C)(C)C)c1] |
| 1.135 | |
| 1.136 | |
| 1.137 | |
| 1.138 | |
| 1.139 | |

TABLE 1A-continued

| Compound No. | Structure |
|---|---|
| 1.140 | 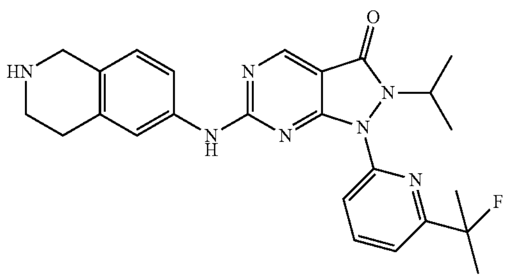 [SMILES: CC(C)n1c(=O)c2cnc(Nc3ccc4c(c3)CCNC4)nc2n1-c1cccc(C(C)(C)F)n1] |
| 1.141 | 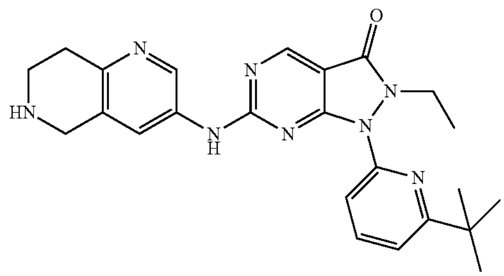 [SMILES: CCn1c(=O)c2cnc(Nc3cnc4c(c3)CNCC4)nc2n1-c1cccc(C(C)(C)C)n1] |
| 1.142 | 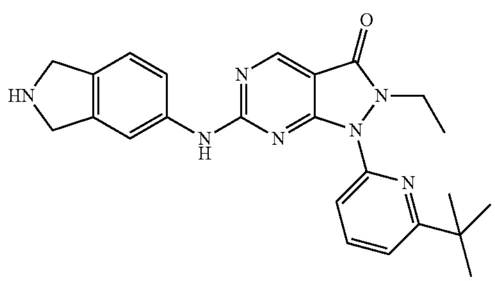 [SMILES: CCn1c(=O)c2cnc(Nc3ccc4c(c3)CNC4)nc2n1-c1cccc(C(C)(C)C)n1] |
| 1.143 | 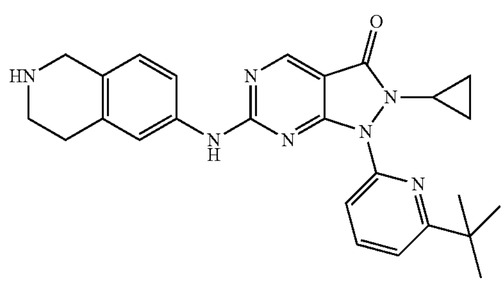 [SMILES: CC(C)(C)c1cccc(-n2c3nc(Nc4ccc5c(c4)CCNC5)ncc3c(=O)n2C2CC2)n1] |
| 1.144 | 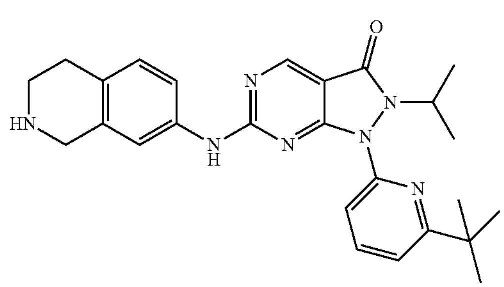 [SMILES: CC(C)n1c(=O)c2cnc(Nc3ccc4c(c3)CNCC4)nc2n1-c1cccc(C(C)(C)C)n1] |
| 1.145 | |
| 1.146 | |
| 1.147 | |
| 1.148 | |
| 1.149 | |

TABLE 1A-continued

| Compound No. | Structure |
|---|---|
| 1.150 | |
| 1.151 | |
| 1.152 | |
| 1.153 | |
| 1.154 | |️
| 1.155 | 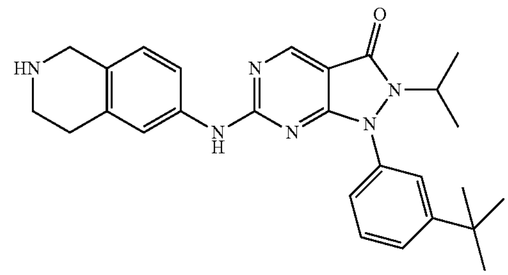 [SMILES: CC(C)n1c(=O)c2cnc(Nc3ccc4c(c3)CCNC4)nc2n1-c1cccc(C(C)(C)C)c1] |
| 1.156 | 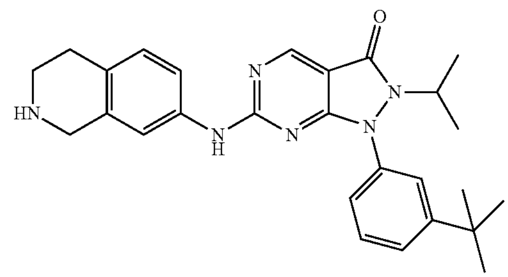 [SMILES: CC(C)n1c(=O)c2cnc(Nc3ccc4c(c3)CNCC4)nc2n1-c1cccc(C(C)(C)C)c1] |
| 1.157 | 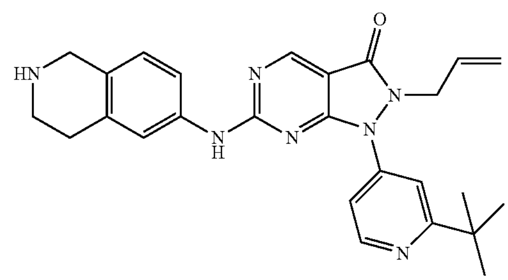 [SMILES: C=CCn1c(=O)c2cnc(Nc3ccc4c(c3)CCNC4)nc2n1-c1ccnc(C(C)(C)C)c1] |
| 1.158 | 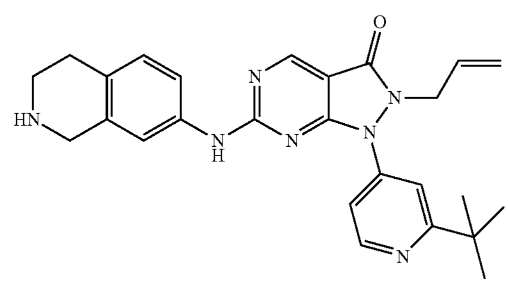 [SMILES: C=CCn1c(=O)c2cnc(Nc3ccc4c(c3)CNCC4)nc2n1-c1ccnc(C(C)(C)C)c1] |
| 1.159 | 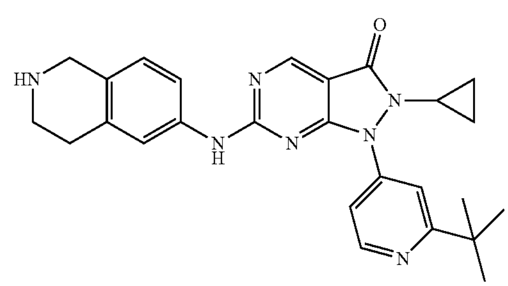 [SMILES: CC(C)(C)c1cc(-n2c3nc(Nc4ccc5c(c4)CCNC5)ncc3c(=O)n2C2CC2)ccn1] |

TABLE 1A-continued

| Compound No. | Structure |
|---|---|
| 1.160 | 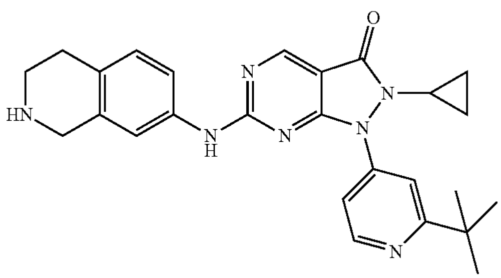 [SMILES: CC(C)(C)c1cc(-n2c3nc(Nc4ccc5c(c4)CNCC5)ncc3c(=O)n2C2CC2)ccn1] |
| 1.161 | 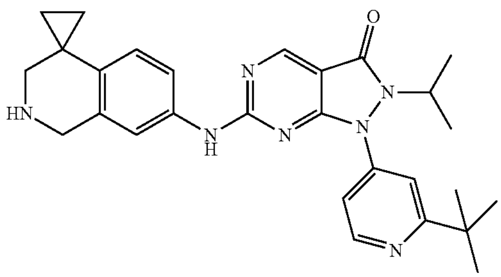 [SMILES: CC(C)n1c(=O)c2cnc(Nc3ccc4c(c3)CNCC43CC3)nc2n1-c1ccnc(C(C)(C)C)c1] |
| 1.162 | 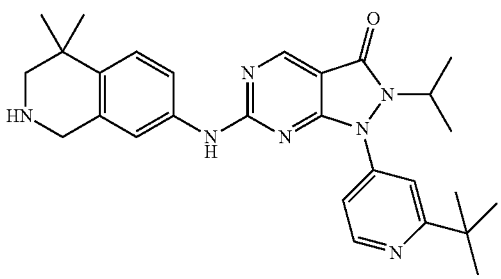 [SMILES: CC(C)n1c(=O)c2cnc(Nc3ccc4c(c3)CNCC4(C)C)nc2n1-c1ccnc(C(C)(C)C)c1] |
| 1.163 | 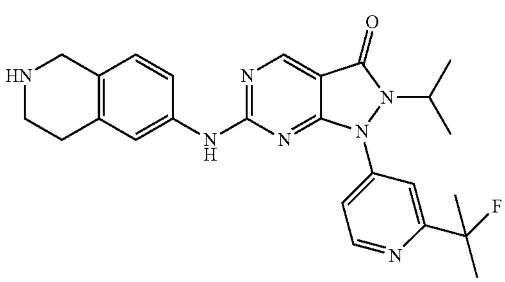 [SMILES: CC(C)n1c(=O)c2cnc(Nc3ccc4c(c3)CCNC4)nc2n1-c1ccnc(C(C)(C)F)c1] |
| 1.164 | 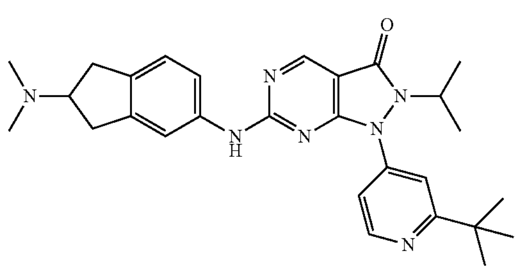 [SMILES: CC(C)n1c(=O)c2cnc(Nc3ccc4c(c3)CC(N(C)C)C4)nc2n1-c1ccnc(C(C)(C)C)c1] |
| 1.165 | |
| 1.166 | |
| 1.167 | |
| 1.168 | |
| 1.169 | |

TABLE 1A-continued
| Compound No. | Structure |
|---|---|
| 1.170 | 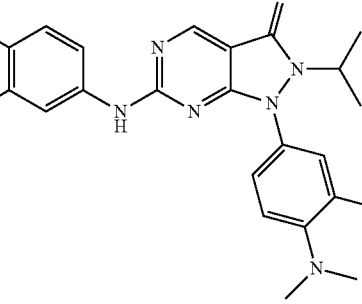 |
| 1.171 | 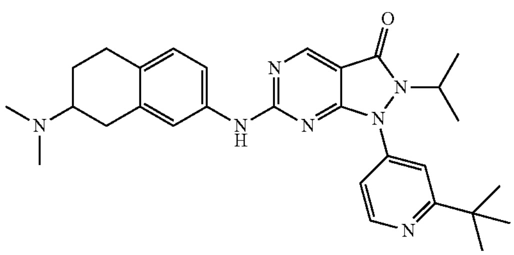 [SMILES: CC(C)n1c(=O)c2cnc(Nc3ccc4c(c3)CC(N(C)C)CC4)nc2n1-c1ccnc(C(C)(C)C)c1] |
| 1.172 | 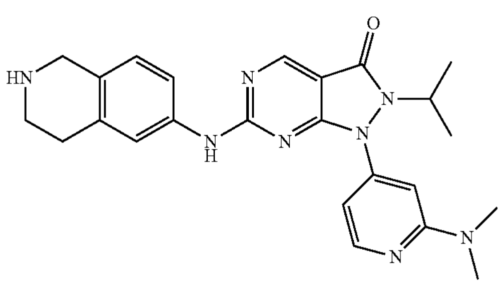 [SMILES: CC(C)n1c(=O)c2cnc(Nc3ccc4c(c3)CCNC4)nc2n1-c1ccnc(N(C)C)c1] |
| 1.173 | 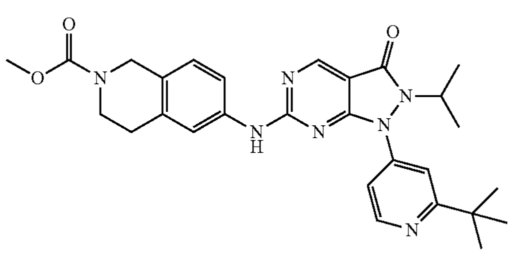 [SMILES: COC(=O)N1CCc2cc(Nc3ncc4c(=O)n(C(C)C)n(-c5ccnc(C(C)(C)C)c5)c4n3)ccc2C1] |
| 1.174 | 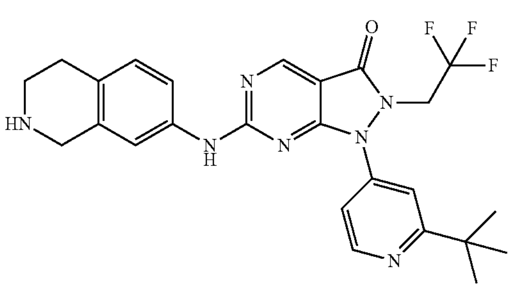 [SMILES: CC(C)(C)c1cc(-n2c3nc(Nc4ccc5c(c4)CNCC5)ncc3c(=O)n2CC(F)(F)F)ccn1] |
TABLE 1A-continued
| Compound No. | Structure |
|---|---|
| 1.175 | 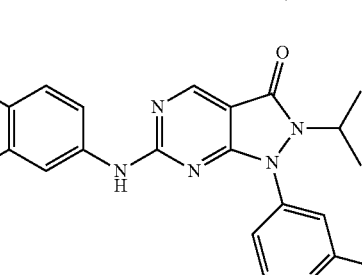 |
| 1.176 | 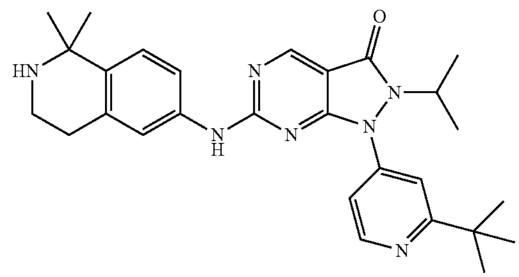 [SMILES: CC(C)n1c(=O)c2cnc(Nc3ccc4c(c3)CCNC4(C)C)nc2n1-c1ccnc(C(C)(C)C)c1] |
| 1.177 | 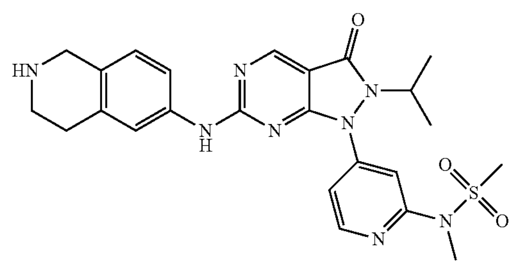 [SMILES: CC(C)n1c(=O)c2cnc(Nc3ccc4c(c3)CCNC4)nc2n1-c1ccnc(N(C)S(C)(=O)=O)c1] |
| 1.178 | 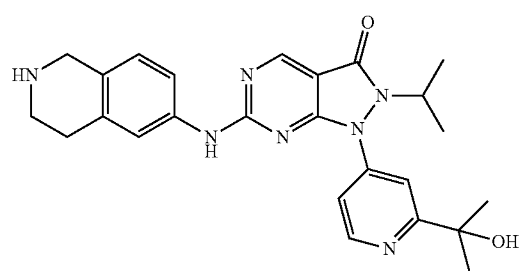 [SMILES: CC(C)n1c(=O)c2cnc(Nc3ccc4c(c3)CCNC4)nc2n1-c1ccnc(C(C)(C)O)c1] |
| 1.179 | 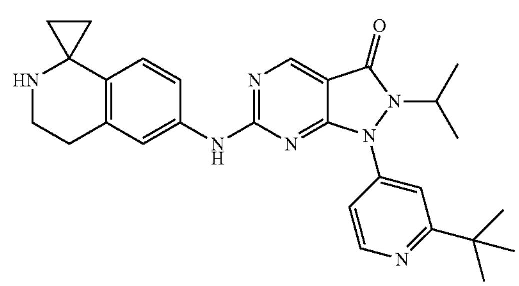 [SMILES: CC(C)n1c(=O)c2cnc(Nc3ccc4c(c3)CCNC43CC3)nc2n1-c1ccnc(C(C)(C)C)c1] |

TABLE 1A-continued

| Compound No. | Structure |
|---|---|
| 1.180 | 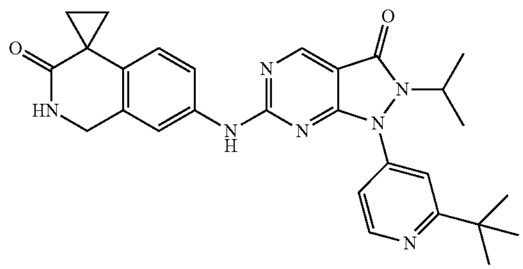 [SMILES: CC(C)n1c(=O)c2cnc(Nc3ccc4c(c3)CNC(=O)C43CC3)nc2n1-c1ccnc(C(C)(C)C)c1] |
| 1.181 | 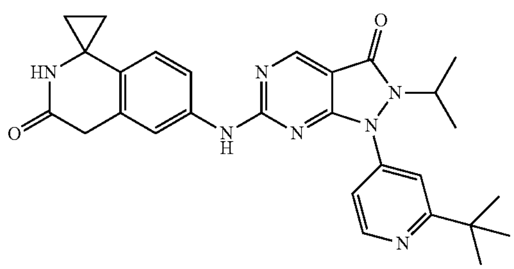 |
| 1.182 | 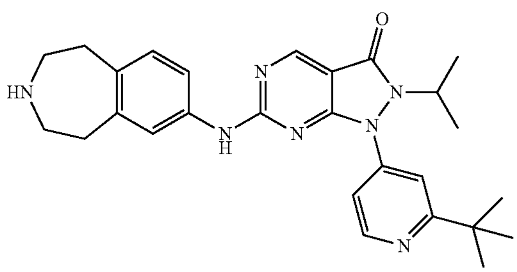 [SMILES: CC(C)n1c(=O)c2cnc(Nc3ccc4c(c3)CCNCC4)nc2n1-c1ccnc(C(C)(C)C)c1] |
| 1.183 | 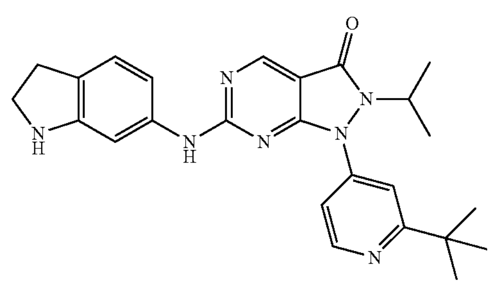 [SMILES: CC(C)n1c(=O)c2cnc(Nc3ccc4c(c3)NCC4)nc2n1-c1ccnc(C(C)(C)C)c1] |
| 1.184 | |ает

TABLE 1A-continued

| Compound No. | Structure |
|---|---|
| 1.185 | 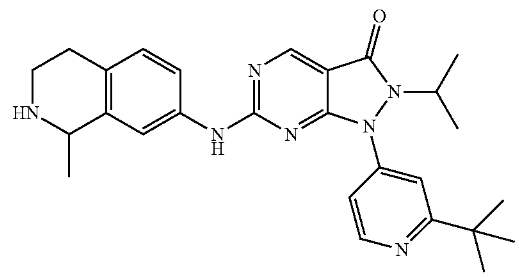 [SMILES: CC1NCCc2ccc(Nc3ncc4c(=O)n(C(C)C)n(-c5ccnc(C(C)(C)C)c5)c4n3)cc21] |
| 1.186 | 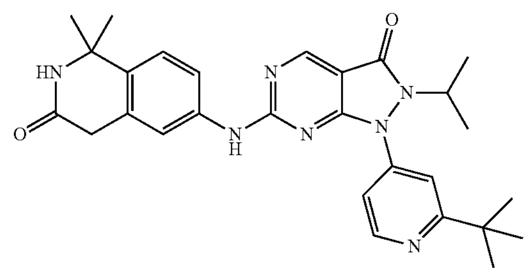 [SMILES: CC(C)n1c(=O)c2cnc(Nc3ccc4c(c3)CC(=O)NC4(C)C)nc2n1-c1ccnc(C(C)(C)C)c1] |
| 1.187 | 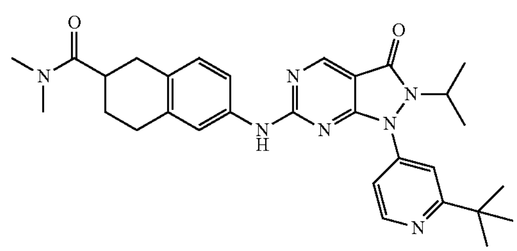 [SMILES: CC(C)n1c(=O)c2cnc(Nc3ccc4c(c3)CCC(C(=O)N(C)C)C4)nc2n1-c1ccnc(C(C)(C)C)c1] |
| 1.188 | 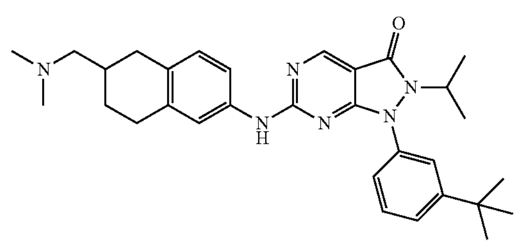 [SMILES: CC(C)n1c(=O)c2cnc(Nc3ccc4c(c3)CCC(CN(C)C)C4)nc2n1-c1cccc(C(C)(C)C)c1] |
| 1.189 | 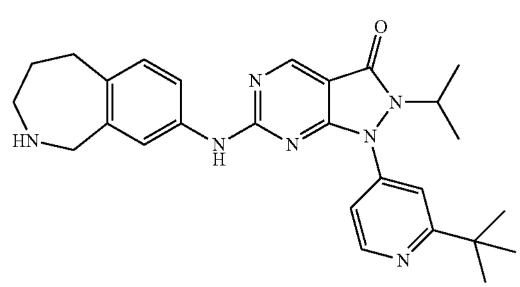 [SMILES: CC(C)n1c(=O)c2cnc(Nc3ccc4c(c3)CNCCC4)nc2n1-c1ccnc(C(C)(C)C)c1] |

TABLE 1A-continued

| Compound No. | Structure |
| --- | --- |
| 1.190 | 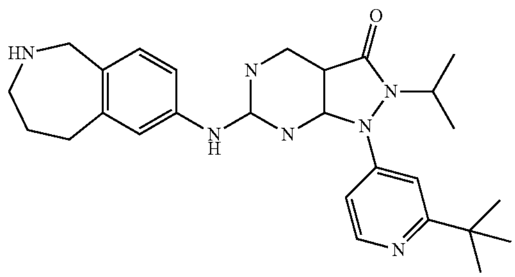 [SMILES: CC(C)N1C(=O)C2CNC(Nc3ccc4c(c3)CCCNC4)NC2N1c1ccnc(C(C)(C)C)c1] |
| 1.191 | 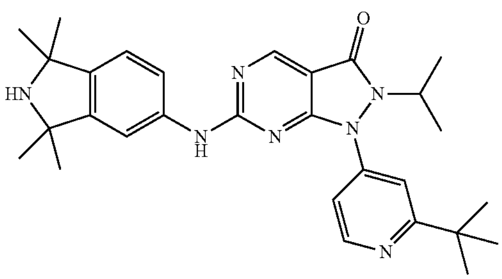 [SMILES: CC(C)n1c(=O)c2cnc(Nc3ccc4c(c3)C(C)(C)NC4(C)C)nc2n1-c1ccnc(C(C)(C)C)c1] |
| 1.192 | 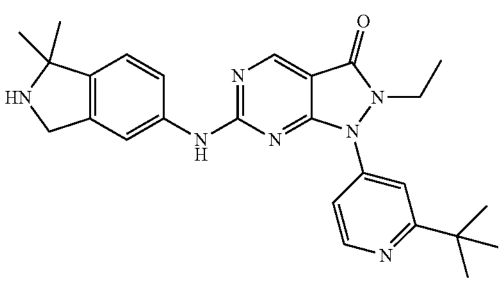 [SMILES: CCn1c(=O)c2cnc(Nc3ccc4c(c3)CNC4(C)C)nc2n1-c1ccnc(C(C)(C)C)c1] |
| 1.193 | 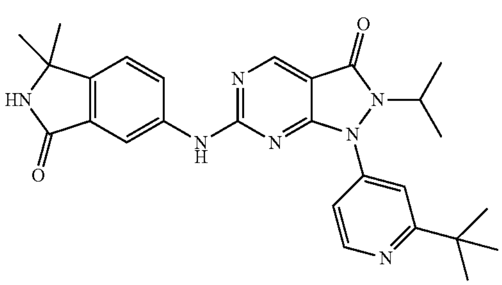 [SMILES: CC(C)n1c(=O)c2cnc(Nc3ccc4c(c3)C(=O)NC4(C)C)nc2n1-c1ccnc(C(C)(C)C)c1] |
| 1.194 | 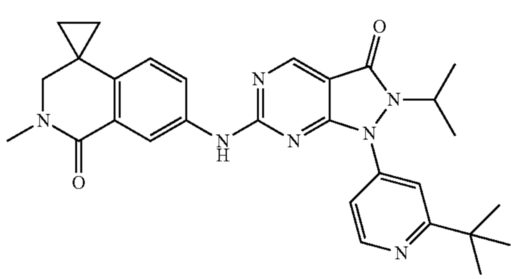 [SMILES: CC(C)n1c(=O)c2cnc(Nc3ccc4c(c3)C(=O)N(C)CC43CC3)nc2n1-c1ccnc(C(C)(C)C)c1] |
| 1.195 | |
| 1.196 | |
| 1.197 | |
| 1.198 | |
| 1.199 | |

TABLE 1A-continued

| Compound No. | Structure |
|---|---|
| 1.200 | 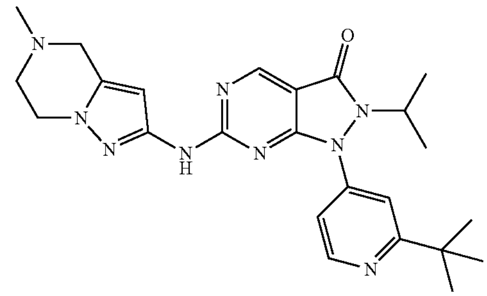 [SMILES: CC(C)n1c(=O)c2cnc(Nc3cc4n(n3)CCN(C)C4)nc2n1-c1ccnc(C(C)(C)C)c1] |
| 1.201 | 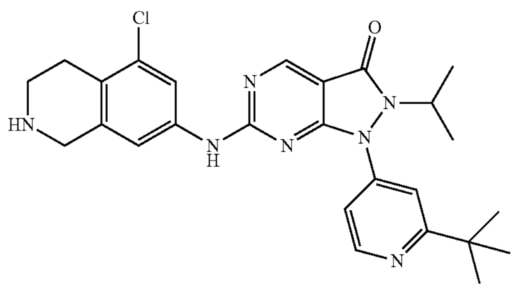 |
| 1.202 | 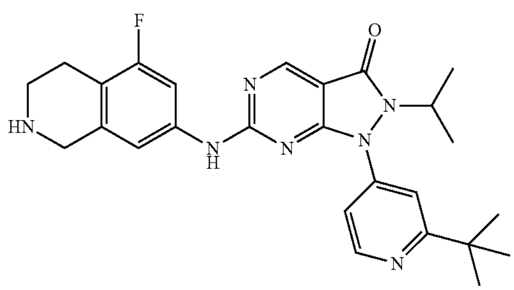 [SMILES: CC(C)n1c(=O)c2cnc(Nc3cc(F)c4c(c3)CNCC4)nc2n1-c1ccnc(C(C)(C)C)c1] |
| 1.203 | 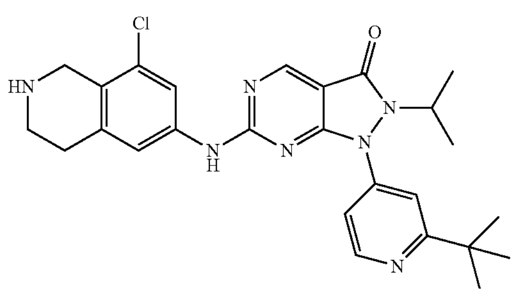 |
| 1.204 | 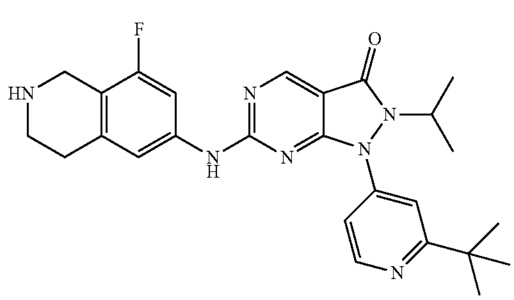 [SMILES: CC(C)n1c(=O)c2cnc(Nc3cc(F)c4c(c3)CCNC4)nc2n1-c1ccnc(C(C)(C)C)c1] |
| 1.205 | |
| 1.206 | |
| 1.207 | |
| 1.208 | |
| 1.209 | |

TABLE 1A-continued
| Compound No. | Structure |
|---|---|
| 1.210 | 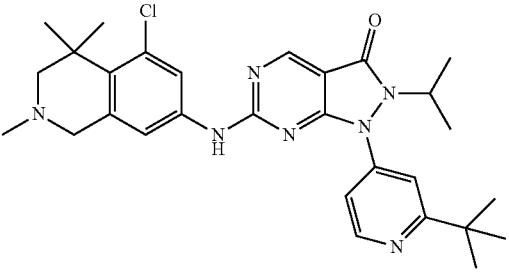 [SMILES: CC(C)n1c(=O)c2cnc(Nc3cc(Cl)c4c(c3)CN(C)CC4(C)C)nc2n1-c1ccnc(C(C)(C)C)c1] |
| 1.211 | 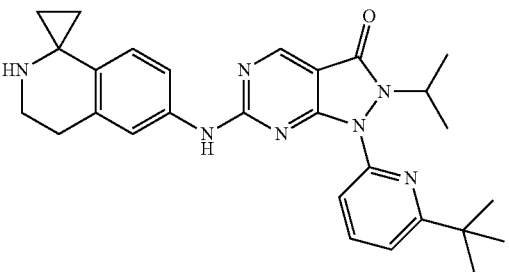 [SMILES: CC(C)n1c(=O)c2cnc(Nc3ccc4c(c3)CCNC43CC3)nc2n1-c1cccc(C(C)(C)C)n1] |
| 1.212 | 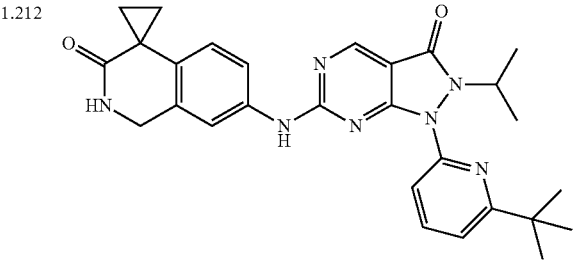 |
| 1.213 | 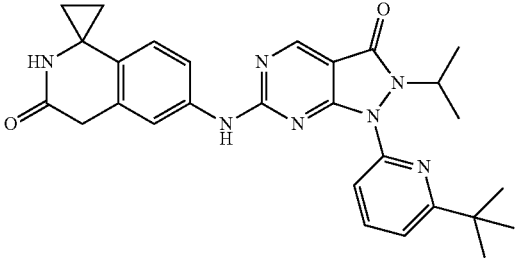 [SMILES: CC(C)n1c(=O)c2cnc(Nc3ccc4c(c3)CC(=O)NC43CC3)nc2n1-c1cccc(C(C)(C)C)n1] |
| 1.214 | 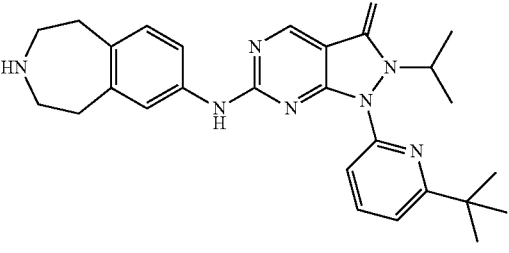 |
TABLE 1A-continued
| Compound No. | Structure |
|---|---|
| 1.215 | 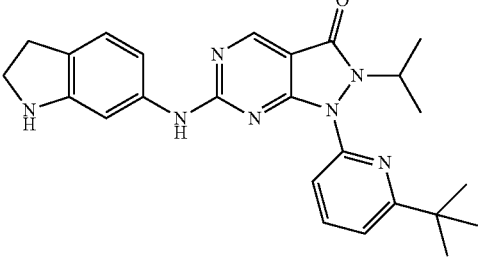 |
| 1.216 | 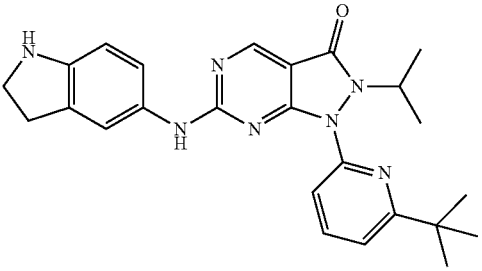 [SMILES: CC(C)n1c(=O)c2cnc(Nc3ccc4c(c3)CCN4)nc2n1-c1cccc(C(C)(C)C)n1] |
| 1.217 | 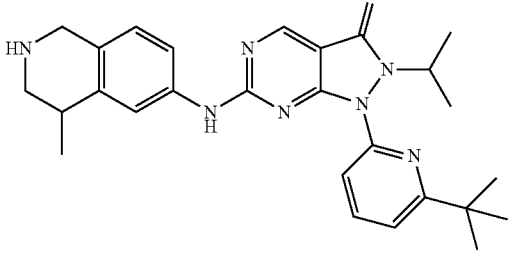 |
| 1.218 | 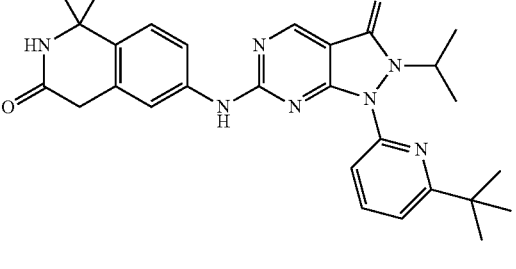 |
| 1.219 | 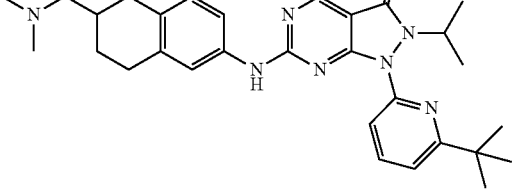 |

TABLE 1A-continued

| Compound No. | Structure |
|---|---|
| 1.220 | 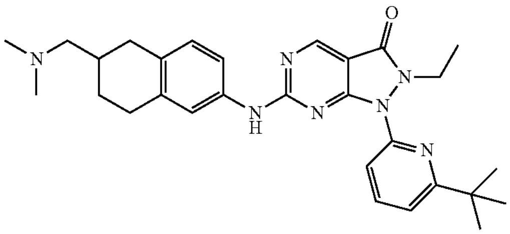 [SMILES: CCn1c(=O)c2cnc(Nc3ccc4c(c3)CCC(CN(C)C)C4)nc2n1-c1cccc(C(C)(C)C)n1] |
| 1.221 | 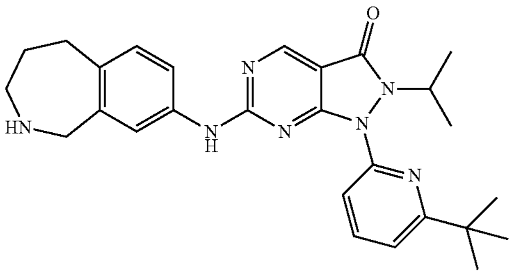 [SMILES: CC(C)n1c(=O)c2cnc(Nc3ccc4c(c3)CNCCC4)nc2n1-c1cccc(C(C)(C)C)n1] |
| 1.222 | 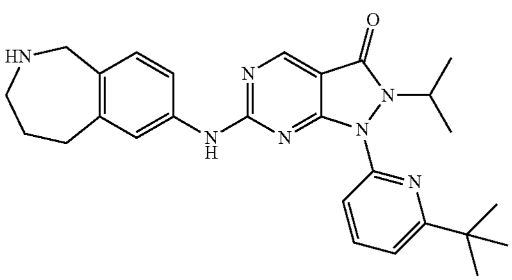 [SMILES: CC(C)n1c(=O)c2cnc(Nc3ccc4c(c3)CCCNC4)nc2n1-c1cccc(C(C)(C)C)n1] |
| 1.223 | 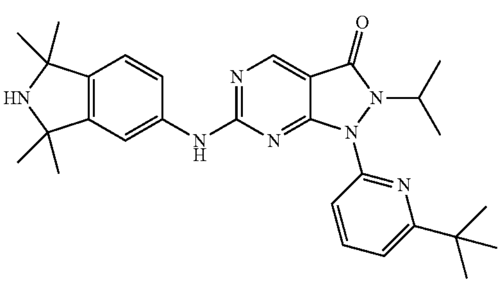 [SMILES: CC(C)n1c(=O)c2cnc(Nc3ccc4c(c3)C(C)(C)NC4(C)C)nc2n1-c1cccc(C(C)(C)C)n1] |
| 1.224 | 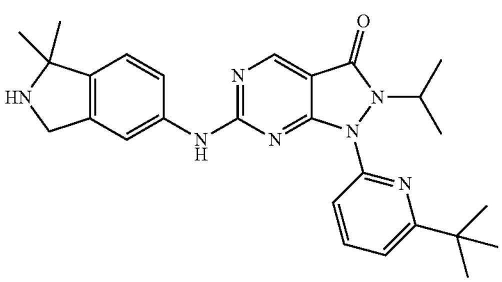 [SMILES: CC(C)n1c(=O)c2cnc(Nc3ccc4c(c3)CNC4(C)C)nc2n1-c1cccc(C(C)(C)C)n1] |
| 1.225 | |
| 1.226 | |
| 1.227 | |
| 1.228 | |
| 1.229 | |

TABLE 1A-continued

| Compound No. | Structure |
|---|---|
| 1.230 | 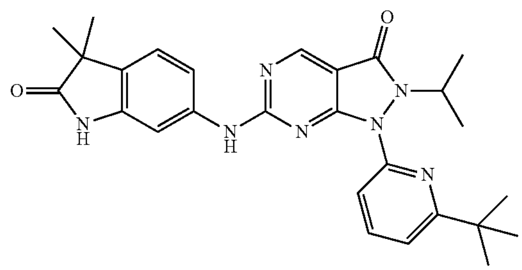 [SMILES: CC(C)n1c(=O)c2cnc(Nc3ccc4c(c3)NC(=O)C4(C)C)nc2n1-c1cccc(C(C)(C)C)n1] |
| 1.231 | 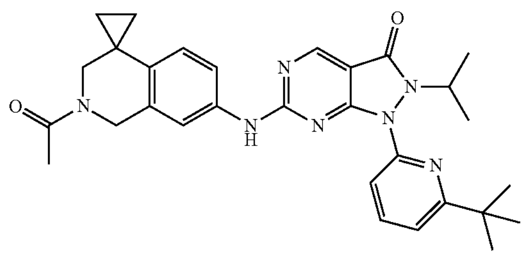 [SMILES: CC(=O)N1Cc2cc(Nc3ncc4c(=O)n(C(C)C)n(-c5cccc(C(C)(C)C)n5)c4n3)ccc2C2(CC2)C1] |
| 1.232 | 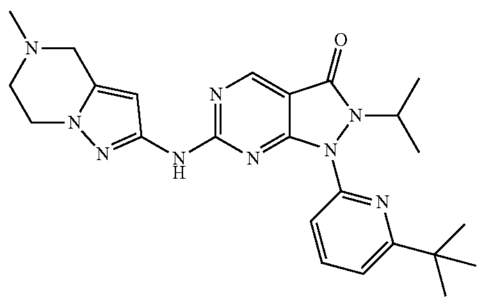 [SMILES: CC(C)n1c(=O)c2cnc(Nc3cc4n(n3)CCN(C)C4)nc2n1-c1cccc(C(C)(C)C)n1] |
| 1.233 | 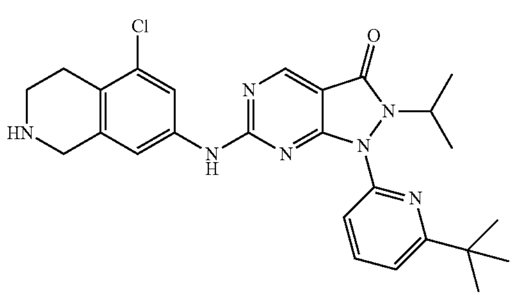 [SMILES: CC(C)n1c(=O)c2cnc(Nc3cc(Cl)c4c(c3)CNCC4)nc2n1-c1cccc(C(C)(C)C)n1] |
| 1.234 | 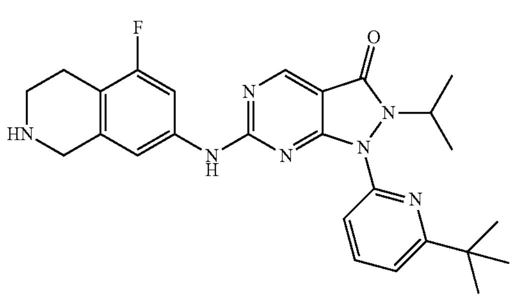 [SMILES: CC(C)n1c(=O)c2cnc(Nc3cc(F)c4c(c3)CNCC4)nc2n1-c1cccc(C(C)(C)C)n1] |
| 1.235 | |
| 1.236 | |
| 1.237 | |
| 1.238 | |
| 1.239 | |

TABLE 1A-continued

| Compound No. | Structure |
|---|---|
| 1.240 | 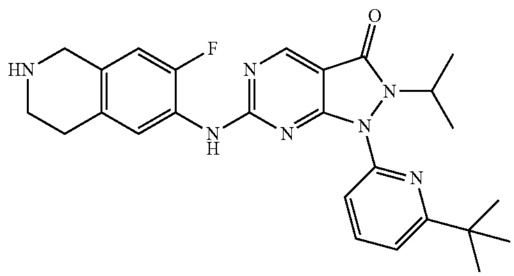 [SMILES: CC(C)n1c(=O)c2cnc(Nc3cc4c(cc3F)CNCC4)nc2n1-c1cccc(C(C)(C)C)n1] |
| 1.241 | 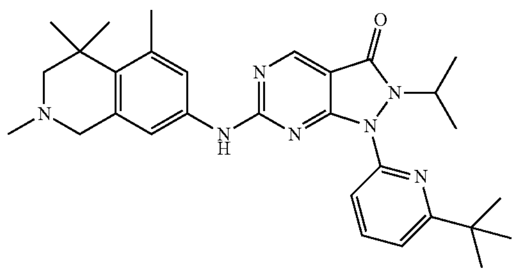 [SMILES: Cc1cc(Nc2ncc3c(=O)n(C(C)C)n(-c4cccc(C(C)(C)C)n4)c3n2)cc2c1C(C)(C)CN(C)C2] |
| 1.242 | 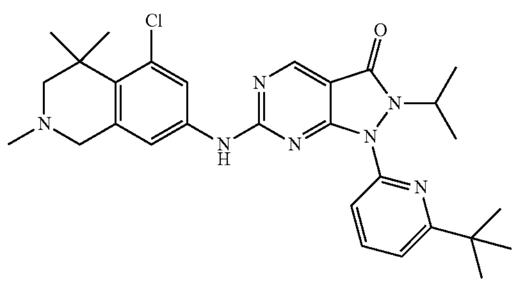 [SMILES: CC(C)n1c(=O)c2cnc(Nc3cc(Cl)c4c(c3)CN(C)CC4(C)C)nc2n1-c1cccc(C(C)(C)C)n1] |
| 1.243 | 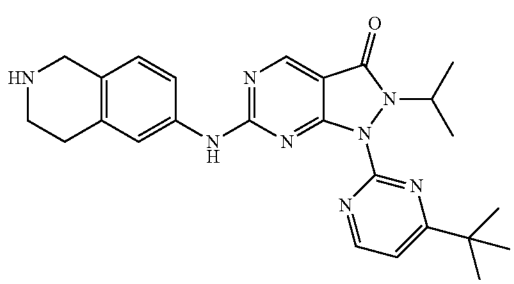 [SMILES: CC(C)n1c(=O)c2cnc(Nc3ccc4c(c3)CCNC4)nc2n1-c1nccc(C(C)(C)C)n1] |
| 1.244 | 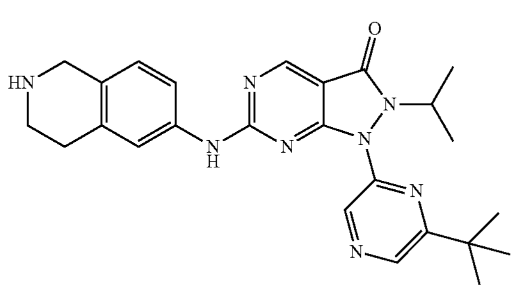 [SMILES: CC(C)n1c(=O)c2cnc(Nc3ccc4c(c3)CCNC4)nc2n1-c1cncc(C(C)(C)C)n1] |
| 1.245 | |
| 1.246 | |
| 1.247 | |
| 1.248 | |
| 1.249 | |

TABLE 1A-continued

| Compound No. | Structure |
|---|---|
| 1.250 | 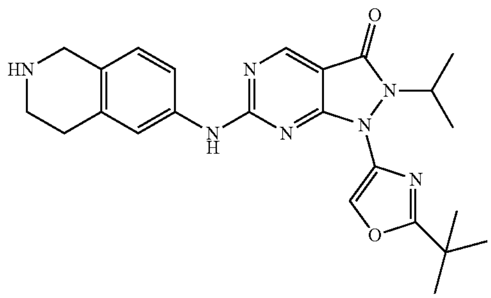 [SMILES: CC(C)n1c(=O)c2cnc(Nc3ccc4c(c3)CCNC4)nc2n1-c1coc(C(C)(C)C)c1] |
| 1.251 | 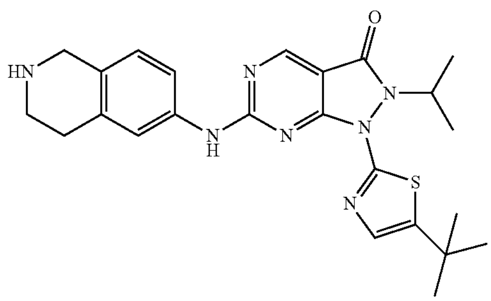 [SMILES: CC(C)n1c(=O)c2cnc(Nc3ccc4c(c3)CCNC4)nc2n1-c1cnc(C(C)(C)C)o1] |
| 1.252 | 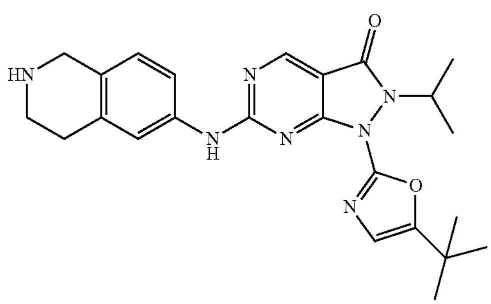 [SMILES: CC(C)n1c(=O)c2cnc(Nc3ccc4c(c3)CCNC4)nc2n1-c1ncc(C(C)(C)C)o1] |
| 1.253 | 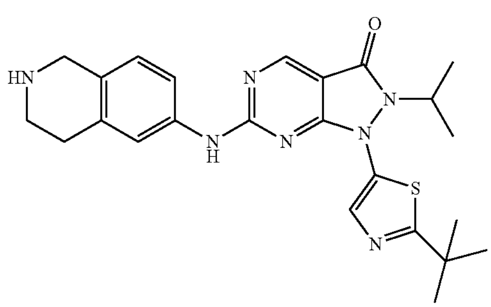 |
| 1.254 | 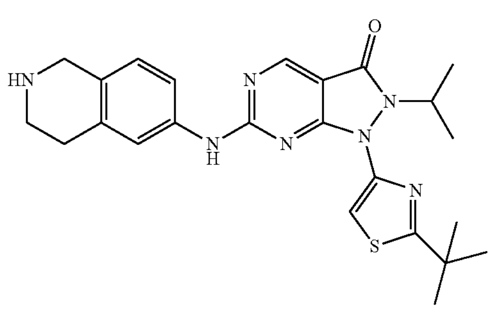 |
| 1.255 | |
| 1.256 | |
| 1.257 | |
| 1.258 | |
| 1.259 | |

TABLE 1A-continued

| Compound No. | Structure |
|---|---|
| 1.260 | 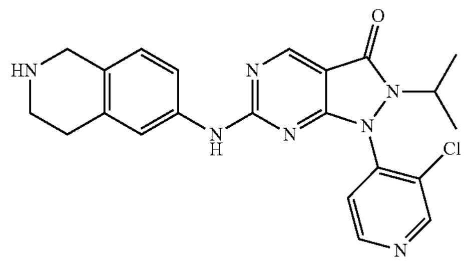 [SMILES: CC(C)n1c(=O)c2cnc(Nc3ccc4c(c3)CCNC4)nc2n1-c1ccncc1Cl] |
| 1.261 | 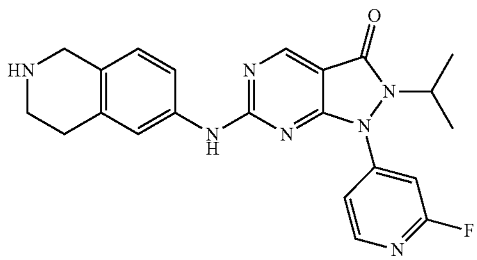 [SMILES: CC(C)n1c(=O)c2cnc(Nc3ccc4c(c3)CCNC4)nc2n1-c1ccnc(F)c1] |
| 1.262 | 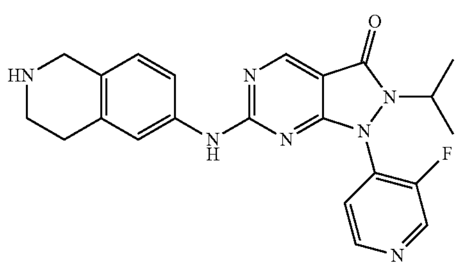 [SMILES: CC(C)n1c(=O)c2cnc(Nc3ccc4c(c3)CCNC4)nc2n1-c1ccncc1F] |
| 1.263 | 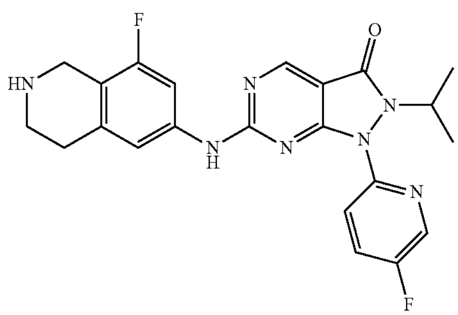 [SMILES: CC(C)n1c(=O)c2cnc(Nc3cc(F)c4c(c3)CCNC4)nc2n1-c1ccc(F)cn1] |
| 1.264 | 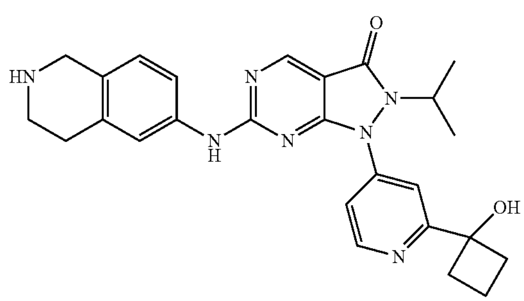 [SMILES: CC(C)n1c(=O)c2cnc(Nc3ccc4c(c3)CCNC4)nc2n1-c1ccnc(C2(O)CCC2)c1] |
| 1.265 | |
| 1.266 | |
| 1.267 | |
| 1.268 | |
| 1.269 | |

TABLE 1A-continued

| Compound No. | Structure |
|---|---|
| 1.270 | 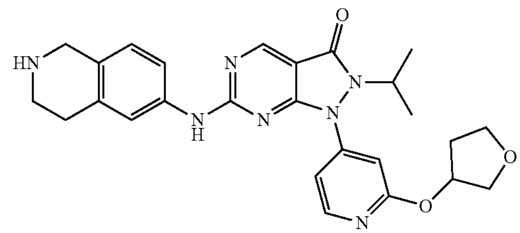 [SMILES: CC(C)n1c(=O)c2cnc(Nc3ccc4c(c3)CCNC4)nc2n1-c1ccnc(OC2CCOC2)c1] |
| 1.271 | 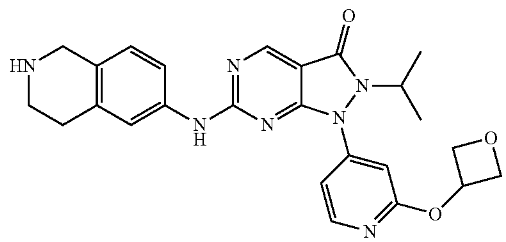 |
| 1.272 | 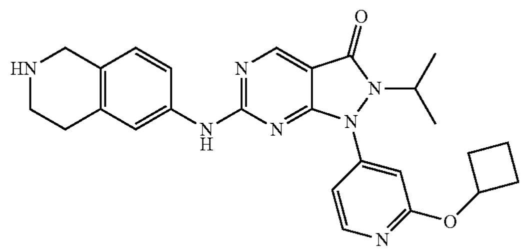 [SMILES: CC(C)n1c(=O)c2cnc(Nc3ccc4c(c3)CCNC4)nc2n1-c1ccnc(OC2CCC2)c1] |
| 1.273 | 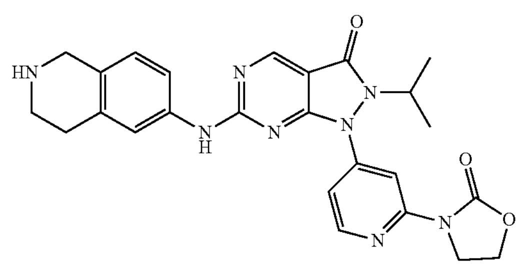 [SMILES: CC(C)n1c(=O)c2cnc(Nc3ccc4c(c3)CCNC4)nc2n1-c1ccnc(N2CCOC2=O)c1] |
| 1.274 | 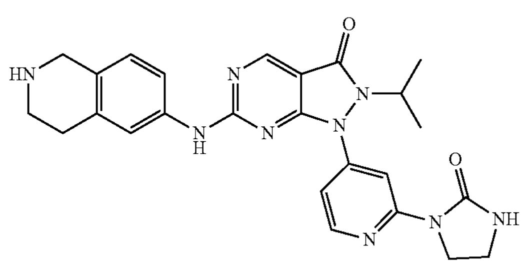 [SMILES: CC(C)n1c(=O)c2cnc(Nc3ccc4c(c3)CCNC4)nc2n1-c1ccnc(N2CCNC2=O)c1] |
| 1.275 | 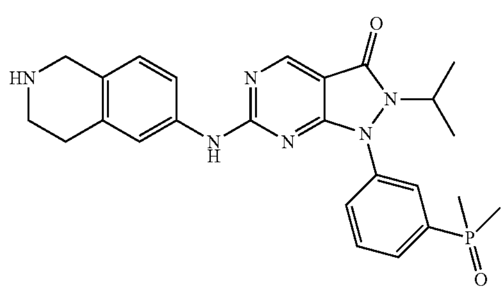 [SMILES: CC(C)n1c(=O)c2cnc(Nc3ccc4c(c3)CCNC4)nc2n1-c1cccc(P(C)(C)=O)c1] |
| 1.276 | |
| 1.277 | |
| 1.278 | |
| 1.279 | |
| 1.280 | |

TABLE 1A-continued

| Compound No. | Structure |
|---|---|
| 1.281 | |
| 1.282 | |
| 1.283 | |
| 1.284 | |
| 1.285 | |
| 1.286 | 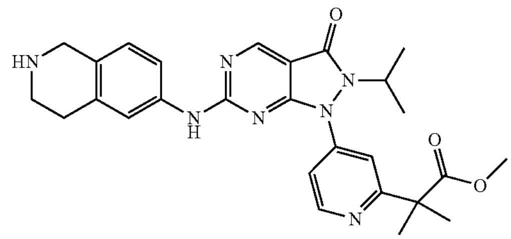 [SMILES: COC(=O)C(C)(C)c1cc(-n2c3nc(Nc4ccc5c(c4)CCNC5)ncc3c(=O)n2C(C)C)ccn1] |
| 1.287 | 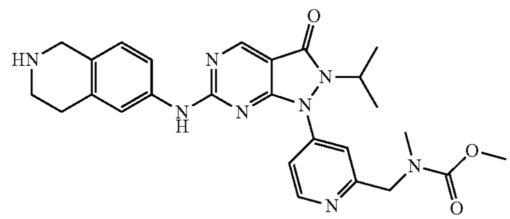 [SMILES: COC(=O)N(C)Cc1cc(-n2c3nc(Nc4ccc5c(c4)CCNC5)ncc3c(=O)n2C(C)C)ccn1] |
| 1.288 | 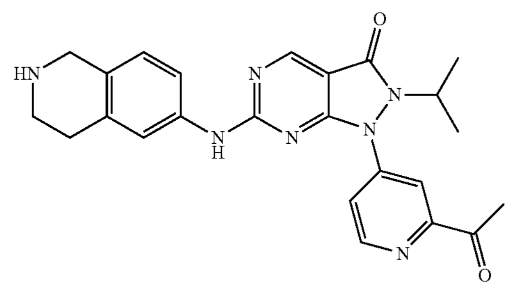 [SMILES: CC(=O)c1cc(-n2c3nc(Nc4ccc5c(c4)CCNC5)ncc3c(=O)n2C(C)C)ccn1] |
| 1.289 | 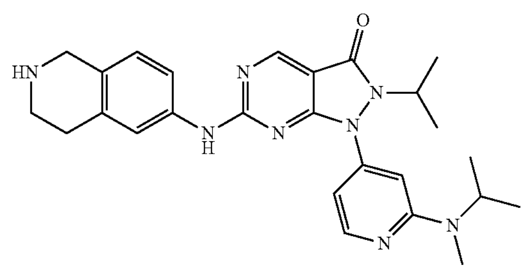 [SMILES: CC(C)N(C)c1cc(-n2c3nc(Nc4ccc5c(c4)CCNC5)ncc3c(=O)n2C(C)C)ccn1] |
| 1.290 | 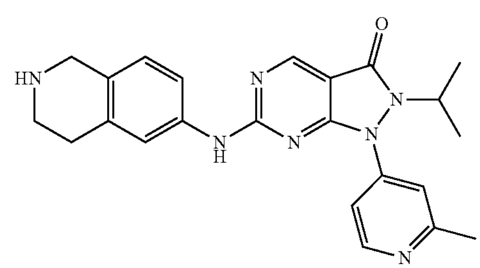 [SMILES: Cc1cc(-n2c3nc(Nc4ccc5c(c4)CCNC5)ncc3c(=O)n2C(C)C)ccn1] |
| 1.291 | 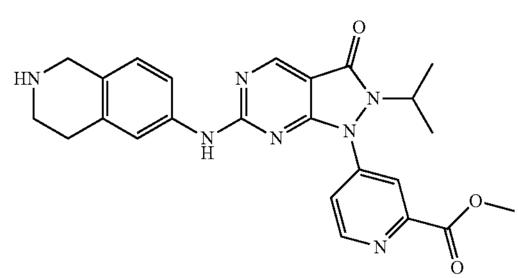 [SMILES: COC(=O)c1cc(-n2c3nc(Nc4ccc5c(c4)CCNC5)ncc3c(=O)n2C(C)C)ccn1] |

TABLE 1A-continued
| Compound No. | Structure |
|---|---|
| 1.292 | 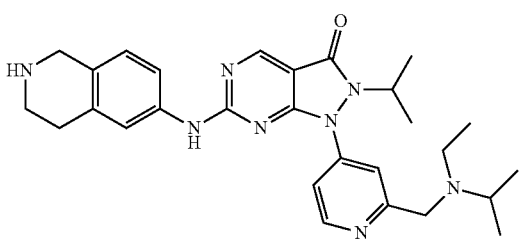 [SMILES: CCN(Cc1cc(-n2c3nc(Nc4ccc5c(c4)CCNC5)ncc3c(=O)n2C(C)C)ccn1)C(C)C] |
| 1.293 | 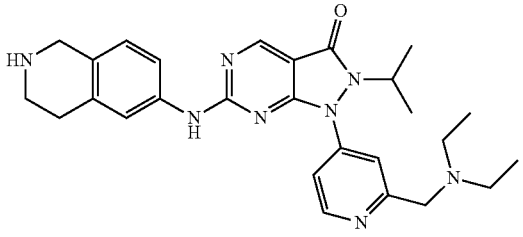 [SMILES: CCN(CC)Cc1cc(-n2c3nc(Nc4ccc5c(c4)CCNC5)ncc3c(=O)n2C(C)C)ccn1] |
| 1.294 | 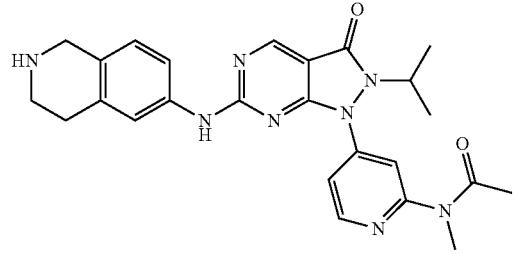 [SMILES: CC(=O)N(C)c1cc(-n2c3nc(Nc4ccc5c(c4)CCNC5)ncc3c(=O)n2C(C)C)ccn1] |
| 1.295 | 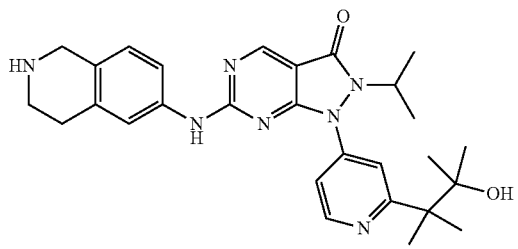 [SMILES: CC(C)n1c(=O)c2cnc(Nc3ccc4c(c3)CCNC4)nc2n1-c1ccnc(C(C)(C)C(C)(C)O)c1] |
| 1.296 | 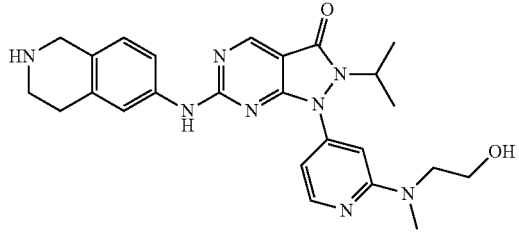 [SMILES: CC(C)n1c(=O)c2cnc(Nc3ccc4c(c3)CCNC4)nc2n1-c1ccnc(N(C)CCO)c1] |
| 1.297 | 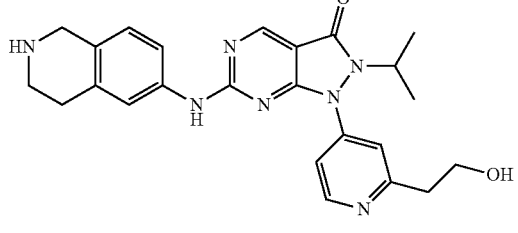 |
| 1.298 | 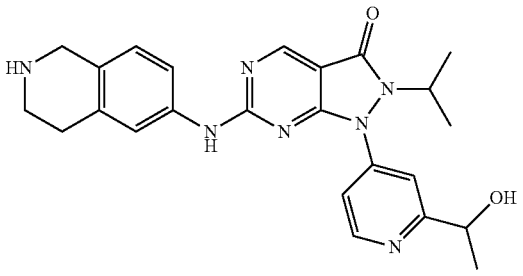 [SMILES: CC(O)c1cc(-n2c3nc(Nc4ccc5c(c4)CCNC5)ncc3c(=O)n2C(C)C)ccn1] |
| 1.299 | 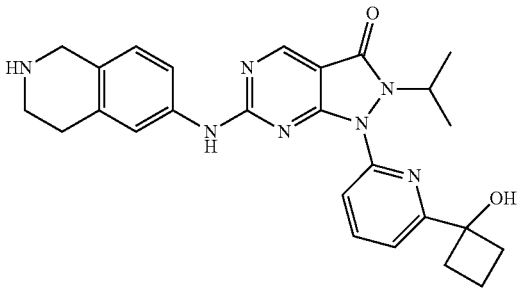 [SMILES: CC(C)n1c(=O)c2cnc(Nc3ccc4c(c3)CCNC4)nc2n1-c1cccc(C2(O)CCC2)n1] |
| 1.300 | 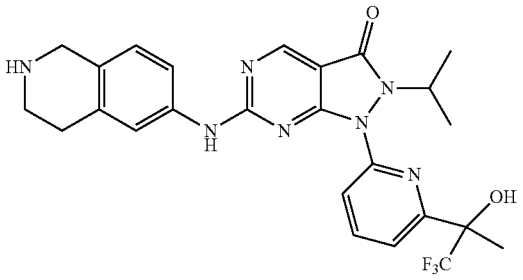 [SMILES: CC(C)n1c(=O)c2cnc(Nc3ccc4c(c3)CCNC4)nc2n1-c1cccc(C(C)(O)C(F)(F)F)n1] |
| 1.301 | 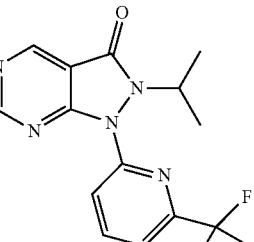 |
| 1.302 | 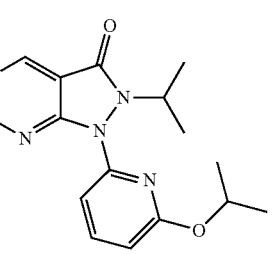 |

TABLE 1A-continued

| Compound No. | Structure |
|---|---|
| 1.303 | 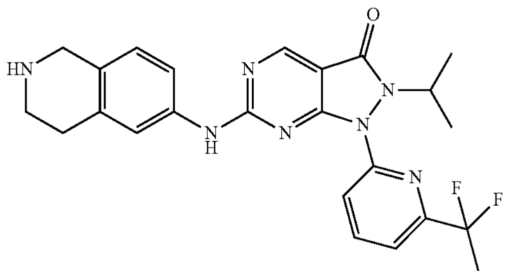 [SMILES: CC(C)n1c(=O)c2cnc(Nc3ccc4c(c3)CCNC4)nc2n1-c1cccc(C(C)(F)F)n1] |
| 1.304 | 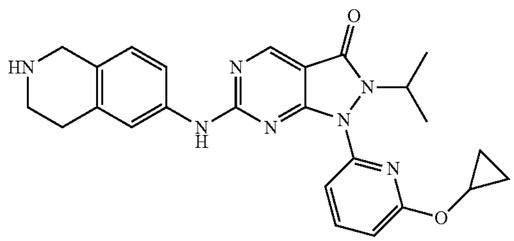 |
| 1.305 | 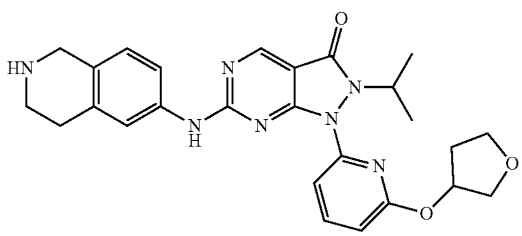 [SMILES: CC(C)n1c(=O)c2cnc(Nc3ccc4c(c3)CCNC4)nc2n1-c1cccc(OC2CCOC2)n1] |
| 1.306 | 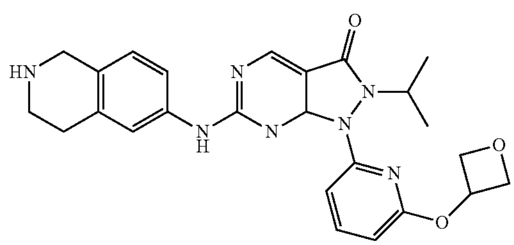 [SMILES: CC(C)N1C(=O)C2=CN=C(Nc3ccc4c(c3)CCNC4)NC2N1c1cccc(OC2COC2)n1] |
| 1.307 | 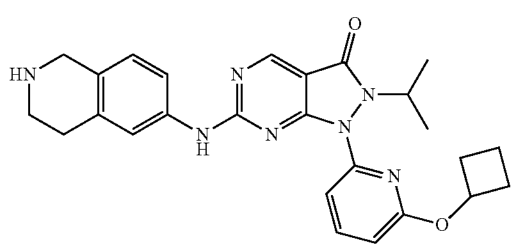 [SMILES: CC(C)n1c(=O)c2cnc(Nc3ccc4c(c3)CCNC4)nc2n1-c1cccc(OC2CCC2)n1] |
| 1.308 | 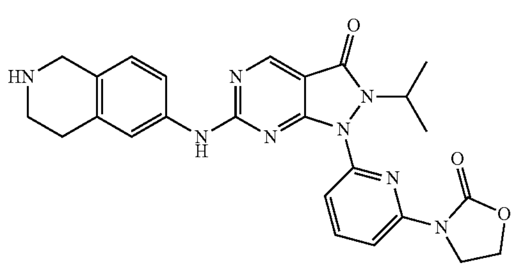 [SMILES: CC(C)n1c(=O)c2cnc(Nc3ccc4c(c3)CCNC4)nc2n1-c1cccc(N2CCOC2=O)n1] |
| 1.309 | |
| 1.310 | |
| 1.311 | |
| 1.312 | |
| 1.313 | |

TABLE 1A-continued
| Compound No. | Structure |
|---|---|
| 1.314 | 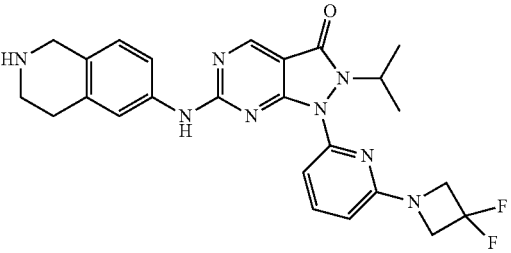 [SMILES: CC(C)n1c(=O)c2cnc(Nc3ccc4c(c3)CCNC4)nc2n1-c1cccc(N2CC(F)(F)C2)n1] |
| 1.315 | 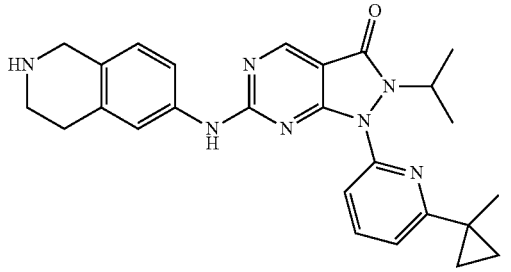 [SMILES: CC(C)n1c(=O)c2cnc(Nc3ccc4c(c3)CCNC4)nc2n1-c1cccc(C2(C)CC2)n1] |
| 1.316 | 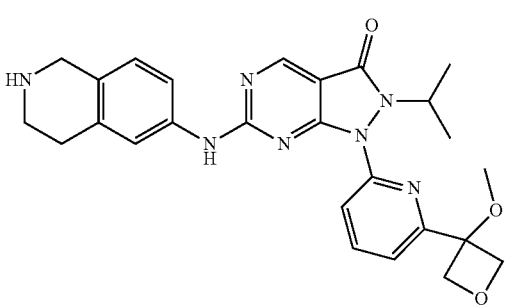 |
| 1.317 |  |
| 1.318 |  |
| 1.319 | 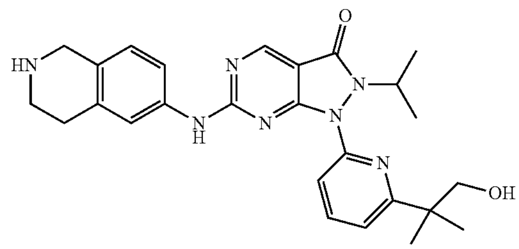 [SMILES: CC(C)n1c(=O)c2cnc(Nc3ccc4c(c3)CCNC4)nc2n1-c1cccc(C(C)(C)CO)n1] |
| 1.320 | 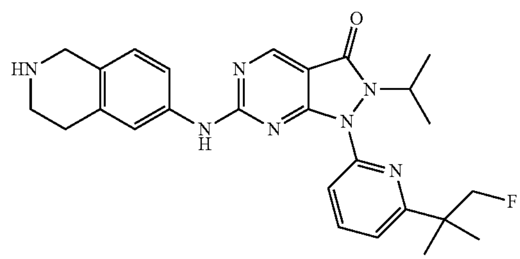 |
| 1.321 | 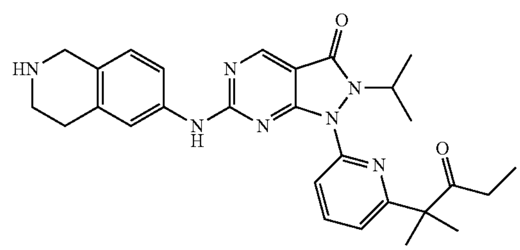 [SMILES: CCC(=O)C(C)(C)c1cccc(-n2c3nc(Nc4ccc5c(c4)CCNC5)ncc3c(=O)n2C(C)C)n1] |
| 1.322 | 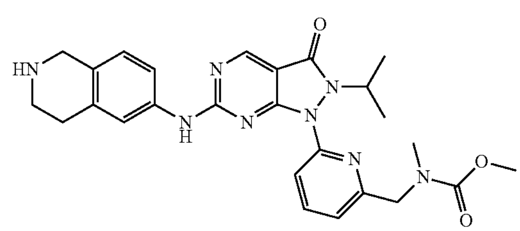 [SMILES: COC(=O)N(C)Cc1cccc(-n2c3nc(Nc4ccc5c(c4)CCNC5)ncc3c(=O)n2C(C)C)n1] |
| 1.323 | 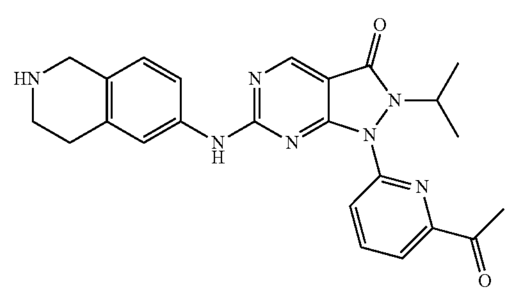 [SMILES: CC(=O)c1cccc(-n2c3nc(Nc4ccc5c(c4)CCNC5)ncc3c(=O)n2C(C)C)n1] |
| 1.324 | 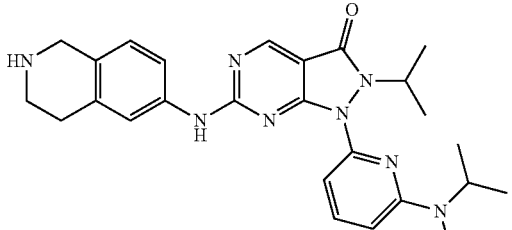 |

TABLE 1A-continued
| Compound No. | Structure |
|---|---|
| 1.325 | 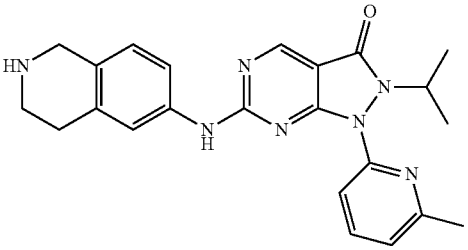 [SMILES: Cc1cccc(-n2c3nc(Nc4ccc5c(c4)CCNC5)ncc3c(=O)n2C(C)C)n1] |
| 1.326 | 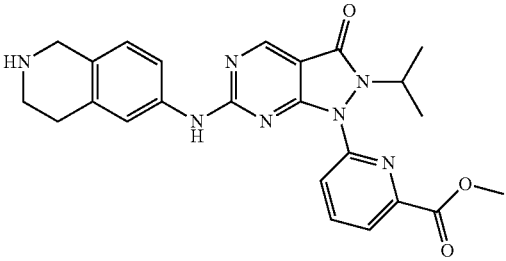 |
| 1.327 | 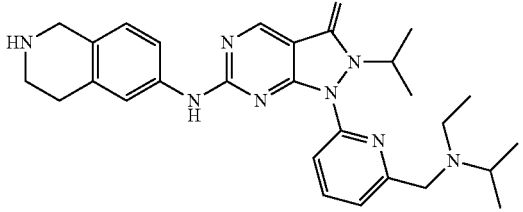 |
| 1.328 | 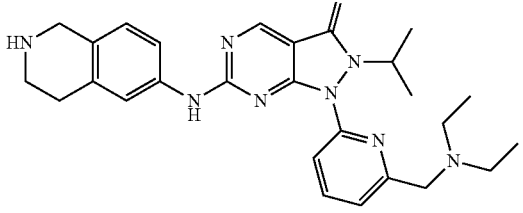 |
| 1.329 | 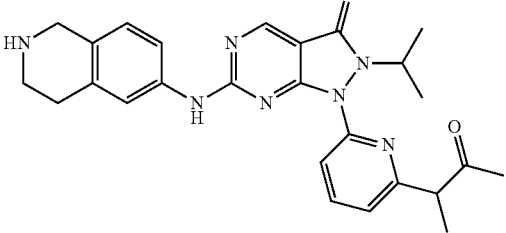 |
| 1.330 | 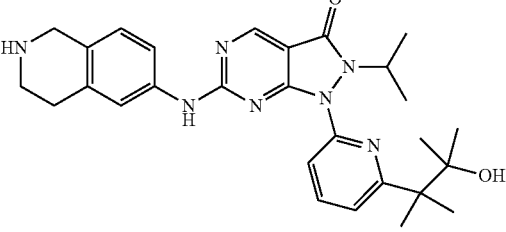 |
| 1.331 | 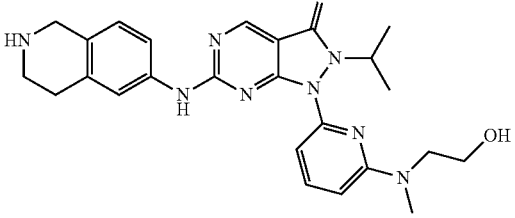 |
| 1.332 | 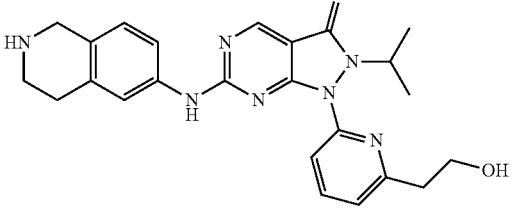 |
| 1.333 | 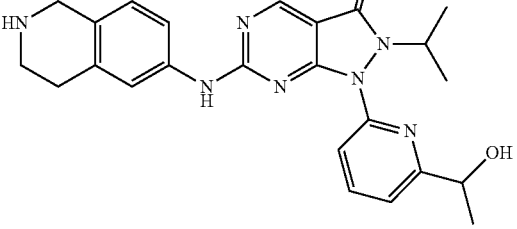 |
| 1.334 | 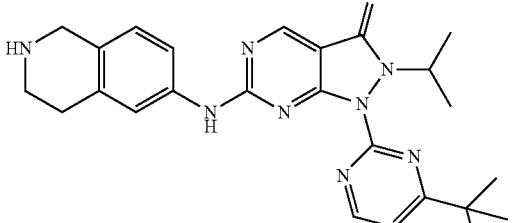 |
| 1.335 | 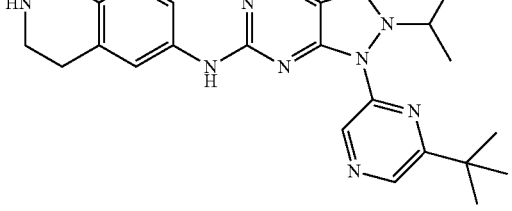 |

TABLE 1A-continued
| Compound No. | Structure |
|---|---|
| 1.336 | 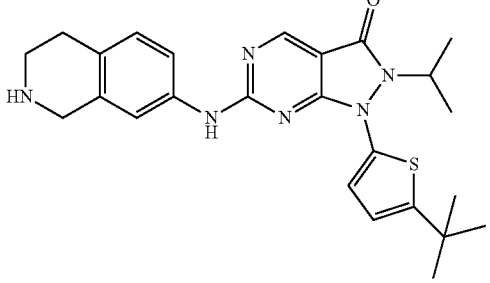 |
| 1.337 | 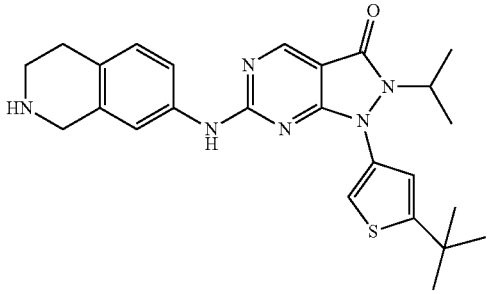 |
| 1.338 | 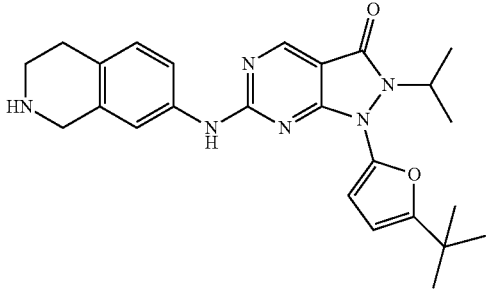 |
| 1.339 | 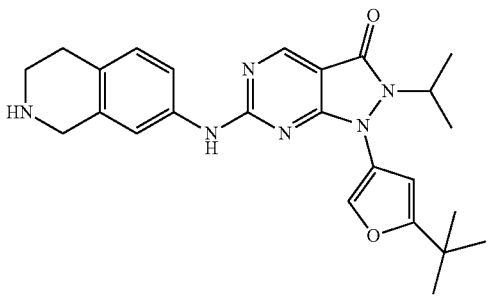 |
| 1.340 | 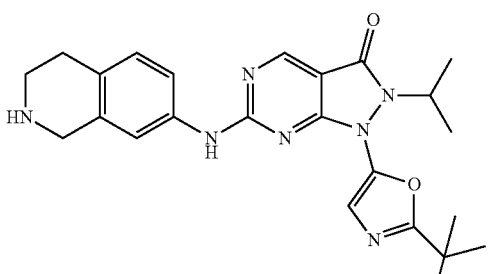 |
TABLE 1A-continued
| Compound No. | Structure |
|---|---|
| 1.341 | 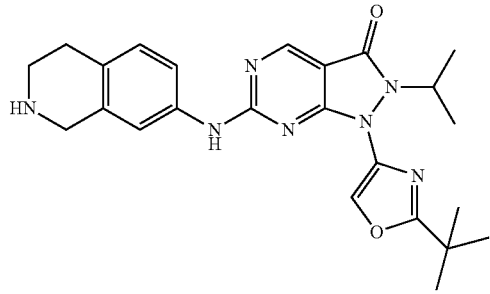 [SMILES: CC(C)n1c(=O)c2cnc(Nc3ccc4c(c3)CNCC4)nc2n1-c1coc(C(C)(C)C)n1] |
| 1.342 | 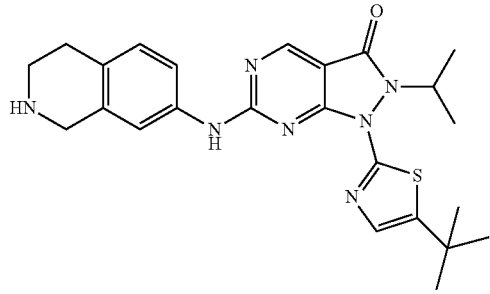 [SMILES: CC(C)n1c(=O)c2cnc(Nc3ccc4c(c3)CNCC4)nc2n1-c1ncc(C(C)(C)C)s1] |
| 1.343 | 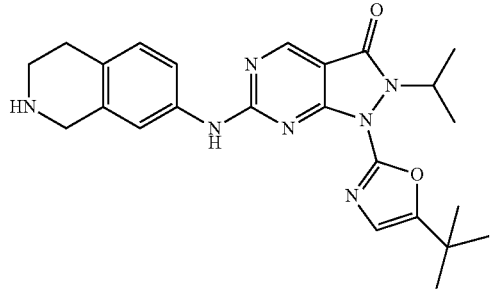 [SMILES: CC(C)n1c(=O)c2cnc(Nc3ccc4c(c3)CNCC4)nc2n1-c1ncc(C(C)(C)C)o1] |
| 1.344 | 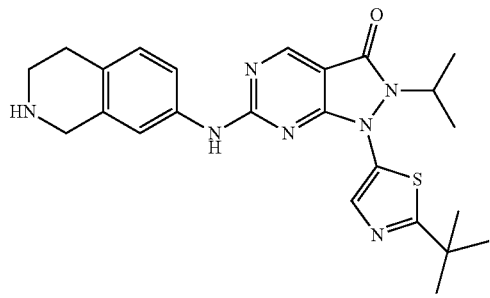 [SMILES: CC(C)n1c(=O)c2cnc(Nc3ccc4c(c3)CNCC4)nc2n1-c1cnc(C(C)(C)C)s1] |
| 1.345 | 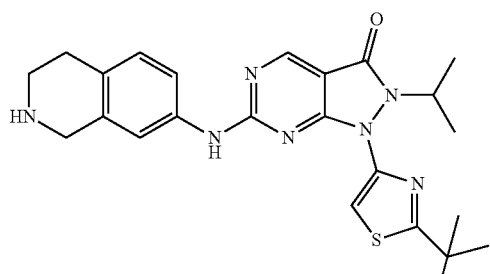 |

TABLE 1A-continued

| Compound No. | Structure |
|---|---|
| 1.346 | 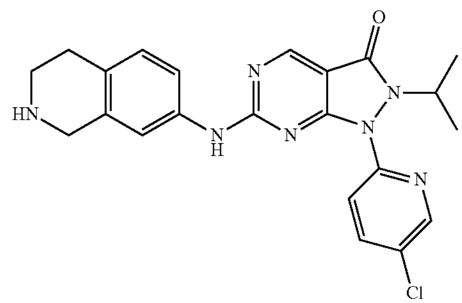 |
| 1.347 | 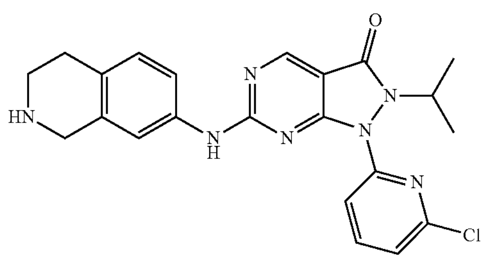 [SMILES: CC(C)n1c(=O)c2cnc(Nc3ccc4c(c3)CNCC4)nc2n1-c1cccc(Cl)n1] |
| 1.348 | 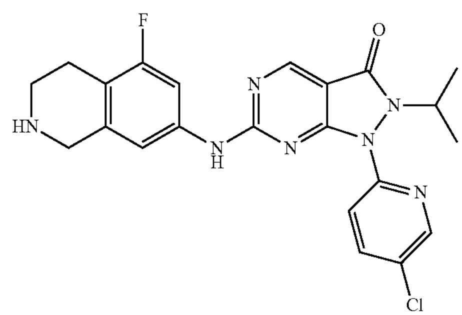 [SMILES: CC(C)n1c(=O)c2cnc(Nc3cc(F)c4c(c3)CNCC4)nc2n1-c1ccc(Cl)cn1] |
| 1.349 | 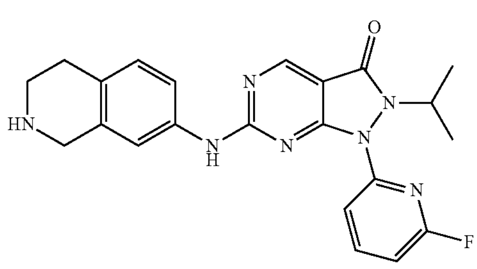 [SMILES: CC(C)n1c(=O)c2cnc(Nc3ccc4c(c3)CNCC4)nc2n1-c1cccc(F)n1] |
| 1.350 | 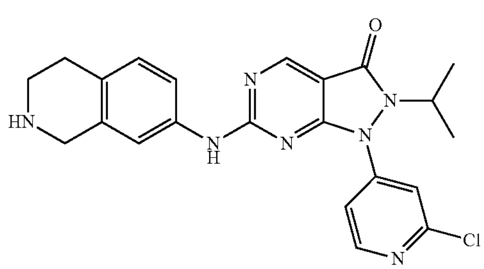 [SMILES: CC(C)n1c(=O)c2cnc(Nc3ccc4c(c3)CNCC4)nc2n1-c1ccnc(Cl)c1] |

TABLE 1A-continued

| Compound No. | Structure |
|---|---|
| 1.351 | 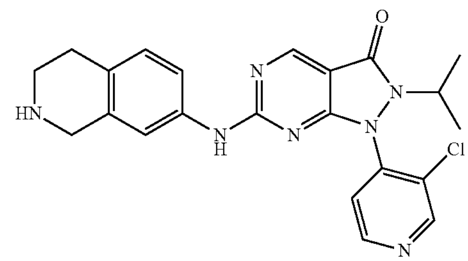 [SMILES: CC(C)n1c(=O)c2cnc(Nc3ccc4c(c3)CNCC4)nc2n1-c1ccncc1Cl] |
| 1.352 | 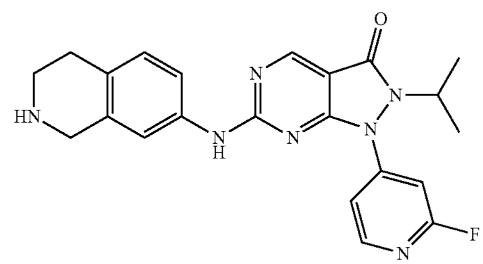 [SMILES: CC(C)n1c(=O)c2cnc(Nc3ccc4c(c3)CNCC4)nc2n1-c1ccnc(F)c1] |
| 1.353 | 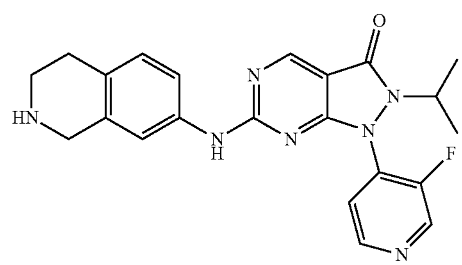 [SMILES: CC(C)n1c(=O)c2cnc(Nc3ccc4c(c3)CNCC4)nc2n1-c1ccncc1F] |
| 1.354 | 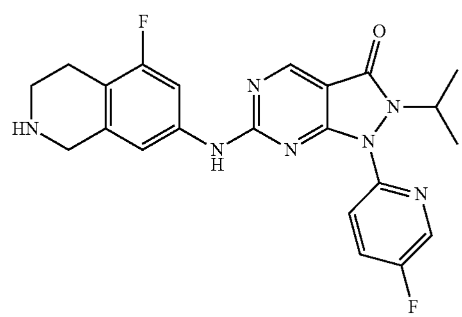 [SMILES: CC(C)n1c(=O)c2cnc(Nc3cc(F)c4c(c3)CNCC4)nc2n1-c1ccc(F)cn1] |
| 1.355 | 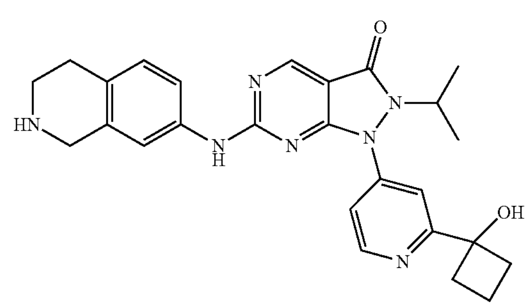 [SMILES: CC(C)n1c(=O)c2cnc(Nc3ccc4c(c3)CNCC4)nc2n1-c1ccnc(C2(O)CCC2)c1] |

TABLE 1A-continued

| Compound No. | Structure |
|---|---|
| 1.356 | |
| 1.357 | |
| 1.358 | |
| 1.359 | |
| 1.360 | |
| 1.361 | 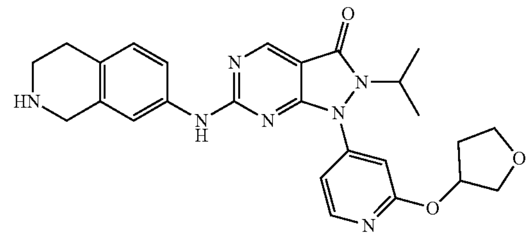 [SMILES: CC(C)n1c(=O)c2cnc(Nc3ccc4c(c3)CNCC4)nc2n1-c1ccnc(OC2CCOC2)c1] |
| 1.362 | 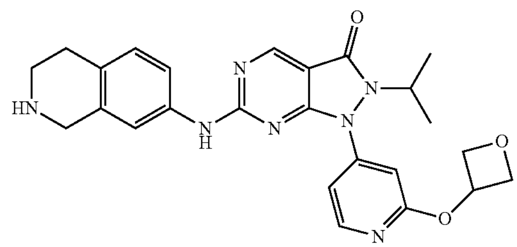 [SMILES: CC(C)n1c(=O)c2cnc(Nc3ccc4c(c3)CNCC4)nc2n1-c1ccnc(OC2COC2)c1] |
| 1.363 | 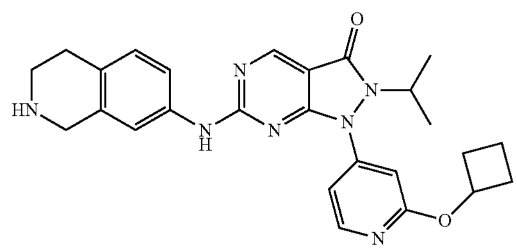 [SMILES: CC(C)n1c(=O)c2cnc(Nc3ccc4c(c3)CNCC4)nc2n1-c1ccnc(OC2CCC2)c1] |
| 1.364 | 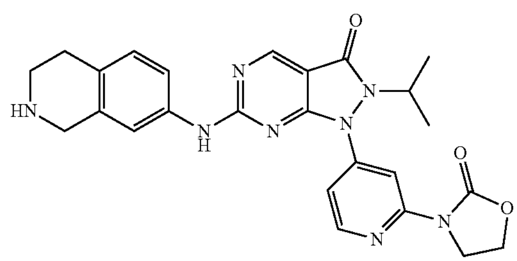 [SMILES: CC(C)n1c(=O)c2cnc(Nc3ccc4c(c3)CNCC4)nc2n1-c1ccnc(N2CCOC2=O)c1] |
| 1.365 | 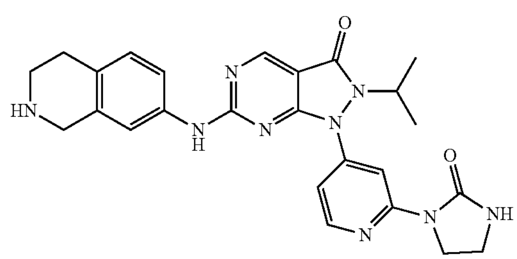 [SMILES: CC(C)n1c(=O)c2cnc(Nc3ccc4c(c3)CNCC4)nc2n1-c1ccnc(N2CCNC2=O)c1] |
| 1.366 | 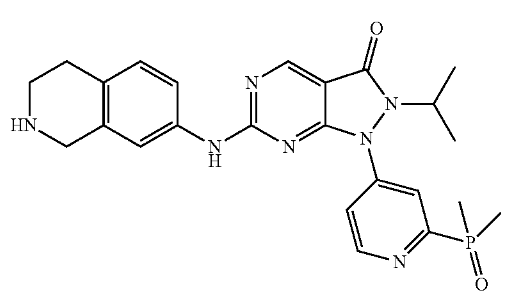 [SMILES: CC(C)n1c(=O)c2cnc(Nc3ccc4c(c3)CNCC4)nc2n1-c1ccnc(P(C)(C)=O)c1] |

TABLE 1A-continued

| Compound No. | Structure |
|---|---|
| 1.367 | 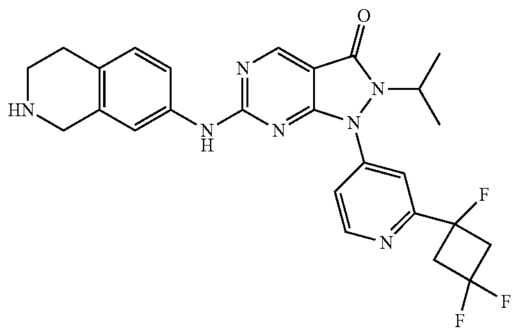 [SMILES: CC(C)n1c(=O)c2cnc(Nc3ccc4c(c3)CNCC4)nc2n1-c1ccnc(C2(F)CC(F)(F)C2)c1] |
| 1.368 | 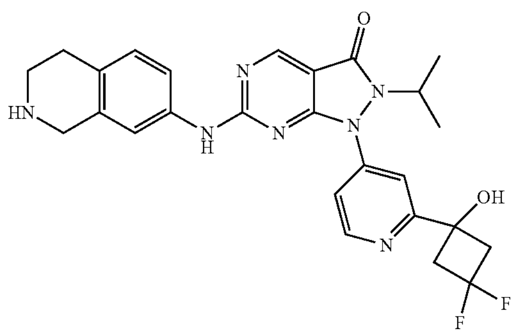 [SMILES: CC(C)n1c(=O)c2cnc(Nc3ccc4c(c3)CNCC4)nc2n1-c1ccnc(C2(O)CC(F)(F)C2)c1] |
| 1.369 | 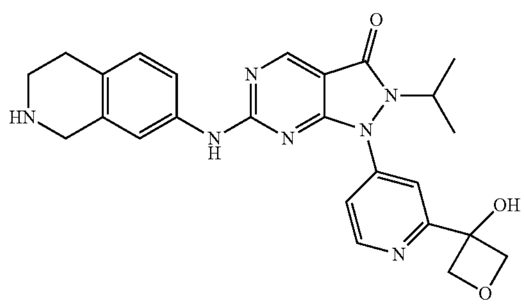 [SMILES: CC(C)n1c(=O)c2cnc(Nc3ccc4c(c3)CNCC4)nc2n1-c1ccnc(C2(O)COC2)c1] |
| 1.370 | 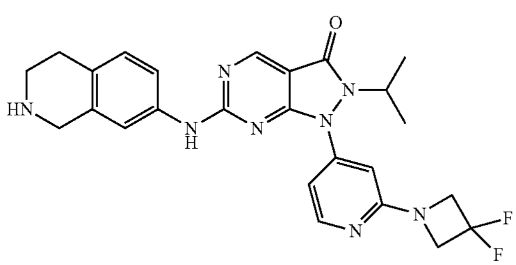 [SMILES: CC(C)n1c(=O)c2cnc(Nc3ccc4c(c3)CNCC4)nc2n1-c1ccnc(N2CC(F)(F)C2)c1] |
| 1.371 | 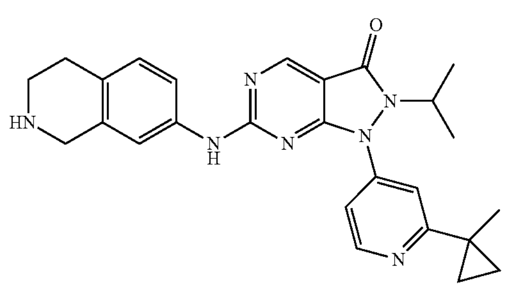 [SMILES: CC(C)n1c(=O)c2cnc(Nc3ccc4c(c3)CNCC4)nc2n1-c1ccnc(C2(C)CC2)c1] |
| 1.372 | 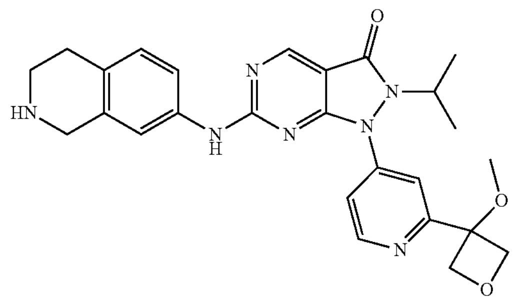 [SMILES: COC1(c2cc(-n3c4nc(Nc5ccc6c(c5)CNCC6)ncc4c(=O)n3C(C)C)ccn2)COC1] |
| 1.373 | 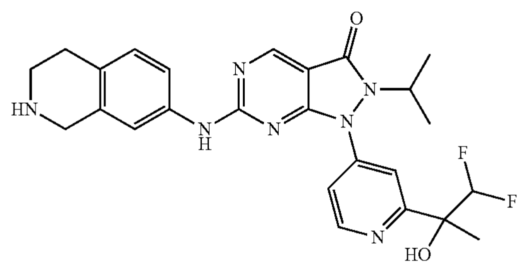 [SMILES: CC(C)n1c(=O)c2cnc(Nc3ccc4c(c3)CNCC4)nc2n1-c1ccnc(C(C)(O)C(F)F)c1] |
| 1.374 | 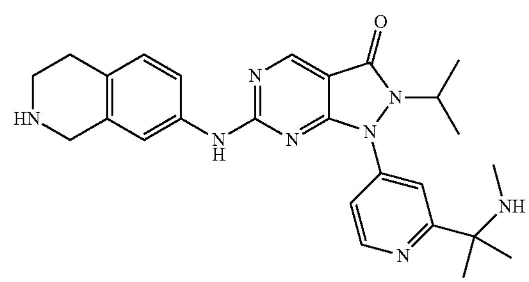 [SMILES: CNC(C)(C)c1cc(-n2c3nc(Nc4ccc5c(c4)CNCC5)ncc3c(=O)n2C(C)C)ccn1] |
| 1.375 | 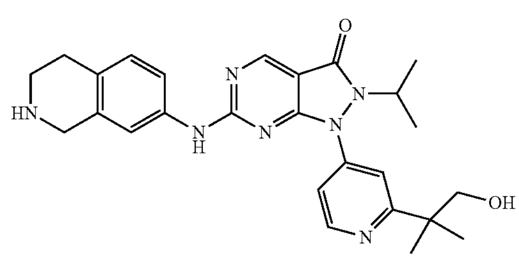 [SMILES: CC(C)n1c(=O)c2cnc(Nc3ccc4c(c3)CNCC4)nc2n1-c1ccnc(C(C)(C)CO)c1] |
| 1.376 | 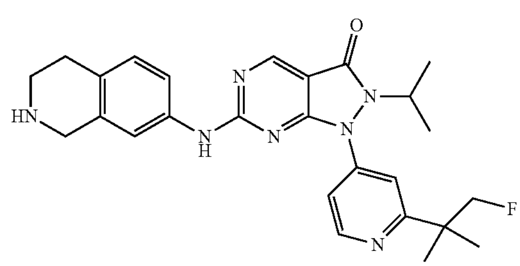 [SMILES: CC(C)n1c(=O)c2cnc(Nc3ccc4c(c3)CNCC4)nc2n1-c1ccnc(C(C)(C)CF)c1] |

TABLE 1A-continued

| Compound No. | Structure |
|---|---|
| 1.377 | |
| 1.378 | |
| 1.379 | |
| 1.380 | |
| 1.381 | |
| 1.382 | 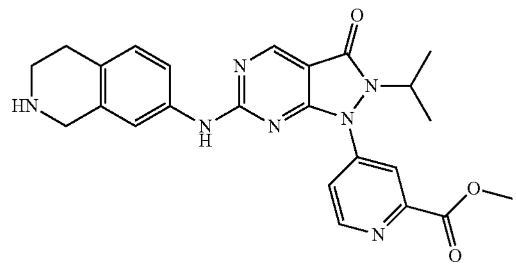 [SMILES: COC(=O)c1cc(-n2c3nc(Nc4ccc5c(c4)CNCC5)ncc3c(=O)n2C(C)C)ccn1] |
| 1.383 | 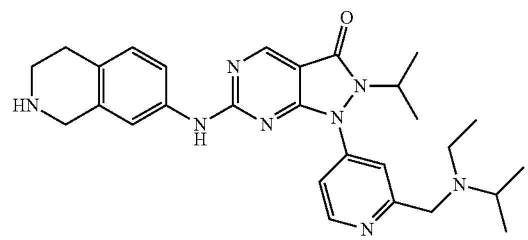 |
| 1.384 | 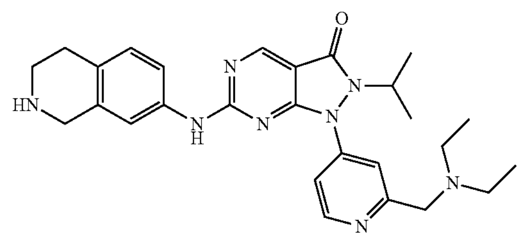 [SMILES: CCN(Cc1cc(-n2c3nc(Nc4ccc5c(c4)CNCC5)ncc3c(=O)n2C(C)C)ccn1)C(C)C] |
| 1.385 | 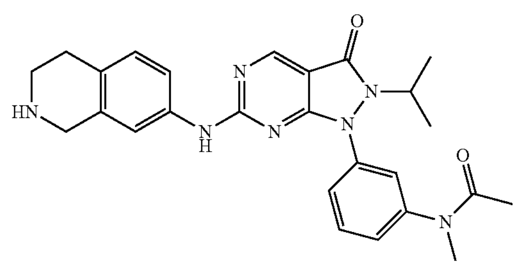 |
| 1.386 | 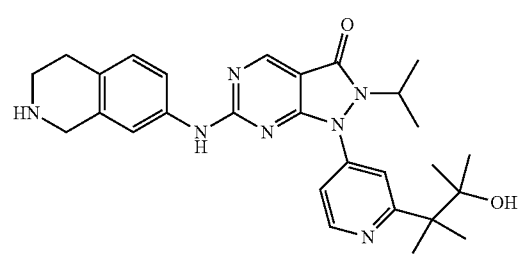 [SMILES: CC(C)n1c(=O)c2cnc(Nc3ccc4c(c3)CNCC4)nc2n1-c1ccnc(C(C)(C)C(C)(C)O)c1] |
| 1.387 | 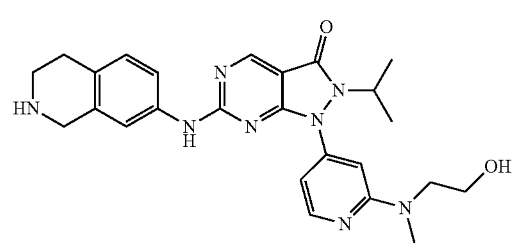 [SMILES: CC(C)n1c(=O)c2cnc(Nc3ccc4c(c3)CNCC4)nc2n1-c1ccnc(N(C)CCO)c1] |

TABLE 1A-continued

| Compound No. | Structure |
|---|---|
| 1.388 | |
| 1.389 | |
| 1.390 | |
| 1.391 | |
| 1.392 | |
| 1.393 | 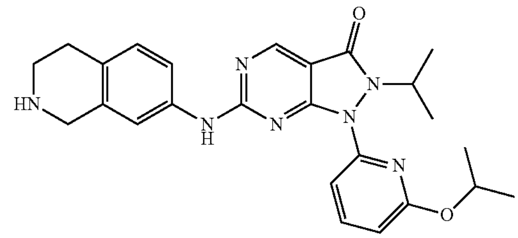 [SMILES: CC(C)Oc1cccc(-n2c3nc(Nc4ccc5c(c4)CNCC5)ncc3c(=O)n2C(C)C)n1] |
| 1.394 | 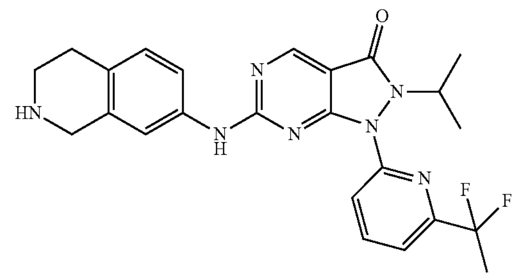 [SMILES: CC(C)n1c(=O)c2cnc(Nc3ccc4c(c3)CNCC4)nc2n1-c1cccc(C(C)(F)F)n1] |
| 1.395 | 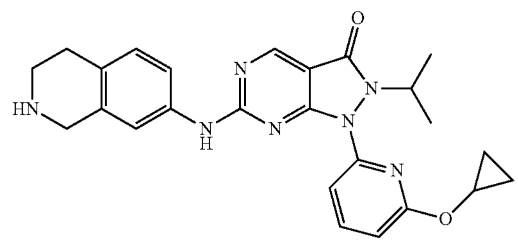 [SMILES: CC(C)n1c(=O)c2cnc(Nc3ccc4c(c3)CNCC4)nc2n1-c1cccc(OC2CC2)n1] |
| 1.396 | 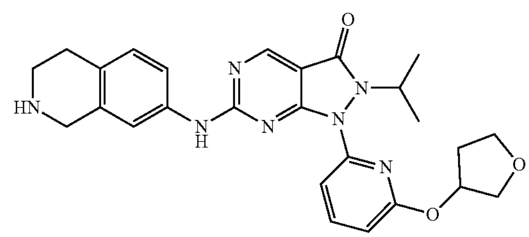 [SMILES: CC(C)n1c(=O)c2cnc(Nc3ccc4c(c3)CNCC4)nc2n1-c1cccc(OC2CCOC2)n1] |
| 1.397 | 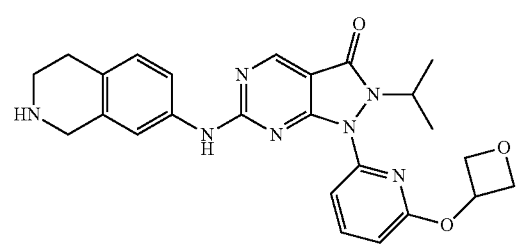 [SMILES: CC(C)n1c(=O)c2cnc(Nc3ccc4c(c3)CNCC4)nc2n1-c1cccc(OC2COC2)n1] |
| 1.398 | 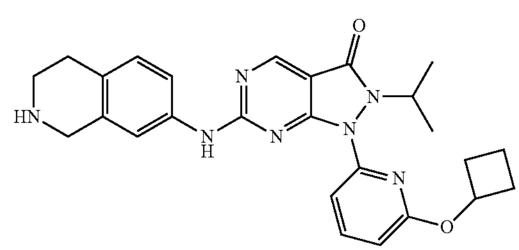 [SMILES: CC(C)n1c(=O)c2cnc(Nc3ccc4c(c3)CNCC4)nc2n1-c1cccc(OC2CCC2)n1] |

TABLE 1A-continued
| Compound No. | Structure |
|---|---|
| 1.399 | 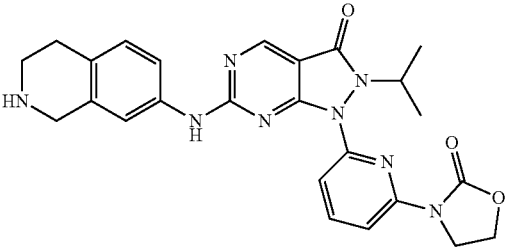 [SMILES: CC(C)n1c(=O)c2cnc(Nc3ccc4c(c3)CNCC4)nc2n1-c1cccc(N2CCOC2=O)n1] |
| 1.400 | 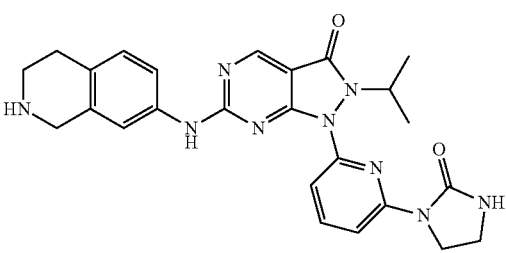 [SMILES: CC(C)n1c(=O)c2cnc(Nc3ccc4c(c3)CNCC4)nc2n1-c1cccc(N2CCNC2=O)n1] |
| 1.401 | 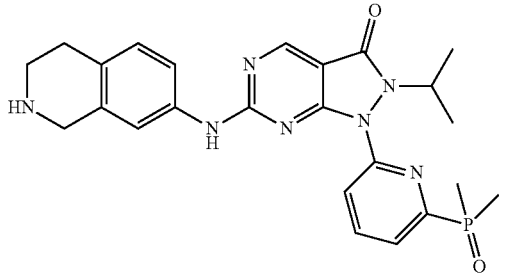 [SMILES: CC(C)n1c(=O)c2cnc(Nc3ccc4c(c3)CNCC4)nc2n1-c1cccc(P(C)(C)=O)n1] |
| 1.402 | 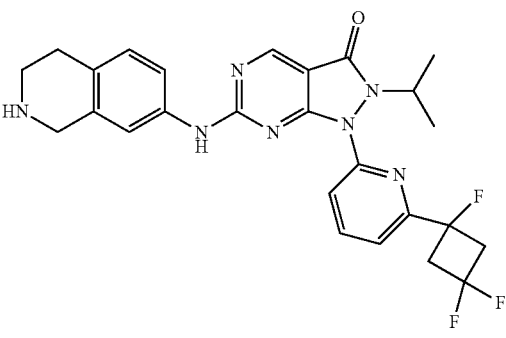 [SMILES: CC(C)n1c(=O)c2cnc(Nc3ccc4c(c3)CNCC4)nc2n1-c1cccc(C2(F)CC(F)(F)C2)n1] |
| 1.403 | 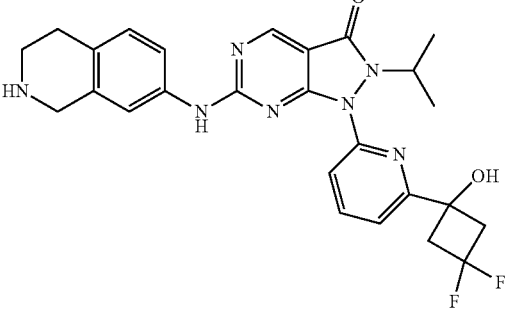 |
| 1.404 | 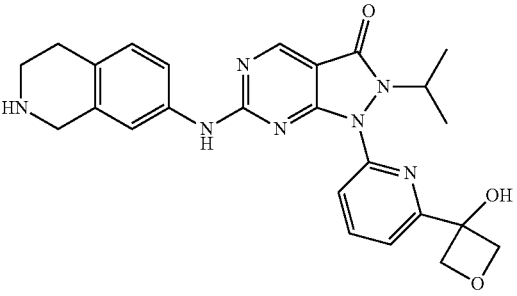 [SMILES: CC(C)n1c(=O)c2cnc(Nc3ccc4c(c3)CNCC4)nc2n1-c1cccc(C2(O)COC2)n1] |
| 1.405 | 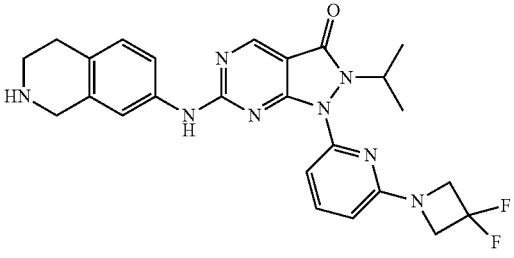 [SMILES: CC(C)n1c(=O)c2cnc(Nc3ccc4c(c3)CNCC4)nc2n1-c1cccc(N2CC(F)(F)C2)n1] |
| 1.406 | 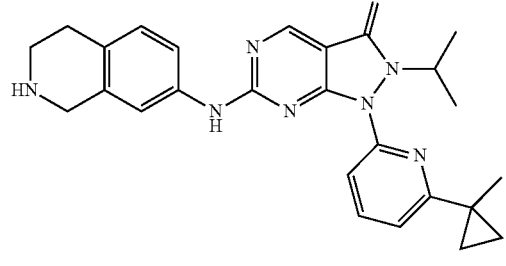 |
| 1.407 | 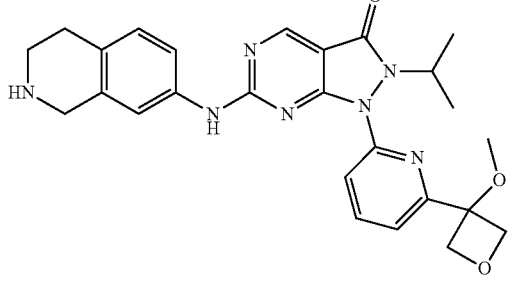 |
| 1.408 | 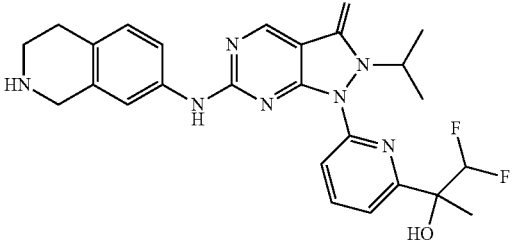 |

TABLE 1A-continued

| Compound No. | Structure |
|---|---|
| 1.409 | 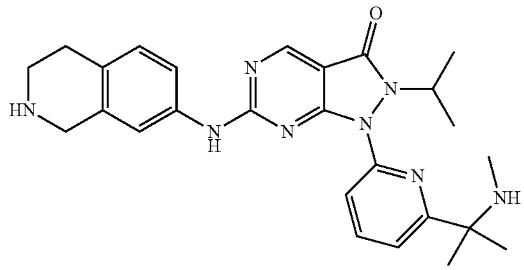 [SMILES: CNC(C)(C)c1cccc(-n2c3nc(Nc4ccc5c(c4)CNCC5)ncc3c(=O)n2C(C)C)n1] |
| 1.410 | 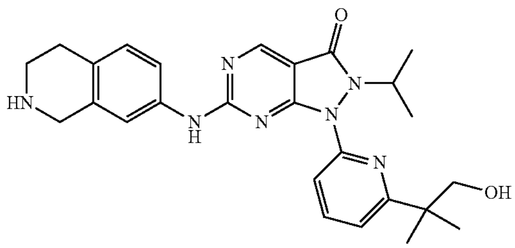 [SMILES: CC(C)n1c(=O)c2cnc(Nc3ccc4c(c3)CNCC4)nc2n1-c1cccc(C(C)(C)CO)n1] |
| 1.411 | 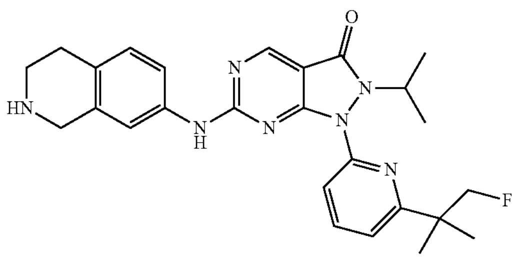 [SMILES: CC(C)n1c(=O)c2cnc(Nc3ccc4c(c3)CNCC4)nc2n1-c1cccc(C(C)(C)CF)n1] |
| 1.412 | 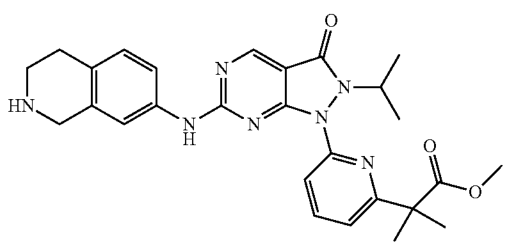 |
| 1.413 | 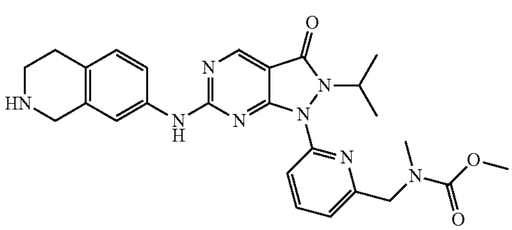 [SMILES: COC(=O)N(C)Cc1cccc(-n2c3nc(Nc4ccc5c(c4)CNCC5)ncc3c(=O)n2C(C)C)n1] |
| 1.414 | 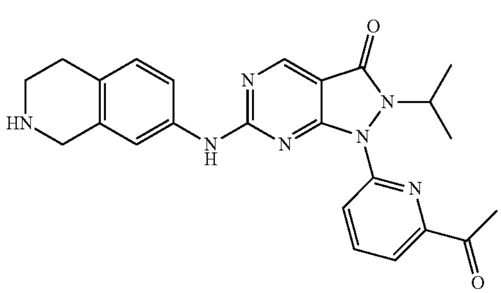 [SMILES: CC(=O)c1cccc(-n2c3nc(Nc4ccc5c(c4)CNCC5)ncc3c(=O)n2C(C)C)n1] |
| 1.415 | |
| 1.416 | |
| 1.417 | |
| 1.418 | |
| 1.419 | |
| 1.420 | |

TABLE 1A-continued
| Compound No. | Structure |
|---|---|
| 1.421 | 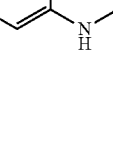 |
| 1.422 | 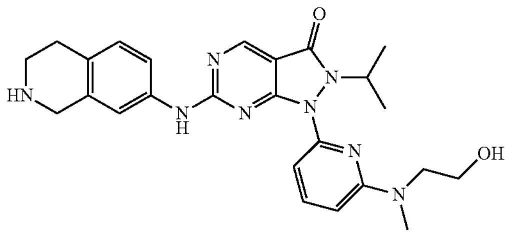 [SMILES: CC(C)n1c(=O)c2cnc(Nc3ccc4c(c3)CNCC4)nc2n1-c1cccc(N(C)CCO)n1] |
| 1.423 | 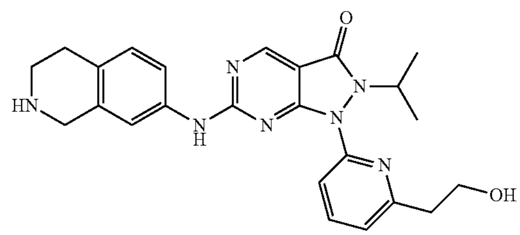 [SMILES: CC(C)n1c(=O)c2cnc(Nc3ccc4c(c3)CNCC4)nc2n1-c1cccc(CCO)n1] |
| 1.424 | 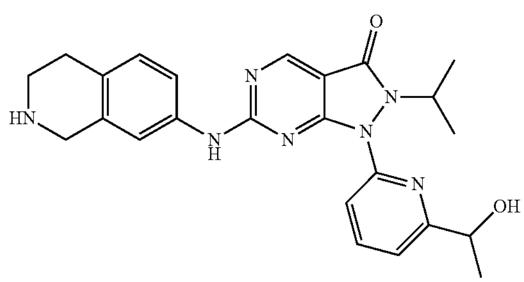 [SMILES: CC(O)c1cccc(-n2c3nc(Nc4ccc5c(c4)CNCC5)ncc3c(=O)n2C(C)C)n1] |
| 1.425 | 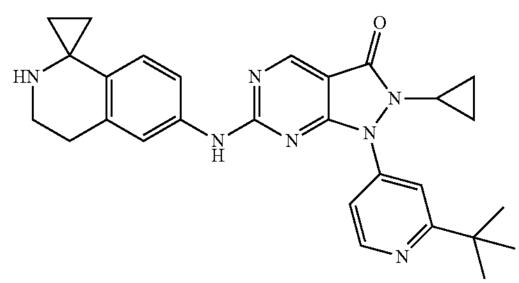 [SMILES: CC(C)(C)c1cc(-n2c3nc(Nc4ccc5c(c4)CCNC54CC4)ncc3c(=O)n2C2CC2)ccn1] |
| 1.426 | 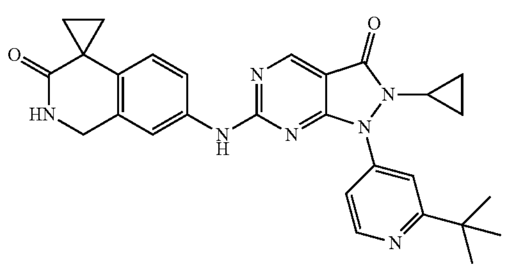 [SMILES: CC(C)(C)c1cc(-n2c3nc(Nc4ccc5c(c4)CNC(=O)C54CC4)ncc3c(=O)n2C2CC2)ccn1] |
TABLE 1A-continued
| Compound No. | Structure |
|---|---|
| 1.427 | 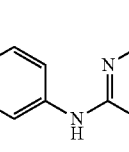 |
| 1.428 | 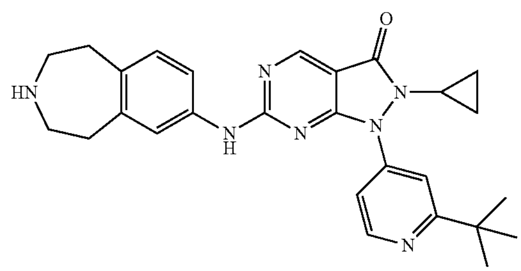 [SMILES: CC(C)(C)c1cc(-n2c3nc(Nc4ccc5c(c4)CCNCC5)ncc3c(=O)n2C2CC2)ccn1] |
| 1.429 | 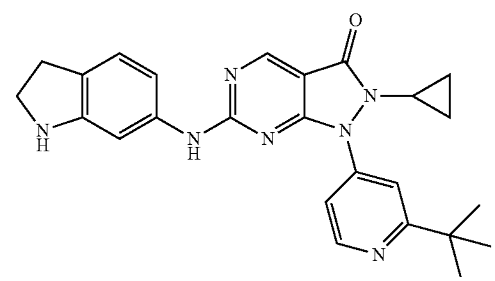 [SMILES: CC(C)(C)c1cc(-n2c3nc(Nc4ccc5c(c4)NCC5)ncc3c(=O)n2C2CC2)ccn1] |
| 1.430 | 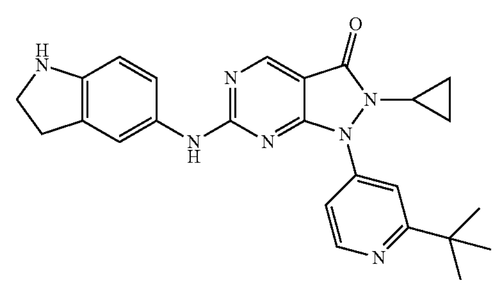 [SMILES: CC(C)(C)c1cc(-n2c3nc(Nc4ccc5c(c4)CCN5)ncc3c(=O)n2C2CC2)ccn1] |
| 1.431 | 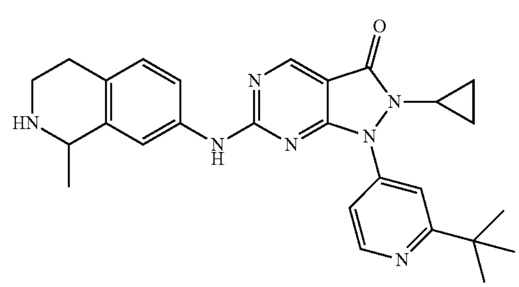 [SMILES: CC1NCCc2ccc(Nc3ncc4c(=O)n(C5CC5)n(-c5ccnc(C(C)(C)C)c5)c4n3)cc21] |

TABLE 1A-continued

| Compound No. | Structure |
|---|---|
| 1.432 | 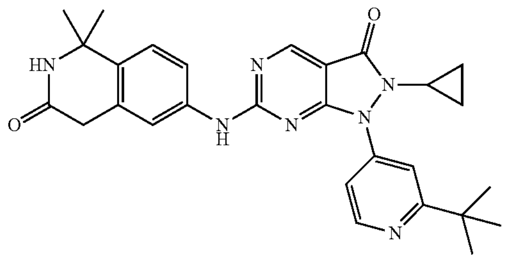 [SMILES: CC(C)(C)c1cc(-n2c3nc(Nc4ccc5c(c4)CC(=O)NC5(C)C)ncc3c(=O)n2C2CC2)ccn1] |
| 1.433 | 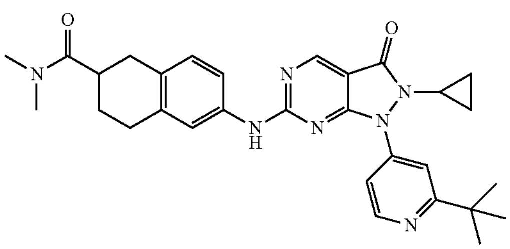 [SMILES: CN(C)C(=O)C1CCc2cc(Nc3ncc4c(=O)n(C5CC5)n(-c5ccnc(C(C)(C)C)c5)c4n3)ccc2C1] |
| 1.434 | 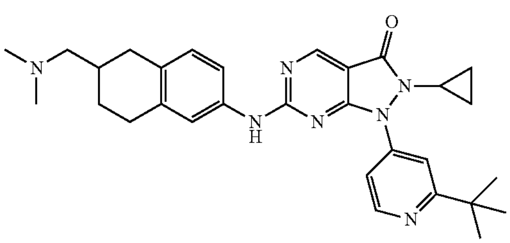 [SMILES: CN(C)CC1CCc2cc(Nc3ncc4c(=O)n(C5CC5)n(-c5ccnc(C(C)(C)C)c5)c4n3)ccc2C1] |
| 1.435 | 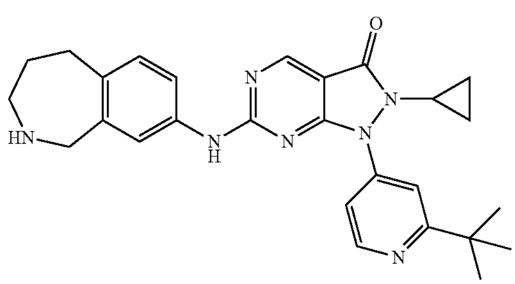 [SMILES: CC(C)(C)c1cc(-n2c3nc(Nc4ccc5c(c4)CNCCC5)ncc3c(=O)n2C2CC2)ccn1] |
| 1.436 | 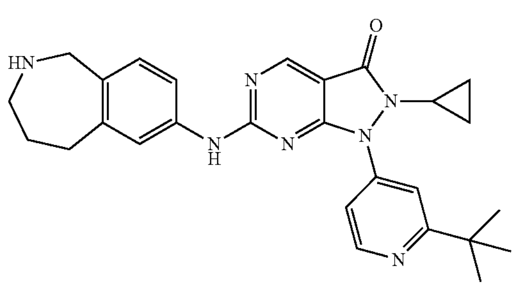 [SMILES: CC(C)(C)c1cc(-n2c3nc(Nc4ccc5c(c4)CCCNC5)ncc3c(=O)n2C2CC2)ccn1] |
| 1.437 | |
| 1.438 | |
| 1.439 | |
| 1.440 | |
| 1.441 | |

TABLE 1A-continued

| Compound No. | Structure |
|---|---|
| 1.442 | 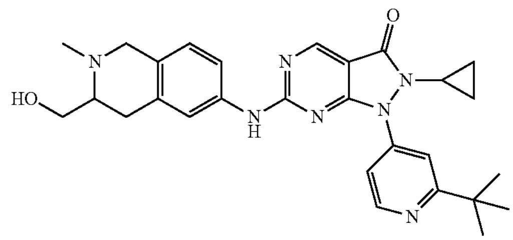 [SMILES: CN1Cc2ccc(Nc3ncc4c(=O)n(C5CC5)n(-c5ccnc(C(C)(C)C)c5)c4n3)cc2CC1CO] |
| 1.443 | 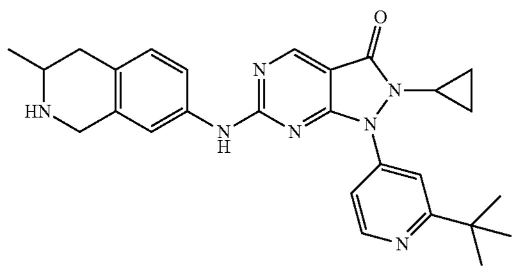 [SMILES: CC1Cc2ccc(Nc3ncc4c(=O)n(C5CC5)n(-c5ccnc(C(C)(C)C)c5)c4n3)cc2CN1] |
| 1.444 | 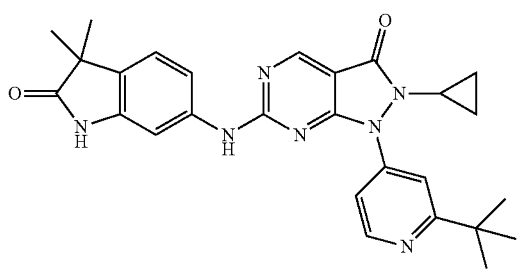 [SMILES: CC(C)(C)c1cc(-n2c3nc(Nc4ccc5c(c4)NC(=O)C5(C)C)ncc3c(=O)n2C2CC2)ccn1] |
| 1.445 | 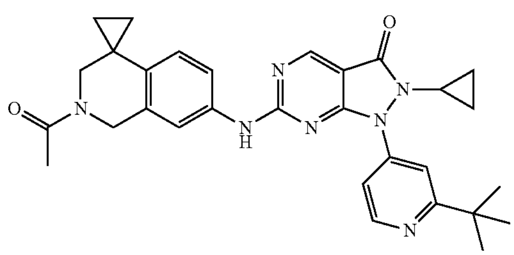 [SMILES: CC(=O)N1Cc2cc(Nc3ncc4c(=O)n(C5CC5)n(-c5ccnc(C(C)(C)C)c5)c4n3)ccc2C2(CC2)C1] |
| 1.446 | 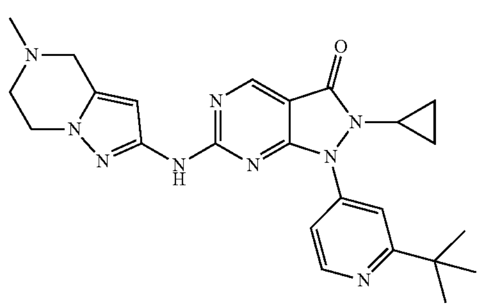 [SMILES: CN1CCn2nc(Nc3ncc4c(=O)n(C5CC5)n(-c5ccnc(C(C)(C)C)c5)c4n3)cc2C1] |

TABLE 1A-continued

| Compound No. | Structure |
|---|---|
| 1.447 | 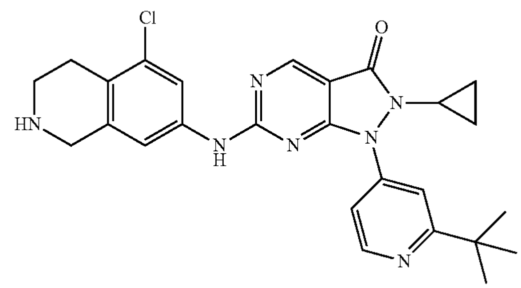 [SMILES: CC(C)(C)c1cc(-n2c3nc(Nc4cc(Cl)c5c(c4)CNCC5)ncc3c(=O)n2C2CC2)ccn1] |
| 1.448 | 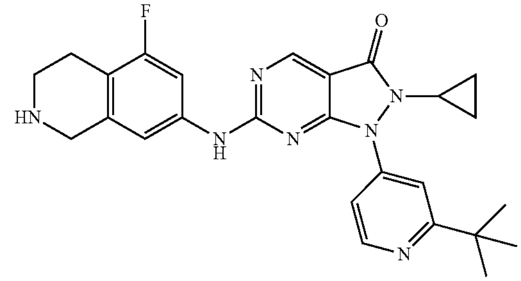 [SMILES: CC(C)(C)c1cc(-n2c3nc(Nc4cc(F)c5c(c4)CNCC5)ncc3c(=O)n2C2CC2)ccn1] |
| 1.449 | 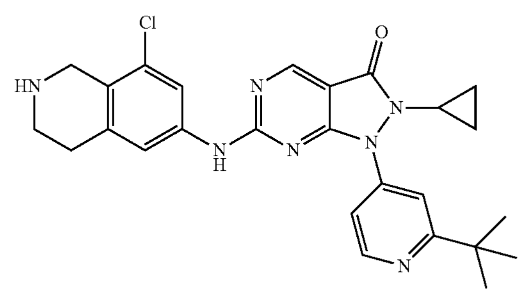 [SMILES: CC(C)(C)c1cc(-n2c3nc(Nc4cc(Cl)c5c(c4)CCNC5)ncc3c(=O)n2C2CC2)ccn1] |
| 1.450 | 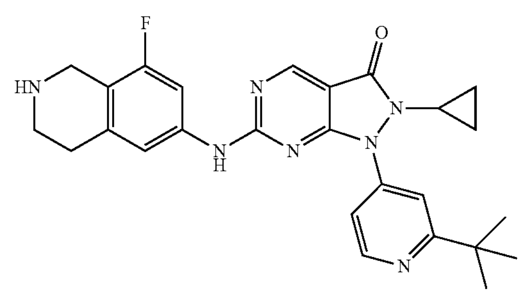 [SMILES: CC(C)(C)c1cc(-n2c3nc(Nc4cc(F)c5c(c4)CCNC5)ncc3c(=O)n2C2CC2)ccn1] |
| 1.451 | 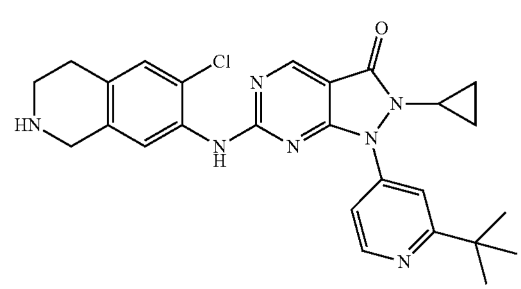 [SMILES: CC(C)(C)c1cc(-n2c3nc(Nc4cc5c(cc4Cl)CCNC5)ncc3c(=O)n2C2CC2)ccn1] |

TABLE 1A-continued
| Compound No. | Structure |
|---|---|
| 1.452 | 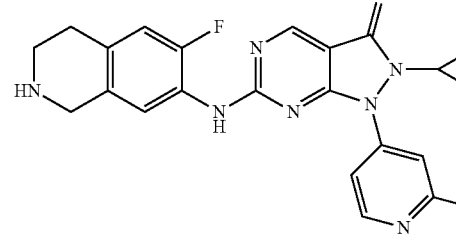 |
| 1.453 | 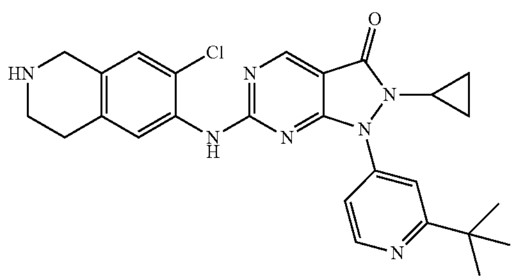 [SMILES: CC(C)(C)c1cc(-n2c3nc(Nc4cc5c(cc4Cl)CNCC5)ncc3c(=O)n2C2CC2)ccn1] |
| 1.454 | 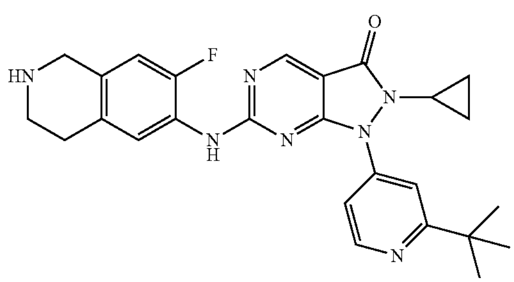 |
| 1.455 | 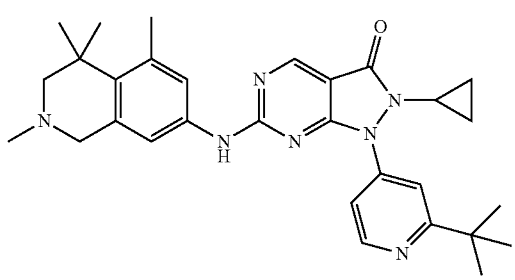 [SMILES: Cc1cc(Nc2ncc3c(=O)n(C4CC4)n(-c4ccnc(C(C)(C)C)c4)c3n2)cc2c1C(C)(C)CN(C)C2] |
| 1.456 | 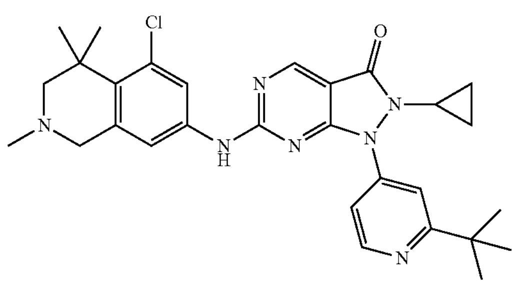 [SMILES: CN1Cc2cc(Nc3ncc4c(=O)n(C5CC5)n(-c5ccnc(C(C)(C)C)c5)c4n3)cc(Cl)c2C(C)(C)C1] |
TABLE 1A-continued
| Compound No. | Structure |
|---|---|
| 1.457 | 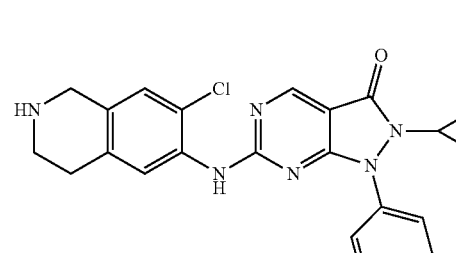 |
| 1.458 | 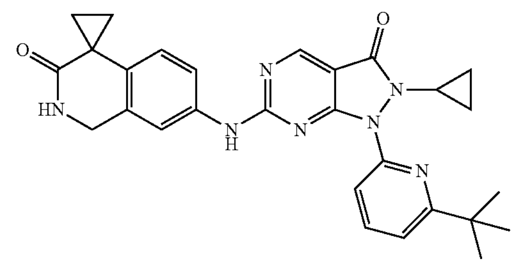 [SMILES: CC(C)(C)c1cccc(-n2c3nc(Nc4ccc5c(c4)CNC(=O)C54CC4)ncc3c(=O)n2C2CC2)n1] |
| 1.459 | 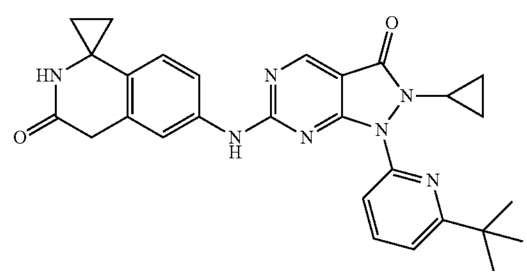 [SMILES: CC(C)(C)c1cccc(-n2c3nc(Nc4ccc5c(c4)CC(=O)NC54CC4)ncc3c(=O)n2C2CC2)n1] |
| 1.460 | 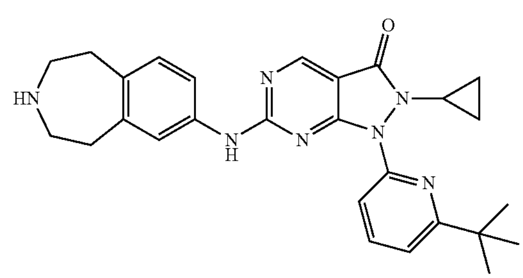 [SMILES: CC(C)(C)c1cccc(-n2c3nc(Nc4ccc5c(c4)CCNCC5)ncc3c(=O)n2C2CC2)n1] |
| 1.461 | 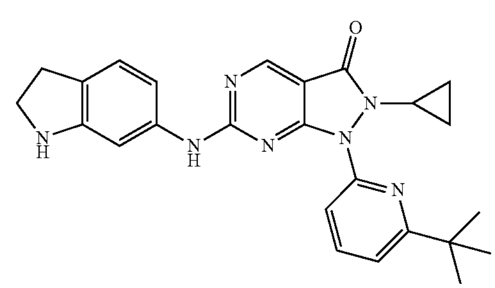 [SMILES: CC(C)(C)c1cccc(-n2c3nc(Nc4ccc5c(c4)NCC5)ncc3c(=O)n2C2CC2)n1] |

TABLE 1A-continued
| Compound No. | Structure |
|---|---|
| 1.462 | 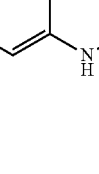 |
| 1.463 | 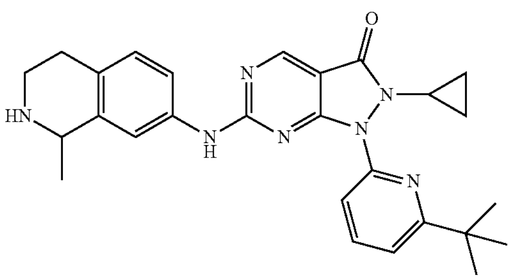 [SMILES: CC1NCCc2ccc(Nc3ncc4c(=O)n(C5CC5)n(-c5cccc(C(C)(C)C)n5)c4n3)cc21] |
| 1.464 | 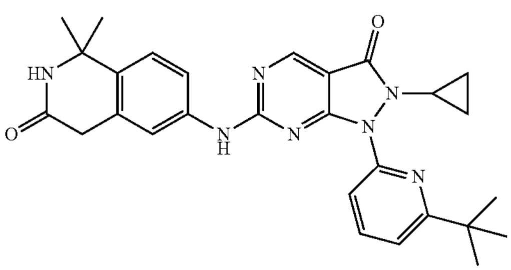 [SMILES: CC(C)(C)c1cccc(-n2c3nc(Nc4ccc5c(c4)CC(=O)NC5(C)C)ncc3c(=O)n2C2CC2)n1] |
| 1.465 | 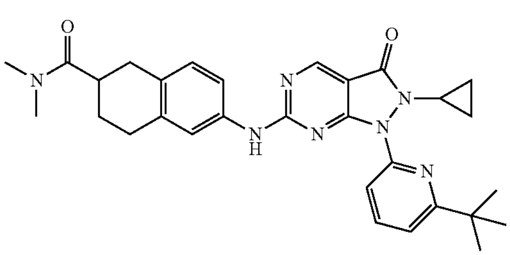 [SMILES: CN(C)C(=O)C1CCc2cc(Nc3ncc4c(=O)n(C5CC5)n(-c5cccc(C(C)(C)C)n5)c4n3)ccc2C1] |
| 1.466 | 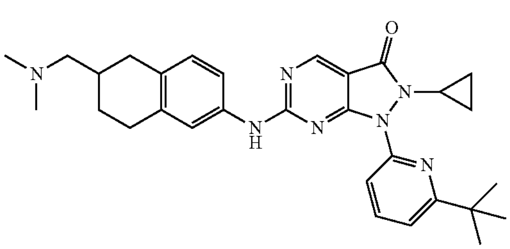 [SMILES: CN(C)CC1CCc2cc(Nc3ncc4c(=O)n(C5CC5)n(-c5cccc(C(C)(C)C)n5)c4n3)ccc2C1] |
TABLE 1A-continued
| Compound No. | Structure |
|---|---|
| 1.467 | 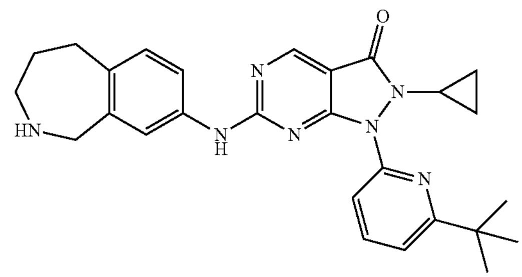 [SMILES: CC(C)(C)c1cccc(-n2c3nc(Nc4ccc5c(c4)CNCCC5)ncc3c(=O)n2C2CC2)n1] |
| 1.468 | 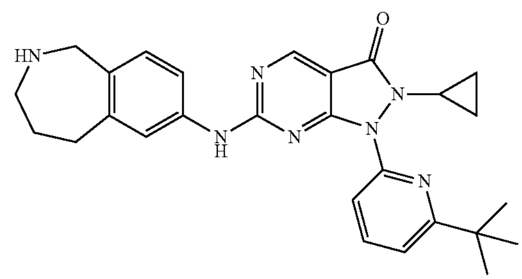 [SMILES: CC(C)(C)c1cccc(-n2c3nc(Nc4ccc5c(c4)CCCNC5)ncc3c(=O)n2C2CC2)n1] |
| 1.469 | 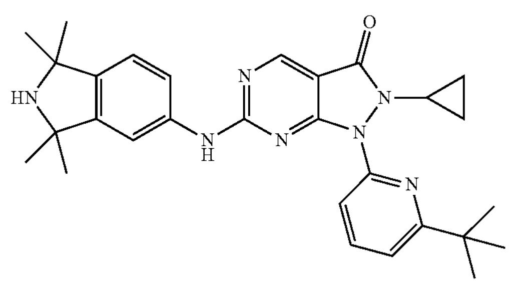 [SMILES: CC(C)(C)c1cccc(-n2c3nc(Nc4ccc5c(c4)C(C)(C)NC5(C)C)ncc3c(=O)n2C2CC2)n1] |
| 1.470 | 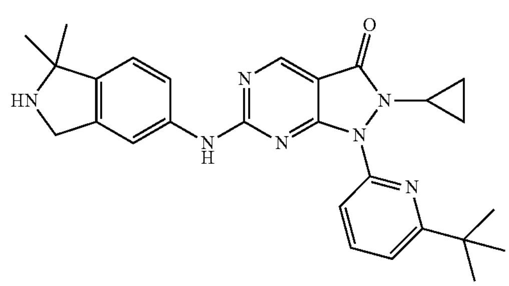 [SMILES: CC(C)(C)c1cccc(-n2c3nc(Nc4ccc5c(c4)CNC5(C)C)ncc3c(=O)n2C2CC2)n1] |
| 1.471 | 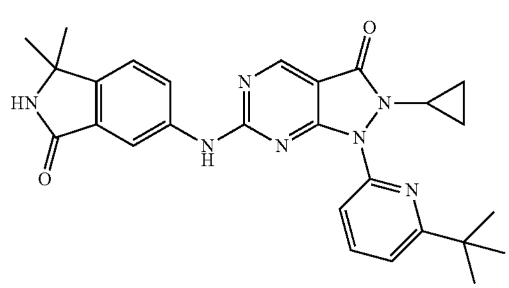 [SMILES: CC(C)(C)c1cccc(-n2c3nc(Nc4ccc5c(c4)C(=O)NC5(C)C)ncc3c(=O)n2C2CC2)n1] |

TABLE 1A-continued

| Compound No. | Structure |
|---|---|
| 1.472 | 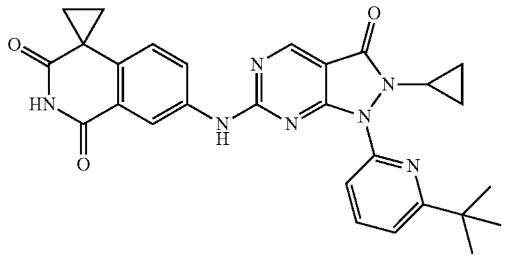 [SMILES: CC(C)(C)c1cccc(-n2c3nc(Nc4ccc5c(c4)C(=O)NC(=O)C54CC4)ncc3c(=O)n2C2CC2)n1] |
| 1.473 | 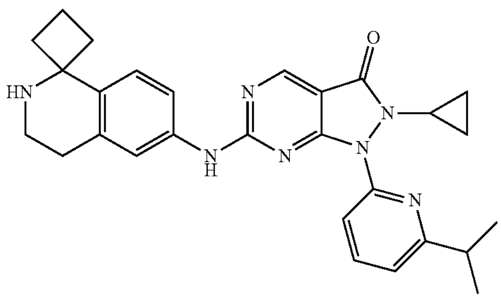 [SMILES: CC(C)c1cccc(-n2c3nc(Nc4ccc5c(c4)CCNC54CCC4)ncc3c(=O)n2C2CC2)n1] |
| 1.474 | 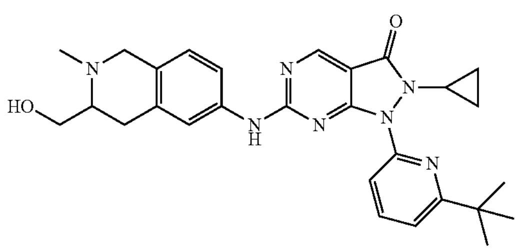 [SMILES: CN1Cc2ccc(Nc3ncc4c(=O)n(C5CC5)n(-c5cccc(C(C)(C)C)n5)c4n3)cc2CC1CO] |
| 1.475 | 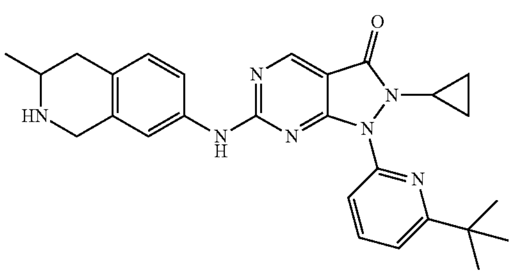 [SMILES: CC1Cc2ccc(Nc3ncc4c(=O)n(C5CC5)n(-c5cccc(C(C)(C)C)n5)c4n3)cc2CN1] |
| 1.476 | 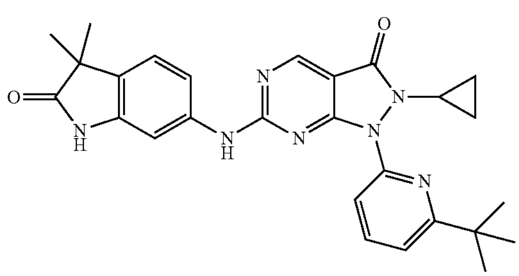 [SMILES: CC(C)(C)c1cccc(-n2c3nc(Nc4ccc5c(c4)NC(=O)C5(C)C)ncc3c(=O)n2C2CC2)n1] |
| 1.477 | 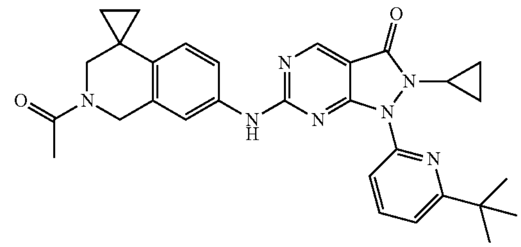 [SMILES: CC(=O)N1Cc2cc(Nc3ncc4c(=O)n(C5CC5)n(-c5cccc(C(C)(C)C)n5)c4n3)ccc2C2(CC2)C1] |
| 1.478 | 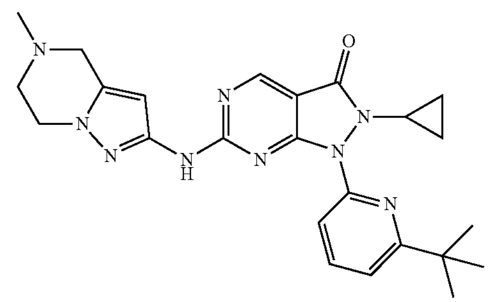 [SMILES: CN1CCn2nc(Nc3ncc4c(=O)n(C5CC5)n(-c5cccc(C(C)(C)C)n5)c4n3)cc2C1] |
| 1.479 | 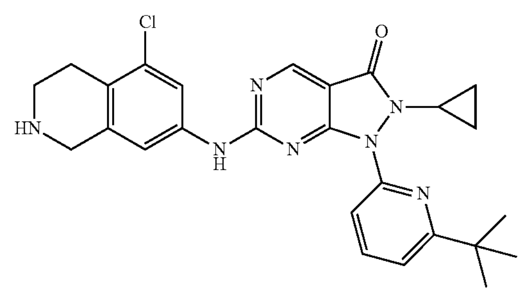 |
| 1.480 | 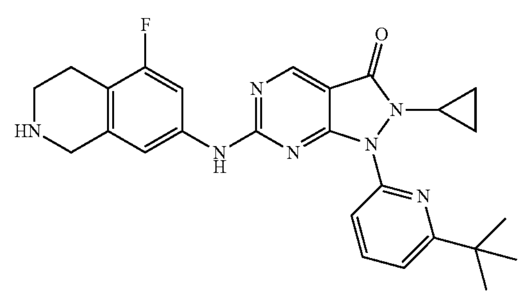 [SMILES: CC(C)(C)c1cccc(-n2c3nc(Nc4cc(F)c5c(c4)CNCC5)ncc3c(=O)n2C2CC2)n1] |
| 1.481 | 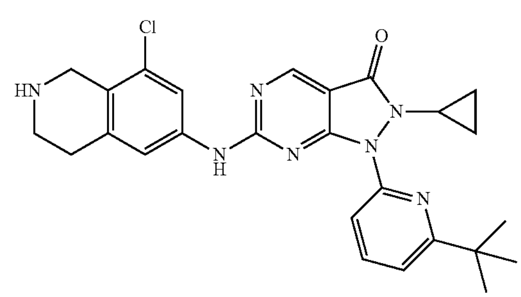 [SMILES: CC(C)(C)c1cccc(-n2c3nc(Nc4cc(Cl)c5c(c4)CCNC5)ncc3c(=O)n2C2CC2)n1] |

TABLE 1A-continued

| Compound No. | Structure |
|---|---|
| 1.482 | 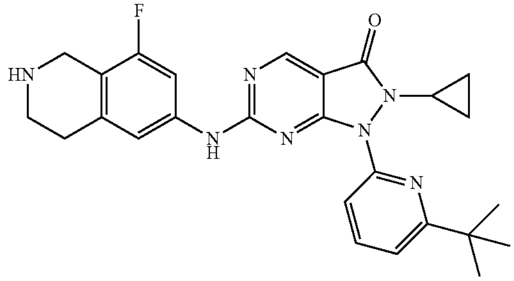 |
| 1.483 | 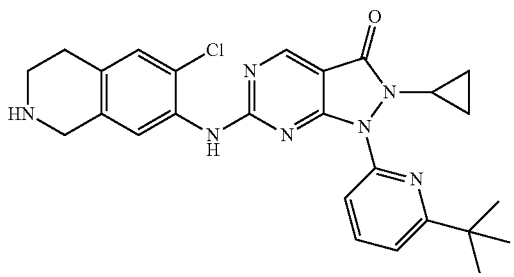 [SMILES: CC(C)(C)c1cccc(-n2c3nc(Nc4cc5c(cc4F)CCNC5)ncc3c(=O)n2C2CC2)n1] |
| 1.484 | 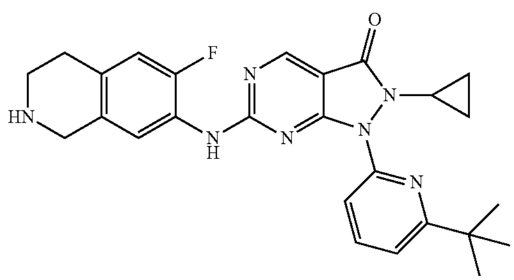 |
| 1.485 | 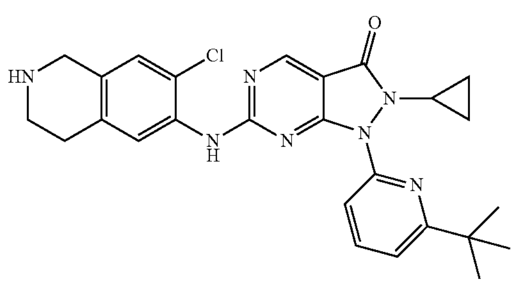 [SMILES: CC(C)(C)c1cccc(-n2c3nc(Nc4cc5c(cc4Cl)CNCC5)ncc3c(=O)n2C2CC2)n1] |
| 1.486 | 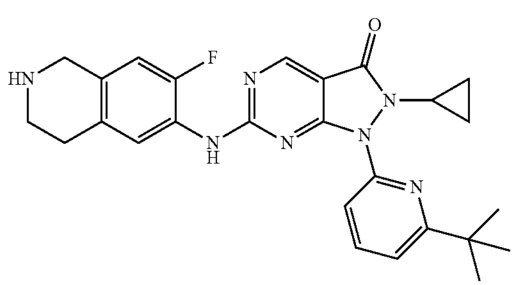 [SMILES: CC(C)(C)c1cccc(-n2c3nc(Nc4cc5c(cc4F)CNCC5)ncc3c(=O)n2C2CC2)n1] |
| 1.487 | |
| 1.488 | |
| 1.489 | |
| 1.490 | |
| 1.491 | |

TABLE 1A-continued
| Compound No. | Structure |
|---|---|
| 1.492 | 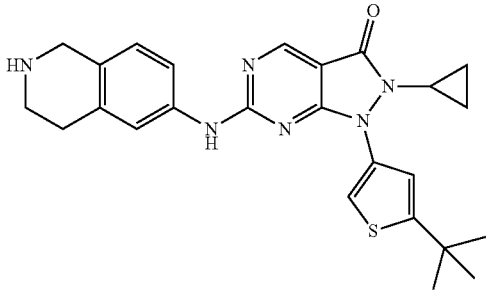 [SMILES: CC(C)(C)c1cc(-n2c3nc(Nc4ccc5c(c4)CCNC5)ncc3c(=O)n2C2CC2)cs1] |
| 1.493 | 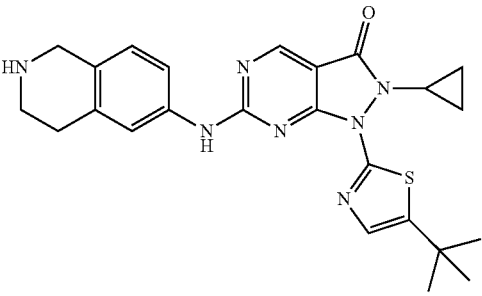 |
| 1.494 | 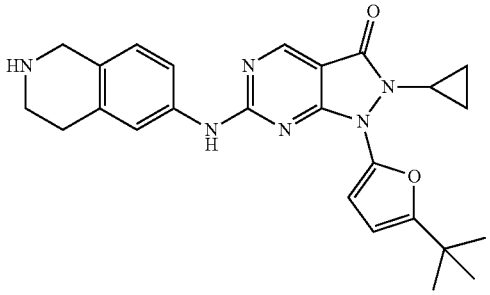 [SMILES: CC(C)(C)c1ccc(-n2c3nc(Nc4ccc5c(c4)CCNC5)ncc3c(=O)n2C2CC2)o1] |
| 1.495 | 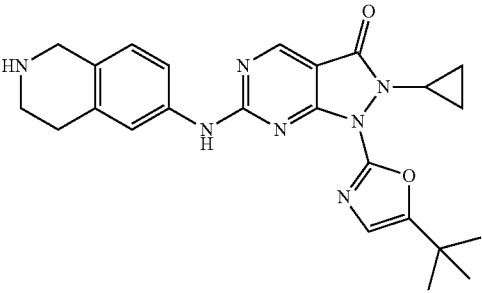 |
| 1.496 | 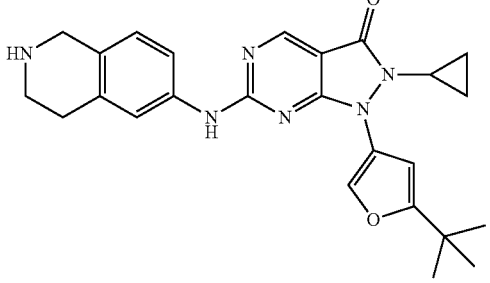 |
| 1.497 | 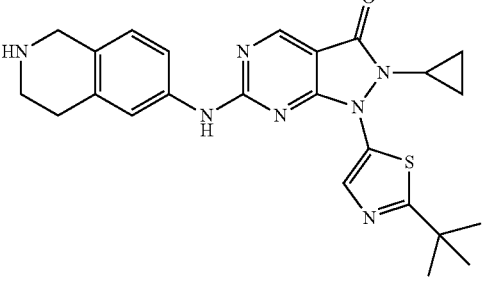 |
| 1.498 | 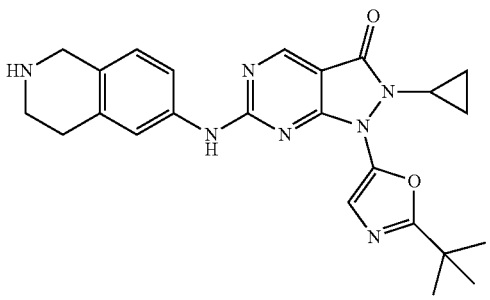 [SMILES: CC(C)(C)c1ncc(-n2c3nc(Nc4ccc5c(c4)CCNC5)ncc3c(=O)n2C2CC2)o1] |
| 1.499 | 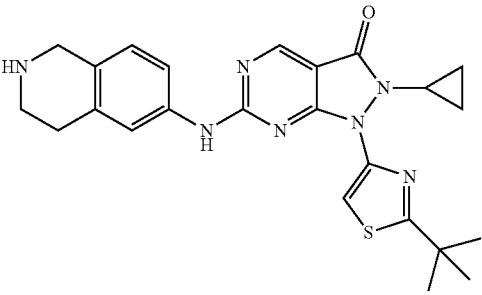 [SMILES: CC(C)(C)c1nc(-n2c3nc(Nc4ccc5c(c4)CCNC5)ncc3c(=O)n2C2CC2)co1] |
| 1.500 | 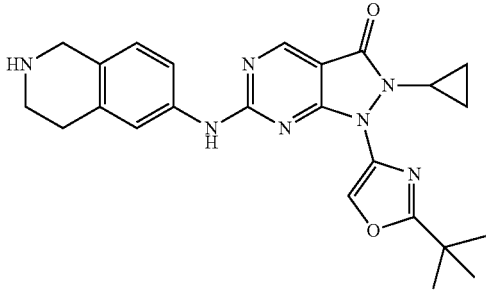 [SMILES: CC(C)(C)c1nc(-n2c3nc(Nc4ccc5c(c4)CCNC5)ncc3c(=O)n2C2CC2)cs1] |
| 1.501 | 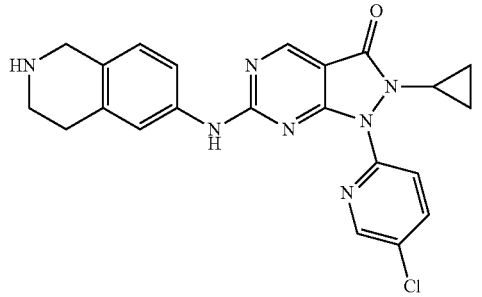 [SMILES: O=c1c2cnc(Nc3ccc4c(c3)CCNC4)nc2n(-c2ccc(Cl)cn2)n1C1CC1] |

TABLE 1A-continued

| Compound No. | Structure |
|---|---|
| 1.502 | 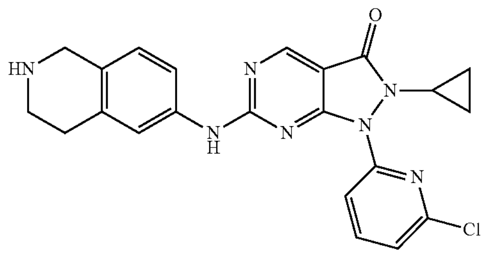 [SMILES: O=c1c2cnc(Nc3ccc4c(c3)CCNC4)nc2n(-c2cccc(Cl)n2)n1C1CC1] |
| 1.503 | 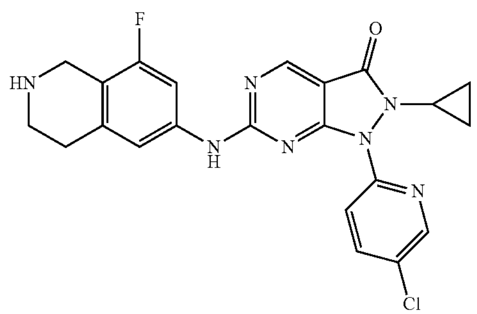 [SMILES: O=c1c2cnc(Nc3cc(F)c4c(c3)CCNC4)nc2n(-c2ccc(Cl)cn2)n1C1CC1] |
| 1.504 | 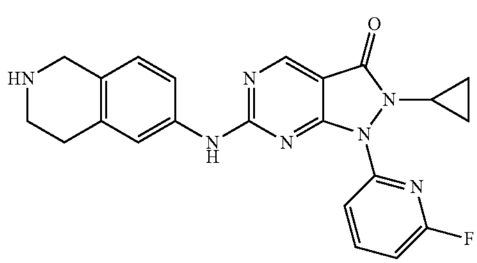 [SMILES: O=c1c2cnc(Nc3ccc4c(c3)CCNC4)nc2n(-c2cccc(F)n2)n1C1CC1] |
| 1.505 | 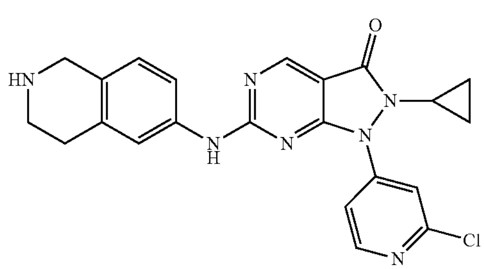 [SMILES: O=c1c2cnc(Nc3ccc4c(c3)CCNC4)nc2n(-c2ccnc(Cl)c2)n1C1CC1] |
| 1.506 | 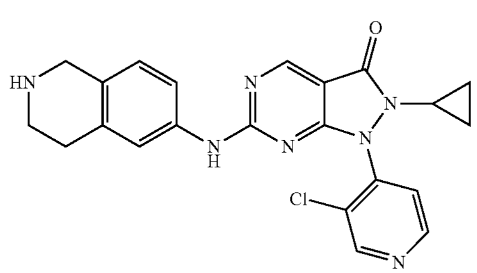 [SMILES: O=c1c2cnc(Nc3ccc4c(c3)CCNC4)nc2n(-c2ccncc2Cl)n1C1CC1] |
| 1.507 | 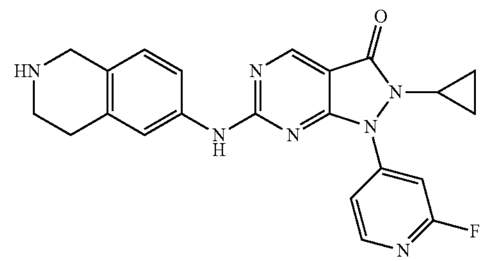 [SMILES: O=c1c2cnc(Nc3ccc4c(c3)CCNC4)nc2n(-c2ccnc(F)c2)n1C1CC1] |
| 1.508 | 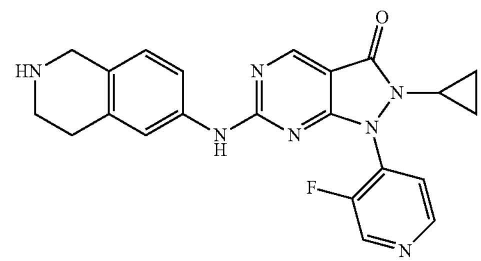 [SMILES: O=c1c2cnc(Nc3ccc4c(c3)CCNC4)nc2n(-c2ccncc2F)n1C1CC1] |
| 1.509 | 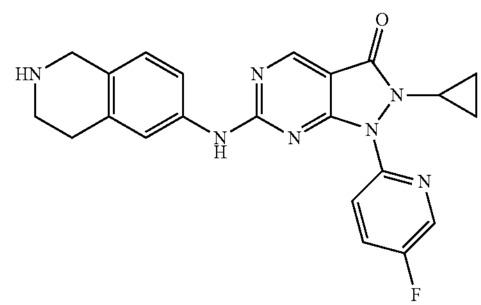 [SMILES: O=c1c2cnc(Nc3ccc4c(c3)CCNC4)nc2n(-c2ccc(F)cn2)n1C1CC1] |
| 1.510 | 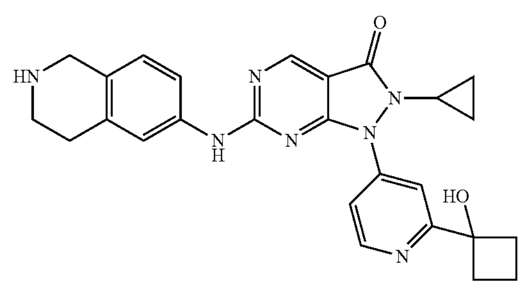 [SMILES: O=c1c2cnc(Nc3ccc4c(c3)CCNC4)nc2n(-c2ccnc(C3(O)CCC3)c2)n1C1CC1] |
| 1.511 | 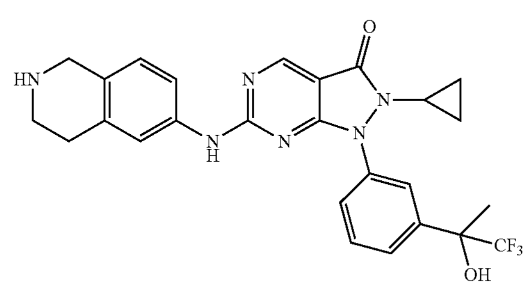 [SMILES: CC(O)(c1cccc(-n2c3nc(Nc4ccc5c(c4)CCNC5)ncc3c(=O)n2C2CC2)c1)C(F)(F)F] |

TABLE 1A-continued

| Compound No. | Structure |
|---|---|
| 1.512 | 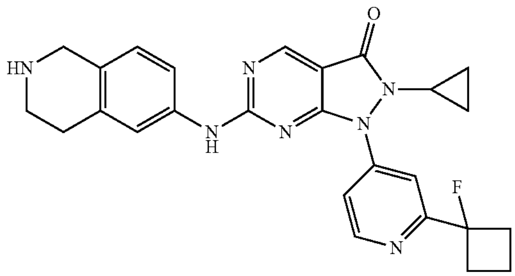 [SMILES: O=c1c2cnc(Nc3ccc4c(c3)CCNC4)nc2n(-c2ccnc(C3(F)CCC3)c2)n1C1CC1] |
| 1.513 | 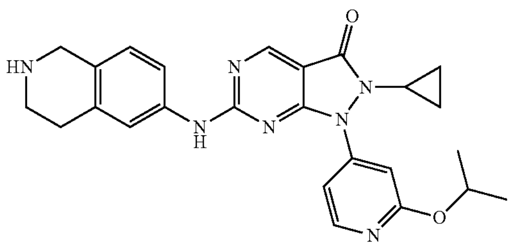 [SMILES: CC(C)Oc1cc(-n2c3nc(Nc4ccc5c(c4)CCNC5)ncc3c(=O)n2C2CC2)ccn1] |
| 1.514 | 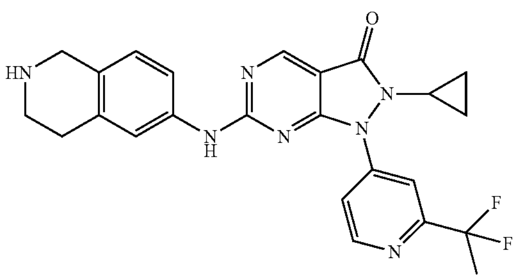 [SMILES: CC(F)(F)c1cc(-n2c3nc(Nc4ccc5c(c4)CCNC5)ncc3c(=O)n2C2CC2)ccn1] |
| 1.515 | 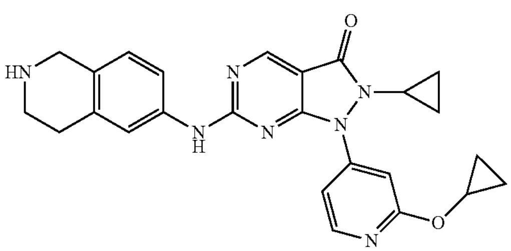 [SMILES: O=c1c2cnc(Nc3ccc4c(c3)CCNC4)nc2n(-c2ccnc(OC3CC3)c2)n1C1CC1] |
| 1.516 | 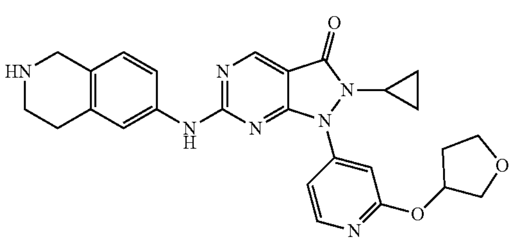 [SMILES: O=c1c2cnc(Nc3ccc4c(c3)CCNC4)nc2n(-c2ccnc(OC3CCOC3)c2)n1C1CC1] |
| 1.517 | 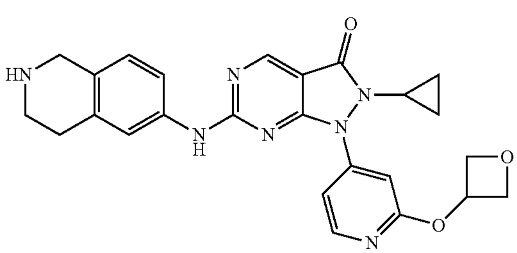 [SMILES: O=c1c2cnc(Nc3ccc4c(c3)CCNC4)nc2n(-c2ccnc(OC3COC3)c2)n1C1CC1] |
| 1.518 | |
| 1.519 | |
| 1.520 | |
| 1.521 | |
| 1.522 | |

TABLE 1A-continued

| Compound No. | Structure |
|---|---|
| 1.523 | |
| 1.524 | |
| 1.525 | |
| 1.526 | |
| 1.527 | |
| 1.528 | 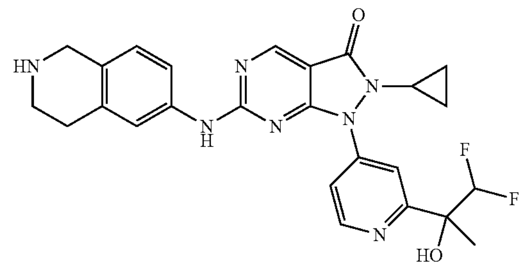 [SMILES: CC(O)(c1cc(-n2c3nc(Nc4ccc5c(c4)CCNC5)ncc3c(=O)n2C2CC2)ccn1)C(F)F] |
| 1.529 | 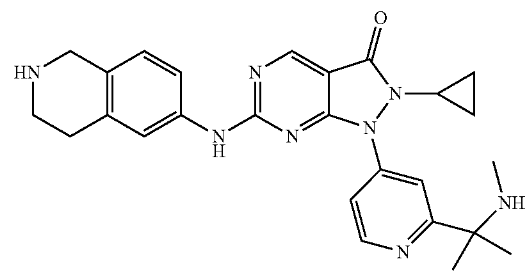 [SMILES: CNC(C)(C)c1cc(-n2c3nc(Nc4ccc5c(c4)CCNC5)ncc3c(=O)n2C2CC2)ccn1] |
| 1.530 | 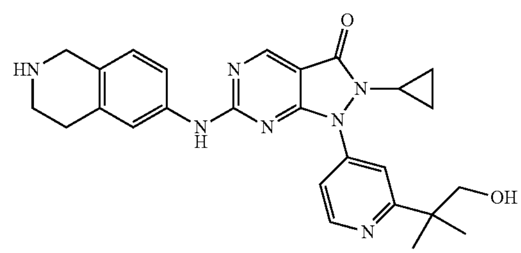 [SMILES: CC(C)(CO)c1cc(-n2c3nc(Nc4ccc5c(c4)CCNC5)ncc3c(=O)n2C2CC2)ccn1] |
| 1.531 | 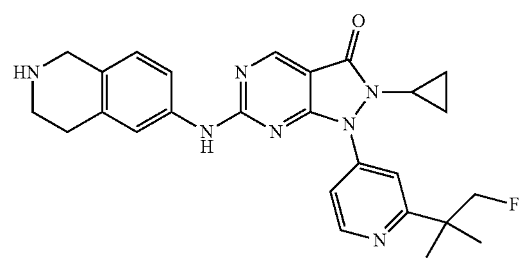 [SMILES: CC(C)(CF)c1cc(-n2c3nc(Nc4ccc5c(c4)CCNC5)ncc3c(=O)n2C2CC2)ccn1] |
| 1.532 | 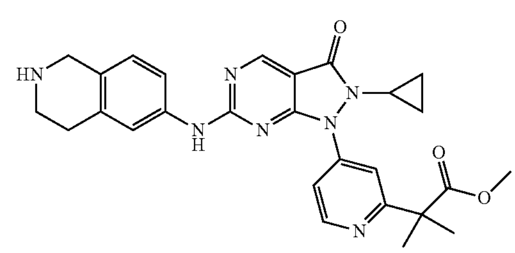 [SMILES: COC(=O)C(C)(C)c1cc(-n2c3nc(Nc4ccc5c(c4)CCNC5)ncc3c(=O)n2C2CC2)ccn1] |
| 1.533 | 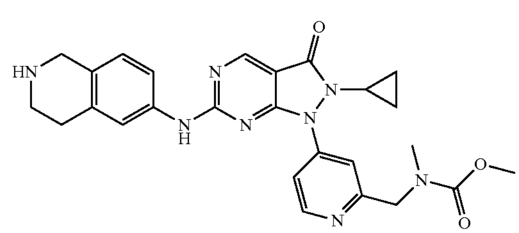 [SMILES: COC(=O)N(C)Cc1cc(-n2c3nc(Nc4ccc5c(c4)CCNC5)ncc3c(=O)n2C2CC2)ccn1] |

TABLE 1A-continued

| Compound No. | Structure |
|---|---|
| 1.534 | 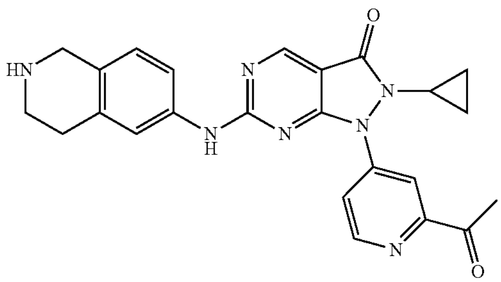 [SMILES: CC(=O)c1cc(-n2c3nc(Nc4ccc5c(c4)CCNC5)ncc3c(=O)n2C2CC2)ccn1] |
| 1.535 | 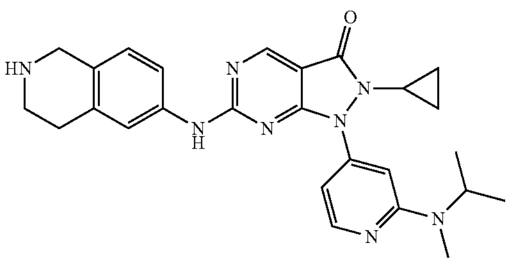 [SMILES: CC(C)N(C)c1cc(-n2c3nc(Nc4ccc5c(c4)CCNC5)ncc3c(=O)n2C2CC2)ccn1] |
| 1.536 | 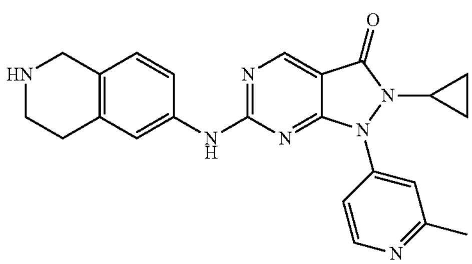 [SMILES: Cc1cc(-n2c3nc(Nc4ccc5c(c4)CCNC5)ncc3c(=O)n2C2CC2)ccn1] |
| 1.537 | 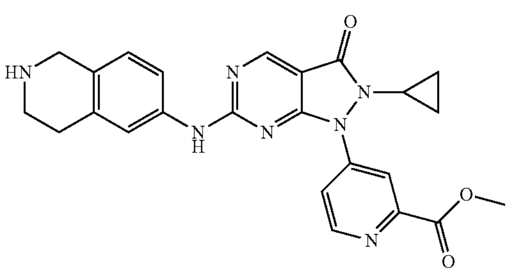 [SMILES: COC(=O)c1cc(-n2c3nc(Nc4ccc5c(c4)CCNC5)ncc3c(=O)n2C2CC2)ccn1] |
| 1.538 | 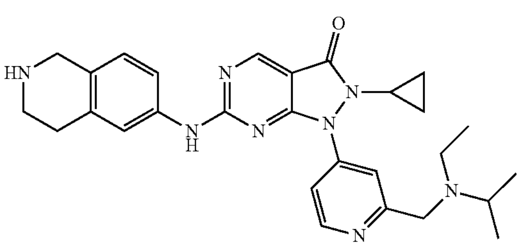 [SMILES: CCN(Cc1cc(-n2c3nc(Nc4ccc5c(c4)CCNC5)ncc3c(=O)n2C2CC2)ccn1)C(C)C] |
| 1.539 | 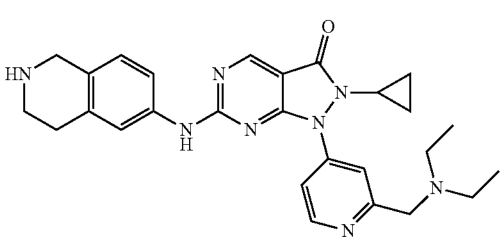 [SMILES: CCN(CC)Cc1cc(-n2c3nc(Nc4ccc5c(c4)CCNC5)ncc3c(=O)n2C2CC2)ccn1] |
| 1.540 | |
| 1.541 | |
| 1.542 | |
| 1.543 | |
| 1.544 | |
| 1.545 | |

TABLE 1A-continued

| Compound No. | Structure |
|---|---|
| 1.546 | |
| 1.547 | |
| 1.548 | |
| 1.549 | |
| 1.550 | |
| 1.551 | 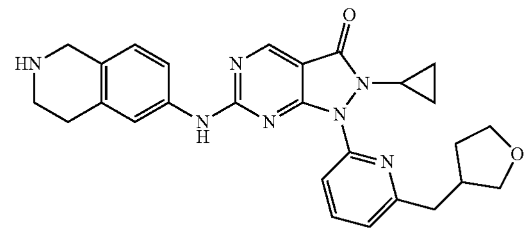 [SMILES: O=c1c2cnc(Nc3ccc4c(c3)CCNC4)nc2n(-c2cccc(CC3CCOC3)n2)n1C1CC1] |
| 1.552 | 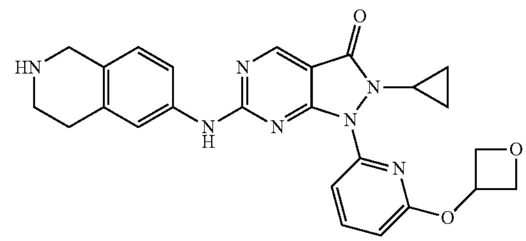 [SMILES: O=c1c2cnc(Nc3ccc4c(c3)CCNC4)nc2n(-c2cccc(OC3COC3)n2)n1C1CC1] |
| 1.553 | 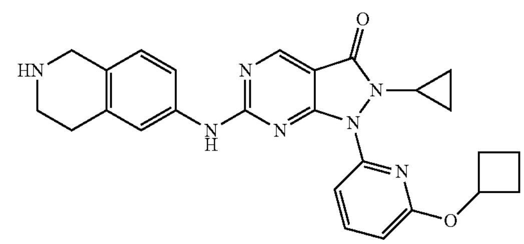 [SMILES: O=c1c2cnc(Nc3ccc4c(c3)CCNC4)nc2n(-c2cccc(OC3CCC3)n2)n1C1CC1] |
| 1.554 | 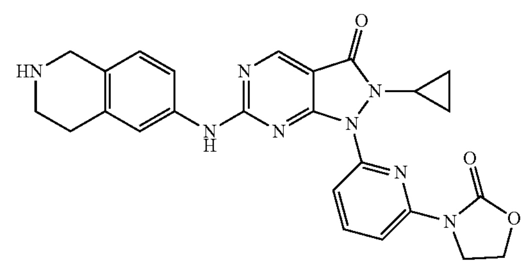 [SMILES: O=C1OCCN1c1cccc(-n2c3nc(Nc4ccc5c(c4)CCNC5)ncc3c(=O)n2C2CC2)n1] |
| 1.555 | 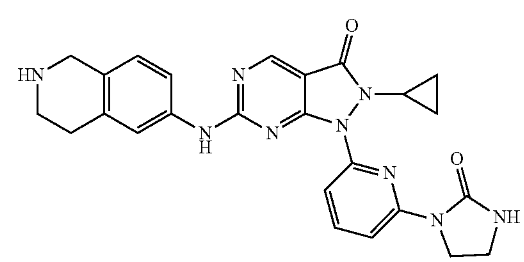 [SMILES: O=C1NCCN1c1cccc(-n2c3nc(Nc4ccc5c(c4)CCNC5)ncc3c(=O)n2C2CC2)n1] |
| 1.556 | 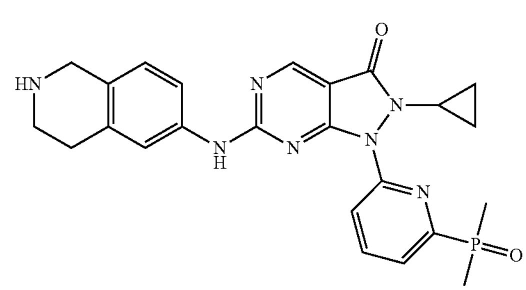 [SMILES: CP(C)(=O)c1cccc(-n2c3nc(Nc4ccc5c(c4)CCNC5)ncc3c(=O)n2C2CC2)n1] |

TABLE 1A-continued
| Compound No. | Structure |
|---|---|
| 1.557 | 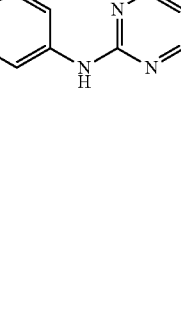 |
| 1.558 | 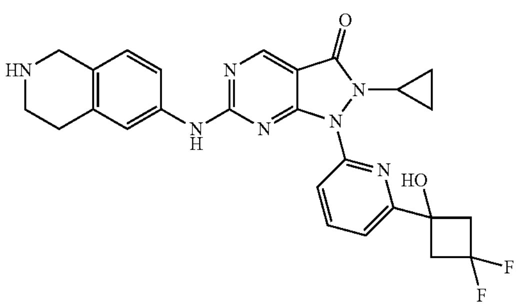 [SMILES: O=c1c2cnc(Nc3ccc4c(c3)CCNC4)nc2n(-c2cccc(C3(O)CC(F)(F)C3)n2)n1C1CC1] |
| 1.559 | 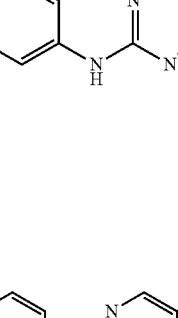 |
| 1.560 | 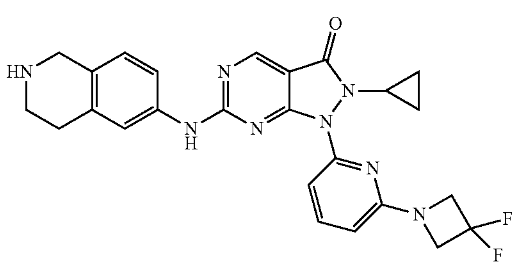 [SMILES: O=c1c2cnc(Nc3ccc4c(c3)CCNC4)nc2n(-c2cccc(N3CC(F)(F)C3)n2)n1C1CC1] |
| 1.561 | 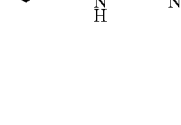 |
| 1.562 | 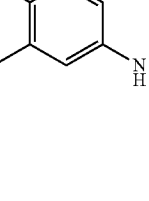 |
| 1.563 | 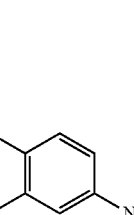 |
| 1.564 |  |
| 1.565 | 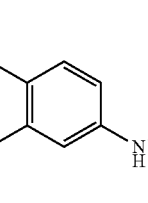 |
| 1.566 | 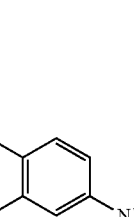 |

TABLE 1A-continued
| Compound No. | Structure |
|---|---|
| 1.567 | 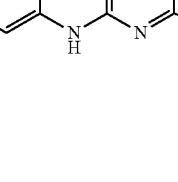 |
| 1.568 | 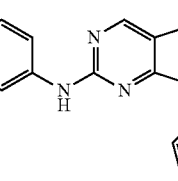 |
| 1.569 | 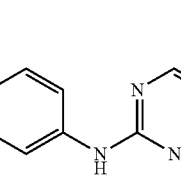 |
| 1.570 | 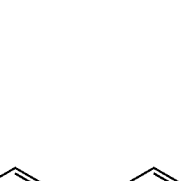 |
| 1.571 | 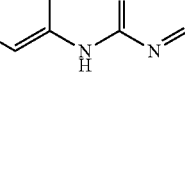 |
| 1.572 | 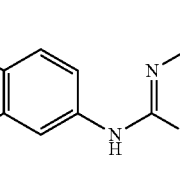 |
| 1.573 | 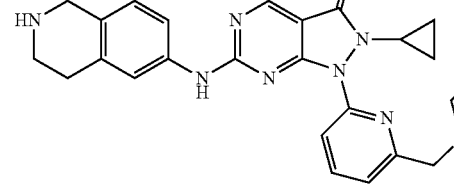 |
| 1.574 | 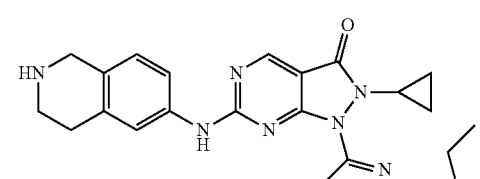 |
| 1.575 | 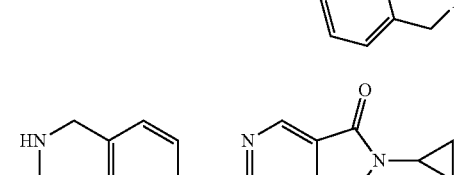 |
| 1.576 | 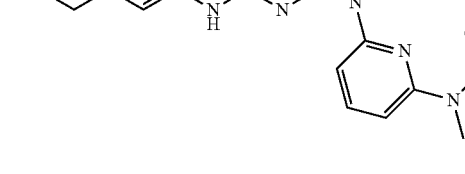 |
| 1.577 | 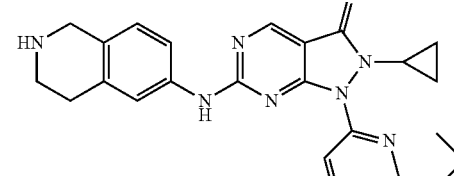 |
| 1.578 | 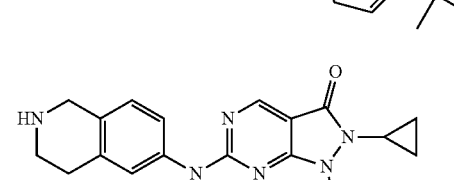 |

TABLE 1A-continued

| Compound No. | Structure |
|---|---|
| 1.579 | 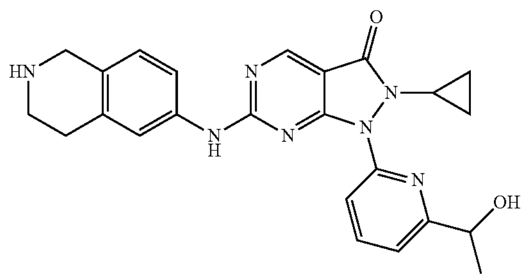 [SMILES: CC(O)c1cccc(-n2c3nc(Nc4ccc5c(c4)CCNC5)ncc3c(=O)n2C2CC2)n1] |
| 1.580 | 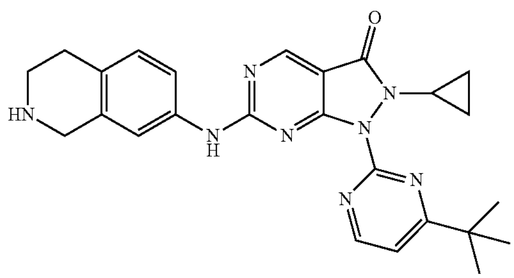 [SMILES: CC(C)(C)c1ccnc(-n2c3nc(Nc4ccc5c(c4)CNCC5)ncc3c(=O)n2C2CC2)n1] |
| 1.581 | 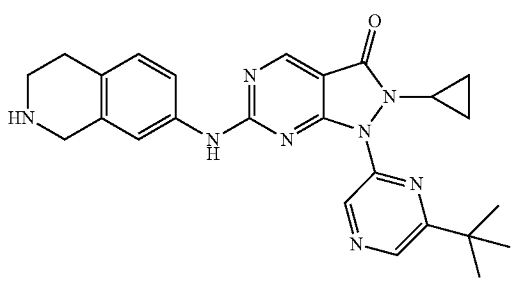 [SMILES: CC(C)(C)c1cncc(-n2c3nc(Nc4ccc5c(c4)CNCC5)ncc3c(=O)n2C2CC2)n1] |
| 1.582 | 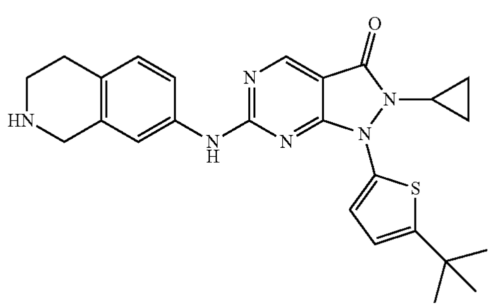 |
| 1.583 | 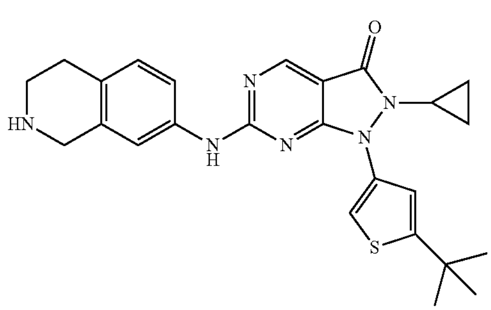 [SMILES: CC(C)(C)c1cc(-n2c3nc(Nc4ccc5c(c4)CNCC5)ncc3c(=O)n2C2CC2)cs1] |
| 1.584 | |
| 1.585 | |
| 1.586 | |
| 1.587 | |
| 1.588 | |

TABLE 1A-continued

| Compound No. | Structure |
|---|---|
| 1.589 | 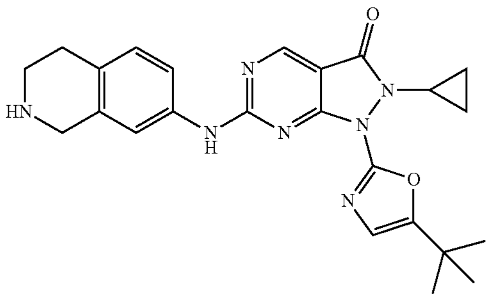 [SMILES: CC(C)(C)c1cnc(-n2c3nc(Nc4ccc5c(c4)CNCC5)ncc3c(=O)n2C2CC2)s1] |
| 1.590 | 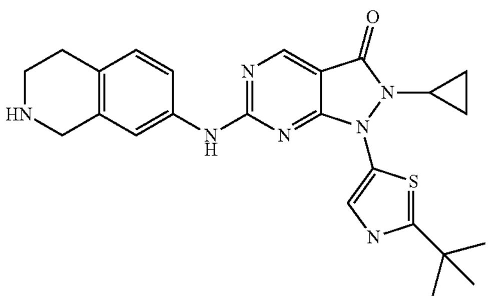 |
| 1.591 | 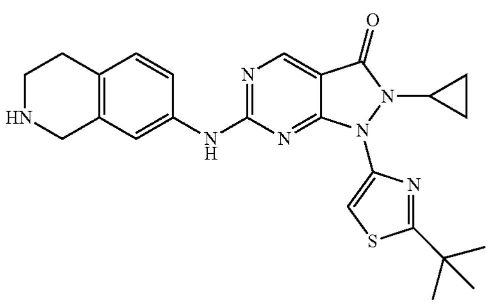 [SMILES: CC(C)(C)c1nc(-n2c3nc(Nc4ccc5c(c4)CNCC5)ncc3c(=O)n2C2CC2)cs1] |
| 1.592 | 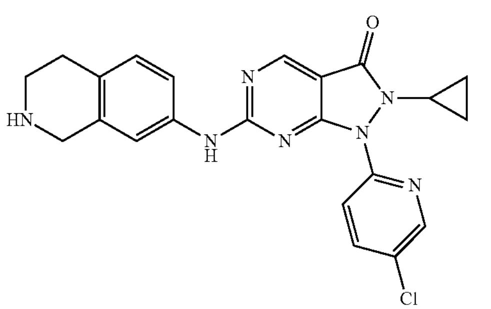 [SMILES: O=c1c2cnc(Nc3ccc4c(c3)CNCC4)nc2n(-c2ccc(Cl)cn2)n1C1CC1] |
| 1.593 | 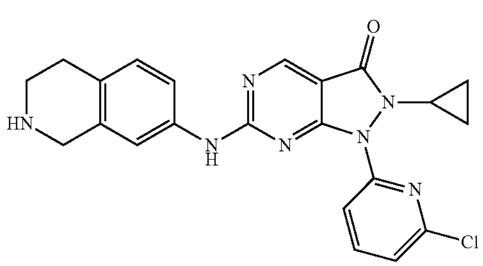 [SMILES: O=c1c2cnc(Nc3ccc4c(c3)CNCC4)nc2n(-c2cccc(Cl)n2)n1C1CC1] |
| 1.594 | |
| 1.595 | |
| 1.596 | |
| 1.597 | |
| 1.598 | |

TABLE 1A-continued

| Compound No. | Structure |
|---|---|
| 1.599 | 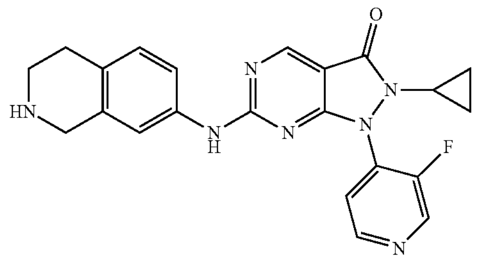 [SMILES: O=c1c2cnc(Nc3ccc4c(c3)CNCC4)nc2n(-c2ccncc2F)n1C1CC1] |
| 1.600 | 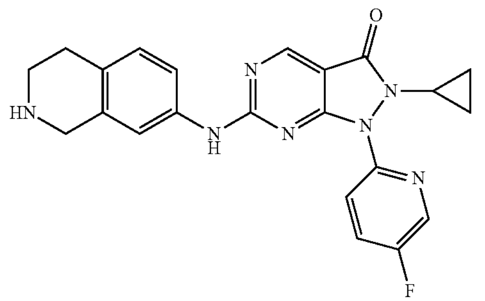 [SMILES: O=c1c2cnc(Nc3ccc4c(c3)CNCC4)nc2n(-c2ccc(F)cn2)n1C1CC1] |
| 1.601 | 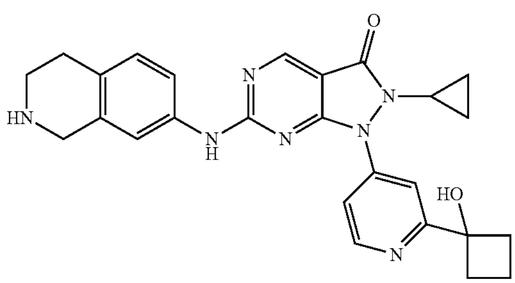 [SMILES: O=c1c2cnc(Nc3ccc4c(c3)CNCC4)nc2n(-c2ccnc(C3(O)CCC3)c2)n1C1CC1] |
| 1.602 | 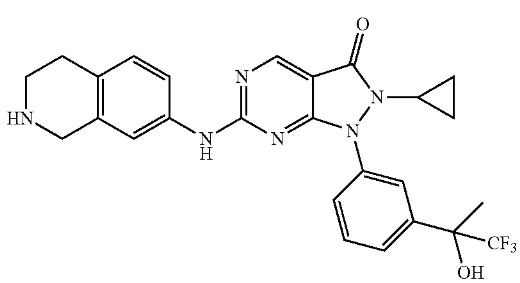 [SMILES: CC(O)(c1cccc(-n2c3nc(Nc4ccc5c(c4)CNCC5)ncc3c(=O)n2C2CC2)c1)C(F)(F)F] |
| 1.603 | 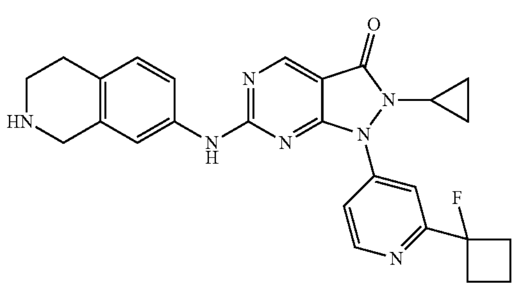 [SMILES: O=c1c2cnc(Nc3ccc4c(c3)CNCC4)nc2n(-c2ccnc(C3(F)CCC3)c2)n1C1CC1] |
| 1.604 | 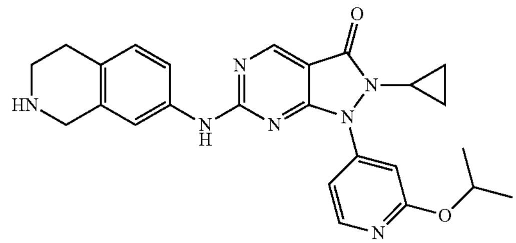 [SMILES: CC(C)Oc1cc(-n2c3nc(Nc4ccc5c(c4)CNCC5)ncc3c(=O)n2C2CC2)ccn1] |
| 1.605 | 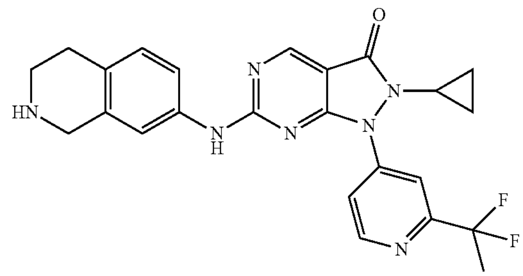 [SMILES: CC(F)(F)c1cc(-n2c3nc(Nc4ccc5c(c4)CNCC5)ncc3c(=O)n2C2CC2)ccn1] |
| 1.606 | 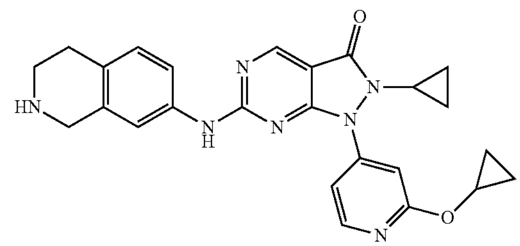 [SMILES: O=c1c2cnc(Nc3ccc4c(c3)CNCC4)nc2n(-c2ccnc(OC3CC3)c2)n1C1CC1] |
| 1.607 | 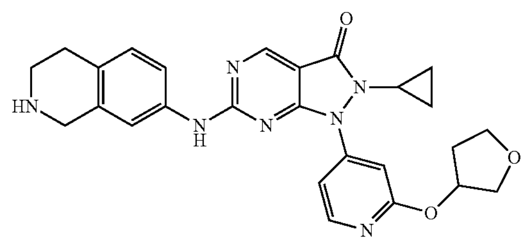 [SMILES: O=c1c2cnc(Nc3ccc4c(c3)CNCC4)nc2n(-c2ccnc(OC3CCOC3)c2)n1C1CC1] |
| 1.608 | 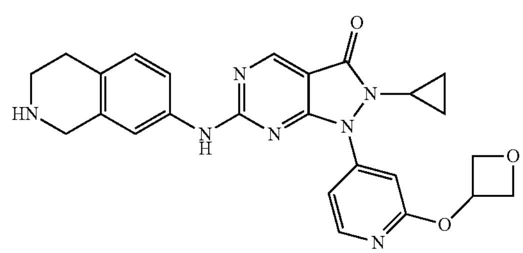 [SMILES: O=c1c2cnc(Nc3ccc4c(c3)CNCC4)nc2n(-c2ccnc(OC3COC3)c2)n1C1CC1] |
| 1.609 | 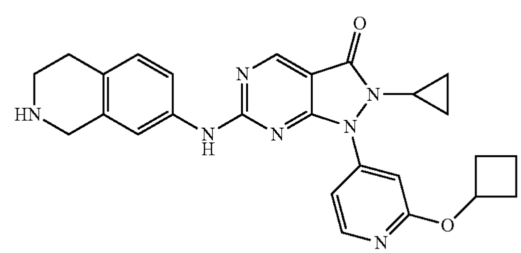 [SMILES: O=c1c2cnc(Nc3ccc4c(c3)CNCC4)nc2n(-c2ccnc(OC3CCC3)c2)n1C1CC1] |

TABLE 1A-continued

| Compound No. | Structure |
|---|---|
| 1.610 | 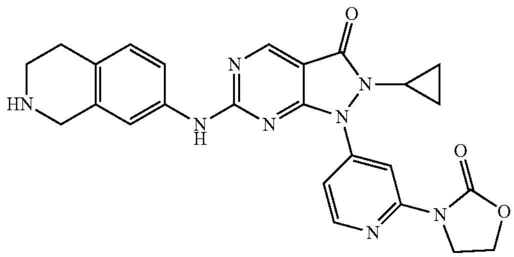 [SMILES: O=C1OCCN1c1cc(-n2c3nc(Nc4ccc5c(c4)CNCC5)ncc3c(=O)n2C2CC2)ccn1] |
| 1.611 | 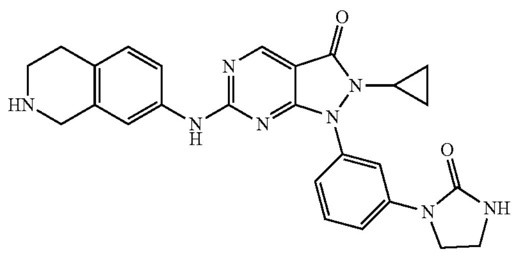 [SMILES: O=C1NCCN1c1cccc(-n2c3nc(Nc4ccc5c(c4)CNCC5)ncc3c(=O)n2C2CC2)c1] |
| 1.612 | 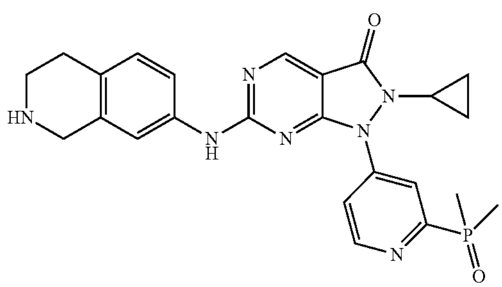 [SMILES: CP(C)(=O)c1cc(-n2c3nc(Nc4ccc5c(c4)CNCC5)ncc3c(=O)n2C2CC2)ccn1] |
| 1.613 | 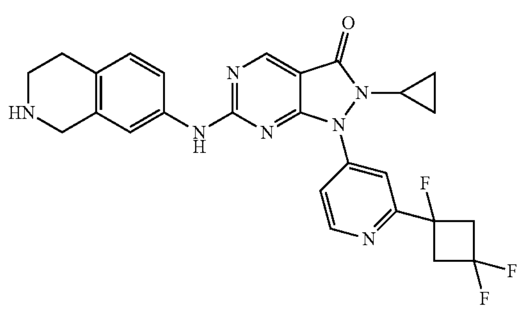 [SMILES: O=c1c2cnc(Nc3ccc4c(c3)CNCC4)nc2n(-c2ccnc(C3(F)CC(F)(F)C3)c2)n1C1CC1] |
| 1.614 | |//

TABLE 1A-continued

| Compound No. | Structure |
|---|---|
| 1.615 | 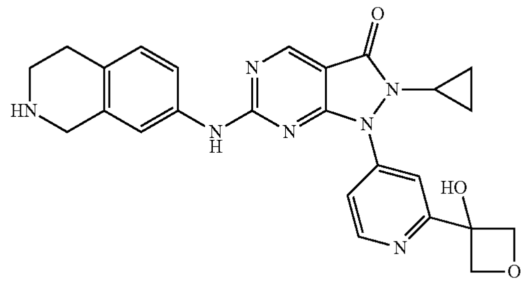 [SMILES: O=c1c2cnc(Nc3ccc4c(c3)CNCC4)nc2n(-c2ccnc(C3(O)COC3)c2)n1C1CC1] |
| 1.616 | 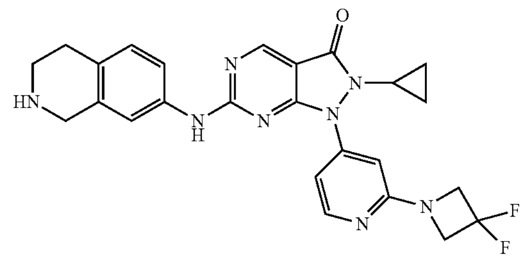 [SMILES: O=c1c2cnc(Nc3ccc4c(c3)CNCC4)nc2n(-c2ccnc(N3CC(F)(F)C3)c2)n1C1CC1] |
| 1.617 | 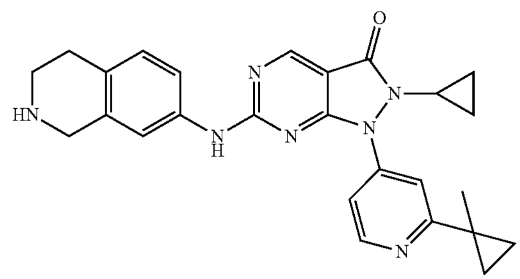 [SMILES: CC1(c2cc(-n3c4nc(Nc5ccc6c(c5)CNCC6)ncc4c(=O)n3C3CC3)ccn2)CC1] |
| 1.618 | 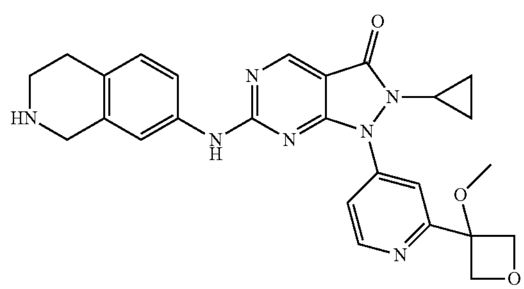 [SMILES: COC1(c2cc(-n3c4nc(Nc5ccc6c(c5)CNCC6)ncc4c(=O)n3C3CC3)ccn2)COC1] |
| 1.619 | 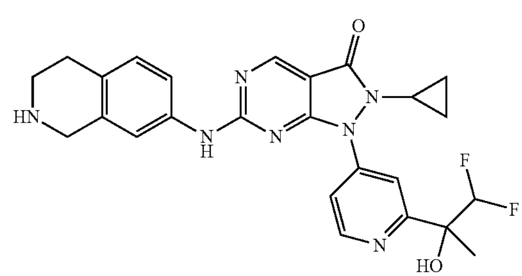 |

TABLE 1A-continued
| Compound No. | Structure |
|---|---|
| 1.620 | 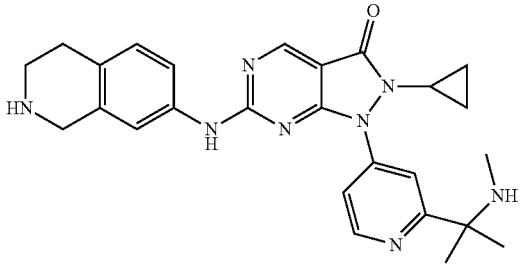 [SMILES: CNC(C)(C)c1cc(-n2c3nc(Nc4ccc5c(c4)CNCC5)ncc3c(=O)n2C2CC2)ccn1] |
| 1.621 | 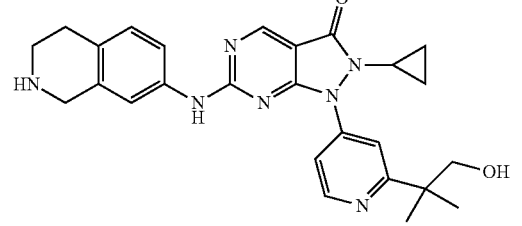 |
| 1.622 | 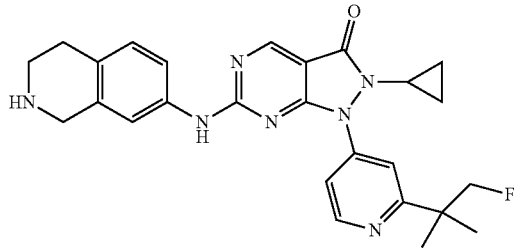 [SMILES: CC(C)(CF)c1cc(-n2c3nc(Nc4ccc5c(c4)CNCC5)ncc3c(=O)n2C2CC2)ccn1] |
| 1.623 | 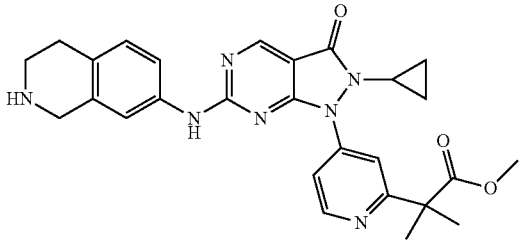 [SMILES: COC(=O)C(C)(C)c1cc(-n2c3nc(Nc4ccc5c(c4)CNCC5)ncc3c(=O)n2C2CC2)ccn1] |
| 1.624 | 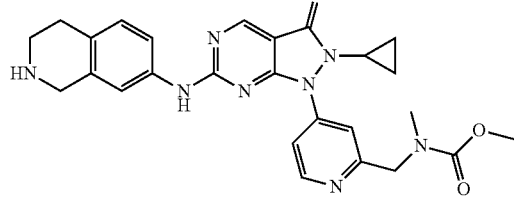 |
| 1.625 | 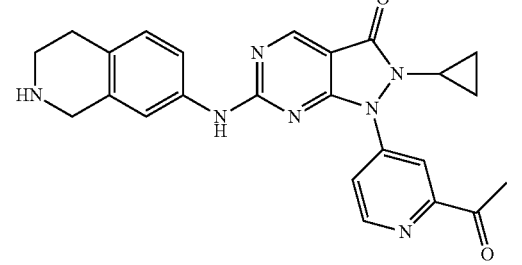 |
| 1.626 | 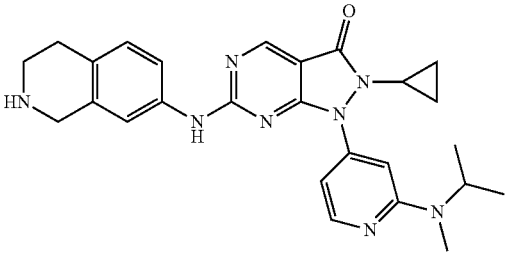 [SMILES: CC(C)N(C)c1cc(-n2c3nc(Nc4ccc5c(c4)CNCC5)ncc3c(=O)n2C2CC2)ccn1] |
| 1.627 | 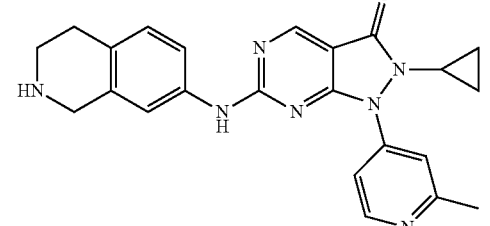 |
| 1.628 | 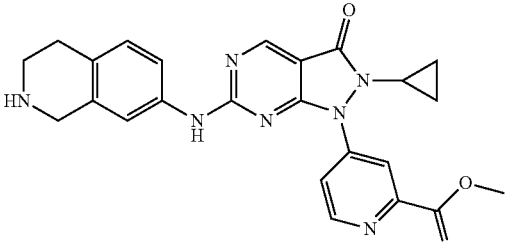 |
| 1.629 | 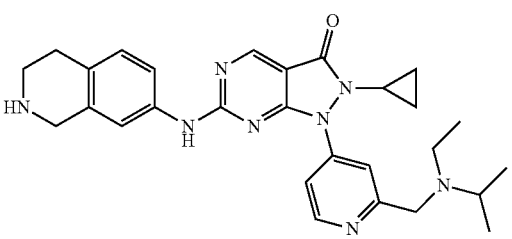 [SMILES: CCN(Cc1cc(-n2c3nc(Nc4ccc5c(c4)CNCC5)ncc3c(=O)n2C2CC2)ccn1)C(C)C] |
| 1.630 | 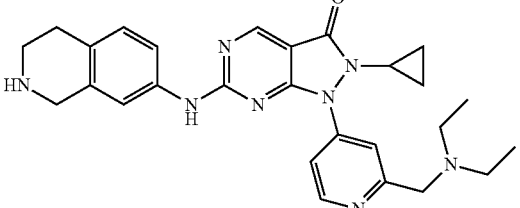 |
| 1.631 | 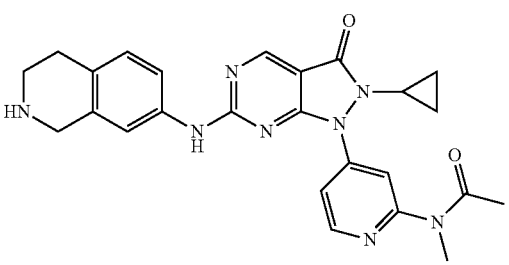 [SMILES: CC(=O)N(C)c1cc(-n2c3nc(Nc4ccc5c(c4)CNCC5)ncc3c(=O)n2C2CC2)ccn1] |

TABLE 1A-continued

| Compound No. | Structure |
|---|---|
| 1.632 | |
| 1.633 | |
| 1.634 | |
| 1.635 | |
| 1.636 | |
| 1.637 | 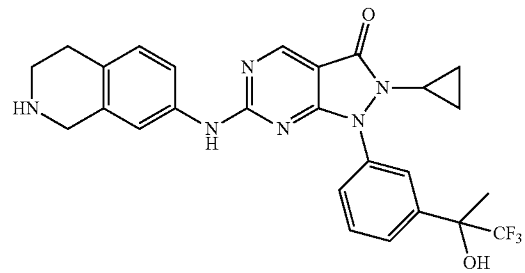 [SMILES: CC(O)(c1cccc(-n2c3nc(Nc4ccc5c(c4)CNCC5)ncc3c(=O)n2C2CC2)c1)C(F)(F)F] |
| 1.638 | 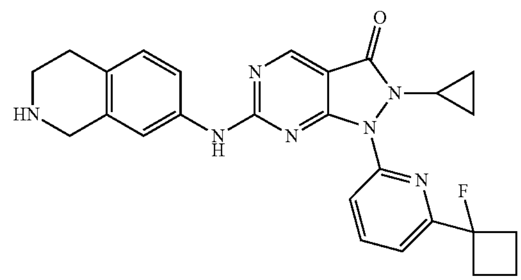 [SMILES: O=c1c2cnc(Nc3ccc4c(c3)CNCC4)nc2n(-c2cccc(C3(F)CCC3)n2)n1C1CC1] |
| 1.639 | 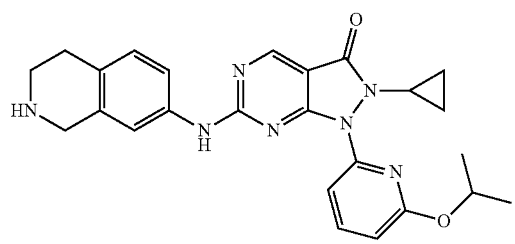 [SMILES: CC(C)Oc1cccc(-n2c3nc(Nc4ccc5c(c4)CNCC5)ncc3c(=O)n2C2CC2)n1] |
| 1.640 | 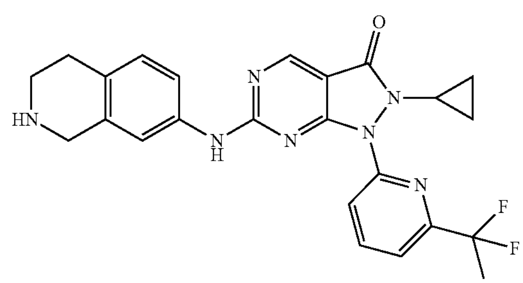 [SMILES: CC(F)(F)c1cccc(-n2c3nc(Nc4ccc5c(c4)CNCC5)ncc3c(=O)n2C2CC2)n1] |
| 1.641 | 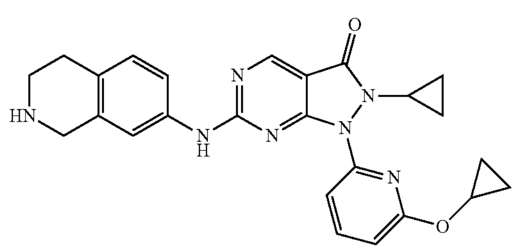 [SMILES: O=c1c2cnc(Nc3ccc4c(c3)CNCC4)nc2n(-c2cccc(OC3CC3)n2)n1C1CC1] |
| 1.642 | 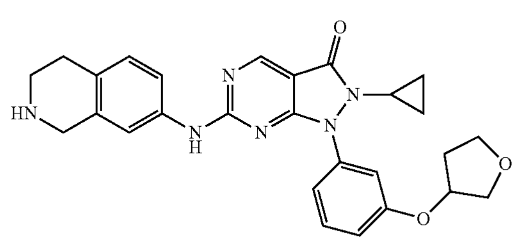 [SMILES: O=c1c2cnc(Nc3ccc4c(c3)CNCC4)nc2n(-c2cccc(OC3CCOC3)c2)n1C1CC1] |

TABLE 1A-continued

| Compound No. | Structure |
|---|---|
| 1.643 | 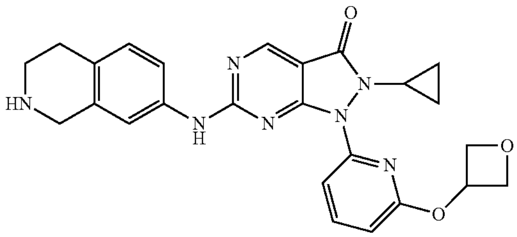 [SMILES: O=c1c2cnc(Nc3ccc4c(c3)CNCC4)nc2n(-c2cccc(OC3COC3)n2)n1C1CC1] |
| 1.644 | 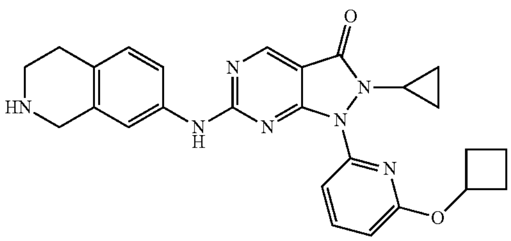 [SMILES: O=c1c2cnc(Nc3ccc4c(c3)CNCC4)nc2n(-c2cccc(OC3CCC3)n2)n1C1CC1] |
| 1.645 | 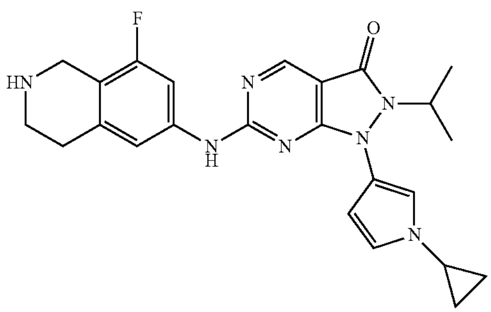 [SMILES: CC(C)n1c(=O)c2cnc(Nc3cc(F)c4c(c3)CCNC4)nc2n1-c1ccn(C2CC2)c1] |
| 1.646 | 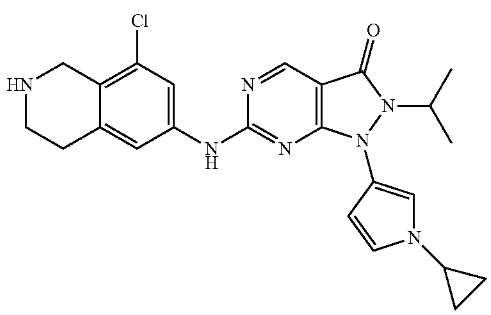 [SMILES: CC(C)n1c(=O)c2cnc(Nc3cc(Cl)c4c(c3)CCNC4)nc2n1-c1ccn(C2CC2)c1] |
| 1.647 | 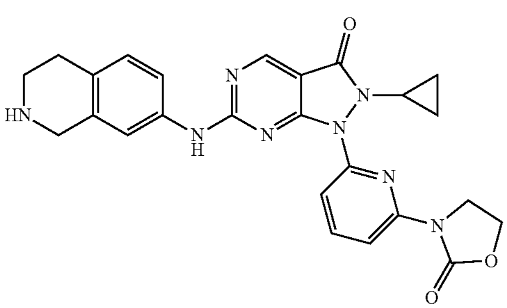 [SMILES: O=C1OCCN1c1cccc(-n2c3nc(Nc4ccc5c(c4)CNCC5)ncc3c(=O)n2C2CC2)n1] |
| 1.648 | |
| 1.649 | |
| 1.650 | |
| 1.651 | |
| 1.652 | |

TABLE 1A-continued

| Compound No. | Structure |
|---|---|
| 1.653 | |
| 1.654 | |
| 1.655 | |
| 1.656 | |
| 1.657 | |
| 1.658 | 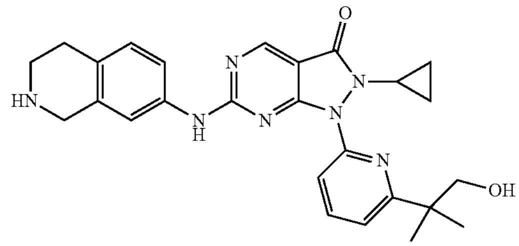 [SMILES: CC(C)(CO)c1cccc(-n2c3nc(Nc4ccc5c(c4)CNCC5)ncc3c(=O)n2C2CC2)n1] |
| 1.659 | 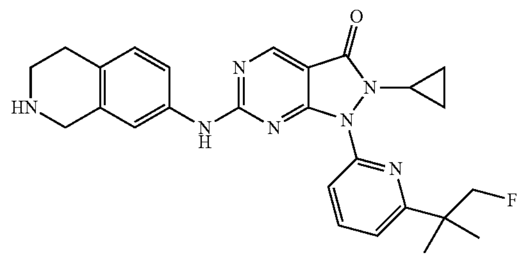 |
| 1.660 | 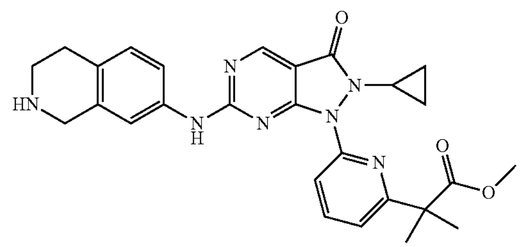 [SMILES: COC(=O)C(C)(C)c1cccc(-n2c3nc(Nc4ccc5c(c4)CNCC5)ncc3c(=O)n2C2CC2)n1] |
| 1.661 | 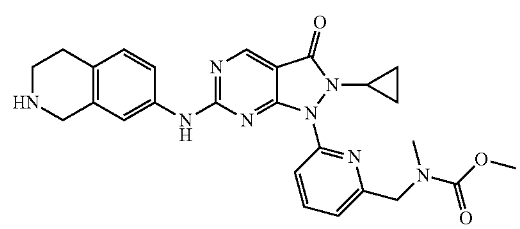 [SMILES: COC(=O)N(C)Cc1cccc(-n2c3nc(Nc4ccc5c(c4)CNCC5)ncc3c(=O)n2C2CC2)n1] |
| 1.662 | 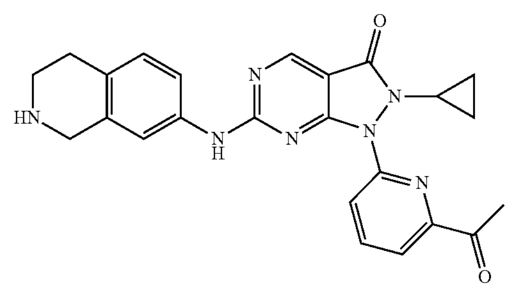 [SMILES: CC(=O)c1cccc(-n2c3nc(Nc4ccc5c(c4)CNCC5)ncc3c(=O)n2C2CC2)n1] |
| 1.663 | 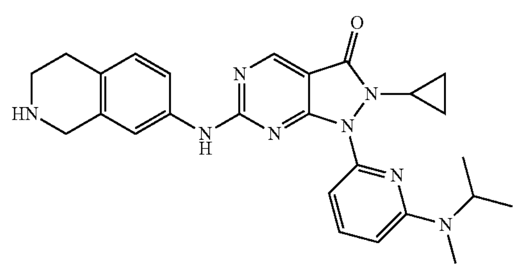 [SMILES: CC(C)N(C)c1cccc(-n2c3nc(Nc4ccc5c(c4)CNCC5)ncc3c(=O)n2C2CC2)n1] |

TABLE 1A-continued

| Compound No. | Structure |
|---|---|
| 1.664 | 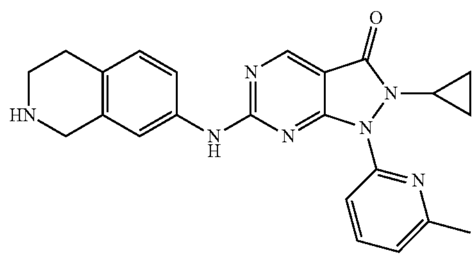 [SMILES: Cc1cccc(-n2c3nc(Nc4ccc5c(c4)CNCC5)ncc3c(=O)n2C2CC2)n1] |
| 1.665 | 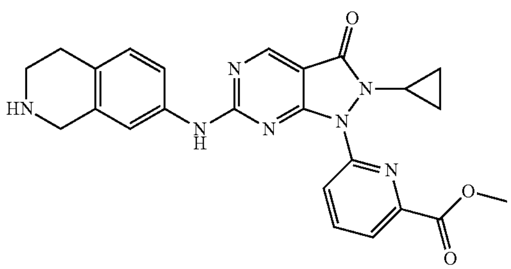 [SMILES: COC(=O)c1cccc(-n2c3nc(Nc4ccc5c(c4)CNCC5)ncc3c(=O)n2C2CC2)n1] |
| 1.666 | 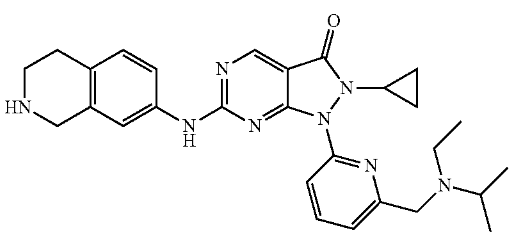 [SMILES: CCN(Cc1cccc(-n2c3nc(Nc4ccc5c(c4)CNCC5)ncc3c(=O)n2C2CC2)n1)C(C)C] |
| 1.667 | 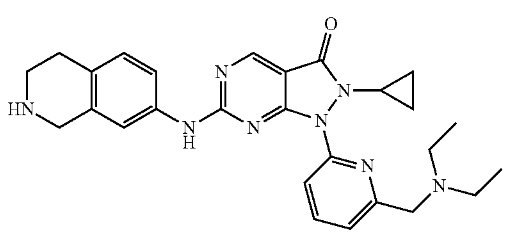 [SMILES: CCN(CC)Cc1cccc(-n2c3nc(Nc4ccc5c(c4)CNCC5)ncc3c(=O)n2C2CC2)n1] |
| 1.668 | 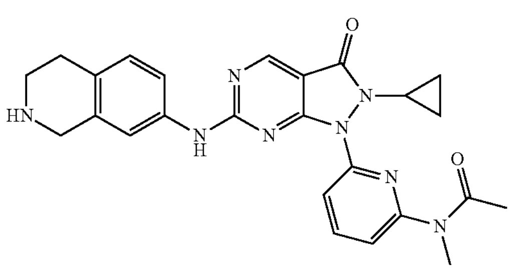 [SMILES: CC(=O)N(C)c1cccc(-n2c3nc(Nc4ccc5c(c4)CNCC5)ncc3c(=O)n2C2CC2)n1] |
| 1.669 | 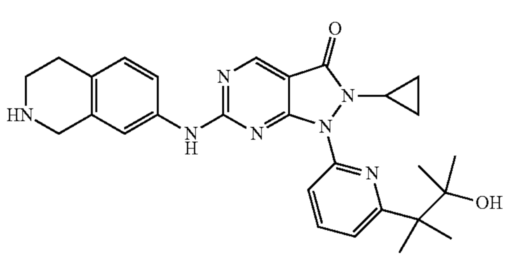 [SMILES: CC(C)(O)C(C)(C)c1cccc(-n2c3nc(Nc4ccc5c(c4)CNCC5)ncc3c(=O)n2C2CC2)n1] |
| 1.670 | |
| 1.671 | |
| 1.672 | |
| 1.673 | |
| 1.674 | |
| 1.675 | |

TABLE 1A-continued

| Compound No. | Structure |
| --- | --- |
| 1.676 | (structure) |
| 1.677 | (structure) |
| 1.678 | (structure) |
| 1.679 | (structure) |
| 1.680 | (structure) |
| 1.681 | (structure) |
| 1.682 | (structure) |
| 1.683 | (structure) |
| 1.684 | (structure) |
| 1.685 | (structure) |

TABLE 1A-continued

| Compound No. | Structure |
|---|---|
| 1.686 | 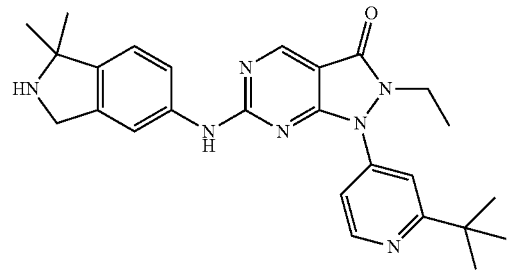 [SMILES: CCn1c(=O)c2cnc(Nc3ccc4c(c3)CNC4(C)C)nc2n1-c1ccnc(C(C)(C)C)c1] |
| 1.687 | 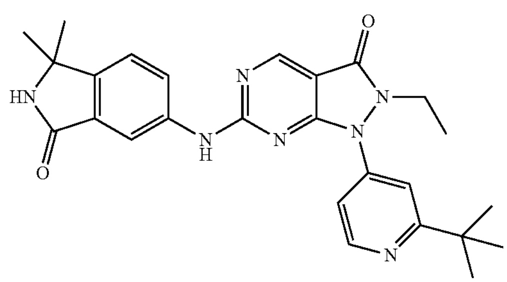 [SMILES: CCn1c(=O)c2cnc(Nc3ccc4c(c3)C(=O)NC4(C)C)nc2n1-c1ccnc(C(C)(C)C)c1] |
| 1.688 | 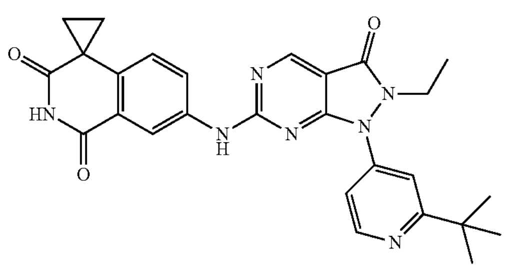 [SMILES: CCn1c(=O)c2cnc(Nc3ccc4c(c3)C(=O)NC(=O)C43CC3)nc2n1-c1ccnc(C(C)(C)C)c1] |
| 1.689 | 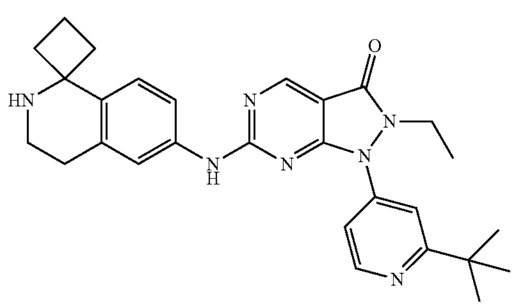 [SMILES: CCn1c(=O)c2cnc(Nc3ccc4c(c3)CCNC43CCC3)nc2n1-c1ccnc(C(C)(C)C)c1] |
| 1.690 | 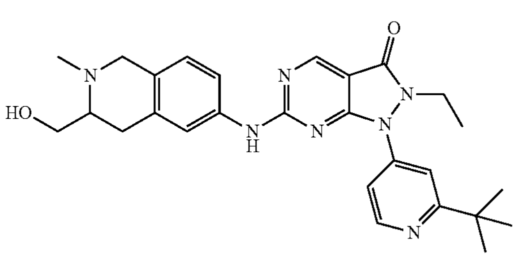 |

TABLE 1A-continued

| Compound No. | Structure |
|---|---|
| 1.691 | |
| 1.692 | |
| 1.693 | |
| 1.694 | |
| 1.695 | |

TABLE 1A-continued
| Compound No. | Structure |
|---|---|
| 1.696 | 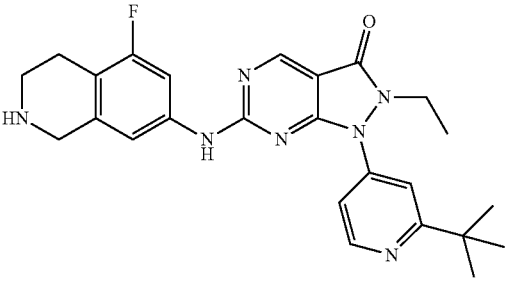 [SMILES: CCn1c(=O)c2cnc(Nc3cc(F)c4c(c3)CNCC4)nc2n1-c1ccnc(C(C)(C)C)c1] |
| 1.697 | 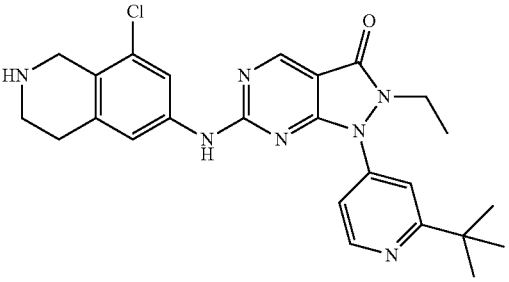 |
| 1.698 | 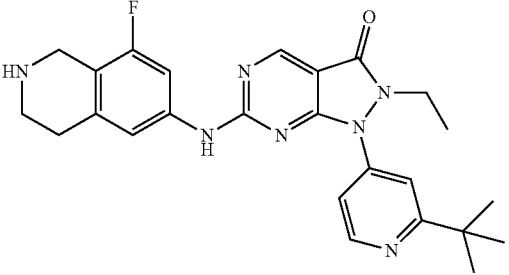 [SMILES: CCn1c(=O)c2cnc(Nc3cc(F)c4c(c3)CCNC4)nc2n1-c1ccnc(C(C)(C)C)c1] |
| 1.699 | 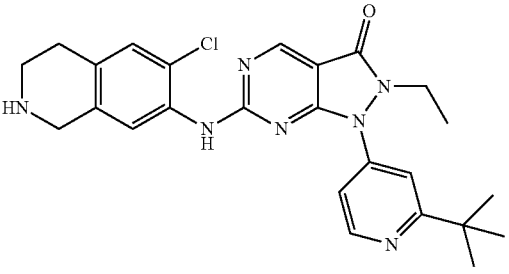 [SMILES: CCn1c(=O)c2cnc(Nc3cc4c(cc3Cl)CCNC4)nc2n1-c1ccnc(C(C)(C)C)c1] |
| 1.700 | 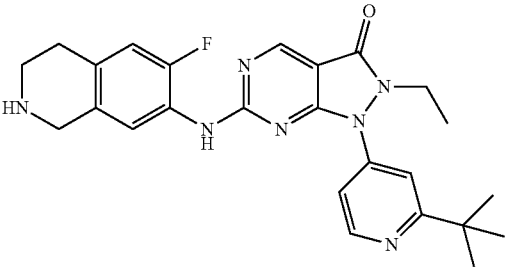 [SMILES: CCn1c(=O)c2cnc(Nc3cc4c(cc3F)CCNC4)nc2n1-c1ccnc(C(C)(C)C)c1] |
TABLE 1A-continued
| Compound No. | Structure |
|---|---|
| 1.701 | 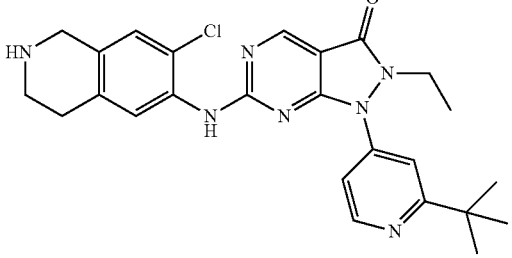 |
| 1.702 | 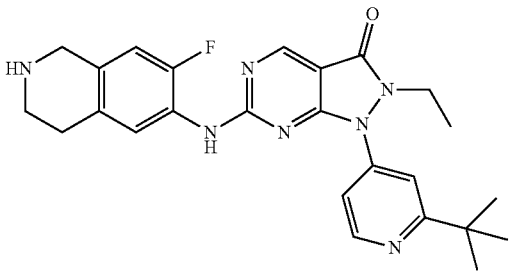 [SMILES: CCn1c(=O)c2cnc(Nc3cc4c(cc3Cl)CNCC4)nc2n1-c1ccnc(C(C)(C)C)c1] |
| 1.703 | 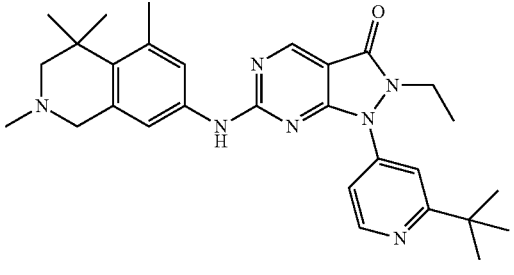 [SMILES: CCn1c(=O)c2cnc(Nc3cc(C)c4c(c3)CN(C)CC4(C)C)nc2n1-c1ccnc(C(C)(C)C)c1] |
| 1.704 | 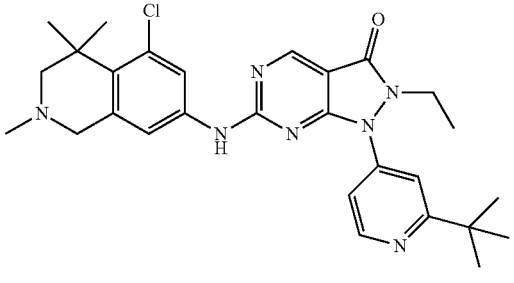 |
| 1.705 | 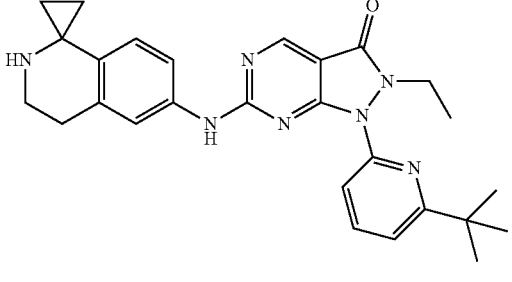 [SMILES: CCn1c(=O)c2cnc(Nc3ccc4c(c3)CCNC43CC3)nc2n1-c1cccc(C(C)(C)C)n1] |

TABLE 1A-continued

| Compound No. | Structure |
|---|---|
| 1.706 | 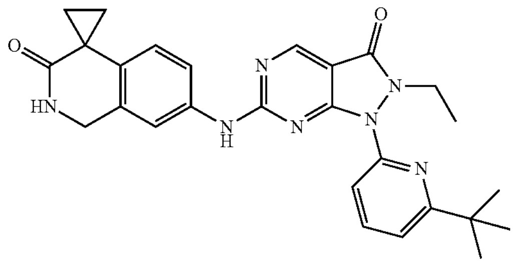 |
| 1.707 | 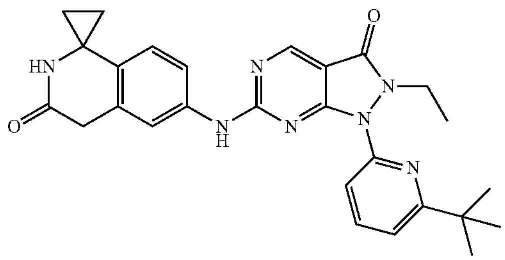 [SMILES: CCn1c(=O)c2cnc(Nc3ccc4c(c3)CC(=O)NC43CC3)nc2n1-c1cccc(C(C)(C)C)n1] |
| 1.708 | 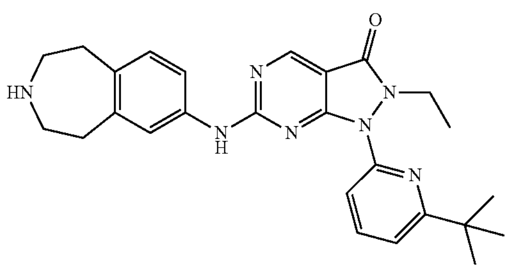 [SMILES: CCn1c(=O)c2cnc(Nc3ccc4c(c3)CCNCC4)nc2n1-c1cccc(C(C)(C)C)n1] |
| 1.709 | 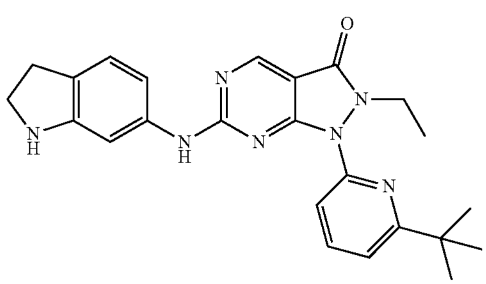 [SMILES: CCn1c(=O)c2cnc(Nc3ccc4c(c3)NCC4)nc2n1-c1cccc(C(C)(C)C)n1] |
| 1.710 | 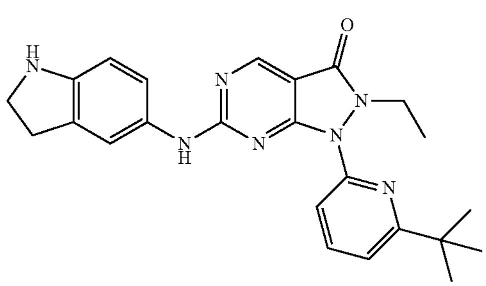 [SMILES: CCn1c(=O)c2cnc(Nc3ccc4c(c3)CCN4)nc2n1-c1cccc(C(C)(C)C)n1] |

TABLE 1A-continued

| Compound No. | Structure |
|---|---|
| 1.711 | 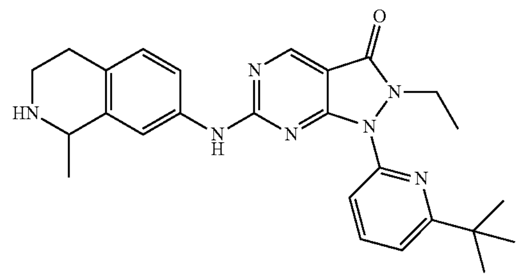 [SMILES: CCn1c(=O)c2cnc(Nc3ccc4c(c3)C(C)NCC4)nc2n1-c1cccc(C(C)(C)C)n1] |
| 1.712 | 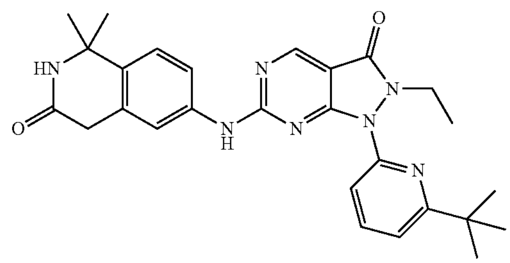 [SMILES: CCn1c(=O)c2cnc(Nc3ccc4c(c3)CC(=O)NC4(C)C)nc2n1-c1cccc(C(C)(C)C)n1] |
| 1.713 | 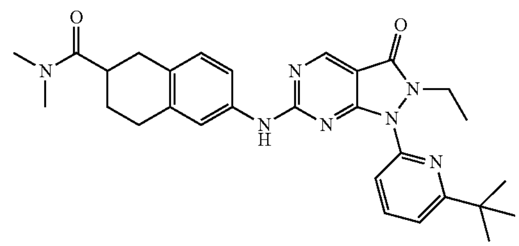 [SMILES: CCn1c(=O)c2cnc(Nc3ccc4c(c3)CCC(C(=O)N(C)C)C4)nc2n1-c1cccc(C(C)(C)C)n1] |
| 1.714 | 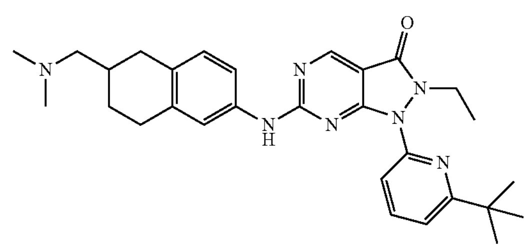 [SMILES: CCn1c(=O)c2cnc(Nc3ccc4c(c3)CCC(CN(C)C)C4)nc2n1-c1cccc(C(C)(C)C)n1] |
| 1.715 | 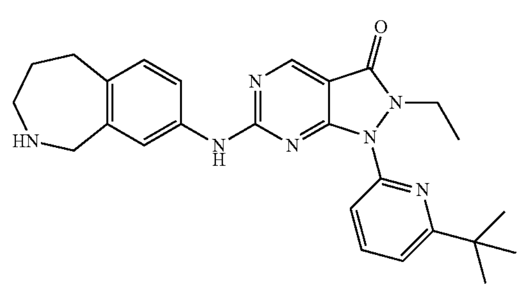 [SMILES: CCn1c(=O)c2cnc(Nc3ccc4c(c3)CNCCC4)nc2n1-c1cccc(C(C)(C)C)n1] |

TABLE 1A-continued

| Compound No. | Structure |
|---|---|
| 1.716 | 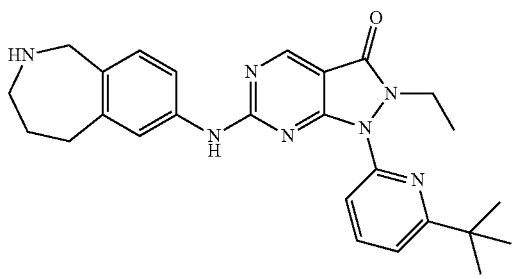 [SMILES: CCn1c(=O)c2cnc(Nc3ccc4c(c3)CCCNC4)nc2n1-c1cccc(C(C)(C)C)n1] |
| 1.717 | 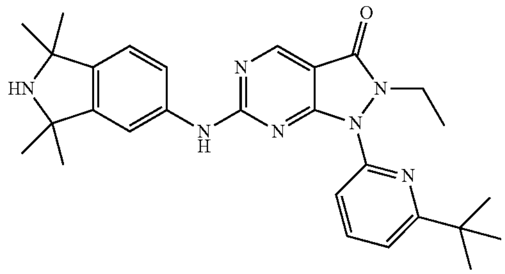 |
| 1.718 | 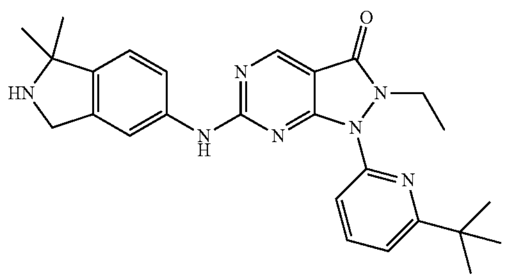 [SMILES: CCn1c(=O)c2cnc(Nc3ccc4c(c3)CNC4(C)C)nc2n1-c1cccc(C(C)(C)C)n1] |
| 1.719 | 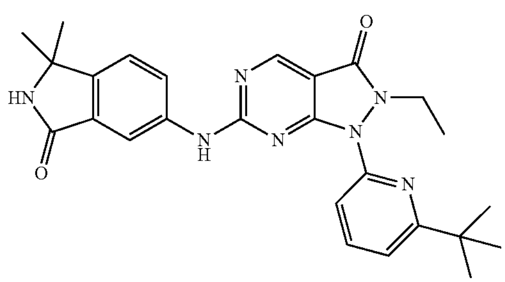 [SMILES: CCn1c(=O)c2cnc(Nc3ccc4c(c3)C(=O)NC4(C)C)nc2n1-c1cccc(C(C)(C)C)n1] |
| 1.720 | 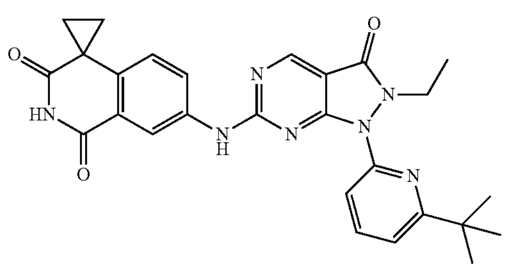 |
| 1.721 | |
| 1.722 | |
| 1.723 | |
| 1.724 | |
| 1.725 | |

TABLE 1A-continued
| Compound No. | Structure |
|---|---|
| 1.726 | 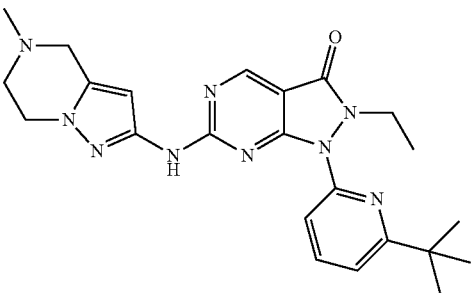 [SMILES: CCn1c(=O)c2cnc(Nc3cc4n(n3)CCN(C)C4)nc2n1-c1cccc(C(C)(C)C)n1] |
| 1.727 | 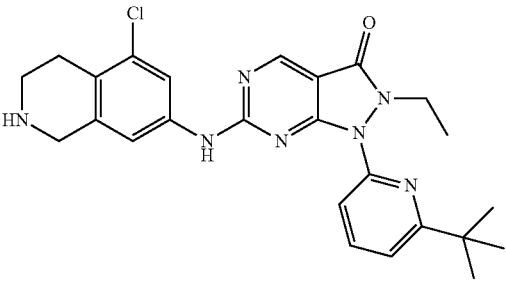 |
| 1.728 | 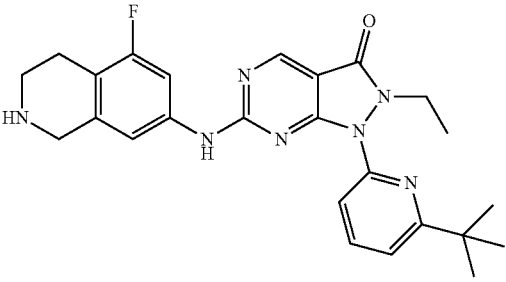 [SMILES: CCn1c(=O)c2cnc(Nc3cc(F)c4c(c3)CNCC4)nc2n1-c1cccc(C(C)(C)C)n1] |
| 1.729 | 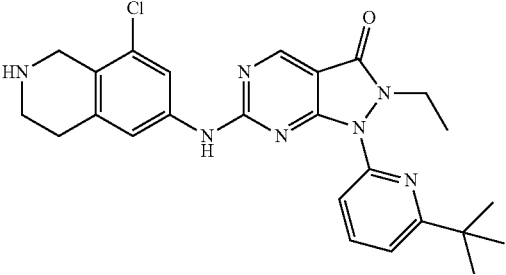 [SMILES: CCn1c(=O)c2cnc(Nc3cc(Cl)c4c(c3)CCNC4)nc2n1-c1cccc(C(C)(C)C)n1] |
| 1.730 | 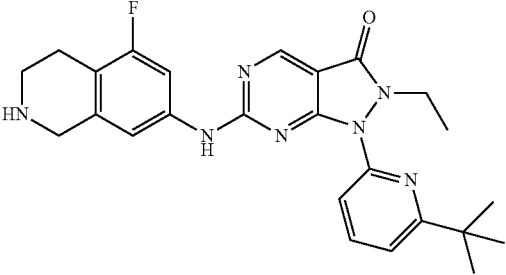 [SMILES: CCn1c(=O)c2cnc(Nc3cc(F)c4c(c3)CNCC4)nc2n1-c1cccc(C(C)(C)C)n1] |
| 1.731 | 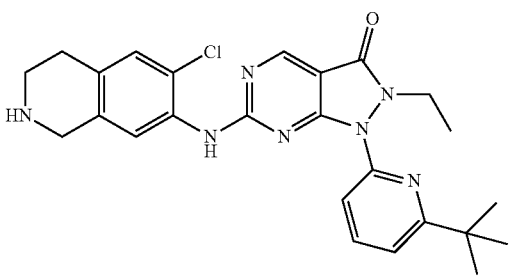 [SMILES: CCn1c(=O)c2cnc(Nc3cc4c(cc3Cl)CCNC4)nc2n1-c1cccc(C(C)(C)C)n1] |
| 1.732 | 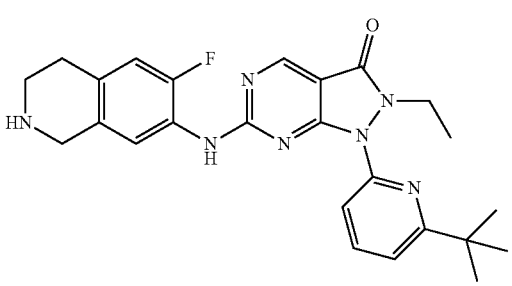 [SMILES: CCn1c(=O)c2cnc(Nc3cc4c(cc3F)CCNC4)nc2n1-c1cccc(C(C)(C)C)n1] |
| 1.733 | 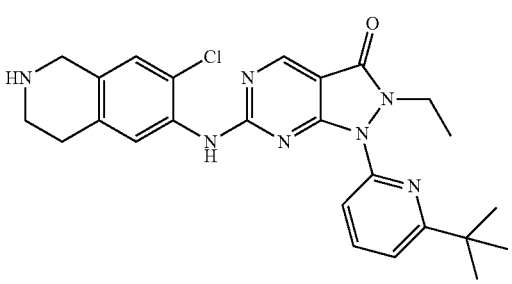 [SMILES: CCn1c(=O)c2cnc(Nc3cc4c(cc3F)CNCC4)nc2n1-c1cccc(C(C)(C)C)n1] |
| 1.734 | 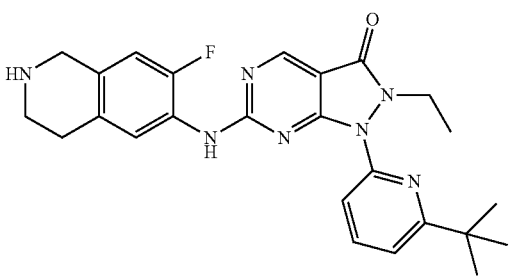 |
| 1.735 | 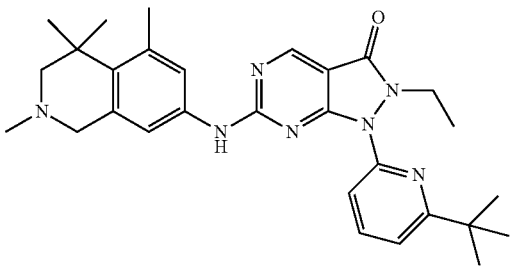 [SMILES: CCn1c(=O)c2cnc(Nc3cc(C)c4c(c3)CN(C)CC4(C)C)nc2n1-c1cccc(C(C)(C)C)n1] |

TABLE 1A-continued

| Compound No. | Structure |
|---|---|
| 1.736 | 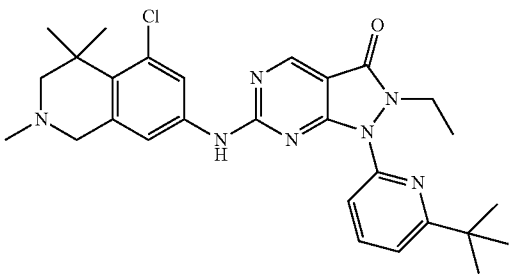 [SMILES: CCn1c(=O)c2cnc(Nc3cc(Cl)c4c(c3)CN(C)CC4(C)C)nc2n1-c1cccc(C(C)(C)C)n1] |
| 1.737 | 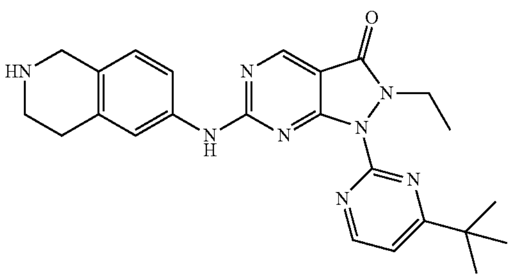 [SMILES: CCn1c(=O)c2cnc(Nc3ccc4c(c3)CCNC4)nc2n1-c1nccc(C(C)(C)C)n1] |
| 1.738 | 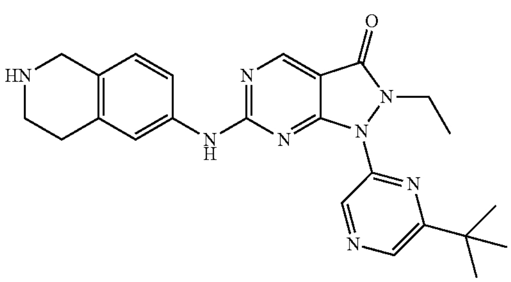 [SMILES: CCn1c(=O)c2cnc(Nc3ccc4c(c3)CCNC4)nc2n1-c1cncc(C(C)(C)C)n1] |
| 1.739 | 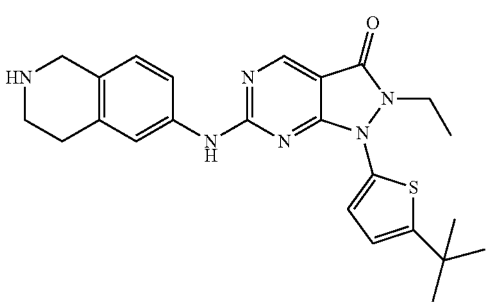 [SMILES: CCn1c(=O)c2cnc(Nc3ccc4c(c3)CCNC4)nc2n1-c1ccc(C(C)(C)C)s1] |
| 1.740 | 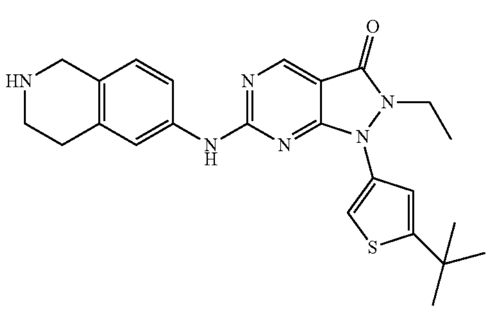 [SMILES: CCn1c(=O)c2cnc(Nc3ccc4c(c3)CCNC4)nc2n1-c1csc(C(C)(C)C)c1] |
| 1.741 | |
| 1.742 | |
| 1.743 | |
| 1.744 | |
| 1.745 | |

TABLE 1A-continued

| Compound No. | Structure |
|---|---|
| 1.746 | 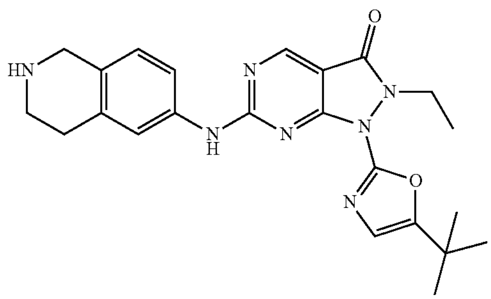 [SMILES: CCn1c(=O)c2cnc(Nc3ccc4c(c3)CCNC4)nc2n1-c1ncc(C(C)(C)C)o1] |
| 1.747 | 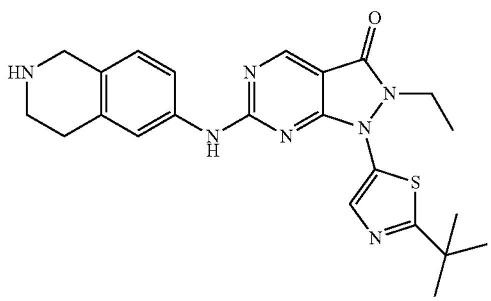 [SMILES: CCn1c(=O)c2cnc(Nc3ccc4c(c3)CCNC4)nc2n1-c1cnc(C(C)(C)C)s1] |
| 1.748 | 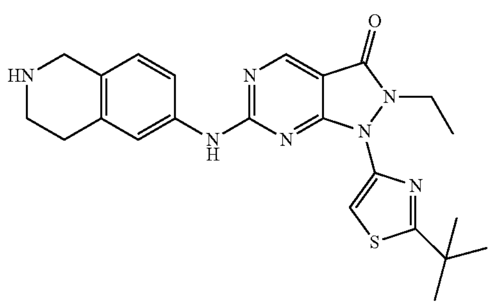 [SMILES: CCn1c(=O)c2cnc(Nc3ccc4c(c3)CCNC4)nc2n1-c1csc(C(C)(C)C)n1] |
| 1.749 | 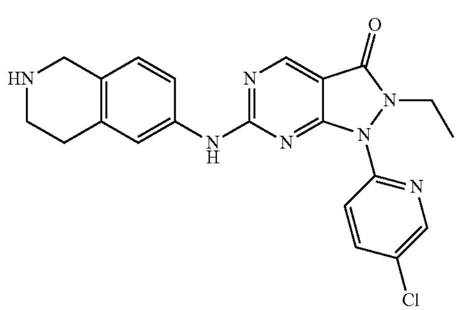 [SMILES: CCn1c(=O)c2cnc(Nc3ccc4c(c3)CCNC4)nc2n1-c1ccc(Cl)cn1] |
| 1.750 | 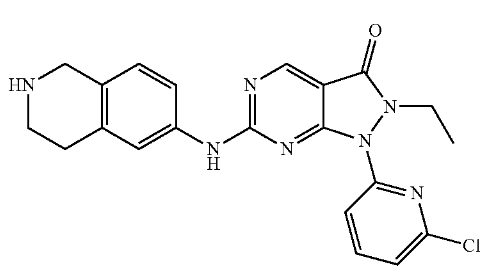 [SMILES: CCn1c(=O)c2cnc(Nc3ccc4c(c3)CCNC4)nc2n1-c1cccc(Cl)n1] |
| 1.751 | |
| 1.752 | |
| 1.753 | |
| 1.754 | |
| 1.755 | |

TABLE 1A-continued

| Compound No. | Structure |
|---|---|
| 1.756 | |
| 1.757 | |
| 1.758 | |
| 1.759 | |
| 1.760 | |
| 1.761 | 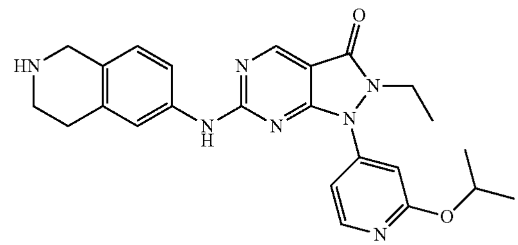 [SMILES: CCn1c(=O)c2cnc(Nc3ccc4c(c3)CCNC4)nc2n1-c1ccnc(OC(C)C)c1] |
| 1.762 | 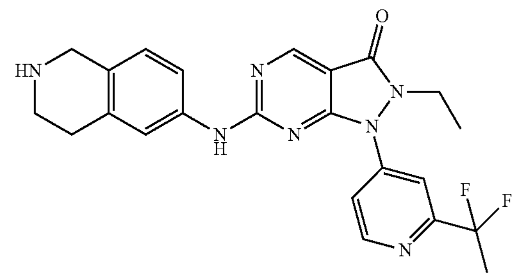 [SMILES: CCn1c(=O)c2cnc(Nc3ccc4c(c3)CCNC4)nc2n1-c1ccnc(C(C)(F)F)c1] |
| 1.763 | 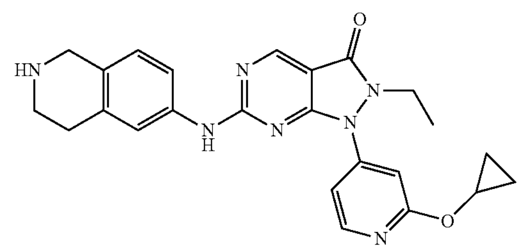 [SMILES: CCn1c(=O)c2cnc(Nc3ccc4c(c3)CCNC4)nc2n1-c1ccnc(OC2CC2)c1] |
| 1.764 | 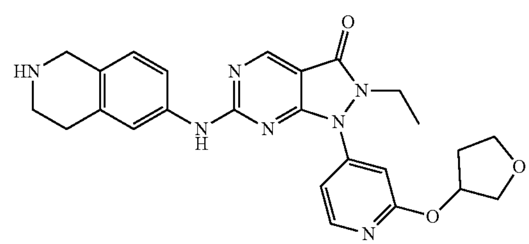 [SMILES: CCn1c(=O)c2cnc(Nc3ccc4c(c3)CCNC4)nc2n1-c1ccnc(OC2CCOC2)c1] |
| 1.765 | 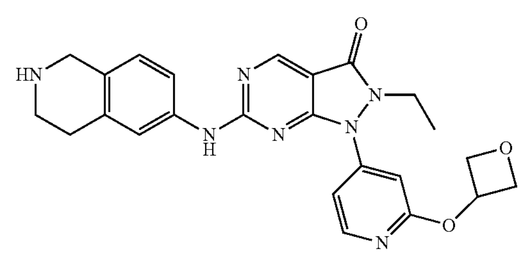 [SMILES: CCn1c(=O)c2cnc(Nc3ccc4c(c3)CCNC4)nc2n1-c1ccnc(OC2COC2)c1] |
| 1.766 | 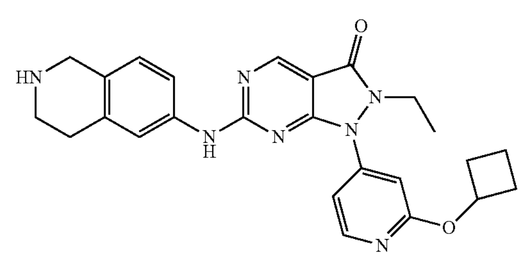 [SMILES: CCn1c(=O)c2cnc(Nc3ccc4c(c3)CCNC4)nc2n1-c1ccnc(OC2CCC2)c1] |

TABLE 1A-continued

| Compound No. | Structure |
|---|---|
| 1.767 | 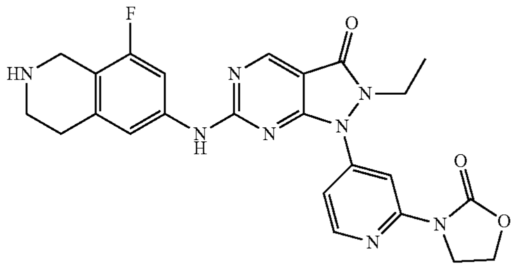 [SMILES: CCn1c(=O)c2cnc(Nc3cc(F)c4c(c3)CCNC4)nc2n1-c1ccnc(N2CCOC2=O)c1] |
| 1.768 | 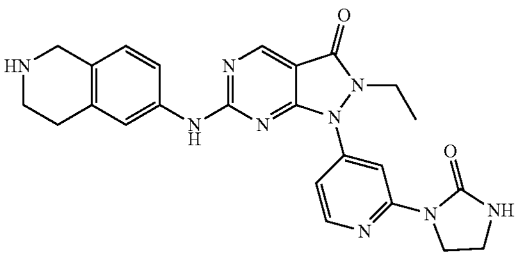 [SMILES: CCn1c(=O)c2cnc(Nc3ccc4c(c3)CCNC4)nc2n1-c1ccnc(N2CCNC2=O)c1] |
| 1.769 | 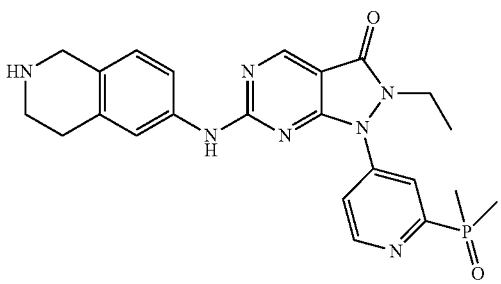 [SMILES: CCn1c(=O)c2cnc(Nc3ccc4c(c3)CCNC4)nc2n1-c1ccnc(P(C)(C)=O)c1] |
| 1.770 | 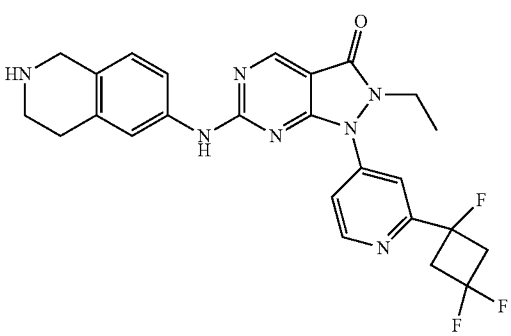 [SMILES: CCn1c(=O)c2cnc(Nc3ccc4c(c3)CCNC4)nc2n1-c1ccnc(C2(F)CC(F)(F)C2)c1] |
| 1.771 | 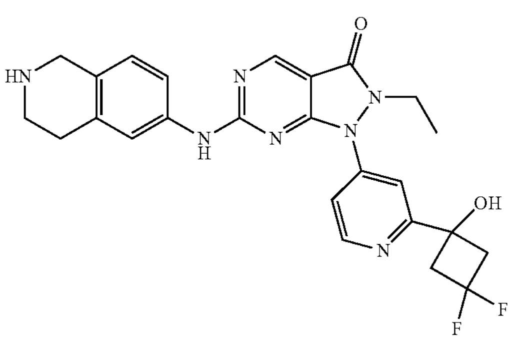 [SMILES: CCn1c(=O)c2cnc(Nc3ccc4c(c3)CCNC4)nc2n1-c1ccnc(C2(O)CC(F)(F)C2)c1] |
| 1.772 | |
| 1.773 | |
| 1.774 | |
| 1.775 | |
| 1.776 | |

TABLE 1A-continued

| Compound No. | Structure |
|---|---|
| 1.777 | 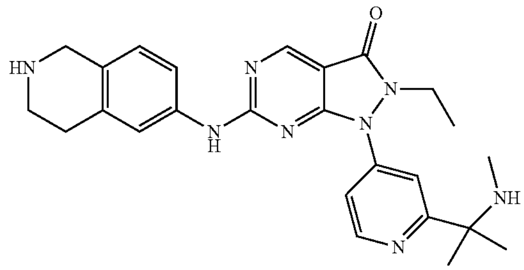 |
| 1.778 | 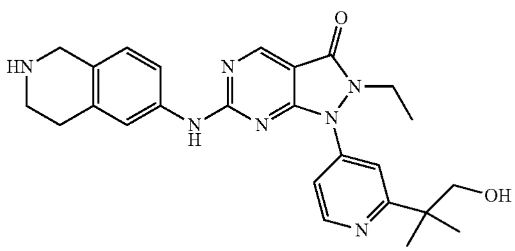 [SMILES: CCn1c(=O)c2cnc(Nc3ccc4c(c3)CCNC4)nc2n1-c1ccnc(C(C)(C)CO)c1] |
| 1.779 | 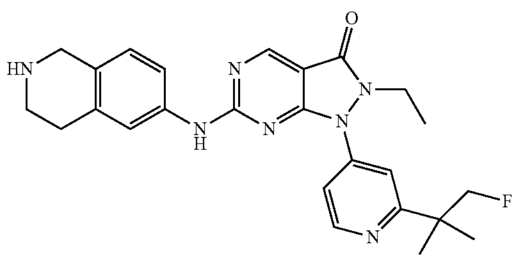 [SMILES: CCn1c(=O)c2cnc(Nc3ccc4c(c3)CCNC4)nc2n1-c1ccnc(C(C)(C)CF)c1] |
| 1.780 | 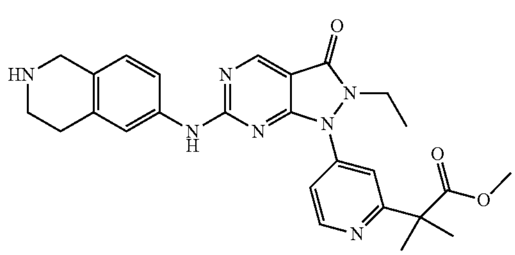 [SMILES: CCn1c(=O)c2cnc(Nc3ccc4c(c3)CCNC4)nc2n1-c1ccnc(C(C)(C)C(=O)OC)c1] |
| 1.781 | 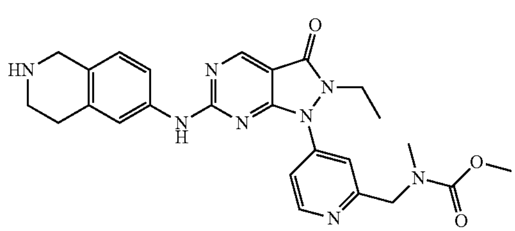 [SMILES: CCn1c(=O)c2cnc(Nc3ccc4c(c3)CCNC4)nc2n1-c1ccnc(CN(C)C(=O)OC)c1] |
| 1.782 | 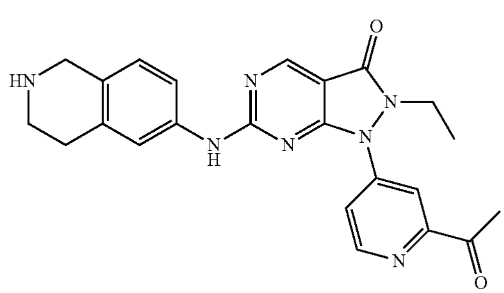 [SMILES: CCn1c(=O)c2cnc(Nc3ccc4c(c3)CCNC4)nc2n1-c1ccnc(C(C)=O)c1] |
| 1.783 | |
| 1.784 | |
| 1.785 | |
| 1.786 | |
| 1.787 | |
| 1.788 | |

TABLE 1A-continued

| Compound No. | Structure |
|---|---|
| 1.789 | 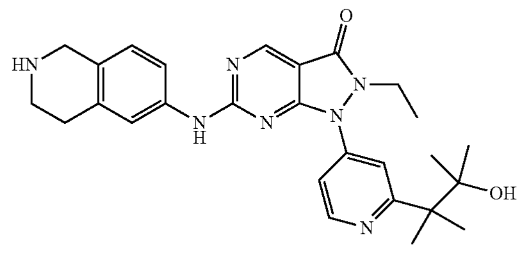 [SMILES: CCn1c(=O)c2cnc(Nc3ccc4c(c3)CCNC4)nc2n1-c1ccnc(C(C)(C)C(C)(C)O)c1] |
| 1.790 | 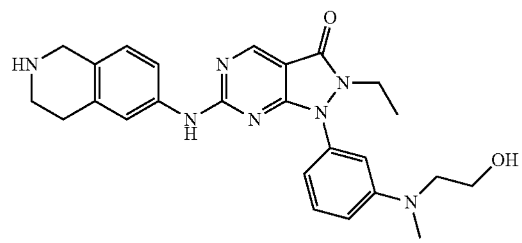 [SMILES: CCn1c(=O)c2cnc(Nc3ccc4c(c3)CCNC4)nc2n1-c1cccc(N(C)CCO)c1] |
| 1.791 | 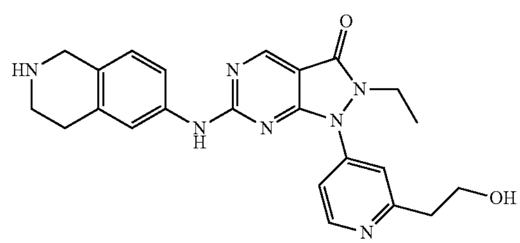 [SMILES: CCn1c(=O)c2cnc(Nc3ccc4c(c3)CCNC4)nc2n1-c1ccnc(CCO)c1] |
| 1.792 | 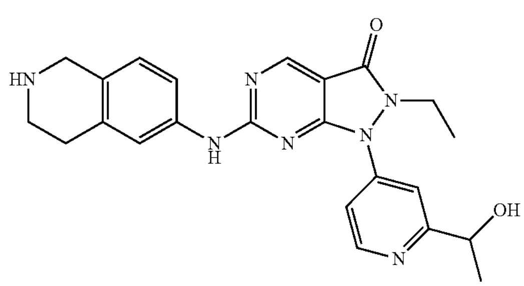 [SMILES: CCn1c(=O)c2cnc(Nc3ccc4c(c3)CCNC4)nc2n1-c1ccnc(C(C)O)c1] |
| 1.793 | 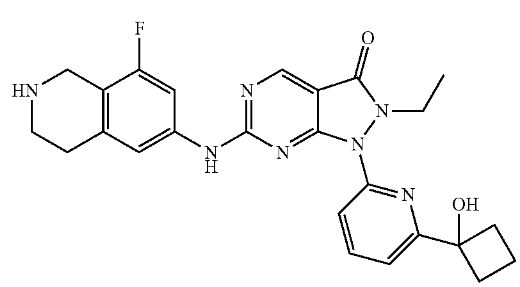 [SMILES: CCn1c(=O)c2cnc(Nc3cc(F)c4c(c3)CCNC4)nc2n1-c1cccc(C2(O)CCC2)n1] |
| 1.794 | 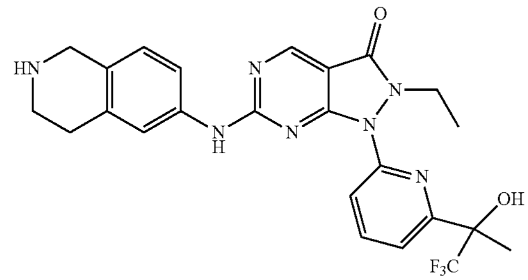 |
| 1.795 | 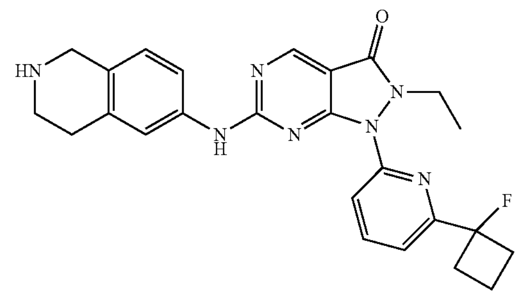 [SMILES: CCn1c(=O)c2cnc(Nc3ccc4c(c3)CCNC4)nc2n1-c1cccc(C2(F)CCC2)n1] |
| 1.796 | 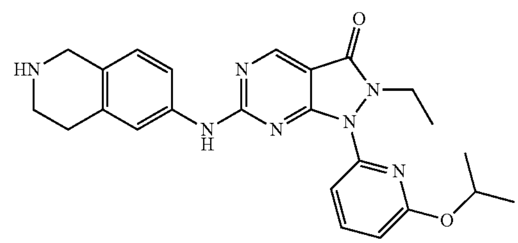 [SMILES: CCn1c(=O)c2cnc(Nc3ccc4c(c3)CCNC4)nc2n1-c1cccc(OC(C)C)n1] |
| 1.797 | 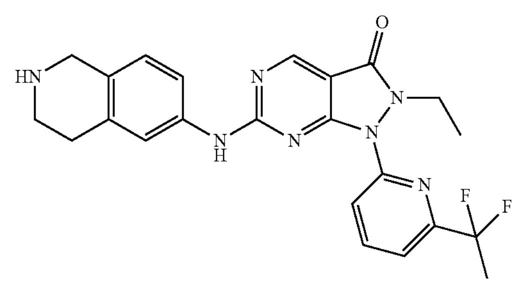 [SMILES: CCn1c(=O)c2cnc(Nc3ccc4c(c3)CCNC4)nc2n1-c1cccc(C(C)(F)F)n1] |
| 1.798 | 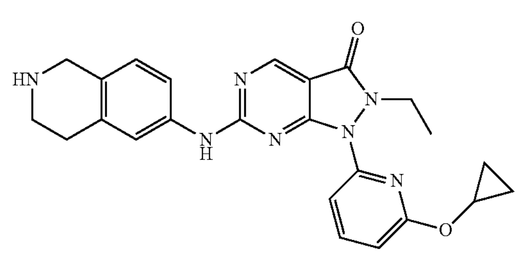 [SMILES: CCn1c(=O)c2cnc(Nc3ccc4c(c3)CCNC4)nc2n1-c1cccc(OC2CC2)n1] |

TABLE 1A-continued

| Compound No. | Structure |
|---|---|
| 1.799 | 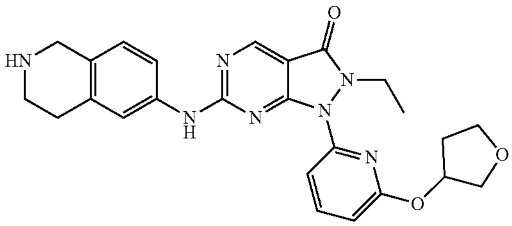 [SMILES: CCn1c(=O)c2cnc(Nc3ccc4c(c3)CCNC4)nc2n1-c1cccc(OC2CCOC2)n1] |
| 1.800 | 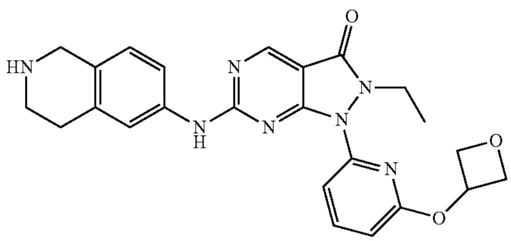 [SMILES: CCn1c(=O)c2cnc(Nc3ccc4c(c3)CCNC4)nc2n1-c1cccc(OC2COC2)n1] |
| 1.801 | 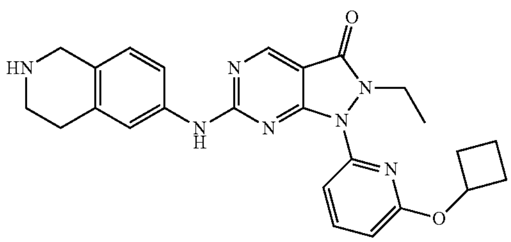 [SMILES: CCn1c(=O)c2cnc(Nc3ccc4c(c3)CCNC4)nc2n1-c1cccc(OC2CCC2)n1] |
| 1.802 | 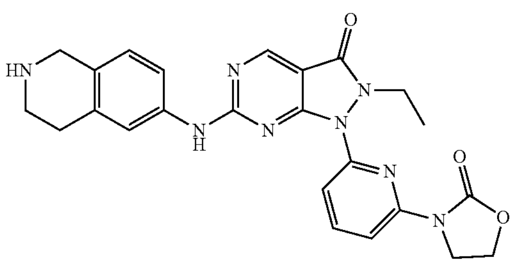 [SMILES: CCn1c(=O)c2cnc(Nc3ccc4c(c3)CCNC4)nc2n1-c1cccc(N2CCOC2=O)n1] |
| 1.803 | 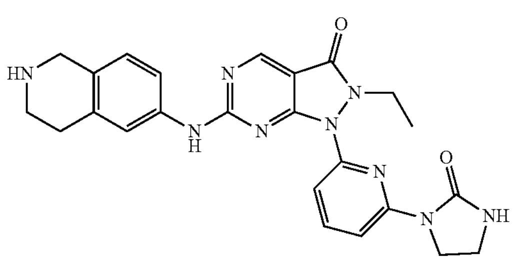 [SMILES: CCn1c(=O)c2cnc(Nc3ccc4c(c3)CCNC4)nc2n1-c1cccc(N2CCNC2=O)n1] |
| 1.804 | 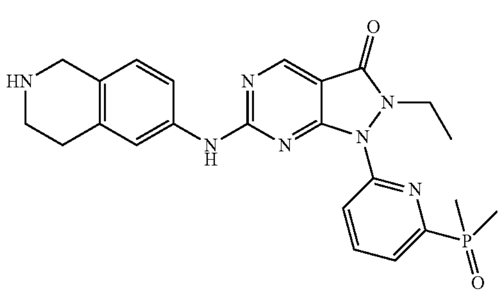 [SMILES: CCn1c(=O)c2cnc(Nc3ccc4c(c3)CCNC4)nc2n1-c1cccc(P(C)(C)=O)n1] |

TABLE 1A-continued

| Compound No. | Structure |
|---|---|
| 1.805 | |
| 1.806 | |
| 1.807 | |
| 1.808 | |
| 1.809 | |

TABLE 1A-continued

| Compound No. | Structure |
|---|---|
| 1.810 | |
| 1.811 | |
| 1.812 | |
| 1.813 | |
| 1.814 | |
| 1.815 | 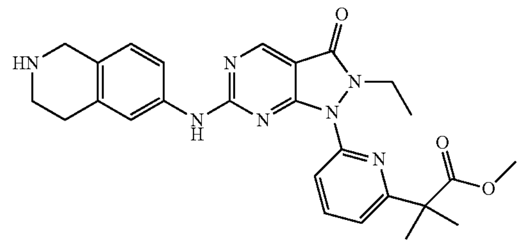 [SMILES: CCn1c(=O)c2cnc(Nc3ccc4c(c3)CCNC4)nc2n1-c1cccc(C(C)(C)C(=O)OC)n1] |
| 1.816 | 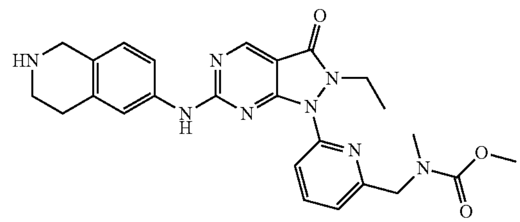 [SMILES: CCn1c(=O)c2cnc(Nc3ccc4c(c3)CCNC4)nc2n1-c1cccc(CN(C)C(=O)OC)n1] |
| 1.817 | 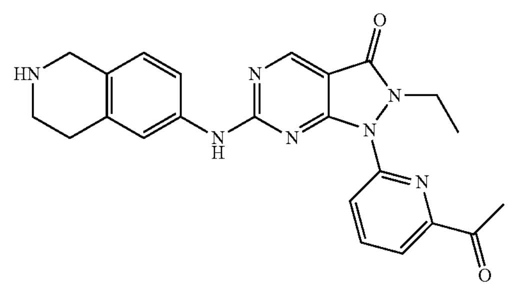 [SMILES: CCn1c(=O)c2cnc(Nc3ccc4c(c3)CCNC4)nc2n1-c1cccc(C(C)=O)n1] |
| 1.818 | 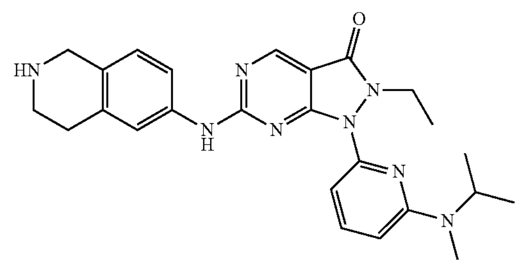 [SMILES: CCn1c(=O)c2cnc(Nc3ccc4c(c3)CCNC4)nc2n1-c1cccc(N(C)C(C)C)n1] |
| 1.819 | 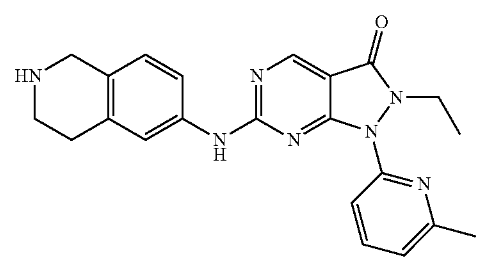 [SMILES: CCn1c(=O)c2cnc(Nc3ccc4c(c3)CCNC4)nc2n1-c1cccc(C)n1] |
| 1.820 | 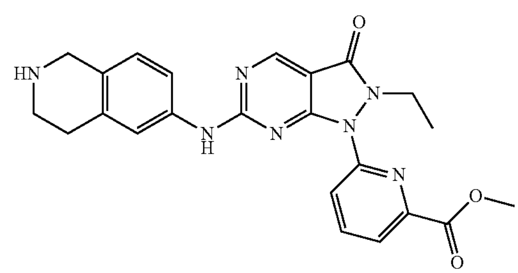 [SMILES: CCn1c(=O)c2cnc(Nc3ccc4c(c3)CCNC4)nc2n1-c1cccc(C(=O)OC)n1] |

TABLE 1A-continued
| Compound No. | Structure |
|---|---|
| 1.821 | 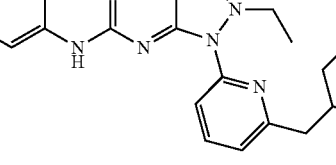 |
| 1.822 | 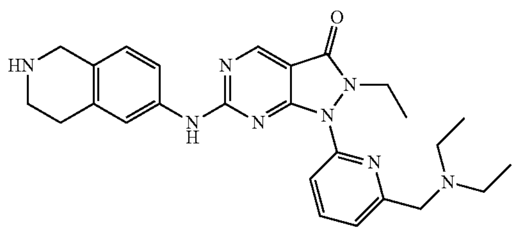 [SMILES: CCN(CC)Cc1cccc(-n2c3nc(Nc4ccc5c(c4)CCNC5)ncc3c(=O)n2CC)n1] |
| 1.823 | 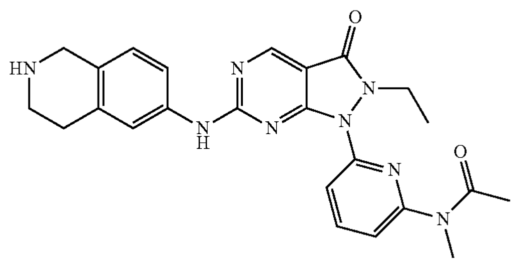 [SMILES: CCn1c(=O)c2cnc(Nc3ccc4c(c3)CCNC4)nc2n1-c1cccc(N(C)C(C)=O)n1] |
| 1.824 | 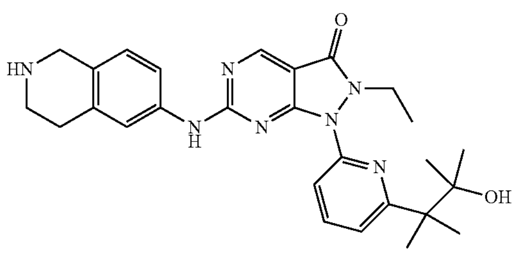 [SMILES: CCn1c(=O)c2cnc(Nc3ccc4c(c3)CCNC4)nc2n1-c1cccc(C(C)(C)C(C)(C)O)n1] |
| 1.825 | 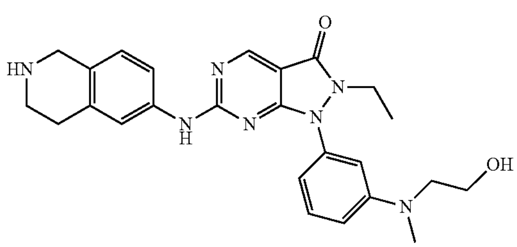 [SMILES: CCn1c(=O)c2cnc(Nc3ccc4c(c3)CCNC4)nc2n1-c1cccc(N(C)CCO)c1] |
| 1.826 | 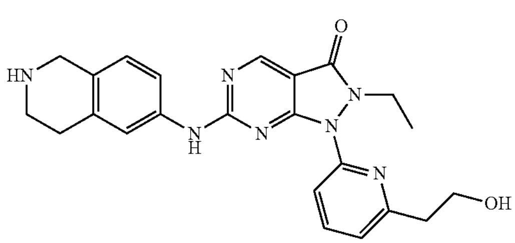 [SMILES: CCn1c(=O)c2cnc(Nc3ccc4c(c3)CCNC4)nc2n1-c1cccc(CCO)n1] |
TABLE 1A-continued
| Compound No. | Structure |
|---|---|
| 1.827 | 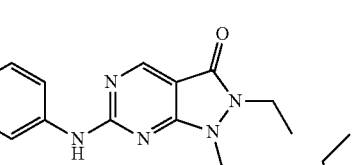 |
| 1.828 | 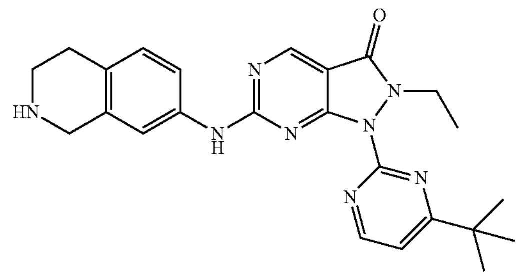 [SMILES: CCn1c(=O)c2cnc(Nc3ccc4c(c3)CNCC4)nc2n1-c1nccc(C(C)(C)C)n1] |
| 1.829 | 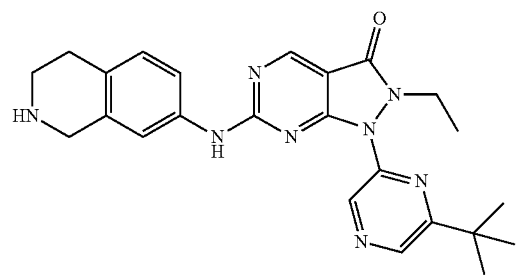 [SMILES: CCn1c(=O)c2cnc(Nc3ccc4c(c3)CNCC4)nc2n1-c1cncc(C(C)(C)C)n1] |
| 1.830 | 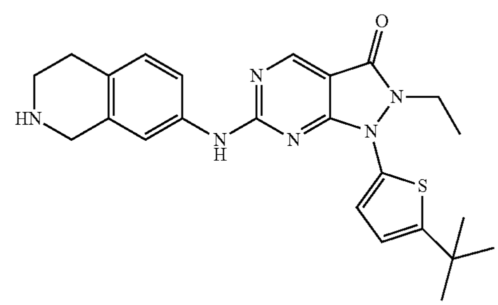 |
| 1.831 | 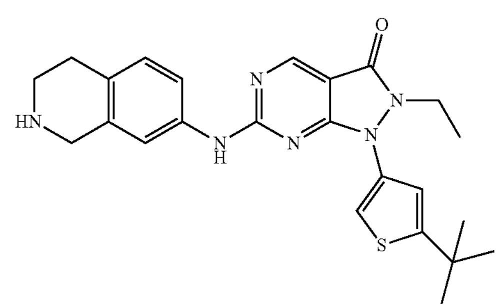 [SMILES: CCn1c(=O)c2cnc(Nc3ccc4c(c3)CNCC4)nc2n1-c1csc(C(C)(C)C)c1] |

TABLE 1A-continued

| Compound No. | Structure |
|---|---|
| 1.832 | 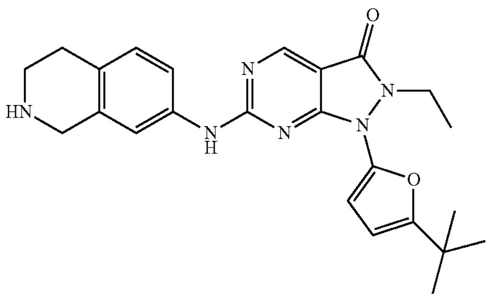 [SMILES: CCn1c(=O)c2cnc(Nc3ccc4c(c3)CNCC4)nc2n1-c1ccc(C(C)(C)C)o1] |
| 1.833 | 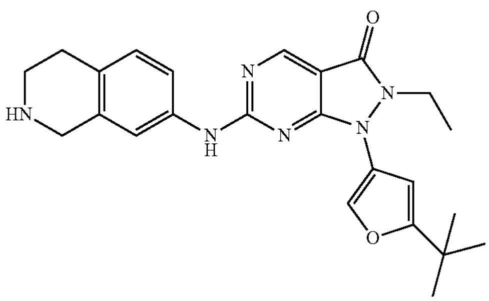 |
| 1.834 | 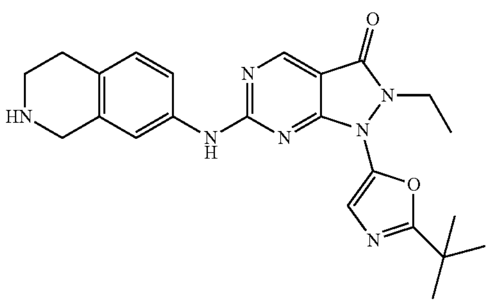 [SMILES: CCn1c(=O)c2cnc(Nc3ccc4c(c3)CNCC4)nc2n1-c1cnc(C(C)(C)C)o1] |
| 1.835 | 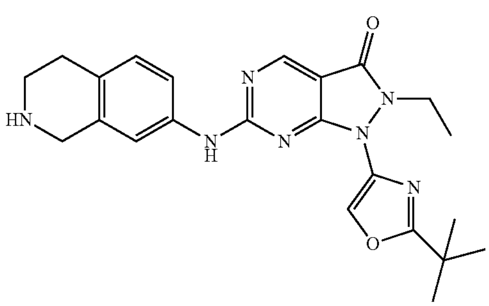 [SMILES: CCn1c(=O)c2cnc(Nc3ccc4c(c3)CNCC4)nc2n1-c1coc(C(C)(C)C)n1] |
| 1.836 | 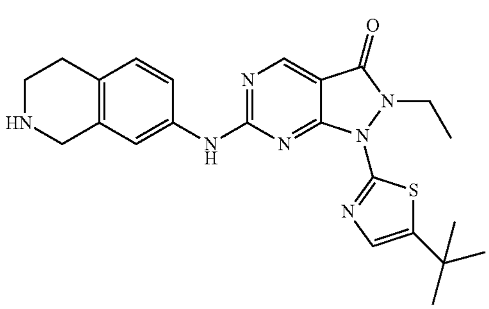 [SMILES: CCn1c(=O)c2cnc(Nc3ccc4c(c3)CNCC4)nc2n1-c1ncc(C(C)(C)C)s1] |
| 1.837 | |
| 1.838 | |
| 1.839 | |
| 1.840 | |
| 1.841 | |

| Compound No. | Structure |
|---|---|
| 1.842 | 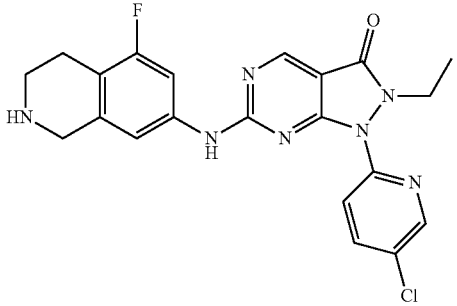 |
| 1.843 | 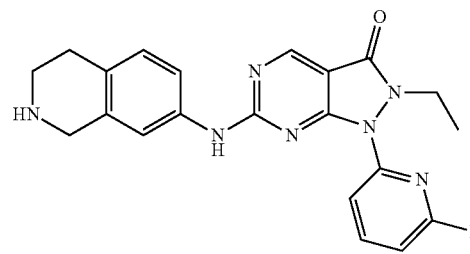 |
| 1.844 | 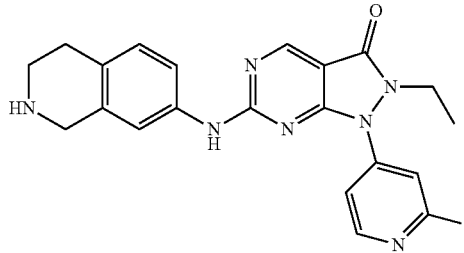 |
| 1.845 | 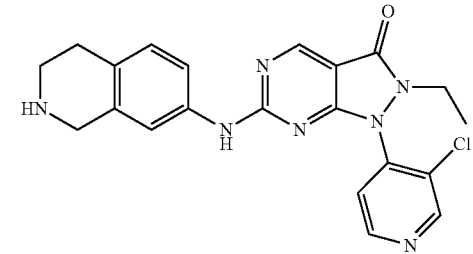 [SMILES: CCn1c(=O)c2cnc(Nc3ccc4c(c3)CNCC4)nc2n1-c1ccncc1Cl] |
| 1.846 | 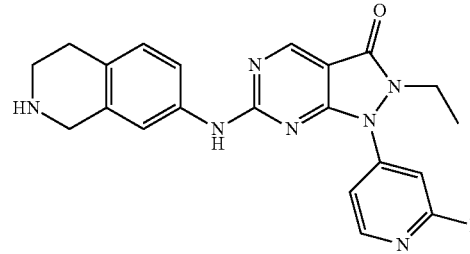 |
| 1.847 | 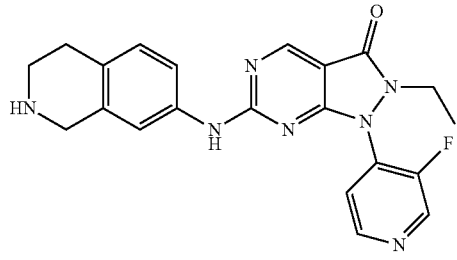 [SMILES: CCn1c(=O)c2cnc(Nc3ccc4c(c3)CNCC4)nc2n1-c1ccncc1F] |
| 1.848 | 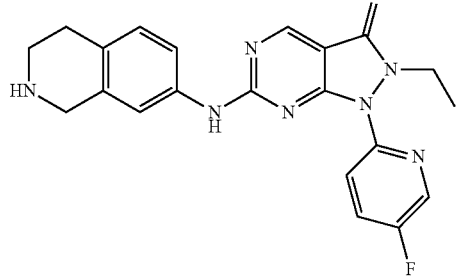 |
| 1.849 | 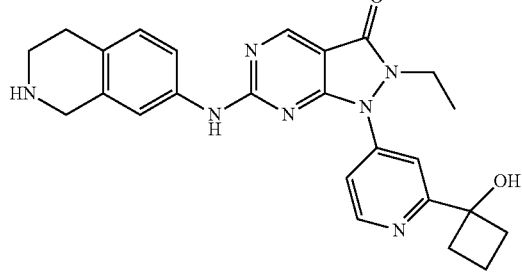 |
| 1.850 | 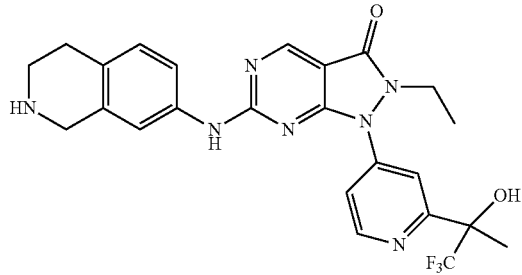 |
| 1.851 | 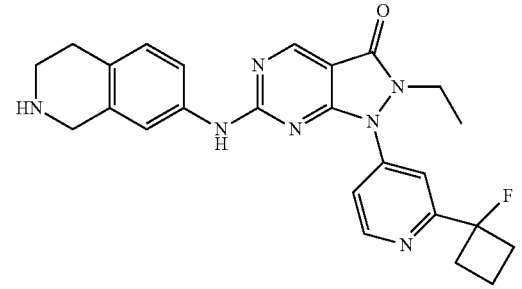 |

TABLE 1A-continued
| Compound No. | Structure |
|---|---|
| 1.852 | 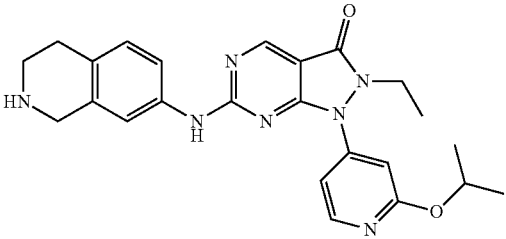 [SMILES: CCn1c(=O)c2cnc(Nc3ccc4c(c3)CNCC4)nc2n1-c1ccnc(OC(C)C)c1] |
| 1.853 | 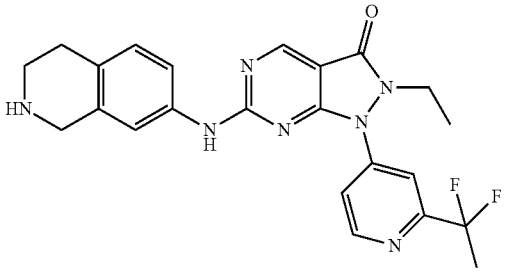 |
| 1.854 | 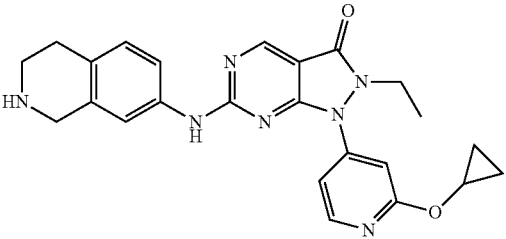 [SMILES: CCn1c(=O)c2cnc(Nc3ccc4c(c3)CNCC4)nc2n1-c1ccnc(OC2CC2)c1] |
| 1.855 | 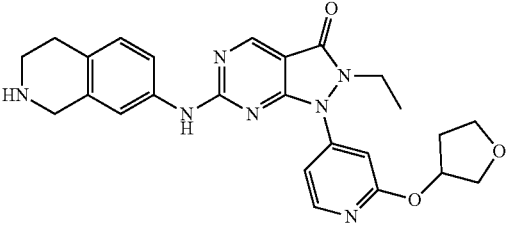 [SMILES: CCn1c(=O)c2cnc(Nc3ccc4c(c3)CNCC4)nc2n1-c1ccnc(OC2CCOC2)c1] |
| 1.856 | 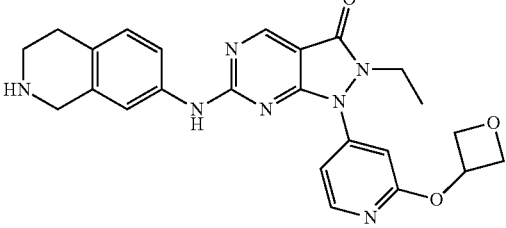 |
| 1.857 | 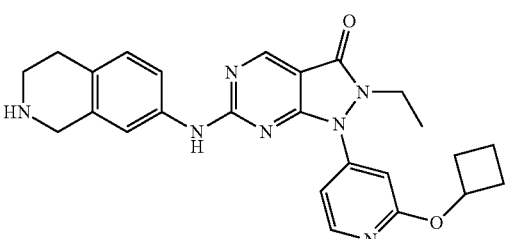 |
| 1.858 | 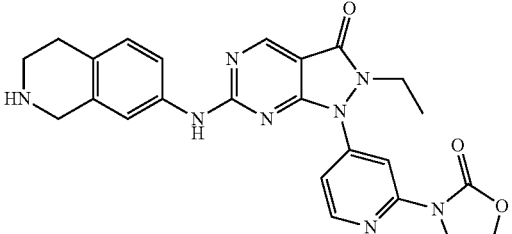 |
| 1.859 | 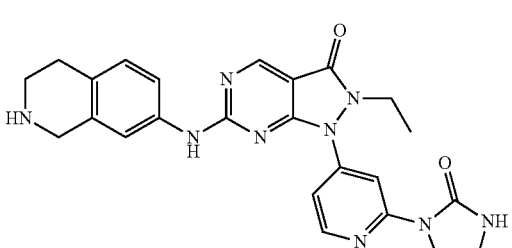 |
| 1.860 | 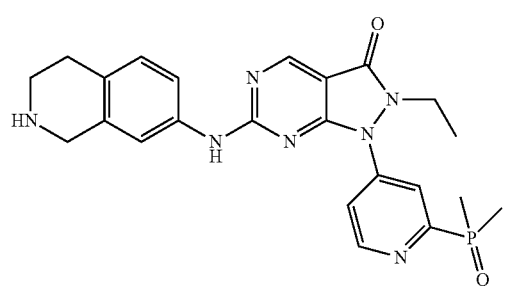 [SMILES: CCn1c(=O)c2cnc(Nc3ccc4c(c3)CNCC4)nc2n1-c1ccnc(P(C)(C)=O)c1] |
| 1.861 | 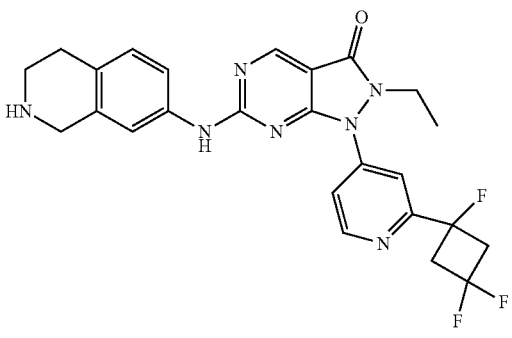 [SMILES: CCn1c(=O)c2cnc(Nc3ccc4c(c3)CNCC4)nc2n1-c1ccnc(C2(F)CC(F)(F)C2)c1] |
| 1.862 | 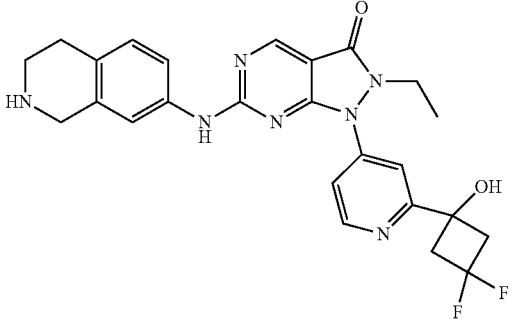 [SMILES: CCn1c(=O)c2cnc(Nc3ccc4c(c3)CNCC4)nc2n1-c1ccnc(C2(O)CC(F)(F)C2)c1] |

TABLE 1A-continued

| Compound No. | Structure |
|---|---|
| 1.863 | |
| 1.864 | |
| 1.865 | |
| 1.866 | |
| 1.867 | |
| 1.868 | 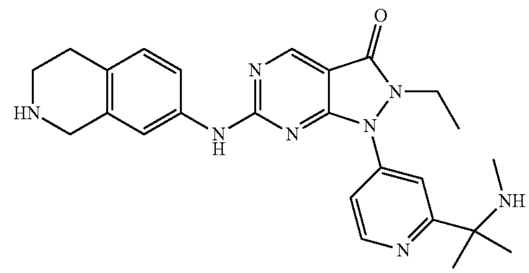 [SMILES: CCn1c(=O)c2cnc(Nc3ccc4c(c3)CNCC4)nc2n1-c1ccnc(C(C)(C)NC)c1] |
| 1.869 | 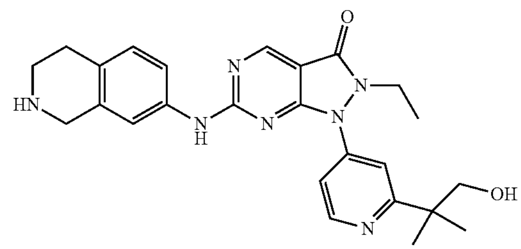 [SMILES: CCn1c(=O)c2cnc(Nc3ccc4c(c3)CNCC4)nc2n1-c1ccnc(C(C)(C)CO)c1] |
| 1.870 | 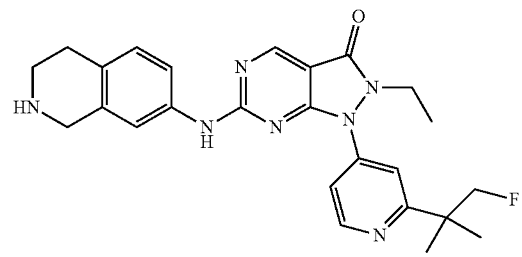 |
| 1.871 | 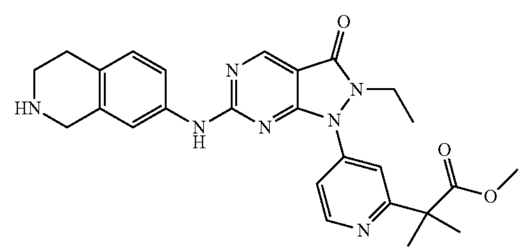 [SMILES: CCn1c(=O)c2cnc(Nc3ccc4c(c3)CNCC4)nc2n1-c1ccnc(C(C)(C)C(=O)OC)c1] |
| 1.872 | 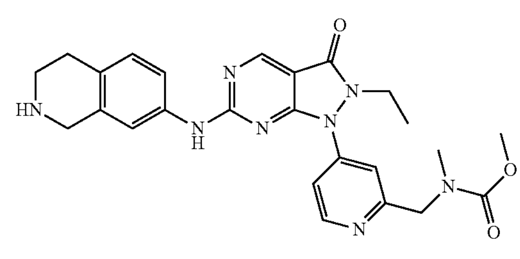 [SMILES: CCn1c(=O)c2cnc(Nc3ccc4c(c3)CNCC4)nc2n1-c1ccnc(CN(C)C(=O)OC)c1] |
| 1.873 | 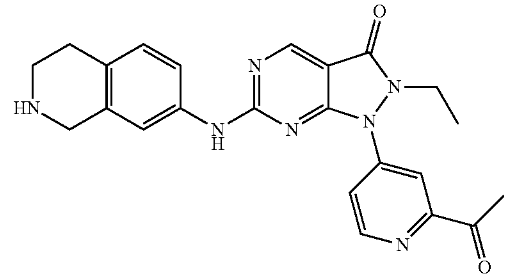 [SMILES: CCn1c(=O)c2cnc(Nc3ccc4c(c3)CNCC4)nc2n1-c1ccnc(C(C)=O)c1] |

TABLE 1A-continued
| Compound No. | Structure |
|---|---|
| 1.874 | 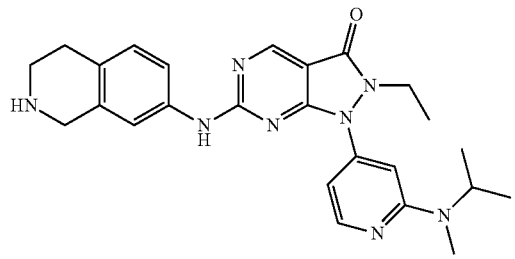 |
| 1.875 | 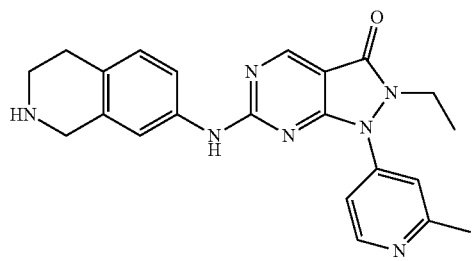 [SMILES: CCn1c(=O)c2cnc(Nc3ccc4c(c3)CNCC4)nc2n1-c1ccnc(C)c1] |
| 1.876 | 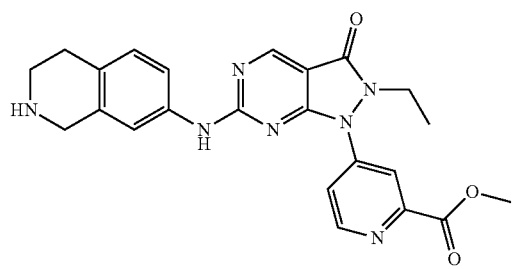 [SMILES: CCn1c(=O)c2cnc(Nc3ccc4c(c3)CNCC4)nc2n1-c1ccnc(C(=O)OC)c1] |
| 1.877 | 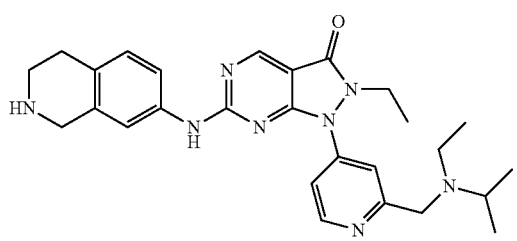 [SMILES: CCN(Cc1cc(-n2c3nc(Nc4ccc5c(c4)CNCC5)ncc3c(=O)n2CC)ccn1)C(C)C] |
| 1.878 | 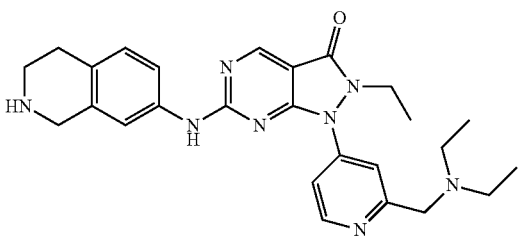 [SMILES: CCN(CC)Cc1cc(-n2c3nc(Nc4ccc5c(c4)CNCC5)ncc3c(=O)n2CC)ccn1] |
| 1.879 | 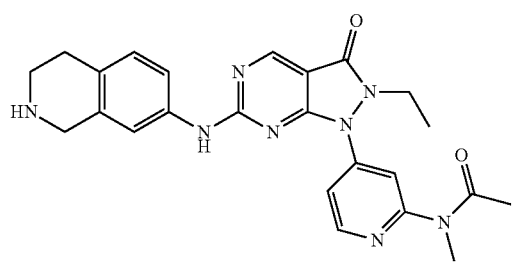 [SMILES: CCn1c(=O)c2cnc(Nc3ccc4c(c3)CNCC4)nc2n1-c1ccnc(N(C)C(C)=O)c1] |
TABLE 1A-continued
| Compound No. | Structure |
|---|---|
| 1.880 | 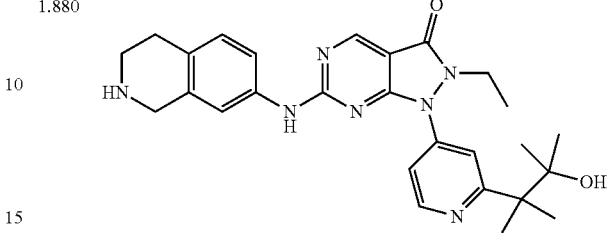 |
| 1.881 | 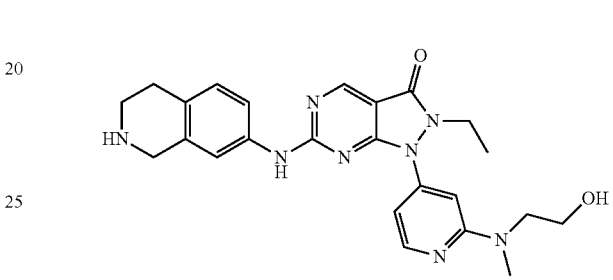 |
| 1.882 | 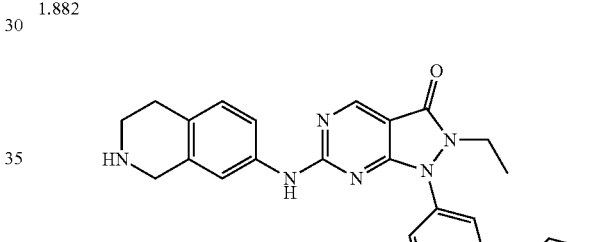 |
| 1.883 | 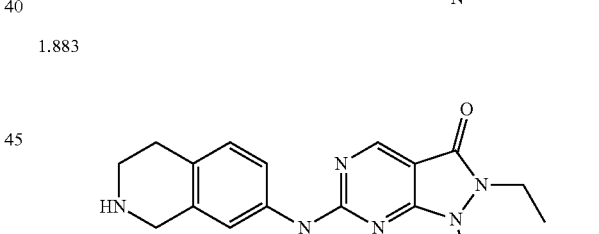 |
| 1.884 | 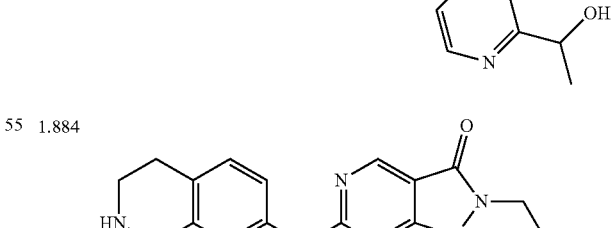 |
| |  |

TABLE 1A-continued

| Compound No. | Structure |
|---|---|
| 1.885 | |
| 1.886 | |
| 1.887 | |
| 1.888 | |
| 1.889 | |
| 1.890 | 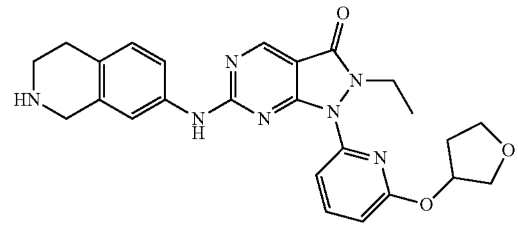 [SMILES: CCn1c(=O)c2cnc(Nc3ccc4c(c3)CNCC4)nc2n1-c1cccc(OC2CCOC2)n1] |
| 1.891 | 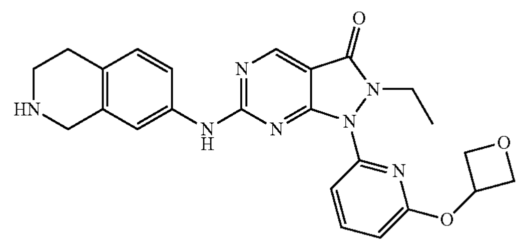 [SMILES: CCn1c(=O)c2cnc(Nc3ccc4c(c3)CNCC4)nc2n1-c1cccc(OC2COC2)n1] |
| 1.892 | 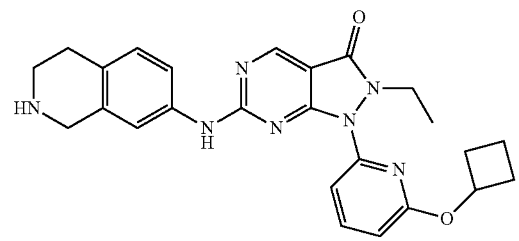 [SMILES: CCn1c(=O)c2cnc(Nc3ccc4c(c3)CNCC4)nc2n1-c1cccc(OC2CCC2)n1] |
| 1.893 | 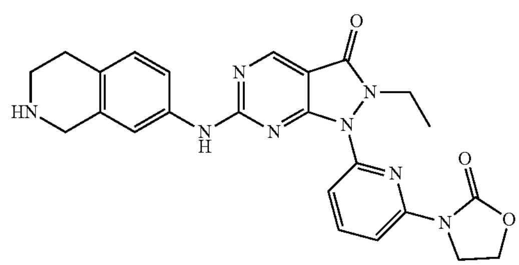 [SMILES: CCn1c(=O)c2cnc(Nc3ccc4c(c3)CNCC4)nc2n1-c1cccc(N2CCOC2=O)n1] |
| 1.894 | 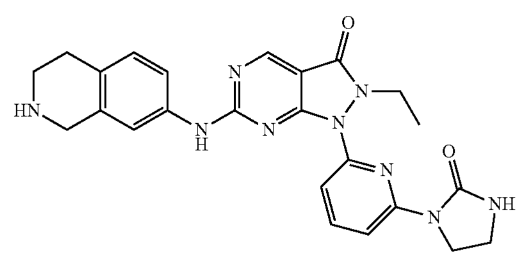 [SMILES: CCn1c(=O)c2cnc(Nc3ccc4c(c3)CNCC4)nc2n1-c1cccc(N2CCNC2=O)n1] |
| 1.895 | 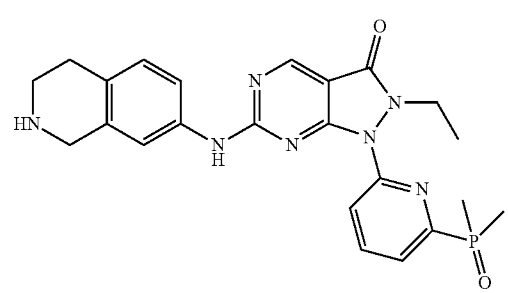 [SMILES: CCn1c(=O)c2cnc(Nc3ccc4c(c3)CNCC4)nc2n1-c1cccc(P(C)(C)=O)n1] |

TABLE 1A-continued

| Compound No. | Structure |
|---|---|
| 1.896 | 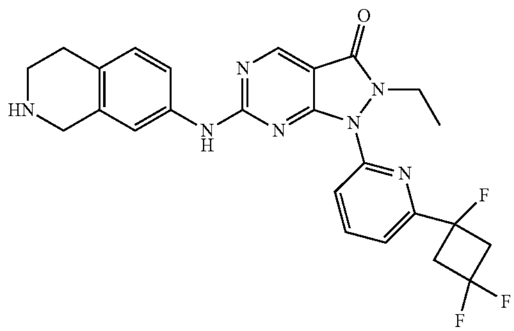 [SMILES: CCn1c(=O)c2cnc(Nc3ccc4c(c3)CNCC4)nc2n1-c1cccc(C2(F)CC(F)(F)C2)n1] |
| 1.897 | 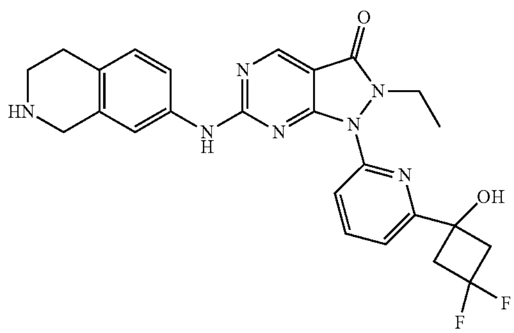 [SMILES: CCn1c(=O)c2cnc(Nc3ccc4c(c3)CNCC4)nc2n1-c1cccc(C2(O)CC(F)(F)C2)n1] |
| 1.898 | 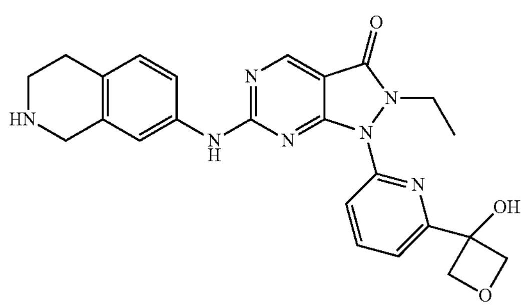 [SMILES: CCn1c(=O)c2cnc(Nc3ccc4c(c3)CNCC4)nc2n1-c1cccc(C2(O)COC2)n1] |
| 1.899 | 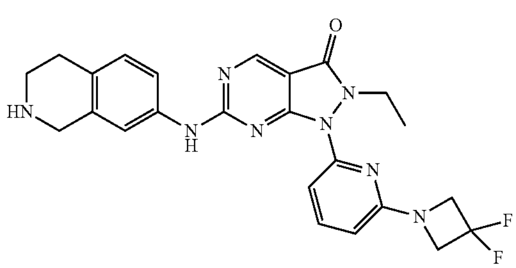 [SMILES: CCn1c(=O)c2cnc(Nc3ccc4c(c3)CNCC4)nc2n1-c1cccc(N2CC(F)(F)C2)n1] |
| 1.900 | 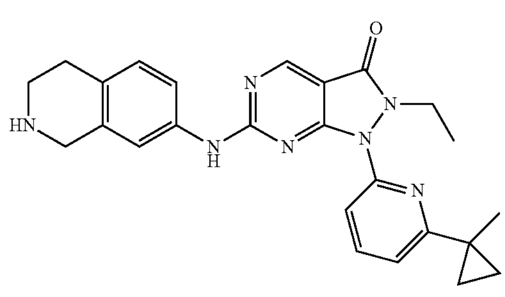 [SMILES: CCn1c(=O)c2cnc(Nc3ccc4c(c3)CNCC4)nc2n1-c1cccc(C2(C)CC2)n1] |
| 1.901 | |
| 1.902 | |
| 1.903 | |
| 1.904 | |
| 1.905 | |

TABLE 1A-continued

| Compound No. | Structure |
|---|---|
| 1.906 | 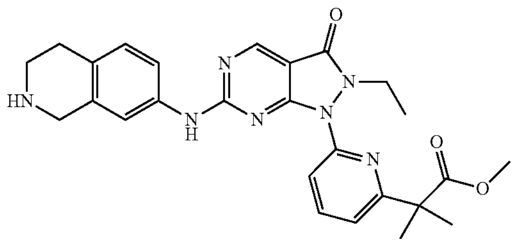 [SMILES: CCn1c(=O)c2cnc(Nc3ccc4c(c3)CNCC4)nc2n1-c1cccc(C(C)(C)C(=O)OC)n1] |
| 1.907 | 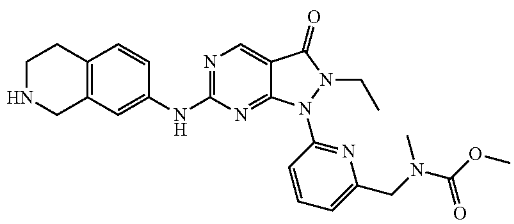 |
| 1.908 | 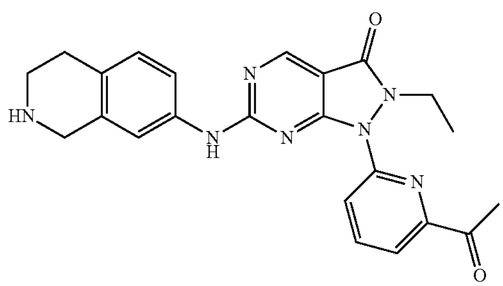 [SMILES: CCn1c(=O)c2cnc(Nc3ccc4c(c3)CNCC4)nc2n1-c1cccc(C(C)=O)n1] |
| 1.909 | 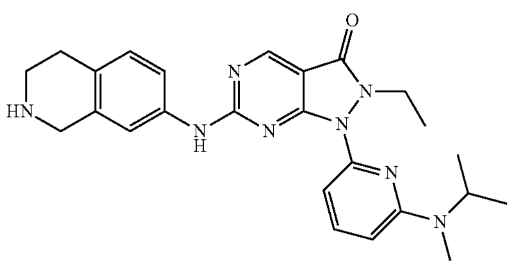 [SMILES: CCn1c(=O)c2cnc(Nc3ccc4c(c3)CNCC4)nc2n1-c1cccc(N(C)C(C)C)n1] |
| 1.910 | 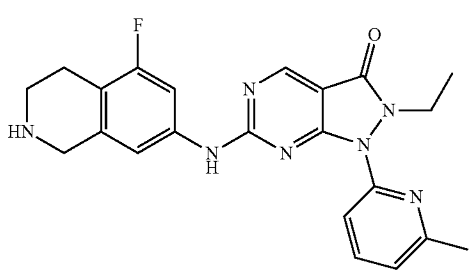 [SMILES: CCn1c(=O)c2cnc(Nc3cc(F)c4c(c3)CNCC4)nc2n1-c1cccc(C)n1] |
| 1.911 | 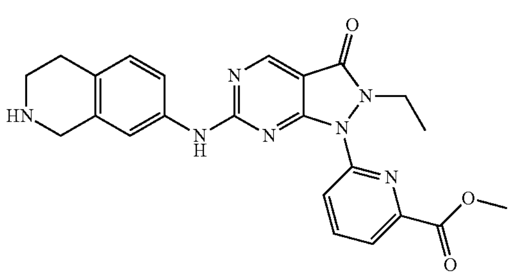 |
| 1.912 | |
| 1.913 | |
| 1.914 | |
| 1.915 | |
| 1.916 | |
| 1.917 | |

TABLE 1A-continued

| Compound No. | Structure |
|---|---|
| 1.918 | 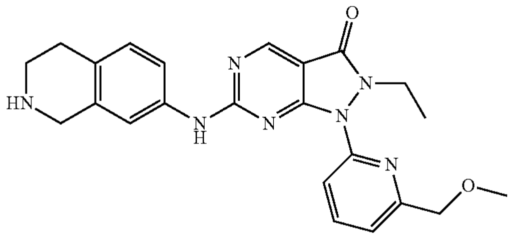 [SMILES: CCn1c(=O)c2cnc(Nc3ccc4c(c3)CNCC4)nc2n1-c1cccc(COC)n1] |
| 1.919 | 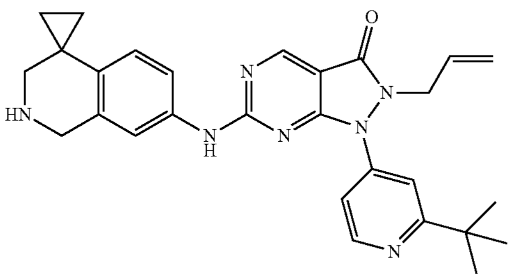 [SMILES: C=CCn1c(=O)c2cnc(Nc3ccc4c(c3)CNCC43CC3)nc2n1-c1ccnc(C(C)(C)C)c1] |
| 1.920 | 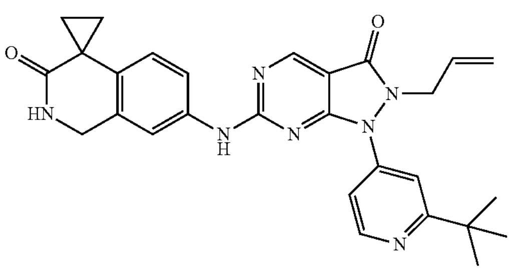 [SMILES: C=CCn1c(=O)c2cnc(Nc3ccc4c(c3)CNC(=O)C43CC3)nc2n1-c1ccnc(C(C)(C)C)c1] |
| 1.921 | 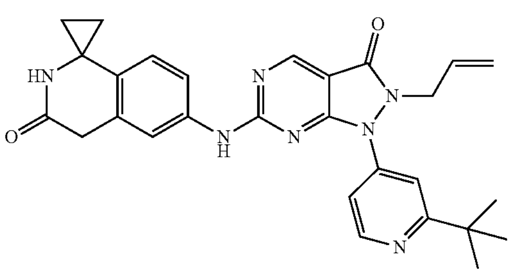 [SMILES: C=CCn1c(=O)c2cnc(Nc3ccc4c(c3)CC(=O)NC43CC3)nc2n1-c1ccnc(C(C)(C)C)c1] |
| 1.922 | 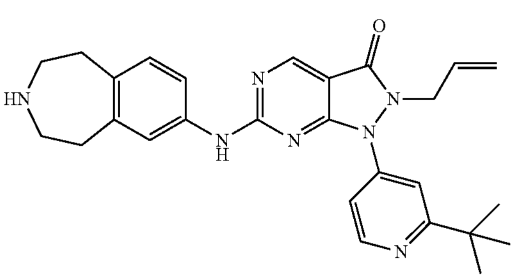 [SMILES: C=CCn1c(=O)c2cnc(Nc3ccc4c(c3)CCNCC4)nc2n1-c1ccnc(C(C)(C)C)c1] |
| 1.923 | |
| 1.924 | |
| 1.925 | |
| 1.926 | |
| 1.927 | |

TABLE 1A-continued

| Compound No. | Structure |
|---|---|
| 1.928 | 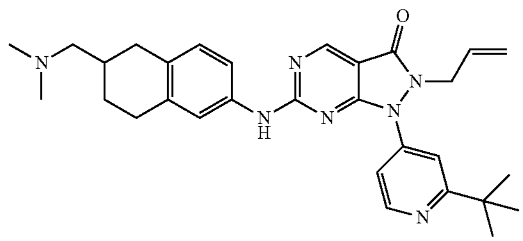 [SMILES: C=CCn1c(=O)c2cnc(Nc3ccc4c(c3)CCC(CN(C)C)C4)nc2n1-c1ccnc(C(C)(C)C)c1] |
| 1.929 | 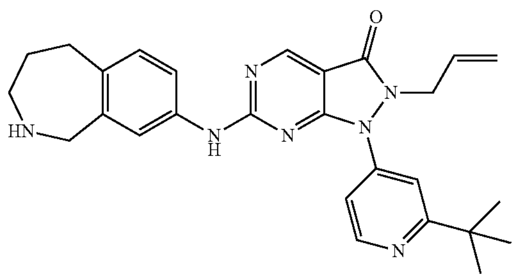 [SMILES: C=CCn1c(=O)c2cnc(Nc3ccc4c(c3)CNCCC4)nc2n1-c1ccnc(C(C)(C)C)c1] |
| 1.930 | 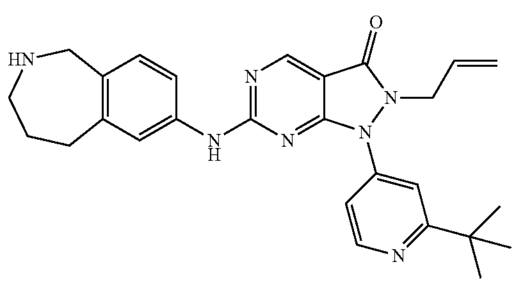 [SMILES: C=CCn1c(=O)c2cnc(Nc3ccc4c(c3)CCCNC4)nc2n1-c1ccnc(C(C)(C)C)c1] |
| 1.931 | 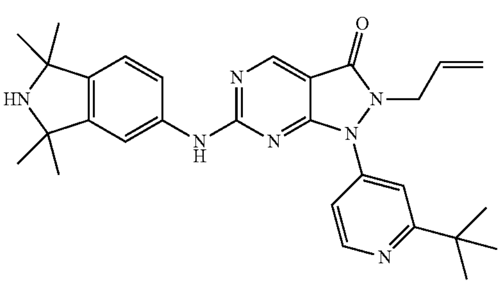 [SMILES: C=CCn1c(=O)c2cnc(Nc3ccc4c(c3)C(C)(C)NC4(C)C)nc2n1-c1ccnc(C(C)(C)C)c1] |
| 1.932 | 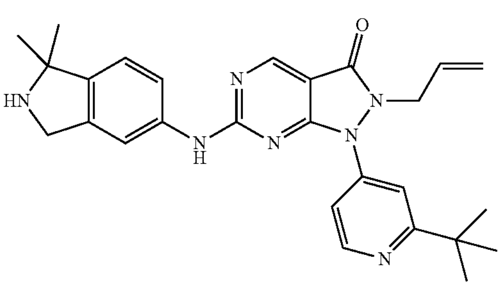 [SMILES: C=CCn1c(=O)c2cnc(Nc3ccc4c(c3)CNC4(C)C)nc2n1-c1ccnc(C(C)(C)C)c1] |
| 1.933 | |
| 1.934 | |
| 1.935 | |
| 1.936 | |
| 1.937 | |

TABLE 1A-continued

| Compound No. | Structure |
| --- | --- |
| 1.938 | 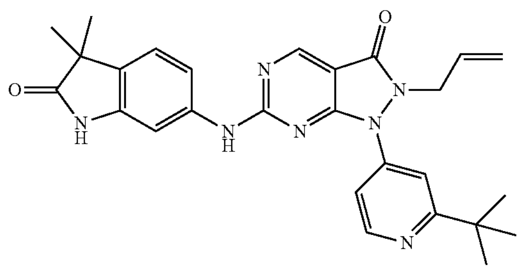 [SMILES: C=CCn1c(=O)c2cnc(Nc3ccc4c(c3)NC(=O)C4(C)C)nc2n1-c1ccnc(C(C)(C)C)c1] |
| 1.939 | 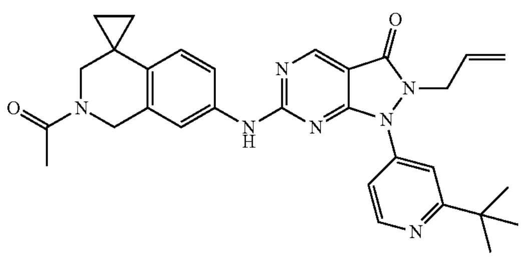 [SMILES: C=CCn1c(=O)c2cnc(Nc3ccc4c(c3)CN(C(C)=O)CC43CC3)nc2n1-c1ccnc(C(C)(C)C)c1] |
| 1.940 | 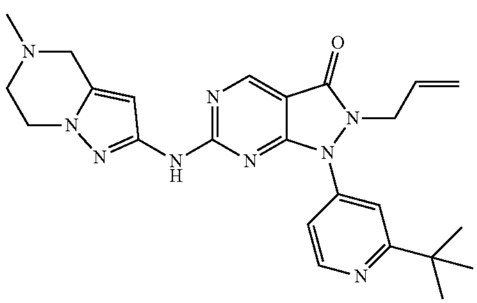 |
| 1.941 | 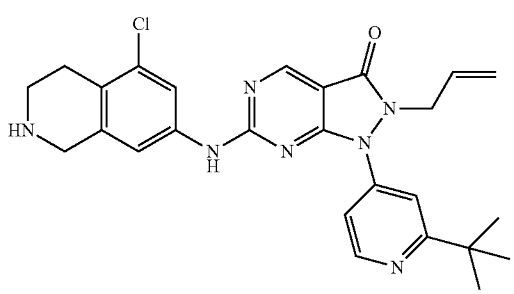 [SMILES: C=CCn1c(=O)c2cnc(Nc3cc(Cl)c4c(c3)CNCC4)nc2n1-c1ccnc(C(C)(C)C)c1] |
| 1.942 | 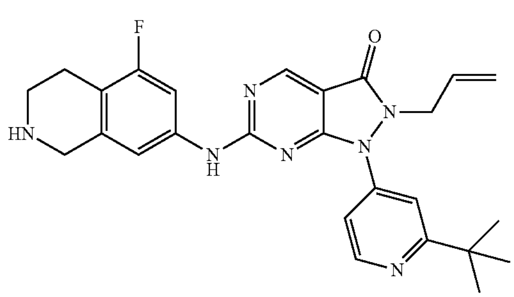 |
| 1.943 | |
| 1.944 | |
| 1.945 | |
| 1.946 | |
| 1.947 | |

TABLE 1A-continued
| Compound No. | Structure |
|---|---|
| 1.948 | 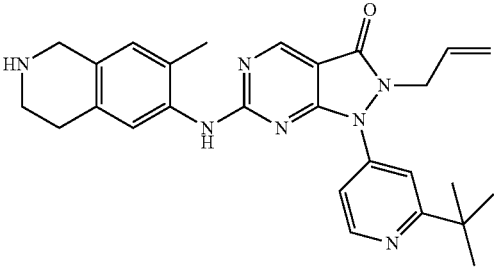 |
| 1.949 | 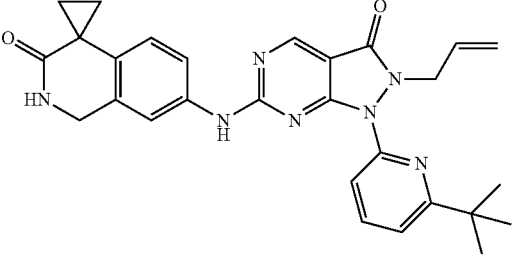 |
| 1.950 | 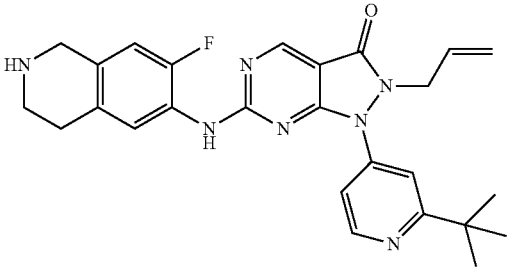 [SMILES: C=CCn1c(=O)c2cnc(Nc3cc4c(cc3Cl)CNCC4)nc2n1-c1ccnc(C(C)(C)C)c1] |
| 1.951 | 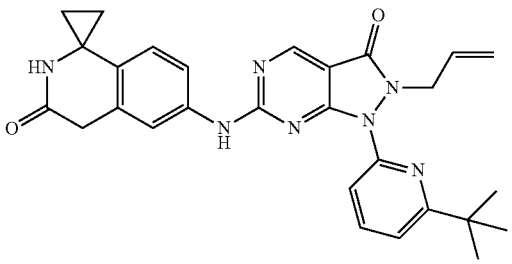 |
| 1.952 | 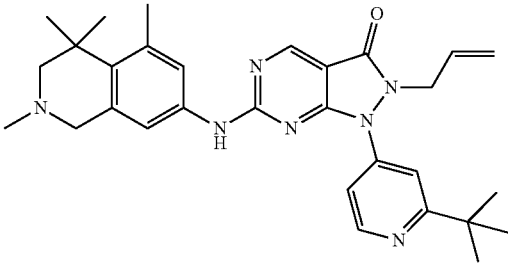 [SMILES: C=CCn1c(=O)c2cnc(Nc3cc(C)c4c(c3)CN(C)CC4(C)C)nc2n1-c1ccnc(C(C)(C)C)c1] |
| 1.953 | 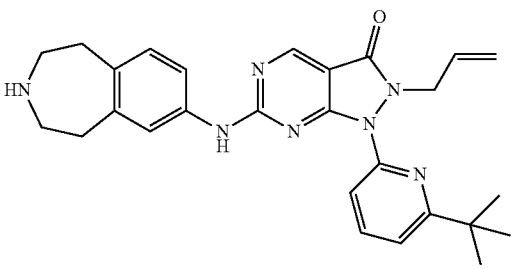 |
| 1.954 | 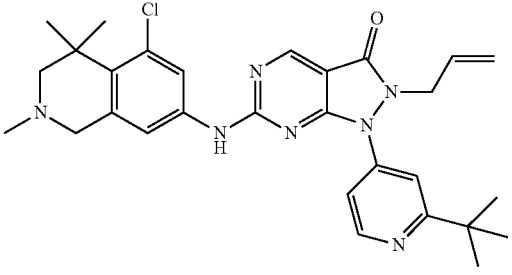 [SMILES: C=CCn1c(=O)c2cnc(Nc3cc(Cl)c4c(c3)CN(C)CC4(C)C)nc2n1-c1ccnc(C(C)(C)C)c1] |
| 1.955 | 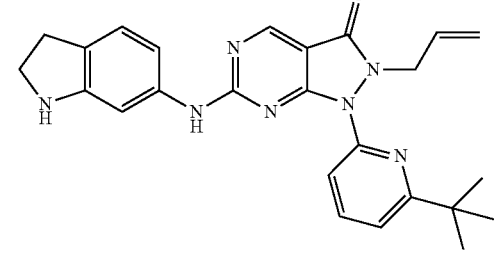 |
| 1.956 | 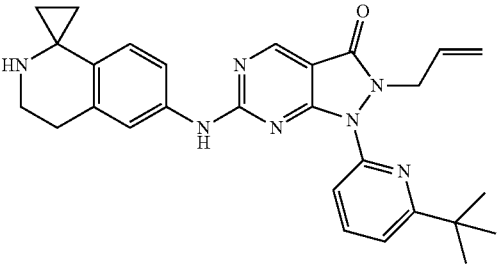 [SMILES: C=CCn1c(=O)c2cnc(Nc3ccc4c(c3)CCNC43CC3)nc2n1-c1cccc(C(C)(C)C)n1] |
| 1.957 | 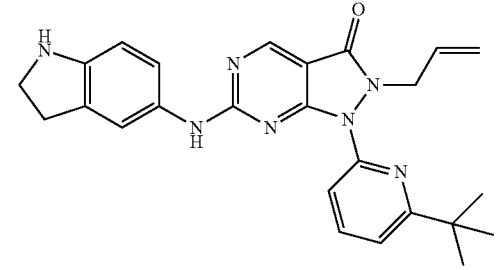 [SMILES: C=CCn1c(=O)c2cnc(Nc3ccc4c(c3)CCN4)nc2n1-c1cccc(C(C)(C)C)n1] |

TABLE 1A-continued
| Compound No. | Structure |
|---|---|
| 1.958 | 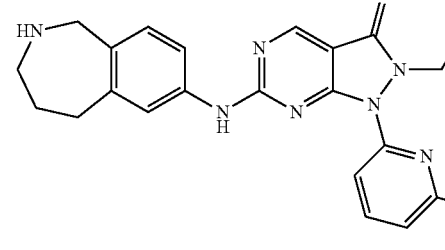 |
| 1.959 | 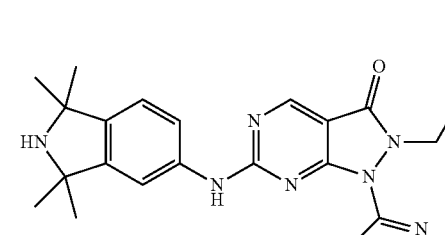 |
| 1.960 | 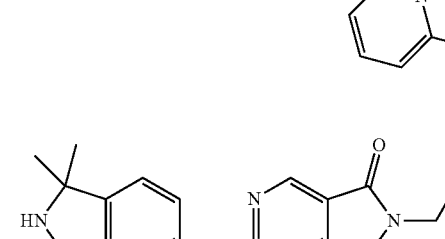 |
| 1.961 | 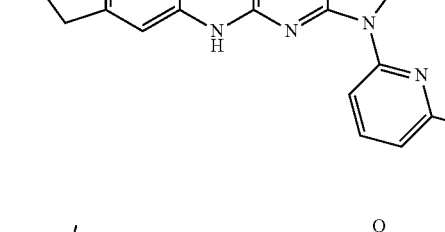 |
| 1.962 | 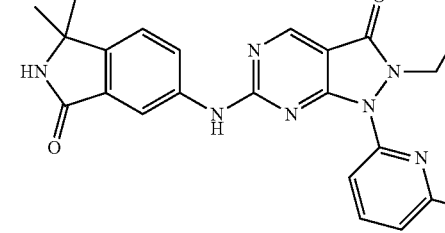 |
TABLE 1A-continued
| Compound No. | Structure |
|---|---|
| 1.963 | 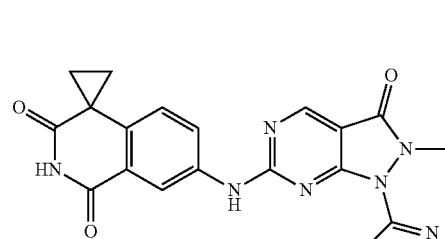 |
| 1.964 | 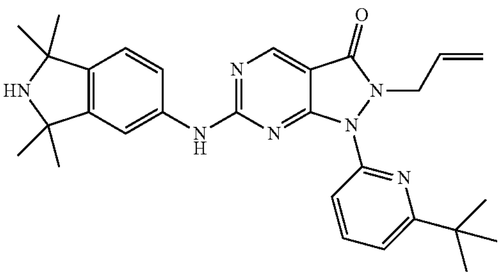 [SMILES: C=CCn1c(=O)c2cnc(Nc3ccc4c(c3)C(C)(C)NC4(C)C)nc2n1-c1cccc(C(C)(C)C)n1] |
| 1.965 | 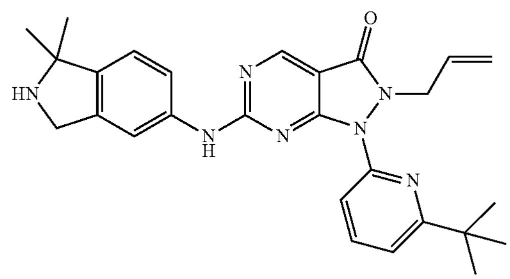 [SMILES: C=CCn1c(=O)c2cnc(Nc3ccc4c(c3)CNC4(C)C)nc2n1-c1cccc(C(C)(C)C)n1] |
| 1.966 | 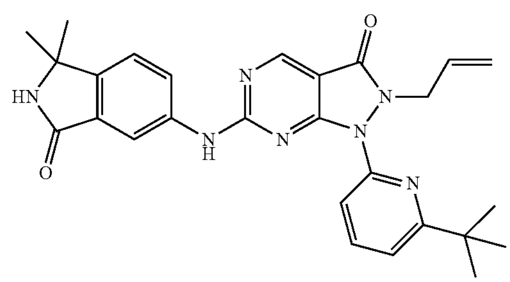 [SMILES: C=CCn1c(=O)c2cnc(Nc3ccc4c(c3)C(=O)NC4(C)C)nc2n1-c1cccc(C(C)(C)C)n1] |
| 1.967 | 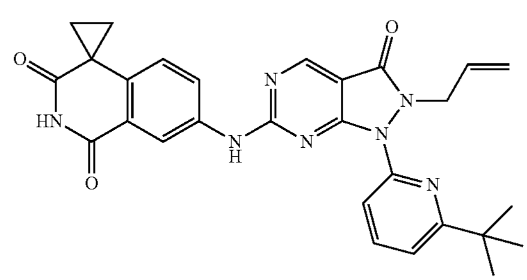 [SMILES: C=CCn1c(=O)c2cnc(Nc3ccc4c(c3)C(=O)NC(=O)C43CC3)nc2n1-c1cccc(C(C)(C)C)n1] |

TABLE 1A-continued

| Compound No. | Structure |
|---|---|
| 1.968 | 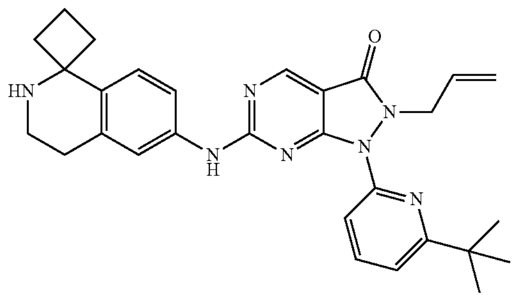 [SMILES: C=CCn1c(=O)c2cnc(Nc3ccc4c(c3)CCNC43CCC3)nc2n1-c1cccc(C(C)(C)C)n1] |
| 1.969 | 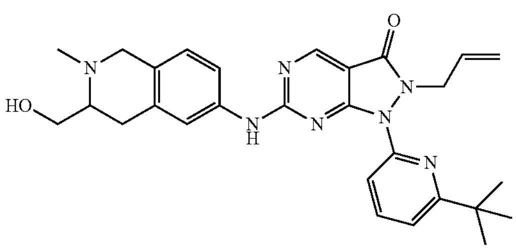 [SMILES: C=CCn1c(=O)c2cnc(Nc3ccc4c(c3)CC(CO)N(C)C4)nc2n1-c1cccc(C(C)(C)C)n1] |
| 1.970 | 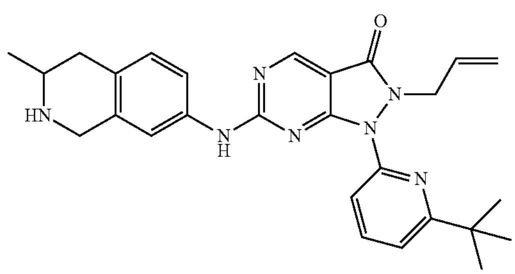 [SMILES: C=CCn1c(=O)c2cnc(Nc3ccc4c(c3)CNC(C)C4)nc2n1-c1cccc(C(C)(C)C)n1] |
| 1.971 | 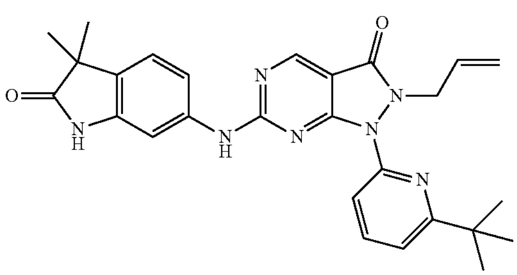 [SMILES: C=CCn1c(=O)c2cnc(Nc3ccc4c(c3)NC(=O)C4(C)C)nc2n1-c1cccc(C(C)(C)C)n1] |
| 1.972 | 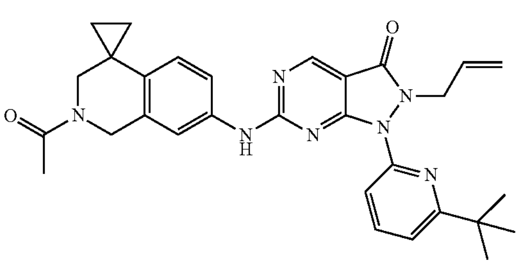 [SMILES: C=CCn1c(=O)c2cnc(Nc3ccc4c(c3)CN(C(C)=O)CC43CC3)nc2n1-c1cccc(C(C)(C)C)n1] |
| 1.973 | |
| 1.974 | |
| 1.975 | |
| 1.976 | |
| 1.977 | |

TABLE 1A-continued

| Compound No. | Structure |
|---|---|
| 1.978 | (structure) |
| 1.979 | (structure) |
| 1.980 | (structure) |
| 1.981 | (structure) |
| 1.982 | (structure) |
| 1.983 | (structure) |
| 1.984 | (structure) |
| 1.985 | (structure) |
| 1.986 | (structure) |
| 1.987 | (structure) |

TABLE 1A-continued

| Compound No. | Structure |
|---|---|
| 1.988 | 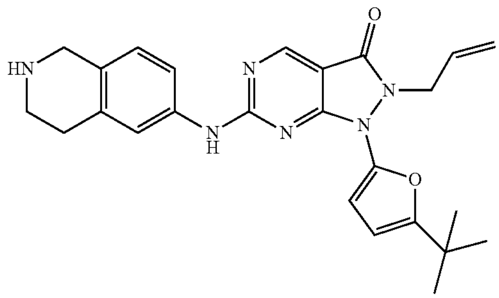 [SMILES: C=CCn1c(=O)c2cnc(Nc3ccc4c(c3)CCNC4)nc2n1-c1ccc(C(C)(C)C)s1] |
| 1.989 | 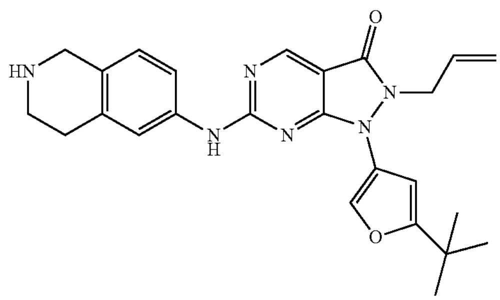 [SMILES: C=CCn1c(=O)c2cnc(Nc3ccc4c(c3)CCNC4)nc2n1-c1coc(C(C)(C)C)c1] |
| 1.990 | 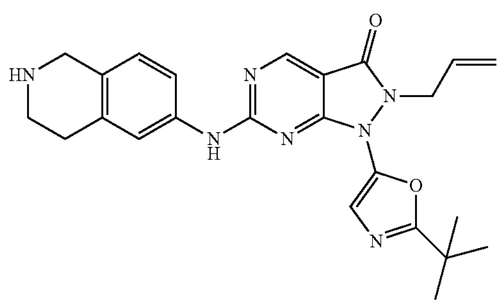 [SMILES: C=CCn1c(=O)c2cnc(Nc3ccc4c(c3)CCNC4)nc2n1-c1cnc(C(C)(C)C)o1] |
| 1.991 | 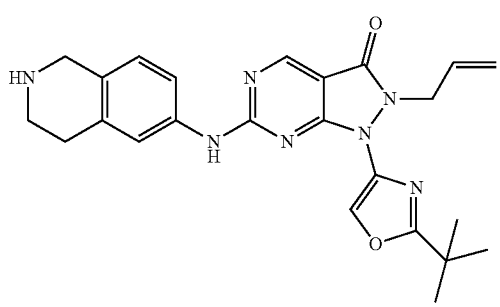 |
| 1.992 | 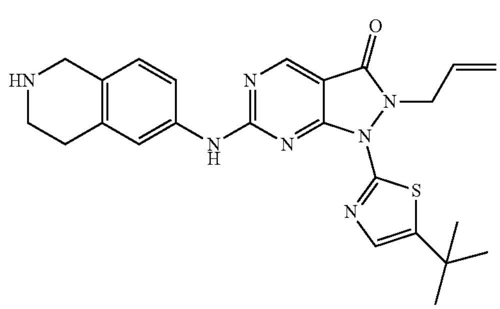 [SMILES: C=CCn1c(=O)c2cnc(Nc3ccc4c(c3)CCNC4)nc2n1-c1ncc(C(C)(C)C)s1] |
| 1.993 | 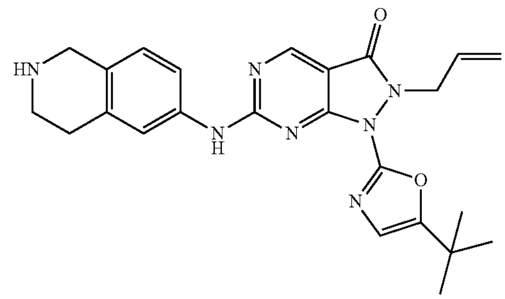 |
| 1.994 | 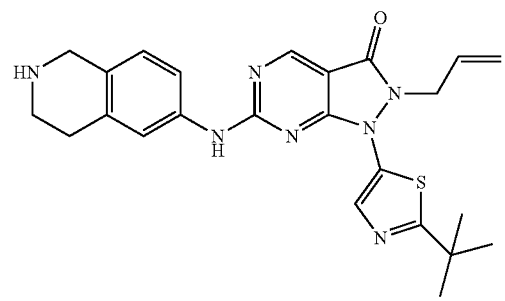 |
| 1.995 | 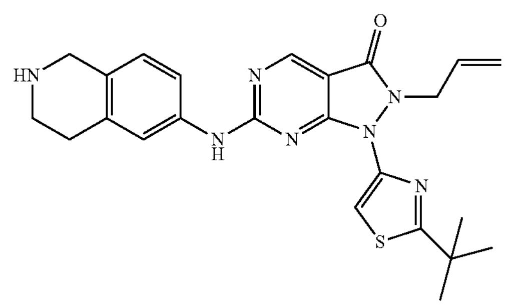 |
| 1.996 | 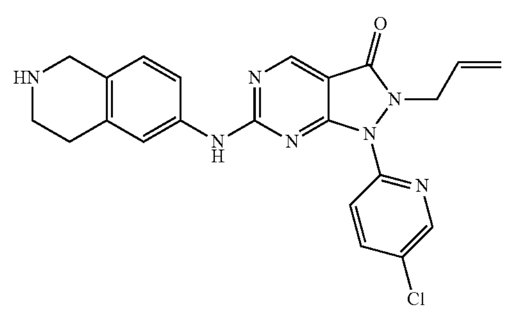 [SMILES: C=CCn1c(=O)c2cnc(Nc3ccc4c(c3)CCNC4)nc2n1-c1ccc(Cl)cn1] |
| 1.997 | 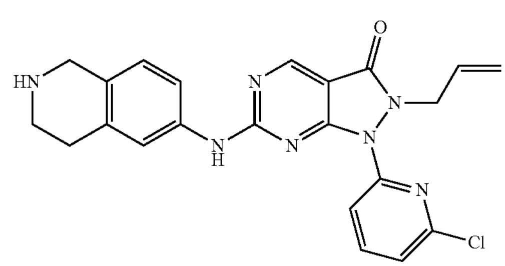 [SMILES: C=CCn1c(=O)c2cnc(Nc3ccc4c(c3)CCNC4)nc2n1-c1cccc(Cl)n1] |

TABLE 1A-continued

| Compound No. | Structure |
|---|---|
| 1,998 | |
| 1,999 | |
| 2,000 | |
| 2,001 | |
| 2,002 | |
| 2,003 | |
| 2,004 | |
| 2,005 | |
| 2,006 | |
| 2,007 | |

TABLE 1A-continued
| Compound No. | Structure |
|---|---|
| 2.008 | 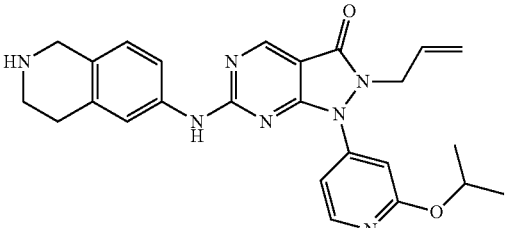 |
| 2.009 | 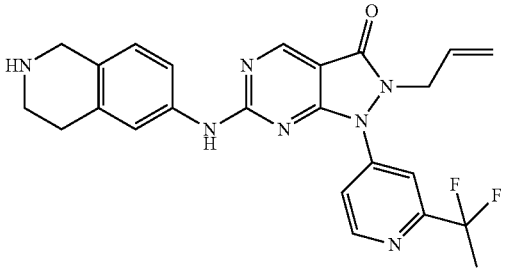 [SMILES: C=CCn1c(=O)c2cnc(Nc3ccc4c(c3)CCNC4)nc2n1-c1ccnc(C(C)(F)F)c1] |
| 2.010 | 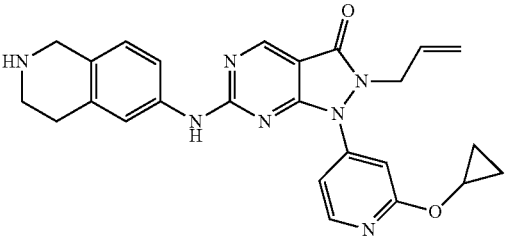 [SMILES: C=CCn1c(=O)c2cnc(Nc3ccc4c(c3)CCNC4)nc2n1-c1ccnc(OC2CC2)c1] |
| 2.011 | 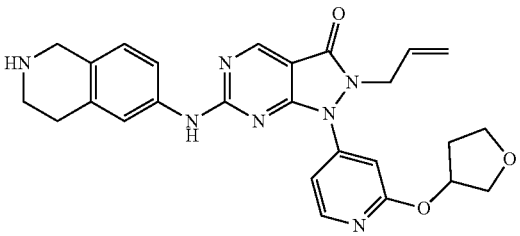 [SMILES: C=CCn1c(=O)c2cnc(Nc3ccc4c(c3)CCNC4)nc2n1-c1ccnc(OC2CCOC2)c1] |
| 2.012 | 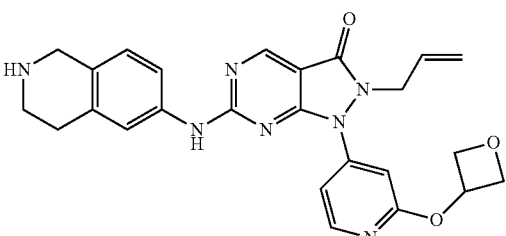 |
| 2.013 | 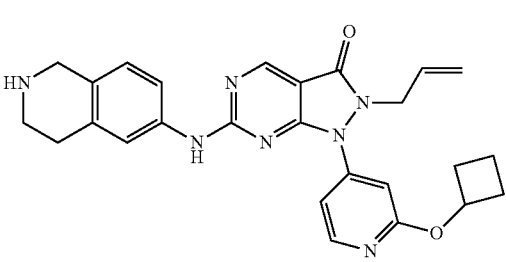 [SMILES: C=CCn1c(=O)c2cnc(Nc3ccc4c(c3)CCNC4)nc2n1-c1ccnc(OC2CCC2)c1] |
| 2.014 | 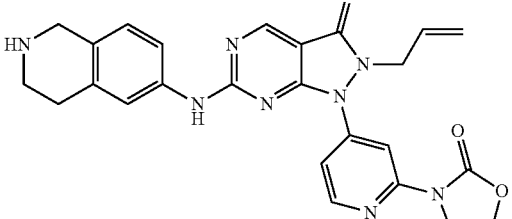 |
| 2.015 | 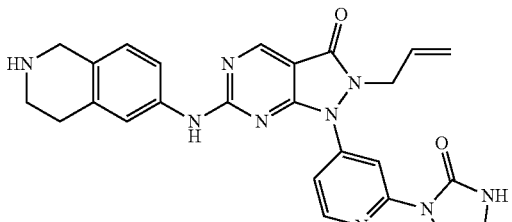 |
| 2.016 | 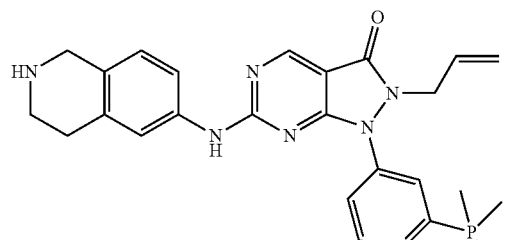 |
| 2.017 | 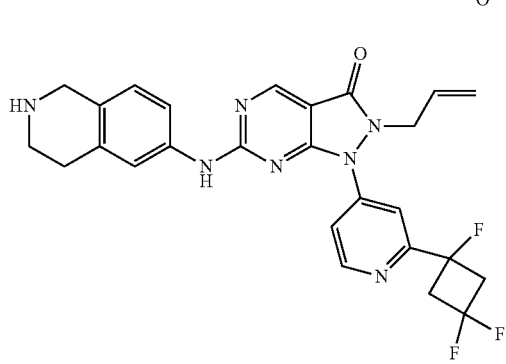 |
| 2.018 | 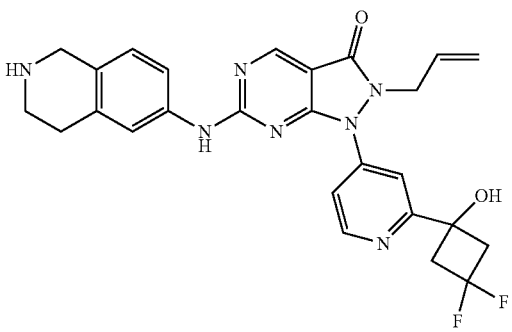 [SMILES: C=CCn1c(=O)c2cnc(Nc3ccc4c(c3)CCNC4)nc2n1-c1ccnc(C2(O)CC(F)(F)C2)c1] |

TABLE 1A-continued

| Compound No. | Structure |
|---|---|
| 2.019 | (structure) |
| 2.020 | (structure) |
| 2.021 | (structure) |
| 2.022 | (structure) |
| 2.023 | (structure) |
| 2.024 | (structure) |
| 2.025 | (structure) |
| 2.026 | (structure) |
| 2.027 | (structure) |
| 2.028 | (structure) |
| 2.029 | (structure) |

TABLE 1A-continued

| Compound No. | Structure |
|---|---|
| 2.030 | 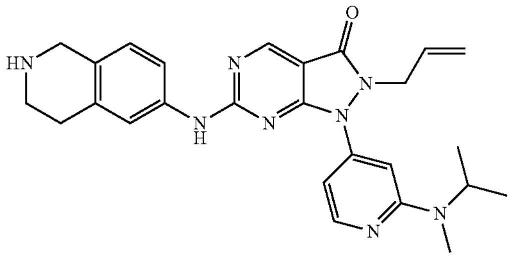 [SMILES: C=CCn1c(=O)c2cnc(Nc3ccc4c(c3)CCNC4)nc2n1-c1ccnc(N(C)C(C)C)c1] |
| 2.031 | 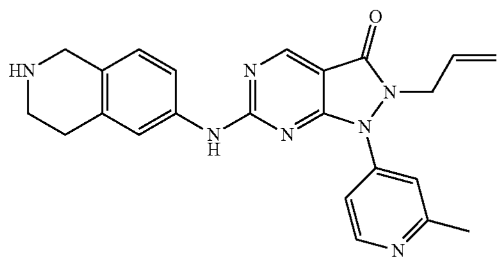 |
| 2.032 | 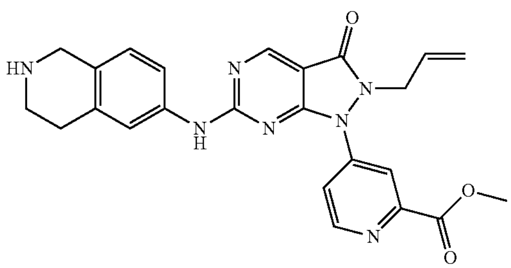 [SMILES: C=CCn1c(=O)c2cnc(Nc3ccc4c(c3)CCNC4)nc2n1-c1ccnc(C(=O)OC)c1] |
| 2.033 | 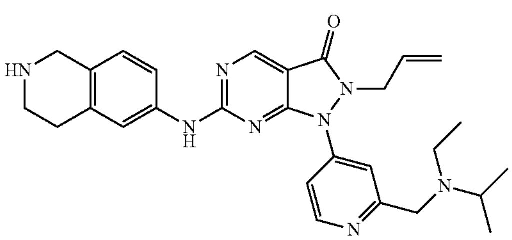 [SMILES: C=CCn1c(=O)c2cnc(Nc3ccc4c(c3)CCNC4)nc2n1-c1ccnc(CN(CC)C(C)C)c1] |
| 2.034 | 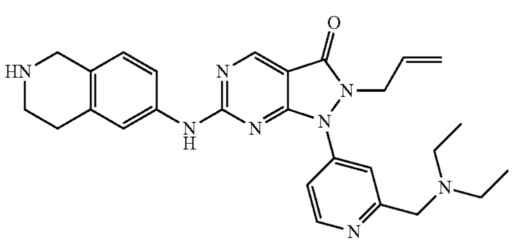 [SMILES: C=CCn1c(=O)c2cnc(Nc3ccc4c(c3)CCNC4)nc2n1-c1ccnc(CN(CC)CC)c1] |
| 2.035 | 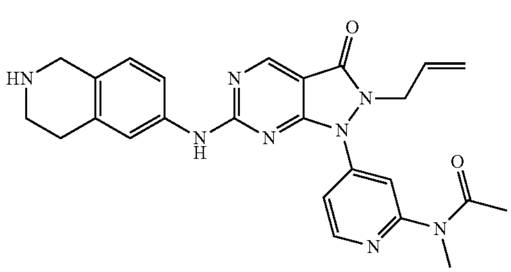 [SMILES: C=CCn1c(=O)c2cnc(Nc3ccc4c(c3)CCNC4)nc2n1-c1ccnc(N(C)C(C)=O)c1] |
| 2.036 | |
| 2.037 | |
| 2.038 | |
| 2.039 | |
| 2.040 | |

TABLE 1A-continued

| Compound No. | Structure |
|---|---|
| 2.041 | (structure) |
| 2.042 | (structure) |
| 2.043 | (structure) |
| 2.044 | (structure) |
| 2.045 | (structure) |
| 2.046 | (structure) |
| 2.047 | (structure) |
| 2.048 | (structure) |
| 2.049 | (structure) |
| 2.050 | (structure) |
| 2.051 | (structure) |

TABLE 1A-continued

| Compound No. | Structure |
|---|---|
| 2.052 | 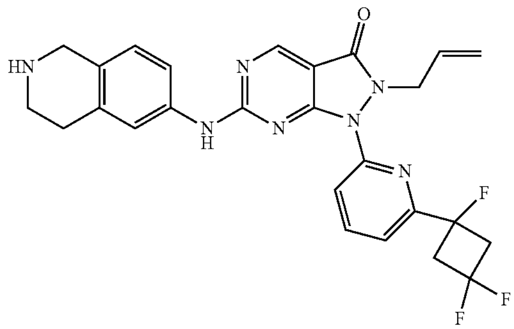 [SMILES: C=CCn1c(=O)c2cnc(Nc3ccc4c(c3)CCNC4)nc2n1-c1cccc(C2(F)CC(F)(F)C2)n1] |
| 2.053 | 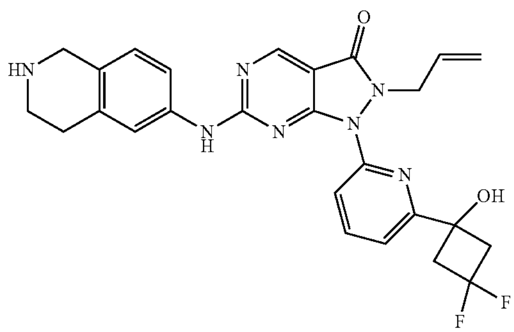 [SMILES: C=CCn1c(=O)c2cnc(Nc3ccc4c(c3)CCNC4)nc2n1-c1cccc(C2(O)CC(F)(F)C2)n1] |
| 2.054 | 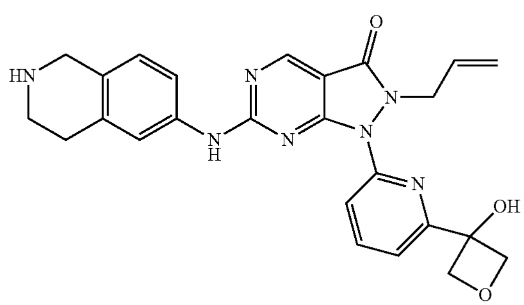 [SMILES: C=CCn1c(=O)c2cnc(Nc3ccc4c(c3)CCNC4)nc2n1-c1cccc(C2(O)COC2)n1] |
| 2.055 | 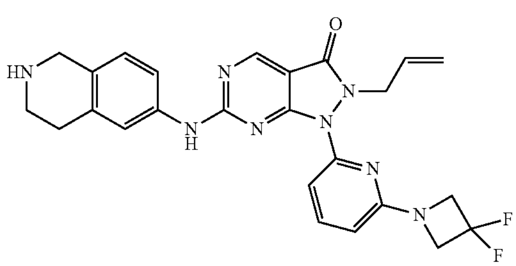 [SMILES: C=CCn1c(=O)c2cnc(Nc3ccc4c(c3)CCNC4)nc2n1-c1cccc(N2CC(F)(F)C2)n1] |
| 2.056 | 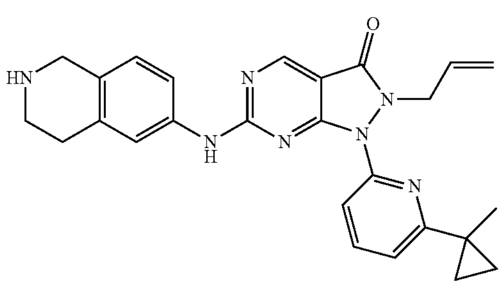 [SMILES: C=CCn1c(=O)c2cnc(Nc3ccc4c(c3)CCNC4)nc2n1-c1cccc(C2(C)CC2)n1] |
| 2.057 | |
| 2.058 | |
| 2.059 | |
| 2.060 | |
| 2.061 | |

TABLE 1A-continued

| Compound No. | Structure |
|---|---|
| 2.062 | *(structure)* |
| 2.063 | *(structure)* |
| 2.064 | *(structure)* |
| 2.065 | *(structure)* |
| 2.066 | *(structure)* |
| 2.067 | *(structure)* |
| 2.068 | *(structure)* |
| 2.069 | *(structure)* |
| 2.070 | *(structure)* |
| 2.071 | *(structure)* |
| 2.072 | *(structure)* |
| 2.073 | *(structure)* |

TABLE 1A-continued
| Compound No. | Structure |
|---|---|
| 2.074 | 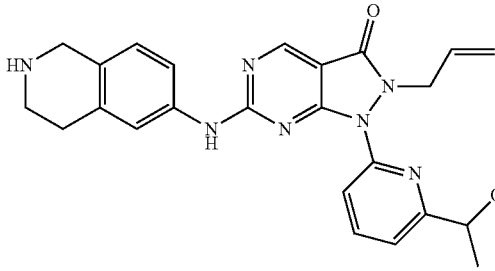 |
| 2.075 | 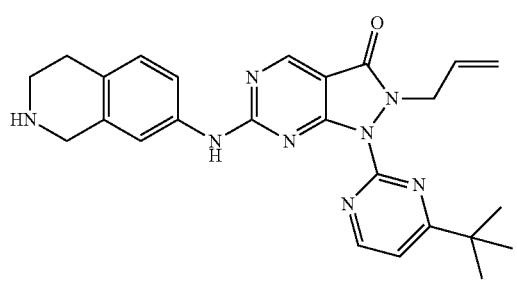 [SMILES: C=CCn1c(=O)c2cnc(Nc3ccc4c(c3)CNCC4)nc2n1-c1nccc(C(C)(C)C)n1] |
| 2.076 | 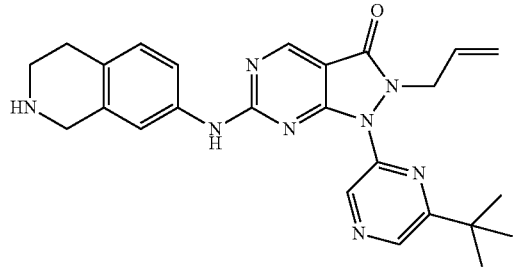 [SMILES: C=CCn1c(=O)c2cnc(Nc3ccc4c(c3)CNCC4)nc2n1-c1cncc(C(C)(C)C)n1] |
| 2.077 | 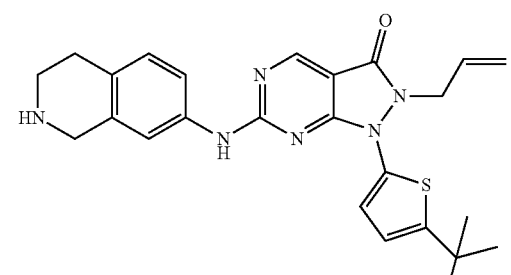 |
| 2.078 | 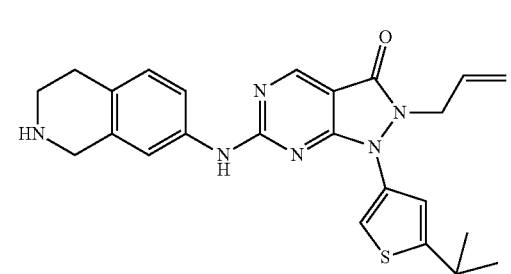 |
TABLE 1A-continued
| Compound No. | Structure |
|---|---|
| 2.079 | 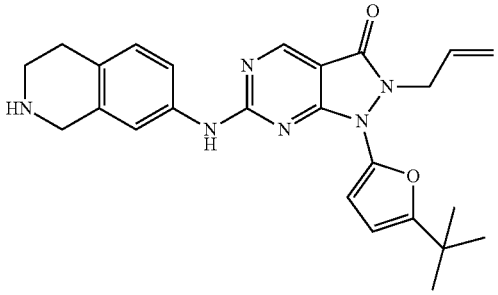 [SMILES: C=CCn1c(=O)c2cnc(Nc3ccc4c(c3)CNCC4)nc2n1-c1ccc(C(C)(C)C)o1] |
| 2.080 | 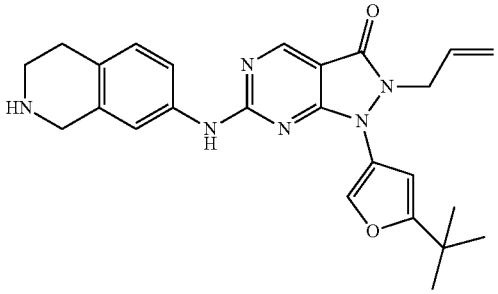 [SMILES: C=CCn1c(=O)c2cnc(Nc3ccc4c(c3)CNCC4)nc2n1-c1coc(C(C)(C)C)c1] |
| 2.081 | 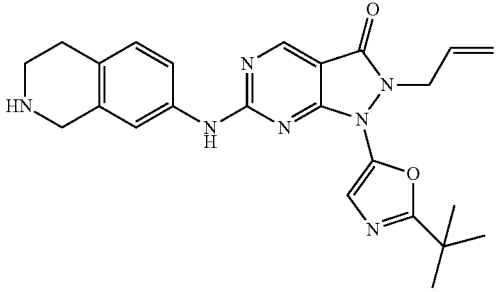 [SMILES: C=CCn1c(=O)c2cnc(Nc3ccc4c(c3)CNCC4)nc2n1-c1cnc(C(C)(C)C)o1] |
| 2.082 | 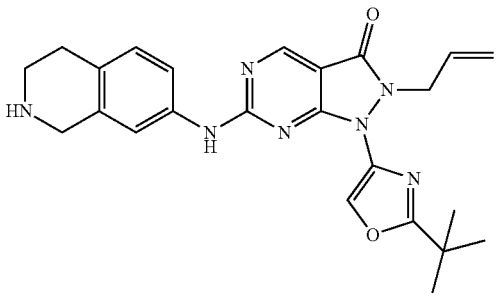 [SMILES: C=CCn1c(=O)c2cnc(Nc3ccc4c(c3)CNCC4)nc2n1-c1coc(C(C)(C)C)n1] |
| 2.083 | 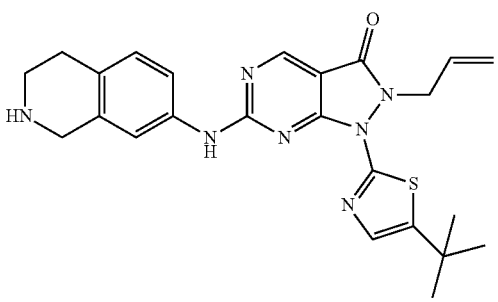 |

TABLE 1A-continued

| Compound No. | Structure |
|---|---|
| 2.084 | 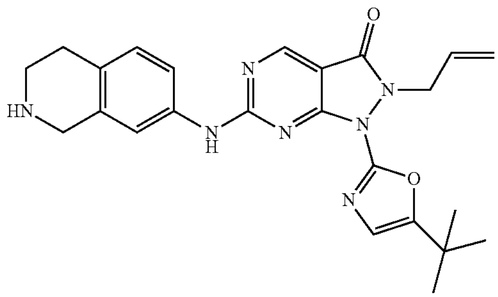 |
| 2.085 | 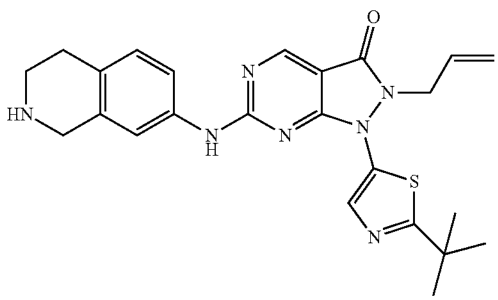 |
| 2.086 | 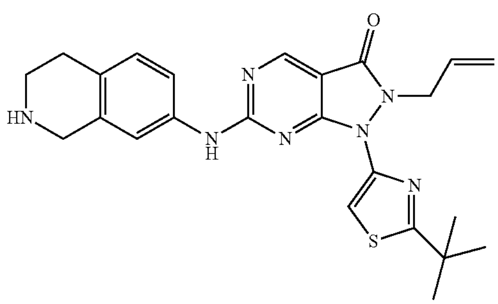 |
| 2.087 | 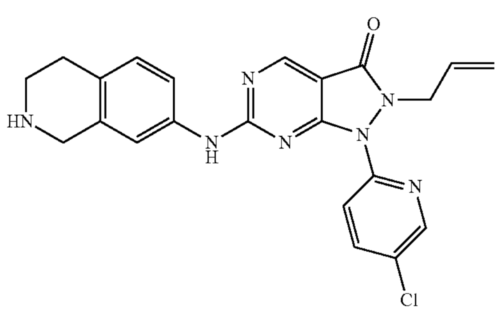 |
| 2.088 | 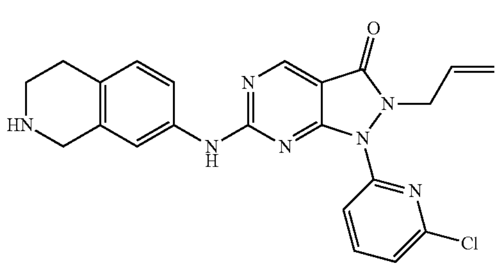 [SMILES: C=CCn1c(=O)c2cnc(Nc3ccc4c(c3)CNCC4)nc2n1-c1cccc(Cl)n1] |
| 2.089 | |
| 2.090 | |
| 2.091 | |
| 2.092 | |
| 2.093 | |

TABLE 1A-continued
| Compound No. | Structure |
|---|---|
| 2.094 | 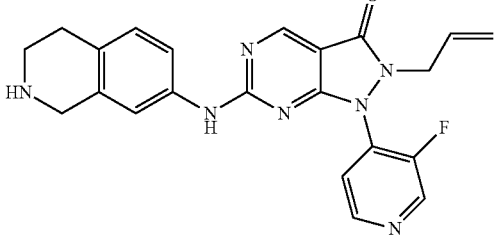 |
| 2.095 | 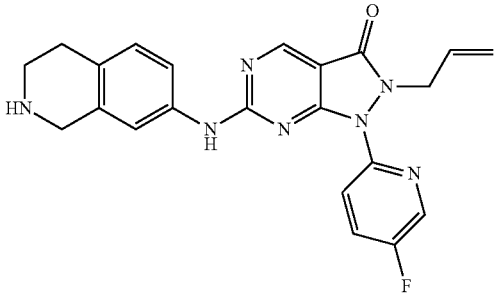 [SMILES: C=CCn1c(=O)c2cnc(Nc3ccc4c(c3)CNCC4)nc2n1-c1ccc(F)cn1] |
| 2.096 | 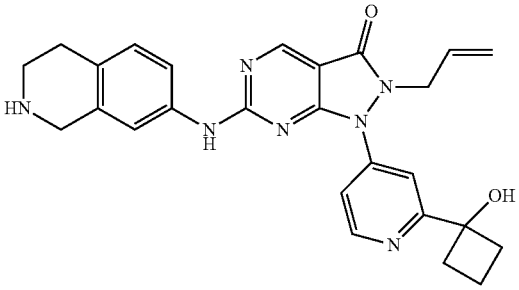 [SMILES: C=CCn1c(=O)c2cnc(Nc3ccc4c(c3)CNCC4)nc2n1-c1ccnc(C2(O)CCC2)c1] |
| 2.097 | 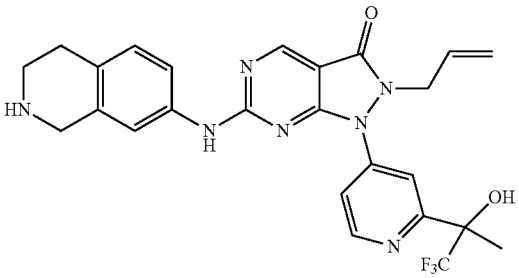 [SMILES: C=CCn1c(=O)c2cnc(Nc3ccc4c(c3)CNCC4)nc2n1-c1ccnc(C(C)(O)C(F)(F)F)c1] |
| 2.098 | 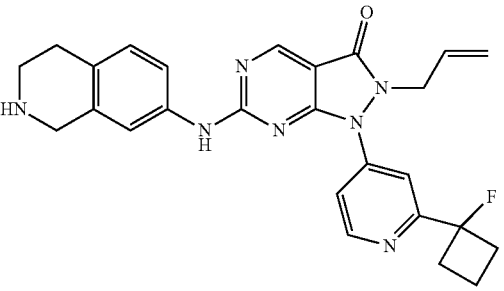 [SMILES: C=CCn1c(=O)c2cnc(Nc3ccc4c(c3)CNCC4)nc2n1-c1ccnc(C2(F)CCC2)c1] |
| 2.099 | 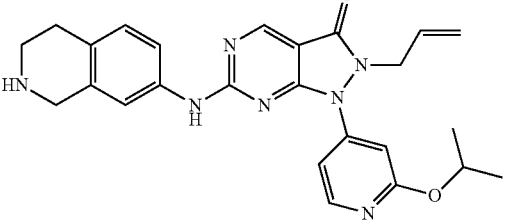 |
| 2.100 | 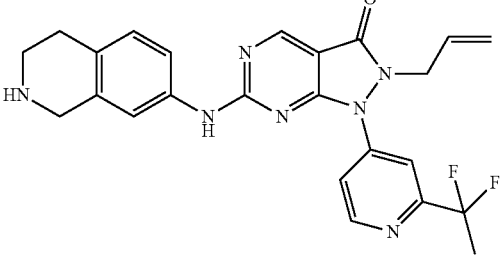 |
| 2.101 | 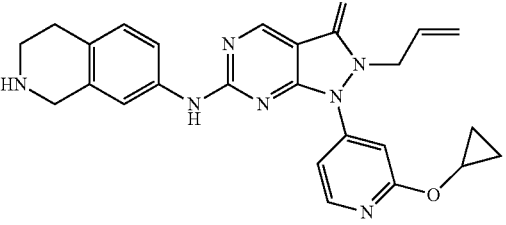 |
| 2.102 | 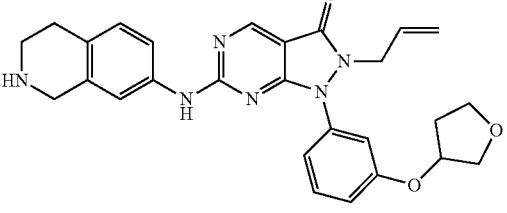 |
| 2.103 | 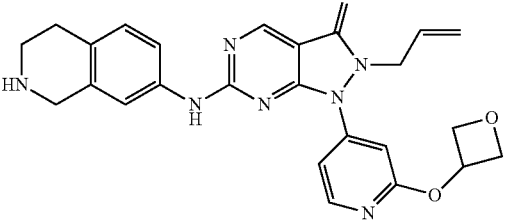 |
| 2.104 | 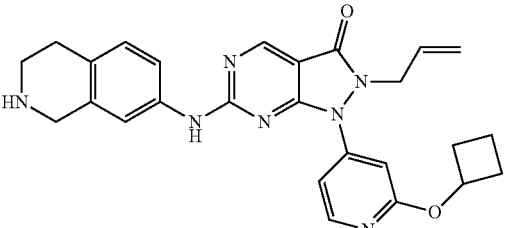 |

TABLE 1A-continued

| Compound No. | Structure |
|---|---|
| 2.105 | 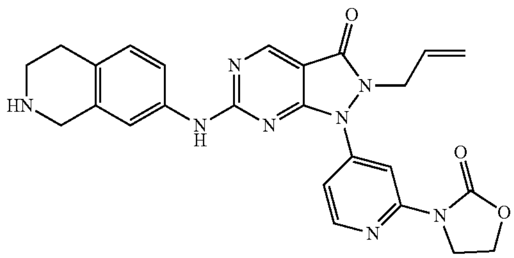 [SMILES: C=CCn1c(=O)c2cnc(Nc3ccc4c(c3)CNCC4)nc2n1-c1ccnc(N2CCOC2=O)c1] |
| 2.106 | 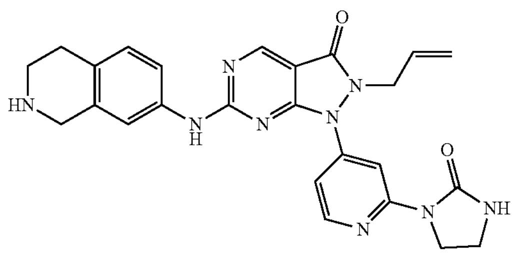 [SMILES: C=CCn1c(=O)c2cnc(Nc3ccc4c(c3)CNCC4)nc2n1-c1ccnc(N2CCNC2=O)c1] |
| 2.107 | 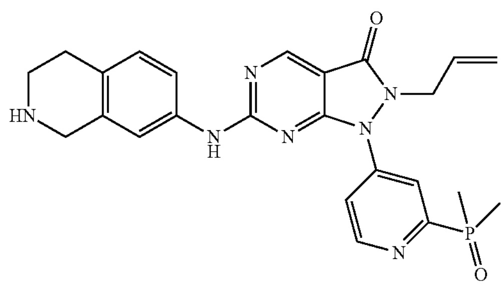 [SMILES: C=CCn1c(=O)c2cnc(Nc3ccc4c(c3)CNCC4)nc2n1-c1ccnc(P(C)(C)=O)c1] |
| 2.108 | 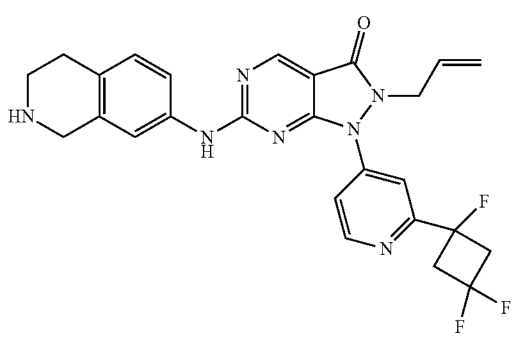 [SMILES: C=CCn1c(=O)c2cnc(Nc3ccc4c(c3)CNCC4)nc2n1-c1ccnc(C2(F)CC(F)(F)C2)c1] |
| 2.109 | 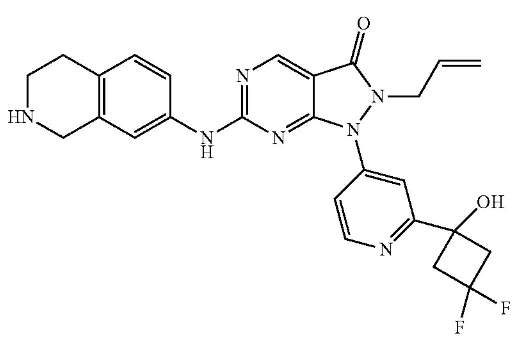 [SMILES: C=CCn1c(=O)c2cnc(Nc3ccc4c(c3)CNCC4)nc2n1-c1ccnc(C2(O)CC(F)(F)C2)c1] |
| 2.110 | |
| 2.111 | |
| 2.112 | |
| 2.113 | |
| 2.114 | |

TABLE 1A-continued

| Compound No. | Structure |
|---|---|
| 2.115 | |
| 2.116 | |
| 2.117 | |
| 2.118 | |
| 2.119 | |
| 2.120 | 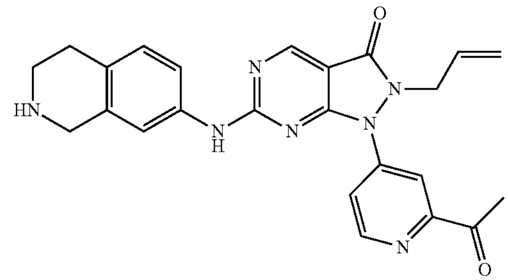 [SMILES: C=CCn1c(=O)c2cnc(Nc3ccc4c(c3)CNCC4)nc2n1-c1ccnc(C(C)=O)c1] |
| 2.121 | 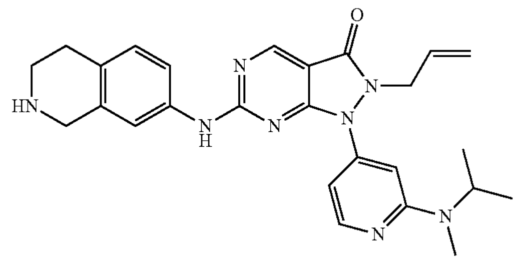 [SMILES: C=CCn1c(=O)c2cnc(Nc3ccc4c(c3)CNCC4)nc2n1-c1ccnc(N(C)C(C)C)c1] |
| 2.122 | 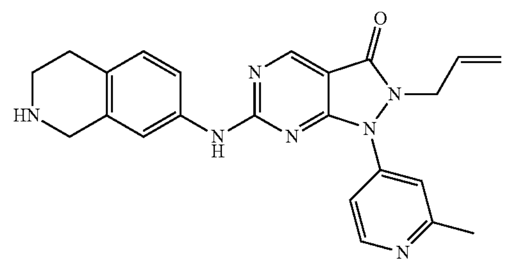 |
| 2.123 | 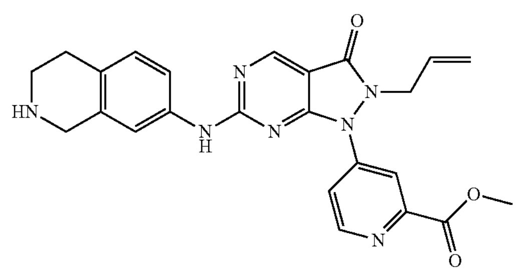 [SMILES: C=CCn1c(=O)c2cnc(Nc3ccc4c(c3)CNCC4)nc2n1-c1ccnc(C(=O)OC)c1] |
| 2.124 | 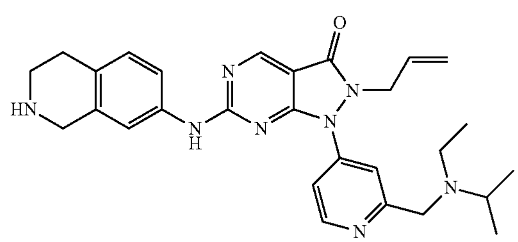 [SMILES: C=CCn1c(=O)c2cnc(Nc3ccc4c(c3)CNCC4)nc2n1-c1ccnc(CN(CC)C(C)C)c1] |
| 2.125 | 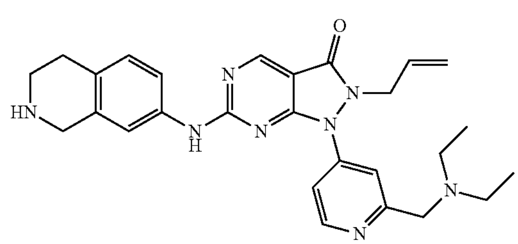 [SMILES: C=CCn1c(=O)c2cnc(Nc3ccc4c(c3)CNCC4)nc2n1-c1ccnc(CN(CC)CC)c1] |

TABLE 1A-continued
| Compound No. | Structure |
|---|---|
| 2.126 | 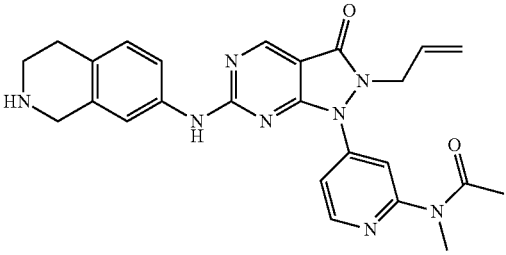 |
| 2.127 | 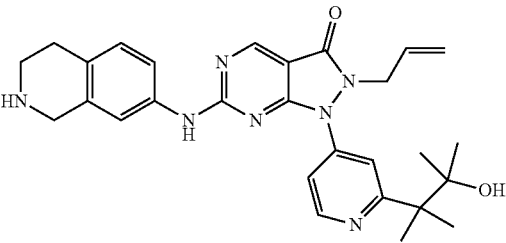 [SMILES: C=CCn1c(=O)c2cnc(Nc3ccc4c(c3)CNCC4)nc2n1-c1ccnc(C(C)(C)C(C)(C)O)c1] |
| 2.128 | 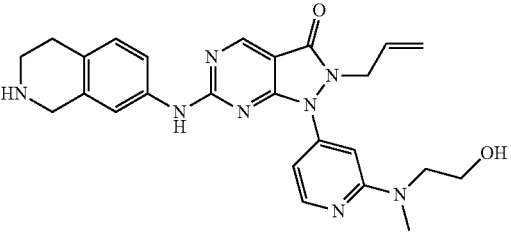 [SMILES: C=CCn1c(=O)c2cnc(Nc3ccc4c(c3)CNCC4)nc2n1-c1ccnc(N(C)CCO)c1] |
| 2.129 | 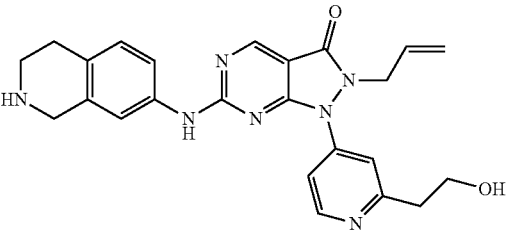 [SMILES: C=CCn1c(=O)c2cnc(Nc3ccc4c(c3)CNCC4)nc2n1-c1ccnc(CCO)c1] |
| 2.130 | 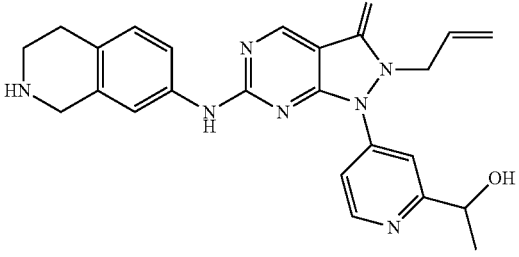 |
| 2.131 | 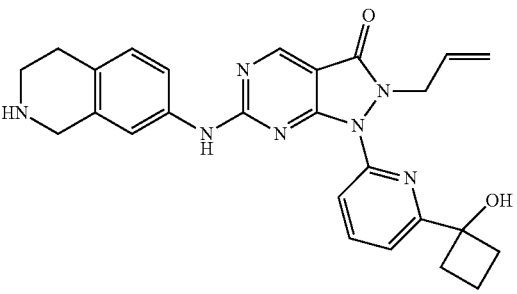 [SMILES: C=CCn1c(=O)c2cnc(Nc3ccc4c(c3)CNCC4)nc2n1-c1cccc(C2(O)CCC2)n1] |
| 2.132 | 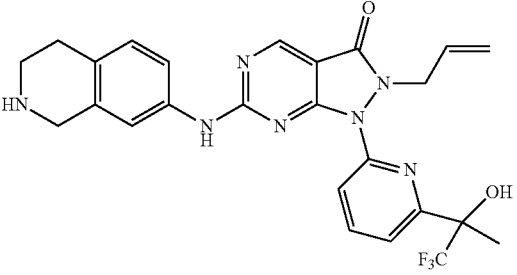 |
| 2.133 | 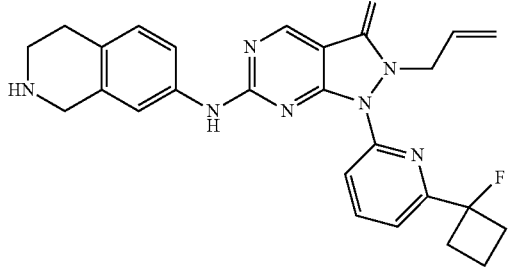 |
| 2.134 | 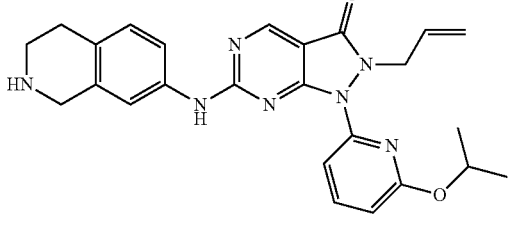 |
| 2.135 | 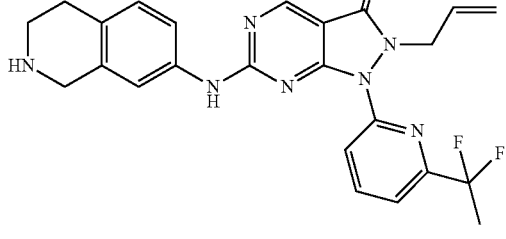 |

TABLE 1A-continued
| Compound No. | Structure |
|---|---|
| 2.136 | 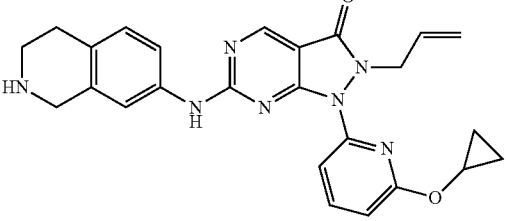 |
| 2.137 | 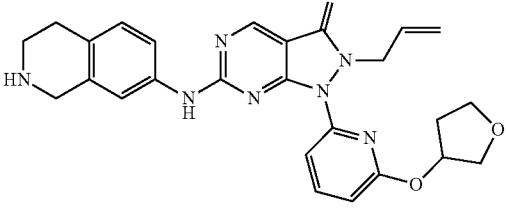 |
| 2.138 | 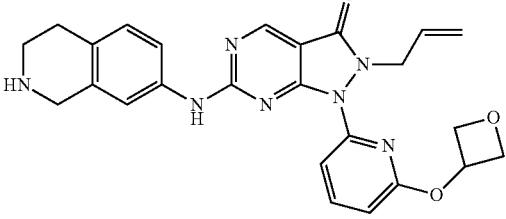 |
| 2.139 | 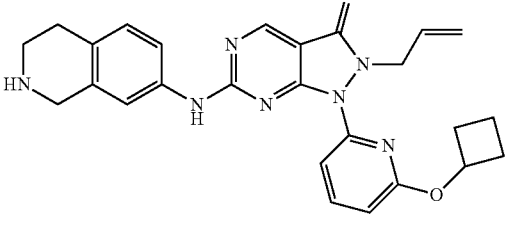 |
| 2.140 | 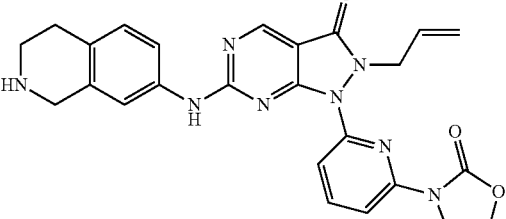 |
| 2.141 | 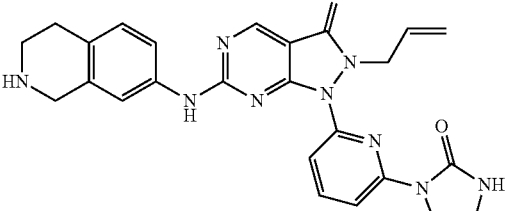 |
| 2.142 | 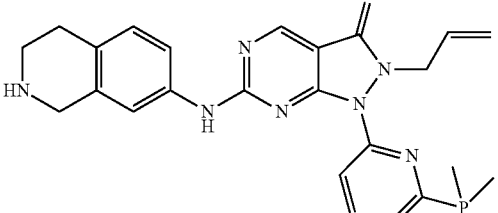 |
| 2.143 | 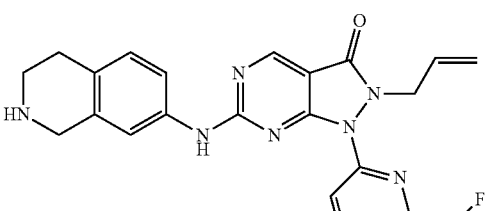 |
| 2.144 | 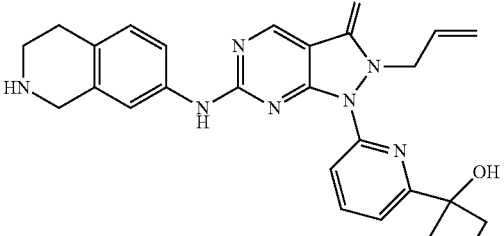 |
| 2.145 | 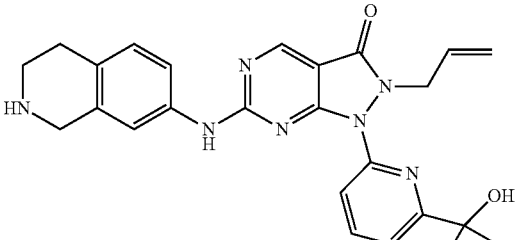 |
| 2.146 | 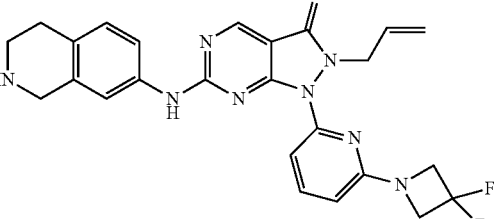 |

TABLE 1A-continued

| Compound No. | Structure |
|---|---|
| 2.147 | |
| 2.148 | |
| 2.149 | |
| 2.150 | |
| 2151 | |
| 2.152 | 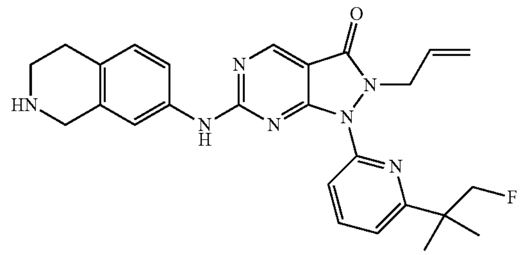 [SMILES: C=CCn1c(=O)c2cnc(Nc3ccc4c(c3)CNCC4)nc2n1-c1cccc(C(C)(C)CF)n1] |
| 2.153 | 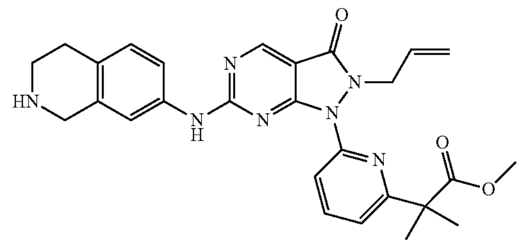 [SMILES: C=CCn1c(=O)c2cnc(Nc3ccc4c(c3)CNCC4)nc2n1-c1cccc(C(C)(C)C(=O)OC)n1] |
| 2.154 | 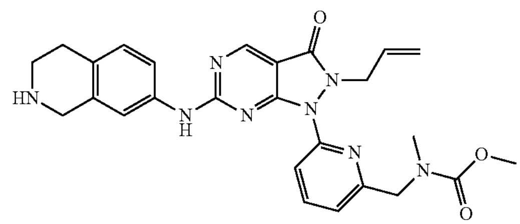 [SMILES: C=CCn1c(=O)c2cnc(Nc3ccc4c(c3)CNCC4)nc2n1-c1cccc(CN(C)C(=O)OC)n1] |
| 2.155 | 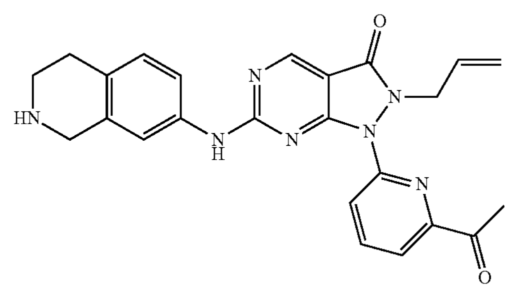 [SMILES: C=CCn1c(=O)c2cnc(Nc3ccc4c(c3)CNCC4)nc2n1-c1cccc(C(C)=O)n1] |
| 2.156 | 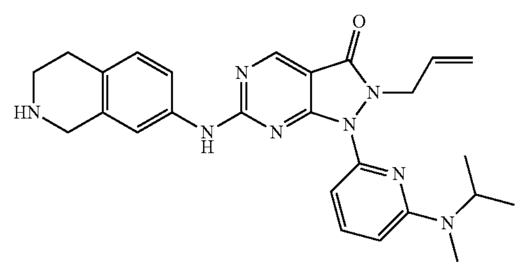 [SMILES: C=CCn1c(=O)c2cnc(Nc3ccc4c(c3)CNCC4)nc2n1-c1cccc(N(C)C(C)C)n1] |
| 2.157 | 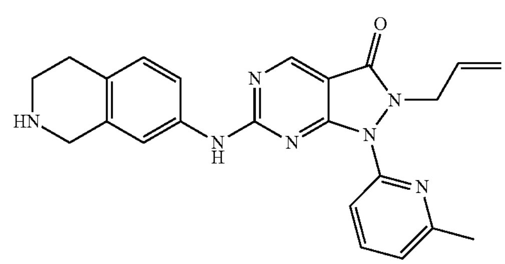 |

TABLE 1A-continued

| Compound No. | Structure |
|---|---|
| 2.158 | 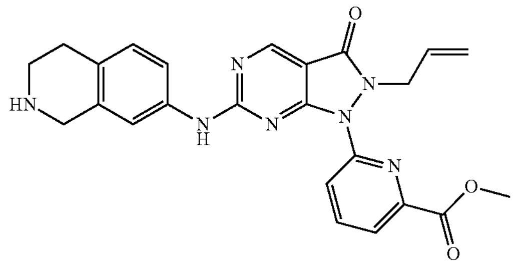 [SMILES: C=CCn1c(=O)c2cnc(Nc3ccc4c(c3)CNCC4)nc2n1-c1cccc(C(=O)OC)n1] |
| 2.159 | 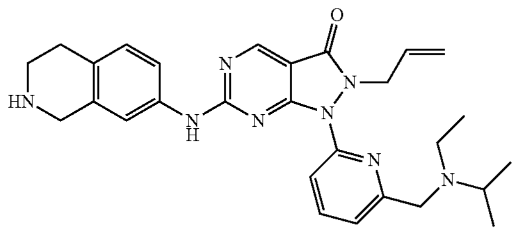 [SMILES: C=CCn1c(=O)c2cnc(Nc3ccc4c(c3)CNCC4)nc2n1-c1cccc(CN(CC)C(C)C)n1] |
| 2.160 | 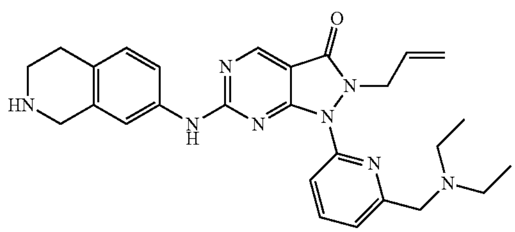 [SMILES: C=CCn1c(=O)c2cnc(Nc3ccc4c(c3)CNCC4)nc2n1-c1cccc(CN(CC)CC)n1] |
| 2.161 | 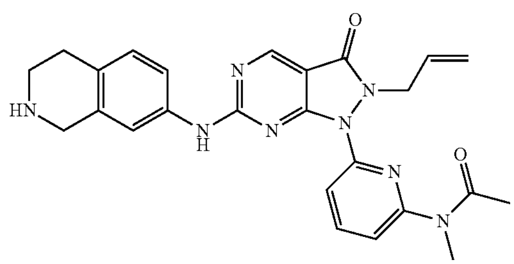 [SMILES: C=CCn1c(=O)c2cnc(Nc3ccc4c(c3)CNCC4)nc2n1-c1cccc(N(C)C(C)=O)n1] |
| 2.162 | 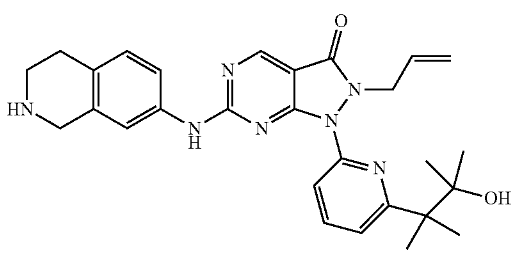 [SMILES: C=CCn1c(=O)c2cnc(Nc3ccc4c(c3)CNCC4)nc2n1-c1cccc(C(C)(C)C(C)(C)O)n1] |
| 2.163 | 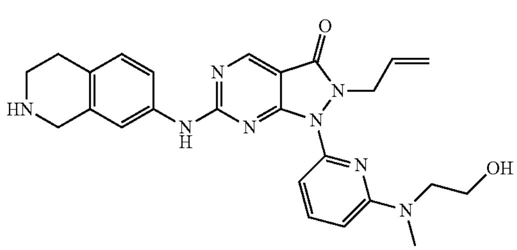 [SMILES: C=CCn1c(=O)c2cnc(Nc3ccc4c(c3)CNCC4)nc2n1-c1cccc(N(C)CCO)n1] |
| 2.164 | 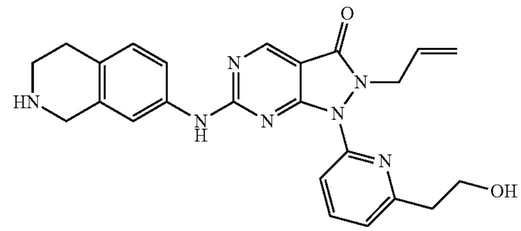 [SMILES: C=CCn1c(=O)c2cnc(Nc3ccc4c(c3)CNCC4)nc2n1-c1cccc(CCO)n1] |
| 2.165 | 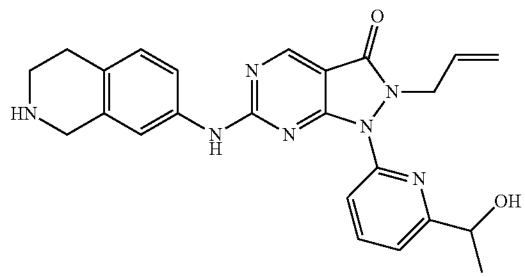 [SMILES: C=CCn1c(=O)c2cnc(Nc3ccc4c(c3)CNCC4)nc2n1-c1cccc(C(C)O)n1] |
| 2.166 | 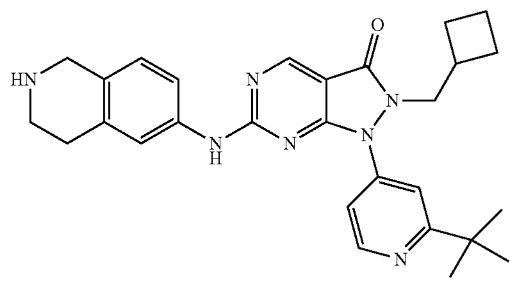 [SMILES: CC(C)(C)c1cc(-n2c3nc(Nc4ccc5c(c4)CCNC5)ncc3c(=O)n2CC2CCC2)ccn1] |
| 2.167 | 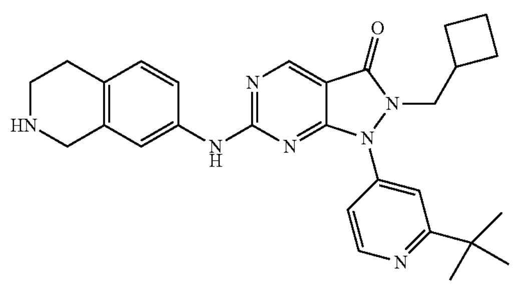 [SMILES: CC(C)(C)c1cc(-n2c3nc(Nc4ccc5c(c4)CNCC5)ncc3c(=O)n2CC2CCC2)ccn1] |
| 2.168 | 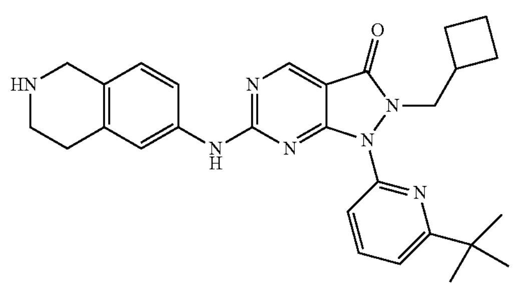 [SMILES: CC(C)(C)c1cccc(-n2c3nc(Nc4ccc5c(c4)CCNC5)ncc3c(=O)n2CC2CCC2)n1] |

TABLE 1A-continued
| Compound No. | Structure |
|---|---|
| 2.169 | 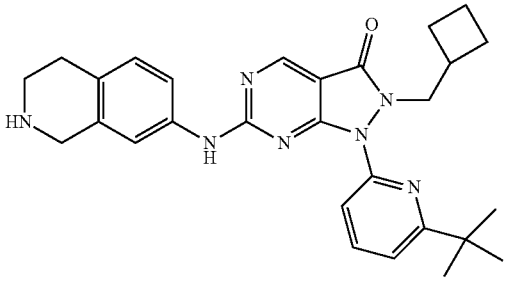 [SMILES: CC(C)(C)c1cccc(-n2c3nc(Nc4ccc5c(c4)CNCC5)ncc3c(=O)n2CC2CCC2)n1] |
| 2.170 | 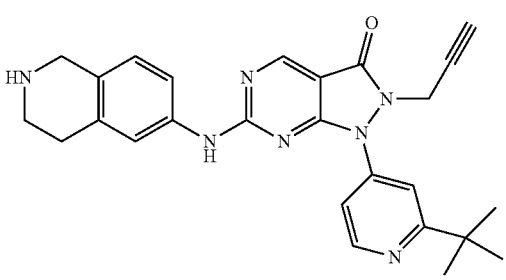 [SMILES: C#CCn1c(=O)c2cnc(Nc3ccc4c(c3)CCNC4)nc2n1-c1ccnc(C(C)(C)C)c1] |
| 2.171 | 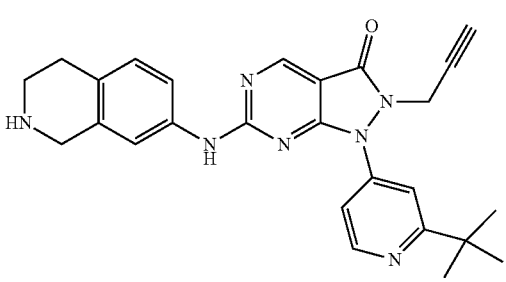 [SMILES: C#CCn1c(=O)c2cnc(Nc3ccc4c(c3)CNCC4)nc2n1-c1ccnc(C(C)(C)C)c1] |
| 2.172 | 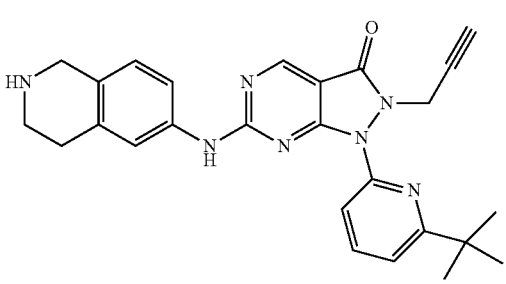 [SMILES: C#CCn1c(=O)c2cnc(Nc3ccc4c(c3)CCNC4)nc2n1-c1cccc(C(C)(C)C)n1] |
| 2.173 | 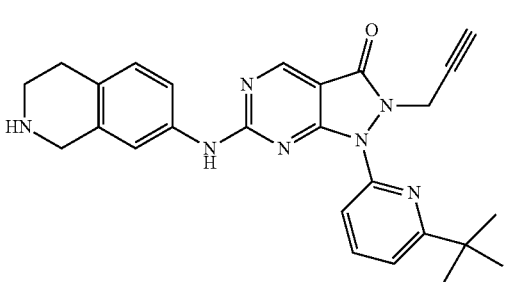 [SMILES: C#CCn1c(=O)c2cnc(Nc3ccc4c(c3)CNCC4)nc2n1-c1cccc(C(C)(C)C)n1] |
| 2.174 | 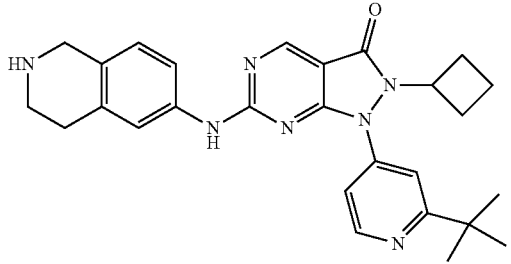 [SMILES: CC(C)(C)c1cc(-n2c3nc(Nc4ccc5c(c4)CCNC5)ncc3c(=O)n2C2CCC2)ccn1] |
| 2.175 | 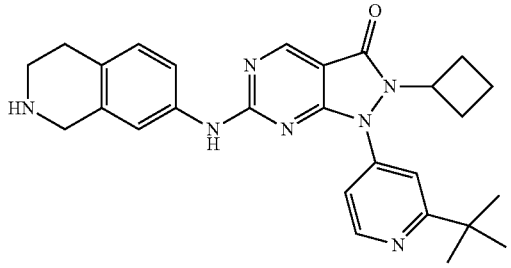 [SMILES: CC(C)(C)c1cc(-n2c3nc(Nc4ccc5c(c4)CNCC5)ncc3c(=O)n2C2CCC2)ccn1] |
| 2.176 | 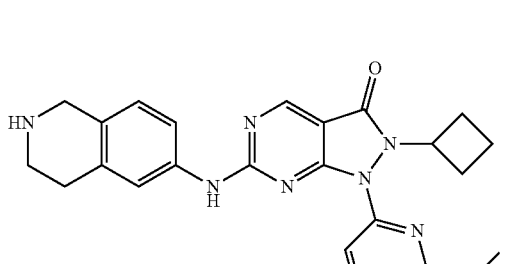 |
| 2.177 | 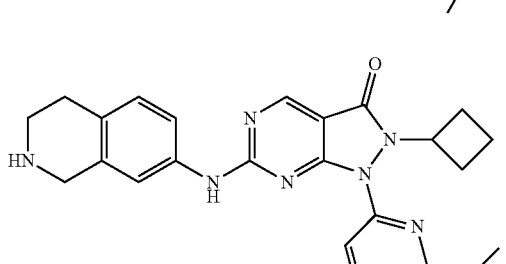 |
| 2.178 | 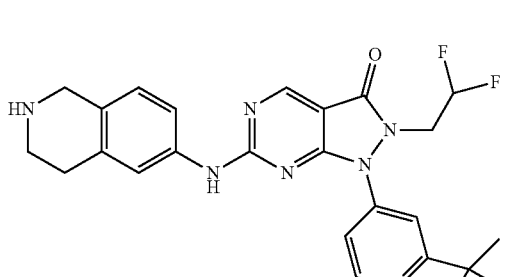 |

TABLE 1A-continued

| Compound No. | Structure |
|---|---|
| 2.179 | 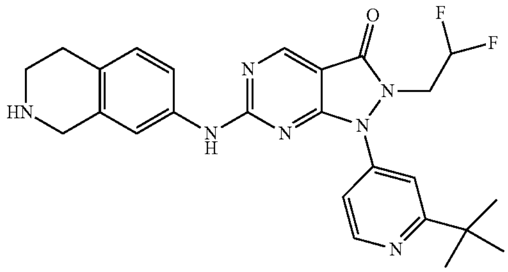 [SMILES: CC(C)(C)c1cc(-n2c3nc(Nc4ccc5c(c4)CNCC5)ncc3c(=O)n2CC(F)F)ccn1] |
| 2.180 | 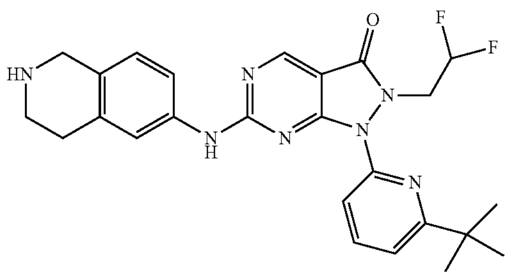 [SMILES: CC(C)(C)c1cccc(-n2c3nc(Nc4ccc5c(c4)CCNC5)ncc3c(=O)n2CC(F)F)n1] |
| 2.181 | 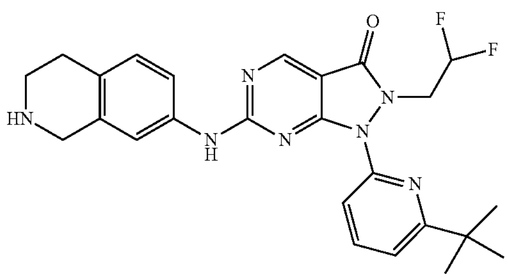 [SMILES: CC(C)(C)c1cccc(-n2c3nc(Nc4ccc5c(c4)CNCC5)ncc3c(=O)n2CC(F)F)n1] |
| 2.182 | 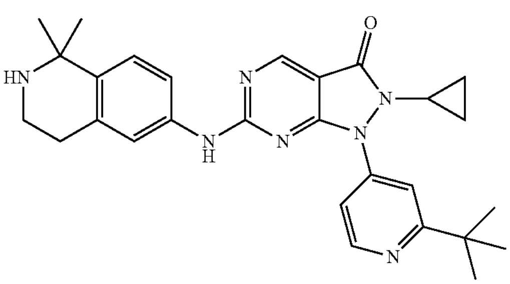 [SMILES: CC(C)(C)c1cc(-n2c3nc(Nc4ccc5c(c4)CCNC5(C)C)ncc3c(=O)n2C2CC2)ccn1] |
| 2.183 | 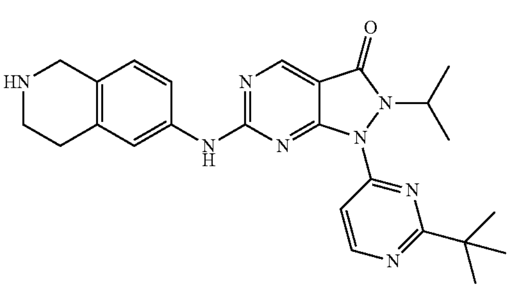 [SMILES: CC(C)n1c(=O)c2cnc(Nc3ccc4c(c3)CCNC4)nc2n1-c1ccnc(C(C)(C)C)n1] |
| 2.184 | |
| 2.185 | |
| 2.186 | |
| 2.187 | |
| 2.188 | |

TABLE 1A-continued

| Compound No. | Structure |
|---|---|
| 2.189 | |
| 2.190 | |
| 2.191 | |
| 2.192 | |
| 2.193 | |
| 2.194 | 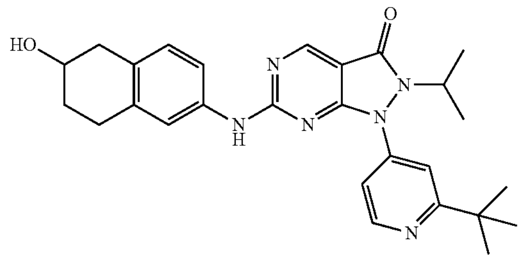 [SMILES: CC(C)n1c(=O)c2cnc(Nc3ccc4c(c3)CCC(O)C4)nc2n1-c1ccnc(C(C)(C)C)c1] |
| 2.195 | 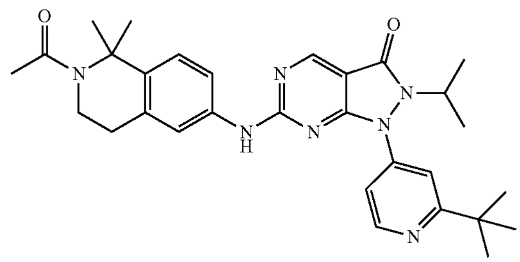 [SMILES: CC(=O)N1CCc2cc(Nc3ncc4c(=O)n(C(C)C)n(-c5ccnc(C(C)(C)C)c5)c4n3)ccc2C1(C)C] |
| 2.196 | 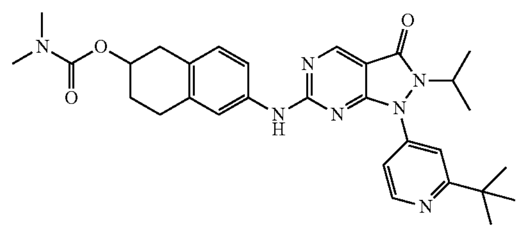 [SMILES: CC(C)n1c(=O)c2cnc(Nc3ccc4c(c3)CCC(OC(=O)N(C)C)C4)nc2n1-c1ccnc(C(C)(C)C)c1] |
| 2.197 | 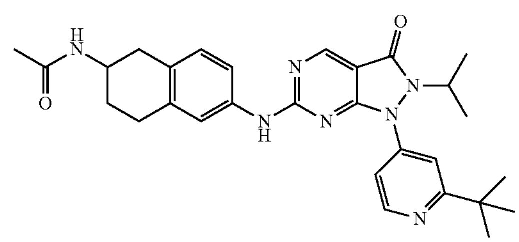 [SMILES: CC(=O)NC1CCc2cc(Nc3ncc4c(=O)n(C(C)C)n(-c5ccnc(C(C)(C)C)c5)c4n3)ccc2C1] |
| 2.198 | 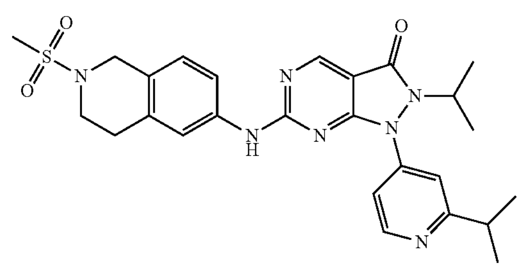 [SMILES: CC(C)c1cc(-n2c3nc(Nc4ccc5c(c4)CCN(S(C)(=O)=O)C5)ncc3c(=O)n2C(C)C)ccn1] |
| 2.199 | 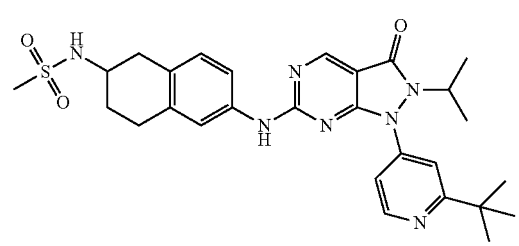 [SMILES: CC(C)n1c(=O)c2cnc(Nc3ccc4c(c3)CCC(NS(C)(=O)=O)C4)nc2n1-c1ccnc(C(C)(C)C)c1] |

TABLE 1A-continued

| Compound No. | Structure |
|---|---|
| 2.200 | 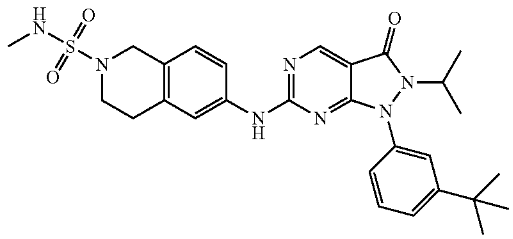 [SMILES: CNS(=O)(=O)N1CCc2cc(Nc3ncc4c(=O)n(C(C)C)n(-c5cccc(C(C)(C)C)c5)c4n3)ccc2C1] |
| 2.201 | 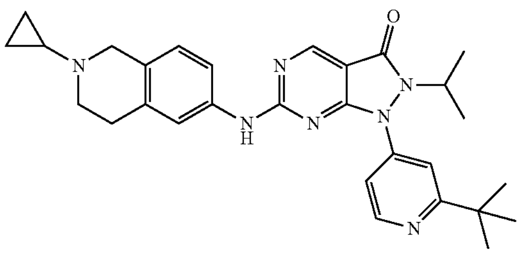 [SMILES: CC(C)n1c(=O)c2cnc(Nc3ccc4c(c3)CCN(C3CC3)C4)nc2n1-c1ccnc(C(C)(C)C)c1] |
| 2.202 | 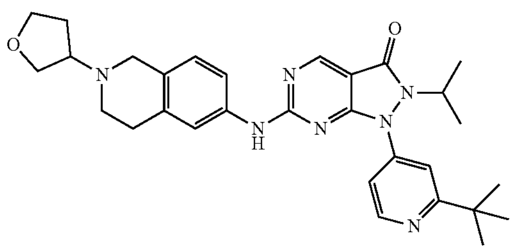 [SMILES: CC(C)n1c(=O)c2cnc(Nc3ccc4c(c3)CCN(C3CCOC3)C4)nc2n1-c1ccnc(C(C)(C)C)c1] |
| 2.203 | 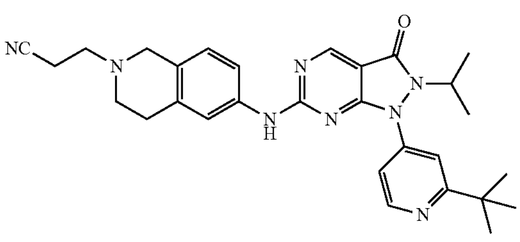 [SMILES: CC(C)n1c(=O)c2cnc(Nc3ccc4c(c3)CCN(CCC#N)C4)nc2n1-c1ccnc(C(C)(C)C)c1] |
| 2.204 | 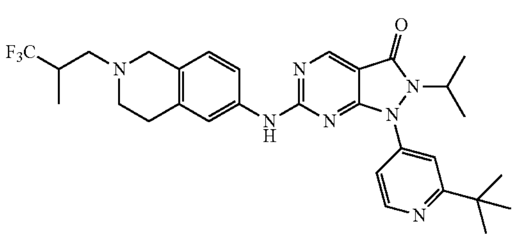 [SMILES: CC(C)n1c(=O)c2cnc(Nc3ccc4c(c3)CCN(CC(C)C(F)(F)F)C4)nc2n1-c1ccnc(C(C)(C)C)c1] |
| 2.205 | 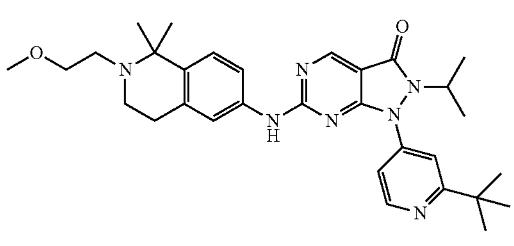 [SMILES: COCCN1CCc2cc(Nc3ncc4c(=O)n(C(C)C)n(-c5ccnc(C(C)(C)C)c5)c4n3)ccc2C1(C)C] |
| 2.206 | 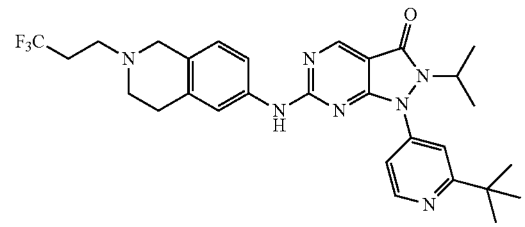 [SMILES: CC(C)n1c(=O)c2cnc(Nc3ccc4c(c3)CCN(CCC(F)(F)F)C4)nc2n1-c1ccnc(C(C)(C)C)c1] |
| 2.207 | 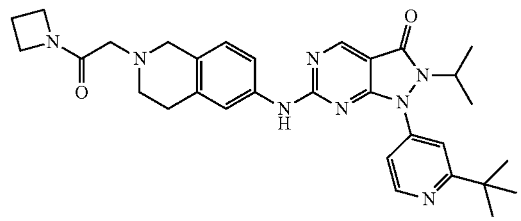 [SMILES: CC(C)n1c(=O)c2cnc(Nc3ccc4c(c3)CCN(CC(=O)N3CCC3)C4)nc2n1-c1ccnc(C(C)(C)C)c1] |
| 2.208 | 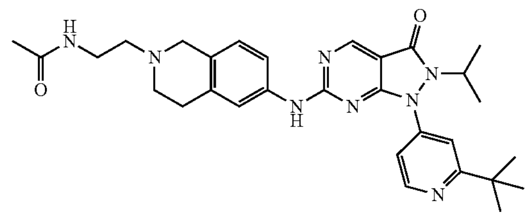 [SMILES: CC(=O)NCCN1CCc2cc(Nc3ncc4c(=O)n(C(C)C)n(-c5ccnc(C(C)(C)C)c5)c4n3)ccc2C1] |
| 2.209 | 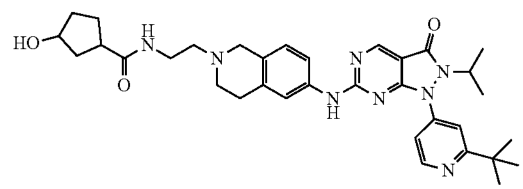 [SMILES: CC(C)n1c(=O)c2cnc(Nc3ccc4c(c3)CCN(CCNC(=O)C3CCC(O)C3)C4)nc2n1-c1ccnc(C(C)(C)C)c1] |
| 2.210 | 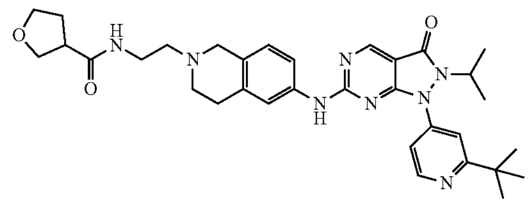 [SMILES: CC(C)n1c(=O)c2cnc(Nc3ccc4c(c3)CCN(CCNC(=O)C3CCOC3)C4)nc2n1-c1ccnc(C(C)(C)C)c1] |
| 2.211 | 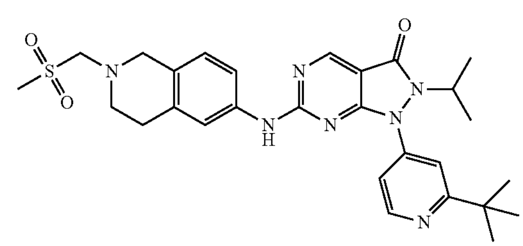 [SMILES: CC(C)n1c(=O)c2cnc(Nc3ccc4c(c3)CCN(CS(C)(=O)=O)C4)nc2n1-c1ccnc(C(C)(C)C)c1] |
| 2.212 | 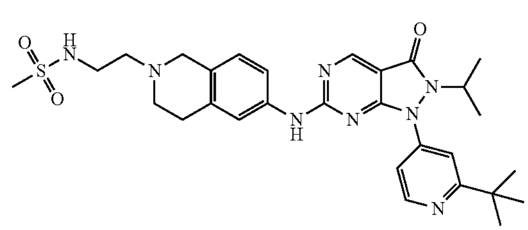 [SMILES: CC(C)n1c(=O)c2cnc(Nc3ccc4c(c3)CCN(CCNS(C)(=O)=O)C4)nc2n1-c1ccnc(C(C)(C)C)c1] |

TABLE 1A-continued

| Compound No. | Structure |
|---|---|
| 2.213 | 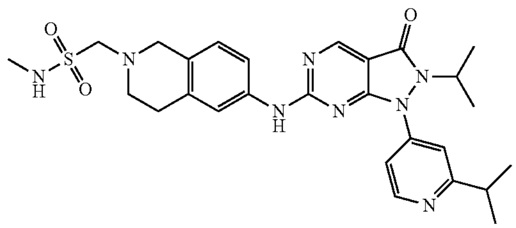 [SMILES: CNS(=O)(=O)CN1CCc2cc(Nc3ncc4c(=O)n(C(C)C)n(-c5ccnc(C(C)C)c5)c4n3)ccc2C1] |
| 2.214 | 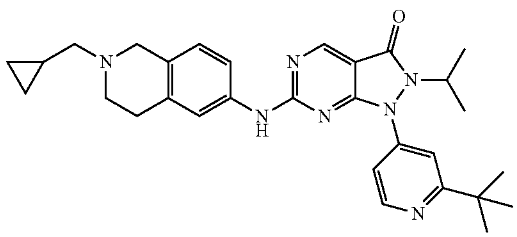 [SMILES: CC(C)n1c(=O)c2cnc(Nc3ccc4c(c3)CCN(CC3CC3)C4)nc2n1-c1ccnc(C(C)(C)C)c1] |
| 2.215 | 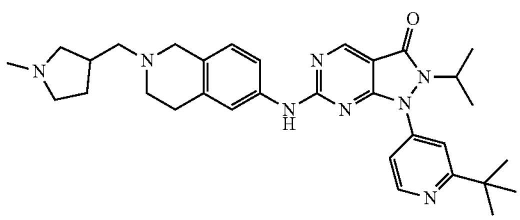 [SMILES: CC(C)n1c(=O)c2cnc(Nc3ccc4c(c3)CCN(CC3CCN(C)C3)C4)nc2n1-c1ccnc(C(C)(C)C)c1] |
| 2.216 | 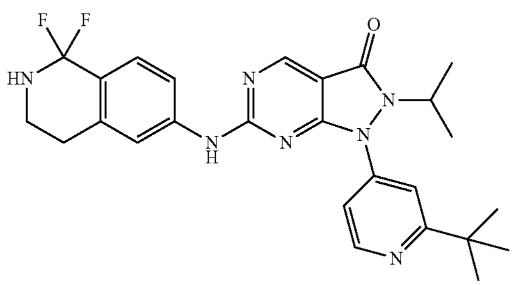 [SMILES: CC(C)n1c(=O)c2cnc(Nc3ccc4c(c3)CCNC4(F)F)nc2n1-c1ccnc(C(C)(C)C)c1] |
| 2.217 | 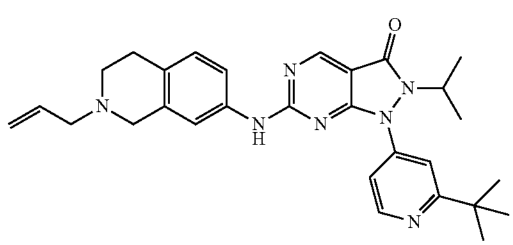 [SMILES: C=CCN1CCc2ccc(Nc3ncc4c(=O)n(C(C)C)n(-c5ccnc(C(C)(C)C)c5)c4n3)cc2C1] |
| 2.218 | 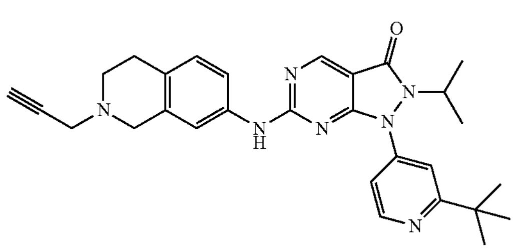 [SMILES: C#CCN1CCc2ccc(Nc3ncc4c(=O)n(C(C)C)n(-c5ccnc(C(C)(C)C)c5)c4n3)cc2C1] |
| 2.219 | |
| 2.220 | |
| 2.221 | |
| 2.222 | |
| 2.223 | |
| 2.224 | |

TABLE 1A-continued

| Compound No. | Structure |
|---|---|
| 2.225 | |
| 2.226 | |
| 2.227 | |
| 2.228 | |
| 2.229 | |
| 2.230 | |
| 2.231 | 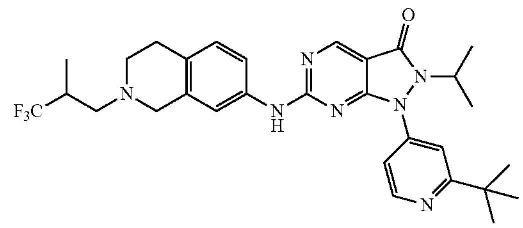 [SMILES: CC(C)n1c(=O)c2cnc(Nc3ccc4c(c3)CN(CC(C)C(F)(F)F)CC4)nc2n1-c1ccnc(C(C)(C)C)c1] |
| 2.232 | 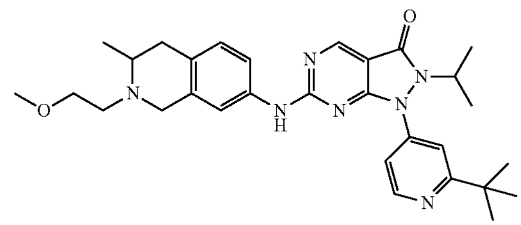 [SMILES: COCCN1Cc2cc(Nc3ncc4c(=O)n(C(C)C)n(-c5ccnc(C(C)(C)C)c5)c4n3)ccc2CC1C] |
| 2.233 | 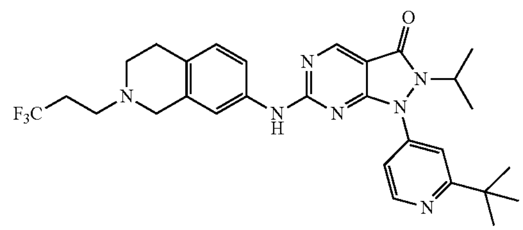 [SMILES: CC(C)n1c(=O)c2cnc(Nc3ccc4c(c3)CN(CCC(F)(F)F)CC4)nc2n1-c1ccnc(C(C)(C)C)c1] |
| 2.234 | 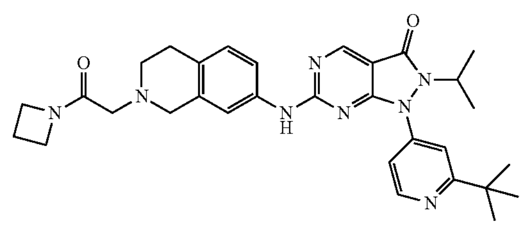 [SMILES: CC(C)n1c(=O)c2cnc(Nc3ccc4c(c3)CN(CC(=O)N3CCC3)CC4)nc2n1-c1ccnc(C(C)(C)C)c1] |
| 2.235 | 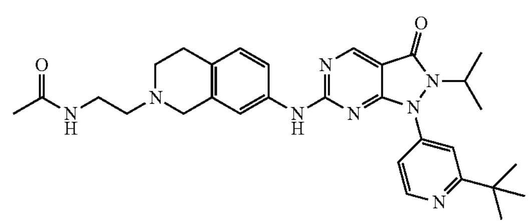 [SMILES: CC(=O)NCCN1CCc2ccc(Nc3ncc4c(=O)n(C(C)C)n(-c5ccnc(C(C)(C)C)c5)c4n3)cc2C1] |
| 2.236 | 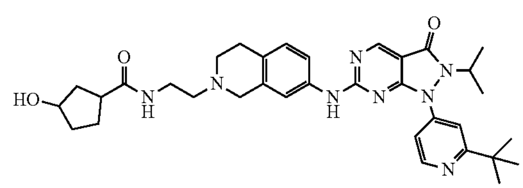 [SMILES: CC(C)n1c(=O)c2cnc(Nc3ccc4c(c3)CN(CCNC(=O)C3CCC(O)C3)CC4)nc2n1-c1ccnc(C(C)(C)C)c1] |
| 2.237 | 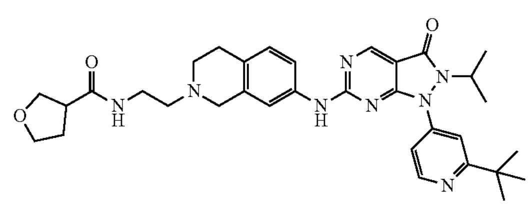 [SMILES: CC(C)n1c(=O)c2cnc(Nc3ccc4c(c3)CN(CCNC(=O)C3CCOC3)CC4)nc2n1-c1ccnc(C(C)(C)C)c1] |

TABLE 1A-continued
| Compound No. | Structure |
|---|---|
| 2.238 | 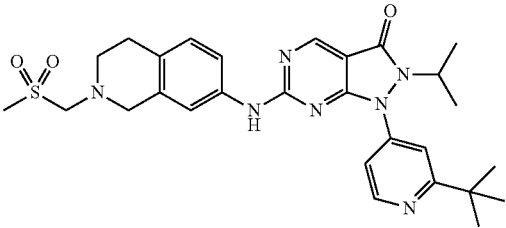 [SMILES: CC(C)n1c(=O)c2cnc(Nc3ccc4c(c3)CN(CS(C)(=O)=O)CC4)nc2n1-c1ccnc(C(C)(C)C)c1] |
| 2.239 | 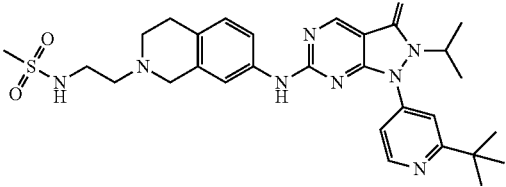 |
| 2.240 | 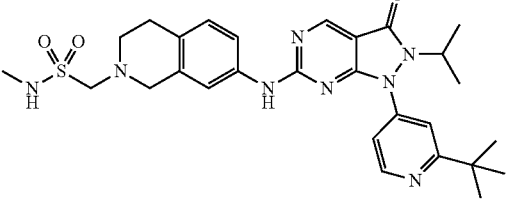 |
| 2.241 | 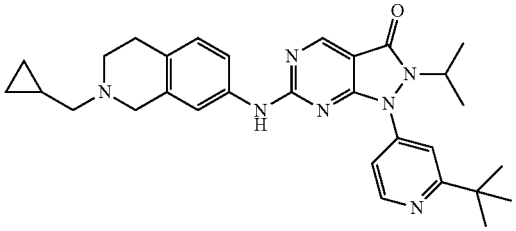 [SMILES: CC(C)n1c(=O)c2cnc(Nc3ccc4c(c3)CN(CC3CC3)CC4)nc2n1-c1ccnc(C(C)(C)C)c1] |
| 2.242 | 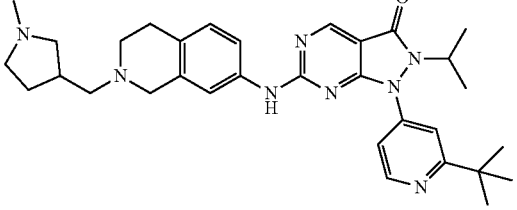 |
| 2.243 | 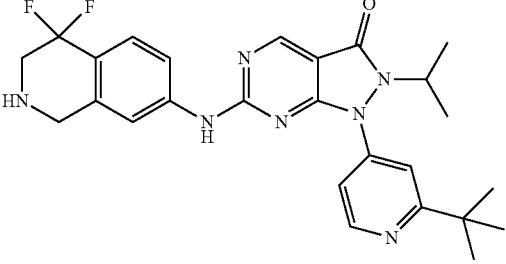 |
| 2.244 | 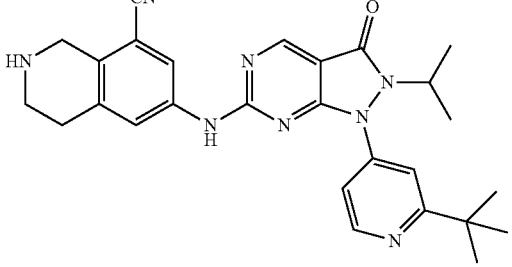 |
| 2.245 | 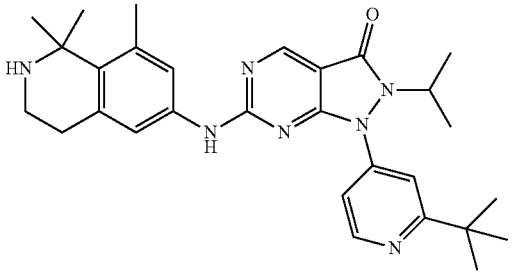 [SMILES: Cc1cc(Nc2ncc3c(=O)n(C(C)C)n(-c4ccnc(C(C)(C)C)c4)c3n2)cc2c1C(C)(C)NCC2] |
| 2.246 | 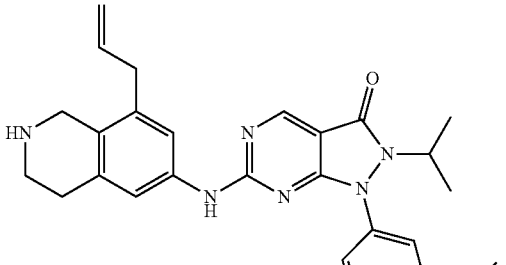 |
| 2.247 | 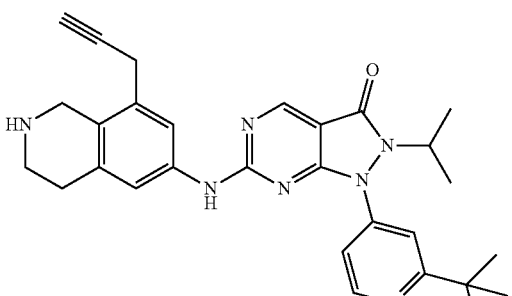 |
| 2.248 | 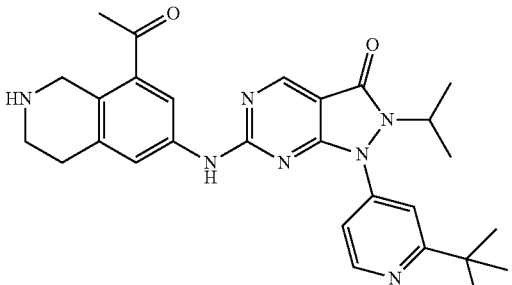 |

TABLE 1A-continued
| Compound No. | Structure |
|---|---|
| 2.249 | 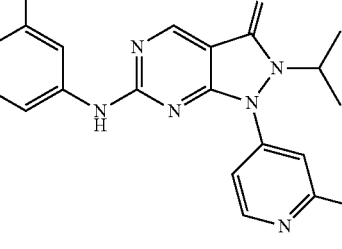 |
| 2.250 | 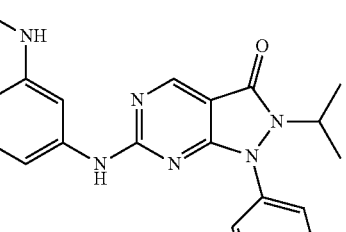 |
| 2.251 | 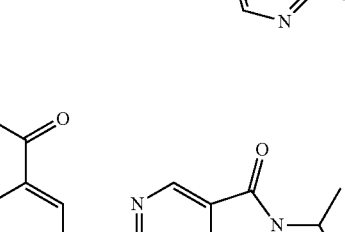 |
| 2.252 | 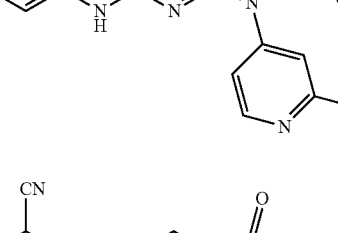 |
| 2.253 | 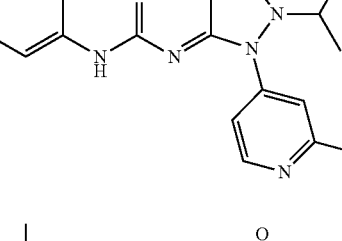 |
| 2.254 | 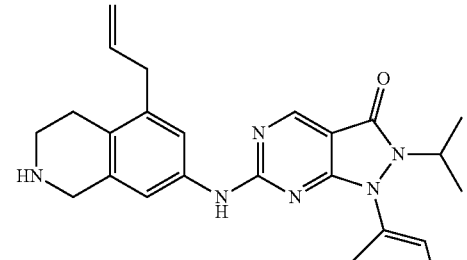 |
| 2.255 | 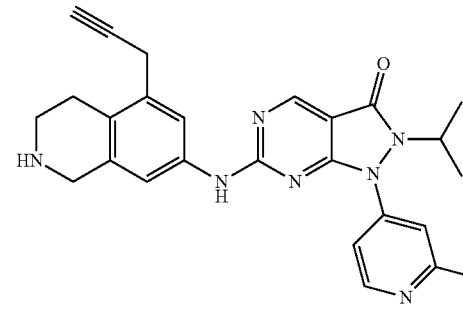 |
| 2.256 | 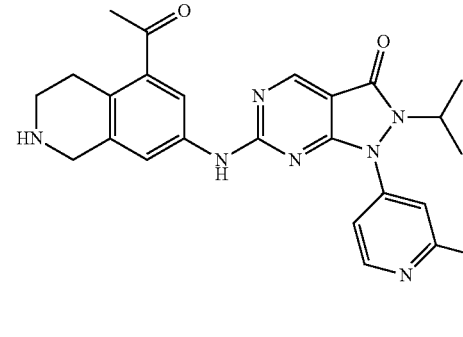 |
| 2.257 | 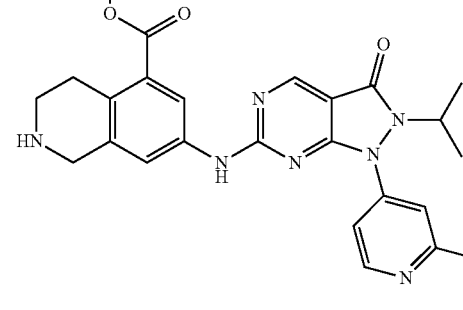 |

TABLE 1A-continued

| Compound No. | Structure |
|---|---|
| 2.258 | 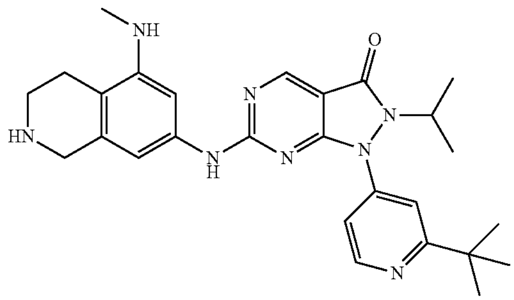 [SMILES: CNc1cc(Nc2ncc3c(=O)n(C(C)C)n(-c4ccnc(C(C)(C)C)c4)c3n2)cc2c1CCNC2] |
| 2.259 | 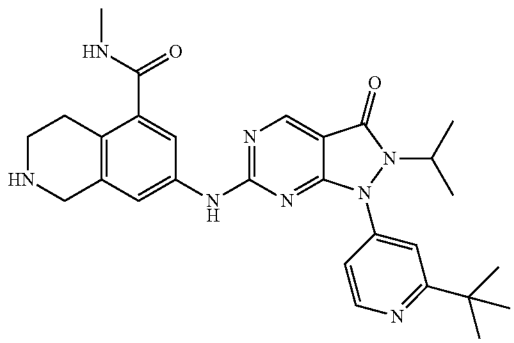 [SMILES: CNC(=O)c1cc(Nc2ncc3c(=O)n(C(C)C)n(-c4ccnc(C(C)(C)C)c4)c3n2)cc2c1CCNC2] |
| 2.260 | 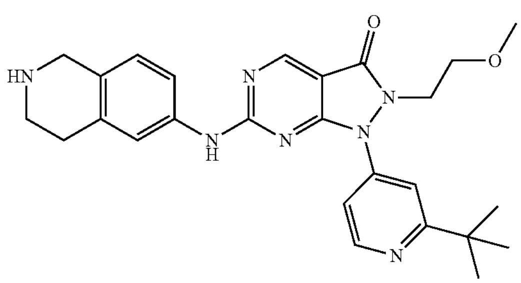 [SMILES: COCCn1c(=O)c2cnc(Nc3ccc4c(c3)CCNC4)nc2n1-c1ccnc(C(C)(C)C)c1] |
| 2.261 | 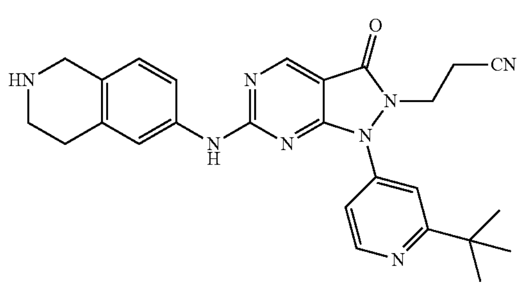 [SMILES: CC(C)(C)c1cc(-n2c3nc(Nc4ccc5c(c4)CCNC5)ncc3c(=O)n2CCC#N)ccn1] |
| 2.262 | 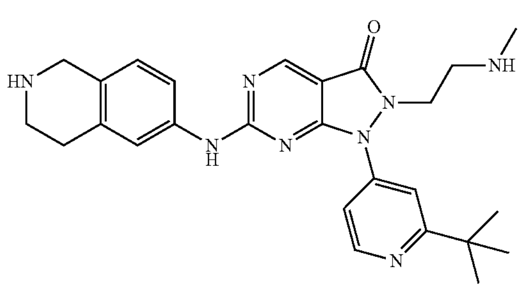 [SMILES: CNCCn1c(=O)c2cnc(Nc3ccc4c(c3)CCNC4)nc2n1-c1ccnc(C(C)(C)C)c1] |
| 2.263 | |
| 2.264 | |
| 2.265 | |
| 2.266 | |
| 2.267 | |

TABLE 1A-continued

| Compound No. | Structure |
|---|---|
| 2.268 | 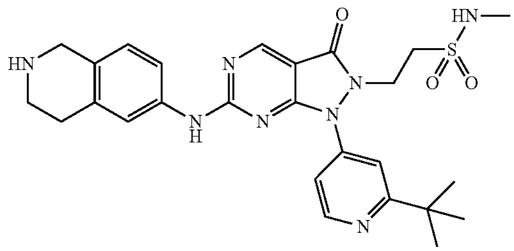 [SMILES: CNS(=O)(=O)CCn1c(=O)c2cnc(Nc3ccc4c(c3)CCNC4)nc2n1-c1ccnc(C(C)(C)C)c1] |
| 2.269 | 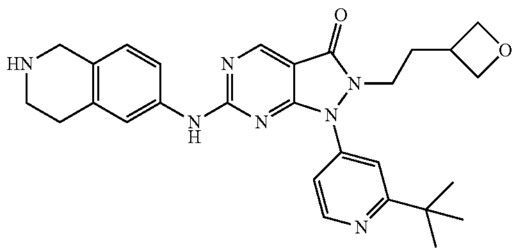 [SMILES: CC(C)(C)c1cc(-n2c3nc(Nc4ccc5c(c4)CCNC5)ncc3c(=O)n2CCC2COC2)ccn1] |
| 2.270 | 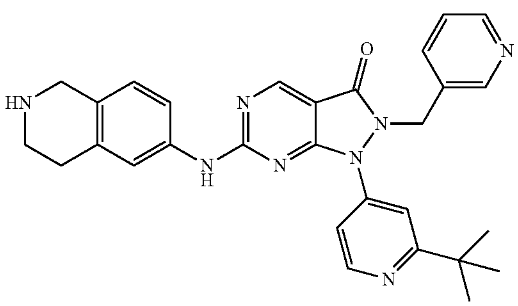 [SMILES: CC(C)(C)c1cc(-n2c3nc(Nc4ccc5c(c4)CCNC5)ncc3c(=O)n2Cc2cccnc2)ccn1] |
| 2.271 | 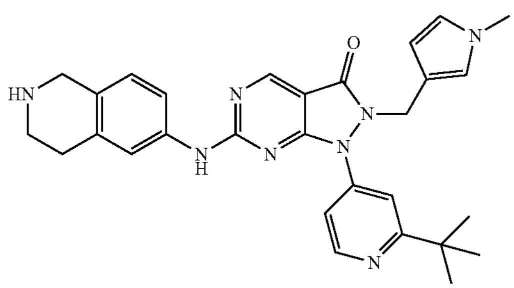 [SMILES: Cn1ccc(Cn2c(=O)c3cnc(Nc4ccc5c(c4)CCNC5)nc3n2-c2ccnc(C(C)(C)C)c2)c1] |
| 2.272 | 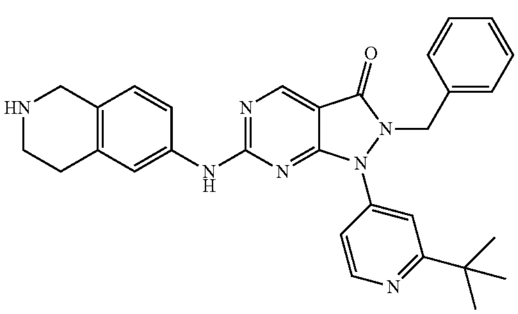 [SMILES: CC(C)(C)c1cc(-n2c3nc(Nc4ccc5c(c4)CCNC5)ncc3c(=O)n2Cc2ccccc2)ccn1] |
| 2.273 | |
| 2.274 | |
| 2.275 | |
| 2.276 | |
| 2.277 | |

TABLE 1A-continued
| Compound No. | Structure |
|---|---|
| 2.278 | 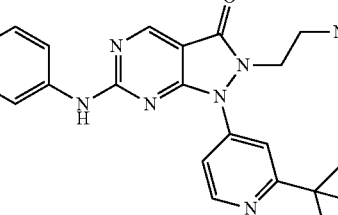 |
| 2.279 | 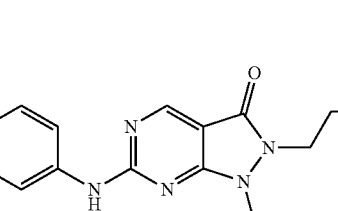 |
| 2.280 | 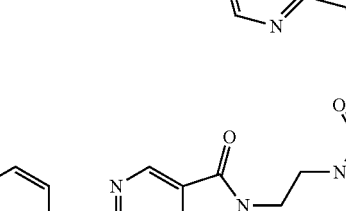 |
| 2.281 | 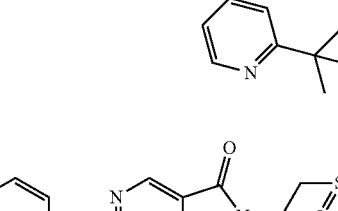 |
| 2.282 | 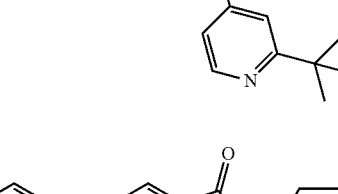 |
TABLE 1A-continued
| Compound No. | Structure |
|---|---|
| 2.283 | 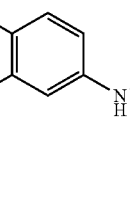 |
| 2.284 | 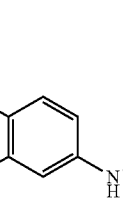 |
| 2.285 | 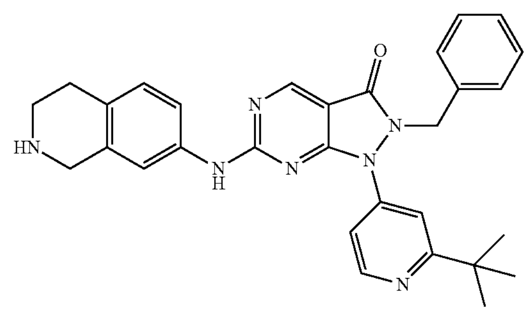 [SMILES: CC(C)(C)c1cc(-n2c3nc(Nc4ccc5c(c4)CNCC5)ncc3c(=O)n2Cc2ccccc2)ccn1] |
| 2.286 | 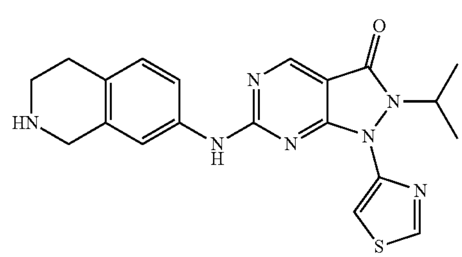 [SMILES: CC(C)n1c(=O)c2cnc(Nc3ccc4c(c3)CNCC4)nc2n1-c1cscn1] |
| 2.287 | 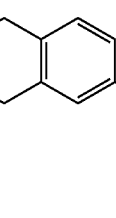 |

TABLE 1A-continued

| Compound No. | Structure |
|---|---|
| 2.288 | 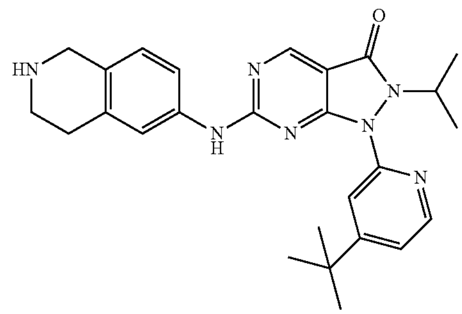 [SMILES: CC(C)n1c(=O)c2cnc(Nc3ccc4c(c3)CCNC4)nc2n1-c1cc(C(C)(C)C)ccn1] |
| 2.289 | 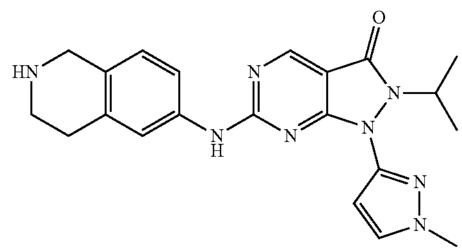 [SMILES: CC(C)n1c(=O)c2cnc(Nc3ccc4c(c3)CCNC4)nc2n1-c1ccn(C)n1] |
| 2.290 | 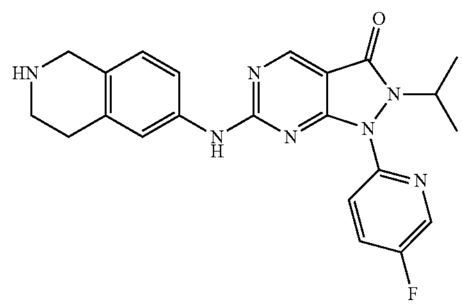 [SMILES: CC(C)n1c(=O)c2cnc(Nc3ccc4c(c3)CCNC4)nc2n1-c1ccc(F)cn1] |
| 2.291 | 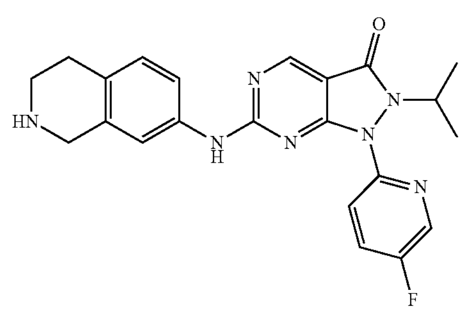 [SMILES: CC(C)n1c(=O)c2cnc(Nc3ccc4c(c3)CNCC4)nc2n1-c1ccc(F)cn1] |
| 2.292 | 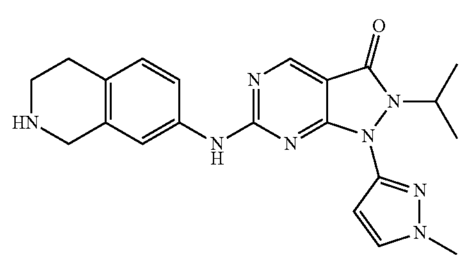 [SMILES: CC(C)n1c(=O)c2cnc(Nc3ccc4c(c3)CNCC4)nc2n1-c1ccn(C)n1] |
| 2.293 | |
| 2.294 | |
| 2.295 | |
| 2.296 | |
| 2.297 | |

TABLE 1A-continued

| Compound No. | Structure |
|---|---|
| 2.298 | 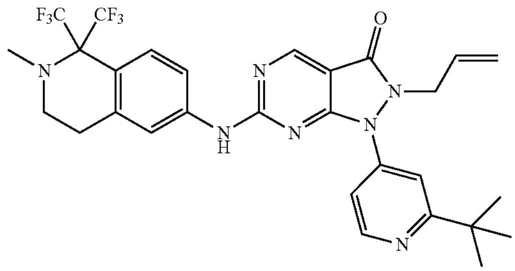 [SMILES: C=CCn1c(=O)c2cnc(Nc3ccc4c(c3)CCN(C)C4(C(F)(F)F)C(F)(F)F)nc2n1-c1ccnc(C(C)(C)C)c1] |
| 2.299 | 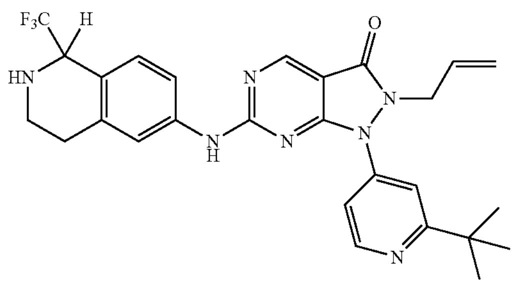 [SMILES: C=CCn1c(=O)c2cnc(Nc3ccc4c(c3)CCNC4C(F)(F)F)nc2n1-c1ccnc(C(C)(C)C)c1] |
| 2.300 | 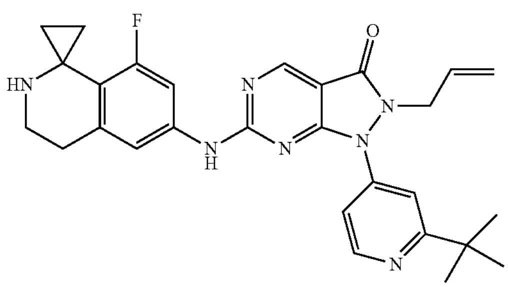 [SMILES: C=CCn1c(=O)c2cnc(Nc3cc(F)c4c(c3)CCNC43CC3)nc2n1-c1ccnc(C(C)(C)C)c1] |
| 2.301 | 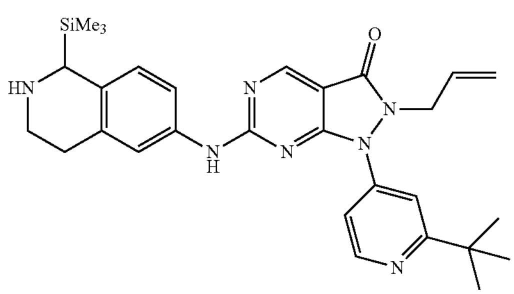 [SMILES: C=CCn1c(=O)c2cnc(Nc3ccc4c(c3)CCNC4[Si](C)(C)C)nc2n1-c1ccnc(C(C)(C)C)c1] |
| 2.302 | 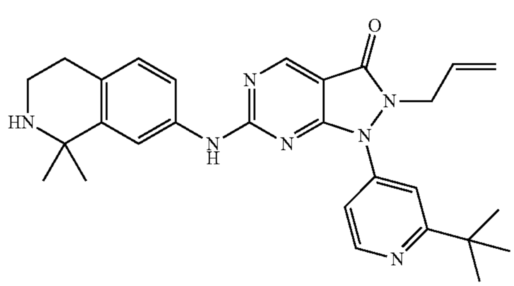 [SMILES: C=CCn1c(=O)c2cnc(Nc3ccc4c(c3)C(C)(C)NCC4)nc2n1-c1ccnc(C(C)(C)C)c1] |
| 2.303 | |
| 2.304 | |
| 2.305 | |
| 2.306 | |
| 2.307 | |

TABLE 1A-continued
| Compound No. | Structure |
|---|---|
| 2.308 | 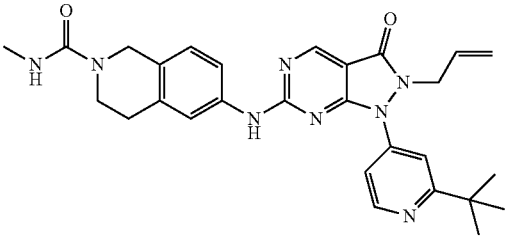 [SMILES: C=CCn1c(=O)c2cnc(Nc3ccc4c(c3)CCN(C(=O)N(C)C)C4)nc2n1-c1ccnc(C(C)(C)C)c1] |
| 2.309 | 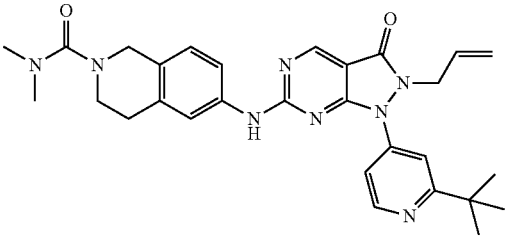 |
| 2.310 | 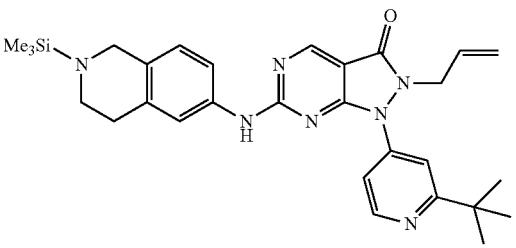 [SMILES: C=CCn1c(=O)c2cnc(Nc3ccc4c(c3)CCN([Si](C)(C)C)C4)nc2n1-c1ccnc(C(C)(C)C)c1] |
| 2.311 | 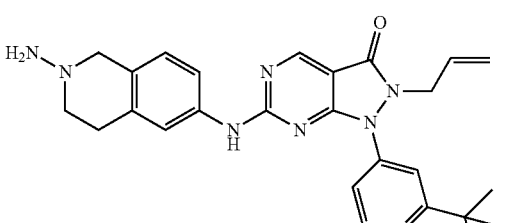 |
| 2.312 | 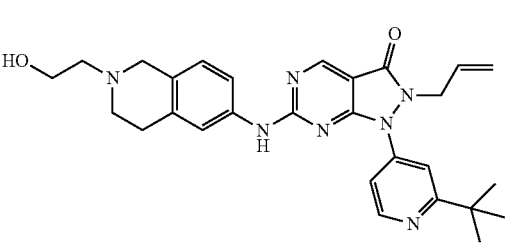 [SMILES: C=CCn1c(=O)c2cnc(Nc3ccc4c(c3)CCN(CCO)C4)nc2n1-c1ccnc(C(C)(C)C)c1] |
| 2.313 | 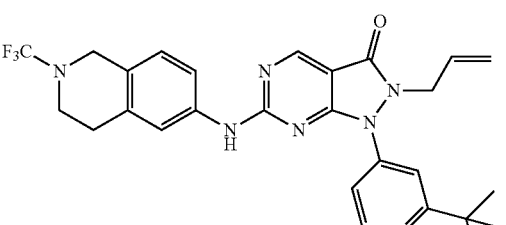 |
TABLE 1A-continued
| Compound No. | Structure |
|---|---|
| 2.314 | 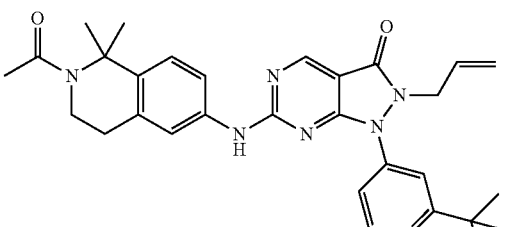 |
| 2.315 | 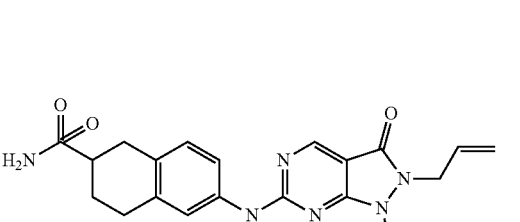 |
| 2.316 | 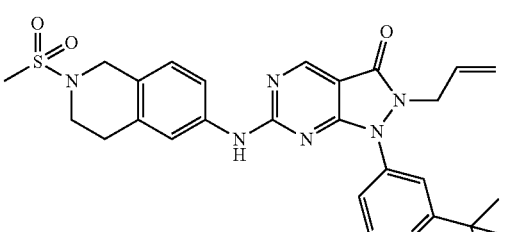 |
| 2.317 | 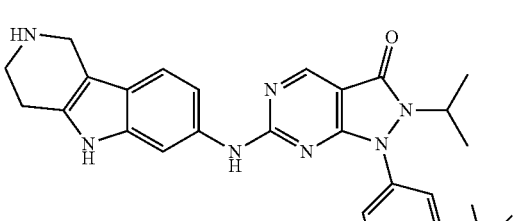 |
| 2.318 | 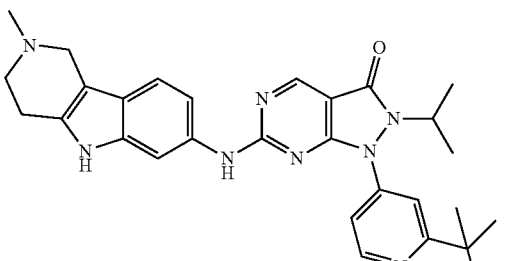 |

TABLE 1A-continued

| Compound No. | Structure |
|---|---|
| 2.319 | |
| 2.320 | |
| 2.321 | |
| 2.322 | |
| 2.323 | |
| 2.324 | 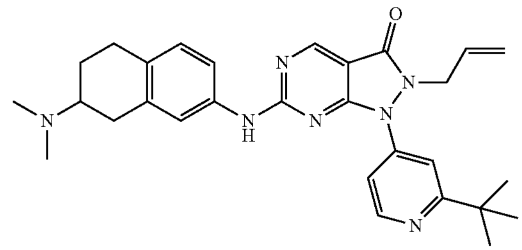 [SMILES: C=CCn1c(=O)c2cnc(Nc3ccc4c(c3)CC(N(C)C)CC4)nc2n1-c1ccnc(C(C)(C)C)c1] |
| 2.325 | 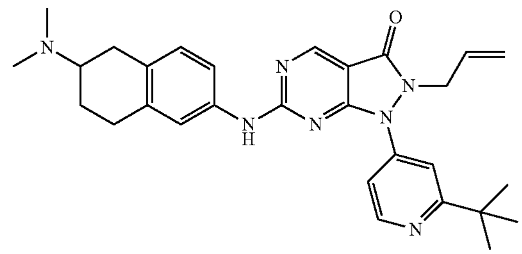 [SMILES: C=CCn1c(=O)c2cnc(Nc3ccc4c(c3)CCC(N(C)C)C4)nc2n1-c1ccnc(C(C)(C)C)c1] |
| 2.326 | 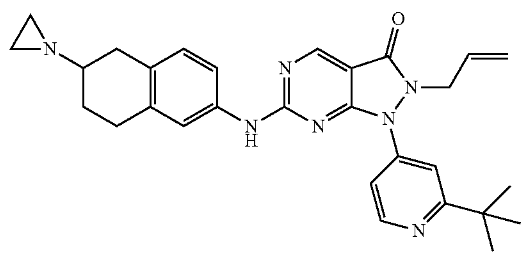 [SMILES: C=CCn1c(=O)c2cnc(Nc3ccc4c(c3)CCC(N3CC3)C4)nc2n1-c1ccnc(C(C)(C)C)c1] |
| 2.327 | 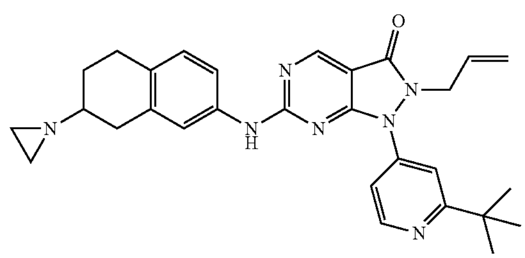 [SMILES: C=CCn1c(=O)c2cnc(Nc3ccc4c(c3)CC(N3CC3)CC4)nc2n1-c1ccnc(C(C)(C)C)c1] |
| 2.328 | 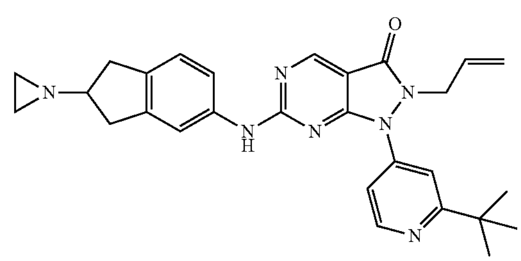 [SMILES: C=CCn1c(=O)c2cnc(Nc3ccc4c(c3)CC(N3CC3)C4)nc2n1-c1ccnc(C(C)(C)C)c1] |
| 2.329 | 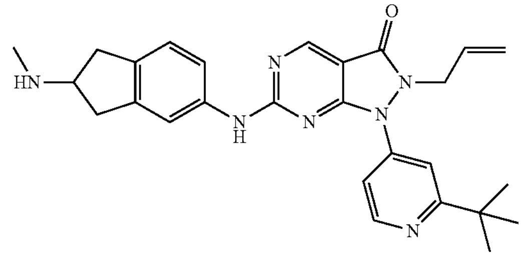 [SMILES: C=CCn1c(=O)c2cnc(Nc3ccc4c(c3)CC(NC)C4)nc2n1-c1ccnc(C(C)(C)C)c1] |

TABLE 1A-continued

| Compound No. | Structure |
|---|---|
| 2.330 | 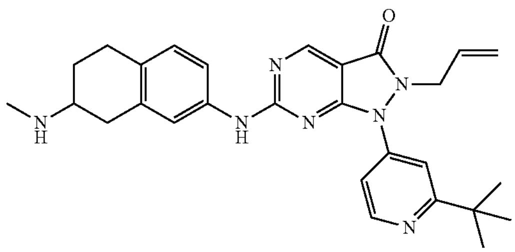 [SMILES: C=CCn1c(=O)c2cnc(Nc3ccc4c(c3)CC(NC)CC4)nc2n1-c1ccnc(C(C)(C)C)c1] |
| 2.331 | 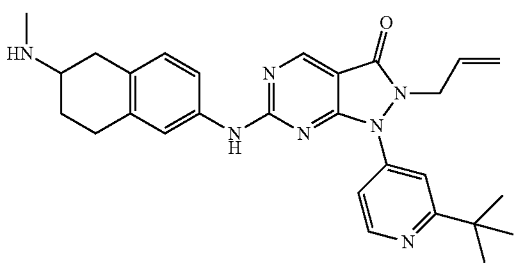 [SMILES: C=CCn1c(=O)c2cnc(Nc3ccc4c(c3)CCC(NC)C4)nc2n1-c1ccnc(C(C)(C)C)c1] |
| 2.332 | 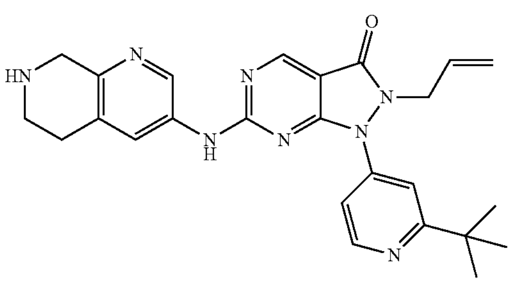 [SMILES: C=CCn1c(=O)c2cnc(Nc3cnc4c(c3)CCNC4)nc2n1-c1ccnc(C(C)(C)C)c1] |
| 2.333 | 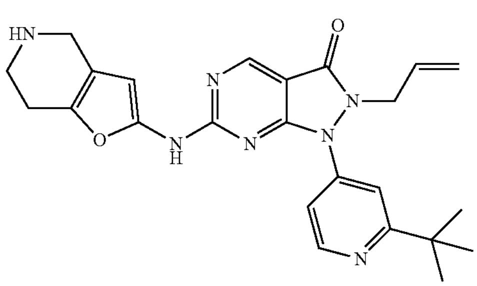 |
| 2.334 | 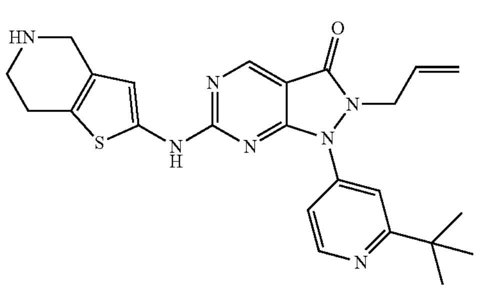 [SMILES: C=CCn1c(=O)c2cnc(Nc3cc4c(o3)CCNC4)nc2n1-c1ccnc(C(C)(C)C)c1] |
| 2.335 | 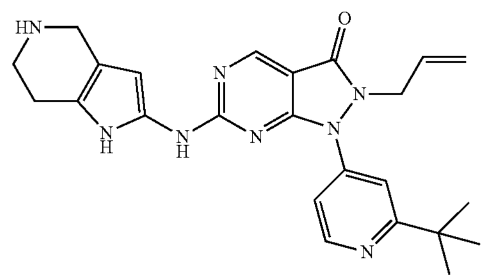 [SMILES: C=CCn1c(=O)c2cnc(Nc3cc4c(s3)CCNC4)nc2n1-c1ccnc(C(C)(C)C)c1] |
| 2.336 | 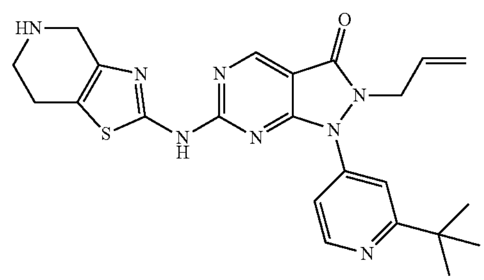 |
| 2.337 | 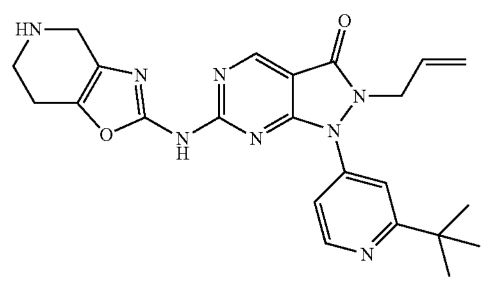 [SMILES: C=CCn1c(=O)c2cnc(Nc3nc4c(o3)CCNC4)nc2n1-c1ccnc(C(C)(C)C)c1] |
| 2.338 | 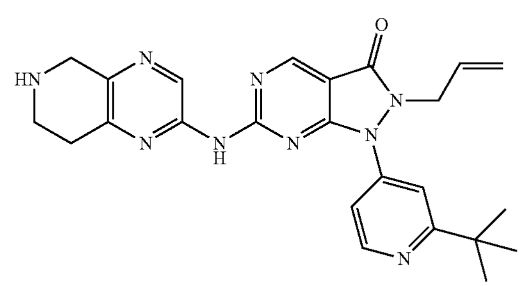 |
| 2.339 | 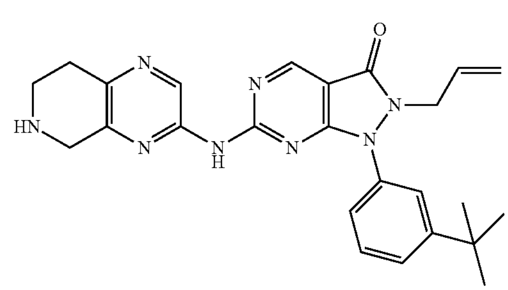 [SMILES: C=CCn1c(=O)c2cnc(Nc3cnc4c(n3)CNCC4)nc2n1-c1cccc(C(C)(C)C)c1] |

TABLE 1A-continued
| Compound No. | Structure |
|---|---|
| 2.340 | 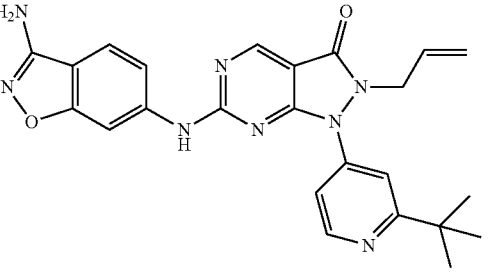 |
| 2.341 | 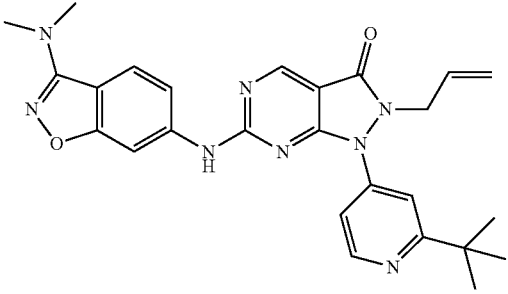 [SMILES: C=CCn1c(=O)c2cnc(Nc3ccc4c(N(C)C)noc4c3)nc2n1-c1ccnc(C(C)(C)C)c1] |
| 2.342 | 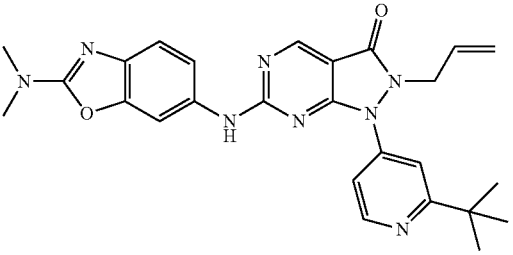 |
| 2.343 | 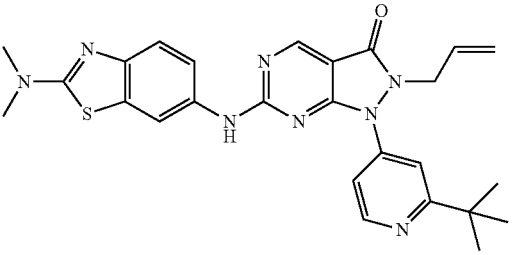 [SMILES: C=CCn1c(=O)c2cnc(Nc3ccc4nc(N(C)C)sc4c3)nc2n1-c1ccnc(C(C)(C)C)c1] |
| 2.344 | 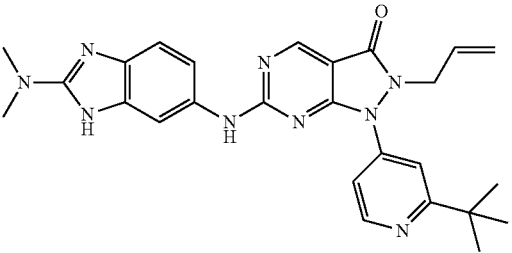 |
| 2.345 | 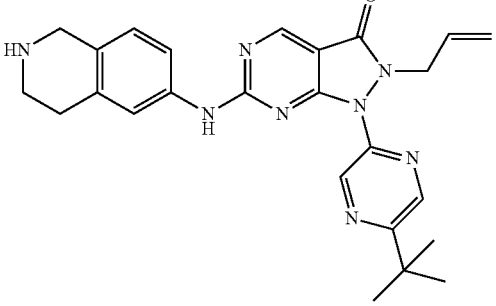 |
| 2.346 | 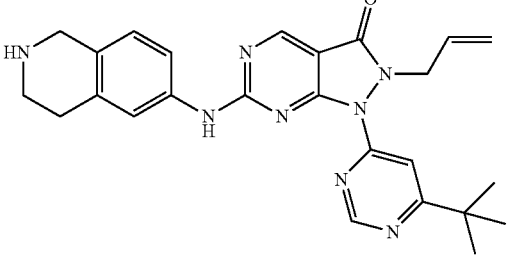 |
| 2.347 | 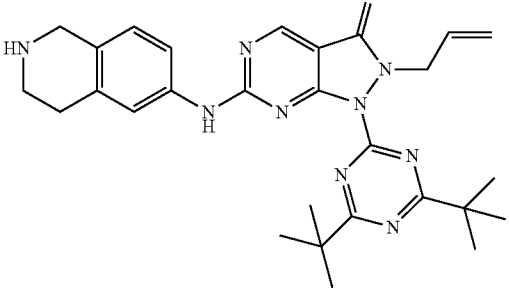 |
| 2.348 | 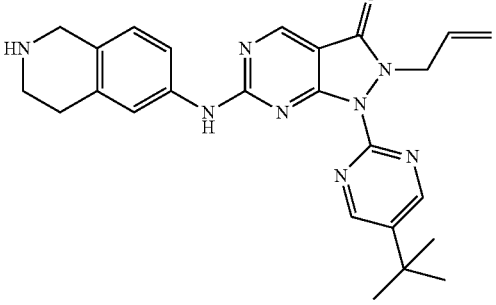 |
| 2.349 | 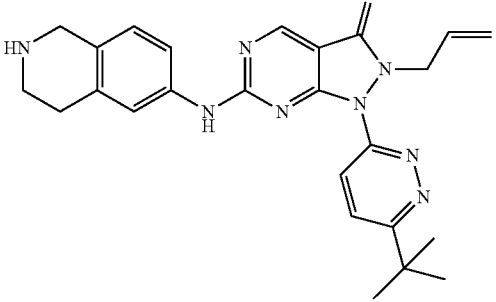 |

TABLE 1A-continued
| Compound No. | Structure |
|---|---|
| 2.350 | 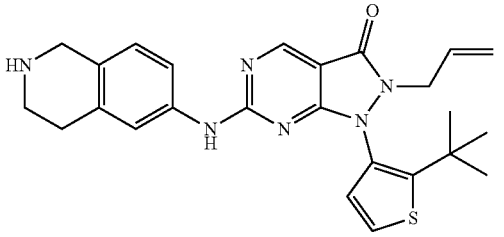 [SMILES: C=CCn1c(=O)c2cnc(Nc3ccc4c(c3)CCNC4)nc2n1-c1ccsc1C(C)(C)C] |
| 2.351 | 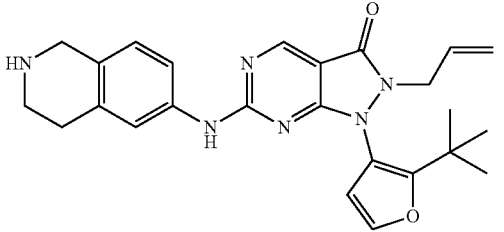 [SMILES: C=CCn1c(=O)c2cnc(Nc3ccc4c(c3)CCNC4)nc2n1-c1ccoc1C(C)(C)C] |
| 2.352 | 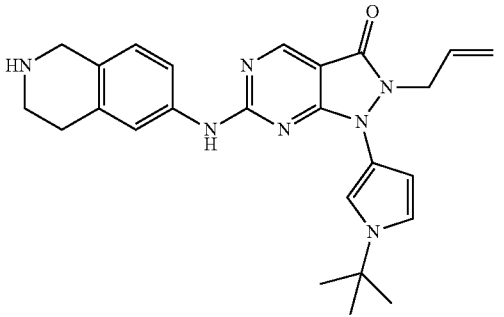 [SMILES: C=CCn1c(=O)c2cnc(Nc3ccc4c(c3)CCNC4)nc2n1-c1ccn(C(C)(C)C)c1] |
| 2.353 | 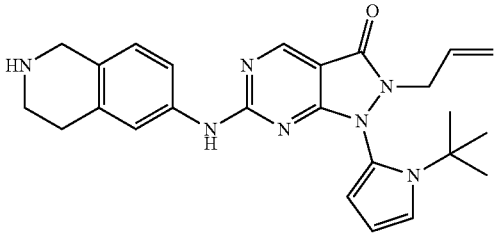 [SMILES: C=CCn1c(=O)c2cnc(Nc3ccc4c(c3)CCNC4)nc2n1-c1cccn1C(C)(C)C] |
| 2.354 | 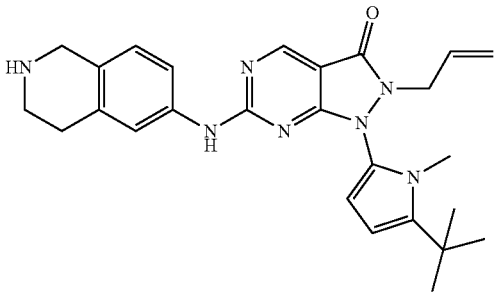 [SMILES: C=CCn1c(=O)c2cnc(Nc3ccc4c(c3)CCNC4)nc2n1-c1ccc(C(C)(C)C)n1C] |
| 2.355 | 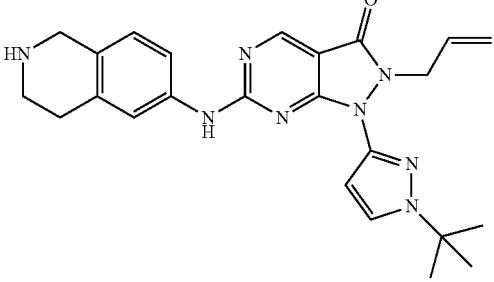 |
| 2.356 | 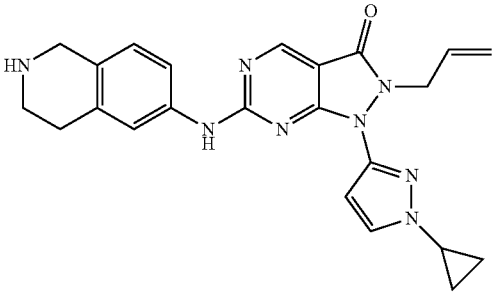 [SMILES: C=CCn1c(=O)c2cnc(Nc3ccc4c(c3)CCNC4)nc2n1-c1ccn(C2CC2)n1] |
| 2.357 | 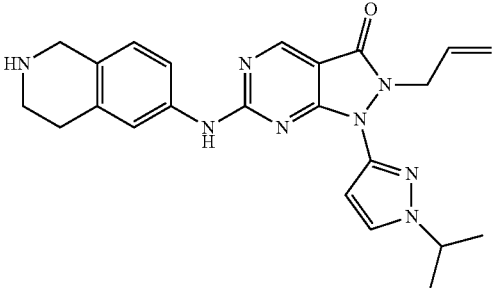 [SMILES: C=CCn1c(=O)c2cnc(Nc3ccc4c(c3)CCNC4)nc2n1-c1ccn(C(C)C)n1] |
| 2.358 | 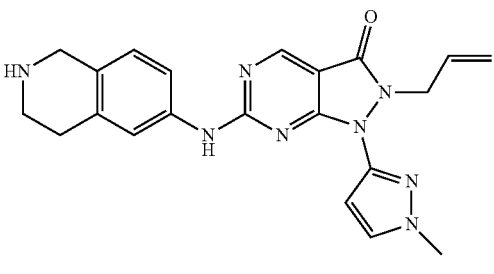 [SMILES: C=CCn1c(=O)c2cnc(Nc3ccc4c(c3)CCNC4)nc2n1-c1ccn(C)n1] |
| 2.359 | 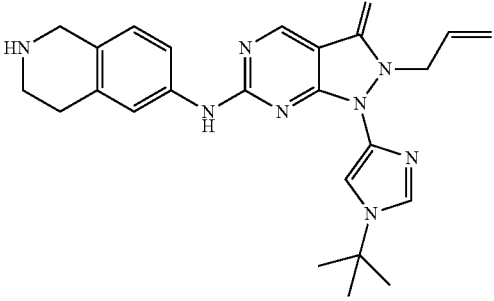 |

TABLE 1A-continued
| Compound No. | Structure |
|---|---|
| 2.360 | 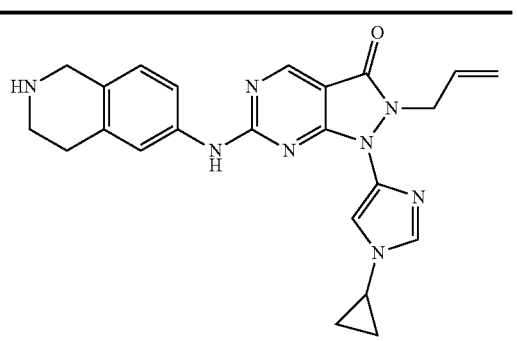 |
| 2.361 | 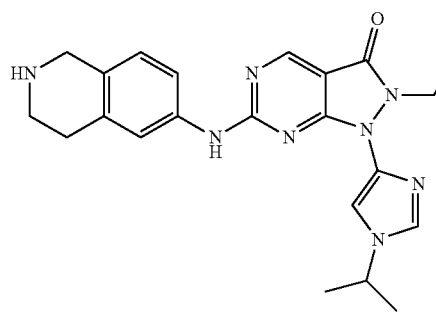 |
| 2.362 | 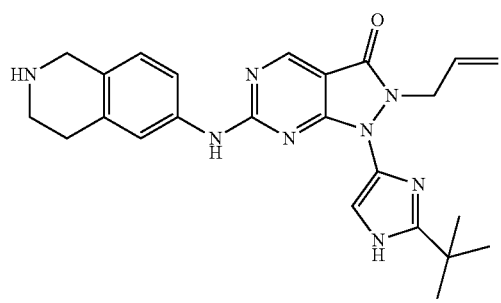 [SMILES: C=CCn1c(=O)c2cnc(Nc3ccc4c(c3)CCNC4)nc2n1-c1c[nH]c(C(C)(C)C)n1] |
| 2.363 | 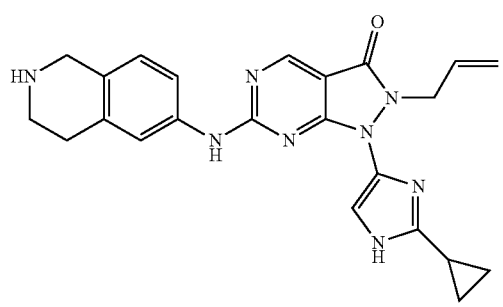 [SMILES: C=CCn1c(=O)c2cnc(Nc3ccc4c(c3)CCNC4)nc2n1-c1c[nH]c(C2CC2)n1] |
| 2.364 | 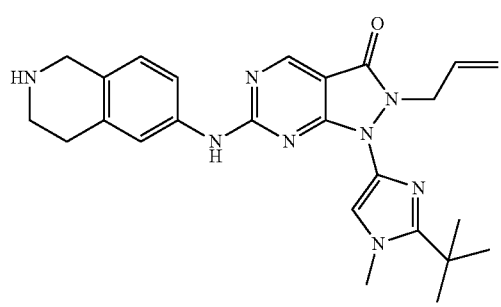 [SMILES: C=CCn1c(=O)c2cnc(Nc3ccc4c(c3)CCNC4)nc2n1-c1cn(C)c(C(C)(C)C)n1] |
| 2.365 | 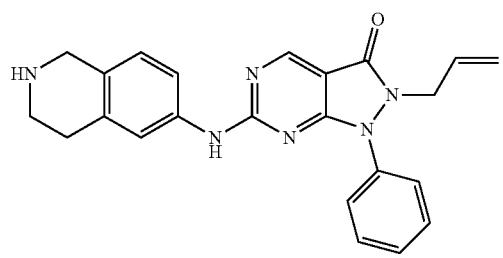 [SMILES: C=CCn1c(=O)c2cnc(Nc3ccc4c(c3)CCNC4)nc2n1-c1ccccc1] |
| 2.366 | 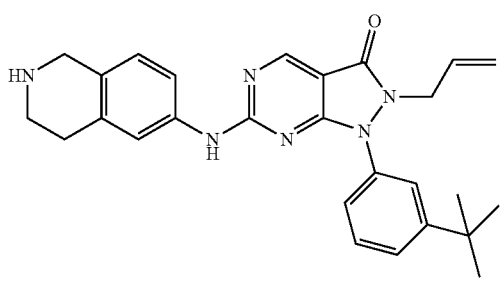 [SMILES: C=CCn1c(=O)c2cnc(Nc3ccc4c(c3)CCNC4)nc2n1-c1cccc(C(C)(C)C)c1] |
| 2.367 | 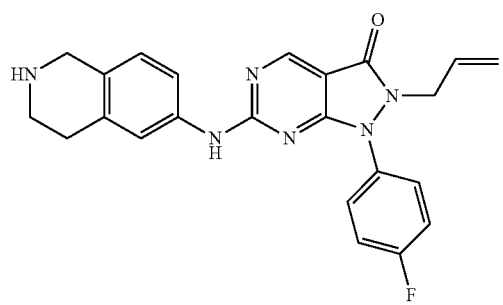 [SMILES: C=CCn1c(=O)c2cnc(Nc3ccc4c(c3)CCNC4)nc2n1-c1ccc(F)cc1] |
| 2.368 | 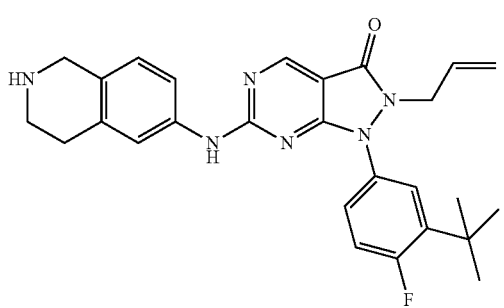 [SMILES: C=CCn1c(=O)c2cnc(Nc3ccc4c(c3)CCNC4)nc2n1-c1ccc(F)c(C(C)(C)C)c1] |
| 2.369 | 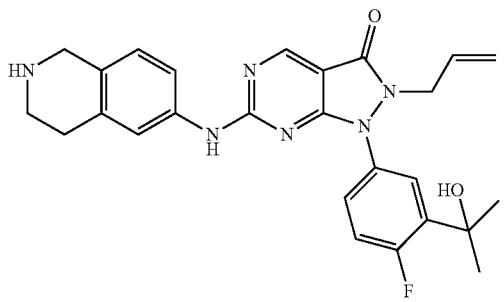 [SMILES: C=CCn1c(=O)c2cnc(Nc3ccc4c(c3)CCNC4)nc2n1-c1ccc(F)c(C(C)(C)O)c1] |

TABLE 1A-continued
| Compound No. | Structure |
|---|---|
| 2.370 | 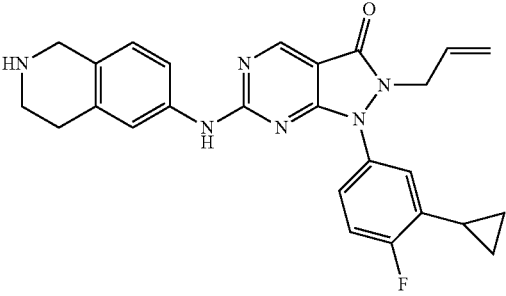 [SMILES: C=CCn1c(=O)c2cnc(Nc3ccc4c(c3)CCNC4)nc2n1-c1ccc(F)c(C2CC2)c1] |
| 2.371 | 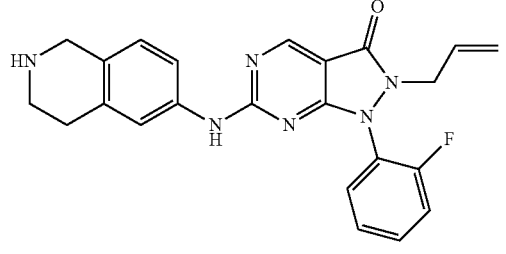 [SMILES: C=CCn1c(=O)c2cnc(Nc3ccc4c(c3)CCNC4)nc2n1-c1ccccc1F] |
| 2.372 | 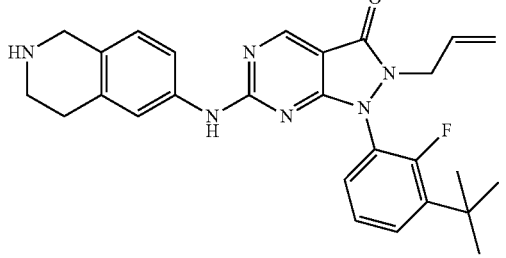 |
| 2.373 | 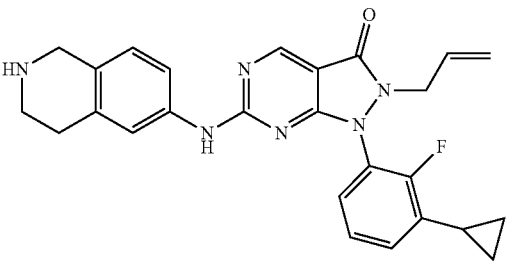 [SMILES: C=CCn1c(=O)c2cnc(Nc3ccc4c(c3)CCNC4)nc2n1-c1cccc(C2CC2)c1F] |
| 2.374 | 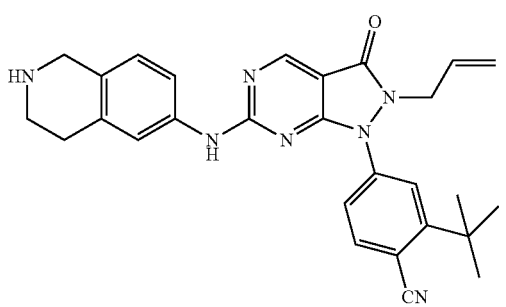 [SMILES: C=CCn1c(=O)c2cnc(Nc3ccc4c(c3)CCNC4)nc2n1-c1ccc(C#N)c(C(C)(C)C)c1] |
TABLE 1A-continued
| Compound No. | Structure |
|---|---|
| 2.375 | 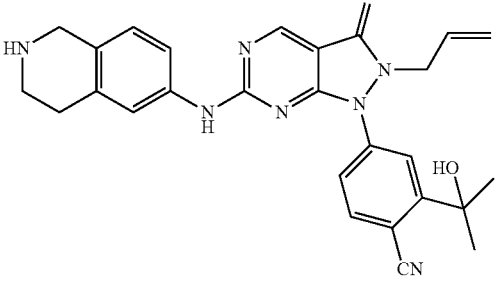 |
| 2.376 | 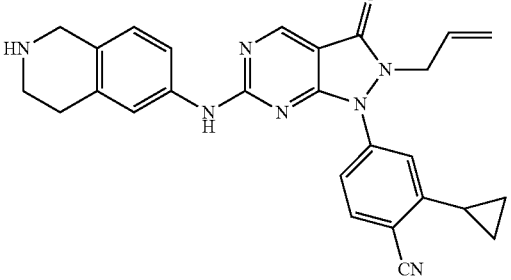 |
| 2.377 | 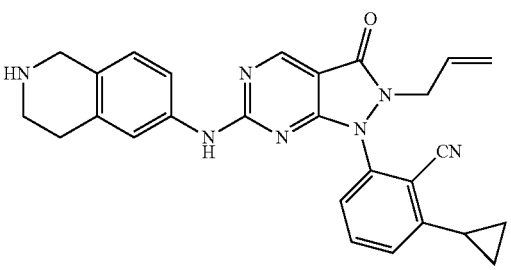 [SMILES: C=CCn1c(=O)c2cnc(Nc3ccc4c(c3)CCNC4)nc2n1-c1cccc(C2CC2)c1C#N] |
| 2.378 | 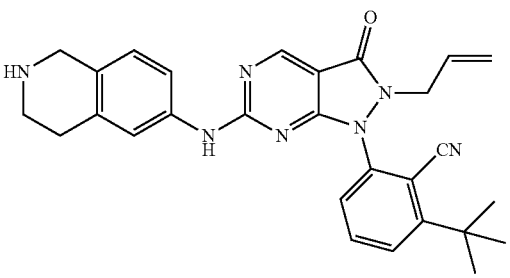 [SMILES: C=CCn1c(=O)c2cnc(Nc3ccc4c(c3)CCNC4)nc2n1-c1cccc(C(C)(C)C)c1C#N] |
| 2.379 | 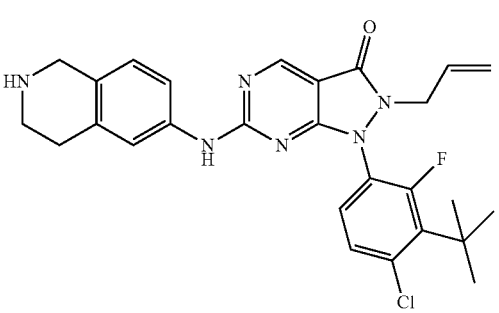 [SMILES: C=CCn1c(=O)c2cnc(Nc3ccc4c(c3)CCNC4)nc2n1-c1ccc(F)c(C(C)(C)C)c1F] |

TABLE 1A-continued
| Compound No. | Structure |
|---|---|
| 2.380 | 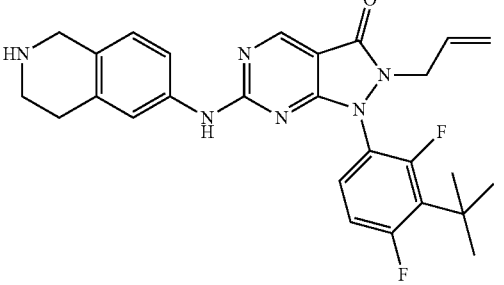 |
| 2.381 | 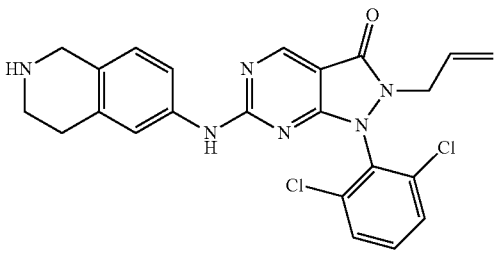 [SMILES: C=CCn1c(=O)c2cnc(Nc3ccc4c(c3)CCNC4)nc2n1-c1c(Cl)cccc1Cl] |
| 2.382 | 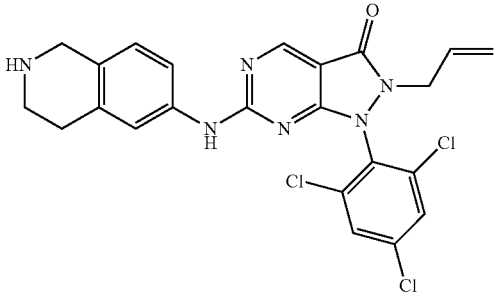 [SMILES: C=CCn1c(=O)c2cnc(Nc3ccc4c(c3)CCNC4)nc2n1-c1c(Cl)cc(Cl)cc1Cl] |
| 2.383 | 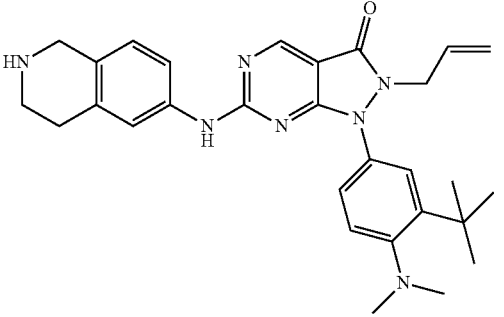 [SMILES: C=CCn1c(=O)c2cnc(Nc3ccc4c(c3)CCNC4)nc2n1-c1ccc(N(C)C)c(C(C)(C)C)c1] |
| 2.384 | 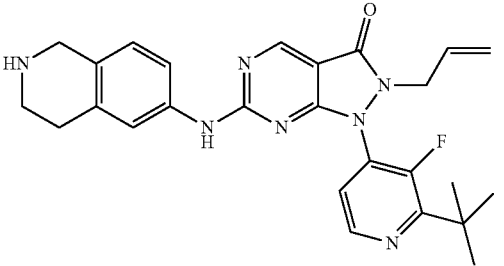 [SMILES: C=CCn1c(=O)c2cnc(Nc3ccc4c(c3)CCNC4)nc2n1-c1ccnc(C(C)(C)C)c1F] |
| 2.385 | 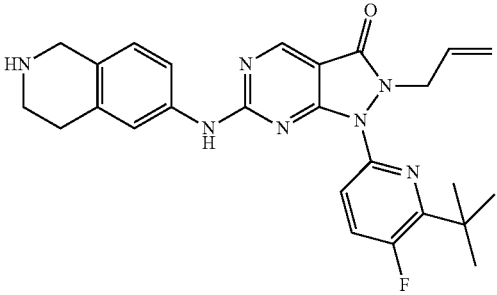 [SMILES: C=CCn1c(=O)c2cnc(Nc3ccc4c(c3)CCNC4)nc2n1-c1ccc(F)c(C(C)(C)C)n1] |
| 2.386 | 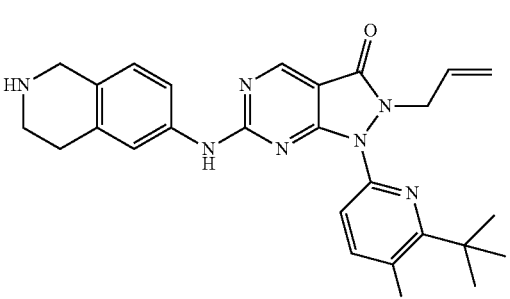 |
| 2.387 | 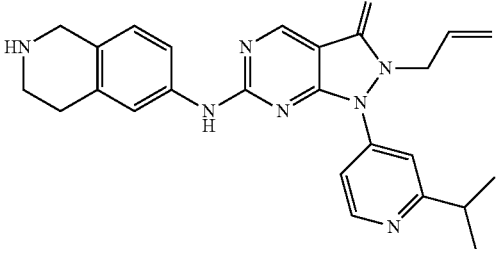 |
| 2.388 | 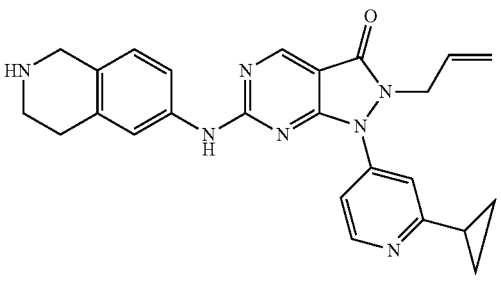 [SMILES: C=CCn1c(=O)c2cnc(Nc3ccc4c(c3)CCNC4)nc2n1-c1ccnc(C2CC2)c1] |
| 2.389 | 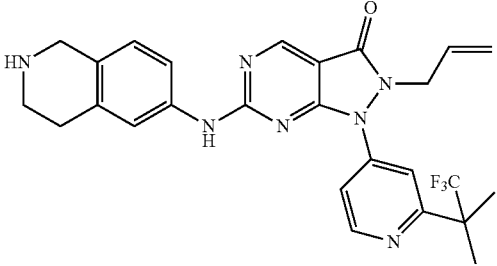 [SMILES: C=CCn1c(=O)c2cnc(Nc3ccc4c(c3)CCNC4)nc2n1-c1ccnc(C(C)(C)C(F)(F)F)c1] |

TABLE 1A-continued

| Compound No. | Structure |
|---|---|
| 2.390 | 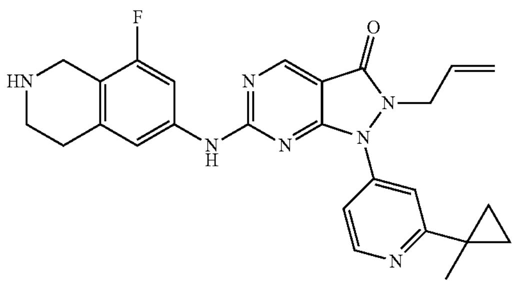 [SMILES: C=CCn1c(=O)c2cnc(Nc3cc(F)c4c(c3)CCNC4)nc2n1-c1ccnc(C2(C)CC2)c1] |
| 2.391 | 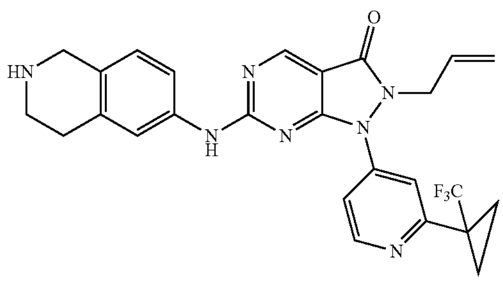 [SMILES: C=CCn1c(=O)c2cnc(Nc3ccc4c(c3)CCNC4)nc2n1-c1ccnc(C2(C(F)(F)F)CC2)c1] |
| 2.392 | 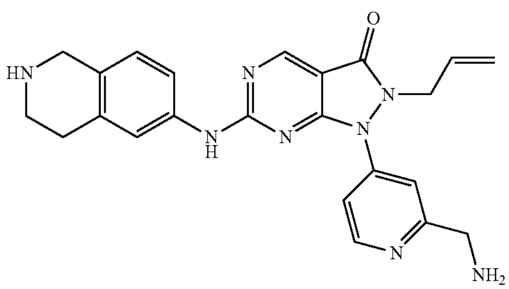 [SMILES: C=CCn1c(=O)c2cnc(Nc3ccc4c(c3)CCNC4)nc2n1-c1ccnc(CN)c1] |
| 2.393 | 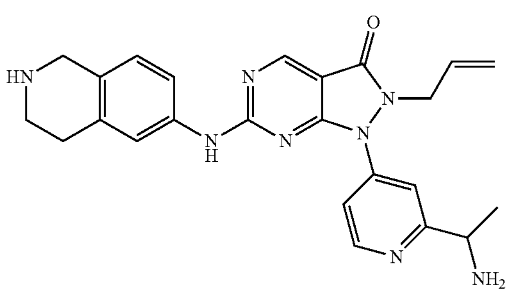 [SMILES: C=CCn1c(=O)c2cnc(Nc3ccc4c(c3)CCNC4)nc2n1-c1ccnc(C(C)N)c1] |
| 2.394 | 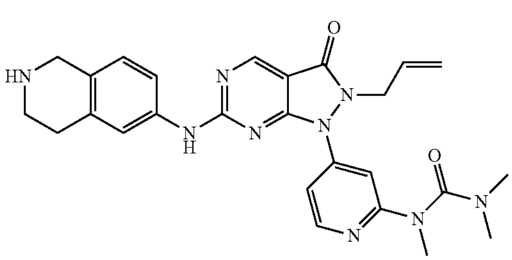 [SMILES: C=CCn1c(=O)c2cnc(Nc3ccc4c(c3)CCNC4)nc2n1-c1ccnc(N(C)C(=O)N(C)C)c1] |
| 2.395 | |
| 2.396 | |
| 2.397 | |
| 2.398 | |
| 2.399 | |

TABLE 1A-continued
| Compound No. | Structure |
|---|---|
| 2.400 | 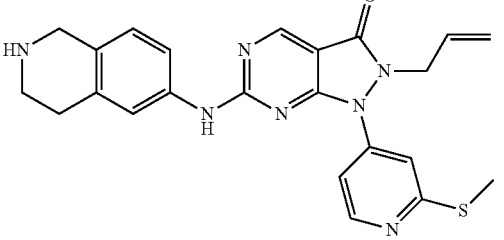 |
| 2.401 | 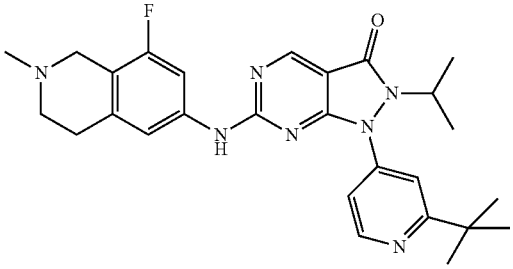 [SMILES: CC(C)n1c(=O)c2cnc(Nc3cc(F)c4c(c3)CCN(C)C4)nc2n1-c1ccnc(C(C)(C)C)c1] |
| 2.402 | 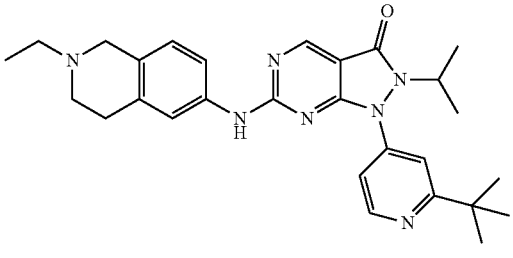 [SMILES: CCN1CCc2cc(Nc3ncc4c(=O)n(C(C)C)n(-c5ccnc(C(C)(C)C)c5)c4n3)ccc2C1] |
| 2.403 | 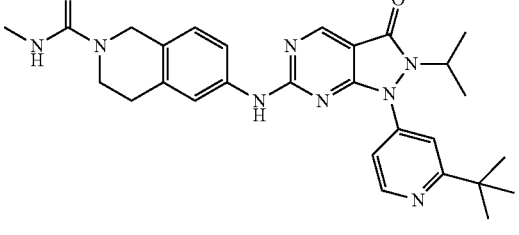 |
| 2.404 | 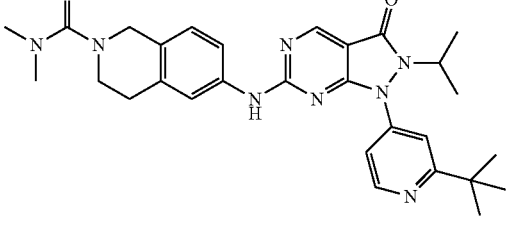 |
| 2.405 | 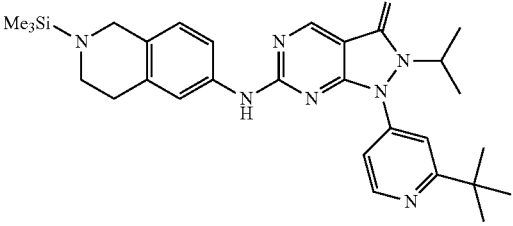 |
| 2.406 | 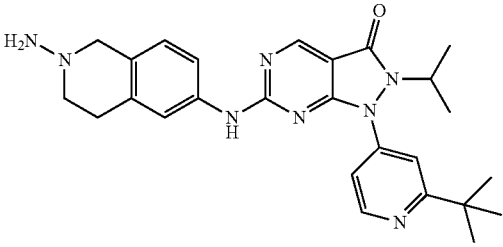 [SMILES: CC(C)n1c(=O)c2cnc(Nc3ccc4c(c3)CCN(C(F)(F)F)C4)nc2n1-c1ccnc(C(C)(C)C)c1] |
| 2.407 | 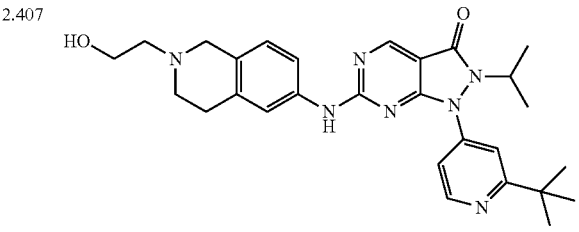 |
| 2.408 | 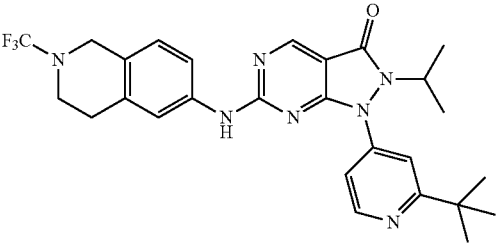 |
| 2.409 | 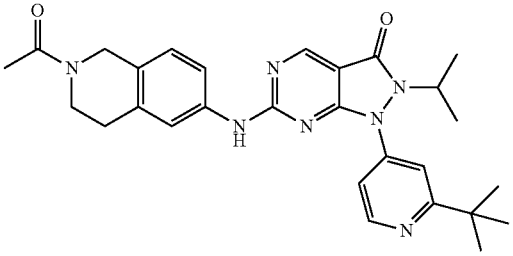 [SMILES: CC(=O)N1CCc2cc(Nc3ncc4c(=O)n(C(C)C)n(-c5ccnc(C(C)(C)C)c5)c4n3)ccc2C1] |
| 2.410 | 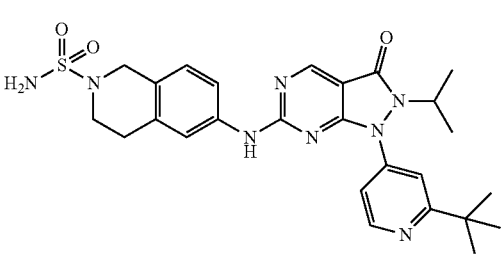 [SMILES: CC(C)n1c(=O)c2cnc(Nc3ccc4c(c3)CCN(S(N)(=O)=O)C4)nc2n1-c1ccnc(C(C)(C)C)c1] |
| 2.411 | 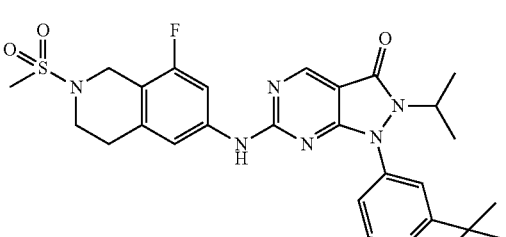 |

TABLE 1A-continued
| Compound No. | Structure |
|---|---|
| 2.412 | 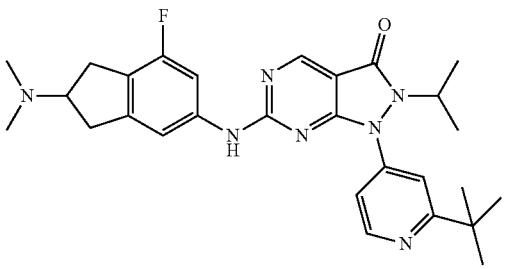 [SMILES: CC(C)n1c(=O)c2cnc(Nc3cc(F)c4c(c3)CC(N(C)C)C4)nc2n1-c1ccnc(C(C)(C)C)c1] |
| 2.413 | 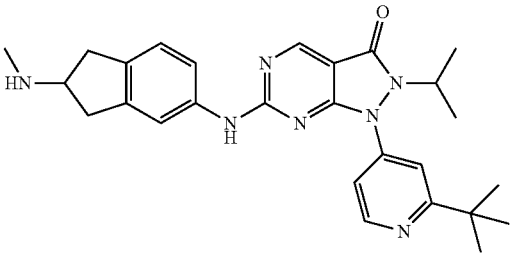 |
| 2.414 | 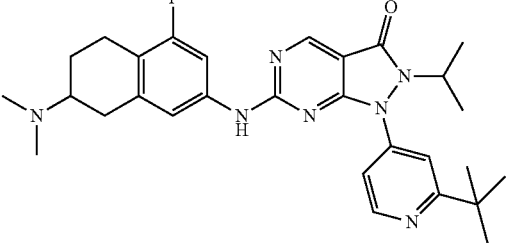 |
| 2.415 | 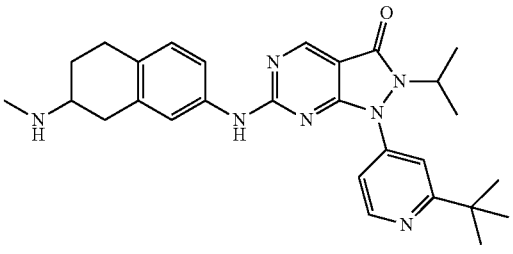 |
| 2.416 | 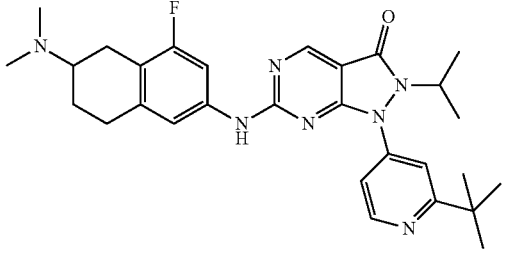 [SMILES: CC(C)n1c(=O)c2cnc(Nc3cc(F)c4c(c3)CCC(N(C)C)C4)nc2n1-c1ccnc(C(C)(C)C)c1] |
| 2.417 | 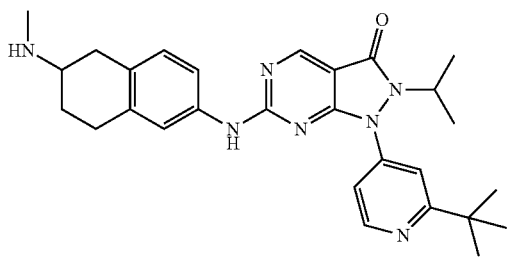 |
| 2.418 | 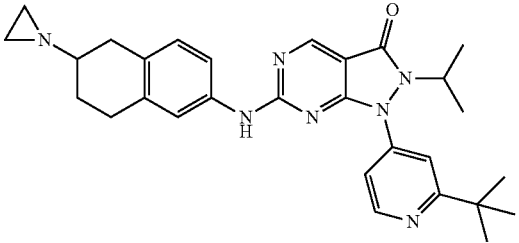 |
| 2.419 | 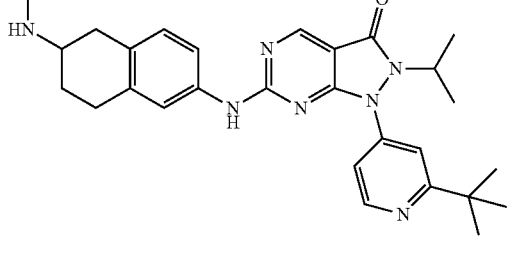 |
| 2.420 | 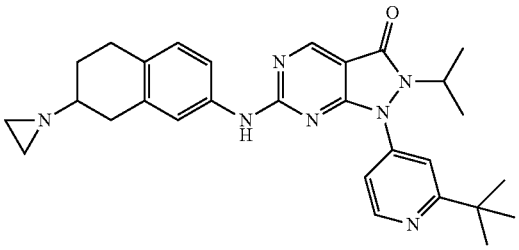 [SMILES: CC(C)n1c(=O)c2cnc(Nc3ccc4c(c3)CC(N3CC3)CC4)nc2n1-c1ccnc(C(C)(C)C)c1] |
| 2.421 | 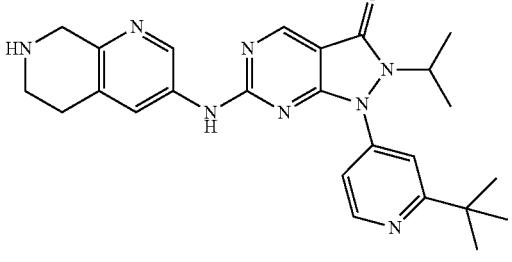 |
| 2.422 | 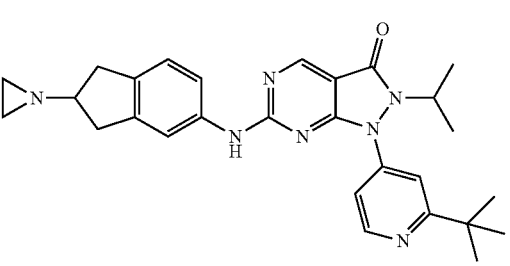 [SMILES: CC(C)n1c(=O)c2cnc(Nc3ccc4c(c3)CC(N3CC3)C4)nc2n1-c1ccnc(C(C)(C)C)c1] |

TABLE 1A-continued

| Compound No. | Structure |
|---|---|
| 2.423 | (structure) |
| 2.424 | (structure) |
| 2.425 | (structure) |
| 2.426 | (structure) |
| 2.427 | (structure) |
| 2.428 | (structure) |
| 2.429 | (structure) |
| 2.430 | (structure) |
| 2.431 | (structure) |
| 2.432 | (structure) |

TABLE 1A-continued

| Compound No. | Structure |
|---|---|
| 2.433 | 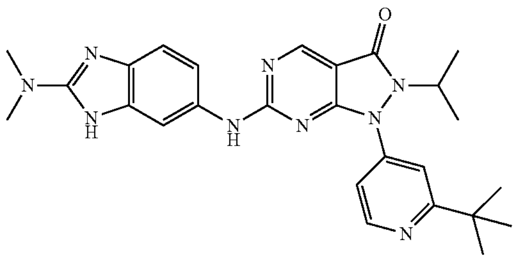 [SMILES: CC(C)n1c(=O)c2cnc(Nc3ccc4nc(N(C)C)[nH]c4c3)nc2n1-c1ccnc(C(C)(C)C)c1] |
| 2.434 | 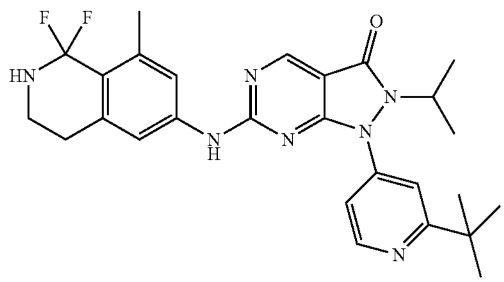 [SMILES: Cc1cc(Nc2ncc3c(=O)n(C(C)C)n(-c4ccnc(C(C)(C)C)c4)c3n2)cc2c1C(F)(F)NCC2] |
| 2.435 | 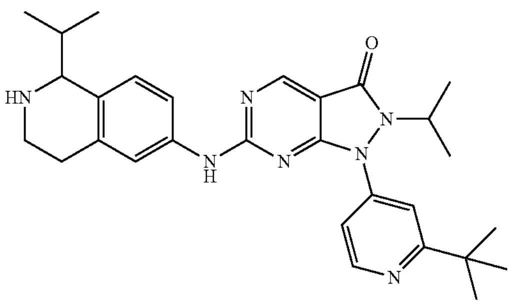 [SMILES: CC(C)C1NCCc2cc(Nc3ncc4c(=O)n(C(C)C)n(-c5ccnc(C(C)(C)C)c5)c4n3)ccc21] |
| 2.436 | 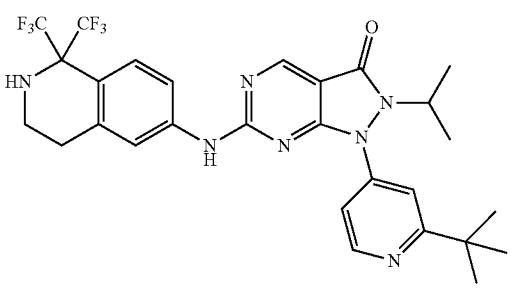 [SMILES: CC(C)n1c(=O)c2cnc(Nc3ccc4c(c3)CCNC4(C(F)(F)F)C(F)(F)F)nc2n1-c1ccnc(C(C)(C)C)c1] |
| 2.437 | 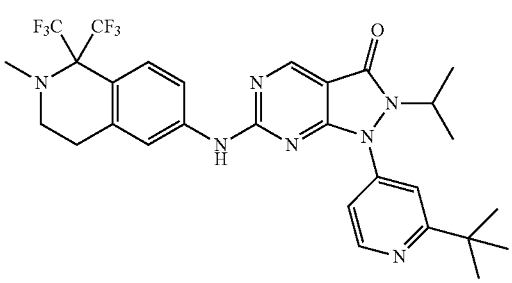 [SMILES: CC(C)n1c(=O)c2cnc(Nc3ccc4c(c3)CCN(C)C4(C(F)(F)F)C(F)(F)F)nc2n1-c1ccnc(C(C)(C)C)c1] |
| 2.438 | 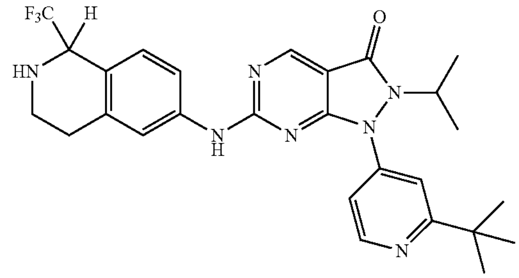 [SMILES: CC(C)n1c(=O)c2cnc(Nc3ccc4c(c3)CCNC4C(F)(F)F)nc2n1-c1ccnc(C(C)(C)C)c1] |
| 2.439 | 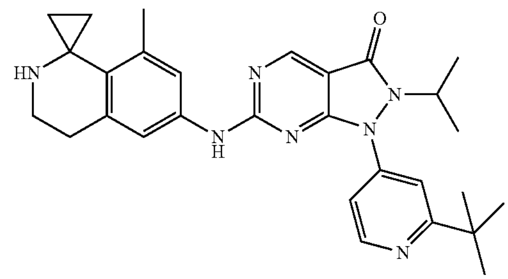 [SMILES: Cc1cc(Nc2ncc3c(=O)n(C(C)C)n(-c4ccnc(C(C)(C)C)c4)c3n2)cc2c1C1(CC1)NCC2] |
| 2.440 | 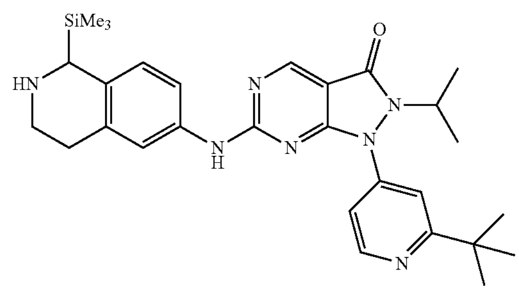 [SMILES: CC(C)n1c(=O)c2cnc(Nc3ccc4c(c3)CCNC4[Si](C)(C)C)nc2n1-c1ccnc(C(C)(C)C)c1] |
| 2.441 | 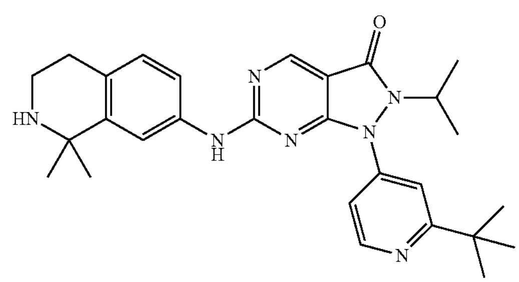 [SMILES: CC(C)n1c(=O)c2cnc(Nc3ccc4c(c3)C(C)(C)NCC4)nc2n1-c1ccnc(C(C)(C)C)c1] |
| 2.442 | 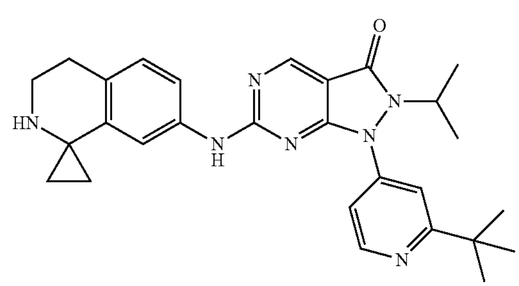 [SMILES: CC(C)n1c(=O)c2cnc(Nc3ccc4c(c3)C3(CC3)NCC4)nc2n1-c1ccnc(C(C)(C)C)c1] |

TABLE 1A-continued
| Compound No. | Structure |
|---|---|
| 2.443 | 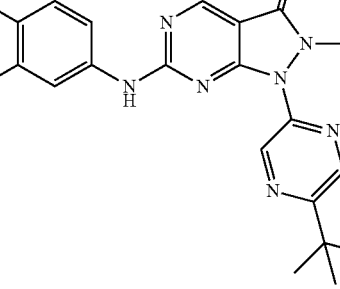 |
| 2.444 | 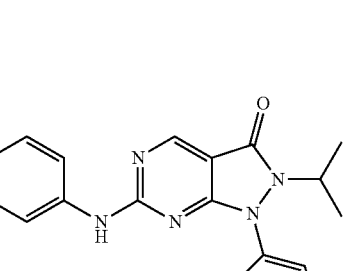 |
| 2.445 | 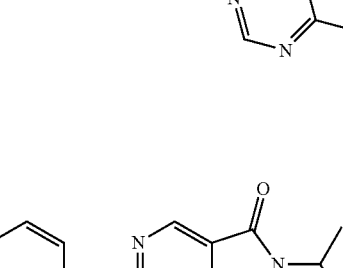 |
| 2.446 | 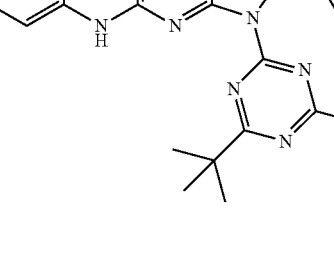 |
TABLE 1A-continued
| Compound No. | Structure |
|---|---|
| 2.447 | 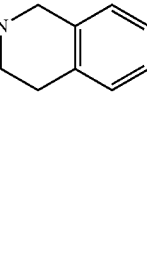 |
| 2.448 | 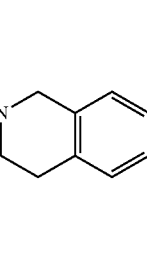 |
| 2.449 | 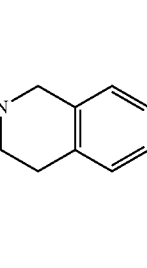 |
| 2.450 | 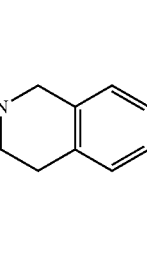 |
| 2.451 | 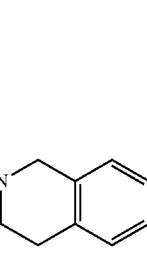 |

TABLE 1A-continued

| Compound No. | Structure |
|---|---|
| 2.452 | 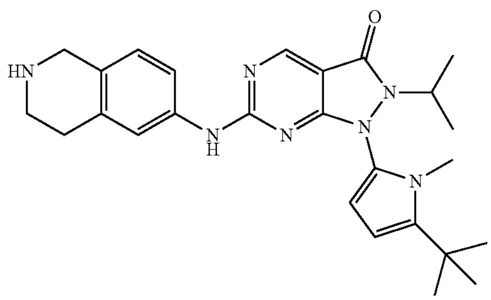 [SMILES: CC(C)n1c(=O)c2cnc(Nc3ccc4c(c3)CCNC4)nc2n1-c1ccc(C(C)(C)C)n1C] |
| 2.453 | 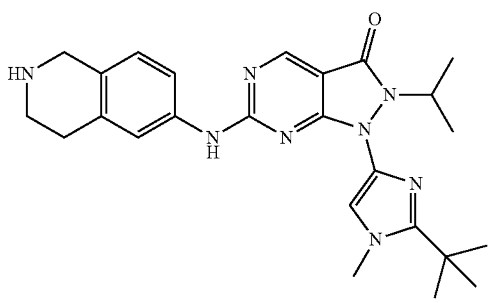 [SMILES: CC(C)n1c(=O)c2cnc(Nc3ccc4c(c3)CCNC4)nc2n1-c1cn(C)c(C(C)(C)C)n1] |
| 2.454 | 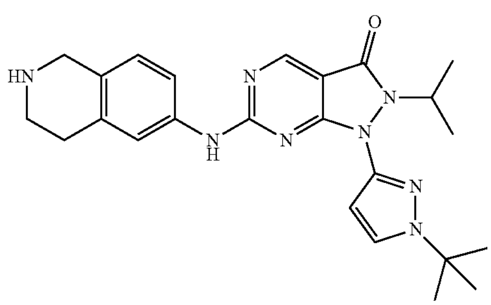 [SMILES: CC(C)n1c(=O)c2cnc(Nc3ccc4c(c3)CCNC4)nc2n1-c1ccn(C(C)(C)C)n1] |
| 2.455 | 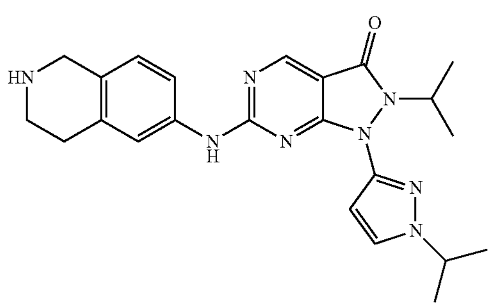 [SMILES: CC(C)n1ccc(-n2c3nc(Nc4ccc5c(c4)CCNC5)ncc3c(=O)n2C(C)C)n1] |
| 2.456 | 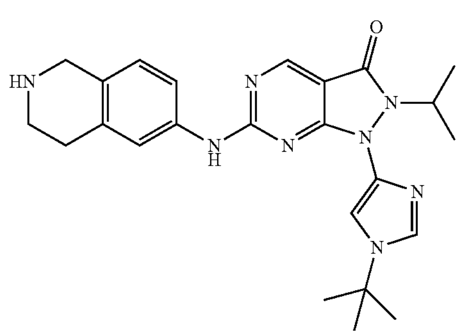 [SMILES: CC(C)n1c(=O)c2cnc(Nc3ccc4c(c3)CCNC4)nc2n1-c1cn(C(C)(C)C)cn1] |
| 2.457 | |
| 2.458 | |
| 2.459 | |
| 2.460 | |
| 2.461 | |

TABLE 1A-continued
| Compound No. | Structure |
|---|---|
| 2.462 | 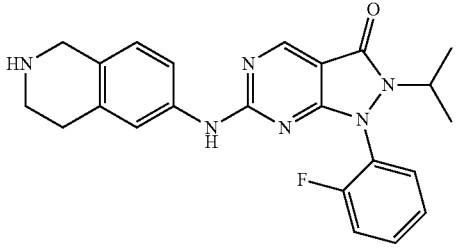 [SMILES: CC(C)n1c(=O)c2cnc(Nc3ccc4c(c3)CCNC4)nc2n1-c1ccccc1F] |
| 2.463 | 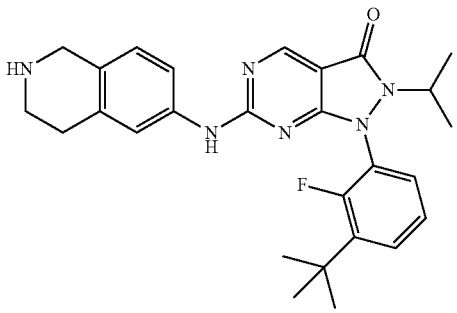 [SMILES: CC(C)n1c(=O)c2cnc(Nc3ccc4c(c3)CCNC4)nc2n1-c1cccc(C(C)(C)C)c1F] |
| 2.464 | 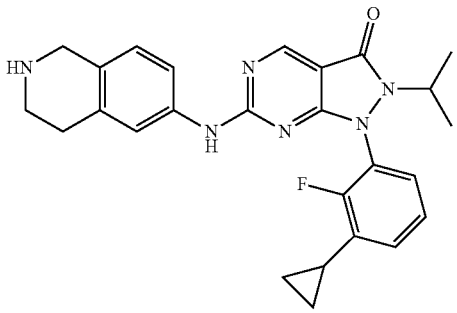 [SMILES: CC(C)n1c(=O)c2cnc(Nc3ccc4c(c3)CCNC4)nc2n1-c1cccc(C2CC2)c1F] |
| 2.465 | 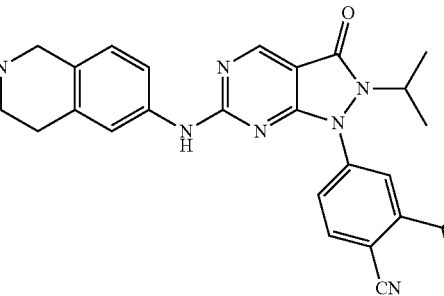 |
| 2.466 | 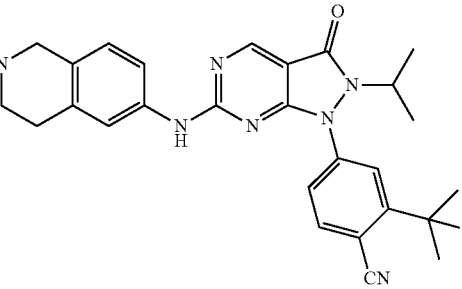 |
| 2.467 | 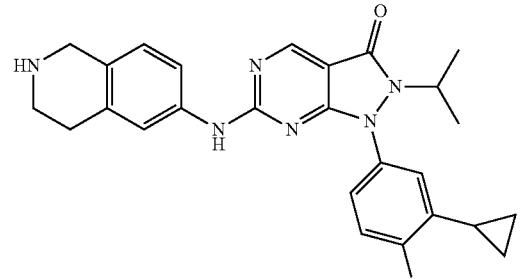 |
| 2.468 | 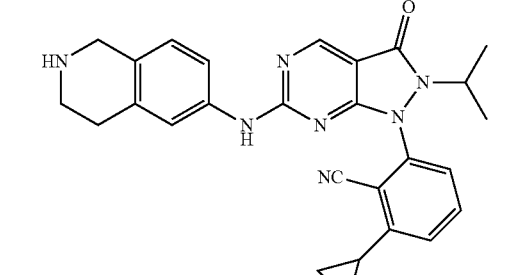 |
| 2.469 | 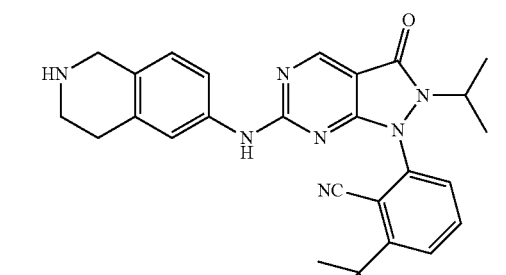 |
| 2.470 | 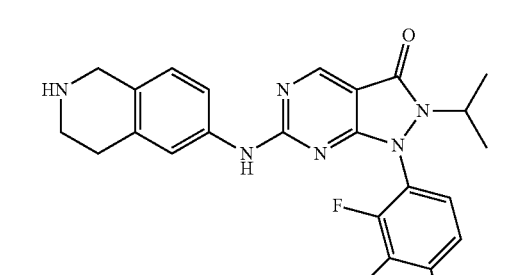 |
| 2.471 | 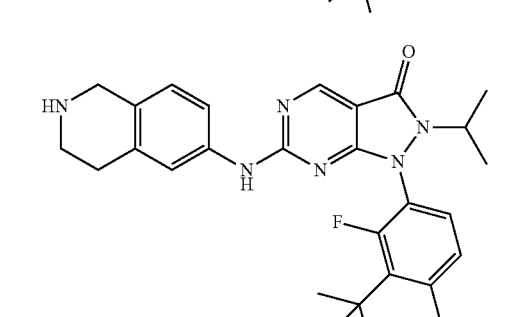 |

TABLE 1A-continued
| Compound No. | Structure |
|---|---|
| 2.472 | 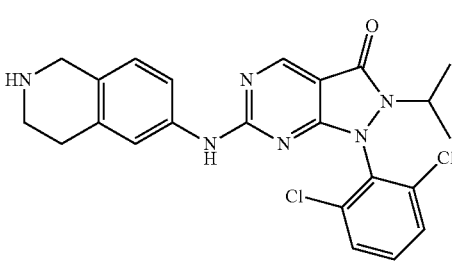 [SMILES: CC(C)n1c(=O)c2cnc(Nc3ccc4c(c3)CCNC4)nc2n1-c1c(Cl)cccc1Cl] |
| 2.473 | 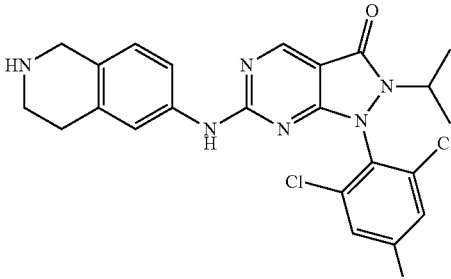 |
| 2.474 | 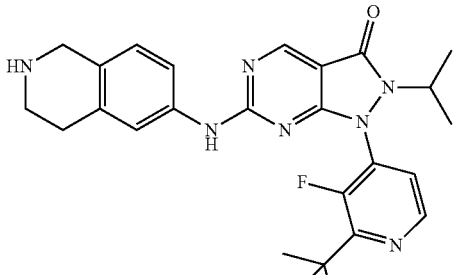 |
| 2.475 | 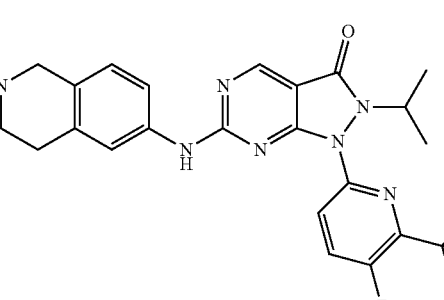 |
| 2.476 | 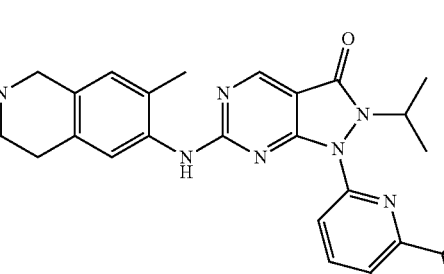 |
| 2.477 | 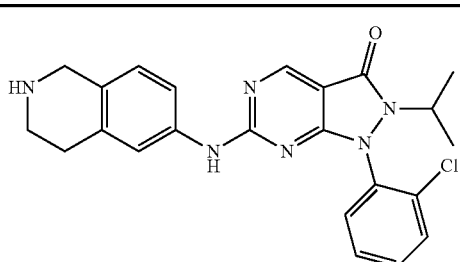 |
| 2.478 | 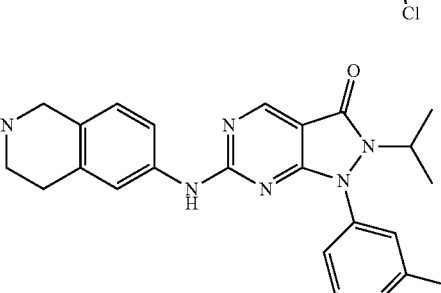 |
| 2.479 | 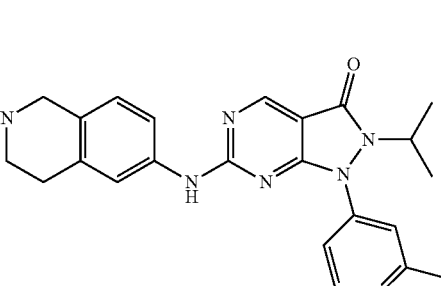 |
| 2.480 | 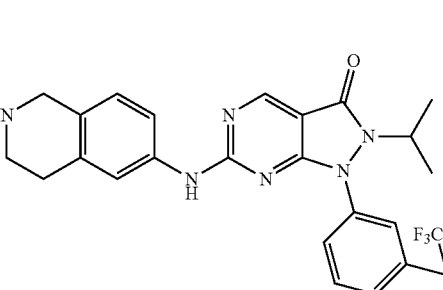 |
| 2.481 | 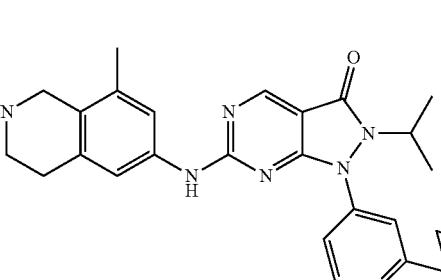 |

TABLE 1A-continued
| Compound No. | Structure |
|---|---|
| 2.482 | 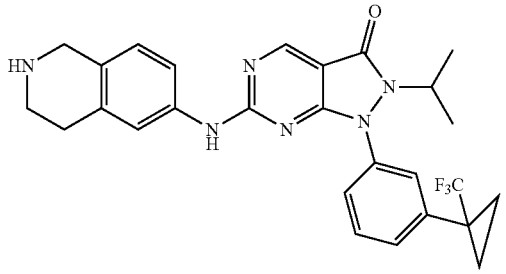 [SMILES: CC(C)n1c(=O)c2cnc(Nc3ccc4c(c3)CCNC4)nc2n1-c1cccc(C2(C(F)(F)F)CC2)c1] |
| 2.483 | 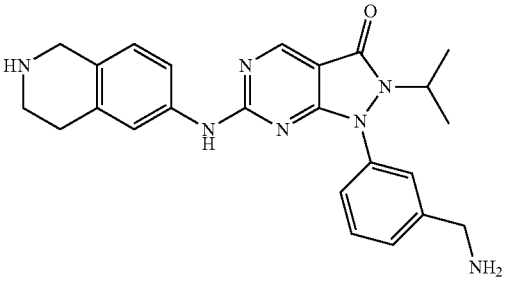 [SMILES: CC(C)n1c(=O)c2cnc(Nc3ccc4c(c3)CCNC4)nc2n1-c1cccc(CN)c1] |
| 2.484 | 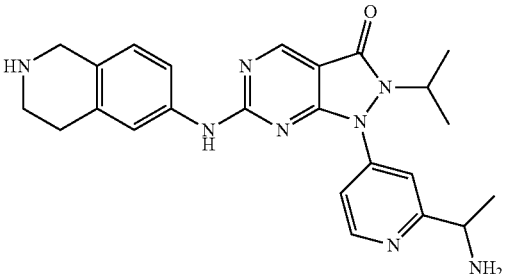 |
| 2.485 | 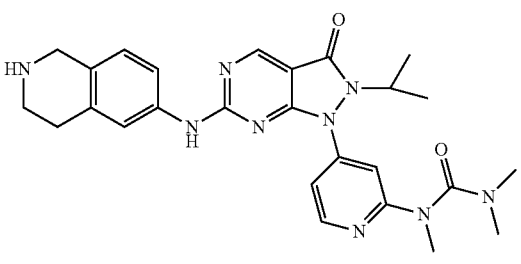 [SMILES: CC(C)n1c(=O)c2cnc(Nc3ccc4c(c3)CCNC4)nc2n1-c1ccnc(N(C)C(=O)N(C)C)c1] |
| 2.486 | 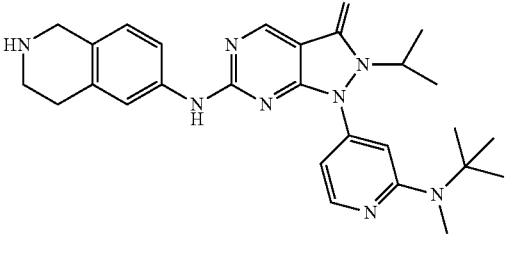 |
TABLE 1A-continued
| Compound No. | Structure |
|---|---|
| 2.487 | 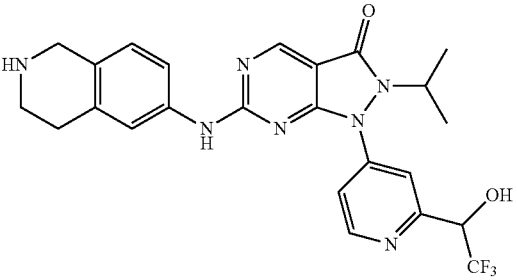 [SMILES: CC(C)n1c(=O)c2cnc(Nc3ccc4c(c3)CCNC4)nc2n1-c1ccnc(C(O)C(F)(F)F)c1] |
| 2.488 | 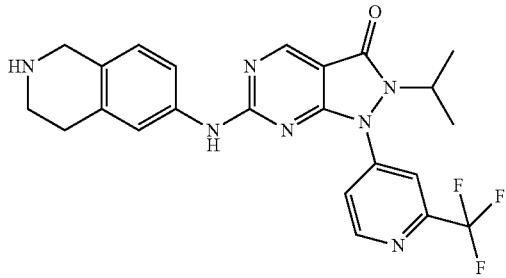 [SMILES: CC(C)n1c(=O)c2cnc(Nc3ccc4c(c3)CCNC4)nc2n1-c1ccnc(C(F)(F)F)c1] |
| 2.489 | 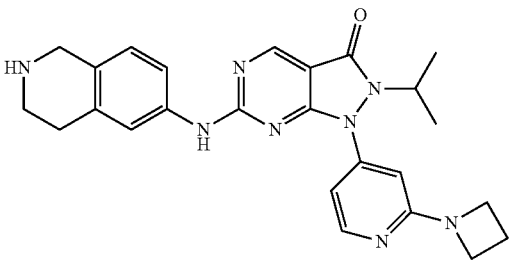 [SMILES: CC(C)n1c(=O)c2cnc(Nc3ccc4c(c3)CCNC4)nc2n1-c1ccnc(N2CCC2)c1] |
| 2.490 | 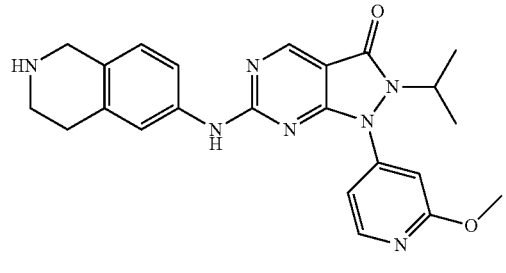 [SMILES: COc1cc(-n2c3nc(Nc4ccc5c(c4)CCNC5)ncc3c(=O)n2C(C)C)ccn1] |
| 2.491 | 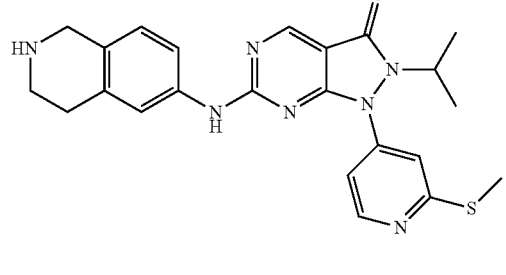 |

TABLE 1A-continued
| Compound No. | Structure |
|---|---|
| 2.492 | 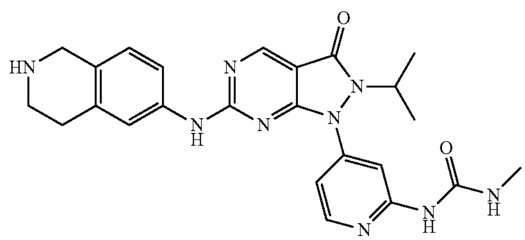 [SMILES: CNC(=O)Nc1cc(-n2c3nc(Nc4ccc5c(c4)CCNC5)ncc3c(=O)n2C(C)C)ccn1] |
| 2.493 | 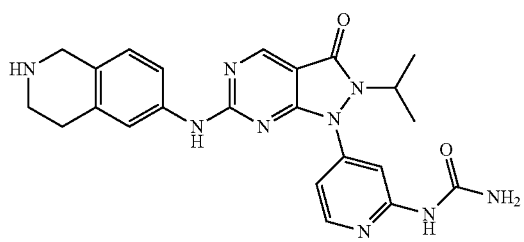 [SMILES: CC(C)n1c(=O)c2cnc(Nc3ccc4c(c3)CCNC4)nc2n1-c1ccnc(NC(N)=O)c1] |
| 2.494 | 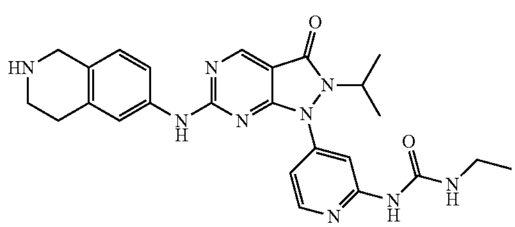 [SMILES: CCNC(=O)Nc1cc(-n2c3nc(Nc4ccc5c(c4)CCNC5)ncc3c(=O)n2C(C)C)ccn1] |
| 2.495 | 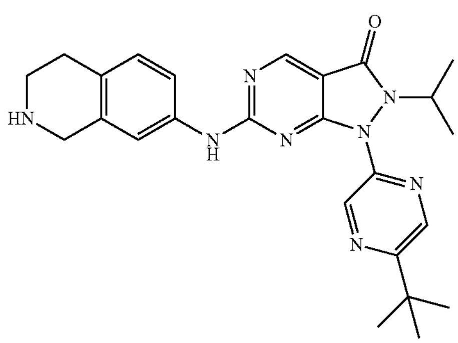 [SMILES: CC(C)n1c(=O)c2cnc(Nc3ccc4c(c3)CNCC4)nc2n1-c1cnc(C(C)(C)C)cn1] |
| 2.496 | 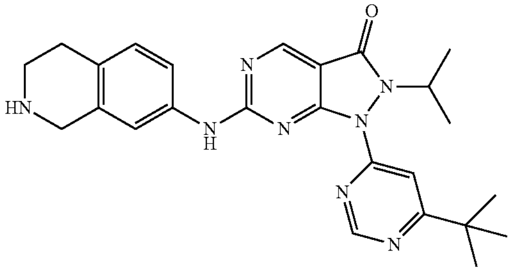 [SMILES: CC(C)n1c(=O)c2cnc(Nc3ccc4c(c3)CNCC4)nc2n1-c1cc(C(C)(C)C)ncn1] |
| 2.497 | |
| 2.498 | |
| 2.499 | |
| 2.500 | |
| 2.501 | |
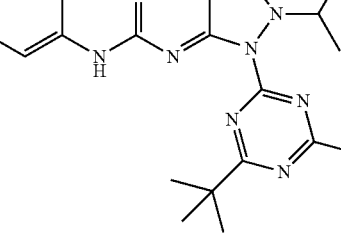

TABLE 1A-continued

| Compound No. | Structure |
|---|---|
| 2.502 | 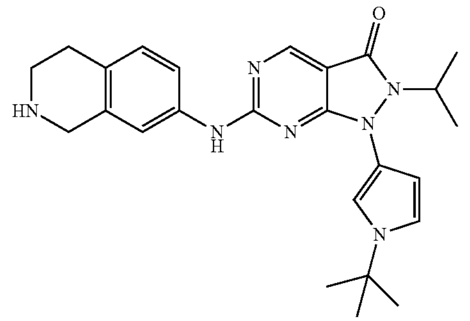 [SMILES: CC(C)n1c(=O)c2cnc(Nc3ccc4c(c3)CNCC4)nc2n1-c1ccn(C(C)(C)C)c1] |
| 2.503 | 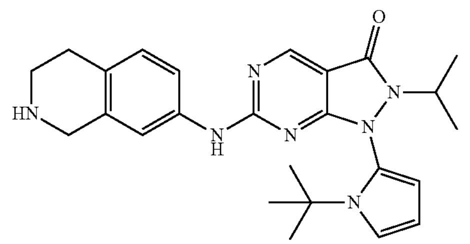 [SMILES: CC(C)n1c(=O)c2cnc(Nc3ccc4c(c3)CNCC4)nc2n1-c1cccn1C(C)(C)C] |
| 2.504 | 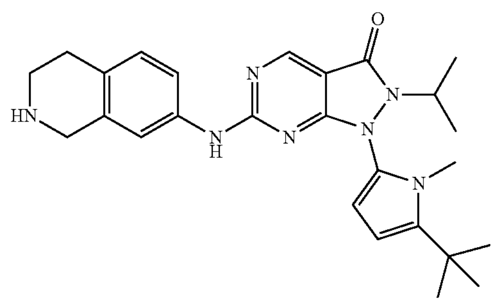 [SMILES: CC(C)n1c(=O)c2cnc(Nc3ccc4c(c3)CNCC4)nc2n1-c1ccc(C(C)(C)C)n1C] |
| 2.505 | 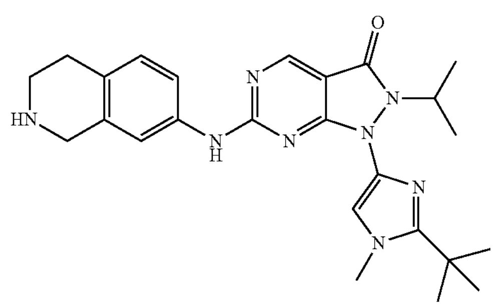 [SMILES: CC(C)n1c(=O)c2cnc(Nc3ccc4c(c3)CNCC4)nc2n1-c1cn(C)c(C(C)(C)C)n1] |
| 2.506 | 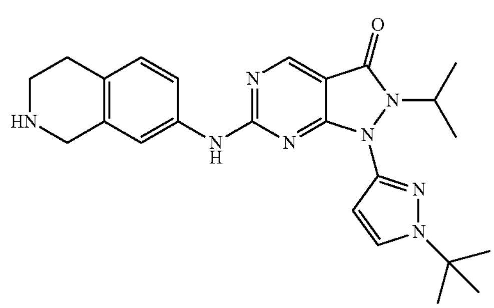 [SMILES: CC(C)n1c(=O)c2cnc(Nc3ccc4c(c3)CNCC4)nc2n1-c1ccn(C(C)(C)C)n1] |
| 2.507 | |
| 2.508 | |
| 2.509 | |
| 2.510 | |
| 2.511 | |

TABLE 1A-continued

| Compound No. | Structure |
|---|---|
| 2.512 | 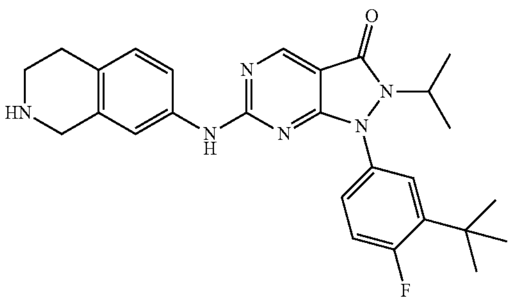 [SMILES: CC(C)n1c(=O)c2cnc(Nc3ccc4c(c3)CNCC4)nc2n1-c1ccc(F)c(C(C)(C)C)c1] |
| 2.513 | 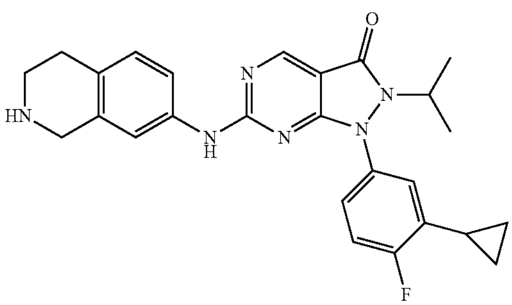 [SMILES: CC(C)n1c(=O)c2cnc(Nc3ccc4c(c3)CNCC4)nc2n1-c1ccc(F)c(C2CC2)c1] |
| 2.514 | 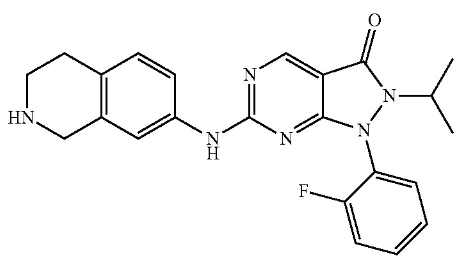 [SMILES: CC(C)n1c(=O)c2cnc(Nc3ccc4c(c3)CNCC4)nc2n1-c1ccccc1F] |
| 2.515 | 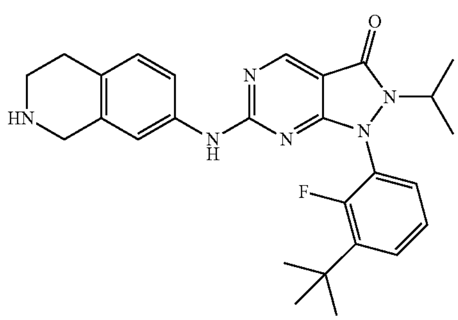 [SMILES: CC(C)n1c(=O)c2cnc(Nc3ccc4c(c3)CNCC4)nc2n1-c1cccc(C(C)(C)C)c1F] |
| 2.516 | 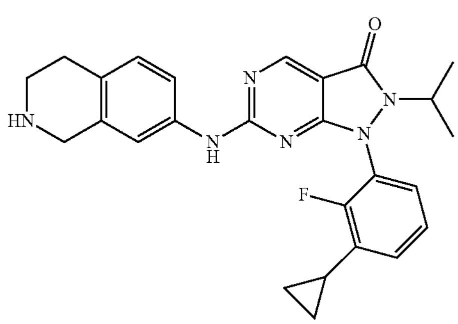 [SMILES: CC(C)n1c(=O)c2cnc(Nc3ccc4c(c3)CNCC4)nc2n1-c1cccc(C2CC2)c1F] |
| 2.517 | |
| 2.518 | |
| 2.519 | |
| 2.520 | |
| 2.521 | |

TABLE 1A-continued
| Compound No. | Structure |
|---|---|
| 2.522 | 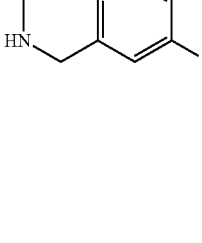 |
| 2.523 | 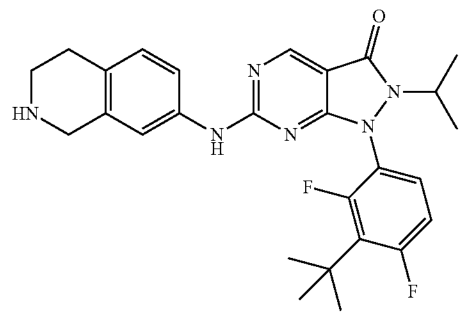 [SMILES: CC(C)n1c(=O)c2cnc(Nc3ccc4c(c3)CNCC4)nc2n1-c1ccc(F)c(C(C)(C)C)c1F] |
| 2.524 | 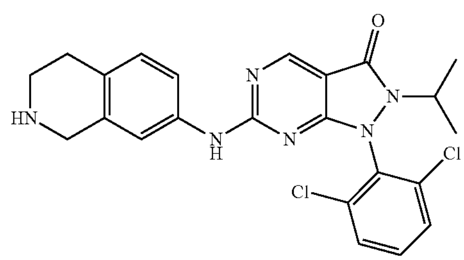 [SMILES: CC(C)n1c(=O)c2cnc(Nc3ccc4c(c3)CNCC4)nc2n1-c1c(Cl)cccc1Cl] |
| 2.525 | 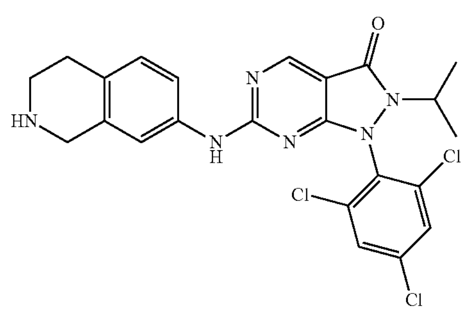 [SMILES: CC(C)n1c(=O)c2cnc(Nc3ccc4c(c3)CNCC4)nc2n1-c1c(Cl)cc(Cl)cc1Cl] |
| 2.526 | 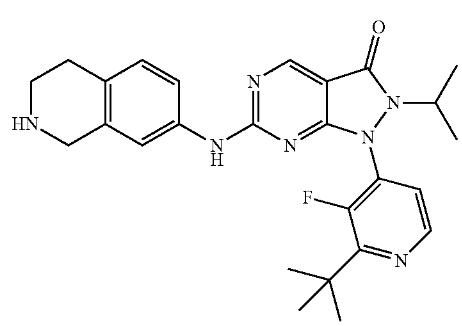 [SMILES: CC(C)n1c(=O)c2cnc(Nc3ccc4c(c3)CNCC4)nc2n1-c1ccnc(C(C)(C)C)c1F] |
| 2.527 | |
| 2.528 | |
| 2.529 | |
| 2.530 | |
| 2.531 | |

TABLE 1A-continued

| Compound No. | Structure |
|---|---|
| 2.532 | 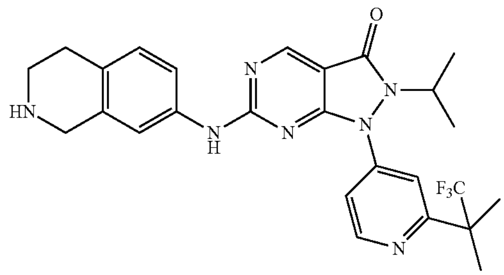 [SMILES: CC(C)n1c(=O)c2cnc(Nc3ccc4c(c3)CNCC4)nc2n1-c1ccnc(C(C)(C)C(F)(F)F)c1] |
| 2.533 | 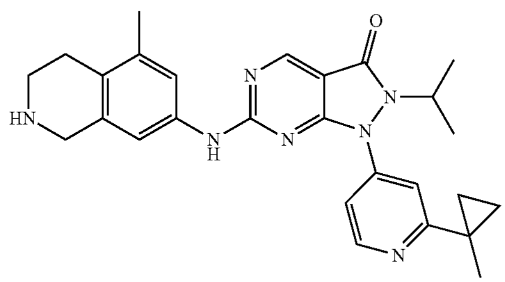 [SMILES: Cc1cc(Nc2ncc3c(=O)n(C(C)C)n(-c4ccnc(C5(C)CC5)c4)c3n2)cc2c1CCNC2] |
| 2.534 | 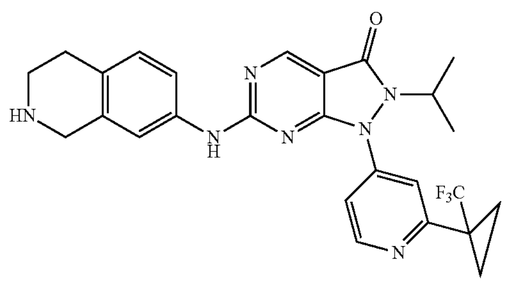 [SMILES: CC(C)n1c(=O)c2cnc(Nc3ccc4c(c3)CNCC4)nc2n1-c1ccnc(C2(C(F)(F)F)CC2)c1] |
| 2.535 | 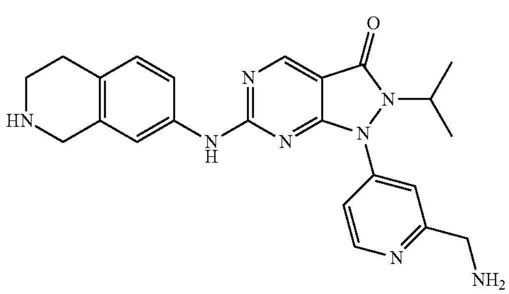 [SMILES: CC(C)n1c(=O)c2cnc(Nc3ccc4c(c3)CNCC4)nc2n1-c1ccnc(CN)c1] |
| 2.536 | 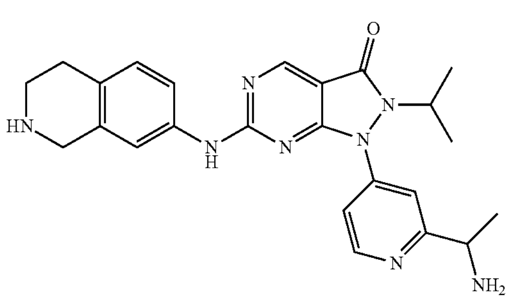 [SMILES: CC(N)c1cc(-n2c3nc(Nc4ccc5c(c4)CNCC5)ncc3c(=O)n2C(C)C)ccn1] |
| 2.537 | |
| 2.538 | |
| 2.539 | |
| 2.540 | |
| 2.541 | |

TABLE 1A-continued

| Compound No. | Structure |
|---|---|
| 2.542 | 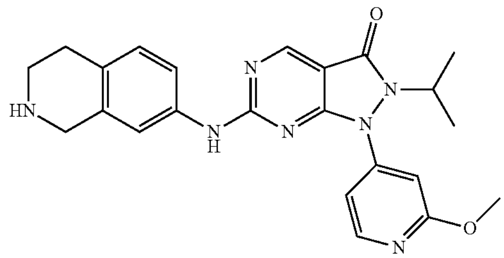 [SMILES: CSc1cc(-n2c3nc(Nc4ccc5c(c4)CNCC5)ncc3c(=O)n2C(C)C)ccn1] |
| 2.543 | 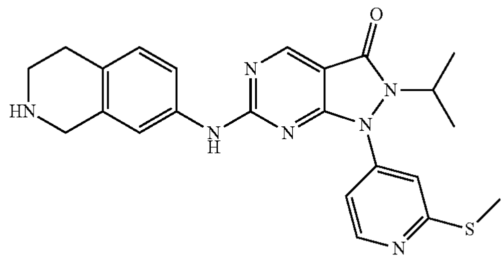 |
| 2.544 | 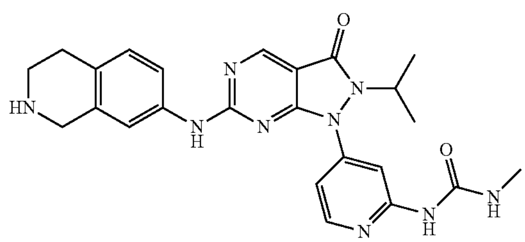 [SMILES: CNC(=O)Nc1cc(-n2c3nc(Nc4ccc5c(c4)CNCC5)ncc3c(=O)n2C(C)C)ccn1] |
| 2.545 | 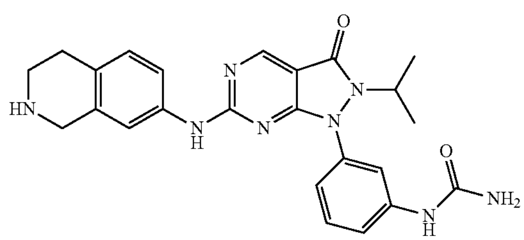 [SMILES: CC(C)n1c(=O)c2cnc(Nc3ccc4c(c3)CNCC4)nc2n1-c1cccc(NC(N)=O)c1] |
| 2.546 | 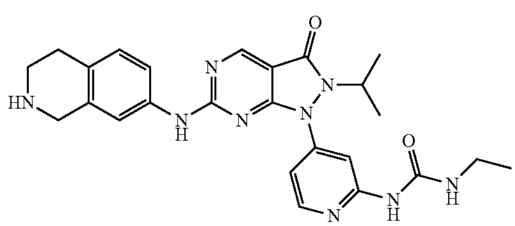 [SMILES: CCNC(=O)Nc1cc(-n2c3nc(Nc4ccc5c(c4)CNCC5)ncc3c(=O)n2C(C)C)ccn1] |
| 2.547 | 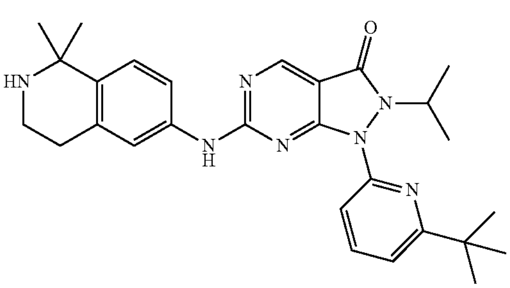 [SMILES: CC(C)n1c(=O)c2cnc(Nc3ccc4c(c3)CCNC4(C)C)nc2n1-c1cccc(C(C)(C)C)n1] |
| 2.548 | |
| 2.549 | |
| 2.550 | |
| 2.551 | |
| 2.552 | |

TABLE 1A-continued
| Compound No. | Structure |
|---|---|
| 2.553 | 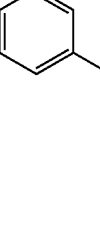 |
| 2.554 | 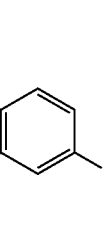 |
| 2.555 | 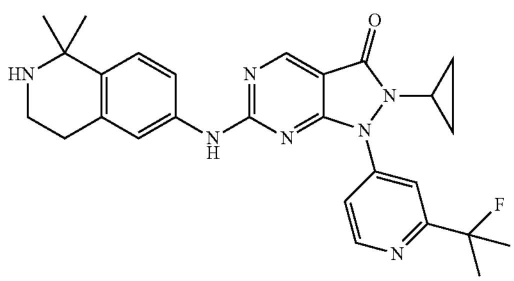 [SMILES: CC(C)(F)c1cc(-n2c3nc(Nc4ccc5c(c4)CCNC5(C)C)ncc3c(=O)n2C2CC2)ccn1] |
| 2.556 | 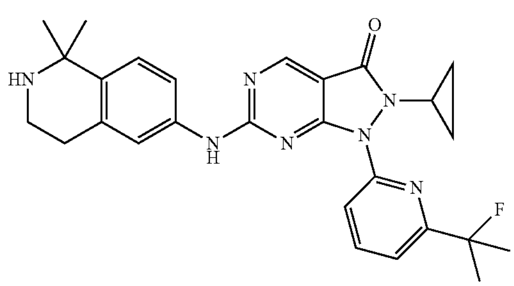 [SMILES: CC(C)(F)c1cccc(-n2c3nc(Nc4ccc5c(c4)CCNC5(C)C)ncc3c(=O)n2C2CC2)n1] |
| 2.557 | 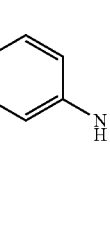 |
| 2.558 | 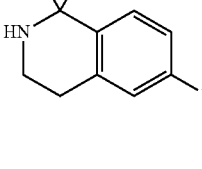 |
| 2.559 | 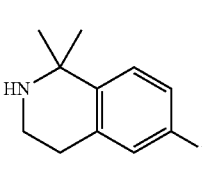 |
| 2.560 | 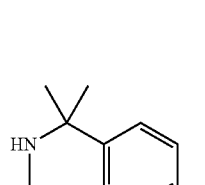 |
| 2.561 |  |
| 2.562 | 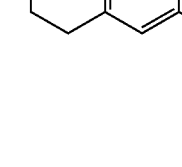 |

TABLE 1A-continued

| Compound No. | Structure |
|---|---|
| 2.563 | 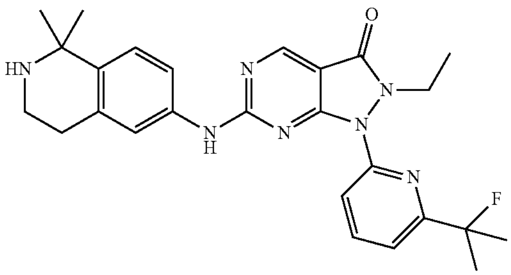 [SMILES: CCn1c(=O)c2cnc(Nc3ccc4c(c3)CCNC4(C)C)nc2n1-c1cccc(C(C)(C)F)n1] |
| 2.564 | 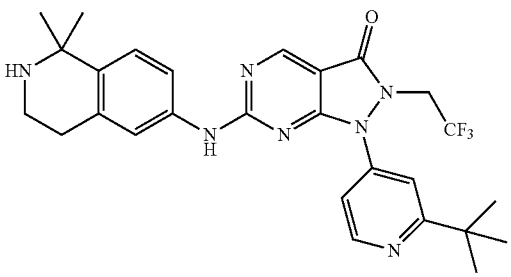 [SMILES: CC(C)(C)c1cc(-n2c3nc(Nc4ccc5c(c4)CCNC5(C)C)ncc3c(=O)n2CC(F)(F)F)ccn1] |
| 2.565 | 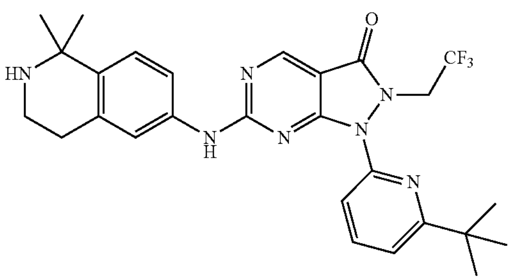 [SMILES: CC(C)(C)c1cccc(-n2c3nc(Nc4ccc5c(c4)CCNC5(C)C)ncc3c(=O)n2CC(F)(F)F)n1] |
| 2.566 | 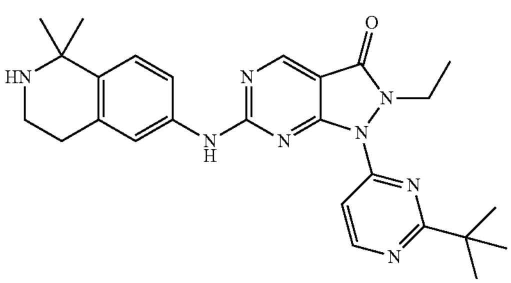 [SMILES: CCn1c(=O)c2cnc(Nc3ccc4c(c3)CCNC4(C)C)nc2n1-c1ccnc(C(C)(C)C)n1] |
| 2.567 | 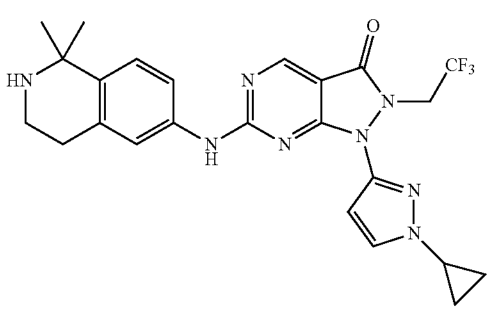 [SMILES: CC1(C)NCCc2cc(Nc3ncc4c(=O)n(CC(F)(F)F)n(-c5ccn(C6CC6)n5)c4n3)ccc21] |
| 2.568 | |
| 2.569 | |
| 2.570 | |
| 2.571 | |
| 2.572 | |

TABLE 1A-continued

| Compound No. | Structure |
|---|---|
| 2.573 | 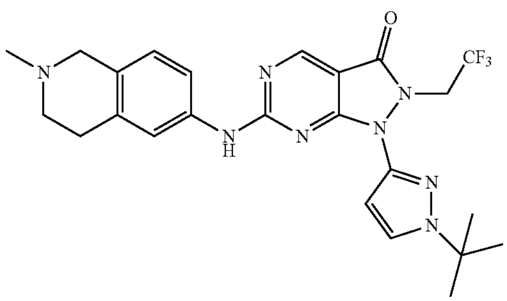 [SMILES: CN1CCc2cc(Nc3ncc4c(=O)n(CC(F)(F)F)n(-c5ccn(C(C)(C)C)n5)c4n3)ccc2C1] |
| 2.574 | 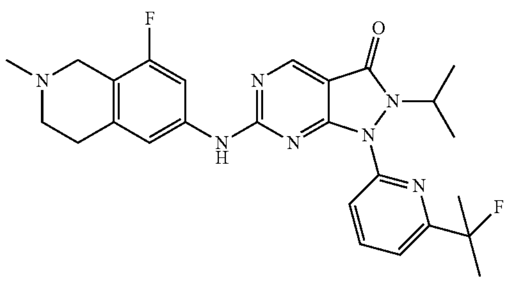 [SMILES: CC(C)n1c(=O)c2cnc(Nc3cc(F)c4c(c3)CCN(C)C4)nc2n1-c1cccc(C(C)(C)F)n1] |
| 2.575 | 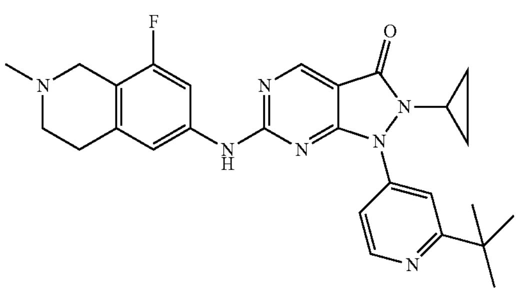 [SMILES: CN1CCc2cc(Nc3ncc4c(=O)n(C5CC5)n(-c5ccnc(C(C)(C)C)c5)c4n3)cc(F)c2C1] |
| 2.576 | 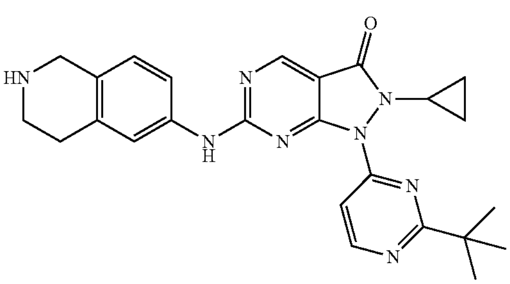 [SMILES: CC(C)(C)c1nccc(-n2c3nc(Nc4ccc5c(c4)CCNC5)ncc3c(=O)n2C2CC2)n1] |
| 2.577 | 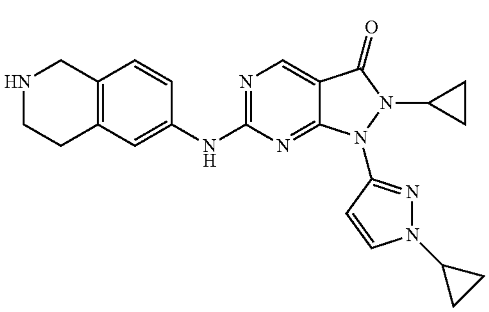 [SMILES: O=c1c2cnc(Nc3ccc4c(c3)CCNC4)nc2n(-c2ccn(C3CC3)n2)n1C1CC1] |
| 2.578 | |
| 2.579 | |
| 2.580 | |
| 2.581 | |
| 2.582 | |

TABLE 1A-continued

| Compound No. | Structure |
|---|---|
| 2.583 | 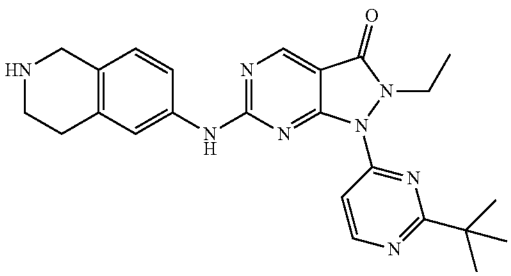 [SMILES: CCn1c(=O)c2cnc(Nc3ccc4c(c3)CCNC4)nc2n1-c1ccnc(C(C)(C)C)n1] |
| 2.584 | 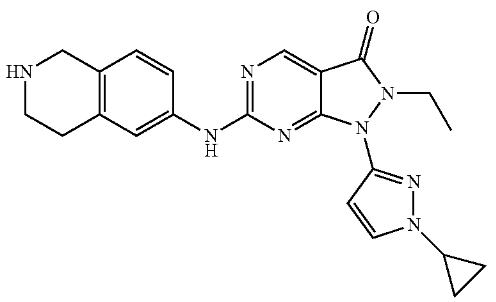 [SMILES: CCn1c(=O)c2cnc(Nc3ccc4c(c3)CCNC4)nc2n1-c1ccn(C2CC2)n1] |
| 2.585 | 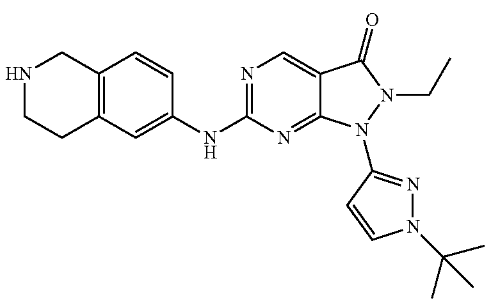 [SMILES: CCn1c(=O)c2cnc(Nc3ccc4c(c3)CCNC4)nc2n1-c1ccn(C(C)(C)C)n1] |
| 2.586 | 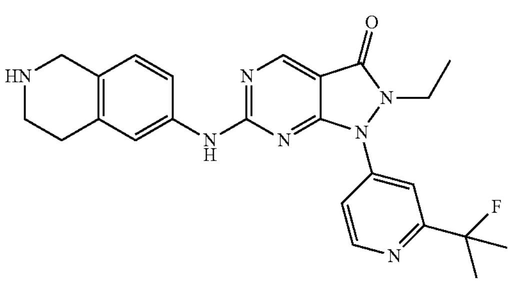 |
| 2.587 | 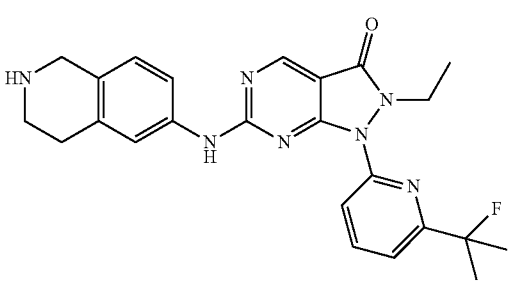 [SMILES: CCn1c(=O)c2cnc(Nc3ccc4c(c3)CCNC4)nc2n1-c1cccc(C(C)(C)F)n1] |
| 2.588 | |
| 2.589 | |
| 2.590 | |
| 2.591 | |
| 2.592 | |

TABLE 1A-continued

| Compound No. | Structure |
|---|---|
| 2.593 | 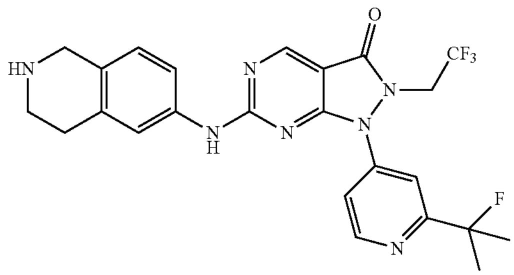 |
| 2.594 | 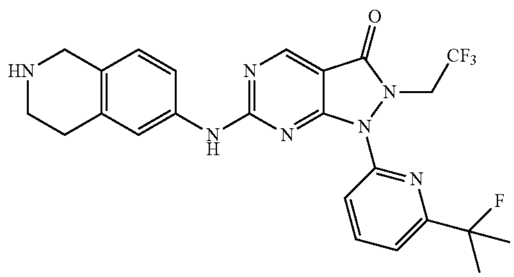 [SMILES: CC(C)(C)c1cccc(-n2c3nc(Nc4ccc5c(c4)CCNC5)ncc3c(=O)n2CC(F)(F)F)n1] |
| 2.595 | 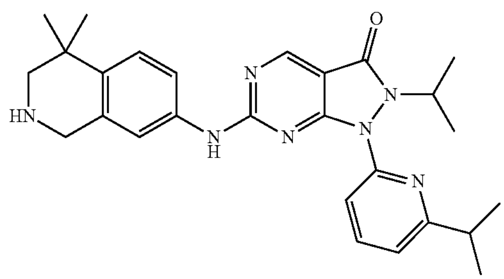 [SMILES: CC(C)c1cccc(-n2c3nc(Nc4ccc5c(c4)CNCC5(C)C)ncc3c(=O)n2C(C)C)n1] |
| 2.596 | 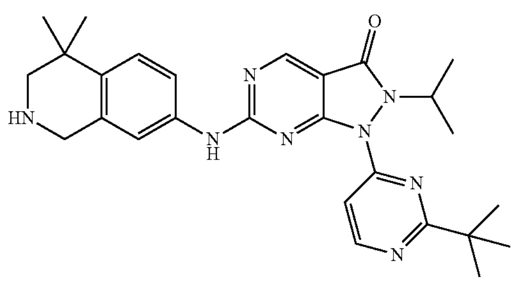 [SMILES: CC(C)n1c(=O)c2cnc(Nc3ccc4c(c3)CNCC4(C)C)nc2n1-c1ccnc(C(C)(C)C)n1] |
| 2.597 | 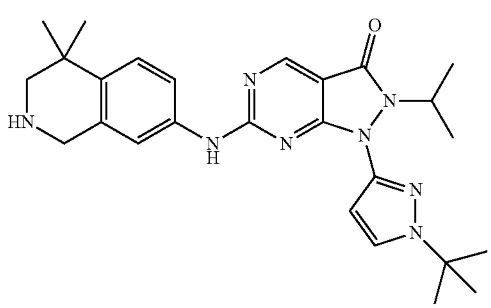 [SMILES: CC(C)n1c(=O)c2cnc(Nc3ccc4c(c3)CNCC4(C)C)nc2n1-c1ccn(C(C)(C)C)n1] |
| 2.598 | |
| 2.599 | |
| 2.600 | |
| 2.601 | |
| 2.602 | |

TABLE 1A-continued

| Compound No. | Structure |
|---|---|
| 2.603 | 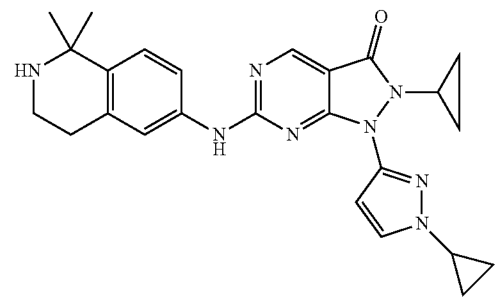 [SMILES: CC1(C)NCCc2cc(Nc3ncc4c(=O)n(C5CC5)n(-c5ccn(C6CC6)n5)c4n3)ccc21] |
| 2.604 | 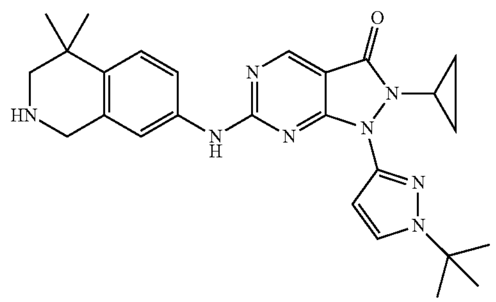 [SMILES: CC1(C)CNCc2cc(Nc3ncc4c(=O)n(C5CC5)n(-c5ccn(C(C)(C)C)n5)c4n3)ccc21] |
| 2.605 | 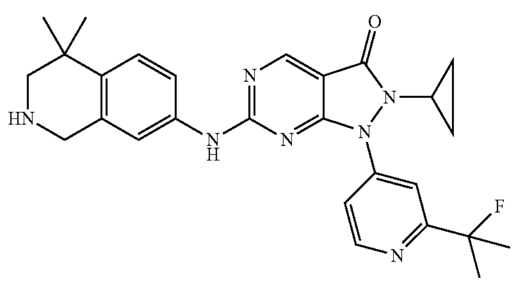 [SMILES: CC(C)(F)c1cc(-n2c3nc(Nc4ccc5c(c4)CNCC5(C)C)ncc3c(=O)n2C2CC2)ccn1] |
| 2.606 | 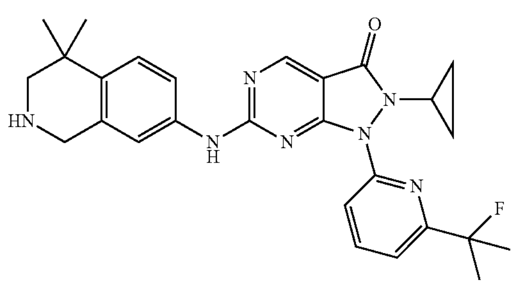 [SMILES: CC(C)(F)c1cccc(-n2c3nc(Nc4ccc5c(c4)CNCC5(C)C)ncc3c(=O)n2C2CC2)n1] |
| 2.607 | 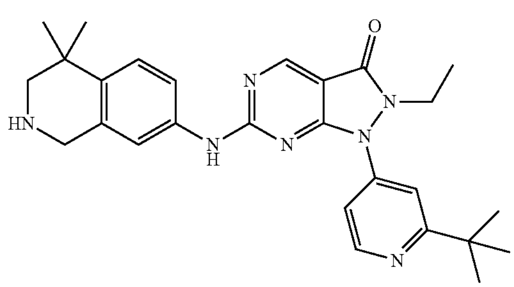 [SMILES: CCn1c(=O)c2cnc(Nc3ccc4c(c3)CNCC4(C)C)nc2n1-c1ccnc(C(C)(C)F)c1] |
| 2.608 | |
| 2.609 | |
| 2.610 | |
| 2.611 | |
| 2.612 | |

TABLE 1A-continued

| Compound No. | Structure |
|---|---|
| 2.613 | 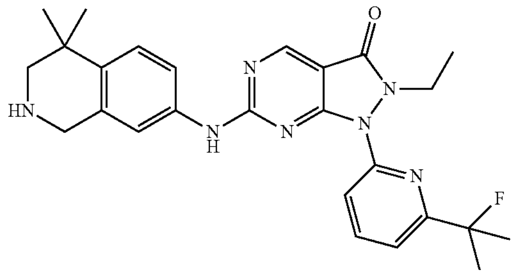 [SMILES: CCn1c(=O)c2cnc(Nc3ccc4c(c3)CNCC4(C)C)nc2n1-c1cccc(C(C)(C)F)n1] |
| 2.614 | 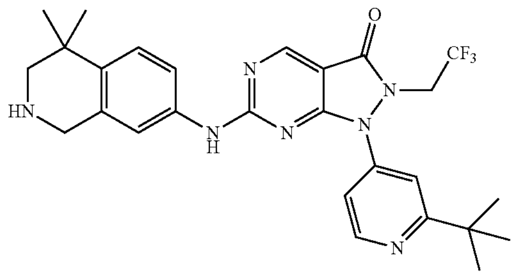 [SMILES: CC(C)(C)c1cc(-n2c3nc(Nc4ccc5c(c4)CNCC5(C)C)ncc3c(=O)n2CC(F)(F)F)ccn1] |
| 2.615 | 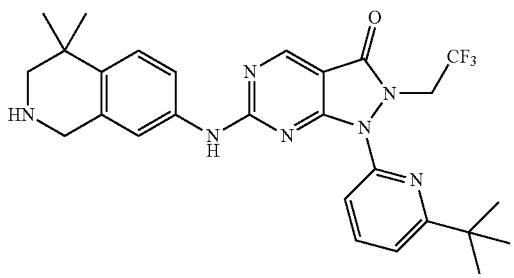 [SMILES: CC(C)(C)c1cccc(-n2c3nc(Nc4ccc5c(c4)CNCC5(C)C)ncc3c(=O)n2CC(F)(F)F)n1] |
| 2.616 | 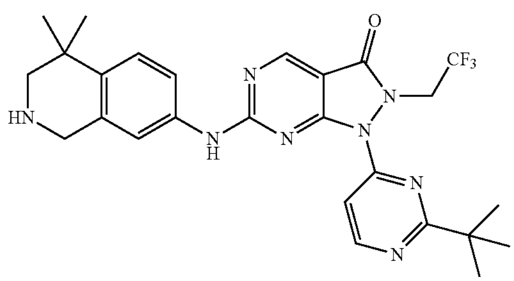 [SMILES: CC(C)(C)c1nccc(-n2c3nc(Nc4ccc5c(c4)CNCC5(C)C)ncc3c(=O)n2CC(F)(F)F)n1] |
| 2.617 | 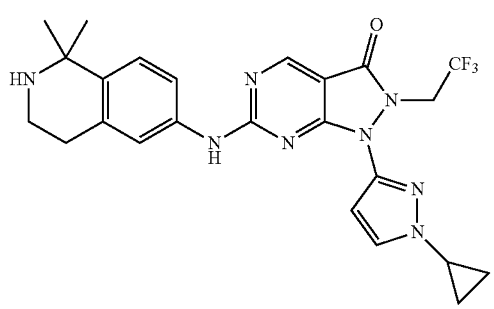 [SMILES: CC1(C)NCCc2cc(Nc3ncc4c(=O)n(CC(F)(F)F)n(-c5ccn(C6CC6)n5)c4n3)ccc21] |
| 2.618 | |
| 2.619 | |
| 2.620 | |
| 2.621 | |
| 2.622 | |

TABLE 1A-continued
| Compound No. | Structure |
|---|---|
| 2.623 | 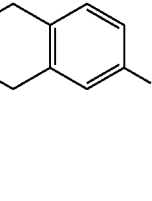 |
| 2.624 | 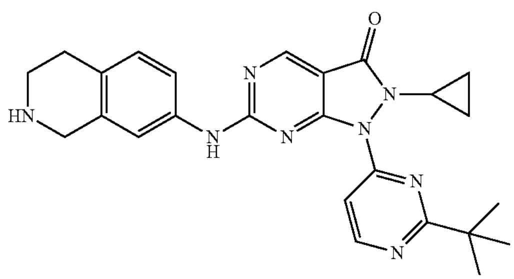 [SMILES: CC(C)(C)c1nccc(-n2c3nc(Nc4ccc5c(c4)CNCC5)ncc3c(=O)n2C2CC2)n1] |
| 2.625 | 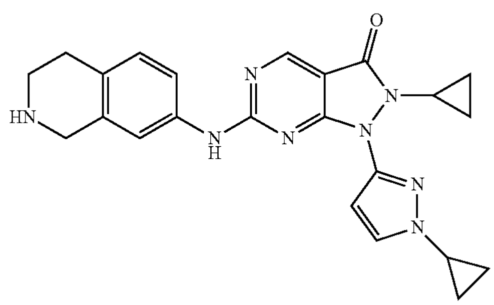 [SMILES: O=c1c2cnc(Nc3ccc4c(c3)CNCC4)nc2n(-c2ccn(C3CC3)n2)n1C1CC1] |
| 2.626 | 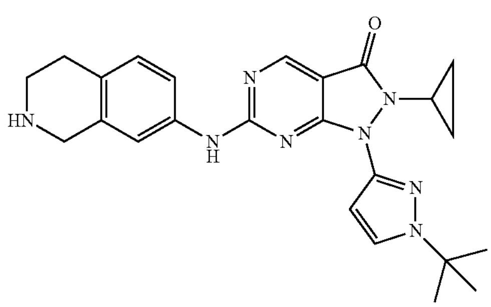 [SMILES: CC(C)(C)n1ccc(-n2c3nc(Nc4ccc5c(c4)CNCC5)ncc3c(=O)n2C2CC2)n1] |
| 2.627 | 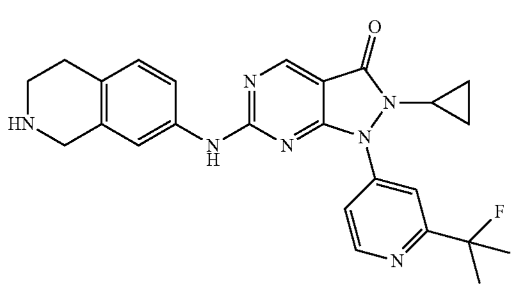 [SMILES: CC(C)(F)c1cc(-n2c3nc(Nc4ccc5c(c4)CNCC5)ncc3c(=O)n2C2CC2)ccn1] |
TABLE 1A-continued
| Compound No. | Structure |
|---|---|
| 2.628 | 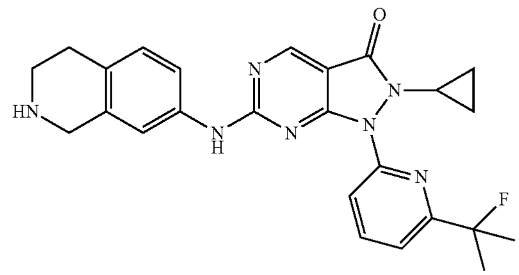 [SMILES: CC(C)(F)c1cccc(-n2c3nc(Nc4ccc5c(c4)CNCC5)ncc3c(=O)n2C2CC2)n1] |
| 2.629 | 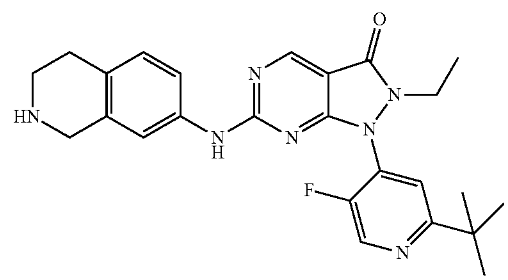 [SMILES: CCn1c(=O)c2cnc(Nc3ccc4c(c3)CNCC4)nc2n1-c1cc(C(C)(C)C)ncc1F] |
| 2.630 | 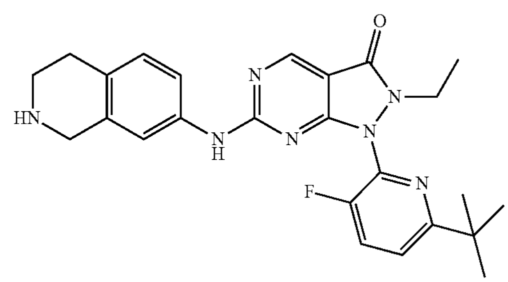 [SMILES: CCn1c(=O)c2cnc(Nc3ccc4c(c3)CNCC4)nc2n1-c1nc(C(C)(C)C)ccc1F] |
| 2.631 | 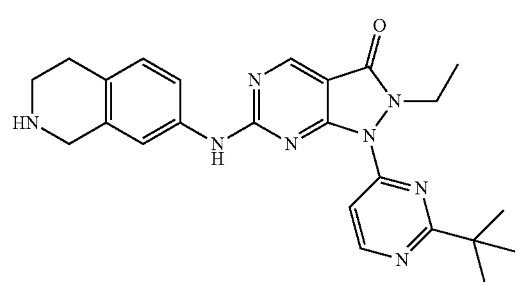 [SMILES: CCn1c(=O)c2cnc(Nc3ccc4c(c3)CNCC4)nc2n1-c1ccnc(C(C)(C)C)n1] |
| 2.632 | 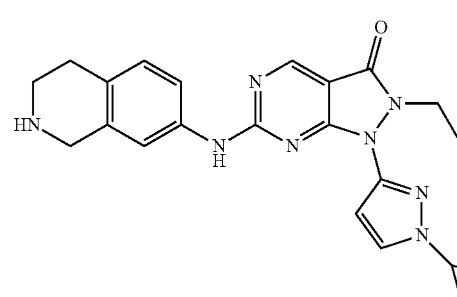 |

TABLE 1A-continued
| Compound No. | Structure |
|---|---|
| 2.633 | 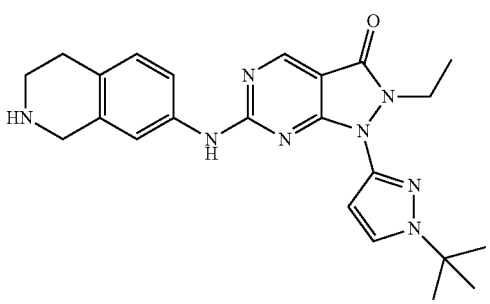 [SMILES: CCn1c(=O)c2cnc(Nc3ccc4c(c3)CNCC4)nc2n1-c1ccn(C(C)(C)C)n1] |
| 2.634 | 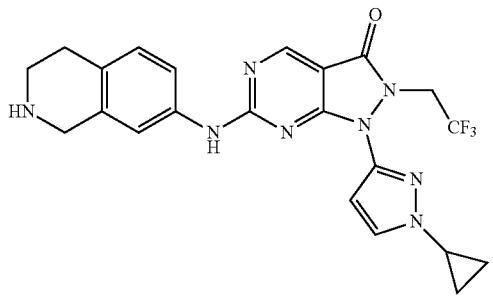 |
| 2.635 | 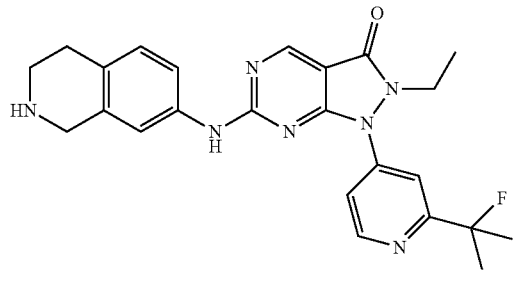 [SMILES: CCn1c(=O)c2cnc(Nc3ccc4c(c3)CNCC4)nc2n1-c1ccnc(C(C)(C)F)c1] |
| 2.636 | 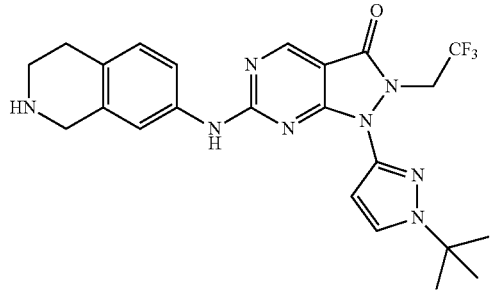 |
| 2.637 | 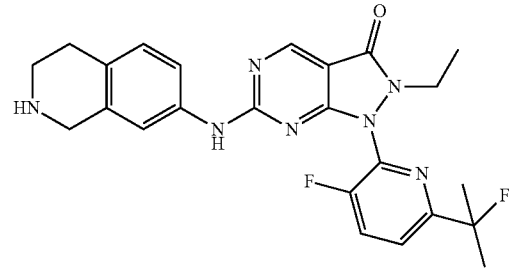 [SMILES: CCn1c(=O)c2cnc(Nc3ccc4c(c3)CNCC4)nc2n1-c1nc(C(C)(C)F)ccc1F] |
TABLE 1A-continued
| Compound No. | Structure |
|---|---|
| 2.638 | 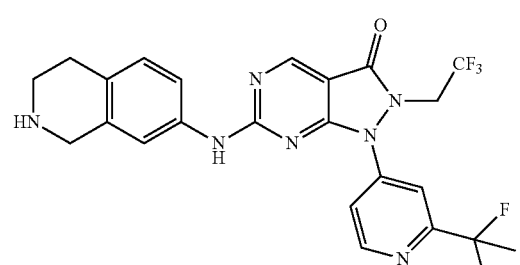 |
| 2.639 | 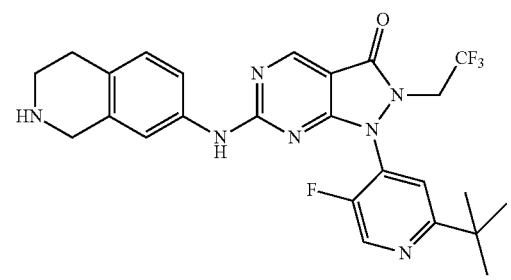 [SMILES: CC(C)(C)c1cc(-n2c3nc(Nc4ccc5c(c4)CNCC5)ncc3c(=O)n2CC(F)(F)F)c(F)cn1] |
| 2.640 | 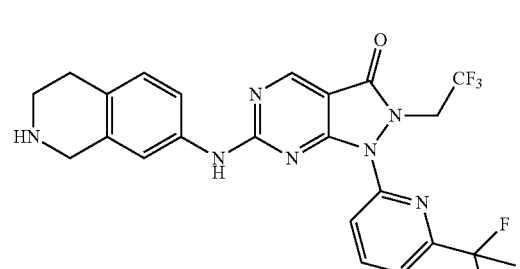 |
| 2.641 | 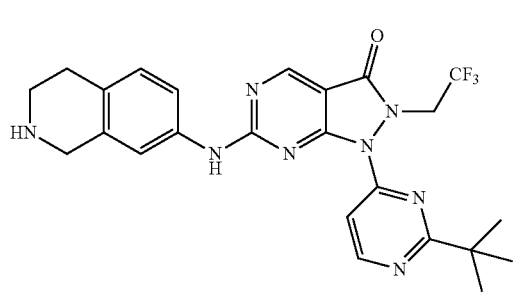 [SMILES: CC(C)(C)c1nccc(-n2c3nc(Nc4ccc5c(c4)CNCC5)ncc3c(=O)n2CC(F)(F)F)n1] |
| 2.642 | 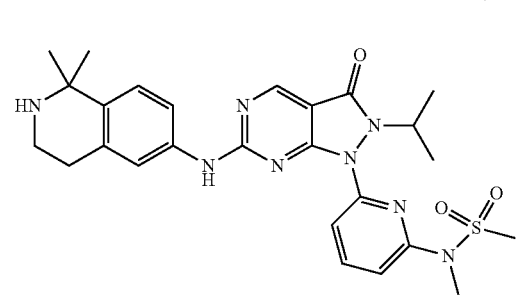 [SMILES: CC(C)n1c(=O)c2cnc(Nc3ccc4c(c3)CCNC4(C)C)nc2n1-c1cccc(N(C)S(C)(=O)=O)n1] |

TABLE 1A-continued

| Compound No. | Structure |
|---|---|
| 2.643 | (structure) |
| 2.644 | (structure) |
| 2.645 | (structure) |
| 2.646 | (structure) |
| 2.647 | (structure) |
| 2.648 | (structure) |
| 2.649 | (structure) |
| 2.650 | (structure) |
| 2.651 | (structure) |
| 2.652 | (structure) |

TABLE 1A-continued

| Compound No. | Structure |
|---|---|
| 2.653 | 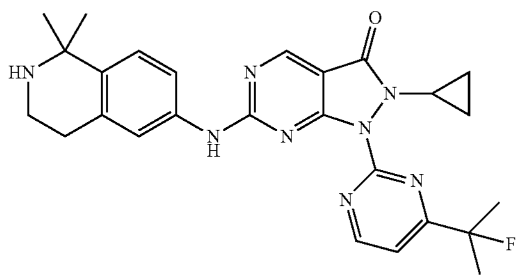 [SMILES: CC(C)(F)c1ccnc(-n2c3nc(Nc4ccc5c(c4)CCNC5(C)C)ncc3c(=O)n2C2CC2)n1] |
| 2.654 | 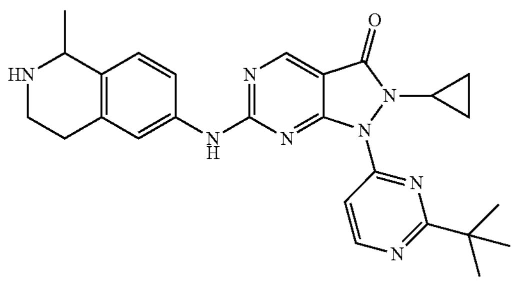 [SMILES: CC1NCCc2cc(Nc3ncc4c(=O)n(C5CC5)n(-c5ccnc(C(C)(C)C)n5)c4n3)ccc21] |
| 2.655 | 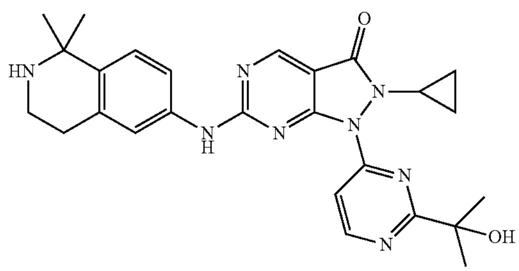 [SMILES: CC(C)(O)c1nccc(-n2c3nc(Nc4ccc5c(c4)CCNC5(C)C)ncc3c(=O)n2C2CC2)n1] |
| 2.656 | 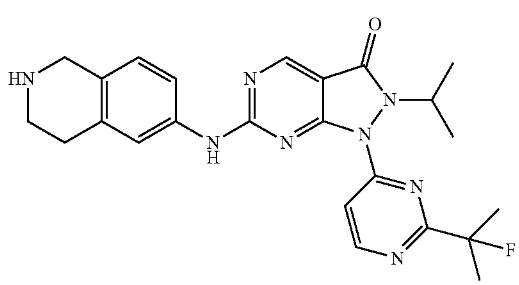 [SMILES: CC(C)n1c(=O)c2cnc(Nc3ccc4c(c3)CCNC4)nc2n1-c1ccnc(C(C)(C)F)n1] |
| 2.657 | 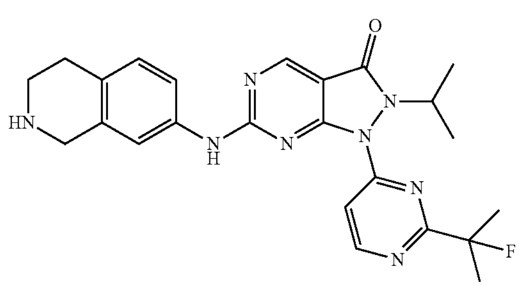 [SMILES: CC(C)n1c(=O)c2cnc(Nc3ccc4c(c3)CNCC4)nc2n1-c1ccnc(C(C)(C)F)n1] |
| 2.658 | |
| 2.659 | |
| 2.660 | |
| 2.661 | |
| 2.662 | |

TABLE 1A-continued

| Compound No. | Structure |
|---|---|
| 2.663 | 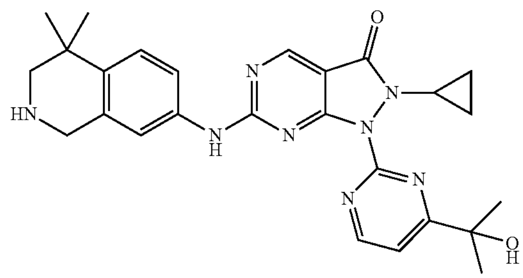 [SMILES: CC(C)(O)c1ccnc(-n2c3nc(Nc4ccc5c(c4)CNCC5(C)C)ncc3c(=O)n2C2CC2)n1] |
| 2.664 | 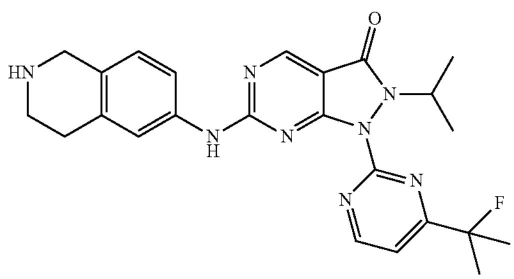 |
| 2.665 | 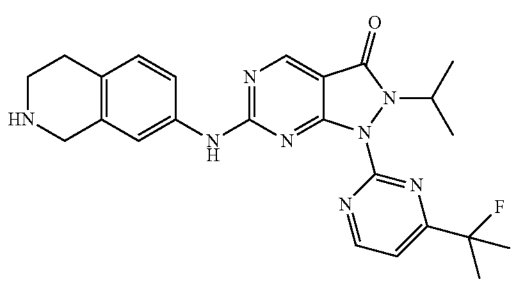 [SMILES: CC(C)n1c(=O)c2cnc(Nc3ccc4c(c3)CNCC4)nc2n1-c1nccc(C(C)(C)F)n1] |
| 2.666 | 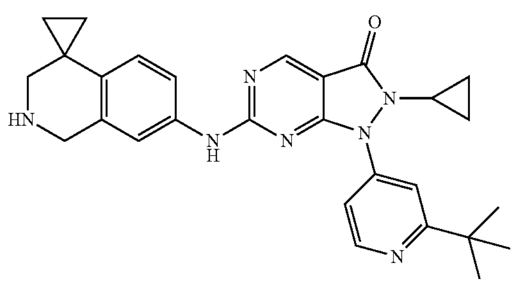 [SMILES: CC(C)(C)c1cc(-n2c3nc(Nc4ccc5c(c4)CNCC54CC4)ncc3c(=O)n2C2CC2)ccn1] |
| 2.667 | 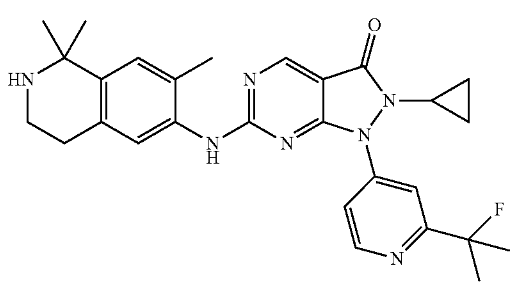 [SMILES: Cc1cc2c(cc1Nc1ncc3c(=O)n(C4CC4)n(-c4ccnc(C(C)(C)F)c4)c3n1)CCNC2(C)C] |
| 2.668 | |
| 2.669 | |
| 2.670 | |
| 2.671 | |
| 2.672 | |

TABLE 1A-continued

| Compound No. | Structure |
| --- | --- |
| 2.673 | 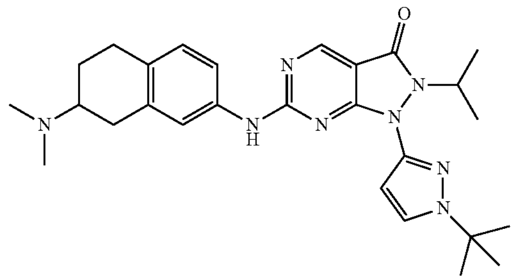 [SMILES: CC(C)n1c(=O)c2cnc(Nc3ccc4c(c3)CC(N(C)C)CC4)nc2n1-c1ccn(C(C)(C)C)n1] |
| 2.674 | 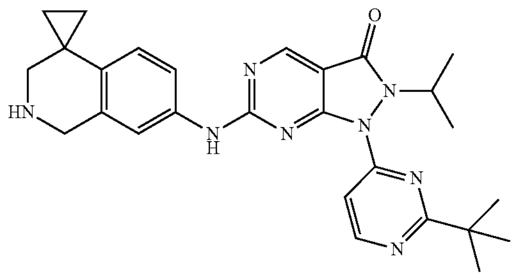 [SMILES: CC(C)n1c(=O)c2cnc(Nc3ccc4c(c3)CNCC43CC3)nc2n1-c1ccnc(C(C)(C)C)n1] |
| 2.675 | 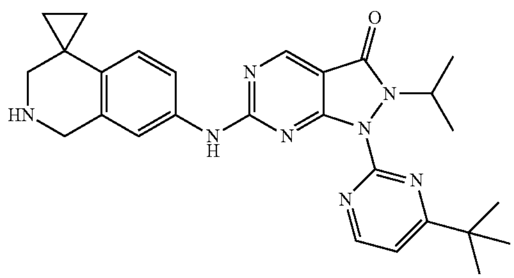 |
| 2.676 | 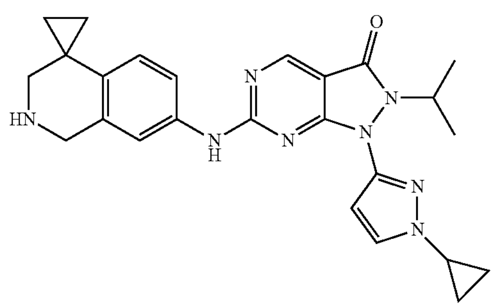 [SMILES: CC(C)n1c(=O)c2cnc(Nc3ccc4c(c3)CNCC43CC3)nc2n1-c1ccn(C2CC2)n1] |
| 2.677 | 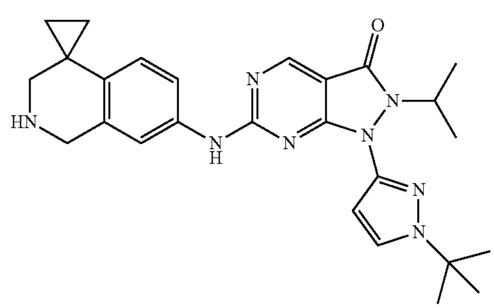 [SMILES: CC(C)n1c(=O)c2cnc(Nc3ccc4c(c3)CNCC43CC3)nc2n1-c1ccn(C(C)(C)C)n1] |
| 2.678 | 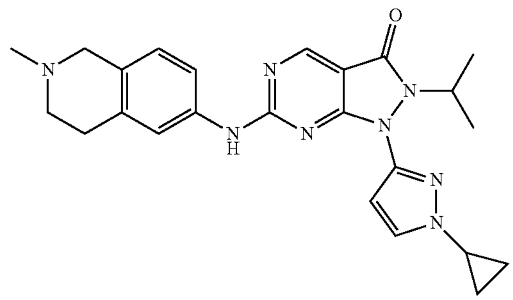 [SMILES: CC(C)n1c(=O)c2cnc(Nc3ccc4c(c3)CCN(C)C4)nc2n1-c1ccn(C2CC2)n1] |
| 2.679 | 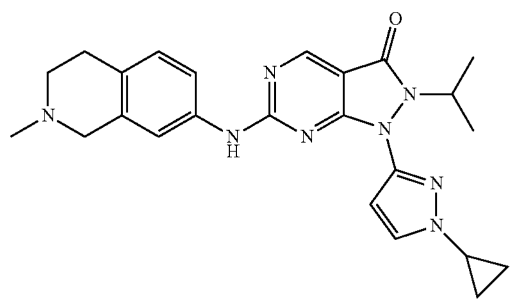 [SMILES: CC(C)n1c(=O)c2cnc(Nc3ccc4c(c3)CN(C)CC4)nc2n1-c1ccn(C2CC2)n1] |
| 2.680 | 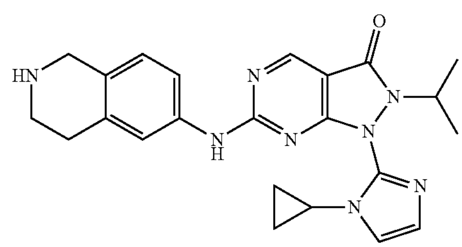 [SMILES: CC(C)n1c(=O)c2cnc(Nc3ccc4c(c3)CCNC4)nc2n1-c1nccn1C1CC1] |
| 2.681 | 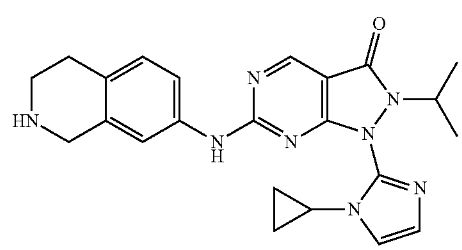 [SMILES: CC(C)n1c(=O)c2cnc(Nc3ccc4c(c3)CNCC4)nc2n1-c1nccn1C1CC1] |
| 2.682 | 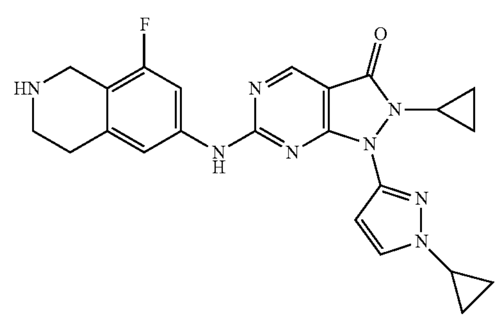 [SMILES: O=c1c2cnc(Nc3cc(F)c4c(c3)CCNC4)nc2n(-c2ccn(C3CC3)n2)n1C1CC1] |

TABLE 1A-continued
| Compound No. | Structure |
|---|---|
| 2.683 | 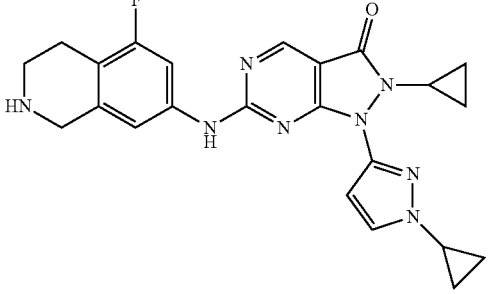 |
| 2.684 | 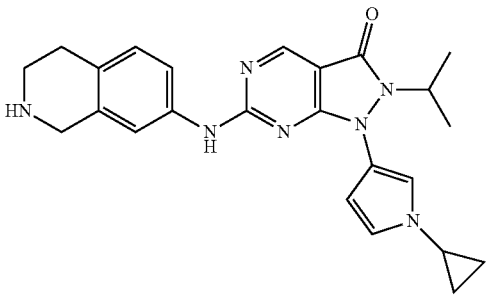 [SMILES: CC(C)n1c(=O)c2cnc(Nc3ccc4c(c3)CNCC4)nc2n1-c1ccn(C2CC2)c1] |
| 2.685 | 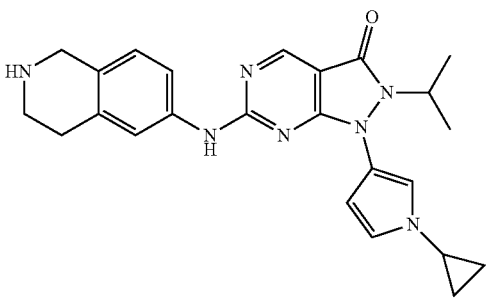 [SMILES: CC(C)n1c(=O)c2cnc(Nc3ccc4c(c3)CCNC4)nc2n1-c1ccn(C2CC2)c1] |
| 2.686 | 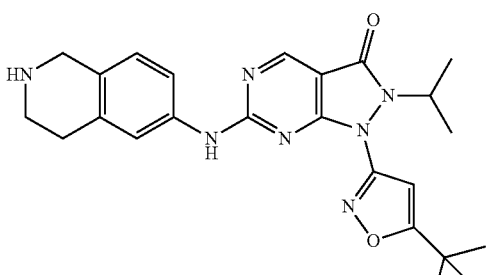 |
| 2.687 | 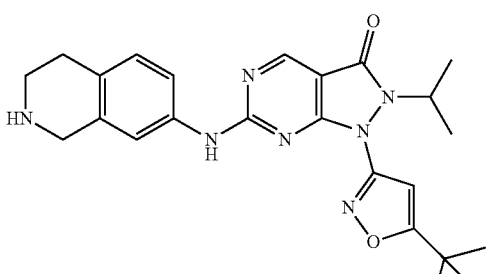 |
| 2.688 | 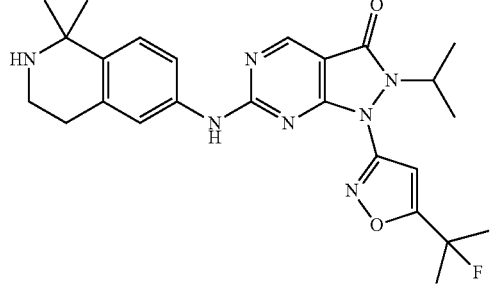 [SMILES: CC(C)n1c(=O)c2cnc(Nc3ccc4c(c3)CCNC4(C)C)nc2n1-c1cc(C(C)(C)F)on1] |
| 2.689 | 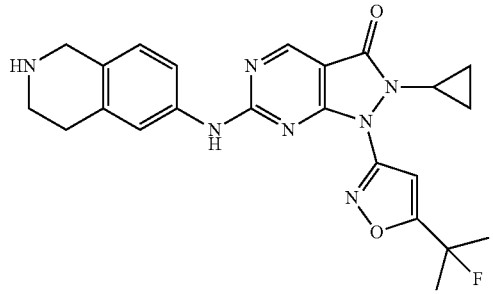 [SMILES: CC(C)(F)c1cc(-n2c3nc(Nc4ccc5c(c4)CCNC5)ncc3c(=O)n2C2CC2)no1] |
| 2.690 | 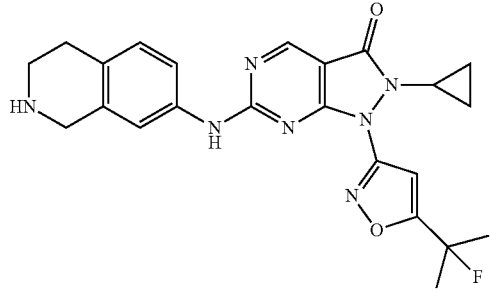 [SMILES: CC(C)(F)c1cc(-n2c3nc(Nc4ccc5c(c4)CNCC5)ncc3c(=O)n2C2CC2)no1] |
| 2.691 | 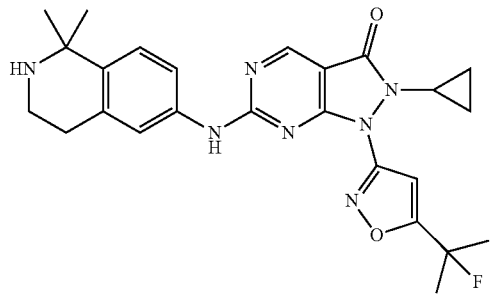 [SMILES: CC(C)(F)c1cc(-n2c3nc(Nc4ccc5c(c4)CCNC5(C)C)ncc3c(=O)n2C2CC2)no1] |
| 2.692 | 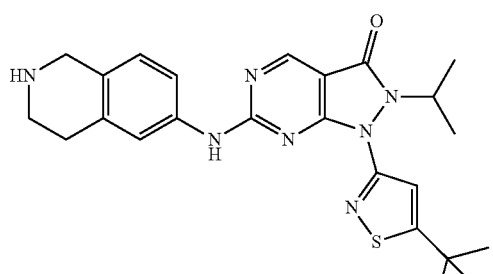 |

US 11,299,493 B2
481
TABLE 1A-continued
| Compound No. | Structure |
|---|---|
| 2.693 | 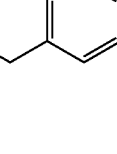 |
| 2.694 | 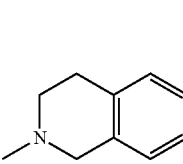 |
| 2.695 | 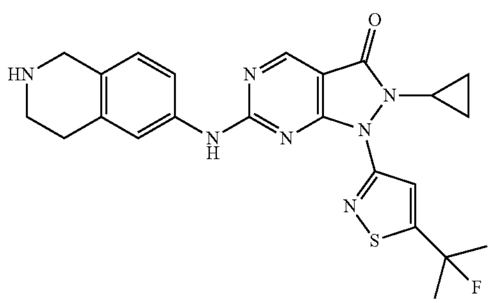 [SMILES: CC(C)(F)c1cc(-n2c3nc(Nc4ccc5c(c4)CCNC5)ncc3c(=O)n2C2CC2)ns1] |
| 2.696 | 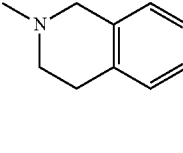 |
| 2.697 | 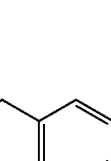 |
482
TABLE 1A-continued
| Compound No. | Structure |
|---|---|
| 2.698 | 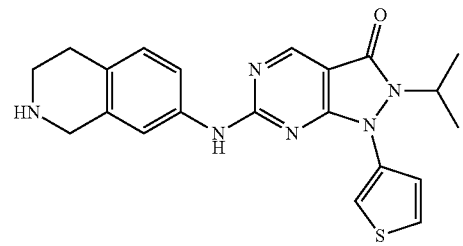 [SMILES: CC(C)n1c(=O)c2cnc(Nc3ccc4c(c3)CNCC4)nc2n1-c1ccsc1] |
| 2.699 | 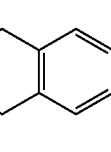 |
| 2.700 | 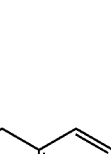 |
| 2.701 | 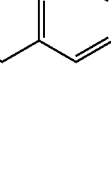 |
| 2.702 | 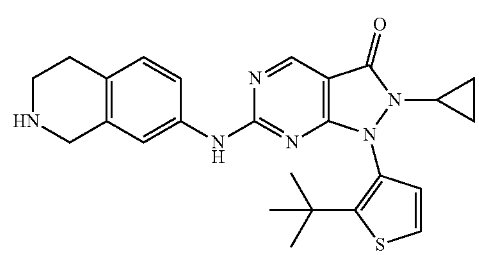 [SMILES: CC(C)(C)c1sccc1-n1c2nc(Nc3ccc4c(c3)CNCC4)ncc2c(=O)n1C1CC1] |
| 2.703 | 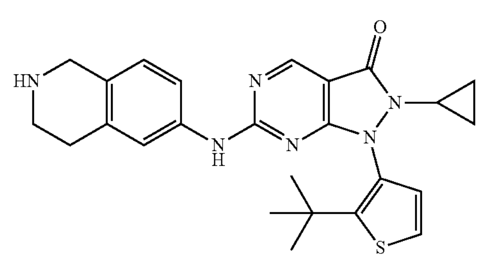 [SMILES: CC(C)(C)c1sccc1-n1c2nc(Nc3ccc4c(c3)CCNC4)ncc2c(=O)n1C1CC1] |

TABLE 1A-continued
| Compound No. | Structure |
|---|---|
| 2.704 | 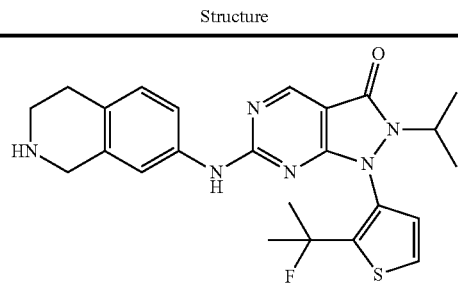 |
| 2.705 | 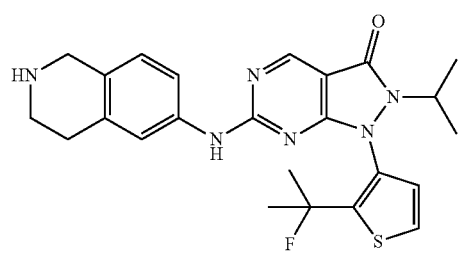 [SMILES: CC(C)n1c(=O)c2cnc(Nc3ccc4c(c3)CCNC4)nc2n1-c1ccsc1C(C)(C)F] |
| 2.706 | 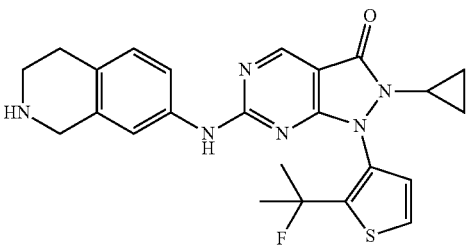 [SMILES: CC(C)(F)c1sccc1-n1c2nc(Nc3ccc4c(c3)CNCC4)ncc2c(=O)n1C1CC1] |
TABLE 1A-continued
| Compound No. | Structure |
|---|---|
| 2.707 | 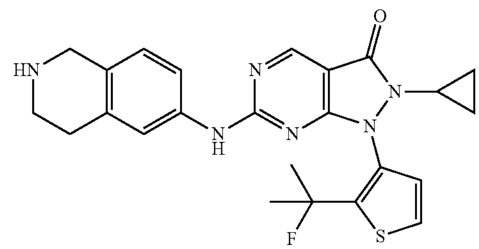 [SMILES: CC(C)(F)c1sccc1-n1c2nc(Nc3ccc4c(c3)CCNC4)ncc2c(=O)n1C1CC1] |
| 2.708 | 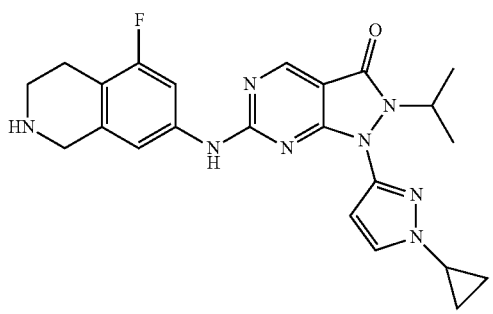 [SMILES: CC(C)n1c(=O)c2cnc(Nc3cc(F)c4c(c3)CNCC4)nc2n1-c1ccn(C2CC2)n1] |
TABLE-1B
| | |
|---|---|
| 2.709 | 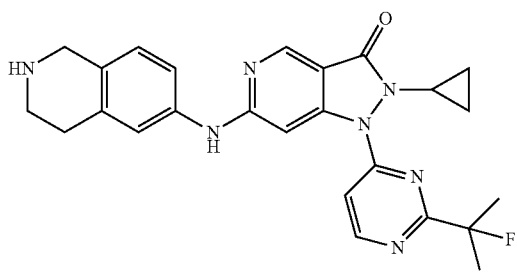 [SMILES: CC(C)(F)c1nccc(-n2c3cc(Nc4ccc5c(c4)CCNC5)ncc3c(=O)n2C2CC2)n1] |
| 2.710 | 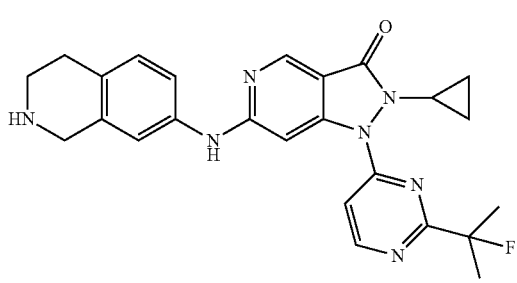 [SMILES: CC(C)(F)c1nccc(-n2c3cc(Nc4ccc5c(c4)CNCC5)ncc3c(=O)n2C2CC2)n1] |

TABLE-1B-continued
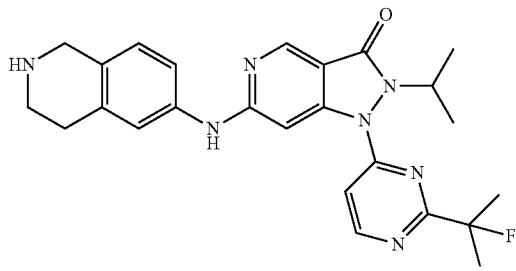 [SMILES: CC(C)n1c(=O)c2cnc(Nc3ccc4c(c3)CCNC4)cc2n1-c1ccnc(C(C)(C)F)n1]
2.711
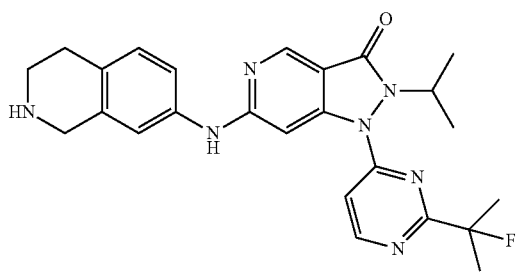
2.712
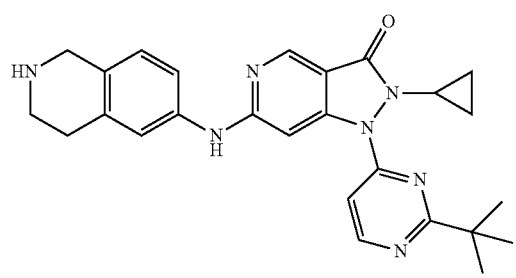 [SMILES: CC(C)(C)c1nccc(-n2c3cc(Nc4ccc5c(c4)CCNC5)ncc3c(=O)n2C2CC2)n1]
2.713
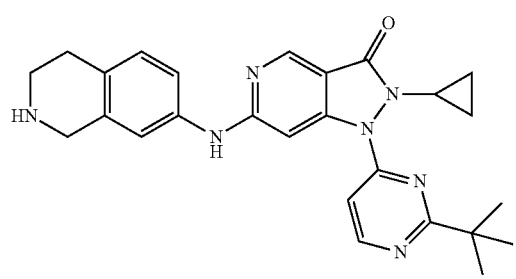 [SMILES: CC(C)(C)c1nccc(-n2c3cc(Nc4ccc5c(c4)CNCC5)ncc3c(=O)n2C2CC2)n1]
2.714
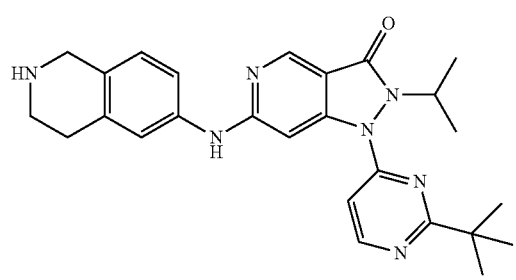 [SMILES: CC(C)n1c(=O)c2cnc(Nc3ccc4c(c3)CCNC4)cc2n1-c1ccnc(C(C)(C)C)n1]
2.715
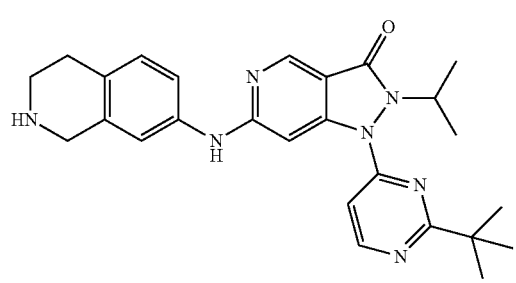 [SMILES: CC(C)n1c(=O)c2cnc(Nc3ccc4c(c3)CNCC4)cc2n1-c1ccnc(C(C)(C)C)n1]
2.716

TABLE-1B-continued
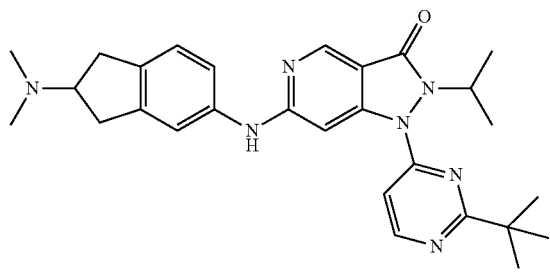 [SMILES: CC(C)n1c(=O)c2cnc(Nc3ccc4c(c3)CC(N(C)C)C4)cc2n1-c1ccnc(C(C)(C)C)n1] 2.717
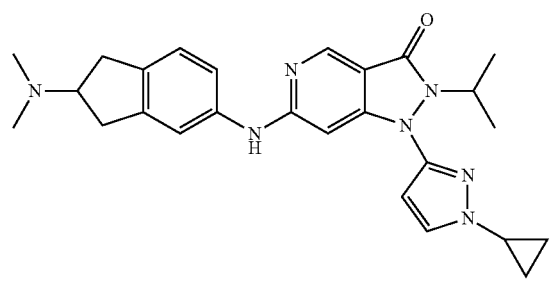 [SMILES: CC(C)n1c(=O)c2cnc(Nc3ccc4c(c3)CC(N(C)C)C4)cc2n1-c1ccn(C2CC2)n1] 2.718
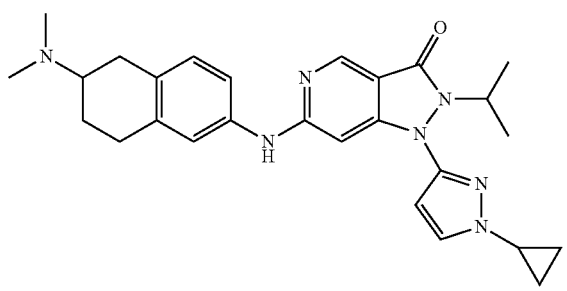 [SMILES: CC(C)n1c(=O)c2cnc(Nc3ccc4c(c3)CCC(N(C)C)C4)cc2n1-c1ccn(C2CC2)n1] 2.719
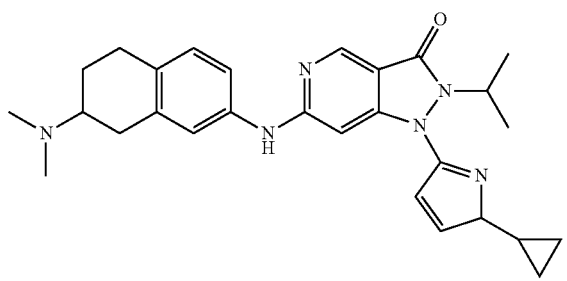 [SMILES: CC(C)n1c(=O)c2cnc(Nc3ccc4c(c3)CC(N(C)C)CC4)cc2n1C1=NC(C2CC2)C=C1] 2.720
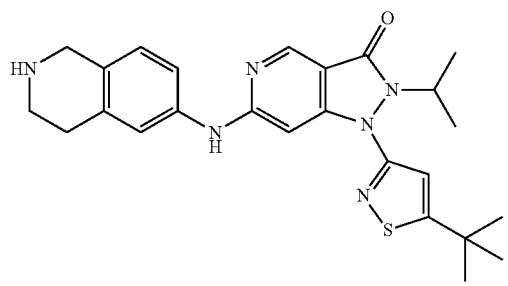 [SMILES: CC(C)n1c(=O)c2cnc(Nc3ccc4c(c3)CCNC4)cc2n1-c1cc(C(C)(C)C)sn1] 2.721

| | |
|---|---|
| 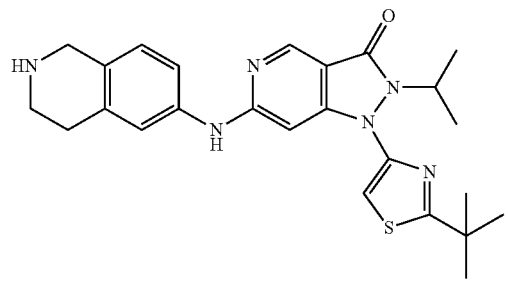 [SMILES: CC(C)n1c(=O)c2cnc(Nc3ccc4c(c3)CCNC4)cc2n1-c1csc(C(C)(C)C)n1] | 2.722 |
| 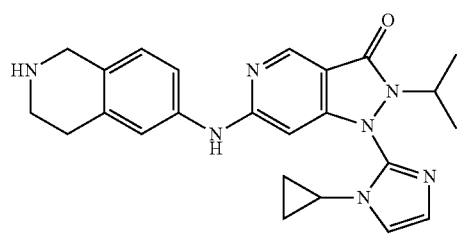 [SMILES: CC(C)n1c(=O)c2cnc(Nc3ccc4c(c3)CCNC4)cc2n1-c1nccn1C1CC1] | 2.723 |
| 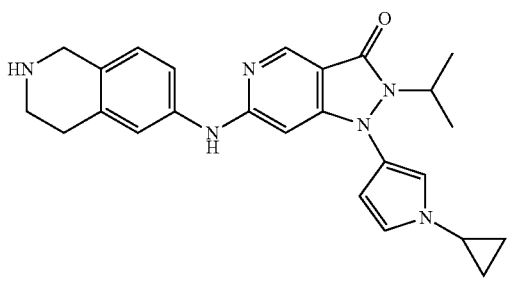 [SMILES: CC(C)n1c(=O)c2cnc(Nc3ccc4c(c3)CCNC4)cc2n1-c1ccn(C2CC2)c1] | 2.724 |
| 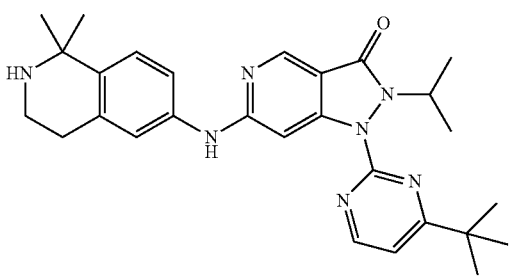 | 2.725 |
| 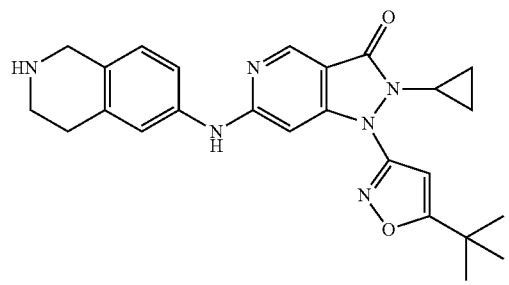 [SMILES: CC(C)(C)c1cc(-n2c3cc(Nc4ccc5c(c4)CCNC5)ncc3c(=O)n2C2CC2)no1] | 2.726 |
| 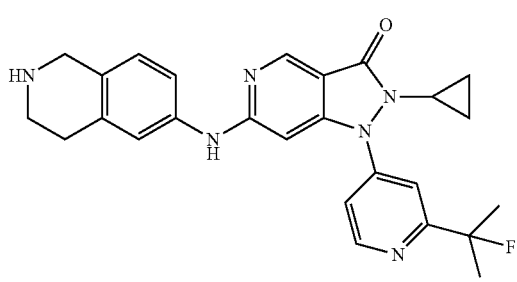 [SMILES: CC(C)(F)c1cc(-n2c3cc(Nc4ccc5c(c4)CCNC5)ncc3c(=O)n2C2CC2)ccn1] | 2.727 |

TABLE-1B-continued
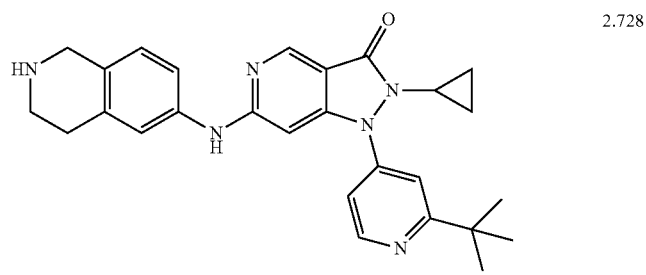
2.728
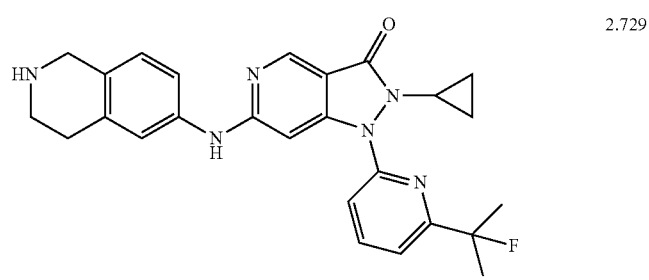
2.729
2.730
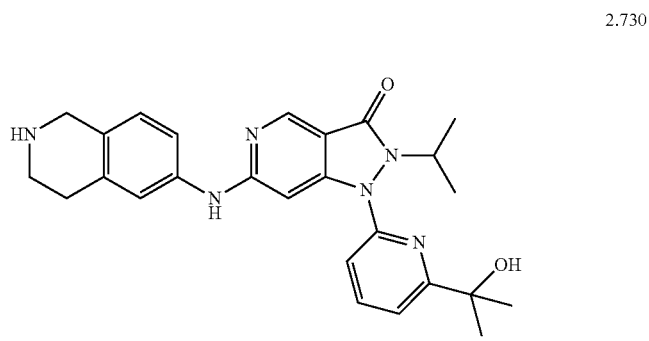
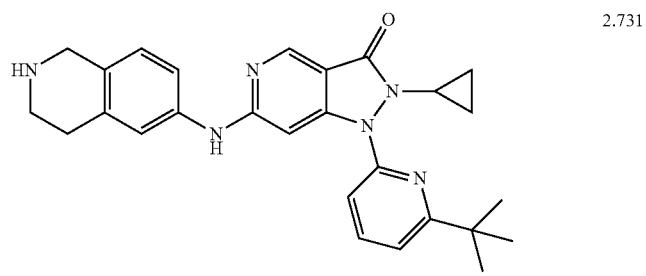
2.731
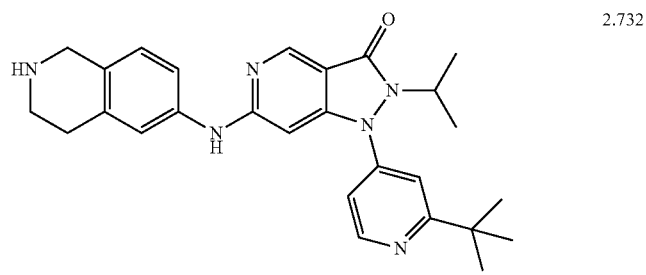
2.732

TABLE-1B-continued
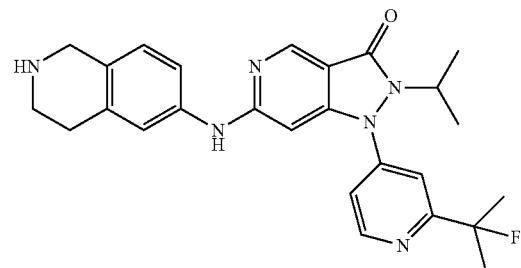 [SMILES: CC(C)n1c(=O)c2cnc(Nc3ccc4c(c3)CCNC4)cc2n1-c1ccnc(C(C)(C)F)c1]
2.733
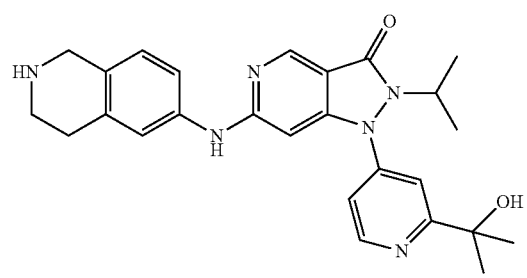 [SMILES: CC(C)n1c(=O)c2cnc(Nc3ccc4c(c3)CCNC4)cc2n1-c1ccnc(C(C)(C)O)c1]
2.734
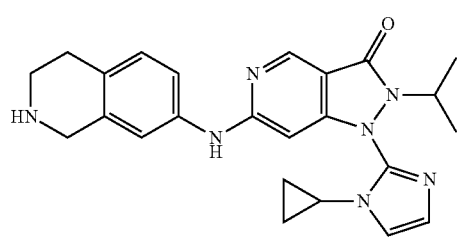 [SMILES: CC(C)n1c(=O)c2cnc(Nc3ccc4c(c3)CNCC4)cc2n1-c1nccn1C1CC1]
2.735
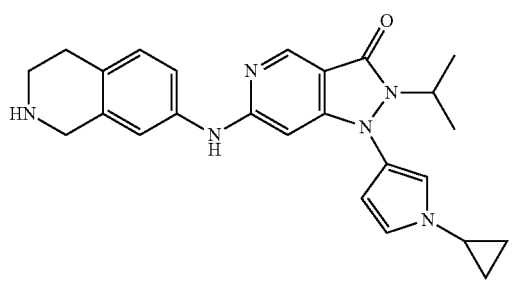 [SMILES: CC(C)n1c(=O)c2cnc(Nc3ccc4c(c3)CNCC4)cc2n1-c1ccn(C2CC2)c1]
2.736
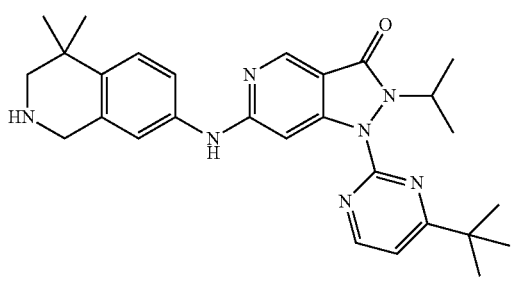 [SMILES: CC(C)n1c(=O)c2cnc(Nc3ccc4c(c3)CNCC4(C)C)cc2n1-c1nccc(C(C)(C)C)n1]
2.737
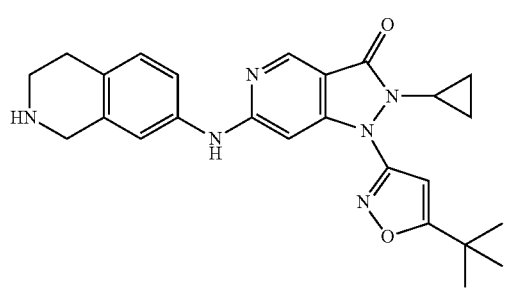 [SMILES: CC(C)(C)c1cc(-n2c3cc(Nc4ccc5c(c4)CNCC5)ncc3c(=O)n2C2CC2)no1]
2.738

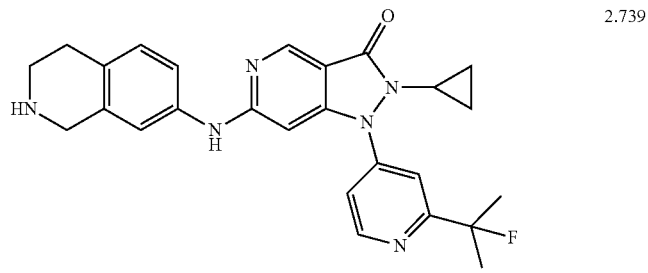
2.739
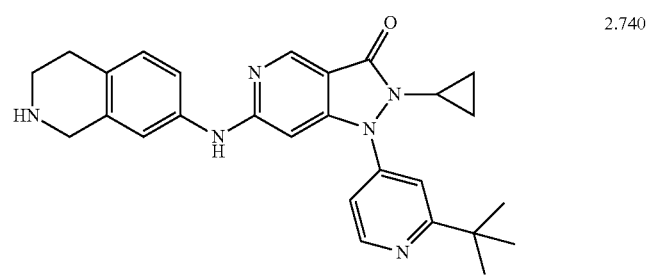
2.740
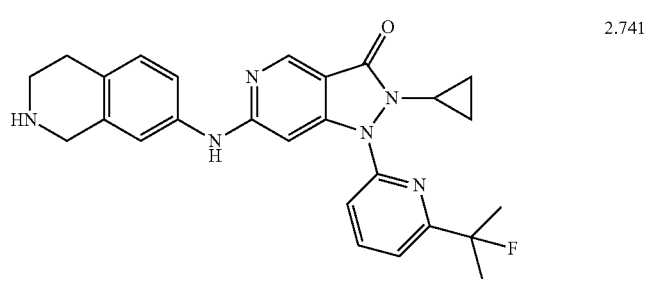
2.741
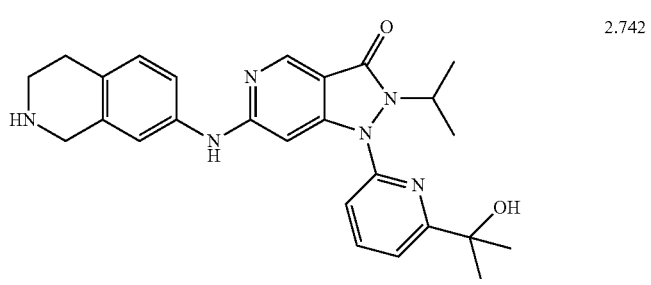
2.742
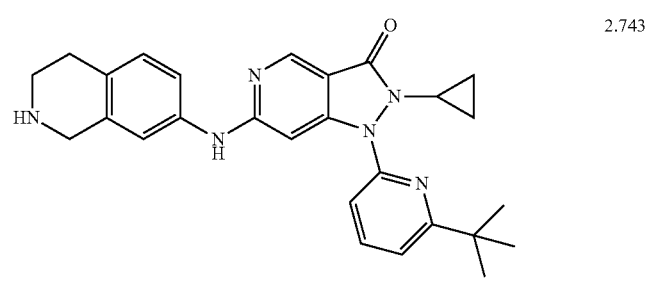
2.743
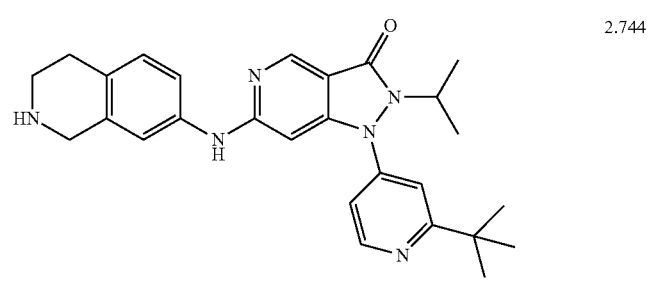
2.744

TABLE-1B-continued
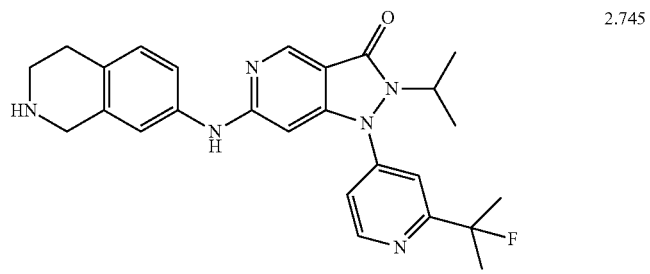
2.745
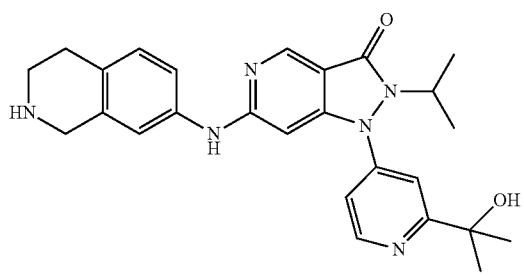 [SMILES: CC(C)n1c(=O)c2cnc(Nc3ccc4c(c3)CNCC4)cc2n1-c1ccnc(C(C)(C)O)c1]
2.746
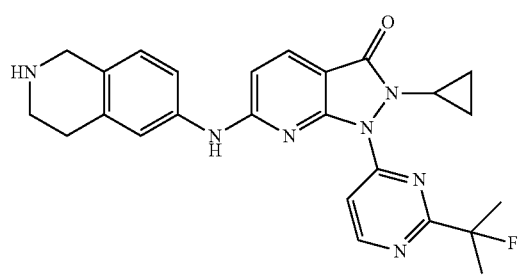 [SMILES: CC(C)(F)c1nccc(-n2c3nc(Nc4ccc5c(c4)CCNC5)ccc3c(=O)n2C2CC2)n1]
2.747
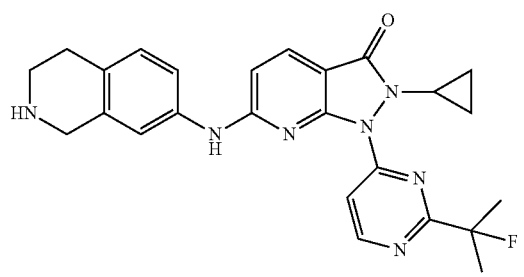
2.748
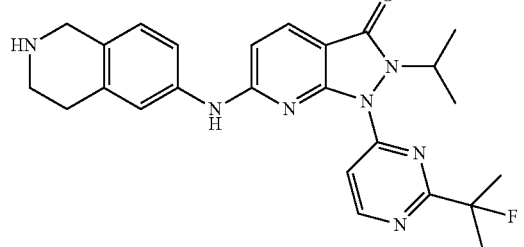
2.749

TABLE-1B-continued
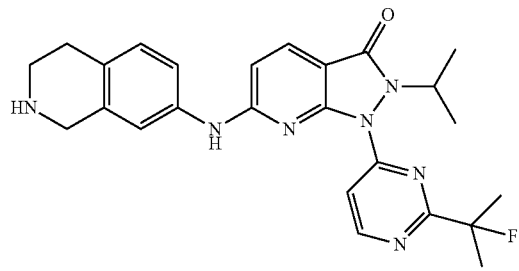 [SMILES: CC(C)n1c(=O)c2ccc(Nc3ccc4c(c3)CNCC4)nc2n1-c1ccnc(C(C)(C)F)n1]
2.750
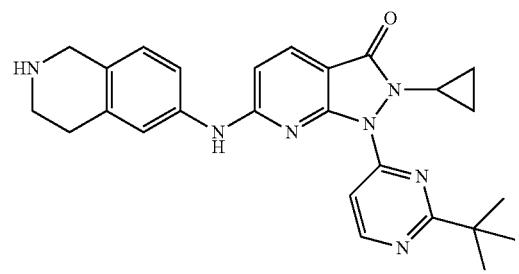 [SMILES: CC(C)(C)c1nccc(-n2c3nc(Nc4ccc5c(c4)CCNC5)ccc3c(=O)n2C2CC2)n1]
2.751
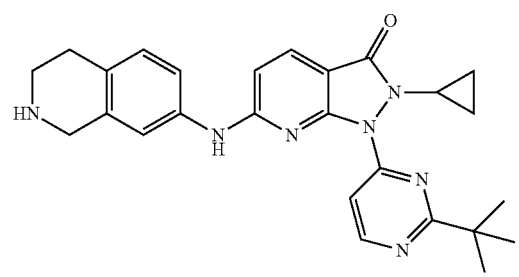
2.752
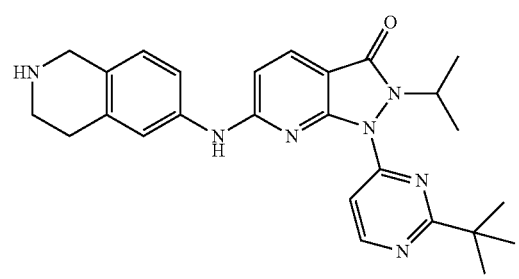 [SMILES: CC(C)n1c(=O)c2ccc(Nc3ccc4c(c3)CCNC4)nc2n1-c1ccnc(C(C)(C)C)n1]
2.753
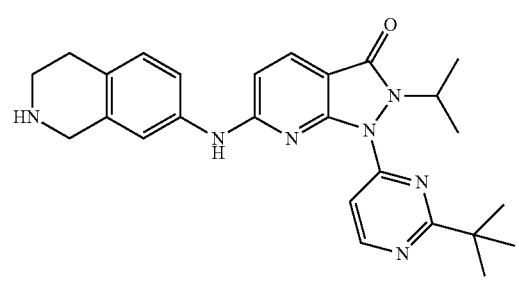
2.754
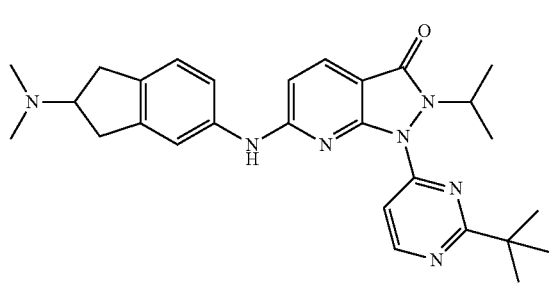 [SMILES: CC(C)n1c(=O)c2ccc(Nc3ccc4c(c3)CC(N(C)C)C4)nc2n1-c1ccnc(C(C)(C)C)n1]
2.755

TABLE-1B-continued
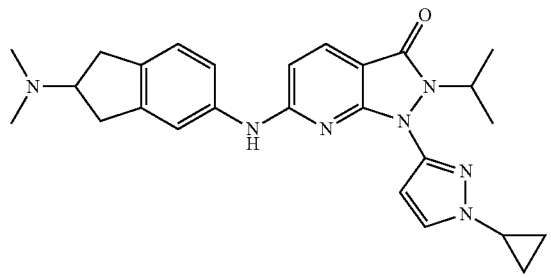 [SMILES: CC(C)n1c(=O)c2ccc(Nc3ccc4c(c3)CC(N(C)C)C4)nc2n1-c1ccn(C2CC2)n1]
2.756
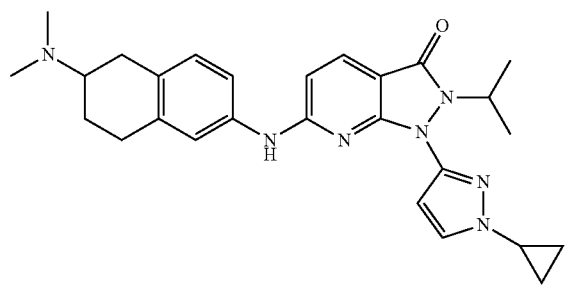 [SMILES: CC(C)n1c(=O)c2ccc(Nc3ccc4c(c3)CCC(N(C)C)C4)nc2n1-c1ccn(C2CC2)n1]
2.757
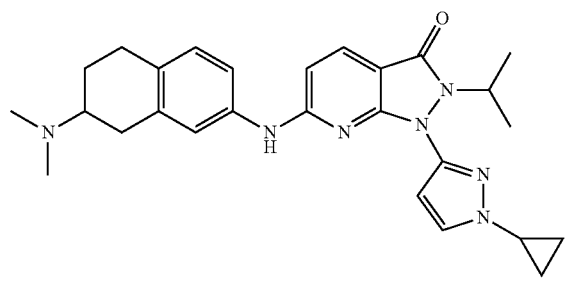 [SMILES: CC(C)n1c(=O)c2ccc(Nc3ccc4c(c3)CC(N(C)C)CC4)nc2n1-c1ccn(C2CC2)n1]
2.758
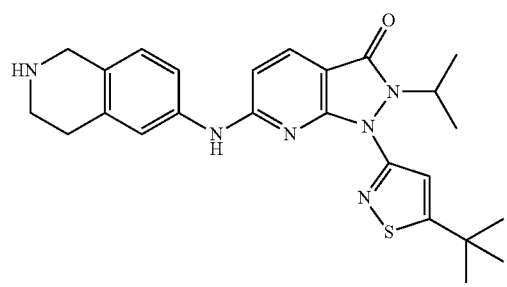
2.759
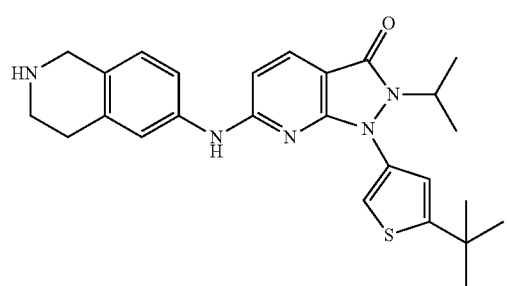 [SMILES: CC(C)n1c(=O)c2ccc(Nc3ccc4c(c3)CCNC4)nc2n1-c1csc(C(C)(C)C)c1]
2.760

TABLE-1B-continued
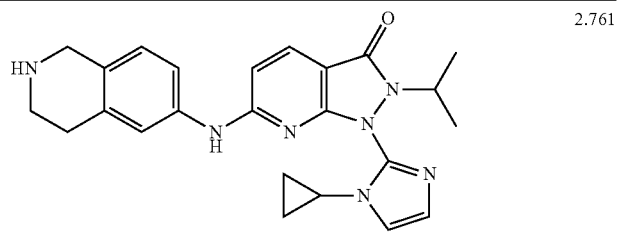
2.761
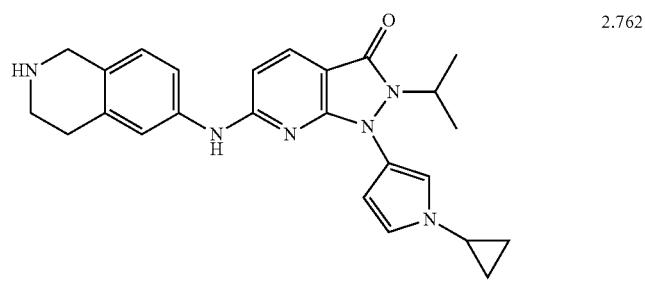
2.762
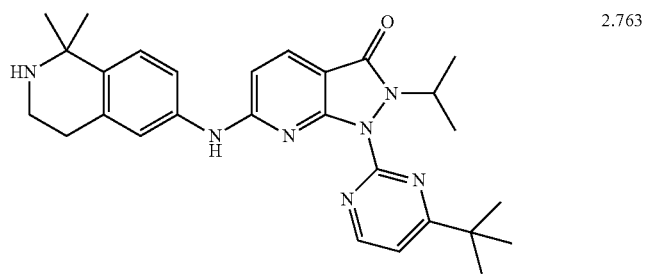
2.763
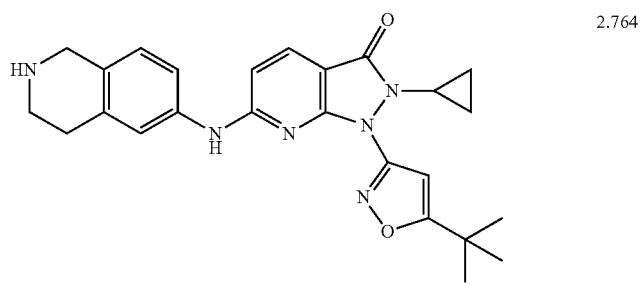
2.764
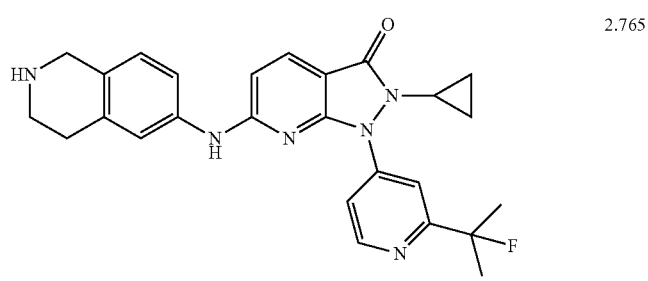
2.765
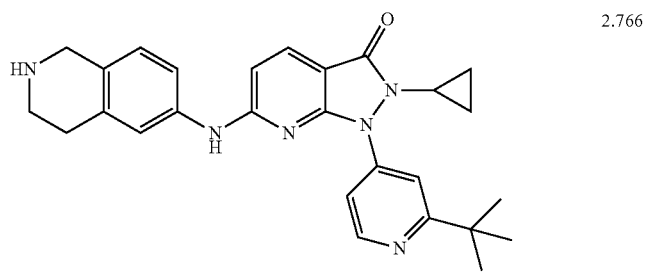
2.766

TABLE-1B-continued
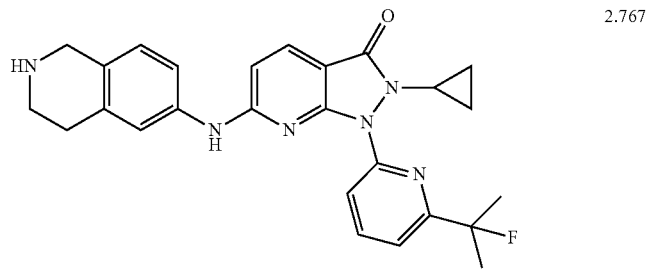
2.767
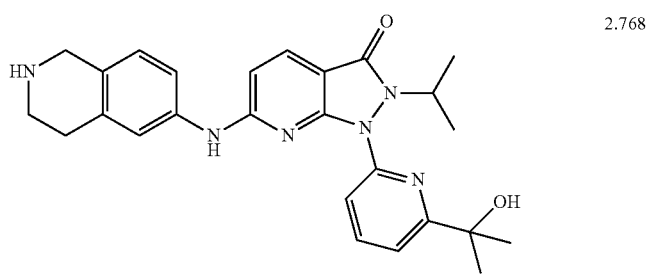
2.768
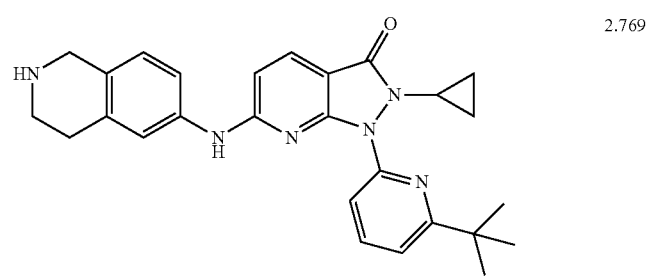
2.769
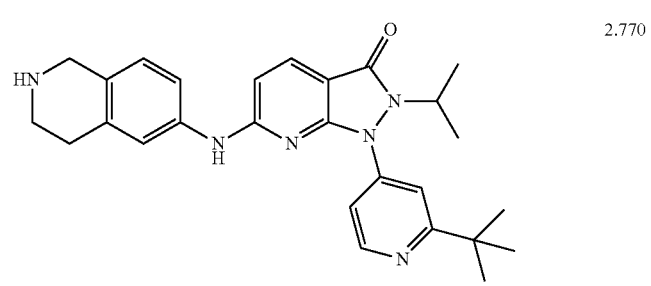
2.770
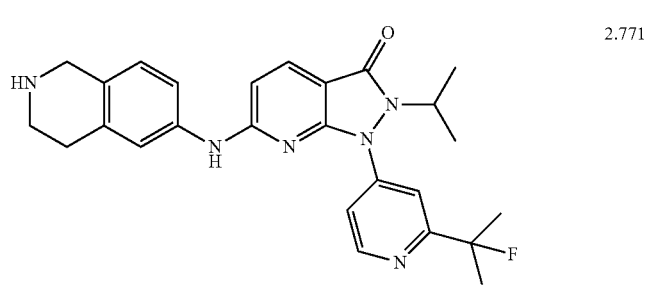
2.771
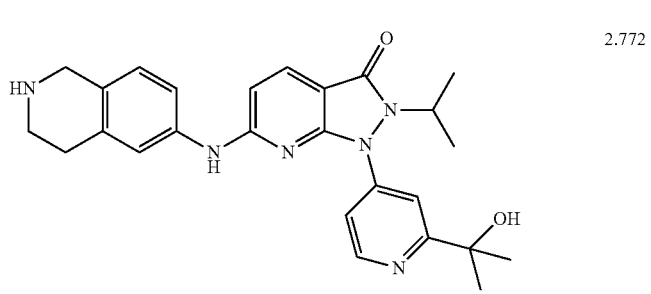
2.772

TABLE-1B-continued
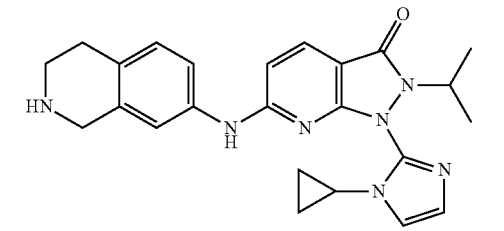 [SMILES: CC(C)n1c(=O)c2ccc(Nc3ccc4c(c3)CNCC4)nc2n1-c1nccn1C1CC1]
2.773
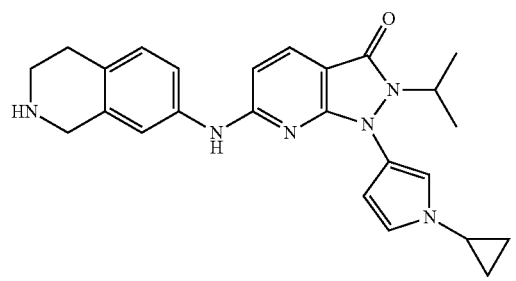 [SMILES: CC(C)n1c(=O)c2ccc(Nc3ccc4c(c3)CNCC4)nc2n1-c1ccn(C2CC2)c1]
2.774
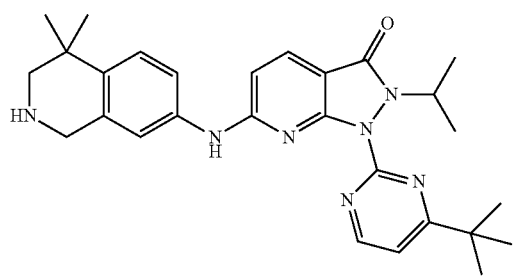 [SMILES: CC(C)n1c(=O)c2ccc(Nc3ccc4c(c3)CNCC4(C)C)nc2n1-c1nccc(C(C)(C)C)n1]
2.775
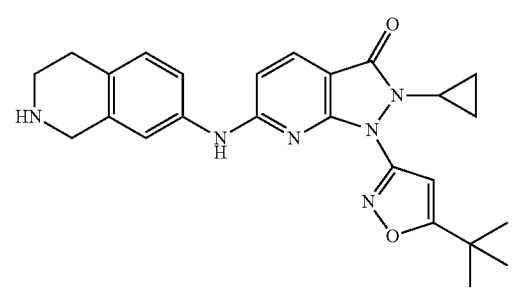 [SMILES: CC(C)(C)c1cc(-n2c3nc(Nc4ccc5c(c4)CNCC5)ccc3c(=O)n2C2CC2)no1]
2.776
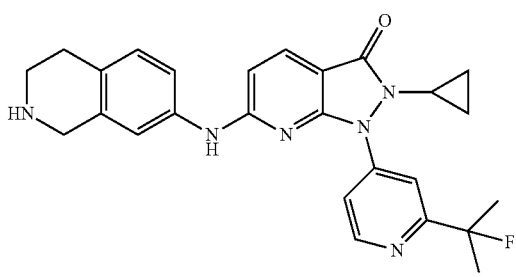 [SMILES: CC(C)(F)c1cc(-n2c3nc(Nc4ccc5c(c4)CNCC5)ccc3c(=O)n2C2CC2)ccn1]
2.777
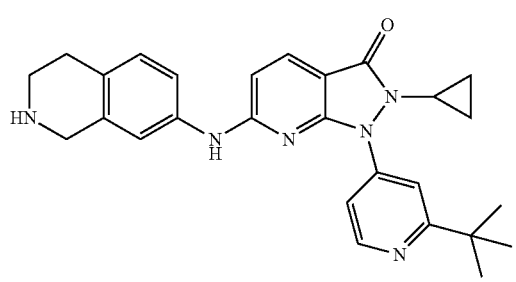 [SMILES: CC(C)(C)c1cc(-n2c3nc(Nc4ccc5c(c4)CNCC5)ccc3c(=O)n2C2CC2)ccn1]
2.778

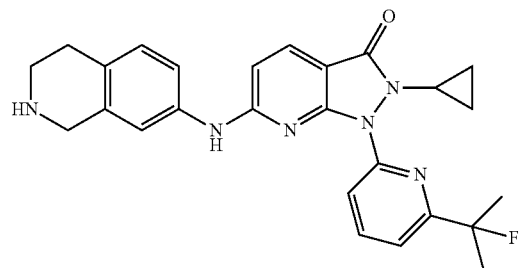 [SMILES: CC(C)(F)c1cccc(-n2c3nc(Nc4ccc5c(c4)CNCC5)ccc3c(=O)n2C2CC2)n1]
2.779
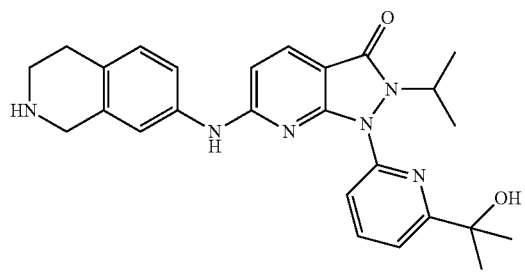 [SMILES: CC(C)n1c(=O)c2ccc(Nc3ccc4c(c3)CNCC4)nc2n1-c1cccc(C(C)(C)O)n1]
2.780
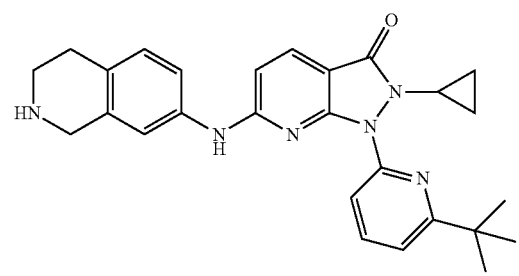 [SMILES: CC(C)(C)c1cccc(-n2c3nc(Nc4ccc5c(c4)CNCC5)ccc3c(=O)n2C2CC2)n1]
2.781
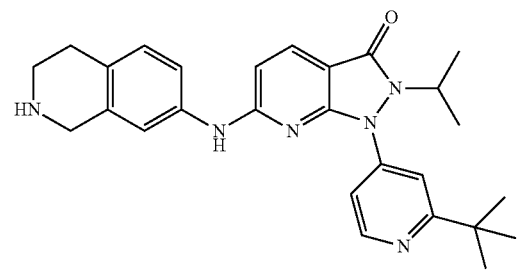
2.782
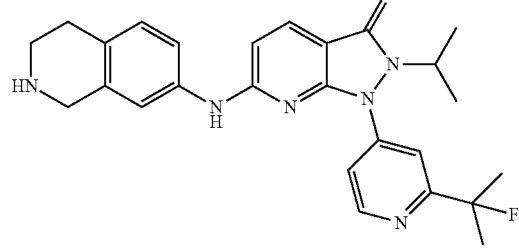
2.783

TABLE-1B-continued
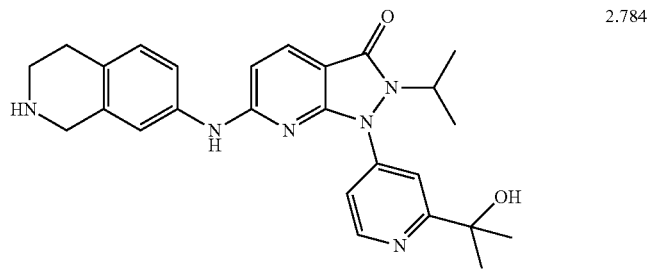
2.784
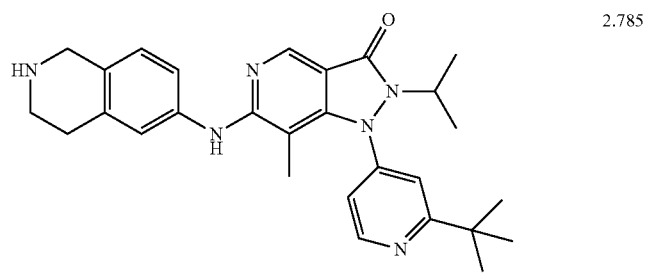
2.785
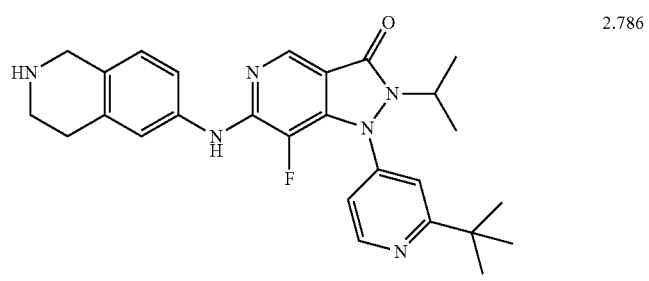
2.786
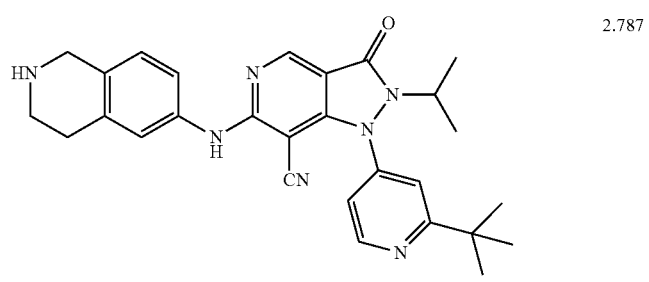
2.787
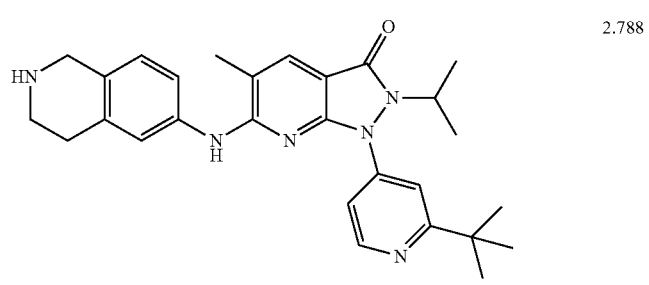
2.788
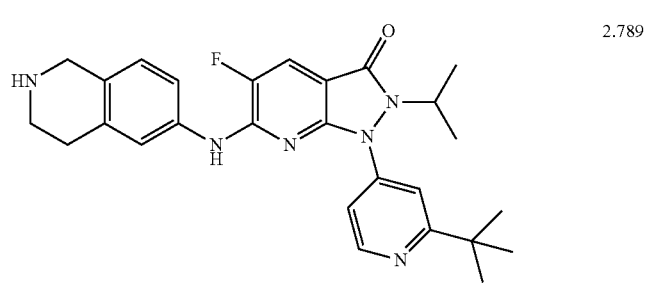
2.789

TABLE-1B-continued
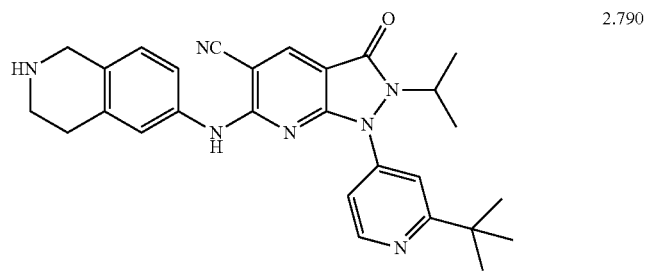 2.790
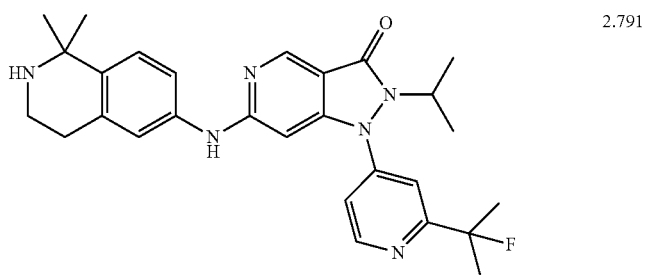 2.791
2.792
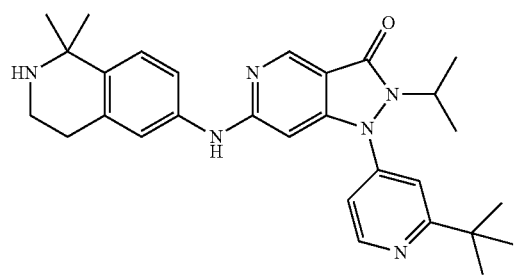 [SMILES: CC(C)n1c(=O)c2cnc(Nc3ccc4c(c3)CCNC4(C)C)cc2n1-c1ccnc(C(C)(C)C)c1] 2.793
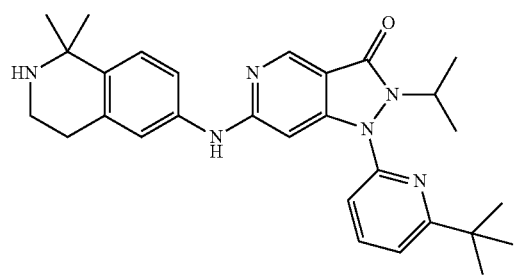 [SMILES: CC(C)n1c(=O)c2cnc(Nc3ccc4c(c3)CCNC4(C)C)cc2n1-c1cccc(C(C)(C)C)n1] 2.794
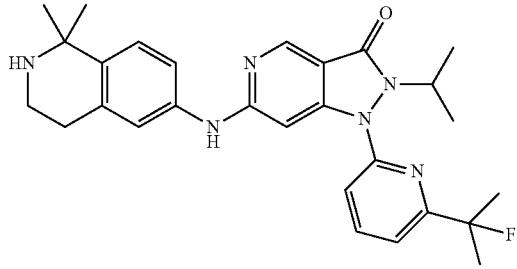 [SMILES: CC(C)n1c(=O)c2cnc(Nc3ccc4c(c3)CCNC4(C)C)cc2n1-c1cccc(C(C)(C)F)n1]

TABLE-1B-continued
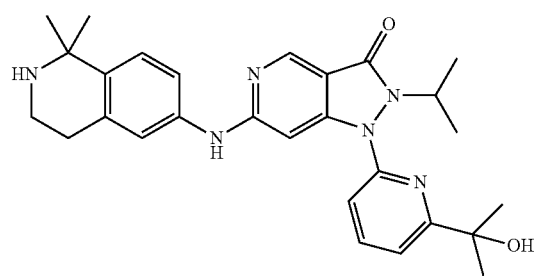 [SMILES: CC(C)n1c(=O)c2cnc(Nc3ccc4c(c3)CCNC4(C)C)cc2n1-c1cccc(C(C)(C)O)n1] 2.795
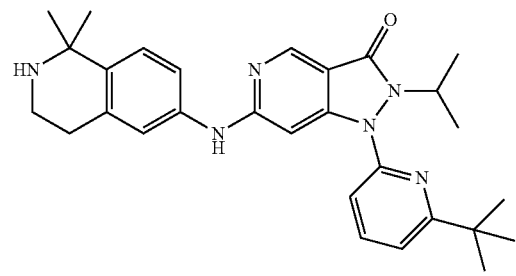 [SMILES: CC(C)n1c(=O)c2cnc(Nc3ccc4c(c3)CCNC4(C)C)cc2n1-c1cccc(C(C)(C)C)n1] 2.796
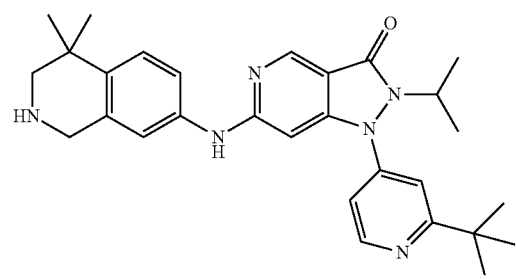 [SMILES: CC(C)n1c(=O)c2cnc(Nc3ccc4c(c3)CNCC4(C)C)cc2n1-c1ccnc(C(C)(C)C)c1] 2.797
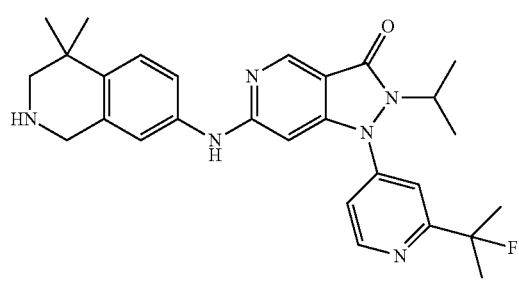 [SMILES: CC(C)n1c(=O)c2cnc(Nc3ccc4c(c3)CNCC4(C)C)cc2n1-c1ccnc(C(C)(C)F)c1] 2.798
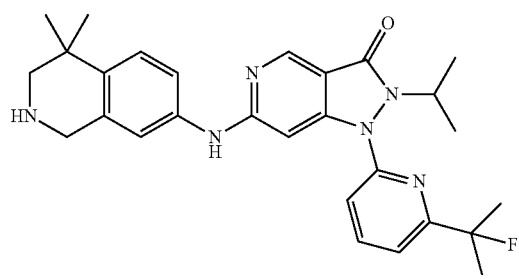 [SMILES: CC(C)n1c(=O)c2cnc(Nc3ccc4c(c3)CNCC4(C)C)cc2n1-c1cccc(C(C)(C)F)n1] 2.799

TABLE-1B-continued
| | |
|---|---|
| 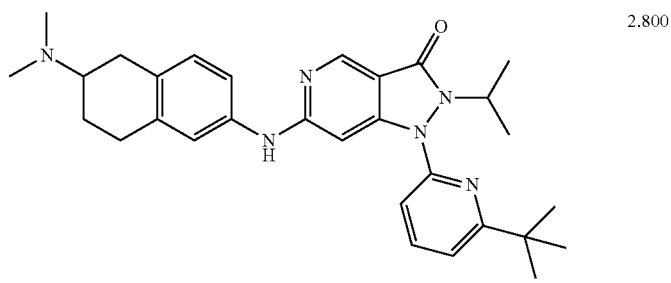 | 2.800 |
| 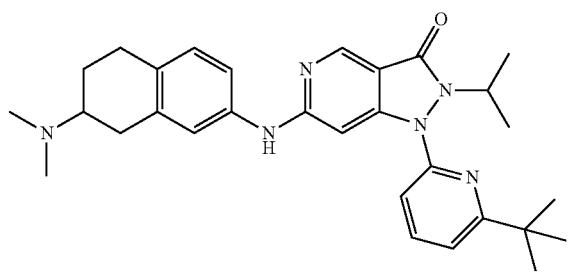 [SMILES: CC(C)n1c(=O)c2cnc(Nc3ccc4c(c3)CC(N(C)C)CC4)cc2n1-c1cccc(C(C)(C)C)n1] | 2.801 |
| 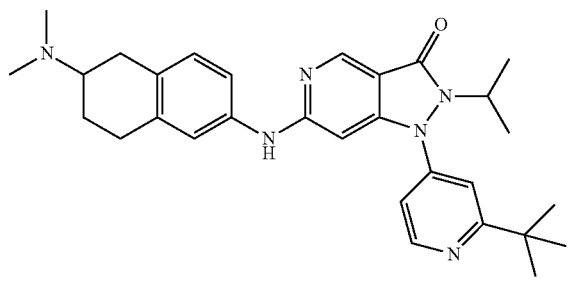 | 2.802 |
| 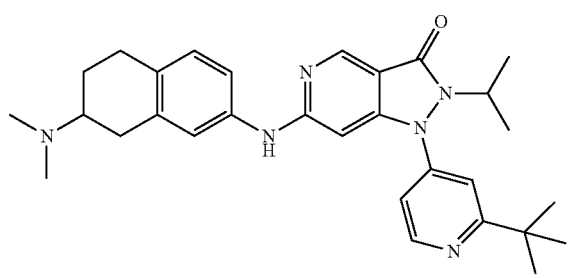 [SMILES: CC(C)n1c(=O)c2cnc(Nc3ccc4c(c3)CC(N(C)C)CC4)cc2n1-c1ccnc(C(C)(C)C)c1] | 2.803 |
| 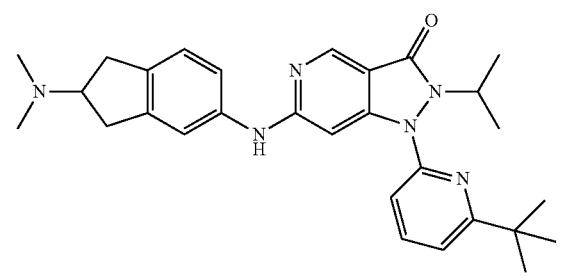 [SMILES: CC(C)n1c(=O)c2cnc(Nc3ccc4c(c3)CC(N(C)C)C4)cc2n1-c1cccc(C(C)(C)C)n1] | 2.804 |

TABLE-1B-continued
| | |
|---|---|
| 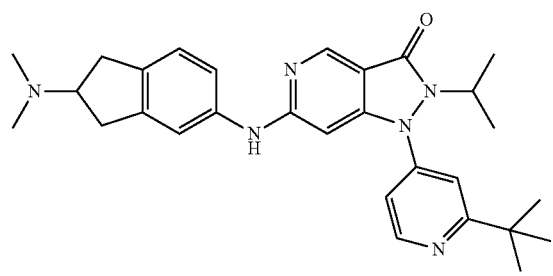 [SMILES: CC(C)n1c(=O)c2cnc(Nc3ccc4c(c3)CC(N(C)C)C4)cc2n1-c1ccnc(C(C)(C)C)c1] | 2.805 |
| 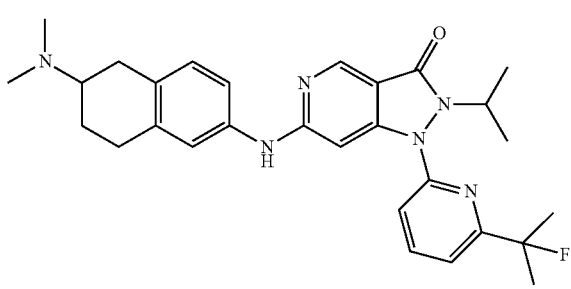 [SMILES: CC(C)n1c(=O)c2cnc(Nc3ccc4c(c3)CCC(N(C)C)C4)cc2n1-c1cccc(C(C)(C)F)n1] | 2.806 |
| 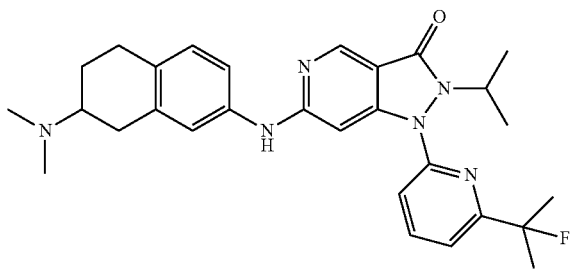 [SMILES: CC(C)n1c(=O)c2cnc(Nc3ccc4c(c3)CC(N(C)C)CC4)cc2n1-c1cccc(C(C)(C)F)n1] | 2.807 |
| 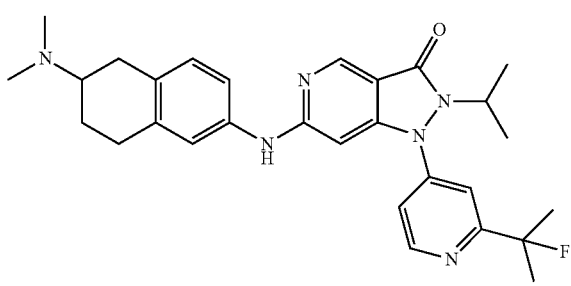 [SMILES: CC(C)n1c(=O)c2cnc(Nc3ccc4c(c3)CCC(N(C)C)C4)cc2n1-c1ccnc(C(C)(C)F)c1] | 2.808 |
| 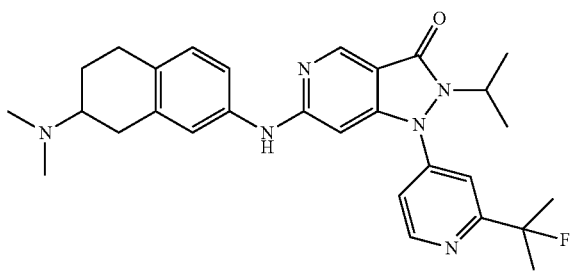 | 2.809 |

TABLE-1B-continued
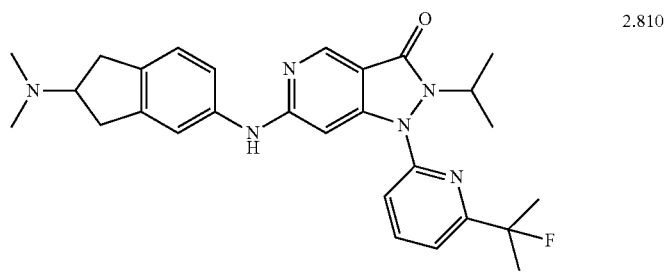
2.810
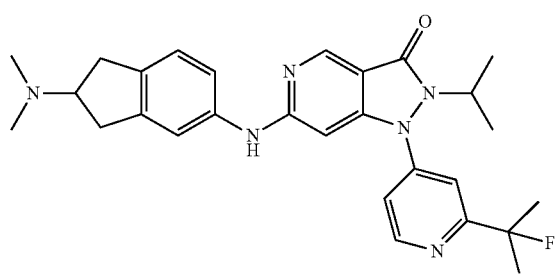 [SMILES: CC(C)n1c(=O)c2cnc(Nc3ccc4c(c3)CC(N(C)C)C4)cc2n1-c1ccnc(C(C)(C)F)c1]
2.811
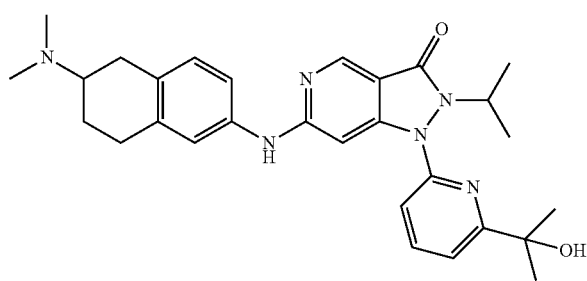 [SMILES: CC(C)n1c(=O)c2cnc(Nc3ccc4c(c3)CCC(N(C)C)C4)cc2n1-c1cccc(C(C)(C)O)n1]
2.812
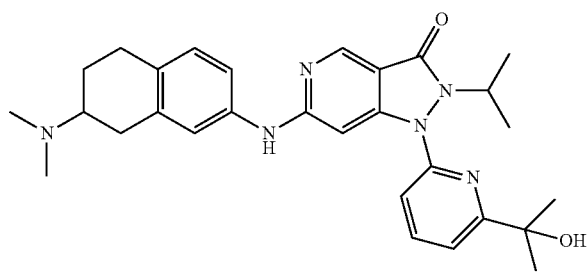
2.813
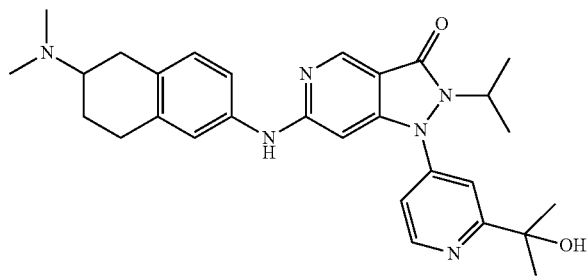
2.814

TABLE-1B-continued
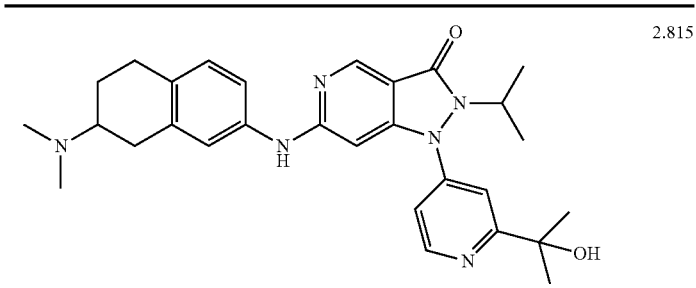
2.815
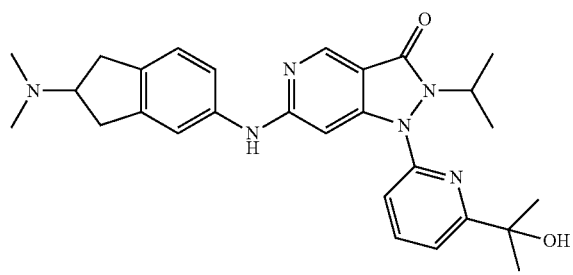 [SMILES: CC(C)n1c(=O)c2cnc(Nc3ccc4c(c3)CC(N(C)C)C4)cc2n1-c1cccc(C(C)(C)O)n1]
2.816
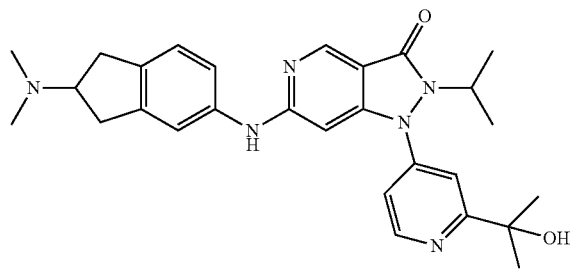
2.817
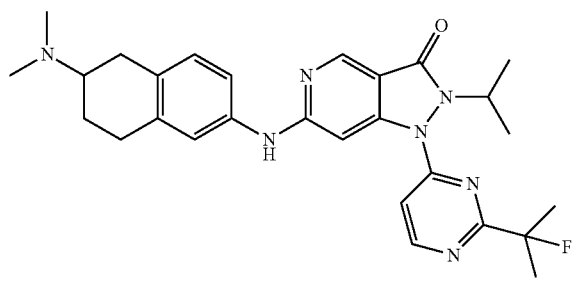 [SMILES: CC(C)n1c(=O)c2cnc(Nc3ccc4c(c3)CCC(N(C)C)C4)cc2n1-c1ccnc(C(C)(C)F)n1]
2.818
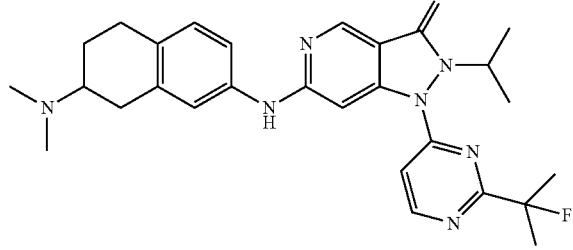
2.819

TABLE-1B-continued
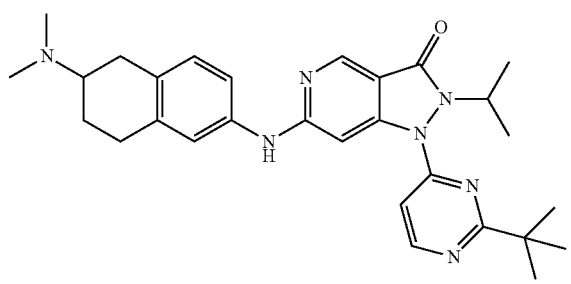 [SMILES: CC(C)n1c(=O)c2cnc(Nc3ccc4c(c3)CCC(N(C)C)C4)cc2n1-c1ccnc(C(C)(C)C)n1]
2.820
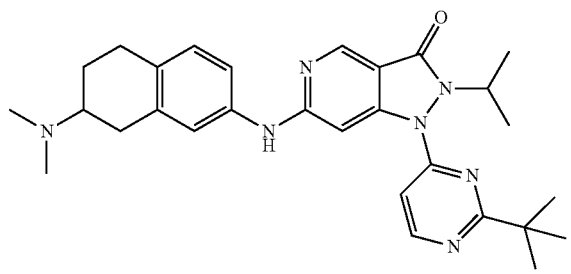 [SMILES: CC(C)n1c(=O)c2cnc(Nc3ccc4c(c3)CC(N(C)C)CC4)cc2n1-c1ccnc(C(C)(C)C)n1]
2.821
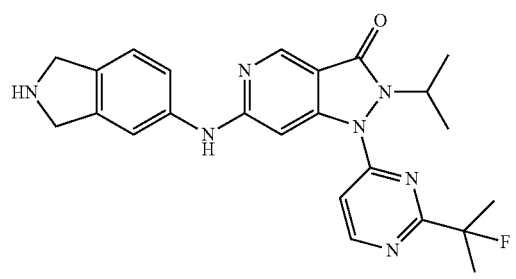 [SMILES: CC(C)n1c(=O)c2cnc(Nc3ccc4c(c3)CNC4)cc2n1-c1ccnc(C(C)(C)F)n1]
2.822
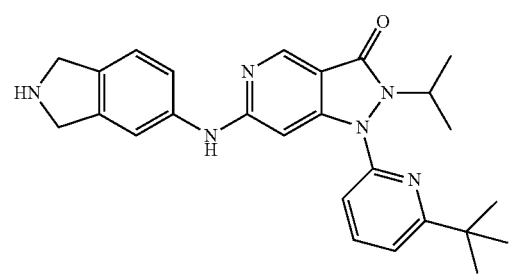 [SMILES: CC(C)n1c(=O)c2cnc(Nc3ccc4c(c3)CNC4)cc2n1-c1cccc(C(C)(C)C)n1]
2.823
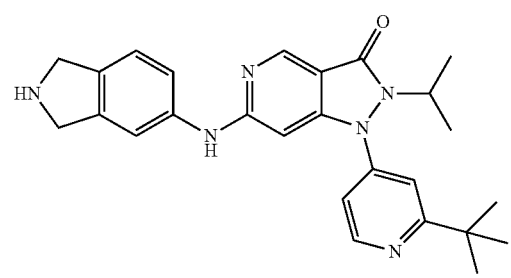 [SMILES: CC(C)n1c(=O)c2cnc(Nc3ccc4c(c3)CNC4)cc2n1-c1ccnc(C(C)(C)C)c1]
2.824

TABLE-1B-continued
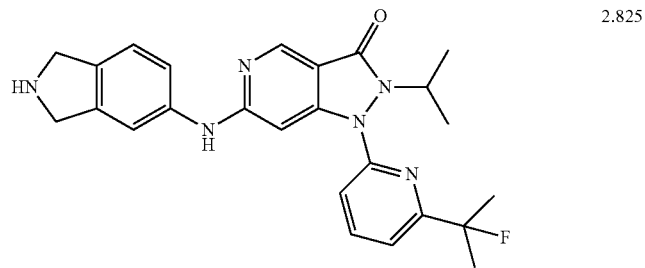
2.825
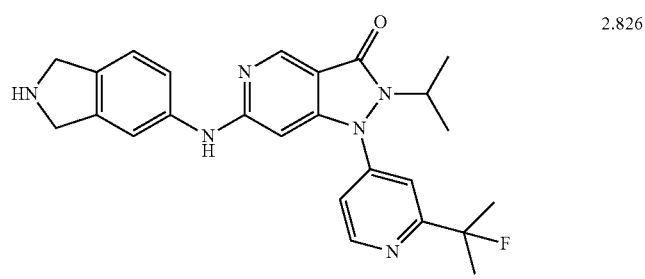
2.826
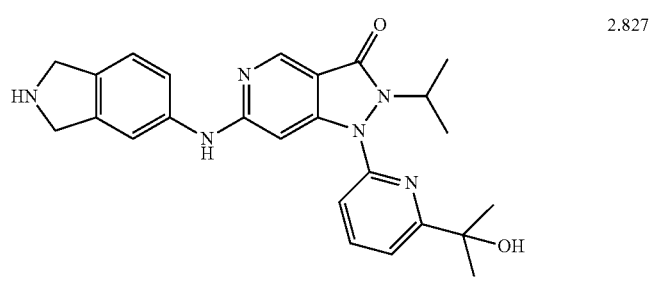
2.827
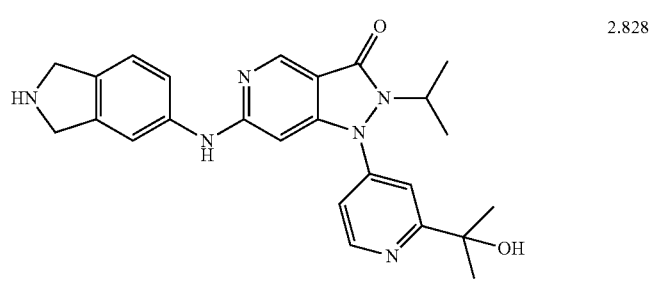
2.828
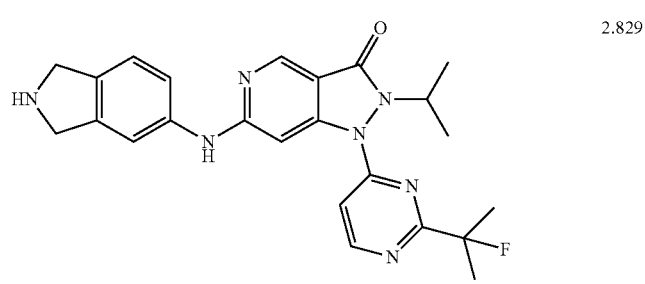
2.829
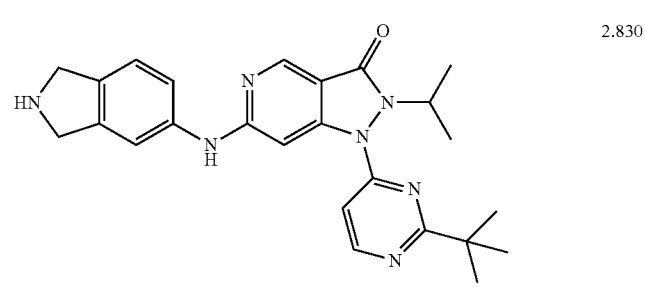
2.830

TABLE-1B-continued
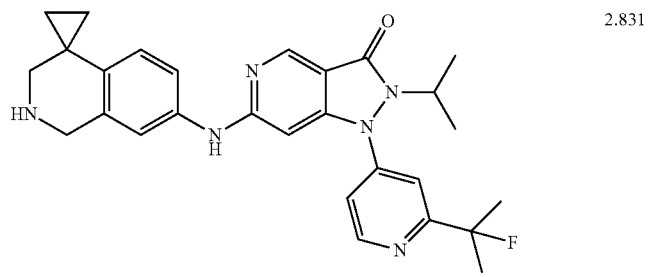
2.831
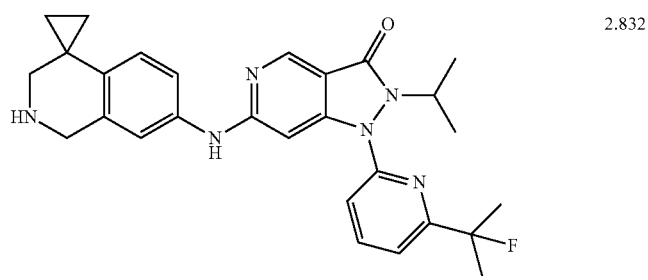
2.832
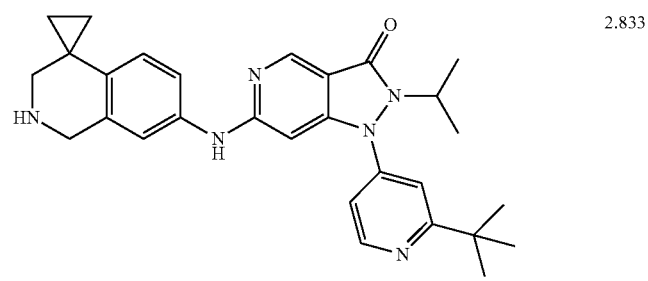
2.833
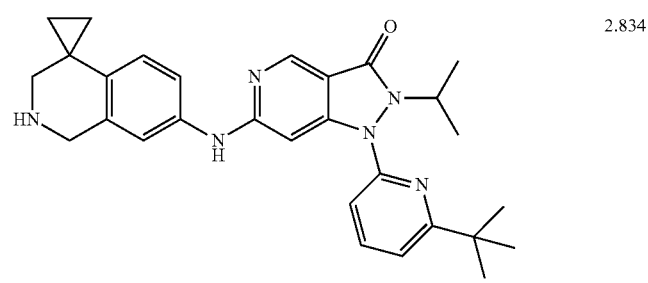
2.834
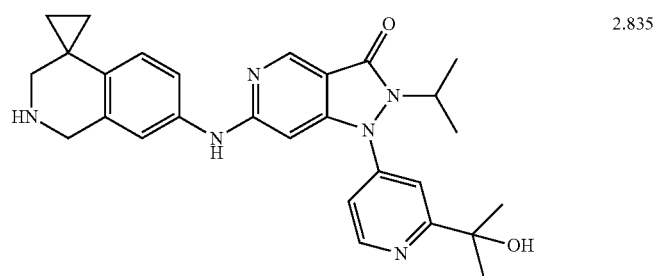
2.835

| | |
|---|---|
| 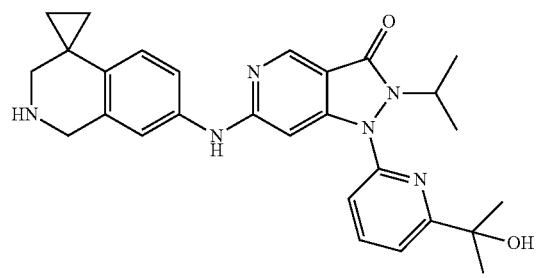 | 2.836 |
| 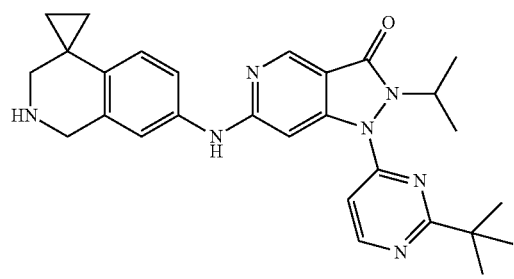 [SMILES: CC(C)n1c(=O)c2cnc(Nc3ccc4c(c3)CNCC43CC3)cc2n1-c1ccnc(C(C)(C)C)n1] | 2.837 |
| 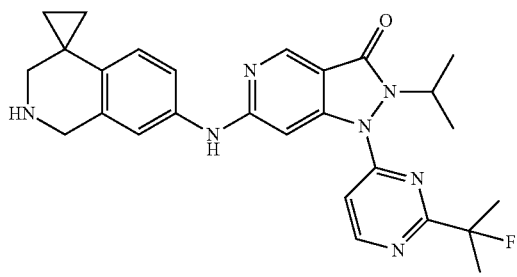 [SMILES: CC(C)n1c(=O)c2cnc(Nc3ccc4c(c3)CNCC43CC3)cc2n1-c1ccnc(C(C)(C)F)n1] | 2.838 |
| 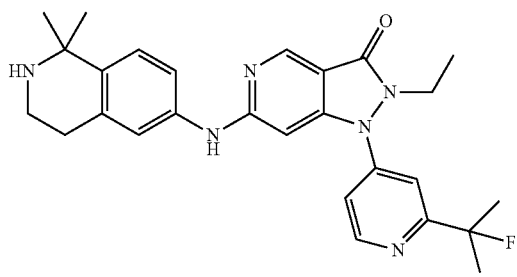 [SMILES: CCn1c(=O)c2cnc(Nc3ccc4c(c3)CCNC4(C)C)cc2n1-c1ccnc(C(C)(C)F)c1] | 2.839 |
| 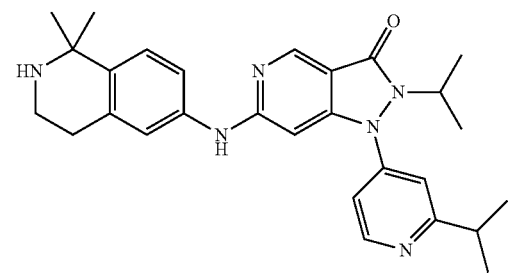 [SMILES: CC(C)c1cc(-n2c3cc(Nc4ccc5c(c4)CCNC5(C)C)ncc3c(=O)n2C(C)C)ccn1] | 2.840 |

TABLE-1B-continued
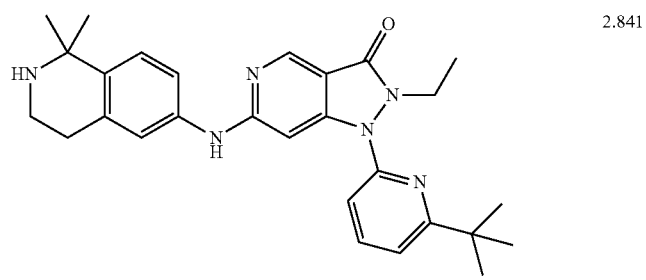 2.841
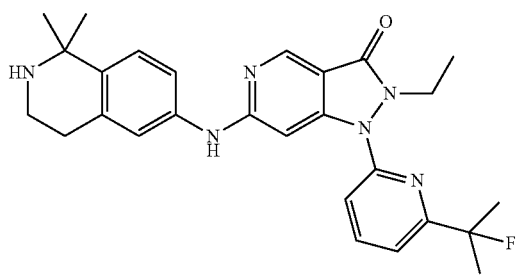 [SMILES: CCn1c(=O)c2cnc(Nc3ccc4c(c3)CCNC4(C)C)cc2n1-c1cccc(C(C)(C)F)n1] 2.842
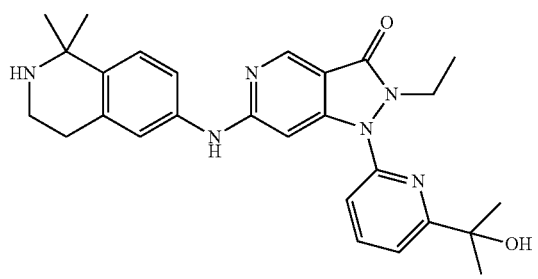 [SMILES: CCn1c(=O)c2cnc(Nc3ccc4c(c3)CCNC4(C)C)cc2n1-c1cccc(C(C)(C)O)n1] 2.843
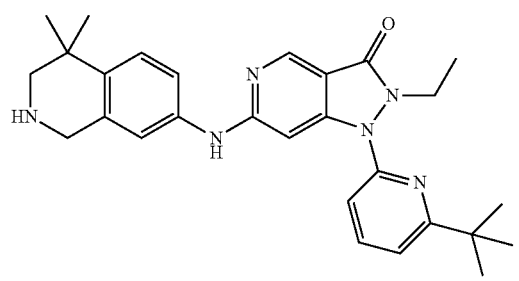 [SMILES: CCn1c(=O)c2cnc(Nc3ccc4c(c3)CNCC4(C)C)cc2n1-c1cccc(C(C)(C)C)n1] 2.844
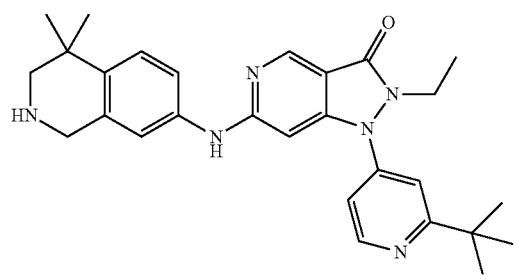 [SMILES: CCn1c(=O)c2cnc(Nc3ccc4c(c3)CNCC4(C)C)cc2n1-c1ccnc(C(C)(C)C)c1] 2.845

TABLE-1B-continued
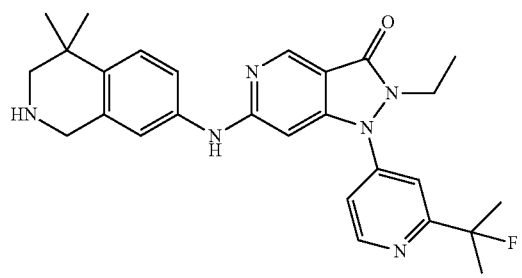 [SMILES: CCn1c(=O)c2cnc(Nc3ccc4c(c3)CNCC4(C)C)cc2n1-c1ccnc(C(C)(C)F)c1]
2.846
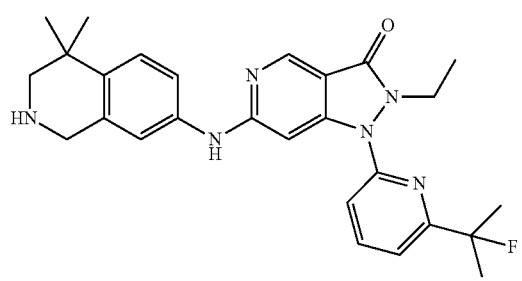 [SMILES: CCn1c(=O)c2cnc(Nc3ccc4c(c3)CNCC4(C)C)cc2n1-c1cccc(C(C)(C)F)n1]
2.847
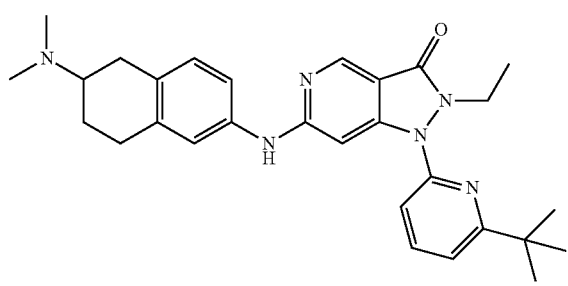 [SMILES: CCn1c(=O)c2cnc(Nc3ccc4c(c3)CCC(N(C)C)C4)cc2n1-c1cccc(C(C)(C)C)n1]
2.848
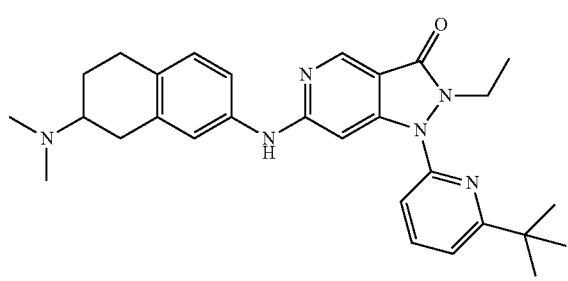 [SMILES: CCn1c(=O)c2cnc(Nc3ccc4c(c3)CC(N(C)C)CC4)cc2n1-c1cccc(C(C)(C)C)n1]
2.849
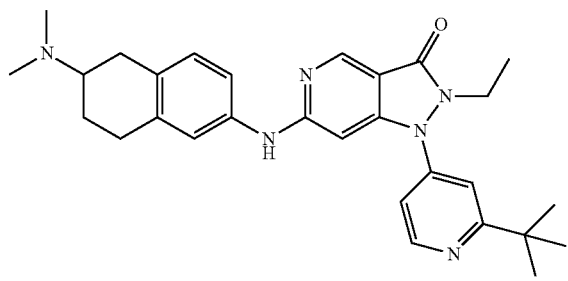 [SMILES: CCn1c(=O)c2cnc(Nc3ccc4c(c3)CCC(N(C)C)C4)cc2n1-c1ccnc(C(C)(C)C)c1]
2.850

TABLE-1B-continued
| | |
|---|---|
| 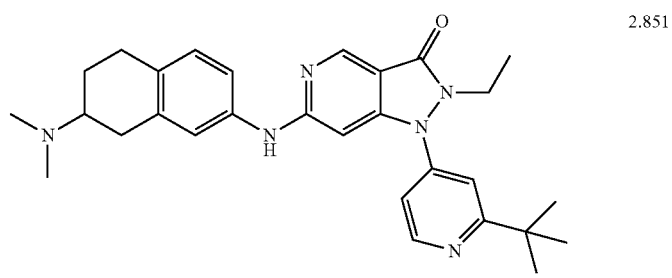 | 2.851 |
| 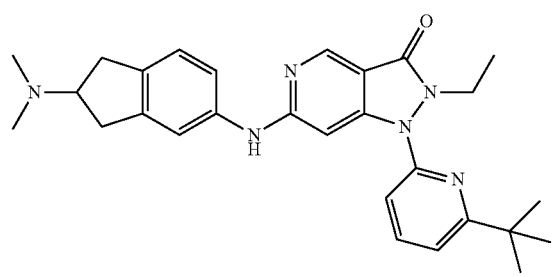 [SMILES: CCn1c(=O)c2cnc(Nc3ccc4c(c3)CC(N(C)C)C4)cc2n1-c1cccc(C(C)(C)C)n1] | 2.852 |
| 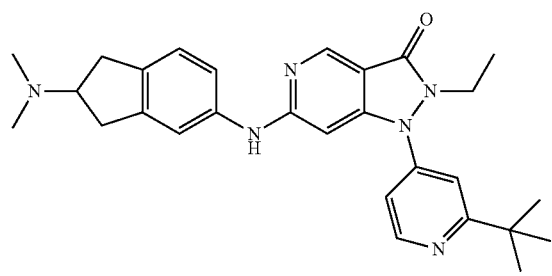 [SMILES: CCn1c(=O)c2cnc(Nc3ccc4c(c3)CC(N(C)C)C4)cc2n1-c1ccnc(C(C)(C)C)c1] | 2.853 |
| 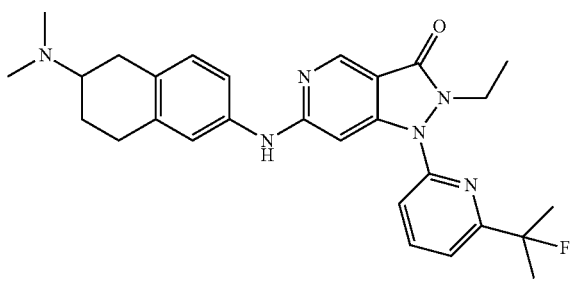 [SMILES: CCn1c(=O)c2cnc(Nc3ccc4c(c3)CCC(N(C)C)C4)cc2n1-c1cccc(C(C)(C)F)n1] | 2.854 |
| 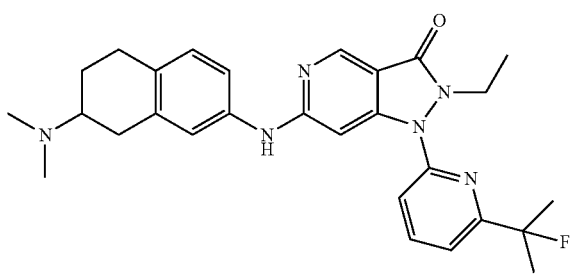 [SMILES: CCn1c(=O)c2cnc(Nc3ccc4c(c3)CC(N(C)C)CC4)cc2n1-c1cccc(C(C)(C)F)n1] | 2.855 |

TABLE-1B-continued
| | |
|---|---|
| 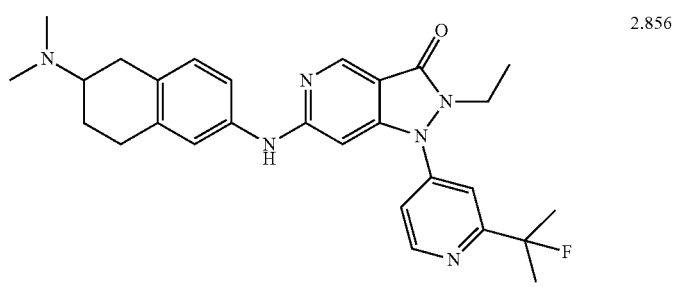 | 2.856 |
| 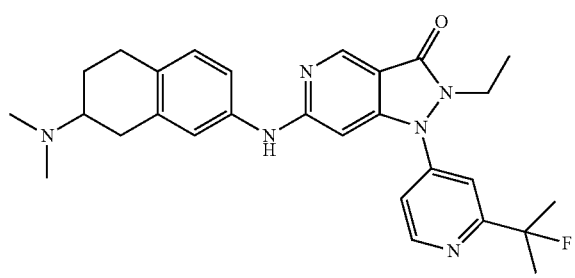 [SMILES: CCn1c(=O)c2cnc(Nc3ccc4c(c3)CC(N(C)C)CC4)cc2n1-c1ccnc(C(C)(C)F)c1] | 2.857 |
| 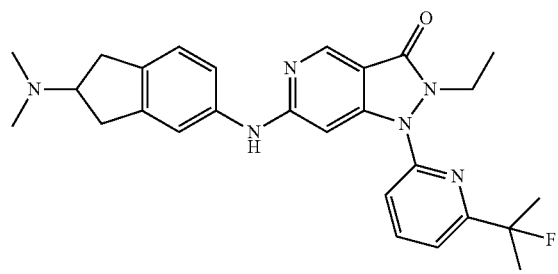 | 2.858 |
| 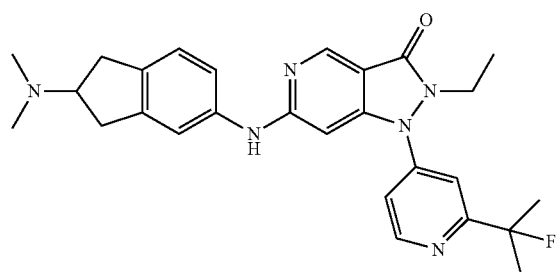 [SMILES: CCn1c(=O)c2cnc(Nc3ccc4c(c3)CC(N(C)C)C4)cc2n1-c1ccnc(C(C)(C)F)c1] | 2.859 |
| 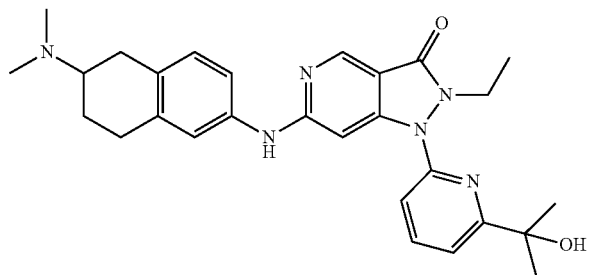 [SMILES: CCn1c(=O)c2cnc(Nc3ccc4c(c3)CCC(N(C)C)C4)cc2n1-c1cccc(C(C)(C)O)n1] | 2.860 |

TABLE-1B-continued
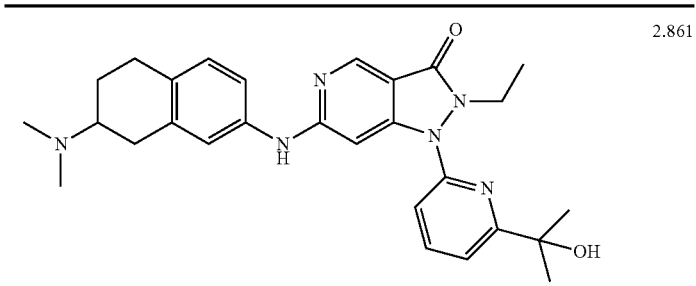 2.861
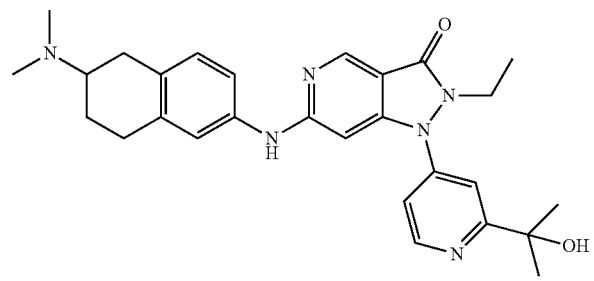 [SMILES: CCn1c(=O)c2cnc(Nc3ccc4c(c3)CCC(N(C)C)C4)cc2n1-c1ccnc(C(C)(C)O)c1] 2.862
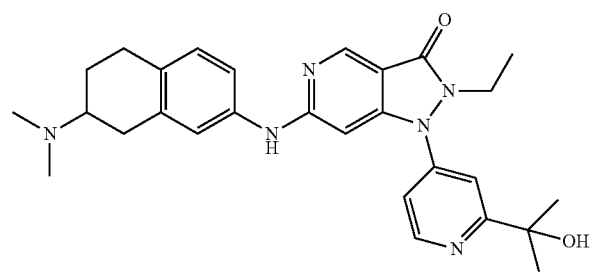 [SMILES: CCn1c(=O)c2cnc(Nc3ccc4c(c3)CC(N(C)C)CC4)cc2n1-c1ccnc(C(C)(C)O)c1] 2.863
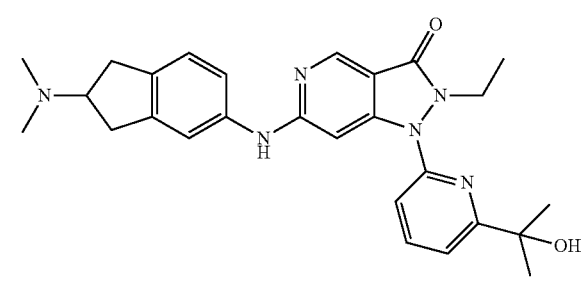 [SMILES: CCn1c(=O)c2cnc(Nc3ccc4c(c3)CC(N(C)C)C4)cc2n1-c1cccc(C(C)(C)O)n1] 2.864
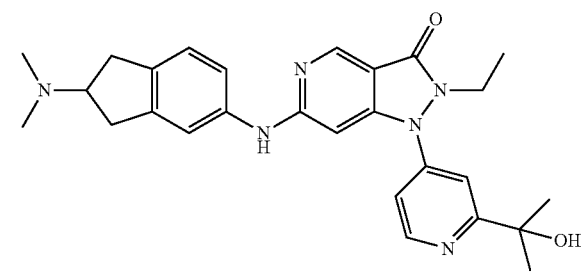 [SMILES: CCn1c(=O)c2cnc(Nc3ccc4c(c3)CC(N(C)C)C4)cc2n1-c1ccnc(C(C)(C)O)c1] 2.865

TABLE-1B-continued
| | |
|---|---|
| 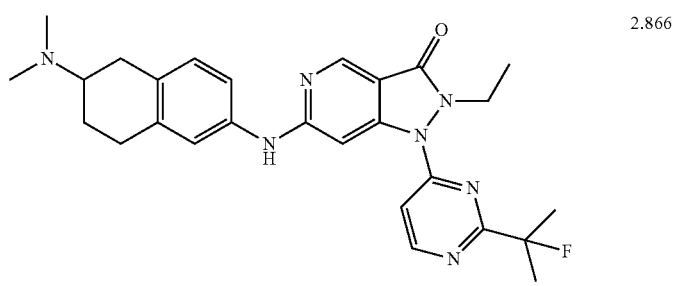 | 2.866 |
| 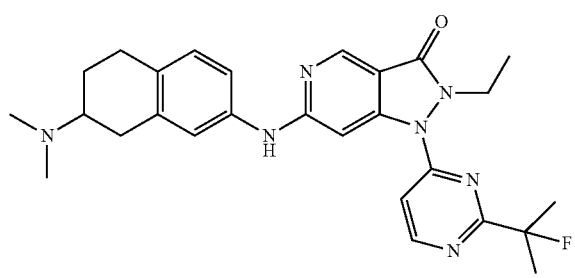 [SMILES: CCn1c(=O)c2cnc(Nc3ccc4c(c3)CC(N(C)C)CC4)cc2n1-c1ccnc(C(C)(C)F)n1] | 2.867 |
| 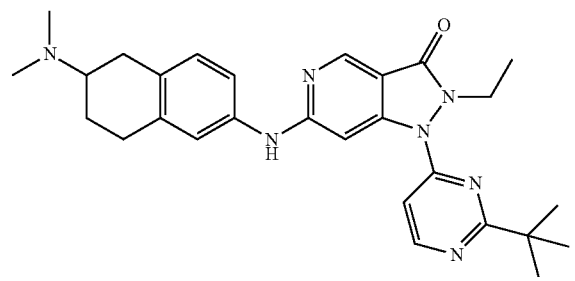 [SMILES: CCn1c(=O)c2cnc(Nc3ccc4c(c3)CCC(N(C)C)C4)cc2n1-c1ccnc(C(C)(C)C)n1] | 2.868 |
| 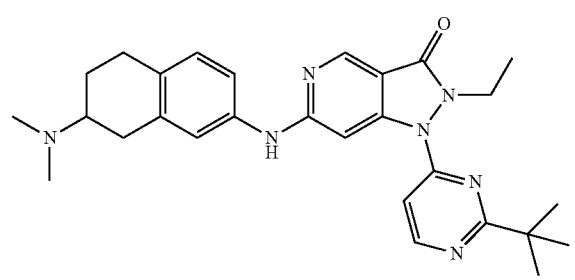 [SMILES: CCn1c(=O)c2cnc(Nc3ccc4c(c3)CC(N(C)C)CC4)cc2n1-c1ccnc(C(C)(C)C)n1] | 2.869 |
| 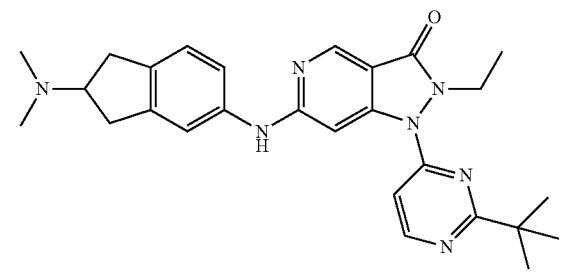 [SMILES: CCn1c(=O)c2cnc(Nc3ccc4c(c3)CC(N(C)C)C4)cc2n1-c1ccnc(C(C)(C)C)n1] | 2.870 |

TABLE-1B-continued
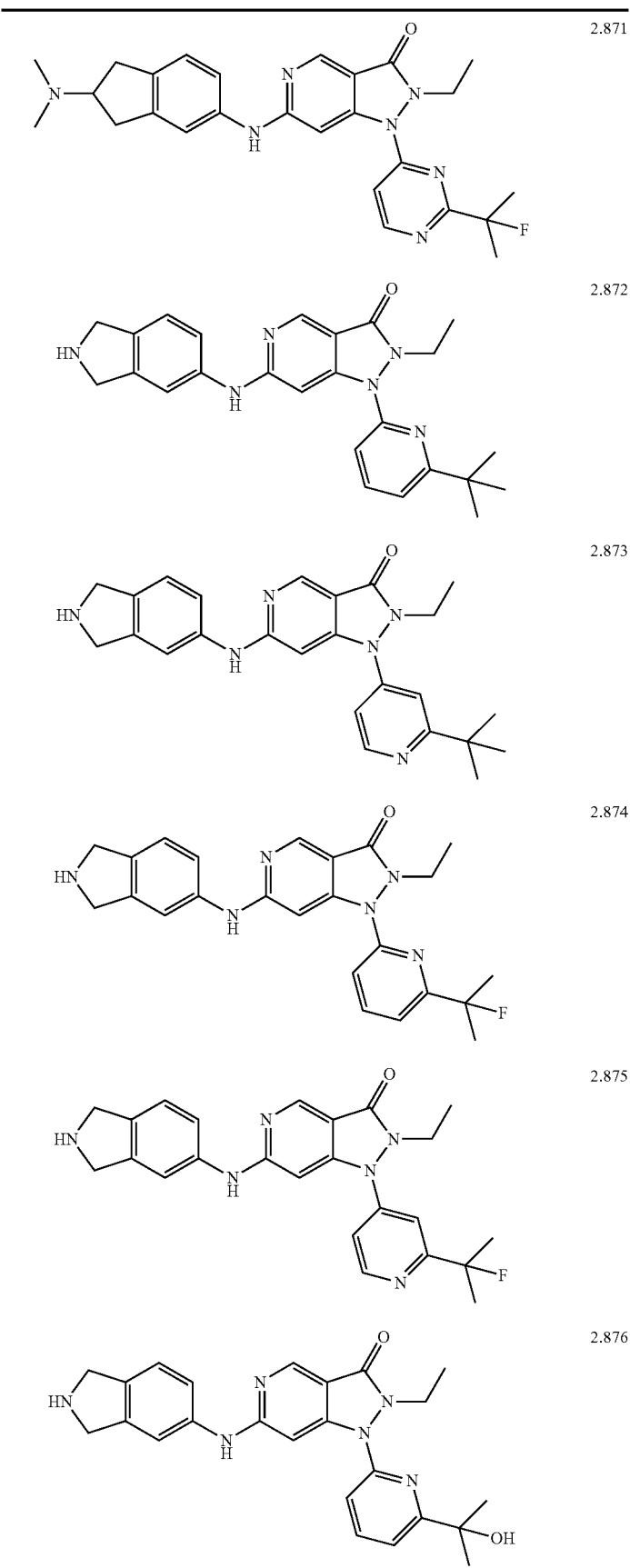
2.871
2.872
2.873
2.874
2.875
2.876

TABLE-1B-continued
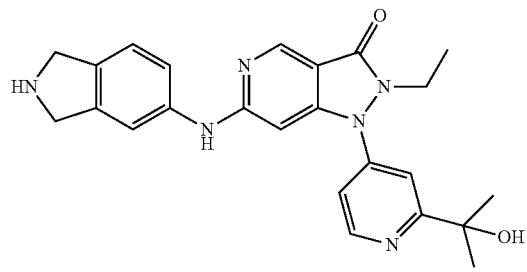 [SMILES: CCn1c(=O)c2cnc(Nc3ccc4c(c3)CNC4)cc2n1-c1ccnc(C(C)(C)O)c1]
2.877
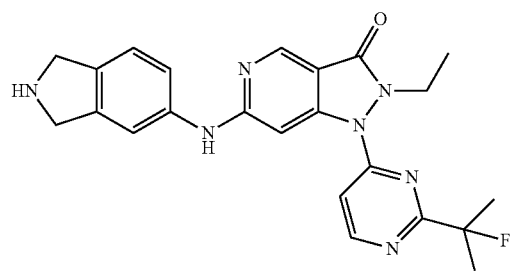 [SMILES: CCn1c(=O)c2cnc(Nc3ccc4c(c3)CNC4)cc2n1-c1ccnc(C(C)(C)F)n1]
2.878
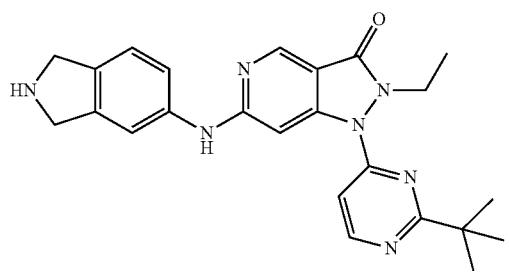 [SMILES: CCn1c(=O)c2cnc(Nc3ccc4c(c3)CNC4)cc2n1-c1ccnc(C(C)(C)C)n1]
2.879
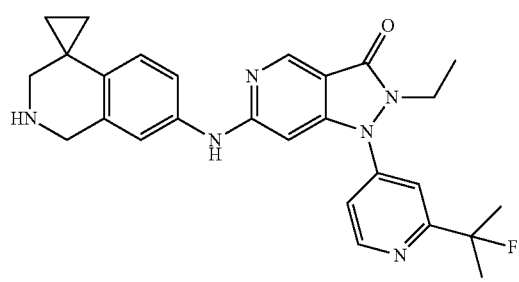 [SMILES: CCn1c(=O)c2cnc(Nc3ccc4c(c3)CNCC43CC3)cc2n1-c1ccnc(C(C)(C)F)c1]
2.880
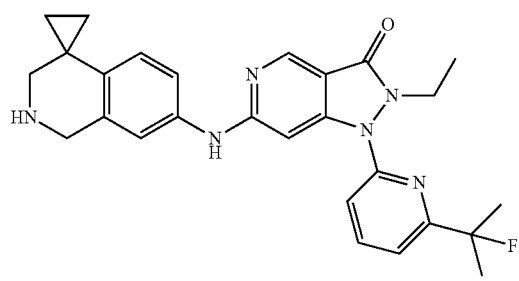
2.881

TABLE-1B-continued
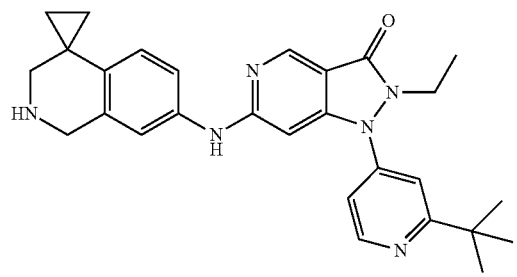 [SMILES: CCn1c(=O)c2cnc(Nc3ccc4c(c3)CNCC43CC3)cc2n1-c1ccnc(C(C)(C)C)c1]
2.882
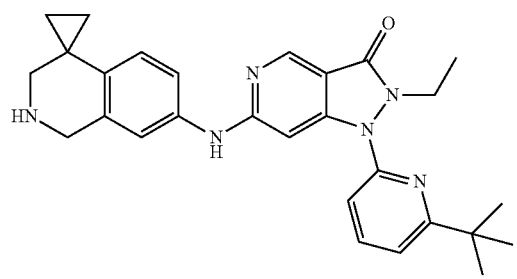 [SMILES: CCn1c(=O)c2cnc(Nc3ccc4c(c3)CNCC43CC3)cc2n1-c1cccc(C(C)(C)C)n1]
2.883
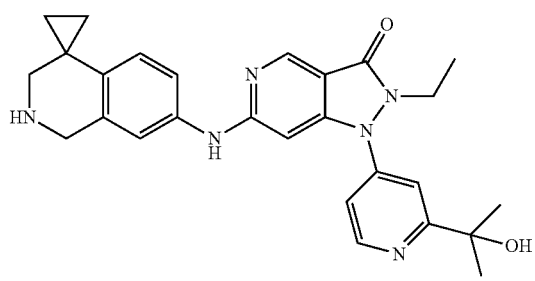 [SMILES: CCn1c(=O)c2cnc(Nc3ccc4c(c3)CNCC43CC3)cc2n1-c1ccnc(C(C)(C)O)c1]
2.884
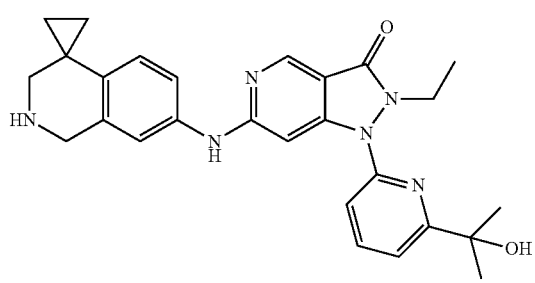 [SMILES: CCn1c(=O)c2cnc(Nc3ccc4c(c3)CNCC43CC3)cc2n1-c1cccc(C(C)(C)O)n1]
2.885
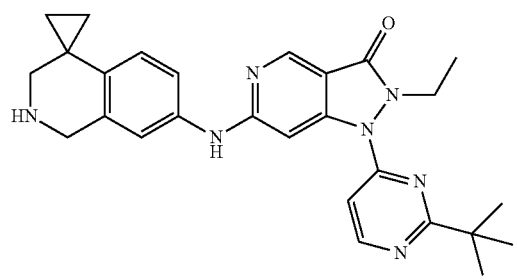 [SMILES: CCn1c(=O)c2cnc(Nc3ccc4c(c3)CNCC43CC3)cc2n1-c1ccnc(C(C)(C)C)n1]
2.886

| | |
|---|---|
| 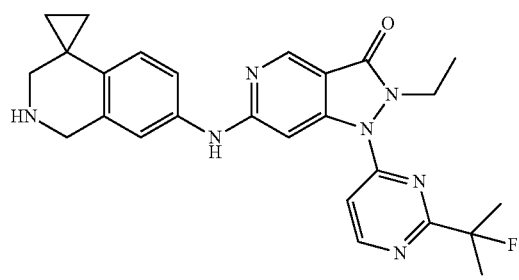 | 2.887 |
| 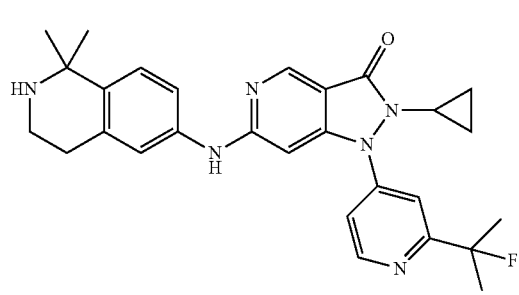 [SMILES: CC(C)(F)c1cc(-n2c3cc(Nc4ccc5c(c4)CCNC5(C)C)ncc3c(=O)n2C2CC2)ccn1] | 2.888 |
| 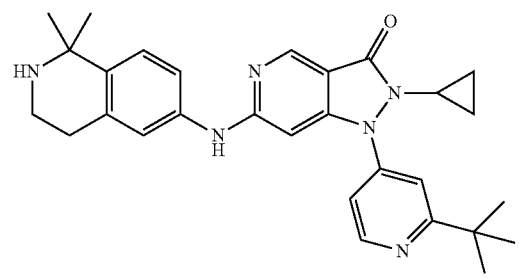 [SMILES: CC(C)(C)c1cc(-n2c3cc(Nc4ccc5c(c4)CCNC5(C)C)ncc3c(=O)n2C2CC2)ccn1] | 2.889 |
| 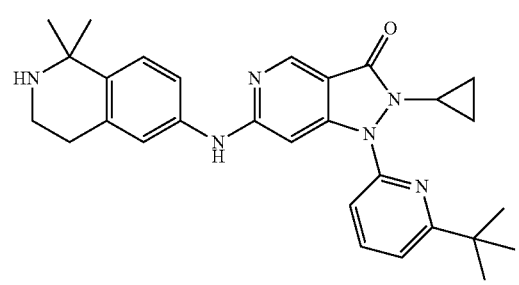 [SMILES: CC(C)(C)c1cccc(-n2c3cc(Nc4ccc5c(c4)CCNC5(C)C)ncc3c(=O)n2C2CC2)n1] | 2.890 |
| 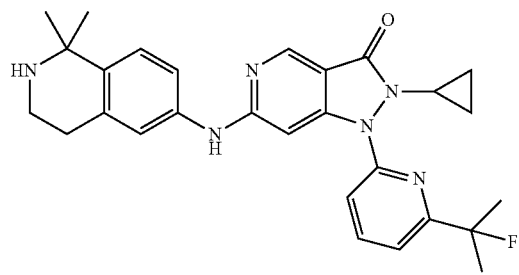 [SMILES: CC(C)(F)c1cccc(-n2c3cc(Nc4ccc5c(c4)CCNC5(C)C)ncc3c(=O)n2C2CC2)n1] | 2.891 |

TABLE-1B-continued
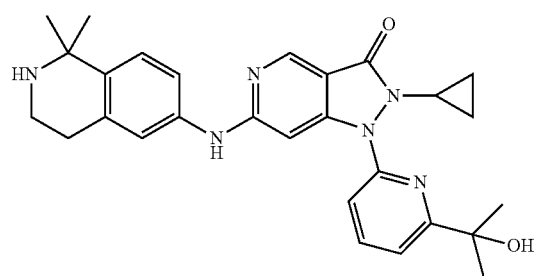 [SMILES: CC(C)(O)c1cccc(-n2c3cc(Nc4ccc5c(c4)CCNC5(C)C)ncc3c(=O)n2C2CC2)n1]
2.892
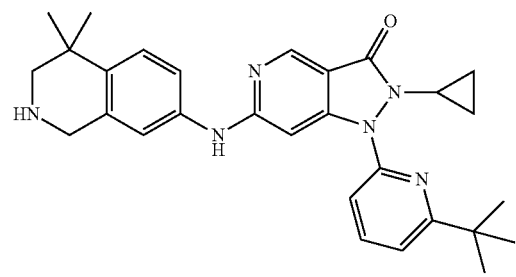 [SMILES: CC(C)(C)c1cccc(-n2c3cc(Nc4ccc5c(c4)CNCC5(C)C)ncc3c(=O)n2C2CC2)n1]
2.893
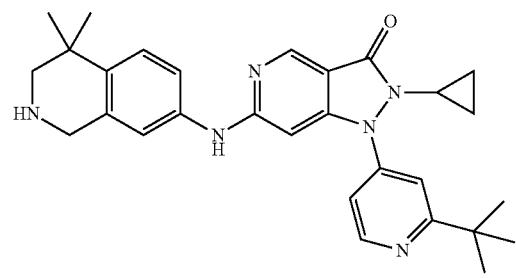 [SMILES: CC(C)(C)c1cc(-n2c3cc(Nc4ccc5c(c4)CNCC5(C)C)ncc3c(=O)n2C2CC2)ccn1]
2.894
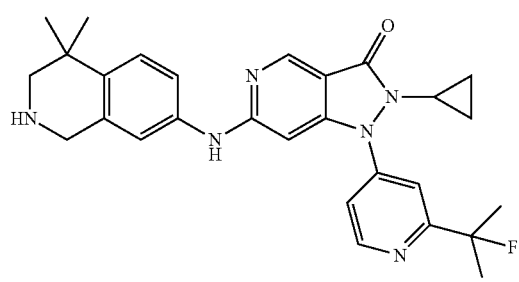 [SMILES: CC(C)(F)c1cc(-n2c3cc(Nc4ccc5c(c4)CNCC5(C)C)ncc3c(=O)n2C2CC2)ccn1]
2.895
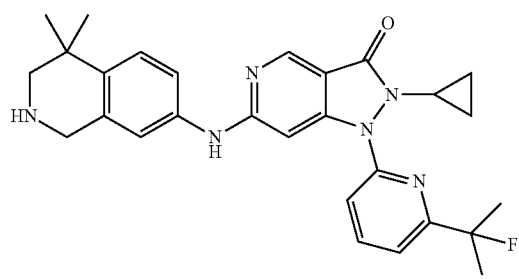 [SMILES: CC(C)(F)c1cccc(-n2c3cc(Nc4ccc5c(c4)CNCC5(C)C)ncc3c(=O)n2C2CC2)n1]
2.896

TABLE-1B-continued
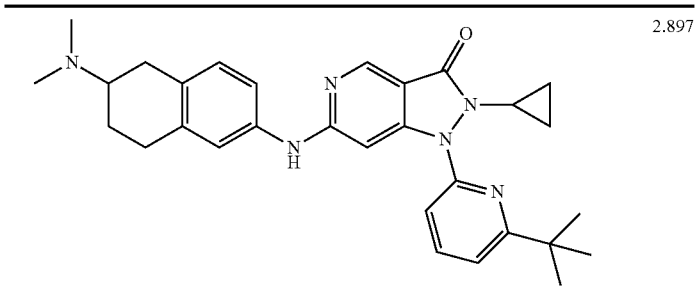
2.897
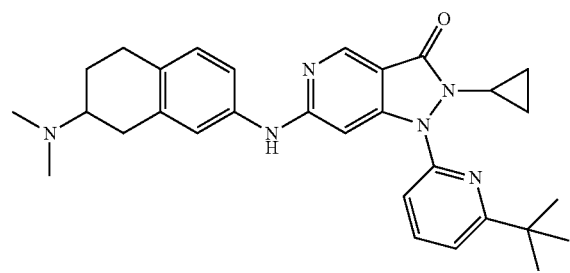
2.898
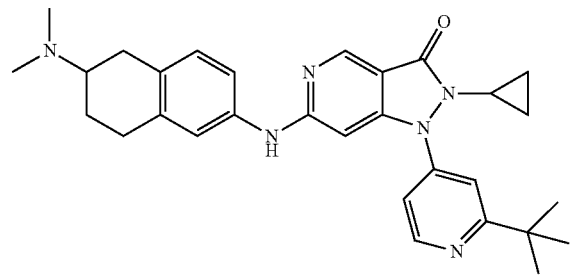 [SMILES: CN(C)C1CCc2cc(Nc3cc4c(cn3)c(=O)n(C3CC3)n4-c3ccnc(C(C)(C)C)c3)ccc2C1]
2.899
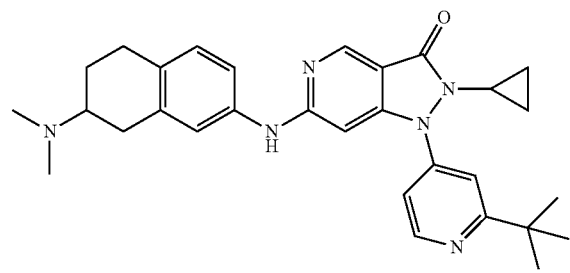
2.900
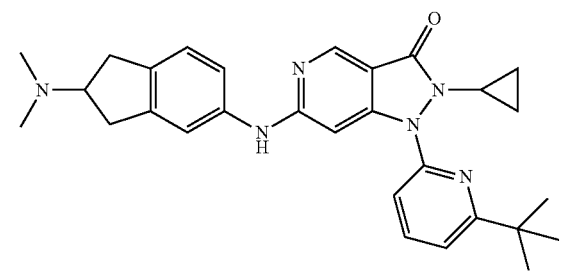
2.901

TABLE-1B-continued
| | |
|---|---|
| 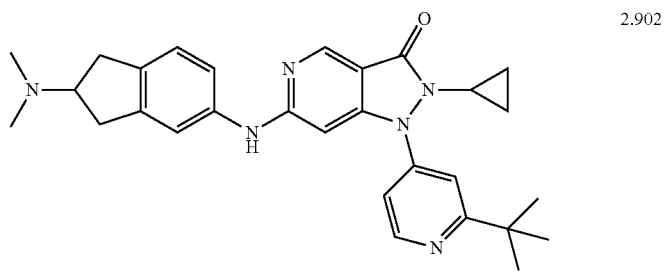 | 2.902 |
| 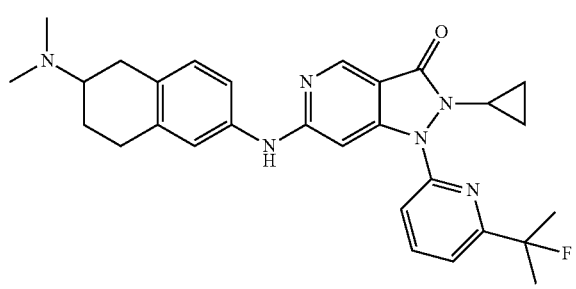 | 2.903 |
| 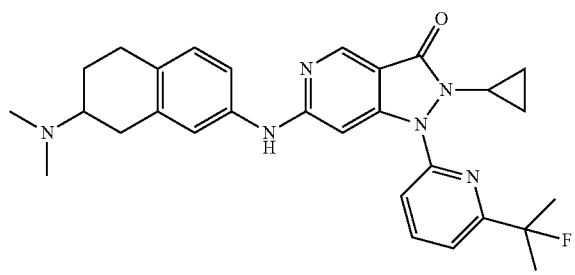 [SMILES: CN(C)C1CCc2ccc(Nc3cc4c(cn3)c(=O)n(C3CC3)n4-c3cccc(C(C)(C)F)n3)cc2C1] | 2.904 |
| 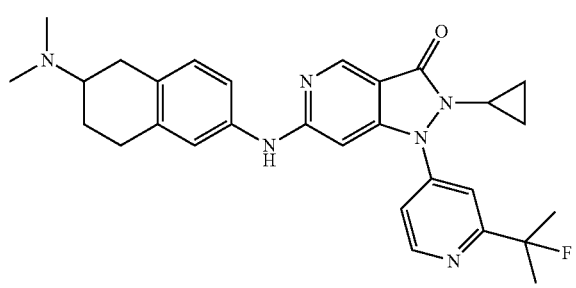 | 2.905 |
| 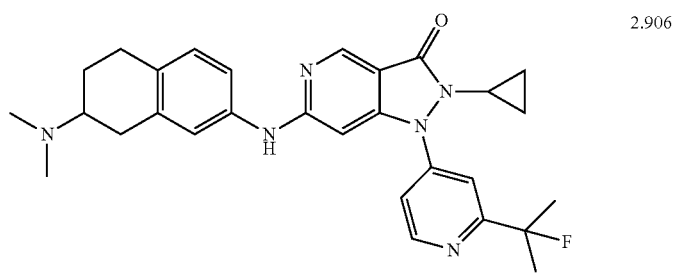 | 2.906 |

TABLE-1B-continued
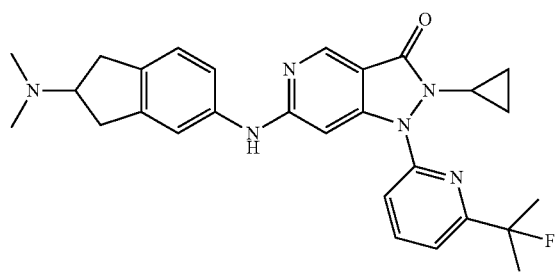 [SMILES: CN(C)C1Cc2ccc(Nc3cc4c(cn3)c(=O)n(C3CC3)n4-c3cccc(C(C)(C)F)n3)cc2C1]
2.907
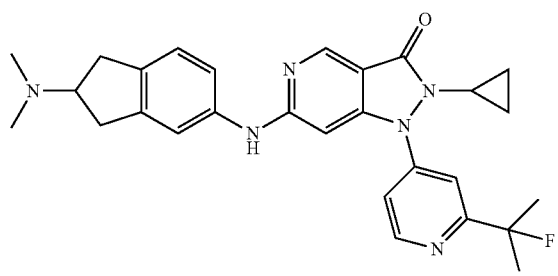 [SMILES: CN(C)C1Cc2ccc(Nc3cc4c(cn3)c(=O)n(C3CC3)n4-c3ccnc(C(C)(C)F)c3)cc2C1]
2.908
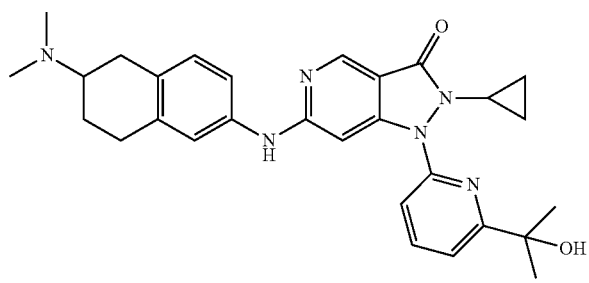 [SMILES: CN(C)C1CCc2cc(Nc3cc4c(cn3)c(=O)n(C3CC3)n4-c3cccc(C(C)(C)O)n3)ccc2C1]
2.909
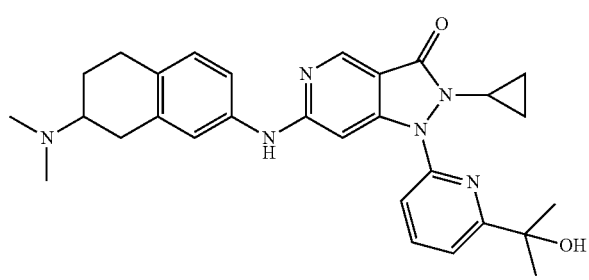 [SMILES: CN(C)C1CCc2ccc(Nc3cc4c(cn3)c(=O)n(C3CC3)n4-c3cccc(C(C)(C)O)n3)cc2C1]
2.910
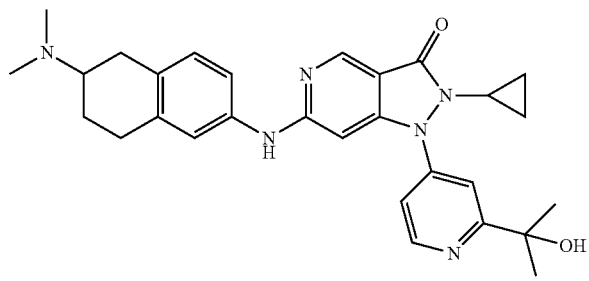 [SMILES: CN(C)C1CCc2cc(Nc3cc4c(cn3)c(=O)n(C3CC3)n4-c3ccnc(C(C)(C)O)c3)ccc2C1]
2.911

TABLE-1B-continued
| | |
|---|---|
| 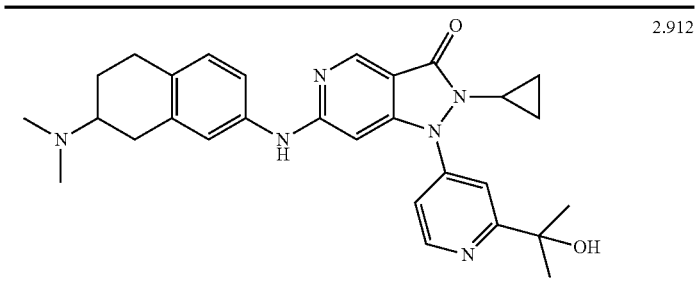 | 2.912 |
| 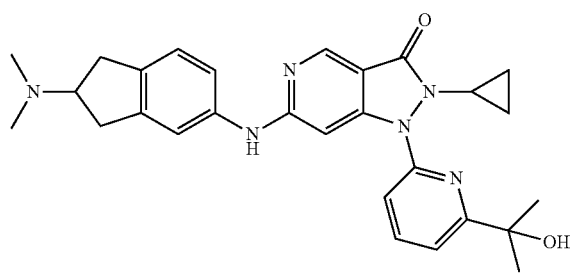 [SMILES: CN(C)C1Cc2ccc(Nc3cc4c(cn3)c(=O)n(C3CC3)n4-c3cccc(C(C)(C)O)n3)cc2C1] | 2.913 |
| 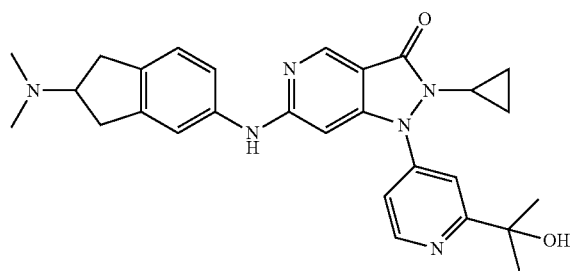 [SMILES: CN(C)C1Cc2ccc(Nc3cc4c(cn3)c(=O)n(C3CC3)n4-c3ccnc(C(C)(C)O)c3)cc2C1] | 2.914 |
| 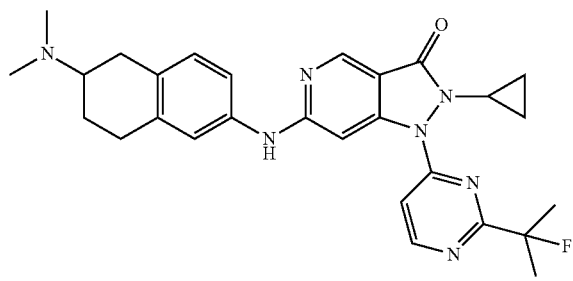 [SMILES: CN(C)C1CCc2cc(Nc3cc4c(cn3)c(=O)n(C3CC3)n4-c3ccnc(C(C)(C)F)n3)ccc2C1] | 2.915 |
| 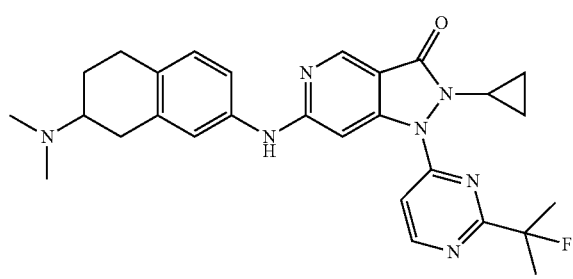 [SMILES: CN(C)C1CCc2ccc(Nc3cc4c(cn3)c(=O)n(C3CC3)n4-c3ccnc(C(C)(C)F)n3)cc2C1] | 2.916 |

TABLE-1B-continued
| | |
|---|---|
| 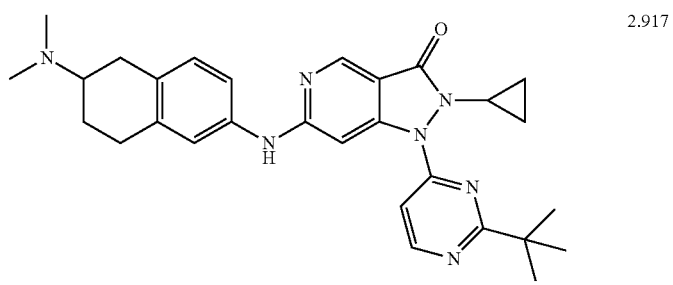 | 2.917 |
| 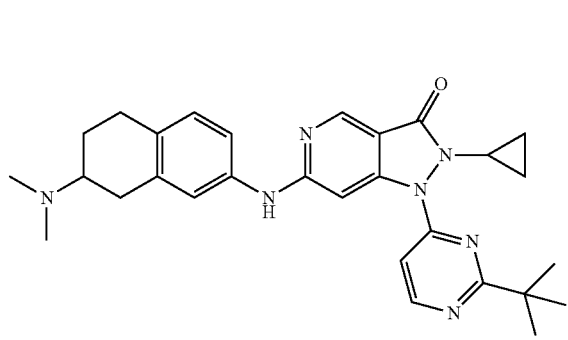 [SMILES: CN(C)C1CCc2ccc(Nc3cc4c(cn3)c(=O)n(C3CC3)n4-c3ccnc(C(C)(C)C)n3)cc2C1] | 2.918 |
| 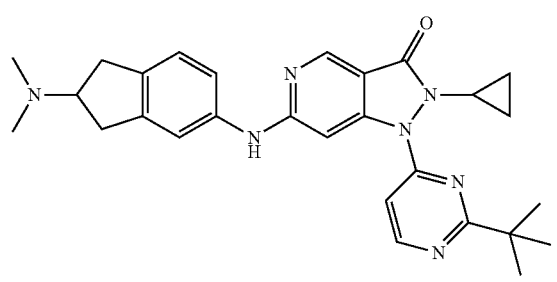 [SMILES: CN(C)C1Cc2ccc(Nc3cc4c(cn3)c(=O)n(C3CC3)n4-c3ccnc(C(C)(C)C)n3)cc2C1] | 2.919 |
| 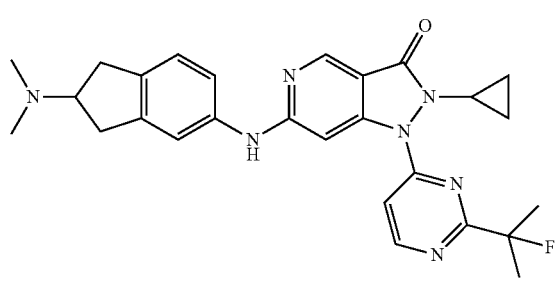 | 2.920 |
| 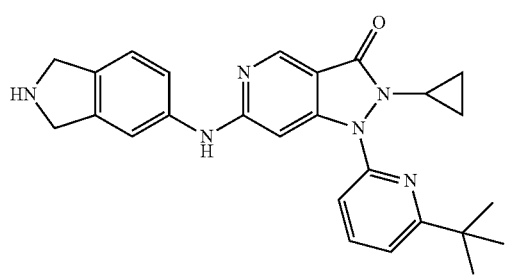 [SMILES: CC(C)(C)c1cccc(-n2c3cc(Nc4ccc5c(c4)CNC5)ncc3c(=O)n2C2CC2)n1] | 2.921 |

TABLE-1B-continued
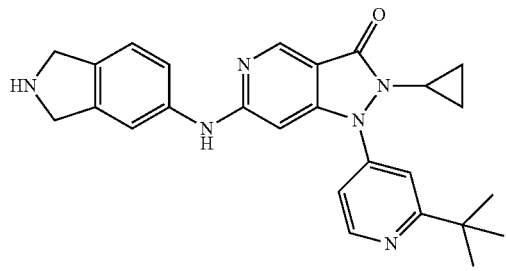 [SMILES: CC(C)(C)c1cc(-n2c3cc(Nc4ccc5c(c4)CNC5)ncc3c(=O)n2C2CC2)ccn1]
2.922
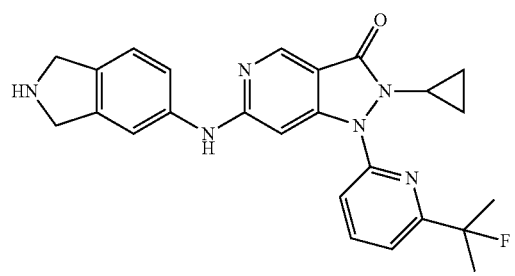 [SMILES: CC(C)(F)c1cccc(-n2c3cc(Nc4ccc5c(c4)CNC5)ncc3c(=O)n2C2CC2)n1]
2.923
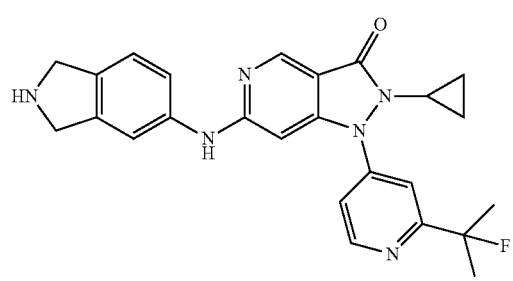 [SMILES: CC(C)(F)c1cc(-n2c3cc(Nc4ccc5c(c4)CNC5)ncc3c(=O)n2C2CC2)ccn1]
2.924
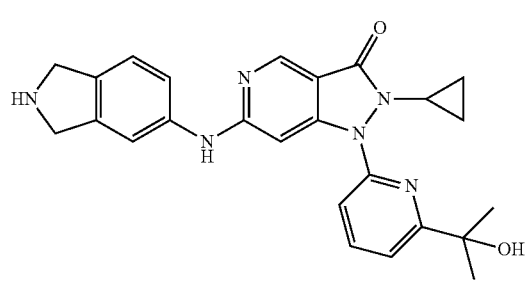 [SMILES: CC(C)(O)c1cccc(-n2c3cc(Nc4ccc5c(c4)CNC5)ncc3c(=O)n2C2CC2)n1]
2.925
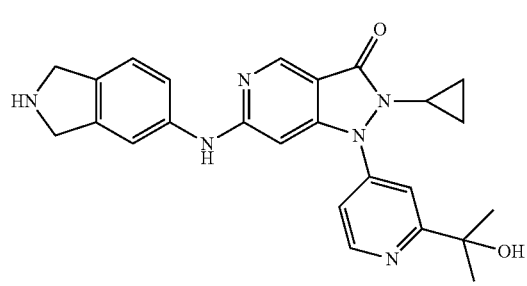 [SMILES: CC(C)(O)c1cc(-n2c3cc(Nc4ccc5c(c4)CNC5)ncc3c(=O)n2C2CC2)ccn1]
2.926
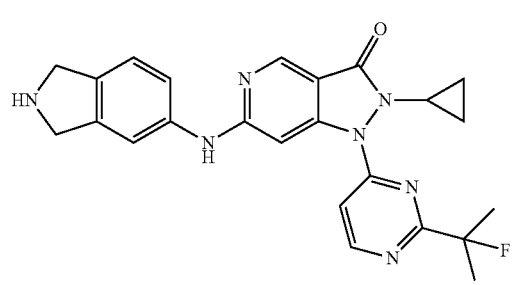 [SMILES: CC(C)(F)c1nccc(-n2c3cc(Nc4ccc5c(c4)CNC5)ncc3c(=O)n2C2CC2)n1]
2.927

TABLE-1B-continued
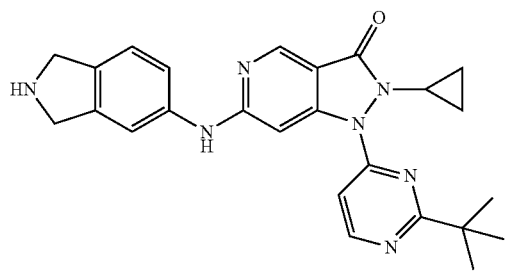 [SMILES: CC(C)(C)c1nccc(-n2c3cc(Nc4ccc5c(c4)CNC5)ncc3c(=O)n2C2CC2)n1]
2.928
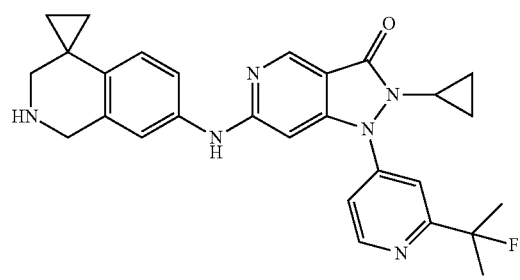
2.929
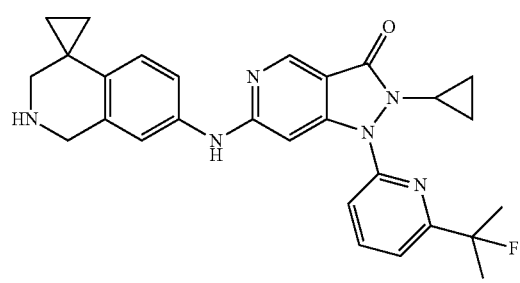 [SMILES: CC(C)(F)c1cccc(-n2c3cc(Nc4ccc5c(c4)CNCC54CC4)ncc3c(=O)n2C2CC2)n1]
2.930
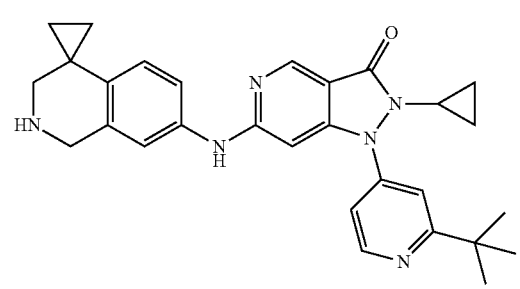 [SMILES: CC(C)(C)c1cc(-n2c3cc(Nc4ccc5c(c4)CNCC54CC4)ncc3c(=O)n2C2CC2)ccn1]
2.931
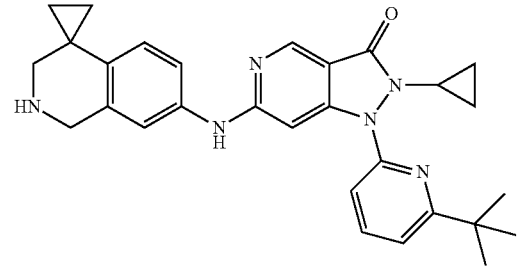 [SMILES: CC(C)(C)c1cccc(-n2c3cc(Nc4ccc5c(c4)CNCC54CC4)ncc3c(=O)n2C2CC2)n1]
2.932

TABLE-1B-continued
| | |
|---|---|
| 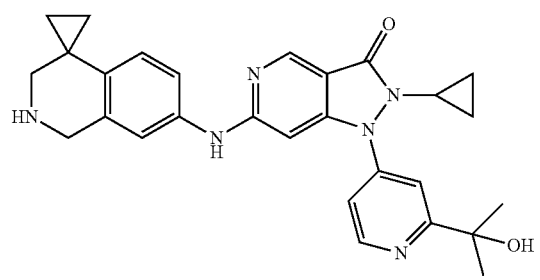 [SMILES: CC(C)(O)c1cc(-n2c3cc(Nc4ccc5c(c4)CNCC54CC4)ncc3c(=O)n2C2CC2)ccn1] | 2.933 |
| 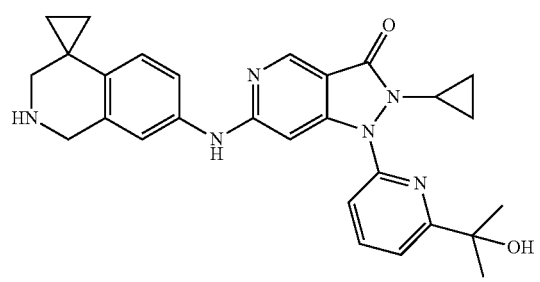 [SMILES: CC(C)(O)c1cccc(-n2c3cc(Nc4ccc5c(c4)CNCC54CC4)ncc3c(=O)n2C2CC2)n1] | 2.934 |
| 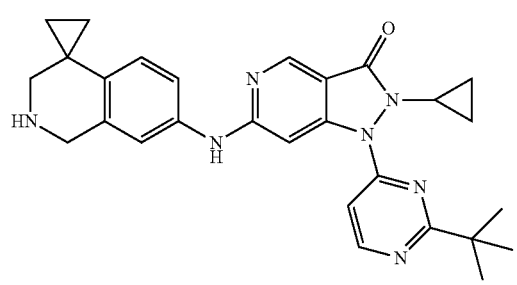 [SMILES: CC(C)(C)c1nccc(-n2c3cc(Nc4ccc5c(c4)CNCC54CC4)ncc3c(=O)n2C2CC2)n1] | 2.935 |
| 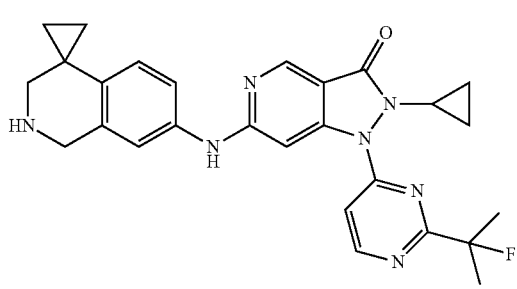 [SMILES: CC(C)(F)c1nccc(-n2c3cc(Nc4ccc5c(c4)CNCC54CC4)ncc3c(=O)n2C2CC2)n1] | 2.936 |
| 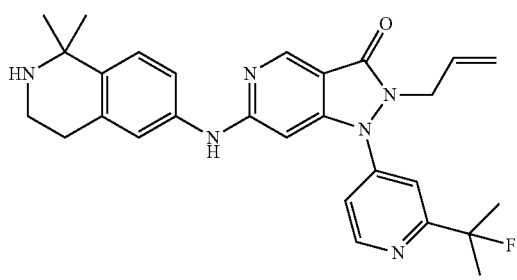 [SMILES: C=CCn1c(=O)c2cnc(Nc3ccc4c(c3)CCNC4(C)C)cc2n1-c1ccnc(C(C)(C)F)c1] | 2.937 |

TABLE-1B-continued
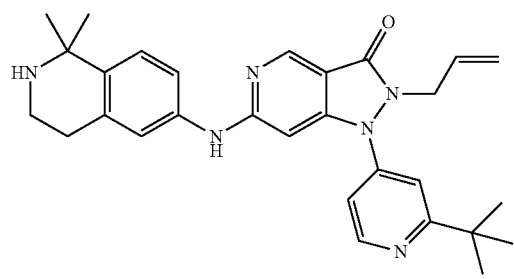 [SMILES: C=CCn1c(=O)c2cnc(Nc3ccc4c(c3)CCNC4(C)C)cc2n1-c1ccnc(C(C)(C)C)c1]
2.938
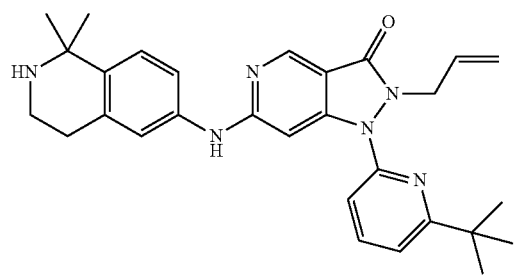 [SMILES: C=CCn1c(=O)c2cnc(Nc3ccc4c(c3)CCNC4(C)C)cc2n1-c1cccc(C(C)(C)C)n1]
2.939
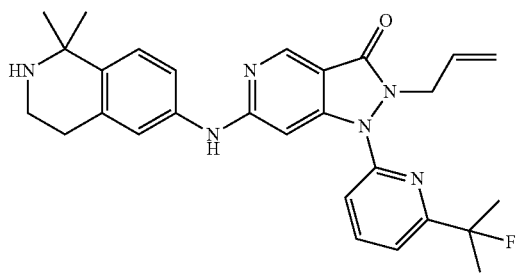 [SMILES: C=CCn1c(=O)c2cnc(Nc3ccc4c(c3)CCNC4(C)C)cc2n1-c1cccc(C(C)(C)F)n1]
2.940
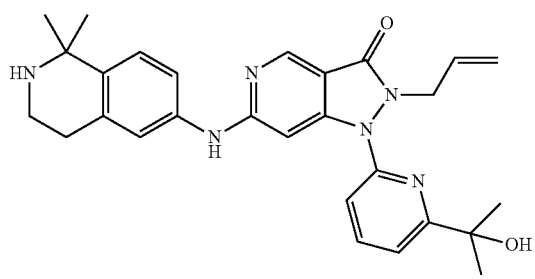 [SMILES: C=CCn1c(=O)c2cnc(Nc3ccc4c(c3)CCNC4(C)C)cc2n1-c1cccc(C(C)(C)O)n1]
2.941
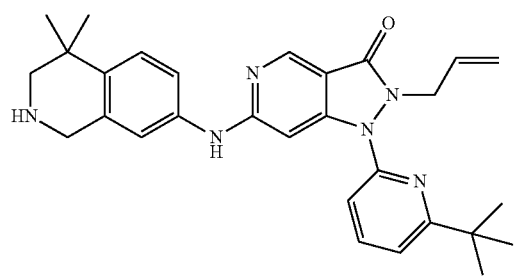 [SMILES: C=CCn1c(=O)c2cnc(Nc3ccc4c(c3)CNCC4(C)C)cc2n1-c1cccc(C(C)(C)C)n1]
2.942

TABLE-1B-continued
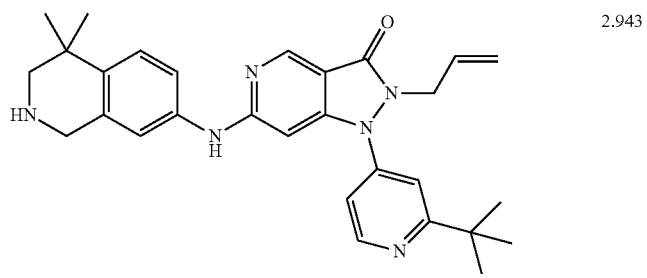
2.943
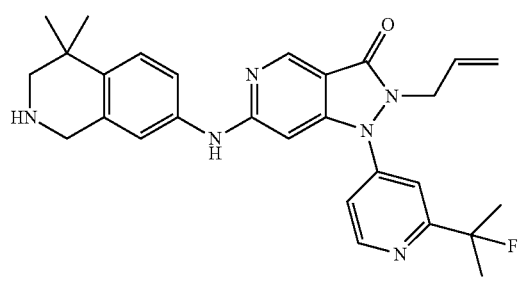 [SMILES: C=CCn1c(=O)c2cnc(Nc3ccc4c(c3)CNCC4(C)C)cc2n1-c1ccnc(C(C)(C)F)c1]
2.944
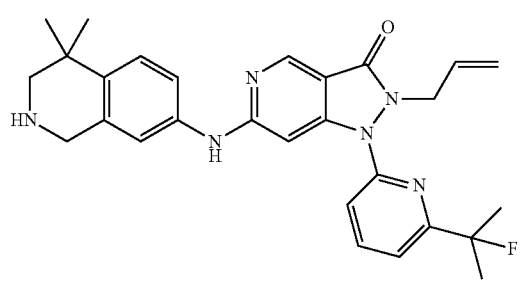 [SMILES: C=CCn1c(=O)c2cnc(Nc3ccc4c(c3)CNCC4(C)C)cc2n1-c1cccc(C(C)(C)F)n1]
2.945
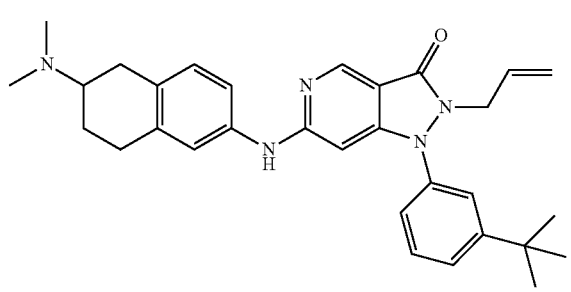 [SMILES: C=CCn1c(=O)c2cnc(Nc3ccc4c(c3)CCC(N(C)C)C4)cc2n1-c1cccc(C(C)(C)C)c1]
2.946
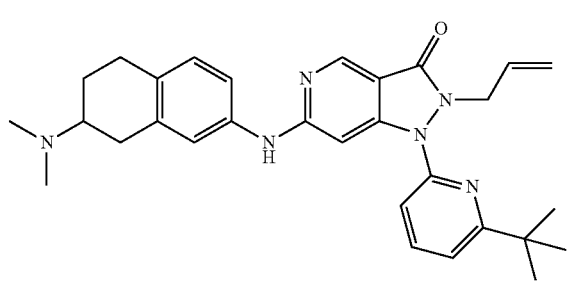 [SMILES: C=CCn1c(=O)c2cnc(Nc3ccc4c(c3)CC(N(C)C)CC4)cc2n1-c1cccc(C(C)(C)C)n1]
2.947

TABLE-1B-continued
| | |
|---|---|
| 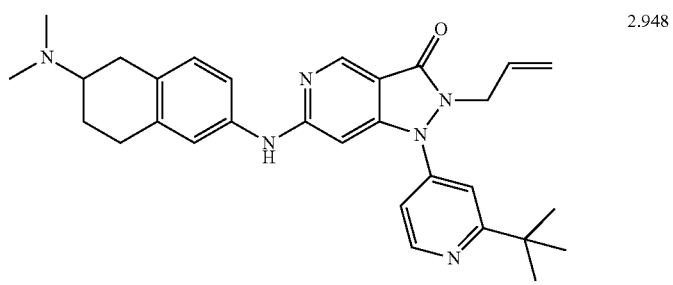 | 2.948 |
| 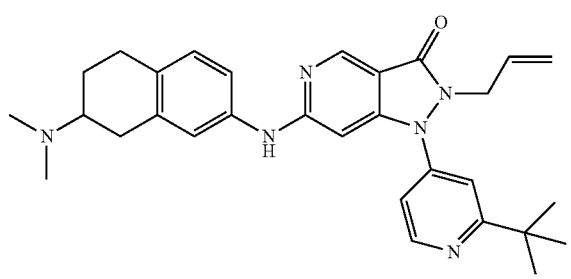 [SMILES: C=CCn1c(=O)c2cnc(Nc3ccc4c(c3)CC(N(C)C)CC4)cc2n1-c1ccnc(C(C)(C)C)c1] | 2.949 |
| 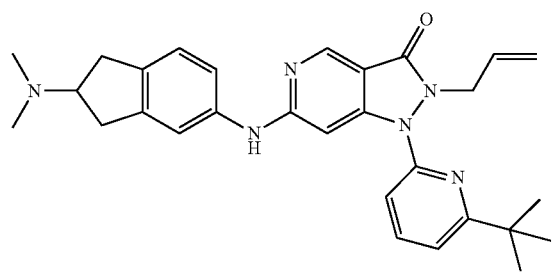 [SMILES: C=CCn1c(=O)c2cnc(Nc3ccc4c(c3)CC(N(C)C)C4)cc2n1-c1cccc(C(C)(C)C)n1] | 2.950 |
| 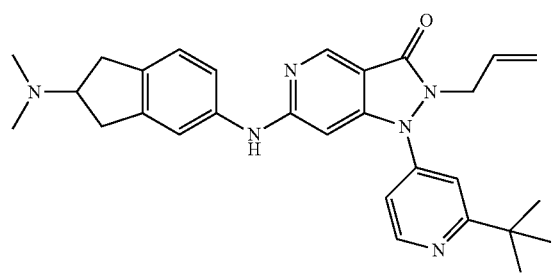 [SMILES: C=CCn1c(=O)c2cnc(Nc3ccc4c(c3)CC(N(C)C)C4)cc2n1-c1ccnc(C(C)(C)C)c1] | 2.951 |
| 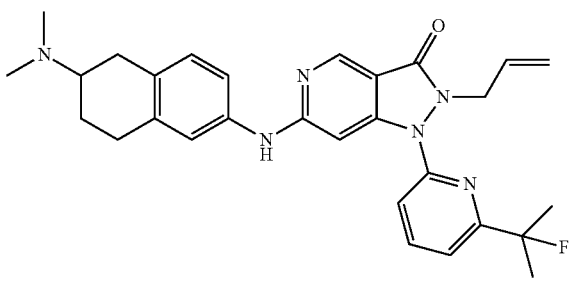 [SMILES: C=CCn1c(=O)c2cnc(Nc3ccc4c(c3)CCC(N(C)C)C4)cc2n1-c1cccc(C(C)(C)F)n1] | 2.952 |

TABLE-1B-continued
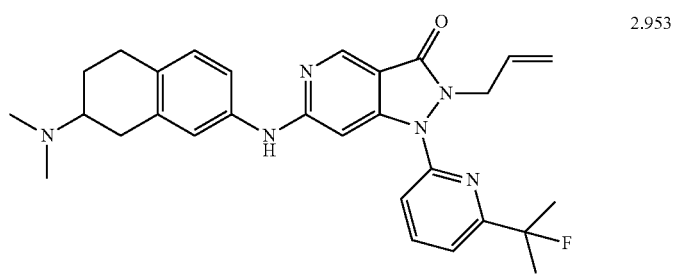
2.953
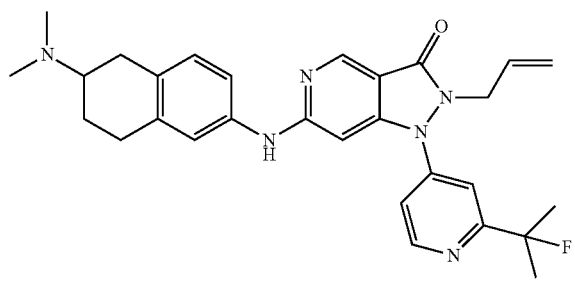
2.954
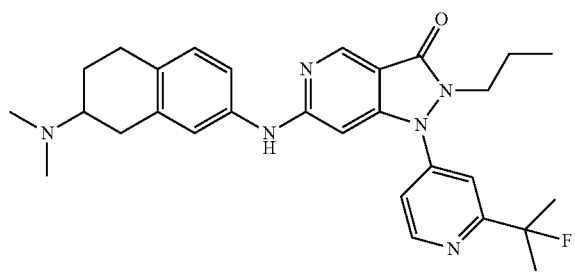 [SMILES: CCCn1c(=O)c2cnc(Nc3ccc4c(c3)CC(N(C)C)CC4)cc2n1-c1ccnc(C(C)(C)F)c1]
2.955
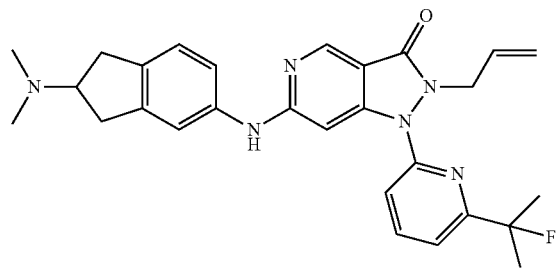 [SMILES: C=CCn1c(=O)c2cnc(Nc3ccc4c(c3)CC(N(C)C)C4)cc2n1-c1cccc(C(C)(C)F)n1]
2.956
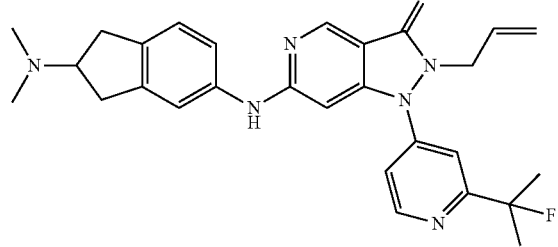
2.957

TABLE-1B-continued
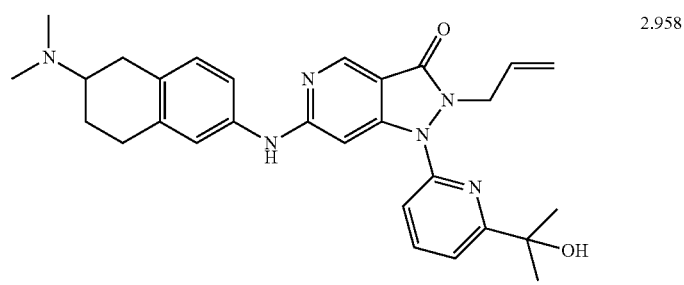
2.958
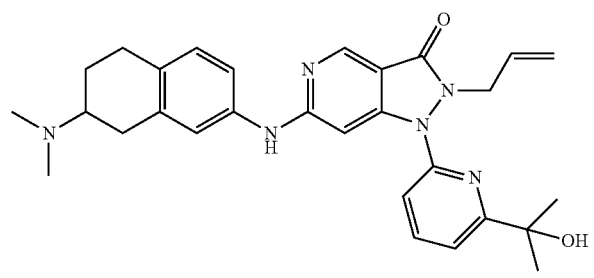
2.959
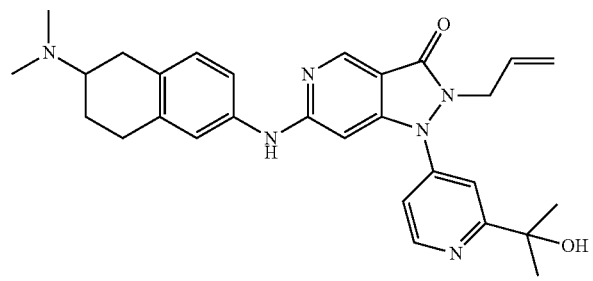 [SMILES: C=CCn1c(=O)c2cnc(Nc3ccc4c(c3)CCC(N(C)C)C4)cc2n1-c1ccnc(C(C)(C)O)c1]
2.960
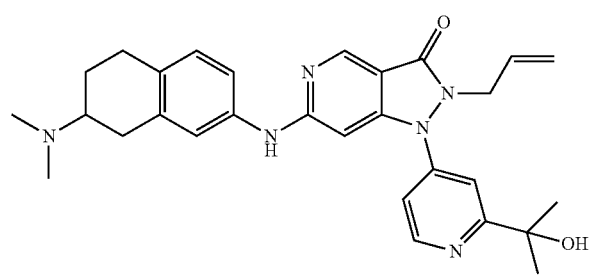 [SMILES: C=CCn1c(=O)c2cnc(Nc3ccc4c(c3)CC(N(C)C)CC4)cc2n1-c1ccnc(C(C)(C)O)c1]
2.961
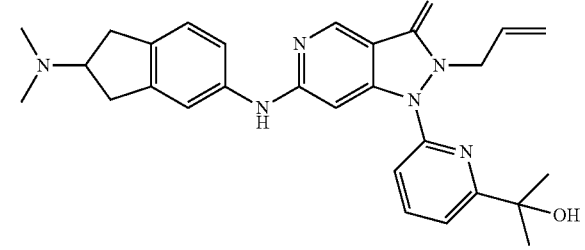
2.962

TABLE-1B-continued
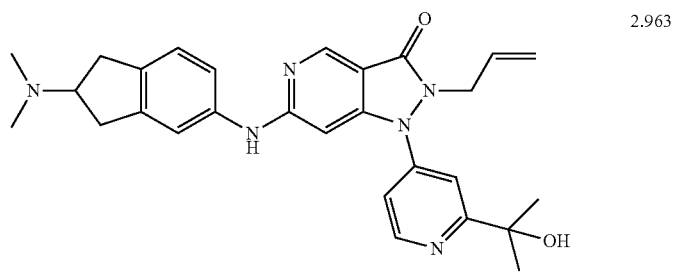
2.963
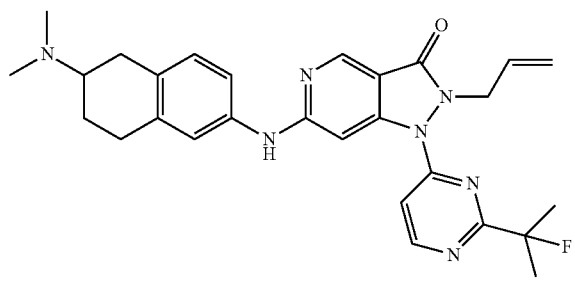 [SMILES: C=CCn1c(=O)c2cnc(Nc3ccc4c(c3)CCC(N(C)C)C4)cc2n1-c1ccnc(C(C)(C)F)n1]
2.964
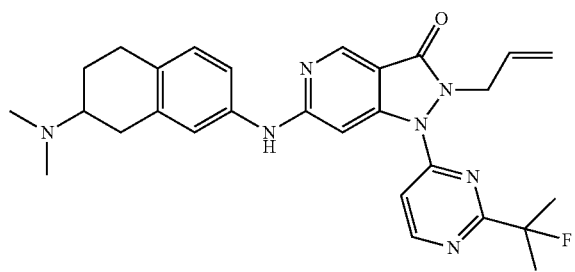 [SMILES: C=CCn1c(=O)c2cnc(Nc3ccc4c(c3)CC(N(C)C)CC4)cc2n1-c1ccnc(C(C)(C)F)n1]
2.965
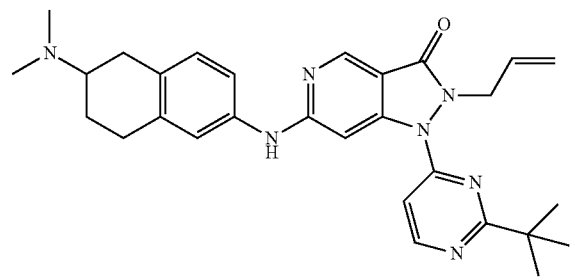 [SMILES: C=CCn1c(=O)c2cnc(Nc3ccc4c(c3)CCC(N(C)C)C4)cc2n1-c1ccnc(C(C)(C)C)n1]
2.966
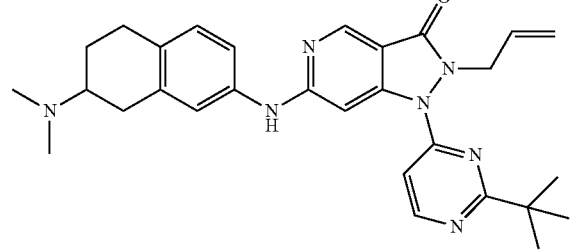
2.967

TABLE-1B-continued
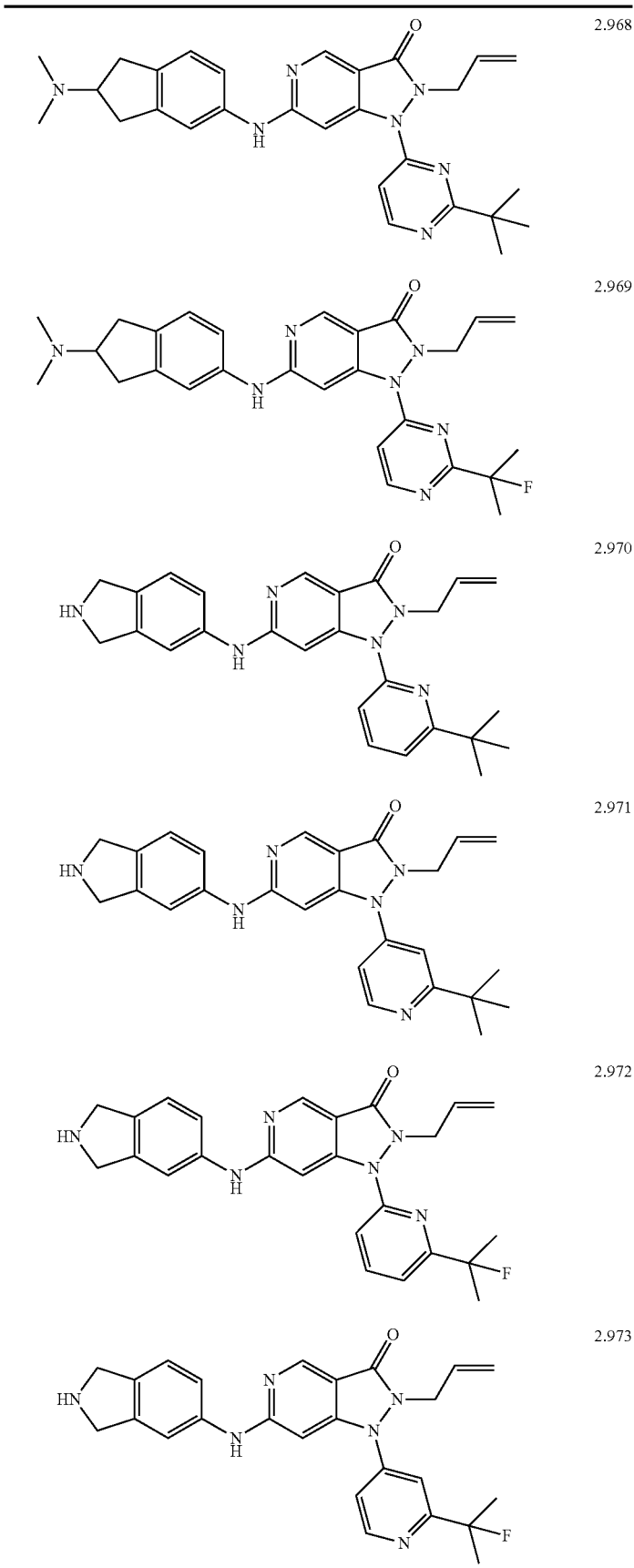
2.968
2.969
2.970
2.971
2.972
2.973

TABLE-1B-continued
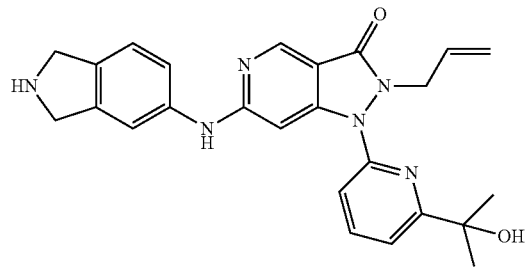 [SMILES: C=CCn1c(=O)c2cnc(Nc3ccc4c(c3)CNC4)cc2n1-c1cccc(C(C)(C)O)n1] 2.974
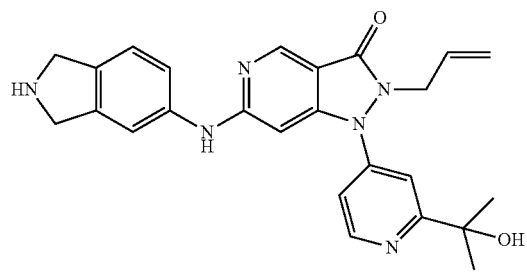 [SMILES: C=CCn1c(=O)c2cnc(Nc3ccc4c(c3)CNC4)cc2n1-c1ccnc(C(C)(C)O)c1] 2.975
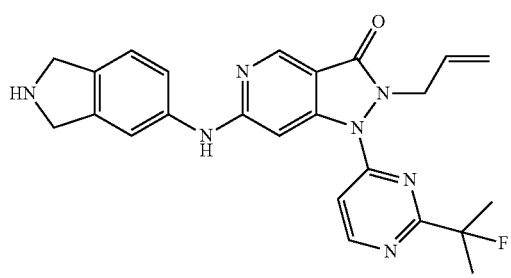 [SMILES: C=CCn1c(=O)c2cnc(Nc3ccc4c(c3)CNC4)cc2n1-c1ccnc(C(C)(C)F)n1] 2.976
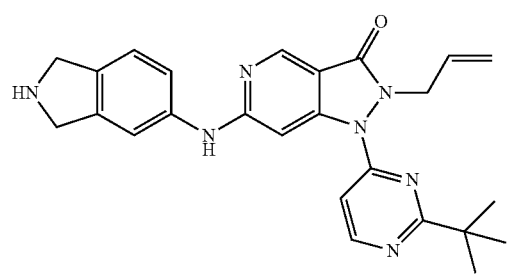 [SMILES: C=CCn1c(=O)c2cnc(Nc3ccc4c(c3)CNC4)cc2n1-c1ccnc(C(C)(C)C)n1] 2.977
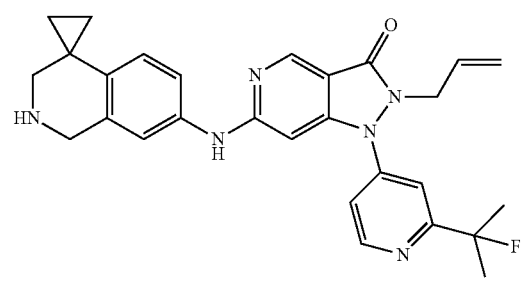 [SMILES: C=CCn1c(=O)c2cnc(Nc3ccc4c(c3)CNCC43CC3)cc2n1-c1ccnc(C(C)(C)F)c1] 2.978

TABLE-1B-continued
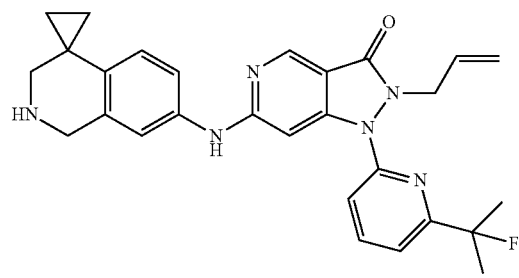 [SMILES: C=CCn1c(=O)c2cnc(Nc3ccc4c(c3)CNCC43CC3)cc2n1-c1cccc(C(C)(C)F)n1]
2.979
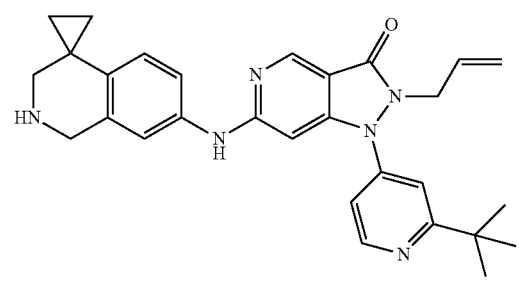
2.980
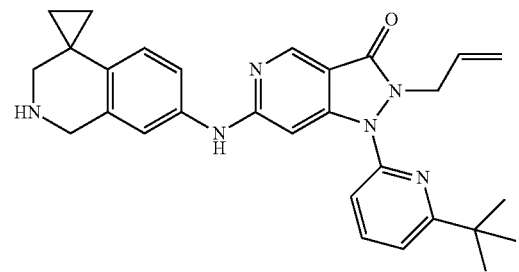 [SMILES: C=CCn1c(=O)c2cnc(Nc3ccc4c(c3)CNCC43CC3)cc2n1-c1cccc(C(C)(C)C)n1]
2.981
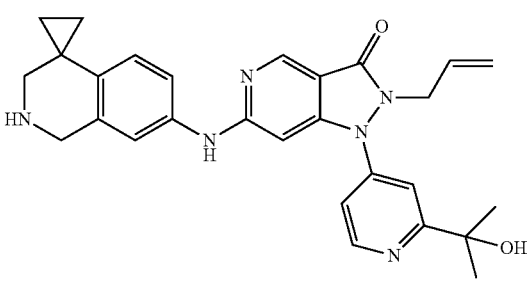 [SMILES: C=CCn1c(=O)c2cnc(Nc3ccc4c(c3)CNCC43CC3)cc2n1-c1ccnc(C(C)(C)O)c1]
2.982
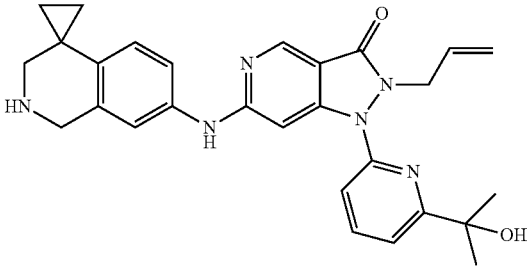 [SMILES: C=CCn1c(=O)c2cnc(Nc3ccc4c(c3)CNCC43CC3)cc2n1-c1cccc(C(C)(C)O)n1]
2.983

TABLE-1B-continued
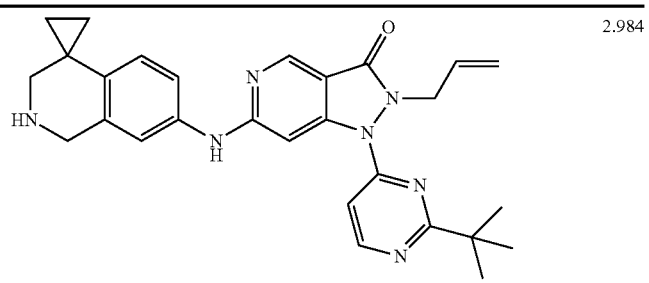
2.984
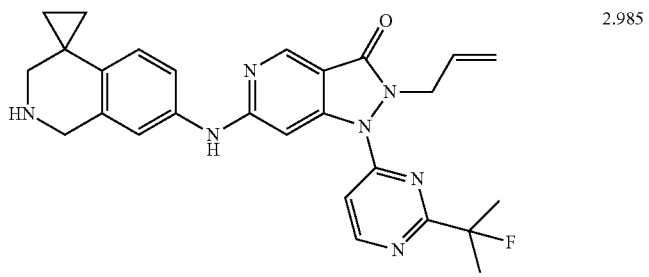
2.985
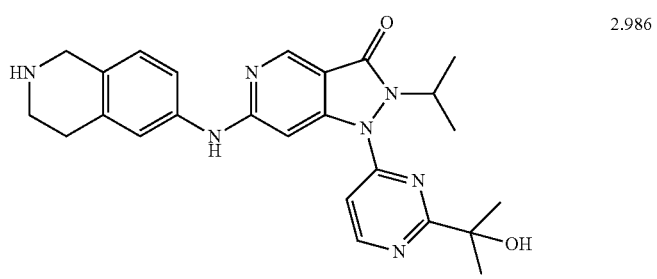
2.986
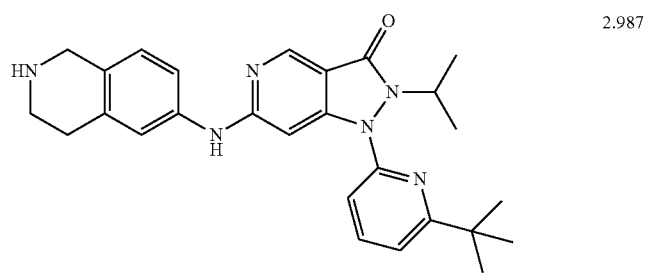
2.987
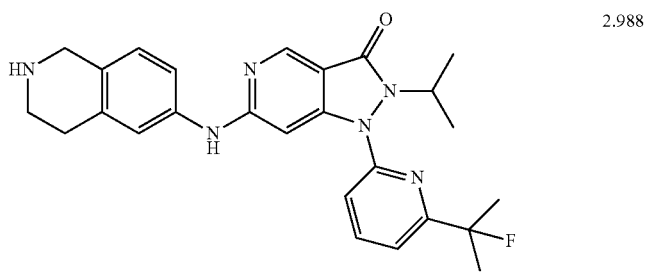
2.988
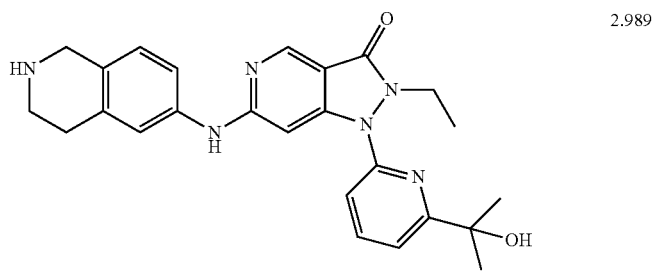
2.989

TABLE-1B-continued
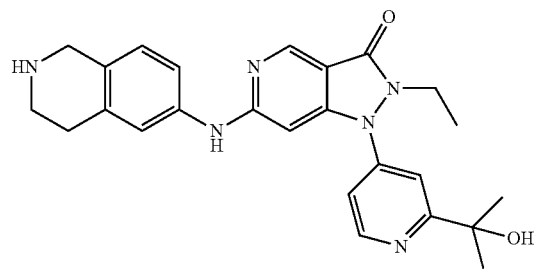 [SMILES: CCn1c(=O)c2cnc(Nc3ccc4c(c3)CCNC4)cc2n1-c1ccnc(C(C)(C)O)c1]
2.990
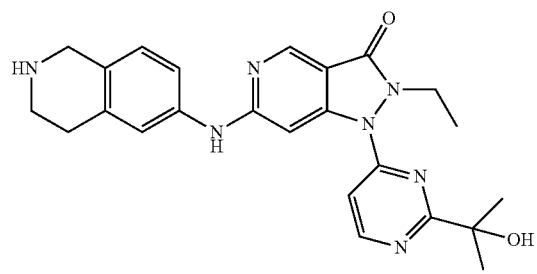 [SMILES: CCn1c(=O)c2cnc(Nc3ccc4c(c3)CCNC4)cc2n1-c1ccnc(C(C)(C)O)n1]
2.991
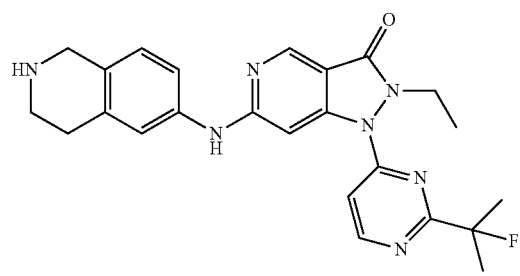
2.992
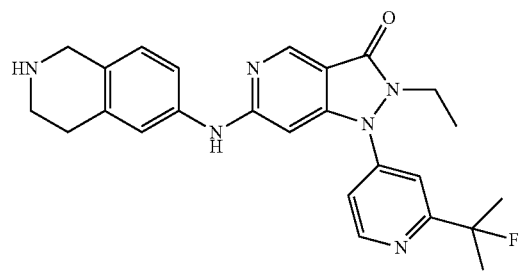 [SMILES: CCn1c(=O)c2cnc(Nc3ccc4c(c3)CCNC4)cc2n1-c1ccnc(C(C)(C)F)n1]
2.993
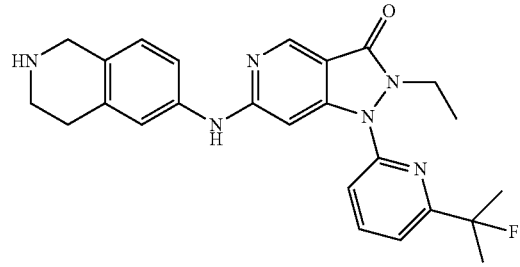 [SMILES: CCn1c(=O)c2cnc(Nc3ccc4c(c3)CCNC4)cc2n1-c1cccc(C(C)(C)F)n1]
2.994

TABLE-1B-continued
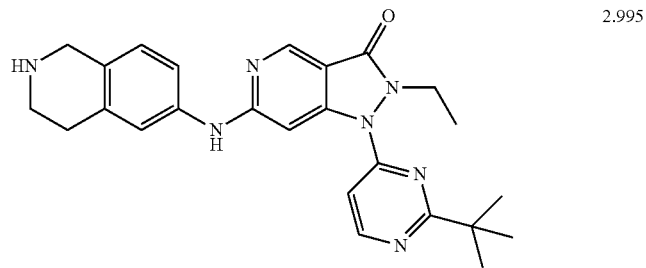
2.995
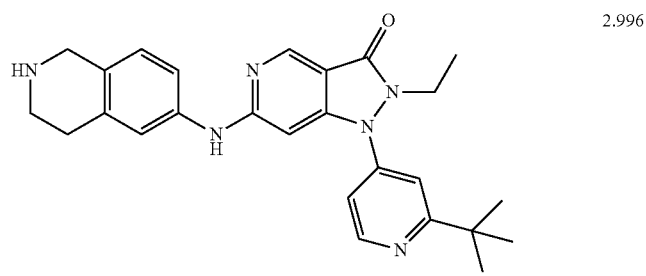
2.996
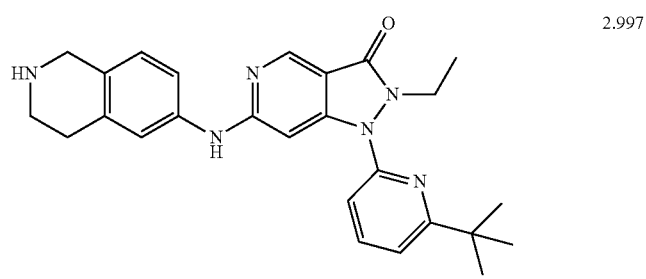
2.997
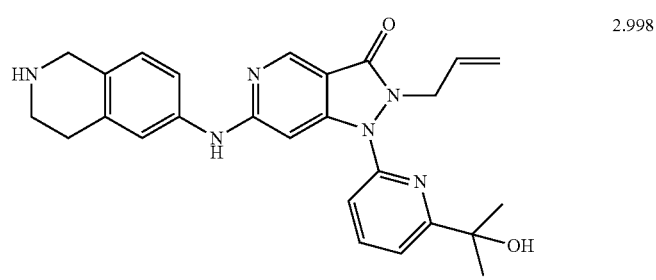
2.998
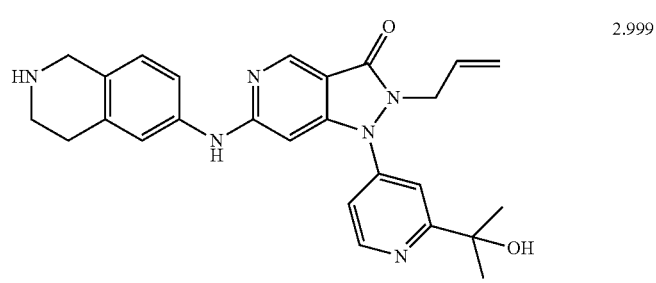
2.999
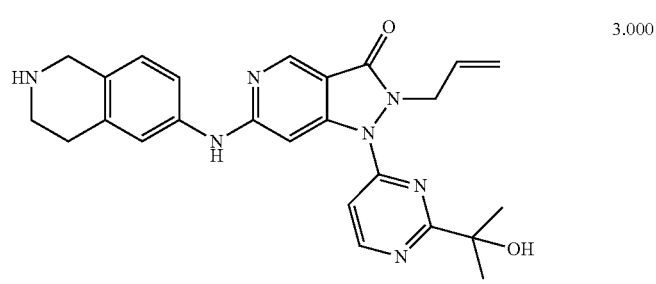
3.000

TABLE-1B-continued
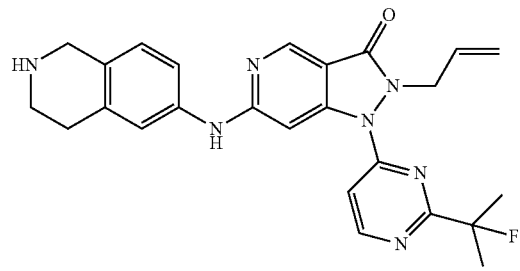 [SMILES: C=CCn1c(=O)c2cnc(Nc3ccc4c(c3)CCNC4)cc2n1-c1ccnc(C(C)(C)F)n1]
3.001
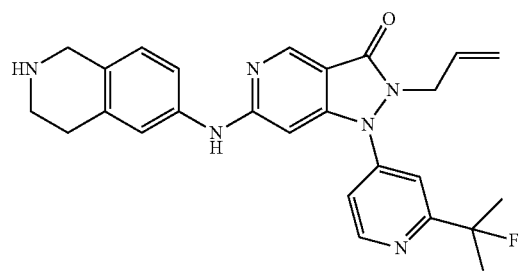 [SMILES: C=CCn1c(=O)c2cnc(Nc3ccc4c(c3)CCNC4)cc2n1-c1ccnc(C(C)(C)F)c1]
3.002
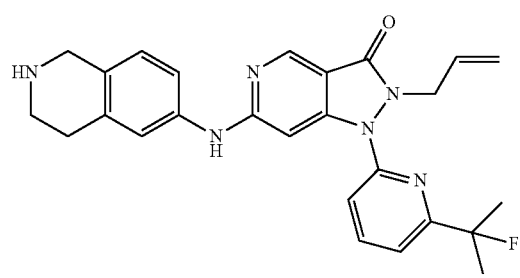
3.003
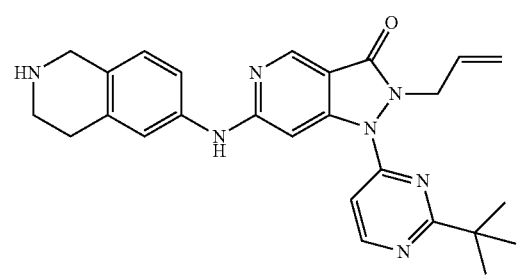 [SMILES: C=CCn1c(=O)c2cnc(Nc3ccc4c(c3)CCNC4)cc2n1-c1ccnc(C(C)(C)C)n1]
3.004
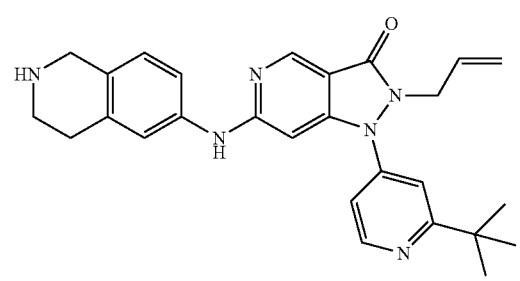
3.005

TABLE-1B-continued
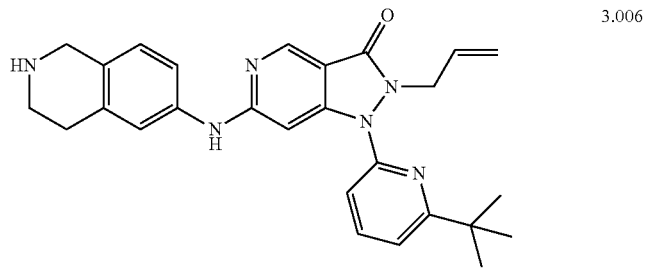 3.006
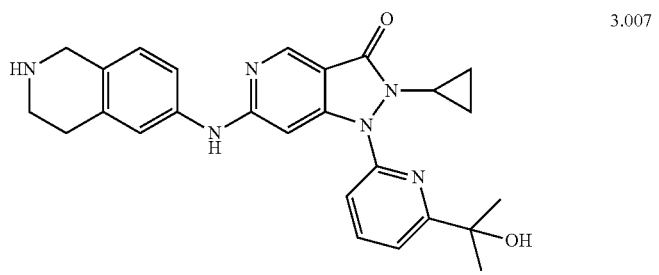 3.007
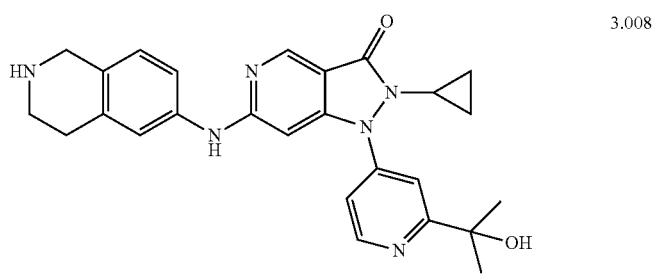 3.008
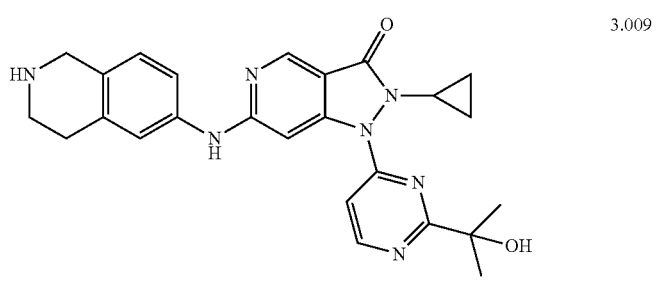 3.009
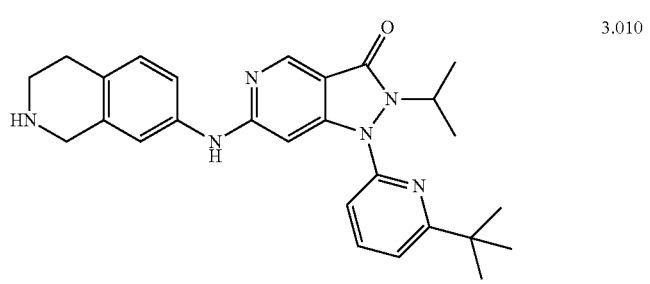 3.010
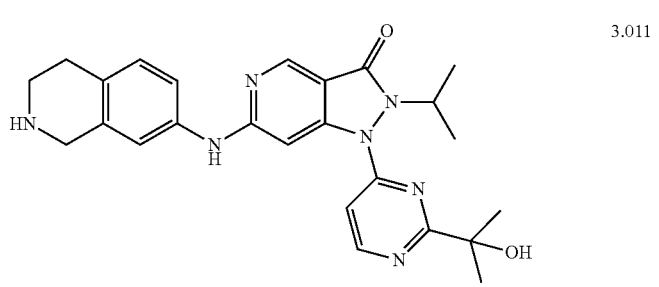 3.011

TABLE-1B-continued
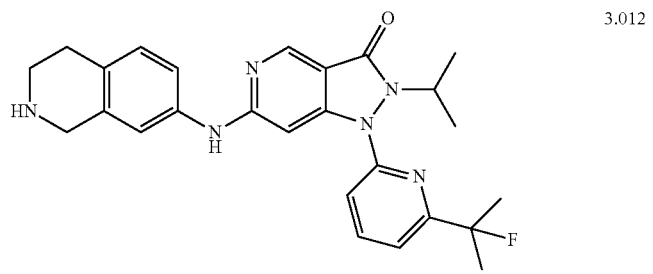
3.012
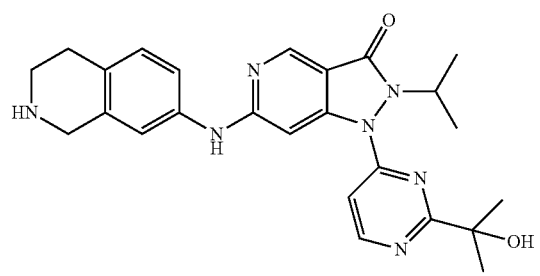 [SMILES: CC(C)n1c(=O)c2cnc(Nc3ccc4c(c3)CNCC4)cc2n1-c1ccnc(C(C)(C)O)n1]
3.013
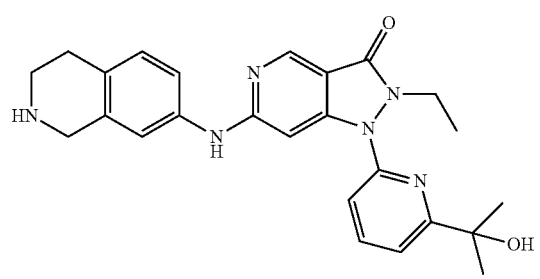 [SMILES: CCn1c(=O)c2cnc(Nc3ccc4c(c3)CNCC4)cc2n1-c1cccc(C(C)(C)O)n1]
3.014
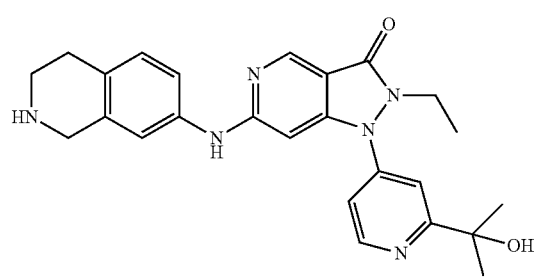 [SMILES: CCn1c(=O)c2cnc(Nc3ccc4c(c3)CNCC4)cc2n1-c1ccnc(C(C)(C)O)c1]
3.015
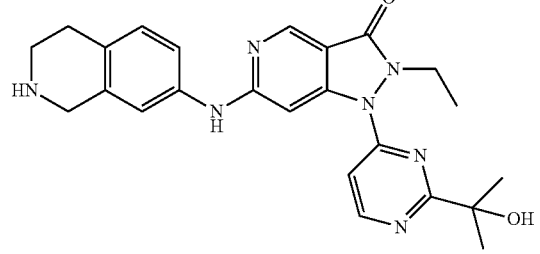
3.016

TABLE-1B-continued
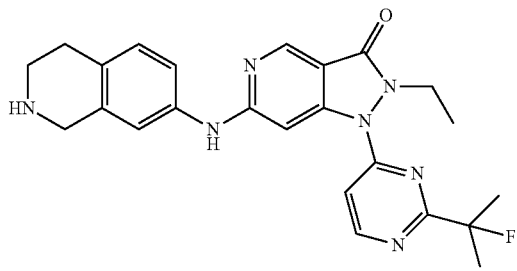 [SMILES: CCn1c(=O)c2cnc(Nc3ccc4c(c3)CNCC4)cc2n1-c1ccnc(C(C)(C)F)n1]
3.017
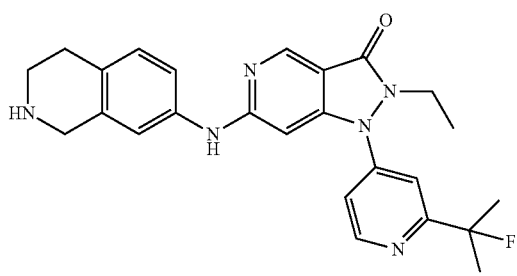 [SMILES: CCn1c(=O)c2cnc(Nc3ccc4c(c3)CNCC4)cc2n1-c1ccnc(C(C)(C)F)c1]
3.018
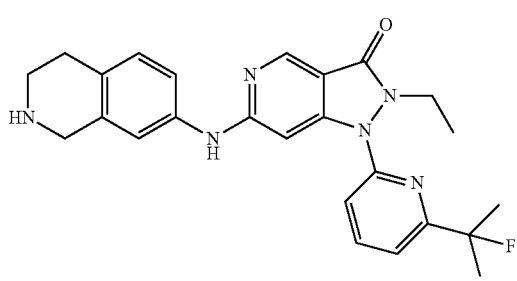 [SMILES: CCn1c(=O)c2cnc(Nc3ccc4c(c3)CNCC4)cc2n1-c1cccc(C(C)(C)F)n1]
3.019
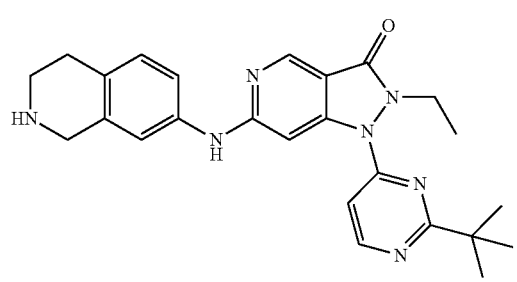 [SMILES: CCn1c(=O)c2cnc(Nc3ccc4c(c3)CNCC4)cc2n1-c1ccnc(C(C)(C)C)n1]
3.020
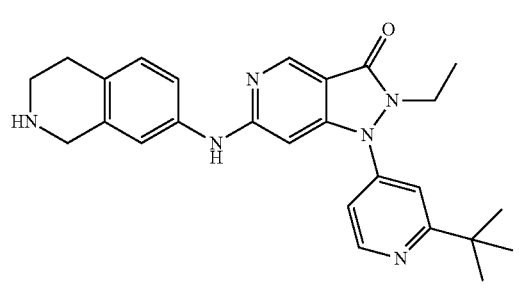 [SMILES: CCn1c(=O)c2cnc(Nc3ccc4c(c3)CNCC4)cc2n1-c1ccnc(C(C)(C)C)c1]
3.021
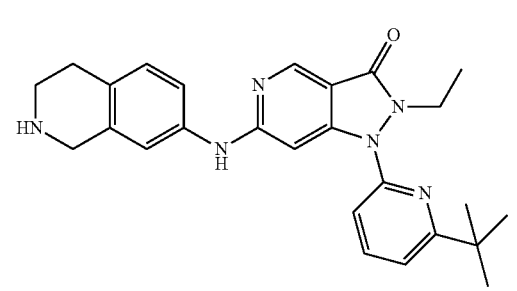 [SMILES: CCn1c(=O)c2cnc(Nc3ccc4c(c3)CNCC4)cc2n1-c1cccc(C(C)(C)C)n1]
3.022

TABLE-1B-continued
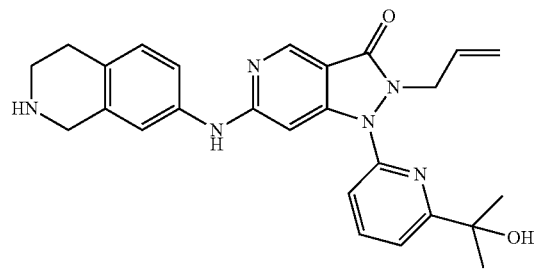 [SMILES: C=CCn1c(=O)c2cnc(Nc3ccc4c(c3)CNCC4)cc2n1-c1cccc(C(C)(C)O)n1]
3.023
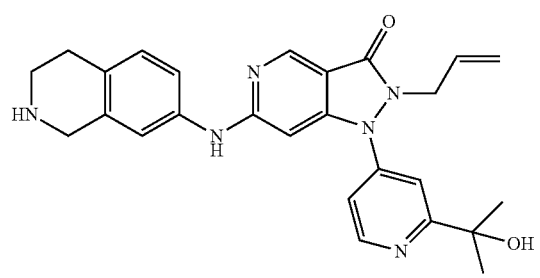 [SMILES: C=CCn1c(=O)c2cnc(Nc3ccc4c(c3)CNCC4)cc2n1-c1ccnc(C(C)(C)O)c1]
3.024
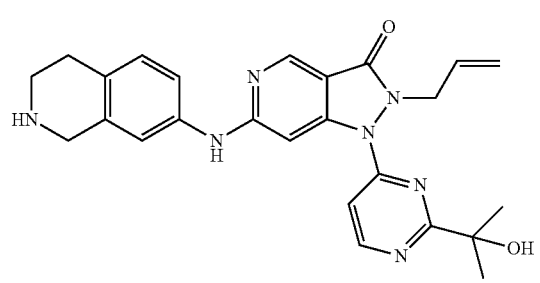 [SMILES: C=CCn1c(=O)c2cnc(Nc3ccc4c(c3)CNCC4)cc2n1-c1ccnc(C(C)(C)O)n1]
3.025
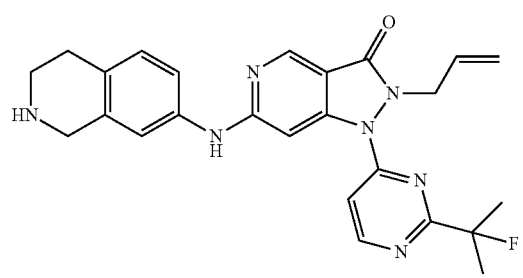 [SMILES: C=CCn1c(=O)c2cnc(Nc3ccc4c(c3)CNCC4)cc2n1-c1ccnc(C(C)(C)F)n1]
3.026
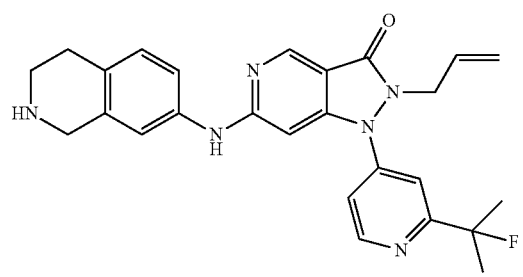 [SMILES: C=CCn1c(=O)c2cnc(Nc3ccc4c(c3)CNCC4)cc2n1-c1ccnc(C(C)(C)F)c1]
3.027

TABLE-1B-continued
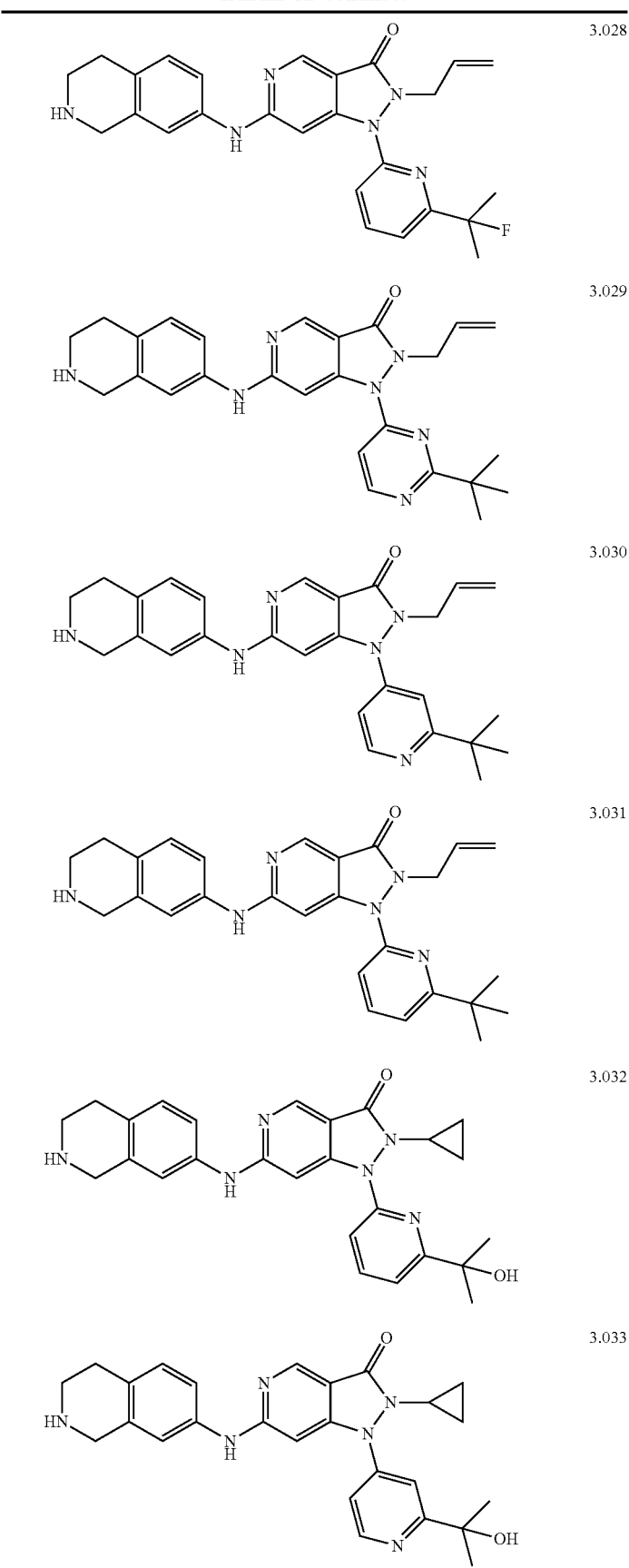

TABLE-1B-continued
| | |
|---|---|
| 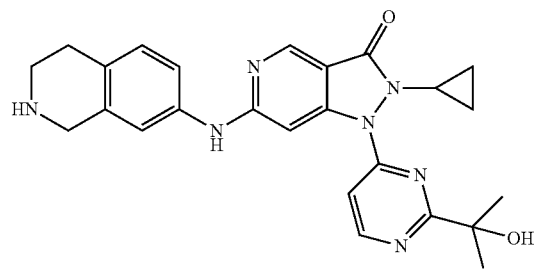 [SMILES: CC(C)(O)c1nccc(-n2c3cc(Nc4ccc5c(c4)CNCC5)ncc3c(=O)n2C2CC2)n1] | 3.034 |
| 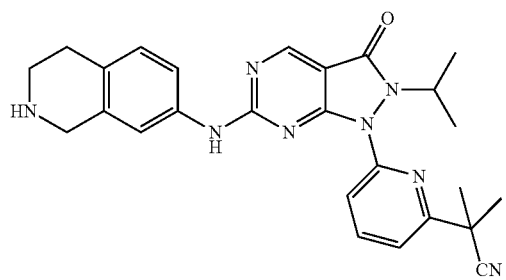 [SMILES: CC(C)n1c(=O)c2cnc(Nc3ccc4c(c3)CNCC4)nc2n1-c1cccc(C(C)(C)C#N)n1] | 3.035 |
| 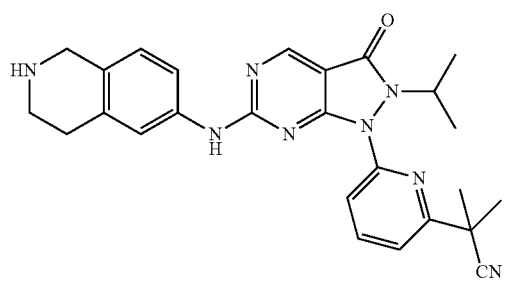 [SMILES: CC(C)n1c(=O)c2cnc(Nc3ccc4c(c3)CCNC4)nc2n1-c1cccc(C(C)(C)C#N)n1] | 3.036 |
| 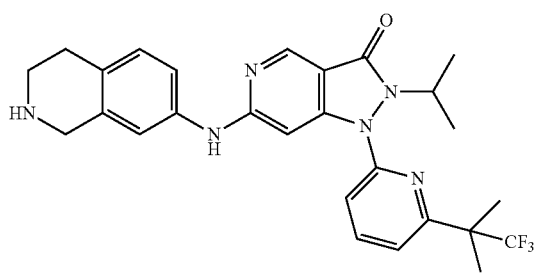 [SMILES: CC(C)n1c(=O)c2cnc(Nc3ccc4c(c3)CNCC4)cc2n1-c1cccc(C(C)(C)C(F)(F)F)n1] | 3.037 |
| 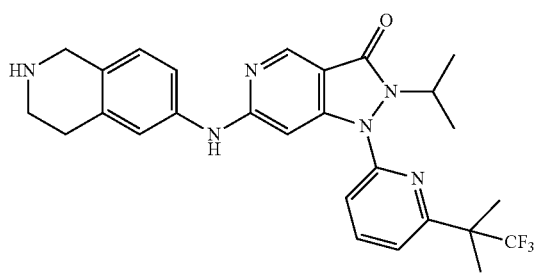 [SMILES: CC(C)n1c(=O)c2cnc(Nc3ccc4c(c3)CCNC4)cc2n1-c1cccc(C(C)(C)C(F)(F)F)n1] | 3.038 |

| | |
|---|---|
| 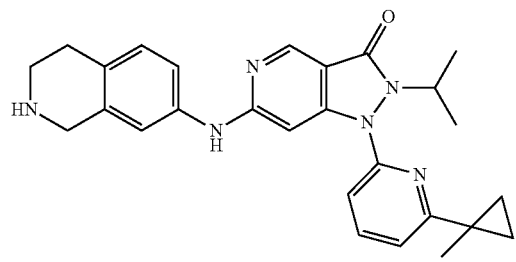 [SMILES: CC(C)n1c(=O)c2cnc(Nc3ccc4c(c3)CNCC4)cc2n1-c1cccc(C2(C)CC2)n1] | 3.039 |
| 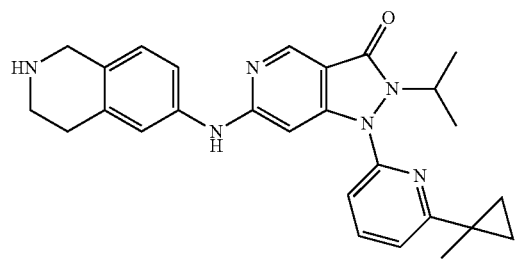 [SMILES: CC(C)n1c(=O)c2cnc(Nc3ccc4c(c3)CCNC4)cc2n1-c1cccc(C2(C)CC2)n1] | 3.040 |
| 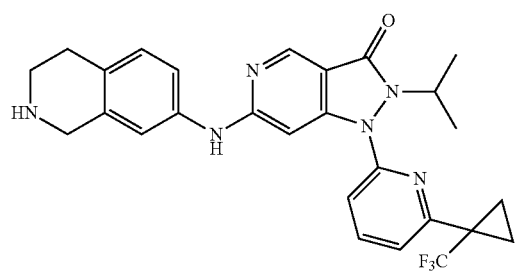 [SMILES: CC(C)n1c(=O)c2cnc(Nc3ccc4c(c3)CNCC4)cc2n1-c1cccc(C2(C(F)(F)F)CC2)n1] | 3.041 |
| 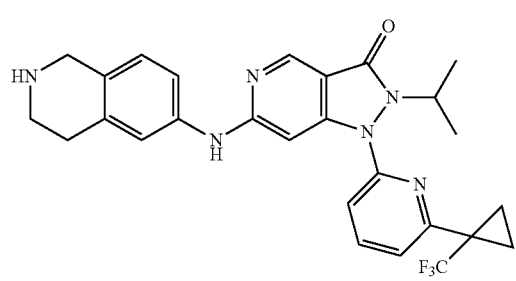 [SMILES: CC(C)n1c(=O)c2cnc(Nc3ccc4c(c3)CCNC4)cc2n1-c1cccc(C2(C(F)(F)F)CC2)n1] | 3.042 |
| 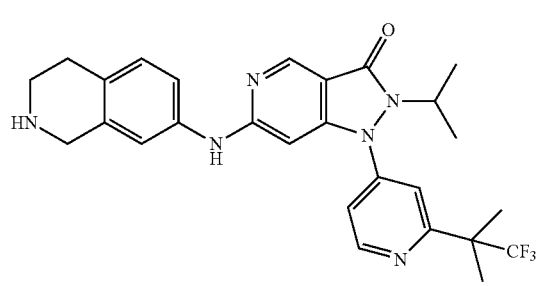 [SMILES: CC(C)n1c(=O)c2cnc(Nc3ccc4c(c3)CNCC4)cc2n1-c1ccnc(C(C)(C)C(F)(F)F)c1] | 3.043 |
| 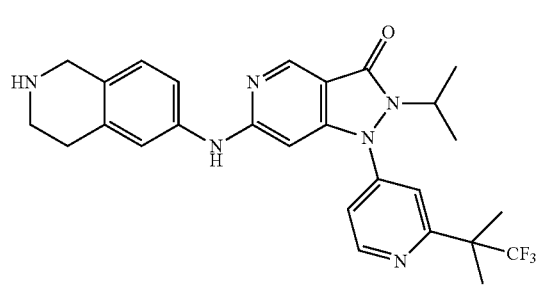 [SMILES: CC(C)n1c(=O)c2cnc(Nc3ccc4c(c3)CCNC4)cc2n1-c1ccnc(C(C)(C)C(F)(F)F)c1] | 3.044 |

TABLE-1B-continued
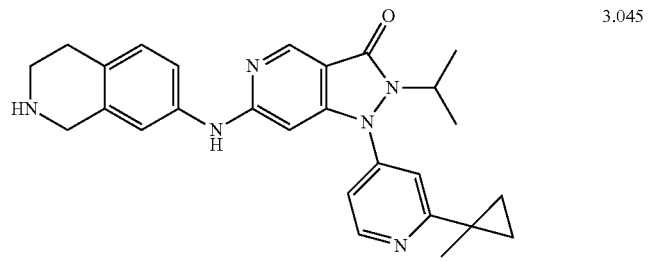 3.045
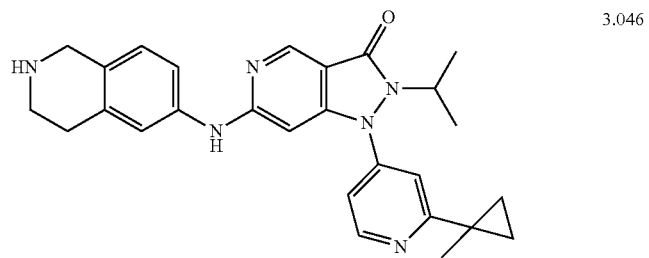 3.046
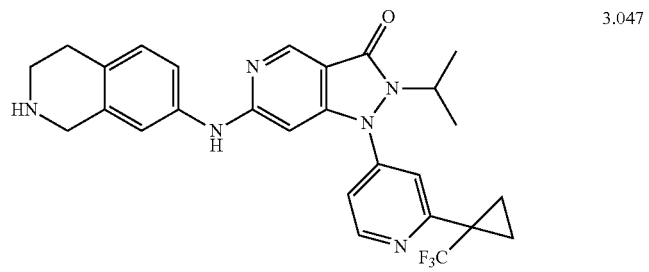 3.047
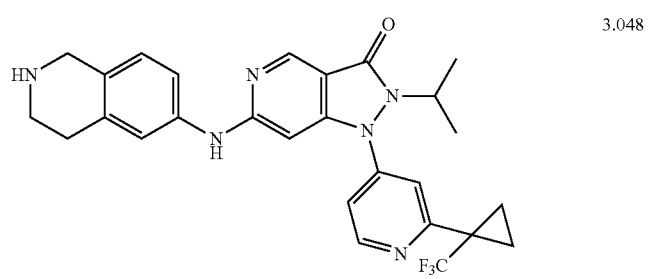 3.048
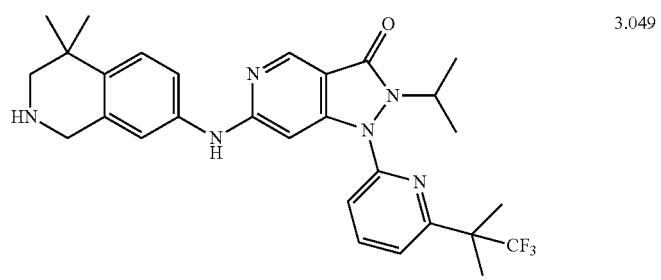 3.049
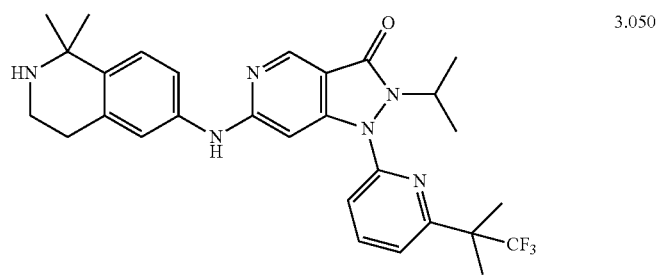 3.050

TABLE-1B-continued
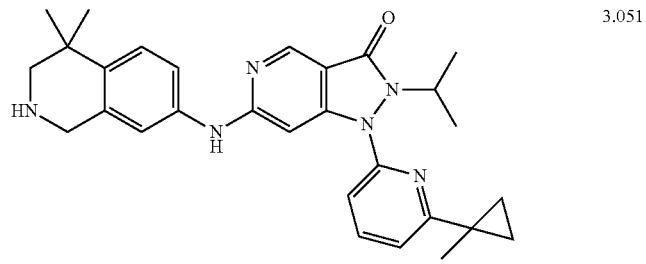
3.051
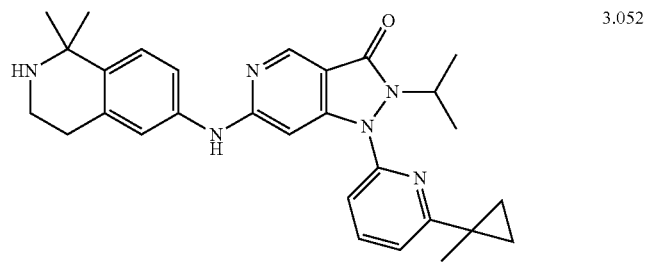
3.052
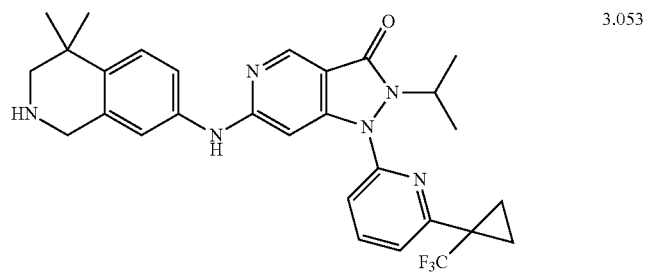
3.053
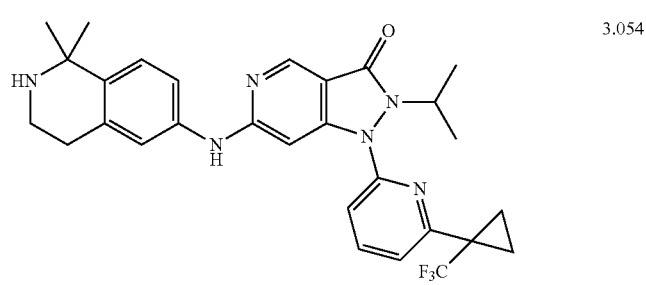
3.054
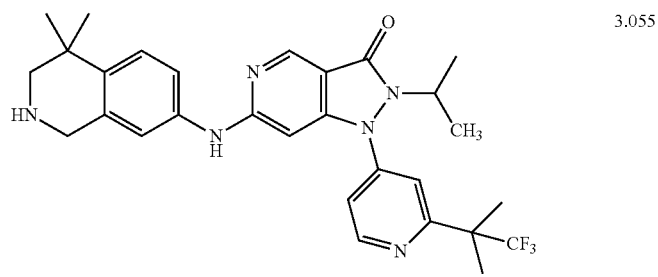
3.055
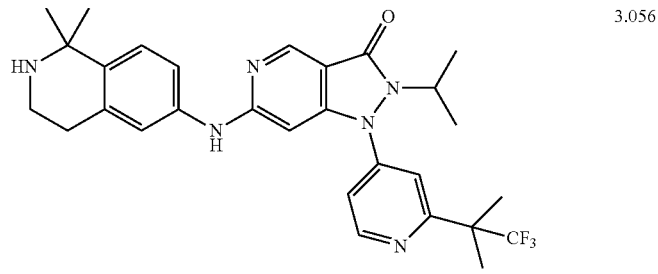
3.056

TABLE-1B-continued
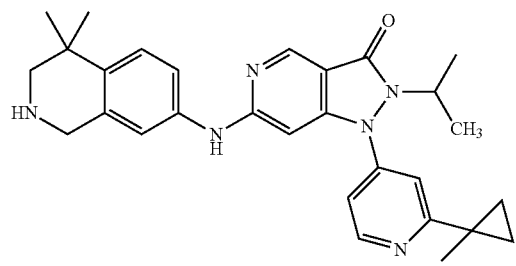 [SMILES: CC(C)n1c(=O)c2cnc(Nc3ccc4c(c3)CNCC4(C)C)cc2n1-c1ccnc(C2(C)CC2)c1]
3.057
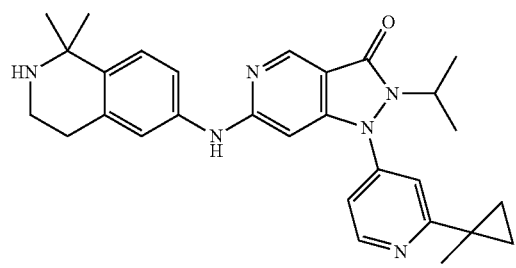 [SMILES: CC(C)n1c(=O)c2cnc(Nc3ccc4c(c3)CCNC4(C)C)cc2n1-c1ccnc(C2(C)CC2)c1]
3.058
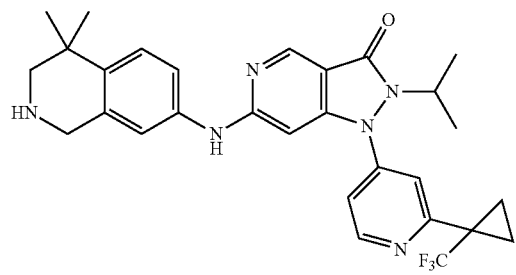 [SMILES: CC(C)n1c(=O)c2cnc(Nc3ccc4c(c3)CNCC4(C)C)cc2n1-c1ccnc(C2(C(F)(F)F)CC2)c1]
3.059
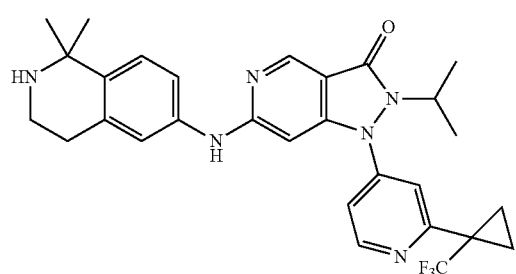
3.060
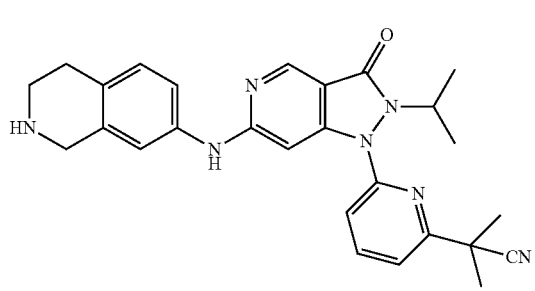 [SMILES: CC(C)n1c(=O)c2cnc(Nc3ccc4c(c3)CNCC4)cc2n1-c1cccc(C(C)(C)C#N)n1]
3.061

TABLE-1B-continued
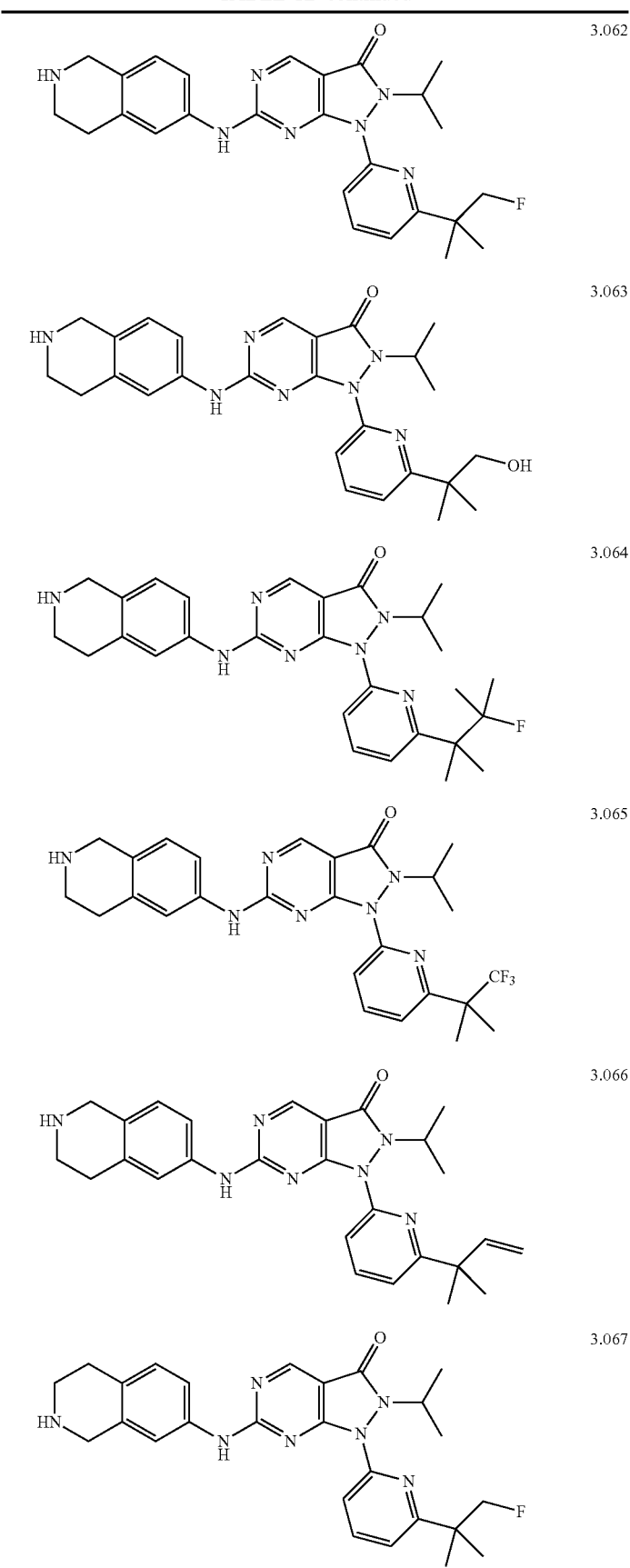
3.062
3.063
3.064
3.065
3.066
3.067

TABLE-1B-continued
| | |
|---|---|
| 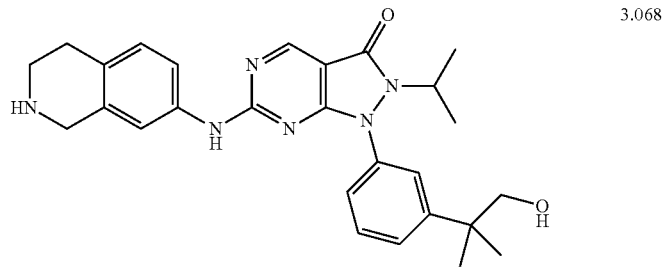 | 3.068 |
| 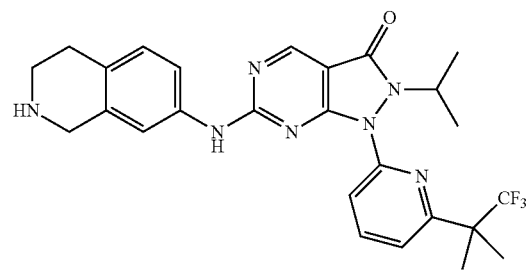 [SMILES: CC(C)n1c(=O)c2cnc(Nc3ccc4c(c3)CNCC4)nc2n1-c1cccc(C(C)(C)C(F)(F)F)n1] | 3.069 |
| 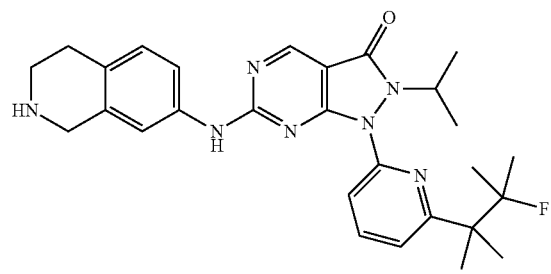 [SMILES: CC(C)n1c(=O)c2cnc(Nc3ccc4c(c3)CNCC4)nc2n1-c1cccc(C(C)(C)C(C)(C)F)n1] | 3.070 |
| 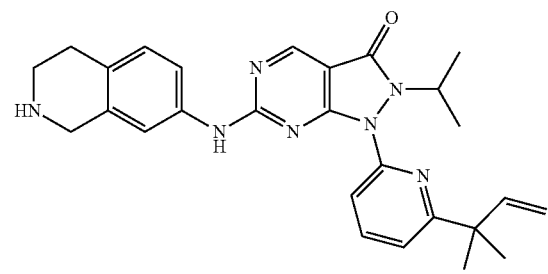 [SMILES: C=CC(C)(C)c1cccc(-n2c3nc(Nc4ccc5c(c4)CNCC5)ncc3c(=O)n2C(C)C)n1] | 3.071 |
| 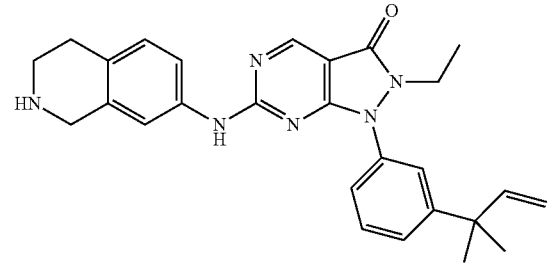 [SMILES: C=CC(C)(C)c1cccc(-n2c3nc(Nc4ccc5c(c4)CNCC5)ncc3c(=O)n2CC)c1] | 3.072 |

TABLE-1B-continued
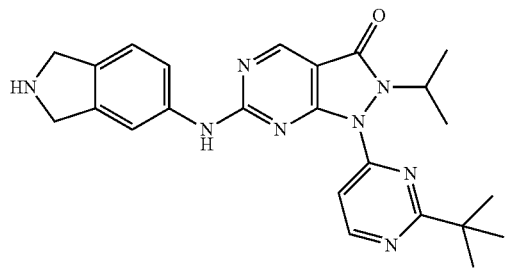 [SMILES: CC(C)n1c(=O)c2cnc(Nc3ccc4c(c3)CNC4)nc2n1-c1ccnc(C(C)(C)C)n1]
3.073
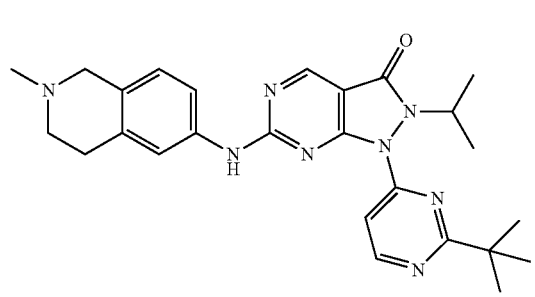 [SMILES: CC(C)n1c(=O)c2cnc(Nc3ccc4c(c3)CCN(C)C4)nc2n1-c1ccnc(C(C)(C)C)n1]
3.074
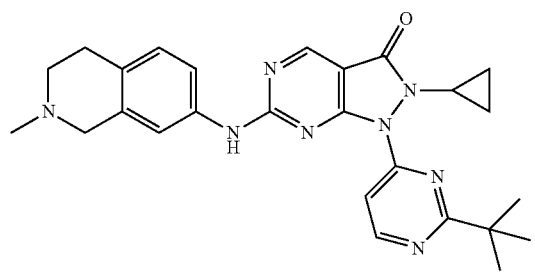 [SMILES: CN1CCc2ccc(Nc3ncc4c(=O)n(C5CC5)n(-c5ccnc(C(C)(C)C)n5)c4n3)cc2C1]
3.075
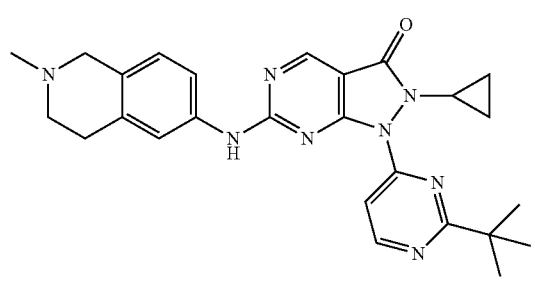 [SMILES: CN1CCc2cc(Nc3ncc4c(=O)n(C5CC5)n(-c5ccnc(C(C)(C)C)n5)c4n3)ccc2C1]
3.076
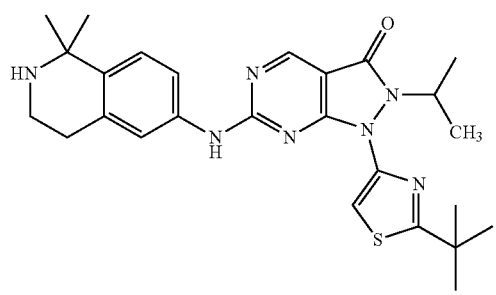 [SMILES: CC(C)n1c(=O)c2cnc(Nc3ccc4c(c3)CCNC4(C)C)nc2n1-c1csc(C(C)(C)C)n1]
3.077

TABLE-1B-continued
| | |
|---|---|
| 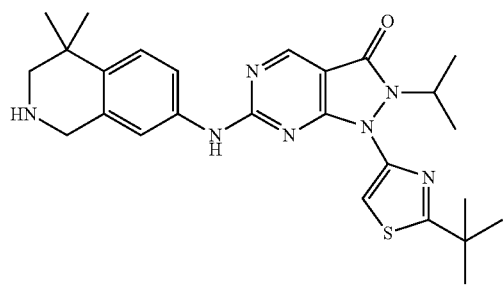 [SMILES: CC(C)n1c(=O)c2cnc(Nc3ccc4c(c3)CNCC4(C)C)nc2n1-c1csc(C(C)(C)C)n1] | 3.078 |
| 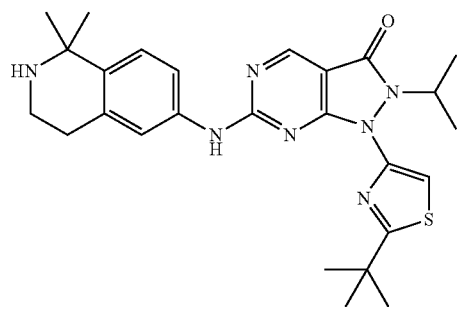 [SMILES: CC(C)n1c(=O)c2cnc(Nc3ccc4c(c3)CCNC4(C)C)nc2n1-c1csc(C(C)(C)C)n1] | 3.079 |
| 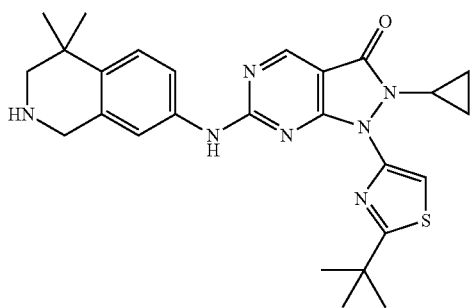 [SMILES: CC(C)(C)c1nc(-n2c3nc(Nc4ccc5c(c4)CNCC5(C)C)ncc3c(=O)n2C2CC2)cs1] | 3.080 |
| 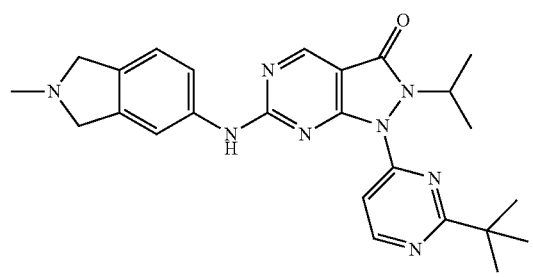 [SMILES: CC(C)n1c(=O)c2cnc(Nc3ccc4c(c3)CN(C)C4)nc2n1-c1ccnc(C(C)(C)C)n1] | 3.081 |
| 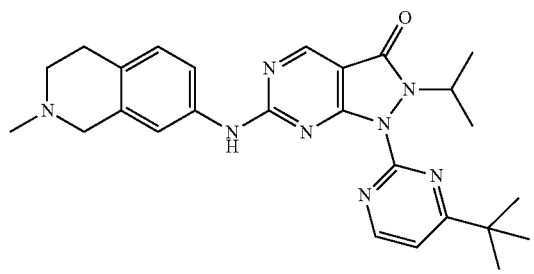 [SMILES: CC(C)n1c(=O)c2cnc(Nc3ccc4c(c3)CN(C)CC4)nc2n1-c1nccc(C(C)(C)C)n1] | 3.082 |

TABLE-1B-continued
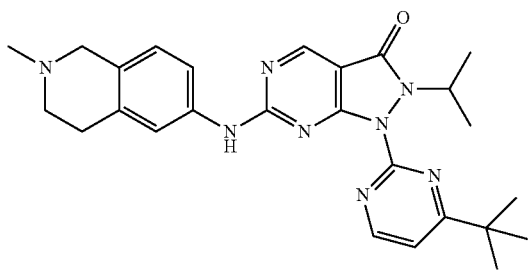 [SMILES: CC(C)n1c(=O)c2cnc(Nc3ccc4c(c3)CCN(C)C4)nc2n1-c1nccc(C(C)(C)C)n1]
3.083
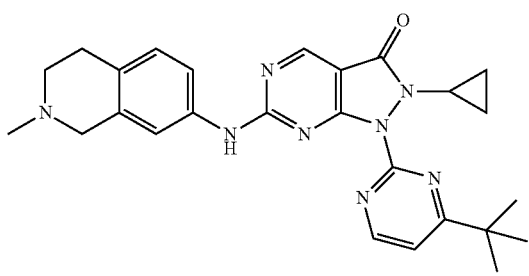 [SMILES: CN1CCc2ccc(Nc3ncc4c(=O)n(C5CC5)n(-c5nccc(C(C)(C)C)n5)c4n3)cc2C1]
3.084
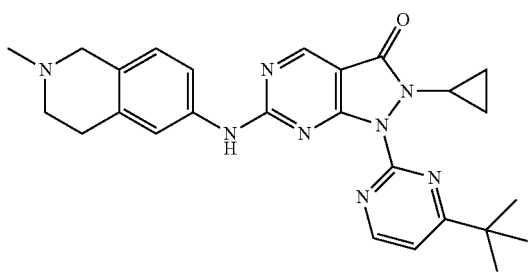 [SMILES: CN1CCc2cc(Nc3ncc4c(=O)n(C5CC5)n(-c5nccc(C(C)(C)C)n5)c4n3)ccc2C1]
3.085
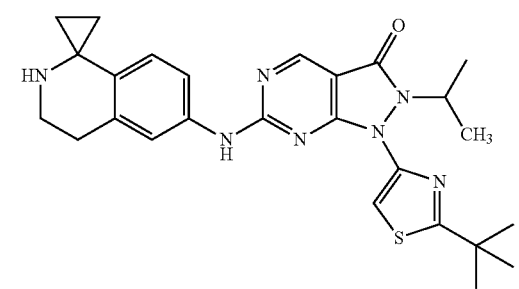 [SMILES: CC(C)n1c(=O)c2cnc(Nc3ccc4c(c3)CCNC43CC3)nc2n1-c1csc(C(C)(C)C)n1]
3.086
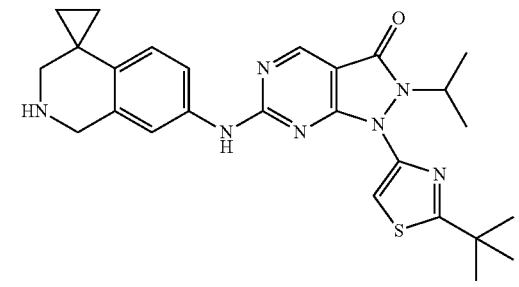 [SMILES: CC(C)n1c(=O)c2cnc(Nc3ccc4c(c3)CNCC43CC3)nc2n1-c1csc(C(C)(C)C)n1]
3.087

TABLE-1B-continued
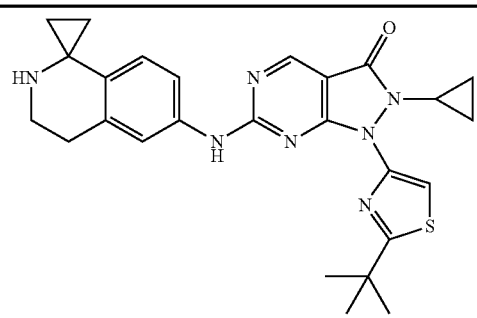
3.088
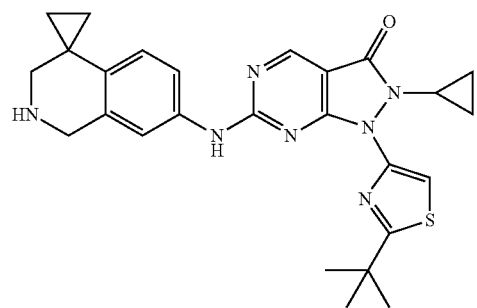 [SMILES: CC(C)(C)c1nc(-n2c3nc(Nc4ccc5c(c4)CNCC54CC4)ncc3c(=O)n2C2CC2)cs1]
3.089
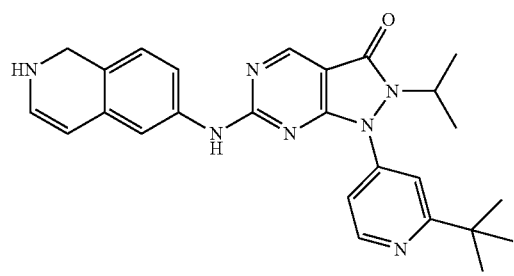 [SMILES: CC(C)n1c(=O)c2cnc(Nc3ccc4c(c3)C=CNC4)nc2n1-c1ccnc(C(C)(C)C)c1]
3.090
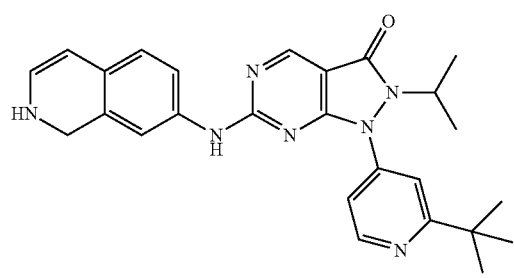 [SMILES: CC(C)n1c(=O)c2cnc(Nc3ccc4c(c3)CNC=C4)nc2n1-c1ccnc(C(C)(C)C)c1]
3.091
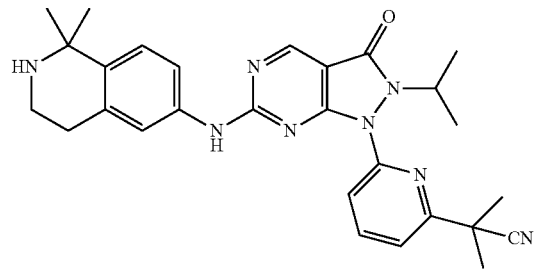 [SMILES: CC(C)n1c(=O)c2cnc(Nc3ccc4c(c3)CCNC4(C)C)nc2n1-c1cccc(C(C)(C)C#N)n1]
3.092

TABLE-1B-continued
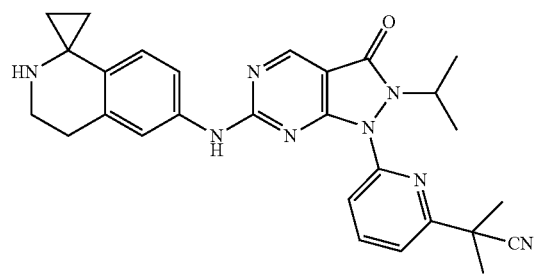
3.093
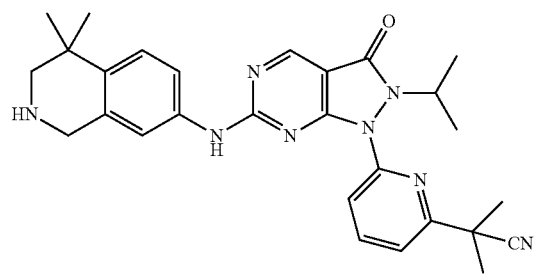 [SMILES: CC(C)n1c(=O)c2cnc(Nc3ccc4c(c3)CNCC4(C)C)nc2n1-c1cccc(C(C)(C)C#N)n1]
3.094
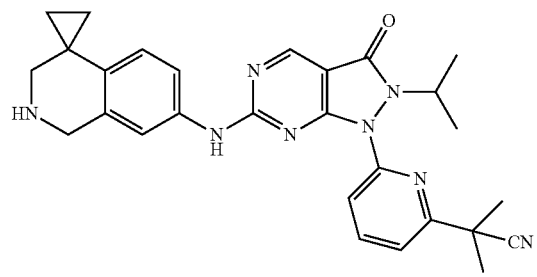 [SMILES: CC(C)n1c(=O)c2cnc(Nc3ccc4c(c3)CNCC43CC3)nc2n1-c1cccc(C(C)(C)C#N)n1]
3.095
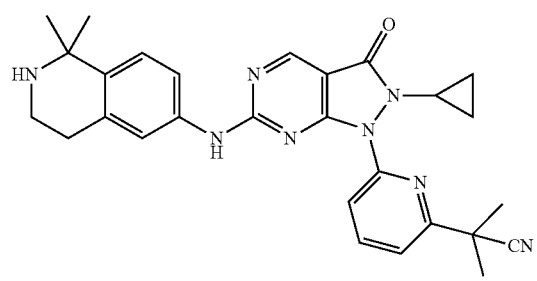 [SMILES: CC(C)(C#N)c1cccc(-n2c3nc(Nc4ccc5c(c4)CCNC5(C)C)ncc3c(=O)n2C2CC2)n1]
3.096
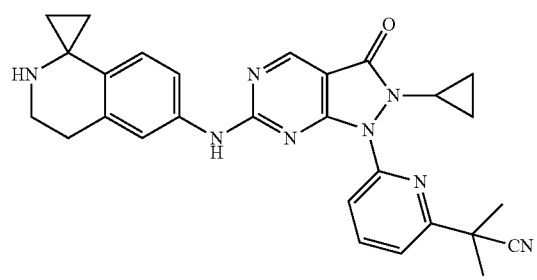 [SMILES: CC(C)(C#N)c1cccc(-n2c3nc(Nc4ccc5c(c4)CCNC54CC4)ncc3c(=O)n2C2CC2)n1]
3.097

TABLE-1B-continued
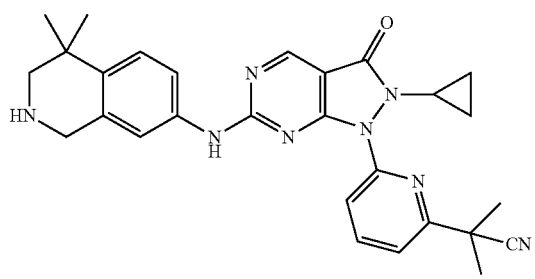 [SMILES: CC(C)(C#N)c1cccc(-n2c3nc(Nc4ccc5c(c4)CNCC5(C)C)ncc3c(=O)n2C2CC2)n1]
3.098
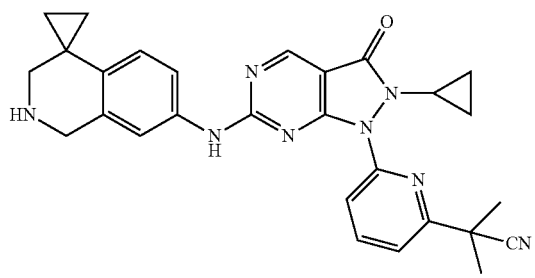 [SMILES: CC(C)(C#N)c1cccc(-n2c3nc(Nc4ccc5c(c4)CNCC54CC4)ncc3c(=O)n2C2CC2)n1]
3.099
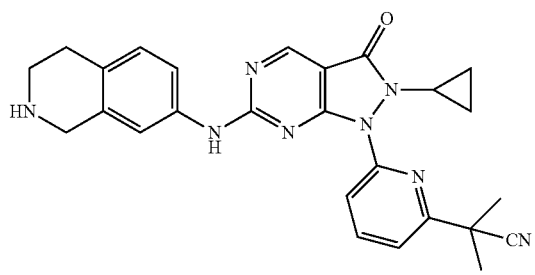 [SMILES: CC(C)(C#N)c1cccc(-n2c3nc(Nc4ccc5c(c4)CNCC5)ncc3c(=O)n2C2CC2)n1]
3.100
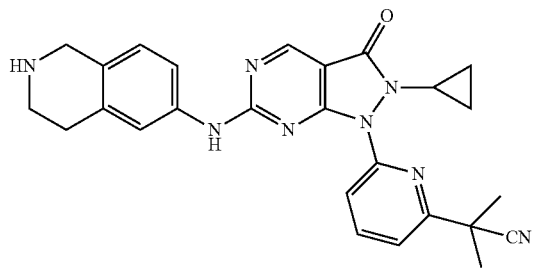 [SMILES: CC(C)(C#N)c1cccc(-n2c3nc(Nc4ccc5c(c4)CCNC5)ncc3c(=O)n2C2CC2)n1]
3.101
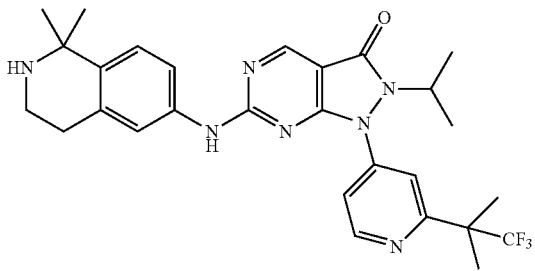 [SMILES: CC(C)n1c(=O)c2cnc(Nc3ccc4c(c3)CCNC4(C)C)nc2n1-c1ccnc(C(C)(C)C(F)(F)F)c1]
3.102

TABLE-1B-continued
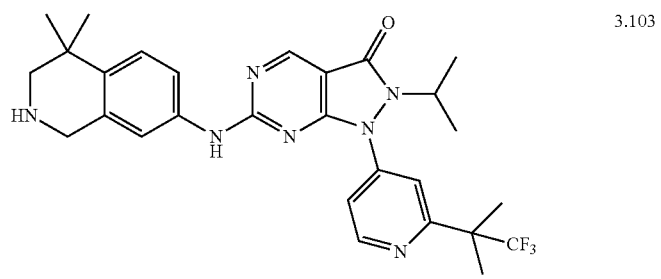 3.103
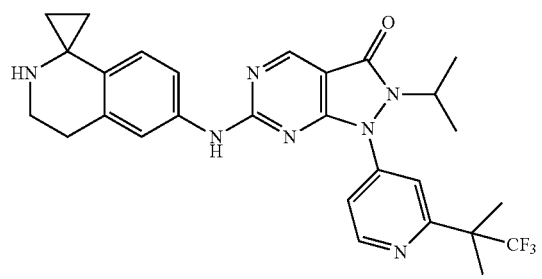 [SMILES: CC(C)n1c(=O)c2cnc(Nc3ccc4c(c3)CCNC43CC3)nc2n1-c1ccnc(C(C)(C)C(F)(F)F)c1] 3.104
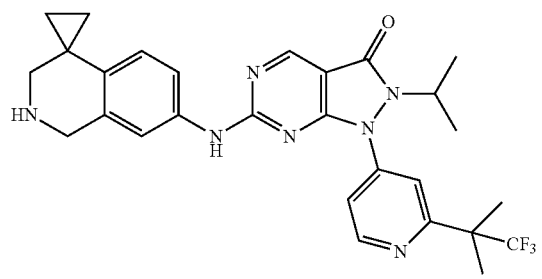 [SMILES: CC(C)n1c(=O)c2cnc(Nc3ccc4c(c3)CNCC43CC3)nc2n1-c1ccnc(C(C)(C)C(F)(F)F)c1] 3.105
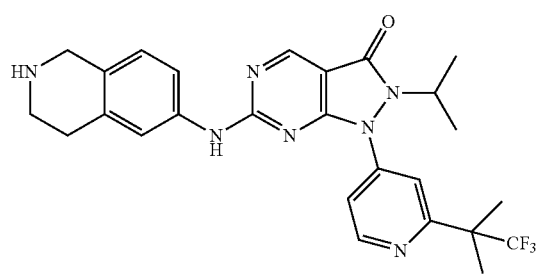 [SMILES: CC(C)n1c(=O)c2cnc(Nc3ccc4c(c3)CCNC4)nc2n1-c1ccnc(C(C)(C)C(F)(F)F)c1] 3.106
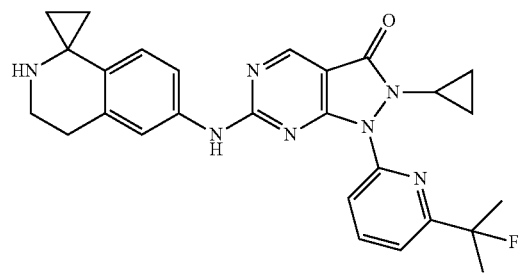 [SMILES: CC(C)(F)c1cccc(-n2c3nc(Nc4ccc5c(c4)CCNC54CC4)ncc3c(=O)n2C2CC2)n1] 3.107

TABLE-1B-continued
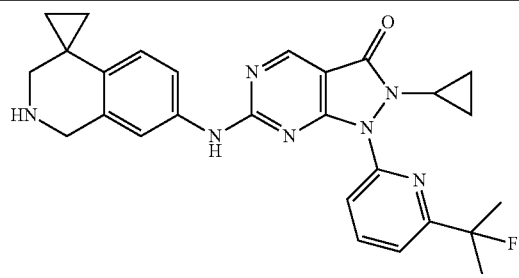
3.108
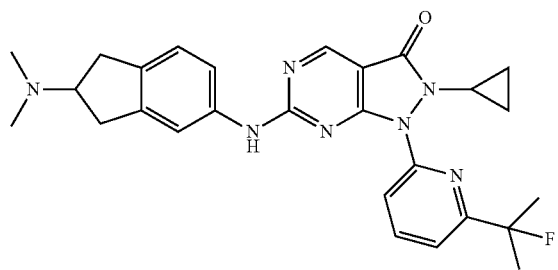 [SMILES: CN(C)C1Cc2ccc(Nc3ncc4c(=O)n(C5CC5)n(-c5cccc(C(C)(C)F)n5)c4n3)cc2C1]
3.109
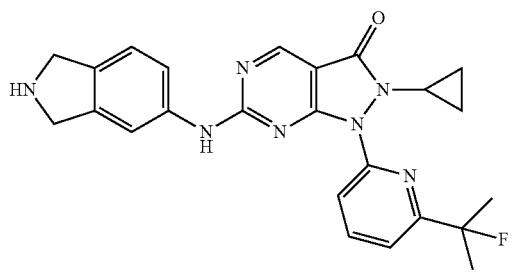 [SMILES: CC(C)(F)c1cccc(-n2c3nc(Nc4ccc5c(c4)CNC5)ncc3c(=O)n2C2CC2)n1]
3.110
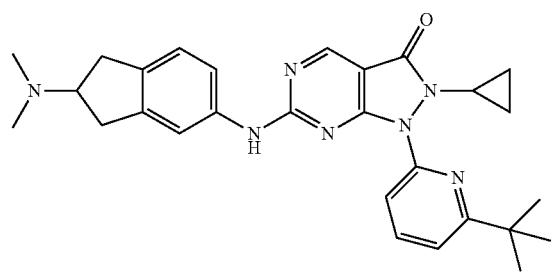 [SMILES: CN(C)C1Cc2ccc(Nc3ncc4c(=O)n(C5CC5)n(-c5cccc(C(C)(C)C)n5)c4n3)cc2C1]
3.111
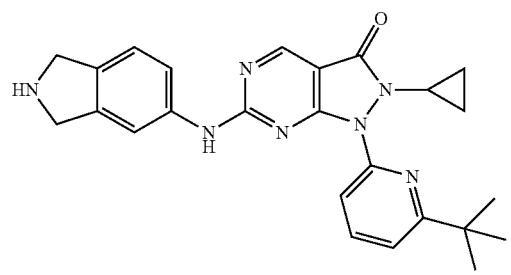 [SMILES: CC(C)(C)c1cccc(-n2c3nc(Nc4ccc5c(c4)CNC5)ncc3c(=O)n2C2CC2)n1]
3.112
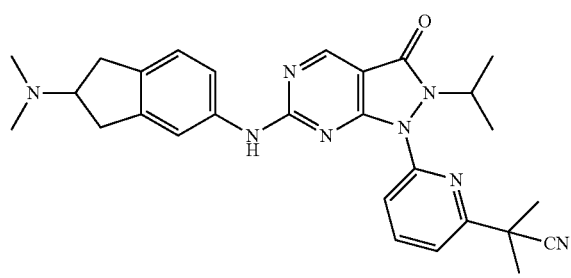 [SMILES: CC(C)n1c(=O)c2cnc(Nc3ccc4c(c3)CC(N(C)C)C4)nc2n1-c1cccc(C(C)(C)C#N)n1]
3.113

TABLE-1B-continued
| | |
|---|---|
| 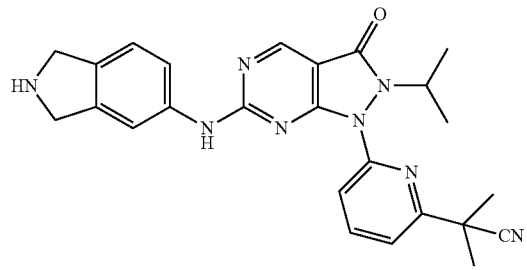 [SMILES: CC(C)n1c(=O)c2cnc(Nc3ccc4c(c3)CNC4)nc2n1-c1cccc(C(C)(C)C#N)n1] | 3.114 |
| 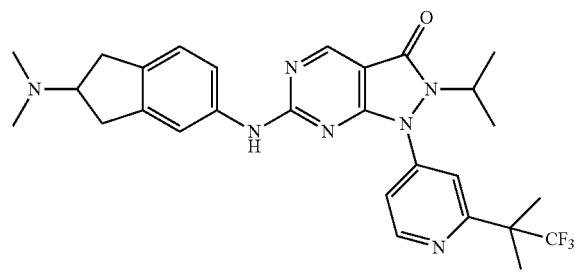 [SMILES: CC(C)n1c(=O)c2cnc(Nc3ccc4c(c3)CC(N(C)C)C4)nc2n1-c1ccnc(C(C)(C)C(F)(F)F)c1] | 3.115 |
| 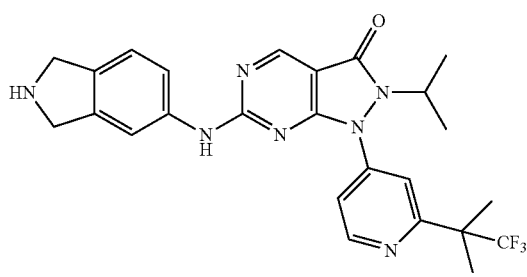 [SMILES: CC(C)n1c(=O)c2cnc(Nc3ccc4c(c3)CNC4)nc2n1-c1ccnc(C(C)(C)C(F)(F)F)c1] | 3.116 |
| 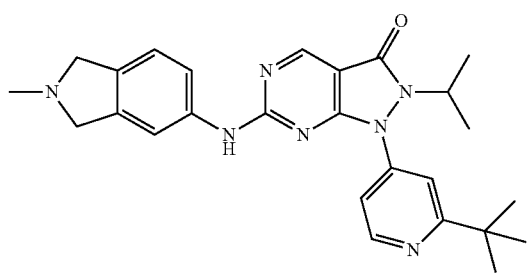 [SMILES: CC(C)n1c(=O)c2cnc(Nc3ccc4c(c3)CN(C)C4)nc2n1-c1ccnc(C(C)(C)C)c1] | 3.117 |
| 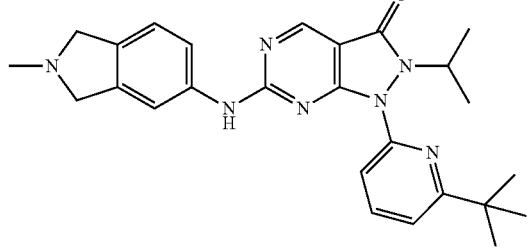 | 3.118 |

TABLE-1B-continued
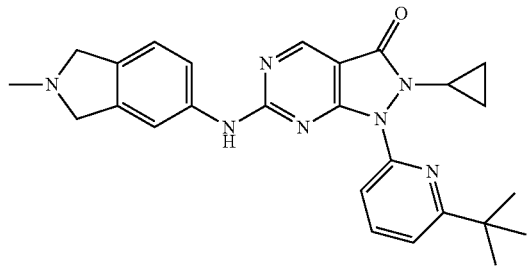 [SMILES: CN1Cc2ccc(Nc3ncc4c(=O)n(C5CC5)n(-c5cccc(C(C)(C)C)n5)c4n3)cc2C1]
3.119
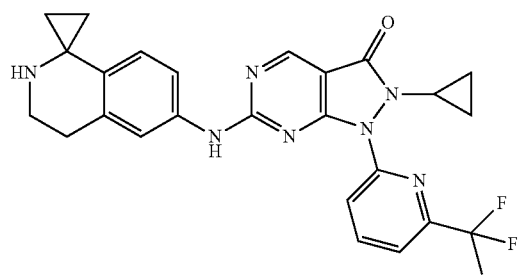 [SMILES: CC(F)(F)c1cccc(-n2c3nc(Nc4ccc5c(c4)CCNC54CC4)ncc3c(=O)n2C2CC2)n1]
3.120
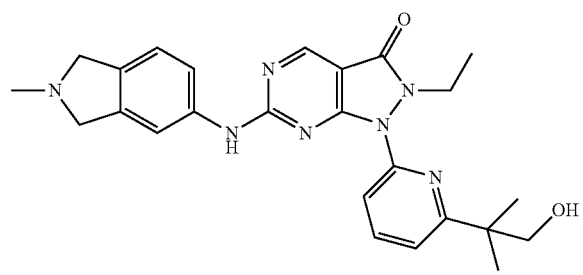 [SMILES: CCn1c(=O)c2cnc(Nc3ccc4c(c3)CN(C)C4)nc2n1-c1cccc(C(C)(C)CO)n1]
3.121
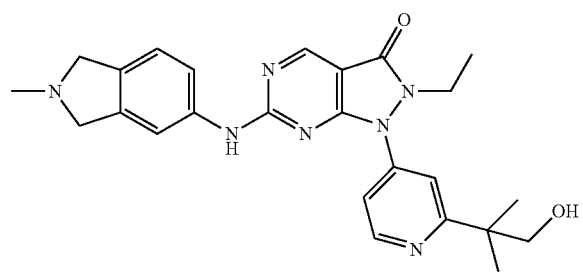 [SMILES: CCn1c(=O)c2cnc(Nc3ccc4c(c3)CN(C)C4)nc2n1-c1ccnc(C(C)(C)CO)c1]
3.122
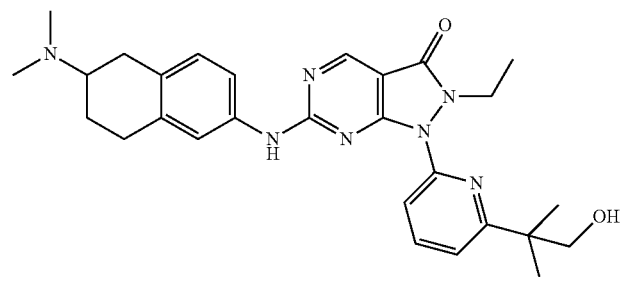 [SMILES: CCn1c(=O)c2cnc(Nc3ccc4c(c3)CCC(N(C)C)C4)nc2n1-c1cccc(C(C)(C)CO)n1]
3.123

TABLE-1B-continued
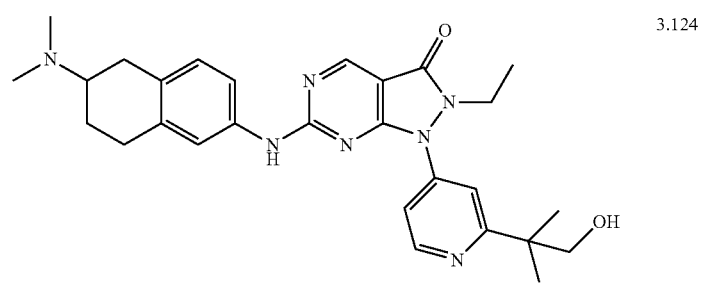
3.124
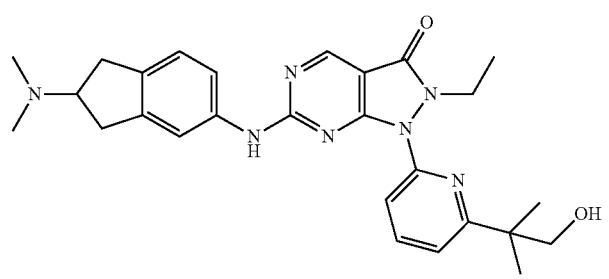 [SMILES: CCn1c(=O)c2cnc(Nc3ccc4c(c3)CC(N(C)C)C4)nc2n1-c1cccc(C(C)(C)CO)n1]
3.125
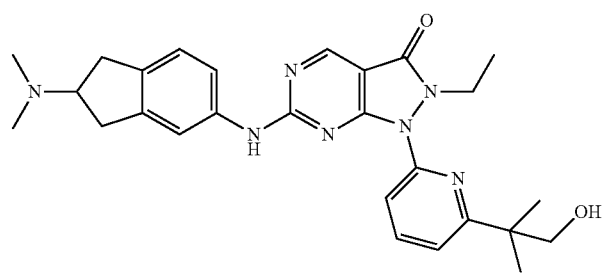 [SMILES: CCn1c(=O)c2cnc(Nc3ccc4c(c3)CC(N(C)C)C4)nc2n1-c1cccc(C(C)(C)CO)n1]
3.126
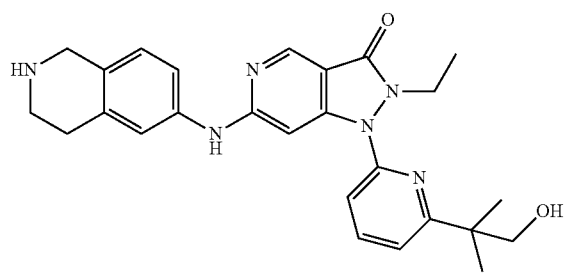 [SMILES: CCn1c(=O)c2cnc(Nc3ccc4c(c3)CCNC4)cc2n1-c1cccc(C(C)(C)CO)n1]
3.127
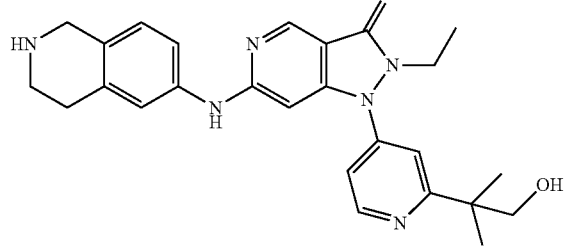
3.128

TABLE-1B-continued
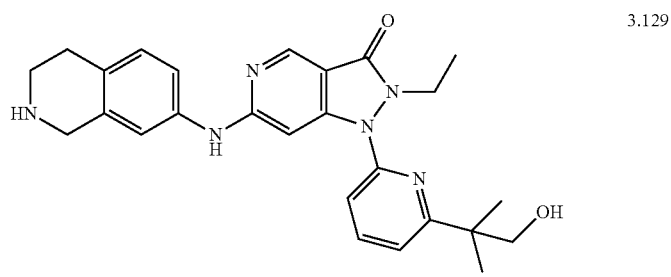
3.129
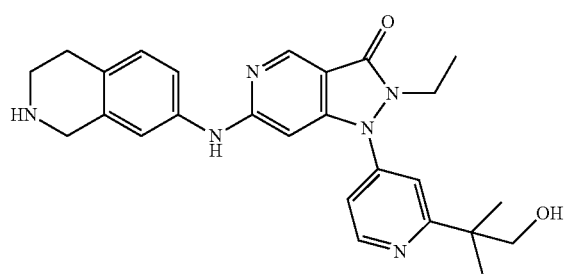 [SMILES: CCn1c(=O)c2cnc(Nc3ccc4c(c3)CNCC4)cc2n1-c1ccnc(C(C)(C)CO)c1]
3.130
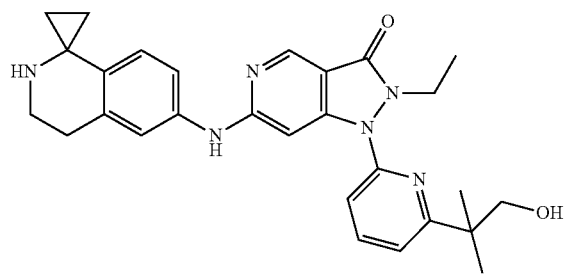 [SMILES: CCn1c(=O)c2cnc(Nc3ccc4c(c3)CCNC43CC3)cc2n1-c1cccc(C(C)(C)CO)n1]
3.131
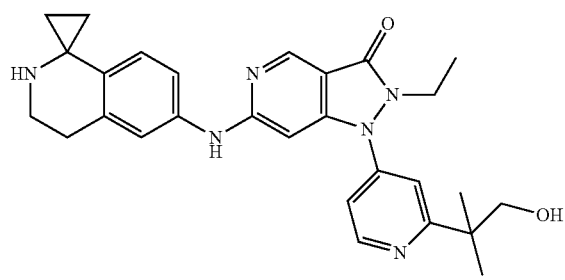 [SMILES: CCn1c(=O)c2cnc(Nc3ccc4c(c3)CCNC43CC3)cc2n1-c1ccnc(C(C)(C)CO)c1]
3.132
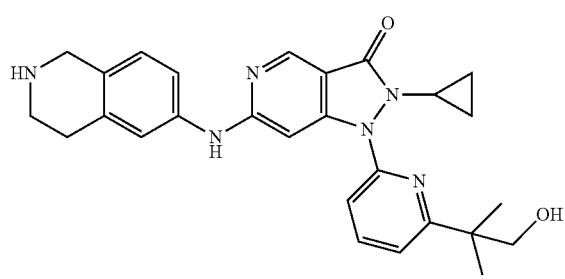 [SMILES: CC(C)(CO)c1cccc(-n2c3cc(Nc4ccc5c(c4)CCNC5)ncc3c(=O)n2C2CC2)n1]
3.133

TABLE-1B-continued

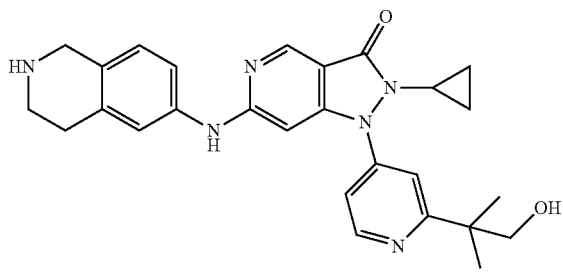 [SMILES: CC(C)(CO)c1cc(-n2c3cc(Nc4ccc5c(c4)CCNC5)ncc3c(=O)n2C2CC2)ccn1]

3.134

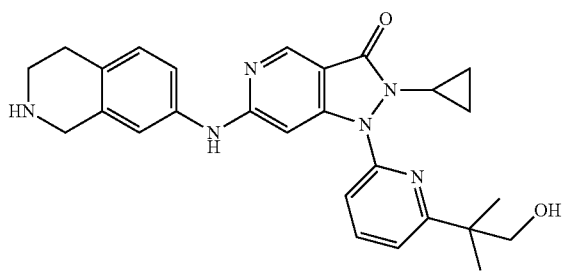 [SMILES: CC(C)(CO)c1cccc(-n2c3cc(Nc4ccc5c(c4)CNCC5)ncc3c(=O)n2C2CC2)n1]

3.135

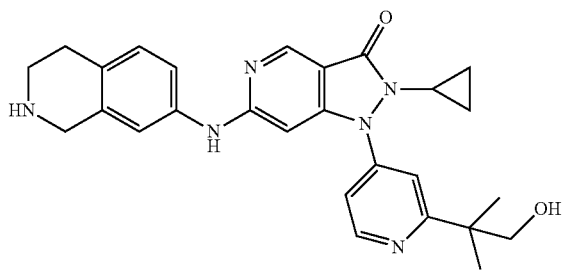 [SMILES: CC(C)(CO)c1cc(-n2c3cc(Nc4ccc5c(c4)CNCC5)ncc3c(=O)n2C2CC2)ccn1]

3.136

In some embodiments, provided herein is a compound described in Table 1A or Table 1B, or a tautomer thereof, or a salt of any of the foregoing, and uses thereof. In some embodiments, provided herein is a compound described in Table 1A or Table 1B or a pharmaceutically acceptable salt thereof. In some embodiments, provided herein is a compound described in Table 1A or Table 1B, or a tautomer or isomer thereof, or a pharmaceutically acceptable salt of any of the foregoing.

The embodiments and variations described herein are suitable for compounds of any formulae detailed herein, where applicable. For example, it is understood that all variations and embodiments for moieties A and B are applicable to any variation of Formula (I) in which such moiety is present. To illustrate, in some embodiments of a compound of Formula (I), or other structure described herein containing moieties A and B, in one variation, B is $C_6$ aryl, 5- to 7-membered heteroaryl, $C_3$-$C_8$ cycloalkyl, or 3- to 8-membered heterocyclyl, each of which is optionally substituted by $R^4$, wherein B is fused to A.

Representative examples of compounds detailed herein, including intermediates and final compounds according to the present disclosure are depicted herein. It is understood that in one aspect, any of the compounds may be used in the methods detailed herein, including, where applicable, intermediate compounds that may be isolated and administered to an individual.

The compounds depicted herein may be present as salts even if salts are not depicted and it is understood that the present disclosure embraces all salts and solvates of the compounds depicted here, as well as the non-salt and non-solvate form of the compound, as is well understood by the skilled artisan. In some embodiments, the salts of the compounds provided herein are pharmaceutically acceptable salts. Where one or more tertiary amine moiety is present in the compound, the N-oxides are also provided and described.

Where tautomeric forms may be present for any of the compounds described herein, each and every tautomeric form is intended even though only one or some of the tautomeric forms may be explicitly depicted. The tautomeric forms specifically depicted may or may not be the predominant forms in solution or when used according to the methods described herein. It is understood that tautomeric forms of a compound of the formulae described herein may be present, for example, when tautomeric forms of a substituent are present, such as when a substituent embraces a keto-enol tautomer or the like.

The present disclosure also includes any or all of the stereochemical forms, including any enantiomeric or diastereomeric forms of the compounds described, such as the compounds of Table 1A or Table 1B. The structure or name is intended to embrace all possible stereoisomers of a compound depicted, and each unique stereoisomer has a compound number bearing a suffix "a", "b", etc. All forms of the compounds are also embraced by the invention, such as crystalline or non-crystalline forms of the compounds. Compositions comprising a compound of the invention are also intended, such as a composition of substantially pure compound, including a specific stereochemical form thereof, or a composition comprising mixtures of compounds of the invention in any ratio, including two or more stereochemical forms, such as in a racemic or non-racemic mixture.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of Formula (I) or variations thereof described herein, where a fraction of one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^{2}H$, $^{3}H$, $^{11}C$, $^{13}C$, $^{14}C$ $^{13}N$, $^{15}O$, $^{17}O$, $^{32}P$, $^{35}S$, $^{18}F$, $^{36}Cl$. Certain isotope labeled compounds (e.g. $^{3}H$ and $^{14}C$) is useful in compound or substrate tissue distribution studies. Incorporation of heavier isotopes such as deuterium ($^{2}H$) can afford certain therapeutic advantages resulting from greater metabolic stability, for example, increased in vivo half-life, or reduced dosage requirements and, hence may be preferred in some instances.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

The invention also includes any or all metabolites of any of the compounds described. The metabolites may include any chemical species generated by a biotransformation of any of the compounds described, such as intermediates and products of metabolism of the compound, such as would be generated in vivo following administration to a human.

Articles of manufacture comprising a compound described herein, or a salt or solvate thereof, in a suitable container are provided. The container may be a vial, jar, ampoule, preloaded syringe, i.v. bag, and the like.

Preferably, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a medicament is for use in any of the methods disclosed herein, e.g., for the treatment of cancer.

General Synthetic Methods

The compounds of the invention may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography.

Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate In some embodiments, compounds of Formula (I), (Ia), (Ia-1 to Ia-12), (Ib), (Ib-1 to Ib-9), (Ic) or (Ic-1 to Ic-9) may be synthesized according to Scheme 1 to Scheme 13.

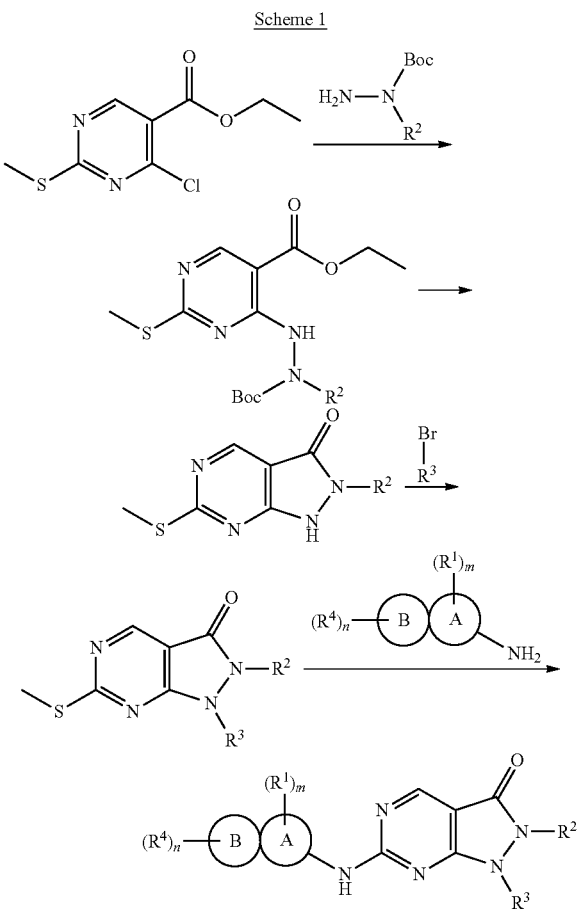

Scheme 1 wherein A, B, $R^1$, $R^2$, $R^3$, and $R^4$ are as defined for Formula (I). Particular examples are provided in the Example Section below.

Scheme 2
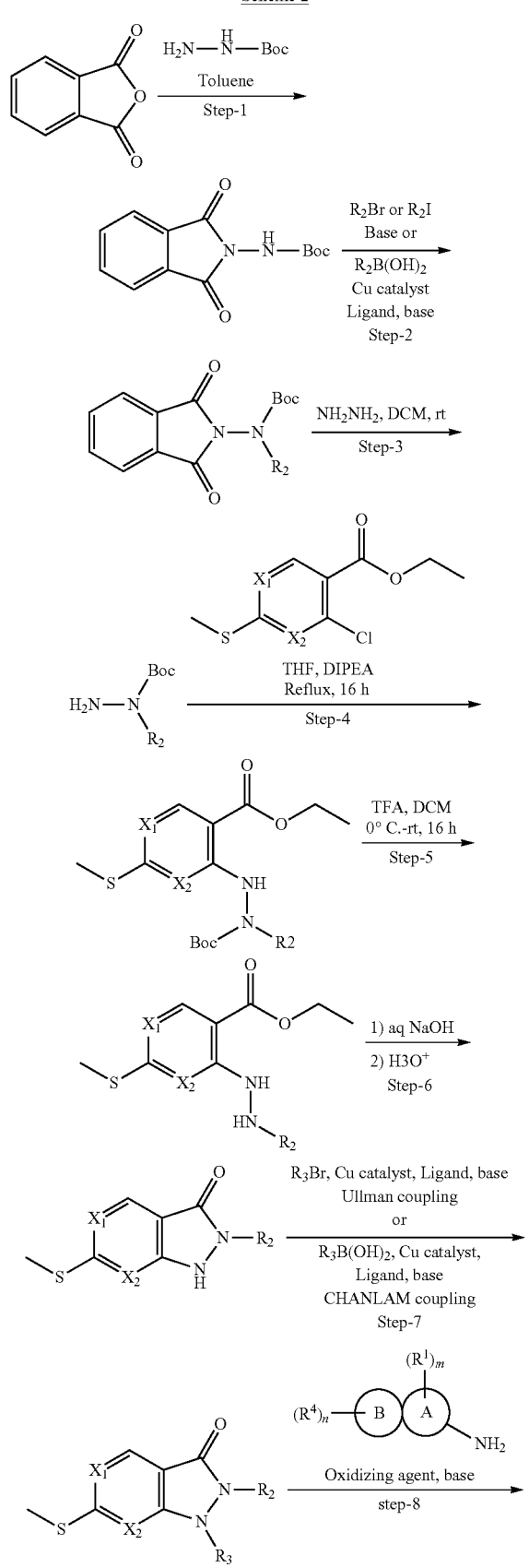
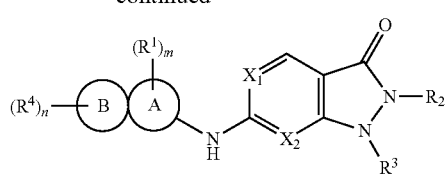
Scheme 3
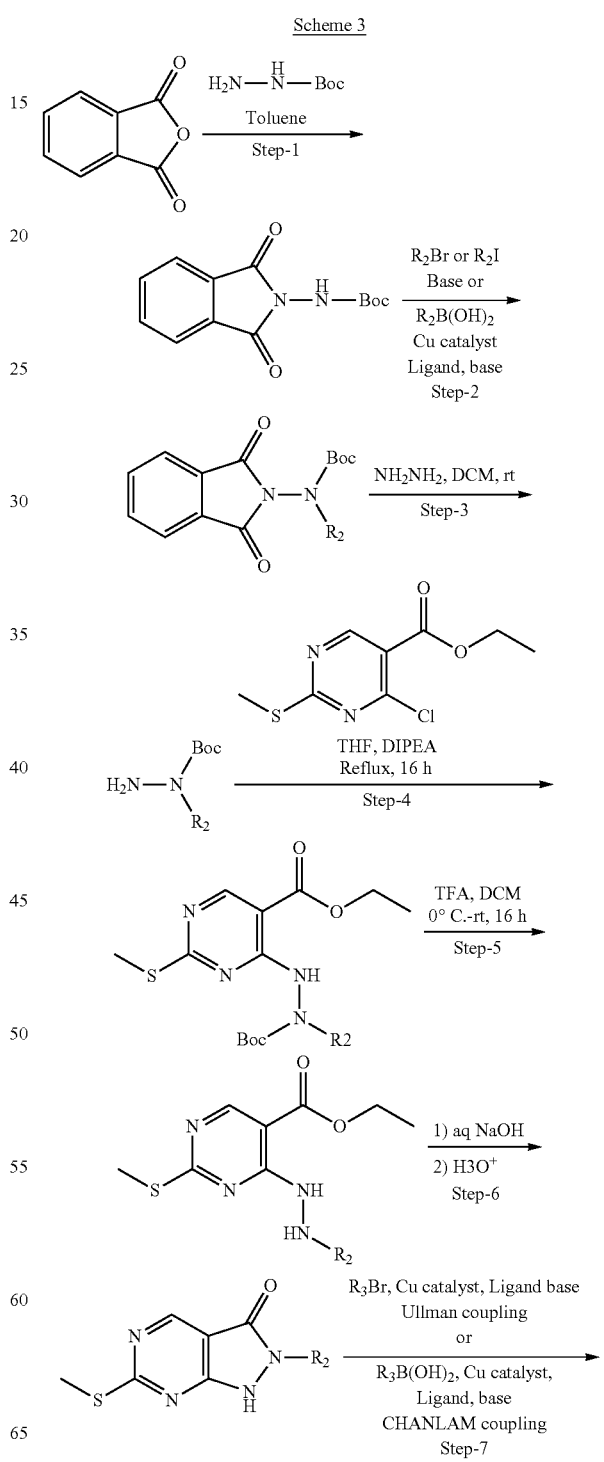

-continued
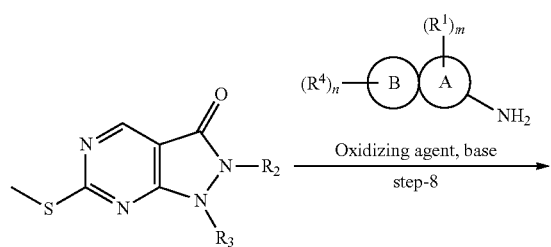
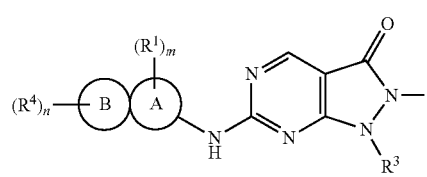
Scheme 4
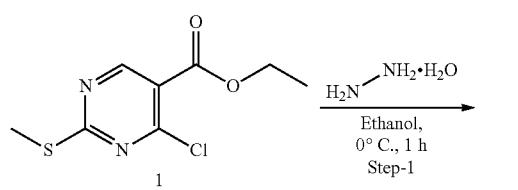
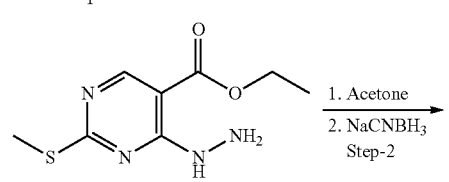
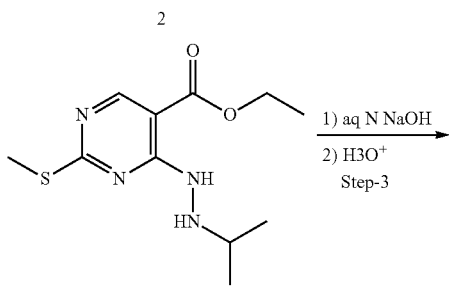
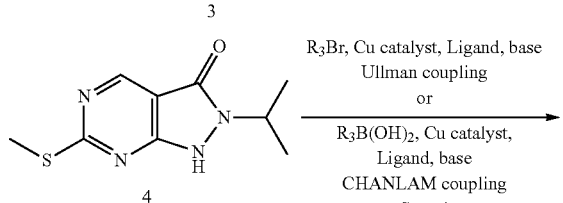
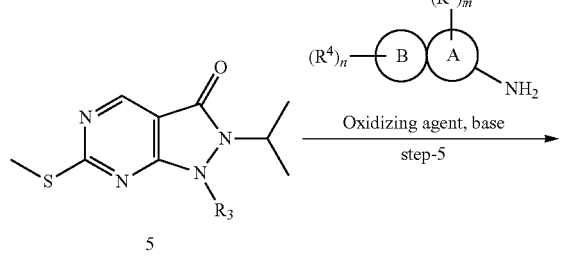
-continued
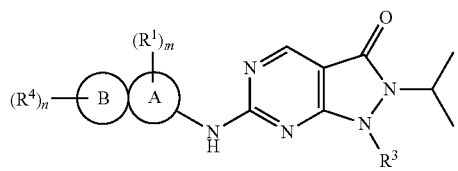
Scheme 5
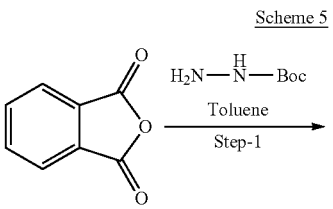
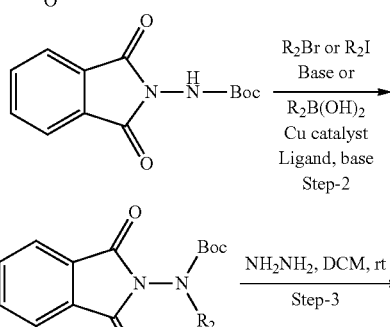
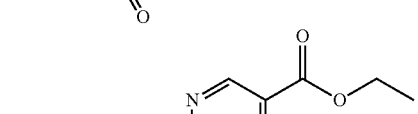
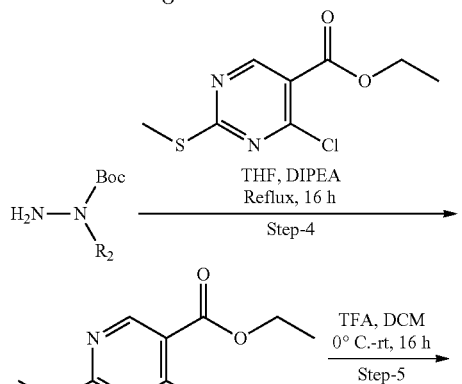
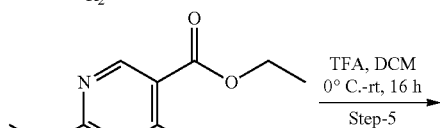
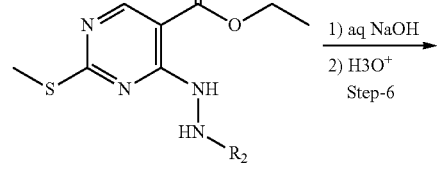
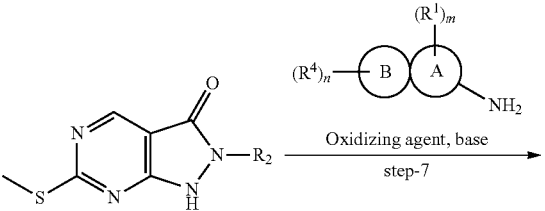

Scheme 6

Scheme 7

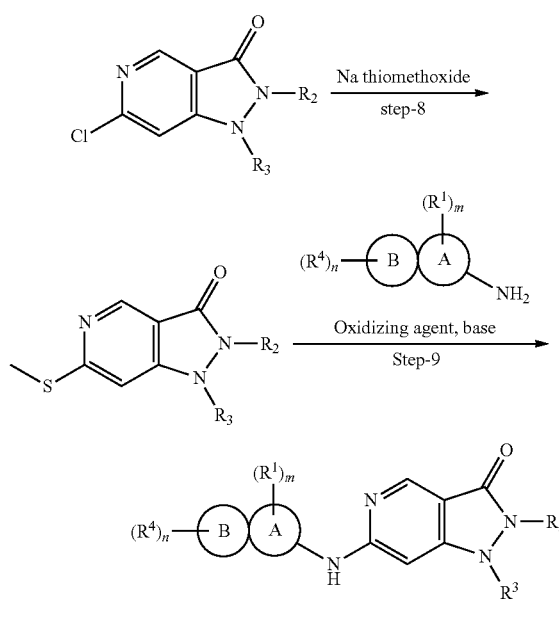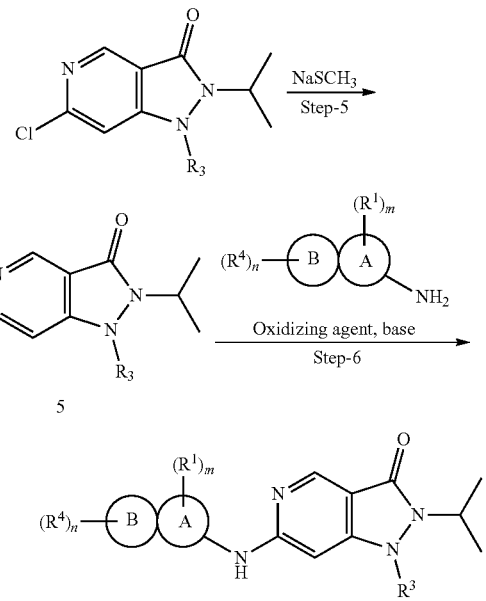
Scheme 8
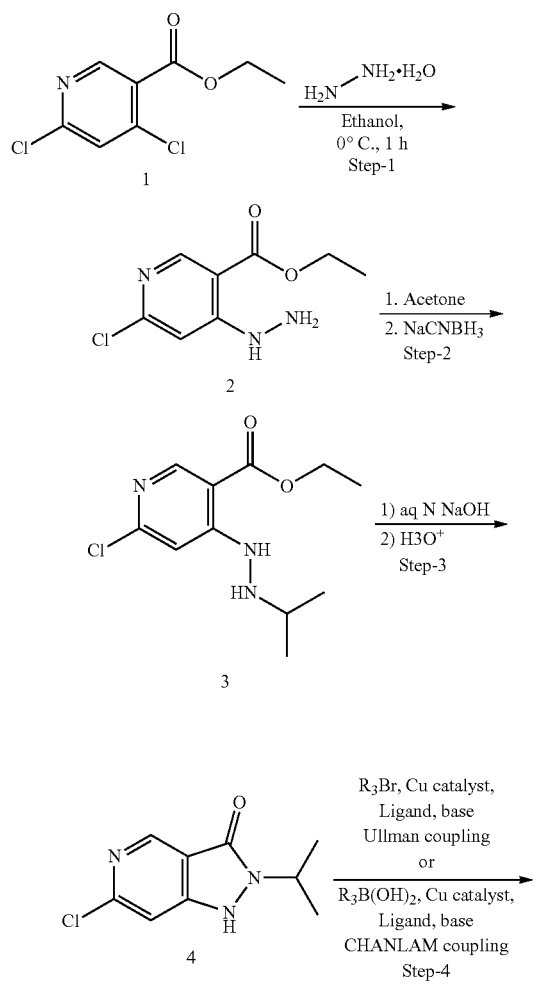
Scheme 9
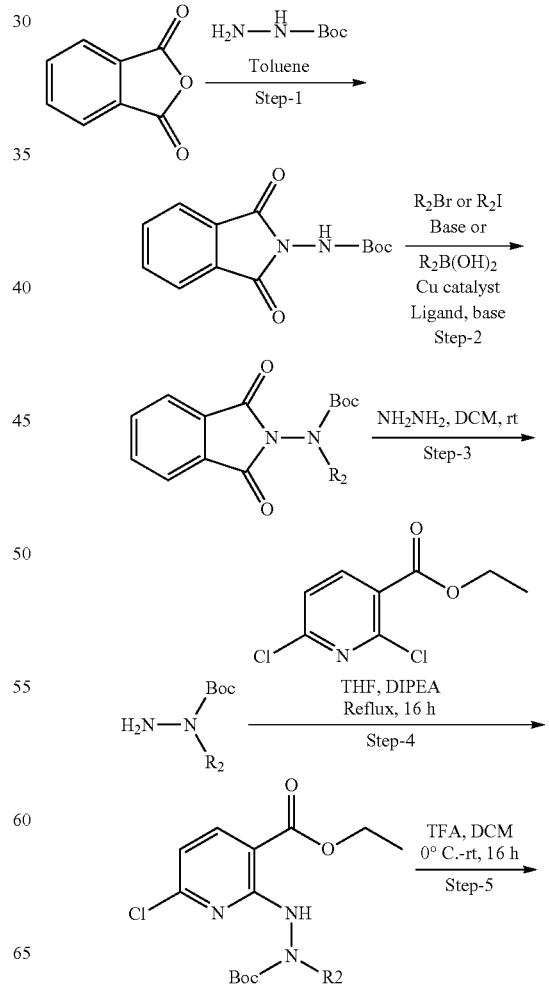

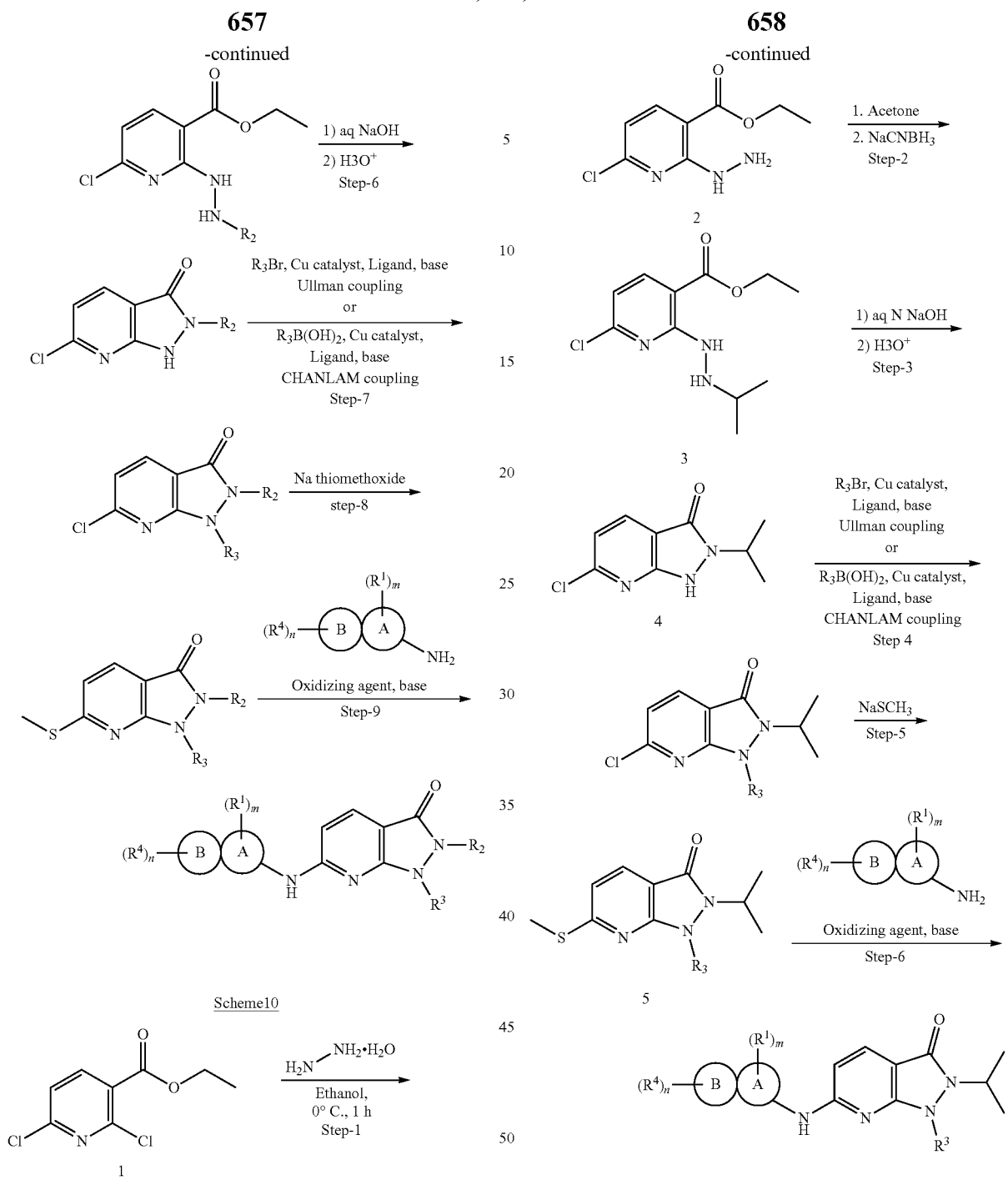

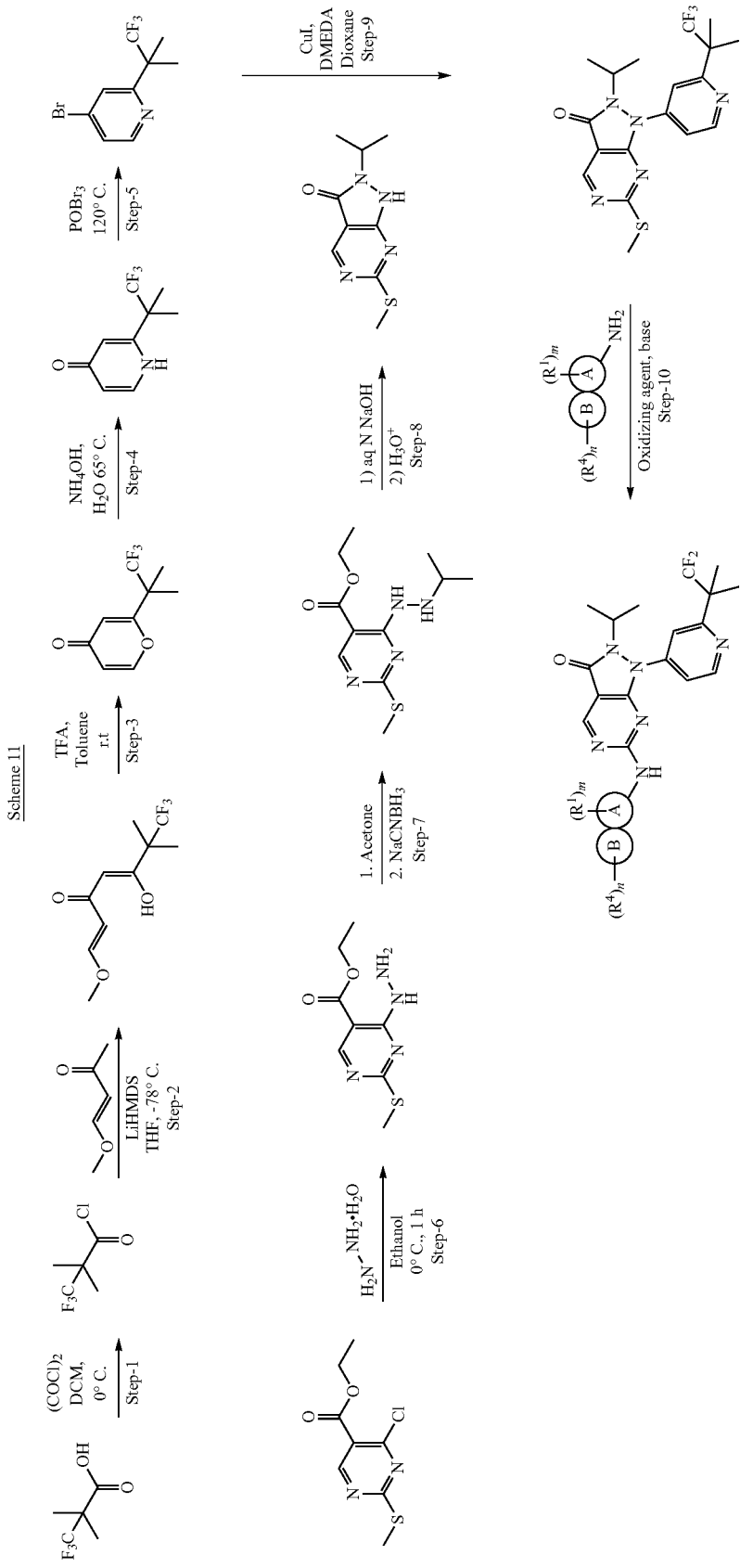

Scheme 12
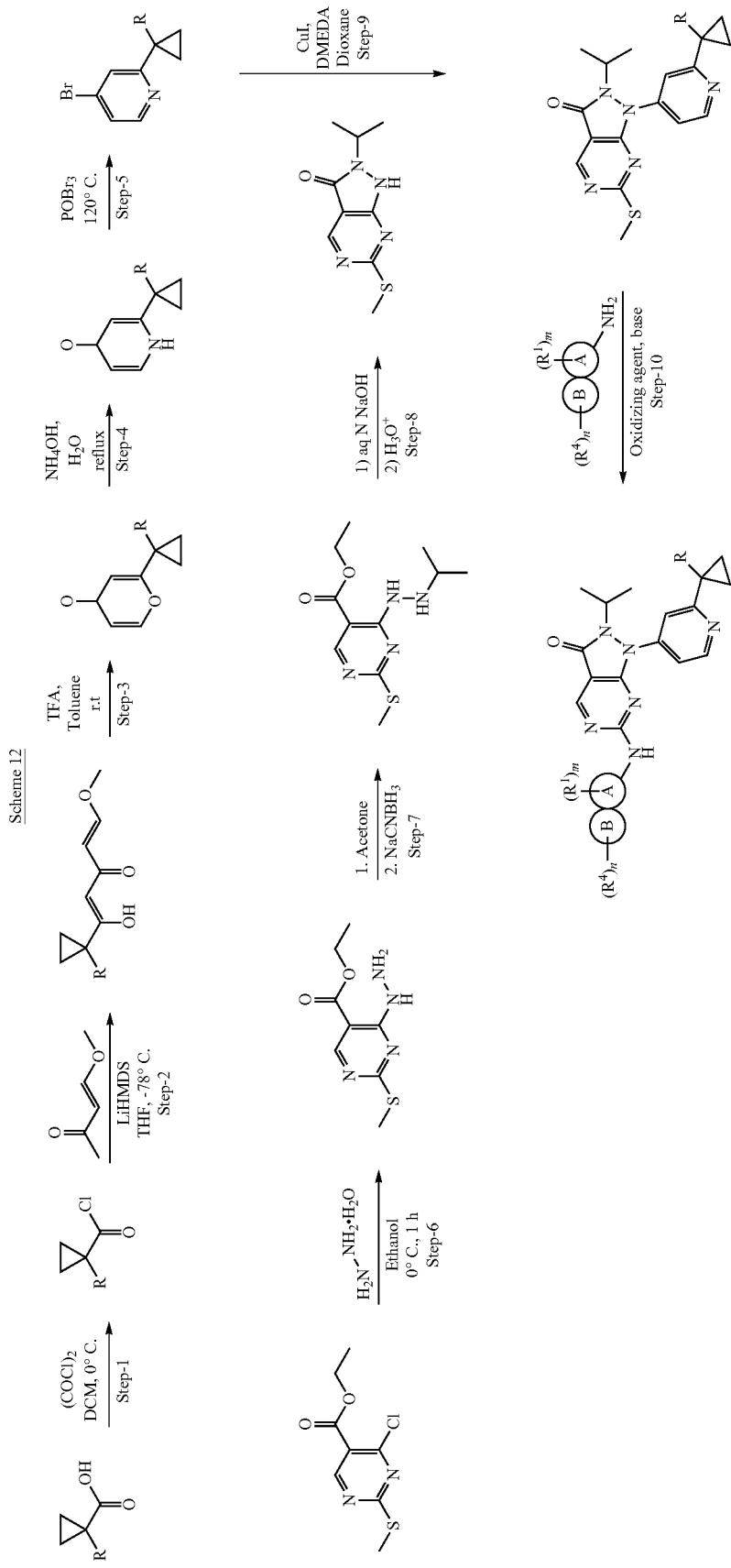
R = CF₃, CH₃

Scheme 13
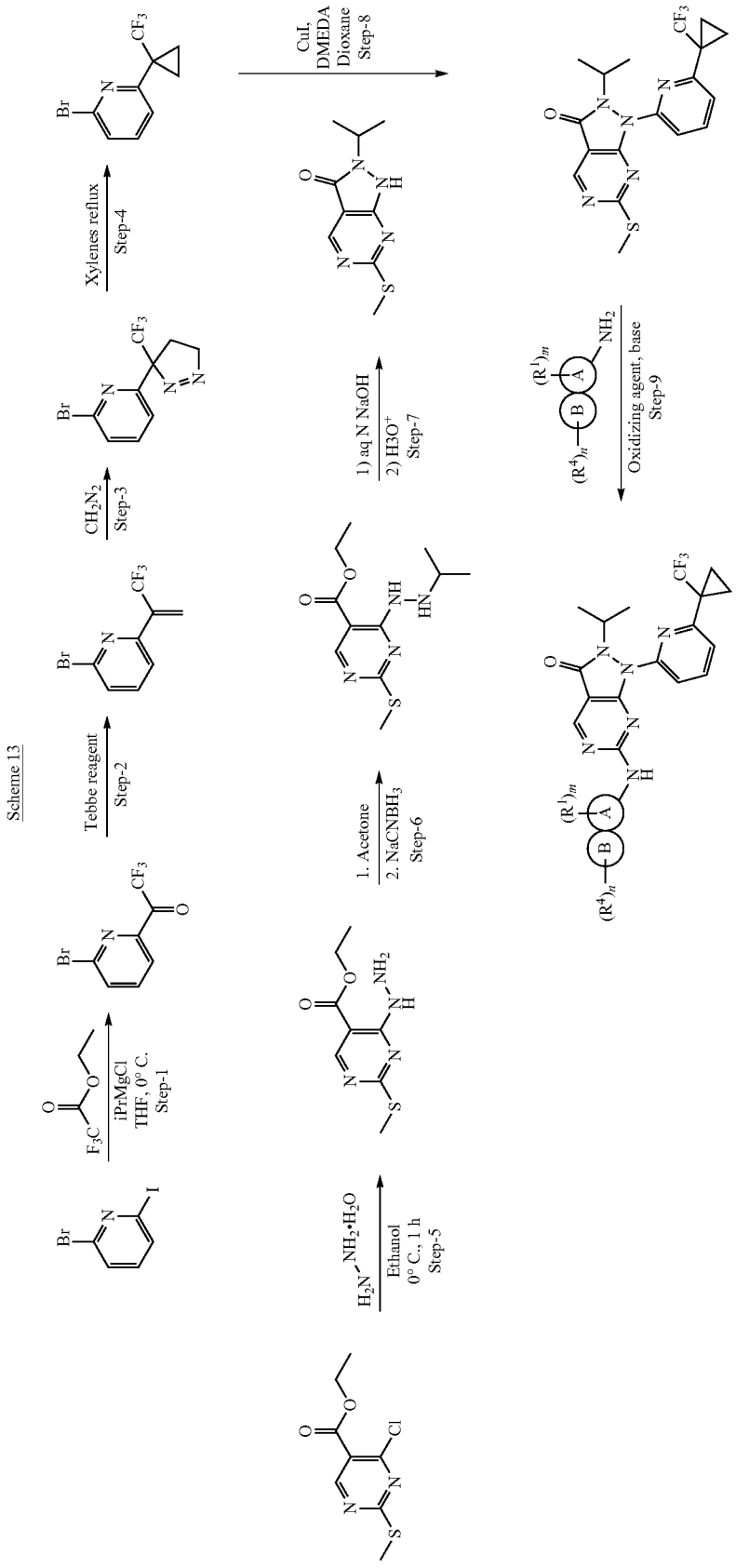
R = CF₃, CH₃ wherein m, n, $X_1$, $X_2$, A, B, $R^1$, $R^2$, $R^3$, and $R^4$ are as defined for Formula (I). Particular examples are provided in the Example Section below.

Pharmaceutical Compositions and Formulations

Pharmaceutical compositions of any of the compounds detailed herein are embraced by this disclosure. Thus, the present disclosure includes pharmaceutical compositions comprising a compound as detailed herein or a salt thereof and a pharmaceutically acceptable carrier or excipient. The present disclosure includes pharmaceutical compositions comprising a compound as detailed herein, or a tautomer or isomer thereof, or a pharmaceutically acceptable salt of any of the foregoing, and a pharmaceutically acceptable carrier or excipient. In one aspect, the pharmaceutically acceptable salt is an acid addition salt, such as a salt formed with an inorganic or organic acid. Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

A compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a salt thereof can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., $20^{th}$ ed. (2000), which is incorporated herein by reference.

Compounds as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a salt thereof can be formulated as a 10 mg tablet.

Compositions comprising a compound provided herein are also described. In one variation, the composition comprises a compound or salt thereof and a pharmaceutically acceptable carrier or excipient. In another variation, a composition of substantially pure compound is provided.

Methods of Use

Compounds and compositions detailed herein, such as a pharmaceutical composition containing a compound of any formula provided herein or a salt thereof and a pharmaceutically acceptable carrier or excipient, may be used in methods of administration and treatment as provided herein. Compounds and compositions detailed herein, such as a pharmaceutical composition containing a compound of any formula provided herein or a tautomer or isomer thereof, or a pharmaceutically acceptable salt of any of the foregoing and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

Provided herein is a method of treating a disease in an individual comprising administering an effective amount of a compound of Formula (I), (Ia), (Ia-1 to Ia-12), (Ib), (Ib-1 to Ib-9), (Ic) or (Ic-1 to Ic-9) or any embodiment, variation or aspect thereof (collectively, a compound of Formula (I), (Ia), (Ia-1 to Ia-12), (Ib), (Ib-1 to Ib-9), (Ic) or (Ic-1 to Ic-9) or the present compounds or the compounds detailed or described herein) or a pharmaceutically acceptable salt thereof, to the individual. Further provided herein is a method of treating a proliferative disease in an individual, comprising administering an effective amount of a compound of Formula (I), (Ia), (Ia-1 to Ia-12), (Ib), (Ib-1 to Ib-9), (Ic) or (Ic-1 to Ic-9) or a pharmaceutically acceptable salt thereof, to the individual. Also provided herein is a method of treating cancer in an individual comprising administering an effective amount of a compound of Formula (I), (Ia), (Ia-1 to Ia-12), (Ib), (Ib-1 to Ib-9), (Ic) or (Ic-1 to Ic-9) or a pharmaceutically acceptable salt thereof, to the individual. In some embodiments, the compound is administered to the individual according to a dosage and/or method of administration described herein.

In some embodiments, the cancer in the individual has one or more TP53 gene mutations or expresses mutant p53.

TP53 is the human gene that encodes p53. In some embodiments, provided herein is a method of treating a cancer in an individual, comprising (a) selecting the individual for treatment based on (i) the presence of one or more mutations of the TP53 gene in the cancer, or (ii) expression of mutant p53 in the cancer, and administering an effective amount of a compound of Formula (I), (Ia), (Ia-1 to Ia-12), (Ib), (Ib-1 to Ib-9), (Ic) or (Ic-1 to Ic-9) or a pharmaceutically acceptable salt thereof, to the individual. In some embodiments, the cancer is assayed for the expression of mutant p53. In some embodiments, the TP53 gene of the cancer is sequenced to detect the one or more mutations. In some embodiments, the TP53 gene is sequenced by biopsying the cancer and sequencing the TP53 gene from the biopsied cancer. In some embodiments, the TP53 gene is sequenced by sequencing circulating-tumor DNA (ctDNA) from the individual.

In some embodiments, provided herein is a method of using a compound of Formula (I), (Ia), (Ia-1 to Ia-12), (Ib), (Ib-1 to Ib-9), (Ic) or (Ic-1 to Ic-9) or any embodiment in the manufacture of a medicament for treatment of a disease. In some embodiments, provided herein is a method of using a compound of Formula (I), (Ia), (Ia-1 to Ia-12), (Ib), (Ib-1 to Ib-9), (Ic) or (Ic-1 to Ic-9) or any embodiment in the manufacture of a medicament for treatment of cancer.

In some embodiments, a compound of Formula (I), (Ia), (Ia-1 to Ia-12), (Ib), (Ib-1 to Ib-9), (Ic) or (Ic-1 to Ic-9) or a salt thereof is used to treat an individual having a proliferative disease, such as cancer as described herein. In some embodiments, the individual is at risk of developing a proliferative disease, such as cancer. In some of these embodiments, the individual is determined to be at risk of developing cancer based upon one or more risk factors. In some of these embodiments, the risk factor is a family history and/or gene associated with cancer.

The present compounds or salts thereof are believed to be effective for treating a variety of diseases and disorders. For example, in some embodiments, the present compositions may be used to treat a proliferative disease, such as cancer. In some embodiments the cancer is a solid tumor. In some embodiments the cancer is any of adult and pediatric oncology, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma, cutaneous T cell lymphoma, Hodgkin's lymphoma, non-Hodgkin's lymphoma, cancer of the adrenal cortex, ACTH-producing tumors, lung cancer, including small cell carcinoma and nonsmall cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, vaginal cancer, cancer of the vulva, uterine cancer and solid tumors in the ovarian follicle, malignancies of the male genital tract, including testicular cancer and penile cancer, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas and osteosarcomas, skin cancers, including melanoma, tumor progression of human skin keratinocytes, squamous cell cancer, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

In some embodiments, the compounds and compositions described herein suppress $G_2$-M checkpoint in a cell (such as a cancer cell). In some embodiments, the cancer cell is a cancer cell from any of the cancer types described herein. Suppression of the $G_2$-M DNA damage checkpoint results in premature mitosis of the cell, and consequently apoptosis. In some embodiments, provided herein is a method of suppressing the $G_2$-M DNA damage checkpoint in a cell comprising administering an effective amount of a compound of Formula (I), (Ia), (Ia-1 to Ia-12), (Ib), (Ib-1 to Ib-9), (Ic) or (Ic-1 to Ic-9) or a pharmaceutically acceptable salt thereof, to the cell. In some embodiments, the $G_2$-M DNA damage checkpoint is suppressed in about 40% or more, about 50% or more, about 60% or more, about 70% or more, about 80% or more, about 85% or more, about 90% or more, about 95% or more, about 96% or more, about 97% or more, about 98% or more, or about 99% or more of cells in a cell population. In some embodiments, the $G_2$-M DNA damage checkpoint is suppressed in up to about 99%, up to about 98%, up to about 97%, up to about 96%, up to about 95%, up to about 90%, up to about 85%, or up to about 80% of cells in the cell population.

In some embodiments, provided herein is a method of inducing premature mitosis in a cell comprising administering an effective amount of a compound of Formula (I), (Ia), (Ia-1 to Ia-12), (Ib), (Ib-1 to Ib-9), (Ic) or (Ic-1 to Ic-9) or a pharmaceutically acceptable salt thereof, to the cell. In some embodiments, premature mitosis is induced in about 40% or more, about 50% or more, about 60% or more, about 70% or more, about 80% or more, about 85% or more, about 90% or more, about 95% or more, about 96% or more, about 97% or more, about 98% or more, or about 99% or more of cells in a cell population. In some embodiments, premature mitosis is induced in up to about 99%, up to about 98%, up to about 97%, up to about 96%, up to about 95%, up to about 90%, up to about 85%, or up to about 80% of cells in the cell population.

In some embodiments, provided herein is a method of inducing apoptosis in a cell comprising administering an effective amount of a compound of Formula (I), (Ia), (Ia-1 to Ia-12), (Ib), (Ib-1 to Ib-9), (Ic) or (Ic-1 to Ic-9) or a pharmaceutically acceptable salt thereof, to the cell. In some embodiments, apoptosis is induced in about 40% or more, about 50% or more, about 60% or more, about 70% or more, about 80% or more, about 85% or more, about 90% or more, about 95% or more, about 96% or more, about 97% or more, about 98% or more, or about 99% or more of cells in a cell population. In some embodiments, apoptosis is induced in up to about 99%, up to about 98%, up to about 97%, up to about 96%, up to about 95%, up to about 90%, up to about 85%, or up to about 80% of cells in the cell population.

In some embodiments, provided herein is a method of inhibiting Wee1 in a cell comprising administering an effective amount of a compound of Formula (I), (Ia), (Ia-1 to Ia-12), (Ib), (Ib-1 to Ib-9), (Ic) or (Ic-1 to Ic-9) or a pharmaceutically acceptable salt thereof, to the cell. In some embodiments, Wee1 is inhibited by about 10% or more, about 20% or more, about 30% or more, about 40% or more, about 50% or more, about 60% or more, about 70% or more, about 75% or more, about 80% or more, about 90% or more, about 95% or more, about 96% or more, about 97% or more, about 98% or more, or about 99% or more. In some embodiments, Wee1 is inhibited up to about 99%, up to about 98%, up to about 97%, up to about 96%, up to about 95%, up to about 90%, up to about 85%, up to about 80%, up to about 70%, or up to about 60%. In some embodiments, the activity of Wee1 is measured according to a kinase assay.

In some embodiments, provided herein is a method of inhibiting Wee1 comprising contacting Wee1 with an effective amount of a compound of Formula (I), (Ia), (Ia-1 to Ia-12), (Ib), (Ib-1 to Ib-9), (Ic) or (Ic-1 to Ic-9) or a pharmaceutically acceptable salt thereof. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof binds to Wee1 with an $IC_{50}$ of less than 1 µM, less than 900 nM, less than 800 nM, less than 700 nM, less than 600 nM, less than 500 nM, less than 400 nM, less than 300 nM, less than 200 nM, less than 100 nM, less than 50 nM, less than 10 nM, less than 5 nM, less than 1 nM, or less than 0.5 nM. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof binds to Wee1 with an $IC_{50}$ between 0.1 nM and 1 nM, between 1 nM and 5 nM, between 5 nM and 10 nM, between 10 nM and 50 nM, between 50 nM and 100 nM, between 100 nM and 200 nM, between 200 nM and 300 nM, between 300 nM and 400 nM, between 400 nM and 500 nM, between 500 nM and 600 nM, between 600 nM and 700 nM, between 700 nM and 800 nM, between 800 nM and 900 nM, or between 900 nM and 1 µM. In some embodiments, the $IC_{50}$ is measured according to a kinase assay. In some embodiments, the $IC_{50}$ is measured according to a cell cytotoxicity assay.

In some embodiments, provided herein is a method of inhibiting the proliferation of a cell, comprising contacting the cell with an effective amount of a compound of Formula (I), (Ia), (Ia-1 to Ia-12), (Ib), (Ib-1 to Ib-9), (Ic) or (Ic-1 to Ic-9) or a pharmaceutically acceptable salt thereof. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is effective in inhibiting the proliferation of the cell with an $IC_{50}$ of less than 5 µM, less than 2 µM, less than 1 µM, less than 900 nM, less than 800 nM, less than 700 nM, less than 600 nM, less than 500 nM, less than 400 nM, less than 300 nM, less than 200 nM, less than 100 nM, or less than 50 nM. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt is effective in inhibiting the proliferation of the cell with an $IC_{50}$ between 10 nM and 20 nM, between 20 nM and 50 nM, between 50 nM and 100 nM, between 100 nM and 500 nM, between 500 nM and 1 µM, between 1 µM and 2 µM, or between 2 µM and 5 µM. In some embodiments, the $IC_{50}$ is measured according to a cell proliferation assay.

Combination Therapy

As provided herein, the presently disclosed compounds or a salt thereof may activate the immune system, for example by inducing apoptosis or suppressing mitosis of cancer cells. Accordingly, the present compounds or a salt thereof may be used in combination with other anti-cancer agents to enhance tumor immunotherapy. In some embodiments, provided herein is a method of treating a disease in an individual comprising administering an effective amount of a compound of Formula (I), (Ia), (Ia-1 to Ia-12), (Ib), (Ib-1 to Ib-9), (Ic) or (Ic-1 to Ic-9) or any embodiment, variation or aspect thereof (collectively, a compound of Formula (I), (Ia), (Ia-1 to Ia-12), (Ib), (Ib-1 to Ib-9), (Ic) or (Ic-1 to Ic-9) or the present compounds or the compounds detailed or described herein) or a pharmaceutically acceptable salt thereof, and an additional therapeutic agent to the individual. In some embodiments, the disease is a proliferative disease such as cancer.

In some embodiments, the additional therapeutic agent is a cancer immunotherapy agent. In some embodiments, the additional therapeutic agent is a chemotherapeutic agent. In some embodiments, the additional therapeutic agent is an immunostimulatory agent. In some embodiments, the additional therapeutic agent targets a checkpoint protein (for example an immune checkpoint inhibitor). In some embodiments, the additional therapeutic agent is effective to stimulate, enhance or improve an immune response against a tumor. In some embodiments, the additional chemotherapeutic agent is a DNA alkylating agent, a platinum-based chemotherapeutic agent, a kinase inhibitor or a DNA damage repair (DDR) pathway inhibitor. In some embodiments, the additional chemotherapeutic agent is a DNA alkylating agent. In some embodiments, the additional chemotherapeutic agent is a platinum-based chemotherapeutic agent. In some embodiments, the additional chemotherapeutic agent is a kinase inhibitor. In some embodiments, the additional chemotherapeutic agent is a DNA damage repair (DDR) pathway inhibitor.

In another aspect, provided herein is a combination therapy for the treatment of a disease, such as cancer. In some embodiments, provided herein is a method of treating a disease in an individual comprising administering an effective amount of a compound of Formula (I), (Ia), (Ia-1 to Ia-12), (Ib), (Ib-1 to Ib-9), (Ic) or (Ic-1 to Ic-9) or any embodiment, variation or aspect thereof (collectively, a compound of Formula (I), (Ia), (Ia-1 to Ia-12), (Ib), (Ib-1 to Ib-9), (Ic) or (Ic-1 to Ic-9) or the present compounds or the compounds detailed or described herein) or a pharmaceutically acceptable salt thereof, in combination with a radiation therapy.

In some embodiments, provided herein is a method of treating a disease in an individual comprising (a) administering an effective amount of a compound of Formula (I), (Ia), (Ia-1 to Ia-12), (Ib), (Ib-1 to Ib-9), (Ic) or (Ic-1 to Ic-9) or any embodiment, variation or aspect thereof (collectively, Formula (I), (Ia), (Ia-1 to Ia-12), (Ib), (Ib-1 to Ib-9), (Ic) or (Ic-1 to Ic-9)) or a pharmaceutically acceptable salt thereof, and (b) administering an effective amount of an additional chemotherapeutic agent. In some embodiments, the chemotherapeutic agent is a kinase inhibitor or an agent that inhibits one or more DNA damage repair (DDR) pathways. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered prior to, after, or simultaneously co-administered with the additional chemotherapeutic agent. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered 1 or more hours (such as 2 or more hours, 4 or more hours, 8 or more hours, 12 or more hours, 24 or more hours, or 48 or more hours) prior to or after the additional chemotherapeutic agent.

Examples of chemotherapeutic agents that can be used in combination with a compound of Formula (I), (Ia), (Ia-1 to Ia-12), (Ib), (Ib-1 to Ib-9), (Ic) or (Ic-1 to Ic-9) or a pharmaceutically acceptable salt thereof include DNA-targeted agents, a DNA alkylating agent (such as cyclophosphamide, mechlorethamine, chlorambucil, melphalan, dacarbazine, or nitrosoureas), a topoisomerase inhibitor (such as a Topoisomerase I inhibitor (e.g., irinotecan or topotecan) or a Topoisomerase II inhibitor (e.g., etoposide or teniposide)), an anthracycline (such as daunorubicin, doxorubicin, epirubicin, idarubicin, mitoxantrone, or valrubicin), a histone deacetylase inhibitor (such as vorinostat or romidepsin), a bromodomain inhibitor, other epigenetic inhibitors, a taxane (such as paclitaxel or docetaxel), a kinase inhibitor (such as bortezomib, erlotinib, gefitinib, imatinib, vemurafenib, or vismodegib), an anti-angiogenic inhibitor, a nucleotide analog or precursor analog (such as azacitidine, azathioprine, capecitabine, cytarabine, doxifluridine, 5-fluorouracil, gemcitabine, hydroxyurea, mercaptopurine, methotrexate, or tioguanine), or a platinum-based chemotherapeutic agent (such as cisplatin, carboplatin, or oxaliplatin), pemetrexed, or a combination thereof. In some embodiments, provided herein is a method of treating a disease in an individual comprising (a) administering an effective amount of a compound of Formula (I), (Ia), (Ia-1 to Ia-12), (Ib), (Ib-1 to Ib-9), (Ic) or (Ic-1 to Ic-9) or any embodiment, variation or aspect thereof (collectively, Formula (I), (Ia), (Ia-1 to Ia-12), (Ib), (Ib-1 to Ib-9), (Ic) or (Ic-1 to Ic-9)) or a pharmaceutically acceptable salt thereof, and (b) administering an effective amount of a kinase inhibitor (such as bortezomib, erlotinib, gefitinib, imatinib, vemurafenib, or vismodegib). In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered prior to, after, or simultaneously co-administered with the kinase inhibitor. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered 1 or more hours (such as 2 or more hours, 4 or more hours, 8 or more hours, 12 or more hours, 24 or more hours, or 48 or more hours) prior to or after the kinase inhibitor.

In some embodiments, provided herein is a method of treating a disease in an individual comprising (a) administering an effective amount of a compound of Formula (I), (Ia), (Ia-1 to Ia-12), (Ib), (Ib-1 to Ib-9), (Ic) or (Ic-1 to Ic-9) or any embodiment, variation or aspect thereof (collectively, Formula (I), (Ia), (Ia-1 to Ia-12), (Ib), (Ib-1 to Ib-9), (Ic) or (Ic-1 to Ic-9)) or a pharmaceutically acceptable salt thereof, and (b) administering an effective amount of a DNA damaging agent. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered prior to, after, or simultaneously co-administered with the DNA damaging agent. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered 1 or more hours (such as 2 or more hours, 4 or more hours, 8 or more hours, 12 or more hours, 24 or more hours, or 48 or more hours) prior to or after the DNA damaging agent.

In some embodiments, provided herein is a method of treating a disease in an individual comprising (a) administering an effective amount of a compound of Formula (I), (Ia), (Ia-1 to Ia-12), (Ib), (Ib-1 to Ib-9), (Ic) or (Ic-1 to Ic-9) or any embodiment, variation or aspect thereof (collectively, Formula (I), (Ia), (Ia-1 to Ia-12), (Ib), (Ib-1 to Ib-9), (Ic) or (Ic-1 to Ic-9)) or a pharmaceutically acceptable salt thereof, and (b) administering an effective amount of a DNA alkylating agent (such as cyclophosphamide, mechlorethamine, chlorambucil, melphalan, dacarbazine, or nitrosoureas). In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered prior to, after, or simultaneously co-administered with the DNA alkylating agent. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered 1 or more hours (such as 2 or more hours, 4 or more hours, 8 or more hours, 12 or more hours, 24 or more hours, or 48 or more hours) prior to or after the DNA alkylating agent.

In some embodiments, provided herein is a method of treating a disease in an individual comprising (a) administering an effective amount of a compound of Formula (I), (Ia), (Ia-1 to Ia-12), (Ib), (Ib-1 to Ib-9), (Ic) or (Ic-1 to Ic-9) or any embodiment, variation or aspect thereof (collectively, Formula (I), (Ia), (Ia-1 to Ia-12), (Ib), (Ib-1 to Ib-9), (Ic) or (Ic-1 to Ic-9)) or a pharmaceutically acceptable salt thereof, and (b) administering an effective amount of a topoisomerase inhibitor (such as a Topoisomerase I inhibitor (e.g., irinotecan or topotecan) or a Topoisomerase II inhibitor (e.g., etoposide or teniposide)). In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered prior to, after, or simultaneously co-administered with the topoisomerase inhibitor. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered 1 or more hours (such as 2 or more hours, 4 or more hours, 8 or more hours, 12 or more hours, 24 or more hours, or 48 or more hours) prior to or after the topoisomerase inhibitor.

In some embodiments, provided herein is a method of treating a disease in an individual comprising (a) administering an effective amount of a compound of Formula (I), (Ia), (Ia-1 to Ia-12), (Ib), (Ib-1 to Ib-9), (Ic) or (Ic-1 to Ic-9) or any embodiment, variation or aspect thereof (collectively, Formula (I), (Ia), (Ia-1 to Ia-12), (Ib), (Ib-1 to Ib-9), (Ic) or (Ic-1 to Ic-9)) or a pharmaceutically acceptable salt thereof, and (b) administering an effective amount of an anthracycline (such as daunorubicin, doxorubicin, epirubicin, idarubicin, mitoxantrone, or valrubicin). In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered prior to, after, or simultaneously co-administered with the anthracycline. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered 1 or more hours (such as 2 or more hours, 4 or more hours, 8 or more hours, 12 or more hours, 24 or more hours, or 48 or more hours) prior to or after the anthracycline.

In some embodiments, provided herein is a method of treating a disease in an individual comprising (a) administering an effective amount of a compound of Formula (I), (Ia), (Ia-1 to Ia-12), (Ib), (Ib-1 to Ib-9), (Ic) or (Ic-1 to Ic-9) or any embodiment, variation or aspect thereof (collectively, Formula (I), (Ia), (Ia-1 to Ia-12), (Ib), (Ib-1 to Ib-9), (Ic) or (Ic-1 to Ic-9)) or a pharmaceutically acceptable salt thereof, and (b) administering an effective amount of a histone deacetylase inhibitor (such as vorinostat or romidepsin). In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered prior to, after, or simultaneously co-administered with the histone deacetylase inhibitor. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered 1 or more hours (such as 2 or more hours, 4 or more hours, 8 or more hours, 12 or more hours, 24 or more hours, or 48 or more hours) prior to or after the histone deacetylase inhibitor.

In some embodiments, provided herein is a method of treating a disease in an individual comprising (a) administering an effective amount of a compound of Formula (I), (Ia), (Ia-1 to Ia-12), (Ib), (Ib-1 to Ib-9), (Ic) or (Ic-1 to Ic-9) or any embodiment, variation or aspect thereof (collectively, Formula (I), (Ia), (Ia-1 to Ia-12), (Ib), (Ib-1 to Ib-9), (Ic) or (Ic-1 to Ic-9)) or a pharmaceutically acceptable salt thereof, and (b) administering an effective amount of a taxane (such as paclitaxel or docetaxel). In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered prior to, after, or simultaneously co-administered with the taxane. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered 1 or more hours (such as 2 or more hours, 4 or more hours, 8 or more hours, 12 or more hours, 24 or more hours, or 48 or more hours) prior to or after the taxane.

In some embodiments, provided herein is a method of treating a disease in an individual comprising (a) administering an effective amount of a compound of Formula (I), (Ia), (Ia-1 to Ia-12), (Ib), (Ib-1 to Ib-9), (Ic) or (Ic-1 to Ic-9) or any embodiment, variation or aspect thereof (collectively, Formula (I), (Ia), (Ia-1 to Ia-12), (Ib), (Ib-1 to Ib-9), (Ic) or (Ic-1 to Ic-9)) or a pharmaceutically acceptable salt thereof, and (b) administering an effective amount of a nucleotide analog or precursor analog (such as azacitidine, azathioprine, capecitabine, cytarabine, doxifluridine, 5-fluorouracil, gemcitabine, hydroxyurea, mercaptopurine, methotrexate, or tioguanine). In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered prior to, after, or simultaneously co-administered with the nucleotide analog or precursor analog. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered 1 or more hours (such as 2 or more hours, 4 or more hours, 8 or more hours, 12 or more hours, 24 or more hours, or 48 or more hours) prior to or after the nucleotide analog or precursor analog.

In some embodiments, provided herein is a method of treating a disease in an individual comprising (a) administering an effective amount of a compound of Formula (I), (Ia), (Ia-1 to Ia-12), (Ib), (Ib-1 to Ib-9), (Ic) or (Ic-1 to Ic-9) or any embodiment, variation or aspect thereof (collectively, Formula (I), (Ia), (Ia-1 to Ia-12), (Ib), (Ib-1 to Ib-9), (Ic) or (Ic-1 to Ic-9)) or a pharmaceutically acceptable salt thereof, and (b) administering an effective amount of a platinum-based chemotherapeutic agent (such as cisplatin, carboplatin, or oxaliplatin). In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered prior to, after, or simultaneously co-administered with the platinum-based chemotherapeutic agent. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered 1 or more hours (such as 2 or more hours, 4 or more hours, 8 or more hours, 12 or more hours, 24 or more hours, or 48 or more hours) prior to or after the platinum-based chemotherapeutic agent.

In some embodiments, provided herein is a method of treating a disease in an individual comprising (a) administering an effective amount of a compound of Formula (I), (Ia), (Ia-1 to Ia-12), (Ib), (Ib-1 to Ib-9), (Ic) or (Ic-1 to Ic-9) or any embodiment, variation or aspect thereof (collectively, Formula (I), (Ia), (Ia-1 to Ia-12), (Ib), (Ib-1 to Ib-9), (Ic) or (Ic-1 to Ic-9)) or a pharmaceutically acceptable salt thereof, and (b) administering an effective amount of pemetrexed. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered prior to, after, or simultaneously co-administered with the pemetrexed. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered 1 or more hours (such as 2 or more hours, 4 or more hours, 8 or more hours, 12 or more hours, 24 or more hours, or 48 or more hours) prior to or after the pemetrexed.

In some embodiments, provided herein is a method of treating a disease in an individual comprising (a) administering an effective amount of a compound of Formula (I), (Ia), (Ia-1 to Ia-12), (Ib), (Ib-1 to Ib-9), (Ic) or (Ic-1 to Ic-9) or any embodiment, variation or aspect thereof (collectively, Formula (I), (Ia), (Ia-1 to Ia-12), (Ib), (Ib-1 to Ib-9), (Ic) or (Ic-1 to Ic-9)) or a pharmaceutically acceptable salt thereof, and (b) administering an effective amount of a DDR pathway inhibitor. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered prior to, after, or simultaneously co-administered with the DDR pathway inhibitor. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered 1 or more hours (such as 2 or more hours, 4 or more hours, 8 or more hours, 12 or more hours, 24 or more hours, or 48 or more hours) prior to or after the DDR pathway inhibitor. Examples of inhibitors of the DDR pathway include poly(ADP-ribose) polymerase (PARP) inhibitors (such as olaparib, rucaparib, niraparib, or talazoparib), ataxia telangiectasia mutated (ATM) protein inhibitors, ataxia telangiectasia and Rad3-related (ATR) protein inhibitors, checkpoint kinase 1 (Chk1) inhibitors, or combinations thereof.

In some embodiments, provided herein is a method of treating a disease in an individual comprising (a) administering an effective amount of a compound of Formula (I), (Ia), (Ia-1 to Ia-12), (Ib), (Ib-1 to Ib-9), (Ic) or (Ic-1 to Ic-9) or any embodiment, variation or aspect thereof (collectively, Formula (I), (Ia), (Ia-1 to Ia-12), (Ib), (Ib-1 to Ib-9), (Ic) or (Ic-1 to Ic-9)) or a pharmaceutically acceptable salt thereof, and (b) administering an effective amount of a PARP inhibitor (such as olaparib, rucaparib, niraparib, or talazoparib). In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered prior to, after, or simultaneously co-administered with the PARP inhibitor. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered 1 or more hours (such as 2 or more hours, 4 or more hours, 8 or more hours, 12 or more hours, 24 or more hours, or 48 or more hours) prior to or after the PARP inhibitor.

In some embodiments, provided herein is a method of treating a disease in an individual comprising (a) administering an effective amount of a compound of Formula (I), (Ia), (Ia-1 to Ia-12), (Ib), (Ib-1 to Ib-9), (Ic) or (Ic-1 to Ic-9) or any embodiment, variation or aspect thereof (collectively, Formula (I), (Ia), (Ia-1 to Ia-12), (Ib), (Ib-1 to Ib-9), (Ic) or (Ic-1 to Ic-9)) or a pharmaceutically acceptable salt thereof, and (b) administering an effective amount of an ATM protein inhibitor. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered prior to, after, or simultaneously co-administered with the ATM protein inhibitor. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered 1 or more hours (such as 2 or more hours, 4 or more hours, 8 or more hours, 12 or more hours, 24 or more hours, or 48 or more hours) prior to or after the ATM protein inhibitor.

In some embodiments, provided herein is a method of treating a disease in an individual comprising (a) administering an effective amount of a compound of Formula (I), (Ia), (Ia-1 to Ia-12), (Ib), (Ib-1 to Ib-9), (Ic) or (Ic-1 to Ic-9) or any embodiment, variation or aspect thereof (collectively, Formula (I), (Ia), (Ia-1 to Ia-12), (Ib), (Ib-1 to Ib-9), (Ic) or (Ic-1 to Ic-9)) or a pharmaceutically acceptable salt thereof, and (b) administering an effective amount of an ATR protein inhibitor. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered prior to, after, or simultaneously co-administered with the ATR protein inhibitor. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered 1 or more hours (such as 2 or more hours, 4 or more hours, 8 or more hours, 12 or more hours, 24 or more hours, or 48 or more hours) prior to or after the ATR protein inhibitor.

In some embodiments, provided herein is a method of treating a disease in an individual comprising (a) administering an effective amount of a compound of Formula (I), (Ia), (Ia-1 to Ia-12), (Ib), (Ib-1 to Ib-9), (Ic) or (Ic-1 to Ic-9) or any embodiment, variation or aspect thereof (collectively, Formula (I), (Ia), (Ia-1 to Ia-12), (Ib), (Ib-1 to Ib-9), (Ic) or (Ic-1 to Ic-9)) or a pharmaceutically acceptable salt thereof, and (b) administering an effective amount of an Chk1 inhibitor. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered prior to, after, or simultaneously co-administered with the Chk1 inhibitor. In some embodiments, a compound of Formula (I), (Ia), (Ia-1 to Ia-12), (Ib), (Ib-1 to Ib-9), (Ic) or (Ic-1 to Ic-9) or a pharmaceutically acceptable salt thereof is administered 1 or more hours (such as 2 or more hours, 4 or more hours, 8 or more hours, 12 or more hours, 24 or more hours, or 48 or more hours) prior to or after the Chk1 inhibitor.

In another aspect, provided herein is a combination therapy in which a compound of Formula (I), (Ia), (Ia-1 to Ia-12), (Ib), (Ib-1 to Ib-9), (Ic) or (Ic-1 to Ic-9) or a salt thereof is coadministered (which may be separately or simultaneously) with one or more additional agents that are effective in stimulating immune responses to thereby further enhance, stimulate or upregulate immune responses in a subject. For example, provided is a method for stimulating an immune response in a subject comprising administering to the subject a compound of Formula (I), (Ia), (Ia-1 to Ia-12), (Ib), (Ib-1 to Ib-9), (Ic) or (Ic-1 to Ic-9) or a salt thereof and one or more immunostimulatory antibodies, such as an anti-PD-1 antibody, an anti-PD-L1 antibody and/or an anti-CTLA-4 antibody, such that an immune response is stimulated in the subject, for example to inhibit tumor growth. In one embodiment, the subject is administered a compound of Formula (I), (Ia), (Ia-1 to Ia-12), (Ib), (Ib-1 to Ib-9), (Ic) or (Ic-1 to Ic-9) or a salt thereof and an anti-PD-1 antibody. In another embodiment, the subject is administered a compound of Formula (I), (Ia), (Ia-1 to Ia-12), (Ib), (Ib-1 to Ib-9), (Ic) or (Ic-1 to Ic-9) or a salt thereof and an anti-PD-L1 antibody. In yet another embodiment, the subject is administered a compound of formula (I) or a salt thereof and an anti-CTLA-4 antibody. In another embodiment, the immunostimulatory antibody (e.g., anti-PD-1, anti-PD-L1 and/or anti-CTLA-4 antibody) is a human antibody. Alternatively, the immunostimulatory antibody can be, for example, a chimeric or humanized antibody (e.g., prepared from a mouse anti-PD-1, anti-PD-L1 and/or anti-CTLA-4 antibody).

In one embodiment, the present disclosure provides a method for treating a proliferative disease (e.g., cancer), comprising administering a compound of Formula (I), (Ia), (Ia-1 to Ia-12), (Ib), (Ib-1 to Ib-9), (Ic) or (Ic-1 to Ic-9) or a salt thereof and an anti-PD-1 antibody to a subject. In further embodiments, a compound of Formula (I), (Ia), (Ia-1 to Ia-12), (Ib), (Ib-1 to Ib-9), (Ic) or (Ic-1 to Ic-9) or a salt thereof is administered at a subtherapeutic dose, the anti-PD-1 antibody is administered at a subtherapeutic dose, or both are administered at a subtherapeutic dose. In another embodiment, the present disclosure provides a method for altering an adverse event associated with treatment of a hyperproliferative disease with an immunostimulatory agent, comprising administering a compound of Formula (I), (Ia), (Ia-1 to Ia-12), (Ib), (Ib-1 to Ib-9), (Ic) or (Ic-1 to Ic-9) or a salt thereof and a subtherapeutic dose of anti-PD-1 antibody to a subject. In certain embodiments, the subject is human. In certain embodiments, the anti-PD-1 antibody is a human sequence monoclonal antibody.

In one embodiment, the present invention provides a method for treating a hyperproliferative disease (e.g., cancer), comprising administering a compound of Formula (I), (Ia), (Ia-1 to Ia-12), (Ib), (Ib-1 to Ib-9), (Ic) or (Ic-1 to Ic-9) or a salt thereof and an anti-PD-L1 antibody to a subject. In further embodiments, a compound of Formula (I), (Ia), (Ia-1 to Ia-12), (Ib), (Ib-1 to Ib-9), (Ic) or (Ic-1 to Ic-9) or a salt thereof is administered at a subtherapeutic dose, the anti-PD-L1 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering a compound of Formula (I), (Ia), (Ia-1 to Ia-12), (Ib), (Ib-1 to Ib-9), (Ic) or (Ic-1 to Ic-9) or a salt thereof and a subtherapeutic dose of anti-PD-L1 antibody to a subject. In certain embodiments, the subject is human. In certain embodiments, the anti-PD-L1 antibody is a human sequence monoclonal antibody.

In certain embodiments, the combination of therapeutic agents discussed herein can be administered concurrently as a single composition in a pharmaceutically acceptable carrier, or concurrently as separate compositions each in a pharmaceutically acceptable carrier. In another embodiment, the combination of therapeutic agents can be administered sequentially. For example, an anti-CTLA-4 antibody and a compound of Formula (I), (Ia), (Ia-1 to Ia-12), (Ib), (Ib-1 to Ib-9), (Ic) or (Ic-1 to Ic-9) or a salt thereof can be administered sequentially, such as anti-CTLA-4 antibody being administered first and a compound of Formula (I), (Ia), (Ia-1 to Ia-12), (Ib), (Ib-1 to Ib-9), (Ic) or (Ic-1 to Ic-9) or a salt thereof second, or a compound of formula Formula (I), (Ia), (Ia-1 to Ia-12), (Ib), (Ib-1 to Ib-9), (Ic) or (Ic-1 to Ic-9) or a salt thereof being administered first and anti-CTLA-4 antibody second. Additionally or alternatively, an anti-PD-1 antibody and a compound of Formula (I), (Ia), (Ia-1 to Ia-12), (Ib), (Ib-1 to Ib-9), (Ic) or (Ic-1 to Ic-9) or a salt thereof can be administered sequentially, such as anti-PD-1 antibody being administered first and a compound of Formula (I), (Ia), (Ia-1 to Ia-12), (Ib), (Ib-1 to Ib-9), (Ic) or (Ic-1 to Ic-9) or a salt thereof second, or a compound of Formula (I), (Ia), (Ia-1 to Ia-12), (Ib), (Ib-1 to Ib-9), (Ic) or (Ic-1 to Ic-9) or a salt thereof being administered first and anti-PD-1 antibody second. Additionally or alternatively, an anti-PD-L1 antibody and a compound of Formula (I), (Ia), (Ia-1 to Ia-12), (Ib), (Ib-1 to Ib-9), (Ic) or (Ic-1 to Ic-9) or a salt thereof can be administered sequentially, such as anti-PD-L1 antibody being administered first and a compound of Formula (I), (Ia), (Ia-1 to Ia-12), (Ib), (Ib-1 to Ib-9), (Ic) or (Ic-1 to Ic-9) or a salt thereof second, or a compound of Formula (I), (Ia), (Ia-1 to Ia-12), (Ib), (Ib-1 to Ib-9), (Ic) or (Ic-1 to Ic-9) or a salt thereof being administered first and anti-PD-L1 antibody second.

Furthermore, if more than one dose of the combination therapy is administered sequentially, the order of the sequential administration can be reversed or kept in the same order at each time point of administration, sequential administrations can be combined with concurrent administrations, or any combination thereof.

Optionally, the combination of a compound of Formula (I), (Ia), (Ia-1 to Ia-12), (Ib), (Ib-1 to Ib-9), (Ic) or (Ic-1 to Ic-9) or a salt thereof can be further combined with an immunogenic agent, such as cancerous cells, purified tumor antigens (including recombinant proteins, peptides, and carbohydrate molecules), cells, and cells transfected with genes encoding immune stimulating cytokines.

A compound of Formula (I), (Ia), (Ia-1 to Ia-12), (Ib), (Ib-1 to Ib-9), (Ic) or (Ic-1 to Ic-9) or a salt thereof can also be further combined with standard cancer treatments. For example, a compound of Formula (I), (Ia), (Ia-1 to Ia-12), (Ib), (Ib-1 to Ib-9), (Ic) or (Ic-1 to Ic-9) or a salt thereof can be effectively combined with chemotherapeutic regimes. In these instances, it is possible to reduce the dose of other chemotherapeutic reagent administered with the combination of the instant disclosure (Mokyr et al. (1998) *Cancer Research* 58: 5301-5304). Other combination therapies with a compound of Formula (I), (Ia), (Ia-1 to Ia-12), (Ib), (Ib-1 to Ib-9), (Ic) or (Ic-1 to Ic-9) or a salt thereof include radiation, surgery, or hormone deprivation. Angiogenesis inhibitors can also be combined with a compound of Formula (I), (Ia), (Ia-1 to Ia-12), (Ib), (Ib-1 to Ib-9), (Ic) or (Ic-1 to Ic-9) or a salt thereof. Inhibition of angiogenesis leads to tumor cell death, which can be a source of tumor antigen fed into host antigen presentation pathways.

In another example, a compound of Formula (I), (Ia), (Ia-1 to Ia-12), (Ib), (Ib-1 to Ib-9), (Ic) or (Ic-1 to Ic-9) or a salt thereof can be used in conjunction with anti-neoplastic antibodies. By way of example and not wishing to be bound by theory, treatment with an anti-cancer antibody or an anti-cancer antibody conjugated to a toxin can lead to cancer cell death (e.g., tumor cells) which would potentiate an immune response mediated by CTLA-4, PD-1, PD-L1 or a compound of Formula (I), (Ia), (Ia-1 to Ia-12), (Ib), (Ib-1 to Ib-9), (Ic) or (Ic-1 to Ic-9) or a salt thereof. In an exemplary embodiment, a treatment of a hyperproliferative disease (e.g., a cancer tumor) can include an anti-cancer antibody in combination with a compound of Formula (I), (Ia), (Ia-1 to Ia-12), (Ib), (Ib-1 to Ib-9), (Ic) or (Ic-1 to Ic-9) or a salt thereof and anti-CTLA-4 and/or anti-PD-1 and/or anti-PD-L1 antibodies, concurrently or sequentially or any combination thereof, which can potentiate anti-tumor immune responses by the host. Other antibodies that can be used to activate host immune responsiveness can be further used in combination with a compound of Formula (I), (Ia), (Ia-1 to Ia-12), (Ib), (Ib-1 to Ib-9), (Ic) or (Ic-1 to Ic-9) or a salt thereof.

In some embodiments, a compound of Formula (I), (Ia), (Ia-1 to Ia-12), (Ib), (Ib-1 to Ib-9), (Ic) or (Ic-1 to Ic-9) or a salt thereof can be combined with an anti-CD73 therapy, such as an anti-CD73 antibody.

In yet further embodiments, a compound of Formula (I), (Ia), (Ia-1 to Ia-12), (Ib), (Ib-1 to Ib-9), (Ic) or (Ic-1 to Ic-9) or a salt thereof is administered in combination with another Wee1 inhibitor.

Dosing and Method of Administration

The dose of a compound administered to an individual (such as a human) may vary with the particular compound or salt thereof, the method of administration, and the particular disease, such as type and stage of cancer, being treated. In some embodiments, the amount of the compound or salt thereof is a therapeutically effective amount.

The effective amount of the compound may in one aspect be a dose of between about 0.01 and about 100 mg/kg. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein or a salt thereof and a pharmaceutically acceptable excipient.

A compound or composition of the invention may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

The compounds provided herein or a salt thereof may be administered to an individual via various routes, including, e.g., intravenous, intramuscular, subcutaneous, oral and transdermal. A compound provided herein can be administered frequently at low doses, known as 'metronomic therapy,' or as part of a maintenance therapy using compound alone or in combination with one or more additional drugs. Metronomic therapy or maintenance therapy can comprise administration of a compound provided herein in cycles. Metronomic therapy or maintenance therapy can comprise intra-tumoral administration of a compound provided herein.

In one aspect, the invention provides a method of treating cancer in an individual by parenterally administering to the individual (e.g., a human) an effective amount of a compound or salt thereof. In some embodiments, the route of administration is intravenous, intra-arterial, intramuscular, or subcutaneous. In some embodiments, the route of administration is oral. In still other embodiments, the route of administration is transdermal.

The invention also provides compositions (including pharmaceutical compositions) as described herein for the use in treating, preventing, and/or delaying the onset and/or development of cancer and other methods described herein. In certain embodiments, the composition comprises a pharmaceutical formulation which is present in a unit dosage form.

Also provided are articles of manufacture comprising a compound of the disclosure or a salt thereof, composition, and unit dosages described herein in suitable packaging for use in the methods described herein. Suitable packaging is known in the art and includes, for example, vials, vessels, ampules, bottles, jars, flexible packaging and the like. An article of manufacture may further be sterilized and/or sealed.

Kits

The present disclosure further provides kits for carrying out the methods of the invention, which comprises one or more compounds described herein or a composition comprising a compound described herein. The kits may employ any of the compounds disclosed herein. In one variation, the kit employs a compound described herein or a salt thereof. The kits may be used for any one or more of the uses described herein, and, accordingly, may contain instructions for the treatment of cancer.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or an additional pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The invention can be further understood by reference to the following examples, which are provided by way of illustration and are not meant to be limiting.

EXAMPLES

Synthetic Examples

Example S1. Synthesis of 2-allyl-1-[6-(1-hydroxy-1-methyl-ethyl)-2-pyridyl]-6-(1,2,3,4-tetrahydroisoquinolin-7-ylamino)pyrazolo[3,4-d]pyrimidin-3-one

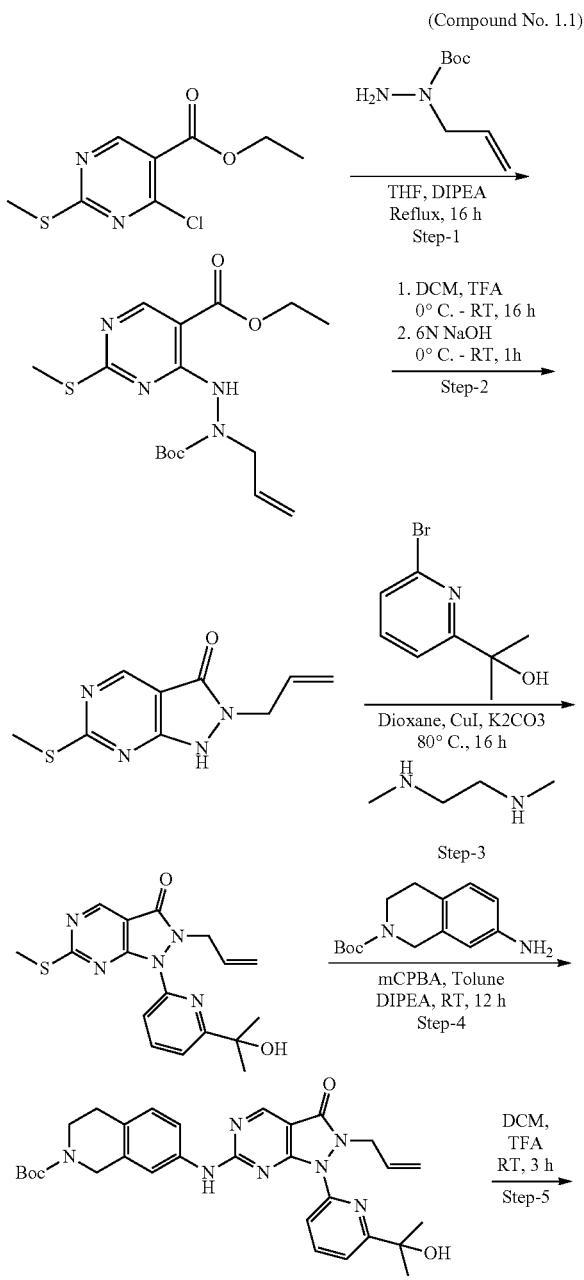

(Compound No. 1.1)

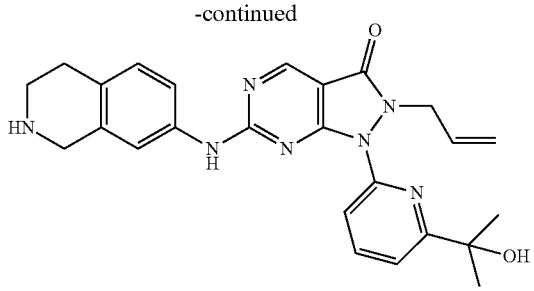

Step-1: Synthesis of ethyl 4-(2-allyl-2-tert-butoxy-carbonyl-hydrazino)-2-methylsulfanyl-pyrimidine-5-carboxylate To a stirred solution of ethyl 4-chloro-2-methylsulfanyl-pyrimidine-5-carboxylate (1.0 g, 4.29 mmol, 1.0 eq) and tert-butyl N-allyl-N-amino-carbamate (960 mg, 5.57 mmol, 1.3 eq) in THF (15 mL) was added DIPEA (1.86 mL, 10.72 mmol, 2.5 eq) and stirred at reflux for 16 h. Solvent was removed under reduced pressure. Residue was diluted with water (20 mL) and extracted with ethyl acetate (50 mL×3). The organic layer was washed with brine solution (20 mL), dried over anhydrous sodium sulphate and concentrated under reduced pressure to obtain crude product which was purified by flash chromatography to afford ethyl 4-(2-allyl-2-tert-butoxycarbonyl-hydrazino)-2-methylsulfanyl-pyrimidine-5-carboxylate (1.10 g, 53.6%) as an oily liquid.

LCMS: 369 [M+1]$^+$ $^1$H NMR (400 MHz, CDCl$_3$): δ 9.50 (br s, 1H), 8.70 (s, 1H), 5.90 (m, 1H), 5.20 (m, 2H), 4.35 (q, 2H), 4.20 (br s, 2H), 2.50 (s, 3H), 1.50-1.25 (m, 12H).

Step-2: Synthesis of 2-allyl-6-methylsulfanyl-1H-pyrazolo[3,4-d]pyrimidin-3-one To a stirred solution of ethyl 4-(2-allyl-2-tert-butoxycarbonyl-hydrazino)-2-methylsulfanyl-pyrimidine-5-carboxylate (3.0 g, 8.19 mmol, 1.0 eq) in CH$_2$Cl$_2$ (10 mL) was added TFA (10 mL) dropwise at 0° C. and allowed to stir at RT for 12 h. After completion of reaction, solvent was removed under reduced pressure. Residue was diluted with EtOH (20 mL) and 6N NaOH solution (10 mL) was added at 0° C. and allowed to stir at RT for 1 h. After completion of reaction, the mixture was acidified by using 6N HCl solution. EtOH was removed under reduced pressure; residue obtained was cooled to RT and extracted with chloroform (50 mL×3). The organic layer was washed with brine solution, dried over anhydrous sodium sulphate and concentrated under reduced pressure to afford 2-allyl-6-methylsulfanyl-1H-pyrazolo[3,4-d]pyrimidin-3-one (1.40 g, 76%) as a yellow solid.

LCMS: 223 [M+1]$^+$

Step-3: Synthesis of 2-allyl-1-[6-(1-hydroxy-1-methyl-ethyl)-2-pyridyl]-6-methylsulfanyl-pyrazolo[3,4-d]pyrimidin-3-one To a stirred solution of 2-allyl-6-methylsulfanyl-1H-pyrazolo[3,4-d]pyrimidin-3-one (200 mg, 0.90 mmol, 1.0 eq) and 2-(6-bromo-2-pyridyl)propan-2-ol (233 mg, 1.08 mmol, 1.20 eq) in 10 mL of dioxane were added copper iodide (171 mg, 0.90 mmol, 1.0 eq), potassium carbonate (186 mg, 1.35 mmol, 1.5 eq) and N,N'-dimethylethylenediamine (87 mg, 0.99 mmol, 1.1 eq) and stirred at 80° C. for overnight. After completion of reaction, solvent was removed under reduced pressure; residue was diluted with water and extracted with ethyl acetate (30 mL×3). Combined organic layer was washed with brine solution, dried over anhydrous sodium sulphate and concentrated under reduced pressure to afford crude product, which was purified by flash chromatography to afford 240 mg (74%) of 2-allyl-1-[6-(1-hydroxy-1-methyl-ethyl)-2-pyridyl]-6-methylsulfanyl-pyrazolo[3,4-d]pyrimidin-3-one.

LCMS: 358 [M+1]$^+$

Step-4: Synthesis of tert-butyl 7-[[2-allyl-1-[6-(1-hydroxy-1-methyl-ethyl)-2-pyridyl]-3-oxo-pyrazolo[3,4-d]pyrimidin-6-yl]amino]-3,4-dihydro-1H-isoquinoline-2-carboxylate To a stirred solution of 2-allyl-1-[6-(1-hydroxy-1-methyl-ethyl)-2-pyridyl]-6-methylsulfanyl-pyrazolo[3,4-d]pyrimidin-3-one (240 mg, 0.67 mmol, 1.0 eq) in 5 mL of toluene was added mCPBA (232 mg, 1.34 mmol, 2.0 eq) and allowed to stir at RT for 20 minutes. Tert-butyl 7-amino-3,4-dihydro-1H-isoquinoline-2-carboxylate (216 mg, 0.87 mmol, 1.3 eq) and DIPEA (260 mg, 2.10 mmol, 3.0 eq) were added and allowed to stir at RT for overnight. Solvent was removed under reduced pressure; residue was diluted with water and extracted with ethyl acetate (30 mL×3). Organic layer was washed with brine solution (20 mL), dried over anhydrous sodium sulphate and concentrated under reduced pressure to afford crude product which was purified by flash chromatography to afford 200 mg (53%) of tert-butyl 7-[[2-allyl-1-[6-(1-hydroxy-1-methyl-ethyl)-2-pyridyl]-3-oxo-pyrazolo[3,4-d]pyrimidin-6-yl]amino]-3,4-dihydro-1H-isoquinoline-2-carboxylate.

LCMS: 558 [M+1]$^+$

Step-5: Synthesis of 2-allyl-1-[6-(1-hydroxy-1-methyl-ethyl)-2-pyridyl]-6-(1,2,3,4-tetrahydroisoquinolin-7-ylamino)pyrazolo[3,4-d]pyrimidin-3-one tert-Butyl 7-[[2-allyl-1-[6-(1-hydroxy-1-methyl-ethyl)-2-pyridyl]-3-oxo-pyrazolo[3,4-d]pyrimidin-6-yl]amino]-3,4-dihydro-1H-isoquinoline-2-carboxylate (200 mg, 0.35 mmol, 1.0 eq) was dissolved in 5 mL of DCM and added TFA (1 mL) and allowed to stir at RT for 3 h. After completion of reaction, solvent was removed under reduced pressure, residue was diluted with aqueous NaHCO$_3$ solution and extracted with ethyl acetate (30 mL×3). Combined organic layer was washed with brine solution (20 mL), dried over anhydrous sodium sulphate and concentrated under reduced pressure to afford crude product which was recrystallized with DCM and n-pentane to afford 4 mg (2.5%) of 2-allyl-1-[6-(1-hydroxy-1-methyl-ethyl)-2-pyridyl]-6-(1,2,3,4-tetrahydroisoquinolin-7-ylamino)pyrazolo[3,4-d]pyrimidin-3-one as white solid. This product was treated with 0.5 mL of 1.25M ethanolic HCl. Solvent was removed under reduced pressure and product was freeze-dried to afford HCl salt of it.

LCMS: 458 [M+1]$^+$ $^1$HNMR (400 MHz, DMSO-d$_6$, HCl salt): δ 10.40 (br s, 1H), 9.50 (br s, 2H), 8.90 (s, 1H), 8.10 (t, J=7.8 Hz, 1H), 7.79 (d, J=8.2 Hz, 1H), 7.75 (br s, 1H) 7.65 (d, J=7.8 Hz, 1H), 7.50 (d, J=7.4 Hz, 1H), 7.18 (d, J=8.2 Hz, 1H), 5.72-5.62 (m, 1H), 5.0 (d, J=10.2 Hz, 1H), 4.80 (d, J=17.2 Hz, 1H), 4.70 (d, J=5.5 Hz, 2H), 4.25 (br s, 2H), 3.39-3.35 (m, 2H), 2.95 (t, J=5.9 Hz, 2H), 1.45 (s, 6H).

Example S2. Synthesis of 2-allyl-6-((2-(2-hydroxy-acetyl)-1,2,3,4-tetrahydroisoquinolin-7-yl)amino)-1-(6-(2-hydroxypropan-2-yl)pyridin-2-yl)-1,2-dihydro-3H-pyrazolo[3,4-d]pyrimidin-3-one

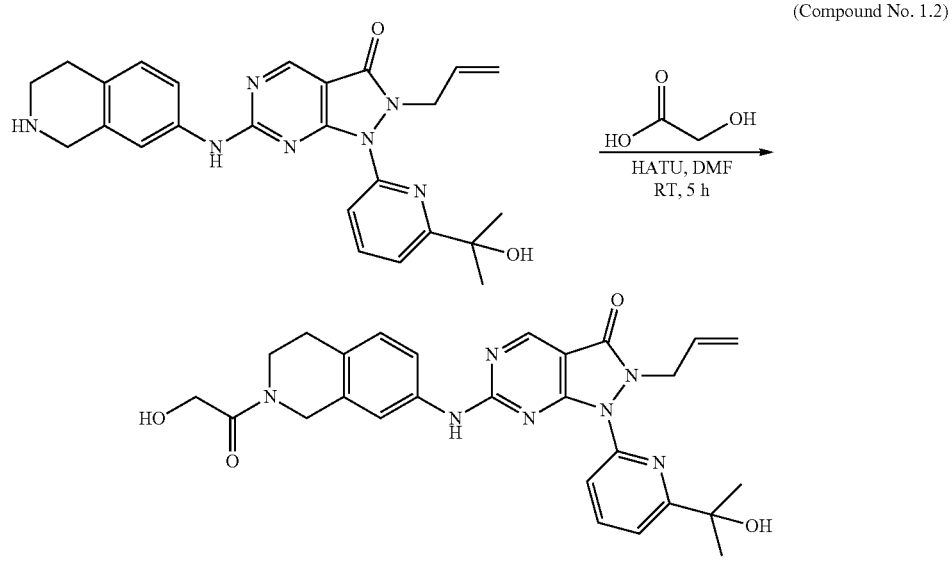

(Compound No. 1.2)

Synthesis of 2-allyl-6-[[2-(2-hydroxyacetyl)-3,4-dihydro-1H-isoquinolin-7yl]amino]-1-[6-(1-hydroxy-1-methyl-ethyl)-2-pyridyl]pyrazolo[3,4-d]pyrimidin-3-one To a stirred solution of glycolic acid (22 mg, 0.288 mmol, 1.2 eq) in 3 mL of DMF was added HATU (136 mg, 0.36 mmol, 1.5 eq) and stirred at RT for 5 minutes. 2-allyl-1-[6-(1-hydroxy-1-methyl-ethyl)-2-pyridyl]-6-(1,2,3,4-tetrahydroisoquinolin-7-ylamino)pyrazolo[3,4-d]pyrimidin-3-one (110 mg, 0.24 mmol, 1.0 eq) and DIPEA (62 mg, 0.48 mmol, 2.0 eq) were added and stirred at RT for 5 h. After completion of reaction, mixture was diluted with ice-cold water and extracted with ethyl acetate (50 mL×2). Combined organic layer was washed with brine solution (20 mL×4), dried over anhydrous sodium sulphate and concentrated under reduced pressure to obtain crude product which was purified by reverse phase chromatography to afford 15 mg (12%) of 2-allyl-6-[[2-(2-hydroxyacetyl)-3,4-dihydro-1H-isoquinolin-7-yl]amino]-1-[6-(1-hydroxy-1-methyl-ethyl)-2-pyridyl]pyrazolo[3,4-d]pyrimidin-3-one as white solid.

LCMS: 516 [M+1]$^+$ $^1$H NMR (400 MHz, DMSO-d$_6$): δ 10.30 (br s, 1H), 8.90 (s, 1H), 8.15-8.07 (m, 1H), 7.81-7.79 (m, 2H), 7.64-7.62 (m, 1H), 7.43-7.36 (m, 1H), 7.10 (d, J=8.2 Hz, 1H), 5.71-5.61 (m, 1H), 5.35 (s, 1H), 5.0 (d, J=10.2 Hz, 1H), 4.80 (d, J=16.4 Hz, 1H), 4.70-4.57 (m, 5H), 4.22-4.19 (m, 2H), 3.71-3.59 (m, 1H), 3.59 (t, J=5.5 Hz, 1H), 2.95-2.80 (m, 2H), 1.45 (s, 6H).

Example S3. Synthesis of 2-allyl-6-((2-(2-hydroxy-2-methylpropanoyl)-4,4-dimethyl-1,2,3,4-tetrahydroisoquinolin-7-yl)amino)-1-(6-(2-hydroxypropan-2-yl)pyridin-2-yl)-1,2-dihydro-3H-pyrazolo[3,4-d]pyrimidin-3-one (Compound No. 1.3)

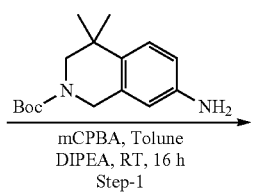

mCPBA, Tolune
DIPEA, RT, 16 h
Step-1

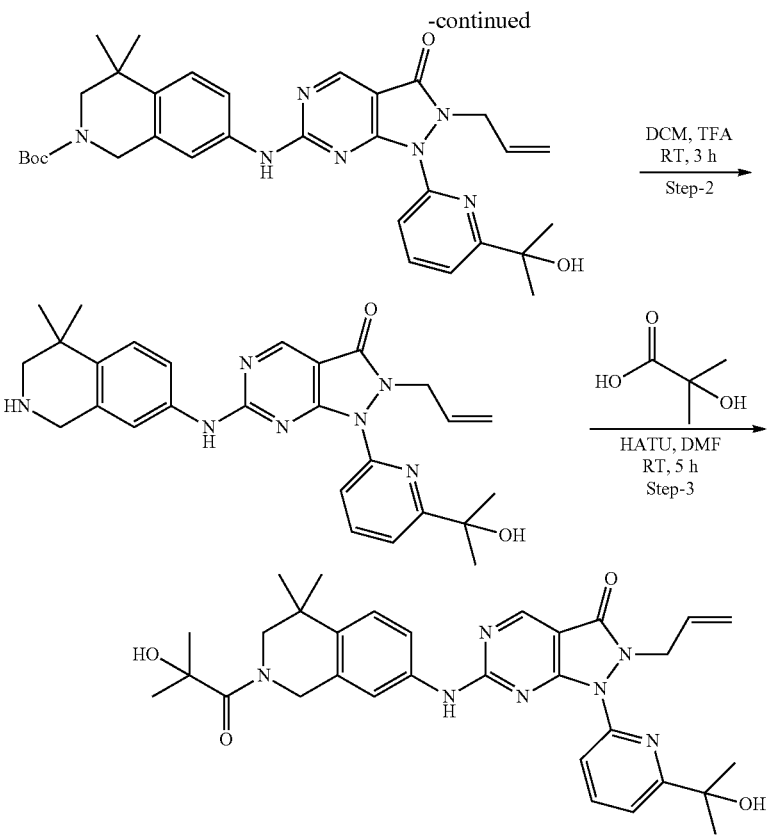

Step-1: Synthesis of tert-butyl 7-[[2-allyl-1-[6-(1-hydroxy-1-methyl-ethyl)-2-pyridyl]-3-oxo-pyrazolo[3,4-d]pyrimidin-6-yl]amino]-4,4-dimethyl-1,3-dihydroisoquinoline-2-carboxylate To a stirred solution of 2-allyl-1-[6-(1-hydroxy-1-methyl-ethyl)-2-pyridyl]-6-methylsulfanyl-pyrazolo[3,4-d]pyrimidin-3-one (500 mg, 1.40 mmol, 1.0 eq) in 5 mL of toluene was added mCPBA (172 mg, 2.80 mmol, 2.0 eq) and allowed to stir at RT for 30 minutes. Tert-butyl 7-amino-4,4-dimethyl-1,3-dihydroisoquinoline-2-carboxylate (424 mg, 1.69 mmol, 1.20 eq) and DIPEA (541 mg, 4.2 mmol, 3.0 eq) were added and allowed to stir at RT for overnight. After completion of reaction, solvent was removed under reduced pressure. Residue was diluted with water and extracted with ethyl acetate (50 mL×2). Combined organic layer was washed with brine solution (20 mL), dried over anhydrous sodium sulphate and concentrated under reduced pressure to afford crude product which was purified by flash chromatography to afford 340 mg (41.4%) of tert-butyl 7-[[2-allyl-1-[6-(1-hydroxy-1-methyl-ethyl)-2-pyridyl]-3-oxo-pyrazolo[3,4-d]pyrimidin-6-yl]amino]-4,4-dimethyl-1,3-dihydroisoquinoline-2-carboxylate.

LCMS: 586 [M+1]$^+$.

Step-2: Synthesis of 2-allyl-6-[(4,4-dimethyl-2,3-dihydro-1H-isoquinolin-7-yl)amino]-1-[6-(1-hydroxy-1-methyl-ethyl)-2-pyridyl]pyrazolo[3,4-d]pyrimidin-3-one Tert-butyl 7-[[2-allyl-1-[6-(1-hydroxy-1-methyl-ethyl)-2-pyridyl]-3-oxo-pyrazolo[3,4-d]pyrimidin-6-yl]amino]-4,4-dimethyl-1,3-dihydroisoquinoline-2-carboxylate (340 mg, 0.581 mmol, 1.0 eq) was dissolved in 5 mL of DCM and added TFA (1 mL) and allowed to stir at RT for 3 h. After completion of reaction, solvent was removed under reduced pressure to obtain crude. Compound was recrystallized with diethyl ether and n-pentane to afford 80 mg (28.3%) of 2-allyl-6-[(4,4-dimethyl-2,3-dihydro-1H-isoquinolin-7-yl)amino]-1-[6-(1-hydroxy-1-methyl-ethyl)-2-pyridyl]pyrazolo[3,4-d]pyrimidin-3-one as white solid.

LCMS: 486 [M+1]$^+$

Step-3: Synthesis of 2-allyl-1-[6-(1-hydroxy-1-methyl-ethyl)-2-pyridyl]-6-[[2-(2-hydroxy-2-methyl-propanoyl)-4,4-dimethyl-1,3-dihydroisoquinolin-7-yl]amino]pyrazolo[3,4 d]pyrimidin-3-one To a stirred solution of 2-hydroxy-2-methyl-propanoic acid (20.60 mg, 0.197 mmol, 1.2 eq) in 2 mL of DMF was added HATU (93.48 mg, 0.246 mmol, 1.5 eq) and stirred at RT for 5 minutes 2-allyl-6-[(4,4-dimethyl-2,3-dihydro-1H-isoquinolin-7-yl)amino]-1-[6-(1-hydroxy-1-methyl-ethyl)-2-pyridyl]pyrazolo[3,4-d]pyrimidin-3-one (80 mg, 0.164 mmol, 1.0 eq) and DIPEA (42.31 mg, 0.328 mmol, 2.0 eq) were added and stirred at RT for 5 h. After completion of reaction, mixture was diluted with ice-cold water and extracted with ethyl acetate (50 mL×2). Combined organic layer was washed with brine solution (20 mL×4), dried over anhydrous sodium sulphate and concentrated under reduced pressure to obtain crude product which was purified by reverse phase chromatography to afford 16.8 mg (18%) 2-allyl-1-[6-(1-hydroxy-1-methyl-ethyl)-2-pyridyl]-6-[[2-(2-hydroxy-2-methyl-propanoyl)-4,4-dimethyl-1,3-dihydroisoquinolin-7-yl]amino]pyrazolo[3,4-d]pyrimidin-3-one as white solid.

LCMS: 572 [M+1]+

¹H NMR (400 MHz, DMSO-d6): δ 10.30 (br s, 1H), 8.90 (s, 1H), 8.20 (br s, 1H), 7.79 (d, J=7.9 Hz, 2H), 7.63 (d, J=7.9 Hz, 1H), 7.40-7.39 (m, 1H), 7.33 (d, d, J=8.0 Hz 1H), 5.72-5.62 (m, 1H), 5.17 (br s, 1H), 5.01-4.98 (m, 2H), 4.84-4.79 (m, 2H), 4.7-4.89 (m, 2H), 1.46 (s, 6H), 1.37 (s, 6H), 1.2 (s, 6H).

Example S4. Synthesis of 2-allyl-6-[(4,4-dimethyl-2,3-dihydro-1H-isoquinolin-7-yl)amino]-1-[6-(1-hydroxy-1-methyl-ethyl)-2-pyridyl]pyrazolo[3,4-d]pyrimidin-3-one

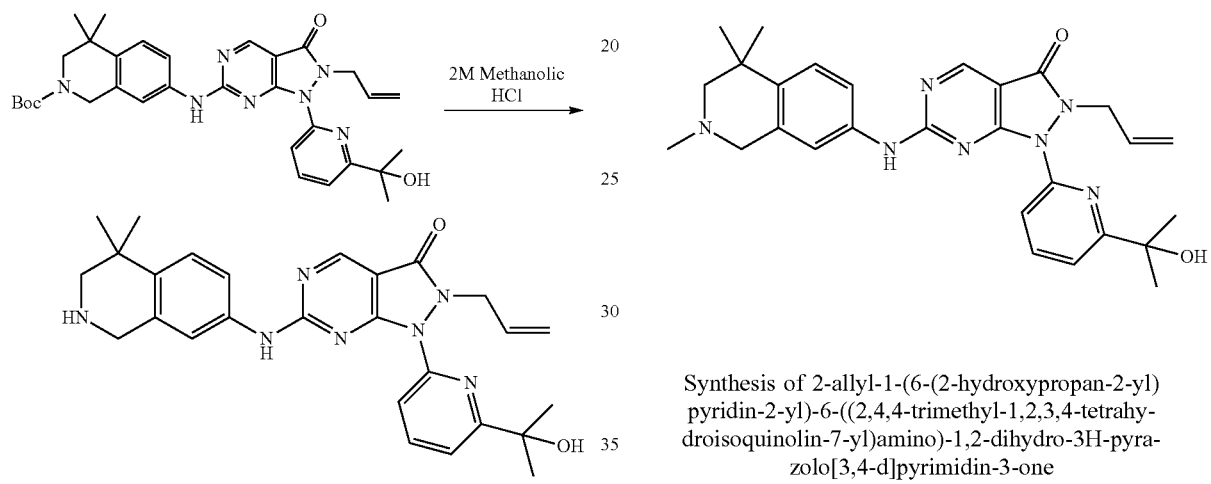

(Compound No. 1.4)

Synthesis of 2-allyl-6-[(4,4-dimethyl-2,3-dihydro-1H-isoquinolin-7-yl)amino]-1-[6-(1-hydroxy-1-methyl-ethyl)-2-pyridyl]pyrazolo[3,4-d]pyrimidin-3-one Tert-butyl 7-[[2-allyl-1-[6-(1-hydroxy-1-methyl-ethyl)-2-pyridyl]-3-oxo-pyrazolo[3,4-d]pyrimidin-6-yl]amino]-4,4-dimethyl-1,3-dihydroisoquinoline-2-carboxylate (60 mg, 0.102 mmol, 1.0 eq) was dissolved in 1 mL of ethanol and added 2M HCl in methanol and allowed to stir at RT for 16 h. After completion of reaction, solvent was removed under reduced pressure to obtain crude. Product was recrystallized with diethyl ether and n-pentane and dried under reduced pressure. Product was freeze-dried to afford 48 mg (90%) HCl salt of 2-allyl-6-[(4,4-dimethyl-2,3-dihydro-1H-isoquinolin-7-yl)amino]-1-[6-(1-hydroxy-1-methyl-ethyl)-2-pyridyl]pyrazolo[3,4-d]pyrimidin-3-one as off-white solid.

LCMS: 486 [M+1]+

¹HNMR (400 MHz, DMSO-d6, HCl Salt): δ 10.39 (br s, 1H), 9.3 (br s, 1H), 8.90 (s, 1H), 8.07 (t, J=7.89 Hz, 1H), 7.8 (d, J=7.45 Hz 1H), 7.71 (br s, 1H), 7.64 (d, J=7.89 Hz, 1H), 7.53 (dd, J=8.77, 2.19 Hz, 1H), 7.44 (d, J=8.33 Hz, 1H), 5.67 (dd, J=17.10, 10.52 Hz, 1H), 5.0 (dd, J 10.30, 1.10 Hz, 1H), 4.80 (dd, J=17.10, 1.32 Hz, 1H), 4.70-4.62 (d, J=5.70 Hz, 2H), 4.23 (s, 2H), 3.23 (d, J=5.70 Hz, 2H), 1.46 (s, 6H), 1.34 (s, 6H).

Example S5. Synthesis of 2-allyl-1-(6-(2-hydroxypropan-2-yl)pyridin-2-yl)-6-((2,4,4-trimethyl-1,2,3,4-tetrahydroisoquinolin-7-yl)amino)-1,2-dihydro-3H-pyrazolo[3,4-d]pyrimidin-3-one

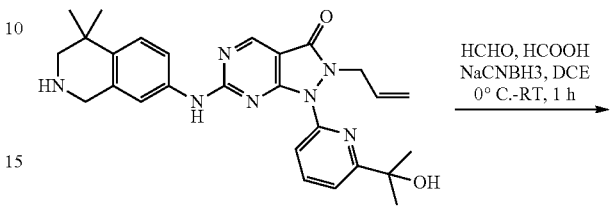

(Compound No. 1.5)

Synthesis of 2-allyl-1-(6-(2-hydroxypropan-2-yl)pyridin-2-yl)-6-((2,4,4-trimethyl-1,2,3,4-tetrahydroisoquinolin-7-yl)amino)-1,2-dihydro-3H-pyrazolo[3,4-d]pyrimidin-3-one To a stirred solution of 2-allyl-6-((4,4-dimethyl-1,2,3,4-tetrahydroisoquinolin-7-yl)amino)-1-(6-(2-hydroxypropan-2-yl)pyridin-2-yl)-1,2-dihydro-3H-pyrazolo[3,4-d]pyrimidin-3-one (110 mg, 0.226 mmol, 1.0 eq) and 37% formaldehyde in water (1.2 mL) in 5 mL of dichloroethane was added dropwise acetic acid (0.068 mL, 1.132 mmol, 5.0 eq) at 0° C. The resulting mixture was stirred at RT for 1 h followed by addition of NaCNBH₄ (56 mg, 0.904 mmol, 4.0 eq) at 0° C. The resulting mixture was stirred at RT for 1 h. The progress of reaction was monitored by LCMS. After completion of reaction, solvent was removed under reduced pressure. Residue was basified with saturated solution of NaHCO₃ (100 mL) and extracted with ethyl acetate (100 mL×2). The combined organic layer was washed with water (50 mL) and brine (50 mL), dried over Na₂SO₄ and concentrated under reduced pressure. Crude was purified by reverse phase chromatography to afford 8 mg free base of 2-allyl-1-(6-(2-hydroxypropan-2-yl)pyridin-2-yl)-6-((2,4,4-trimethyl-1,2,3,4-tetrahydroisoquinolin-7-yl)amino)-1,2-dihydro-3H-pyrazolo[3,4-d]pyrimidin-3-one as brown solid.

LCMS: 501 [M+1]+

¹H NMR (400 MHz, CDCl₃): δ 10.21 (s, 1H), 8.84 (br s, 1H), 8.03-8.0 (m, 1H), 7.73 (d, J 7.89 Hz, 1H), 7.66 (d, J=7.89 Hz, 1H), 7.57-7.52 (m, 1H), 7.40 (d, J=8.77 Hz, 1H), 7.30 (d, J 8.33 Hz, 1H), 5.71-5.61 (m, 1H), 5.35 (br s, 1H), 4.99 (d, J=10.96 Hz, 1H), 4.81 (d, J=18 Hz, 1H), 4.68 (d, J=6.58 Hz, 2H), 2.46-2.31 (m, 3H), 1.60 (s, 3H), 1.49 (br s, 6H), 1.25 (br s, 6H).

Example S6. Synthesis of 2-allyl-6-[[2-(2-hydroxyacetyl)-4,4-dimethyl-1,3-dihydroisoquinolin-7-yl]amino]-1-[6-(1-hydroxy-1-methyl-ethyl)-2-pyridyl]pyrazolo[3,4-d]pyrimidin-3-one

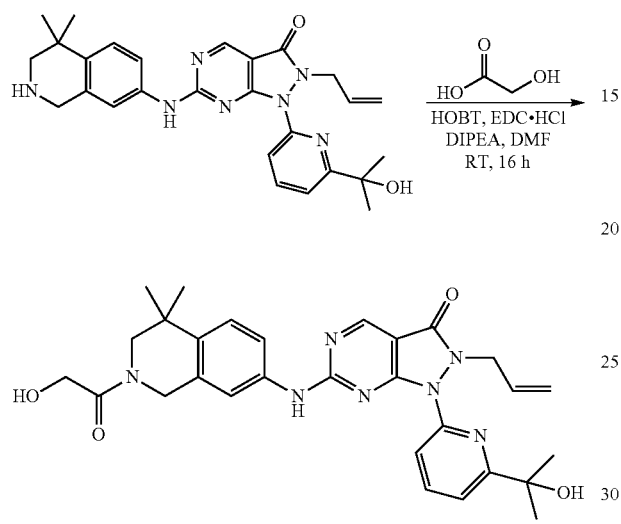

Synthesis of 2-allyl-6-[[2-(2-hydroxyacetyl)-4,4-dimethyl-1,3-dihydroisoquinolin-7-yl]amino]-1-[6-(1-hydroxy-1-methyl-ethyl)-2-pyridyl]pyrazolo[3,4-d]pyrimidin-3-one To a stirred solution of 2-hydroxyacetic acid (23.50 mg, 0.309 mmol, 1.5 eq) in 2 mL of DMF were added EDC*HCl (39.34 mg, 0.206 mmol, 1.0 eq) & HOBT (2.78 mg, 0.0206 mmol, 0.1 eq) and stirred at RT for 5 min. 2-Allyl-6-[(4,4-dimethyl-2,3-dihydro-1H-isoquinolin-7-yl)amino]-1-[6-(1-hydroxy-1-methyl-ethyl)-2-pyridyl]pyrazolo[3,4-d]pyrimidin-3-one (100 mg, 0.206 mmol, 1.0 eq) and DIPEA (79.72 mg, 0.618 mmol, 3.0 eq) were added and stirred at RT for 16 h. The progress of reaction was monitored by LCMS. After completion of reaction, mixture was diluted with ice-cold water and extracted with ethyl acetate (50 mL×2). Combined organic layers was washed with brine solution (20 mL×4), dried over anhydrous sodium sulphate and concentrated under reduced pressure to obtain crude product which was purified by reverse phase chromatography to afford 8 mg (7%) of 2-allyl-6-[[2-(2-hydroxyacetyl)-4,4-dimethyl-1,3-dihydroisoquinolin-7-yl]amino]-1-[6-(1-hydroxy-1-methyl-ethyl)-2-pyridyl]pyrazolo[3,4-d]pyrimidin-3-one as off white solid.

LCMS: 544 [M+1]+

$^{1}$H NMR (400 MHz, DMSO-d6): δ 10.30 (br s, 1H), 8.90 (s, 1H), 8.18 (br s, 1H), 7.83-7.79 (m, 1H), 7.65-7.62 (m, 1H), 7.45-7.23 (m, 2H), 5.75-5.6 (m, 1H), 5.35 (br s, 1H), 5.0 (dd, J=10.41, 1.21 Hz, 1H), 4.84-4.79 (m, 1H), 4.71-4.62 (m, 3H), 4.6 (s, 1H), 4.28-4.26 (m, 1H), 4.22-4.20 (m, 1H), 3.52-3.5 (m, 2H), 1.46 (s, 6H), 1.21 (d, J=11.40 Hz, 6H).

Example S7. Synthesis of 2-ethyl-1-(6-(2-hydroxypropan-2-yl)pyridin-2-yl)-6-((1,2,3,4-tetrahydroisoquinolin-7-yl)amino)-1,2-dihydro-3H-pyrazolo[3,4-d]pyrimidin-3-one (Compound No. 1.7)

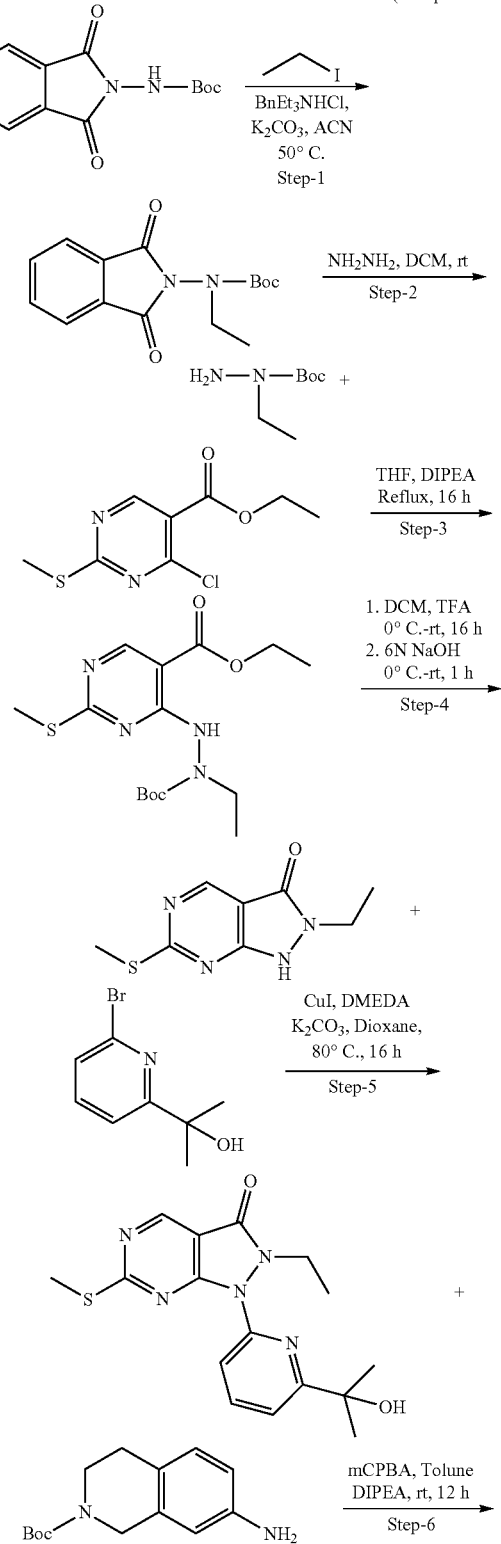

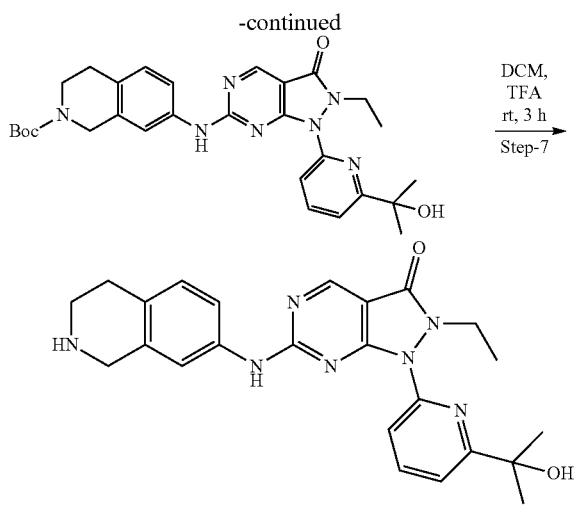

Step-1: Synthesis of tert-butyl (1,3-dioxoisoindolin-2-yl)(ethyl)carbamate

To a stirred solution of tert-butyl (1,3-dioxoisoindolin-2-yl)carbamate (5.0 g, 19.064 mmol, 1.0 eq), in $CH_3CN$ (100 mL) was added ethyliodide (1.83 mL, 22.877 mmol, 1.2 eq), $BnEt_3N^+Cl^-$ (435 mg, 1.906 mmol, 0.1 eq) and $K_2CO_3$ (5.27 g, 38.128 mmol, 2.0 eq) at RT. The resulting mixture was heated at 55° C. for 12 h. The progress of reaction was monitored by LCMS. The reaction mixture was diluted with water (50 mL), extracted with EtOAc (2×100 mL). The combined organic layers were washed with water (50 mL), with brine (50 mL), dried over $Na_2SO_4$, concentrated and purified by recrystallization to afford the desired compound, tert-butyl (1,3-dioxoisoindolin-2-yl)(ethyl)carbamate (5.21 g, 94.19%) as light yellow solid.
LCMS: 291.1[M+1]$^+$

Step-2: Synthesis of tert-butyl 1-ethylhydrazine-1-carboxylate

To a stirred solution of tert-butyl (1,3-dioxoisoindolin-2-yl)(ethyl)carbamate. (5.0 g, 17.22 mmol, 1.0 eq), in $CH_2Cl_2$ (100 mL) was added $NH_2NH_2*H_2O$ (2.16 mL, 34.44 mmol, 2.0 eq) at RT. The resulting mixture was stirred at RT for 12 h, after which formation of white precipitates was obr served. Progress of the reaction was monitored by $^1H$ NMR. The reaction mixture was filtered and the filtrate was concentrated and purified by n-pentane to afford the desired compound, tert-butyl 1-ethylhydrazine-1-carboxylate (2.1 g, 75.26%) as light yellow liquid.
$^1H$ NMR (400 MHz, $CDCl_3$): δ 3.95 (br s, 2H), 3.40 (q, 2H), 1.47 (s, 9H), 1.12 (t, 3H).

Step-3: Synthesis of ethyl 4-(2-(tert-butoxycarbonyl)-2-ethylhydrazinyl)-2-(methylthio) pyrimidine-5-carboxylate To a stirred solution of ethyl 4-chloro-2-methylsulfanyl-pyrimidine-5-carboxylate (2.0 g, 8.595 mmol, 1.0 eq) and tert-butyl 1-ethylhydrazine-1-carboxylate (2.06 g, 12.893 mmol, 1.5 eq) in (50 mL) of THF was added DIPEA (3.73 mL, 21.487 mmol, 2.5 eq) and stirred at 60° C. for 16 h. Solvent was removed under reduced pressure. Residue was diluted with water (50 mL) and extracted with EtOAc (50 mL×2). Organic layer was washed with brine solution (50 mL), dried over anhydrous $Na_2SO_4$ and concentrated under reduced pressure to afford the desired compound, ethyl 4-(2-(tert-butoxycarbonyl)-2-ethylhydrazinyl)-2-(methylthio)pyrimidine-5-carboxylate (2.91 g, 95.03%) as light yellow liquid.
LCMS: 356.0 [M+1]$^+$

Step-4: Synthesis of 2-ethyl-6-(methylthio)-1,2-dihydro-3H-pyrazolo[3,4-d]pyrimidin-3-one To a stirred solution of ethyl 4-(2-(tert-butoxycarbonyl)-2-ethylhydrazinyl)-2-(methylthio) pyrimidine-5-carboxylate (2.90 g, 8.136 mmol, 1.0 eq) in $CH_2Cl$ (50 mL) was added TFA (8.136 mL) dropwise at 0° C. and allowed to stir at RT for 12 h. After completion of reaction, solvent was removed under reduced pressure. Residue was diluted with EtOH (20 mL). 6N NaOH solution (10 mL) was added in to above at 0° C. and allowed to stir at RT for 1 h. After completion of reaction, mixture was acidified by using 6N HCl solution. EtOH was removed under reduced pressure; residue obtained was cooled to RT and extracted with chloroform (100 mL×3). Organic layer was washed with brine solution, dried over anhydrous sodium sulphate and concentrated under reduced pressure to afford the desired compound, 2-ethyl-6-(methylthio)-1,2-dihydro-3H-pyrazolo[3,4-d]pyrimidin-3-one (1.15 g, 67.25%) as yellow solid.
LCMS: 211.1 [M+1]$^+$

Step-5: Synthesis of 2-ethyl-1-(6-(2-hydroxypropan-2-yl)pyridin-2-yl)-6-(methylthio)-1,2-dihydro-3H-pyrazolo[3,4-d]pyrimidin-3-one To a stirred solution of 2-ethyl-6-(methylthio)-1,2-dihydro-3H-pyrazolo[3,4-d]pyrimidin-3-one (250 mg, 1.189 mmol, 1.0 eq) and 2-(6-bromo-2-pyridyl)propan-2-ol (308 mg, 1.426 mmol, 1.20 eq) in dioxane (10 mL) were added $K_2CO_3$ (328 mg, 2.378 mmol, 2.0 eq) and the resulting mixture was purged with nitrogen for 10 min followed by addition of CuI (45 mg, 0.237 mmol, 0.2 eq), and DIPEA (42 mg, 0.475 mmol, 0.4 eq) and again purged with nitrogen for 10 min, stirred at 90° C. for 12 h. After completion of reaction, the reaction mixture was diluted with water and extracted with EtOAc (50 mL×2). Combined organic layer was washed with water (50 mL) brine solution (50 mL), dried over anhydrous sodium sulphate and concentrated under reduced pressure to afford crude product, which was purified by flash chromatography to afford the desired compound, 2-ethyl-1-(6-(2-hydroxypropan-2-yl)pyridin-2-yl)-6-(methylthio)-1,2-dihydro-3H-pyrazolo[3,4-d]pyrimidin-3-one (170 mg, 40.24%) as off white viscous.
LCMS: 346.2 [M+1]$^+$

Step-6: Synthesis of tert-butyl 7-((2-ethyl-1-(6-(2-hydroxypropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate To a stirred solution of 2-ethyl-1-(6-(2-hydroxypropan-2-yl)pyridin-2-yl)-6-(methylthio)-1,2-dihydro-3H-pyrazolo[3,4-d]pyrimidin-3-one (165 mg, 0.477 mmol, 1.0 eq) in toluene (10 mL) was added m-CPBA (165 mg, 0.954 mmol, 2.0 eq) and allowed to stir at RT for 30 min. Tert-butyl 7-amino-3,4-dihydro-1H-isoquinoline-2-carboxylate (131 mg, 0.525 mmol, 1.3 eq) and DIPEA (0.331 mL, 1.908 mmol, 4.0 eq) were added and allowed to stir at RT for 12 h. The formation of precipitate was observed which was filtered to afford the desired compound, tert-butyl 7-((2-ethyl-1-(6-(2-hydroxypropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate (110 mg, 42.30%) as off white solid.

LCMS: 546.4 [M+1]+

Step-7: Synthesis of 2-ethyl-1-(6-(2-hydroxypropan-2-yl)pyridin-2-yl)-6-((1,2,3,4-tetrahydroisoquinolin-7-yl)amino)-1,2-dihydro-3H-pyrazolo[3,4-d]pyrimidin-3-one tert-butyl 7-((2-ethyl-1-(6-(2-hydroxypropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate (105 mg, 0.192 mmol, 1.0 eq) was dissolved in dioxane (2 mL) and added 4M HCl (2 mL) and allowed to stir at RT for 1 h. After completion of reaction, the reaction mixture was filtered and dried under reduced pressure to afford the desired compound, 2-ethyl-1-(6-(2-hydroxypropan-2-yl)pyridin-2-yl)-6-((1,2,3,4-tetrahydroisoquinolin-7-yl)amino)-1,2-dihydro-3H-pyrazolo[3,4-d]pyrimidin-3-one (65 mg, 75.82%) as HCl salt yellow solid.

LCMS: 446.3 [M+1]+

$^1$H NMR (400 MHz, DMSO-d$_6$): δ 10.35 (brs, 1H), 9.36 (brs, 2H), 8.88 (s, 1H), 8.11 (t, J=7.89 Hz, 1H), 7.85 (d, J=7.89 Hz, 1H), 7.75 (brs, 1H), 7.66 (d, J=7.89 Hz, 1H), 7.51 (d, J=8.33 Hz, 1H), 7.18 (d, J=8.77 Hz, 1H), 4.26 (brs, 2H), 4.05 (d, J=7.02 Hz, 2H), 3.36 (brs, 2H), 2.89-3.04 (m, 2H), 1.44 (s, 6H), 0.98 (t, J=7.02 Hz, 3H).

Example S8. Synthesis of 2-allyl-1-(6-(2-hydroxypropan-2-yl)pyridin-2-yl)-6-(1,2,3,4-tetrahydroisoquinolin-6-ylamino)-1H-pyrazolo[3,4-d]pyrimidin-3(2H)-one (Compound No. 1.8)

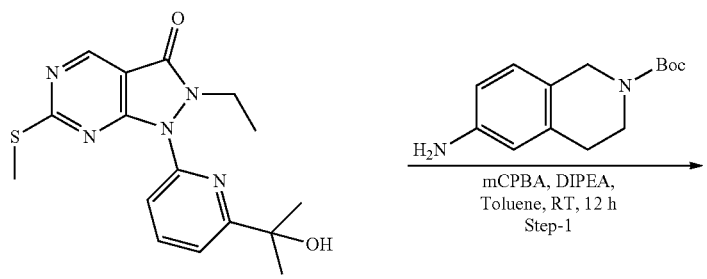

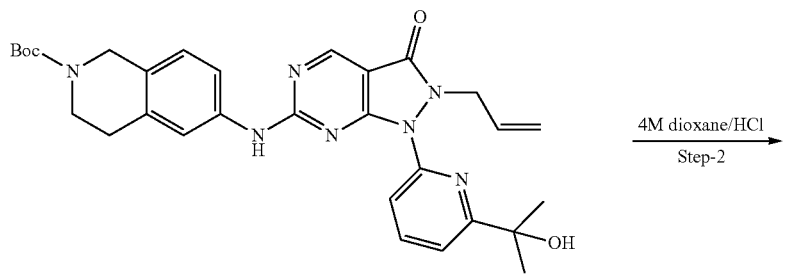

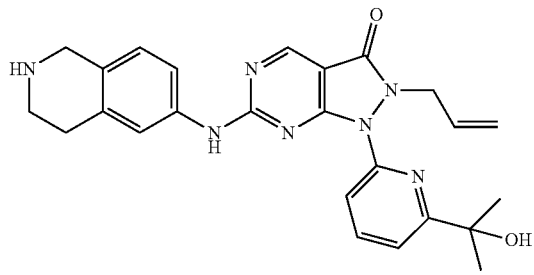

Step-1: Synthesis of tert-butyl 6-(2-allyl-1-(6-(2-hydroxypropan-2-yl)pyridin-2-yl)-3-oxo-2,3-dihydro-1H-pyrazolo[3,4-d]pyrimidin-6-ylamino)-3,4-dihydroisoquinoline-2(1H)-carboxylate To a stirred solution of 2-allyl-1-(6-(2-hydroxypropan-2-yl)pyridin-2-yl)-6-(methylthio)-1H-pyrazolo[3,4-d]pyrimidin-3(2H)-one (300 mg, 0.84 mmol, 1.0 eq) in toluene (5 mL) was added m-CPBA (361 mg, 2.10 mmol, 2.5 eq) and allowed to stir at RT for 30 min. tert-Butyl 6-amino-3,4-dihydroisoquinoline-2(1H)-carboxylate (208 mg, 0.84 mmol, 1.0 eq) and DIPEA (433 mg, 3.36 mmol, 4.0 eq) were added and allowed to stir at RT for 12 h. Progress of reaction was monitored by LCMS. After completion of reaction, precipitated compound was filtered off, washed with toluene (3 mL) and dried under reduced pressure to obtain tert-butyl 6-(2-allyl-1-(6-(2-hydroxypropan-2-yl)pyridin-2-yl)-3-oxo-2,3-dihydro-1H-pyrazolo[3,4-d]pyrimidin-6-ylamino)-3,4-dihydroisoquinoline-2(1H)-carboxylate (220 mg, 47.00%).

LCMS: 558 [M+1]$^+$

Step-2: Synthesis of 2-allyl-1-(6-(2-hydroxypropan-2-yl)pyridin-2-yl)-6-(1,2,3,4-tetrahydroisoquinolin-6-ylamino)-1H-pyrazolo[3,4-d]pyrimidin-3(2H)-one tert-Butyl 6-(2-allyl-1-(6-(2-hydroxypropan-2-yl)pyridin-2-yl)-3-oxo-2,3-dihydro-1H-pyrazolo[3,4-d]pyrimidin-6-ylamino)-3,4-dihydroisoquinoline-2(1H)-carboxylate (220 mg, 0.395 mmol, 1.0 eq) was dissolved in 4N HCl in dioxane (5 mL) at 0° C. Reaction was stirred at RT for 30 min. Progress of reaction was monitored by LCMS. After completion of reaction, precipitated compound was filtered off and dried under reduced pressure. Solid was triturated with diethyl ether (10 mL), filtered off and dried under reduced pressure to obtain 2-allyl-1-(6-(2-hydroxypropan-2-yl)pyridin-2-yl)-6-(1,2,3,4-tetrahydroisoquinolin-6-ylamino)-1H-pyrazolo[3,4-d]pyrimidin-3(2H)-one (150 mg, 77.3%) as HCl salt.

LCMS: 448 [M+1]$^+$ $^1$H NMR (400 MHz, DMSO-d$_6$, HCl salt): δ 10.38 (br s, 1H), 9.25 (s, 1H), 8.90 (s, 1H), 8.05 (t, J=7.89 Hz, 1H), 7.80 (d, J=8.33 Hz, 2H), 7.65 (d, J=7.45 Hz, 1H), 7.50 (d, J=8.33 Hz, 1H), 7.20 (d, J=8.33 Hz, 1H), 5.72-5.62 (m, 1H), 5.00 (d, J=9.21 Hz, 1H), 4.90 (d, J=17.10 Hz, 1H), 4.70 (d, J=6.14 Hz, 2H), 4.25-4.2 (m, 2H), 3.41-3.36 (m, 2H), 3.02-2.99 (m, 2H), 1.50 (s, 6H).

Example S9. Synthesis of 2-allyl-1-(6-(2-hydroxypropan-2-yl)pyridin-2-yl)-6-((2-methyl-1,2,3,4-tetrahydroisoquinolin-7-yl)amino)-1,2-dihydro-3H-pyrazolo[3,4-d]pyrimidin-3-one (Compound No. 1.9)

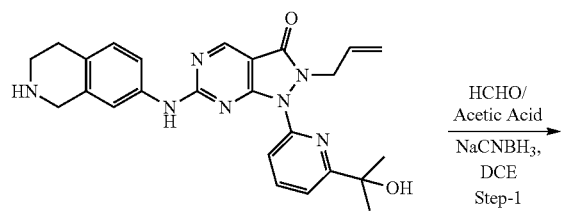

HCHO/
Acetic Acid
—————→
NaCNBH$_3$,
DCE
Step-1

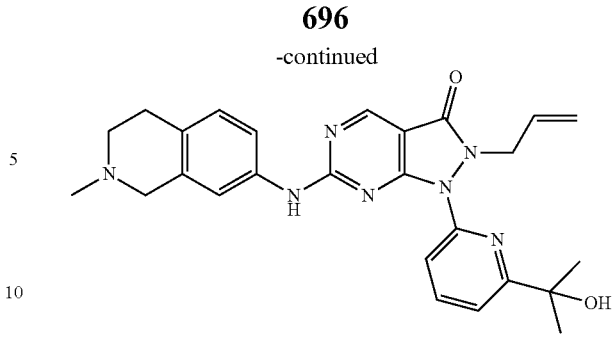

Synthesis of 2-allyl-1-(6-(2-hydroxypropan-2-yl)pyridin-2-yl)-6-((2-methyl-1,2,3,4-tetrahydroisoquinolin-7-yl)amino)-1,2-dihydro-3H-pyrazolo[3,4-d]pyrimidin-3-one To a stirred solution of 2-allyl-1-(6-(2-hydroxypropan-2-yl)pyridin-2-yl)-6-((1,2,3,4-tetrahydroisoquinolin-7-yl)amino)-1,2-dihydro-3H-pyrazolo[3,4-d]pyrimidin-3-one (170 mg, 0.3715 mmol, 1.0 eq) and HCHO (0.1 mL) in dichloroethane (7 mL) was added acetic acid (111.45 mg, 1.85 mmol, 5.0 eq) dropwise at 0° C. The resulting mixture was stirred at RT for 1 h followed by addition of NaCNBH$_3$ (70.2 mg, 1.1145 mmol, 3.0 eq) at 0° C. The resulting mixture was stirred at RT for 1 h. The progress of reaction was monitored by LCMS. The reaction mixture was concentrated, basified with saturated solution of NaHCO$_3$ (100 mL) extracted with EtOAc (2×100 mL). The combined organic layer extracts were washed with water (50 mL), with brine (50 mL) dried over Na$_2$SO$_4$ and concentrated under reduced and purified by reversed phase chromatography to afford the desired compound, 2-allyl-1-(6-(2-hydroxypropan-2-yl)pyridin-2-yl)-6-((2-methyl-1,2,3,4-tetrahydroisoquinolin-7-yl)amino)-1,2-dihydro-3H-pyrazolo[3,4-d]pyrimidin-3-one (0.023 g, 13.14%) as off white solid.

LCMS: 472 [M+1]$^+$ $^1$H NMR (400 MHz, DMSO-d$_6$): δ 10.22 (br s, 1H), 8.87 (s, 1H), 8.15 (s, 1H), 8.01 (t, J=7.89 Hz, 1H), 7.76 (d, J=8.33 Hz, 1H), 7.64 (d, J=7.89 Hz, 1H), 7.57 (br s, 1H), 7.40 (d, J=8.77 Hz, 1H), 7.05 (d, J=8.77 Hz, 1H), 5.70-5.64 (m, 1H), 5.36-5.29 (m, 1H), 4.99 (d, J=10.52 Hz, 1H), 4.81 (d, 1H), 4.68 (d, J=4.82 Hz, 2H), 3.49 (br s, 2H), 2.77 (br s, 2H), 2.61 (br s, 2H), 2.38 (s, 3H), 1.46 (s, 6H).

Example S10. Synthesis of 1-(6-(2-hydroxypropan-2-yl)pyridin-2-yl)-2-isopropyl-6-((1,2,3,4-tetrahydroisoquinolin-7-yl)amino)-1,2-dihydro-3H-pyrazolo[3,4-d]pyrimidin-3-one (Compound No. 1.10)

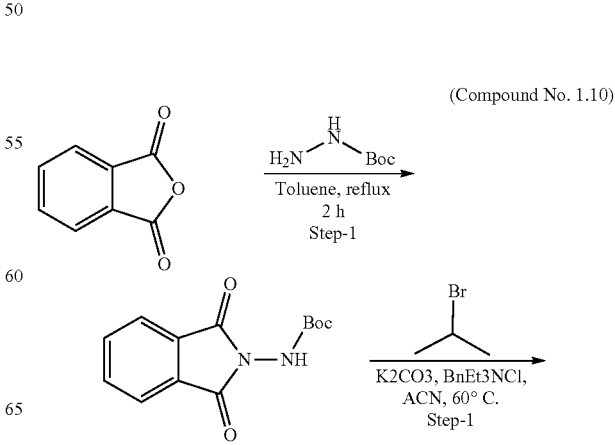

-continued

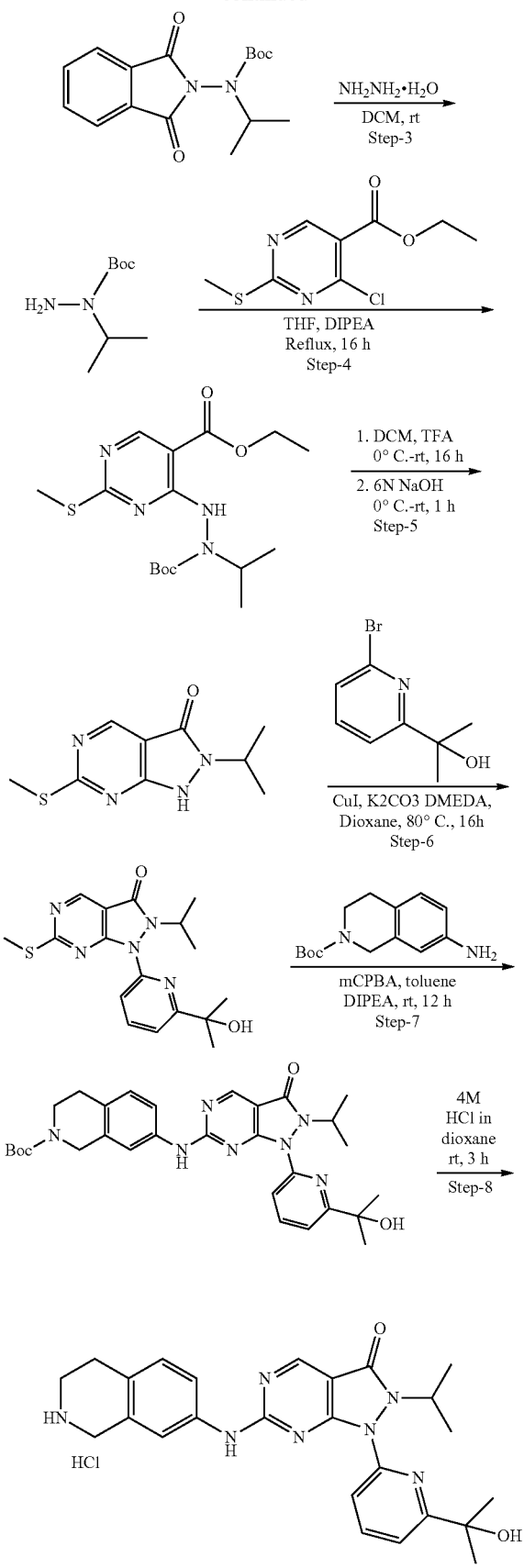

Step-1: Synthesis of tert-butyl (1,3-dioxoisoindolin-2-yl)carbamate

A mixture of phthalic anhydride (15 g, 101.2 mmol) and tert-butylcarbazate (13.3 g, 101.2 mmol) in toluene (200 mL) was refluxed for 3 h. The mixture was allowed to cool and filtered. The white solid product obtained was dissolved in ethyl acetate and washed with water and brine (100 mL×3). The organic layer was dried over anhydrous sodium sulphate and concentrated under reduced pressure to give tert-butyl (1,3-dioxoisoindolin-2-yl)carbamate (15 g, 56%) as a white solid.
LCMS: 263.1 [M+1]$^+$

Step-2: Synthesis of tert-butyl (1,3-dioxoisoindolin-2-yl)(isopropyl)carbamate To a solution of tert-butyl 1,3-dioxoisoindolin-2-ylcarbamate (10.0 g, 38.12 mmol) in CH$_3$CN (100 mL), K$_2$CO$_3$ (21.07 g, 152.5 mmol), triethylbenzylammonium chloride (1.736 g, 7.62 mmol) was added under stirring. Further, 2-bromopropane (5.62 g, 45.75 mmol) was added dropwise under stirring. The reaction was purged with nitrogen and mixture was heated at 60° C. 12 h. After completion the reaction, mixture was cooled to RT and solvent was evaporated. The residue was diluted with water, and extracted with EtOAc (100 mL×5). The combined extracts were washed with brine, dried over sodium sulphate, and concentrated to give the title compound as a white solid (9.88 g, 85%).
LCMS: 305.1 [M+1]$^+$

Step-3: Synthesis of tert-butyl 1-isopropylhydrazine-1-carboxylate

To a solution of tert-butyl (1,3-dioxoisoindolin-2-yl)(isopropyl)carbamate (9.88 g, 32.5 mmol) in dry CH$_2$Cl$_2$ (50 mL), NH$_2$NH$_2$.H$_2$O (3.25 g, 65.0 mmol) was added dropwise at 0° C. under inert atmosphere. The resulting mixture was stirred at RT for 72 h. The progress of the reaction was monitored by TLC. After completion, the solvent was removed under reduced pressure and the resulting mass was washed with pentane. The resulting precipitate formed if any was removed by filtration. The filtrate was concentrated to give the title compound as yellow oil (2.62 g, 46%).
LCMS: 175.1 [M+1]$^+$

Step-4: Synthesis of ethyl 4-(2-(tert-butoxycarbonyl)-2-isopropylhydrazinyl)-2-(methylthio)pyrimidine-5-carboxylate To a stirred solution of ethyl 4-chloro-2-methylsulfanyl-pyrimidine-5-carboxylate (2 g, 11.47 mmol, 1.0 eq) and tert-butyl 1-isopropylhydrazine-1-carboxylate (2.66 g, 11.47 mmol, 1.0 eq) in dry THF (50 mL), DIPEA (4.99 mL, 28.69 mmol, 2.5 eq) was added and the resulting solution was stirred at reflux temperature for 16 h. After completion of reaction, solvent was removed under reduced pressure. Residue was diluted with water (20 mL) and extracted with ethyl acetate (20 mL×3). The combined organic layer was washed with brine solution (10 mL×2), dried over anhydrous sodium sulphate and concentrated under reduced pressure to obtain crude product which was purified by flash chromatography (MeOH:CH$_2$Cl$_2$ 1-10%) to afford ethyl 4-(2-(tert-butoxycarbonyl)-2-isopropylhydrazinyl)-2-(methylthio)pyrimidine-5-carboxylate (1.2 g, 38%) as oily liquid.
LCMS: 371.1 [M+1]$^+$ Step-5: Synthesis of 2-isopropyl-6-(methylthio)-1,2-dihydro-3H-pyrazolo[3,4-d]pyrimidin-3-one To a stirred solution of ethyl 4-(2-(tert-butoxycarbonyl)-2-isopropylhydrazinyl)-2-(methylthio)pyrimidine-5-carboxylate (1 g, 2.96 mmol, 1.0 eq) in CH$_2$Cl$_2$ (10 mL) was added TFA (2.0 mL) dropwise at 0° C. and the resulting solution was allowed to stir at RT for 12 h. After completion of reaction, solvent was removed under reduced pressure. The residue was diluted with EtOH (10 mL) and 6N NaOH solution (3 mL) was added at 0° C. and the resulting solution was allowed to stir at RT for 1 h. After completion of reaction, mixture was acidified with 6N HCl solution (3 mL). Solvent was removed under reduced pressure; residue obtained was cooled to RT and extracted with CH$_2$Cl$_2$ (10 mL×3). The combined organic layer was washed with brine solution, dried over anhydrous Na$_2$SO$_4$ and concentrated under reduced pressure to afford 2-isopropyl-6-(methylthio)-1,2-dihydro-3H-pyrazolo[3,4-d]pyrimidin-3-one (0.27 g, 45%) as yellow solid.

LCMS: 225 [M+1]$^+$

Step-6: Synthesis of 1-(6-(2-hydroxypropan-2-yl)pyridin-2-yl)-2-isopropyl-6-(methylthio)-1,2-dihydro-3H-pyrazolo[3,4-d]pyrimidin-3-one To a stirred solution of 2-isopropyl-6-(methylthio)-1,2-dihydro-3H-pyrazolo[3,4-d]pyrimidin-3-one (0.26 g, 1.16 mmol, 1.0 eq) and 2-(6-bromo-2-pyridyl)propan-2-ol (0.3 g, 1.39 mmol, 1.20 eq) in dioxane (10 mL) were added CuI (0.044 g, 0.23 mmol, 1.0 eq), K$_2$CO$_3$ (0.32 g, 2.32 mmol, 2 eq) and DIPEA (0.041 g, 0.46 mmol, 0.4 eq) and stirred at 80° C. 12 h. After completion of reaction, solvent was removed under reduced pressure; residue was diluted with water and extracted with ethyl acetate (10 mL×3). Combined organic layer was washed with brine solution, dried over anhydrous sodium sulphate and concentrated under reduced pressure to afford crude product, which was purified by flash chromatography to afford 1-(6-(2-hydroxypropan-2-yl)pyridin-2-yl)-2-isopropyl-6-(methylthio)-1,2-dihydro-3H-pyrazolo[3,4-d]pyrimidin-3-one (55 mg, 13+%) as yellow oil.

LCMS: 360 [M+1]$^+$

Step-7: Synthesis of tert-butyl 7-((1-(6-(2-hydroxypropan-2-yl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(6-(2-hydroxypropan-2-yl)pyridin-2-yl)-2-isopropyl-6-(methylthio)-1,2-dihydro-3H-pyrazolo[3,4-d]pyrimidin-3-one (50 mg, 0.14 mmol, 1.0 eq) in toluene (5 mL) was added m-CPBA (48.0 mg, 027 mmol, 2.0 eq) and allowed to stir at RT for 30 min. Further, tert-butyl 7-amino-3,4-dihydro-1H-isoquinoline-2-carboxylate (38 mg, 0.15 mmol, 1.1 eq) and DIPEA (0.09 mL, 0.55 mmol, 4 eq) were added and allowed to stir at RT for 12 h. After completion of reaction, solvent was removed under reduced pressure; residue was diluted with water and extracted with ethyl acetate (5 mL×3). The combined organic layer was washed with brine solution (10 mL), dried over anhydrous Na$_2$SO$_4$ and concentrated under reduced pressure to afford crude product which was purified by flash chromatography to afford tert-butyl 7-[[2-allyl-1-[6-(1-hydroxy-1-methyl-ethyl)-2-pyridyl]-3-oxo-pyrazolo[3,4-d]pyrimidin-6-yl]amino]-3,4-dihydro-1H-isoquinoline-2-carboxylate (28 mg, 36%).

LCMS: 560 [M+1]$^+$

Step-8: Synthesis of 1-(6-(2-hydroxypropan-2-yl)pyridin-2-yl)-2-isopropyl-6-((1,2,3,4-tetrahydroisoquinolin-7-yl)amino)-1,2-dihydro-3H-pyrazolo[3,4-d]pyrimidin-3-one 4M HCl in dioxane (1 mL) was added to tert-butyl 7-[[2-allyl-1-[6-(1-hydroxy-1-methyl-ethyl)-2-pyridyl]-3-oxo-pyrazolo[3,4-d]pyrimidin-6-yl]amino]-3,4-dihydro-1H-isoquinoline-2-carboxylate (28 mg, 0.05 mmol, 1.0 eq) and the resulting solution was allowed to stir at RT for 3 h. After completion of reaction, solvent was removed under reduced pressure, and the resulting solid was filtered and washed with ether, dried to afford HCl salt of 1-(6-(2-hydroxypropan-2-yl)pyridin-2-yl)-2-isopropyl-6-((1,2,3,4-tetrahydroisoquinolin-7-yl)amino)-1,2-dihydro-3H-pyrazolo[3,4-d]pyrimidin-3-one (15 mg, 60%) as a white solid.

LCMS: 460.2 [M+1]$^+$ $^1$H NMR (400 MHz, DMSO-d$_6$, FB): δ 10.1 (br s, 1H), 8.7 (br s, 1H), 8.07-8.01 (m, 1H), 7.74 (d, J=7.89 Hz, 1H), 7.67 (d, J=7.45 Hz, 1H), 7.51 (br s, 1H), 7.35-7.33 (m, 1H), 6.98 (d, J=8.77 Hz, 1H), 5.33 (br s, 1H), 4.07-4.22 (m, 1H), 3.80 (s, 2H), 2.93 (t, J=5.92 Hz, 2H), 2.59-2.70 (m, 2H), 1.44 (s, 6H), 1.37 (d, J=7.02 Hz, 6H).

Example S11. Synthesis of 2-(cyclopropylmethyl)-1-(6-(2-hydroxypropan-2-yl)pyridin-2-yl)-6-((1,2,3,4-tetrahydroisoquinolin-7-yl)amino)-1,2-dihydro-3H-pyrazolo[3,4-d]pyrimidin-3-one hydrochloride (Compound No. 1.11)

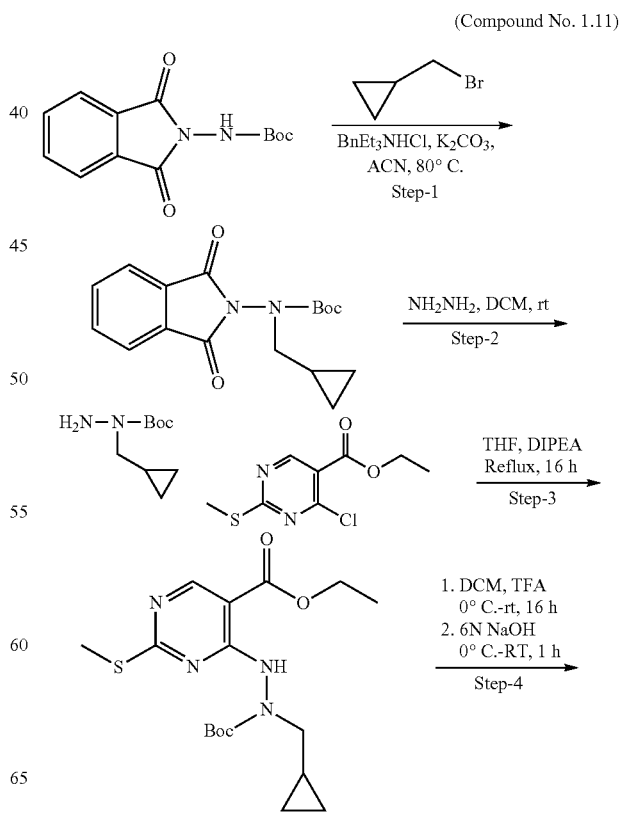

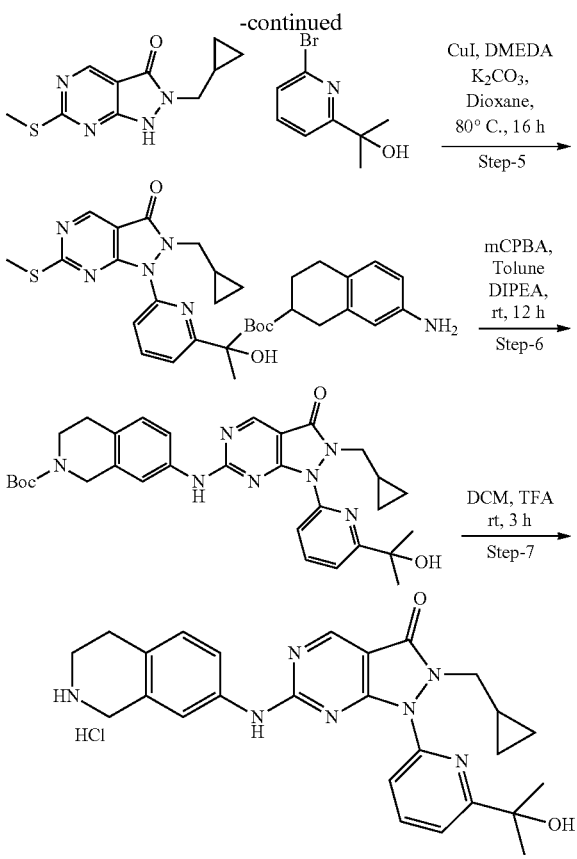

Step-1: tert-butyl (cyclopropylmethyl)(1,3-dioxoisoindolin-2-yl)carbamate

To a stirred solution of tert-butyl (1,3-dioxoisoindolin-2-yl)carbamate (10.0 g, 38.12 mmol, 1.0 eq), in $CH_3CN$ (100 mL) was added (bromomethyl)cyclopropane (4.44 mL, 45.75 mmol, 1.2 eq), $BnEt_3N^+Cl^-$ (1.73 g, 7.624 mmol, 0.2 eq) and $K_2CO_3$ (21.07 g, 152.48 mmol, 4.0 eq) at RT. The resulting mixture was heated at 80° C. for 12 h. The progress of reaction was monitored by LCMS. The reaction mixture was diluted with water (100 mL), extracted with EtOAc (2×200 mL). The combined organic layers were washed with water (100 mL), with brine (50 mL), dried over $Na_2SO_4$, concentrated and purified by recrystallization to afford the desired compound, tert-butyl (cyclopropylmethyl) (1,3-dioxoisoindolin-2-yl)carbamate (6.8 g, 56.38%) as light yellow liquid.
LCMS: 317.1 [M+1]$^+$ Step-2: tert-butyl 1-(cyclopropylmethyl)hydrazine-1-carboxylate To a stirred solution of tert-butyl (cyclopropylmethyl)(1,3-dioxoisoindolin-2-yl)carbamate (6.8 g, 21.49 mmol, 1.0 eq), in $CH_2Cl_2$ (100 mL) was added $NH_2NH_2.H_2O$ (2.04 mL, 42.98 mmol, 2.0 eq) at RT. The resulting mixture was stirred at RT for 12 h, formation of white precipitates was observed. The progress of reaction was monitored by $^1$HNMR. The reaction mixture was filtered and the filtrate was concentrated and purified by pentane to afford the desired compound, tert-butyl 1-(cyclopropylmethyl)hydrazine-1-carboxylate (3.90 g, 97.5%) as light yellow liquid.
LCMS: 187.1 [M+1]$^+$ Step-3: Synthesis of ethyl 4-(2-(tert-butoxycarbonyl)-2-(cyclopropylmethyl)hydrazinyl)-2-(methylthio)pyrimidine-5-carboxylate To a stirred solution of ethyl 4-chloro-2-methylsulfanyl-pyrimidine-5-carboxylate (3.48 g, 14.99 mmol, 1.0 eq) and tert-butyl 1-(cyclopropylmethyl)hydrazine-1-carboxylate (3.90 g, 20.98 mmol, 1.5 eq) in THF (36 mL) was added DIPEA (6.48 mL, 37.47 mmol, 2.5 eq) and stirred at 80° C. for 16 h. Solvent was removed under reduced pressure. Residue was diluted with water (50 mL) and extracted with EtOAc (50 mL×2). Organic layer was washed with brine solution (50 mL), dried over anhydrous $Na_2SO_4$ and concentrated under reduced pressure to afford the desired compound, ethyl 4-(2-(tert-butoxycarbonyl)-2-(cyclopropylmethyl)hydrazinyl)-2-(methylthio)pyrimidine-5-carboxylate (3.0 g, 52.34%) as light yellow solid.
LCMS: 237.0 [M+1]$^+$ Step-4: Synthesis of 2-(cyclopropylmethyl)-6-(methylthio)-1,2-dihydro-3H-pyrazolo[3,4-d]pyrimidin-3-one To a stirred solution of ethyl 4-(2-(tert-butoxycarbonyl)-2-(cyclopropylmethyl)hydrazinyl)-2-(methylthio)pyrimidine-5-carboxylate (3.0 g, 7.84 mmol, 1.0 eq) in $CH_2Cl_2$ (50 mL) was added TFA (7.84 mL) dropwise at 0° C. and allowed to stir at RT for 12 h. After completion of reaction, solvent was removed under reduced pressure. Residue was diluted with EtOH (20 mL). 6N NaOH solution (10 mL) was added in to above solution at 0° C. and allowed to stir at RT for 1 h. After completion, the reaction mixture was acidified by using 6N HCl solution. EtOH was removed under reduced pressure; residue obtained was cooled to RT and extracted with chloroform (100 mL×3). Organic layer was washed with brine solution, dried over anhydrous $Na_2SO_4$ and concentrated under reduced pressure to afford the desired compound, 2-(cyclopropylmethyl)-6-(methylthio)-1,2-dihydro-3H-pyrazolo[3,4-d]pyrimidin-3-one (1.0 g, 54.05%) as yellow solid.
LCMS: 237.1 [M+1]$^+$ Step-5: Synthesis of 2-(cyclopropylmethyl)-1-(6-(2-hydroxypropan-2-yl)pyridin-2-yl)-6-(methylthio)-1,2-dihydro-3H-pyrazolo[3,4-d]pyrimidin-3-one To a stirred solution of 2-(cyclopropylmethyl)-6-(methylthio)-1,2-dihydro-3H-pyrazolo[3,4-d]pyrimidin-3-one (1.0 g, 4.23 mmol, 1.0 eq) and 2-(6-bromo-2-pyridyl)propan-2-ol (1.09 g, 5.07 mmol, 1.20 eq) in dioxane (10 mL) were added $K_2CO_3$ (1.16 g, 8.46 mmol, 2.0 eq) and the resulting mixture was purged with nitrogen for 10 min followed by addition of CuI (161 mg, 0.84 mmol, 0.2 eq), and DIPEA (149 mg, 1.69 mmol, 0.4 eq) and again purged with nitrogen for 10 min, stirred at 90° C. for 12 h. After completion of reaction, the reaction mixture was diluted with water and extracted with EtOAc (50 mL×2). Combined organic layer was washed with water (50 mL) and brine solution (50 mL), dried over anhydrous sodium sulphate and concentrated under reduced pressure to afford crude product, which was purified by flash chromatography to afford the desired compound, 2-(cyclopropylmethyl)-1-(6-(2-hydroxypropan-2-yl)pyridin-2-yl)-6-(methylthio)-1,2-dihydro-3H-pyrazolo[3,4-d]pyrimidin-3-one (500 mg, 31.84%) as an off white solid.
LCMS: 372.2 [M+1]$^+$

Step-6: Synthesis of tert-butyl 7-((2-(cyclopropylmethyl)-1-(6-(2-hydroxypropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate To a stirred solution of 2-(cyclopropylmethyl)-1-(6-(2-hydroxypropan-2-yl)pyridin-2-yl)-6-(methylthio)-1,2-dihydro-3H-pyrazolo[3,4-d]pyrimidin-3-one (500 mg, 1.34 mmol, 1.0 eq) in toluene (10 mL) was added m-CPBA (465 mg, 2.692 mmol, 2.0 eq) and allowed to stir at RT for 30 min. tert-Butyl 7-amino-3,4-dihydro-1H-isoquinoline-2-carboxylate (401 mg, 1.615 mmol, 1.3 eq) and DIPEA (0.9 mL, 5.384 mmol, 4.0 eq) were added and allowed to stir at RT for 12 h. The formation of precipitates was obr served which was filtered to afford the desired compound, tert-butyl 7-((2-(cyclopropylmethyl)-1-(6-(2-hydroxypropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate (400 mg, 51.98%) as an off white solid.

LCMS: 546.4 [M+1]$^+$

Step-7: Synthesis of 2-(cyclopropylmethyl)-1-(6-(2-hydroxypropan-2-yl)pyridin-2-yl)-6-((1,2,3,4-tetrahydroisoquinolin-7-yl)amino)-1,2-dihydro-3H-pyrazolo[3,4-d]pyrimidin-3-one hydrochloride Tert-butyl 7-((2-(cyclopropylmethyl)-1-(6-(2-hydroxypropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate (78 mg, 0.136 mmol, 1.0 eq) was dissolved in dioxane (2 mL) and added 4M dioxane-HCl (2 mL) and allowed to stir at RT for 1 h. After completion of reaction, the reaction mixture was filtered and dried under reduced pressure to afford the desired compound, 2-(cyclopropylmethyl)-1-(6-(2-hydroxypropan-2-yl)pyridin-2-yl)-6-((1,2,3,4-tetrahydroisoquinolin-7-yl)amino)-1,2-dihydro-3H-pyrazolo[3,4-d]pyrimidin-3-one hydrochloride (40 mg, 57.71%) as an off white solid.

LCMS: 472.3 [M+1]$^+$ $^1$H NMR (400 MHz, DMSO-d$_6$, HCl salt): δ 10.3 (br s, 1H), 9.1 (br s, 1H), 8.83 (s, 1H), 8.08 (t, J=7.67 Hz, 1H), 7.80 (d, J=7.89 Hz, 1H), 7.60-7.69 (m, 1H), 7.49 (d, 1H), 7.19 (d, J=8.33 Hz, 1H), 5.48-5.65 (m, 1H), 4.78-4.93 (m, 2H), 4.24 (br s, 2H), 4.13 (t, J=7.00 Hz, 2H), 3.37-3.34 (m, 2H), 2.95 (t, J=6.14 Hz, 2H), 2.00-2.16 (m, 2H), 1.42 (s, 6H).

Example S12. Synthesis of 2-ethyl-1-(6-(2-hydroxypropan-2-yl)pyridin-2-yl)-6-((1,2,3,4-tetrahydroisoquinolin-6-yl)amino)-1,2-dihydro-3H-pyrazolo[3,4-d]pyrimidin-3-one (Compound No. 1.12)

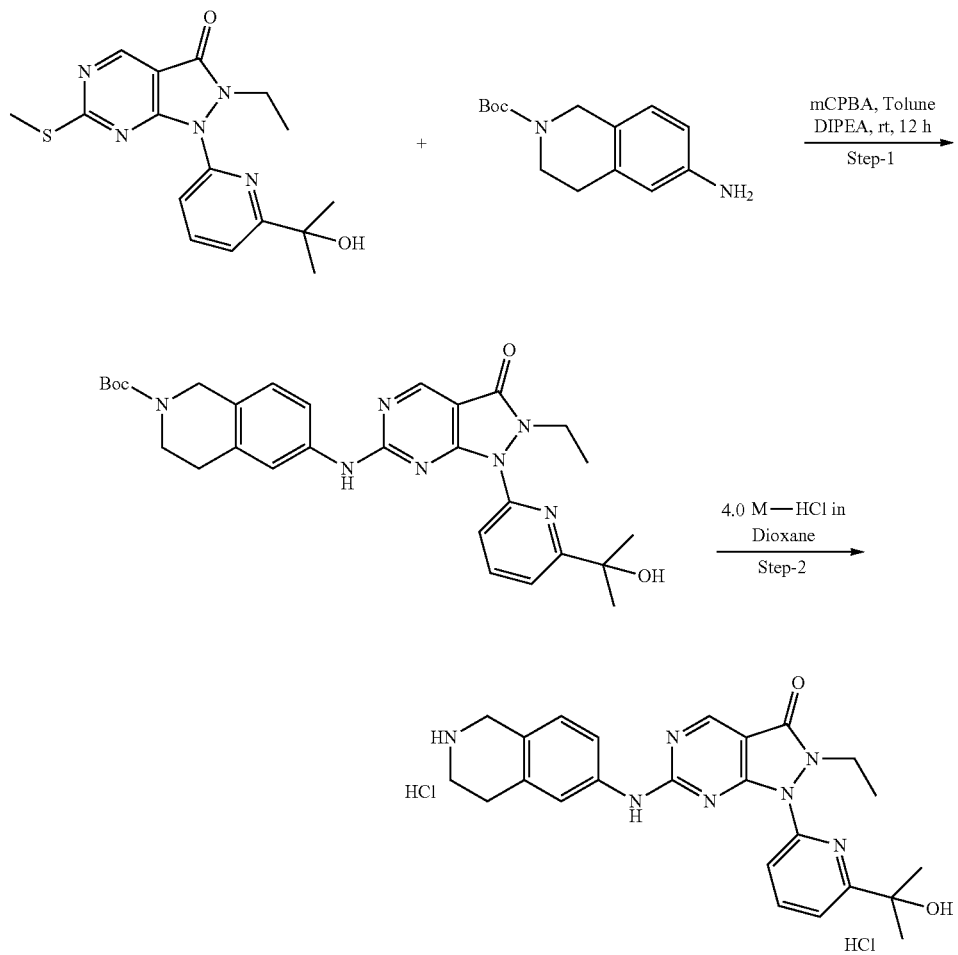

Step-1: Synthesis of tert-butyl 6-((2-ethyl-1-(6-(2-hydroxypropan-2-yl)pyridin-2-yl)-3-oxo-2,3-dihydro-1-pyrazolo[3,4-d]pyrimidin-6-yl)amino)-3,4-dihydroisoquinoline-2(1H)-carboxylate To a stirred solution of 2-ethyl-1-(6-(2-hydroxypropan-2-yl)pyridin-2-yl)-6-(methylthio)-1,2-dihydro-3H-pyrazolo[3,4-d]pyrimidin-3-one (200 mg, 0.579 mmol, 1.0 eq) in toluene (10 mL) was added m-CPBA (200 mg, 1.158 mmol, 2.0 eq) and allowed to stir at RT for 30 min. tert-Butyl 6-amino-3,4-dihydroisoquinoline-2(1H)-carboxylate (158 mg, 0.636 mmol, 1.1 eq) and DIPEA (0.404 mL, 2.316 mmol, 4.0 eq) were added and allowed to stir at RT 12 h. The formation of precipitate was obr served which was filtered and purified by flash chromatography [elution 0-30% EtOAc in hexane] to afford the desired compound, tert-butyl 6-((2-ethyl-1-(6-(2-hydroxypropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate (115 mg, 36.50%) as an off white solid.
LCMS: 546.5 [M+1]+

Step-2: Synthesis of 2-ethyl-1-(6-(2-hydroxypropan-2-yl)pyridin-2-yl)-6-((1,2,3,4-tetrahydroisoquinolin-6-yl)amino)-1,2-dihydro-3H-pyrazolo[3,4-d]pyrimidin-3-one dihydrochloride tert-butyl 6-((2-ethyl-1-(6-(2-hydroxypropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate (110 mg, 0.201 mmol, 1.0 eq) was dissolved in 4M HCl in dioxane (2 mL) and allowed to stir at RT for 1 h. After completion of reaction, the reaction mixture was filtered and dried under reduced pressure to afford the desired compound, 2-ethyl-1-(6-(2-hydroxypropan-2-yl)pyridin-2-yl)-6-((1,2,3,4-tetrahydroisoquinolin-6-yl)amino)-1,2-dihydro-3H-pyrazolo[3,4-d]pyrimidin-3-one dihydrochloride (51 mg, 49.03%) as yellow solid.
LCMS: 446.4 [M+1]+
1H NMR (400 MHz, DMSO-d6): δ 10.33 (brs, 1H), 9.27 (brs, 2H), 8.88 (s, 1H), 8.09 (t, J=8.11 Hz, 1H), 7.85 (s, 1H), 7.78 (brs, 1H), 7.66 (d, J=7.89 Hz, 1H), 7.49 (d, J=7.45 Hz, 1H), 7.17 (d, J=8.33 Hz, 1H), 4.21 (brs, 2H), 4.05 (d, J=7.02 Hz, 2H), 3.39 (brs, 2H), 3.01 (brs, 2H), 1.44 (s, 6H), 0.98 (t, J=6.80 Hz, 3H).

Example S13. Synthesis of 6-((4,4-dimethyl-1,2,3,4-tetrahydroisoquinolin-7-yl)amino)-2-ethyl-1-(6-(2-hydroxypropan-2-yl)pyridin-2-yl)-1,2-dihydro-3H-pyrazolo[3,4-d]pyrimidin-3-one dihydrochloride (Compound No. 1.13)

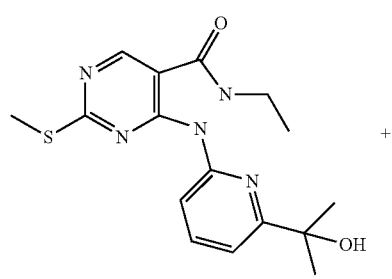

+

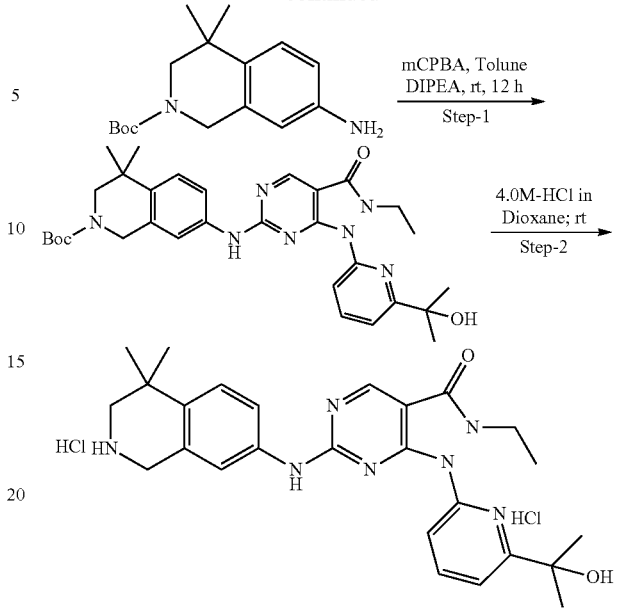

Step-1: Synthesis of tert-butyl 7-((2-ethyl-1-(6-(2-hydroxypropan-2-yl)pyridin-2-yl)-3-oxo-2,3-dihydro-1H-pyrazolo[3,4-d]pyrimidin-6-yl)amino)-4,4-dimethyl-3,4-dihydroisoquinoline-2(1H)-carboxylate To a stirred solution of 2-ethyl-1-(6-(2-hydroxypropan-2-yl)pyridin-2-yl)-6-(methylthio)-1,2-dihydro-3H-pyrazolo[3,4-d]pyrimidin-3-one (1.1 g, 3.184 mmol, 1.0 eq) in toluene (20 mL) was added m-CPBA (1.57 g, 6.368 mmol, 2.0 eq) and allowed to stir at RT for 30 min. tert-Butyl 7-amino-4,4-dimethyl-3,4-dihydroisoquinoline-2(1H)-carboxylate (0.968 g, 3.502 mmol, 1.1 eq) and DIPEA (2.2 mL, 12.736 mmol, 4.0 eq) were added and allowed to stir at RT 12 h. The reaction mixture was diluted with water (50 mL) and extracted with EtOAc (2×50 mL). The combined organic layers were washed with water (50 mL), brine (50 mL), dried over Na2SO4, filtered, concentrated and purified by flash chromatography [elution 0-30% EtOAc in Hexane] to afford the desired compound, tert-butyl 7-((2-ethyl-1-(6-(2-hydroxypropan-2-yl)pyridin-2-yl)-3-oxo-2,3-dihydro-1H-pyrazolo[3,4-d]pyrimidin-6-yl)amino)-4,4-dimethyl-3,4-dihydroiso quinoline-2(1H)-carboxylate (630 mg, 34.61%) as light yellow solid.
LCMS: 574.4 [M+1]+

Step-2: Synthesis of 6-((4,4-dimethyl-1,2,3,4-tetrahydroisoquinolin-7-yl)amino)-2-ethyl-1-(6-(2-hydroxypropan-2-yl)pyridin-2-yl)-1,2-dihydro-3H-pyrazolo[3,4-d]pyrimidin-3-one dihydrochloride tert-butyl 7-((2-ethyl-1-(6-(2-hydroxypropan-2-yl)pyridin-2-yl)-3-oxo-2,3-dihydro-1H-pyrazolo[3,4-d]pyrimidin-6-yl)amino)-4,4-dimethyl-3,4-dihydroisoquinoline-2(1H)-carboxylate (500 mg, 0.871 mmol, 1.0 eq) was dissolved in 4M HCl in dioxane (5 mL) and allowed to stir at RT for 1 h. After completion of reaction, the reaction mixture was filtered and dried under reduced pressure and purified by diethyl ether to afford the desired compound, 6-((4,4-dimethyl-1,2,3,4-tetrahydroisoquinolin-7-yl)amino)-2-ethyl-1-

(6-(2-hydroxypropan-2-yl)pyridin-2-yl)-1,2-dihydro-3H-pyrazolo[3,4-d]pyrimidin-3-one dihydrochloride (475 mg, 99.99%) as yellow solid.

LCMS: 474.4 [M+1]+

$^1$H NMR (400 MHz, DMSO-d$_6$): δ 10.33 (brs, 1H), 9.34 (brs, 2H), 8.87 (s, 1H), 8.11 (t, J=7.89 Hz, 1H), 7.86 (d, J=7.89 Hz, 1H), 7.70 (brs, 1H), 7.66 (d, J=7.45 Hz, 1H), 7.54 (d, J=8.33 Hz, 1H), 7.44 (d, J=8.77 Hz, 1H), 4.25 (brs, 2H), 4.01-4.08 (m, 2H), 3.21 (brs, 2H), 1.44 (s, 6H), 1.35 (s, 6H), 0.98 (t, J=7.02 Hz, 3H).

Example S14. Synthesis of 2-ethyl-6-((2-(2-hydroxyacetyl)-4,4-dimethyl-1,2,3,4-tetrahydroisoquinolin-7-yl)amino)-1-(6-(2-hydroxypropan-2-yl)pyridin-2-yl)-1,2-dihydro-3H-pyrazolo[3,4-d]pyrimidin-3-one

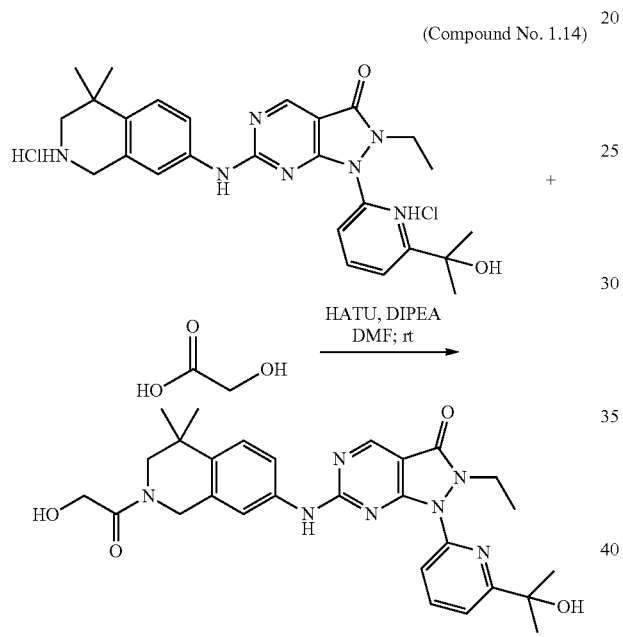

Step-1: Synthesis of 2-ethyl-6-((2-(2-hydroxyacetyl)-4,4-dimethyl-1,2,3,4-tetrahydroisoquinolin-7-yl)amino)-1-(6-(2-hydroxypropan-2-yl)pyridin-2-yl)-1,2-dihydro-3H-pyrazolo[3,4-d]pyrimidin-3-one To a stirred solution of glycolic acid (31 mg, 0.401 mmol, 1.1 eq) in DMF (5 mL) was added HATU (208 mg, 0.547 mmol, 1.5 eq) at RT. The resulting mixture was stirred at RT for 5 min, followed by addition of 6-((4,4-dimethyl-1,2,3,4-tetrahydroisoquinolin-7-yl)amino)-2-ethyl-1-(6-(2-hydroxypropan-2-yl)pyridin-2-yl)-1,2-dihydro-3H-pyrazolo[3,4-d]pyrimidin-3-one dihydrochloride (200 mg, 0.365 mmol, 1.0 eq) and DIPEA (0.128 mL, 0.730 mmol, 2.0 eq) and stirred at RT for 1 h. The reaction mixture was diluted with water (50 mL) and extracted with ethyl acetate (2×50 mL). The combined organic extracts were washed with water (50 mL) and brine (50 mL) dried over Na$_2$SO$_4$, concentrated under reduced and purified by flash chromatography [elution 0-3% MeOH in CH2CL2] to afford the desired compound, 2-ethyl-6-((2-(2-hydroxyacetyl)-4,4-dimethyl-1,2,3,4-tetrahydroisoquinolin-7-yl) amino)-1-(6-(2-hydroxypropan-2-yl)pyridin-2-yl)-1,2-dihydro-3H-pyrazolo[3,4-d]pyrimidin-3-one (70 mg, 35.89%) as off white solid.

LCMS: 532.3 [M+2]+

$^1$H NMR (400 MHz, DMSO-d$_6$): δ 10.27 (brs, 1H), 8.86 (s, 1H), 8.15 (brs, 1H), 7.87 (t, J=7.67 Hz, 1H), 7.58-7.79 (m, 2H), 7.43 (d, J=7.89 Hz, 1H), 7.26-7.40 (m, 1H), 5.34 (s, 1H), 4.64-4.76 (m, 2H), 4.61 (brs, 1H), 4.27 (d, J=5.26 Hz, 1H), 4.21 (d, J=5.70 Hz, 1H), 4.05 (d, J=7.02 Hz, 2H), 3.51 (brs, 1H), 3.38 (brs, 1H), 1.44 (s, 6H), 1.23 (s, 3H), 1.20 (s, 3H), 0.91-1.07 (m, 3H).

Example S15. Synthesis of 1-(6-(2-hydroxypropan-2-yl)pyridin-2-yl)-2-propyl-6-((1,2,3,4-tetrahydroisoquinolin-7-yl)amino)-1,2-dihydro-3H-pyrazolo[3,4-d]pyrimidin-3-one

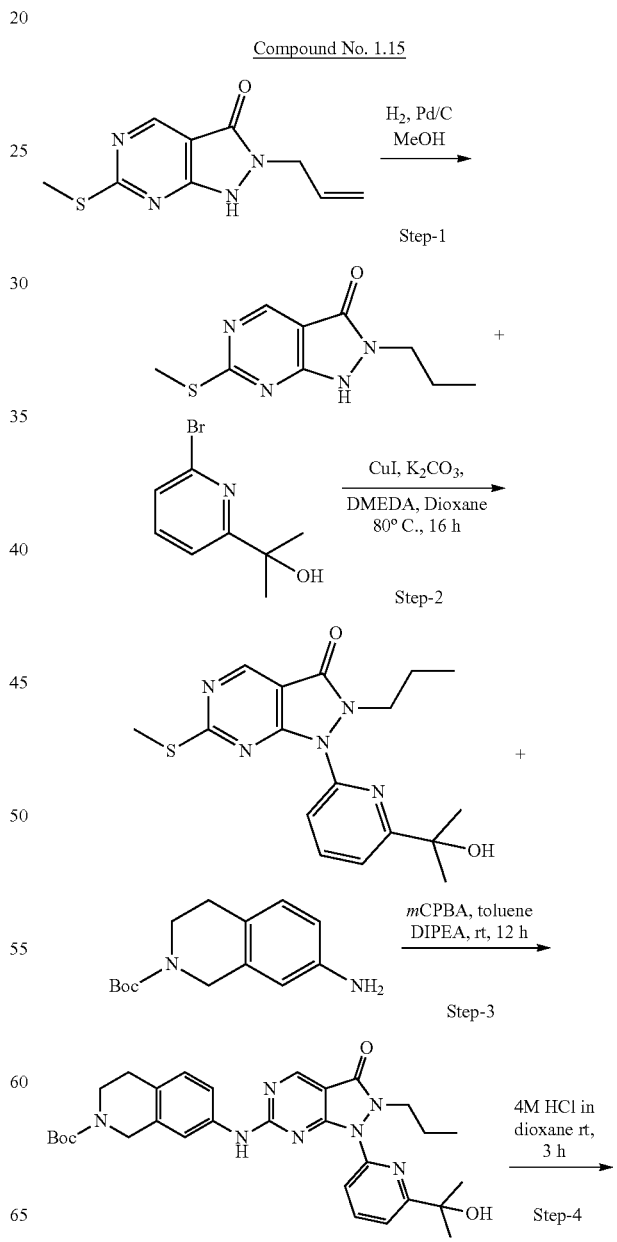

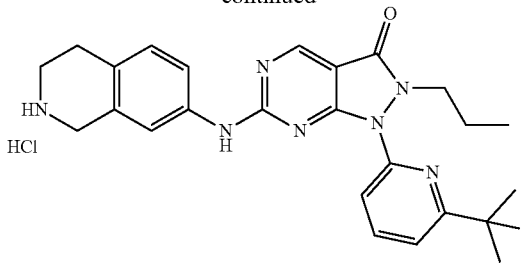

Step-1: Synthesis of 6-(methylthio)-2-propyl-1,2-dihydro-3H-pyrazolo[3,4-d]pyrimidin-3-one To a stirred solution of 2-allyl-6-(methylthio)-1,2-dihydro-3H-pyrazolo[3,4-d]pyrimidin-3-on (2.0 g, 8.9 mmol, 1.0 eq) in dry MeOH (50 mL), Pd/C (10 wt %) (200 mg) was added under stirring under inert atmosphere in Parr vessel. The reaction was stirred in Parr reactor at 60 psi hydrogen pressure 12 h. The reaction was monitored by LCMS. After completion the mixture was filtered through celite and concentrated to afford, 6-(methylthio)-2-propyl-1,2-dihydro-3H-pyrazolo[3,4-d]pyrimidin-3-one as yellow solid (1.318 g, 65%).

LCMS: 225.1 [M+1]$^+$

Step-2: Synthesis of 1-(6-(2-hydroxypropan-2-yl)pyridin-2-yl)-6-(methylthio)-2-propyl-1,2-dihydro-3H-pyrazolo[3,4-d]pyrimidin-3-one To a stirred solution of 6-(methylthio)-2-propyl-1,2-dihydro-3H-pyrazolo[3,4-d]pyrimidin-3-one (1.318 g, 5.88 mmol, 1.0 eq) and 2-(6-bromo-2-pyridyl)propan-2-ol (1.525 g, 7.06 mmol, 1.20 eq) in dioxane (50 mL) were added CuI (224 mg, 1.17 mmol, 0.2 eq), K$_2$CO$_3$ (1.626 g, 11.76 mmol, 2 eq) and DIPEA (2.35 g, 2.35 mmol, 0.4 eq) and stirred at 80° C. 12 h. The reaction was monitored by LCMS. After completion of reaction, solvent was removed under reduced pressure; residue was diluted with water and extracted with ethyl acetate (30 mL×3). The combined organic layer was washed with brine solution, dried over anhydrous Na$_2$SO$_4$ and concentrated under reduced pressure to afford crude product, which was purified by flash chromatography (elution: 0-10% MeOH in CH$_2$Cl$_2$) to afford 1-(6-(2-hydroxypropan-2-yl)pyridin-2-yl)-2-isopropyl-6-(methylthio)-1,2-dihydro-3H-pyrazolo[3,4-d]pyrimidin-3-one (1.035 g, 49%) as yellow solid.

LCMS: 360.1 [M+1]$^+$

Step-3: Synthesis of tert-butyl 7-((1-(6-(2-hydroxypropan-2-yl)pyridin-2-yl)-3-oxo-2-propyl-2,3-dihydro-1H-pyrazolo[3,4-d]pyrimidin-6-yl)amino)-3,4-dihydroisoquinoline-2(1H)-carboxylate To a stirred solution of 1-(6-(2-hydroxypropan-2-yl)pyridin-2-yl)-2-isopropyl-6-(methylthio)-1,2-dihydro-3H-pyrazolo[3,4-d]pyrimidin-3-one (1.035 g, 2.87 mmol, 1.0 eq) in toluene (50 mL), m-CPBA (0.99 g, 5.75 mmol, 2.0 eq) was added under stirring and resulting mixture was allowed to stir at RT for 30 min. Further, tert-butyl 7-amino-3,4-dihydro-1H-isoquinoline-2-carboxylate (0.786 g, 3.16 mmol, 1.1 eq) and DIPEA (1.48 g, 11.51 mmol, 4 eq) were added and the reaction was allowed to stir at RT for 12 h. The reaction was monitored by LCMS. After completion reaction was quenched with water (30 mL) and extracted with ethyl acetate (30 mL×3). The combined organic layer was washed with brine solution (50 mL), dried over anhydrous Na$_2$SO$_4$ and concentrated under reduced pressure to afford crude product which was purified by flash chromatography (elution: 0-10% MeOH in CH$_2$Cl$_2$) to afford tert-butyl 7-((1-(6-(2-hydroxypropan-2-yl)pyridin-2-yl)-3-oxo-2-propyl-2,3-dihydro-1H-pyrazolo[3,4-d]pyrimidin-6-yl)amino)-3,4-dihydroisoquinoline-2(1H)-carboxylate (2.5 g, 78%) as yellow solid.

LCMS: 560.3 [M+1]$^+$

Step-4: Synthesis of 1-(6-(2-hydroxypropan-2-yl)pyridin-2-yl)-2-propyl-6-((1,2,3,4-tetrahydroisoquinolin-7-yl)amino)-1,2-dihydro-3H-pyrazolo[3,4-d]pyrimidin-3-one 20% HCl in dioxane (2 mL) was added to a stirred solution of tert-butyl 7-((1-(6-(2-hydroxypropan-2-yl)pyridin-2-yl)-3-oxo-2-propyl-2,3-dihydro-1H-pyrazolo[3,4-d]pyrimidin-6-yl)amino)-3,4-dihydroisoquinoline-2(1H)-carboxylate (105 mg, 0.18 mmol, 1.0 eq) at 0° C. and the resulting solution was allowed to stir at RT for 3 h. After completion of reaction, solvent was removed under reduced pressure, and the resulting solid was filtered and washed with ether, dried to afford HCl salt of 1-(6-(2-hydroxypropan-2-yl)pyridin-2-yl)-2-propyl-6-((1,2,3,4-tetrahydroisoquinolin-7-yl)amino)-1,2-dihydro-3H-pyrazolo[3,4-d]pyrimidin-3-one (60 mg, 65%) as a white solid.

LCMS: 460.3 [M+1]$^+$ $^1$H NMR (400 MHz, DMSO-d$_6$, HCl salt): δ 10.36 (br s, 1H), 9.21 (br s, 2H), 8.39 (s, 1H), 8.09 (t, J=7.89 Hz, 1H), 7.84 (d, J=7.89 Hz, 1H), 7.74 (br s, 1H), 7.66 (d, J=7.89 Hz, 1H), 7.46-7.53 (m, 1H), 4.28-4.26 (m, 2H), 4.03 (t, J=7.24 Hz, 2H), 3.41-3.66 (m, 2H), 2.96 (t, J=6.14 Hz, 2H), 1.44 (s, 6H), 1.29-1.41 (m, 2H), 0.68 (t, J=7.45 Hz, 3H).

Example S16. Synthesis of 2-ethyl-1-(6-(2-hydroxypropan-2-yl)pyridin-2-yl)-6-((2,4,4-trimethyl-1,2,3,4-tetrahydroisoquinolin-7-yl)amino)-1,2-dihydro-3H-pyrazolo[3,4-d]pyrimidin-3-one (Compound No. 1.16)

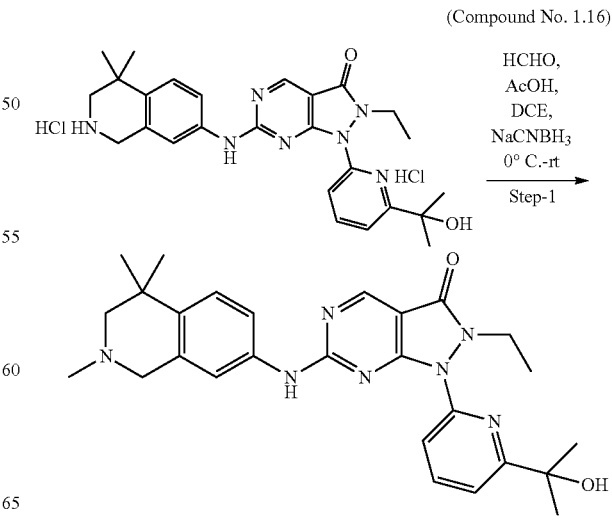

Synthesis of 2-ethyl-1-(6-(2-hydroxypropan-2-yl)pyridin-2-yl)-6-((2,4,4-trimethyl-1,2,3,4-tetrahydroisoquinolin-7-yl)amino)-1,2-dihydro-3H-pyrazolo[3,4-d]pyrimidin-3-one To a stirred solution of 6-((4,4-dimethyl-1,2,3,4-tetrahydroisoquinolin-7-yl)amino)-2-ethyl-1-(6-(2-hydroxypropan-2-yl)pyridin-2-yl)-1,2-dihydro-3H-pyrazolo[3,4-d]pyrimidin-3-one dihydrochloride (200 mg, 0.366 mmol, 1.0 eq) and HCHO (0.15 mL, 1.83 mmol, 5.0 eq) in DCE (10 mL) was dropwise added acetic acid (0.11 mL, 1.83 mmol, 5.0 eq) at 0° C. The resulting mixture was stirred at RT for 1 h followed by addition of NaCNBH$_3$ (69 mg, 1.098 mmol, 3.0 eq) at 0° C. The resulting mixture was stirred at RT for 1 h. The progress of reaction was monitored by LCMS. The reaction mixture was concentrated, basified with saturated solution of NaHCO$_3$ (50 mL), extracted with EtOAc (2×50 mL). The combined organic extracts were washed with water (50 mL), with brine (50 mL) dried over Na$_2$SO$_4$ and concentrated under reduced and purified by reversed phase chromatography to afford the desired compound, 2-ethyl-1-(6-(2-hydroxypropan-2-yl)pyridin-2-yl)-6-((2,4,4-trimethyl-1,2,3,4-tetrahydroisoquinolin-7-yl)amino)-1,2-dihydro-3H-pyrazolo[3,4-d]pyrimidin-3-one (0.02 g, 11.23%) as white solid.

LCMS: 488.4 [M+1]$^+$ $^1$H NMR (400 MHz, DMSO-d$_6$): δ 10.16 (brs, 1H), 8.84 (s, 1H), 8.05 (t, J=7.89 Hz, 1H), 7.82 (d, J=7.89 Hz, 1H), 7.67 (d, J=7.89 Hz, 1H), 7.52 (brs, 1H), 7.42 (d, J=7.89 Hz, 1H), 7.28 (d, J=8.33 Hz, 1H), 5.33 (s, 1H), 4.03 (d, J=7.02 Hz, 2H), 3.43 (s, 2H), 2.34 (d, J=9.21 Hz, 5H), 1.44 (s, 6H), 1.23 (s, 6H), 0.97 (t, J=7.02 Hz, 3H).

Example S17. Synthesis of 2-cyclopropyl-1-(6-(2-hydroxypropan-2-yl)pyridin-2-yl)-6-((1,2,3,4-tetrahydroisoquinolin-7-yl)amino)-1,2-dihydro-3H-pyrazolo[3,4-d]pyrimidin-3-one (Compound No. 1.17)

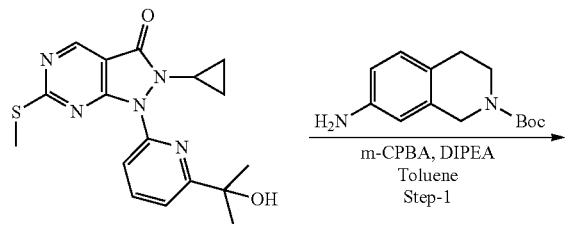

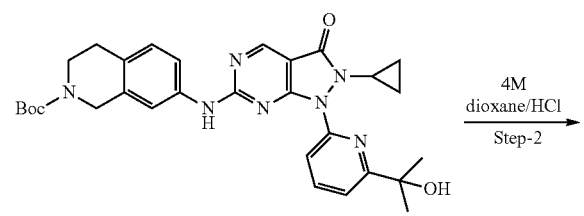

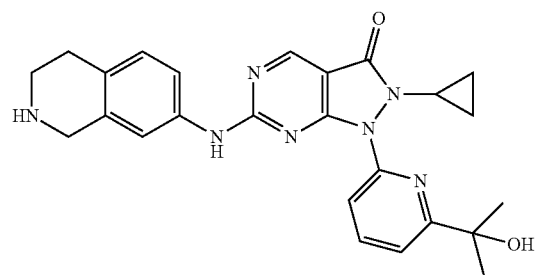

Step-1: Synthesis of tert-butyl 7-((2-cyclopropyl-1-(6-(2-hydroxypropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate To a stirred solution of 2-cyclopropyl-1-(6-(2-hydroxypropan-2-yl)pyridin-2-yl)-6-(methylthio)-1,2-dihydro-3H-pyrazolo[3,4-d]pyrimidin-3-one (130 mg, 0.364 mmol, 1.0 eq) in toluene (10 mL) was added m-CPBA (126 mg, 0.728 mmol, 2.0 eq) and allowed to stir at RT for 30 min. tert-Butyl-7-amino-3,4-dihydroisoquinoline-2(1H)-carboxylate (108 mg, 0.436 mmol, 2.0 eq) and DIPEA (0.25 mL, 1.45 mmol, 4.0 eq) were added and allowed to stir at RT for 12 h. The formation of precipitate was obr served which was filtered to afford the desired compound, tert-butyl 7-((2-cyclopropyl-1-(6-(2-hydroxypropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate (87 mg, 42.89%) as an off white solid.

LCMS: 558.3 [M+1]$^+$

Step-2: Synthesis of 2-cyclopropyl-1-(6-(2-hydroxypropan-2-yl)pyridin-2-yl)-6-((1,2,3,4-tetrahydroisoquinolin-7-yl)amino)-1,2-dihydro-3H-pyrazolo[3,4-d]pyrimidin-3-one Tert-butyl-7-((2-cyclopropyl-1-(6-(2-hydroxypropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate (35 mg, 0.056 mmol, 1.0 eq) was dissolved in dioxane (0.5 mL) and added 6M dioxane-HCl (1 mL) and allowed to stir at RT for 1 h. After completion of reaction, the reaction mixture was filtered and dried under reduced pressure to afford the desired compound, 2-cyclopropyl-1-(6-(2-hydroxypropan-2-yl)pyridin-2-yl)-6-((1,2,3,4-tetrahydroisoquinolin-7-yl)amino)-1,2-dihydro-3H-pyrazolo[3,4-d]pyrimidin-3-one (12 mg, 16.81%) as an off white solid.

LCMS: 458.3 [M+1]$^+$ $^1$H NMR (400 MHz, DMSO-d6): δ 10.18 (brs, 1H), 8.79 (s, 1H), 8.06 (t, J=7.67 Hz, 1H), 7.75 (d, J=7.89 Hz, 1H), 7.65 (d, J=7.45 Hz, 2H), 7.42 (d, J=8.33 Hz, 1H), 7.09 (d, J=7.89 Hz, 1H), 5.32 (s, 1H), 4.05 (br s, 2H), 3.17 (br s, 4H), 2.80 (br s, 2H), 1.44 (s, 6H), 0.81 (brs, 4H).

Example S18. Synthesis of 2-ethyl-1-(6-methoxy-pyridin-2-yl)-6-((1,2,3,4-tetrahydroisoquinolin-7-yl)amino)-1,2-dihydro-3H-pyrazolo[3,4-d]pyrimidin-3-one (Compound No. 1.18)

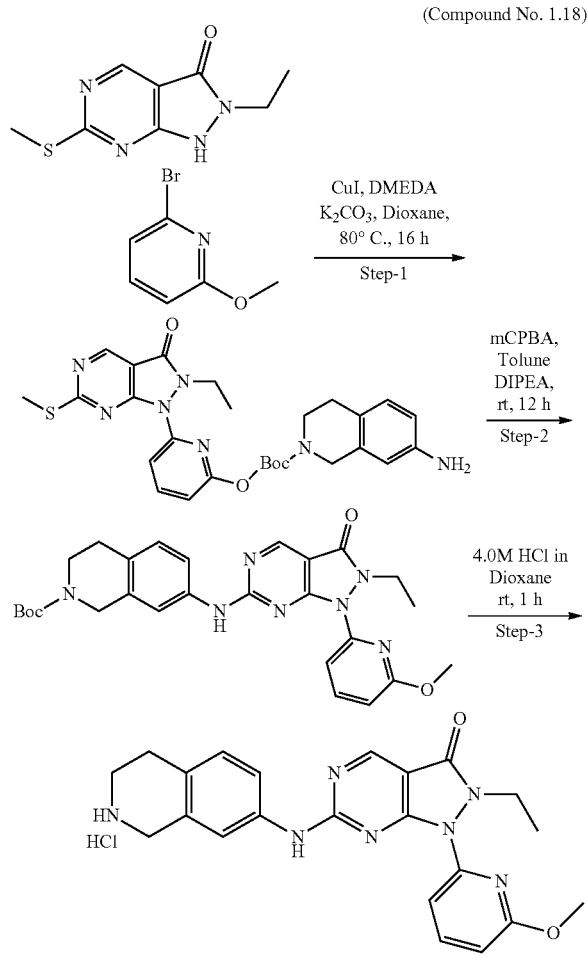

Step-1: Synthesis of 2-ethyl-1-(6-methoxypyridin-2-yl)-6-(methylthio)-1,2-dihydro-3H-pyrazolo[3,4-d]pyrimidin-3-one To a stirred solution of 2-ethyl-6-(methylthio)-1,2-dihydro-3H-pyrazolo[3,4-d]pyrimidin-3-one (450 mg, 2.140 mmol, 1.0 eq) and 2-bromo-6-methoxypyridine (483 mg, 2.568 mmol, 1.20 eq) in dioxane (20 mL) were added $K_2CO_3$ (591 mg, 4.28 mmol, 2.0 eq) and the resulting mixture was purged with nitrogen for 10 min followed by addition of CuI (82 mg, 0.428 mmol, 0.2 eq), and DIPEA (0.092 mL, 0.856 mmol, 0.4 eq). Reaction was again purged with nitrogen for 10 min and stirred at 90° C. for 12 h. After completion of reaction, the reaction mixture was diluted with water (20 mL) and extracted with EtOAc (50 mL×2). Combined organic layer was washed with water (50 mL) brine solution (50 mL), dried over anhydrous $Na_2SO_4$ and concentrated under reduced pressure to afford crude product, which was purified by flash chromatography (elution 0-30% EtOAc in Hexane) to afford the desired compound, 2-ethyl-1-(6-methoxypyridin-2-yl)-6-(methylthio)-1,2-dihydro-3H-pyrazolo[3,4-d]pyrimidin-3-one (300 mg, 44.18%) as an off white solid.

LCMS: 318.1 [M+1]$^+$

Step-2: Synthesis of tert-butyl 7-((2-ethyl-1-(6-methoxypyridin-2-yl)-3-oxo-2,3-dihydro-1H-pyrazolo[3,4-d]pyrimidin-6-yl)amino)-3,4-dihydroisoquinoline-2(1H)-carboxylate To a stirred solution of 2-ethyl-1-(6-methoxypyridin-2-yl)-6-(methylthio)-1,2-dihydro-3H-pyrazolo[3,4-d]pyrimidin-3-one (150 mg, 0.472 mmol, 1.0 eq) in toluene (5.0 mL) was added m-CPBA (233 mg, 0.944 mmol, 2.0 eq) and allowed to stir at RT for 30 min. tert-Butyl-7-amino-3,4-dihydro-1H-isoquinoline-2-carboxylate (130 mg, 0.519 mmol, 1.1 eq) and DIPEA (0.331 mL, 1.888 mmol, 4.0 eq) were added and allowed to stir at RT for 12 h. The formation of precipitate was obr served which was filtered to afford the desired compound, tert-butyl 7-((2-ethyl-1-(6-methoxypyridin-2-yl)-3-oxo-2,3-dihydro-1H-pyrazolo[3,4-d]pyrimidin-6-yl)amino)-3,4-dihydroisoquinoline-2(1H)-carboxylate (125 mg, 49.18%) as off white solid.

LCMS: 518.3 [M+1]$^+$

Step-3: Synthesis of 2-ethyl-1-(6-methoxypyridin-2-yl)-6-((1,2,3,4-tetrahydroisoquinolin-7-yl)amino)-1,2-dihydro-3H-pyrazolo[3,4-d]pyrimidin-3-one hydrochloride tert-Butyl 7-((2-ethyl-1-(6-methoxypyridin-2-yl)-3-oxo-2,3-dihydro-1H-pyrazolo[3,4-d]pyrimidin-6-yl)amino)-3,4-dihydroisoquinoline-2(1H)-carboxylate (120 mg, 0.231 mmol, 1.0 eq) was dissolved in 4M HCl in dioxane (2 mL) and allowed to stir at RT for 1 h. After completion of reaction, the reaction mixture was filtered and dried under reduced pressure to afford the desired compound, 2-ethyl-1-(6-methoxypyridin-2-yl)-6-((1,2,3,4-tetrahydroisoquinolin-7-yl)amino)-1,2-dihydro-3H-pyrazolo[3,4-d]pyrimidin-3-one hydrochloride (85 mg, 88.54%) as yellow solid.

LCMS: 418.3 [M+1]$^+$ $^1$H NMR (400 MHz, DMSO-d$_6$): δ 10.34 (br s, 1H), 9.37 (br s, 2H), 8.87 (s, 1H), 8.02 (t, J=7.89 Hz 1H), 7.73 (br s, 1H), 7.52 (d, J=7.89 Hz, 2H), 7.17 (d, J=8.77 Hz, 1H), 6.85 (d, J=7.89 Hz, 1H), 4.23 (br s, 2H), 4.04 (q, J=6.72 Hz, 2H), 3.87 (s, 3H), 3.36 (br s, 2H), 2.96 (t, J=6.14 Hz 2H), 1.01 (t, J=6.80 Hz, 3H).

Example S19. Synthesis of 2-ethyl-1-(6-methoxy-pyridin-2-yl)-6-((1,2,3,4-tetrahydroisoquinolin-6-yl)amino)-1,2-dihydro-3H-pyrazolo[3,4-d]pyrimidin-3-one (Compound No. 1.23)

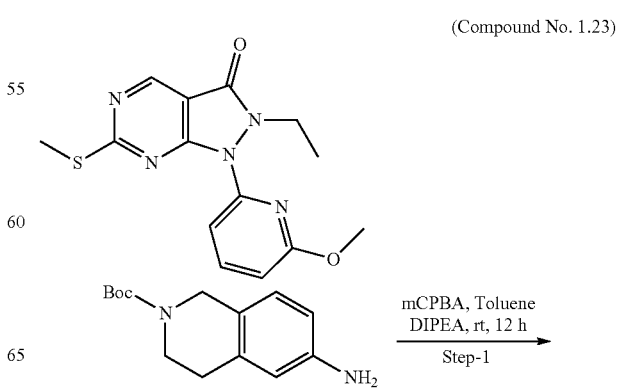

715

-continued

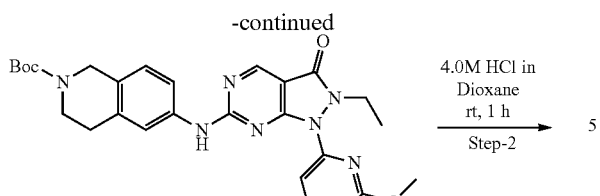

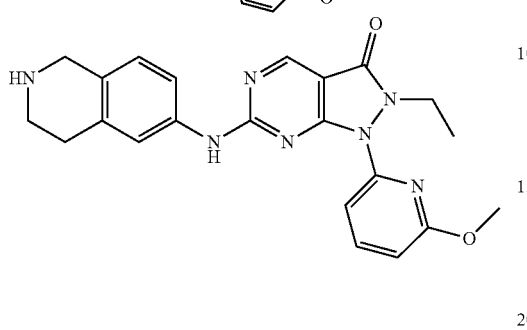

Step-1: Synthesis of tert-butyl 6-((2-ethyl-1-(6-methoxypyridin-2-yl)-3-oxo-2,3-dihydro-1H-pyrazolo[3,4-d]pyrimidin-6-yl)amino)-3,4-dihydroisoquinoline-2(1H)-carboxylate To a stirred solution of 2-ethyl-1-(6-methoxypyridin-2-yl)-6-(methylthio)-1,2-dihydro-3H-pyrazolo[3,4-d]pyrimidin-3-one (150 mg, 0.472 mmol, 1.0 eq) in toluene (5.0 mL) was added m-CPBA (233 mg, 0.944 mmol, 2.0 eq) and allowed to stir at rt for 30 min. tert-Butyl 6-amino-3,4-dihydroisoquinoline-2(1H)-carboxylate (130 mg, 0.519 mmol, 1.1 eq) and DIPEA (0.331 mL, 1.888 mmol, 4.0 eq) were added and allowed to stir at RT for overnight. The formation of precipitates was observed which was filtered to afford the desired compound, tert-butyl 6-((2-ethyl-1-(6-methoxypyridin-2-yl)-3-oxo-2,3-dihydro-1H-pyrazolo[3,4-d]pyrimidin-6-yl)amino)-3,4-dihydroisoquinoline-2(1H)-carboxylate (120 mg, 49%) as off white solid.

LCMS: [M+1]$^+$: 518.3

Step-2: Synthesis of 2-ethyl-1-(6-methoxypyridin-2-yl)-6-((1,2,3,4-tetrahydroisoquinolin-6-yl)amino)-1,2-dihydro-3H-pyrazolo[3,4-d]pyrimidin-3-one tert-Butyl 6-((2-ethyl-1-(6-methoxypyridin-2-yl)-3-oxo-2,3-dihydro-1H-pyrazolo[3,4-d]pyrimidin-6-yl) amino)-3,4-dihydroisoquinoline-2(1H)-carboxylate (120 mg, 0.231 mmol, 1.0 eq) was dissolved in (3 mL) 4M HCl in dioxane and allowed to stir at RT for 1 h. After completion of reaction, the reaction mixture was filtered and dried under reduced pressure and purified by SFC to afford the desired compound, 2-ethyl-1-(6-methoxypyridin-2-yl)-6-((1,2,3,4-tetrahydroisoquinolin-7-yl)amino)-1,2-dihydro-3H-pyrazolo[3,4-d]pyrimidin-3-one (40 mg, 42%) as light yellow solid.

LCMS [M+1]$^+$: 418.3

UPLC @ 254 nm=91.26% and @ 220 nm=93.54%.

$^1$H NMR (400 MHz, DMSO-d$_6$): δ 10.17 (br s, 1H), 8.84 (s, 1H), 7.97 (t, J=7.67 Hz, 1H), 7.61 (br s, 1H), 7.50 (d, J=7.45 Hz, 1H), 7.38 (d, J=8.33 Hz, 1H), 6.95 (d, J=8.33 Hz, 1H), 6.85 (d, J=8.33 Hz, 1H), 4.03 (d, J=6.58 Hz, 2H), 3.86 (s, 3H), 3.82 (br s, 2H), 2.97 (br s, 2H), 2.67 (br s, 2H), 1.00 (t, J=6.80 Hz, 3H).

716

Example S20. Synthesis of 1-(6-(2-hydroxypropan-2-yl)pyridin-2-yl)-2-isopropyl-6-((1,2,3,4-tetrahydroisoquinolin-6-yl)amino)-1,2-dihydro-3H-pyrazolo[3,4-d]pyrimidin-3-one hydrochloride (Compound No. 1.69)

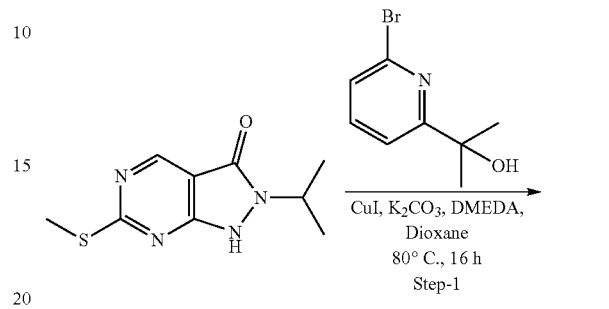

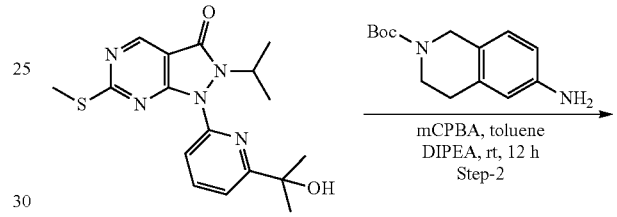

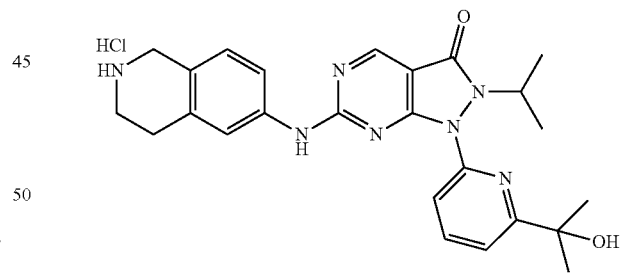

Step-1: Synthesis of 1-(6-(2-hydroxypropan-2-yl)pyridin-2-yl)-2-isopropyl-6-(methylthio)-1,2-dihydro-3H-pyrazolo[3,4-d]pyrimidin-3-one To a stirred solution of 2-isopropyl-6-(methylthio)-1,2-dihydro-3H-pyrazolo[3,4-d]pyrimidin-3-one (0.5 g, 2.23 mmol, 1.0 eq) and 2-(6-bromo-2-pyridyl)propan-2-ol (0.578 g, 2.67 mmol, 1.2 eq) in dioxane (30 mL) were added CuI (0.084 g, 0.44 mmol, 0.2 eq), K$_2$CO$_3$ (0.62 g, 4.46 mmol, 2 eq) and DMEDA (0.078 g, 0.89 mmol, 0.4 eq) and the resulting mixture was stirred at 80° C. for 16 h. After completion of reaction, solvent was removed under reduced pressure; residue was diluted with water (20 mL) and extracted with ethyl acetate (10 mL×3). The combined organic layer was washed with brine (5 mL×3), dried over anhydrous Na$_2$SO$_4$ and concentrated under reduced pressure to afford crude product, which was purified by flash chromatography (EtOAc/hexane 10-70%) to afford 1-(6-(2-hydroxypropan-2-yl)pyridin-2-yl)-2-isopropyl-6-(methylthio)-1,2-dihydro-3H-pyrazolo[3,4-d]pyrimidin-3-one (556 mg, 69%) as yellow oil.

LCMS: 360 [M+1]$^+$

Step-2: Synthesis of tert-butyl 6-((1-(6-(2-hydroxypropan-2-yl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(6-(2-hydroxypropan-2-yl)pyridin-2-yl)-2-isopropyl-6-(methylthio)-1,2-dihydro-3H-pyrazolo[3,4-d]pyrimidin-3-one (250 mg, 0.69 mmol, 1.0 eq) in toluene (3 mL) was added m-CPBA (300.3 mg, 1.74 mmol, 2.5 eq) and allowed to stir at rt for 30 min. Further, tert-butyl 6-amino-3,4-dihydroisoquinoline-2(1H)-carboxylate (190.15 mg, 0.76 mmol, 1.1 eq) and DIPEA (0.49 mL, 2.76 mmol, 4 eq) were added to the above mixture and allowed to stir at rt for 12 h. After completion of reaction, solvent was removed under reduced pressure; residue was diluted with water (10 mL) and extracted with ethyl acetate (5 mL×3). The combined organic layer was washed with brine solution (5 mL×3), dried over anhydrous Na$_2$SO$_4$ and concentrated under reduced pressure to afford crude product which was purified by flash chromatography (MeOH/CH$_2$Cl$_2$ 1-5%) to afford tert-butyl 6-((1-(6-(2-hydroxypropan-2-yl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (270 mg, 69%) as yellow solid.

LCMS: 560 [M+1]$^+$

Step-3: Synthesis of 1-(6-(2-hydroxypropan-2-yl)pyridin-2-yl)-2-isopropyl-6-((1,2,3,4-tetrahydroisoquinolin-6-yl)amino)-1,2-dihydro-3H-pyrazolo[3,4-d]pyrimidin-3-one hydrochloride 20% HCl in dioxane (2 mL) was added to a solution of tert-butyl 6-((1-(6-(2-hydroxypropan-2-yl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (260 mg, 0.46 mmol, 1.0 eq) in dioxane (1 mL) at 0° C. and the resulting solution was allowed to stir at rt for 3 h. After completion of reaction, solvent was removed under reduced pressure and the resulting solid was filtered and washed with diethyl ether (5 mL×3), dried to afford 1-(6-(2-hydroxypropan-2-yl)pyridin-2-yl)-2-isopropyl-6-((1,2,3,4-tetrahydroisoquinolin-6-yl)amino)-1,2-dihydro-3H-pyrazolo[3,4-d]pyrimidin-3-one hydrochloride (165 mg, 71%) as a yellow solid.

LCMS: 460 [M+1]$^+$

UPLC @ 254 nm=98.23% and @ 220 nm=97.37%

$^1$H NMR (400 MHz, DMSO-d$_6$, HCl salt): δ 10.3 (br s, 1H), 9.27 (br s, 1H), 8.79 (s, 1H), 8.07-8.03 (m, 1H), 7.70-7.63 (m, 3H), 7.42 (d, J=8 Hz, 1H), 7.12 (d, J=8 Hz, 1H) 4.18 (br. s., 1H), 3.36-3.33 (m, 2H), 2.97-2.95 (m, 2H), 1.40 (s, 6H), 1.32 (d, J=6.58 Hz, 6H).

Example S21. Synthesis of 6-(2',3'-dihydro-1'H-spiro[cyclopropane-1,4'-isoquinoline]-7'-ylamino)-2-ethyl-1-(6-(2-hydroxypropan-2-yl)pyridin-2-yl)-1H-pyrazolo[3,4-d]pyrimidin-3(2H)-one (Compound No. 1.70)

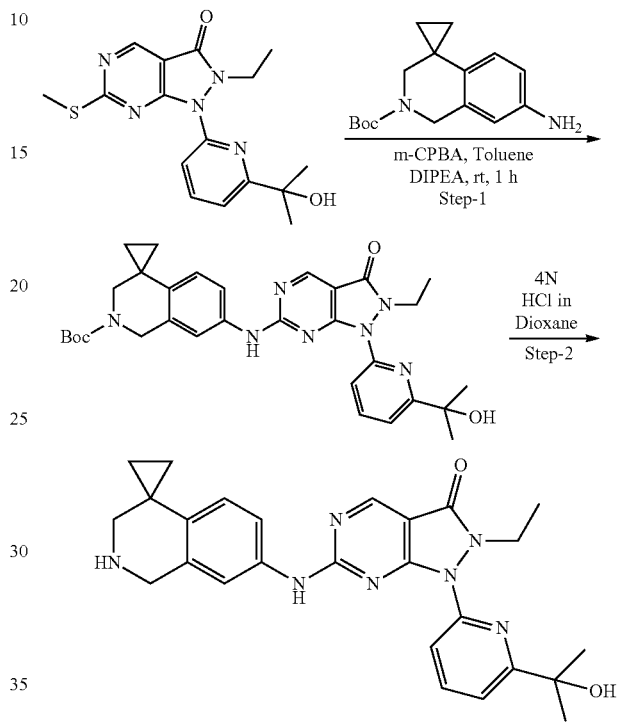

Step-1: Synthesis of tert-butyl 7'-(2-ethyl-1-(6-(2-hydroxypropan-2-yl)pyridin-2-yl)-3-oxo-2,3-dihydro-1H-pyrazolo[3,4-d]pyrimidin-6-ylamino)-1'H-spiro[cyclopropane-1,4'-isoquinoline]-2'(3'H)-carboxylate To a stirred solution of 2-ethyl-1-(6-(2-hydroxypropan-2-yl)pyridin-2-yl)-6-(methylthio)-1H-pyrazolo[3,4-d]pyrimidin-3(2H)-one (200 mg, 0.58 mmol, 1.0 eq) in toluene (5 mL) was added m-CPBA (250 mg, 1.45 mmol, 2.5 eq.) and allowed to stir at RT for 30 min. tert-Butyl 7'-amino-1'H-spiro[cyclopropane-1,4'-isoquinoline]-2'(3'H)-carboxylate (160 mg, 0.58 mmol, 1.0 eq) and DIPEA (300 mg, 2.32 mmol, 4.0 eq) were added and allowed to stir at RT for 1 h. Progress of reaction was monitored by LCMS. After completion of reaction solvent was removed under reduced pressure, residue was diluted with water (20 mL) and extracted with ethyl acetate (50 mL×3). Combined organic layer was washed with water (20 mL×3), dried over anhydrous Na$_2$SO$_4$ and concentrated under reduced pressure. Crude was purified by flash chromatography to obtain tert-butyl 7'-(2-ethyl-1-(6-(2-hydroxypropan-2-yl)pyridin-2-yl)-3-oxo-2,3-dihydro-1H-pyrazolo[3,4-d]pyrimidin-6-ylamino)-1'H-spiro[cyclopropane-1,4'-isoquinoline]-2' (3'H)-carboxylate (150 mg, 45.3%).

LCMS: 572 [M+1]$^+$

Step-2: Synthesis of 6-(2',3'-dihydro-1'H-spiro[cyclopropane-1,4'-isoquinoline]-7'-ylamino)-2-ethyl-1-(6-(2-hydroxypropan-2-yl)pyridin-2-yl)-1H-pyrazolo[3,4-d]pyrimidin-3(2H)-one tert-butyl 7'-(2-ethyl-1-(6-(2-hydroxypropan-2-yl)pyridin-2-yl)-3-oxo-2,3-dihydro-1H-pyrazolo[3,4-d]pyrimidin-6-ylamino)-1'H-spiro[cyclopropane-1,4'-isoquinoline]-2'(3'H)-carboxylate (150 mg, 0.262 mmol, 1.0 eq) was dissolved in 4N HCl in dioxane (5 mL) at 0° C. Reaction was stirred at RT for 30 min. Progress of reaction was monitored by LCMS. After completion of reaction, precipitated compound was filtered off and dried under vacuum to obtain 6-(2',3'-dihydro-1'H-spiro[cyclopropane-1,4'-isoquinoline]-7'-ylamino)-2-ethyl-1-(6-(2-hydroxypropan-2-yl)pyridin-2-yl)-1H-pyrazolo[3,4-d]pyrimidin-3 (2H)-one (35 mg, 28.4%) as HCl salt.

LCMS: 472 [M+1]$^+$

UPLC @ 254 nm=90.35% and @ 220 nm=94.63%

$^1$H NMR (400 MHz, DMSO-d$_6$): δ 10.31 (br s, 1H), 9.52 (br s, 2H), 8.86 (s, 1H), 8.11 (t, J=7.89 Hz, 1H), 7.84 (d, J=7.89 Hz, 1H), 7.72 (br s, 1H), 7.66 (d, J=7.45 Hz, 1H), 7.48 (d, J=8.77 Hz, 1H), 6.83 (d, J=8.33 Hz, 1H), 4.36 (br s, 2H), 4.04 (d, J=7.02 Hz, 2H), 3.24 (br s, 2H), 1.44 (s, 6H), 1.08 (br s, 4H), 0.97 (t, J=7.02 Hz, 3H).

Example S22. Synthesis of 2-ethyl-1-(6-(2-hydroxypropan-2-yl)pyridin-2-yl)-6-(1,2,3,4-tetrahydroisoquinolin-5-ylamino)-1H-pyrazolo[3,4-d]pyrimidin-3(2H)-one (Compound No. 1.125)

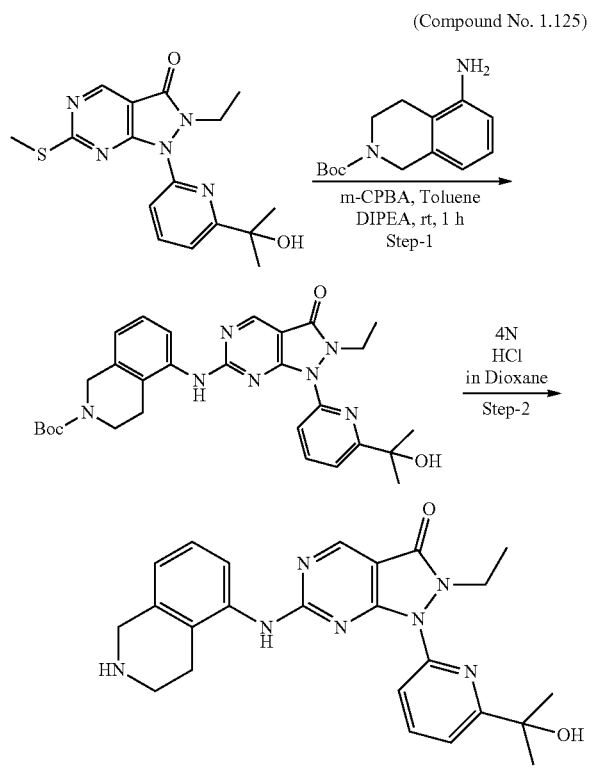

Step-1: Synthesis of tert-butyl 5-(2-ethyl-1-(6-(2-hydroxypropan-2-yl)pyridin-2-yl)-3-oxo-2,3-dihydro-1H-pyrazolo[3,4-d]pyrimidin-6-ylamino)-3,4-dihydroisoquinoline-2(1H)-carboxylate To a stirred solution of 2-ethyl-1-(6-(2-hydroxypropan-2-yl)pyridin-2-yl)-6-(methylthio)-1H-pyrazolo[3,4-d]pyrimidin-3(2H)-one (200 mg, 0.58 mmol, 1.0 eq) in 5 mL of Toluene was added m-CPBA (250 mg, 1.45 mmol, 2.5 eq.) and allowed to stir at rt for 30 minutes. tert-butyl 5-amino-3,4-dihydroisoquinoline-2(1H)-carboxylate (140 mg, 0.58 mmol, 1.0 eq) and DIPEA (300 mg, 2.32 mmol, 4.0 eq) were added and allowed to stir at rt for 1 h. Progress of reaction was monitored by LCMS. After completion of reaction solvent was removed under reduced pressure, residue was diluted with 20 ml of water and extracted with ethyl acetate (50 mL×3). Combined organic layer was washed with water (20 ml×3), dried over anhydrous sodium sulfate and concentrated under reduced pressure. Crude was purified by flash chromatography to obtain 170 mg (53.79%) of tert-butyl 5-(2-ethyl-1-(6-(2-hydroxypropan-2-yl)pyridin-2-yl)-3-oxo-2,3-dihydro-1H-pyrazolo[3,4-d]pyrimidin-6-ylamino)-3,4-dihydroisoquinoline-2(1H)-carboxylate.

LCMS: 546 [M+1]$^+$

Step-2: Synthesis of 2-ethyl-1-(6-(2-hydroxypropan-2-yl)pyridin-2-yl)-6-(1,2,3,4-tetrahydroisoquinolin-5-ylamino)-1H-pyrazolo[3,4-d]pyrimidin-3(2H)-one tert-butyl 5-(2-ethyl-1-(6-(2-hydroxypropan-2-yl)pyridin-2-yl)-3-oxo-2,3-dihydro-1H-pyrazolo[3,4-d]pyrimidin-6-ylamino)-3,4-dihydroisoquinoline-2(1H)-carboxylate (170 mg, 0.311 mmol, 1.0 eq) was dissolved in 5 mL of 4N HCl in dioxane solution at 0° C. Reaction was stirred at rt for 30 min. Progress of reaction was monitored by LCMS. After completion of reaction, precipitated compound was filtered off and dried under vacuum. Crude was basified with saturated NaHCO$_3$ solution; precipitated compound was filtered off and dried under vacuum and purified by reverse phase chromatography to obtain 30 mg (21.7%) free base of 2-ethyl-1-(6-(2-hydroxypropan-2-yl)pyridin-2-yl)-6-(1,2,3,4-tetrahydroisoquinolin-5-ylamino)-1H-pyrazolo[3,4-d]pyrimidin-3 (2H)-one.

LCMS: 446 [M+1]$^+$ $^1$H NMR (400 MHz, DMSO-d$_6$) δ 9.56 (brs, 1H), 8.77 (s, 1H), 7.89 (brs, 1H), 7.69 (d, J=6.14 Hz, 1H), 7.58 (d, J=7.45 Hz, 1H), 7.33 (brs, 1H), 7.19 (t, J=7.67 Hz, 1H), 6.97 (d, J=7.89 Hz, 1H), 5.30 (brs, 1H), 3.96-4.07 (m, 4H), 3.04 (brs, 2H), 2.69 (brs, 2H), 1.37-1.49 (m, 7H), 0.95 (t, J=6.80 Hz, 3H).

Example S23. Synthesis of 2-cyclopropyl-1-(6-(2-hydroxypropan-2-yl)pyridin-2-yl)-6-((1,2,3,4-tetrahydroisoquinolin-6-yl)amino)-1,2-dihydro-3H-pyrazolo[3,4-d]pyrimidin-3-one (Compound No. 1.24)

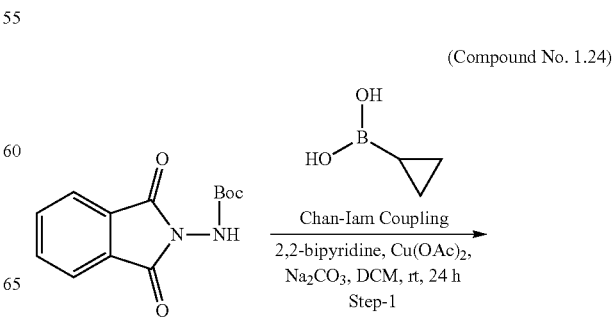

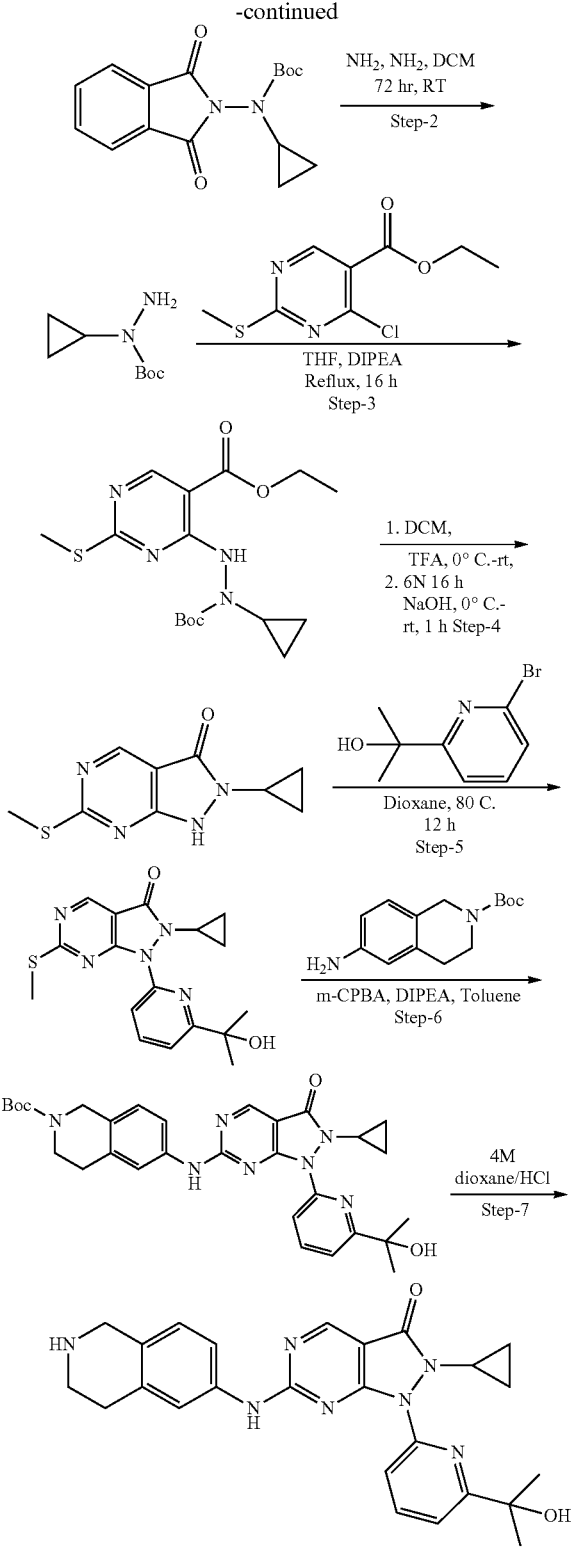

Step-1: Synthesis of tert-butyl cyclopropyl(1,3-dioxoisoindolin-2-yl)carbamate

To a stirred solution of tert-butyl (1,3-dioxoisoindolin-2-yl)carbamate (5.0 g, 19.06 mmol, 1.0 eq), in DCM (120 mL) were added cyclopropylboronic acid (4.61 g, 38.12 mmol, 2.0 eq), 2,2-bipyridine, (5.95 g, 38.12 mmol, 2.0 eq), Cu(OAc)2 (6.92 g, 38.12 mmol, 2.0 eq) and Na2CO3 (6.06 g, 57.18 mmol, 3.0 eq) at rt. The resulting mixture was stirred in open bottle for 24 h. The progress of reaction was monitored by LCMS. The reaction mixture was diluted with water (100 mL), extracted with DCM (2×200 mL). The combined organic layers were washed with water (100 mL), with brine (50 mL), dried over Na2SO4, concentrated and purified by column chromatography (Combiflash, elution, 0-15% EtOAC in hexane) to afford the desired compound tert-butyl cyclopropyl(1,3-dioxoisoindolin-2-yl)carbamate (64.3 g, 74.65%) as white solid.

LCMS: 303.1 [M+1]+

Step-2: Synthesis of tert-butyl 1-cyclopropylhydrazine-1-carboxylate

To a stirred solution of tert-butyl cyclopropyl(1,3-dioxoisoindolin-2-yl)carbamate (4.3 g, 14.22 mmol, 1.0 eq), in DCM (60 mL) was added NH2NH2.H2O (1.35 mL, 28.44 mmol, 2.0 eq) at rt. The resulting mixture stirred at rt for overnight, formation of white precipitates was observed. The progress of reaction was monitored by $^1$HNMR. The reaction mixture was filtered and the filtrate was concentrated and purified by pentane to afford the desired compound, tert-butyl 1-cyclopropylhydrazine-1-carboxylate (2.2 g, 90.16%) as light yellow liquid.

LCMS: 173.1 [M+1]+

Step-3: Synthesis of ethyl 4-(2-(tert-butoxycarbonyl)-2-cyclopropylhydrazinyl)-2-(methylthio)pyrimidine-5-carboxylate To a stirred solution of tert-butyl 1-cyclopropylhydrazine-1-carboxylate (1.98 g, 8.51 mmol, 1.0 eq) and tert-butyl 1-(cyclopropylmethyl)hydrazine-1-carboxylate (2.2 g, 12.77 mmol, 1.5 eq) in (24 mL) of THF was added DIPEA (3.68 mL, 21.27 mmol, 2.5 eq) and stirred at 80° C. for 16 h. Solvent was removed under reduced pressure. Residue was diluted with water (50 mL) and extracted with EtOAc (50 mL×2). The organic layers were washed with brine solution (50 mL), dried over anhydrous sodium sulphate and concentrated under reduced pressure, purified by column chromatography (Combiflash, elution-0-40% EtOAc in Hexane) to afford the desired compound, ethyl 4-(2-(tert-butoxycarbonyl)-2-cyclopropylhydrazinyl)-2-(methylthio) pyrimidine-5-carboxylate (2.2 g, 70.28%) as off white solid.

LCMS: 369.1 [M+1]+

Step-4: Synthesis of 2-cyclopropyl-6-(methylthio)-1,2-dihydro-3H-pyrazolo[3,4-d]pyrimidin-3-one To a stirred solution of ethyl 4-(2-(tert-butoxycarbonyl)-2-cyclopropylhydrazinyl)-2-(methylthio)pyrimidine-5-carboxylate (2.2 g, 5.97 mmol, 1.0 eq) in 24 mL of DCM was added TFA (5.97 mL) dropwise at 0° C. and allowed to stir at rt for overnight. After completion of reaction, solvent was removed under reduced pressure. Residue was diluted with ethanol (12 mL), 6N NaOH solution (12 mL) was added in to above solution at 0° C. and allowed to stir at rt for 1 h. After completion, the reaction mixture was acidified by using 6N HCl solution. Ethanol was removed under reduced pressure; residue obtained was cooled to rt and extracted with chloroform (100 mL×3). The organic layers were washed with brine solution, dried over anhydrous sodium sulphate and concentrated under reduced pressure to afford the desired compound, 2-cyclopropyl-6-(methylthio)-1,2-dihydro-3H-pyrazolo[3,4-d]pyrimidin-3-one (1.0 g, 75.75%) as yellow solid.

LCMS: 223.1 [M+1]+

Step-5: Synthesis of 2-cyclopropyl-1-(6-(2-hydroxypropan-2-yl)pyridin-2-yl)-6-(methylthio)-1,2-dihydro-3H-pyrazolo[3,4-d]pyrimidin-3-one To a stirred solution of 2-(cyclopropylmethyl)-6-(methylthio)-1,2-dihydro-3H-pyrazolo[3,4-d]pyrimidin-3-one (1.0 g, 4.49 mmol, 1.0 eq) and 2-(6-bromo-2-pyridyl)propan-2-ol (1.16 g, 5.39 mmol, 1.20 eq) in (10 mL) of dioxane were added Potassium carbonate (1.24 g, 8.98 mmol, 2.0 eq) and the resulting mixture was purged with nitrogen for 10 min, followed by addition of copper iodide (171 mg, 0.89 mmol, 0.2 eq), and N,N'-dimethylethylenediamine (DMEDA) (158 mg, 1.79 mmol, 0.4 eq) and again purged with nitrogen for 10 min, stirred at 90° C. for overnight. After completion of reaction, the reaction mixture was diluted with water and extracted with EtOAc (50 mL×2). The combined organic layers were washed with water (50 mL), brine solution (50 mL), dried over anhydrous sodium sulphate and concentrated under reduced pressure to afford crude product, which was purified by flash chromatography to afford the desired compound, 2-cyclopropyl-1-(6-(2-hydroxypropan-2-yl)pyridin-2-yl)-6-(methylthio)-1,2-dihydro-3H-pyrazolo[3,4-d]pyrimidin-3-one (600 mg, 37.50%) as an off white solid.

LCMS: 358.2 [M+1]+

Step-6: Synthesis of tert-butyl 6-((2-cyclopropyl-1-(6-(2-hydroxypropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate To a stirred solution of 2-cyclopropyl-1-(6-(2-hydroxypropan-2-yl)pyridin-2-yl)-6-(methylthio)-1,2-dihydro-3H-pyrazolo[3,4-d]pyrimidin-3-one (100 mg, 0.280 mmol, 1.0 eq) in (3 mL) of toluene was added m-CPBA (97 mg, 0.560 mmol, 2.0 eq) and allowed to stir at rt for 30 min. tert-butyl 6-amino-3,4-dihydroisoquinoline-2(1H)-carboxylate (83 mg, 0.336 mmol, 2.0 eq) and DIPEA (0.2 mL, 1.12 mmol, 4.0 eq) were added and allowed to stir at rt for overnight. The formation of precipitates was observed which was filtered to afford the desired compound, tert-butyl 6-((2-cyclopropyl-1-(6-(2-hydroxypropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate (50 mg, 32.04%) as an off white solid.

LCMS: 558.3 [M+1]+

Step-7: Synthesis of 2-cyclopropyl-1-(6-(2-hydroxypropan-2-yl)pyridin-2-yl)-6-((1,2,3,4-tetrahydroisoquinolin-6-yl)amino)-1,2-dihydro-3H-pyrazolo[3,4-d]pyrimidin-3-one tert-butyl 6-((2-cyclopropyl-1-(6-(2-hydroxypropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate (50 mg, 0.089 mmol, 1.0 eq) was dissolved in (0.5 mL) of dioxane and added 6M dioxane-HCl (1 mL) and allowed to stir at rt for 1 h. After completion of reaction, the reaction mixture was filtered and dried under reduced pressure to afford the desired compound, 2-cyclopropyl-1-(6-(2-hydroxypropan-2-yl)pyridin-2-yl)-6-((1,2,3,4-tetrahydroisoquinolin-6-yl)amino)-1,2-dihydro-3H-pyrazolo[3,4-d]pyrimidin-3-one (12 mg, 29.25%) as an off white solid.

LCMS: 458.3 [M+1]+; UPLC @ 254 nm=99.73% and @ 220 nm=99.78%.

1H NMR (400 MHz, DMSO-d6): δ 10.09 (br. s., 1H), 8.77 (s, 1H), 8.04-8.13 (m, 1H), 7.64 (br. s., 2H), 7.35 (br. s., 1H), 6.91-7.01 (m, 2H), 4.40 (br. s., 1H), 3.78 (br. s., 2H), 3.52 (br. s., 3H), 3.20 (br. s., 2H), 2.94 (br. s., 2H), 2.66 (br. s., 3H), 1.59 (s, 3H), 1.44 (s, 7H), 0.81 (br. s., 4H).

Example S24. Synthesis of 2-ethyl-1-(6-(2-oxopyrrolidin-1-yl)pyridin-2-yl)-6-((1,2,3,4-tetrahydroisoquinolin-7-yl)amino)-1,2-dihydro-3H-indazol-3-one dihydrochloride (Compund No. 1.31)

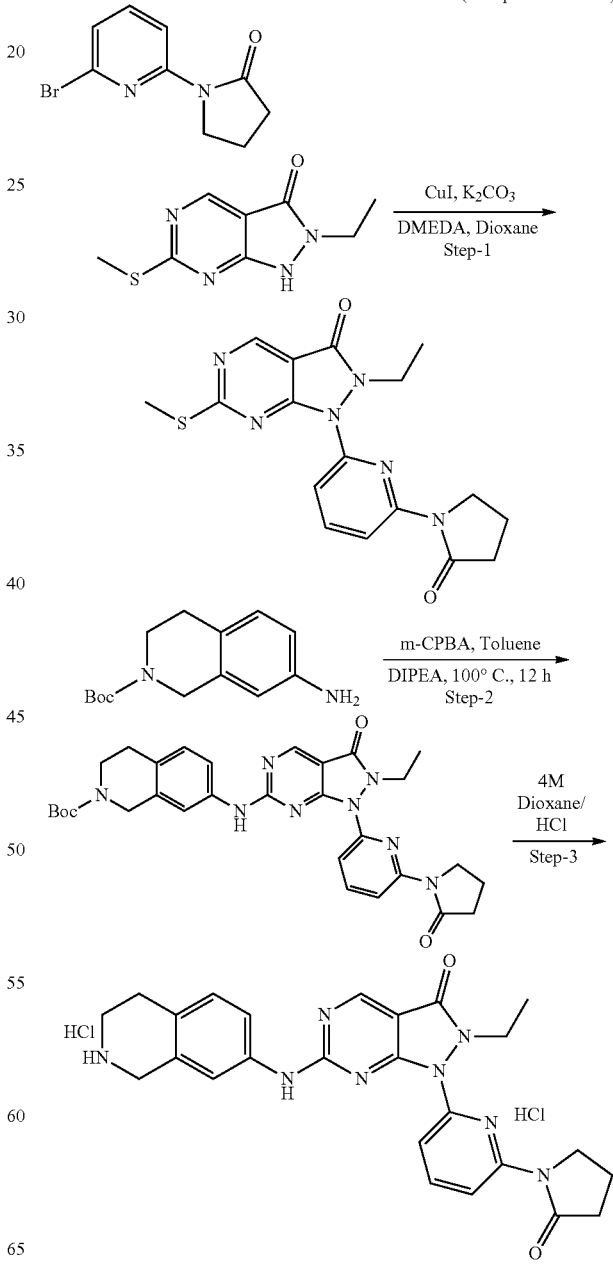

Step-1: Synthesis of 2-ethyl-6-(methylthio)-1-(6-(2-oxopyrrolidin-1-yl)pyridin-2-yl)-1,2-dihydro-3H-indazol-3-one To a stirred solution of 2-ethyl-6-(methylthio)-1,2-dihydro-3H-indazol-3-one (400 mg, 1.90 mmol, 1.0 eq) and 1-(6-bromopyridin-2-yl)pyrrolidin-2-one (459 mg, 2.28 mmol, 1.20 eq) in (20 mL) of dioxane was added Potassium carbonate (525 mg, 3.80 mmol, 2.0 eq) and the resulting mixture was purged with nitrogen for 10 min followed by addition of copper iodide (72 mg, 0.38 mmol, 0.2 eq), and N,N'-dimethylethylenediamine (DMEDA) (0.08 mL, 0.76 mmol, 0.4 eq) and again purged with nitrogen for 10 min, stirred at 90° C. for overnight. After completion of reaction, the reaction mixture was diluted with water and extracted with EtOAc (50 mL×2). Combined organic layer was washed with water (50 mL) brine solution (50 mL), dried over anhydrous sodium sulphate and concentrated under reduced pressure to afford crude product, which was purified by flash chromatography [silica gel 100-200 mesh; elution 0-30% EtOAc in hexane] to afford the desired compound 2-ethyl-6-(methylthio)-1-(6-(2-oxopyrrolidin-1-yl)pyridin-2-yl)-1,2-dihydro-3H-indazol-3-one (200 mg, 28.26%) as light yellow solid.

LCMS: 371.3 [M+1]+

Step-2: Synthesis of tert-butyl 7-((2-ethyl-3-oxo-1-(6-(2-oxopyrrolidin-1-yl)pyridin-2-yl)-2,3-dihydro-1H-indazol-6-yl)amino)-3,4-dihydroisoquinoline-2(1H)-carboxylate To a stirred solution of 2-ethyl-6-(methylthio)-1-(6-(2-oxopyrrolidin-1-yl)pyridin-2-yl)-1,2-dihydro-3H-indazol-3-one (200 mg, 0.539 mmol, 1.0 eq) in (5.0 mL) of toluene was added m-CPBA (283 mg, 1.347 mmol, 2.0 eq) and allowed to stir at rt for 30 minutes. tert-butyl 7-amino-3,4-dihydroisoquinoline-2(1H)-carboxylate (147 mg, 0.593 mmol, 1.1 eq) and DIPEA (0.37 mL, 2.156 mmol, 4.0 eq) were added and allowed to stir at rt for overnight. The formation of precipitates was observed which was filtered to afford the desired compound tert-butyl 7-((2-ethyl-3-oxo-1-(6-(2-oxopyrrolidin-1-yl)pyridin-2-yl)-2,3-dihydro-1H-indazol-6-yl)amino)-3,4-dihydroisoquinoline-2(1H)-carboxylate (200 mg, 64.91%) as white solid. LCMS: 571.4 [M+1]+

Step-3: Synthesis of 2-ethyl-1-(6-(2-oxopyrrolidin-1-yl)pyridin-2-yl)-6-((1,2,3,4-tetrahydroisoquinolin-7-yl)amino)-1,2-dihydro-3H-indazol-3-one dihydrochloride tert-butyl 7-((2-ethyl-3-oxo-1-(6-(2-oxopyrrolidin-1-yl)pyridin-2-yl)-2,3-dihydro-1H-indazol-6-yl)amino)-3,4-dihydroisoquinoline-2(1H)-carboxylate (200 mg, 0.350 mmol, 1.0 eq) was dissolved in (0.5 mL) of dioxane and added 6M dioxane-HCl (1 mL) and allowed to stir at rt for 1 h. After completion of reaction, the reaction mixture was filtered and dried under reduced pressure to afford the desired compound, 2-ethyl-1-(6-(2-oxopyrrolidin-1-yl)pyridin-2-yl)-6-((1,2,3,4-tetrahydroisoquinolin-7-yl)amino)-1,2-dihydro-3H-indazol-3-one dihydrochloride (90 mg, 54.57%) as an off white solid.

LCMS: 469.3 [M+1]+; UPLC @ 254 nm=95.67% and @ 220 nm=96.28%.

1H NMR (400 MHz, DMSO-d6): δ 10.34 (br. s., 1H), 9.15 (br. s., 2H), 8.88 (s, 1H), 8.29 (d, J=7.89 Hz, 1H), 8.12 (t, J=8.33 Hz, 1H), 7.70-7.76 (m, 1H), 7.51 (d, J=8.33 Hz, 1H), 7.18 (d, J=8.77 Hz, 1H), 4.26 (br. s., 2H), 4.02-4.13 (m, 2H), 3.98 (t, J=7.02 Hz, 2H), 3.57 (s, 2H), 3.39 (br. s., 2H), 2.96 (br. s., 2H), 2.67 (br. s., 1H), 2.59-2.64 (m, 2H), 2.00-2.12 (m, 3H), 0.99 (t, J=7.02 Hz, 3H).

Example S25. Synthesis of 2-ethyl-1-(6-(methylamino)pyridin-2-yl)-6-((1,2,3,4-tetrahydroisoquinolin-7-yl)amino)-1,2-dihydro-3H-pyrazolo[3,4-d]pyrimidin-3-one dihydrochloride (Compound No. 1.27)

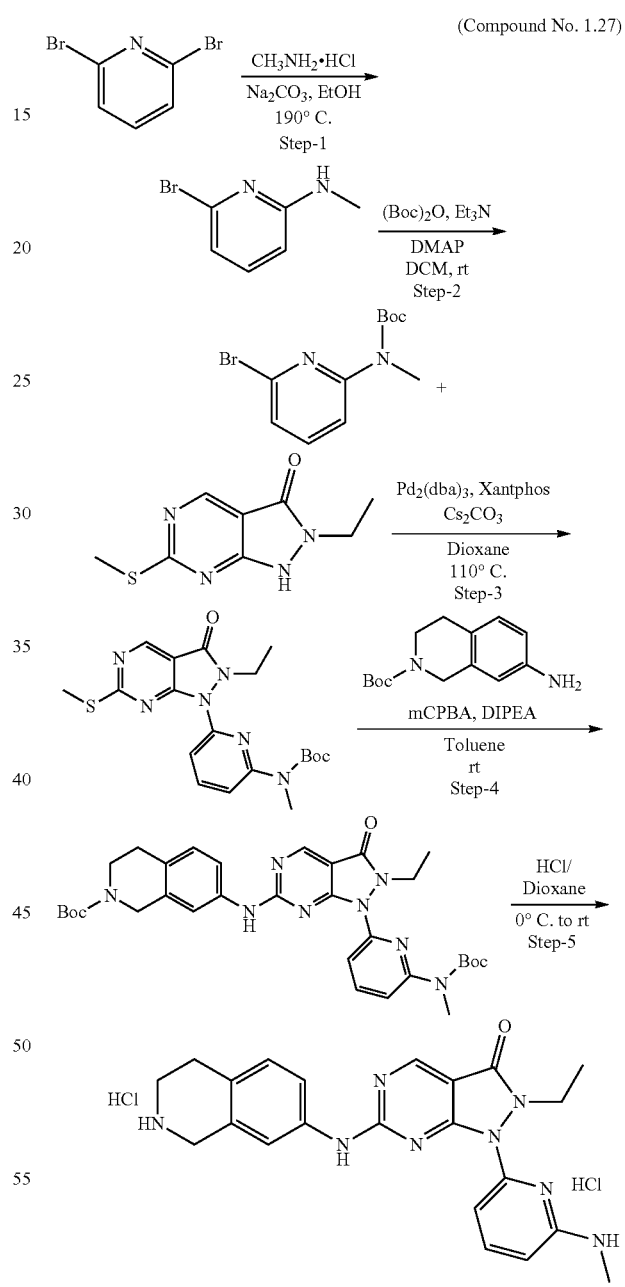

Step-1: Synthesis of 6-bromo-N-methylpyridin-2-amine

To a solution of 2,6-dibromopyridine (5 g, 21.1, 1 eq) in EtOH (50 mL), methyl amine hydrochloride (1.71 g, 25.3 mmol, 1.2 eq) and Na2CO3 (6.71 g, 63.3 mmol, 3 eq) were added under stirring at rt. The mixture was heated at 190° C. for 12 h. The progress of the reaction was monitored by LCMS. After completion the mixture was cooled to rt, concentrated under vacuo to remove solvent. Water (10 mL×3) was added followed by extraction using EtOAc (20 mL×3). The combined organic layer was dried over Na₂SO₄ and concentrated. The residue was purified by flash chromatography (20% EtOAc/pet ether) to give 6-bromo-N-methylpyridin-2-amine (2.8 g, 71%) as colourless oil.

LCMS: 187 [M+1]⁺

Step-2: Synthesis of tert-butyl (6-bromopyridin-2-yl)(methyl)carbamate

To a solution of 6-bromo-N-methylpyridin-2-amine (2.3 g, 12.2, 1 eq) in dry DCM (50 mL), Et₃N (2.57 mL, 18.4 mmol, 1.5 eq) followed by DMAP (0.3 g, 2.45 mmol, 0.2 eq) were added under stirring at rt under inert atmosphere. The resulting solution was stirred for 15-20 min at rt followed by dropwise addition of Boc-anhydride (4.23 mL, 18.4 mmol, 1.5 eq). The resulting solution was stirred at rt for 16 h. The progress of the reaction was monitored by LCMS. After completion, reaction was quenched with water (20 mL×3) and extracted using DCM (10 mL×3). The combined organic layer was dried over Na₂SO₄, concentrated and purified by flash chromatography (20% EtOAc/pet ether) to give tert-butyl (6-bromopyridin-2-yl)(methyl)carbamate (2.5 g, 71%) as colourless liquid.

LCMS: 287 [M+1]⁺

Step-3: Synthesis of tert-butyl (6-(2-ethyl-6-(methylthio)-3-oxo-2,3-dihydro-1H-pyrazolo[3,4-d]pyrimidin-1-yl)pyridin-2-yl)(methyl)carbamate To a stirring solution of 2-ethyl-6-(methylthio)-1,2-dihydro-3H-pyrazolo[3,4-d]pyrimidin-3-one (400 mg, 1.9 mmol, 1 eq) in dioxane (20 mL), tert-butyl (6-bromopyridin-2-yl)(methyl)carbamate (0.655 g, 2.28 mmol, 1.2 eq) and Cs₂CO₃ (1.23 g, 3.8 mmol, 2 eq) were added. The mixture was degassed for 10-15 min followed addition of Pd₂(dba)₃ (174.2 mg, 0.19 mmol, 0.1 eq) and xantphos (165.1 mg, 3.8 mmol, 2 eq). The reaction was heated at 100° C. for 16 h. After completion, the reaction mixture was filtered through celite and water (20 mL) was added to it. Extraction was carried out using MeOH/DCM (20 mL×3). The combined organic layer was dried, concentrated and purified by flash chromatography (MeOH/DCM 1-5%) to give tert-butyl (6-(2-ethyl-6-(methylthio)-3-oxo-2,3-dihydro-1H-pyrazolo[3,4-d]pyrimidin-1-yl)pyridin-2-yl)(methyl)carbamate (145 mg, 19%) as yellow solid.

LCMS: 416 ([M+1]⁺

Step-4: Synthesis of tert-butyl 7-((1-(6-((tert-butoxycarbonyl)(methyl)amino)pyridin-2-yl)-2-ethyl-3-oxo-2,3-dihydro-1H-pyrazolo[3,4-d]pyrimidin-6-yl)amino)-3,4-dihydroisoquinoline-2(1H)-carboxylate To a stirred solution of tert-butyl (6-(2-ethyl-6-(methylthio)-3-oxo-2,3-dihydro-1H-pyrazolo[3,4-d]pyrimidin-1-yl)pyridin-2-yl)(methyl)carbamate (140 mg, 0.33 mmol, 1.0 eq) in toluene (4 mL); m-CPBA (145 mg, 0.84 mmol, 2.5 eq) was added under stirring and resulting mixture was allowed to stir at rt for 30 minutes. tert-butyl 7-amino-3,4-dihydroisoquinoline-2(1H)-carboxylate (243.1 mg, 0.36 mmol, 1.1 eq) and DIPEA (0.23 mL, 1.34 mmol, 4 eq) were then added and the reaction was allowed to stir at rt for 16 h. The progress of the reaction was monitored by LCMS. After completion reaction was quenched with water and extracted with MeOH/DCM (10 mL×3). The combined organic layer was washed with brine solution (20 mL), dried over anhydrous Na₂SO₄ and concentrated under reduced pressure to afford crude product which was purified by flash chromatography (1-10% MeOH/DCM) to afford tert-butyl 7-((1-(6-((tert-butoxycarbonyl)(methyl)amino)pyridin-2-yl)-2-ethyl-3-oxo-2,3-dihydro-1H-pyrazolo[3,4-d]pyrimidin-6-yl)amino)-3,4-dihydroisoquinoline-2(1H)-carboxylate (100 mg, 48%) as yellow solid.

LCMS: 616 [M+1]⁺

Step-5: Synthesis of 2-ethyl-1-(6-(methylamino)pyridin-2-yl)-6-((1,2,3,4-tetrahydroisoquinolin-7-yl)amino)-1,2-dihydro-3H-pyrazolo[3,4-d]pyrimidin-3-one dihydrochloride 20% HCl in dioxane (2 mL) was added to a stirred solution of tert-butyl 7-((1-(6-((tert-butoxycarbonyl)(methyl)amino)pyridin-2-yl)-2-ethyl-3-oxo-2,3-dihydro-1H-pyrazolo[3,4-d]pyrimidin-6-yl)amino)-3,4-dihydroisoquinoline-2(1H)-carboxylate (97 mg, 0.15 mmol, 1.0 eq) in dioxane (2 mL) at 0° C. under inert atmosphere and the resulting solution was allowed to stir at rt for 3 h. After completion, solvent was removed under reduced pressure and the resulting solid was filtered and washed with ether, dried to afford 2-ethyl-1-(6-(methylamino)pyridin-2-yl)-6-((1,2,3,4-tetrahydroisoquinolin-7-yl)amino)-1,2-dihydro-3H-pyrazolo[3,4-d]pyrimidin-3-one dihydrochloride (22 mg, 29%) as a yellow solid.

LCMS: 416 [M+1]⁺; UPLC: @220 nm=91.97% @254 nm=90.07% HPLC: @220 nm=97.13% @254 nm=96.03%

¹H NMR (400 MHz, DMSO-d₆, Formate): δ 10.13 (br s, 1H), 8.81 (s, 1H), 8.24 (br s, 1H), 7.65-7.61 (m, 2H), 7.41-7.61 (m, 1H), 7.01 (d, J=8.33 Hz, 1H), 6.96-6.94 (m, 1H), 6.88-6.84 (m, 1H), 6.44 (d, J=7.89 Hz, 1H), 4 (q, J=7 Hz, 2H), 3.89 (br s, 2H), 3.04-3.01 (m, 2H), 2.75 (d, J=4.82 Hz, 2H), 2.7-2.67 (m, 3H), 1.01 (t, J=7.02 Hz, 3H).

Example S26. Synthesis of 6-(2-ethyl-3-oxo-6-((1,2,3,4-tetrahydroisoquinolin-7-yl)amino)-2,3-dihydro-1H-pyrazolo[3,4-d]pyrimidin-1-yl)-N-methylpicolinamide hydrochloride

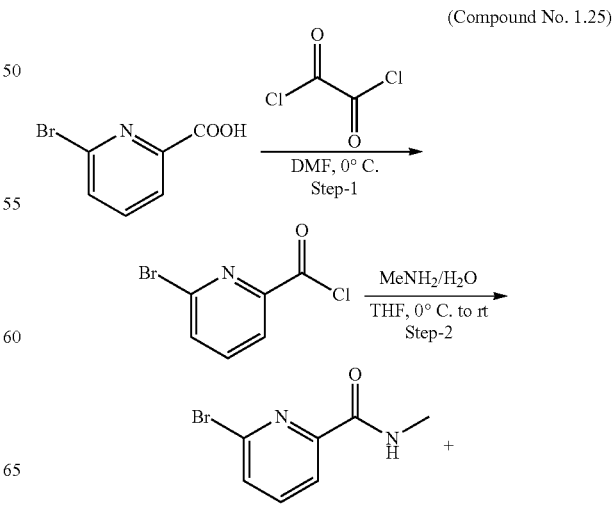

(Compound No. 1.25)

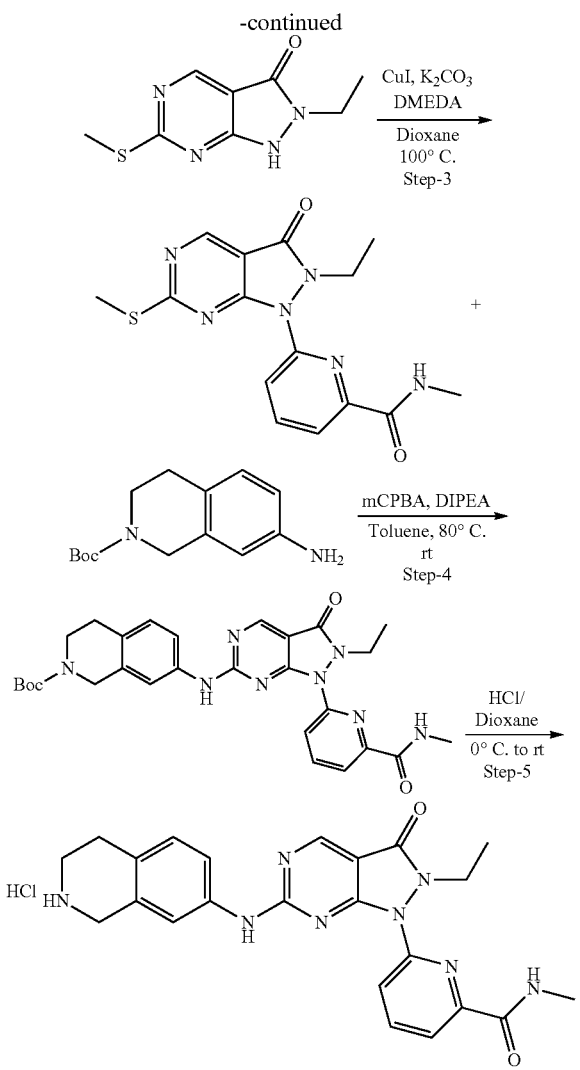

Step-1: Synthesis of 6-bromopicolinoyl chloride

To a solution of 6-bromopicolinic acid (1 g, 4.95, 1 eq) in dry DCM (100 mL), oxalyl chloride (1.27 mL, 14.85 mmol, 3 eq) was added followed by addition of DMF (0.1 mL) under stirring at 0° C. under inert atmosphere. The resulting mixture was stirred at rt for 3-4 h. After completion the mixture was concentrated under vacuo to remove oxalyl chloride to give 6-bromopicolinoyl chloride (0.95 g, 88%) as yellow solid.
LCMS: 220.1 [M+1]$^+$ Step-2: Synthesis of 6-bromo-N-methylpicolinamide To a solution of 6-bromopicolinoyl chloride (0.9 g, 4.08, 1 eq) in dry THF (25 mL), MeNH$_2$ (40 wt % in H$_2$O, 10 mL, 122.4 mmol, 30 eq) in dry THF (25 mL) was added under stirring at 0° C. under inert atmosphere. The resulting solution was stirred at rt for 16 h. The progress of the reaction was monitored by LCMS. After completion, reaction was quenched with water (20 mL×3) and extracted using DCM (10 mL×3). The combined organic layer was dried over Na$_2$SO$_4$, concentrated to give 6-bromo-N-methylpicolinamide (0.8 g, 82%) as yellow liquid which was used without further purification.
LCMS: 214 [M+1]$^+$ Step-3: Synthesis of 6-(2-ethyl-6-(methylthio)-3-oxo-2,3-dihydro-1H-pyrazolo[3,4-d]pyrimidin-1-yl)-N-methylpicolinamide To a stirring solution of 2-ethyl-6-(methylthio)-1,2-dihydro-3H-pyrazolo[3,4-d]pyrimidin-3-one (300 mg, 1.42 mmol, 1 eq) in dioxane (10 mL), K$_2$CO$_3$ (349.3 mg, 2.85 mmol, 2 eq) and 6-bromo-N-methylpicolinamide (368.2 mg, 1.71 mmol, 1.2 eq) were added under stirring at rt. The mixture was degassed for 10-15 min followed addition of CuI (54.3 mg, 0.28 mmol, 0.2 eq) and DMEDA (0.06 mL, 0.57 mmol, 0.4 eq). The reaction was heated at 100° C. for 16 h. The progress of the reaction was monitored by LCMS. After completion, the reaction mixture was filtered through celite and water (20 mL) was added to it. Extraction was carried out using MeOH/DCM (10 mL×3). The combined organic layer was dried, concentrated and purified by flash chromatography (MeOH/DCM 1-5%) to give 6-(2-ethyl-6-(methylthio)-3-oxo-2,3-dihydro-1H-pyrazolo[3,4-d]pyrimidin-1-yl)-N-methylpicolinamide (75 mg, 15%) as yellow solid.
LCMS: 344 [M+1]$^+$ Step-4: Synthesis of tert-butyl 7-((2-ethyl-1-(6-(methylcarbamoyl)pyridin-2-yl)-3-oxo-2,3-dihydro-1H-pyrazolo[3,4-d]pyrimidin-6-yl)amino)-3,4-dihydroisoquinoline-2(1H)-carboxylate To a stirred solution of 6-(2-ethyl-6-(methylthio)-3-oxo-2,3-dihydro-1H-pyrazolo[3,4-d]pyrimidin-1-yl)-N-methylpicolinamide (70 mg, 0.20 mmol, 1.0 eq) in toluene (3 mL); m-CPBA (87.6 mg, 0.50 mmol, 2.5 eq) was added under stirring and resulting mixture was allowed to stir at rt for 30 minutes. tert-butyl 7-amino-3,4-dihydroisoquinoline-2(1H)-carboxylate (55.5 mg, 0.22 mmol, 1.1 eq) and DIPEA (0.16 mL, 0.81 mmol, 4 eq) were then added and the reaction was heated at 80° C. for 16 h. The progress of the reaction was monitored by LCMS. After completion reaction was quenched with water (10 mL) and extracted with MeOH/DCM (10 mL×3). The combined organic layer was washed with brine solution (20 mL), dried over anhydrous Na$_2$SO$_4$ and concentrated under reduced pressure to afford crude product which was purified by flash chromatography (1-10% MeOH/DCM) to afford tert-butyl 7-((2-ethyl-1-(6-(methylcarbamoyl)pyridin-2-yl)-3-oxo-2,3-dihydro-1H-pyrazolo[3,4-d]pyrimidin-6-yl)amino)-3,4-dihydroisoquinoline-2(1H)-carboxylate (72 mg, 65%) as yellow solid.
LCMS: 544 [M+1]$^+$ Step-5: Synthesis of 6-(2-ethyl-3-oxo-6-((1,2,3,4-tetrahydroisoquinolin-7-yl)amino)-2,3-dihydro-1H-pyrazolo[3,4-d]pyrimidin-1-yl)-N-methylpicolinamide hydrochloride 20% HCl in dioxane (2 mL) was added to a stirred solution of tert-butyl 7-((2-ethyl-1-(6-(methylcarbamoyl)pyridin-2-yl)-3-oxo-2,3-dihydro-1H-pyrazolo[3,4-d]pyrimidin-6-yl)amino)-3,4-dihydroisoquinoline-2(1H)-carboxylate (70 mg, 0.12 mmol, 1.0 eq) in dioxane (1 mL) at 0° C. under inert atmosphere and the resulting solution was allowed to stir at rt for 3 h. The progress of the reaction was monitored by LCMS. After completion, solvent was removed under reduced pressure and the resulting solid was filtered and washed with ether, dried to afford 6-(2-ethyl-3-oxo-6-((1,2,3,4-tetrahydroisoquinolin-7-yl)amino)-2,3-dihydro-1H-pyrazolo[3,4-d]pyrimidin-1-yl)-N-methylpicolinamide hydrochloride (5 mg, 8%) as a yellow solid.

LCMS: 444 [M+1]$^+$; UPLC: @ 220 nm=97.02% @ 254 nm=96.19%

$^1$H NMR (400 MHz, DMSO-d$_6$, Formate): δ 10.32 (br s, 1H), 8.89 (s, 1H), 8.31-8.26 (m, 1H), 8.21 (br s, 1H), 8.14-8.1 (m, 1H), 8.03-8.0 (m, 1H), 7.65-7.62 (m, 1H), 7.47-7.43 (m, 1H), 7.13-7.09 (m, 1H), 4.12 (br s, 2H), 4.04 (q, J=7 Hz, 2H), 3.37-3.29 (m, 2H), 2.97-2.9 (m, 2H), 2.81 (s, 3H), 0.93 (t, J=7.02 Hz, 3H)

Example S27. Synthesis of 2-ethyl-1-(6-(2-hydroxypropan-2-yl)pyridin-2-yl)-6-(5,6,7,8-tetrahydro-1,6-naphthyridin-3-ylamino)-1H-pyrazolo[3,4-d]pyrimidin-3(2H)-one (Compound No. 1.127)

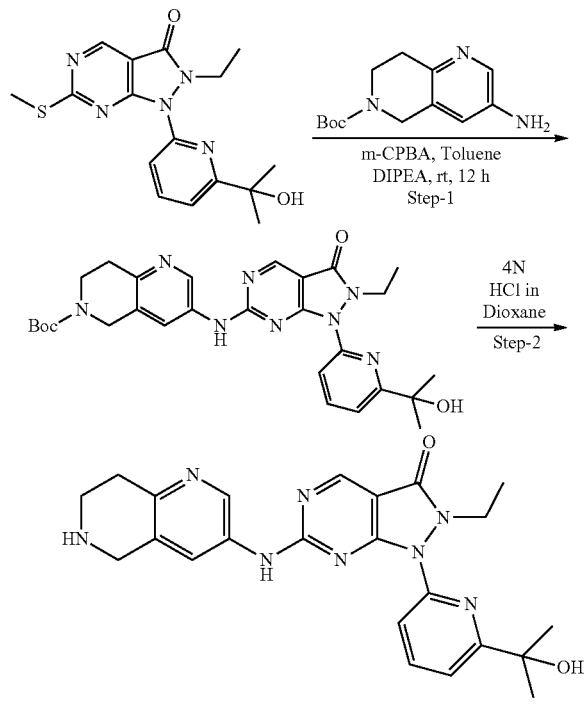

Step-1: Synthesis of tert-butyl 3-(2-ethyl-1-(6-(2-hydroxypropan-2-yl)pyridin-2-yl)-3-oxo-2,3-dihydro-1H-pyrazolo[3,4-d]pyrimidin-6-ylamino)-7,8-dihydro-1,6-naphthyridine-6(5H)-carboxylate To a stirred solution of 2-ethyl-1-(6-(2-hydroxypropan-2-yl)pyridin-2-yl)-6-(methylthio)-1H-pyrazolo[3,4-d]pyrimidin-3(2H)-one (200 mg, 0.58 mmol, 1.0 eq) in 5 mL of Toluene was added m-CPBA (250 mg, 1.45 mmol, 2.5 eq.) and allowed to stir at rt for 30 minutes. tert-butyl 3-amino-7,8-dihydro-1,6-naphthyridine-6(5H)-carboxylate (150 mg, 0.58 mmol, 1.0 eq) and DIPEA (300 mg, 2.32 mmol, 4.0 eq) were added and allowed to stir at rt for 12 h. Progress of reaction was monitored by LCMS. After completion of reaction solvent was removed under reduced pressure, residue was diluted with 20 ml of water and extracted with ethyl acetate (50 mL×3). Combined organic layer was washed with water (20 ml×3), dried over anhydrous sodium sulfate and concentrated under reduced pressure. Crude was purified by reverse phase chromatography to obtain 20 mg (6.30%) of tert-butyl 3-(2-ethyl-1-(6-(2-hydroxypropan-2-yl)pyridin-2-yl)-3-oxo-2,3-dihydro-1H-pyrazolo[3,4-d]pyrimidin-6-ylamino)-7,8-dihydro-1,6-naphthyridine-6(5H)-carboxylate.

LCMS: 547 [M+1]$^+$

Step-2: Synthesis of 2-ethyl-1-(6-(2-hydroxypropan-2-yl)pyridin-2-yl)-6-(5,6,7,8-tetrahydro-1,6-naphthyridin-3-ylamino)-1H-pyrazolo[3,4-d]pyrimidin-3 (2H)-one tert-butyl 3-(2-ethyl-1-(6-(2-hydroxypropan-2-yl)pyridin-2-yl)-3-oxo-2,3-dihydro-1H-pyrazolo[3,4-d]pyrimidin-6-ylamino)-7,8-dihydro-1,6-naphthyridine-6(5H)-carboxylate (20 mg, 0.037 mmol, 1.0 eq) was dissolved in 1 mL of 4N HCl in dioxane solution at 0° C. Reaction was stirred at rt for 30 min. Progress of reaction was monitored by LCMS. After completion of reaction, precipitated compound was filtered off and dried under vacuum to obtain 10 mg (62.5%) HCl of 2-ethyl-1-(6-(2-hydroxypropan-2-yl)pyridin-2-yl)-6-(5,6,7,8-tetrahydro-1,6-naphthyridin-3-ylamino)-1H-pyrazolo[3,4-d]pyrimidin-3 (2H)-one.

LCMS: 447 [M+1]$^+$ $^1$H NMR (400 MHz, DMSO-d$_6$) δ 10.62 (br. s., 1H), 9.56 (br. s., 2H), 8.94 (s, 1H), 8.78 (br. s., 1H), 8.23 (br. s., 1H), 8.13 (t, J=7.89 Hz, 1H), 7.84 (d, J=7.89 Hz, 1H), 7.67 (d, J=7.89 Hz, 1H), 4.37 (br. s., 2H), 4.05 (d, J=7.45 Hz, 3H), 3.48 (br. s., 2H), 3.12 (br. s., 2H), 1.44 (s, 3H), 1.23 (br. s., 1H), 0.99 (t, J=7.24 Hz, 2H), 0.84 (d, J=7.45 Hz, 1H).

Example S28. Synthesis of 1-(6-(tert-butyl)pyridin-2-yl)-2-ethyl-6-((1,2,3,4-tetrahydroisoquinolin-7-yl)amino)-1,2-dihydro-3H-pyrazolo[3,4-d]pyrimidin-3-one dihydrochloride (Compound No. 1.126)

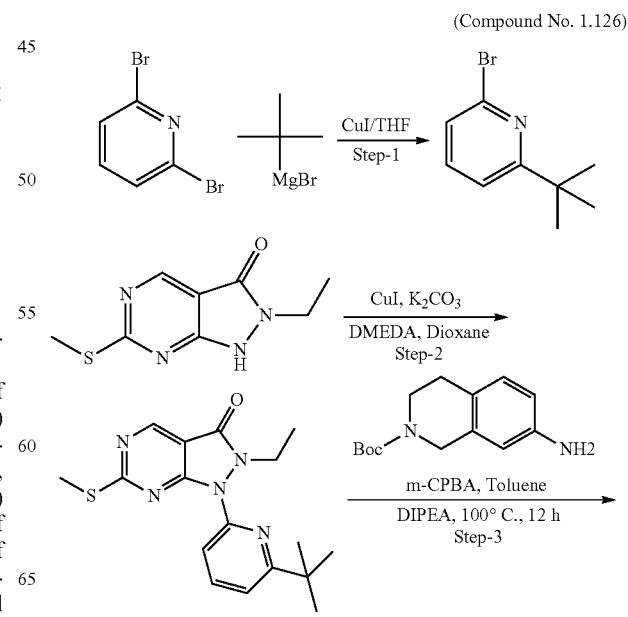

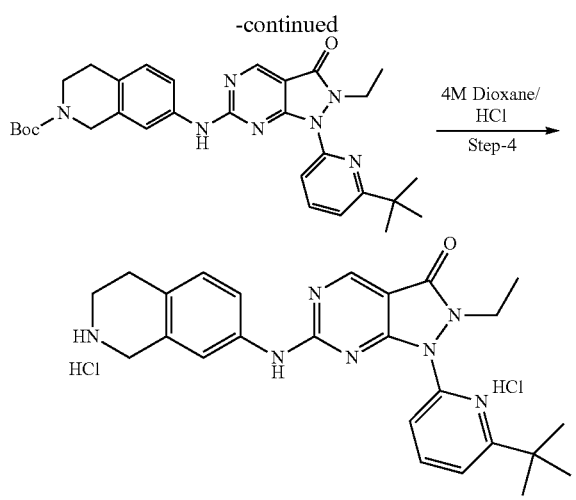

Step-1: Synthesis of 2-bromo-6-(tert-butyl)pyridine

To a stirred solution of 2,6-dibromopyridine (1.0 g, 4.221 mmol, 1.0 eq) in (30.0 mL) of THF was added CuI (40 mg, 0.211 mmol, 0.05 eq) followed by addition of 2.0M solution of tert-butylmagnesium bromide (8.44 mL, 16.885 mmol, 4.0 eq) at 0° C. The reaction mixture was stirred at RT for 1 h. The progress of reaction was monitored by LCMS. The reaction mixture was quenched with saturated solution of NH$_4$Cl (50 mL), extracted with EtOAc (2×100 mL), the combined organic layers were washed with water (50 mL), dried over Na$_2$SO$_4$, concentrated to afford the desired compound 2-bromo-6-(tert-butyl)pyridine (790 mg, 87.19%) as Light yellow liquid.

LCMS: 214.1 [M+1]$^+$

Step-2: Synthesis of 1-(6-(tert-butyl)pyridin-2-yl)-2-ethyl-6-(methylthio)-1,2-dihydro-3H-pyrazolo[3,4-d]pyrimidin-3-one To a stirred solution of 2-ethyl-6-(methylthio)-1,2-dihydro-3H-pyrazolo[3,4-d]pyrimidin-3-one (600 mg, 2.853 mmol, 1.0 eq) and 2-bromo-6-(tert-butyl)pyridine (734 mg, 3.424 mmol, 1.20 eq) in (20 mL) of dioxane was added Potassium carbonate (788 mg, 5.706 mmol, 2.0 eq) and the resulting mixture was purged with nitrogen for 10 min followed by addition of copper iodide (109 mg, 0.570 mmol, 0.2 eq), and N,N'-dimethylethylenediamine (DMEDA) (0.123 mL, 1.141 mmol, 0.4 eq) and again purged with nitrogen for 10 min, stirred at 90° C. for overnight. After completion of reaction, the reaction mixture was diluted with water and extracted with EtOAc (50 mL×2). Combined organic layer was washed with water (50 mL) brine solution (50 mL), dried over anhydrous sodium sulphate and concentrated under reduced pressure to afford crude product, which was purified by flash chromatography [silica gel 100-200 mesh; elution 0-30% EtOAc in hexane] to afford the desired compound 1-(6-(tert-butyl)pyridin-2-yl)-2-ethyl-6-(methylthio)-1,2-dihydro-3H-pyrazolo[3,4-d]pyrimidin-3-one (380 mg, 38.77%) as light yellow solid.

LCMS: 344.3 [M+1]$^+$

Step-3: Synthesis of tert-butyl 7-((1-(6-(tert-butyl)pyridin-2-yl)-2-ethyl-3-oxo-2,3-dihydro-1H-pyrazolo[3,4-d]pyrimidin-6-yl)amino)-3,4-dihydroisoquinoline-2(1H)-carboxylate To a stirred solution of 1-(6-(tert-butyl)pyridin-2-yl)-2-ethyl-6-(methylthio)-1,2-dihydro-3H-pyrazolo[3,4-d]pyrimidin-3-one (200 mg, 0.582 mmol, 1.0 eq) in (5.0 mL) of toluene was added m-CPBA (287 mg, 1.164 mmol, 2.0 eq) and allowed to stir at rt for 30 minutes. tert-butyl 7-amino-3,4-dihydroisoquinoline-2(1H)-carboxylate (174 mg, 0.698 mmol, 1.2 eq) and DIPEA (0.40 mL, 2.328 mmol, 4.0 eq) were added and allowed to stir at rt for overnight. The formation of precipitates was observed which was filtered to afford the desired compound tert-butyl 7-((1-(6-(tert-butyl)pyridin-2-yl)-2-ethyl-3-oxo-2,3-dihydro-1H-pyrazolo[3,4-d]pyrimidin-6-yl)amino)-3,4-dihydroisoquinoline-2(1H)-carboxylate (158 mg, 49.84%) as white solid.

LCMS: 544.4 [M+1]$^+$

Step-4: Synthesis of 1-(6-(tert-butyl)pyridin-2-yl)-2-ethyl-6-((1,2,3,4-tetrahydroisoquinolin-7-yl)amino)-1,2-dihydro-3H-pyrazolo[3,4-d]pyrimidin-3-one dihydrochloride tert-butyl 7-((1-(6-(tert-butyl)pyridin-2-yl)-2-ethyl-3-oxo-2,3-dihydro-1H-pyrazolo[3,4-d]pyrimidin-6-yl)amino)-3,4-dihydroisoquinoline-2(1H)-carboxylate (158 mg, 0.290 mmol, 1.0 eq) was dissolved in (1 mL) of dioxane and added 4.0M-HCl (2 mL) and allowed to stir at rt for 1 h. After completion of reaction, the reaction mixture was filtered and dried under reduced pressure to afford the desired compound 1-(6-(tert-butyl)pyridin-2-yl)-2-ethyl-6-((1,2,3,4-tetrahydroisoquinolin-7-yl)amino)-1,2-dihydro-3H-pyrazolo[3,4-d]pyrimidin-3-one dihydrochloride (125 mg, 83.33%) as yellow solid.

LCMS: 444.4 [M+1]$^+$; UPLC @ 254 nm=99.12% and @ 220 nm=99.47%.

$^1$H NMR (400 MHz, DMSO-d$_6$) δ 10.33 (brs, 1H), 9.26 (brs, 2H), 8.88 (s, 1H), 8.06 (t, J=7.67 Hz, 1H), 7.84 (d, J=8.33 Hz, 1H), 7.73 (brs, 1H), 7.52 (d, J=8.33 Hz, 1H), 7.43 (d, J=7.89 Hz, 1H), 7.19 (d, J=8.33 Hz, 1H), 4.27 (brs, 2H), 4.08 (d, J=7.45 Hz, 2H), 3.37 (brs, 2H), 2.96 (brs, 2H), 1.33 (s, 9H), 0.98 (t, J=7.02 Hz, 3H).

Example S29. Synthesis of N-(6-(2-ethyl-3-oxo-6-((1,2,3,4-tetrahydroisoquinolin-7-yl)amino)-2,3-dihydro-1H-pyrazolo[3,4-d]pyrimidin-1-yl)pyridin-2-yl)acetamide dihydrochloride (Compound No. 1.47)

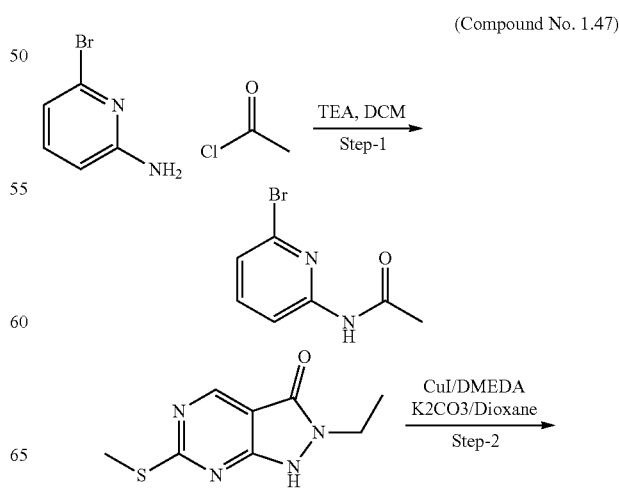

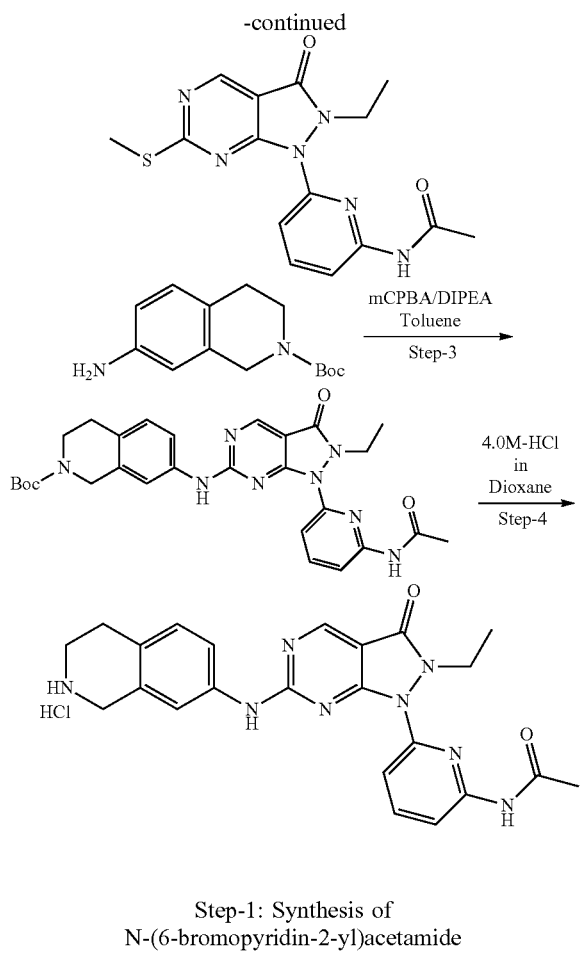

Step-1: Synthesis of N-(6-bromopyridin-2-yl)acetamide

To a stirred solution of 6-bromopyridin-2-amine (1.0 g, 5.78 mmol, 1.0 eq) in (30.0 mL) of DCM was added TEA (1.61 mL, 11.567 mmol, 2.0 eq) followed by addition of actyl chloride (0.62 mL, 8.67 mmol, 1.5 eq) at 0° C. The reaction mixture was stirred at RT for overnight. The progress of reaction was monitored by LCMS. The reaction mixture was quenched with saturated solution of NaHCO₃ (100 mL), extracted with EtOAc (2×100 mL), the combined organic layers were washed with water (50 mL), dried over Na₂SO₄, concentrated and purified by combiflash chromatography [silica gel 100-200 mesh; elution 0-10% EtOAc in hexane] to afford the desired compound N-(6-bromopyridin-2-yl)acetamide (355 mg, 28.62%) as white solid.

LCMS: 215.1 [M+1]$^+$

Step-2: Synthesis of N-(6-(2-ethyl-6-(methylthio)-3-oxo-2,3-dihydro-1H-pyrazolo[3,4-d]pyrimidin-1-yl)pyridin-2-yl)acetamide To a stirred solution of 2-ethyl-6-(methylthio)-1,2-dihydro-3H-indazol-3-one (285 mg, 1.356 mmol, 1.0 eq) and N-(6-bromopyridin-2-yl)acetamide (350 mg, 1.627 mmol, 1.20 eq) in (10 mL) of dioxane was added Potassium carbonate (375 mg, 2.712 mmol, 2.0 eq) and the resulting mixture was purged with nitrogen for 10 min followed by addition of copper iodide (52 mg, 0.271 mmol, 0.2 eq), and N,N'-dimethylethylenediamine (DMEDA) (0.06 mL, 0.542 mmol, 0.4 eq) and again purged with nitrogen for 10 min, stirred at 90° C. for overnight. After completion of reaction, the reaction mixture was diluted with water and extracted with EtOAc (50 mL×2). Combined organic layer was washed with water (50 mL) brine solution (50 mL), dried over anhydrous sodium sulfate and concentrated under reduced pressure to afford crude product, which was purified by flash chromatography [silica gel 100-200 mesh; elution 0-3% MeOH in DCM] to afford the desired compound N-(6-(2-ethyl-6-(methylthio)-3-oxo-2,3-dihydro-1H-pyrazolo[3,4-d]pyrimidin-1-yl)pyridin-2-yl)acetamide (1420 mg, 30.47%) as white solid.

LCMS: 345.3 [M+1]$^+$

Step-3: Synthesis of tert-butyl 7-((1-(6-acetamidopyridin-2-yl)-2-ethyl-3-oxo-2,3-dihydro-1H-pyrazolo[3,4-d]pyrimidin-6-yl)amino)-3,4-dihydroisoquinoline-2(1H)-carboxylate To a stirred solution of N-(6-(2-ethyl-6-(methylthio)-3-oxo-2,3-dihydro-1H-pyrazolo[3,4-d]pyrimidin-1-yl)pyridin-2-yl)acetamide (140 mg, 0.407 mmol, 1.0 eq) in (2.0 mL) of toluene was added m-CPBA (200 mg, 0.814 mmol, 2.0 eq) and allowed to stir at rt for 30 minutes. tert-butyl 7-amino-3,4-dihydroisoquinoline-2(1H)-carboxylate (121 mg, 0.488 mmol, 1.2 eq) and DIPEA (0.285 mL, 1.628 mmol, 4.0 eq) were added and allowed to stir at rt for overnight. The formation of precipitates was observed which was filtered to afford the desired compound tert-butyl 7-((1-(6-acetamidopyridin-2-yl)-2-ethyl-3-oxo-2,3-dihydro-1H-pyrazolo[3,4-d]pyrimidin-6-yl)amino)-3,4-dihydroisoquinoline-2(1H)-carboxylate (105 mg, 47.51%) as white solid.

LCMS: 545.5 [M+1]$^+$

Step-4: Synthesis of N-(6-(2-ethyl-3-oxo-6-((1,2,3,4-tetrahydroisoquinolin-7-yl)amino)-2,3-dihydro-1H-pyrazolo[3,4-d]pyrimidin-1-yl)pyridin-2-yl)acetamide dihydrochloride tert-butyl 7-((1-(6-acetamidopyridin-2-yl)-2-ethyl-3-oxo-2,3-dihydro-1H-pyrazolo[3,4-d]pyrimidin-6-yl)amino)-3,4-dihydroisoquinoline-2(1H)-carboxylate (105 mg, 0.193 mmol, 1.0 eq) was dissolved in 4.0M-HCl (3 mL) and allowed to stir at rt for 1 h. After completion of reaction, the reaction mixture was filtered and dried under reduced pressure to afford the desired compound N-(6-(2-ethyl-3-oxo-6-((1,2,3,4-tetrahydroisoquinolin-7-yl)amino)-2,3-dihydro-1H-pyrazolo[3,4-d]pyrimidin-1-yl)pyridin-2-yl)acetamide dihydrochloride (80 mg, 80.80%) as yellow solid.

LCMS: 445.3 [M+1]$^+$; UPLC @ 254 nm=94.71% and @ 220 nm=96.31%.

$^1$H NMR (400 MHz, DMSO-d₆) δ 10.66 (s, 1H), 10.35 (brs, 1H), 9.33 (brs, 2H), 8.87 (s, 1H), 8.08 (d, J=3.95 Hz, 2H), 7.73 (brs, 1H), 7.58-7.68 (m, 1H), 7.50 (d, J=7.02 Hz, 1H), 7.17 (d, J=7.89 Hz, 1H), 4.23 (brs, 2H), 4.00 (d, J=7.45 Hz, 2H), 3.36 (brs, 2H), 2.96 (brs, 2H), 2.11 (s, 3H), 0.97 (t, J=7.02 Hz, 3H).

Example S30. 2-ethyl-6-((2-(2-hydroxyethyl)-1,2,3,4-tetrahydroisoquinolin-7-yl)amino)-1-(6-(2-hydroxypropan-2-yl)pyridin-2-yl)-1,2-dihydro-3H-pyrazolo[3,4-d]pyrimidin-3-one (Compound No. 1.128)

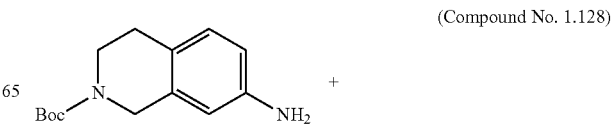

+

737

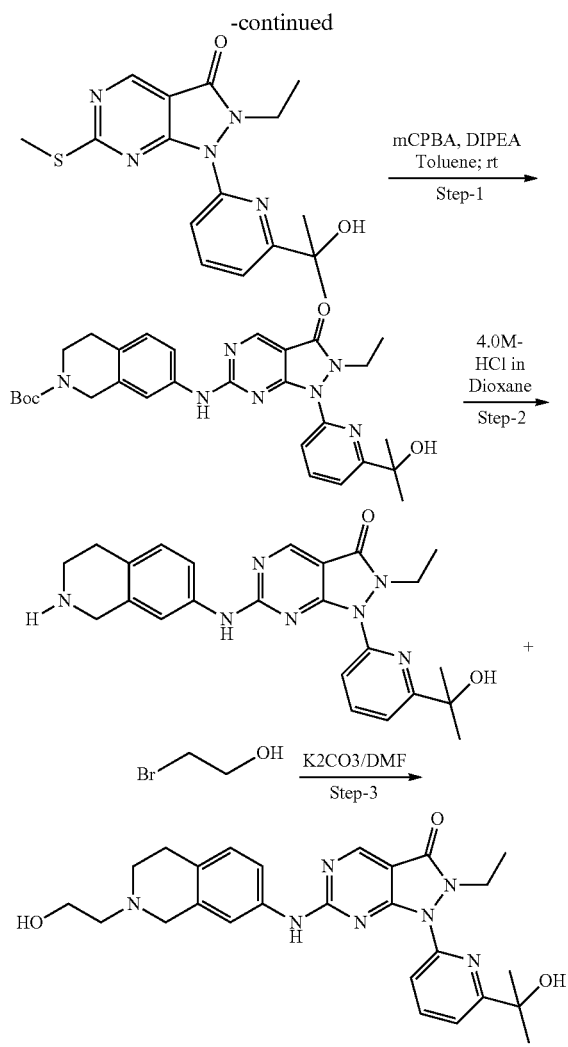

Step-1: tert-butyl 7-((2-ethyl-1-(6-(2-hydroxypropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate To a stirred solution of 2-ethyl-1-(6-(2-hydroxypropan-2-yl)pyridin-2-yl)-6-(methylthio)-1,2-dihydro-3H-pyrazolo[3,4-d]pyrimidin-3-one (0.2 g 0.5790 mmol, 1.0 eq) in (5.0 mL) of toluene was added m-CPBA (0.280 g, 1.158 mmol, 2 eq) and allowed to stir at rt for 30 min. followed by addition of tert-butyl 7-amino-3,4-dihydroisoquinoline-2 (1H)-carboxylate (0.186 g, 0.7527 mmol, 1.3 eq) and DIPEA (0.224 g 1.737 mmol, 3.0 eq) and allowed to stir at rt for overnight. The reaction mixture was diluted with water (20 mL) and extracted with EtOAc (2×20 mL). The combined organic layers were washed with water (30 mL), brine (30 mL), dried over Na$_2$SO$_4$, concentrated and purified by combi flash [silica gel-100-200 mesh; elution 0-35% EtOAc in Hexane] to afford the desired compound, tert-butyl 4-(4-((3-(2,6-dichlorophenyl)-4-oxo-3,4-dihydro-2H-pyrimido [5,4-e][1,3]oxazin-7-yl)amino)phenyl)-2-(hydroxymethyl) piperazine-1-carboxylate (0.110 g, 49.52%) as white solid.

LCMS: 546.4 [M+1]$^+$

738

Step-2: Synthesis of 2-ethyl-1-(6-(2-hydroxypropan-2-yl)pyridin-2-yl)-6-((1,2,3,4-tetrahydroisoquinolin-7-yl)amino)-1,2-dihydro-3H-pyrazolo[3,4-d]pyrimidin-3-one tert-butyl 7-((2-ethyl-1-(6-(2-hydroxypropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate (0.110 mg, 0.2017 mmol, 1.0 eq) was dissolved in 4.0M-HCl in dioxane (3 mL) and allowed to stir at rt for 1 h. After completion of reaction, the reaction mixture was filtered and dried under reduced pressure and purified by diethyl ether to afford the desired compound, 2-ethyl-1-(6-(2-hydroxypropan-2-yl)pyridin-2-yl)-6-((1,2,3,4-tetrahydroisoquinolin-7-yl)amino)-1,2-dihydro-3H-pyrazolo[3,4-d]pyrimidin-3-one (86 mg, 63.84%) as white solid.

LCMS: 446.5 [M+1]$^+$

Step-3: 2-ethyl-6-((2-(2-hydroxyethyl)-1,2,3,4-tetrahydroisoquinolin-7-yl)amino)-1-(6-(2-hydroxypropan-2-yl)pyridin-2-yl)-1,2-dihydro-3H-pyrazolo[3,4-d]pyrimidin-3-one To a stirred solution of 2-ethyl-1-(6-(2-hydroxypropan-2-yl)pyridin-2-yl)-6-((1,2,3,4-tetrahydroisoquinolin-7-yl) amino)-1,2-dihydro-3H-pyrazolo[3,4-d]pyrimidin-3-one (0.086 g, 0.1931 mmol, 1.0 eq) and 2-bromoethan-1-ol (0.026 g, 0.2124 mmol, 1.1 eq) in DMF (2 mL) was added potassium carbonate (0.054 g, 0.3862 mmol, 2.0 eq) at rt. The resulting mixture was stirred at 90° C. for overnight. The progress of reaction was monitored by LCMS. The reaction mixture was poured into ice cold water (100 mL), stirred for 5 min, formation of precipitates was observed, which was filtered and dried under vacuum to afford the desired compound, 2-ethyl-6-((2-(2-hydroxyethyl)-1,2,3,4-tetrahydroisoquinolin-7-yl)amino)-1-(6-(2-hydroxypropan-2-yl)pyridin-2-yl)-1,2-dihydro-3H-pyrazolo[3,4-d]pyrimidin-3-one (15 mg, 15.87%) as white solid.

LCMS: 490.3 [M+1]$^+$ $^1$H NMR (400 MHz, DMSO-d$_6$): δ 10.39 (br. s., 2H), 8.95 (s, 1H), 8.20 (t, J=7.67 Hz, 1H), 7.91 (d, J=7.89 Hz, 1H), 7.81 (br. s., 1H), 7.74 (d, J=7.89 Hz, 1H), 7.60 (d, J=8.77 Hz, 1H), 7.27 (d, J=8.77 Hz, 1H), 4.60 (d, J=14.91 Hz, 1H), 4.48 (d, J=7.89 Hz, 1H), 4.12 (d, J=7.45 Hz, 2H), 3.96 (br. s., 2H), 3.80 (br. s., 2H), 3.42 (br. s., 2H), 3.23 (br. s., 2H), 3.05 (d, J=17.10 Hz, 1H), 1.51 (s, 5H), 1.42 (br. s., 1H), 1.30 (br. s., 4H), 0.99-1.10 (m, 3H), 0.91 (d, J=7.02 Hz, 1H)

Example S31. 2-(7-((2-ethyl-1-(6-(2-hydroxypropan-2-yl)pyridin-2-yl)-3-oxo-2,3-dihydro-1H-pyrazolo[3,4-d]pyrimidin-6-yl)amino)-3,4-dihydroisoquinolin-2(1H)-yl)-N,N-dimethylacetamide (Compound No. 1.129)

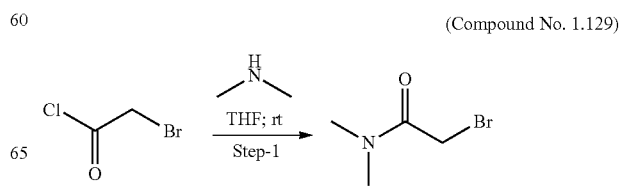

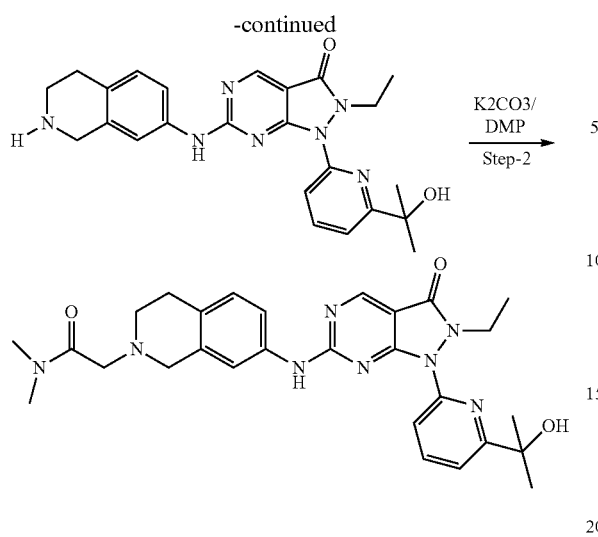

Step-1: 2-bromo-N,N-dimethylacetamide

To a stirred solution of 2-bromo-N,N-dimethylacetamide (0.5 g, 3.1768 mmol, 1.0 eq) and dimethylamine (0.026 g, 0.2124 mmol, 1.1 eq) in THF (5 mL) at rt. The resulting mixture was stirred at RT for overnight. The progress of reaction was monitored by LCMS. Solvent was removed under reduce pressure, residue was diluted with water (5 ml) and extracted using DCM (50 ml). The combined organic layer was washed with water (10 ml), brine (10 ml) and concentrated to afford desired compound (120 mg, 22.77%) as white solid.

$^1$H NMR (400 MHz, CDCl3) δ 2.97 (s, 3H), 3.1 (s, 3H), 3.86 (s, 2H).

Step-2: 2-(7-((2-ethyl-1-(6-(2-hydroxypropan-2-yl)pyridin-2-yl)-3-oxo-2,3-dihydro-1H-pyrazolo[3,4-d]pyrimidin-6-yl)amino)-3,4-dihydroisoquinolin-2(1H)-yl)-N,N-dimethylacetamide To a stirred solution of 2-ethyl-1-(6-(2-hydroxypropan-2-yl)pyridin-2-yl)-6-((1,2,3,4-tetrahydroisoquinolin-7-yl)amino)-1,2-dihydro-3H-pyrazolo[3,4-d]pyrimidin-3-one (0.150 g, 0.3368 mmol, 1.0 eq) and 2-bromo-N,N-dimethylacetamide (0.061 g, 0.3705 mmol, 1.1 eq) in DMF (2 mL) was added potassium carbonate (0.093 g, 0.6736 mmol, 2.0 eq) at rt. The resulting mixture was stirred at 90° C. for overnight. The progress of reaction was monitored by LCMS. The reaction mixture was poured into ice cold water (100 mL), stirred for 5 min, formation of precipitates was observed, which was filtered and dried under vacuum to afford the desired compound, 2-(7-((2-ethyl-1-(6-(2-hydroxypropan-2-yl)pyridin-2-yl)-3-oxo-2,3-dihydro-1H-pyrazolo[3,4-d]pyrimidin-6-yl)amino)-3,4-dihydroisoquinolin-2(1H)-yl)-N,N-dimethylacetamide (13 mg, 07.27%) as white solid.

LCMS: 531.4 [M+1]$^+$; UPLC @254 nm=94.98%, @220 nm=95.59%

$^1$H NMR (400 MHz, DMSO-d$_6$): δ 10.22 (br. s., 1H), 8.84 (s, 1H), 8.10 (t, J=7.89 Hz, 1H), 7.82 (d, J=8.33 Hz, 1H), 7.71 (br. s., 1H), 7.65 (br. s., 1H), 7.33 (d, J=7.45 Hz, 1H), 7.05 (d, J=8.33 Hz, 1H), 5.33 (s, 1H), 4.04 (d, J=6.58 Hz, 2H), 3.62 (br. s., 2H), 3.36 (br. s., 2H), 3.07 (s, 3H), 2.88 (s, 3H), 2.76 (br. s., 3H), 1.44 (s, 6H), 1.23 (br. s., 1H), 0.98 (t, J=6.80 Hz, 3H)

Example S32. Synthesis of 2-ethyl-1-(pyridin-2-yl)-6-((1,2,3,4-tetrahydroisoquinolin-7-yl)amino)-1,2-dihydro-3H-pyrazolo[3,4-d]pyrimidin-3-one dihydrochloride (Compound No. 1.130)

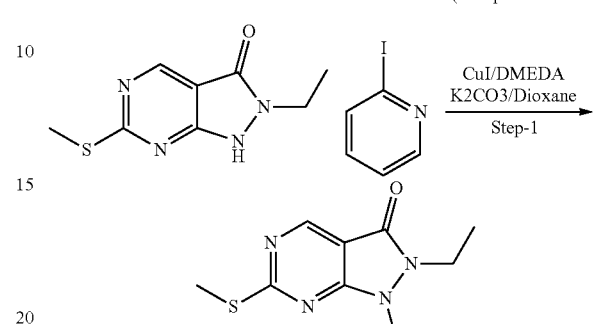

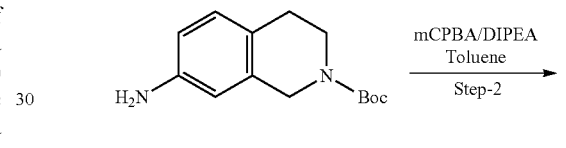

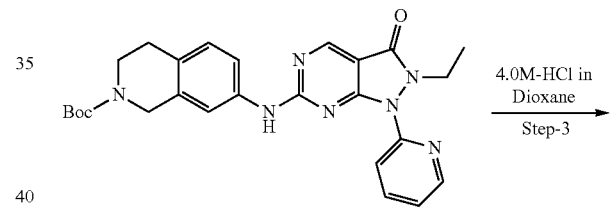

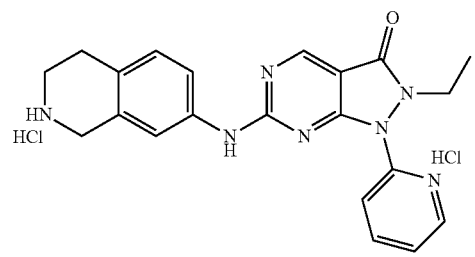

Step-1: Synthesis of 2-ethyl-6-(methylthio)-1-(pyridin-2-yl)-1,2-dihydro-3H-pyrazolo[3,4-d]pyrimidin-3-one To a stirred solution of 2-ethyl-6-(methylthio)-1,2-dihydro-3H-indazol-3-one (500 mg, 2.378 mmol, 1.0 eq) and 2-iodopyridine (585 mg, 2.854 mmol, 1.2 eq) in (10 mL) of dioxane was added Potassium carbonate (657 mg, 4.756 mmol, 2.0 eq) and the resulting mixture was purged with nitrogen for 10 min followed by addition of copper iodide (91 mg, 0.475 mmol, 0.2 eq), and N,N'-dimethylethylenediamine (DMEDA) (0.1 mL, 0.951 mmol, 0.4 eq) and again purged with nitrogen for 10 min, stirred at 90° C. for overnight. After completion of reaction, the reaction mixture was diluted with water and extracted with EtOAc (50 mL×2). Combined organic layer was washed with water (50 mL) brine solution (50 mL), dried over anhydrous sodium sulfate and concentrated under reduced pressure to afford crude product, which was purified by flash chromatography [silica gel 100-200 mesh; elution 0-30% EtOAc in Hexane] to afford the desired compound 2-ethyl-6-(methylthio)-1-(pyridin-2-yl)-1,2-dihydro-3H-pyrazolo[3,4-d]pyrimidin-3-one (450 mg, 65.88%) as light yellow viscous.

LCMS: 288.2 [M+1]+

Step-2: Synthesis of tert-butyl 7-((2-ethyl-3-oxo-1-(pyridin-2-yl)-2,3-dihydro-1H-pyrazolo[3,4-d]py-rimidin-6-yl)amino)-3,4-dihydroisoquinoline-2(1H)-carboxylate To a stirred solution of 2-ethyl-6-(methylthio)-1-(pyridin-2-yl)-1,2-dihydro-3H-pyrazolo[3,4-d]pyrimidin-3-one (200 mg, 0.696 mmol, 1.0 eq) in (2.0 mL) of toluene was added m-CPBA (343 mg, 1.392 mmol, 2.0 eq) and allowed to stir at rt for 30 minutes. tert-butyl 7-amino-3,4-dihydroisoqui-noline-2(1H)-carboxylate (207 mg, 0.835 mmol, 1.2 eq) and DIPEA (0.485 mL, 2.784 mmol, 4.0 eq) were added and allowed to stir at rt for overnight. The formation of precipitates was observed which was filtered to afford the desired compound tert-butyl 7-((2-ethyl-3-oxo-1-(pyridin-2-yl)-2,3-dihydro-1H-pyrazolo[3,4-d]pyrimidin-6-yl)amino)-3,4-di-hydroisoquinoline-2(1H)-carboxylate (158 mg, 46.60%) as white solid.

LCMS: 488.4 [M+1]+

Step-3: Synthesis of 2-ethyl-1-(pyridin-2-yl)-6-((1,2,3,4-tetrahydroisoquinolin-7-yl)amino)-1,2-di-hydro-3H-pyrazolo[3,4-d]pyrimidin-3-one dihydro-chloride tert-butyl 7-((2-ethyl-3-oxo-1-(pyridin-2-yl)-2,3-dihydro-1H-pyrazolo[3,4-d]pyrimidin-6-yl)amino)-3,4-dihydroiso-quinoline-2(1H)-carboxylate (158 mg, 0.324 mmol, 1.0 eq) was dissolved in 4.0M-HCl in dioxane (2 mL) and allowed to stir at rt for 1 h. After completion of reaction, the reaction mixture was filtered and dried under reduced pressure to afford the desired compound 2-ethyl-1-(pyridin-2-yl)-6-((1,2,3,4-tetrahydroisoquinolin-7-yl)amino)-1,2-dihydro-3H-pyrazolo[3,4-d]pyrimidin-3-one dihydrochloride (120 mg, 80.0%) as brown solid.

LCMS: 388.3 [M+1]+; UPLC @ 254 nm=96.60% and @ 220 nm=98.10%.

$^1$H NMR (400 MHz, DMSO-$d_6$) δ 10.35 (brs, 1H), 9.50 (brs, 2H), 8.88 (s, 1H), 8.57 (d, J=4.38 Hz, 1H), 8.14 (t, J=7.89 Hz, 1H), 7.96 (d, J=8.33 Hz, 1H), 7.73 (brs, 1H), 7.49 (d, J=8.77 Hz, 1H), 7.34-7.46 (m, 1H), 7.17 (d, J=8.33 Hz, 1H), 4.24 (brs, 2H), 3.96 (d, J=7.02 Hz, 2H), 3.35 (brs, 2H), 2.96 (brs, 2H), 0.98 (t, J=7.02 Hz, 3H).

Example S33. Synthesis of 1-(6-(tert-butyl)pyridin-2-yl)-2-ethyl-6-((1,2,3,4-tetrahydroisoquinolin-6-yl)amino)-1,2-dihydro-3H-pyrazolo[3,4-d]pyrimidin-3-one hydrochloride (Compound No. 1.131)

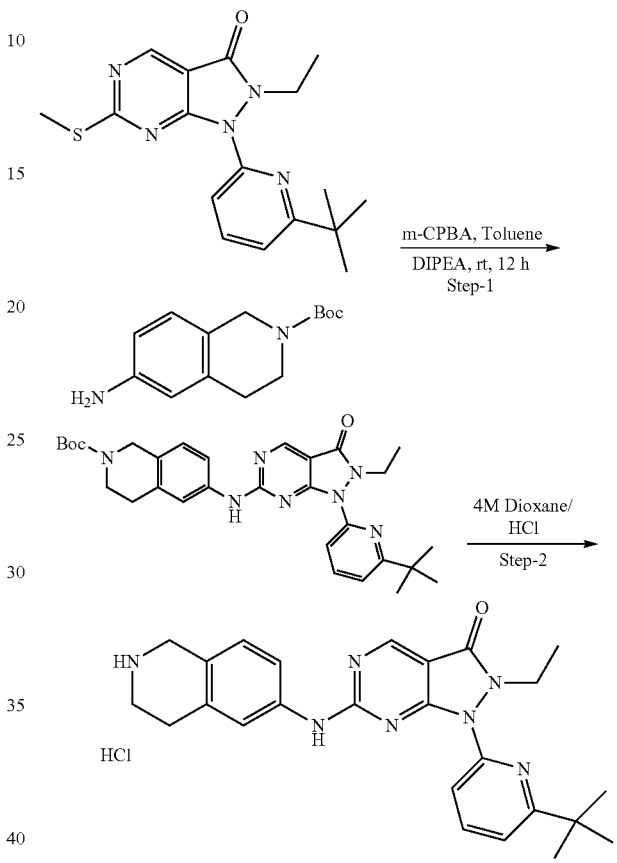

Step-1: Synthesis of tert-butyl 6-((1-(6-(tert-butyl)pyridin-2-yl)-2-ethyl-3-oxo-2,3-dihydro-1H-pyra-zolo[3,4-d]pyrimidin-6-yl)amino)-3,4-dihydroisoqui-noline-2(1H)-carboxylate To a stirred solution of 1-(6-(tert-butyl)pyridin-2-yl)-2-ethyl-6-(methylthio)-1,2-dihydro-3H-pyrazolo[3,4-d]py-rimidin-3-one (100 mg, 0.291 mmol, 1.0 eq) in (2.0 mL) of toluene was added m-CPBA (143 mg, 0.582 mmol, 2.0 eq) and allowed to stir at rt for 30 minutes. tert-butyl 6-amino-3,4-dihydroisoquinoline-2(1H)-carboxylate (87 mg, 0.349 mmol, 1.2 eq) and DIPEA (0.20 mL, 1.164 mmol, 4.0 eq) were added and allowed to stir at rt for overnight. After completion of reaction, the reaction mixture was diluted with water (50 mL) and extracted with EtOAc (50 mL×2). Combined organic layer was washed with water (50 mL) brine solution (50 mL), dried over anhydrous sodium sulfate and concentrated under reduced pressure to afford crude product, which was purified by flash chromatography [silica gel 100-200 mesh; elution 0-30% EtOAc in Hexane] to afford the desired compound tert-butyl 6-((1-(6-(tert-butyl)pyridin-2-yl)-2-ethyl-3-oxo-2,3-dihydro-1H-pyrazolo[3,4-d]pyrimidin-6-yl)amino)-3,4-dihydroisoquinoline-2(1H)-carboxylate (80 mg, 50.63%) as brown solid.

LCMS: 544.4 [M+1]+

Step-2: Synthesis of 1-(6-(tert-butyl)pyridin-2-yl)-2-ethyl-6-((1,2,3,4-tetrahydroisoquinolin-6-yl)amino)-1,2-dihydro-3H-pyrazolo[3,4-d]pyrimidin-3-one hydrochloride tert-butyl 6-((1-(6-(tert-butyl)pyridin-2-yl)-2-ethyl-3-oxo-2,3-dihydro-1H-pyrazolo[3,4-d]pyrimidin-6-yl)amino)-3,4-dihydroisoquinoline-2(1H)-carboxylate (80 mg, 0.147 mmol, 1.0 eq) was dissolved in 4.0M-HCl (2 mL) and allowed to stir at rt for 1 h. After completion of reaction, the reaction mixture was filtered and dried under reduced pressure to afford the desired compound 1-(6-(tert-butyl)pyridin-2-yl)-2-ethyl-6-((1,2,3,4-tetrahydroisoquinolin-6-yl)amino)-1,2-dihydro-3H-pyrazolo[3,4-d]pyrimidin-3-one hydrochloride (44 mg, 62.85%) as light brown solid.

LCMS: 444.4 [M+1]$^+$; UPLC @ 254 nm=96.64% and @ 220 nm=97.96%.

$^1$H NMR (400 MHz, DMSO-d$_6$) δ 10.32 (brs, 1H), 9.02 (brs, 2H), 8.88 (s, 1H), 8.04 (t, J=7.89 Hz, 1H), 7.75-7.87 (m, 2H), 7.51 (d, J=7.02 Hz, 1H), 7.44 (d, J=7.45 Hz, 1H), 7.17 (d, J=8.33 Hz, 1H), 4.23 (brs, 2H), 4.04-4.13 (m, 2H), 3.40 (brs, 2H), 3.00 (brs, 2H), 1.48 (brs, 1H), 1.33 (s, 7H), 0.98 (t, J=7.02 Hz, 3H).

Example S34. Synthesis of 2-ethyl-1-(6-(2-hydroxypropan-2-yl)pyridin-2-yl)-6-(isoindolin-5-ylamino)-1,2-dihydro-3H-pyrazolo[3,4-d]pyrimidin-3-one

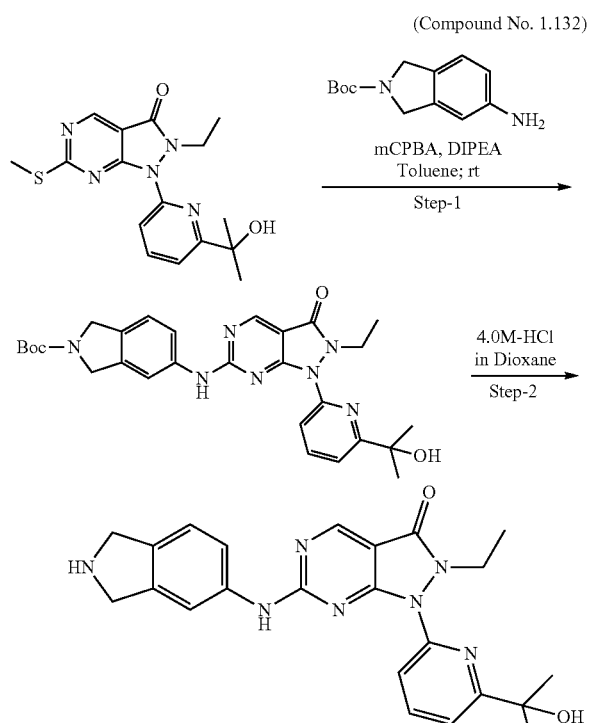

(Compound No. 1.132)

Step-1: tert-butyl 5-((2-ethyl-1-(6-(2-hydroxypropan-2-yl)pyridin-2-yl)-3-oxo-2,3-dihydro-1H-pyrazolo[3,4-d]pyrimidin-6-yl)amino)isoindoline-2-carboxylate To a stirred solution of 2-ethyl-1-(6-(2-hydroxypropan-2-yl)pyridin-2-yl)-6-(methylthio)-1,2-dihydro-3H-pyrazolo[3,4-d]pyrimidin-3-one (0.2 g 0.5790 mmol, 1.0 eq) in (5.0 mL) of toluene was added m-CPBA (0.280 g, 1.158 mmol, 2 eq) and allowed to stir at rt for 30 min. followed by addition of tert-butyl 5-aminoisoindoline-2-carboxylate (0.176 g, 0.7527 mmol, 1.3 eq) and DIPEA (0.3 ml 1.737 mmol, 3.0 eq) and allowed to stir at rt for overnight. The reaction mixture was diluted with water (20 mL) and extracted with EtOAc (2×20 mL). The combined organic layers were washed with water (30 mL), brine (30 mL), dried over Na$_2$SO$_4$, concentrated and purified by combi flash [silica gel-100-200 mesh; elution 0-35% EtOAc in Hexane] to afford the desired compound, tert-butyl 5-((2-ethyl-1-(6-(2-hydroxypropan-2-yl)pyridin-2-yl)-3-oxo-2,3-dihydro-1H-pyrazolo[3,4-d]pyrimidin-6-yl)amino)isoindoline-2-carboxylate (0.100 g, 49.52%) as white solid.

LCMS: 532.4 [M+1]$^+$

Step-2: Synthesis of 2-ethyl-1-(6-(2-hydroxypropan-2-yl)pyridin-2-yl)-6-(isoindolin-5-ylamino)-1,2-dihydro-3H-pyrazolo[3,4-d]pyrimidin-3-one tert-butyl 5-((2-ethyl-1-(6-(2-hydroxypropan-2-yl)pyridin-2-yl)-3-oxo-2,3-dihydro-1H-pyrazolo[3,4-d]pyrimidin-6-yl)amino)isoindoline-2-carboxylate (0.100 mg, 0.1881 mmol, 1.0 eq) was dissolved in 4.0M-HCl in dioxane (3 mL) and allowed to stir at rt for 1 h. After completion of reaction, the reaction mixture was filtered and dried under reduced pressure and purified by diethyl ether to afford the desired compound, 2-ethyl-1-(6-(2-hydroxypropan-2-yl)pyridin-2-yl)-6-((1,2,3,4-tetrahydroisoquinolin-7-yl)amino)-1,2-dihydro-3H-pyrazolo[3,4-d]pyrimidin-3-one (70 mg, 63.84%) as white solid.

LCMS: 432.3 [M+1]$^+$ $^1$H NMR (400 MHz, DMSO-d$_6$): δ 10.42 (br. s., 1H), 9.66 (br. s., 2H), 8.89 (s, 1H), 8.08 (t, J=7.67 Hz, 1H), 7.90 (br. s., 1H), 7.83 (d, J=8.33 Hz, 1H), 7.61-7.70 (m, 2H), 7.35 (d, J=8.77 Hz, 1H), 4.52 (br. s., 2H), 4.46 (br. s., 2H), 4.05 (d, J=7.02 Hz, 2H), 3.57 (s, 2H), 1.44 (s, 6H), 0.98 (t, J=6.80 Hz, 3H)

Example S35. Synthesis of 2-ethyl-6-((1,2,3,4-tetrahydroisoquinolin-7-yl)amino)-1-(6-(trifluoromethyl)pyridin-2-yl)-1,2-dihydro-3H-pyrazolo[3,4-d]pyrimidin-3-one hydrochloride

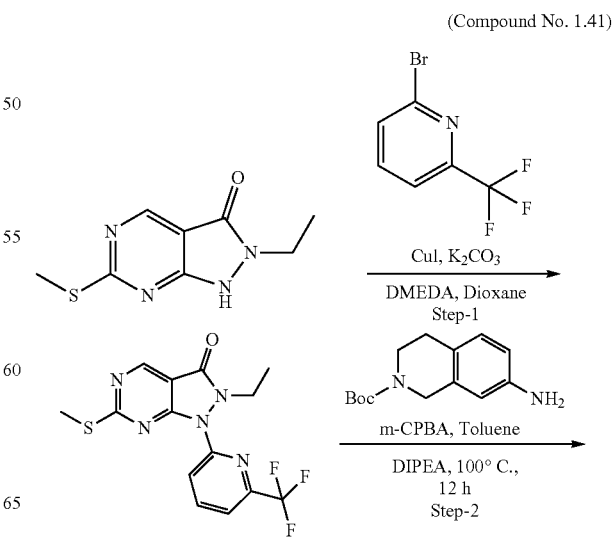

(Compound No. 1.41)

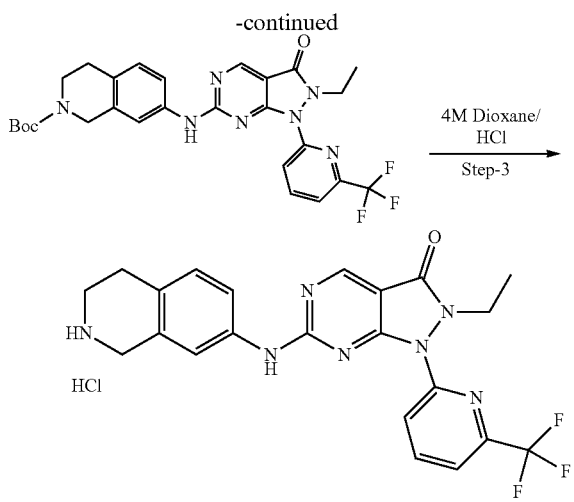

Step-1: Synthesis of 2-ethyl-6-(methylthio)-1-(6-(trifluoromethyl)pyridin-2-yl)-1,2-dihydro-3H-pyrazolo[3,4-d]pyrimidin-3-one To a stirred solution of 2-ethyl-6-(methylthio)-1,2-dihydro-3H-indazol-3-one (500 mg, 2.375 mmol, 1.0 eq) and 2-bromo-6-(trifluoromethyl)pyridine (644 mg, 2.850 mmol, 1.2 eq) in (30 mL) of dioxane was added Potassium carbonate (656 mg, 4.75 mmol, 2.0 eq) and the resulting mixture was purged with nitrogen for 10 min followed by addition of copper iodide (91 mg, 0.475 mmol, 0.2 eq), and N,N'-dimethylethylenediamine (DMEDA) (0.1 mL, 0.951 mmol, 0.4 eq) and again purged with nitrogen for 10 min, stirred at 90° C. for overnight. After completion of reaction, the reaction mixture was diluted with water and extracted with EtOAc (50 mL×2). Combined organic layer was washed with water (50 mL) brine solution (50 mL), dried over anhydrous sodium sulfate and concentrated under reduced pressure to afford crude product, which was purified by flash chromatography [silica gel 100-200 mesh; elution 0-30% EtOAc in Hexane] to afford the desired compound 2-ethyl-6-(methylthio)-1-(6-(trifluoromethyl)pyridin-2-yl)-1,2-dihydro-3H-pyrazolo[3,4-d]pyrimidin-3-one (450 mg, 53.25%) as light yellow viscous.

LCMS: 356.1 [M+1]$^+$

Step-2: Synthesis of tert-butyl 7-((2-ethyl-3-oxo-1-(6-(trifluoromethyl)pyridin-2-yl)-2,3-dihydro-1H-pyrazolo[3,4-d]pyrimidin-6-yl)amino)-3,4-dihydroisoquinoline-2(1H)-carboxylate To a stirred solution of 2-ethyl-6-(methylthio)-1-(6-(trifluoromethyl)pyridin-2-yl)-1,2-dihydro-3H-pyrazolo[3,4-d]pyrimidin-3-one (200 mg, 0.562 mmol, 1.0 eq) in (3.0 mL) of toluene was added m-CPBA (277 mg, 1.124 mmol, 2.0 eq) and allowed to stir at rt for 30 minutes. tert-butyl 7-amino-3,4-dihydroisoquinoline-2(1H)-carboxylate (168 mg, 0.675 mmol, 1.2 eq) and DIPEA (0.39 mL, 2.248 mmol, 4.0 eq) were added and allowed to stir at rt for overnight. The formation of precipitates was observed which was filtered to afford the desired compound tert-butyl 7-((2-ethyl-3-oxo-1-(6-(trifluoromethyl)pyridin-2-yl)-2,3-dihydro-1H-pyrazolo[3,4-d]pyrimidin-6-yl)amino)-3,4-dihydroisoquinoline-2(1H)-carboxylate (97 mg, 30.99%) as white solid.

LCMS: 556.3 [M+1]$^+$

Step-3: Synthesis of 2-ethyl-6-((1,2,3,4-tetrahydroisoquinolin-7-yl)amino)-1-(6-(trifluoromethyl)pyridin-2-yl)-1,2-dihydro-3H-pyrazolo[3,4-d]pyrimidin-3-one hydrochloride tert-butyl 7-((2-ethyl-3-oxo-1-(6-(trifluoromethyl)pyridin-2-yl)-2,3-dihydro-1H-pyrazolo[3,4-d]pyrimidin-6-yl)amino)-3,4-dihydroisoquinoline-2(1H)-carboxylate (95 mg, 0.171 mmol, 1.0 eq) was dissolved in 4.0M-HCl in dioxane (2 mL) and allowed to stir at rt for 1 h. After completion of reaction, the reaction mixture was filtered and dried under reduced pressure to afford the desired compound 2-ethyl-6-((1,2,3,4-tetrahydroisoquinolin-7-yl)amino)-1-(6-(trifluoromethyl)pyridin-2-yl)-1,2-dihydro-3H-pyrazolo[3,4-d]pyrimidin-3-one hydrochloride (60 mg, 71.42%) as light yellow solid.

LCMS: 456.3 [M+1]$^+$; UPLC @ 254 nm=98.86% and @ 220 nm=99.25%.

$^1$H NMR (400 MHz, DMSO-d$_6$) δ 10.44 (brs, 1H), 9.37 (brs, 2H), 8.92 (s, 1H), 8.31-8.44 (m, 2H), 7.90 (d, J=7.45 Hz, 1H), 7.65 (brs, 1H), 7.55 (d, J=8.33 Hz, 1H), 7.21 (d, J=8.33 Hz, 1H), 4.28 (brs, 3H), 3.92-4.05 (m, 3H), 3.37 (brs, 2H), 2.93-3.04 (m, 2H), 1.02 (t, J=7.02 Hz, 3H).

Example S36. Synthesis of 6-((2-(dimethylamino)-2,3-dihydro-1H-inden-5-yl)amino)-2-ethyl-1-(6-(2-hydroxypropan-2-yl)pyridin-2-yl)-1,2-dihydro-3H-pyrazolo[3,4-d]pyrimidin-3-one (Compound No. 1.133)

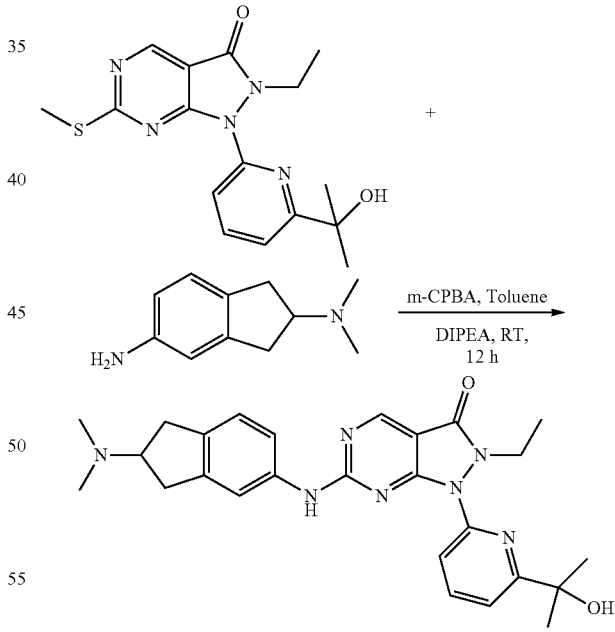

To a stirred solution of 2-ethyl-1-(6-(2-hydroxypropan-2-yl)pyridin-2-yl)-6-(methylthio)-1,2-dihydro-3H-pyrazolo[3,4-d]pyrimidin-3-one (195 mg, 0565 mmol, 1.0 eq) in (3.0 mL) of toluene was added m-CPBA (278 mg, 1.13 mmol, 2.0 eq) and allowed to stir at rt for 30 minutes. N2,N2-dimethyl-2,3-dihydro-1H-indene-2,5-diamine (140 mg, 0.679 mmol, 1.2 eq) and DIPEA (0.395 mL, 2.26 mmol, 4.0 eq) were added and allowed to stir at rt for overnight. After completion of reaction, the reaction mixture was diluted with water (50 mL) and extracted with EtOAc (50 mL×2). Combined organic layer was washed with water (50 mL) brine solution (50 mL), dried over anhydrous sodium sulfate and concentrated under reduced pressure to afford crude product, which was purified by reverse phase purification to afford the desired compound 6-((2-(dimethylamino)-2,3-dihydro-1H-inden-5-yl)amino)-2-ethyl-1-(6-(2-hydroxypropan-2-yl)pyridin-2-yl)-1,2-dihydro-3H-pyrazolo[3,4-d]pyrimidin-3-one (5.0 mg, 1.87%) as brown solid.

LCMS: 474.3 [M+1]$^+$; UPLC @ 254 nm=76.60% and @ 220 nm=85.51%.

$^1$H NMR (400 MHz, DMSO-d$_6$) δ 10.18 (brs, 1H), 8.84 (s, 1H), 8.32 (d, J=9.65 Hz, 1H), 7.99-8.07 (m, 1H), 7.82 (d, J=7.89 Hz, 1H), 7.65 (d, J=7.89 Hz, 2H), 7.42 (d, J=7.89 Hz, 1H), 7.13 (d, J=8.33 Hz, 1H), 4.01-4.09 (m, 2H), 3.17 (s, 2H), 2.88-3.11 (m, 4H), 2.60-2.85 (m, 3H), 2.22 (s, 6H), 1.32-1.50 (m, 6H), 1.23 (brs, 1H), 0.97 (t, J=7.02 Hz, 3H).

Example S37. Synthesis of 1-(2-(tert-butyl)pyridin-4-yl)-2-ethyl-6-((1,2,3,4-tetrahydroisoquinolin-7-yl)amino)-1,2-dihydro-3H-pyrazolo[3,4-d]pyrimidin-3-one dihydrochloride (Compound No. 1.134)

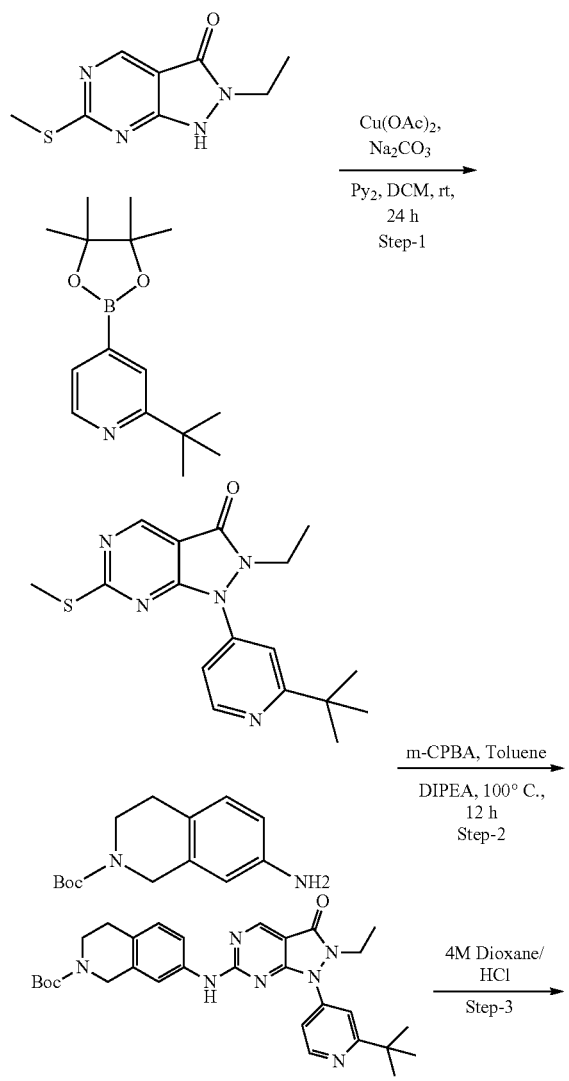

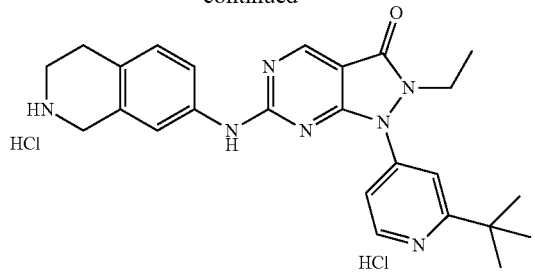

Step-1: Synthesis of 1-(2-(tert-butyl)pyridin-4-yl)-2-ethyl-6-(methylthio)-1,2-dihydro-3H-pyrazolo[3,4-d]pyrimidin-3-one To a stirred solution of 2-ethyl-6-(methylthio)-1,2-dihydro-3H-pyrazolo[3,4-d]pyrimidin-3-one (300 mg, 1.42 mmol) and 2-(tert-butyl)-4-(4,4,5,5-tetramethyl-1,3,2-dioxaborolan-2-yl)pyridine (445 mg, 2.85 mmol) in DCM (50 mL) was added 2,2-bipyridine (445 mg, 2.85 mmol), copper acetate (518 mg, 2.85 mmol) and Na$_2$CO$_3$ (451 mg, 4.26 mmol). The reaction mixture was stirred at rt for 24 h in open air. The progress of reaction was monitored by TLC. After completion, the reaction mixture was filtered over celite to remove inorganic impurities. The filtrate was washed with water, dried over Na$_2$SO$_4$, concentrated and purified by column chromatography (Combiflash, Elution: 0-30% EtOAc in Hexane) to afford the desired product, 1-(2-(tert-butyl)pyridin-4-yl)-2-ethyl-6-(methylthio)-1,2-dihydro-3H-pyrazolo[3,4-d]pyrimidin-3-one (180 mg, 36.73%) as an off white solid.

LCMS: 344.2 [M+1]$^+$

Step-2: Synthesis of tert-butyl 7-((1-(2-(tert-butyl)pyridin-4-yl)-2-ethyl-3-oxo-2,3-dihydro-1H-pyrazolo[3,4-d]pyrimidin-6-yl)amino)-3,4-dihydroisoquinoline-2(1H)-carboxylate To a stirred solution of 1-(2-(tert-butyl)pyridin-4-yl)-2-ethyl-6-(methylthio)-1,2-dihydro-3H-pyrazolo[3,4-d]pyrimidin-3-one (100 mg, 0.291 mmol, 1.0 eq) in (6.0 mL) of toluene was added m-CPBA (100 mg, 0.582 mmol, 2.0 eq) and allowed to stir at rt for 1 h. tert-butyl 7-amino-3,4-dihydroisoquinoline-2(1H)-carboxylate (87 mg, 0.349 mmol, 1.2 eq) and DIPEA (0.2 mL, 1.164 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 7-((1-(2-(tert-butyl)pyridin-4-yl)-2-ethyl-3-oxo-2,3-dihydro-1H-pyrazolo[3,4-d]pyrimidin-6-yl)amino)-3,4-dihydroisoquinoline-2(1H)-carboxylate (27 mg, 17.05%) as an off white solid.

LCMS: 544.3 [M+1]$^+$

Step-3: Synthesis of 1-(2-(tert-butyl)pyridin-4-yl)-2-ethyl-6-((1,2,3,4-tetrahydroisoquinolin-7-yl)amino)-1,2-dihydro-3H-pyrazolo[3,4-d]pyrimidin-3-one dihydrochloride tert-butyl 7-((1-(2-(tert-butyl)pyridin-4-yl)-2-ethyl-3-oxo-2,3-dihydro-1H-pyrazolo[3,4-d]pyrimidin-6-yl)

amino)-3,4-dihydroisoquinoline-2(1H)-carboxylate (27 mg, 0.049 mmol, 1.0 eq) was dissolved in dioxane (0.5 mL), followed by dropwise addition of 4.0M-HCl (0.5 mL) and allowed to stir at rt for 1 h. After completion of reaction, the reaction mixture was filtered and dried under reduced pressure to afford the desired compound, 1-(2-(tert-butyl)pyridin-4-yl)-2-ethyl-6-((1,2,3,4-tetrahydroisoquinolin-7-yl)amino)-1,2-dihydro-3H-pyrazolo[3,4-d]pyrimidin-3-one dihydrochloride (18 mg, 70.20%) as light yellow solid.

LCMS: 444.4 [M+1]$^+$; UPLC @ 254 nm=94.74% and @ 220 nm=93.98%.

$^1$H NMR (400 MHz, DMSO-d$_6$): δ 10.54 (br. s., 1H), 9.47 (br. s., 2H), 8.94 (s, 1H), 8.82 (d, J=6.14 Hz, 1H), 7.88 (br. s., 1H), 7.59 (d, J=7.45 Hz, 2H), 7.53 (br. s., 1H), 7.22 (d, J=7.89 Hz, 1H), 4.28 (br. s., 4H), 3.83 (d, J=7.02 Hz, 2H), 3.36 (br. s., 2H), 2.99 (br. s., 2H), 1.42 (br. s., 9H), 0.97 (t, J=6.80 Hz, 3H)

Example S38. 6-{[7-(dimethylamino)-5,6,7,8-tetrahydronaphthalen-2-yl]amino}-2-ethyl-1-[6-(2-hydroxypropan-2-yl)pyridin-2-yl]-1H,2H,3H-pyrazolo[3,4-d]pyrimidin-3-one (PK-II: Compound No. 1.135)

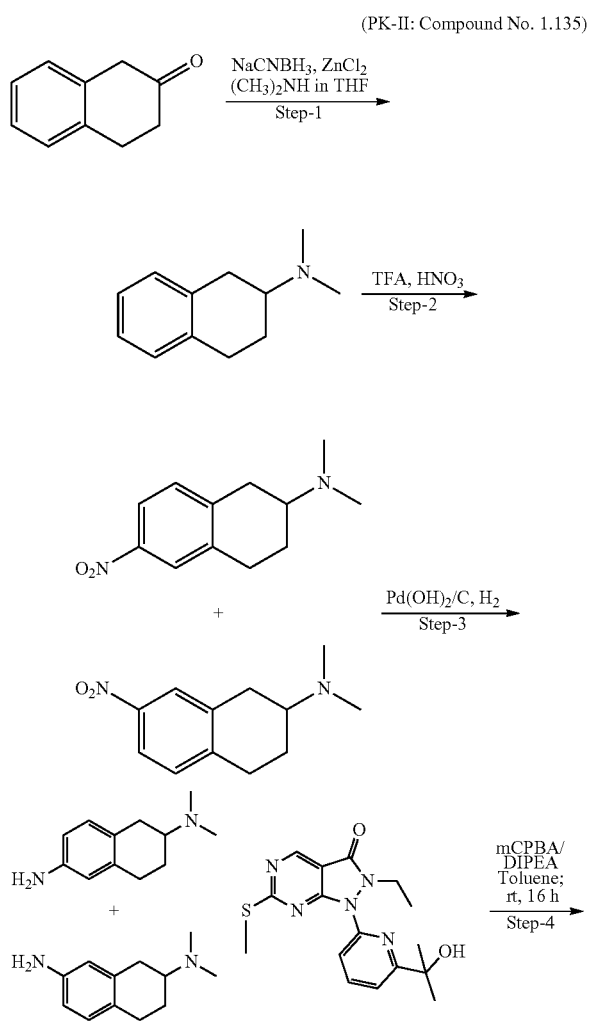

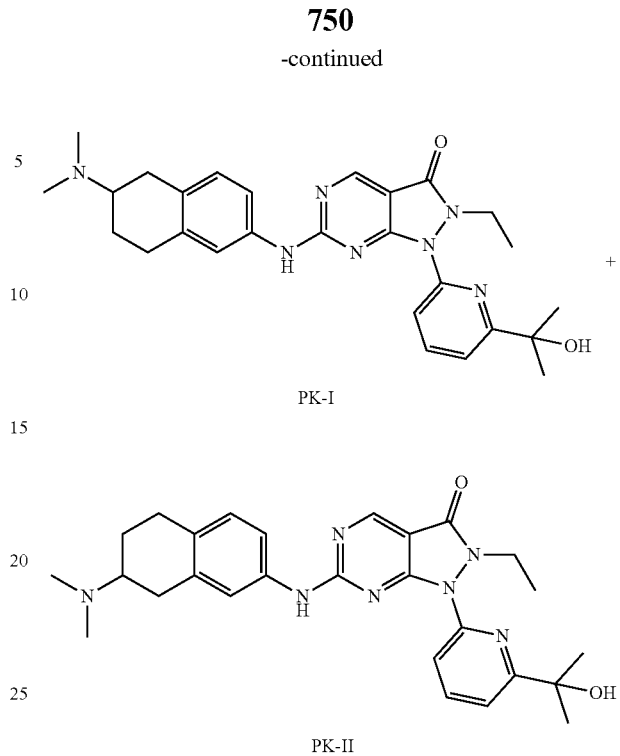

PK-I

PK-II

Step-1: Synthesis of N,N-dimethyl-1,2,3,4-tetrahydronaphthalen-2-amine 46 mL of a methanol solution of NaCNBH$_3$ (0.87 g, 13.825 mmol, 1.0 eq) and ZnCl$_2$ (0.94 g, 6.914 mmol, 0.5 eq) and 6.9 mL of a THF solution of 2M dimethyl amine, were added to a THF solution (10 mL) of 3,4-dihydronaphthalen-2(1H)-one (2.02 g, 13.828 mmol, 1.0 eq) at 0° C. The resulting mixture was stirred at rt for overnight. The progress of reaction was monitored by LCMS. The reaction mixture was concentrated, acidified with 1N-HCl (50 mL), washed with EtOAc (2×50 mL), then made alkaline with aqueous 5N NaOH solution, extracted with EtOAc (2×50 mL). The combined organic layers were washed with water (50 mL), with brine (50 mL), dried over Na$_2$SO$_4$ concentrated and purified by combiflash chromatography [basic alumina, elution 0-10% EtOAc in Hexane] to afford the desired compound N,N-dimethyl-1,2,3,4-tetrahydronaphthalen-2-amine (845 mg, 34.77%) as colorless liquid.

LCMS: 176.3 4 [M+1]$^+$

Step-2: Synthesis of N,N-dimethyl-6-nitro-1,2,3,4-tetrahydronaphthalen-2-amine and N,N-dimethyl-7-nitro-1,2,3,4-tetrahydronaphthalen-2-amine 1.2 mL of nitric acid (specific gravity, 1.41) to a TFA (5.0 mL) solution of N,N-dimethyl-1,2,3,4-tetrahydronaphthalen-2-amine (0.840 g, 4.792 mmol, 1.0 eq) at 0° C. The resulting mixture was stirred at rt for overnight. The progress of reaction was monitored by LCMS. The reaction mixture was poured into ice cold water (100 mL), then made alkaline with aqueous 5M solution of NaOH added there to and extracted with EtOAc (2×100 mL). The combined organic layers were washed with water (50 mL), with brine (50 mL), dried over Na$_2$SO$_4$ concentrated and purified by combiflash chromatography [basic alumina, elution 0-10% EtOAc in Hexane] to afford the mixture of N,N-dimethyl-6-nitro-1,2,3,4-tetrahydronaphthalen-2-amine and N,N-dimethyl-7-nitro-1,2,3,4-tetrahydronaphthalen-2-amine (900 mg, 85.30%) as brown viscous.

LCMS: 221.3 4 [M+1]$^+$

Step-3: Synthesis of N2,N2-dimethyl-1,2,3,4-tetrahydronaphthalene-2,6-diamine and N2,N2-dimethyl-1,2,3,4-tetrahydronaphthalene-2,7-diamine 130 mg of palladium hydroxide-carbon (20%) was added to a solution of N,N-dimethyl-6-nitro-1,2,3,4-tetrahydronaphthalen-2-amine and N,N-dimethyl-7-nitro-1,2,3,4-tetrahydronaphthalen-2-amine (0.900 g, 4.085 mmol, 1.0 eq) in EtOH (10 mL) at rt. The resulting mixture was stirred at rt for overnight in hydrogen atmosphere. The catalyst was removed though filtration, the filtrate was concentrated, and stirred in hexane, filtered and concentrated to afford the mixture of N2,N2-dimethyl-1,2,3,4-tetrahydronaphthalene-2,6-diamine and N2,N2-dimethyl-1,2,3,4-tetrahydro naphthalene-2,7-diamine (730 mg, 93.95%) as brown viscous.

LCMS: 191.3 4 [M+1]$^+$

Step-4: Synthesis of 6-{[7-(dimethylamino)-5,6,7,8-tetrahydronaphthalen-2-yl]amino}-2-ethyl-1-[6-(2-hydroxypropan-2-yl)pyridin-2-yl]-1H,2H,3H-pyrazolo[3,4-d]pyrimidin-3-one (PK-II)

To a stirred solution of 2-ethyl-1-(6-(2-hydroxypropan-2-yl)pyridin-2-yl)-6-(methylthio)-1,2-dihydro-3H-pyrazolo[3,4-d]pyrimidin-3-one (1.05 g, 3.065 mmol, 1.0 eq) in (20.0 mL) of toluene was added m-CPBA (1.51 g, 6.13 mmol, 2.0 eq) and allowed to stir at rt for 30 minutes. N2,N2-dimethyl-1,2,3,4-tetrahydronaphthalene-2,6-diamine and N2,N2-dimethyl-1,2,3,4-tetrahydro naphthalene-2,7-diamine (700 mg, 3.678 mmol, 1.2 eq) and DIPEA (2.14 mL, 12.26 mmol, 4.0 eq) were added and allowed to stir at rt for overnight. After completion of reaction, the reaction mixture was filtered and dried under reduced pressure to afford the mixture of 6-((6-(dimethylamino)-5,6,7,8-tetrahydronaphthalen-2-yl)amino)-2-ethyl-1-(6-(2-hydroxypropan-2-yl)pyridin-2-yl)-1,2-dihydro-3H-pyrazolo[3,4-d]pyrimidin-3-one (PK-I) and 6-((7-(dimethylamino)-5,6,7,8-tetrahydronaphthalen-2-yl)amino)-2-ethyl-1-(6-(2-hydroxypropan-2-yl) pyridin-2-yl)-1,2-dihydro-3H-pyrazolo[3,4-d]pyrimidin-3-one (PK-II), which was purified by reverse phase purification to obtain peak-II (5.0 mg, 1.87%) as brown solid.

LCMS: 474.3 4 [M+1]$^+$; UPLC @ 254 nm=76.60% and @ 220 nm=85.51%.

$^1$H NMR (400 MHz, DMSO-d$_6$): δ 10.18 (brs, 1H), 8.84 (s, 1H), 8.32 (d, J=9.65 Hz, 1H), 7.99-8.07 (m, 1H), 7.82 (d, J=7.89 Hz, 1H), 7.65 (d, J=7.89 Hz, 2H), 7.42 (d, J=7.89 Hz, 1H), 7.13 (d, J=8.33 Hz, 1H), 4.01-4.09 (m, 2H), 3.17 (s, 2H), 2.88-3.11 (m, 4H), 2.60-2.85 (m, 3H), 2.22 (s, 6H), 1.32-1.50 (m, 6H), 1.23 (brs, 1H), 0.97 (t, J=7.02 Hz, 3H).

Example S39. Synthesis of 1-(2-(tert-butyl)pyridin-4-yl)-2-ethyl-6-((1,2,3,4-tetrahydroisoquinolin-6-yl)amino)-1,2-dihydro-3H-pyrazolo[3,4-d]pyrimidin-3-one dihydrochloride (Compound No. 1.136)

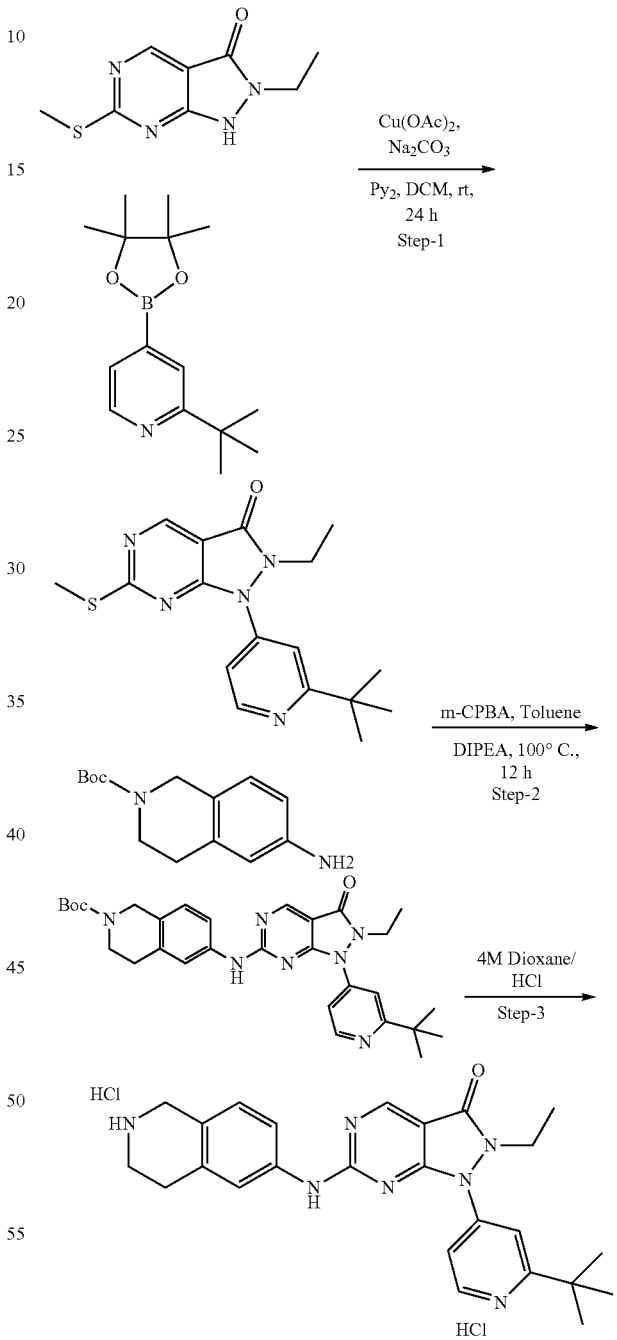

Step-1: Synthesis of 1-(2-(tert-butyl)pyridin-4-yl)-2-ethyl-6-(methylthio)-1,2-dihydro-3H-pyrazolo[3,4-d]pyrimidin-3-one To a stirred solution of 2-ethyl-6-(methylthio)-1,2-dihydro-3H-pyrazolo[3,4-d]pyrimidin-3-one (300 mg, 1.42 mmol) and 2-(tert-butyl)-4-(4,4,5,5-tetramethyl-1,3,2-dioxaborolan-2-yl)pyridine (445 mg, 2.85 mmol) in DCM (50 mL) was added 2,2-bipyridine (445 mg, 2.85 mmol), copper acetate (518 mg, 2.85 mmol) and Na$_2$CO$_3$ (451 mg, 4.26 mmol). The reaction mixture was stirred at rt for 24 h in open air. The progress of reaction was monitored by TLC. After completion, the reaction mixture was filtered over celite to remove inorganic impurities. The filtrate was washed with water, dried over Na$_2$SO$_4$, concentrated and purified by column chromatography (Combiflash, Elution: 0-30% EtOAc in Hexane) to afford the desired product, 1-(2-(tert-butyl)pyridin-4-yl)-2-ethyl-6-(methylthio)-1,2-dihydro-3H-pyrazolo[3,4-d]pyrimidin-3-one (180 mg, 36.73%) as an off white solid.

LCMS: 344.2 [M+1]$^+$

Step-2: Synthesis of tert-butyl 6-((1-(2-(tert-butyl)pyridin-4-yl)-2-ethyl-3-oxo-2,3-dihydro-1H-pyrazolo[3,4-d]pyrimidin-6-yl)amino)-3,4-dihydroisoquinoline-2(1H)-carboxylate To a stirred solution of 1-(2-(tert-butyl)pyridin-4-yl)-2-ethyl-6-(methylthio)-1,2-dihydro-3H-pyrazolo[3,4-d]pyrimidin-3-one (100 mg, 0.291 mmol, 1.0 eq) in (6.0 mL) of toluene was added m-CPBA (100 mg, 0.582 mmol, 2.0 eq) and allowed to stir at rt for 1 h. tert-butyl 6-amino-3,4-dihydroisoquinoline-2(1H)-carboxylate (87 mg, 0.349 mmol, 1.2 eq) and DIPEA (0.2 mL, 1.164 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((1-(2-(tert-butyl)pyridin-4-yl)-2-ethyl-3-oxo-2,3-dihydro-1H-pyrazolo[3,4-d]pyrimidin-6-yl)amino)-3,4-dihydroisoquinoline-2(1H)-carboxylate (50 mg, 33.26%) as an off white solid.

LCMS: 544.3 [M+1]$^+$

Step-3: Synthesis of 1-(2-(tert-butyl)pyridin-4-yl)-2-ethyl-6-((1,2,3,4-tetrahydroisoquinolin-6-yl)amino)-1,2-dihydro-3H-pyrazolo[3,4-d]pyrimidin-3-one dihydrochloride tert-butyl 6-((1-(2-(tert-butyl)pyridin-4-yl)-2-ethyl-3-oxo-2,3-dihydro-1H-pyrazolo[3,4-d]pyrimidin-6-yl)amino)-3,4-dihydroisoquinoline-2(1H)-carboxylate (100 mg, 0.179 mmol, 1.0 eq) was dissolved in dioxane (1 mL), followed by dropwise addition of 4.0M-HCl (2 mL) and allowed to stir at rt for 1 h. After completion of reaction, the reaction mixture was filtered and dried under reduced pressure to afford the desired compound, 1-(2-(tert-butyl)pyridin-4-yl)-2-ethyl-6-((1,2,3,4-tetrahydroisoquinolin-6-yl)amino)-1,2-dihydro-3H-pyrazolo[3,4-d]pyrimidin-3-one dihydrochloride (70 mg, 73.59%) as light yellow solid.

LCMS: 444.3 [M+1]$^+$; UPLC @ 254 nm=93.80% and @ 220 nm=93.41%.

$^1$H NMR (400 MHz, DMSO-d$_6$): δ 10.48 (br. s., 1H), 9.33 (br. s., 2H), 8.94 (s, 1H), 8.77 (d, J=5.70 Hz, 1H), 7.79 (br. s., 1H), 7.58 (br. s., 3H), 7.21 (s, 1H), 4.23 (br. s., 2H), 3.02 (br. s., 2H), 1.28-1.57 (m, 9H), 0.97 (t, J=6.80 Hz, 3H).

Example S40. Synthesis of 1-(2-(tert-butyl)pyridin-4-yl)-2-isopropyl-6-((1,2,3,4-tetrahydroisoquinolin-7-yl)amino)-1,2-dihydro-3H-pyrazolo[3,4-d]pyrimidin-3-one dihydrochloride (Compound No. 1.137)

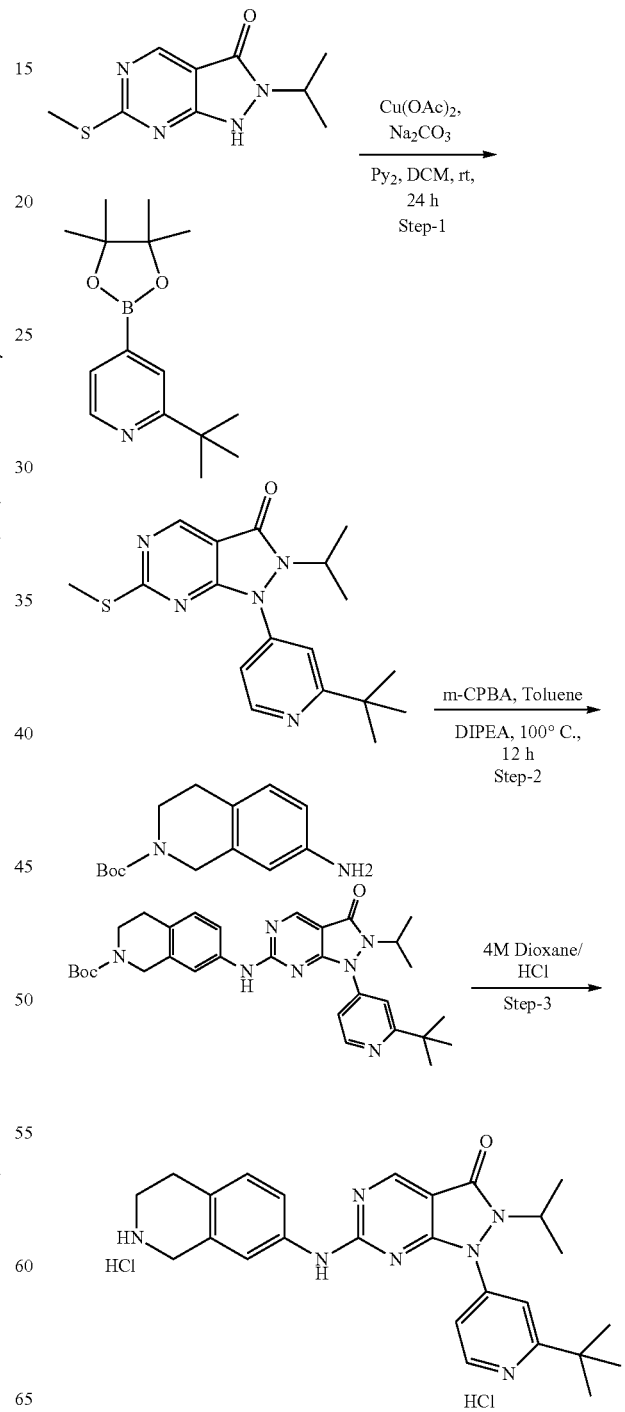

Step-1: Synthesis of 1-(2-(tert-butyl)pyridin-4-yl)-2-isopropyl-6-(methylthio)-1,2-dihydro-3H-pyrazolo[3,4-d]pyrimidin-3-one To a stirred solution of 2-isopropyl-6-(methylthio)-1,2-dihydro-3H-pyrazolo[3,4-d]pyrimidin-3-one (600 mg, 2.67 mmol) and 2-(tert-butyl)-4-(4,4,5,5-tetramethyl-1,3,2-dioxaborolan-2-yl)pyridine (1.39 g, 5.35 mmol) in DCM (100 mL) was added 2,2-bipyridine (836 mg, 5.35 mmol), copper acetate (972 mg, 5.35 mmol) and Na$_2$CO$_3$ (849 mg, 8.01 mmol). The reaction mixture was stirred at rt for 24 h in open air. The progress of reaction was monitored by TLC. After completion, the reaction mixture was filtered over celite to remove inorganic impurities. The filtrate was washed with water, dried over Na$_2$SO$_4$, concentrated and purified by column chromatography (Combiflash, Elution: 0-30% EtOAc in Hexane) to afford the desired product, 1-(2-(tert-butyl)pyridin-4-yl)-2-isopropyl-6-(methylthio)-1,2-dihydro-3H-pyrazolo[3,4-d]pyrimidin-3-one (450 mg, 47.05%) as an off white solid.
LCMS: 358.2 [M+1]$^+$

Step-2: Synthesis of tert-butyl 7-((1-(2-(tert-butyl)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(2-(tert-butyl)pyridin-4-yl)-2-isopropyl-6-(methylthio)-1,2-dihydro-3H-pyrazolo[3,4-d]pyrimidin-3-one (225 mg, 0.629 mmol, 1.0 eq) in (6.0 mL) of toluene was added m-CPBA (217 mg, 1.258 mmol, 2.0 eq) and allowed to stir at rt for 1 h. tert-butyl 7-amino-3,4-dihydroisoquinoline-2(1H)-carboxylate (188 mg, 0.755 mmol, 1.2 eq) and DIPEA (0.43 mL, 2.516 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound tert-butyl 7-((1-(2-(tert-butyl)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate (80 mg, 22.78%) as an off white solid.
LCMS: 558.3 [M+1]$^+$

Step-3: Synthesis of 1-(2-(tert-butyl)pyridin-4-yl)-2-isopropyl-6-((1,2,3,4-tetrahydroisoquinolin-7-yl)amino)-1,2-dihydro-3H-pyrazolo[3,4-d]pyrimidin-3-one dihydrochloride tert-butyl 7-((1-(2-(tert-butyl)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate (80 mg, 0.143 mmol, 1.0 eq) was dissolved in dioxane (1 mL), followed by dropwise addition of 4.0M-HCl (2 mL) and allowed to stir at rt for 1 h. After completion of reaction, the reaction mixture was filtered and dried under reduced pressure to afford the desired compound, 1-(2-(tert-butyl)pyridin-4-yl)-2-isopropyl-6-((1,2,3,4-tetrahydroisoquinolin-7-yl)amino)-1,2-dihydro-3H-pyrazolo[3,4-d]pyrimidin-3-one dihydrochloride (45 mg, 59.14%) as light yellow solid.
LCMS: 458.4 [M+1]$^+$; UPLC @ 254 nm=95.58% and @ 220 nm=96.94%.

$^1$H NMR (400 MHz, DMSO-d$_6$): δ 10.56 (br. s., 1H), 9.57 (br. s., 3H), 8.90 (s, 1H), 8.82 (br. s., 1H), 7.90 (br. s., 1H), 7.52 (br. s., 1H), 7.22 (d, J=8.33 Hz, 1H), 4.28 (br. s., 2H), 3.95 (br. s., 1H), 3.36 (br. s., 2H), 2.99 (br. s., 2H), 1.29-1.53 (m, 15H)

Example S41. Synthesis of 1-(2-(tert-butyl)pyridin-4-yl)-2-isopropyl-6-((1,2,3,4-tetrahydroisoquinolin-6-yl)amino)-1,2-dihydro-3H-pyrazolo[3,4-d]pyrimidin-3-one dihydrochloride (Compound No. 1.138)

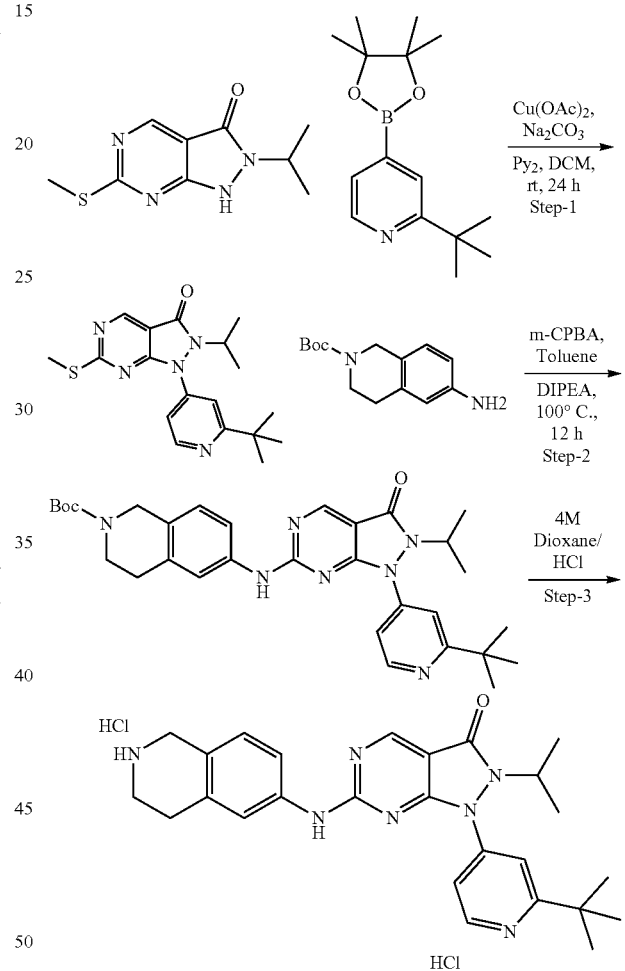

Step-1: Synthesis of 1-(2-(tert-butyl)pyridin-4-yl)-2-isopropyl-6-(methylthio)-1,2-dihydro-3H-pyrazolo[3,4-d]pyrimidin-3-one To a stirred solution of 2-isopropyl-6-(methylthio)-1,2-dihydro-3H-pyrazolo[3,4-d]pyrimidin-3-one (600 mg, 2.67 mmol) and 2-(tert-butyl)-4-(4,4,5,5-tetramethyl-1,3,2-dioxaborolan-2-yl)pyridine (1.39 g, 5.35 mmol) in DCM (100 mL) was added 2,2-bipyridine (836 mg, 5.35 mmol), copper acetate (972 mg, 5.35 mmol) and Na$_2$CO$_3$ (849 mg, 8.01 mmol). The reaction mixture was stirred at rt for 24 h in open air. The progress of reaction was monitored by TLC. After completion, the reaction mixture was filtered over celite to remove inorganic impurities. The filtrate was washed with water, dried over Na₂SO₄, concentrated and purified by column chromatography (Combiflash, Elution: 0-30% EtOAc in Hexane) to afford the desired product, 1-(2-(tert-butyl)pyridin-4-yl)-2-isopropyl-6-(methylthio)-1,2-dihydro-3H-pyrazolo[3,4-d]pyrimidin-3-one (450 mg, 47.05%) as an off white solid.

LCMS: 358.2 [M+1]⁺

Step-2: Synthesis of tert-butyl 6-((1-(2-(tert-butyl)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(2-(tert-butyl)pyridin-4-yl)-2-isopropyl-6-(methylthio)-1,2-dihydro-3H-pyrazolo[3,4-d]pyrimidin-3-one (225 mg, 0.629 mmol, 1.0 eq) in (6.0 mL) of toluene was added m-CPBA (217 mg, 1.258 mmol, 2.0 eq) and allowed to stir at rt for 1 h. tert-butyl 6-amino-3,4-dihydroisoquinoline-2(1H)-carboxylate (188 mg, 0.755 mmol, 1.2 eq) and DIPEA (0.43 mL, 2.516 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((1-(2-(tert-butyl)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate (100 mg, 28.48%) as an off white solid.

LCMS: 558.3 [M+1]⁺

Step-3: Synthesis of 1-(2-(tert-butyl)pyridin-4-yl)-2-isopropyl-6-((1,2,3,4-tetrahydroisoquinolin-6-yl)amino)-1,2-dihydro-3H-pyrazolo[3,4-d]pyrimidin-3-one dihydrochloride tert-butyl 6-((1-(2-(tert-butyl)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate (100 mg, 0.179 mmol, 1.0 eq) was dissolved in dioxane (1 mL), followed by dropwise addition of 4.0M-HCl (2 mL) and allowed to stir at rt for 1 h. After completion of reaction, the reaction mixture was filtered and dried under reduced pressure to afford the desired compound, 1-(2-(tert-butyl)pyridin-4-yl)-2-isopropyl-6-((1,2,3,4-tetrahydroisoquinolin-6-yl)amino)-1,2-dihydro-3H-pyrazolo[3,4-d]pyrimidin-3-one dihydrochloride (70 mg, 73.59%) as light yellow solid.

LCMS: 458.4 [M+1]⁺; UPLC @ 254 nm=95.47% and @ 220 nm=97.76%.

¹H NMR (400 MHz, DMSO-d₆): δ 10.58 (br. s., 1H), 9.61 (br. s., 2H), 8.91 (s, 1H), 8.81 (d, J=6.14 Hz, 1H), 7.93 (br. s., 1H), 7.66 (br. s., 1H), 7.58 (d, J=7.89 Hz, 1H), 7.52 (br. s., 1H), 7.23 (d, J=8.33 Hz, 1H), 4.23 (br. s., 3H), 3.95 (td, J=6.80, 13.59 Hz, 1H), 3.36 (br. s., 2H), 3.04 (br. s., 2H), 1.32-1.58 (m, 15H)

Example S42. Synthesis of 1-(6-(2-fluoropropan-2-yl)pyridin-2-yl)-2-isopropyl-6-(1,2,3,4-tetrahydroisoquinolin-7-ylamino)-1H-pyrazolo[3,4-d]pyrimidin-3(2H)-one dihydrochloride (Compound No. 1.139)

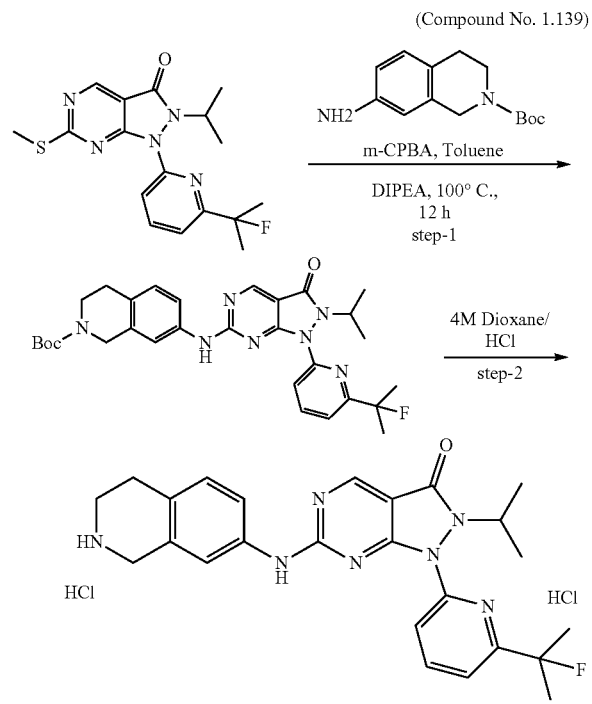

Step-1: Synthesis of tert-butyl 7-((1-(6-(2-fluoropropan-2-yl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(6-(tert-butyl)pyridin-2-yl)-2-isopropyl-6-(methylthio)-1,2-dihydro-3H-pyrazolo[3,4-d]pyrimidin-3-one (150 mg, 0.4155 mmol, 1.0 eq) in (5.0 mL) of toluene was added m-CPBA (143 mg, 0.831 mmol, 2.0 eq) and allowed to stir at rt for 30 minutes. tert-butyl 7-amino-3,4-dihydroisoquinoline-2(1H)-carboxylate (124 mg, 0.5 mmol, 1.2 eq) and DIPEA (0.3 mL, 1.662 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((2-isopropyl-1-(6-(2-fluoropropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate (80 mg, 34.32%) as an off white solid.

¹H NMR (400 MHz, DMSO-d₆): δ 10.22 (brs, 1H), 8.81 (s, 1H), 8.10-8.17 (m, 1H), 7.96 (d, J=8.77 Hz, 1H), 7.7-7.3 (m, 3H), 7.06 (d, 1H), 4.5 (brs, 2H), 4.06 (s, 1H), 3.6 (brs, 2H), 2.7 (brs, 2H), 1.7 (d, 6H), 1.5-1.3 (m, 15H).

Step-2: Synthesis of 1-(6-(2-fluoropropan-2-yl)pyridin-2-yl)-2-isopropyl-6-((1,2,3,4-tetrahydroisoquinolin-7-yl)amino)-1,2-dihydro-3H-pyrazolo[3,4-d]pyrimidin-3-one tert-butyl 6-((1-(6-(tert-butyl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (80 mg, 0. mmol, 1.0 eq) was dissolved in dioxane (1 mL), followed by dropwise addition of 4.0M-HCl (2 mL) and allowed to stir at rt for 1 h. After completion of reaction, the reaction mixture was filtered and dried under reduced pressure to afford the desired compound, 2-isopropyl-1-(6-(2-fluoropropan-2-yl)pyridin-2-yl)-6-((1,2,3,4-tetrahydroisoquinolin-6-yl)amino)-1,2-dihydro-3H-pyrazolo[3,4-d]pyrimidin-3-one (45 mg, 30.16%) as light yellow solid.

LCMS: 462.3 [M+1]⁺; UPLC @ 254 nm=94.68% and @ 220 nm=97.66%.

¹H NMR (400 MHz, DMSO-$d_6$): δ 10.22 (brs, 1H), 9.22 (brs, 2H), 8.81 (s, 1H), 8.20-8.10 (m, 1H), 7.88 (d, 1H), 7.64 (brs, 1H), 7.55-7.42 (m, 2H), 7.18 (d, 1H), 4.28-4.16 (m, 3H), 3.4 (brs, 2H), 2.98 (brs, 2H), 1.66 (s, 3H), 1.62 (s, 3H), 1.40 (d, 6H).

Example S43. Synthesis of 2-isopropyl-1-(6-(2-fluoropropan-2-yl)pyridin-2-yl)-6-((1,2,3,4-tetrahydroisoquinolin-6-yl)amino)-1,2-dihydro-3H-pyrazolo[3,4-d]pyrimidin-3-one (Compound No. 1.140)

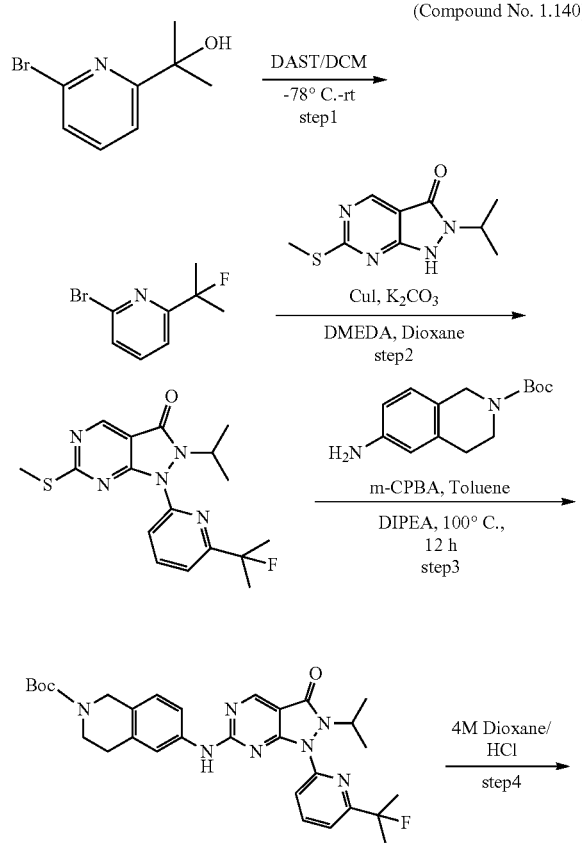

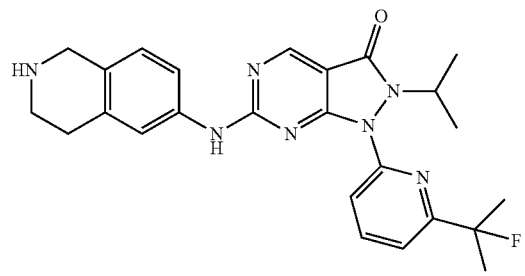

Step)-1: Synthesis of 2-bromo-6-(2-fluoropropan-2-yl)pyridine

To a stirred solution of 2-(6-bromo-pyridine-2-yl)-propane-2-ol (0.500 g, 2.313 mmol, 1.0 eq) in DCM (10 mL), DAST (0.36 mL, 2.545 mmol, 1.1 eq) was added at −78° C. The reaction mixture was stirred at rt for 12 h. After completion of reaction, the reaction mixture was quenched with saturated sodium bicarbonate solution and was extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-10% EtOAc in hexane] to afford the desired compound, tert-butyl 6-((2-cyclopropyl-1-(6-(2-fluoropropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate (355 mg, 70.43%) as colorless liquid. LCMS: 217.99 [M+1]⁺

Step-2: Synthesis of 2-isopropyl-1-(6-(2-fluoropropan-2-yl)pyridin-2-yl)-6-(methylthio)-1,2-dihydro-3H-pyrazolo[3,4-d]pyrimidin-3-one To a stirred solution of 2-isopropyl-6-(methylthio)-1,2-dihydro-3H-pyrazolo[3,4-d]pyrimidin-3-one (300 mg, 1.337 mmol, 1.0 eq) and 2-bromo-6-(2-fluoropropan-2-yl)pyridine (294 mg, 1.36 mmol, 1.20 eq) in (8 mL) of dioxane was added potassium carbonate (370 mg, 2.674 mmol, 2.0 eq) and the resulting mixture was purged with nitrogen for 10 min, followed by addition of copper iodide (51 mg, 0.27 mmol, 0.2 eq), and N,N'-dimethylethylenediamine (DMEDA) (47 mg, 0.535 mmol, 0.4 eq) and again purged with nitrogen for 10 min, stirred at 90° C. for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-30% EtOAc in hexane] to afford the desired product, 2-isopropyl-1-(6-(2-fluoropropan-2-yl)pyridin-2-yl)-6-(methylthio)-1,2-dihydro-3H-pyrazolo[3,4-d]pyrimidin-3-one (310 mg, 64%) as an off white solid.

LCMS: 362.3 [M+1]⁺

Step-3: Synthesis of tert-butyl 6-((2-isopropyl-1-(6-(2-fluoropropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate To a stirred solution of 1-(6-(tert-butyl)pyridin-2-yl)-2-isopropyl-6-(methylthio)-1,2-dihydro-3H-pyrazolo[3,4-d]pyrimidin-3-one (150 mg, 0.4155 mmol, 1.0 eq) in (5.0 mL) of toluene was added m-CPBA (143 mg, 0.831 mmol, 2.0 eq) and allowed to stir at rt for 30 minutes. tert-butyl 6-amino-3,4-dihydroisoquinoline-2(1H)-carboxylate (124 mg, 0.5 mmol, 1.2 eq) and DIPEA (0.3 mL, 1.662 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((2-isopropyl-1-(6-(2-fluoropropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate (80 mg, %) as an off white solid.

$^1$H NMR (400 MHz, DMSO-$d_6$): δ 10.22 (brs, 1H), 8.81 (s, 1H), 8.10-8.17 (m, 1H), 7.88 (d, J=8.77 Hz, 1H), 7.6-7.4 (m, 3H), 7.10 (brs, 1H), 4.9 (brs, 1H), 4.10-4.46 (m, 4H), 3.4 (brs, 2H), 1.86 (d, 6H), 1.4 (m, 15H).

Step-4: Synthesis of 2-isopropyl-1-(6-(2-fluoropropan-2-yl)pyridin-2-yl)-6-((1,2,3,4-tetrahydroisoquinolin-6-yl)amino)-1,2-dihydro-3H-pyrazolo[3,4-d]pyrimidin-3-one tert-butyl 6-((1-(6-(tert-butyl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (80 mg, 0. mmol, 1.0 eq) was dissolved in dioxane (1 mL), followed by dropwise addition of 4.0M-HCl (2 mL) and allowed to stir at rt for 1 h. After completion of reaction, the reaction mixture was filtered and dried under reduced pressure to afford the desired compound, 2-isopropyl-1-(6-(2-fluoropropan-2-yl)pyridin-2-yl)-6-((1,2,3,4-tetrahydroisoquinolin-6-yl)amino)-1,2-dihydro-3H-pyrazolo[3,4-d]pyrimidin-3-one (45 mg, 30.16%) as light yellow solid.

LCMS: 462.3 [M+1]$^+$; UPLC @ 254 nm=94.72% and @ 220 nm=96.31%.

$^1$H NMR (400 MHz, DMSO-$d_6$): δ 10.22 (brs, 1H), 9.22 (brs, 2H), 8.81 (s, 1H), 8.10-8.17 (m, 1H), 7.88 (d, 1H), 7.69 (brs, 1H), 7.55-7.40 (m, 2H), 7.18 (d, 1H), 4.22-4.16 (m, 3H), 3.4 (brs, 2H), 3.24 (brs, 2H), 1.66 (s, 3H), 1.62 (s, 3H), 1.40 (d, 6H).

Example S44. Synthesis of 1-(6-(tert-butyl)pyridin-2-yl)-2-ethyl-6-((5,6,7,8-tetrahydro-1,6-naphthyridin-3-yl)amino)-1,2-dihydro-3H-pyrazolo[3,4-d]pyrimidin-3-one trihydrochloride (Compound No. 1.141)

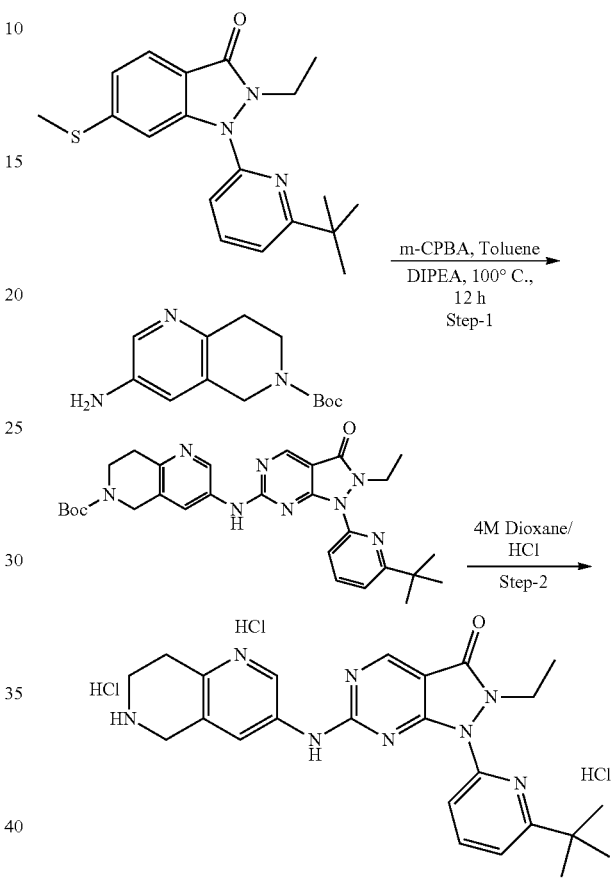

Step-1: Synthesis of tert-butyl 3-((1-(6-(tert-butyl)pyridin-2-yl)-2-ethyl-3-oxo-2,3-dihydro-1H-pyrazolo[3,4-d]pyrimidin-6-yl)amino)-7,8-dihydro-1,6-naphthyridine-6(5H)-carboxylate To a stirred solution of 1-(6-(tert-butyl)pyridin-2-yl)-2-ethyl-6-(methylthio)-1,2-dihydro-3H-indazol-3-one (200 mg, 0.582 mmol, 1.0 eq) in (2.0 mL) of toluene was added m-CPBA (287 mg, 1.164 mmol, 2.0 eq) and allowed to stir at rt for 30 minutes. tert-butyl 3-amino-7,8-dihydro-1,6-naphthyridine-6(5H)-carboxylate (174 mg, 0.698 mmol, 1.2 eq) and DIPEA (0.40 mL, 2.328 mmol, 4.0 eq) were added and allowed to stir at rt for overnight. The formation of precipitates were observed which were filtered to afford the desired compound tert-butyl 3-((1-(6-(tert-butyl)pyridin-2-yl)-2-ethyl-3-oxo-2,3-dihydro-1H-pyrazolo[3,4-d]pyrimidin-6-yl)amino)-7,8-dihydro-1,6-naphthyridine-6(5H)-carboxylate (50 mg, 15.82%) as brown solid.

LCMS: 545.4 [M+1]$^+$

763

Step-2: Synthesis of 1-(6-(tert-butyl)pyridin-2-yl)-2-ethyl-6-((5,6,7,8-tetrahydro-1,6-naphthyridin-3-yl)amino)-1,2-dihydro-3H-pyrazolo[3,4-d]pyrimidin-3-one trihydrochloride tert-butyl 3-((1-(6-(tert-butyl)pyridin-2-yl)-2-ethyl-3-oxo-2,3-dihydro-1H-pyrazolo[3,4-d]pyrimidin-6-yl)amino)-7,8-dihydro-1,6-naphthyridine-6(5H)-carboxylate (45 mg, 0.0826 mmol, 1.0 eq) was dissolved in 4.0M-HCl (1 mL) and allowed to stir at rt for 1 h. After completion of reaction, the reaction mixture was filtered and dried under reduced pressure to afford the desired compound 1-(6-(tert-butyl)pyridin-2-yl)-2-ethyl-6-((5,6,7,8-tetrahydro-1,6-naphthyridin-3-yl)amino)-1,2-dihydro-3H-pyrazolo[3,4-d]pyrimidin-3-one trihydrochloride (35 mg, 87.50%) as yellow solid.

LCMS: 445.3.4 [M+1]$^+$; UPLC @ 254 nm=92.74% and @ 220 nm=95.09%.

$^1$H NMR (400 MHz, DMSO-d$_6$) δ 10.53 (brs, 1H), 9.27 (brs, 2H), 8.93 (s, 1H), 8.71 (brs, 1H), 8.17 (brs, 1H), 8.05 (t, J=7.89 Hz, 1H), 7.82 (d, J=7.89 Hz, 1H), 7.45 (d, J=7.45 Hz, 1H), 4.35 (brs, 2H), 4.08 (d, J=6.58 Hz, 2H), 3.51 (brs, 2H), 3.07 (brs, 2H), 1.32 (s, 9H), 0.98 (t, J=6.80 Hz, 3H).

Example S45. Synthesis of 1-(6-(tert-butyl)pyridin-2-yl)-2-ethyl-6-(isoindolin-5-ylamino)-1,2-dihydro-3H-pyrazolo[3,4-d]pyrimidin-3-one dihydrochloride (Compound No. 1.142)

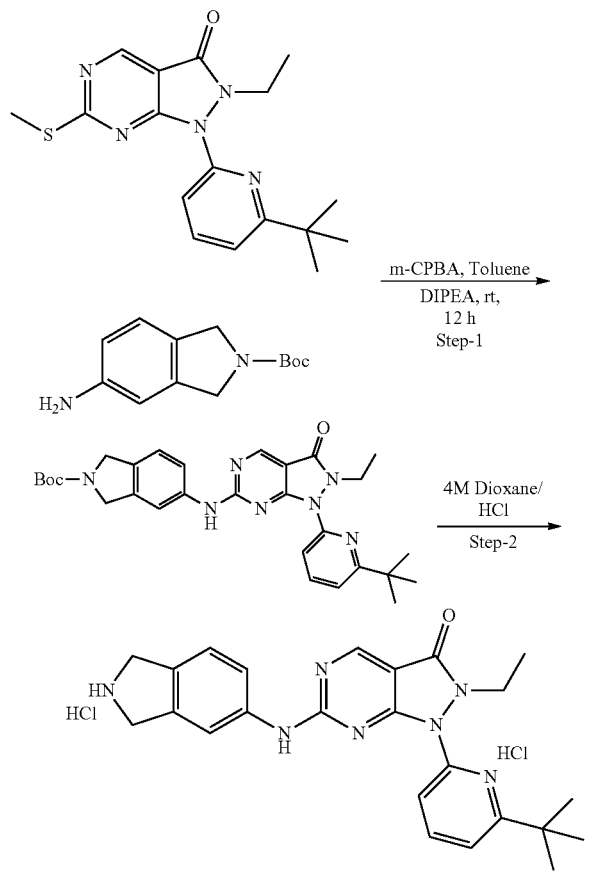

764

Step-1: Synthesis of tert-butyl 5-((1-(6-(tert-butyl)pyridin-2-yl)-2-ethyl-3-oxo-2,3-dihydro-1H-pyrazolo[3,4-d]pyrimidin-6-yl)amino)isoindoline-2-carboxylate To a stirred solution of 1-(6-(tert-butyl)pyridin-2-yl)-2-ethyl-6-(methylthio)-1,2-dihydro-3H-indazol-3-one (200 mg, 0.582 mmol, 1.0 eq) in (2.0 mL) of toluene was added m-CPBA (287 mg, 1.164 mmol, 2.0 eq) and allowed to stir at rt for 30 minutes. tert-butyl 5-aminoisoindoline-2-carboxylate (164 mg, 0.698 mmol, 1.2 eq) and DIPEA (0.40 mL, 2.328 mmol, 4.0 eq) were added and allowed to stir at rt for overnight. The formation of precipitates were observed which were filtered to afford the desired compound tert-butyl 5-((1-(6-(tert-butyl)pyridin-2-yl)-2-ethyl-3-oxo-2,3-dihydro-1H-pyrazolo[3,4-d]pyrimidin-6-yl)amino)isoindoline-2-carboxylate (135 mg, 43.83%) as brown solid.

LCMS: 530.4 [M+1]$^+$

Step-2: Synthesis of 1-(6-(tert-butyl)pyridin-2-yl)-2-ethyl-6-(isoindolin-5-ylamino)-1,2-dihydro-3H-pyrazolo[3,4-d]pyrimidin-3-one dihydrochloride tert-butyl 5-((1-(6-(tert-butyl)pyridin-2-yl)-2-ethyl-3-oxo-2,3-dihydro-1H-pyrazolo[3,4-d]pyrimidin-6-yl)amino)isoindoline-2-carboxylate (130 mg, 1.321 mmol, 1.0 eq) was dissolved in 4.0M-HCl (1.5 mL) and allowed to stir at rt for 1 h. After completion of reaction, the reaction mixture was filtered and dried under reduced pressure to afford the desired compound 1-(6-(tert-butyl)pyridin-2-yl)-2-ethyl-6-(isoindolin-5-ylamino)-1,2-dihydro-3H-pyrazolo[3,4-d]pyrimidin-3-one dihydrochloride (105 mg, 94.92%) as yellow solid.

LCMS: 430.4 [M+1]$^+$; UPLC @ 254 nm=95.23% and @ 220 nm=96.75%.

$^1$H NMR (400 MHz, DMSO-d$_6$) δ 10.42 (brs, 1H), 9.91 (brs, 2H), 8.89 (s, 1H), 8.05 (t, J=7.45 Hz, 1H), 7.89 (brs, 1H), 7.81 (d, J=7.89 Hz, 1H), 7.62 (d, J=7.89 Hz, 1H), 7.43 (d, J=7.45 Hz, 1H), 7.35 (d, J=7.89 Hz, 1H), 4.51 (brs, 2H), 4.45 (brs, 3H), 4.08 (d, J=6.58 Hz, 3H), 1.23-1.38 (m, 9H), 0.98 (t, J=6.58 Hz, 3H).

Example S46. Synthesis of 1-(6-(tert-butyl)pyridin-2-yl)-2-cyclopropyl-6-((1,2,3,4-tetrahydroisoquinolin-6-yl)amino)-1,2-dihydro-3H-pyrazolo[3,4-d]pyrimidin-3-one dihydrochloride (Compound No. 1.143)

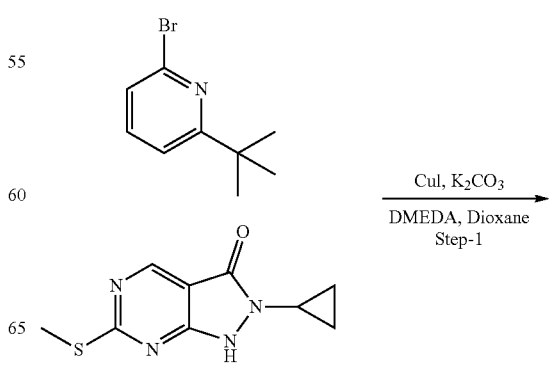

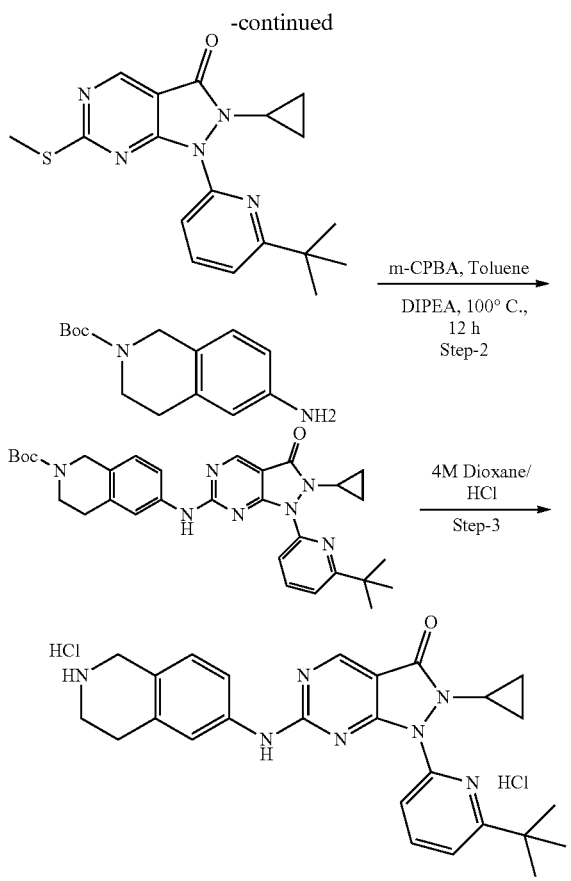

Step-1: Synthesis of 1-(6-(tert-butyl)pyridin-2-yl)-2-cyclopropyl-6-(methylthio)-1,2-dihydro-3H-pyrazolo[3,4-d]pyrimidin-3-one To a stirred solution of 2-cyclopropyl-6-(methylthio)-1,2-dihydro-3H-pyrazolo[3,4-d]pyrimidin-3-one (500 mg, 2.242 mmol, 1.0 eq) and 2-bromo-6-(tert-butyl)pyridine (586 mg, 2.690 mmol, 1.20 eq) in (12 mL) of dioxane was added potassium carbonate (619 mg, 4.484 mmol, 2.0 eq) and the resulting mixture was purged with nitrogen for 10 min followed by addition of copper iodide (85 mg, 0.448 mmol, 0.2 eq), and N,N'-dimethylethylenediamine (DMEDA) (80 mg, 0.896 mmol, 0.4 eq) and again purged with nitrogen for 10 min, stirred at 90° C. for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-30% EtOAc in hexane] to afford the desired product, 1-(6-(tert-butyl)pyridin-2-yl)-2-cyclopropyl-6-(methylthio)-1,2-dihydro-3H-pyrazolo[3,4-d]pyrimidin-3-one (300 mg, 37.51%) as light yellow viscous.

LCMS: 356.2 [M+1]$^+$

Step-2: Synthesis of tert-butyl 6-((1-(6-(tert-butyl)pyridin-2-yl)-2-cyclopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(6-(tert-butyl)pyridin-2-yl)-2-cyclopropyl-6-(methylthio)-1,2-dihydro-3H-pyrazolo[3,4-d]pyrimidin-3-one (140 mg, 0.393 mmol, 1.0 eq) in (2.0 mL) of toluene was added m-CPBA (135 mg, 0.786 mmol, 2.0 eq) and allowed to stir at rt for 30 minutes. tert-butyl 6-amino-3,4-dihydroisoquinoline-2(1H)-carboxylate (195 mg, 0.786 mmol, 1.2 eq) and DIPEA (0.27 mL, 1.572 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((1-(6-(tert-butyl)pyridin-2-yl)-2-cyclopropyl-3-oxo-2,3-dihydro-1H-pyrazolo[3,4-d]pyrimidin-6-yl)amino)-3,4-dihydroisoquinoline-2(1H)-carboxylate (76 mg, 34.72%) as white solid.

LCMS: 556.3 [M+1]$^+$

Step-3: Synthesis of 1-(6-(tert-butyl)pyridin-2-yl)-2-cyclopropyl-6-((1,2,3,4-tetrahydroisoquinolin-6-yl)amino)-1,2-dihydro-3H-pyrazolo[3,4-d]pyrimidin-3-one dihydrochloride tert-butyl 6-((1-(6-(tert-butyl)pyridin-2-yl)-2-cyclopropyl-3-oxo-2,3-dihydro-1H-pyrazolo[3,4-d]pyrimidin-6-yl)amino)-3,4-dihydroisoquinoline-2(1H)-carboxylate (76 mg, 0.136 mmol, 1.0 eq) was dissolved in dioxane (1 mL), followed by dropwise addition of 4.0M-HCl (2 mL) and allowed to stir at rt for 1 h. After completion of reaction, the reaction mixture was filtered and dried under reduced pressure to afford the desired compound, 1-(6-(tert-butyl)pyridin-2-yl)-2-cyclopropyl-6-((1,2,3,4-tetrahydroisoquinolin-6-yl)amino)-1,2-dihydro-3H-pyrazolo[3,4-d]pyrimidin-3-one dihydrochloride (52 mg, 71.65%) as light yellow solid.

LCMS: 456.3 [M+1]$^+$; UPLC @ 254 nm=96.94% and @ 220 nm=96.60%.

$^1$H NMR (400 MHz, DMSO-d$_6$): δ 10.25 (brs, 1H), 9.24 (brs, 2H), 8.81 (s, 1H), 8.03 (t, J=7.89 Hz, 1H), 7.70-7.79 (m, 2H), 7.40-7.51 (m, 2H), 7.16 (d, J=8.33 Hz, 1H), 4.21 (brs, 2H), 3.37 (brs, 2H), 3.23 (brs, 2H), 2.95-3.04 (m, 2H), 1.32 (s, 9H), 0.82 (brs, 4H).

Example S47. Synthesis of 1-(6-(tert-butyl)pyridin-2-yl)-2-isopropyl-6-((1,2,3,4-tetrahydroisoquinolin-7-yl)amino)-1,2-dihydro-3H-pyrazolo[3,4-d]pyrimidin-3-one dihydrochloride (Compound No. 1.144)

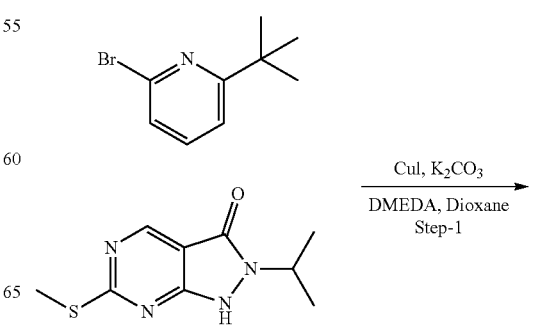

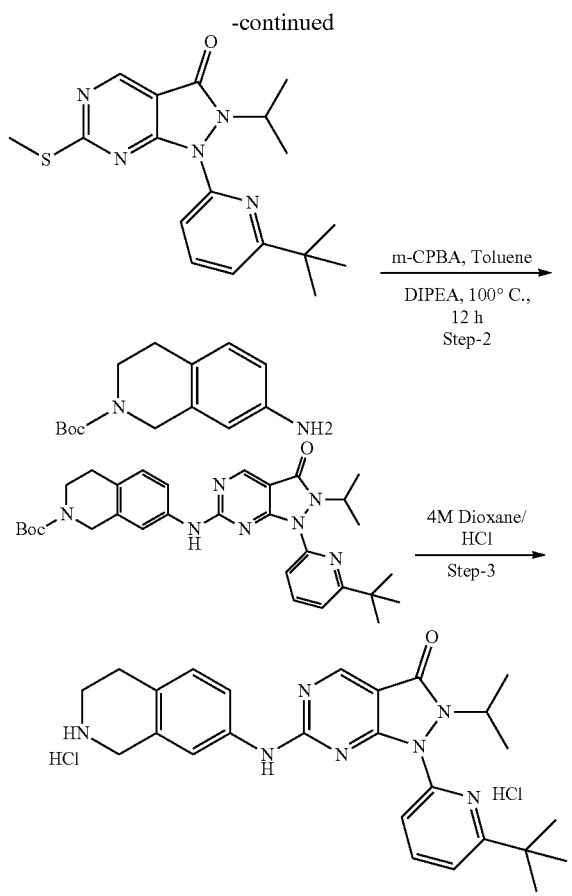

Step-1: Synthesis of 1-(6-(tert-butyl)pyridin-2-yl)-2-isopropyl-6-(methylthio)-1,2-dihydro-3H-pyrazolo[3,4-d]pyrimidin-3-one To a stirred solution of 2-isopropyl-6-(methylthio)-1,2-dihydro-3H-pyrazolo[3,4-d]pyrimidin-3-one (400 mg, 1.78 mmol, 1.0 eq) and 2-bromo-6-(tert-butyl)pyridine (458 mg, 2.14 mmol, 1.20 eq) in (12 mL) of dioxane was added potassium carbonate (492 mg, 3.56 mmol, 2.0 eq) and the resulting mixture was purged with nitrogen for 10 min followed by addition of copper iodide (68 mg, 0.356 mmol, 0.2 eq), and N,N'-dimethylethylenediamine (DMEDA) (63 mg, 0.712 mmol, 0.4 eq) and again purged with nitrogen for 10 min, stirred at 90° C. for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-30% EtOAc in hexane] to afford the desired product, 1-(6-(tert-butyl)pyridin-2-yl)-2-isopropyl-6-(methylthio)-1,2-dihydro-3H-pyrazolo[3,4-d]pyrimidin-3-one (366 mg, 57.40%) as colorless liquid. LCMS: 358.2 [M+1]$^+$ Step-2: Synthesis of tert-butyl 7-((1-(6-(tert-butyl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(6-(tert-butyl)pyridin-2-yl)-2-isopropyl-6-(methylthio)-1,2-dihydro-3H-pyrazolo[3,4-d]pyrimidin-3-one (180 mg, 0.503 mmol, 1.0 eq) in (6.0 mL) of toluene was added m-CPBA (174 mg, 1.006 mmol, 2.0 eq) and allowed to stir at rt for 30 minutes. tert-butyl 7-amino-3,4-dihydroisoquinoline-2(1H)-carboxylate (150 mg, 0.604 mmol, 1.2 eq) and DIPEA (0.34 mL, 2.012 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 7-((1-(6-(tert-butyl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (127 mg, 45.22%) as an off white solid.

LCMS: 558.3 [M+1]$^+$

Step-3: Synthesis of 1-(6-(tert-butyl)pyridin-2-yl)-2-isopropyl-6-((1,2,3,4-tetrahydroisoquinolin-7-yl)amino)-1,2-dihydro-3H-pyrazolo[3,4-d]pyrimidin-3-one dihydrochloride tert-butyl 7-((1-(6-(tert-butyl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (127 mg, 0.227 mmol, 1.0 eq) was dissolved in dioxane (1 mL), followed by dropwise addition of 4.0M-HCl (2 mL) and allowed to stir at rt for 1 h. After completion of reaction, the reaction mixture was filtered and dried under reduced pressure to afford the desired compound, 1-(6-(tert-butyl)pyridin-2-yl)-2-isopropyl-6-((1,2,3,4-tetrahydroisoquinolin-7-yl)amino)-1,2-dihydro-3H-pyrazolo[3,4-d]pyrimidin-3-one dihydrochloride (96 mg, 79.47%) as light yellow solid.

LCMS: 458.3 [M+1]$^+$; UPLC @ 254 nm=96.17% and @ 220 nm=96.72%.

$^1$H NMR (400 MHz, DMSO-d$_6$): δ 10.31 (brs, 1H), 9.20 (brs, 2H), 8.83 (s, 1H), 8.04 (t, J=7.89 Hz, 1H), 7.76 (d, J=8.33 Hz, 1H), 7.69 (brs, 1H), 7.50 (d, J=7.89 Hz, 1H), 7.44 (d, J=7.45 Hz, 1H), 7.16 (d, J=8.33 Hz, 1H), 4.25 (brs, 2H), 4.12-4.21 (m, 1H), 3.36 (brs, 2H), 2.95 (t, J=5.70 Hz, 2H), 1.38 (d, J=6.58 Hz, 4H), 1.32 (s, 6H).

Example S48. Synthesis of 1-(6-(tert-butyl)pyridin-2-yl)-2-isopropyl-6-((1,2,3,4-tetrahydroisoquinolin-6-yl)amino)-1,2-dihydro-3H-pyrazolo[3,4-d]pyrimidin-3-one dihydrochloride (Compound No. 1.145)

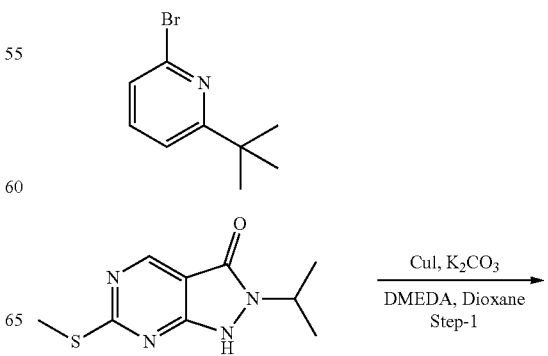

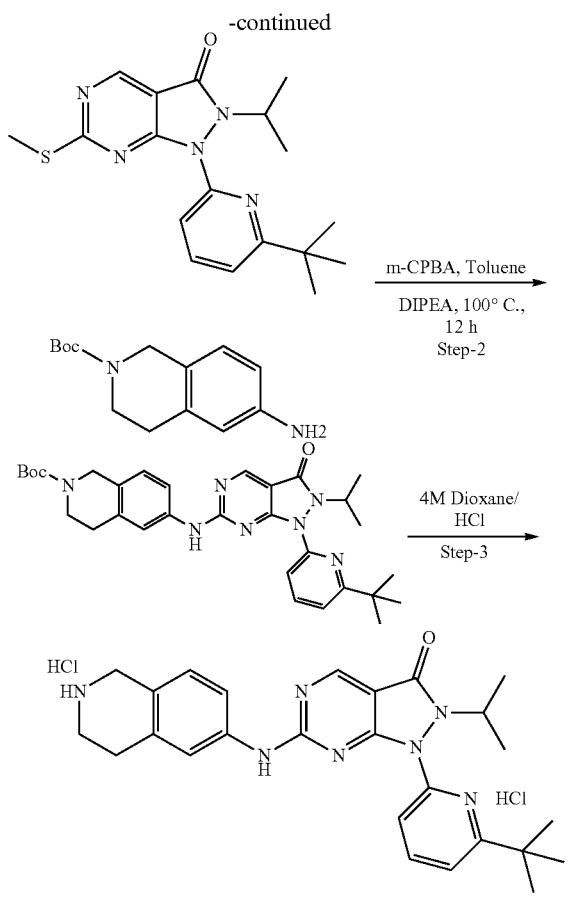

Step-1: Synthesis of 1-(6-(tert-butyl)pyridin-2-yl)-2-isopropyl-6-(methylthio)-1,2-dihydro-3H-pyrazolo[3,4-d]pyrimidin-3-one To a stirred solution of 2-isopropyl-6-(methylthio)-1,2-dihydro-3H-pyrazolo[3,4-d]pyrimidin-3-one (400 mg, 1.78 mmol, 1.0 eq) and 2-bromo-6-(tert-butyl)pyridine (458 mg, 2.14 mmol, 1.20 eq) in (12 mL) of dioxane was added potassium carbonate (492 mg, 3.56 mmol, 2.0 eq) and the resulting mixture was purged with nitrogen for 10 min followed by addition of copper iodide (68 mg, 0.356 mmol, 0.2 eq), and N,N'-dimethylethylenediamine (DMEDA) (63 mg, 0.712 mmol, 0.4 eq) and again purged with nitrogen for 10 min, stirred at 90° C. for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-30% EtOAc in hexane] to afford the desired product, 1-(6-(tert-butyl)pyridin-2-yl)-2-isopropyl-6-(methylthio)-1,2-dihydro-3H-pyrazolo[3,4-d]pyrimidin-3-one (366 mg, 57.40%) as colorless liquid.

LCMS: 358.2 [M+1]$^+$

Step-2: Synthesis of tert-butyl 6-((1-(6-(tert-butyl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(6-(tert-butyl)pyridin-2-yl)-2-isopropyl-6-(methylthio)-1,2-dihydro-3H-pyrazolo[3,4-d]pyrimidin-3-one (180 mg, 0.503 mmol, 1.0 eq) in (6.0 mL) of toluene was added m-CPBA (174 mg, 1.006 mmol, 2.0 eq) and allowed to stir at rt for 30 minutes. tert-butyl 6-amino-3,4-dihydroisoquinoline-2(1H)-carboxylate (150 mg, 0.604 mmol, 1.2 eq) and DIPEA (0.34 mL, 2.012 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((1-(6-(tert-butyl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (120 mg, 42.73%) as an off white solid.

LCMS: 558.3 [M+1]$^+$

Step-3: Synthesis of 1-(6-(tert-butyl)pyridin-2-yl)-2-isopropyl-6-((1,2,3,4-tetrahydroisoquinolin-6-yl)amino)-1,2-dihydro-3H-pyrazolo[3,4-d]pyrimidin-3-one dihydrochloride tert-butyl 7-((1-(6-(tert-butyl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (120 mg, 0.215 mmol, 1.0 eq) was dissolved in dioxane (1 mL), followed by dropwise addition of 4.0M-HCl (2 mL) and allowed to stir at rt for 1 h. After completion of reaction, the reaction mixture was filtered and dried under reduced pressure to afford the desired compound, 1-(6-(tert-butyl)pyridin-2-yl)-2-isopropyl-6-((1,2,3,4-tetrahydroisoquinolin-6-yl)amino)-1,2-dihydro-3H-pyrazolo[3,4-d]pyrimidin-3-one dihydrochloride (81 mg, 70.96%) as light yellow solid.

LCMS: 458.3 [M+1]$^+$; UPLC @ 254 nm=95.25% and @ 220 nm=97.03%.

$^1$H NMR (400 MHz, DMSO-d$_6$): δ 10.30 (brs, 1H), 9.29 (brs, 2H), 8.83 (s, 1H), 8.02 (d, J=7.89 Hz, 1H), 7.74 (d, J=7.45 Hz, 2H), 7.41-7.54 (m, 2H), 7.15 (d, J=8.33 Hz, 1H), 4.20 (brs, 3H), 3.37 (brs, 2H), 2.98 (brs, 2H), 1.38 (d, J=6.14 Hz, 4H), 1.32 (s, 6H)

Example S49. Synthesis of 2-cyclopropyl-1-(6-(2-fluoropropan-2-yl)pyridin-2-yl)-6-((1,2,3,4-tetrahydroisoquinolin-6-yl)amino)-1,2-dihydro-3H-pyrazolo[3,4-d]pyrimidin-3-one (Compound No. 1.146)

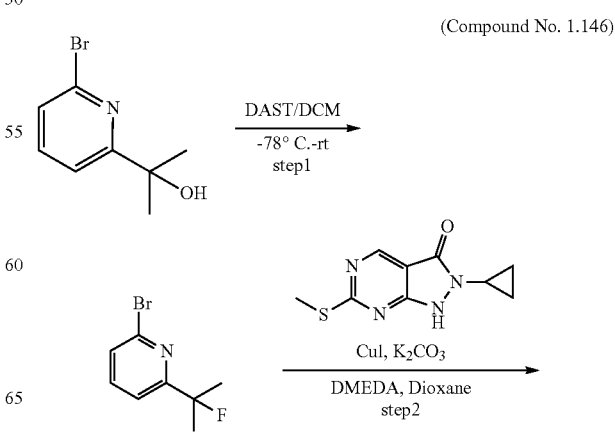

-continued

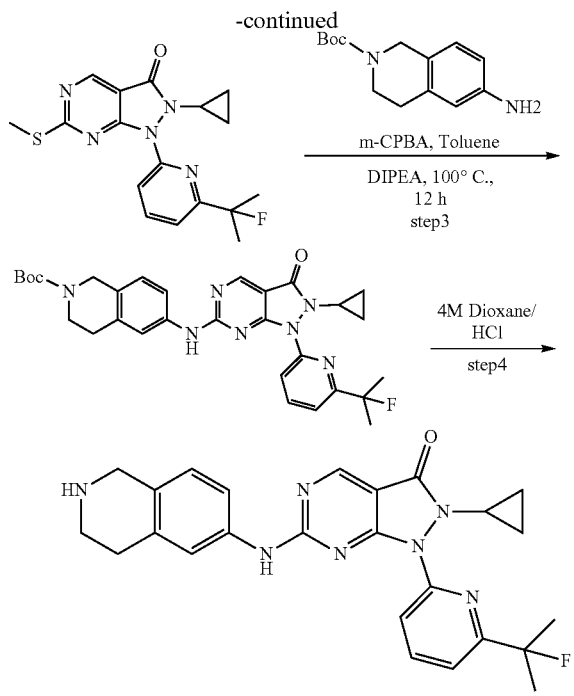

Step-1: Synthesis of 2-bromo-6-(2-fluoropropan-2-yl)pyridine

To a stirred solution of 2-(6-bromo-pyridine-2-yl)-propane-2-ol (0.500 g, 2.313 mmol, 1.0 eq) in DCM (10 mL), DAST (0.36 mL, 2.545 mmol, 1.1 eq) was added at −78° C. The reaction mixture was stirred at rt for 12 h. After completion of reaction, the reaction mixture was quenched with saturated sodium bicarbonate solution and was extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-10% EtOAc in hexane] to afford the desired compound, tert-butyl 6-((2-cyclopropyl-1-(6-(2-fluoropropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate (355 mg, 70.43%) as colorless liquid.

LCMS: 217.99 [M+1]$^+$

Step-2: Synthesis of 2-cyclopropyl-1-(6-(2-fluoropropan-2-yl)pyridin-2-yl)-6-(methylthio)-1,2-dihydro-3H-pyrazolo[3,4-d]pyrimidin-3-on To a stirred solution of 2-isopropyl-6-(methylthio)-1,2-dihydro-3H-pyrazolo[3,4-d]pyrimidin-3-one (300 mg, 1.345 mmol, 1.0 eq) and 2-bromo-6-(2-fluoropropan-2-yl)pyridine (351 mg, 1.614 mmol, 1.20 eq) in (10 mL) of dioxane was added potassium carbonate (371 mg, 2.690 mmol, 2.0 eq) and the resulting mixture was purged with nitrogen for 10 min, followed by addition of copper iodide (51 mg, 0.269 mmol, 0.2 eq), and N,N'-dimethylethylenediamine (DMEDA) (47 mg, 0.538 mmol, 0.4 eq) and again purged with nitrogen for 10 min, stirred at 90° C. for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-30% EtOAc in hexane] to afford the desired product, 2-cyclopropyl-1-(6-(2-fluoropropan-2-yl)pyridin-2-yl)-6-(methylthio)-1,2-dihydro-3H-pyrazolo[3,4-d]pyrimidin-3-one (260 mg, 52.63%) as an off white solid.

LCMS: (M+1): 359.12 [M+1]$^+$

Step-3: Synthesis of tert-butyl 6-((2-cyclopropyl-1-(6-(2-fluoropropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate To a stirred solution of 1-(6-(tert-butyl)pyridin-2-yl)-2-cyclopropyl-6-(methylthio)-1,2-dihydro-3H-pyrazolo[3,4-d]pyrimidin-3-one (260 mg, 0.722 mmol, 1.0 eq) in (5.0 mL) of toluene was added m-CPBA (249 mg, 1.444 mmol, 2.0 eq) and allowed to stir at rt for 30 minutes. tert-butyl 6-amino-3,4-dihydroisoquinoline-2(1H)-carboxylate (358 mg, 1.444 mmol, 2.0 eq) and DIPEA (0.5 mL, 2.888 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((2-cyclopropyl-1-(6-(2-fluoropropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate (100 mg, 24.75%) as an off white solid.

LCMS: 560.27 [M+1]$^+$

Step-4: Synthesis of 2-cyclopropyl-1-(6-(2-fluoropropan-2-yl)pyridin-2-yl)-6-((1,2,3,4-tetrahydroisoquinolin-6-yl)amino)-1,2-dihydro-3H-pyrazolo[3,4-d]pyrimidin-3-one tert-butyl 6-((1-(6-(tert-butyl)pyridin-2-yl)-2-cyclopropyl-3-oxo-2,3-dihydro-1H-pyrazolo[3,4-d]pyrimidin-6-yl)amino)-3,4-dihydroisoquinoline-2(1H)-carboxylate (100 mg, 0.178 mmol, 1.0 eq) was dissolved in dioxane (1 mL), followed by dropwise addition of 4.0M-HCl (2 mL) and allowed to stir at rt for 1 h. After completion of reaction, the reaction mixture was filtered and dried under reduced pressure to afford the desired compound, 2-cyclopropyl-1-(6-(2-fluoropropan-2-yl)pyridin-2-yl)-6-((1,2,3,4-tetrahydroisoquinolin-6-yl)amino)-1,2-dihydro-3H-pyrazolo[3,4-d]pyrimidin-3-one (25 mg, 30.16%) as light yellow solid.

LCMS: 460.22 [M+1]$^+$; UPLC @ 254 nm=96.72% and @ 220 nm=98.03%.

$^1$H NMR (400 MHz, DMSO-d$_6$): δ 10.22 (brs, 1H), 8.81 (s, 1H), 8.10-8.17 (m, 1H), 7.88 (d, J=8.77 Hz, 2H), 7.69 (brs, 1H), 7.55 (brs, 1H), 7.43 (brs, 1H), 7.10 (brs, 1H), 4.07 (brs, 2H), 3.24 (brs, 2H), 2.88 (brs, 2H), 1.70 (s, 3H), 1.64 (s, 3H), 0.82 (d, J=5.26 Hz, 4H).

Example S50. Synthesis of 1-(6-(tert-butyl)pyridin-2-yl)-2-cyclopropyl-6-((1,2,3,4-tetrahydroisoquinolin-7-yl)amino)-1,2-dihydro-3H-pyrazolo[3,4-d]pyrimidin-3-one dihydrochloride (Compound No. 1.147)

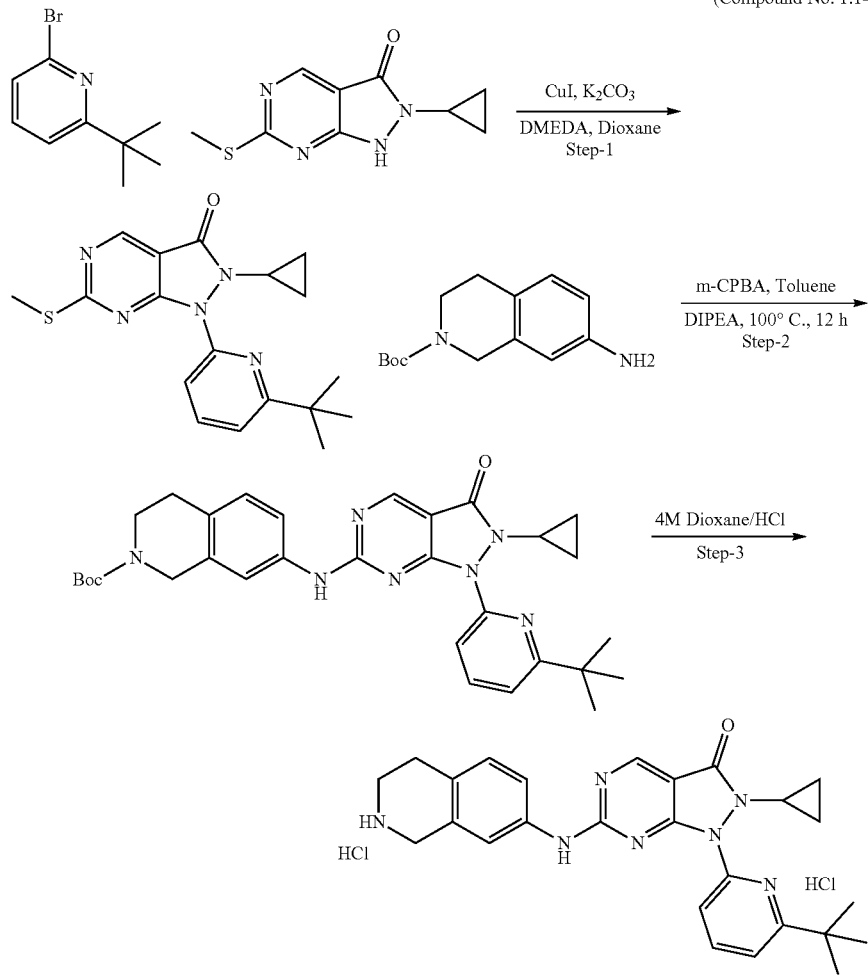

Step-1: Synthesis of 1-(6-(tert-butyl)pyridin-2-yl)-2-cyclopropyl-6-(methylthio)-1,2-dihydro-3H-pyrazolo[3,4-d]pyrimidin-3-one To a stirred solution of 2-cyclopropyl-6-(methylthio)-1,2-dihydro-3H-pyrazolo[3,4-d]pyrimidin-3-one (500 mg, 2.242 mmol, 1.0 eq) and 2-bromo-6-(tert-butyl)pyridine (586 mg, 2.690 mmol, 1.20 eq) in (12 mL) of dioxane was added potassium carbonate (619 mg, 4.484 mmol, 2.0 eq) and the resulting mixture was purged with nitrogen for 10 min followed by addition of copper iodide (85 mg, 0.448 mmol, 0.2 eq), and N,N'-dimethylethylenediamine (DMEDA) (80 mg, 0.896 mmol, 0.4 eq) and again purged with nitrogen for 10 min, stirred at 90° C. for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-30% EtOAc in hexane] to afford the desired product, 1-(6-(tert-butyl)pyridin-2-yl)-2-cyclopropyl-6-(methylthio)-1,2-dihydro-3H-pyrazolo[3,4-d]pyrimidin-3-one (300 mg, 37.51%) as light yellow viscous.

LCMS: 356.2 [M+1]$^+$

Step-2: Synthesis of tert-butyl 7-((1-(6-(tert-butyl)pyridin-2-yl)-2-cyclopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(6-(tert-butyl)pyridin-2-yl)-2-cyclopropyl-6-(methylthio)-1,2-dihydro-3H-pyrazolo[3,4-d]pyrimidin-3-one (140 mg, 0.393 mmol, 1.0 eq) in (2.0 mL) of toluene was added m-CPBA (135 mg, 0.786 mmol, 2.0 eq) and allowed to stir at rt for 30 minutes. tert-butyl 7-amino-3,4-dihydroisoquinoline-2(1H)-carboxylate (195 mg, 0.786 mmol, 1.2 eq) and DIPEA (0.27 mL, 1.572 mmol, 4.0 eq) were added and allowed to stir at rt for overnight.

After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 7-((1-(6-(tert-butyl)pyridin-2-yl)-2-cyclopropyl-3-oxo-2,3-dihydro-1H-pyrazolo[3,4-d]pyrimidin-6-yl)amino)-3,4-dihydroisoquinoline-2(1H)-carboxylate (81 mg, 37.01%) as white solid.

LCMS: 556.3 [M+1]+

Step-3: Synthesis of 1-(6-(tert-butyl)pyridin-2-yl)-2-cyclopropyl-6-((1,2,3,4-tetrahydroisoquinolin-7-yl)amino)-1,2-dihydro-3H-pyrazolo[3,4-d]pyrimidin-3-one dihydrochloride tert-butyl 7-((1-(6-(tert-butyl)pyridin-2-yl)-2-cyclopropyl-3-oxo-2,3-dihydro-1H-pyrazolo[3,4-d]pyrimidin-6-yl)amino)-3,4-dihydroisoquinoline-2(1H)-carboxylate (81 mg, 0.145 mmol, 1.0 eq) was dissolved in dioxane (1 mL), followed by dropwise addition of 4.0M-HCl (2 mL) and allowed to stir at rt for 1 h. After completion of reaction, the reaction mixture was filtered and dried under reduced pressure to afford the desired compound, 1-(6-(tert-butyl)pyridin-2-yl)-2-cyclopropyl-6-((1,2,3,4-tetrahydroisoquinolin-7-yl)amino)-1,2-dihydro-3H-pyrazolo[3,4-d]pyrimidin-3-one dihydrochloride (58 mg, 75.29%) as light yellow solid.

LCMS: 456.3 [M+1]+; UPLC @ 254 nm=96.46% and @ 220 nm=97.00%.

1H NMR (400 MHz, DMSO-d6): δ 10.25 (brs, 1H), 9.27 (brs, 3H), 8.81 (s, 1H), 8.04 (t, J=7.89 Hz, 1H), 7.67-7.79 (m, 3H), 7.51 (d, J=10.09 Hz, 1H), 7.43 (d, J=7.89 Hz, 1H), 7.17 (d, J=8.77 Hz, 1H), 4.25 (brs, 2H), 3.36 (brs, 2H), 3.23 (brs, 1H), 2.95 (t, J=5.70 Hz, 3H), 1.33 (s, 9H), 0.82 (brs, 4H).

Example S51. Synthesis of 1-(6-cyclopropylpyridin-2-yl)-2-isopropyl-6-((1,2,3,4-tetrahydroisoquinolin-7-yl)amino)-1,2-dihydro-3H-pyrazolo[3,4-d]pyrimidin-3-one dihydrochloride (Compound No. 1.148)

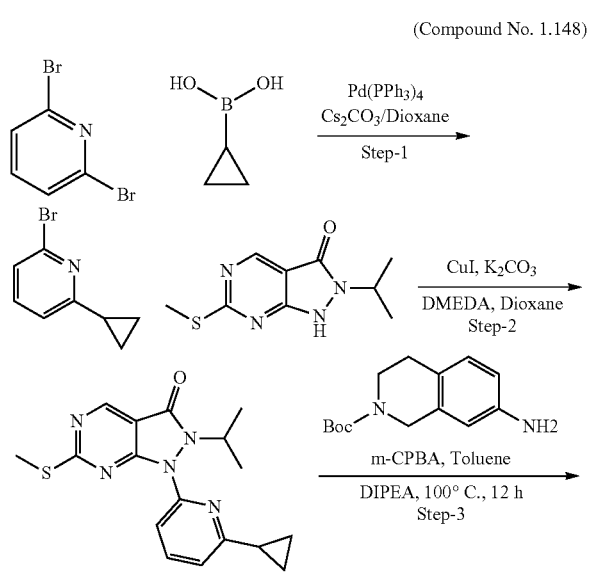

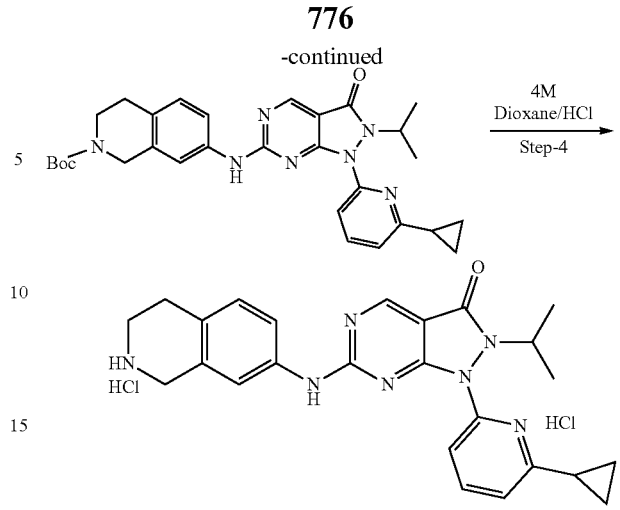

Step-1: Synthesis of 2-bromo-6-cyclopropylpyridine

To a stirred solution of 2,6-dibromopyridine (1.0 g, 4.221 mmol, 1.0 eq) in (30.0 mL) of dioxane was added Cs2CO3 (8.25 g, 25.329 mmol, 3.0 eq) at rt. The resulting mixture was purged with nitrogen for 10 min, followed by addition of Pd(PPh3)4 (487 mg, 0.422 mmol, 0.05 eq) and again purged with nitrogen for 10 min. The reaction mixture was stirred at 100° C. for 2 h. The progress of reaction was monitored by LCMS. The reaction mixture was diluted with water (50 mL), extracted with EtOAc (2×50 mL), the combined organic layers were washed with water (50 mL), dried over Na2SO4, concentrated and purified by combi flash chromatography [silica gel 100-200 mesh, elution 0-2% EtOAc in hexane] to afford the desired compound, 2-bromo-6-cyclopropylpyridine (500 mg, 29.92%) as colorless liquid.

LCMS: 198.9 [M+1]+

Step-2: Synthesis of 1-(6-cyclopropylpyridin-2-yl)-2-isopropyl-6-(methylthio)-1,2-dihydro-3H-pyrazolo[3,4-d]pyrimidin-3-one To a stirred solution of 2-isopropyl-6-(methylthio)-1,2-dihydro-3H-pyrazolo[3,4-d]pyrimidin-3-one (400 mg, 1.783 mmol, 1.0 eq) and 2-bromo-6-cyclopropylpyridine (423 mg, 2.140 mmol, 1.20 eq) in (20 mL) of dioxane was added potassium carbonate (493 mg, 3.566 mmol, 2.0 eq) and the resulting mixture was purged with nitrogen for 10 min followed by addition of copper iodide (68 mg, 0.356 mmol, 0.2 eq), and N,N'-dimethylethylenediamine (DMEDA) (63 mg, 0.713 mmol, 0.4 eq) and again purged with nitrogen for 10 min, stirred at 90° C. for overnight. After completion of reaction, the reaction mixture was diluted with water and extracted with EtOAc (50 mL×2). Combined organic layer was washed with water (50 mL) brine solution (50 mL), dried over anhydrous sodium sulfate and concentrated under reduced pressure to afford crude product, which was purified by flash chromatography [silica gel 100-200 mesh; elution 0-30% EtOAc in hexane] to afford the desired compound 1-(6-cyclopropylpyridin-2-yl)-2-isopropyl-6-(methylthio)-1,2-dihydro-3H-pyrazolo[3,4-d]pyrimidin-3-one (500 mg, 82.10%) as light yellow viscous.

LCMS: 342.2 [M+1]+

Step-3: Synthesis of tert-butyl 7-((1-(6-cyclopropylpyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(6-cyclopropylpyridin-2-yl)-2-isopropyl-6-(methylthio)-1,2-dihydro-3H-pyrazolo[3,4-d]pyrimidin-3-one (200 mg, 0.586 mmol, 1.0 eq) in (2.0 mL) of toluene was added m-CPBA (289 mg, 1.172 mmol, 2.0 eq) and allowed to stir at rt for 30 minutes. tert-butyl 7-amino-3,4-dihydroisoquinoline-2(1H)-carboxylate (175 mg, 0.702 mmol, 1.2 eq) and DIPEA (0.40 mL, 2.344 mmol, 4.0 eq) were added and allowed to stir at rt for overnight. After completion of reaction, the reaction mixture was diluted with water and extracted with EtOAc (50 mL×2). Combined organic layer was washed with water (50 mL) brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound tert-butyl 7-((1-(6-cyclopropylpyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (170 mg, 53.63%) as white solid.

LCMS: 542.5 [M+1]$^+$

Step-4: Synthesis of 1-(6-cyclopropylpyridin-2-yl)-2-isopropyl-6-((1,2,3,4-tetrahydroisoquinolin-7-yl)amino)-1,2-dihydro-3H-pyrazolo[3,4-d]pyrimidin-3-one dihydrochloride tert-butyl 7-((1-(6-cyclopropylpyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (160 mg, 0.295 mmol, 1.0 eq) was dissolved in 4.0M-HCl (2 mL) and allowed to stir at rt for 1 h. After completion of reaction, the reaction mixture was filtered and dried under reduced pressure to afford the desired compound 1-(6-cyclopropylpyridin-2-yl)-2-isopropyl-6-((1,2,3,4-tetrahydroisoquinolin-7-yl)amino)-1,2-dihydro-3H-pyrazolo[3,4-d]pyrimidin-3-one dihydrochloride (140 mg, 92.71%) as yellow solid.

LCMS: 442.3 [M+1]$^+$; UPLC @ 254 nm=94.55% and @ 220 nm=97.17%.

$^1$H NMR (400 MHz, DMSO-d$_6$) δ 10.30 (brs, 1H), 9.44 (brs, 2H), 8.81 (s, 1H), 7.95 (t, J=7.67 Hz, 1H), 7.68 (brs, 1H), 7.63 (d, J=7.89 Hz, 1H), 7.49 (d, J=6.58 Hz, 1H), 7.35 (d, J=7.45 Hz, 1H), 7.15 (d, J=8.33 Hz, 1H), 4.22 (brs, 2H), 4.10 (td, J=6.63, 13.48 Hz, 1H), 3.35 (brs, 2H), 2.95 (t, J=5.70 Hz, 2H), 2.17 (dt, J=4.17, 8.44 Hz, 1H), 1.34 (d, J=7.02 Hz, 6H), 0.95-1.03 (m, 2H), 0.87-0.95 (m, 2H).

Example S52. Synthesis of 1-(6-cyclopropylpyridin-2-yl)-2-isopropyl-6-((1,2,3,4-tetrahydroisoquinolin-6-yl)amino)-1,2-dihydro-3H-pyrazolo[3,4-d]pyrimidin-3-one dihydrochloride (Compound No. 1.149)

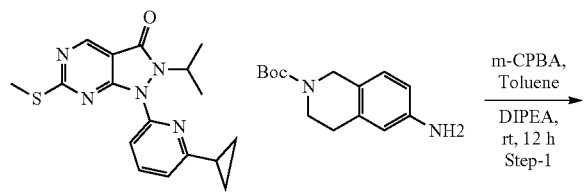

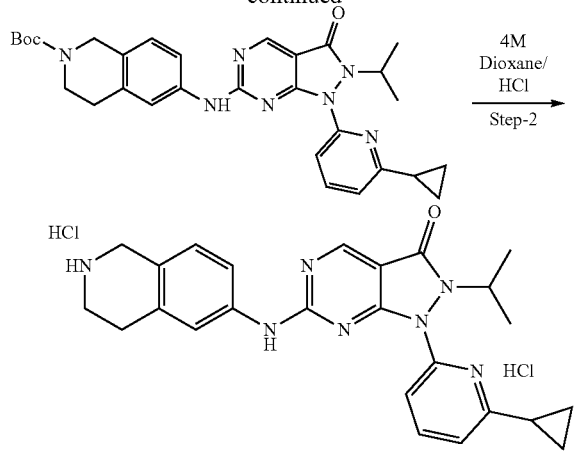

Step-1: Synthesis of tert-butyl 6-((1-(6-cyclopropylpyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(6-cyclopropylpyridin-2-yl)-2-isopropyl-6-(methylthio)-1,2-dihydro-3H-pyrazolo[3,4-d]pyrimidin-3-one (200 mg, 0.586 mmol, 1.0 eq) in (2.0 mL) of toluene was added m-CPBA (289 mg, 1.172 mmol, 2.0 eq) and allowed to stir at rt for 30 minutes. tert-butyl 6-amino-3,4-dihydroisoquinoline-2(1H)-carboxylate (175 mg, 0.702 mmol, 1.2 eq) and DIPEA (0.40 mL, 2.344 mmol, 4.0 eq) were added and allowed to stir at rt for overnight. After completion of reaction, the reaction mixture was diluted with water and extracted with EtOAc (50 mL×2). Combined organic layer was washed with water (50 mL) brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound tert-butyl 6-((1-(6-cyclopropylpyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (150 mg, 47.31%) as white solid.

LCMS: 542.5 [M+1]$^+$

Step-2: Synthesis of 1-(6-cyclopropylpyridin-2-yl)-2-isopropyl-6-((1,2,3,4-tetrahydroisoquinolin-6-yl)amino)-1,2-dihydro-3H-pyrazolo[3,4-d]pyrimidin-3-one dihydrochloride tert-butyl 6-((1-(6-cyclopropylpyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (150 mg, 0.276 mmol, 1.0 eq) was dissolved in 4.0M-HCl (2 mL) and allowed to stir at rt for 1 h. After completion of reaction, the reaction mixture was filtered and dried under reduced pressure to afford the desired compound 1-(6-cyclopropylpyridin-2-yl)-2-isopropyl-6-((1,2,3,4-tetrahydroisoquinolin-6-yl)amino)-1,2-dihydro-3H-pyrazolo[3,4-d]pyrimidin-3-one dihydrochloride (110 mg, 77.46%) as yellow solid.

LCMS: 442.3 [M+1]$^+$; UPLC @ 254 nm=95.97% and @ 220 nm=94.33%.

$^1$H NMR (400 MHz, DMSO-d$_6$) δ 10.28 (brs, 1H), 9.33 (brs, 2H), 8.82 (s, 1H), 7.93 (t, J=7.67 Hz, 1H), 7.72 (brs, 1H), 7.61 (d, J=7.89 Hz, 1H), 7.48 (d, J=7.45 Hz, 1H), 7.35

(d, J=7.45 Hz, 1H), 7.14 (d, J=8.33 Hz, 1H), 4.20 (brs, 3H), 3.37 (brs, 3H), 2.93-3.02 (m, 2H), 2.12-2.22 (m, 1H), 1.34 (d, J=6.58 Hz, 6H), 0.99 (d, J=7.89 Hz, 2H), 0.92 (brs, 2H).

Example S53. Synthesis of 1-(6-tert-butylpyridin-2-yl)-6-(1,2,3,4-tetrahydroisoquinolin-7-ylamino)-2-(1,1,1-trifluoropropan-2-yl)-1H-pyrazolo[3,4-d]pyrimidin-3(2H)-one hydrochloride (Compound No. 1.150)

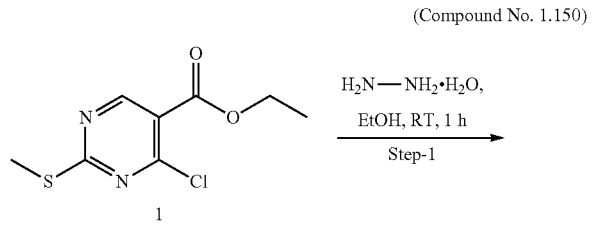

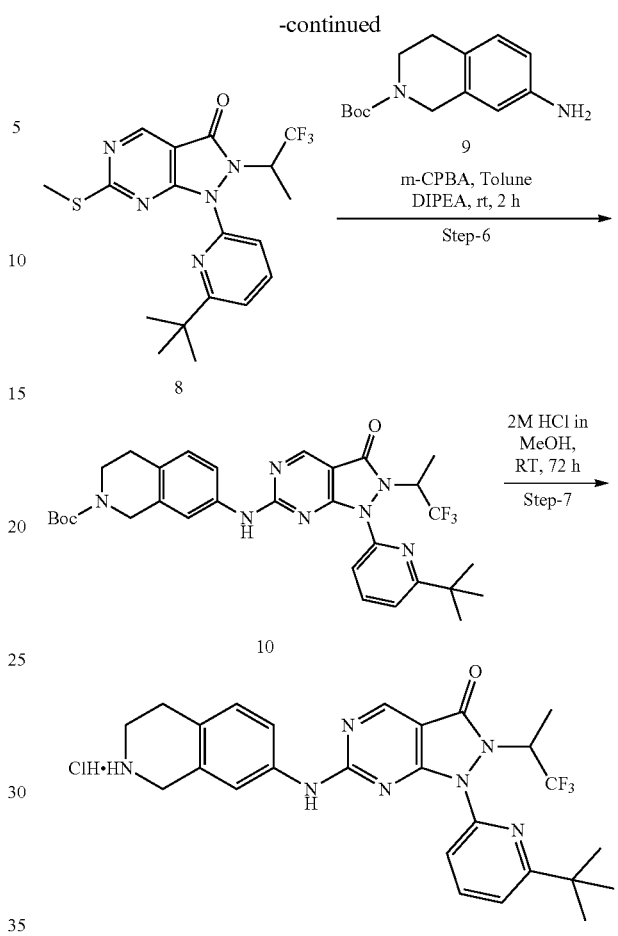

Step-1: Synthesis of ethyl 4-hydrazinyl-2-(methylthio)pyrimidine-5-carboxylate

To a stirred solution of hydrazine hydrate (3.5 mL, 107.44 mmol, 5 eq) in EtOH (50 mL) was added the solution of ethyl 4-chloro-2-(methylthio)pyrimidine-5-carboxylate (5 g, 21.488 mmol, 1 eq) in EtOH (100 mL) at 0° C. The resulting mixture was stirred at RT for 1 h. The progress of reaction was monitored by TLC. The reaction mixture was diluted with water (100 mL), extracted with EtOAc (2×200 mL). The combined organic layers were washed with water (100 mL), with brine (100 mL), dried over $Na_2SO_4$, concentrated under reduced pressure to afford ethyl 4-hydrazinyl-2-(methylthio)pyrimidine-5-carboxylate (4.21 g, 85.71%) as an off white solid.

LCMS: 229 [M+1]$^+$

Step-2: Synthesis of (E)-ethyl 2-(methylthio)-4-(2-(1,1,1-trifluoropropan-2-ylidene)hydrazinyl)pyrimidine-5-carboxylate To a stirred solution of ethyl 4-hydrazinyl-2-(methylthio)pyrimidine-5-carboxylate (4.2 g, 21.01 mmol, 1 eq) in EtOH (10 mL) was added 1,1,1-trifluoropropan-2-one (2.35 g, 21.02 mmol, 1 eq) at RT. The resulting mixture was heated at 50° C. for 2 h. The progress of reaction was monitored by TLC. The reaction mixture was diluted with water (100 mL), extracted with EtOAc (2×200 mL). The combined organic layers were washed with water (100 mL), with brine (100 mL), dried over $Na_2SO_4$, concentrated under reduced pressure to afford (E)-ethyl 2-(methylthio)-4-(2-(1,1,1-trifluoropropan-2-ylidene)hydrazinyl)pyrimidine-5-carboxylate (3.5 g, 59.32%) as an off-white solid.

LCMS: 323 [M+1]+

Step-3: Synthesis of ethyl 2-(methylthio)-4-(2-(1,1,1-trifluoropropan-2-yl)hydrazinyl) pyrimidine-5-carboxylate To a stirred solution of (E)-ethyl 2-(methylthio)-4-(2-(1,1,1-trifluoropropan-2-ylidene)hydrazinyl)pyrimidine-5-carboxylate (2.2 g, 6.825 mmol, 1 eq) in THF (50 mL) was portion wise added LiBH$_4$ (0.178 g, 8.19 mmol, 1.2 eq) at −30° C. The resulting mixture was warmed at 0° C. for 20 min. The progress of reaction was monitored by TLC. The reaction mixture was diluted with water (100 mL), extracted with EtOAc (2×200 mL). The combined organic layers were washed with water (100 mL), with brine (100 mL), dried over Na$_2$SO$_4$, concentrated under reduced pressure to afford crude which was purified using combi flash chromatography (Teledyne Isco Rf+); compound eluting 30% EtOAc/Hexane to afford ethyl 2-(methylthio)-4-(2-(1,1,1-trifluoropropan-2-yl)hydrazinyl) pyrimidine-5-carboxylate (0.28 g, 12.27%) as an off-white solid.

LCMS: 325 [M+1]+

Step-4: Synthesis of 6-(methylthio)-2-(1,1,1-trifluoropropan-2-yl)-1H-pyrazolo[3,4-d]pyrimidin-3(2H)-one To a stirred solution of ethyl 2-(methylthio)-4-(2-(1,1,1-trifluoropropan-2-yl)hydrazinyl) pyrimidine-5-carboxylate (0.28 g, 0.864 mmol, 1 eq) in EtOH (5 mL) was portion wise added NaOEt (0.235 g, 3.456 mmol, 4 eq) at RT. The resulting mixture was heated at 50° C. for 16 h. The progress of reaction was monitored by TLC. The reaction mixture was diluted with water (50 mL), extracted with EtOAc (2×75 mL). The combined organic layers were washed with water (50 mL), with brine (50 mL), dried over Na$_2$SO$_4$, concentrated under reduced pressure to afford crude which was purified using combi flash chromatography (Teledyne Isco Rf+); compound eluting 20% MeOH/DCM to afford 6-(methylthio)-2-(1,1,1-trifluoropropan-2-yl)-1H-pyrazolo[3,4-d]pyrimidin-3(2H)-one (0.125 g, 52.08%) as an off-white solid.

LCMS: 279 [M+1]+

Step-5: Synthesis of 1-(6-tert-butylpyridin-2-yl)-6-(methylthio)-2-(1,1,1-trifluoropropan-2-yl)-1H-pyrazolo[3,4-d]pyrimidin-3(2H)-one To a stirred solution of 6-(methylthio)-2-(1,1,1-trifluoropropan-2-yl)-1H-pyrazolo[3,4-d]pyrimidin-3(2H)-one (100 mg, 0.359 mmol, 1.0 eq) and 2-bromo-6-tert-butylpyridine (92.33 mg, 0.431 mmol, 1.2 eq) in 1,4 dioxane (5 mL) was added potassium carbonate (99.2 mg, 0.718 mmol, 2.0 eq) and the resulting mixture was purged with nitrogen for 30 min followed by addition of copper iodide (13.67 mg, 0.0718 mmol, 0.2 eq), and N,N'-dimethylethylenediamine (DMEDA) (12.65 mg, 0.143 mmol, 0.4 eq) and again purged with nitrogen for 10 min. The resultant mixture was heated at 100° C. for 16 h. The reaction was monitored by TLC. After completion of reaction, the reaction mixture was diluted with water and extracted with EtOAc (50 mL×2). Combined organic layer was washed with water (50 mL) brine solution (50 mL), dried over anhydrous Na$_2$SO$_4$ and concentrated under reduced pressure to afford crude product which was purified by flash chromatography (Teledyne Isco Rf+); to afford 1-(6-tert-butylpyridin-2-yl)-6-(methylthio)-2-(1,1,1-trifluoropropan-2-yl)-1H-pyrazolo[3,4-d]pyrimidin-3 (2H)-one (100 mg, 68.02%) as off white solid.

LCMS: 412 [M+1]+

Step-6: Synthesis of tert-butyl 7-(1-(6-tert-butylpyridin-2-yl)-3-oxo-2-(1,1,1-trifluoropropan-2-yl)-2,3-dihydro-1H-pyrazolo[3,4-d]pyrimidin-6-ylamino)-3,4-dihydroisoquinoline-2(1H)-carboxylate To a stirred solution of -(6-tert-butylpyridin-2-yl)-6-(methylthio)-2-(1,1,1-trifluoropropan-2-yl)-1H-pyrazolo[3,4-d]pyrimidin-3(2H)-one (90 mg, 0.218 mmol, 1.0 eq) in toluene (2 mL) was added m-CPBA (150.4 mg, 0.872 mmol, 4.0 eq) and allowed to stir at RT for 1 h. tert-butyl 7-amino-3,4-dihydroisoquinoline-2(1H)-carboxylate (59.75 mg, 0.24 mmol, 1.1 eq) and DIPEA (168.8 mg, 1.308 mmol, 6.0 eq) were then added and the mixture was allowed to stir at RT for 1 h. The reaction was monitored by TLC. After completion of reaction, the reaction mixture was diluted with water and extracted with EtOAc (50 mL×2). Combined organic layer was washed with water (50 mL) brine solution (50 mL), dried over anhydrous Na$_2$SO$_4$ and concentrated under reduced pressure to afford crude which was purified by reversed-phase chromatography to afford tert-butyl 7-(1-(6-tert-butylpyridin-2-yl)-3-oxo-2-(1,1,1-trifluoropropan-2-yl)-2,3-dihydro-1H-pyrazolo[3,4-d]pyrimidin-6-ylamino)-3,4-dihydroisoquinoline-2(1H)-carboxylate (30 mg, 22.55%) as off white solid.

LCMS: 612 [M+1]+

Step-7: Synthesis of 1-(6-tert-butylpyridin-2-yl)-6-(1,2,3,4-tetrahydroisoquinolin-7-ylamino)-2-(1,1,1-trifluoropropan-2-yl)-1H-pyrazolo[3,4-d]pyrimidin-3 (2H)-one hydrochloride The solution of tert-butyl 7-(1-(6-tert-butylpyridin-2-yl)-3-oxo-2-(1,1,1-trifluoropropan-2-yl)-2,3-dihydro-1H-pyrazolo[3,4-d]pyrimidin-6-ylamino)-3,4-dihydroisoquinoline-2 (1H)-carboxylate (30 mg, 0.049 mmol, 1.0 eq) in 2M HCl in methanol (10 mL) was stirred at RT for 72 h. The reaction was monitored by TLC. After completion of reaction, the volatiles are removed under reduced pressure to afford 1-(6-tert-butylpyridin-2-yl)-6-(1,2,3,4-tetrahydroisoquinolin-7-ylamino)-2-(1,1,1-trifluoropropan-2-yl)-1H-pyrazolo[3,4-d]pyrimidin-3(2H)-one as a hydrochloride salt (11 mg, 42.38%) as off white solid.

LCMS: 512 [M+1]+

$^1$H NMR: (400 MHz, MeOD) δ 8.86 (s, 1H), 7.99 (s, 1H), 7.59-7.68 (m, 2H), 7.46-7.55 (m, 2H), 7.19 (d, J=8.33 Hz, 1H), 5.03 (br. s., 1H), 4.31 (br. s., 2H), 3.51 (t, J=6.36 Hz, 2H), 3.09 (t, J=6.36 Hz, 2H), 1.71 (d, J=7.02 Hz, 3H), 1.36 (s, 9H).

Example S54. Synthesis of 2-tert-butyl-1-(6-tert-butylpyridin-2-yl)-6-(1,2,3,4-tetrahydroisoquinolin-7-ylamino)-1H-pyrazolo[3,4-d]pyrimidin-3(2H)-one (Compound No. 1.151)

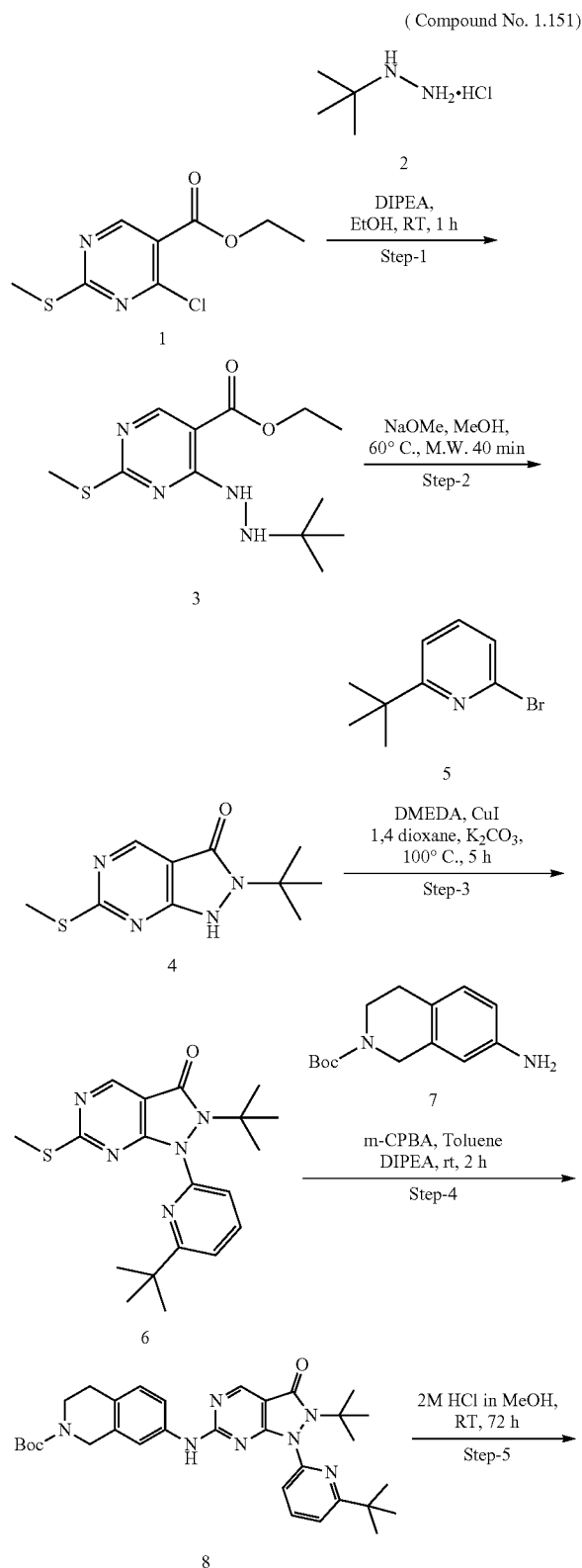

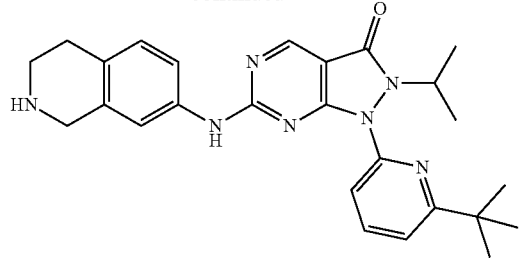

Step-1: Synthesis of ethyl 4-(2-tert-butylhydrazinyl)-2-(methylthio)pyrimidine-5-carboxylate To a stirred solution of ethyl 4-chloro-2-(methylthio) pyrimidine-5-carboxylate (1.66 g, 10.3 mmol, 1.2 eq) in EtOH (50 mL) was added DIPEA (4.48 g, 34.3 mmol, 4 eq) at RT. The resulting reaction mixture was stirred at RT for 30 min, followed by addition of 1 (2 g, 8.621 mmol, 1 eq) at RT. The resulting reaction mixture was stirred at RT for 3 h. The progress of reaction was monitored by TLC. Upon completion, the reaction mixture was diluted with water (100 mL), extracted with EtOAc (2×200 mL). The combined organic layers were washed with water (100 mL), with brine (100 mL), dried over $Na_2SO_4$, concentrated under reduced pressure to afford ethyl 4-(2-tert-butylhydrazinyl)-2-(methylthio)pyrimidine-5-carboxylate (2.19 g, 89.38%) as off white solid.

LCMS: 285 [M+1]$^+$

Step-2: Synthesis of 2-tert-butyl-6-(methylthio)-1H-pyrazolo[3,4-d]pyrimidin-3(2H)-one To a stirred solution of ethyl 4-(2-tert-butylhydrazinyl)-2-(methylthio)pyrimidine-5-carboxylate (1.2 g, 4.21 mmol, 1 eq) in MeOH (10 mL) was added NaOMe (0.455 g, 1.68 mmol, 4 eq) at RT. The resulting mixture was irradiated in microwave at 60° C. for 40 min. The progress of reaction was monitored by TLC. Upon completion, the reaction mixture was diluted with water (100 mL), extracted with EtOAc (2×200 mL). The combined organic layers were washed with water (100 mL), with brine (100 mL), dried over $Na_2SO_4$, concentrated under reduced pressure to afford crude which was purified using combi flash chromatography (Teledyne Isco Rf+); compound eluting 90% EtOAc/Hexane to afford 2-tert-butyl-6-(methylthio)-1H-pyrazolo[3,4-d]pyrimidin-3(2H)-one (0.12 g, 12%) as an off-white solid.

LCMS: 239 [M+1]$^+$

Step-3: Synthesis of 2-tert-butyl-1-(6-tert-butylpyridin-2-yl)-6-(methylthio)-1H-pyrazolo[3,4-d]pyrimidin-3(2H)-one To a stirred solution of 2-tert-butyl-6-(methylthio)-1H-pyrazolo[3,4-d]pyrimidin-3(2H)-one (180 mg, 0.756 mmol, 1.0 eq) and 2-bromo-6-tert-butylpyridine (194.3 mg, 0.907 mmol, 1.2 eq) in 1,4 dioxane (5 mL) was added potassium carbonate (208.9 mg, 1.512 mmol, 2.0 eq) and the resulting mixture was purged with nitrogen for 30 min followed by addition of copper iodide (28.7 mg, 0.151 mmol, 0.2 eq), and N,N'-dimethylethylenediamine (DMEDA) (26.05 mg, 0.302 mmol, 0.4 eq) and again purged with nitrogen for 10 min. The resultant mixture was heated at 100° C. for 5 h. The reaction was monitored by TLC. After completion of reaction, the reaction mixture was diluted with water and extracted with EtOAc (50 mL×2). Combined organic layer was washed with water (50 mL) brine solution (50 mL), dried over anhydrous Na₂SO₄ and concentrated under reduced pressure to afford crude which was purified by flash chromatography (Teledyne Isco Rf+); compound eluting 30% EtOAc/Hexane to afford 2-tert-butyl-1-(6-tert-butylpyridin-2-yl)-6-(methylthio)-1H-pyrazolo[3,4-d]pyrimidin-3(2H)-one (100 mg, 35.71%) as off white solid.

LCMS: 372 [M+H]⁺

Step-4: Synthesis of tert-butyl 7-(2-tert-butyl-1-(6-tert-butylpyridin-2-yl)-3-oxo-2,3-dihydro-1H-pyrazolo[3,4-d]pyrimidin-6-ylamino)-3,4-dihydroisoquinoline-2(1H)-carboxylate To a stirred solution of 2-tert-butyl-1-(6-tert-butylpyridin-2-yl)-6-(methylthio)-1H-pyrazolo[3,4-d]pyrimidin-3(2H)-one (100 mg, 0.269 mmol, 1.0 eq) in toluene (2 mL) was added m-CPBA (185.6 mg, 1.076 mmol, 4.0 eq) and allowed to stir at RT for 1 h, followed by addition of 7 (84.1 mg, 0.296 mmol, 1.1 eq) and DIPEA (208.3 mg, 1.614 mmol, 6.0 eq) were added and allowed to stir at 55° C. for 6 h. The reaction was monitored by TLC. After completion of reaction, the reaction mixture was diluted with water and extracted with EtOAc (50 mL×2). Combined organic layer was washed with water (50 mL) brine solution (50 mL), dried over anhydrous Na₂SO₄ and concentrated under reduced pressure to afford crude which was purified by flash chromatography (Teledyne Isco Rf+); compound eluting 30% EtOAc/Hexane to afford tert-butyl 7-(2-tert-butyl-1-(6-tert-butylpyridin-2-yl)-3-oxo-2,3-dihydro-1H-pyrazolo[3,4-d]pyrimidin-6-ylamino)-3,4-dihydroisoquinoline-2(1H)-carboxylate (95 mg, 54.28%) as off white solid.

LCMS: 572 [M+1]⁺

Step-5: Synthesis of 2-tert-butyl-1-(6-tert-butylpyridin-2-yl)-6-(1,2,3,4-tetrahydro isoquinolin-7-ylamino)-1H-pyrazolo[3,4-d]pyrimidin-3(2H)-one The solution of tert-butyl 7-(2-tert-butyl-1-(6-tert-butylpyridin-2-yl)-3-oxo-2,3-dihydro-1H-pyrazolo[3,4-d]pyrimidin-6-ylamino)-3,4-dihydroisoquinoline-2(1H)-carboxylate (95 mg, 0.166 mmol, 1.0 eq) in 2M HCl in methanol (10 mL) was stirred at RT for 72 h. The reaction was monitored by TLC. After completion of reaction, the volatiles are removed under reduced pressure and the residue was taken in saturated NaHCO₃ and extracted with EtOAc (150 mL×2). Combined organic layer was washed with water (50 mL) brine solution (50 mL), dried over anhydrous Na₂SO₄ and concentrated under reduced pressure to afford crude which was purified by reversed-phase chromatography to afford 2-tert-butyl-1-(6-tert-butylpyridin-2-yl)-6-(1,2,3,4-tetrahydro isoquinolin-7-ylamino)-1H-pyrazolo[3,4-d]pyrimidin-3(2H)-one (13 mg, 16.66%) as off white solid.

LCMS: 472 [M+1]⁺

¹H NMR: (400 MHz, MeOD) δ 8.77 (s, 1H), 7.94 (s, 1H), 7.59 (br. s., 1H), 7.52 (d, J=7.89 Hz, 2H), 7.44 (d, J=7.89 Hz, 1H), 7.17 (d, J=8.33 Hz, 1H), 4.33 (s, 2H), 3.51 (t, J=6.58 Hz, 2H), 3.08 (t, J=6.14 Hz, 2H), 1.47 (s, 9H), 1.35 (s, 9H).

Example S55. Synthesis of 1-(6-tert-butylpyridin-2-yl)-6-(1,2,3,4-tetrahydroisoquinolin-7-ylamino)-2-(2,2,2-trifluoroethyl)-1H-pyrazolo[3,4-d]pyrimidin-3(2H)-one (Compound No. 1.152)

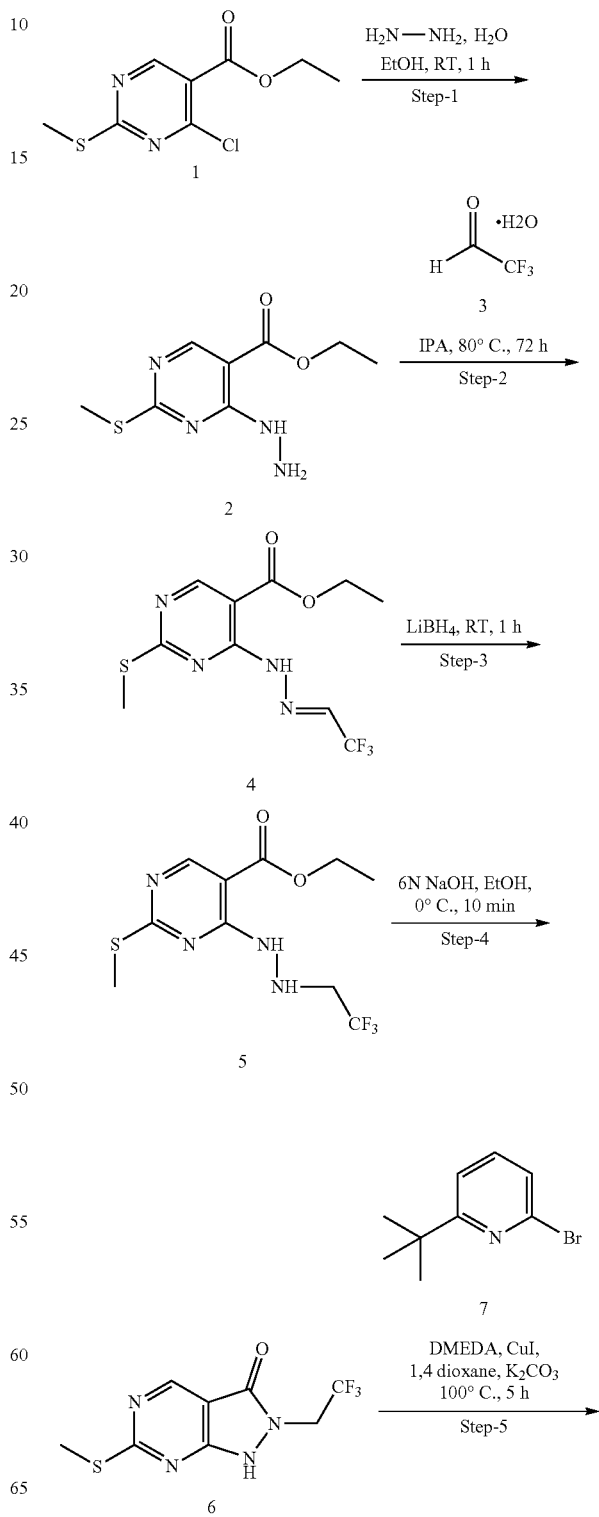

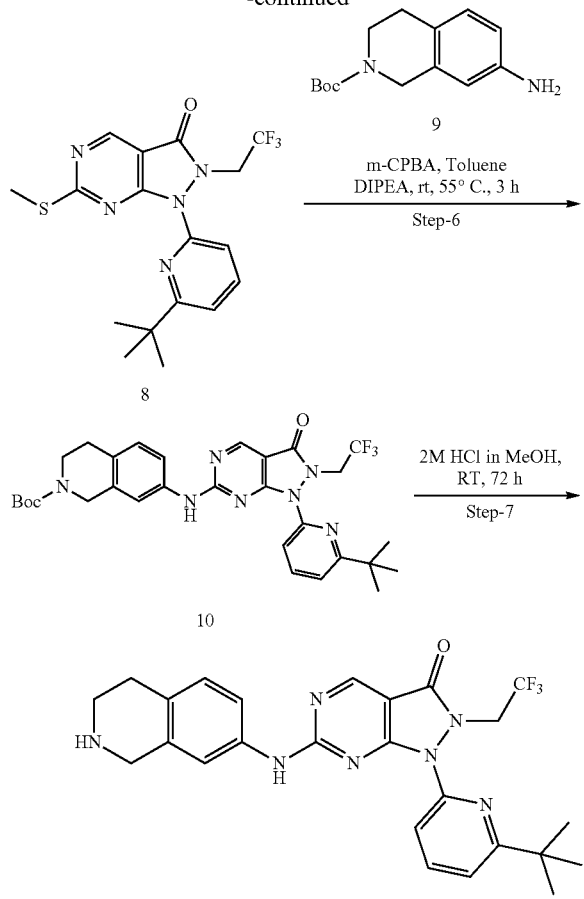

Step-1: Synthesis of ethyl 4-hydrazinyl-2-(methylthio)pyrimidine-5-carboxylate To a stirred solution of hydrazine hydrate (3.5 mL, 107.44 mmol, 5 eq) in EtOH (50 mL) was added the solution of ethyl 4-chloro-2-(methylthio)pyrimidine-5-carboxylate (5 g, 21.488 mmol, 1 eq) in EtOH (100 mL) at 0° C. The resulting mixture was stirred at RT for 1 h. The progress of reaction was monitored by TLC. The reaction mixture was diluted with water (100 mL), extracted with EtOAc (2×200 mL). The combined organic layers were washed with water (100 mL), with brine (100 mL), dried over Na$_2$SO$_4$, concentrated under reduced pressure to afford ethyl 4-hydrazinyl-2-(methylthio)pyrimidine-5-carboxylate (4.21 g, 85.71%) as an off white solid.

LCMS: 229 [M+1]$^+$

Step-2: Synthesis of (E)-ethyl 2-(methylthio)-4-(2-(2,2,2-trifluoroethylidene) hydrazinyl) pyrimidine-5-carboxylate To a stirred solution of (E)-ethyl 2-(methylthio)-4-(2-(2,2,2-trifluoroethylidene) hydrazinyl) pyrimidine-5-carboxylate (4 g, 17.541 mmol, 1 eq) in IPA (20 mL) was added 2,2,2-trifluoroacetaldehyde hydrate (6.1 g, 52.523 mmol, 3 eq) at RT. The resulting mixture was heated at 80° C. for 72 h. The progress of reaction was monitored by TLC. Upon completion, the resulting reaction mixture was quenched in to water to follow out solid, filtered through Buchner funnel washed with water and hexane to afford (E)-ethyl 2-(methylthio)-4-(2-(2,2,2-trifluoroethylidene) hydrazinyl) pyrimidine-5-carboxylate (2.59 g, 48.05%) as an off-white solid.

LCMS: 309 [M+1]$^+$

Step-3: Synthesis of ethyl 2-(methylthio)-4-(2-(2,2,2-trifluoroethyl)hydrazinyl)pyrimidine-5-carboxylate To a stirred solution of (E)-ethyl 2-(methylthio)-4-(2-(2,2,2-trifluoroethylidene) hydrazinyl) pyrimidine-5-carboxylate (2 g, 6.425 mmol, 1 eq) in THF (50 mL) was added LiBH$_4$ (0.169 g, 7.79 mmol, 1.2 eq) at 0° C. portion wise. The resulting mixture was stirred at RT for 1 h. The progress of reaction was monitored by TLC. Upon completion, the reaction mixture was diluted with water (100 mL), extracted with EtOAc (2×200 mL). The combined organic layers were washed with water (100 mL), with brine (100 mL), dried over Na$_2$SO$_4$, concentrated under reduced pressure to afford crude which was purified using combi flash chromatography (Teledyne Isco Rf+); compound eluting 30% EtOAc/Hexane to afford ethyl 2-(methylthio)-4-(2-(2,2,2-trifluoroethyl)hydrazinyl)pyrimidine-5-carboxylate (0.6 g, 30%) as an off-white solid.

LCMS: 311 [M+1]$^+$

Step-4: Synthesis of 6-(methylthio)-2-(2,2,2-trifluoroethyl)-1H-pyrazolo[3,4-d]pyrimidin-3(2H)-one To a stirred solution of ethyl 2-(methylthio)-4-(2-(2,2,2-trifluoroethyl)hydrazinyl)pyrimidine-5-carboxylate (0.4 g, 1.29 mmol, 1 eq) in EtOH (7 mL) was added 6N-NaOH (2 mL) at 0° C. The resulting mixture was stirred at 0° C. for 10 min. The progress of reaction was monitored by TLC. Upon completion, the reaction mixture was quenched in 1N HCl solution, extracted with EtOAc (2×200 mL). The combined organic layers were washed with water (100 mL), with brine (100 mL), dried over Na$_2$SO$_4$, concentrated under reduced pressure to afford crude which was purified using combi flash chromatography (Teledyne Isco Rf+); compound eluting 5% MeOH/DCM to afford pure 6-(methylthio)-2-(2,2,2-trifluoroethyl)-1H-pyrazolo[3,4-d]pyrimidin-3(2H)-one (0.19 g, 55.88%) as an off-white solid.

LCMS: 265 [M+1]$^+$

Step-5: Synthesis of 1-(6-tert-butylpyridin-2-yl)-6-(methylthio)-2-(2,2,2-trifluoroethyl)-1H-pyrazolo[3,4-d]pyrimidin-3(2H)-one To a stirred solution of 6-(methylthio)-2-(2,2,2-trifluoroethyl)-1H-pyrazolo[3,4-d]pyrimidin-3(2H)-one (90 mg, 0.719 mmol, 1.0 eq) and 2-bromo-6-tert-butylpyridine (184.7 mg, 0.862 mmol, 1.2 eq) in 1,4 dioxane (3 mL) was added potassium carbonate (198.7 mg, 1.438 mmol, 2.0 eq) and the resulting mixture was purged with nitrogen for 30 min followed by addition of copper iodide (27.38 mg, 0.143 mmol, 0.2 eq), and N,N'-dimethylethylenediamine (DMEDA) (25.35 mg, 0.287 mmol, 0.4 eq) and again purged with nitrogen for 10 min. The resulting mixture was heated at 100° C. for 5 h. The reaction was monitored by TLC. After completion of reaction, the reaction mixture was diluted with water and extracted with EtOAc (150 mL×2). The combined organic layers were washed with water (50 mL) brine solution (50 mL), dried over anhydrous Na$_2$SO$_4$ and concentrated under reduced pressure to afford crude which was purified by flash chromatography (Teledyne Isco Rf+);

compound eluting 30% EtOAc/Hexane to afford pure 1-(6-tert-butylpyridin-2-yl)-6-(methylthio)-2-(2,2,2-trifluoroethyl)-1H-pyrazolo[3,4-d]pyrimidin-3(2H)-one (180 mg, 63.15%) as off white solid.

LCMS: 398 [M+1]⁺

Step-6: Synthesis of tert-butyl 7-(1-(6-tert-butylpyridin-2-yl)-3-oxo-2-(2,2,2-trifluoroethyl)-2,3-dihydro-1H-pyrazolo[3,4-d]pyrimidin-6-ylamino)-3,4-dihydroisoquinoline-2(1H)-carboxylate To a stirred solution of 1-(6-tert-butylpyridin-2-yl)-6-(methylthio)-2-(2,2,2-trifluoroethyl)-1H-pyrazolo[3,4-d]pyrimidin-3(2H)-one (150 mg, 0.377 mmol, 1.0 eq) in toluene (3 mL) was added m-CPBA (260.2 mg, 1.508 mmol, 4.0 eq) and allowed to stir at RT for 1 h, followed by addition of 9 (118.04 mg, 0.415 mmol, 1.1 eq) and DIPEA (292.02 mg, 2.262 mmol, 6.0 eq) were added and allowed to stir at 55° C. for 3 h. The reaction was monitored by TLC. After completion of reaction, the reaction mixture was diluted with water and extracted with EtOAc (100 mL×2). The combined organic layers were washed with water (50 mL) brine solution (50 mL), dried over anhydrous $Na_2SO_4$ and concentrated under reduced pressure to afford crude tert-butyl 7-(1-(6-tert-butylpyridin-2-yl)-3-oxo-2-(2,2,2-trifluoroethyl)-2,3-dihydro-1H-pyrazolo[3,4-d]pyrimidin-6-ylamino)-3,4-dihydroisoquinoline-2(1H)-carboxylate (200 mg, 88.88%) as off white solid.

LCMS: 598 [M+1]⁺

Step-7: Synthesis of 1-(6-tert-butylpyridin-2-yl)-6-(1,2,3,4-tetrahydroisoquinolin-7-ylamino)-2-(2,2,2-trifluoroethyl)-1H-pyrazolo[3,4-d]pyrimidin-3(2H)-one The solution of tert-butyl 7-(1-(6-tert-butylpyridin-2-yl)-3-oxo-2-(2,2,2-trifluoroethyl)-2,3-dihydro-1H-pyrazolo[3,4-d]pyrimidin-6-ylamino)-3,4-dihydroisoquinoline-2(1H)-carboxylate (200 mg, 0.335 mmol, 1.0 eq) in 2M HCl in methanol (20 mL) was stirred at RT for 72 h. The reaction was monitored by TLC. After completion of reaction, the volatiles are removed under reduced pressure and the residue was taken in saturated $NaHCO_3$ and extracted with EtOAc (200 mL×2). Combined organic layer was washed with water (150 mL) brine solution (100 mL), dried over anhydrous $Na_2SO_4$ and concentrated under reduced pressure to afford crude which was purified by reversed-phase chromatography to afford 1-(6-tert-butylpyridin-2-yl)-6-(1,2,3,4-tetrahydroisoquinolin-7-ylamino)-2-(2,2,2-trifluoroethyl)-1H-pyrazolo[3,4-d]pyrimidin-3 (2H)-one (30 mg, 12.5%) as off white solid.

LCMS: 498 [M+1]⁺

¹H NMR: (400 MHz, MeOD) δ 8.90 (s, 1H), 7.99 (s, 1H), 7.85 (d, J=8.33 Hz, 1H), 7.69 (s, 1H), 7.54 (d, J=8.33 Hz, 1H), 7.45 (d, J=7.89 Hz, 1H), 7.22 (d, J=8.33 Hz, 1H), 5.02-5.13 (m, 2H), 4.31 (br. s., 2H), 3.47 (br. s., 2H), 3.07 (br. s., 2H), 1.39 (s, 9H).

Example S56. Synthesis of 1-(6-tert-butylpyridin-2-yl)-2-(1-hydroxypropan-2-yl)-6-(1,2,3,4-tetrahydroisoquinolin-7-ylamino)-1H-pyrazolo[3,4-d]pyrimidin-3(2H)-one (Compound No. 1.153)

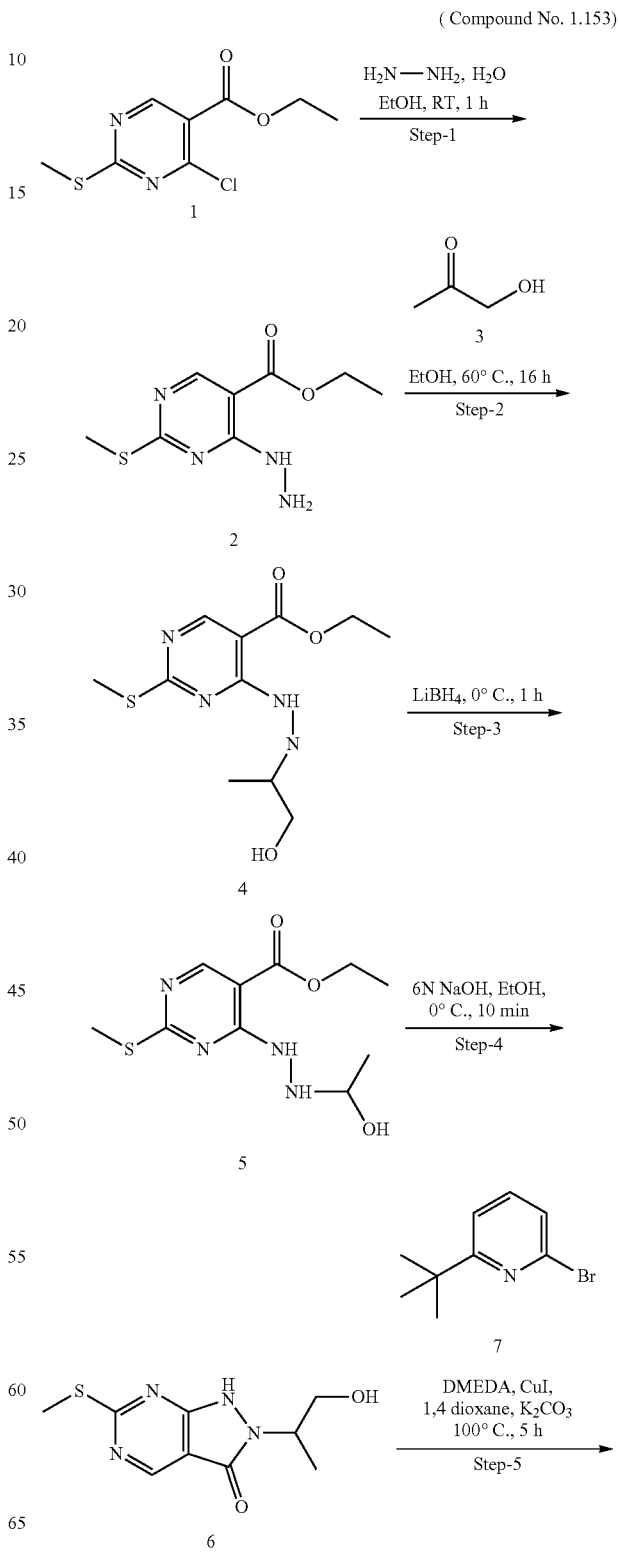

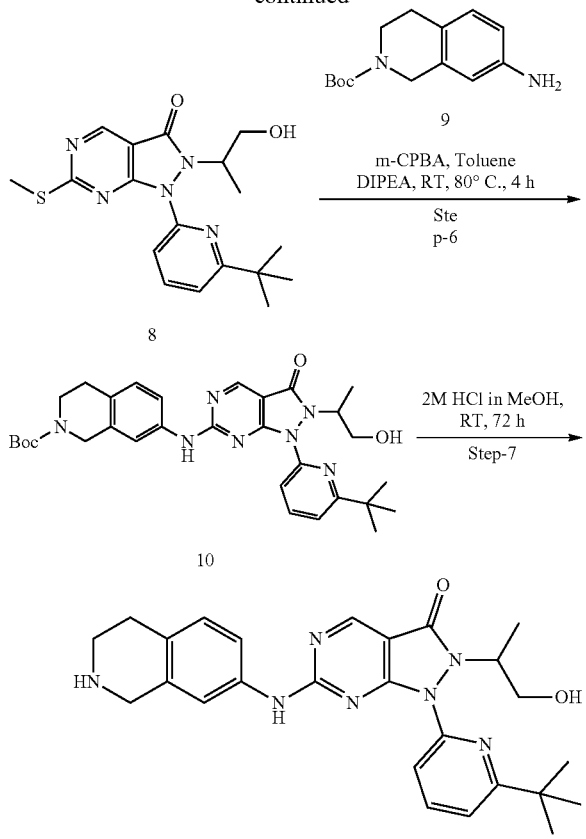

Step-1: Synthesis of ethyl 4-hydrazinyl-2-(methylthio)pyrimidine-5-carboxylate To a stirred solution of hydrazine hydrate (3.5 mL, 107.44 mmol, 5 eq) in EtOH (50 mL) was added the solution of ethyl 4-chloro-2-(methylthio)pyrimidine-5-carboxylate (5 g, 21.488 mmol, 1 eq) in EtOH (100 mL) at 0° C. The resulting mixture was stirred at RT for 1 h. The progress of reaction was monitored by TLC. Upon completion, the reaction mixture was diluted with water (100 mL), extracted with EtOAc (2×200 mL). The combined organic layers were washed with water (100 mL), with brine (100 mL), dried over Na$_2$SO$_4$, concentrated under reduced pressure to afford ethyl 4-hydrazinyl-2-(methylthio)pyrimidine-5-carboxylate (4.21 g, 85.71%) as off white solid.

LCMS: 229 [M+1]$^+$

Step-2: Synthesis of (E)-ethyl 4-(2-(1-hydroxypropan-2-ylidene)hydrazinyl)-2-(methylthio) pyrimidine-5-carboxylate To a stirred solution of ethyl 4-hydrazinyl-2-(methylthio) pyrimidine-5-carboxylate (4.7 g, 26.6 mmol, 1 eq) in EtOH (70 mL) was added 1-hydroxypropan-2-one (7.63 g, 103.6 mmol, 5 eq) at RT. The resulting mixture was heated at 60° C. for 16 h. The progress of reaction was monitored by TLC. Upon completion, the reaction mixture was diluted with water (100 mL), extracted with EtOAc (2×200 mL). The combined organic layers were washed with water (100 mL), with brine (100 mL), dried over Na$_2$SO$_4$, concentrated under reduced pressure to afford crude which was purified using combi flash chromatography (Teledyne Isco Rf+); compound eluting 30% EtOAc/Hexane to afford (E)-ethyl 4-(2-(1-hydroxypropan-2-ylidene)hydrazinyl)-2-(methylthio) pyrimidine-5-carboxylate (4 g, 68.96%) as an off-white solid.

LCMS: 284 [M+1]$^+$

Step-3: Synthesis of ethyl 4-(2-(1-hydroxypropan-2-yl)hydrazinyl)-2-(methylthio) pyrimidine-5-carboxylate To a stirred solution of (E)-ethyl 4-(2-(1-hydroxypropan-2-ylidene)hydrazinyl)-2-(methylthio) pyrimidine-5-carboxylate (2 g, 7.425 mmol, 1 eq) in THF (50 mL) was portion wise added LiBH$_4$ (0.199 g, 9.1 mmol, 1.3 eq) at 0° C. The resulting mixture was stirred at 0° C. for 1 h. The progress of reaction was monitored by TLC. Upon completion, the reaction mixture was diluted with water (100 mL), extracted with EtOAc (2×200 mL). The combined organic layers were washed with water (100 mL), with brine (100 mL), dried over Na$_2$SO$_4$, concentrated under reduced pressure to afford crude which was purified using combi flash chromatography (Teledyne Isco Rf+); compound eluting 95% EtOAc/Hexane to afford ethyl 4-(2-(1-hydroxypropan-2-yl)hydrazinyl)-2-(methylthio) pyrimidine-5-carboxylate (0.5 g, 24.87%) as an off-white solid.

LCMS: 287 [M+1]$^+$

Step-4: Synthesis of 2-(1-hydroxypropan-2-yl)-6-(methylthio)-1H-pyrazolo[3,4-d]pyrimidin-3(2H)-one To a stirred solution of ethyl 4-(2-(1-hydroxypropan-2-yl)hydrazinyl)-2-(methylthio) pyrimidine-5-carboxylate (0.45 g, 0.0015 mmol, 1 eq) in EtOH (7 mL) was added 6N NaOH (2.2 mL) at 0° C. The resulting mixture was stirred at 0° C. for 10 min. The progress of reaction was monitored by TLC. Upon completion, the reaction mixture was quenched in 1N HCl solution, extracted with EtOAc (2×200 mL). The combined organic layers were washed with water (100 mL), with brine (100 mL), dried over Na$_2$SO$_4$, concentrated under reduced pressure to afford 2-(1-hydroxypropan-2-yl)-6-(methylthio)-1H-pyrazolo[3,4-d]pyrimidin-3(2H)-one (0.225 g, 59.36%) as an off-white solid.

LCMS: 241 [M+1]$^+$

Step-5: Synthesis of 1-(6-tert-butylpyridin-2-yl)-2-(1-hydroxypropan-2-yl)-6-(methylthio)-1H-pyrazolo[3,4-d]pyrimidin-3(2H)-one To a stirred solution of 2-(1-hydroxypropan-2-yl)-6-(methylthio)-1H-pyrazolo[3,4-d]pyrimidin-3(2H)-one (200 mg, 0.833 mmol, 1.0 eq) and 2-bromo-6-tert-butylpyridine (214 mg, 0.999 mmol, 1.2 eq) in 1,4 dioxane (3 mL) was added potassium carbonate (230 mg, 1.666 mmol, 2.0 eq) and the resulting mixture was purged with nitrogen for 30 min followed by addition of copper iodide (31 mg, 0.666 mmol, 0.2 eq), and N,N'-dimethylethylenediamine (DMEDA) (30 mg, 0.333 mmol, 0.4 eq) and again purged with nitrogen for 10 min. The resultant mixture was heated at 100° C. for 5 h. The reaction was monitored by TLC. After completion of reaction, the reaction mixture was diluted with water and extracted with EtOAc (150 mL×2). Combined organic layer was washed with water (50 mL) brine solution (50 mL), dried over anhydrous Na$_2$SO$_4$ and concentrated under reduced pressure to afford crude which was purified by flash chromatography (Teledyne Isco Rf+); compound eluting 95% EtOAc/Hexane to afford 1-(6-tertbutylpyridin-2-yl)-2-(1-hydroxypropan-2-yl)-6-(methylthio)-1H-pyrazolo[3,4-d]pyrimidin-3(2H)-one (100 mg, 32.25%) as off white solid.

LCMS: 374 [M+1]$^+$

Step-6: Synthesis of tert-butyl 7-(1-(6-tert-butylpyridin-2-yl)-2-(1-hydroxypropan-2-yl)-3-oxo-2,3-dihydro-1H-pyrazolo[3,4-d]pyrimidin-6-ylamino)-3,4-dihydroisoquinoline-2(1H)-carboxylate To a stirred solution of 1-(6-tert-butylpyridin-2-yl)-2-(1-hydroxypropan-2-yl)-6-(methylthio)-1H-pyrazolo[3,4-d]pyrimidin-3(2H)-one (100 mg, 0.268 mmol, 1.0 eq) in toluene (3 mL) was added m-CPBA (184 mg, 1.072 mmol, 4.0 eq) and allowed to stir at RT for 1 h, followed by addition of tert-butyl 7-amino-3,4-dihydroisoquinoline-2(1H)-carboxylate (83 mg, 0.294 mmol, 1.1 eq) and DIPEA (207 mg, 1.608 mmol, 6.0 eq) were added and allowed to stir at 80° C. for 4 h. The reaction was monitored by TLC. After completion of reaction, the reaction mixture was diluted with water and extracted with EtOAc (100 mL×2). Combined organic layer was washed with water (50 mL) brine solution (50 mL), dried over anhydrous $Na_2SO_4$ and concentrated under reduced pressure to afford crude tert-butyl 7-(1-(6-tert-butylpyridin-2-yl)-2-(1-hydroxypropan-2-yl)-3-oxo-2,3-dihydro-1H-pyrazolo[3,4-d]pyrimidin-6-ylamino)-3,4-dihydroisoquinoline-2(1H)-carboxylate (130 mg, 84.96%) as off white solid.

LCMS: 574 [M+1]$^+$

Step-7: Synthesis of 1-(6-tert-butylpyridin-2-yl)-2-(1-hydroxypropan-2-yl)-6-(1,2,3,4-tetrahydro isoquinolin-7-ylamino)-1H-pyrazolo[3,4-d]pyrimidin-3(2H)-one The solution of tert-butyl 7-(1-(6-tert-butylpyridin-2-yl)-2-(1-hydroxypropan-2-yl)-3-oxo-2,3-dihydro-1H-pyrazolo[3,4-d]pyrimidin-6-ylamino)-3,4-dihydroisoquinoline-2(1H)-carboxylate (200 mg, 0.349 mmol, 1.0 eq) in 2M HCl in methanol (20 mL) was stirred at RT for 72 h. The reaction was monitored by TLC. After completion of reaction, the volatiles are removed under reduced pressure and the residue was taken in saturated $NaHCO_3$ and extracted with EtOAc (200 mL×2). Combined organic layer was washed with water (150 mL) brine solution (100 mL), dried over anhydrous $Na_2SO_4$ and concentrated under reduced pressure to afford crude which was purified by reversed-phase chromatography to afford 1-(6-tert-butylpyridin-2-yl)-2-(1-hydroxypropan-2-yl)-6-(1,2,3,4-tetrahydroisoquinolin-7-ylamino)-1H-pyrazolo[3,4-d]pyrimidin-3(2H)-one (14 mg, 8.48%) as off white solid.

LCMS: 474 [M+1]$^+$ $^1$H NMR: (400 MHz, MeOD) δ 8.82 (s, 1H), 8.52 (br. s., 1H), 7.98 (t, J=7.89 Hz, 1H), 7.71 (d, J=7.89 Hz, 1H), 7.64 (br. s., 1H), 7.46-7.54 (m, 2H), 7.17 (d, J=8.77 Hz, 1H), 4.29-4.35 (m, 1H), 4.26 (s, 2H), 4.02 (dd, J=7.67, 11.18 Hz, 1H), 3.83 (dd, J=5.70, 10.96 Hz, 1H), 3.41-3.49 (m, 2H), 3.04 (t, J=6.14 Hz, 2H), 1.47 (d, J=7.02 Hz, 3H), 1.38 (s, 9H)

Example S57. Synthesis of 1-(6-tert-butylpyridin-2-yl)-2-(2-methoxyethyl)-6-(1,2,3,4-tetrahydro isoquinolin-7-ylamino)-1H-pyrazolo[3,4-d]pyrimidin-3(2H)-one (Compound No. 1.154)

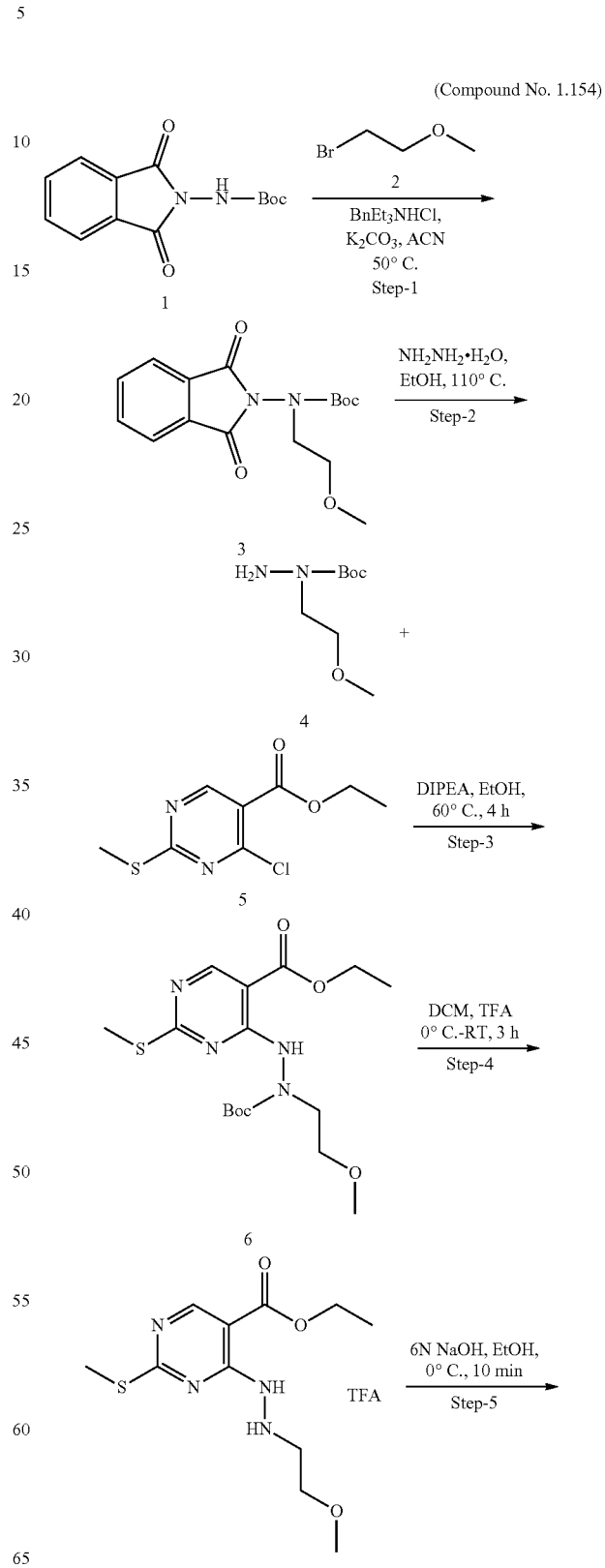

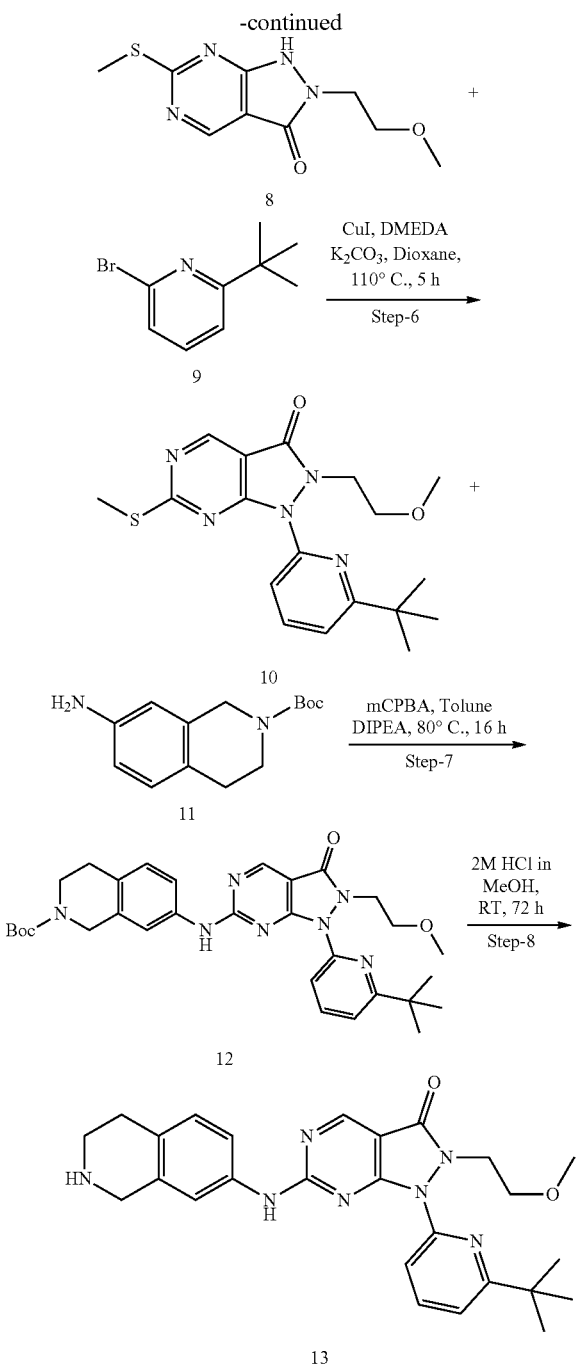

Step-1: Synthesis of tert-butyl 1,3-dioxoisoindolin-2-yl(2-methoxyethyl)carbamate To a stirred solution of tert-butyl 1,3-dioxoisoindolin-2-ylcarbamate (1 g, 3.8526 mmol, 1.0 eq) in ACN (100 mL) was added 2 (1.06 g, 7.625 mmol, 2 eq), BnEt$_3$N$^+$Cl$^-$ (347 mg, 1.506 mmol, 0.4 eq) and K$_2$CO$_3$ (1.57 g, 11.258 mmol, 3.0 eq) at RT. The resulting mixture was heated at 55° C. for overnight. The progress of reaction was monitored by TLC. Upon completion, the reaction mixture was diluted with water (100 mL), extracted with EtOAc (2×200 mL). The combined organic layers were washed with water (50 mL), with brine (50 mL), dried over Na$_2$SO$_4$, concentrated and purified by crystallization to afford tert-butyl 1,3-dioxoisoindolin-2-yl(2-methoxyethyl)carbamate (1.1 g, 91.66%) as light yellow solid.

LCMS: 321 [M+1]$^+$

Step-2: Synthesis of tert-butyl 1-(2-methoxyethyl)hydrazinecarboxylate

To a stirred solution of afford tert-butyl 1,3-dioxoisoindolin-2-yl(2-methoxyethyl)carbamate (1.4 g, 4.375 mmol, 1.0 eq) in EtOH (25 mL) was added NH$_2$NH$_2$.H$_2$O (1.4 mL) at RT. The resulting mixture was stirred at 110° C. for 1 h, formation of white precipitates was observed. The progress of reaction was monitored by TLC. Upon completion, the reaction mixture was diluted with water (100 mL), extracted with EtOAc (2×200 mL). The combined organic layers were washed with water (50 mL), with brine (50 mL), dried over Na$_2$SO$_4$, concentrated and purified by crystallization to afford tert-butyl 1-(2-methoxyethyl)hydrazinecarboxylate (0.41 g, 49.41%) as light yellow solid.

LCMS: 191 [M+1]$^+$

Step-3: Synthesis of ethyl 4-(2-(tert-butoxycarbonyl)-2-(2-methoxyethyl)hydrazinyl)-2-(methylthio)pyrimidine-5-carboxylate To a stirred solution of ethyl 4-(2-(tert-butoxycarbonyl)-2-(2-methoxyethyl)hydrazinyl)-2-(methylthio)pyrimidine-5-carboxylate (0.402 g, 2.114 mmol, 1.2 eq) in EtOH (10 mL) was added DIPEA (0.909 g, 7.048 mmol, 4 eq) at RT. The reaction was stirred at RT for 30 min, followed by addition of 5 (0.41 g, 1.762 mmol, 1 eq) and stirred at 60° C. for 4 h. Upon completion, reaction was diluted with water (50 mL) and extracted with EtOAc (50 mL×2). Organic layer was washed with brine solution (50 mL), dried over anhydrous sodium sulphate and concentrated under reduced pressure to afford crude product, which was purified by flash chromatography (Teledyne Isco Rf+); compound eluting 30% EtOAc/Hexane to afford ethyl 4-(2-(tert-butoxycarbonyl)-2-(2-methoxyethyl)hydrazinyl)-2-(methylthio)pyrimidine-5-carboxylate (0.5 g, 73.31%).

LCMS: 387 [M+1]$^+$

Step-4: Synthesis of ethyl 4-(2-(2-methoxyethyl)hydrazinyl)-2-(methylthio)pyrimidine-5-carboxylate To a stirred solution of ethyl 4-(2-(tert-butoxycarbonyl)-2-(2-methoxyethyl)hydrazinyl)-2-(methylthio)pyrimidine-5-carboxylate (0.5 g, 1.295 mmol, 1.0 eq.) in 10 mL of DCM was added TFA (5 mL) dropwise at 0° C. and allowed to stir at RT for 3 h. Upon completion, solvent was removed under reduced pressure to afford ethyl 4-(2-(2-methoxyethyl)hydrazinyl)-2-(methylthio)pyrimidine-5-carboxylate (0.41 g, 82.99%) as off white solid.

LCMS: 383 [M+1]$^+$

Step-5: Synthesis of 2-(2-methoxyethyl)-6-(methylthio)-1H-pyrazolo[3,4-d]pyrimidin-3(2H)-one To a stirred solution of ethyl 4-(2-(2-methoxyethyl)hydrazinyl)-2-(methylthio)pyrimidine-5-carboxylate (400 mg, 1.044 mmol, 1 eq) in EtOH (10 mL) was added 6N NaOH solution (2 mL) at 0° C. and allowed to stir at 0° C. for 10 min. Upon completion, reaction was acidified by using 1N HCl solution. Ethanol was removed under reduced pressure; residue obtained was cooled to RT and extracted with DCM (100 mL×3). Organic layer was washed with brine solution, dried over anhydrous sodium sulphate and concentrated under reduced pressure to afford 2-(2-methoxyethyl)-6-(methylthio)-1H-pyrazolo[3,4-d]pyrimidin-3(2H)-one (300 mg, 84.26%) as an off white solid.
LCMS: 341 [M+1]+

Step-6: Synthesis of 1-(6-tert-butylpyridin-2-yl)-2-(2-methoxyethyl)-6-(methylthio)-1H-pyrazolo[3,4-d]pyrimidin-3(2H)-one To a stirred solution of 2-(2-methoxyethyl)-6-(methylthio)-1H-pyrazolo[3,4-d]pyrimidin-3(2H)-one (300 mg, 1.248 mmol, 1.0 eq) and 2-bromo-6-tert-butylpyridine (320 mg, 1.497 mmol, 1.2 eq) in dioxane (6 mL) was added potassium carbonate (344.7 mg, 2.496 mmol, 2.0 eq) and the resulting mixture was purged with nitrogen for 30 min followed by addition of copper iodide (47.53 mg, 0.249 mmol, 0.2 eq), and N,N'-dimethylethylenediamine (DMEDA) (44 mg, 0.499 mmol, 0.4 eq) and again purged with nitrogen for 30 min. The resultant mixture was heated at 110° C. for 5 h. Upon completion, the reaction mixture was diluted with water and extracted with EtOAc (150 mL×2). Combined organic layer was washed with water (50 mL) brine solution (50 mL), dried over anhydrous sodium sulphate and concentrated under reduced pressure to afford crude product, which was purified by flash chromatography (Teledyne Isco Rf+); compound eluting 50% EtOAc/Hexane to afford pure to afford 1-(6-tert-butylpyridin-2-yl)-2-(2-methoxyethyl)-6-(methylthio)-1H-pyrazolo[3,4-d]pyrimidin-3 (2H)-one (200 mg, 42.91%).
LCMS: 373 [M+1]+

Step-7: Synthesis of tert-butyl 7-(1-(6-tert-butylpyridin-2-yl)-2-(2-methoxyethyl)-3-oxo-2,3-dihydro-1H-pyrazolo[3,4-d]pyrimidin-6-ylamino)-3,4-dihydroisoquinoline-2(1H)-carboxylate To a stirred solution of 10 (200 mg, 0.535 mmol, 1.0 eq) in toluene (5 mL) was added m-CPBA (369 mg, 2.14 mmol, 4.0 eq) and allowed to stir at RT for 1 h, followed by addition of 11 (146.28 mg, 0.589 mmol, 1.1 eq) and DIPEA (414.4 mg, 3.21 mmol, 6.0 eq) at RT and allowed to stir at 80° C. for 16 h. Upon completion, the reaction mixture was diluted with water (50 mL) and extracted with EtOAc (150 mL×2). Combined organic layer was washed with water (50 mL) brine solution (50 mL), dried over anhydrous sodium sulphate and concentrated under reduced pressure to afford crude tert-butyl 7-(1-(6-tert-butylpyridin-2-yl)-2-(2-methoxyethyl)-3-oxo-2,3-dihydro-1H-pyrazolo[3,4-d]pyrimidin-6-ylamino)-3,4-dihydroisoquinoline-2(1H)-carboxylate (300 mg, 98.68%).
LCMS: 574 [M+1]+

Step-8: Synthesis of 1-(6-tert-butylpyridin-2-yl)-2-(2-methoxyethyl)-6-(1,2,3,4-tetrahydro isoquinolin-7-ylamino)-1H-pyrazolo[3,4-d]pyrimidin-3(2H)-one The solution of tert-butyl 7-(1-(6-tert-butylpyridin-2-yl)-2-(2-methoxyethyl)-3-oxo-2,3-dihydro-1H-pyrazolo[3,4-d]pyrimidin-6-ylamino)-3,4-dihydroisoquinoline-2(1H)-carboxylate (300 mg, 0.523 mmol, 1.0 eq) in 2M HCl in methanol (20 mL) was stirred at RT for 72 h. The reaction was monitored by TLC. Upon completion, the volatiles are removed under reduced pressure and the residue was taken in saturated NaHCO₃ and extracted with EtOAc (200 mL×2). Combined organic layer was washed with water (150 mL) brine solution (100 mL), dried over anhydrous Na₂SO₄ and concentrated under reduced pressure to afford crude which was purified by reversed-phase chromatography to afford 1-(6-tert-butylpyridin-2-yl)-2-(2-methoxyethyl)-6-(1,2,3,4-tetrahydro isoquinolin-7-ylamino)-1H-pyrazolo[3,4-d]pyrimidin-3(2H)-one (34 mg, 13.76%) as off white solid.
LCMS: 474 [M+1]+
¹H NMR: (400 MHz, MeOD) δ 8.84 (s, 1H), 7.97 (d, J=7.89 Hz, 1H), 7.82 (d, J=7.89 Hz, 1H), 7.72 (br. s., 1H), 7.54 (br. s., 1H), 7.43 (d, J=7.89 Hz, 1H), 7.21 (d, J=8.33 Hz, 1H), 4.44 (t, J=5.48 Hz, 2H), 4.33 (s, 2H), 3.42-3.51 (m, 4H), 3.18 (s, 3H), 3.08 (t, J=6.14 Hz, 2H), 1.38 (s, 9H)

Example S58. Synthesis of 1-(3-(tert-butyl)phenyl)-2-isopropyl-6-((1,2,3,4-tetrahydroisoquinolin-6-yl)amino)-1,2-dihydro-3H-pyrazolo[3,4-d]pyrimidin-3-one (Compound No. 1.155)

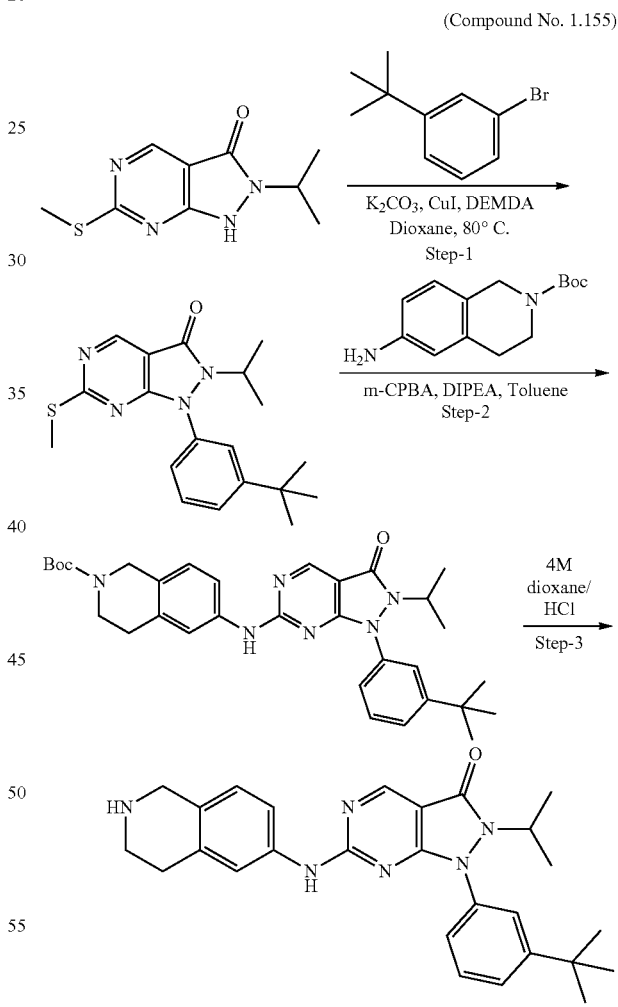

Step-1: Synthesis of 1-(3-(tert-butyl)phenyl)-2-isopropyl-6-(methylthio)-1,2-dihydro-3H-pyrazolo[3,4-d]pyrimidin-3-one To a stirred solution of 2-(cyclopropylmethyl)-6-(methylthio)-1,2-dihydro-3H-pyrazolo[3,4-d]pyrimidin-3-one (0.400 g, 1.777 mmol, 1.0 eq) and 1-bromo-3-(tert-butyl)

benzene (0.36 mL, 2.133 mmol, 1.2 eq) in (5 mL) of dioxane was added Potassium carbonate (0.491 g, 3.554 mmol, 2.0 eq) and the resulting mixture was purged with nitrogen for 10 min, followed by addition of copper iodide (67 mg, 0.355 mmol, 0.2 eq), and N,N'-dimethylethylenediamine (DMEDA) (62 mg, 0.710 mmol, 0.4 eq) and again purged with nitrogen for 10 minutes and stirred at 80° C. for overnight. After completion of reaction, the reaction mixture was diluted with water and extracted with EtOAc (50 mL×2). The combined organic layers were washed with water (50 mL), brine solution (50 mL), dried over anhydrous sodium sulphate and concentrated under reduced pressure. The crude product obtained was purified by flash chromatography (Combiflash, Elution: 0-70% EtOAc in Hexane) to afford the desired compound, 1-(3-(tert-butyl)phenyl)-2-isopropyl-6-(methylthio)-1,2-dihydro-3H-pyrazolo[3,4-d]pyrimidin-3-one (160 mg, 25.27%) as an off white solid.

LCMS: 357.2 [M+1]$^+$

Step-2: Synthesis of tert-butyl 6-((1-(3-(tert-butyl)phenyl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(3-(tert-butyl)phenyl)-2-isopropyl-6-(methylthio)-1,2-dihydro-3H-pyrazolo[3,4-d]pyrimidin-3-one (80 mg, 0.224 mmol, 1.0 eq) in (1 mL) of toluene was added m-CPBA (77 mg, 0.448 mmol, 2.0 eq) and allowed to stir at rt for 30 min. tert-butyl 6-amino-3,4-dihydroisoquinoline-2(1H)-carboxylate (66 mg, 0.268 mmol, 1.2 eq) and DIPEA (0.3 mL, 0.896 mmol, 4.0 eq) were added and allowed to stir at rt for overnight. The formation of precipitates was observed which was filtered to afford the desired compound, tert-butyl 6-((1-(3-(tert-butyl)phenyl)-2-isopropyl-3-oxo-2,3-dihydro-1H-pyrazolo[3,4-d]pyrimidin-6-yl)amino)-3,4-dihydroisoquinoline-2(1H)-carboxylate (70 mg, 56.45%) as an off white solid.

LCMS: 557.3 [M+1]$^+$

Step-3: Synthesis of 1-(3-(tert-butyl)phenyl)-2-isopropyl-6-((1,2,3,4-tetrahydroisoquinolin-6-yl)amino)-1,2-dihydro-3H-pyrazolo[3,4-d]pyrimidin-3-one tert-butyl 6-((1-(3-(tert-butyl)phenyl)-2-isopropyl-3-oxo-2,3-dihydro-1H-pyrazolo[3,4-d]pyrimidin-6-yl)amino)-3,4-dihydroisoquinoline-2(1H)-carboxylate (70 mg, 0.125 mmol, 1.0 eq) was dissolved in (0.9 mL) of dioxane and added 4M dioxane-HCl (0.9 mL) and allowed to stir at rt for 1 h. After completion of reaction, the reaction mixture was filtered and dried under reduced pressure to afford the desired compound, 1-(3-(tert-butyl)phenyl)-2-isopropyl-6-((1,2,3,4-tetrahydroisoquinolin-6-yl)amino)-1,2-dihydro-3H-pyrazolo[3,4-d]pyrimidin-3-one (35 mg, 39.32%) as an off white solid.

LCMS: 457.3 [M+1]$^+$; UPLC @ 254 nm=90.86% and @ 220 nm=94.62%.

$^1$H NMR (400 MHz, DMSO-d$_6$): δ 10.21 (br. s., 1H), 9.22 (br. s., 2H), 8.82 (s, 1H), 7.63 (br. s., 1H), 7.52 (d, J=7.45 Hz, 2H), 7.48 (br. s., 2H), 7.39 (br. s., 1H), 7.08 (d, J=8.77 Hz, 1H), 4.18 (br. s., 2H), 4.06 (br. s., 1H), 3.35 (br. s., 3H), 2.93 (br. s., 2H), 1.20-1.38 (m, 15H)

Example S59. Synthesis of 1-(3-(tert-butyl)phenyl)-2-isopropyl-6-((1,2,3,4-tetrahydroisoquinolin-7-yl)amino)-1,2-dihydro-3H-pyrazolo[3,4-d]pyrimidin-3-one (Compound No. 1.156)

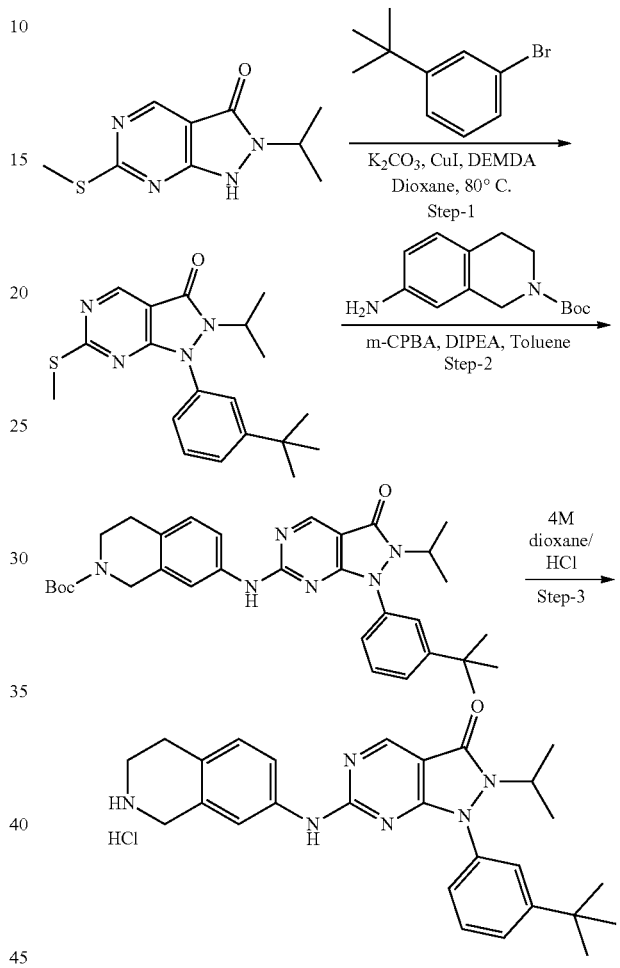

Step-1: Synthesis 1-(3-(tert-butyl)phenyl)-2-isopropyl-6-(methylthio)-1,2-dihydro-3H-pyrazolo[3,4-d]pyrimidin-3-one To a stirred solution of 2-(cyclopropylmethyl)-6-(methylthio)-1,2-dihydro-3H-pyrazolo[3,4-d]pyrimidin-3-one (0.400 g, 1.777 mmol, 1.0 eq) and 1-bromo-3-(tert-butyl)benzene (0.36 mL, 2.133 mmol, 1.2 eq) in (5 mL) of dioxane were added Potassium carbonate (0.491 g, 3.554 mmol, 2.0 eq) and the resulting mixture was purged with nitrogen for 10 min, followed by addition of copper iodide (67 mg, 0.355 mmol, 0.2 eq), and N,N'-dimethylethylenediamine (DMEDA) (62 mg, 0.710 mmol, 0.4 eq) and again purged with nitrogen for 10 min, stirred at 90° C. for overnight. After completion of reaction, the reaction mixture was diluted with water and extracted with EtOAc (50 mL×2). The combined organic layers were washed with water (50 mL), brine solution (50 mL), dried over anhydrous sodium sulphate and concentrated under reduced pressure to afford crude product, which was purified by flash chromatography

801 to afford the desired compound, 1-(3-(tert-butyl)phenyl)-2-isopropyl-6-(methylthio)-1,2-dihydro-3H-pyrazolo[3,4-d]pyrimidin-3-one (160 mg, 25.27%) as an off white solid.
LCMS: 358.2 [M+1]⁺

Step-2: Synthesis of tert-butyl 6-((1-(3-(tert-butyl)phenyl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(3-(tert-butyl)phenyl)-2-isopropyl-6-(methylthio)-1,2-dihydro-3H-pyrazolo[3,4-d]pyrimidin-3-one (80 mg, 0.224 mmol, 1.0 eq) in (1 mL) of toluene was added m-CPBA (77 mg, 0.448 mmol, 2.0 eq) and allowed to stir at rt for 30 min. tert-butyl 7-amino-3,4-dihydroisoquinoline-2(1H)-carboxylate (66 mg, 0.268 mmol, 1.2 eq) and DIPEA (0.3 mL, 0.896 mmol, 4.0 eq) were added and allowed to stir at rt for overnight. The formation of precipitates was observed which was filtered to afford the desired compound tert-butyl 7-((1-(3-(tert-butyl)phenyl)-2-isopropyl-3-oxo-2,3-dihydro-1H-pyrazolo[3,4-d]pyrimidin-6-yl)amino)-3,4-dihydroisoquinoline-2(1H)-carboxylate (70 mg, 56.45%) as an off white solid.
LCMS: 556.3 [M+1]⁺

Step-3: Synthesis of 1-(3-(tert-butyl)phenyl)-2-isopropyl-6-((1,2,3,4-tetrahydroisoquinolin-7-yl)amino)-1,2-dihydro-3H-pyrazolo[3,4-d]pyrimidin-3-one tert-butyl 7-((1-(3-(tert-butyl)phenyl)-2-isopropyl-3-oxo-2,3-dihydro-1H-pyrazolo[3,4-d]pyrimidin-6-yl)amino)-3,4-dihydroisoquinoline-2(1H)-carboxylate (70 mg, 0.125 mmol, 1.0 eq) was dissolved in (0.9 mL) of dioxane and added 6M dioxane-HCl (0.9 mL) and allowed to stir at rt for 1 h. After completion of reaction, the reaction mixture was filtered and dried under reduced pressure to afford the desired compound, 1-(3-(tert-butyl)phenyl)-2-isopropyl-6-((1,2,3,4-tetrahydroisoquinolin-7-yl)amino)-1,2-dihydro-3H-pyrazolo[3,4-d]pyrimidin-3-one (45 mg, 39.32%) as an off white solid.
LCMS: 456.4 [M+1]⁺; UPLC @ 254 nm=98.86% and @ 220 nm=97.62%.
¹H NMR (400 MHz, DMSO-d₆): δ 10.24 (br. s., 1H), 9.34 (br. s., 2H), 8.81 (br. s., 1H), 7.60 (br. s., 1H), 7.52 (br. s., 2H), 7.47 (br. s., 2H), 7.39 (br. s., 1H), 7.10 (br. s., 1H), 4.18 (br. s., 2H), 4.06 (br. s., 1H), 3.34 (br. s., 2H), 2.93 (br. s., 2H), 1.31 (br. s., 15H)

Example S60. Synthesis of 2-allyl-1-(2-(tert-butyl)pyridin-4-yl)-6-((1,2,3,4-tetrahydroisoquinolin-6-yl)amino)-1,2-dihydro-3H-pyrazolo[3,4-d]pyrimidin-3-one (Compound No. 1.157)

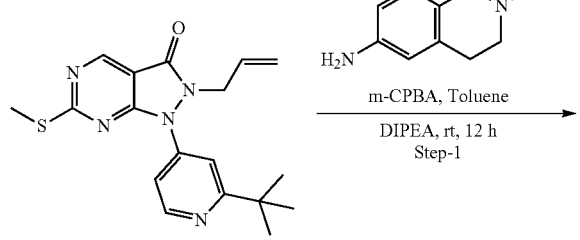

802

-continued

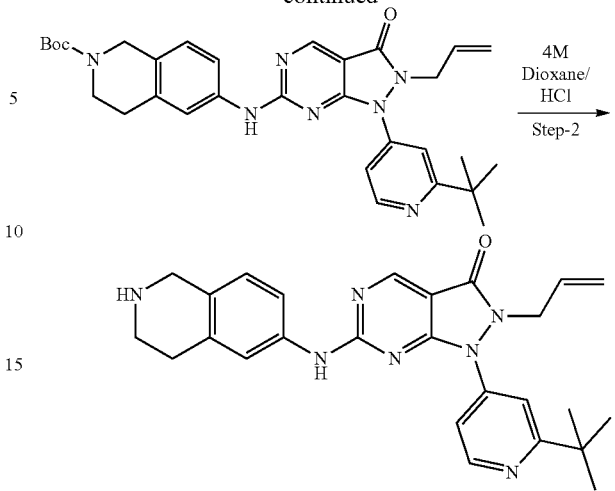

Step-1: Synthesis of tert-butyl tert-butyl 6-((2-allyl-1-(2-(tert-butyl)pyridin-4-yl)-3-oxo-2,3-dihydro-1H-pyrazolo[3,4-d]pyrimidin-6-yl)amino)-3,4-dihydroisoquinoline-2(1H)-carboxylate To a stirred solution of 2-allyl-1-(2-(tert-butyl)pyridin-4-yl)-6-(methylthio)-1,2-dihydro-3H-pyrazolo[3,4-d]pyrimidin-3-one (170 mg, 0.5 mmol, 1.0 eq) in (2.0 mL) of toluene was added m-CPBA (247 mg, 1.0 mmol, 2 eq) and allowed to stir at rt for 1 h. tert-butyl-6-amino-3,4-dihydroisoquinoline-2(1H)-carboxylate (149 mg, 0.6 mmol, 1.2 eq) and DIPEA (0.36 mL, 2.0 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((2-allyl-1-(2-(tert-butyl)pyridin-4-yl)-3-oxo-2,3-dihydro-1H-pyrazolo[3,4-d]pyrimidin-6-yl)amino)-3,4-dihydroisoquinoline-2(1H)-carboxylate (40 mg, 14.38%) as an off white solid. LCMS: 556.6 [M+1]⁺

Step-2: Synthesis of 2-allyl-1-(2-(tert-butyl)pyridin-4-yl)-6-((1,2,3,4-tetrahydroisoquinolin-6-yl)amino)-1,2-dihydro-3H-pyrazolo[3,4-d]pyrimidin-3-one tert-butyl 6-((2-allyl-1-(2-(tert-butyl)pyridin-4-yl)-3-oxo-2,3-dihydro-1H-pyrazolo[3,4-d]pyrimidin-6-yl)amino)-3,4-dihydroisoquinoline-2(1H)-carboxylate (30 mg, 0.054 mmol, 1.0 eq) was dissolved in dioxane (0.6 mL), followed by dropwise addition of 4.0M-HCl (0.6 mL) and allowed to stir at rt for 1 h. After completion of reaction, the reaction mixture was filtered and dried under reduced pressure to afford the desired compound, 2-allyl-1-(2-(tert-butyl)pyridin-4-yl)-6-((1,2,3,4-tetrahydroisoquinolin-6-yl)amino)-1,2-dihydro-3H-pyrazolo[3,4-d]pyrimidin-3-one (12 mg, 50%) as off white solid.
LCMS: 456.3 [M+1]⁺; UPLC @ 254 nm=87.26% and @ 220 nm=90.52%.
¹H NMR (400 MHz, DMSO-d₆) δ 10.53 (s, 1H), 9.37 (br. s., 2H), 8.95 (s, 1H), 8.76 (d, J=6.14 Hz, 1H), 7.78 (br. s., 1H), 7.57 (d, J=8.33 Hz, 3H), 7.21 (br. s., 1H), 5.68-5.77 (m, 1H), 5.12 (d, J=10.09 Hz, 1H), 5.05 (br. s., 1H), 4.39 (d, J=5.70 Hz, 2H), 4.23 (br. s., 2H), 3.37 (br. s., 2H), 2.97-3.02 (m, 2H), 1.28-1.49 (m, 9H)

Example S61. Synthesis of 2-allyl-1-(2-(tert-butyl)pyridin-4-yl)-6-((1,2,3,4-tetrahydroisoquinolin-7-yl)amino)-1,2-dihydro-3H-pyrazolo[3,4-d]pyrimidin-3-one (Compound No.1.158)

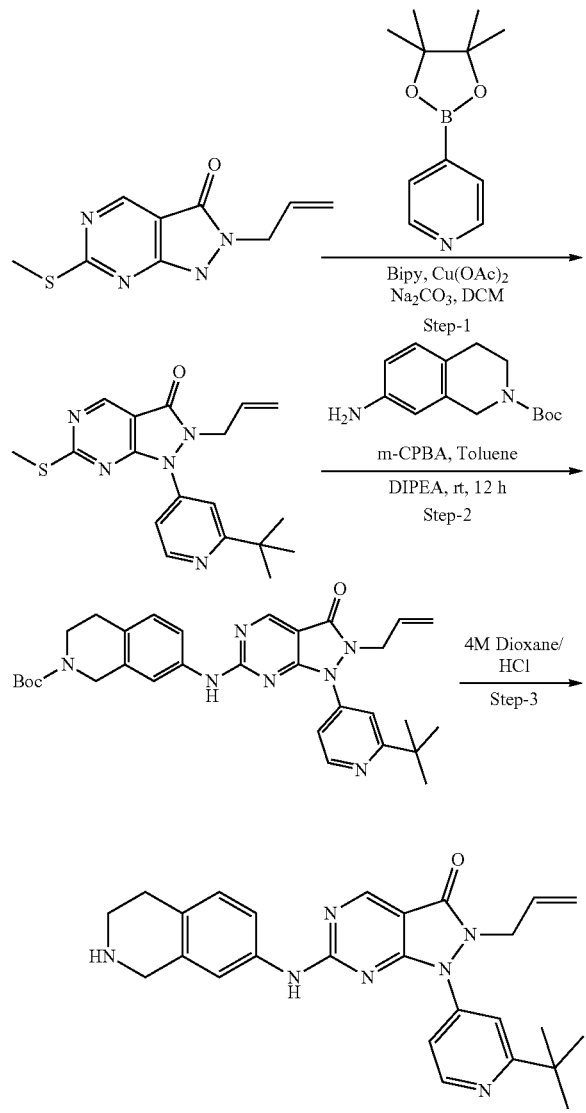

Step-1: 2-allyl-1-(2-(tert-butyl)pyridin-4-yl)-6-(methylthio)-1,2-dihydro-3H-pyrazolo[3,4-d]pyrimidin-3-one To a stirred solution of 2-allyl-6-(methylthio)-1,2-dihydro-3H-pyrazolo[3,4-d]pyrimidin-3-one (540 mg, 2.43 mmol, 1 eq) and 2-(tert-butyl)-4-(4,4,5,5-tetramethyl-1,3,2-dioxaborolan-2-yl)pyridine (1.26 g, 4.84 mmol, 2 eq) in DCM (50 mL) was added 2,2-bipyridine (756 mg, 4.84 mmol, 2 eq), copper acetate (880 mg, 4.84 mmol, 2 eq) and Na$_2$CO$_3$ (773 mg, 7.29 mmol, 3 eq). The reaction mixture was stirred at rt for 24 h in open air. The progress of reaction was monitored by TLC. After completion, the reaction mixture was filtered over celite to remove inorganic impurities. The filtrate was washed with water, dried over Na$_2$SO$_4$, concentrated and purified by column chromatography (Combiflash, Elution: 0-30% EtOAc in Hexane) to afford the desired product, 2-allyl-1-(2-(tert-butyl)pyridin-4-yl)-6-(methylthio)-1,2-dihydro-3H-pyrazolo[3,4-d]pyrimidin-3-one (380 mg, 44%) as yellow solid.

LCMS: 356.3 [M+1]$^+$

Step-2: Synthesis of tert-butyl 7-((2-allyl-1-(2-(tert-butyl)pyridin-4-yl)-3-oxo-2,3-dihydro-1H-pyrazolo[3,4-d]pyrimidin-6-yl)amino)-3,4-dihydroisoquinoline-2(1H)-carboxylate To a stirred solution of 2 2-allyl-1-(2-(tert-butyl)pyridin-4-yl)-6-(methylthio)-1,2-dihydro-3H-pyrazolo[3,4-d]pyrimidin-3-one (170 mg, 0.5 mmol, 1.0 eq) in (2.0 mL) of toluene was added m-CPBA (247 mg, 1.0 mmol, 2 eq) and allowed to stir at rt for 1 h. tert-butyl-7-amino-3,4-dihydroisoquinoline-2(1H)-carboxylate (149 mg, 0.6 mmol, 1.2 eq) and DIPEA (0.36 mL, 2.0 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 7-((2-allyl-1-(2-(tert-butyl)pyridin-4-yl)-3-oxo-2,3-dihydro-1H-pyrazolo[3,4-d]pyrimidin-6-yl)amino)-3,4-dihydroisoquinoline-2(1H)-carboxylate (30 mg, 13.14%) as an off white solid.

LCMS: 556.6 [M+1]$^+$

Step-3: Synthesis of 2-allyl-1-(2-(tert-butyl)pyridin-4-yl)-6-((1,2,3,4-tetrahydroisoquinolin-7-yl)amino)-1,2-dihydro-3H-pyrazolo[3,4-d]pyrimidin-3-one tert-butyl 7-((2-allyl-1-(2-(tert-butyl)pyridin-4-yl)-3-oxo-2,3-dihydro-1H-pyrazolo[3,4-d]pyrimidin-6-yl)amino)-3,4-dihydroisoquinoline-2(1H)-carboxylate (30 mg, 0.054 mmol, 1.0 eq) was dissolved in dioxane (0.6 mL), followed by dropwise addition of 4.0M-HCl (0.6 mL) and allowed to stir at rt for 1 h. After completion of reaction, the reaction mixture was filtered and dried under reduced pressure to afford the desired compound, 2-allyl-1-(2-(tert-butyl)pyridin-4-yl)-6-((1,2,3,4-tetrahydroisoquinolin-7-yl)amino)-1,2-dihydro-3H-pyrazolo[3,4-d]pyrimidin-3-one (36 mg, 75.70%) as off white solid.

LCMS: 456.3 [M+1]$^+$; UPLC @ 254 nm=91.79% and @ 220 nm=89.02%.

$^1$H NMR (400 MHz, DMSO-d$_6$) δ 10.56 (br. s., 1H), 9.47 (br. s., 2H), 8.96 (s, 1H), 8.74-8.83 (m, 1H), 7.85 (br. s., 1H), 7.49-7.61 (m, 3H), 7.22 (d, J=7.89 Hz, 1H), 6.55 (s, 1H), 5.66-5.78 (m, 1H), 5.12 (d, J=10.52 Hz, 1H), 5.05 (d, J=17.10 Hz, 1H), 4.39 (d, J=5.70 Hz, 2H), 4.28 (br. s., 2H), 3.36 (br. s., 2H), 2.99 (d, J=5.70 Hz, 2H), 1.34-1.49 (m, 9H).

Example S62. Synthesis of 1-(2-(tert-butyl)pyridin-4-yl)-2-cyclopropyl-6-((1,2,3,4-tetrahydroisoquinolin-6-yl)amino)-1,2-dihydro-3H-pyrazolo[3,4-d]pyrimidin-3-one dihydrochloride (Compound No. 1.159)

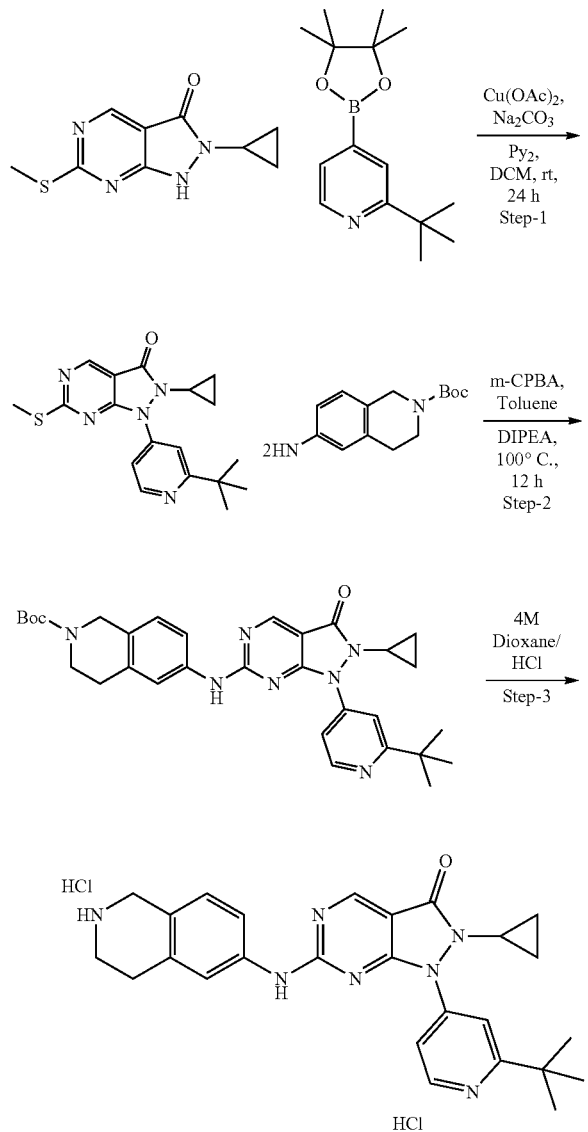

Step-1: Synthesis of 1-(2-(tert-butyl)pyridin-4-yl)-2-cyclopropyl-6-(methylthio)-1,2-dihydro-3H-pyrazolo[3,4-d]pyrimidin-3-one To a stirred solution of 2-cyclopropyl-6-(methylthio)-1,2-dihydro-3H-pyrazolo[3,4-d]pyrimidin-3-one (600 mg, 2.69 mmol, 1 eq) and 2-(tert-butyl)-4-(4,4,5,5-tetramethyl-1,3,2-dioxaborolan-2-yl)pyridine (1.05 g, 4.04 mmol, 1.5 eq) in DCM (100 mL) was added 2,2-bipyridine (840 mg, 5.38 mmol, 2 eq), copper acetate (977 mg, 5.38 mmol, 2 eq) and $Na_2CO_3$ (855 mg, 8.07 mmol, 3 eq). The reaction mixture was stirred at rt for 24 h in open air. The progress of reaction was monitored by TLC. After completion, the reaction mixture was filtered over celite to remove inorganic impurities. The filtrate was washed with water, dried over $Na_2SO_4$, concentrated and purified by column chromatography (Combiflash, Elution: 0-30% EtOAc in Hexane) to afford the desired product, 1-(2-(tert-butyl)pyridin-4-yl)-2-cyclopropyl-6-(methylthio)-1,2-dihydro-3H-pyrazolo[3,4-d]pyrimidin-3-one (392 mg, 40.85%) as an off white solid.

LCMS: 356.2 $[M+1]^+$

Step-2: Synthesis of tert-butyl 6-((1-(2-(tert-butyl)pyridin-4-yl)-2-cyclopropyl-3-oxo-2,3-dihydro-1H-pyrazolo[3,4-d]pyrimidin-6-yl)amino)-3,4-dihydroisoquinoline-2(1H)-carboxylate)

To a stirred solution of 1-(2-(tert-butyl)pyridin-4-yl)-2-cyclopropyl-6-(methylthio)-1,2-dihydro-3H-pyrazolo[3,4-d]pyrimidin-3-one (196 mg, 0.548 mmol, 1.0 eq) in (6.0 mL) of toluene was added m-CPBA (189 mg, 1.096 mmol, 2.0 eq) and allowed to stir at rt for 1 h. tert-butyl 6-amino-3,4-dihydroisoquinoline-2(1H)-carboxylate (163 mg, 0.657 mmol, 1.2 eq) and DIPEA (0.37 mL, 2.192 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((1-(2-(tert-butyl)pyridin-4-yl)-2-cyclopropyl-3-oxo-2,3-dihydro-1H-pyrazolo[3,4-d]pyrimidin-6-yl)amino)-3,4-dihydroisoquinoline-2(1H)-carboxylate (50 mg, 16.31%) as an off white solid.

LCMS: 556.3 $[M+1]^+$

Step-3: Synthesis of 1-(2-(tert-butyl)pyridin-4-yl)-2-cyclopropyl-6-((1,2,3,4-tetrahydroisoquinolin-6-yl)amino)-1,2-dihydro-3H-pyrazolo[3,4-d]pyrimidin-3-one dihydrochloride tert-butyl 6-((1-(2-(tert-butyl)pyridin-4-yl)-2-cyclopropyl-3-oxo-2,3-dihydro-1H-pyrazolo[3,4-d]pyrimidin-6-yl)amino)-3,4-dihydroisoquinoline-2(1H)-carboxylate (50 mg, 0.179 mmol, 1.0 eq) was dissolved in dioxane (0.6 mL), followed by dropwise addition of 4.0M-HCl (0.6 mL) and allowed to stir at rt for 1 h. After completion of reaction, the reaction mixture was filtered and dried under reduced pressure to afford the desired compound, 1-(2-(tert-butyl)pyridin-4-yl)-2-cyclopropyl-6-((1,2,3,4-tetrahydroisoquinolin-6-yl)amino)-1,2-dihydro-3H-pyrazolo[3,4-d]pyrimidin-3-one dihydrochloride (36 mg, 75.70%) as light yellow solid.

LCMS: 456.4 $[M+1]^+$; UPLC @ 254 nm=89.33% and @ 220 nm=87.71%.

$^1$H NMR (400 MHz, DMSO-$d_6$): δ 10.39 (br. s., 1H), 9.39 (br. s., 2H), 8.87 (s, 1H), 8.76 (d, J=6.14 Hz, 1H), 7.86 (br. s., 1H), 7.71 (br. s., 1H), 7.56 (br. s., 2H), 7.19 (d, J=8.77 Hz, 1H), 4.22 (br. s., 2H), 3.37 (br. s., 2H), 3.21 (br. s., 1H), 3.01 (br. s., 2H), 1.41 (s, 9H), 0.88 (d, J=6.14 Hz, 2H), 0.83 (br. s., 2H).

Example S63. Synthesis of 1-(2-(tert-butyl)pyridin-4-yl)-2-cyclopropyl-6-((1,2,3,4-tetrahydroisoquinolin-7-yl)amino)-1,2-dihydro-3H-pyrazolo[3,4-d]pyrimidin-3-one dihydrochloride (Compound No. 1.160)

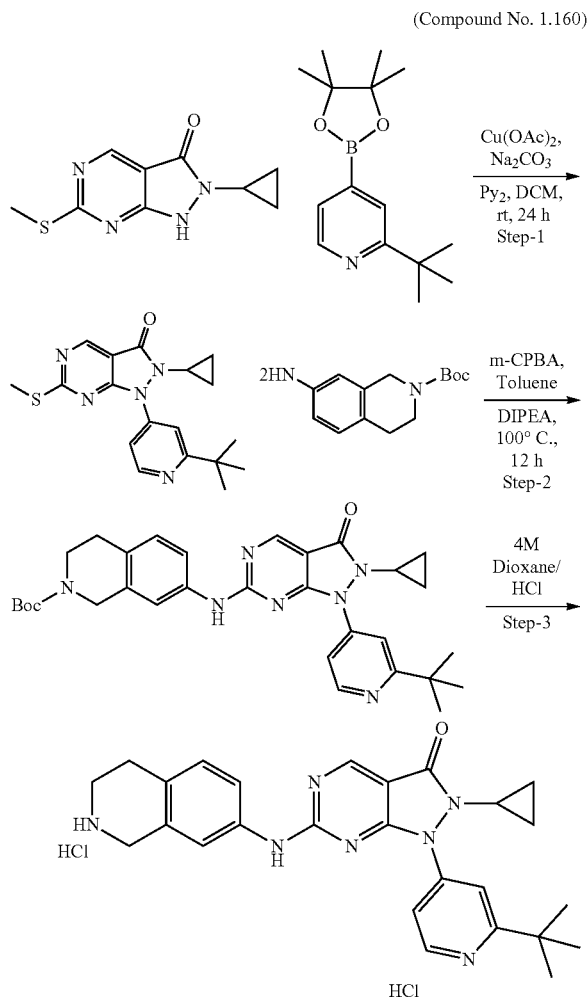

Step-1: Synthesis of 1-(2-(tert-butyl)pyridin-4-yl)-2-cyclopropyl-6-(methylthio)-1,2-dihydro-3H-pyrazolo[3,4-d]pyrimidin-3-one To a stirred solution of 2-cyclopropyl-6-(methylthio)-1,2-dihydro-3H-pyrazolo[3,4-d]pyrimidin-3-one (600 mg, 2.69 mmol, 1 eq) and 2-(tert-butyl)-4-(4,4,5,5-tetramethyl-1,3,2-dioxaborolan-2-yl)pyridine (1.05 g, 4.04 mmol, 1.5 eq) in DCM (100 mL) was added 2,2-bipyridine (840 mg, 5.38 mmol, 2 eq), copper acetate (977 mg, 5.38 mmol, 2 eq) and Na$_2$CO$_3$ (855 mg, 8.07 mmol, 3 eq). The reaction mixture was stirred at rt for 24 h in open air. The progress of reaction was monitored by TLC. After completion, the reaction mixture was filtered over celite to remove inorganic impurities. The filtrate was washed with water, dried over Na$_2$SO$_4$, concentrated and purified by column chromatography (Combiflash, Elution: 0-30% EtOAc in Hexane) to afford the desired product, 1-(2-(tert-butyl)pyridin-4-yl)-2-cyclopropyl-6-(methylthio)-1,2-dihydro-3H-pyrazolo[3,4-d]pyrimidin-3-one (392 mg, 40.85%) as an off white solid.
LCMS: 356.2 [M+1]$^+$

Step-2: Synthesis of tert-butyl 7-((1-(2-(tert-butyl)pyridin-4-yl)-2-cyclopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(2-(tert-butyl)pyridin-4-yl)-2-cyclopropyl-6-(methylthio)-1,2-dihydro-3H-pyrazolo[3,4-d]pyrimidin-3-one (196 mg, 0.548 mmol, 1.0 eq) in (6.0 mL) of toluene was added m-CPBA (189 mg, 1.096 mmol, 2.0 eq) and allowed to stir at rt for 1 h. tert-butyl 6-amino-3,4-dihydroisoquinoline-2(1H)-carboxylate (163 mg, 0.657 mmol, 1.2 eq) and DIPEA (0.37 mL, 2.192 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 7-((1-(2-(tert-butyl)pyridin-4-yl)-2-cyclopropyl-3-oxo-2,3-dihydro-1H-pyrazolo[3,4-d]pyrimidin-6-yl)amino)-3,4-dihydroisoquinoline-2(1H)-carboxylate (100 mg, 32.63%) as an off white solid.
LCMS: 556.3 [M+1]$^+$

Step-3: Synthesis of 1-(2-(tert-butyl)pyridin-4-yl)-2-cyclopropyl-6-((1,2,3,4-tetrahydroisoquinolin-7-yl)amino)-1,2-dihydro-3H-pyrazolo[3,4-d]pyrimidin-3-one dihydrochloride tert-butyl 7-((1-(2-(tert-butyl)pyridin-4-yl)-2-cyclopropyl-3-oxo-2,3-dihydro-1H-pyrazolo[3,4-d]pyrimidin-6-yl)amino)-3,4-dihydroisoquinoline-2(1H)-carboxylate (100 mg, 0.179 mmol, 1.0 eq) was dissolved in dioxane (1.2 mL), followed by dropwise addition of 4.0M-HCl (1.2 mL) and allowed to stir at rt for 1 h. After completion of reaction, the reaction mixture was filtered and dried under reduced pressure to afford the desired compound, 1-(2-(tert-butyl)pyridin-4-yl)-2-cyclopropyl-6-((1,2,3,4-tetrahydroisoquinolin-7-yl)amino)-1,2-dihydro-3H-pyrazolo[3,4-d]pyrimidin-3-one dihydrochloride (66 mg, 69.40%) as light yellow solid.
LCMS: 456.4 [M+1]$^+$; UPLC @ 254 nm=93.54% and @ 220 nm=92.28%.
$^1$H NMR (400 MHz, DMSO-d$_6$): δ 10.41 (br. s., 1H), 9.40 (br. s., 2H), 8.87 (s, 1H), 8.78 (d, J=6.14 Hz, 1H), 7.89 (br. s., 1H), 7.72 (br. s., 1H), 7.51-7.59 (m, 2H), 7.21 (d, J=8.77 Hz, 1H), 4.27 (br. s., 2H), 3.37 (br. s., 2H), 3.22 (br. s., 1H), 2.95-3.01 (m, 2H), 1.44 (br. s., 1H), 1.41 (s, 9H), 0.89 (d, J=6.58 Hz, 2H), 0.76-0.84 (m, 2H).

Example S64. Synthesis of 1-(4-(tert-butyl)pyridin-2-yl)-2-isopropyl-6-((1,2,3,4-tetrahydroisoquinolin-7-yl)amino)-1,2-dihydro-3H-pyrazolo[3,4-d]pyrimidin-3-one (Compound No. 2.287)

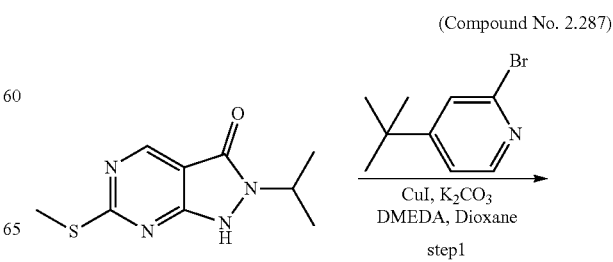

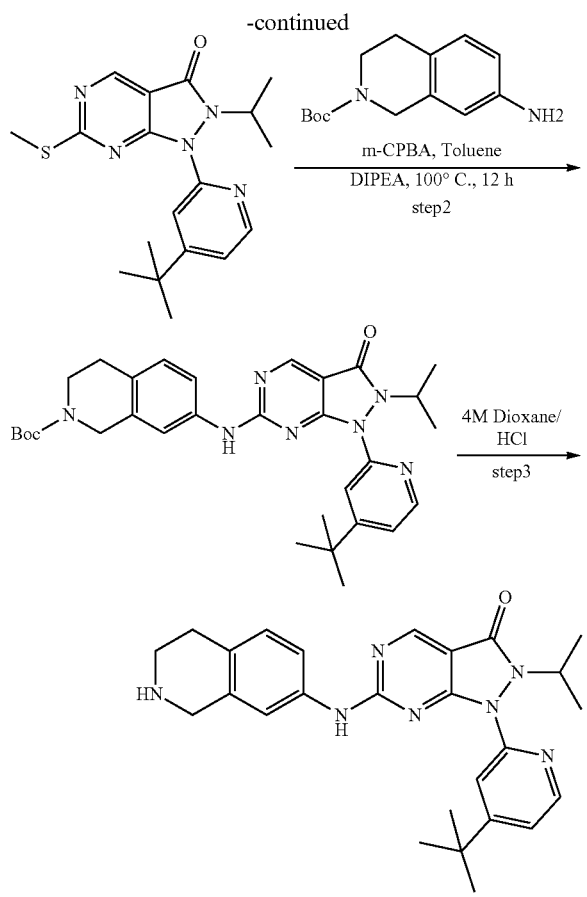

Step-1: Synthesis of 1-(4-(tert-butyl)pyridin-2-yl)-2-isopropyl-6-(methylthio)-1,2-dihydro-3H-pyrazolo[3,4-d]pyrimidin-3-one To a stirred solution of 2-isopropyl-6-(methylthio)-1,2-dihydro-3H-pyrazolo[3,4-d]pyrimidin-3-one (300 mg, 1.337 mmol, 1.0 eq) and 2-bromo-4-(tert-butyl)pyridine (294 mg, 1.36 mmol, 1.20 eq) in (8 mL) of dioxane was added potassium carbonate (370 mg, 2.674 mmol, 2.0 eq) and the resulting mixture was purged with nitrogen for 10 min, followed by addition of copper iodide (51 mg, 0.27 mmol, 0.2 eq), and N,N'-dimethylethylenediamine (DMEDA) (47 mg, 0.535 mmol, 0.4 eq) and again purged with nitrogen for 10 min, stirred at 90° C. for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-30% EtOAc in hexane] to afford the desired product, 1-(4-(tert-butyl)pyridin-2-yl)-2-isopropyl-6-(methylthio)-1,2-dihydro-3H-pyrazolo[3,4-d]pyrimidin-3-one (270 mg, 56.5%) as yellow solid.

LCMS: 359.3 [M+1]$^+$

Step-2: tert-butyl 7-((1-(4-(tert-butyl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(4-(tert-butyl)pyridin-2-yl)-2-isopropyl-6-(methylthio)-1,2-dihydro-3H-pyrazolo[3,4-d]pyrimidin-3-one (120 mg, 0.34 mmol, 1.0 eq) in (2.0 mL) of toluene was added mCPBA (91 mg, 0.37, 1.1 eq) and allowed to stir at rt for 30 minutes. tert-butyl 7-amino-3,4-dihydroisoquinoline-2(1H)-carboxylate (102 mg, 0.408 mmol, 1.2 eq) and DIPEA (0.30 mL, 1.7 mmol, 5.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography to afford the desired product, tert-butyl 7-((1-(4-(tert-butyl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (68 mg, 35.98%) as brown solid.

LCMS: 558.5 [M+1]$^+$

Step-3: Synthesis of 1-(4-(tert-butyl)pyridin-2-yl)-2-isopropyl-6-((1,2,3,4-tetrahydroisoquinolin-7-yl)amino)-1,2-dihydro-3H-pyrazolo[3,4-d]pyrimidin-3-one tert-butyl 7-((1-(4-(tert-butyl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (65 mg, 0.117 mmol, 1.0 eq) was dissolved in dioxane (1 mL), followed by dropwise addition of 4.0M-HCl (0.5 mL) and allowed to stir at rt for 1 h. After completion of reaction, the reaction mixture was filtered and dried under reduced pressure to afford the desired compound 1-(4-(tert-butyl)pyridin-2-yl)-2-isopropyl-6-((1,2,3,4-tetrahydroisoquinolin-7-yl)amino)-1,2-dihydro-3H-pyrazolo[3,4-d]pyrimidin-3-one (46 mg, 95.83%) as an off white solid.

LCMS: 458.3 [M+1]$^+$; UPLC @ 254 nm=98.87% and @ 220 nm=99.76%.

$^1$H NMR (400 MHz, DMSO-d$_6$): δ 10.22 (br. s., 1H), 9.31 (br. s., 2H), 8.83 (s, 1H), 8.50 (d, J=5.26 Hz, 1H), 7.65 (s, 2H), 7.49 (d, J=3.95 Hz, 1H), 7.42 (br. s., 1H), 7.09 (d, J=8.33 Hz, 1H), 4.17 (br. s., 2H), 3.33 (br. s., 2H), 2.90-2.97 (m, 2H), 1.33 (s, 9H), 1.26 (d, J=7.02 Hz, 6H).

Example S65. Synthesis of 1-(4-(tert-butyl)pyridin-2-yl)-2-isopropyl-6-((1,2,3,4-tetrahydroisoquinolin-6-yl)amino)-1,2-dihydro-3H-pyrazolo[3,4-d]pyrimidin-3-one (Compound No. 2.288)

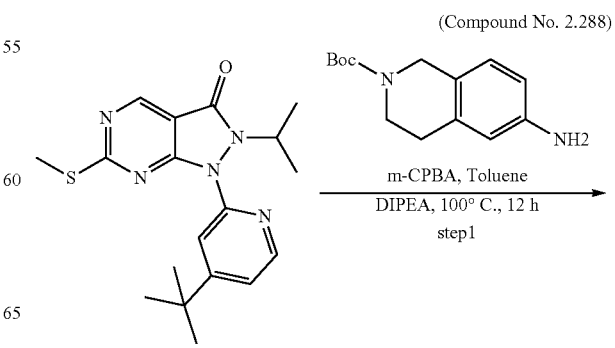

811

-continued

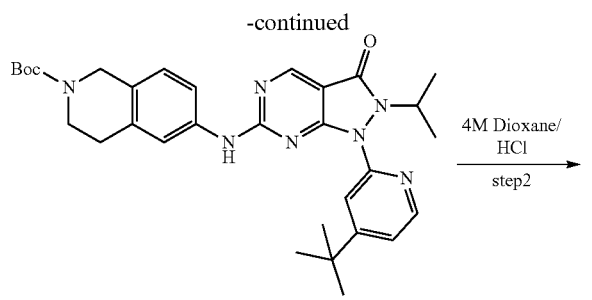

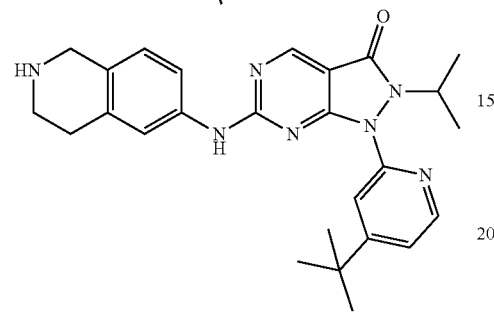

Step-1: tert-butyl 6-((1-(4-(tert-butyl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(4-(tert-butyl)pyridin-2-yl)-2-isopropyl-6-(methylthio)-1,2-dihydro-3H-pyrazolo[3,4-d]pyrimidin-3-one (120 mg, 0.34 mmol, 1.0 eq) in (2.0 mL) of toluene was added mCPBA (91 mg, 0.37, 1.1 eq) and allowed to stir at rt for 30 minutes. tert-butyl 6-amino-3,4-dihydroisoquinoline-2(1H)-carboxylate (102 mg, 0.408 mmol, 1.2 eq) and DIPEA (0.30 mL, 1.7 mmol, 5.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography to afford the desired product, tert-butyl 6-((1-(4-(tert-butyl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (50 mg, 26.24%) as brown solid.

LCMS: 558.5 [M+1]$^+$

Step-2: Synthesis of 1-(4-(tert-butyl)pyridin-2-yl)-2-isopropyl-6-((1,2,3,4-tetrahydroisoquinolin-6-yl)amino)-1,2-dihydro-3H-pyrazolo[3,4-d]pyrimidin-3-one tert-butyl 6-((1-(4-(tert-butyl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (50 mg, 0.09 mmol, 1.0 eq) was dissolved in dioxane (1 mL), followed by dropwise addition of 4.0M-HCl (0.5 mL) and allowed to stir at rt for 1 h. After completion of reaction, the reaction mixture was filtered and dried under reduced pressure to afford the desired compound 1-(4-(tert-butyl)pyridin-2-yl)-2-isopropyl-6-((1,2,3,4-tetrahydroisoquinolin-6-yl)amino)-1,2-dihydro-3H-pyrazolo[3,4-d]pyrimidin-3-one (40 mg, 97.5%) as light brown solid.

812

LCMS: 458.3 [M+1]$^+$; UPLC @ 254 nm=96.51% and @ 220 nm=99.29%.

$^1$H NMR (400 MHz, DMSO-d$_6$): δ 10.22 (br. s., 1H), 9.42 (br. s., 2H), 8.84 (s, 1H), 8.51 (d, J=5.26 Hz, 1H), 7.59-7.69 (m, 2H), 7.44-7.52 (m, 2H), 7.07 (d, J=8.33 Hz, 1H), 4.12-4.21 (m, 3H), 3.33 (br. s., 2H), 2.92 (br. s., 2H), 1.33 (s, 9H), 1.25 (d, J=6.58 Hz, 6H).

Example S66. Synthesis of 1-(2-(tert-butyl)pyridin-4-yl)-6-((2',3'-dihydro-1'H-spiro[cyclopropane-1,4'-isoquinolin]-7'-yl)amino)-2-isopropyl-1,2-dihydro-3H-pyrazolo[3,4-d]pyrimidin-3-one dihydrochloride (Compound No. 1.161)

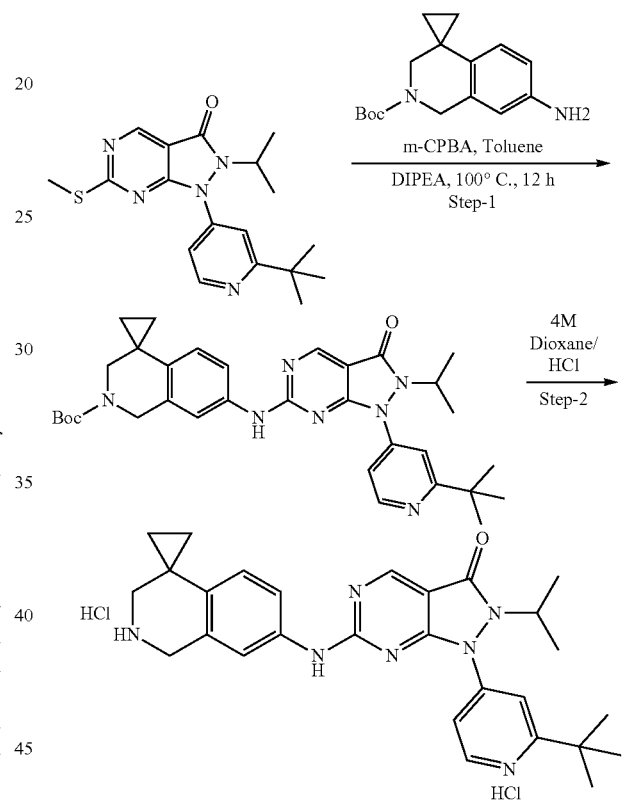

Step-1: Synthesis of tert-butyl 7'-((1-(2-(tert-butyl)pyridin-4-yl)-2-isopropyl-3-oxo-2,3-dihydro-1H-pyrazolo[3,4-d]pyrimidin-6-yl)amino)-1'H-spiro[cyclopropane-1,4'-isoquinoline]-2'(3'H)-carboxylate To a stirred solution of 1-(2-(tert-butyl)pyridin-4-yl)-2-isopropyl-6-(methylthio)-1,2-dihydro-3H-pyrazolo[3,4-d]pyrimidin-3-one (150 mg, 0.419 mmol, 1.0 eq) in (6.0 mL) of toluene was added m-CPBA (145 mg, 0.838 mmol, 2.0 eq) and allowed to stir at rt for 1 h. tert-butyl 7'-amino-1'H-spiro[cyclopropane-1,4'-isoquinoline]-2'(3'H)-carboxylate (138 mg, 0.503 mmol, 1.2 eq) and DIPEA (0.28 mL, 1.676 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 7'-((1-(2-(tert-butyl)pyridin-4-yl)-2-isopropyl-3-oxo-2,3-dihydro-1H-pyrazolo[3,4-d]pyrimidin-6-yl)amino)-1'H-spiro[cyclopropane-1,4'-isoquinoline]-2'(3'H)-carboxylate (110 mg, 61.24%) as an off white solid.

LCMS: 584.3 [M+1]$^+$

Step-2: Synthesis of 1-(2-(tert-butyl)pyridin-4-yl)-6-((2',3'-dihydro-1'H-spiro[cyclopropane-1,4'-isoquinolin]-7'-yl)amino)-2-isopropyl-1,2-dihydro-3H-pyrazolo[3,4-d]pyrimidin-3-one dihydrochloride tert-butyl 7'-((1-(2-(tert-butyl)pyridin-4-yl)-2-isopropyl-3-oxo-2,3-dihydro-1H-pyrazolo[3,4-d]pyrimidin-6-yl)amino)-1'H-spiro[cyclopropane-1,4'-isoquinoline]-2'(3'H)-carboxylate (110 mg, 0.188 mmol, 1.0 eq) was dissolved in dioxane (1 mL), followed by dropwise addition of 4.0M-HCl (2 mL) and allowed to stir at rt for 1 h. After completion of reaction, the reaction mixture was filtered and dried under reduced pressure to afford the desired compound, 1-(2-(tert-butyl)pyridin-4-yl)-6-((2',3'-dihydro-1'H-spiro[cyclopropane-1,4'-isoquinolin]-7'-yl)amino)-2-isopropyl-1,2-dihydro-3H-pyrazolo[3,4-d]pyrimidin-3-one dihydrochloride (63 mg, 60.07%) as light yellow solid.

LCMS: 484.4 [M+1]$^+$; UPLC @ 254 nm=95.36% and @ 220 nm=97.34%.

$^1$H NMR (400 MHz, DMSO-d$_6$): δ 10.53 (br. s., 1H), 9.49 (br. s., 2H), 8.88 (s, 1H), 8.80 (br. s., 1H), 7.80 (br. s., 1H), 7.54 (br. s., 3H), 6.85 (d, J=8.33 Hz, 1H), 4.39 (br. s., 2H), 3.26 (br. s., 3H), 1.25-1.52 (m, 14H), 1.09 (br. s., 4H).

Example S67. Synthesis of 1-(2-(tert-butyl)pyridin-4-yl)-6-((4,4-dimethyl-1,2,3,4-tetrahydroisoquinolin-7-yl)amino)-2-isopropyl-1,2-dihydro-3H-pyrazolo[3,4-d]pyrimidin-3-one dihydrochloride (Compound No. 1.162)

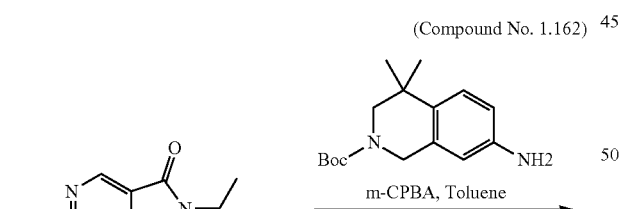

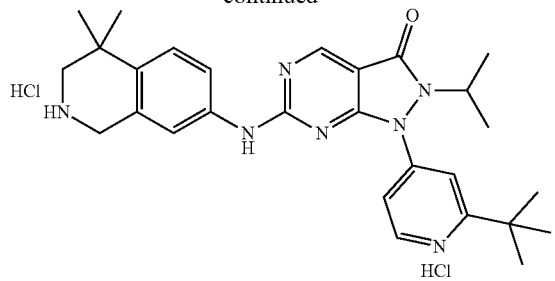

Step-1: Synthesis of tert-butyl 7-((1-(2-(tert-butyl)pyridin-4-yl)-2-isopropyl-3-oxo-2,3-dihydro-1H-pyrazolo[3,4-d]pyrimidin-6-yl)amino)-4,4-dimethyl-3,4-dihydroisoquinoline-2(1H)-carboxylate To a stirred solution of 1-(2-(tert-butyl)pyridin-4-yl)-2-isopropyl-6-(methylthio)-1,2-dihydro-3H-pyrazolo[3,4-d]pyrimidin-3-one (150 mg, 0.419 mmol, 1.0 eq) in (6.0 mL) of toluene was added m-CPBA (145 mg, 0.838 mmol, 2.0 eq) and allowed to stir at rt for 1 h. tert-butyl 7-amino-4,4-dimethyl-3,4-dihydroisoquinoline-2(1H)-carboxylate (138 mg, 0.503 mmol, 1.2 eq) and DIPEA (0.28 mL, 1.676 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 7-((1-(2-(tert-butyl)pyridin-4-yl)-2-isopropyl-3-oxo-2,3-dihydro-1H-pyrazolo[3,4-d]pyrimidin-6-yl)amino)-4,4-dimethyl-3,4-dihydroisoquinoline-2(1H)-carboxylate (60 mg, 24.41%) as an off white solid.

LCMS: 586.3 [M+1]$^+$

Step-2: Synthesis of 1-(2-(tert-butyl)pyridin-4-yl)-6-((4,4-dimethyl-1,2,3,4-tetrahydroisoquinolin-7-yl)amino)-2-isopropyl-1,2-dihydro-3H-pyrazolo[3,4-d]pyrimidin-3-one dihydrochloride tert-butyl 7-((1-(2-(tert-butyl)pyridin-4-yl)-2-isopropyl-3-oxo-2,3-dihydro-1H-pyrazolo[3,4-d]pyrimidin-6-yl)amino)-4,4-dimethyl-3,4-dihydroisoquinoline-2(1H)-carboxylate (60 mg, 0.102 mmol, 1.0 eq) was dissolved in dioxane (1 mL), followed by dropwise addition of 4.0M-HCl (2 mL) and allowed to stir at rt for 1 h. After completion of reaction, the reaction mixture was filtered and dried under reduced pressure to afford the desired compound, 1-(2-(tert-butyl)pyridin-4-yl)-6-((4,4-dimethyl-1,2,3,4-tetrahydroisoquinolin-7-yl)amino)-2-isopropyl-1,2-dihydro-3H-pyrazolo[3,4-d]pyrimidin-3-one dihydrochloride (36 mg, 62.92%) as light yellow solid.

LCMS: 486.4 [M+1]$^+$; UPLC @ 254 nm=96.12% and @ 220 nm=97.81%.

$^1$H NMR (400 MHz, DMSO-d$_6$): δ 10.48 (br. s., 1H), 9.31 (br. s., 2H), 8.88 (s, 1H), 8.76 (br. s., 1H), 7.72 (br. s., 1H), 7.45-7.58 (m, 3H), 7.43 (br. s., 1H), 4.27 (br. s., 2H), 3.89-4.01 (m, 2H), 3.23 (br. s., 2H), 1.16-1.44 (m, 21H).

815

Example S68. Synthesis of 1-(2-(2-fluoropropan-2-yl)pyridin-4-yl)-2-isopropyl-6-((1,2,3,4-tetrahydroisoquinolin-6-yl)amino)-1,2-dihydro-3H-pyrazolo[3,4-d]pyrimidin-3-one dihydrochloride (Compound No. 1.163)

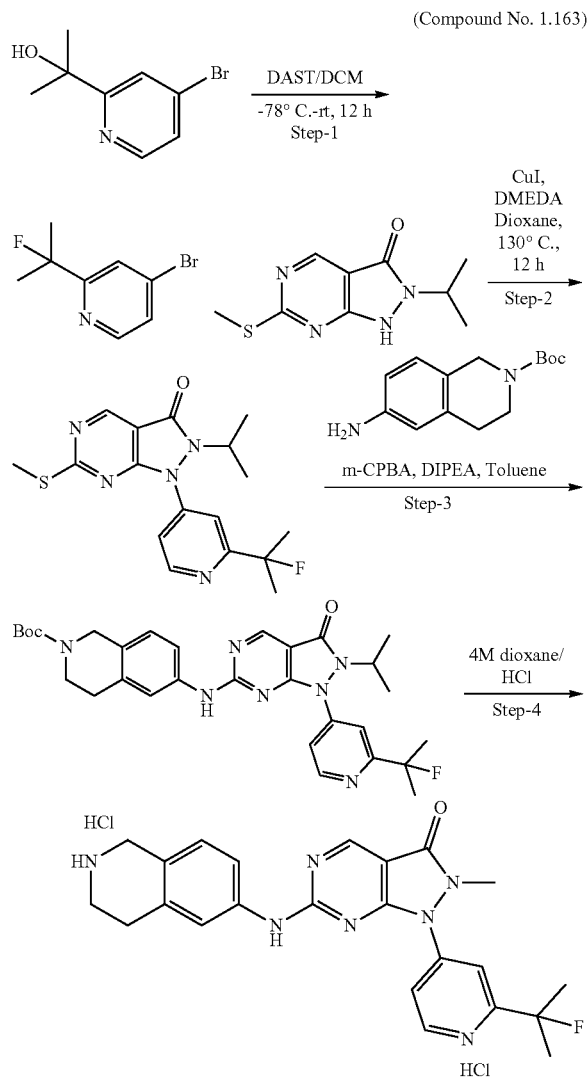

Step-1: Synthesis of 4-bromo-2-(2-fluoropropan-2-yl)pyridine

To a stirred solution of 2-(4-bromopyridin-2-yl)propan-2-ol (0.5 g, 2.313 mmol, 1.0 eq) in DCM (7 mL) was added DAST (0.33 mL, 2.545 mmol, 1.1 eq) at −78° C. The reaction mixture was stirred at rt for 12 h. After completion of reaction, the reaction mixture was quenched with NaHCO₃ solution and was extracted with DCM (100 mL×2). The combined organic layer were dried over Na2SO4, concentrated under reduced pressure and purified by column chromatography [Combiflash, elution: 0-50% EtOAc in hexane] to afford the desired compound, 4-bromo-2-(2-fluoropropan-2-yl)pyridine (250 mg, 49.54%) as yellow liquid.

LCMS: 218.2/220.2 [M+2]$^+$

816

Step-2: Synthesis of 1-(2-(2-fluoropropan-2-yl)pyridin-4-yl)-2-isopropyl-6-(methylthio)-1,2-dihydro-3H-pyrazolo[3,4-d]pyrimidin-3-one To a stirred solution of 2-isopropyl-6-(methylthio)-1,2-dihydro-3H-pyrazolo[3,4-d]pyrimidin-3-one (500 mg, 2.22 mmol, 1.0 eq) and 4-bromo-2-(2-fluoropropan-2-yl)pyridine (580 mg, 2.675 mmol, 1.2 eq) in (8 mL) of dioxane were added Potassium carbonate (620 mg, 4.45 mmol, 2.0 eq) and the resulting mixture was purged with nitrogen for 10 min, followed by addition of copper iodide (85 mg, 0.44 mmol, 0.2 eq), and N,N'-dimethylethylenediamine (DMEDA) (0.1 mL, 0.891 mmol, 2 eq) and again purged with nitrogen for 10 min, stirred at 130° C. for overnight. After completion of reaction, the reaction mixture was diluted with water and extracted with EtOAc (30 mL×2). The combined organic layers were washed with water (30 mL), brine solution (30 mL), dried over anhydrous sodium sulphate and concentrated under reduced pressure to afford crude product, which was purified by flash chromatography to afford the desired compound, 2-isopropyl-1-(6-(2-hydroxypropan-2-yl)pyridin-2-yl)-6-(methylthio)-1,2-dihydro-3H-pyrazolo[3,4-d]pyrimidin-3-one (150 mg, 68.19%) as an off white solid.

LCMS: 362.3 [M+1]$^+$

Step-3: Synthesis of tert-butyl 6-((1-(2-(2-fluoropropan-2-yl)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(2-(2-fluoropropan-2-yl)pyridin-4-yl)-2-isopropyl-6-(methylthio)-1,2-dihydro-3H-pyrazolo[3,4-d]pyrimidin-3-one (150 mg, 0.415 mmol, 1.0 eq) in (5 mL) of toluene was added m-CPBA (143.4 mg, 0.830 mmol, 2.0 eq) and allowed to stir at rt for 30 min. tert-butyl 6-amino-3,4-dihydroisoquinoline-2(1H)-carboxylate (123 mg, 0.498 mmol, 1.2 eq) and DIPEA (0.3 mL, 1.662 mmol, 4.0 eq) were added and allowed to stir at 80° C. for overnight. Solvent was evaporated and reaction mass was diluted with water and extracted with EtOAc (30 mL×2). The combined organic layer were dried over sodium sulphate, concentrated under reduced pressure purified by column chromatography (Combiflash, elution-0-70% EtOAc in Hexane) to afford the desired compound, tert-butyl 6-((1-(2-(2-fluoropropan-2-yl)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate (52 mg, 22.30%) as yellow liquid.

LCMS: 562.5 [M+1]$^+$

Step-4: Synthesis of 1-(2-(2-fluoropropan-2-yl)pyridin-4-yl)-2-isopropyl-6-((1,2,3,4-tetrahydroisoquinolin-6-yl)amino)-1,2-dihydro-3H-pyrazolo[3,4-d]pyrimidin-3-one dihydrochloride To a stirred solution of tert-butyl 6-((1-(2-(2-fluoropropan-2-yl)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate (52 mg, 92.691 mmol, 1.0 eq) in (1 mL) of dioxane was added 4M dioxane-HCl (0.6 mL) and allowed to stir at rt for 2 h. After completion of reaction, the reaction mixture was filtered and dried under reduced pressure to afford the desired compound, 1-(2-(2-fluoropropan-2-yl)pyridin-4-yl)-2-isopropyl-6-((1,2,3,4-tetrahydroisoquinolin-6-yl)amino)-1,2-dihydro-3H-pyrazolo[3,4-d]pyrimidin-3-one dihydrochloride (20 mg, 40.42%) as yellow solid.

LCMS: 462.3 [M+1]⁺, UPLC @ 254 nm=86.26% and @ 220 nm=92.47%.
¹H NMR (400 MHz, DMSO-$d_6$): 10.48 (br. s., 1H), 9.08 (br. s., 2H), 8.87 (s, 1H), 8.72 (d, J=5.26 Hz, 1H), 7.60 (s, 1H), 7.63 (s, 2H), 7.18 (d, J=7.89 Hz, 1H), 4.23 (br. s., 2H), 3.97 (d, J=6.14 Hz, 2H), 3.63 (br. s., 8H), 3.01 (br. s., 2H), 1.72 (s, 2H), 1.67 (s, 2H), 1.36 (d, J=6.58 Hz, 7H), 1.24 (br. s., 1H)

Example S69. Synthesis of 1-(2-(tert-butyl)pyridin-4-yl)-6-((2-(dimethylamino)-2,3-dihydro-1H-inden-5-yl)amino)-2-isopropyl-1,2-dihydro-3H-pyrazolo[3,4-d]pyrimidin-3-one

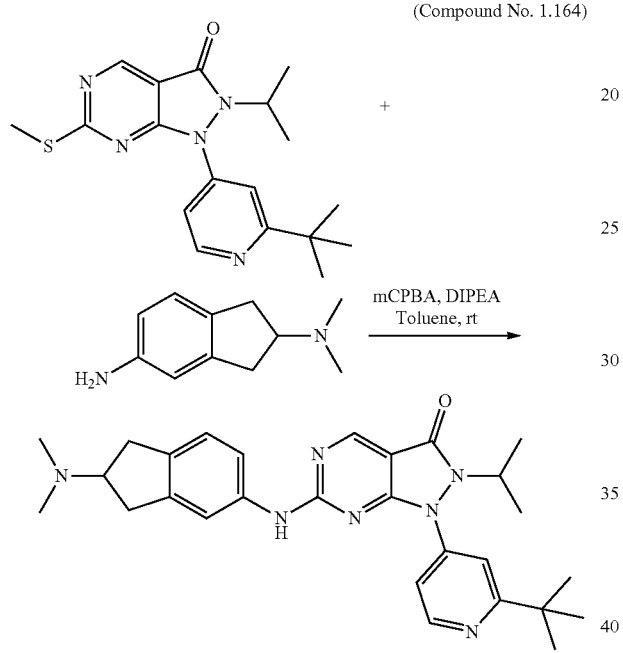

(Compound No. 1.164)

To a stirred solution of 1-(2-(tert-butyl)pyridin-4-yl)-2-isopropyl-6-(methylthio)-1,2-dihydro-3H-pyrazolo[3,4-d]pyrimidin-3-one (90 mg, 0.251 mmol, 1.0 eq) in (2.0 mL) of toluene was added mCPBA (124 mg, 0.502 mmol, 2.0 eq) and allowed to stir at rt for 30 minutes. N2,N2-dimethyl-2,3-dihydro-1H-indene-2,5-diamine (62 mg, 0.302 mmol, 1.2 eq) and DIPEA (0.175 mL, 1.004 mmol, 4.0 eq) were added and allowed to stir at 100° C. for overnight. After completion of reaction, the reaction mixture was diluted with water (20 mL) and extracted with EtOAc (20 mL×2). Combined organic layer was washed with water (50 mL) brine solution (50 mL), dried over anhydrous sodium sulfate and concentrated under reduced pressure to afford crude product, which was purified by reverse phase chromatography to afford the desired 1-(2-(tert-butyl)pyridin-4-yl)-6-((2-(dimethylamino)-2,3-dihydro-1H-inden-5-yl)amino)-2-isopropyl-1,2-dihydro-3H-pyrazolo[3,4-d]pyrimidin-3-one (6.0 mg, 4.91%) as off white solid.
LCMS: 486.4 [M+1]⁺; UPLC @ 254 nm=97.62% and @ 220 nm=96.06%.
¹H NMR (400 MHz, DMSO-$d_6$) δ 10.28 (brs, 1H), 8.81 (s, 1H), 8.64 (d, J=5.26 Hz, 1H), 7.68 (brs, 1H), 7.52 (brs, 1H), 7.43 (brs, 2H), 7.12 (d, J=7.89 Hz, 1H), 3.94 (d, J=6.58 Hz, 1H), 3.66 (brs, 2H), 2.96 (brs, 2H), 2.70 (brs, 2H), 2.20 (s, 6H), 1.28-1.43 (m, 15H).

Example S70. Synthesis of 1-(2-(tert-butyl)pyridin-4-yl)-6-(isoindolin-5-ylamino)-2-isopropyl-1,2-dihydro-3H-pyrazolo[3,4-d]pyrimidin-3-one

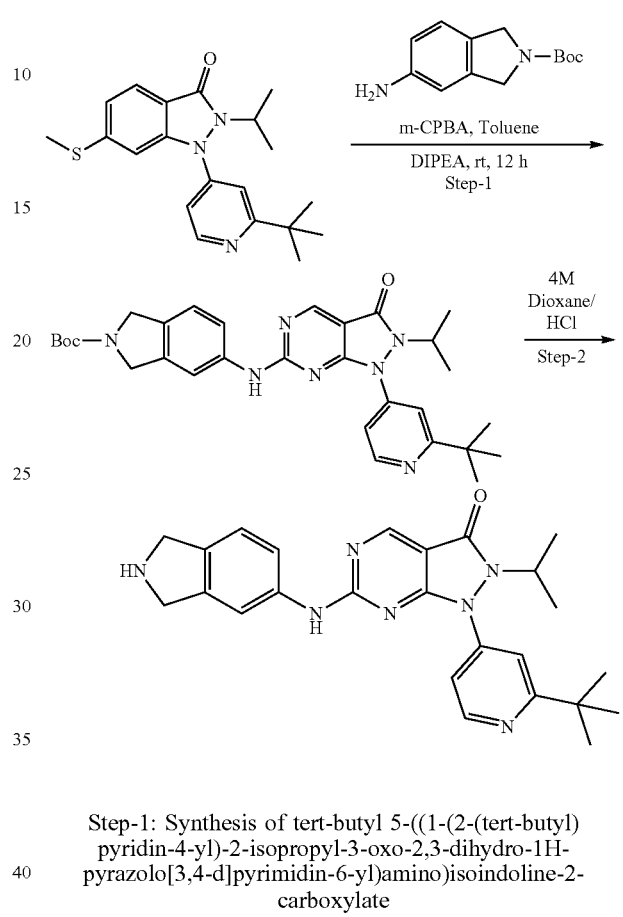

(Compound No. 1.165)

Step-1: Synthesis of tert-butyl 5-((1-(2-(tert-butyl)pyridin-4-yl)-2-isopropyl-3-oxo-2,3-dihydro-1H-pyrazolo[3,4-d]pyrimidin-6-yl)amino)isoindoline-2-carboxylate To a stirred solution of 1-(2-(tert-butyl)pyridin-4-yl)-2-isopropyl-6-(methylthio)-1,2-dihydro-3H-indazol-3-one (120 mg, 0.34 mmol, 1.0 eq) in (2.0 mL) of toluene was added m-CPBA (91 mg, 0.37, 1.1 eq) and allowed to stir at rt for 30 minutes. tert-butyl 5-aminoisoindoline-2-carboxylate (102 mg, 408 mmol, 1.2 eq) and DIPEA (0.30 mL, 1.7 mmol, 5.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography to afford the desired product, tert-butyl 5-((1-(2-(tert-butyl)pyridin-4-yl)-2-isopropyl-3-oxo-2,3-dihydro-1H-pyrazolo[3,4-d]pyrimidin-6-yl)amino)isoindoline-2-carboxylate (40 mg, 21.73%) as brown solid.
LCMS: 544.6 [M+1]⁺

Step-2: Synthesis of 1-(2-(tert-butyl)pyridin-4-yl)-6-(isoindolin-5-ylamino)-2-isopropyl-1,2-dihydro-3H-pyrazolo[3,4-d]pyrimidin-3-one tert-butyl 5-((1-(6-(tert-butyl)pyridin-2-yl)-2-ethyl-3-oxo-2,3-dihydro-1H-pyrazolo[3,4-d]pyrimidin-6-yl)amino)

isoindoline-2-carboxylate (130 mg, 1.321 mmol, 1.0 eq) was dissolved in 4.0M-HCl (1.5 mL) and allowed to stir at rt for 1 h. After completion of reaction, the reaction mixture was filtered and dried under reduced pressure to afford the desired compound 1-(6-(tert-butyl)pyridin-2-yl)-2-ethyl-6-(isoindolin-5-ylamino)-1,2-dihydro-3H-pyrazolo[3,4-d]pyrimidin-3-one dihydrochloride (11 mg, 27.50%) as brown solid.

LCMS: 444.3 [M+1]$^+$; UPLC @ 254 nm=90.44% and @ 220 nm=96.36%.

$^1$H NMR (400 MHz, DMSO-d$_6$) δ 10.62 (br. s., 1H), 9.99 (br. s., 2H), 8.91 (s, 1H), 8.79 (d, J=4.38 Hz, 1H), 7.85 (br. s., 1H), 7.74 (br. s., 1H), 7.56-7.68 (m, 3H), 7.39 (d, J=8.33 Hz, 2H), 4.53 (br. s., 2H), 4.47 (br. s., 2H), 3.96 (m, 1H), 1.35-1.45 (m, 15H).

Example S71. Synthesis of 1-(4-fluorophenyl)-2-isopropyl-6-((1,2,3,4-tetrahydroisoquinolin-6-yl)amino)-1,2-dihydro-3H-pyrazolo[3,4-d]pyrimidin-3-one hydrochloride added 2,2-bipyridine (520 mg, 3.33 mmol), copper acetate (605 mg, 3.33 mmol) and Na$_2$CO$_3$ (706 mg, 6.66 mmol). The reaction mixture was stirred at rt for 24 h in open air. The progress of reaction was monitored by TLC. After completion, the reaction mixture was filtered over celite to remove inorganic impurities. The filtrate was washed with water, dried over Na$_2$SO$_4$, concentrated and purified by column chromatography (Combiflash, Elution: 0-30% EtOAc in Hexane) to afford the desired product, 1-(4-fluorophenyl)-2-isopropyl-6-(methylthio)-1,2-dihydro-3H-pyrazolo[3,4-d]pyrimidin-3-one (270 mg, 38.04%) as an off white solid.

LCMS: 319.2 [M+1]$^+$

Step-2: Synthesis of tert-butyl 6-((1-(4-fluorophenyl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(4-fluorophenyl)-2-isopropyl-6-(methylthio)-1,2-dihydro-3H-pyrazolo[3,4-d]pyrimidin-3-

(Compound No. 1.166)

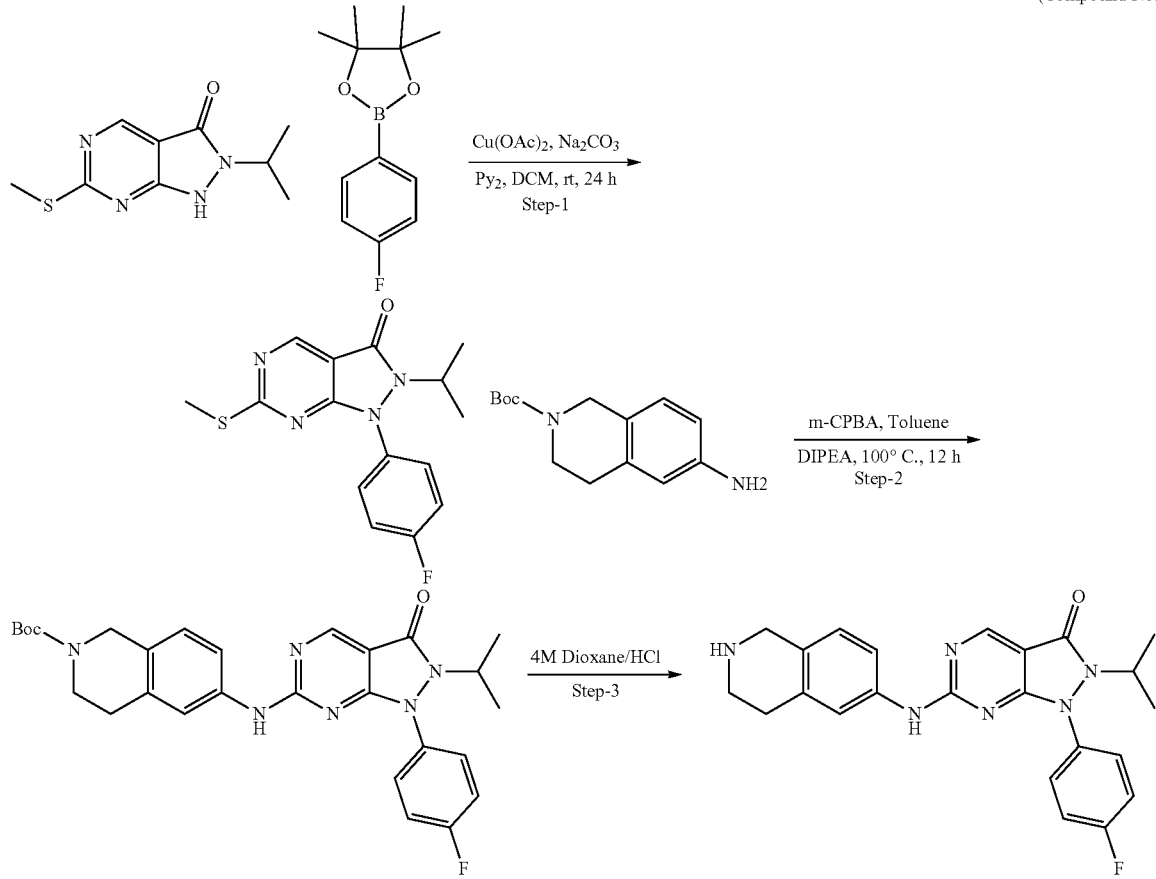

Step-1: Synthesis of 1-(4-fluorophenyl)-2-isopropyl-6-(methylthio)-1,2-dihydro-3H-pyrazolo[3,4-d]pyrimidin-3-one To a stirred solution of 2-isopropyl-6-(methylthio)-1,2-dihydro-3H-pyrazolo[3,4-d]pyrimidin-3-one (500 mg, 2.22 mmol) and 2-(4-fluorophenyl)-4,4,5,5-tetramethyl-1,3,2-dioxaborolane (374 g, 2.67 mmol) in DCM (100 mL) was one (135 mg, 0.424 mmol, 1.0 eq) in (6.0 mL) of toluene was added m-CPBA (146 mg, 0.848 mmol, 2.0 eq) and allowed to stir at rt for 1 h. tert-butyl 6-amino-3,4-dihydroisoquinoline-2(1H)-carboxylate (126 mg, 0.508 mmol, 1.2 eq) and DIPEA (0.29 mL, 1.69 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((1-(4-fluorophenyl)-2-isopropyl-3-oxo-2,3-dihydro-1H-pyrazolo[3,4-d]pyrimidin-6-yl)amino)-3,4-dihydroisoquinoline-2(1H)-carboxylate (50 mg, 22.73%) as an off white solid.

LCMS: 519.3 [M+1]⁺

Step-3: Synthesis of 1-(4-fluorophenyl)-2-isopropyl-6-((1,2,3,4-tetrahydroisoquinolin-6-yl)amino)-1,2-dihydro-3H-pyrazolo[3,4-d]pyrimidin-3-one hydrochloride tert-butyl 6-((1-(4-fluorophenyl)-2-isopropyl-3-oxo-2,3-dihydro-1H-pyrazolo[3,4-d]pyrimidin-6-yl)amino)-3,4-dihydroisoquinoline-2(1H)-carboxylate (50 mg, 0.179 mmol, 1.0 eq) was dissolved in dioxane (0.6 mL), followed by dropwise addition of 4.0M-HCl (0.6 mL) and allowed to stir at rt for 1 h. After completion of reaction, the reaction mixture was filtered and dried under reduced pressure to afford the desired compound, 1-(4-fluorophenyl)-2-isopropyl-6-((1,2,3,4-tetrahydroisoquinolin-6-yl)amino)-1,2-dihydro-3H-pyrazolo[3,4-d]pyrimidin-3-one hydrochloride (10 mg, 24.78%) as light yellow solid.

LCMS: 419.3 [M+1]⁺; UPLC @ 254 nm=98.11% and @ 220 nm=98.37%.

¹H NMR (400 MHz, DMSO-d₆): δ 10.29 (brs, 1H), 9.05 (brs, 2H), 8.83 (s, 1H), 7.69 (brs, 1H), 7.61 (d, J=4.82 Hz, 2H), 7.29-7.49 (m, 3H), 7.13 (d, J=8.77 Hz, 1H), 4.20 (brs, 2H), 4.02-4.12 (m, 1H), 2.93 (brs, 2H), 1.35 (brs, 1H), 1.27 (d, J=6.58 Hz, 6H).

Example S72. Synthesis of 1-(4-fluorophenyl)-2-isopropyl-6-((1,2,3,4-tetrahydroisoquinolin-7-yl)amino)-1,2-dihydro-3H-pyrazolo[3,4-d]pyrimidin-3-one (Compound No. 1.167)

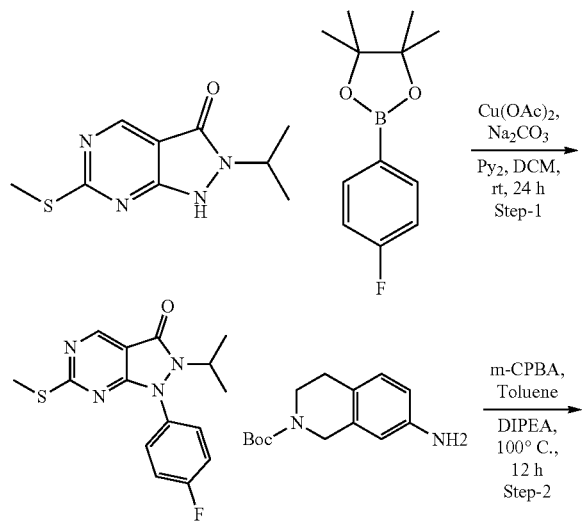

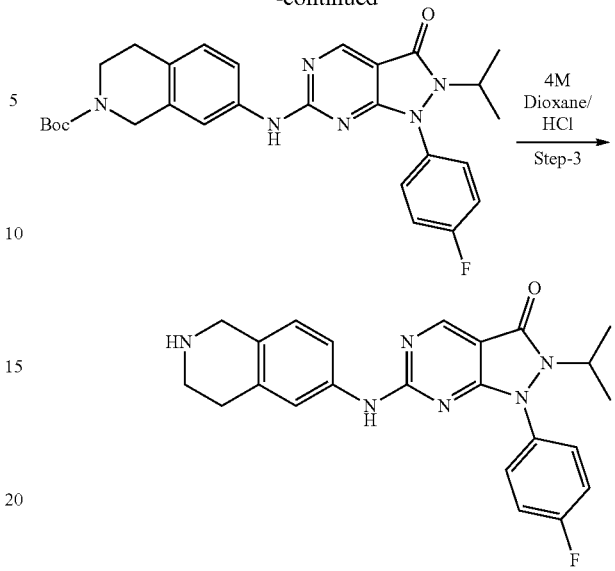

Step-1: Synthesis of 1-(4-fluorophenyl)-2-isopropyl-6-(methylthio)-1,2-dihydro-3H-pyrazolo[3,4-d]pyrimidin-3-one To a stirred solution of 2-isopropyl-6-(methylthio)-1,2-dihydro-3H-pyrazolo[3,4-d]pyrimidin-3-one (500 mg, 2.22 mmol) and 2-(4-fluorophenyl)-4,4,5,5-tetramethyl-1,3,2-dioxaborolane (374 g, 2.67 mmol) in DCM (100 mL) was added 2,2-bipyridine (520 mg, 3.33 mmol), copper acetate (605 mg, 3.33 mmol) and Na₂CO₃ (706 mg, 6.66 mmol). The reaction mixture was stirred at rt for 24 h in open air. The progress of reaction was monitored by TLC. After completion, the reaction mixture was filtered over celite to remove inorganic impurities. The filtrate was washed with water, dried over Na₂SO₄, concentrated and purified by column chromatography (Combiflash, Elution: 0-30% EtOAc in Hexane) to afford the desired product, 1-(4-fluorophenyl)-2-isopropyl-6-(methylthio)-1,2-dihydro-3H-pyrazolo[3,4-d]pyrimidin-3-one (270 mg, 38.04%) as an off white solid.

LCMS: 319.2 [M+1]⁺

Step-2: Synthesis of tert-butyl 7-((1-(4-fluorophenyl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(4-fluorophenyl)-2-isopropyl-6-(methylthio)-1,2-dihydro-3H-pyrazolo[3,4-d]pyrimidin-3-one (135 mg, 0.424 mmol, 1.0 eq) in (6.0 mL) of toluene was added m-CPBA (146 mg, 0.848 mmol, 2.0 eq) and allowed to stir at rt for 1 h. tert-butyl 7-amino-3,4-dihydroisoquinoline-2(1H)-carboxylate (126 mg, 0.508 mmol, 1.2 eq) and DIPEA (0.29 mL, 1.69 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 7-((1-(4-fluorophenyl)-2-isopropyl-3-oxo-2,3-dihydro-1H-pyrazolo[3,4-d]pyrimidin-6-yl)amino)-3,4-dihydroisoquinoline-2(1H)-carboxylate (50 mg, 22.73%) as an off white solid.
LCMS: 519.3 [M+1]+

Step-3: Synthesis of 1-(4-fluorophenyl)-2-isopropyl-6-((1,2,3,4-tetrahydroisoquinolin-7-yl)amino)-1,2-dihydro-3H-pyrazolo[3,4-d]pyrimidin-3-one tert-butyl 7-((1-(4-fluorophenyl)-2-isopropyl-3-oxo-2,3-dihydro-1H-pyrazolo[3,4-d]pyrimidin-6-yl)amino)-3,4-dihydroisoquinoline-2(1H)-carboxylate (50 mg, 0.179 mmol, 1.0 eq) was dissolved in dioxane (0.6 mL), followed by dropwise addition of 4.0M-HCl (0.6 mL) and allowed to stir at rt for 1 h. After completion of reaction, the reaction mixture was filtered and dried under reduced pressure to afford the desired compound, 1-(4-fluorophenyl)-2-isopropyl-6-((1,2,3,4-tetrahydroisoquinolin-7-yl)amino)-1,2-dihydro-3H-pyrazolo[3,4-d]pyrimidin-3-one (10 mg, 24.78%) as light yellow solid.
LCMS: 419.3 [M+1]+; UPLC @ 254 nm=98.25% and @ 220 nm=98.37%.
1H NMR (400 MHz, DMSO-d6): δ 10.26 (brs, 1H), 9.05 (brs, 2H), 8.83 (s, 1H), 7.70 (brs, 1H), 7.55-7.66 (m, 2H), 7.30-7.47 (m, 3H), 7.11 (d, J=8.33 Hz, 1H), 4.19 (brs, 2H), 4.06-4.14 (m, 1H), 2.92 (brs, 2H), 1.27 (d, J=7.02 Hz, 6H).

Example S73. Synthesis of 1-(2-(2-fluoropropan-2-yl)pyridin-4-yl)-2-isopropyl-6-((1,2,3,4-tetrahydroquinolin-7-yl)amino)-1,2-dihydro-3H-pyrazolo[3,4-d]pyrimidin-3-one dihydrochloride Step-1: Synthesis of tert-butyl 7-((1-(2-(2-fluoropropan-2-yl)pyridin-4-yl)-2-isopropyl-3-oxo-2,3-dihydro-1H-pyrazolo[3,4-d]pyrimidin-6-yl)amino)-3,4-dihydroquinoline-1(2H)-carboxylate To a stirred solution of 1-(2-(2-fluoropropan-2-yl)pyridin-4-yl)-2-isopropyl-6-(methylthio)-1,2-dihydro-3H-pyrazolo[3,4-d]pyrimidin-3-one (150 mg, 0.415 mmol, 1.0 eq) in (5 mL) of toluene was added m-CPBA (143.4 mg, 0.830 mmol, 2.0 eq) and allowed to stir at rt for 30 min. tert-butyl 7-amino-3,4-dihydroquinoline-1(2H)-carboxylate, (123 mg, 0.498 mmol, 1.2 eq) and DIPEA (0.3 mL, 1.662 mmol, 4.0 eq) were added and allowed to stir at 80° C. for overnight. Solvent was evaporated and reaction mass was diluted with water and extracted with EtOAc (30 mL×2). The combined organic layer were dried over sodium sulphate, concentrated under reduced pressure purified by column chromatography (Combiflash, elution-0-70% EtOAc in Hexane) to afford the desired compound, tert-butyl 7-((1-(2-(2-fluoropropan-2-yl)pyridin-4-yl)-2-isopropyl-3-oxo-2,3-dihydro-1H-pyrazolo[3,4-d]pyrimidin-6-yl)amino)-3,4-dihydroquinoline-1(2H)-carboxylate, (82 mg, 35.17%) as yellow liquid.
LCMS: 562.5 [M+1]+

Step-2: Synthesis of 1-(2-(2-fluoropropan-2-yl)pyridin-4-yl)-2-isopropyl-6-((1,2,3,4-tetrahydroquinolin-7-yl)amino)-1,2-dihydro-3H-pyrazol[3,4-d]pyrimidin-3-one dihydrochloride tert-butyl 7-((1-(2-(2-fluoropropan-2-yl)pyridin-4-yl)-2-isopropyl-3-oxo-2,3-dihydro-1H-pyrazolo[3,4-d]pyrimidin-6-yl)amino)-3,4-dihydroquinoline-1 (2H)-carboxylate (82 mg, 0.146 mmol, 1.0 eq) was dissolved in (1 mL) of dioxane and added 4M dioxane-HCl (0.8 mL) and allowed to stir at rt for 2 h. After completion of reaction, the reaction mixture was filtered and dried under reduced pressure to afford the desired compound, 1-(2-(2-fluoropropan-2-yl)pyridin-4-yl)-2-isopropyl-6-((1,2,3,4-tetrahydroquinolin-7-yl)amino)-1,2-dihydro-3H-pyrazolo[3,4-d]pyrimidin-3-one dihydrochloride (25 mg, 32.04%) as white solid.
LCMS: 462.3 [M+1]+, UPLC @ 254 nm=91.28% and @ 220 nm=99.61%.
1H NMR (400 MHz, DMSO-d6): δ 8.84 (s, 1H), 8.72 (d, J=4.82 Hz, 1H), 7.66 (brs, 1H), 7.58 (brs, 1H), 7.03 (brs, 2H), 3.95 (d, J=5.70 Hz, 2H), 3.28 (brs, 1H), 2.71 (brs, 2H), 1.89 (brs, 2H), 1.72 (s, 3H), 1.67 (s, 3H), 1.36 (d, J=6.58 Hz, 6H).

Example S74. Synthesis of 1-(2-(2-fluoropropan-2-yl)pyridin-4-yl)-2-isopropyl-6-((1,2,3,4-tetrahydroisoquinolin-7-yl)amino)-1,2-dihydro-3H-pyrazolo[3,4-d]pyrimidin-3-one dihydrochloride (Compound No. 1.168)

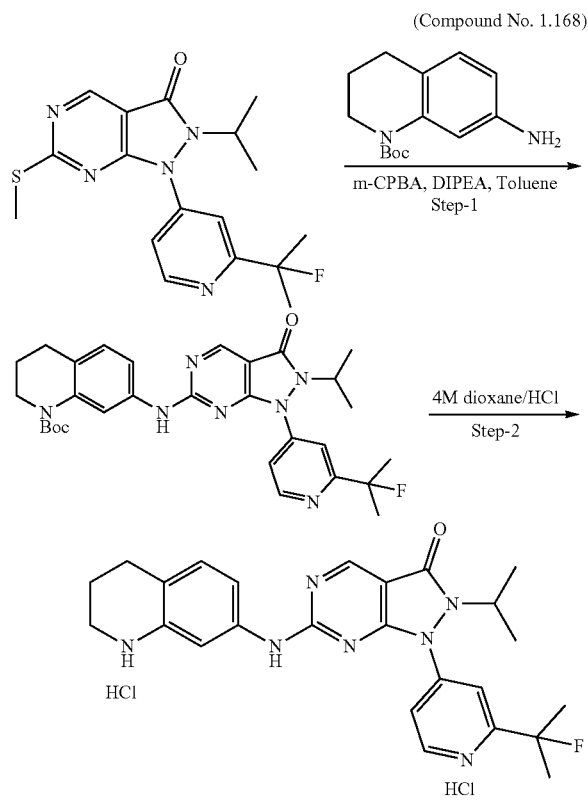

(Compound No. 1.169)

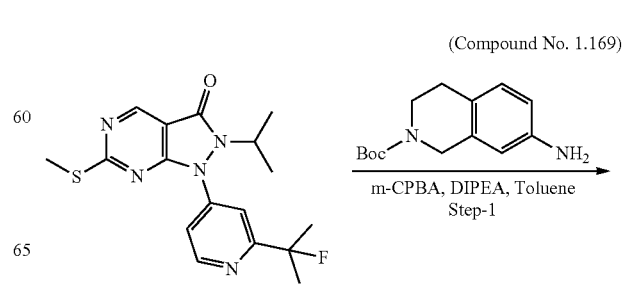

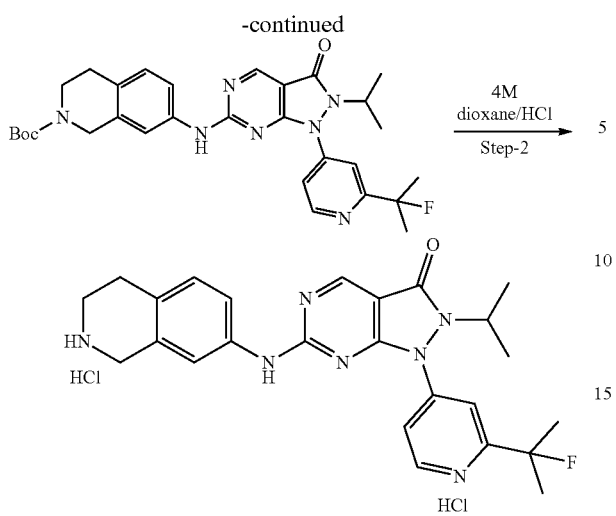

Step-1: Synthesis of tert-butyl 7-((1-(2-(2-fluoropropan-2-yl)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(2-(2-fluoropropan-2-yl)pyridin-4-yl)-2-isopropyl-6-(methylthio)-1,2-dihydro-3H-pyrazolo[3,4-d]pyrimidin-3-one (140 mg, 0.387 mmol, 1.0 eq) in (6 mL) of toluene was added m-CPBA (133.6 mg, 0.775 mmol, 2.0 eq) and allowed to stir at rt for 30 min. tert-butyl 7-amino-3,4-dihydroisoquinoline-2(1H)-carboxylate, (115 mg, 0.465 mmol, 1.2 eq) and DIPEA (0.27 mL, 1.551 mmol, 4.0 eq) were added and allowed to stir at 80° C. for overnight. Solvent was evaporated and reaction mass was diluted with water and extracted with EtOAc (30 mL×2). The combined organic layer were dried over sodium sulphate, concentrated under reduced pressure purified by column chromatography (Combiflash, elution-0-70% EtOAc in Hexane) to afford the desired compound, tert-butyl 7-amino-3,4-dihydroisoquinoline-2(1H)-carboxylateAc in Hexane) to afford the desired compound, tert-butyl 7-((1-(2-(2-fluoropropan-2-yl)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate (70 mg, 32.17%) as yellow liquid.

LCMS: 562.5 [M+1]+

Step-2: Synthesis of 1-(2-(2-fluoropropan-2-yl)pyridin-4-yl)-2-isopropyl-6-((1,2,3,4-tetrahydroisoquinolin-7-yl)amino)-1,2-dihydro-3H-pyrazolo[3,4-d]pyrimidin-3-one dihydrochloride tert-butyl 7-((1-(2-(2-fluoropropan-2-yl)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate (70 mg, 0.124 mmol, 1.0 eq) was dissolved in (2 mL) of dioxane and added 4M dioxane-HCl (0.7 mL) and allowed to stir at rt for 2 h. After completion of reaction, the reaction mixture was filtered and dried under reduced pressure to afford the desired compound, 1-(2-(2-fluoropropan-2-yl)pyridin-4-yl)-2-isopropyl-6-((1,2,3,4-tetrahydroisoquinolin-7-yl)amino)-1,2-dihydro-3H-pyrazolo[3,4-d]pyrimidin-3-one dihydrochloride (15 mg, 26.07%) as white solid.

LCMS: 462.3 [M+1]+, UPLC @ 254 nm=95.42% and @ 220 nm=97.82%.

1H NMR (400 MHz, DMSO-d6): δ 9.05 (brs, 2H), 8.87 (s, 1H), 8.72 (brs, 1H), 7.63 (brs, 2H), 7.56 (brs, 1H), 7.20 (d, J=8.77 Hz, 1H), 4.29 (brs, 3H), 3.96 (brs., 2H), 2.96 (brs, 2H), 1.72 (s, 3H), 1.66 (s, 3H), 1.36 (d, J=6.58 Hz, 6H).

Example S75a. Synthesis of 1-(2-tert-butylpyridin-4-yl)-6-{[6-(dimethylamino)-5,6,7,8-tetrahydronaphthalen-2-yl]amino}-2-(propan-2-yl)-1H,2H,3H-pyrazolo[3,4-d]pyrimidin-3-one (Peak-I:Compound No. 1.170); and Example S75b. Synthesis of 1-(2-tert-butylpyridin-4-yl)-6-{[7-(dimethylamino)-5,6,7,8-tetrahydronaphthalen-2-yl]amino}-2-(propan-2-yl)-1H,2H,3H-pyrazolo[3,4-d]pyrimidin-3-one (Peak II: Compound No. 1.171)

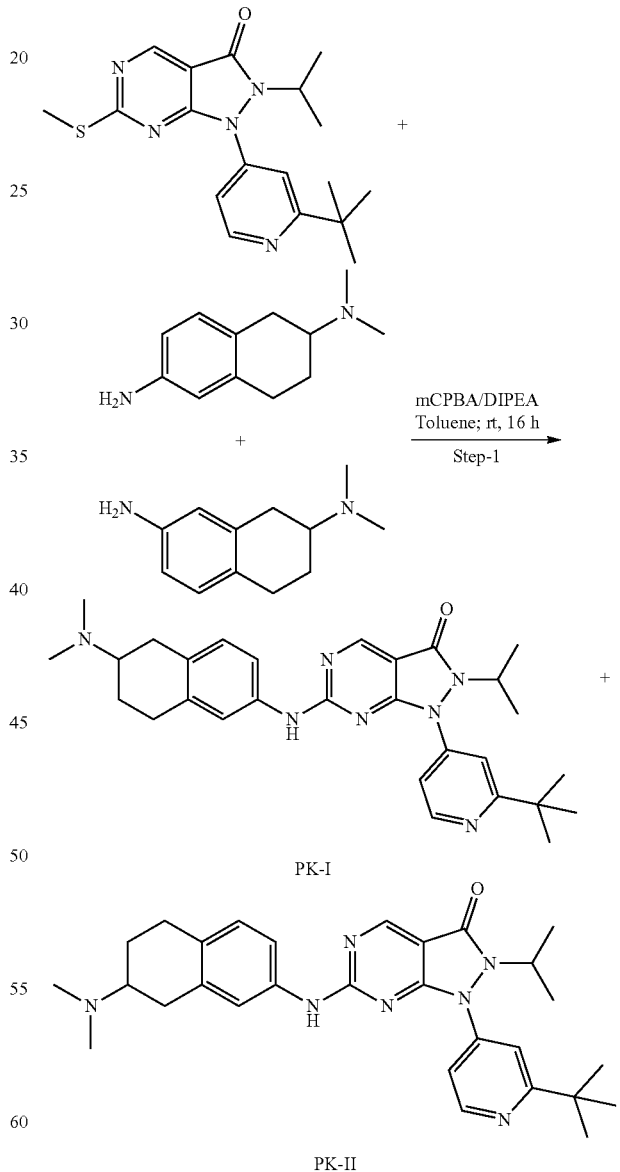

To a stirred solution of 1-(2-(tert-butyl)pyridin-4-yl)-2-isopropyl-6-(methylthio)-1,2-dihydro-3H-pyrazolo[3,4-d]pyrimidin-3-one (210 mg, 0.587 mmol, 1.0 eq) in (5.0 mL) of toluene was added mCPBA (290 mg, 1.174 mmol, 2.0 eq)

and allowed to stir at rt for 30 minutes. N2,N2-dimethyl-1,2,3,4-tetrahydronaphthalene-2,6-diamine and N2,N2-dimethyl-1,2,3,4-tetrahydro naphthalene-2,7-diamine (135 mg, 0.704 mmol, 1.2 eq) and DIPEA (0.41 mL, 2.348 mmol, 4.0 eq) were added and allowed to stir at rt for overnight. After completion of reaction, the reaction mixture was diluted with water (50 mL) extracted with EtOAc (2×50 mL). The combined organic extracts were washed with water (50 mL), with brine (50 mL) dried over Na₂SO₄ and concentrated under reduced pressure to afford mixture of desired compound 1-(2-(tert-butyl)pyridin-4-yl)-6-((6-(dimethylamino)-5,6,7,8-tetrahydronaphthalen-2-yl)amino)-2-isopropyl-1,2-dihydro-3H-pyrazolo[3,4-d]pyrimidin-3-one and 1-(2-(tert-butyl)pyridin-4-yl)-6-((7-(dimethylamino)-5,6,7,8-tetrahydronaphthalen-2-yl)amino)-2-isopropyl-1,2-dihydro-3H-pyrazolo[3,4-d]pyrimidin-3-one, which was purified by reverse phase purification as PK-I and PK-II (PK-I; 10.0 mg, 3.41%, PK-II; 11.0 mg, 3.75%) both as white solid.

LCMS: 500.4 [M+1]⁺; PK-I; UPLC @ 254 nm=97.35% and @ 220 nm=97.52%.

PK-II; UPLC @ 254 nm=99.89% and @ 220 nm=99.87%.

PK-I: ¹H NMR (400 MHz, DMSO-d₆) δ 10.30 (brs, 1H), 8.83 (s, 1H), 8.67 (d, J=5.26 Hz, 1H), 7.44-7.57 (m, 3H), 7.40 (brs, 1H), 7.07 (d, J=8.77 Hz, 1H), 3.95 (brs, 1H), 3.01 (brs, 1H), 2.87 (brs, 3H), 2.67 (brs, 6H), 2.20 (brs, 2H), 1.72 (brs, 1H), 1.49 (brs, 1H), 1.28-1.42 (m, 15H).

PK-II: ¹H NMR (400 MHz, DMSO-d₆) δ 10.29 (brs, 1H), 8.82 (s, 1H), 8.66 (brs, 1H), 7.53 (brs, 1H), 7.48 (brs, 1H), 7.40 (brs, 2H), 7.03 (d, J=8.77 Hz, 1H), 3.95 (brs, 1H), 2.90 (brs, 2H), 2.82 (brs, 2H), 2.73 (brs, 2H), 2.67 (br., 2H), 2.10 (brs, 1H), 1.62 (brs, 1H), 1.25-1.48 (m, 15H).

Example S76. Synthesis of 1-(2-(dimethylamino) pyridin-4-yl)-2-isopropyl-6-((1,2,3,4-tetrahydroisoquinolin-6-yl)amino)-1,2-dihydro-3H-pyrazolo[3,4-d]pyrimidin-3-one (Compound No. 1.172)

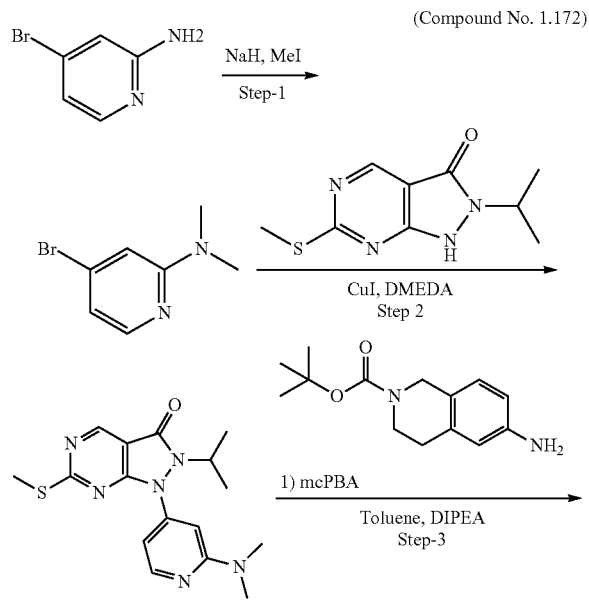

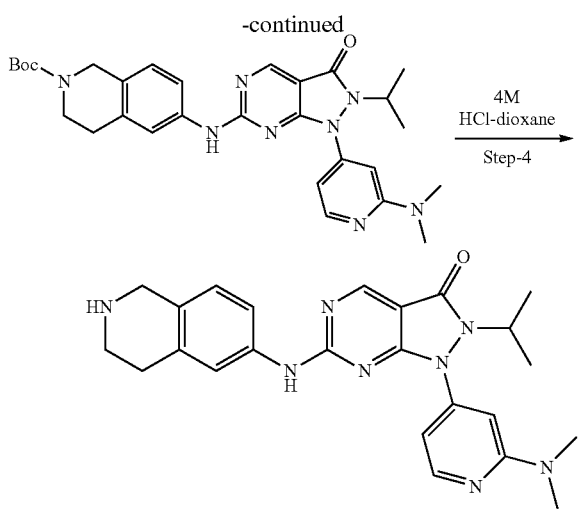

Step-1: Synthesis of 4-bromo-N,N-dimethylpyridin-2-amine

To a solution of compound 2-amino-4-bromopyridine (704 mg, 4.0 mmol, 1.0 eq) in THF at 0° C. was added NaH (352 mg, 8.8 mmol, 2.2 eq) and the reaction mixture was stirred for 30 minutes. To this solution was added methyl iodide at 0° C. (0.622 mL, 10 mmol, 2.5 eq) and reaction mixture was warmed to rt. Reaction was allowed to stir at rt for 16 h and the progress of the reaction was monitored by TLC. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, 4-bromo-N,N-dimethylpyridin-2-amine (500 mg, 62.5%) as a brown solid.

LCMS: 201.0 [M+1]⁺

Step-2: Synthesis of 1-(2-(dimethylamino)pyridin-4-yl)-2-isopropyl-6-(methylthio)-1,2-dihydro-3H-pyrazolo[3,4-d]pyrimidin-3-one To a stirred solution of 2-isopropyl-6-(methylthio)-1,2-dihydro-3H-pyrazolo[3,4-d]pyrimidin-3-one (300 mg, 1.337 mmol, 1.0 eq) and -bromo-N,N-dimethylpyridin-2-amine (321 mg, 1.60 mmol, 1.20 eq) in (8 mL) of dioxane was added potassium carbonate (370 mg, 2.674 mmol, 2.0 eq) and the resulting mixture was purged with nitrogen for 10 min, followed by addition of copper iodide (51 mg, 0.27 mmol, 0.2 eq), and N,N'-dimethylethylenediamine (DMEDA) (47 mg, 0.535 mmol, 0.4 eq) and again purged with nitrogen for 10 min, stirred at 90° C. for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-30% EtOAc in hexane] to afford the desired product, 1-(2-(dimethylamino)pyridin-4-yl)-2-isopropyl-6-(methylthio)-1,2-dihydro-3H-pyrazolo[3,4-d]pyrimidin-3-one (60 mg, 13.1%) as brown solid.

LCMS: 345.2 [M+1]⁺

Step-3: Synthesis of tert-butyl 6-((1-(2-(dimethyl-amino)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(2-(dimethylamino)pyridin-4-yl)-2-isopropyl-6-(methylthio)-1,2-dihydro-3H-pyrazolo[3,4-d]pyrimidin-3-one (55 mg, 0.145 mmol, 1.0 eq) in (2.0 mL) of toluene was added mCPBA (40 mg, 0.16, 1.1 eq) and allowed to stir at rt for 30 minutes. tert-butyl 6-amino-3,4-dihydroisoquinoline-2(1H)-carboxylate (43 mg, 0.174 mmol, 1.2 eq) and DIPEA (0.13 mL, 0.725 mmol, 5.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography to afford the desired product, tert-butyl 6-((1-(2-(dimethyl-amino)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate (20 mg, 25.3%) as brown solid.
LCMS: 546.3 [M+1]+

Step-4: Synthesis of 1-(2-(dimethylamino)pyridin-4-yl)-2-isopropyl-6-((1,2,3,4-tetrahydroisoquinolin-6-yl)amino)-1,2-dihydro-3H-pyrazolo[3,4-d]pyrimidin-3-one tert-butyl 6-((1-(2-(dimethylamino)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate (20 mg, 0.036 mmol, 1.0 eq) was dissolved in dioxane (0.3 mL), followed by dropwise addition of 4.0M-HCl (0.3 mL) and allowed to stir at rt for 1 h. After completion of reaction, the reaction mixture was filtered and dried. Purified product was obtained by preparative chromatography to give 1-(2-(dimethylamino)pyridin-4-yl)-2-isopropyl-6-((1,2,3,4-tetrahydroisoquinolin-6-yl)amino)-1,2-dihydro-3H-pyrazolo[3,4-d]pyrimidin-3-one (10 mg, 62%) as off white solid.
LCMS: 445.3 [M+1]+; UPLC @ 254 nm=83.56% and @ 220 nm=88.54%.
1H NMR (400 MHz, DMSO-d6): δ 10.53 (brs, 1H), 9.53 (brs, 2H), 8.90 (s, 1H), 8.14 (d, J=6.58 Hz, 1H), 7.49-7.61 (m, 2H), 7.13-7.23 (m, 2H), 6.99 (brs, 1H), 4.22 (brs, 2H), 3.98 (brs, 1H), 3.35 (brs, 2H), 3.23 (brs, 6H), 2.99 (brs, 2H), 1.38 (d, J=6.58 Hz, 6H).

Example S77. Synthesis of methyl 6-((1-(2-(tert-butyl)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate (Compound No. 1.173)

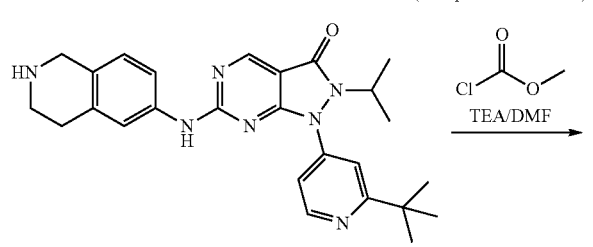

-continued

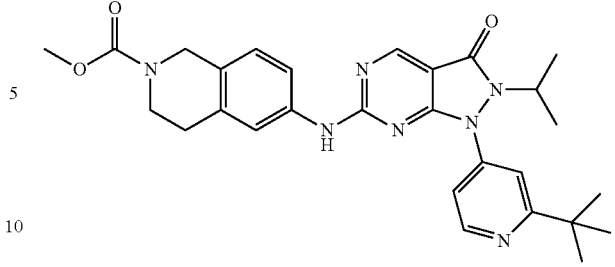

To a stirred solution of 1-(2-(tert-butyl)pyridin-4-yl)-2-isopropyl-6-((1,2,3,4-tetrahydroisoquinolin-6-yl)amino)-1,2-dihydro-3H-pyrazolo[3,4-d]pyrimidin-3-one (110 mg, 0.240 mmol) in DMF (3 mL) was added TEA (0.1 mL, 0.720 mmol), followed by addition of methyl carbonochloridate (0.02 mL, 0.288 mmol) at 0° C. The reaction mixture was stirred at rt for 1 h. The reaction mixture was diluted with water (10 mL), extracted with EtOAc (50 mL×2). The combined organic layers were dried over Na2SO4, concentrated and purified by column chromatography (Combiflash, Elution: 0-70% EtOAc in Hexane) to afford the desired product, 1-(2-(tert-butyl)pyridin-4-yl)-2-isopropyl-6-(methylthio)-1,2-dihydro-3H-pyrazolo[3,4-d]pyrimidin-3-one (36 mg, 29.04%) as an off white solid.
LCMS: 516.4 [M+1]+; UPLC @ 254 nm=95.88% and @ 220 nm=97.00%.
1H NMR (400 MHz, DMSO-d6): δ 10.35 (brs, 1H), 8.84 (s, 1H), 8.69 (d, J=5.26 Hz, 1H), 7.47-7.58 (m, 3H), 7.42 (brs, 1H), 7.13 (d, J=7.45 Hz, 1H), 4.51 (brs, 2H), 3.94 (d, J=6.58 Hz, 1H), 3.60-3.67 (m, 4H), 2.79 (brs, 2H), 1.26-1.44 (m, 15H).

Example S78. Synthesis of 1-(2-tert-butylpyridin-4-yl)-6-(1,2,3,4-tetrahydroisoquinolin-7-ylamino)-2-(2,2,2-trifluoroethyl)-1H-pyrazolo[3,4-d]pyrimidin-3 (2H)-one (Compound No. 1.174)

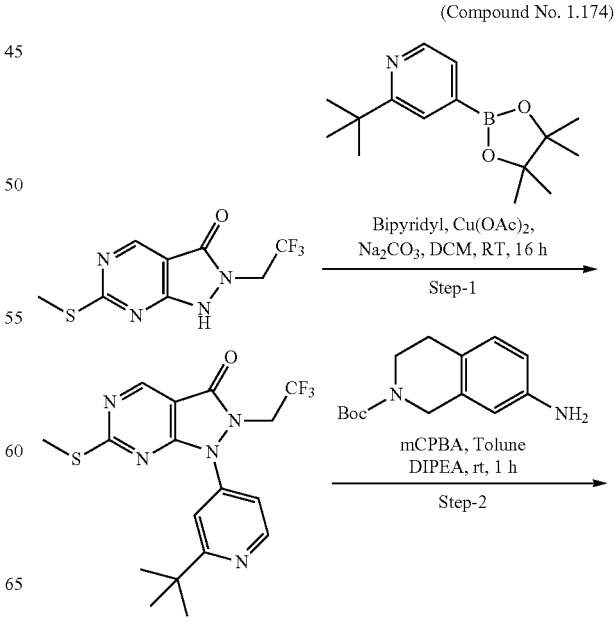

-continued

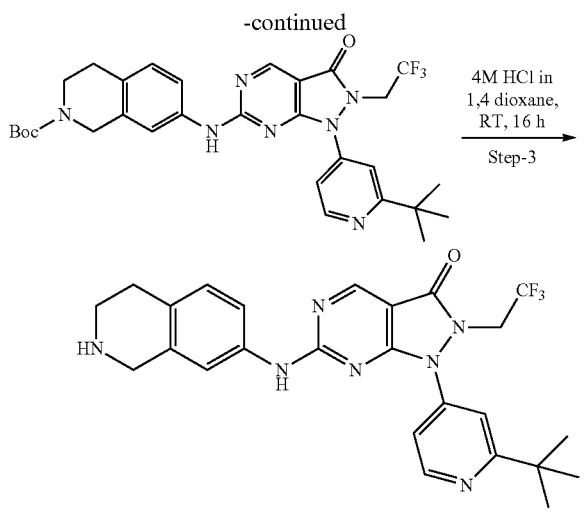

4M HCl in
1,4 dioxane,
RT, 16 h
Step-3

Step-1: Synthesis of 1-(2-tert-butylpyridin-4-yl)-6-(methylthio)-2-(2,2,2-trifluoroethyl)-1H-pyrazolo[3,4-d]pyrimidin-3(2H)-one To a stirred solution of 6-(methylthio)-2-(2,2,2-trifluoroethyl)-1H-pyrazolo[3,4-d]pyrimidin-3(2H)-one (440 mg, 1.665 mmol, 1.0 eq) and 2-tert-butyl-4-(4,4,5,5-tetramethyl-1,3,2-dioxaborolan-2-yl)pyridine (652 mg, 2.49 mmol, 1.5 eq) in DCM (20 mL) was added $Na_2CO_3$ (529 mg, 4.99 mmol, 3.0 eq), $Cu(OAc)_2$ (604 mg, 3.33 mmol, 2.0 eq) and Bipyridyl (520 mg, 3.33 mmol, 2 eq) and the mixture was stirred in presence of oxygen at Rt for 16 h. The reaction was monitored by TLC. After completion of reaction, the volatiles are removed under reduced pressure and the residue was taken in water and extracted with EtOAc (150 mL×2). The combined organic layers were washed with water (50 mL), brine (50 mL), dried over anhydrous $Na_2SO_4$ and concentrated under reduced pressure to afford crude which was purified by flash chromatography (Teledyne Isco Rf+); compound eluting 50% EtOAc/Hexane to afford 1-(2-tert-butylpyridin-4-yl)-6-(methylthio)-2-(2,2,2-trifluoroethyl)-1H-pyrazolo[3,4-d]pyrimidin-3(2H)-one (350 mg, 53%) as an off white solid.

LCMS: 398 [M+1]$^+$

Step-2: Synthesis of tert-butyl 7-(1-(2-tert-butylpyridin-4-yl)-3-oxo-2-(2,2,2-trifluoroethyl)-2,3-dihydro-1H-pyrazolo[3,4-d]pyrimidin-6-ylamino)-3,4-dihydroisoquinoline-2(1H)-carboxylate To a stirred solution of 1-(2-tert-butylpyridin-4-yl)-6-(methylthio)-2-(2,2,2-trifluoroethyl)-1H-pyrazolo[3,4-d]pyrimidin-3(2H)-one (150 mg, 0.377 mmol, 1.0 eq) in toluene (3 mL) was added m-CPBA (260.2 mg, 1.508 mmol, 4.0 eq) at 0° C. and the mixture was allowed to stir at RT for 1 h, followed by addition of DIPEA (292.02 mg, 2.262 mmol, 6.0 eq) and tert-butyl 7-amino-3,4-dihydroisoquinoline-2(1H)-carboxylate (118.04 mg, 0.415 mmol, 1.1 eq) and the mixture was allowed to stir at RT for 1 h. The reaction was monitored by TLC. After completion of reaction, the mixture was diluted with water and extracted with EtOAc (100 mL×2). The combined organic layers were washed with water (50 mL), brine (50 mL), dried over anhydrous $Na_2SO_4$ and concentrated under reduced pressure to afford a crude which was purified by flash chromatography (Teledyne Isco Rf+); compound eluting 70% EtOAc/Hexane to afford tert-butyl 7-(1-(2-tert-butylpyridin-4-yl)-3-oxo-2-(2,2,2-trifluoroethyl)-2,3-dihydro-1H-pyrazolo[3,4-d]pyrimidin-6-ylamino)-3,4-dihydroisoquinoline-2(1H)-carboxylate (30 mg, 13%) as off white solid.

LCMS: 598 [M+1]$^+$

Step-3: Synthesis of 1-(2-tert-butylpyridin-4-yl)-6-(1,2,3,4-tetrahydroisoquinolin-7-ylamino)-2-(2,2,2-trifluoroethyl)-1H-pyrazolo[3,4-d]pyrimidin-3(2H)-one The tert-butyl 7-(1-(2-tert-butylpyridin-4-yl)-3-oxo-2-(2,2,2-trifluoroethyl)-2,3-dihydro-1H-pyrazolo[3,4-d]pyrimidin-6-ylamino)-3,4-dihydroisoquinoline-2(1H)-carboxylate (30 mg, 0.0502 mmol, 1.0 eq) was added 4N-HCl in 1,4-Dioxane (2 mL) and the mixture was stirred was stirred at RT for 16 h. The reaction was monitored by TLC. After completion, the volatiles are removed under reduced pressure and the residue was taken in saturated $NaHCO_3$ (100 mL) and extracted with EtOAc (200 mL×2). The combined organic layers were washed with water (150 mL), brine (100 mL), dried over anhydrous $Na_2SO_4$ and concentrated under reduced pressure to afford crude which was purified by reversed-phase chromatography to afford 1-(2-tert-butylpyridin-4-yl)-6-(1,2,3,4-tetrahydroisoquinolin-7-ylamino)-2-(2,2,2-trifluoroethyl)-1H-pyrazolo[3,4-d]pyrimidin-3(2H)-one (3 mg, 13%) as a formate salt (off-white solid).

LCMS: 498 [M+1]$^+$ $^1$H NMR (400 MHz, DMSO-d$_6$): δ 8.90 (s, 1H), 8.64 (d, 1H), 7.61-7.42 (m, 4H), 7.22 (d, 1H), 4.26 (s, 2H), 3.23 (m, 2H), 3.03 (m, 2H), 2.16 (s, 1H), 1.40 (s, 6H).

Example S79. Synthesis of 1-(3-(tert-butyl)-4-(dimethylamino)phenyl)-2-isopropyl-6-((1,2,3,4-tetrahydroisoquinolin-6-yl)amino)-1,2-dihydro-3H-pyrazolo[3,4-d]pyrimidin-3-one (Compound No. 1.175)

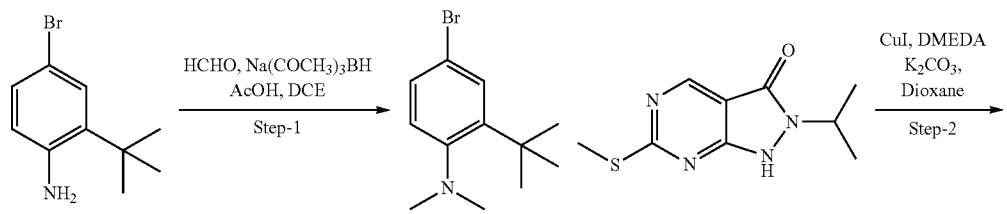

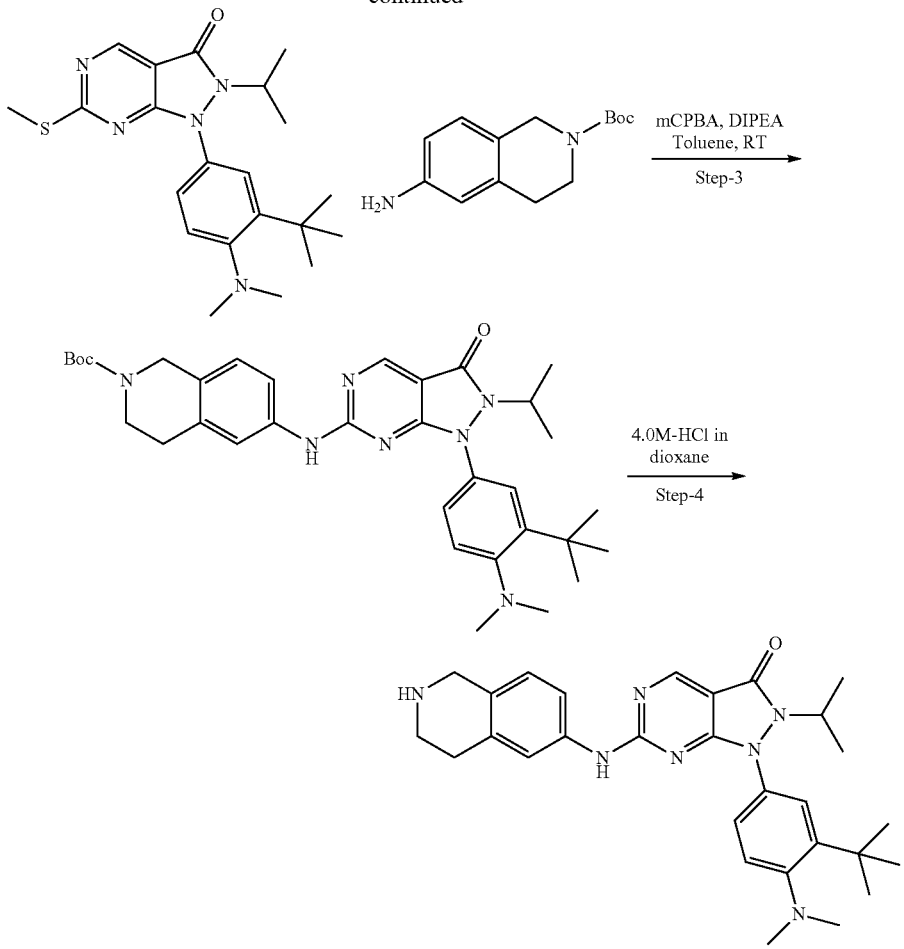

Step-1: Synthesis of 4-bromo-2-(tert-butyl)-N,N-dimethylaniline

To a stirred solution of 4-bromo-2-(tert-butyl)aniline (500 mg, 2.192 mmol, 1.0 eq) and HCHO (0.822 mL, 10.92 mmol, 5.0 eq) in dichloroethane (10 mL) was dropwise added acetic acid (0.65 mL, 10.92 mmol, 5.0 eq) at 0° C. The resulting mixture was stirred at rt for 1 h, followed by addition of Na(COCH$_3$)$_3$BH (1.4 g, 6.576 mmol, 3.0 eq) at 0° C. The resulting mixture was stirred at rt for 1 h. The progress of reaction was monitored by LCMS. The resection mixture was concentrated, basified with saturated solution of NaHCO$_3$ (50 mL) extracted with EtOAc (2×50 mL). The combined organic extracts were washed with water (50 mL), with brine (50 mL) dried over Na$_2$SO$_4$ and concentrated under reduced and purified by combi flash chromatography [silica gel, 100-200 mesh; elution 0-1% EtOAc in hexane] to afford the desired compound 4-bromo-2-(tert-butyl)-N,N-dimethylaniline (350 mg, 62.38%) as white solid.

LCMS: 256.0 [M+1]$^+$

Step-2: Synthesis of 1-(3-(tert-butyl)-4-(dimethylamino)phenyl)-2-isopropyl-6-(methylthio)-1,2-dihydro-3H-pyrazolo[3,4-d]pyrimidin-3-one To a stirred solution of 2-isopropyl-6-(methylthio)-1,2-dihydro-3H-pyrazolo[3,4-d]pyrimidin-3-one (550 mg, 2.452 mmol, 1.0 eq) and 4-bromo-2-(tert-butyl)-N,N-dimethylaniline (700 mg, 2.697 mmol, 1.10 eq) in (20 mL) of dioxane was added Potassium carbonate (678 mg, 4.904 mmol, 2.0 eq) and the resulting mixture was purged with nitrogen for 10 min., followed by addition of copper iodide (103 mg, 0.539 mmol, 0.2 eq), and N,N'-dimethylethylenediamine (DMEDA) (0.13 mL, 1.226 mmol, 0.4 eq) and again purged with nitrogen for 10 min, stirred at 90° C. for overnight. After completion of reaction, the reaction mixture was diluted with water and extracted with EtOAc (50 mL×2). Combined organic layer was washed with water (50 mL) brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound 1-(3-(tert-butyl)-4-(dimethylamino)phenyl)-2-isopropyl-6-(methylthio)-1,2-dihydro-3H-pyrazolo[3,4-d]pyrimidin-3-one (60 mg, 6.12%) as light yellow solid.

LCMS: 400.2 [M+1]$^+$

Step-3: Synthesis of tert-butyl 6-((1-(3-(tert-butyl)-4-(dimethylamino)phenyl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(3-(tert-butyl)-4-(dimethylamino)phenyl)-2-isopropyl-6-(methylthio)-1,2-dihydro-3H-pyrazolo[3,4-d]pyrimidin-3-one (60 mg, 0.150 mmol, 1.0 eq) in (2.0 mL) of toluene was added m-CPBA (74 mg, 0.30 mmol, 2.0 eq) and allowed to stir at rt for 30 min. tert-butyl 6-amino-3,4-dihydroisoquinoline-2(1H)-carboxylate (41 mg, 0.165 mmol, 1.1 eq) and DIPEA (0.104 mL, 0.600 mmol, 4.0 eq) were added and allowed to stir at rt for overnight. After completion of reaction, the reaction mixture was diluted with water and extracted with EtOAc (20 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-60% EtOAc in hexane] to afford the desired compound, tert-butyl 6-((1-(3-(tert-butyl)-4-(dimethylamino)phenyl)-2-isopropyl-3-oxo-2,3-dihydro-1H-pyrazolo[3,4-d]pyrimidin-6-yl)amino)-3,4-dihydroisoquinoline-2(1H)-carboxylate (62 mg, 68.88%) as brown viscous.

LCMS: 600.4 [M+1]$^+$

Step-4: Synthesis of 1-(3-(tert-butyl)-4-(dimethylamino)phenyl)-2-isopropyl-6-((1,2,3,4-tetrahydroisoquinolin-6-yl)amino)-1,2-dihydro-3H-pyrazolo[3,4-d]pyrimidin-3-one tert-butyl 6-((1-(3-(tert-butyl)-4-(dimethylamino)phenyl)-2-isopropyl-3-oxo-2,3-dihydro-1H-pyrazolo[3,4-d]pyrimidin-6-yl)amino)-3,4-dihydroisoquinoline-2(1H)-carboxylate (60 mg, 1.00 mmol, 1.0 eq) was dissolved in 4.0M-HCl (1.5 mL) and allowed to stir at rt for 1 h. After completion of reaction, the reaction mixture was basified with NaHCO$_3$ water and extracted with EtOAc (20 mL×2). The combined organic layers were washed with water (50 mL) brine solution (50 mL), dried over anhydrous sodium sulfate and concentrated under reduced pressure to afford crude product, which was purified by reverse phase chromatography to afford the desired compound 1-(3-(tert-butyl)-4-(dimethylamino)phenyl)-2-isopropyl-6-((1,2,3,4-tetrahydroisoquinolin-6-yl)amino)-1,2-dihydro-3H-pyrazolo[3,4-d]pyrimidin-3-one (4.0 mg, 8.16%) as white solid.

LCMS: 500.4 [M+1]$^+$; UPLC @ 254 nm=94.68% and @ 220 nm=95.49%.

$^1$H NMR (400 MHz, DMSO-d$_6$) δ 10.08 (s, 1H), 8.77 (s, 1H), 8.29 (s, 1H), 7.63 (d, J=8.33 Hz, 1H), 7.46-7.55 (m, 2H), 7.40 (s, 1H), 7.28 (br. s., 1H), 6.91 (d, J=8.33 Hz, 1H), 4.01 (d, J=6.14 Hz, 1H), 3.83 (brs, 2H), 2.98 (brs, 2H), 2.66 (d, J=5.70 Hz, 2H), 2.59 (s, 6H), 1.42 (s, 9H), 1.30 (d, J=7.02 Hz, 6H).

Example S80. Synthesis of 1-(2-(tert-butyl)pyridin-4-yl)-6-((1,1-dimethyl-1,2,3,4-tetrahydroisoquinolin-6-yl)amino)-2-isopropyl-1,2-dihydro-3H-pyrazolo[3,4-d]pyrimidin-3-one dihydrochloride (Compound No. 1.176)

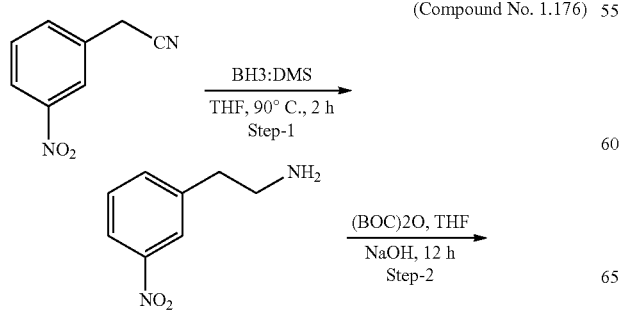

Step-1: Synthesis of 2-(3-nitrophenyl)ethan-1-amine

To a stirred solution of 3-nitrophenylacetonitril (5.0 g, 30.83 mmol, 1 eq), (3.22 mL, 1.5 eq) of borane-dimethyl sulfide complex was added to THF (100 mL) and stirred under reflux for 2 h. The reaction mixture was cooled to room temperature, and 40 mL of 5% HCl/methanol solution was added to it, and heated under reflux for 1 h. The solvent was evaporated, and diethyl ether was added to it to obtain, 2-(3-nitrophenyl) ethan-1-amine (3.5 g, 68.35%) as yellowish solid.

LCMS: 166.1 [M+1]$^+$

Step-2: Synthesis of tert-butyl (3-nitrophenethyl) carbamate

To a stirred solution of 2-(3-nitrophenyl) ethan-1-amine (3.5 g, 21.08 mmol, 1 eq) in THF (50 mL) were added, 5M sodium hydroxide (7 mL) and di-tert-butyl dicarboxylic anhydride (4.68 g, 21.08 mmol, 1 eq), and stirred overnight at room temperature. The reaction mixture was diluted with water (100 mL), extracted with EtOAc (200 mL×2). The combined organic layers were dried over Na$_2$SO$_4$, concentrated and purified by column chromatography (Combiflash, Elution: 0-70% EtOAc in Hexane) to afford the desired product, tert-butyl (3-nitrophenethyl) carbamate (4.0 g, 71.42%) as colorless oil.

LCMS: 266.1 [M+1]$^+$

Step-3: Synthesis of tert-butyl (3-aminophenethyl) carbamate

To a stirred solution of tert-butyl (3-nitrophenethyl) carbamate (4.0 g, 15.03 mmol, 1 eq), in THF: Methanol (150 mL, 2:1 ratio), palladium hydroxide-carbon (1.21 g) was added and the reaction mixture was stirred under hydrogen atmosphere overnight. The catalyst was removed through filtration, and the filtrate was concentrated to obtain, tert-butyl (3-aminophenethyl) carbamate (3.0 g, 84.75%) as colorless liquid.

LCMS: 237.0 [M+1]$^+$

Step-4: Synthesis of 3-(2-aminoethyl) aniline

A solution of tert-butyl (3-aminophenethyl) carbamate (3.0 g, 12.71 mmol, 1 eq) in TFA (10 mL) was stirred at room temperature for 1 h. The reaction liquid was concentrated to obtain, 3-(2-aminoethyl) aniline (2.5 g, crude) as brown liquid.

LCMS: 137.0 [M+1]$^+$

Step-5: Synthesis of 1,1-dimethyl-1,2,3,4-tetrahydroisoquinolin-6-amine

A mixture of 3-(2-aminoethyl) aniline (2.5 g, 18.38 mmol, 1 eq), 6.5 mL of 85% phosphoric acid and 1.8 mL of 2,2-dimethoxypropane was stirred at 70° C. for 3 days. Further, 1 mL of 2,2-dimethoxypropane was added to it, and reacted at 140° C. for 3 h using a microwave reactor. The reaction mixture was diluted with water (50 mL), basified with K2CO3 and extracted with 10% methanol in dichloromethane (100 mL×2), dried with anhydrous Na$_2$SO$_4$, and the solvent was evaporated to obtain, 1,1-dimethyl-1,2,3,4-tetrahydroisoquinolin-6-amine (1.24 g, crude) as brown solid.

LCMS: 176.9 [M+1]$^+$

Step-6: Synthesis of tert-butyl 6-amino-1,1-dimethyl-3,4-dihydroisoquinoline-2(1H)-carboxylate To a stirred solution of 1,1-dimethyl-1,2,3,4-tetrahydroisoquinolin-6-amine (1.24 g, 7.045 mmol, 1.0 eq) in (10.0 mL) of THF was added di-tert-butyl dicarboxylic anhydride (1.84 g, 8.45 mmol, 1.2 eq) and allowed to stir at rt for 12 h and allowed to stir at rt for overnight. After completion of reaction, the reaction mixture was diluted with water (50 mL) and extracted with EtOAc (50 mL×2). The combined organic layers were washed with water (50 mL), brine solution (50 mL), dried over anhydrous sodium sulfate and concentrated under reduced pressure to afford crude product, which was purified by flash chromatography [silica gel 100-200 mesh; elution 0-40% EtOAc in hexane] to afford the desired compound (0.7 g) as brown solid.

LCMS: 276.9 [M+1]$^+$

Step-7: Synthesis of tert-butyl 6-((1-(2-(tert-butyl)pyridin-4-yl)-2-isopropyl-3-oxo-2,3-dihydro-1H-pyrazolo[3,4-d]pyrimidin-6-yl)amino)-1,1-dimethyl-3,4-dihydroisoquinoline-2(1H)-carboxylate To a stirred solution of tert-butyl 6-amino-1,1-dimethyl-3,4-dihydroisoquinoline-2(1H)-carboxylate (200 mg, 0.560 mmol, 1.0 eq) in (6.0 mL) of toluene was added m-CPBA (194 mg, 1.120 mmol, 2.0 eq) and allowed to stir at rt for 1 h. 1, 1-dimethyl-1,2,3,4-tetrahydroisoquinolin-6-amine (186 mg, 0.672 mmol, 1.2 eq) and DIPEA (0.43 mL, 2.2408 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((1-(2-(tert-butyl)pyridin-4-yl)-2-isopropyl-3-oxo-2,3-dihydro-1H-pyrazolo[3,4-d]pyrimidin-6-yl)amino)-1,1-dimethyl-3, 4-dihydroisoquinoline-2(1H)-carboxylate (50 mg, 15.25%) as an off white solid.

LCMS: 586.4 [M+1]$^+$

Step-8: Synthesis of 1-(2-(tert-butyl)pyridin-4-yl)-6-((1,1-dimethyl-1,2,3,4-tetrahydroisoquinolin-6-yl)amino)-2-isopropyl-1,2-dihydro-3H-pyrazolo[3,4-d]pyrimidin-3-one dihydrochloride tert-butyl 6-((1-(2-(tert-butyl)pyridin-4-yl)-2-isopropyl-3-oxo-2,3-dihydro-1H-pyrazolo[3,4-d]pyrimidin-6-yl)amino)-1,1-dimethyl-3,4-dihydroisoquinoline-2(1H)-carboxylate (50 mg, 0.0854 mmol, 1.0 eq) was dissolved in dioxane (1 mL), followed by dropwise addition of 4.0M-HCl (2 mL) and allowed to stir at rt for 1 h. After completion of reaction, the reaction mixture was filtered and dried under reduced pressure to afford the desired compound, 1-(2-(tert-butyl)pyridin-4-yl)-6-((1,1-dimethyl-1,2,3,4-tetrahydroisoquinolin-6-yl)amino)-2-isopropyl-1,2-dihydro-3H-pyrazolo[3,4-d]pyrimidin-3-one dihydrochloride (21 mg, 44.05%) as light yellow solid.

LCMS: 486.4 [M+1]$^+$; UPLC @ 254 nm=91.54% and @ 220 nm=93.66%.

$^1$H NMR (400 MHz, DMSO-d$_6$): δ 10.48 (br. s., 1H), 9.75 (br. s., 1H), 8.87 (s, 1H) 8.58 (d, J=5.26 Hz, 1H) 7.90 (br. s., 1H) 7.58 (d, J=4.82 Hz, 2H) 7.48 (s, 1H) 7.19 (d, J=8.33 Hz, 1H) 3.94-3.99 (m, 1H) 3.35 (t, 2H) 3.03 (t, 2H), 1.62 (s, 6H), 1.42 (d, 6H), 1.37 (s, 9H).

839

Example S81. Synthesis of N-(4-(2-isopropyl-3-oxo-6-((1,2,3,4-tetrahydroisoquinolin-6-yl)amino)-2,3-dihydro-1H-pyrazolo[3,4-d]pyrimidin-1-yl)pyridin-2-yl)-N-methylmethanesulfonamide dihydrochloride (Compound No. 1.177)

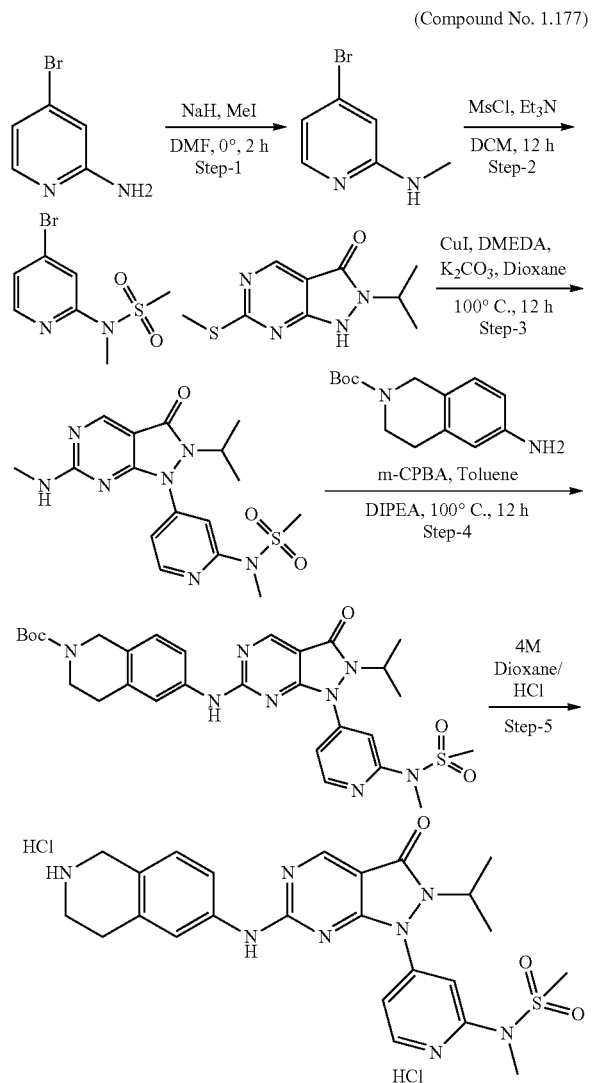

Step-1: Synthesis of 4-bromo-N-methylpyridin-2-amine

To a stirred solution of 4-bromopyridin-2-amine (3.0 g, 17.34 mmol, 1 eq), in DMF (10 mL) and NaH (0.5 g, 19.07 mmol, 1 eq), was added at 0° C. & stirred for 30 min. MeI (1.62 mL, 26.01 mmol, 1.5 eq) was added dropwise & stirred for 1 h. After completion of reaction, the reaction mixture was diluted with water and extracted with EtOAc (50 mL×2). The combined organic layers were washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, 4-bromo-N-methylpyridin-2-amine (600 mg, 18.51%) as white solid.

LCMS: 187.0 [M+1]$^+$

840

Step-2: Synthesis of N-(4-bromopyridin-2-yl)-N-methylmethanesulfonamide

To a stirred solution of 4-bromo-N-methylpyridin-2-amine (0.6 g, 3.22 mmol, 1 eq), in (50 mL) of DCM, was added TEA (1 mL, 7.09 mmol, 2.2 eq), followed by addition of methane sulphonyl chloride (0.4 mL, 4.83 mmol, 1.5 eq) and stirred overnight at room temperature. The reaction mixture was basified with saturated sodium bicarbonate solution and extracted with EtOAc (50 mL×2). The combined organic layers were washed with water (50 mL), brine solution (50 mL), dried over anhydrous sodium sulfate and the solvent was evaporated under reduced pressure to afford crude product, which was purified by flash chromatography [silica gel 100-200 mesh; elution 0-50% EtOAc in hexane] to afford the desired compound, N-(4-bromopyridin-2-yl)-N-methylmethanesulfonamide (563 mg, 66.19%) as white solid.

LCMS: 265.0 [M+1]$^+$

Step-3: Synthesis of N-(4-(2-isopropyl-6-(methylthio)-3-oxo-2, 3-dihydro-1H-pyrazolo [3, 4-d] pyrimidin-1-yl) pyridin-2-yl)-N-methylmethanesulfonamide To a stirred solution of 2-isopropyl-6-(methylthio)-1,2-dihydro-3H-pyrazolo[3,4-d]pyrimidin-3-one (400 mg, 1.77 mmol, 1.0 eq) and N-(4-bromopyridin-2-yl)-N-methylmethanesulfonamide (563 mg, 2.13 mmol, 1.2 eq) in (10 mL) of dioxane was added Potassium carbonate (490 mg, 3.55 mmol, 2 eq) and the resulting mixture was purged with nitrogen for 10 min, followed by addition of copper iodide (68 mg, 0.35 mmol, 0.2 eq), and N,N'-dimethylethylenediamine (DMEDA) (62 mg, 0.710 mmol, 0.4 eq) and again purged with nitrogen for 10 min, stirred at 90° C. for overnight. After completion of reaction, the reaction mixture was diluted with water and extracted with EtOAc (50 mL×2). Combined organic layers were washed with water (50 mL) brine solution (50 mL), dried over anhydrous sodium sulphate and concentrated under reduced pressure to afford crude product, which was purified by flash chromatography to afford the desired compound, N-(4-(2-isopropyl-6-(methylthio)-3-oxo-2,3-dihydro-1H-pyrazolo [3, 4-d] pyrimidin-1-yl) pyridin-2-yl)-N-methylmethanesulfonamide (120 mg, 16.47%) as an off white solid.

LCMS: 409.1 [M+1]$^+$

Step-4: Synthesis of tert-butyl 6-((2-isopropyl-1-(2-(N-methylmethylsulfonamido)pyridin-4-yl)-3-oxo-2,3-dihydro-1H-pyrazolo[3,4-d]pyrimidin-6-yl) amino)-3,4-dihydroisoquinoline-2(1H)-carboxylate To a stirred solution of N-(4-(2-isopropyl-6-(methylthio)-3-oxo-2,3-dihydro-1H-pyrazolo [3, 4-d] pyrimidin-1-yl) pyridin-2-yl)-N-methylmethanesulfonamide (120 mg, 0.294 mmol, 1.0 eq) in (3.0 mL) of toluene was added m-CPBA (102 mg, 0.5882 mmol, 2.0 eq) and allowed to stir at rt for 1 h. tert-butyl 6-amino-3,4-dihydroisoquinoline-2(1H)-carboxylate (102 mg, 0.3529 mmol, 1.2 eq) and DIPEA (0.2 mL, 1.18 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((2-isopropyl-1-(2-(N-methylmethylsulfonamido)pyridin-4-yl)-3-oxo-2,3-dihydro-1H-pyrazolo[3,4-d]pyrimidin-6-yl)amino)-3,4-dihydroisoquinoline-2(1H)-carboxylate (40 mg, 22.37%) as an off white solid.

LCMS: 609.3 [M+1]$^+$

Step-5: Synthesis of N-(4-(2-isopropyl-3-oxo-6-((1,2,3,4-tetrahydroisoquinolin-6-yl)amino)-2,3-dihydro-1H-pyrazolo[3,4-d]pyrimidin-1-yl)pyridin-2-yl)-N-methylmethanesulfonamide dihydrochloride tert-butyl 6-((2-isopropyl-1-(2-(N-methylmethylsulfonamido)pyridin-4-yl)-3-oxo-2,3-dihydro-1H-pyrazolo[3,4-d]pyrimidin-6-yl)amino)-3,4-dihydroisoquinoline-2(1H)-carboxylate (30 mg, 0.0495 mmol, 1.0 eq) was dissolved in dioxane (1 mL), followed by dropwise addition of 4.0M-HCl (2 mL) and allowed to stir at rt for 1 h. After completion of reaction, the reaction mixture was filtered and dried under reduced pressure to afford the desired compound, N-(4-(2-isopropyl-3-oxo-6-((1,2,3,4-tetrahydroisoquinolin-6-yl)amino)-2,3-dihydro-1H-pyrazolo[3,4-d]pyrimidin-1-yl)pyridin-2-yl)-N-methylmethanesulfonamide dihydrochloride (11 mg, 38.39%) as light yellow solid.

LCMS: 509.3 [M+1]$^+$; UPLC @ 254 nm=85.04% and @ 220 nm=87.09%.

$^1$H NMR (400 MHz, DMSO-d$_6$): δ 10.48 (br. s., 1H), 9.17 (br. s., 1H), 8.87 (s, 1H) 8.58 (d, J=5.26 Hz, 1H) 7.74 (br. s., 1H) 7.58 (d, J=4.82 Hz, 2H) 7.48 (s, 1H) 7.19 (d, J=8.33 Hz, 1H) 4.22 (br. s., 2H) 3.94-3.99 (m, 1H) 3.35 (t, 2H) 3.25 (br. s., 3H) 3.17 (t, 2H) 3.03 (br. s., 3H) 1.37 (d, J=7.02 Hz, 6H).

Example S82. Synthesis of 1-(2-(2-hydroxypropan-2-yl)pyridin-4-yl)-2-isopropyl-6-((1,2,3,4-tetrahydroisoquinolin-6-yl)amino)-1,2-dihydro-3H-pyrazolo[3,4-d]pyrimidin-3-one (Compound No. 1.178)

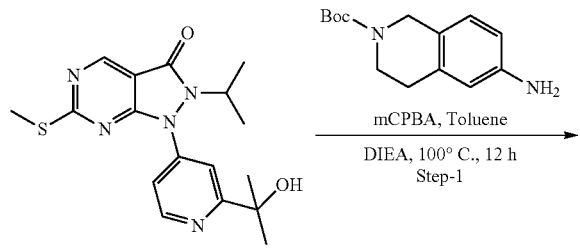

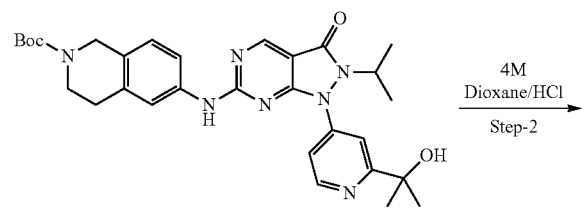

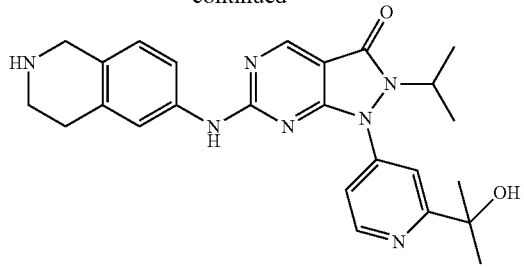

Step-1: Synthesis of tert-butyl 6-((1-(2-(2-hydroxypropan-2-yl)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(2-(2-hydroxypropan-2-yl)pyridin-4-yl)-2-isopropyl-6-(methylthio)-1,2-dihydro-3H-pyrazolo[3,4-d]pyrimidin-3-one (200 mg, 0.5571 mmol, 1.0 eq) in (3.0 mL) of toluene was added m-CPBA (270 mg, 1.1142 mmol, 2.0 eq) and allowed to stir at rt for 1 h. tert-butyl 6-amino-3,4-dihydroisoquinoline-2(1H)-carboxylate (166 mg, 0.6685 mmol, 1.2 eq) and DIPEA (0.4 mL, 2.2284 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((1-(2-(2-hydroxypropan-2-yl)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate (110 mg, 35.32%) as an off white solid.

LCMS: 560.4[M+1]$^+$

Step-2: Synthesis of 1-(2-(2-hydroxypropan-2-yl)pyridin-4-yl)-2-isopropyl-6-((1,2,3,4-tetrahydroisoquinolin-6-yl)amino)-1,2-dihydro-3H-pyrazolo[3,4-d]pyrimidin-3-one tert-butyl 6-((1-(2-(2-hydroxypropan-2-yl)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate (50 mg, 0.089 mmol, 1.0 eq) was dissolved in dioxane (1 mL), followed by dropwise addition of 4.0M-HCl (1 mL) and allowed to stir at rt for 1 h. After completion of reaction, the reaction mixture was filtered and dried under reduced pressure and purified by prep purification to afford the desired compound, 1-(2-(2-hydroxypropan-2-yl)pyridin-4-yl)-2-isopropyl-6-((1,2,3,4-tetrahydroisoquinolin-6-yl)amino)-1,2-dihydro-3H-pyrazolo[3,4-d]pyrimidin-3-one (10 mg, 24.35%) as light yellow solid.

LCMS: 460.4 [M+1]$^+$; UPLC @ 254 nm=97.95% and @ 220 nm=98.46%.

$^1$H NMR (400 MHz, DMSO-d$_6$): δ 10.29 (br. s. 1H), 8.82 (s, 1H) 8.63 (d, J=5.26 Hz, 1H) 7.72 (br. s., 1H) 7.55 (d, J=4.38 Hz, 2H) 7.46 (br. s., 1H) 7.01 (d, J=7.45 Hz, 1H) 5.35 (br. s., 1H) 3.96 (d, J=6.14 Hz, 2H) 3.80 (t, 2H) 2.95 (br. s., 1H) 2.67 (t, 2H) 1.75 (s, 1H) 1.46 (s, 6H) 1.35 (d, J=6.58 Hz, 6H).

843

Example S83. Synthesis of 1-(2-(tert-butyl)pyridin-4-yl)-2-cyclopropyl-6-((1,1-dimethyl-1,2,3,4-tetrahydroisoquinolin-6-yl)amino)-1,2-dihydro-3H-pyrazolo[3,4-d]pyrimidin-3-one dihydrochloride (Compound No. 2.182)

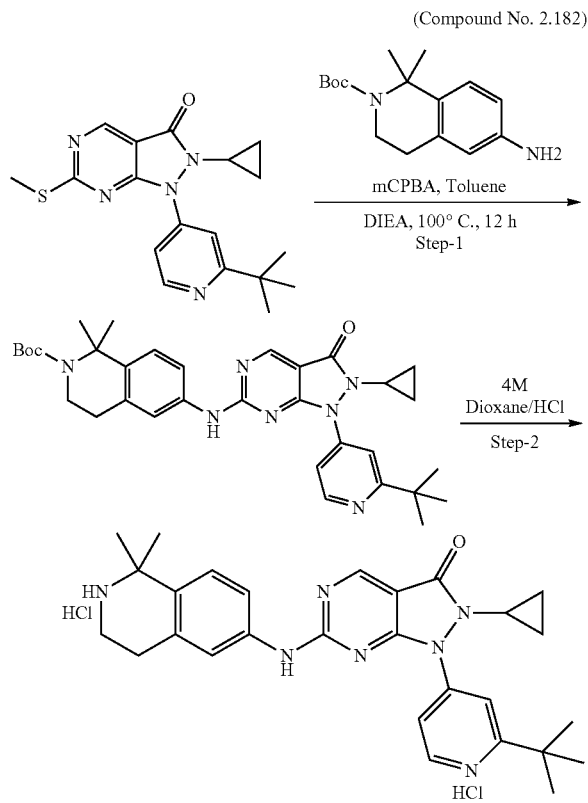

Step-1: Synthesis of tert-butyl 6-((1-(2-(tert-butyl)pyridin-4-yl)-2-cyclopropyl-3-oxo-2,3-dihydro-1H-pyrazolo[3,4-d]pyrimidin-6-yl)amino)-1,1-dimethyl-3,4-dihydroisoquinoline-2(1H)-carboxylate To a stirred solution of 1-(2-(tert-butyl)pyridin-4-yl)-2-cyclopropyl-6-(methylthio)-1,2-dihydro-3H-pyrazolo[3,4-d]pyrimidin-3-one (150 mg, 0.421 mmol, 1.0 eq) in (6.0 mL) of toluene was added m-CPBA (145 mg, 0.842 mmol, 2.0 eq) and allowed to stir at rt for 1 h. tert-butyl 6-amino-1,1-dimethyl-3,4-dihydroisoquinoline-2(1H)-carboxylate (140 mg, 0.506 mmol, 1.2 eq) and DIPEA (0.29 mL, 1.684 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((1-(2-(tert-butyl)pyridin-4-yl)-2-cyclopropyl-3-oxo-2,3-dihydro-1H-pyrazolo[3,4-d]pyrimidin-6-yl)amino)-1,1-dimethyl-3,4-dihydroisoquinoline-2(1H)-carboxylate (60 mg, 24.35%) as an off white solid.

LCMS: 584.3 [M+1]$^+$

844

Step-2: Synthesis of 1-(2-(tert-butyl)pyridin-4-yl)-2-cyclopropyl-6-((1,1-dimethyl-1,2,3,4-tetrahydroisoquinolin-6-yl)amino)-1,2-dihydro-3H-pyrazolo[3,4-d]pyrimidin-3-one dihydrochloride tert-butyl 6-((1-(2-(tert-butyl)pyridin-4-yl)-2-cyclopropyl-3-oxo-2,3-dihydro-1H-pyrazolo[3,4-d]pyrimidin-6-yl)amino)-1,1-dimethyl-3,4-dihydroisoquinoline-2(1H)-carboxylate (60 mg, 0.102 mmol, 1.0 eq) was dissolved in dioxane (1 mL), followed by dropwise addition of 4.0M-HCl (2 mL) and allowed to stir at rt for 1 h. After completion of reaction, the reaction mixture was filtered and dried under reduced pressure to afford the desired compound, 1-(2-(tert-butyl)pyridin-4-yl)-2-cyclopropyl-6-((1,1-dimethyl-1,2,3,4-tetrahydroisoquinolin-6-yl)amino)-1,2-dihydro-3H-pyrazolo[3,4-d]pyrimidin-3-one dihydrochloride (36 mg, 62.93%) as an off white solid.

LCMS: 486.4 [M+1]$^+$; UPLC @ 254 nm=96.12% and @ 220 nm=97.81%.

$^1$H NMR (400 MHz, DMSO-d$_6$): δ δ 10.33 (brs, 1H), 9.34 (brs, 2H), 8.86 (brs, 1H), 8.73 (brs, 1H), 7.58 (brs, 3H), 7.36 (d, J=7.45 Hz, 1H), 3.17 (brs, 2H), 3.04 (brs, 3H), 1.65 (s, 6H), 1.38 (s, 9H), 0.84 (brs, 4H)

Example S84. Synthesis of 1-(2-(tert-butyl)pyrimidin-4-yl)-2-isopropyl-6-(((1,2,3,4-tetrahydroisoquinolin-6-yl)amino)-1,2-dihydro-3H-pyrazolo[3,4-d]pyrimidin-3-one hydrochloride (Compound No. 2.183)

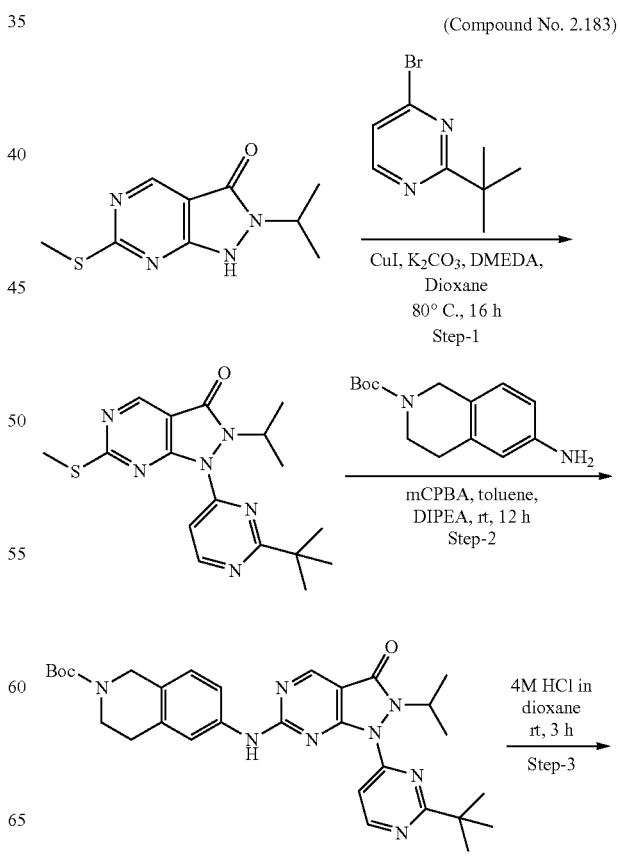

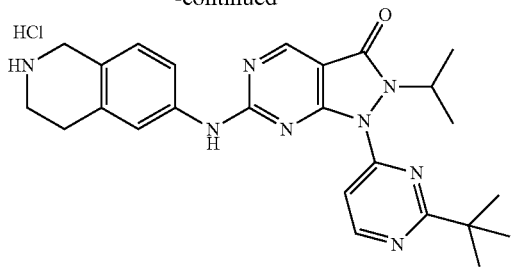

Step 1: Synthesis of 1-(2-(tert-butyl)pyrimidin-4-yl)-2-isopropyl-6-(methylthio)-1,2-dihydro-3H-pyrazolo[3,4-d]pyrimidin-3-one To a stirred solution of 2-isopropyl-6-(methylthio)-1,2-dihydro-3H-pyrazolo[3,4-d]pyrimidin-3-one (417 mg, 1.85 mmol, 1.0 eq.) and 4-bromo-2-(tert-butyl)pyrimidine (400 mg, 1.85 mmol, 1.2 eq.) in 30 mL of dioxane were added copper iodide (71 mg, 0.37 mmol, 0.2 eq.), Potassium carbonate (514 mg, 3.71 mmol, 2 eq.) and DMEDA (0.08 mL, 0.74 mmol, 0.4 eq.) and stirred at 110° C. overnight. After completion of reaction, solvent was removed under reduced pressure; residue was diluted with water and extracted with ethyl acetate (100 mL×3). The combined organic layer were washed with brine solution, dried over anhydrous sodium sulphate and concentrated under reduced pressure to afford crude product, which was purified by flash chromatography to afford 1-(2-(tert-butyl)pyrimidin-4-yl)-2-isopropyl-6-(methylthio)-1,2-dihydro-3H-pyrazolo[3,4-d]pyrimidin-3-one (352 mg, 52.81%) as an off white solid.

LCMS: 359.2 [M+1]+

Step 2: Synthesis of tert-butyl 6-((1-(2-(tert-butyl)pyrimidin-4-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(2-(tert-butyl)pyrimidin-4-yl)-2-isopropyl-6-(methylthio)-1,2-dihydro-3H-pyrazolo[3,4-d]pyrimidin-3-one (176 mg, 0.49 mmol, 1.0 eq.) in 3 mL of toluene was added m-CPBA (169 mg, 0.98 mmol, 2 eq.) and allowed to stir at rt for 1 h. Further, tert-butyl 6-amino-3,4-dihydroisoquinoline-2(1H)-carboxylate (146 mg, 0.58 mmol, 1.2 eq.) and DIPEA (0.33 mL, 1.96 mmol, 4 eq.) were added and allowed to stir at rt for overnight. After completion of reaction, solvent was removed under reduced pressure; residue was diluted with water and extracted with ethyl acetate (50 mL×3). The combined organic layer was washed with brine solution (10 mL), dried over anhydrous sodium sulphate and concentrated under reduced pressure to afford crude product which was purified by flash chromatography to afford tert-butyl 6-((1-(2-(tert-butyl)pyrimidin-4-yl)-2-isopropyl-3-oxo-2,3-dihydro-1H-pyrazolo[3,4-d]pyrimidin-6-yl)amino)-3,4-dihydroisoquinoline-2(1H)-carboxylate (120 mg, 43.74%) as yellow solid.

LCMS: 559.3 [M+1]+

Step 3: Synthesis of 1-(2-(tert-butyl)pyrimidin-4-yl)-2-isopropyl-6-((1,2,3,4-tetrahydroisoquinolin-6-yl)amino)-1,2-dihydro-3H-pyrazolo[3,4-d]pyrimidin-3-one hydrochloride tert-butyl 7-((1-(2-(tert-butyl)pyridin-4-yl)-2-cyclopropyl-3-oxo-2,3-dihydro-1H-pyrazolo[3,4-d]pyrimidin-6-yl)amino)-4,4-dimethyl-3,4-dihydroisoquinoline-2(1H)-carboxylate (120 mg, 0.214 mmol, 1.0 eq) was dissolved in dioxane (1 mL), followed by dropwise addition of 4.0M-HCl (2 mL) and allowed to stir at rt for 1 h. After completion of reaction, the reaction mixture was filtered and dried under reduced pressure to afford the desired compound, 1-(2-(tert-butyl)pyrimidin-4-yl)-2-isopropyl-6-((1,2,3,4-tetrahydroisoquinolin-6-yl)amino)-1,2-dihydro-3H-pyrazolo[3,4-d]pyrimidin-3-one hydrochloride (64 mg, 60.19%) as an off white solid.

LCMS: 459.4 [M+1]+; UPLC @ 254 nm=96.17% and @ 220 nm=95.77%.

$^1$H NMR (400 MHz, DMSO-$d_6$): δ 10.48 (brs, 1H), 9.48 (brs, 2H), 8.84-8.95 (m, 2H), 7.99 (brs, 1H), 7.72 (brs, 1H), 7.47 (brs, 1H), 7.23 (d, J=8.33 Hz, 1H), 4.20-4.31 (m, 3H), 3.39 (brs, 2H), 3.06 (brs, 2H), 1.39-1.55 (m, 6H), 1.38 (s, 9H).

Example S85. Synthesis of 1-(2-(tert-butyl)pyrimidin-4-yl)-2-isopropyl-6-((1,2,3,4-tetrahydroisoquinolin-7-yl)amino)-1,2-dihydro-3H-pyrazolo[3,4-d]pyrimidin-3-one hydrochloride (Compound No. 2.184)

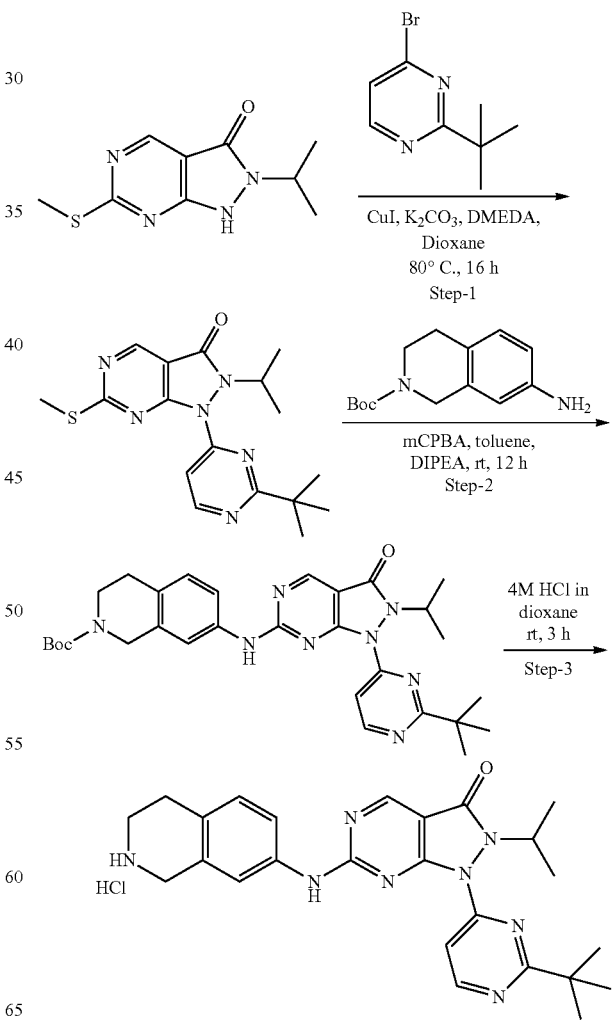

Step 1: Synthesis of 1-(2-(tert-butyl)pyrimidin-4-yl)-2-isopropyl-6-(methylthio)-1,2-dihydro-3H-pyrazolo[3,4-d]pyrimidin-3-one To a stirred solution of 2-isopropyl-6-(methylthio)-1,2-dihydro-3H-pyrazolo[3,4-d]pyrimidin-3-one (417 mg, 1.85 mmol, 1.0 eq.) and 4-bromo-2-(tert-butyl)pyrimidine (400 mg, 1.85 mmol, 1.2 eq.) in 30 mL of dioxane were added copper iodide (71 mg, 0.37 mmol, 0.2 eq.), Potassium carbonate (514 mg, 3.71 mmol, 2 eq.) and DMEDA (0.08 mL, 0.74 mmol, 0.4 eq.) and stirred at 110° C. overnight. After completion of reaction, solvent was removed under reduced pressure; residue was diluted with water and extracted with ethyl acetate (100 mL×3). The combined organic layer were washed with brine solution, dried over anhydrous sodium sulphate and concentrated under reduced pressure to afford crude product, which was purified by flash chromatography to afford 1-(2-(tert-butyl)pyrimidin-4-yl)-2-isopropyl-6-(methylthio)-1,2-dihydro-3H-pyrazolo[3,4-d]pyrimidin-3-one (352 mg, 52.81%) as an off white solid.
LCMS: 359.2 [M+1]$^+$

Step 2: Synthesis of tert-butyl 7-((1-(2-(tert-butyl)pyrimidin-4-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(2-(tert-butyl)pyrimidin-4-yl)-2-isopropyl-6-(methylthio)-1,2-dihydro-3H-pyrazolo[3,4-d]pyrimidin-3-one (176 mg, 0.49 mmol, 1.0 eq.) in 3 mL of toluene was added m-CPBA (169 mg, 0.98 mmol, 2 eq.) and allowed to stir at rt for 1 h. Further, tert-butyl 7-amino-3,4-dihydroisoquinoline-2(1H)-carboxylate (146 mg, 0.58 mmol, 1.2 eq.) and DIPEA (0.33 mL, 1.96 mmol, 4 eq.) were added and allowed to stir at rt for overnight. After completion of reaction, solvent was removed under reduced pressure; residue was diluted with water and extracted with ethyl acetate (50 mL×3). The combined organic layer was washed with brine solution (10 mL), dried over anhydrous sodium sulphate and concentrated under reduced pressure to afford crude product which was purified by flash chromatography to afford tert-butyl 7-((1-(2-(tert-butyl)pyrimidin-4-yl)-2-isopropyl-3-oxo-2,3-dihydro-1H-pyrazolo[3,4-d]pyrimidin-6-yl)amino)-3,4-dihydroisoquinoline-2(1H)-carboxylate (120 mg, 43.74%) as yellow solid.
LCMS: 559.3 [M+1]$^+$

Step 3: Synthesis of 1-(2-(tert-butyl)pyrimidin-4-yl)-2-isopropyl-6-((1,2,3,4-tetrahydroisoquinolin-7-yl)amino)-1,2-dihydro-3H-pyrazolo[3,4-d]pyrimidin-3-one hydrochloride tert-butyl 7-((1-(2-(tert-butyl)pyrimidin-4-yl)-2-isopropyl-3-oxo-2,3-dihydro-1H-pyrazolo[3,4-d]pyrimidin-6-yl)amino)-3,4-dihydroisoquinoline-2(1H)-carboxylate (120 mg, 0.214 mmol, 1.0 eq) was dissolved in dioxane (1 mL), followed by dropwise addition of 4.0M-HCl (2 mL) and allowed to stir at rt for 1 h. After completion of reaction, the reaction mixture was filtered and dried under reduced pressure to afford the desired compound, 1-(2-(tert-butyl)pyrimidin-4-yl)-2-isopropyl-6-((1,2,3,4-tetrahydroisoquinolin-7-yl)amino)-1,2-dihydro-3H-pyrazolo[3,4-d]pyrimidin-3-one hydrochloride (98 mg, 92.17%) as an off white solid.
LCMS: 459.4 [M+1]$^+$; UPLC @ 254 nm=95.93% and @ 220 nm=96.06%.
$^1$H NMR (400 MHz, DMSO-d$_6$): δ 10.49 (brs, 1H), 9.19 (brs, 2H), 8.84-8.95 (m, 2H), 8.00 (brs, 1H), 7.71 (brs, 1H), 7.47 (brs, 1H), 7.24 (d, J=8.33 Hz, 1H), 4.18-4.39 (m, 3H), 3.40 (brs, 3H), 2.99 (brs, 2H), 1.47 (d, J=7.02 Hz, 6H), 1.38 (s, 9H).

Example S86. Synthesis of 1-(4-fluoro-3-(2-hydroxypropan-2-yl)phenyl)-2-isopropyl-6-((1,2,3,4-tetrahydroisoquinolin-6-yl)amino)-1,2-dihydro-3H-pyrazolo[3,4-d]pyrimidin-3-one (Compound No. 2.185)

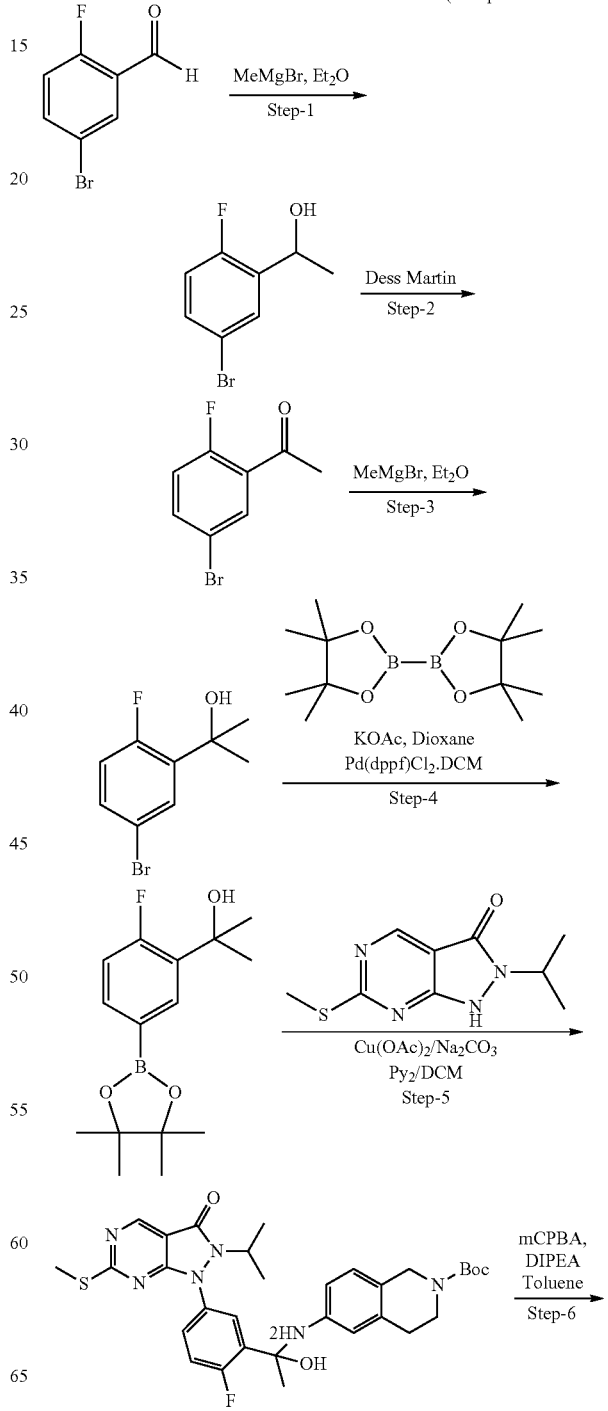

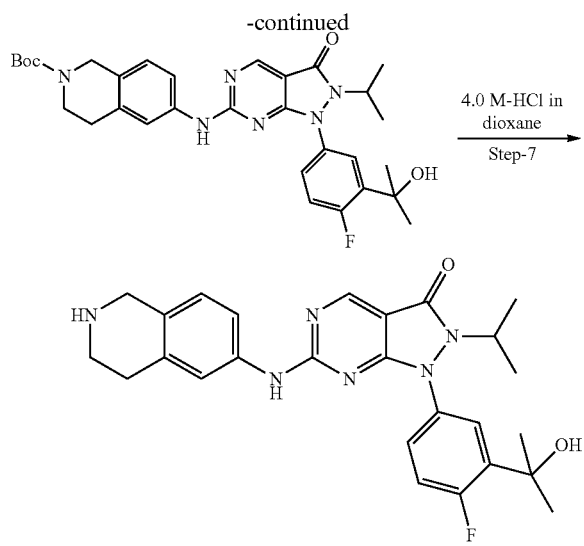

Step-1: Synthesis of 1-(5-bromo-2-fluorophenyl)ethan-1-ol

To a stirred solution of 5-bromo-2-fluorobenzaldehyde (5.0 g, 24.63 mmol, 1.0 eq) in diethylether (50 mL) was dropwise added methylmagnesium bromide (12.3 mL, 36.94 mmol, 1.5 eq) at 0° C. The resulting mixture was stirred at 0° C. for 15 min. The progress of reaction was monitored by LCMS. The resection mixture was quenched with saturated solution of NH$_4$Cl (50 mL) extracted with EtOAc (2×50 mL). The combined organic extracts were washed with water (50 mL), with brine (50 mL) dried over Na$_2$SO$_4$ and concentrated under reduced to afford the desired compound 1-(5-bromo-2-fluorophenyl)ethan-1-ol (5.31 g, 98.51%) as yellow liquid.

$^1$H NMR (400 MHz, CDCl$_3$) 7.64 (dd, J=2.41, 6.36 Hz, 1H), 7.35 (ddd, J=2.63, 4.60, 8.55 Hz, 1H), 6.91 (dd, J=8.77, 9.65 Hz, 1H), 5.16 (d, J=5.26 Hz, 1H), 1.88 (brs, 1H), 1.50 (d, J=6.14 Hz, 3H).

Step-2: Synthesis of 1-(5-bromo-2-fluorophenyl)ethan-1-one

To a stirred solution of 1-(5-bromo-2-fluorophenyl)ethan-1-ol (5.3 g, 24.195 mmol, 1.0 eq) in THF (50 mL) was added Dess-martin peridionane (12.314 g, 29.034 mmol, 1.2 eq) at 0° C. The resulting mixture was stirred at rt for 15 min. The progress of reaction was monitored by LCMS. The resection mixture was quenched with saturated solution of NaHCO$_3$ (50 mL) extracted with EtOAc (2×50 mL). The combined organic extracts were washed with water (50 mL), with brine (50 mL) dried over Na$_2$SO$_4$ and concentrated under reduced pressure and purified by flash chromatography [silica gel 100-200 mesh; elution 0-5% EtOAc in hexane] to afford the desired compound 1-(5-bromo-2-fluorophenyl)ethan-1-one (3.78 g, 72.00%) as yellow liquid.

$^1$H NMR (400 MHz, CDCl$_3$) δ 7.99 (dd, J=2.63, 6.58 Hz, 1H), 7.61 (ddd, J=2.63, 4.39, 8.77 Hz, 1H), 7.05 (dd, J=8.77, 10.09 Hz, 1H), 2.64 (d, J=4.82 Hz, 3H).

Step-3: Synthesis of 2-(5-bromo-2-fluorophenyl)propan-2-ol

To a stirred solution of 1-(5-bromo-2-fluorophenyl)ethan-1-one (3.70 g, 17.047 mmol, 1.0 eq) in diethylether (30 mL) was dropwise added methylmagnesium bromide (8.53 mL, 25.571 mmol, 1.5 eq) at 0° C. The resulting mixture was stirred at 0° C. for 15 min. The progress of reaction was monitored by LCMS. The resection mixture was quenched with saturated solution of NH$_4$Cl (50 mL) extracted with EtOAc (2×50 mL). The combined organic extracts were washed with water (50 mL), with brine (50 mL) dried over Na$_2$SO$_4$ and concentrated under reduced pressure and purified by flash chromatography [silica gel 100-200 mesh; elution 0-5% EtOAc in hexane] to afford the desired compound 2-(5-bromo-2-fluorophenyl)propan-2-ol (3.2 g, 93.02%) as yellow liquid.

$^1$H NMR (400 MHz, CDCl$_3$) δ 7.73 (dd, J=2.63, 7.45 Hz, 1H), 7.34 (ddd, J=2.63, 4.38, 8.77 Hz, 1H), 6.91 (dd, J=8.33, 11.40 Hz, 1H), 2.02 (d, J=17.54 Hz, 1H), 1.61-1.64 (m, 6H).

Step-4: Synthesis of 2-(2-fluoro-5-(4,4,5,5-tetramethyl-1,3,2-dioxaborolan-2-yl)phenyl)propan-2-ol To a stirred solution of 2-(5-bromo-2-fluorophenyl)propan-2-ol (1.0 g, 4.290 mmol, 1.0 eq) and 4,4,4',4',5,5,5',5'-octamethyl-2,2'-bi(1,3,2-dioxaborolane) (1.30 g, 5.148 mmol, 1.2 eq) in dioxane (30 mL) was added KoAc (1.05 g, 10.725 mmol, 2.5 eq) at rt. The resulting mixture was purged with N$_2$ for 10 min. followed by addition of Pd(dppf)Cl$_2$.DCM (175 mg, 0.214 mmol, 0.05 eq) and again purged with N$_2$ for 10 min. The resulting mixture was stirred at 70° C. for overnight. The progress of reaction was monitored by LCMS. The resection mixture was diluted with water (50 mL) extracted with EtOAc (2×50 mL). The combined organic extracts were washed with water (50 mL), with brine (50 mL) dried over Na$_2$SO$_4$ and concentrated under reduced pressure and purified by flash chromatography [silica gel 100-200 mesh; elution 0-5% EtOAc in hexane] to afford the desired compound 2-(2-fluoro-5-(4,4,5,5-tetramethyl-1,3,2-dioxaborolan-2-yl)phenyl)propan-2-ol (705 mg, 58.75%) as yellow viscous.

$^1$H NMR (400 MHz, CDCl$_3$) δ 7.98 (dd, J=1.53, 8.99 Hz, 1H), 7.64-7.74 (m, 1H), 7.02 (dd, J=8.11, 12.50 Hz, 1H), 2.14 (brs, 1H), 1.61-1.70 (m, 6H), 1.34 (s, 12H).

Step-5: Synthesis of 1-(4-fluoro-3-(2-hydroxypropan-2-yl)phenyl)-2-isopropyl-6-(methylthio)-1,2-dihydro-3H-pyrazolo[3,4-d]pyrimidin-3-one To a stirred solution of 2-isopropyl-6-(methylthio)-1,2-dihydro-3H-pyrazolo[3,4-d]pyrimidin-3-one (280 mg, 1.249 mmol, 1.0 eq) and 2-(2-fluoro-5-(4,4,5,5-tetramethyl-1,3,2-dioxaborolan-2-yl)phenyl)propan-2-ol (700 mg, 2.498 mmol, 2.0 eq) in (50 mL) of CH$_2$Cl$_2$ was added Na$_2$CO$_3$ (397 mg, 3.747 mmol, 3.0 eq), Cu(OAc)$_2$ (442 mg, 2.498 mmol, 2.0 eq), Py$_2$ (390 mg, 2.498 mmol, 2.0 eq), and the resulting mixture was stirred at rt for 48 h. After completion of reaction, the reaction mixture was diluted with water (50.0 mL) and extracted with EtOAc (50 mL×2). Combined organic layer was washed with water (50 mL) brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound 1-(4-fluoro-3-(2-hydroxypropan-2-yl)phenyl)-2- isopropyl-6-(methylthio)-1,2-dihydro-3H-pyrazolo[3,4-d]pyrimidin-3-one (220 mg, 46.80%) as light yellow viscous.

LCMS: 377.2 [M+1]⁺

Step-6: Synthesis of tert-butyl 6-((1-(4-fluoro-3-(2-hydroxypropan-2-yl)phenyl)-2-isopropyl-3-oxo-2,3-dihydro-1H-pyrazolo[3,4-d]pyrimidin-6-yl)amino)-3,4-dihydro isoquinoline-2(1H)-carboxylate To a stirred solution of 1-(4-fluoro-3-(2-hydroxypropan-2-yl)phenyl)-2-isopropyl-6-(methylthio)-1,2-dihydro-3H-pyrazolo[3,4-d]pyrimidin-3-one (100 mg, 0.265 mmol, 1.0 eq) in (2.0 mL) of toluene was added mCPBA (130 mg, 0.530 mmol, 2.0 eq) and allowed to stir at rt for 30 minutes. tert-butyl 6-amino-3,4-dihydroisoquinoline-2(1H)-carboxylate (80 mg, 0.318 mmol, 1.2 eq) and DIPEA (0.180 mL, 1.06 mmol, 4.0 eq) were added and allowed to stir at rt for overnight. After completion of reaction, the reaction mixture was diluted with water and extracted with EtOAc (20 mL×2). Combined organic layer was washed with water (50 mL) brine solution (50 mL), dried over anhydrous sodium sulfate and concentrated under reduced pressure to afford crude product, which was purified by flash chromatography [silica gel 100-200 mesh; elution 0-60% EtOAc in hexane] to afford the desired compound tert-butyl 6-((1-(4-fluoro-3-(2-hydroxypropan-2-yl)phenyl)-2-isopropyl-3-oxo-2,3-dihydro-1H-pyrazolo[3,4-d]pyrimidin-6-yl)amino)-3,4-dihydro isoquinoline-2(1H)-carboxylate (60 mg, 39.21%) as brown viscous.

LCMS: 577.4 [M+1]⁺

Step-7: Synthesis of 1-(4-fluoro-3-(2-hydroxypropan-2-yl)phenyl)-2-isopropyl-6-((1,2,3,4-tetrahydroisoquinolin-6-yl)amino)-1,2-dihydro-3H-pyrazolo[3,4-d]pyrimidin-3-one tert-butyl 6-((1-(4-fluoro-3-(2-hydroxypropan-2-yl)phenyl)-2-isopropyl-3-oxo-2,3-dihydro-1H-pyrazolo[3,4-d]pyrimidin-6-yl)amino)-3,4-dihydro isoquinoline-2(1H)-carboxylate (60 mg, 1.00 mmol, 1.0 eq) was dissolved in 4.0M-HCl (1.5 mL) and allowed to stir at rt for 1 h. After completion of reaction, the reaction mixture was basified with NaHCO₃ water and extracted with EtOAc (20 mL×2). Combined organic layer was washed with water (50 mL) brine solution (50 mL), dried over anhydrous sodium sulfate and concentrated under reduced pressure to afford crude product, which was purified by reverse phase chromatography to afford the desired compound 1-(4-fluoro-3-(2-hydroxypropan-2-yl)phenyl)-2-isopropyl-6-((1,2,3,4-tetrahydroisoquinolin-6-yl)amino)-1,2-dihydro-3H-pyrazolo[3,4-d]pyrimidin-3-one (7.0 mg, 14.28%) as white solid.

LCMS: 477.4 [M+1]⁺; UPLC @ 254 nm=95.78% and @ 220 nm=96.10%.

¹H NMR (400 MHz, DMSO-d₆): δ 10.26 (brs, 1H), 9.10 (brs, 2H), 8.84 (s, 1H), 7.66 (brs, 1H), 7.60 (brs, 1H), 7.54 (d, J=7.02 Hz, 2H), 7.28-7.38 (m, 1H), 7.12 (d, J=8.77 Hz, 1H), 5.47 (brs, 1H), 4.19 (brs, 2H), 4.05-4.13 (m, 1H), 2.92 (brs, 2H), 1.50 (s, 6H), 1.26 (d, J=6.58 Hz, 6H).

Example S87. Synthesis of 1-(4-fluoro-3-(2-hydroxypropan-2-yl)phenyl)-2-isopropyl-6-((1,2,3,4-tetrahydroisoquinolin-7-yl)amino)-1,2-dihydro-3H-pyrazolo[3,4-d]pyrimidin-3-one (Compound No. 2.186)

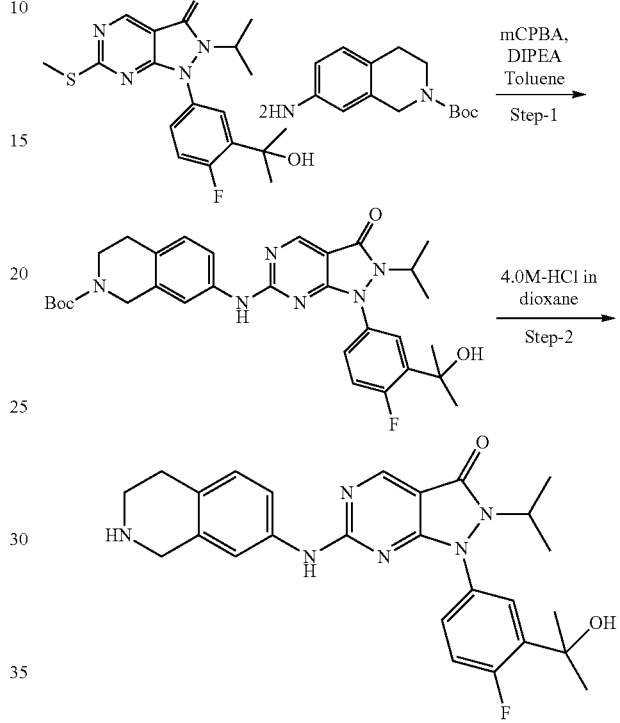

Step-1: Synthesis of tert-butyl 7-((1-(4-fluoro-3-(2-hydroxypropan-2-yl)phenyl)-2-isopropyl-3-oxo-2,3-dihydro-1H-pyrazolo[3,4-d]pyrimidin-6-yl)amino)-3,4-dihydro isoquinoline-2(1H)-carboxylate To a stirred solution of 1-(4-fluoro-3-(2-hydroxypropan-2-yl)phenyl)-2-isopropyl-6-(methylthio)-1,2-dihydro-3H-pyrazolo[3,4-d]pyrimidin-3-one (100 mg, 0.265 mmol, 1.0 eq) in (2.0 mL) of toluene was added mCPBA (130 mg, 0.530 mmol, 2.0 eq) and allowed to stir at rt for 30 minutes. tert-butyl 7-amino-3,4-dihydroisoquinoline-2(1H)-carboxylate (80 mg, 0.318 mmol, 1.2 eq) and DIPEA (0.180 mL, 1.06 mmol, 4.0 eq) were added and allowed to stir at rt for overnight. After completion of reaction, the reaction mixture was diluted with water and extracted with EtOAc (20 mL×2). Combined organic layer was washed with water (50 mL) brine solution (50 mL), dried over anhydrous sodium sulfate and concentrated under reduced pressure to afford crude product, which was purified by flash chromatography [silica gel 100-200 mesh; elution 0-60% EtOAc in hexane] to afford the desired compound tert-butyl 7-((1-(4-fluoro-3-(2-hydroxypropan-2-yl)phenyl)-2-isopropyl-3-oxo-2,3-dihydro-1H-pyrazolo[3,4-d]pyrimidin-6-yl)amino)-3,4-dihydro isoquinoline-2(1H)-carboxylate (40 mg, 26.14%) as brown viscous.

LCMS: 577.4 [M+1]⁺

Step-2: Synthesis of 1-(4-fluoro-3-(2-hydroxypropan-2-yl)phenyl)-2-isopropyl-6-((1,2,3,4-tetrahydroisoquinolin-7-yl)amino)-1,2-dihydro-3H-pyrazolo[3,4-d]pyrimidin-3-one tert-butyl 7-((1-(4-fluoro-3-(2-hydroxypropan-2-yl)phenyl)-2-isopropyl-3-oxo-2,3-dihydro-1H-pyrazolo[3,4-d]pyrimidin-6-yl)amino)-3,4-dihydro isoquinoline-2(1H)-carboxylate (40 mg, 0.069 mmol, 1.0 eq) was dissolved in 4.0M-HCl (1.5 mL) and allowed to stir at rt for 1 h. After completion of reaction, the reaction mixture was basified with NaHCO$_3$ water and extracted with EtOAc (20 mL×2). Combined organic layer was washed with water (50 mL) brine solution (50 mL), dried over anhydrous sodium sulfate and concentrated under reduced pressure to afford crude product, which was purified by reverse phase chromatography to afford the desired compound 1-(4-fluoro-3-(2-hydroxypropan-2-yl)phenyl)-2-isopropyl-6-((1,2,3,4-tetrahydroisoquinolin-7-yl)amino)-1,2-dihydro-3H-pyrazolo[3,4-d]pyrimidin-3-one (9.0 mg, 27.27%) as white solid.

LCMS: 477.4 [M+1]$^+$; UPLC @ 254 nm=98.89% and @ 220 nm=98.54%.

$^1$H NMR (400 MHz, DMSO-d$_6$) δ 10.28 (brs, 1H), 9.12 (brs, 2H), 8.83 (s, 1H), 7.66 (brs, 1H), 7.55 (s, 1H), 7.58 (s, 2H), 7.36 (d, J=10.96 Hz, 1H), 7.14 (d, J=7.89 Hz, 2H), 5.48 (brs, 1H), 4.21 (brs, 2H), 4.05-4.11 (m, 1H), 2.93 (brs, 2H), 1.51 (s, 6H), 1.26 (d, J=6.58 Hz, 6H).

Example S88. Synthesis of 6-((1,1-dimethyl-1,2,3,4-tetrahydroisoquinolin-6-yl)amino)-1-(2-(2-fluoropropan-2-yl)pyridin-4-yl)-2-isopropyl-1,2-dihydro-3H-pyrazolo[3,4-d]pyrimidin-3-one dihydrochloride (Compound No. 2.187)

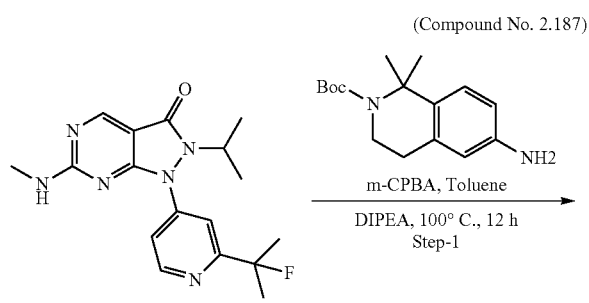

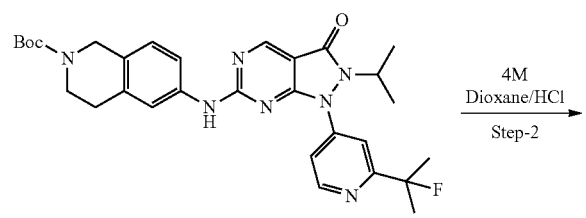

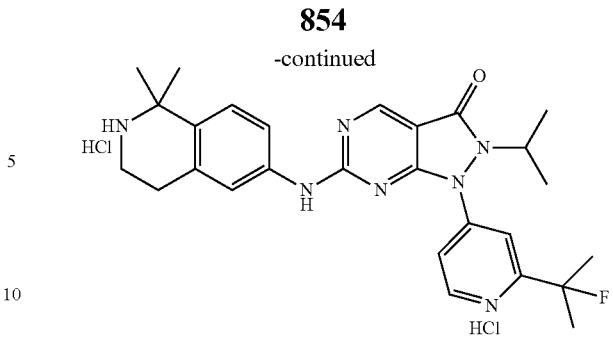

Step-1: Synthesis of tert-butyl 6-((1-(2-(2-fluoropropan-2-yl)pyridin-4-yl)-2-isopropyl-3-oxo-2,3-dihydro-1H-pyrazolo[3,4-d]pyrimidin-6-yl)amino)-1,1-dimethyl-3,4-dihydroisoquinoline-2(1H)-carboxylate To a stirred solution of 1-(2-(2-fluoropropan-2-yl)pyridin-4-yl)-2-isopropyl-6-(methylthio)-1,2-dihydro-3H-pyrazolo[3,4-d]pyrimidin-3-one (95 mg, 0.262 mmol, 1.0 eq) in (6.0 mL) of toluene was added m-CPBA (90 mg, 0.524 mmol, 2.0 eq) and allowed to stir at rt for 1 h. tert-butyl 6-amino-1,1-dimethyl-3,4-dihydroisoquinoline-2(1H)-carboxylate (87 mg, 0.315 mmol, 1.2 eq) and DIPEA (0.18 mL, 1.048 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((1-(2-(2-fluoropropan-2-yl)pyridin-4-yl)-2-isopropyl-3-oxo-2,3-dihydro-1H-pyrazolo[3,4-d]pyrimidin-6-yl)amino)-1,1-dimethyl-3,4-dihydroisoquinoline-2(1H)-carboxylate (60 mg, 38.70%) as an off white solid.

LCMS: 590.3 [M+1]$^+$

Step-2: Synthesis of 6-((1,1-dimethyl-1,2,3,4-tetrahydroisoquinolin-6-yl)amino)-1-(2-(2-fluoropropan-2-yl)pyridin-4-yl)-2-isopropyl-1,2-dihydro-3H-pyrazolo[3,4-d]pyrimidin-3-one dihydrochloride tert-butyl 6-((1-(2-(2-fluoropropan-2-yl)pyridin-4-yl)-2-isopropyl-3-oxo-2,3-dihydro-1H-pyrazolo[3,4-d]pyrimidin-6-yl)amino)-1,1-dimethyl-3,4-dihydroisoquinoline-2(1H)-carboxylate (60 mg, 0.102 mmol, 1.0 eq) was dissolved in dioxane (1 mL), followed by dropwise addition of 4.0M-HCl (2 mL) and allowed to stir at rt for 1 h. After completion of reaction, the reaction mixture was filtered and dried under reduced pressure to afford the desired compound, 6-((1,1-dimethyl-1,2,3,4-tetrahydroisoquinolin-6-yl)amino)-1-(2-(2-fluoropropan-2-yl)pyridin-4-yl)-2-isopropyl-1,2-dihydro-3H-pyrazolo[3,4-d]pyrimidin-3-one dihydrochloride (36 mg, 62.90%) as an off white solid.

LCMS: 490.3 [M+1]$^+$; UPLC @ 254 nm=96.29% and @ 220 nm=96.60%.

$^1$H NMR (400 MHz, DMSO-d$_6$): δ 10.47 (brs, 1H), 9.53 (brs, 2H), 8.87 (s, 1H), 8.74 (d, J=5.70 Hz, 1H), 7.63 (d, J=7.02 Hz, 2H), 7.53 (brs, 1H), 7.34 (d, J=8.77 Hz, 1H), 3.41 (brs, 2H), 3.05 (br., 2H), 1.72 (s, 3H), 1.53-1.67 (m, 9H), 1.36 (d, J=6.58 Hz, 4H).

Example S89. Synthesis of 1-(1-cyclopropyl-1H-pyrazol-3-yl)-2-isopropyl-6-((1,2,3,4-tetrahydroisoquinolin-6-yl)amino)-1,2-dihydro-3H-pyrazolo[3,4-d]pyrimidin-3-one hydrochloride (Compound No. 2.188)

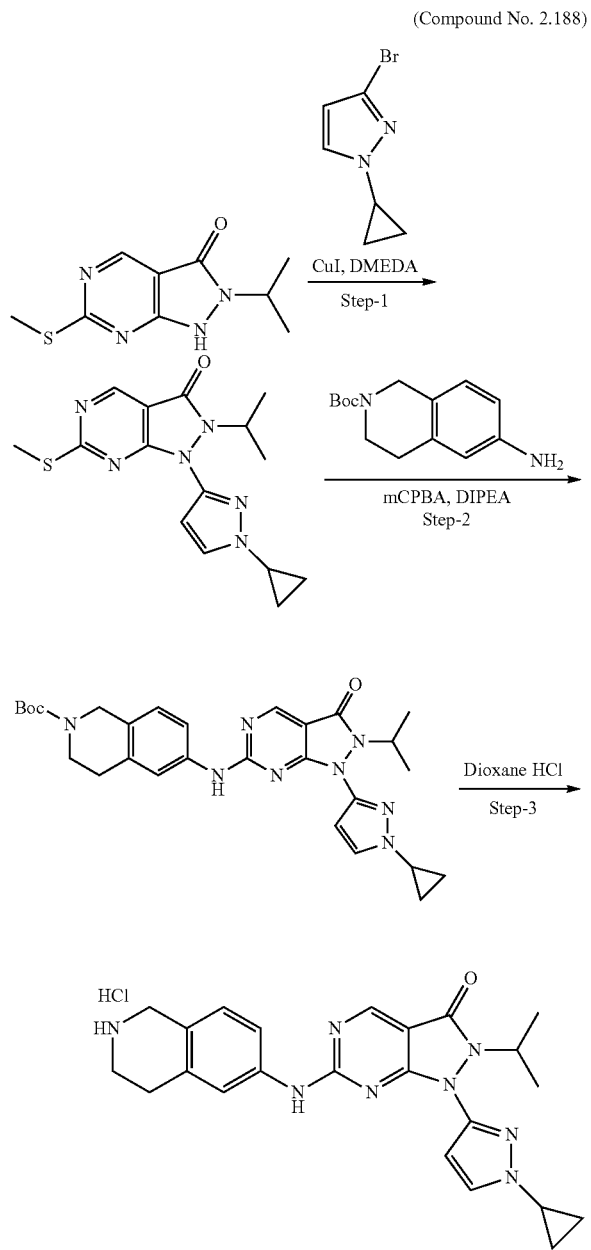

Step-1: Synthesis of 1-(1-cyclopropyl-1H-pyrazol-3-yl)-2-isopropyl-6-(methylthio)-1,2-dihydro-3H-pyrazolo[3,4-d]pyrimidin-3-one To a stirred solution of 2-isopropyl-6-(methylthio)-1,2-dihydro-3H-pyrazolo[3,4-d]pyrimidin-3-one (1.0 g, 4.45 mmol, 1.0 eq) and 3-bromo-1-cyclopropyl-1H-pyrazole (1.0 g, 5.34 mmol, 1.2 eq) in (30 mL) of dioxane was added Potassium carbonate (1.23 g, 8.9 mmol, 2.0 eq) and the resulting mixture was purged with nitrogen for 10 min, followed by addition of copper iodide (0.17 g, 0.89 mmol, 0.2 eq) and N,N'-dimethylethylenediamine (DMEDA) (0.20 mL, 1.78 mmol, 2 eq) and again purged with nitrogen for 10 min, stirred at 130° C. for overnight. After completion of reaction, the reaction mixture was diluted with water and extracted with EtOAc (50 mL×2). The combined organic layers were washed with water (30 mL), brine solution (30 mL), dried over anhydrous sodium sulphate and concentrated under reduced pressure to afford crude product, which was purified by flash chromatography to afford the desired compound, 1-(1-cyclopropyl-1H-pyrazol-3-yl)-2-isopropyl-6-(methylthio)-1,2-dihydro-3H-pyrazolo[3,4-d]pyrimidin-3-one (180 mg, 12.24%) as an off white solid.

LCMS: 331.1 [M+1]$^+$

Step-2: Synthesis of tert-butyl 6-((1-(1-cyclopropyl-1H-pyrazol-3-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(1-cyclopropyl-1H-pyrazol-3-yl)-2-isopropyl-6-(methylthio)-1,2-dihydro-3H-pyrazolo[3,4-d]pyrimidin-3-one (180 mg, 0.545 mmol, 1.0 eq) in (2 mL) of toluene was added m-CPBA (188 mg, 1.09 mmol, 2.0 eq) and allowed to stir at rt for 1 h. Tert-butyl 6-amino-3,4-dihydroisoquinoline-2(1H)-carboxylate (162.4 mg, 0.654 mmol, 1.2 eq) and DIPEA (0.377 mL, 2.18 mmol, 4.0 eq) were added and allowed to stir at rt for overnight. The reaction mixture was diluted with water (30 mL) and extracted with EtOAc (30 mL×2). The combined organic layer were dried over sodium sulphate, concentrated under reduced pressure purified by column chromatography (Combiflash, elution-0-60% EtOAc in Hexane) to afford the desired compound, tert-butyl 6-((1-(1-cyclopropyl-1H-pyrazol-3-yl)-2-isopropyl-3-oxo-2,3-dihydro-1H-pyrazolo[3,4-d]pyrimidin-6-yl)amino)-3,4-dihydroisoquinoline-2(1H)-carboxylate (95 mg, 32.86%) as yellow liquid.

LCMS: 531.4 [M+1]$^+$

Step-3: Synthesis of 1-(1-cyclopropyl-1H-pyrazol-3-yl)-2-isopropyl-6-(((1,2,3,4-tetrahydroisoquinolin-6-yl)amino)-1,2-dihydro-3H-pyrazolo[3,4-d]pyrimidin-3-one hydrochloride To a stirred solution of tert-butyl 6-((1-(1-cyclopropyl-1H-pyrazol-3-yl)-2-isopropyl-3-oxo-2,3-dihydro-1H-pyrazolo[3,4-d]pyrimidin-6-yl)amino)-3,4-dihydroisoquinoline-2(1H)-carboxylate (95 mg, 0.17 mmol, 1.0 eq) in (1 mL) of dioxane was added 4M dioxane-HCl (1 mL) and allowed to stir at rt for 2 h. After completion of reaction, the reaction mixture was filtered and dried under reduced pressure to afford the desired compound, 1-(1-cyclopropyl-1H-pyrazol-3-yl)-2-isopropyl-6-(((1,2,3,4-tetrahydroisoquinolin-6-yl)amino)-1,2-dihydro-3H-pyrazolo[3,4-d]pyrimidin-3-one hydrochloride (64 mg, 76.55%) as light yellow solid.

LCMS: 431.2 [M+1]$^+$, UPLC @ 254 nm=97.16% and @ 220 nm=98.13%.

$^1$H NMR (400 MHz, DMSO-d$_6$): δ 10.23 (brs, 1H), 9.30 (brs, 2H), 8.81 (s, 1H), 7.97 (d, J=2.19 Hz, 1H), 7.65 (brs, 1H), 7.51 (d, J=7.89 Hz, 1H), 7.11 (d, J=8.77 Hz, 1H), 6.46 (d, J=2.19 Hz, 1H), 4.24-4.33 (m, 1H), 4.18 (brs, 2H), 3.81 (dd, J=3.51, 7.45 Hz, 1H), 3.34 (brs, 2H), 2.88-2.97 (m, 2H), 1.24 (d, J=6.58 Hz, 6H), 1.00-1.09 (m, 4H).

Example S90. Synthesis of 1-(1-cyclopropyl-1H-pyrazol-3-yl)-2-isopropyl-6-((1,2,3,4-tetrahydroisoquinolin-7-yl)amino)-1,2-dihydro-3H-pyrazolo[3,4-d]pyrimidin-3-one (Compound No. 2.189)

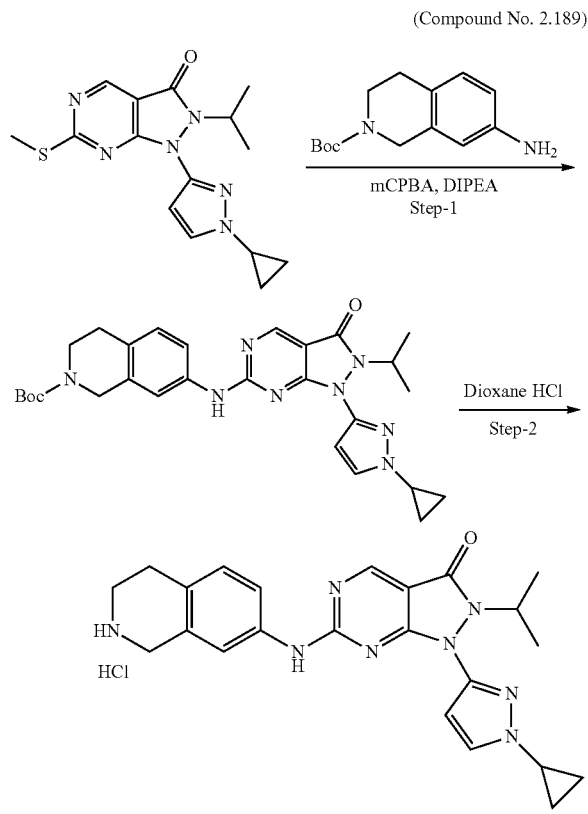

Step-1: Synthesis of tert-butyl 7-((1-(1-cyclopropyl-1H-pyrazol-3-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(1-cyclopropyl-1H-pyrazol-3-yl)-2-isopropyl-6-(methylthio)-1,2-dihydro-3H-pyrazolo[3,4-d]pyrimidin-3-one (85 mg, 0.257 mmol, 1.0 eq) in (1.5 mL) of toluene was added m-CPBA (88.70 mg, 0.514 mmol, 2.0 eq) and allowed to stir at rt for 1 h. Tert-butyl 7-amino-3,4-dihydroisoquinoline-2(1H)-carboxylate (76.6 mg, 0.308 mmol, 1.2 eq) and DIPEA (0.17 mL, 2.18 mmol, 4.0 eq) were added and allowed to stir at rt for overnight. The reaction mixture was diluted with water (30 mL) and extracted with EtOAc (30 mL×2). The combined organic layer were dried over sodium sulphate, concentrated under reduced pressure purified by column chromatography (Combiflash, elution-0-60% EtOAc in Hexane) to afford the desired compound, tert-butyl 7-((1-(1-cyclopropyl-1H-pyrazol-3-yl)-2-isopropyl-3-oxo-2,3-dihydro-1H-pyrazolo[3,4-d]pyrimidin-6-yl)amino)-3,4-dihydroisoquinoline-2(1H)-carboxylate (36 mg, 26.37%) as yellow liquid.

LCMS: 531.4 [M+1]$^+$

Step-2: Synthesis of 1-(1-cyclopropyl-1H-pyrazol-3-yl)-2-isopropyl-6-((1,2,3,4-tetrahydroisoquinolin-7-yl)amino)-1,2-dihydro-3H-pyrazolo[3,4-d]pyrimidin-3-one To a stirred solution of tert-butyl 7-((1-(1-cyclopropyl-1H-pyrazol-3-yl)-2-isopropyl-3-oxo-2,3-dihydro-1H-pyrazolo[3,4-d]pyrimidin-6-yl)amino)-3,4-dihydroisoquinoline-2(1H)-carboxylate (36 mg, 0.067 mmol, 1.0 eq) in (0.6 mL) of dioxane was added 4M dioxane-HCl (0.6 mL) and allowed to stir at rt for 2 h. After completion of reaction, the reaction mixture was filtered and dried under reduced pressure to afford the desired compound, of 1-(1-cyclopropyl-1H-pyrazol-3-yl)-2-isopropyl-6-((1,2,3,4-tetrahydroisoquinolin-7-yl)amino)-1,2-dihydro-3H-pyrazolo[3,4-d]pyrimidin-3-one (18 mg, 58.59%) as light yellow solid.

LCMS: 431.2 [M+1]$^+$, UPLC @ 254 nm=95.48% and @ 220 nm=96.05%.

$^1$H NMR (400 MHz, DMSO-d$_6$): δ 10.23 (brs, 1H), 9.23 (brs, 2H), 8.81 (s, 1H), 7.95 (d, J=2.63 Hz, 1H), 7.63 (brs, 1H), 7.53 (d, J=8.33 Hz, 1H), 7.12 (d, J=7.89 Hz, 1H), 6.46 (d, J=2.19 Hz, 1H), 4.22-4.31 (m, 1H), 4.19 (brs, 2H), 3.74-3.87 (m, 2H), 3.35 (brs, 2H), 2.93 (t, J=6.14 Hz, 2H), 1.24 (d, J=6.58 Hz, 6H), 0.93-1.10 (m, 4H).

Example S91. Synthesis of 2-isopropyl-1-(1-methyl-1H-pyrazol-3-yl)-6-((1,2,3,4-tetrahydroisoquinolin-6-yl)amino)-1,2-dihydro-3H-pyrazolo[3,4-d]pyrimidin-3-one hydrochloride (Compound No. 2.289)

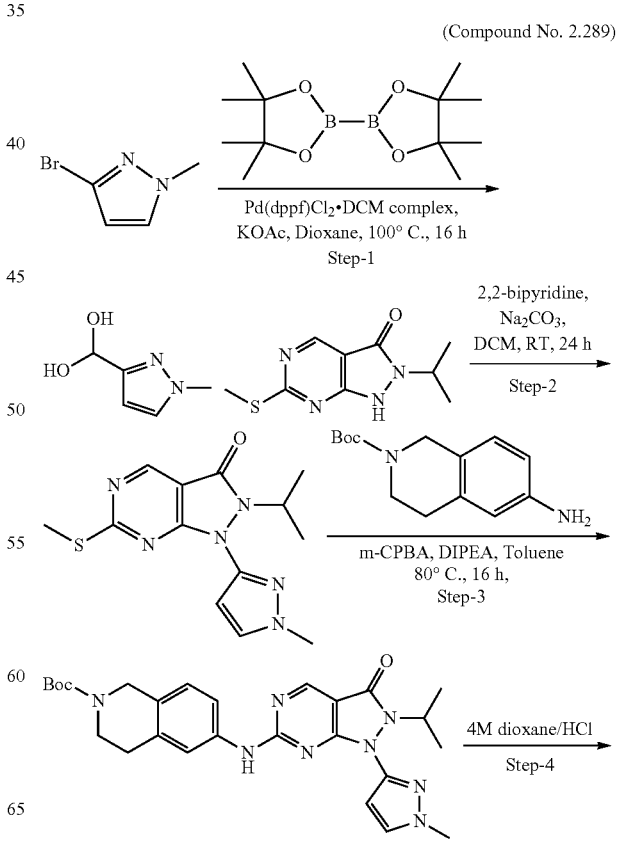

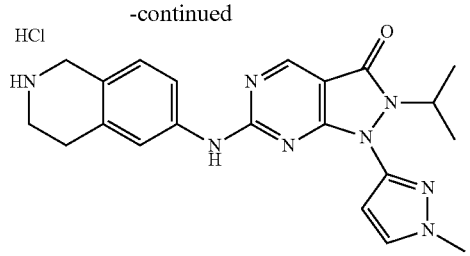

Step-1: Synthesis of (1-methyl-1H-pyrazol-3-yl)boronic acid

To a stirred solution of 3-bromo-1-methyl-1H-pyrazole (10 g, 62.11 mmol, 1 eq.) and 4,4,4',4',5,5,5',5'-octamethyl-2,2'-bi(1,3,2-dioxaborolane) (23.6 g, 93.167 mmol, 1.5 eq.) in 120 mL of dioxane was added potassium acetate (18.28 g, 186.33 mmol, 3.0 eq.). The reaction mixture was purged with $N_2$ for about 5 min and Pd(dppf)Cl$_2$.DCM complex (2.5 g, 3.105 mmol, 0.05 eq.) was added. The reaction mixture was re-purged with $N_2$ and heated at 100° C. for 16 h. Following this reaction mixture was allowed to cool to rt and filtered through celite bed and washed with ethyl acetate (200 mL). The obtained organic layer was concentrated under reduced pressure to get desired product, (1-methyl-1H-pyrazol-3-yl)boronic acid (6.5 g, 89.28%) as an off white solid.

LCMS: 127.0 [M+1]$^+$

Step-2: Synthesis of 2-isopropyl-1-(1-methyl-1H-pyrazol-3-yl)-6-(methylthio)-1,2-dihydro-3H-pyrazolo[3,4-d]pyrimidin-3-one To a stirred solution of 2-isopropyl-6-(methylthio)-1,2-dihydro-3H-pyrazolo[3,4-d]pyrimidin-3-one (300 mg, 1.337 mmol, 1 eq.) and (1-methyl-1H-pyrazol-3-yl)boronic acid (340 mg, 2.675 mmol, 2.0 eq) in DCM (10 mL) was added 2,2-bipyridine (417 mg, 2.675 mmol, 2.0 eq.), copper acetate (474 mg, 2.675 mmol, 2.0 eq.) and $Na_2CO_3$ (425 mg, 4.012 mmol, 3.0 eq). The reaction mixture was stirred at rt for 24 h in open air. The progress of reaction was monitored by TLC. The reaction mass was diluted with water (200 mL) and extracted with ethyl acetate (200 mL×2) and the organic layer was dried over $Na_2SO_4$, concentrated and purified by column chromatography (Combiflash, Elution: 0-30% EtOAc in Hexane) to afford the desired product, 2-isopropyl-1-(1-methyl-1H-pyrazol-3-yl)-6-(methylthio)-1,2-dihydro-3H-pyrazolo[3,4-d]pyrimidin-3-one (100 mg, 24.6%) as brown solid.

LCMS: 305.2 [M+1]$^+$

Step-3: Synthesis of tert-butyl 6-((2-isopropyl-1-(1-methyl-1H-pyrazol-3-yl)-3-oxo-2,3-dihydro-1H-pyrazolo[3,4-d]pyrimidin-6-yl)amino)-3,4-dihydroisoquinoline-2(1H)-carboxylate To a stirred solution of 2-isopropyl-1-(1-methyl-1H-pyrazol-3-yl)-6-(methylthio)-1,2-dihydro-3H-pyrazolo[3,4-d]pyrimidin-3-one (100 mg, 0.328 mmol, 1.0 eq) in (6 mL) of toluene was added m-CPBA (113 mg, 0.657 mmol, 2.0 eq) and allowed to stir at rt for 1 h. Tert-butyl 6-amino-3,4-dihydroisoquinoline-2(1H)-carboxylate (98 mg, 0.394 mmol, 1.2 eq) and DIPEA (0.23 mL, 1.315 mmol, 4.0 eq) were added and allowed to stir at 80° C. for overnight. Toluene was evaporated and the reaction mass was diluted with water (200 mL) and extracted with ethyl acetate (200 mL×2). The organic layer was dried over $Na_2SO_4$, concentrated and purified by column chromatography (Combiflash, elution-0-70% EtOAc in Hexane) to afford the desired compound, tert-butyl 6-((2-isopropyl-1-(1-methyl-1H-pyrazol-3-yl)-3-oxo-2,3-dihydro-1H-pyrazolo[3,4-d]pyrimidin-6-yl)amino)-3,4-dihydroisoquinoline-2(1H)-carboxylate (33 mg, 19.95%) as brown solid.

LCMS: 504.26 [M+1]$^+$

Step-4: Synthesis of 2-isopropyl-1-(1-methyl-1H-pyrazol-3-yl)-6-((1,2,3,4-tetrahydroisoquinolin-6-yl)amino)-1,2-dihydro-3H-pyrazolo[3,4-d]pyrimidin-3-one hydrochloride To a stirred solution of tert-butyl 6-((2-isopropyl-1-(1-methyl-1H-pyrazol-3-yl)-3-oxo-2,3-dihydro-1H-pyrazolo[3,4-d]pyrimidin-6-yl)amino)-3,4-dihydroisoquinoline-2 (1H)-carboxylate (33 mg, 65.476 mmol, 1.0 eq) was dissolved in (1 mL) of dioxane and added 4M dioxane-HCl (0.6 mL) and allowed to stir at rt for 3 h. After completion of reaction, the reaction mixture was filtered and dried under reduced pressure to afford the desired compound, 2-isopropyl-1-(1-methyl-1H-pyrazol-3-yl)-6-((1,2,3,4-tetrahydroisoquinolin-6-yl)amino)-1,2-dihydro-3H-pyrazolo[3,4-d]pyrimidin-3-one hydrochloride (10 mg, 37.80%) as an off white solid.

LCMS: 404.26 [M+1]$^+$, UPLC @ 254 nm=96.95% and @ 220 nm=97.27%.

$^1$H NMR (400 MHz, DMSO-d$_6$): δ ppm 10.22 (br. s., 1H), 9.14 (br. s., 1H), 8.82 (s, 1H), 7.86 (s, 1H), 7.67 (br. s., 1H), 7.50 (d, J=7.89 Hz, 1H), 7.11 (d, J=8.77 Hz, 1H), 6.45 (d, J=2.19 Hz, 1H), 4.27 (m, 1H), 4.19 (d., 2H), 3.91 (s, 3H), 3.40 (d, 2H), 2.92 (d., 2H) 1.26 (d, J=6.58 Hz, 6H).

Example S92. Synthesis of 1-(5-fluoropyridin-2-yl)-2-isopropyl-6-((1,2,3,4-tetrahydroisoquinolin-6-yl)amino)-1,2-dihydro-3H-pyrazolo[3,4-d]pyrimidin-3-one dihydrochloride (Compound No. 2.290)

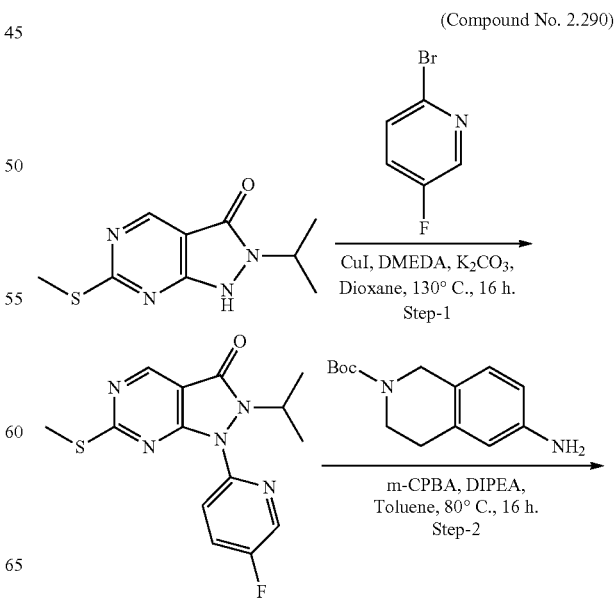

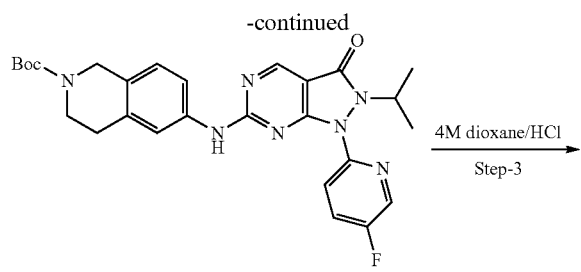

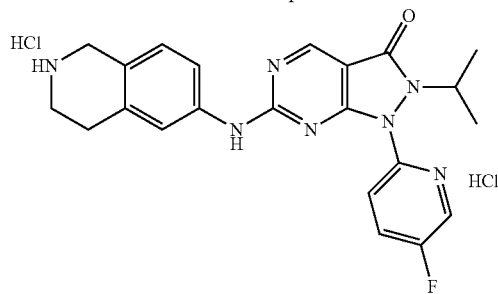

Step-1: Synthesis of 1-(5-fluoropyridin-2-yl)-2-isopropyl-6-(methylthio)-1, 2-dihydro-3H-pyrazolo [3,4-d] pyrimidin-3-one To a stirred solution of 2-isopropyl-6-(methylthio)-1,2-dihydro-3H-pyrazolo[3,4-d]pyrimidin-3-one, (300 mg, 1.337 mmol, 1.0 eq) and 2-bromo-5-fluoropyridine (282 mg, 1.605 mmol, 1.2 eq) in (6 mL) of dioxane was added Potassium carbonate (370 mg, 2.675 mmol, 2.0 eq) and the resulting mixture was purged with nitrogen for 10 min, followed by addition of copper iodide (51 mg, 0.267 mmol, 0.2 eq), and N,N'-dimethylethylenediamine (DMEDA) (0.06 mL, 0.535 mmol, 0.4 eq) and again purged with nitrogen for 10 min, stirred at 130° C. for overnight. After completion of reaction, the reaction mixture was diluted with water (50 mL) and extracted with EtOAc (30 mL×2). The combined organic layers were washed with water (30 mL), brine solution (30 mL), dried over anhydrous sodium sulphate and concentrated under reduced pressure to afford crude product, which was purified by flash chromatography to afford the desired compound, 1-(5-fluoropyridin-2-yl)-2-isopropyl-6-(methylthio)-1,2-dihydro-3H-pyrazolo[3,4-d]pyrimidin-3-one (265 mg, 62.10%) as an sticky yellow liquid.

LCMS: 320.10 [M+1]$^+$

Step-2: Synthesis of tert-butyl 6-((1-(5-fluoropyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(5-fluoropyridin-2-yl)-2-isopropyl-6-(methylthio)-1, 2-dihydro-3H-pyrazolo[3,4-d]pyrimidin-3-one (130 mg, 0.407 mmol, 1.0 eq) in (6 mL) of toluene was added m-CPBA (141 mg, 0.814 mmol, 2.0 eq) and allowed to stir at rt for 1 h., tert-butyl 6-amino-3,4-dihydroisoquinoline-2(1H)-carboxylate (121.4 mg, 0.489 mmol, 1.2 eq) and DIPEA (0.3 mL, 1.628 mmol, 4.0 eq) were added and allowed to stir at 80° C. for overnight. Toluene was evaporated and reaction mixture was diluted with water (50 mL) and extracted with EtOAc (30 mL×2), the organic layer was dried over sodium sulphate, concentrated under reduced pressure purified by column chromatography (Combiflash, elution-0-70% EtOAc in Hexane) to afford the desired compound. tert-butyl 6-((1-(5-fluoropyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (100 mg, 47.31%) as yellow semi solid.

LCMS: 520.24 [M+1]$^+$

Step-3: Synthesis of 1-(5-fluoropyridin-2-yl)-2-isopropyl-6-((1,2,3,4-tetrahydroisoquinolin-6-yl)amino)-1,2-dihydro-3H-pyrazolo[3,4-d]pyrimidin-3-one dihydrochloride To a stirred solution of tert-butyl 6-((1-(5-fluoropyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (100 mg, 0.192 mmol, 1.0 eq) in (1 mL) of dioxane and added 4M dioxane-HCl (0.8 mL) and allowed to stir at rt for 3 h. After completion of reaction, the reaction mixture was filtered and dried under reduced pressure to afford the desired compound, 1-(5-fluoropyridin-2-yl)-2-isopropyl-6-((1,2,3,4-tetrahydroisoquinolin-6-yl)amino)-1,2-dihydro-3H-pyrazolo[3,4-d]pyrimidin-3-one dihydrochloride (63 mg, 78.3%) as an off white solid.

LCMS: 420.3 [M+1]$^+$, UPLC @ 254 nm=95.96% and @ 220 nm=96.53%.

$^1$H NMR (400 MHz, DMSO-d$_6$): δ ppm 10.32 (br. s., 1H) 9.23 (br. s., 1H) 8.85 (s, 1H) 8.62 (d, J=2.63 Hz, 2H) 8.08 (d, J=8.55 Hz, 1H) 7.45 (d, J=7.89 Hz, 1H) 7.14 (d, J=8.33 Hz, 2H) 4.09-4.30 (m, 1H), 3.48 (s, 2H) 3.36 (d, 2H) 2.96 (d, 2H) 1.16-1.32 (m, 6H).

Example S93. Synthesis of 1-(5-fluoropyridin-2-yl)-2-isopropyl-6-((1,2,3,4-tetrahydroisoquinolin-7-yl)amino)-1,2-dihydro-3H-pyrazolo[3,4-d]pyrimidin-3-one dihydrochloride (Compound No. 2.291)

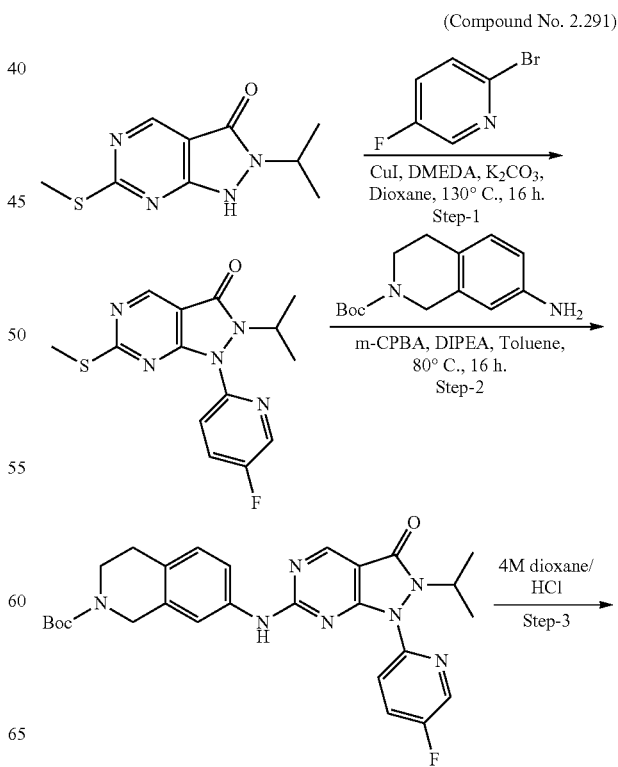

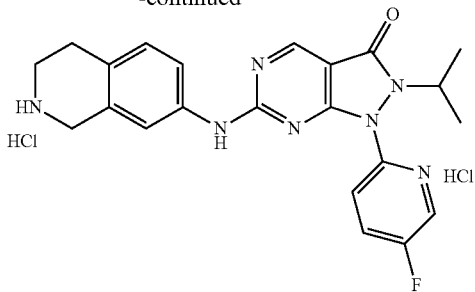

Step-1: Synthesis of 1-(5-fluoropyridin-2-yl)-2-isopropyl-6-(methylthio)-1, 2-dihydro-3H-pyrazolo [3,4-d] pyrimidin-3-one To a stirred solution of 2-isopropyl-6-(methylthio)-1,2-dihydro-3H-pyrazolo[3,4-d]pyrimidin-3-one, (300 mg, 1.337 mmol, 1.0 eq) and 2-bromo-5-fluoropyridine (282 mg, 1.605 mmol, 1.2 eq) in (6 mL) of dioxane was added Potassium carbonate (370 mg, 2.675 mmol, 2.0 eq) and the resulting mixture was purged with nitrogen for 10 min, followed by addition of copper iodide (51 mg, 0.267 mmol, 0.2 eq), and N,N'-dimethylethylenediamine (DMEDA) (0.06 mL, 0.535 mmol, 0.4 eq) and again purged with nitrogen for 10 min, stirred at 130° C. for overnight. After completion of reaction, the reaction mixture was diluted with water (30 mL) and extracted with EtOAc (30 mL×2). The combined organic layers were washed with water (30 mL), brine solution (30 mL), dried over anhydrous sodium sulphate and concentrated under reduced pressure to afford crude product, which was purified by flash chromatography to afford the desired compound, 1-(5-fluoropyridin-2-yl)-2-isopropyl-6-(methylthio)-1,2-dihydro-3H-pyrazolo[3,4-d]pyrimidin-3-one (265 mg, 62.10%) as an sticky yellow liquid.

LCMS: 320.10 [M+1]$^+$

Step-2: Synthesis of tert-butyl 7-((1-(5-fluoropyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(5-fluoropyridin-2-yl)-2-isopropyl-6-(methylthio)-1, 2-dihydro-3H-pyrazolo[3,4-d]pyrimidin-3-one (130 mg, 0.407 mmol, 1.0 eq) in (6 mL) of toluene was added m-CPBA (141 mg, 0.814 mmol, 2.0 eq) and allowed to stir at rt for 30 min., tert-butyl 7-amino-3,4-dihydroisoquinoline-2(1H)-carboxylate (121.4 mg, 0.489 mmol, 1.2 eq) and DIPEA (0.3 mL, 1.628 mmol, 4.0 eq) were added and allowed to stir at 80° C. for overnight. Toluene was evaporated and reaction mixture was diluted with water (30 mL) and extracted with EtOAc (30 mL×2), the organic layer was dried over sodium sulphate, concentrated under reduced pressure purified by column chromatography (Combiflash, elution-0-70% EtOAc in Hexane) to afford the desired compound. tert-butyl 7-((1-(5-fluoropyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate. (70 mg, 33.12%) as yellow semi solid.

LCMS: 520.24 [M+1]$^+$

Step-3: Synthesis of 1-(5-fluoropyridin-2-yl)-2-isopropyl-6-((1,2,3,4-tetrahydroisoquinolin-7-yl)amino)-1,2-dihydro-3H-pyrazolo[3,4-d]pyrimidin-3-one dihydrochloride To a stirred solution of tert-butyl 7-((1-(5-fluoropyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate. (70 mg, 0.134 mmol, 1.0 eq) was dissolved in (3 mL) of dioxane and added 4M dioxane-HCl (0.9 mL) and allowed to stir at rt for 3 h. After completion of reaction, the reaction mixture was filtered and dried under reduced pressure to afford the desired compound, 1-(5-fluoropyridin-2-yl)-2-isopropyl-6-((1,2,3,4-tetrahydroisoquinolin-7-yl)amino)-1,2-dihydro-3H-pyrazolo[3,4-d]pyrimidin-3-one dihydrochloride (33 mg, 58.7%).

LCMS: 420.3 [M+1]$^+$, UPLC @ 254 nm=95.51% and @ 220 nm=94.28%.

$^1$H NMR (400 MHz, DMSO-d$_6$): δ ppm 10.32 (br. s., 1H) 9.23 (br. s., 1H) 8.85 (s, 1H) 8.62 (d, J=2.63 Hz, 2H) 8.08 (d, J=8.55 Hz, 1H) 7.45 (d, J=7.89 Hz, 1H) 7.14 (d, J=8.33 Hz, 2H) 4.09-4.30 (m, 1H), 3.48 (s, 2H) 3.36 (d, 2H) 2.96 (d, 2H) 1.16-1.32 (m, 6H).

Example S94. Synthesis of 2-isopropyl-1-(1-methyl-1H-pyrazol-3-yl)-6-((1,2,3,4-tetrahydroisoquinolin-7-yl)amino)-1,2-dihydro-3H-pyrazolo[3,4-d]pyrimidin-3-one hydrochloride (Compound No. 2.292)

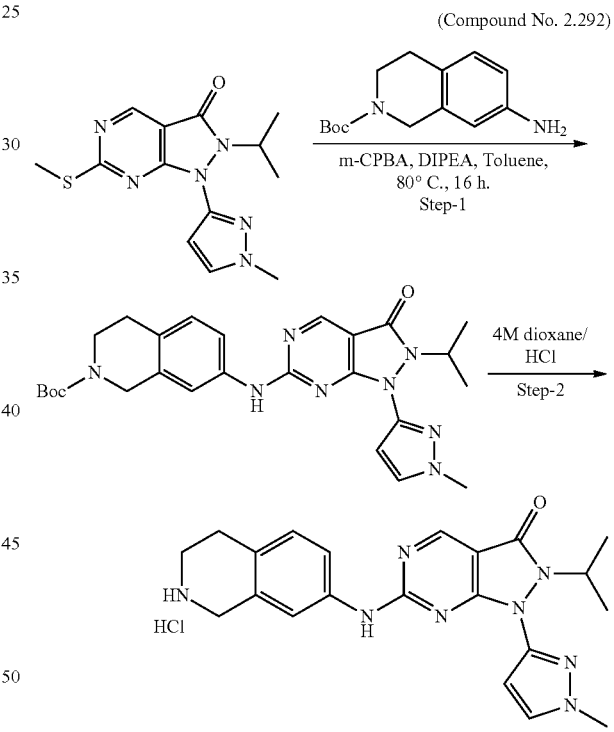

Step-1: Synthesis of tert-butyl 7-((2-isopropyl-1-(1-methyl-1H-pyrazol-3-yl)-3-oxo-2,3-dihydro-1H-pyrazolo[3,4-d]pyrimidin-6-yl)amino)-3,4-dihydroisoquinoline-2(1H)-carboxylate To a stirred solution of 2-isopropyl-1-(1-methyl-1H-pyrazol-3-yl)-6-(methylthio)-1,2-dihydro-3H-pyrazolo[3,4-d]pyrimidin-3-one (100 mg, 0.328 mmol, 1.0 eq) in (6 mL) of toluene was added m-CPBA (113 mg, 0.657 mmol, 2.0 eq) and allowed to stir at rt for 30 min. tert-butyl 7-amino-3,4-dihydroisoquinoline-2(1H)-carboxylate (98 mg, 0.394 mmol, 1.2 eq) and DIPEA (0.23 mL, 1.315 mmol, 4.0 eq) were added and allowed to stir at 80° C. for overnight.

Tolene was evaporated and reaction mass was diluted with ethyl acetate and water, organic layer was dried over sodium sulphate, concentrated under reduced pressure purified by column chromatography (Combiflash, elution-0-70% EtOAc in Hexane) to afford the desired compound, tert-butyl 7-((2-isopropyl-1-(1-methyl-1H-pyrazol-3-yl)-3-oxo-2,3-dihydro-1H-pyrazolo[3,4-d]pyrimidin-6-yl)amino)-3,4-dihydroisoquinoline-2(1H)-carboxylate (35 mg, 21.16%) as brown solid.

LCMS: 504.26 [M+1]+

Step-2: Synthesis of (2-isopropyl-1-(1-methyl-1H-pyrazol-3-yl)-6-((1,2,3,4-tetrahydroisoquinolin-7-yl)amino)-1,2-dihydro-3H-pyrazolo[3,4-d]pyrimidin-3-one hydrochloride To a stirred solution of tert-butyl 7-((2-isopropyl-1-(1-methyl-1H-pyrazol-3-yl)-3-oxo-2,3-dihydro-1H-pyrazolo[3,4-d]pyrimidin-6-yl)amino)-3,4-dihydroisoquinoline-2(1H)-carboxylate (35 mg 69.44 mmol, 1.0 eq) was dissolved in (1 mL) of dioxane and added 4M dioxane-HCl (0.6 mL) and allowed to stir at rt for 3 h. After completion of reaction, the reaction mixture was filtered and dried under reduced pressure to afford the desired compound, 2-isopropyl-1-(1-methyl-1H-pyrazol-3-yl)-6-((1,2,3,4-tetrahydroisoquinolin-7-yl)amino)-1,2-dihydro-3H-pyrazolo[3,4-d]pyrimidin-3-one hydrochloride (15 mg, 53.47%) as an off white solid.

LCMS: 404.26 [M+1]+, UPLC @ 254 nm=98.84% and @ 220 nm=99.25%.

1H NMR: (400 MHz, DMSO-d6): δ ppm 10.22 (br. s., 1H), 9.14 (br. s., 1H), 8.82 (s, 1H), 7.86 (s, 1H), 7.67 (br. s., 1H), 7.50 (d, J=7.89 Hz, 1H), 7.11 (d, J=8.77 Hz, 1H), 6.45 (d, J=2.19 Hz, 1H), 4.27 (m, 1H), 4.19 (d., 2H), 3.91 (s, 3H), 3.40 (d, 2H), 2.92 (d., 2H) 1.26 (d, J=6.58 Hz, 6H).

Example S95. Synthesis of 2-isopropyl-1-(2-(2-methoxypropan-2-yl)pyridin-4-yl)-6-((1,2,3,4-tetrahydroisoquinolin-6-yl)amino)-1,2-dihydro-3H-pyrazolo[3,4-d]pyrimidin-3-one (Compound No. 2.293)

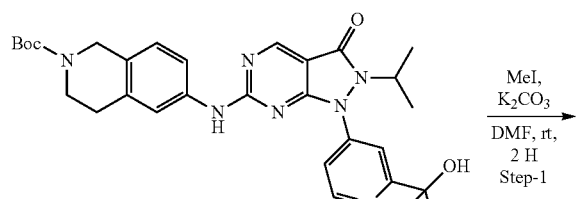

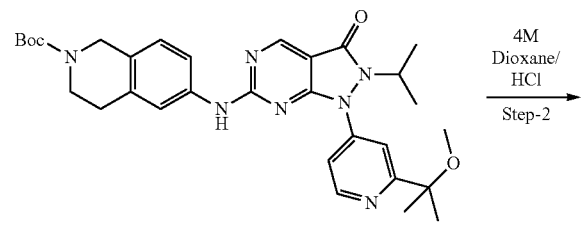

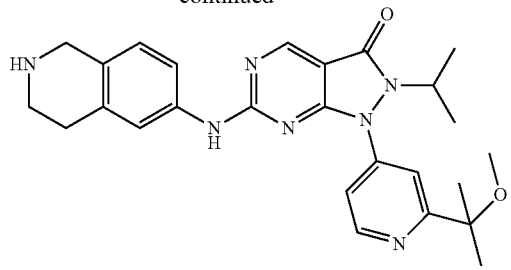

Step-1: Synthesis of tert-butyl 6-((2-isopropyl-1-(2-(2-methoxypropan-2-yl)pyridin-4-yl)-3-oxo-2,3-dihydro-1H-pyrazolo[3,4-d]pyrimidin-6-yl)amino)-3,4-dihydroisoquinoline-2(1H)-carboxylate To a stirred solution of tert-butyl 6-((1-(2-(2-hydroxypropan-2-yl)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate (50 mg, 0.0892 mmol, 1.0 eq) in (3.0 mL) of DMF was added K2CO3 (14 mg, 0.0982 mmol, 1.1 eq) and allowed to stir at 00 for 15 min. to that methyl iodide (0.1 mL, 0.0982 mmol, 1.1 eq) were added and allowed to stir at rt for 2 h. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-80% EtOAc in hexane] to afford the desired compound, tert-butyl 6-((1-(2-(2-hydroxypropan-2-yl)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate (35 mg, 68.62%) as an off white solid.

LCMS: 574.4 [M+1]+

Step-2: Synthesis of 2-isopropyl-1-(2-(2-methoxypropan-2-yl)pyridin-4-yl)-6-((1,2,3,4-tetrahydroisoquinolin-6-yl)amino)-1,2-dihydro-3H-pyrazolo[3,4-d]pyrimidin-3-one tert-butyl 6-((1-(2-(2-hydroxypropan-2-yl)pyridin-4-yl)-2-isopropyl-3-oxo-2,3-dihydro-1H-pyrazolo[3,4-d]pyrimidin-6-yl)amino)-3,4-dihydroisoquinoline-2(1H)-carboxylate (35 mg, 0.0609 mmol, 1.0 eq) was dissolved in dioxane (1 mL), followed by dropwise addition of 4.0M-HCl (1 mL) and allowed to stir at rt for 1 h. After completion of reaction, the reaction mixture was filtered and dried under reduced pressure and purified by prep purification to afford the desired compound, 2-isopropyl-1-(2-(2-methoxypropan-2-yl)pyridin-4-yl)-6-((1,2,3,4-tetrahydroisoquinolin-6-yl)amino)-1,2-dihydro-3H-pyrazolo[3,4-d]pyrimidin-3-one (2 mg, 7.14%) as an off white solid.

LCMS: 474.4 [M+1]+; UPLC @ 254 nm=97.91% and @ 220 nm=97.81%.

1H NMR (400 MHz, DMSO-d6): δ 10.29 (br. s. 1H), 8.82 (s, 1H) 8.63 (d, J=5.26 Hz, 1H) 7.72 (br. s., 1H) 7.55 (d, J=4.38 Hz, 2H) 7.46 (br. s., 1H) 7.01 (d, J=7.45 Hz, 1H) 3.96 (d, J=6.14 Hz, 2H) 3.80 (t, 2H), 3.45 (s, 3H), 2.95 (br. s., 1H) 2.67 (t, 2H) 1.75 (s, 1H) 1.46 (s, 6H) 1.35 (d, J=6.58 Hz, 6H).

Example S96. Synthesis of N-(6-(6-((1,1-dimethyl-1,2,3,4-tetrahydroisoquinolin-6-yl)amino)-2-isopropyl-3-oxo-2,3-dihydro-1H-pyrazolo[3,4-d]pyrimidin-1-yl)pyridin-2-yl)-N-methylmethanesulfonamide dihydrochloride (Compound No. 2.642)

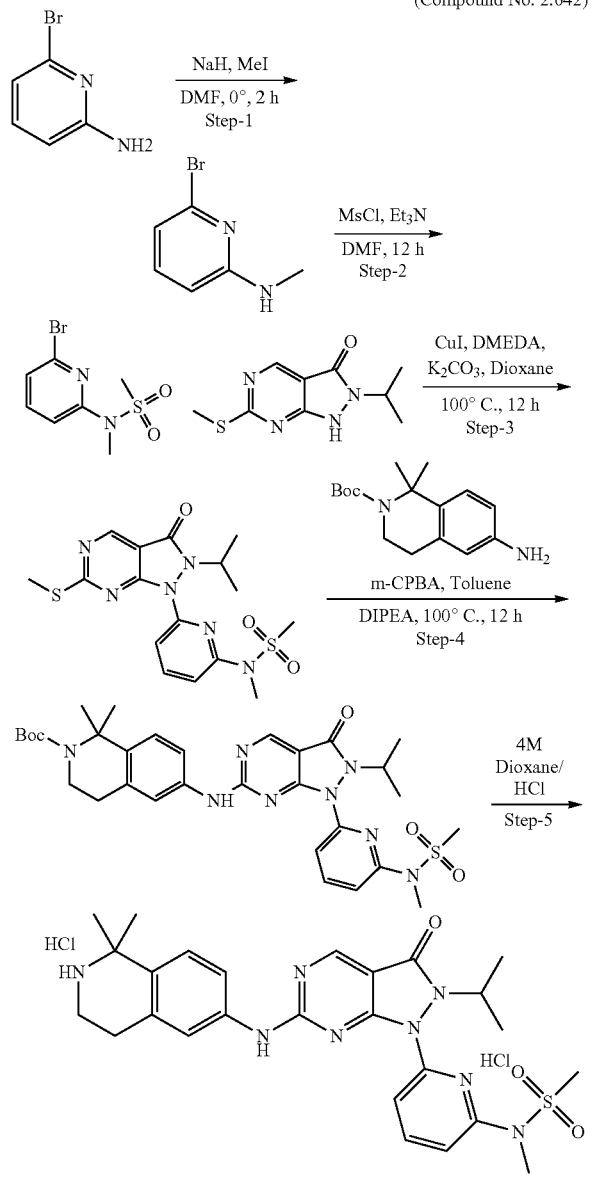

Step-1: Synthesis of 6-bromo-N-methylpyridin-2-amine

To a stirred solution of 6-bromopyridin-2-amine (5.0 g, 28.90 mmol, 1 eq), in DMF (50 mL) and NaH (1.2 g, 31.79 mmol, 1.1 eq), was added at 0° C. & stirred for 30 min. MeI (2.7 mL, 43.35 mmol, 1.5 eq) was added dropwise & stirred for 1 h. After completion of reaction, the reaction mixture was diluted with water and extracted with EtOAc (50 mL×2). The combined organic layers were washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, 6-bromo-N-methylpyridin-2-amine (2.0 g, 37.03%) as white solid.
LCMS: 187.0 [M+1]$^+$ Step-2: Synthesis of N-(6-bromopyridin-2-yl)-N-methylmethanesulfonamide To a stirred solution of 6-bromo-N-methylpyridin-2-amine (2.0 g, 10.75 mmol, 1 eq), in (50 mL) of DCM, was added TEA (3.31 mL, 23.65 mmol, 2.2 eq), followed by addition of methane sulphonyl chloride (1.25 mL, 16.12 mmol, 1.5 eq) and stirred overnight at room temperature. The reaction mixture was basified with saturated sodium bicarbonate solution and extracted with EtOAc (50 mL×2). The combined organic layers were washed with water (50 mL), brine solution (50 mL), dried over anhydrous sodium sulfate and the solvent was evaporated under reduced pressure to afford crude product, which was purified by flash chromatography [silica gel 100-200 mesh; elution 0-50% EtOAc in hexane] to afford the desired compound, N-(6-bromopyridin-2-yl)-N-methylmethanesulfonamide (2.8 g, 98.93%) as white solid.
LCMS: 265.0 [M+1]$^+$ Step-3: Synthesis of N-(6-(2-isopropyl-6-(methylthio)-3-oxo-2,3-dihydro-1H-pyrazolo[3,4-d]pyrimidin-1-yl)pyridin-2-yl)-N-methylmethanesulfonamide To a stirred solution of N-(6-bromopyridin-2-yl)-N-methylmethanesulfonamide (1.0 g, 4.45 mmol, 1.0 eq) and N-(4-bromopyridin-2-yl)-N-methylmethanesulfonamide (1.41 g, 5.34 mmol, 1.2 eq) in (10 mL) of dioxane was added Potassium carbonate (1.23 g, 8.9 mmol, 2 eq) and the resulting mixture was purged with nitrogen for 10 min, followed by addition of copper iodide (170 mg, 0.89 mmol, 0.2 eq), and N,N'-dimethylethylenediamine (DMEDA) (0.2 mL, 1.78 mmol, 0.4 eq) and again purged with nitrogen for 10 min, stirred at 90° C. for overnight. After completion of reaction, the reaction mixture was diluted with water and extracted with EtOAc (50 mL×2). Combined organic layers were washed with water (50 mL) brine solution (50 mL), dried over anhydrous sodium sulphate and concentrated under reduced pressure to afford crude product, which was purified by flash chromatography to afford the desired compound, N-(6-(2-isopropyl-6-(methylthio)-3-oxo-2,3-dihydro-1H-pyrazolo[3,4-d]pyrimidin-1-yl)pyridin-2-yl)-N-methylmethanesulfonamide (1.2 g, 65.93%) as an off white solid.
LCMS: 409.1 [M+1]$^+$ Step-4: Synthesis of tert-butyl 6-((2-isopropyl-1-(6-(N-methylmethylsulfonamido)pyridin-2-yl)-3-oxo-2,3-dihydro-1H-pyrazolo[3,4-d]pyrimidin-6-yl)amino)-1,1-dimethyl-3,4-dihydroisoquinoline-2(1H)-carboxylate To a stirred solution of N-(6-(2-isopropyl-6-(methylthio)-3-oxo-2,3-dihydro-1H-pyrazolo[3,4-d]pyrimidin-1-yl)pyridin-2-yl)-N-methylmethanesulfonamide (200 mg, 0.489 mmol, 1.0 eq) in (3.0 mL) of toluene was added m-CPBA (169 mg, 0.978 mmol, 2.0 eq) and allowed to stir at rt for 1 h. tert-butyl 6-amino-1,1-dimethyl-3,4-dihydroisoquinoline-2(1H)-carboxylate (135 mg, 0.489 mmol, 1.0 eq) and DIPEA (0.33 mL, 1.95 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((2-isopropyl-1-(6-(N-methylmethylsulfonamido)pyridin-2-yl)-3-oxo-2,3-dihydro-1H-pyrazolo[3,4-d]pyrimidin-6-yl)amino)-1,1-dimethyl-3,4-dihydroisoquinoline-2(1H)-carboxylate (90 mg, 28.86%) as an off white solid.

LCMS: 637.3 [M+1]⁺

Step-5: Synthesis of N-(6-(6-(((1,1-dimethyl-1,2,3,4-tetrahydroisoquinolin-6-yl)amino)-2-isopropyl-3-oxo-2,3-dihydro-1H-pyrazolo[3,4-d]pyrimidin-1-yl)pyridin-2-yl)-N-methylmethanesulfonamide dihydrochloride tert-butyl 6-((2-isopropyl-1-(6-(N-methylmethylsulfonamido)pyridin-2-yl)-3-oxo-2,3-dihydro-1H-pyrazolo[3,4-d]pyrimidin-6-yl)amino)-1,1-dimethyl-3,4-dihydroisoquinoline-2(1H)-carboxylate (90 mg, 0.141 mmol, 1.0 eq) was dissolved in dioxane (1 mL), followed by dropwise addition of 4.0M-HCl (1 mL) and allowed to stir at rt for 1 h. After completion of reaction, the reaction mixture was filtered and dried under reduced pressure to afford the desired compound, N-(6-(6-(((1,1-dimethyl-1,2,3,4-tetrahydroisoquinolin-6-yl)amino)-2-isopropyl-3-oxo-2,3-dihydro-1H-pyrazolo[3,4-d]pyrimidin-1-yl)pyridin-2-yl)-N-methylmethanesulfonamide dihydrochloride (29 mg, 33.66%) as an off white solid.

LCMS: 537.5 [M+1]⁺; UPLC @ 254 nm=98.68% and @ 220 nm=99.14%.

¹H NMR (400 MHz, DMSO-d₆): δ 10.32 (brs, 1H), 9.37 (brs, 2H), 8.84 (s, 1H), 8.14 (t, J=7.83 Hz, 1H), 7.72 (d, J=7.83 Hz, 1H), 7.67 (brs, 1H), 7.51 (d, J=7.83 Hz, 1H), 7.43 (d, J=8.31 Hz, 1H), 7.35 (d, J=8.31 Hz, 1H), 4.17-4.22 (m, 1H), 3.43 (brs, 2H), 3.32 (s, 3H), 3.21 (s, 3H), 3.01 (brs, 2H), 1.64 (s, 6H), 1.36 (d, J=6.85 Hz, 6H).

Example S97. Synthesis of 1-(1-cyclopropyl-1H-pyrazol-3-yl)-6-((1,1-dimethyl-1,2,3,4-tetrahydroisoquinolin-6-yl)amino)-2-isopropyl-1,2-dihydro-3H-pyrazolo[3,4-d]pyrimidin-3-one hydrochloride (Compound No. 2.643)

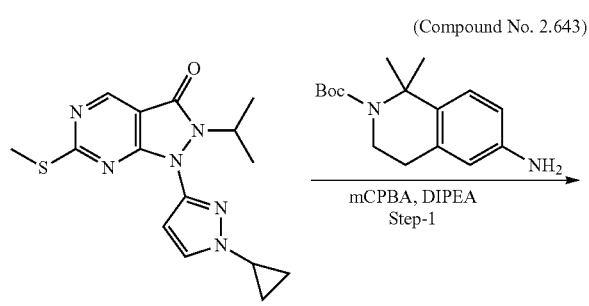

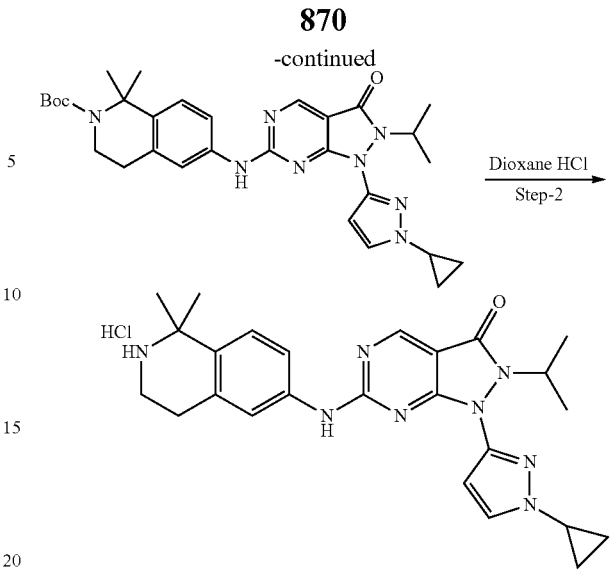

Step-1: Synthesis of tert-butyl 6-((1-(1-cyclopropyl-1H-pyrazol-3-yl)-2-isopropyl-3-oxo-2,3-dihydro-1H-pyrazolo[3,4-d]pyrimidin-6-yl)amino)-1,1-dimethyl-3,4-dihydroisoquinoline-2(1H)-carboxylate To a stirred solution of 1-(1-cyclopropyl-1H-pyrazol-3-yl)-2-isopropyl-6-(methylthio)-1,2-dihydro-3H-pyrazolo[3,4-d]pyrimidin-3-one (95 mg, 0.287 mmol, 1.0 eq) in (1.5 mL) of toluene was added m-CPBA (99 mg, 0.574 mmol, 2.0 eq) and allowed to stir at rt for 1 h. Tert-butyl 6-amino-1,1-dimethyl-3,4-dihydroisoquinoline-2(1H)-carboxylate (95.18 mg, 0.344 mmol, 1.2 eq) and DIPEA (0.19 mL, 1.14 mmol, 4.0 eq) were added and allowed to stir at rt for overnight. Reaction mixture was diluted with water and extracted with EtOAc (30 mL×2). The combined organic layer were dried over sodium sulphate, concentrated under reduced pressure purified by column chromatography (Combiflash, elution-0-60% EtOAc in Hexane) to afford the desired compound, tert-butyl 6-((1-(1-cyclopropyl-1H-pyrazol-3-yl)-2-isopropyl-3-oxo-2,3-dihydro-1H-pyrazolo[3,4-d]pyrimidin-6-yl)amino)-1,1-dimethyl-3,4-dihydroisoquinoline-2(1H)-carboxylate (20 mg, 12.46%) as yellow liquid.

LCMS: 559.4 [M+1]⁺

Step-2: Synthesis of 1-(1-cyclopropyl-1H-pyrazol-3-yl)-6-((1,1-dimethyl-1,2,3,4-tetrahydroisoquinolin-6-yl)amino)-2-isopropyl-1,2-dihydro-3H-pyrazolo[3,4-d]pyrimidin-3-one hydrochloride To a stirred solution of tert-butyl 6-((1-(1-cyclopropyl-1H-pyrazol-3-yl)-2-isopropyl-3-oxo-2,3-dihydro-1H-pyrazolo[3,4-d]pyrimidin-6-yl)amino)-1,1-dimethyl-3,4-dihydroisoquinoline-2(1H)-carboxylate (20 mg, 0.035 mmol, 1.0 eq) in (0.3 mL) of dioxane was added 4M dioxane-HCl (0.3 mL) and allowed to stir at rt for 2 h. After completion of reaction, the reaction mixture was filtered and dried under reduced pressure to afford the desired compound, of 1-(1-cyclopropyl-1H-pyrazol-3-yl)-6-((1,1-dimethyl-1,2,3,4-tetrahydroisoquinolin-6-yl)amino)-2-isopropyl-1,2-dihydro-3H-pyrazolo[3,4-d]pyrimidin-3-one hydrochloride (7.8 mg, 44.01%) as an off white solid.

LCMS: 459.4 [M+1]⁺, UPLC @ 254 nm=90.87% and @ 220 nm=91.88%.

¹H NMR (400 MHz, DMSO-d₆): δ 10.21 (brs, 1H), 9.21 (brs, 2H), 8.81 (s, 1H), 7.97 (brs, 1H), 7.62 (brs, 1H), 7.49 (brs, 1H), 7.29 (brs, 1H), 6.46 (d, J=2.19 Hz, 1H), 4.26 (d, J=6.58 Hz, 1H), 3.81 (d, J=4.39 Hz, 2H), 2.94 (brs, 2H), 1.62 (s, 6H), 1.24 (d, J=6.58 Hz, 6H), 0.84-1.10 (m, 4H).

Example S98. Synthesis of 1-(2-(tert-butyl)pyridin-4-yl)-2-isopropyl-6-((2-methyl-1,2,3,4-tetrahydroisoquinolin-6-yl)amino)-1,2-dihydro-3H-pyrazolo[3,4-d]pyrimidin-3-one dihydrochloride (Compound No. 2.644)

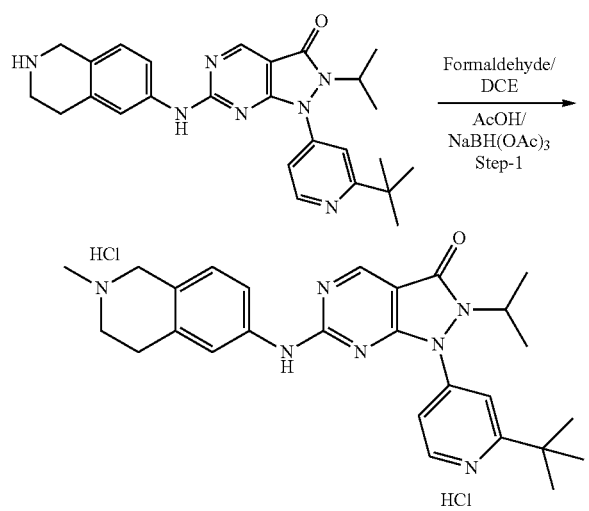

To a stirred solution of 1-(2-(tert-butyl)pyridin-4-yl)-2-isopropyl-6-((1,2,3,4-tetrahydroisoquinolin-6-yl)amino)-1,2-dihydro-3H-pyrazolo[3,4-d]pyrimidin-3-one (50 mg, 0.094 mmol, 1.0 eq) and HCHO (8.49 mg, 0.282 mmol, 3.0 eq) in dichloroethane (10 mL) acetic acid (5.6 mg, 0.094 mmol, 1.0 eq) was added drop-wise at 0° C. The resulting mixture was stirred at rt for 1 h, followed by addition of NaBH(OAc)₃ (20 mg, 0.094 mmol, 1.0 eq) at 0° C. The resulting mixture was stirred at rt for 1 h. The progress of reaction was monitored by LCMS. After completion of reaction, solvent was removed under reduced pressure, residue was basified with saturated solution of NaHCO₃ (50 mL) and extracted with ethyl acetate (100 mL×2). The combined organic layers were washed with water (50 mL) and brine (50 mL), dried over anhydrous Na₂SO₄ and concentrated under reduced pressure. Crude residue was purified by flash chromatography to afford, 1-(2-(tert-butyl)pyridin-4-yl)-2-isopropyl-6-((2-methyl-1,2,3,4-tetrahydroisoquinolin-6-yl)amino)-1,2-dihydro-3H-pyrazolo[3,4-d]pyrimidin-3-one dihydrochloride (3 mg, 5.04%) as an off white solid. HCl salt of this compound was synthesized using 4M dioxane/HCl.

LCMS: 472.5 [M+1]⁺, UPLC @ 254 nm=95.82% and @ 220 nm=95.59%.

¹H NMR (400 MHz, DMSO-d₆): δ 10.47 (brs, 1H), 10.26 (brs, 1H), 8.88 (s, 1H), 8.73 (d, J=4.82 Hz, 1H), 7.51-7.72 (m, 3H), 7.43 (brs, 1H), 7.15 (d, J=8.77 Hz, 1H), 4.45 (d, J=14.47 Hz, 2H), 4.24 (brs, 2H), 3.97 (brs, 2H), 3.66 (brs, 3H), 3.19 (brs, 2H), 3.04 (d, J=16.66 Hz, 2H), 2.93 (d, J=4.82 Hz, 3H), 1.35 (s, 15H).

Example S99. Synthesis of N-(6-(2-isopropyl-3-oxo-6-((1,2,3,4-tetrahydroisoquinolin-6-yl)amino)-2,3-dihydro-1H-pyrazolo[3,4-d]pyrimidin-1-yl)pyridin-2-yl)-N-methylmethanesulfonamide dihydrochloride (Compound No. 2.645)

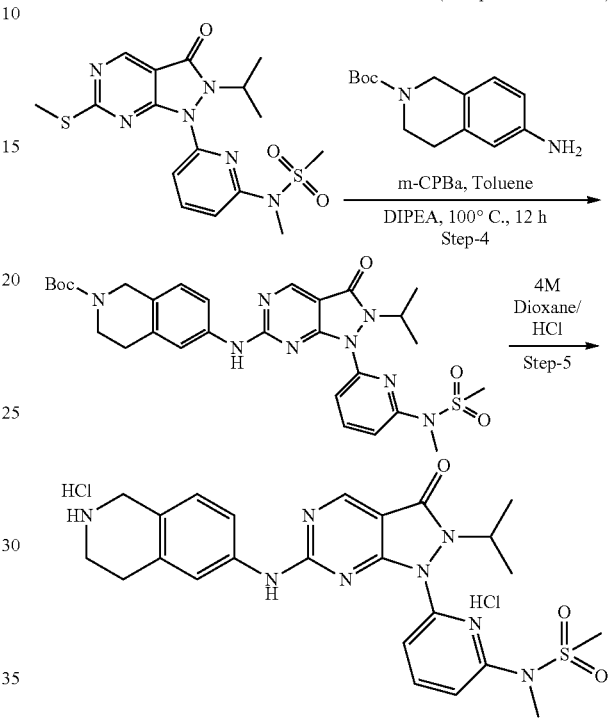

Step-1: Synthesis of tert-butyl 6-((2-isopropyl-1-(6-(N-methylmethylsulfonamido)pyridin-2-yl)-3-oxo-2,3-dihydro-1-pyrazolo[3,4-d]pyrimidin-6-yl)amino)-3,4-dihydroisoquinoline-2(1H)-carboxylate To a stirred solution of N-(6-(2-isopropyl-6-(methylthio)-3-oxo-2,3-dihydro-1H-pyrazolo[3,4-d]pyrimidin-1-yl)pyridin-2-yl)-N-methylmethanesulfonamide (200 mg, 0.489 mmol, 1.0 eq) in (3.0 mL) of toluene was added m-CPBA (169 mg, 0.978 mmol, 2.0 eq) and allowed to stir at rt for 1 h tert-butyl 6-amino-3,4-dihydroisoquinoline-2(1H)-carboxylate (146 mg, 0.58 mmol, 1.2 eq) and DIPEA (0.33 mL, 1.95 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((2-isopropyl-1-(6-(N-methylmethylsulfonamido)pyridin-2-yl)-3-oxo-2,3-dihydro-1H-pyrazolo[3,4-d]pyrimidin-6-yl)amino)-3,4-dihydroisoquinoline-2(1H)-carboxylate (90 mg, 30.19%) as an off white solid.

LCMS: 609.3 [M+1]⁺

Step-2: Synthesis of N-(6-(2-isopropyl-3-oxo-6-((1,2,3,4-tetrahydroisoquinolin-6-yl)amino)-2,3-dihydro-1H-pyrazolo[3,4-d]pyrimidin-1-yl)pyridin-2-yl)-N-methylmethanesulfonamide dihydrochloride tert-butyl 6-((2-isopropyl-1-(6-(N-methylmethylsulfonamido)pyridin-2-yl)-3-oxo-2,3-dihydro-1H-pyrazolo[3,4-d]pyrimidin-6-yl)amino)-3,4-dihydroisoquinoline-2(1H)-carboxylate (90 mg, 0.147 mmol, 1.0 eq) was dissolved in dioxane (1 mL), followed by dropwise addition of 4.0M-HCl (1 mL) and allowed to stir at rt for 1 h. After completion of reaction, the reaction mixture was filtered and dried under reduced pressure to afford the desired compound, N-(6-(2-isopropyl-3-oxo-6-(((1,2,3,4-tetrahydroisoquinolin-6-yl)amino)-2,3-dihydro-1H-pyrazolo[3,4-d]pyrimidin-1-yl)pyridin-2-yl)-N-methylmethanesulfonamide dihydrochloride (78 mg, 90.72%) as light yellow solid.

LCMS: 509.4 [M+1]$^+$; UPLC @ 254 nm=97.44% and @ 220 nm=97.61%.

$^1$H NMR (400 MHz, DMSO-d$_6$): δ10.34 (brs, 1H), 9.33 (brs, 2H), 8.84 (s, 1H), 8.11-8.16 (m, 1H), 7.73 (d, J=7.89 Hz, 2H), 7.39-7.49 (m, 2H), 7.16 (d, J=8.77 Hz, 1H), 4.20 (brs, 3H), 3.36 (brs, 2H), 3.32 (s, 3H), 3.21 (s, 3H), 2.96-3.04 (m, 2H), 1.36 (d, J=6.58 Hz, 6H).

Example S00. Synthesis of 1-(1-cyclopropyl-1H-pyrazol-3-yl)-6-((4,4-dimethyl-1,2,3,4-tetrahydroisoquinolin-7-yl)amino)-2-isopropyl-1,2-dihydro-3H-pyrazolo[3,4-d]pyrimidin-3-one hydrochloride (Compound No. 2.646)

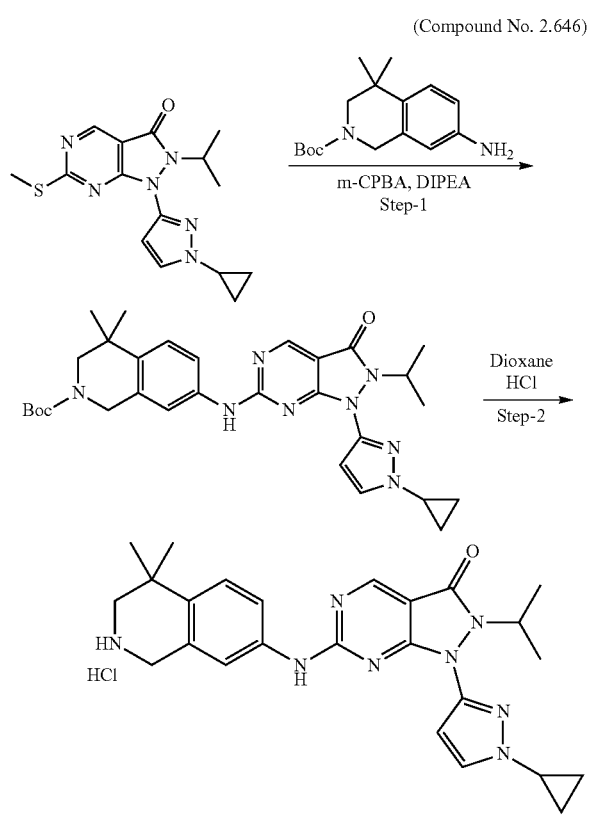

Step-1: Synthesis of tert-butyl 7-((1-(1-cyclopropyl-1H-pyrazol-3-yl)-2-isopropyl-3-oxo-2,3-dihydro-1H-pyrazolo[3,4-d]pyrimidin-6-yl)amino)-4,4-dimethyl-3,4-dihydroisoquinoline-2(1H)-carboxylate To a stirred solution of 1-(1-cyclopropyl-1H-pyrazol-3-yl)-2-isopropyl-6-(methylthio)-1,2-dihydro-3H-pyrazolo[3,4-d]pyrimidin-3-one (95 mg, 0.287 mmol, 1.0 eq) in (1.5 mL) of toluene was added m-CPBA (99 mg, 0.574 mmol, 2.0 eq) and allowed to stir at rt for 1 h. Tert-butyl 7-amino-4,4-dimethyl-3,4-dihydroisoquinoline-2(1H)-carboxylate (95.18 mg, 0.344 mmol, 1.2 eq) and DIPEA (0.19 mL, 1.14 mmol, 4.0 eq) were added and allowed to stir at rt for overnight. The reaction mixture was diluted with water (25 mL) and extracted with EtOAc (30 mL×2). The combined organic layer were dried over sodium sulphate, concentrated under reduced pressure purified by column chromatography (Combiflash, elution-0-60% EtOAc in Hexane) to afford the desired compound, tert-butyl 7-((1-(1-cyclopropyl-1H-pyrazol-3-yl)-2-isopropyl-3-oxo-2,3-dihydro-1H-pyrazolo[3,4-d]pyrimidin-6-yl)amino)-4,4-dimethyl-3,4-dihydroisoquinoline-2(1H)-carboxylate (50 mg, 31.12%) as yellow liquid.

LCMS: 559.2 [M+1]$^+$

Step-2: Synthesis of 1-(1-cyclopropyl-1H-pyrazol-3-yl)-6-((4,4-dimethyl-1,2,3,4-tetrahydroisoquinolin-7-yl)amino)-2-isopropyl-1,2-dihydro-3H-pyrazolo[3,4-d]pyrimidin-3-one hydrochloride To a stirred solution of tert-butyl 7-((1-(1-cyclopropyl-1H-pyrazol-3-yl)-2-isopropyl-3-oxo-2,3-dihydro-1H-pyrazolo[3,4-d]pyrimidin-6-yl)amino)-4,4-dimethyl-3,4-dihydroisoquinoline-2(1H)-carboxylate (50 mg, 0.089 mmol, 1.0 eq) in (0.6 mL) of dioxane was added 4M dioxane-HCl (0.6 mL) and allowed to stir at rt for 2 h. After completion of reaction, the reaction mixture was filtered and dried under reduced pressure to afford the desired compound, 1-(1-cyclopropyl-1H-pyrazol-3-yl)-6-((4,4-dimethyl-1,2,3,4-tetrahydroisoquinolin-7-yl)amino)-2-isopropyl-1,2-dihydro-3H-pyrazolo[3,4-d]pyrimidin-3-one hydrochloride (36 mg, 81.26%) as light yellow solid.

LCMS: 459.4 [M+1]$^+$, UPLC @ 254 nm=92.32% and @ 220 nm=89.51%.

$^1$H NMR (400 MHz, DMSO-d$_6$): δ 10.23 (brs, 1H), 9.35 (brs, 2H), 8.80 (s, 1H), 7.95 (d, J=2.19 Hz, 1H), 7.60 (brs, 1H), 7.54 (brs, 1H), 7.37 (d, J=8.77 Hz, 2H), 6.46 (d, J=2.19 Hz, 1H), 4.23-4.31 (m, 1H), 4.16 (brs, 2H), 3.82 (d, J=3.95 Hz, 2H), 3.18 (brs, 2H), 1.12-1.40 (m, 18H), 0.99-1.09 (m, 4H).

Example S101. Synthesis of 2-isopropyl-6-((1,2,3,4-tetrahydroisoquinolin-6-yl)amino)-1-(thiophen-3-yl)-1,2-dihydro-3H-pyrazolo[3,4-d]pyrimidin-3-one hydrochloride (Compound No. 2.647)

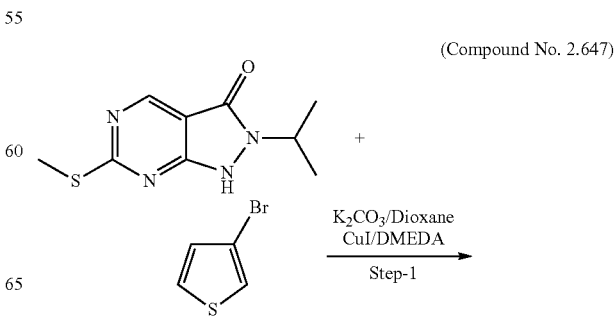

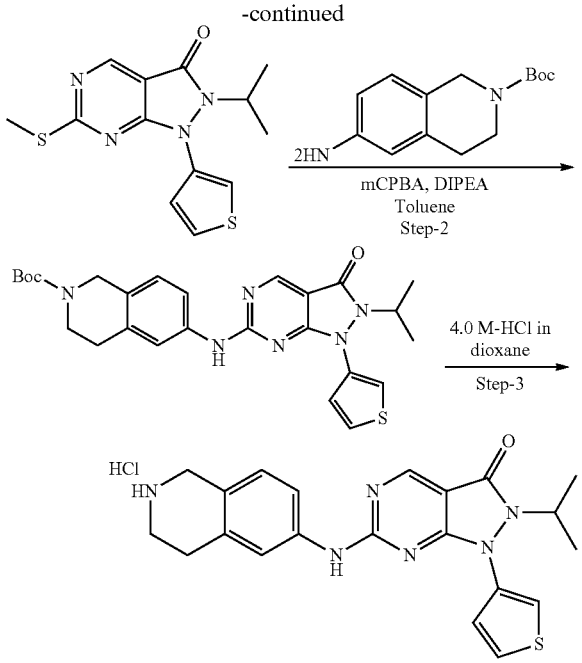

Step-1: Synthesis of 2-isopropyl-6-(methylthio)-1-(thiophen-3-yl)-1,2-dihydro-3H-pyrazolo[3,4-d]pyrimidin-3-one To a stirred solution of 2-isopropyl-6-(methylthio)-1,2-dihydro-3H-pyrazolo[3,4-d]pyrimidin-3-one (300 mg, 1.33 mmol) and 3-bromothiophene (221 g, 1.36 mmol) in Dioxane (10 mL) was added CuI (51 mg, 0.26 mmol), DMEDA (47 mg, 0.53 mmol). The reaction mixture was stirred at 130° C. for 14 h. The progress of reaction was monitored by TLC. After completion, the reaction mixture was extracted with EtOAc (3×50 mL) dried over Na₂SO₄, concentrated and purified by column chromatography (Combiflash, Elution: 0-30% EtOAc in Hexane) to afford the desired product, 2-isopropyl-6-(methylthio)-1-(thiophen-3-yl)-1,2-dihydro-3H-pyrazolo[3,4-d]pyrimidin-3-one (130 mg, 31.71%) as an off white solid.

LCMS: 307.1 [M+1]⁺

Step-2: Synthesis of tert-butyl 6-((2-isopropyl-3-oxo-1-(thiophen-3-yl)-2,3-dihydro-1H-pyrazolo[3,4-d]pyrimidin-6-yl)amino)-3,4-dihydroisoquinoline-2(1H)-carboxylate To a stirred solution of 2-isopropyl-6-(methylthio)-1-(thiophen-3-yl)-1,2-dihydro-3H-pyrazolo[3,4-d]pyrimidin-3-one (130 mg, 0.424 mmol, 1.0 eq) in (6.0 mL) of toluene was added m-CPBA (146 mg, 0.84 mmol, 2 eq) and allowed to stir at rt for 1 h. Tert-butyl 6-amino-3,4-dihydroisoquinoline-2(1H)-carboxylate (125 mg, 0.51 mmol, 1.2 eq) and DIPEA (0.36 mL, 2.1 mmol, 4.0 eq) were added and allowed to stir at rt for overnight. After completion of reaction, the reaction mixture was diluted with water and extracted with EtOAc (20 mL×3). The organic layer was dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((2-isopropyl-3-oxo-1-(thiophen-3-yl)-2,3-dihydro-1H-pyrazolo[3,4-d]pyrimidin-6-yl)amino)-3,4-dihydroisoquinoline-2(1H)-carboxylate (40 mg, 18.60%) as an off white solid.

LCMS: 507.2 [M+1]⁺

Step-3: Synthesis of 2-isopropyl-6-((1,2,3,4-tetrahydroisoquinolin-6-yl)amino)-1-(thiophen-3-yl)-1,2-dihydro-3H-pyrazolo[3,4-d]pyrimidin-3-one hydrochloride tert-butyl 6-((2-isopropyl-3-oxo-1-(thiophen-3-yl)-2,3-dihydro-1H-pyrazolo[3,4-d]pyrimidin-6-yl)amino)-3,4-dihydroisoquinoline-2(1H)-carboxylate (40 mg, 0.079 mmol, 1.0 eq) was dissolved in dioxane (1 mL), followed by dropwise addition of 4.0M-HCl in dioxane (1 mL) and allowed to stir at rt for 1 h. After completion of reaction, the reaction mixture was filtered and dried under reduced pressure to afford the desired compound, 2-isopropyl-6-((1,2,3,4-tetrahydroisoquinolin-6-yl)amino)-1-(thiophen-3-yl)-1,2-dihydro-3H-pyrazolo[3,4-d]pyrimidin-3-one hydrochloride (3 mg, 8.57%) as an off white solid.

LCMS: 407.3 [M+1]⁺; UPLC @ 254 nm=97.46% and @ 220 nm=98.32%.

¹H NMR (400 MHz, DMSO-d₆): δ 10.26 (s, 1H), 8.99 (brs, 2H), 8.82 (s, 1H), 7.82 (brs, 1H), 7.72-7.79 (m, 1H), 7.44 (brs, 1H), 7.29 (d, J=4.38 Hz, 1H), 7.11 (d, J=8.77 Hz, 1H), 4.08-4.24 (m, 3H), 2.94 (brs, 2H), 1.29 (d, J=6.58 Hz, 6H).

Example S102. Synthesis of 1-(1-(tert-butyl)-1H-pyrazol-3-yl)-2-isopropyl-6-((1,2,3,4-tetrahydroisoquinolin-6-yl)amino)-1,2-dihydro-3H-pyrazolo[3,4-d]pyrimidin-3-one hydrochloride (Compound No. 2.454)

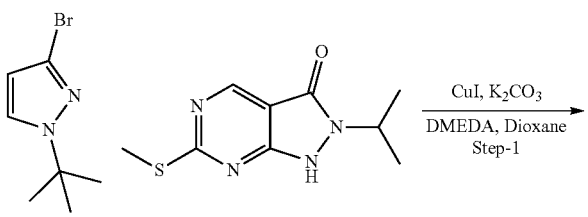

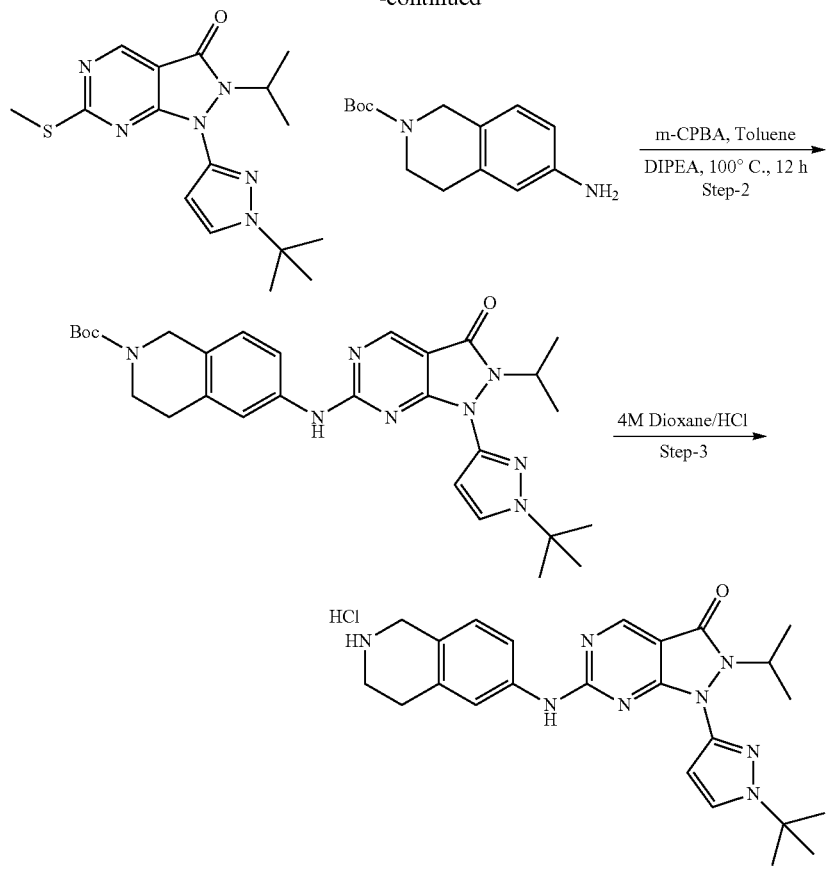

Step-1: Synthesis of 1-(1-(tert-butyl)-1H-pyrazol-3-yl)-2-isopropyl-6-(methylthio)-1,2-dihydro-3H-pyrazolo[3,4-d]pyrimidin-3-one To a stirred solution of 2-isopropyl-6-(methylthio)-1,2-dihydro-3H-pyrazolo[3,4-d]pyrimidin-3-one (442 mg, 1.96 mmol, 1.0 eq) and 3-bromo-1-(tert-butyl)-1H-pyrazole (400 mg, 1.96 mmol, 1.0 eq) in (12 mL) of dioxane was added potassium carbonate (542 mg, 3.92 mmol, 2.0 eq) and the resulting mixture was purged with nitrogen for 10 min followed by addition of copper iodide (75 mg, 0.392 mmol, 0.2 eq), and N,N'-dimethylethylenediamine (DMEDA) (0.08 mL, 0.784 mmol, 0.4 eq) and again purged with nitrogen for 10 min, stirred at 90° C. for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-30% EtOAc in hexane] to afford the desired product, 1-(1-(tert-butyl)-1H-pyrazol-3-yl)-2-isopropyl-6-(methylthio)-1,2-dihydro-3H-pyrazolo[3,4-d]pyrimidin-3-one (366 mg, 14.64%) as colorless liquid.
LCMS: 347.2 [M+1]$^+$ Step-2: Synthesis of tert-butyl 6-((1-(1-(tert-butyl)-1H-pyrazol-3-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 1-(1-(tert-butyl)-1H-pyrazol-3-yl)-2-isopropyl-6-(methylthio)-1,2-dihydro-3H-pyrazolo[3,4-d]pyrimidin-3-one (100 mg, 0.288 mmol, 1.0 eq) in (6.0 mL) of toluene was added m-CPBA (99 mg, 0.576 mmol, 2.0 eq) and allowed to stir at rt for 30 minutes. tert-butyl 6-amino-3,4-dihydroisoquinoline-2(1H)-carboxylate (86 mg, 0.604 mmol, 1.2 eq) and DIPEA (0.2 mL, 1.15 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((1-(1-(tert-butyl)-1H-pyrazol-3-yl)-2-isopropyl-3-oxo-2,3-dihydro-1H-pyrazolo[3,4-d]pyrimidin-6-yl)amino)-3,4-dihydroisoquinoline-2(1H)-carboxylate (17 mg, 10.77%) as an off white solid.
LCMS: 547.3 [M+1]$^+$ Step-3: Synthesis of 1-(1-(tert-butyl)-1H-pyrazol-3-yl)-2-isopropyl-6-((1,2,3,4-tetrahydroisoquinolin-6-yl)amino)-1,2-dihydro-3H-pyrazolo[3,4-d]pyrimidin-3-one hydrochloride tert-butyl 6-((1-(1-(tert-butyl)-1H-pyrazol-3-yl)-2-isopropyl-3-oxo-2,3-dihydro-1H-pyrazolo[3,4-d]pyrimidin-6-yl)amino)-3,4-dihydroisoquinoline-2(1H)-carboxylate (17 mg, 0.031 mmol, 1.0 eq) was dissolved in dioxane (0.3 mL), followed by dropwise addition of 4.0M-HCl (0.3 mL) and allowed to stir at rt for 1 h. After completion of reaction, the reaction mixture was filtered and dried under reduced pressure to afford the desired compound, 1-(1-(tert-butyl)-1H-pyrazol-3-yl)-2-isopropyl-6-((1,2,3,4-tetrahydroisoquinolin-6-yl)amino)-1,2-dihydro-3H-pyrazolo[3,4-d]pyrimidin-3-one hydrochloride (96 mg, 46.60%) as light yellow solid.

LCMS: 447.3 [M+1]+; UPLC @ 254 nm=90.92% and @ 220 nm=88.16%.

¹H NMR (400 MHz, DMSO-d₆): δ 10.22 (br. s., 1H) 9.21 (br. s., 2H) 8.82 (s, 1H) 7.99 (br. s., 1H) 7.63 (br. s., 1H) 7.54 (d, J=8.80 Hz, 1H) 7.08 (d, J=8.31 Hz, 1H) 6.47 (d, J=1.96 Hz, 1H) 4.30-4.39 (m, 1H) 4.18 (br. s., 2H) 3.15-3.20 (d, 2H) 2.91 (br. s., 2H) 1.44-1.61 (m, 9H) 1.19-1.32 (m, 6H).

Example S103. Synthesis of 1-(2-(tert-butyl)pyridin-4-yl)-2-cyclopropyl-6-((4,4-dimethyl-1,2,3,4-tetrahydroisoquinolin-7-yl)amino)-1,2-dihydro-3H-pyrazolo[3,4-d]pyrimidin-3-one dihydrochloride (Compound No. 2.600)

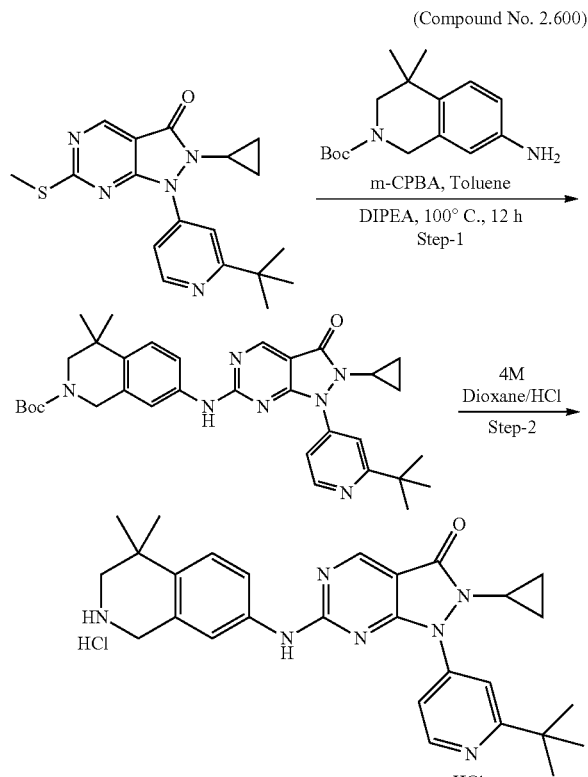

Step-1: Synthesis of tert-butyl 7-((1-(2-(tert-butyl)pyridin-4-yl)-2-cyclopropyl-3-oxo-2,3-dihydro-1H-pyrazolo[3,4-d]pyrimidin-6-yl)amino)-4,4-dimethyl-3,4-dihydroisoquinoline-2(1H)-carboxylate To a stirred solution of 1-(2-(tert-butyl)pyridin-4-yl)-2-cyclopropyl-6-(methylthio)-1,2-dihydro-3H-pyrazolo[3,4-d]pyrimidin-3-one (100 mg, 0.281 mmol, 1.0 eq) in (6.0 mL) of toluene was added m-CPBA (97 mg, 0.562 mmol, 2.0 eq) and allowed to stir at rt for 1 h. tert-butyl 7-amino-4,4-dimethyl-3,4-dihydroisoquinoline-2(1H)-carboxylate (93 mg, 0.337 mmol, 1.2 eq) and DIPEA (0.2 mL, 1.124 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 7-((1-(2-(tert-butyl)pyridin-4-yl)-2-cyclopropyl-3-oxo-2,3-dihydro-1H-pyrazolo[3,4-d]pyrimidin-6-yl)amino)-4,4-dimethyl-3,4-dihydroisoquinoline-2(1H)-carboxylate (60 mg, 36.53%) as an off white solid.

LCMS: 584.3 [M+1]+

Step-2: Synthesis of 1-(2-(tert-butyl)pyridin-4-yl)-2-cyclopropyl-6-((4,4-dimethyl-1,2,3,4-tetrahydroisoquinolin-7-yl)amino)-1,2-dihydro-3H-pyrazolo[3,4-d]pyrimidin-3-one dihydrochloride tert-butyl 7-((1-(2-(tert-butyl)pyridin-4-yl)-2-cyclopropyl-3-oxo-2,3-dihydro-1H-pyrazolo[3,4-d]pyrimidin-6-yl)amino)-4,4-dimethyl-3,4-dihydroisoquinoline-2(1H)-carboxylate (60 mg, 0.102 mmol, 1.0 eq) was dissolved in dioxane (0.6 mL), followed by dropwise addition of 4.0M-HCl (0.6 mL) and allowed to stir at rt for 1 h. After completion of reaction, the reaction mixture was filtered and dried under reduced pressure to afford the desired compound, 1-(2-(tert-butyl)pyridin-4-yl)-2-cyclopropyl-6-((4,4-dimethyl-1,2,3,4-tetrahydroisoquinolin-7-yl)amino)-1,2-dihydro-3H-pyrazolo[3,4-d]pyrimidin-3-one dihydrochloride (36 mg, 52.44%) as an off white solid.

LCMS: 486.5 [M+1]+; UPLC @ 254 nm=93.71% and @ 220 nm=94.78%.

¹H NMR (400 MHz, DMSO-d₆): δ 10.40 (br. s., 1H) 9.60 (br. s., 2H) 8.80-8.92 (m, 2H) 7.99 (br. s., 1H) 7.80 (br. s., 1H) 7.62 (d, J=8.31 Hz, 1H) 7.38-7.49 (m, 2H) 4.25 (br. s., 2H), 4.10 (s., 2H) 3.90-3.99 (m, 1H) 3.10-3.27 (d, 4H) 1.39-1.55 (m, 9H) 1.37 (m, 6H).

Example S104. Synthesis of 1-(2-(tert-butyl)pyridin-4-yl)-2-isopropyl-6-((1,2,3,4-tetrahydroisoquinolin-6-yl)amino)-1,2-dihydro-3H-pyrazolo[4,3-c]pyridin-3-one trihydrochloride (Compound No. 2.732)

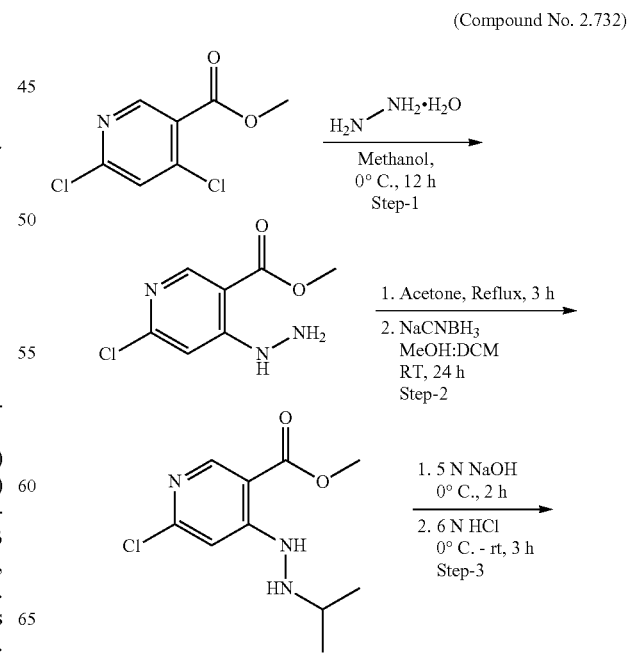

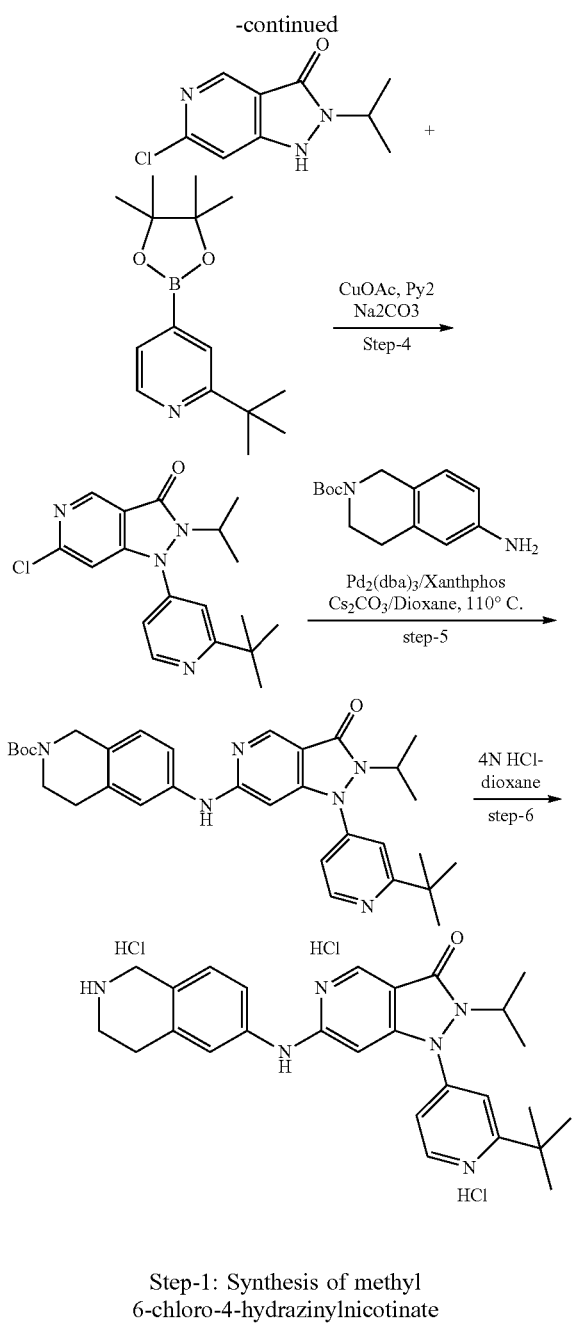

Step-1: Synthesis of methyl
6-chloro-4-hydrazinylnicotinate

Hydrazine hydrate (4.76 mL, 97.06 mmol, 2 eq) was dissolved in methanol (50 mL) and cooled to 0° C. methyl 4,6-dichloronicotinate (10.0 g, 48.53 mmol, 1 eq) was added. The reaction mixture was stirred at same temperature for 12 h. Solid obtained was filtered under vacuum to get the desired product, methyl 6-chloro-4-hydrazinylnicotinate (6.19 g, 63.29%) as an off white solid.
LCMS: 202.1 [M+1]$^+$ Step-2: Synthesis of methyl
6-chloro-4-(2-isopropylhydrazinyl)nicotinate Methyl 6-chloro-4-hydrazinylnicotinate (6.19 g, 3.07 mmol, 1.0 eq) was suspended in Acetone and reflux for 4 h, after the completion of reaction, the reaction mixture was evaporated under reduced pressure to afford 6.20 g of methyl 6-chloro-4-(2-(propan-2-ylidene)hydrazinyl)nicotinate. The crude product obtained, 6-chloro-4-(2-(propan-2-ylidene)hydrazinyl)nicotinate (6.20 g, 25.65 mmol, 1 eq) was dissolved in Methanol: Dichloromethane (3:1) (160 mL) and cooled at 0° C. A solution of Sodium cynoborohydride (9.67 g, 153.92 mmol, 6.0 eq) in Methanol (40 mL) and concentrated Hydrochloric acid (1.2 mL) solution was added drop wise to the reaction mixture. The reaction mixture was stirred at ambient temperature for 24 h. Saturated aqueous solution of sodium bicarbonate was added to reaction mixture till pH 7-8 and organic phase was extracted with ethyl acetate (500 mL×3). The combined organic layers were dried over anhydrous sodium sulfate and concentrated under reduced pressure to afford, methyl 6-chloro-4-(2-isopropylhydrazinyl)nicotinate (5.91 g, 79.01%) as an off white solid.
LCMS: 244.1 [M+1]$^+$ Step-3: Synthesis of 6-chloro-2-isopropyl-1,2-dihydro-3H-pyrazolo[4,3-c]pyridin-3-one Methyl 6-chloro-4-(2-isopropylhydrazinyl)nicotinate (5.91 g, 24.25 mmol, 1 eq) was dissolved in Methanol (55 mL) and solution was cooled to 0° C. A solution of sodium hydroxide in water (5N, 173 mL) was added drop wise to reaction solution and reaction mixture was stirred at same temperature for 2 h. Hydrochloric acid in water (5N) was added drop wise to make pH-2 and stirred for 3 h at ambient temperature. After completion of reaction, dichloromethane (500 mL×2) was added in to reaction mixture and organic phase was extracted. Organic layer was dried over anhydrous Sodium sulfate and concentrated under reduced pressure. Solid obtained was washed with pentane (100 mL×2) to afford 6-chloro-2-isopropyl-1,2-dihydro-3H-pyrazolo[4,3-c]pyridin-3-one (1.5 g, 24.25%) as yellow solid.
LCMS: 212.2 [M+1]$^+$ Step-4: Synthesis of 1-(2-(tert-butyl)pyridin-4-yl)-6-chloro-2-isopropyl-1,2-dihydro-3H-pyrazolo[4,3-c]pyridin-3-one To a stirred solution of 6-chloro-2-isopropyl-1,2-dihydro-3H-pyrazolo[4,3-c]pyridin-3-one (1.5 g, 7.08 mmol, 1 eq) and 2-(tert-butyl)-4-(4,4,5,5-tetramethyl-1,3,2-dioxaborolan-2-yl)pyridine (2.77 g, 10.63 mmol, 1.5 eq) in DCM (100 mL) was added 2,2-bipyridine (2.21 g, 14.16 mmol, 2 eq), copper acetate (2.57 g, 14.16 mmol, 2 eq) and Na$_2$CO$_3$ (2.25 g, 21.24 mmol, 3 eq). The reaction mixture was stirred at rt for 24 h in open air. The progress of reaction was monitored by TLC. After completion, the reaction mixture was filtered over celite to remove inorganic impurities. The filtrate was washed with water, dried over Na$_2$SO$_4$, concentrated and purified by column chromatography (Combiflash, Elution: 0-30% EtOAc in Hexane) to afford the desired product, 1-(2-(tert-butyl)pyridin-4-yl)-6-chloro-2-isopropyl-1,2-dihydro-3H-pyrazolo[4,3-c]pyridin-3-one (900 mg, 37.50%) as an off white solid.
LCMS: 345.2 [M+1]$^+$ Step-5: Synthesis of tert-butyl 6-((1-(2-(tert-butyl)pyridin-4-yl)-2-isopropyl-3-oxo-2,3-dihydro-1H-pyrazolo[4,3-c]pyridin-6-yl)amino)-3,4-dihydroisoquinoline-2(1H)-carboxylate To a stirring solution of 1-(2-(tert-butyl)pyridin-4-yl)-6-chloro-2-isopropyl-1,2-dihydro-3H-pyrazolo[4,3-c]pyridin-3-one (200 mg, 0.579 mmol, 1 eq) in dioxane (20 mL), tert-butyl 6-amino-3,4-dihydroisoquinoline-2(1H)-carboxylate (173 mg, 0.695 mmol, 1.2 eq) and Cs$_2$CO$_3$ (377 mg, 1.158 mmol, 2 eq) were added. The mixture was degassed for 10-15 min followed by addition of Pd$_2$(dba)$_3$ (64 mg, 0.069 mmol, 0.12 eq) and xantphos (50 mg, 0.086 mmol, 1.5 eq). The reaction was heated at 110° C. for 1 h under microwave irradiation. After completion, the reaction mixture was filtered through celite using EtOAc. The combined organic layer was dried, concentrated and purified by flash chromatography (EtOAc-Hexane 0-70%) to give tert-butyl 6-((1-(2-(tert-butyl)pyridin-4-yl)-2-isopropyl-3-oxo-2,3-dihydro-1H-pyrazolo[4,3-c]pyridin-6-yl)amino)-3,4-dihydroisoquinoline-2(1H)-carboxylate (60 mg, 18.58%) as yellow solid.)

LCMS: 557.3 [M+1]$^+$

Step-6: Synthesis of 1-(2-(tert-butyl)pyridin-4-yl)-2-isopropyl-6-((1,2,3,4-tetrahydroisoquinolin-6-yl)amino)-1,2-dihydro-3H-pyrazolo[4,3-c]pyridin-3-one trihydrochloride tert-butyl 6-((1-(2-(tert-butyl)pyridin-4-yl)-2-isopropyl-3-oxo-2,3-dihydro-1H-pyrazolo[4,3-c]pyridin-6-yl)amino)-3,4-dihydroisoquinoline-2(1H)-carboxylate (60 mg, 0.107 mmol, 1.0 eq) was dissolved in dioxane (1 mL), followed by dropwise addition of 4.0M-HCl (1 mL) and allowed to stir at rt for 1 h. After completion of reaction, the reaction mixture was filtered and dried under reduced pressure to afford the desired compound, 1-(2-(tert-butyl)pyridin-4-yl)-2-isopropyl-6-((1,2,3,4-tetrahydroisoquinolin-6-yl)amino)-1,2-dihydro-3H-pyrazolo[4,3-c]pyridin-3-one trihydrochloride (42 mg, 68.86%) as light yellow solid.

LCMS: 457.5 [M+1]$^+$; UPLC @ 254 nm=96.90% and @ 220 nm=98.32%.

$^1$H NMR (400 MHz, DMSO-d$_6$): δ 9.86 (br. s., 1H) 9.40 (br. s., 1H) 8.75 (d, J=5.87 Hz, 1H) 8.63 (s, 1H) 7.60 (s, 2H) 7.64 (m, 2H) 7.14 (d, J=8.80 Hz, 1H) 6.81 (br. s., 1H) 4.18 (br. s., 2H) 3.96 (m, 1H) 3.33 (br. s., 2H) 2.92-3.01 (m, 2H) 2.81 (d, J=4.40 Hz, 2H) 1.45 (s, 9H) 1.28-1.41 (m, 6H).

Example S105. Synthesis of 2-cyclopropyl-6-((1,1-dimethyl-1,2,3,4-tetrahydroisoquinolin-6-yl)amino)-1-(2-(2-fluoropropan-2-yl)pyridin-4-yl)-1,2-dihydro-3H-pyrazolo[3,4-d]pyrimidin-3-one (Compound No. 2.555)

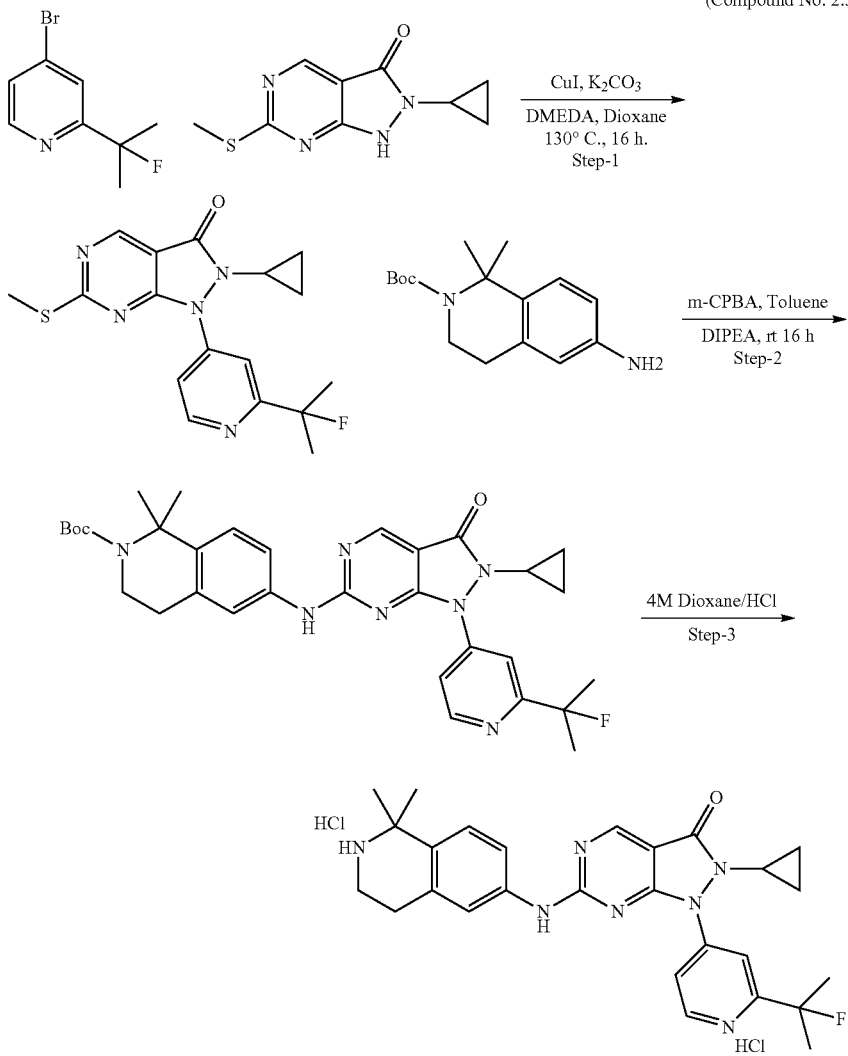

Step-1: Synthesis of 2-cyclopropyl-1-(2-(2-fluoro-propan-2-yl) pyridin-4-yl)-6-(methylthio)-1, 2-dihydro-3H-pyrazolo [3, 4-d] pyrimidin-3-one To a stirred solution of 2-cyclopropyl-6-(methylthio)-1,2-dihydro-3H-pyrazolo[3,4-d]pyrimidin-3-one (250 mg, 1.124 mmol, 1.0 eq) and 4-bromo-2-(2-fluoropropan-2-yl) pyridine (293 mg, 1.349 mmol, 1.2 eq) in (6 mL) of dioxane was added potassium carbonate (310 mg, 2.249 mmol, 2.0 eq) and the resulting mixture was purged with nitrogen for 10 min followed by addition of copper iodide (43 mg, 0.224 mmol, 0.2 eq), and N,N'-dimethylethylenediamine (DMEDA) (0.04 mL, 0.449 mmol, 0.4 eq) and again purged with nitrogen for 10 min, stirred at 130° C. for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired product 2-cyclopropyl-1-(2-(2-fluoro-propan-2-yl) pyridin-4-yl)-6-(methylthio)-1,2-dihydro-3H-pyrazolo [3, 4-d] pyrimidin-3-one. (50 mg, 12.3%) as yellow semi solid.

LCMS: 359.2 [M+1]$^+$

Step-2: Synthesis of tert-butyl 6-((2-cyclopropyl-1-(2-(2-fluoropropan-2-yl)pyridin-4-yl)-3-oxo-2,3-dihydro-1H-pyrazolo[3,4-d]pyrimidin-6-yl)amino)-1,1-dimethyl-3,4-dihydroisoquinoline-2(1H)-carboxylate To a stirred solution of 2-cyclopropyl-1-(2-(2-fluoropro-pan-2-yl) pyridin-4-yl)-6-(methylthio)-1,2-dihydro-3H-pyrazolo [3, 4-d] pyrimidin-3-one (50 mg, 0.139 mmol, 1.0 eq) in (2.0 mL) of toluene was added m-CPBA (48 mg, 0.278 mmol, 2.0 eq) and allowed to stir at rt for 60 minutes. tert-butyl 6-amino-1,1-dimethyl-3,4-dihydroisoquinoline-2 (1H)-carboxylate (46 mg, 0.167 mmol, 1.2 eq) and DIPEA (0.09 mL, 0.557 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((2-cyclopropyl-1-(2-(2-fluoropropan-2-yl)pyridin-4-yl)-3-oxo-2,3-dihydro-1H-pyrazolo[3,4-d]pyrimidin-6-yl) amino)-1,1-dimethyl-3,4-dihydroisoquinoline-2(1H)-carboxylate (12 mg, 14.70%) as light yellow solid.

LCMS: 587.25 [M+1]$^+$

Step-3: Synthesis of 2-cyclopropyl-6-((1,1-dimethyl-1,2,3,4-tetrahydroisoquinolin-6-yl)amino)-1-(2-(2-fluoropropan-2-yl)pyridin-4-yl)-1,2-dihydro-3H-pyrazolo[3,4-d]pyrimidin-3-one tert-butyl 6-((2-cyclopropyl-1-(2-(2-fluoropropan-2-yl) pyridin-4-yl)-3-oxo-2,3-dihydro-1H-pyrazolo[3,4-d]pyrimi-din-6-yl)amino)-1,1-dimethyl-3,4-dihydroisoquinoline-2 (1H)-carboxylate (15 mg, 25.55 mmol, 1.0 eq) was dissolved in dioxane (1.5 mL), followed by dropwise addition of 4.0M-HCl (0.4 mL) and allowed to stir at rt for 2 h. After completion of reaction, the reaction mixture was filtered and dried under reduced pressure to afford the desired compound, 2-cyclopropyl-6-((1,1-dimethyl-1,2,3,4-tetrahydroisoquinolin-6-yl)amino)-1-(2-(2-fluoropropan-2-yl)pyridin-4-yl)-1,2-dihydro-3H-pyrazolo[3,4-d]pyrimidin-3-one (3.5 mg, 28.11%) as light yellow solid.

LCMS: 487.25 [M+1]$^+$; UPLC @ 254 nm=93.48% and @ 220 nm=92.49%.

$^1$H NMR (400 MHz, DMSO-d$_6$): δ ppm 10.35 (br. s., 1H) 9.43 (br. s., 1H) 8.84 (s, 1H) 8.72 (d, J=5.38 Hz, 2H) 7.59-7.79 (m, 2H) 7.51 (s, 1H) 7.33 (d, J=8.31 Hz, 2H) 3.42 (s., 6H) 3.11 (s., 2H) 3.03 (s, 2H) 3.0 (d 2H) 1.74 (s, 2H) 1.49-1.71 (m, 6H).

Example S106. Synthesis of 2-cyclopropyl-6-((4,4-dimethyl-1,2,3,4-tetrahydroisoquinolin-7-yl)amino)-1-(2-(2-fluoropropan-2-yl)pyridin-4-yl)-1,2-dihydro-3H-pyrazolo[3,4-d]pyrimidin-3-one (Compound No. 2.605)

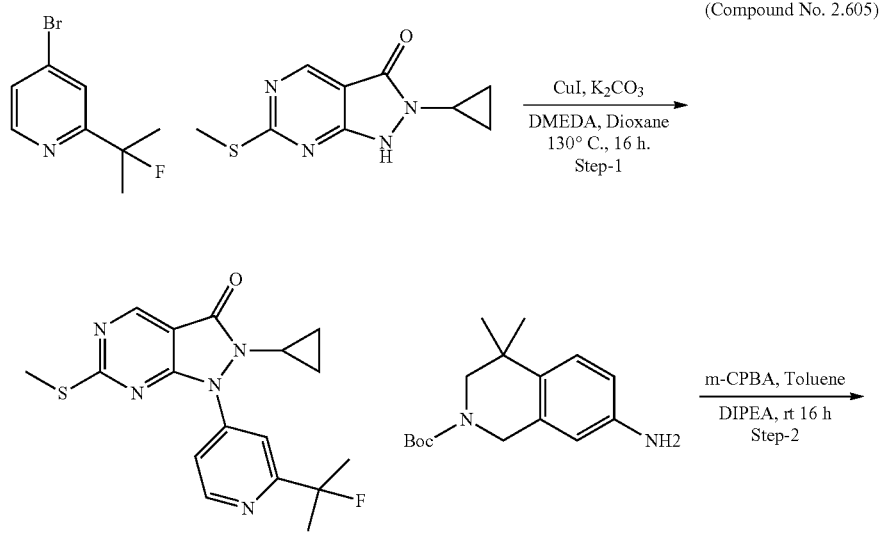

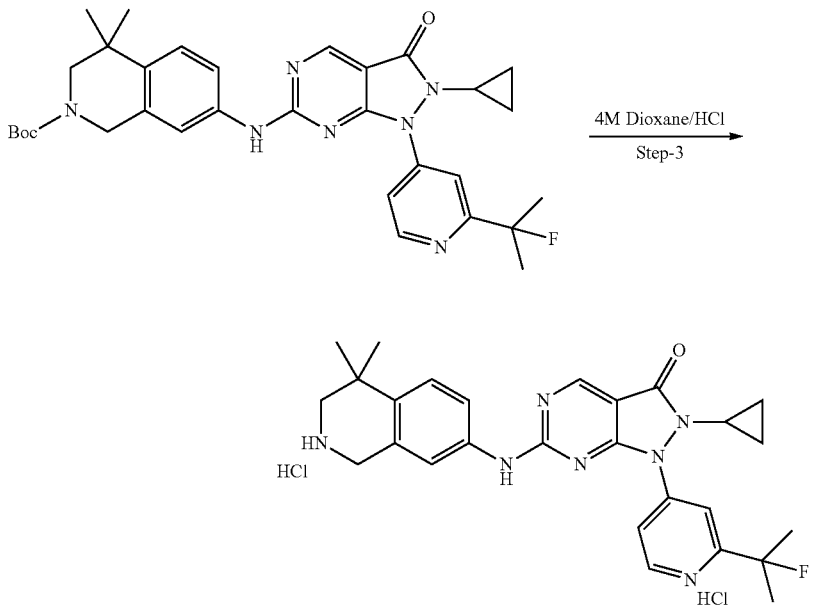

Step-1: Synthesis of 2-cyclopropyl-1-(2-(2-fluoropropan-2-yl)pyridin-4-yl)-6-(methylthio)-1,2-dihydro-3H-pyrazolo[3,4-d]pyrimidin-3-one To a stirred solution of 2-cyclopropyl-6-(methylthio)-1,2-dihydro-3H-pyrazolo[3,4-d]pyrimidin-3-one (250 mg, 1.124 mmol, 1.0 eq) and 4-bromo-2-(2-fluoropropan-2-yl)pyridine (293 mg, 1.349 mmol, 1.2 eq) in (5 mL) of dioxane was added potassium carbonate (310 mg, 2.249 mmol, 2.0 eq) and the resulting mixture was purged with nitrogen for 10 min followed by addition of copper iodide (43 mg, 0.224 mmol, 0.2 eq), and N,N'-dimethylethylenediamine (DMEDA) (0.04 mL, 0.449 mmol, 0.4 eq) and again purged with nitrogen for 10 min, stirred at 130° C. for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-30% EtOAc in hexane] to afford the desired product, 2-cyclopropyl-1-(2-(2-fluoropropan-2-yl)pyridin-4-yl)-6-(methylthio)-1,2-dihydro-3H-pyrazolo[3,4-d]pyrimidin-3-one (50 mg, 12.39%) as light yellow viscous.

LCMS: 359.2 [M+1]$^+$

Step-2: Synthesis of tert-butyl 7-((2-cyclopropyl-1-(2-(2-fluoropropan-2-yl)pyridin-4-yl)-3-oxo-2,3-dihydro-1H-pyrazolo[3,4-d]pyrimidin-6-yl)amino)-4,4-dimethyl-3,4-dihydroisoquinoline-2(1H)-carboxylate To a stirred solution of 2-cyclopropyl-1-(2-(2-fluoropropan-2-yl)pyridin-4-yl)-6-(methylthio)-1,2-dihydro-3H-pyrazolo[3,4-d]pyrimidin-3-one (50 mg, 0.139 mmol, 1.0 eq) in (2.0 mL) of toluene was added m-CPBA (48 mg, 0.278 mmol, 2.0 eq) and allowed to stir at rt for 60 minutes. tert-butyl 7-amino-4,4-dimethyl-3,4-dihydroisoquinoline-2 (1H)-carboxylate (46 mg, 0.167 mmol, 1.2 eq) and DIPEA (0.09 mL, 0.557 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 7-((2-cyclopropyl-1-(2-(2-fluoropropan-2-yl)pyridin-4-yl)-3-oxo-2,3-dihydro-1H-pyrazolo[3,4-d]pyrimidin-6-yl)amino)-4,4-dimethyl-3,4-dihydroisoquinoline-2(1H)-carboxylate (18 mg, 22.06%) as white solid. LCMS: 587.25 (M+1)$^+$

Step-3: Synthesis of 2-cyclopropyl-6-((4,4-dimethyl-1,2,3,4-tetrahydroisoquinolin-7-yl)amino)-1-(2-(2-fluoropropan-2-yl)pyridin-4-yl)-1,2-dihydro-3H-pyrazolo[3,4-d]pyrimidin-3-one tert-butyl 7-((2-cyclopropyl-1-(2-(2-fluoropropan-2-yl)pyridin-4-yl)-3-oxo-2,3-dihydro-1H-pyrazolo[3,4-d]pyrimidin-6-yl)amino)-4,4-dimethyl-3,4-dihydroisoquinoline-2 (1H)-carboxylate (18 mg, 30.66 mmol, 1.0 eq) was dissolved in dioxane (1.5 mL), followed by dropwise addition of 4.0M-HCl (0.5 mL) and allowed to stir at rt for 2 h. After completion of reaction, the reaction mixture was filtered and dried under reduced pressure to afford the desired compound, 2-cyclopropyl-6-((4,4-dimethyl-1,2,3,4-tetrahydroisoquinolin-7-yl)amino)-1-(2-(2-fluoropropan-2-yl)pyridin-4-yl)-1,2-dihydro-3H-pyrazolo[3,4-d]pyrimidin-3-one (5 mg, 33.48%) as light yellow solid.

LCMS: 487.26 [M+1]$^+$; UPLC @ 254 nm=92.57% and @ 220 nm=91.91%.

$^1$H NMR (400 MHz, DMSO-d$_6$): δ ppm 10.36 (br. s., 1H) 9.06 (d., 2H) 8.84 (s, 1H) 8.71 (d, J=5.38 Hz, 2H) 7.72 (br. s., 1H) 7.67 (d, J=3.91 Hz, 2H) 7.27-7.56 (m, 3H) 4.26 (s., 2H) 3.23 (s., 3H) 3.11 (s., 3H) 1.74 (m, 4H) 1.69 (s, 3H) 1.34 (s, 3H).

Example S107. Synthesis of 2-(6-(2-isopropyl-3-oxo-6-((1,2,3,4-tetrahydroisoquinolin-7-yl)amino)-2,3-dihydro-1H-pyrazolo[3,4-d]pyrimidin-1-yl)pyridin-2-yl)-2-methylpropanenitrile dihydrochloride Compound No. 3.035

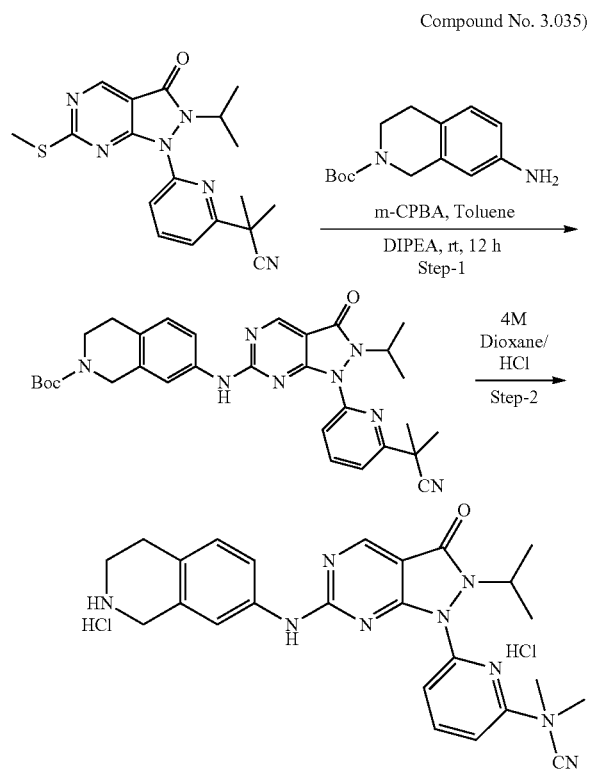

Step-1: Synthesis of tert-butyl 7-((1-(6-(2-cyanopropan-2-yl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 2-(6-(2-isopropyl-6-(methylthio)-3-oxo-2,3-dihydro-1H-pyrazolo[3,4-d]pyrimidin-1-yl)pyridin-2-yl)-2-methylpropanenitrile (125 mg, 0.339 mmol, 1.0 eq) in (3.0 mL) of toluene was added m-CPBA (117 mg, 0.6792 mmol, 2.0 eq) and allowed to stir at rt for 1 h. tert-butyl 7-amino-3,4-dihydroisoquinoline-2(1H)-carboxylate (101 mg, 0.4076 mmol, 1.2 eq) and DIPEA (0.25 mL, 1.3584 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 7-((1-(6-(2-cyanopropan-2-yl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (55 mg, 28.49%) as an off white solid.

LCMS: 569.2 [M+1]⁺

Step-2: Synthesis of 2-(6-(2-isopropyl-3-oxo-6-((1,2,3,4-tetrahydroisoquinolin-7-yl)amino)-2,3-dihydro-1H-pyrazolo[3,4-d]pyrimidin-1-yl)pyridin-2-yl)-2-methylpropanenitrile dihydrochloride tert-butyl 7-((1-(6-(2-cyanopropan-2-yl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (55 mg, 0.149 mmol, 1.0 eq) was dissolved in dioxane (1 mL), followed by dropwise addition of 4.0M-HCl (2 mL) and allowed to stir at rt for 1 h. After completion of reaction, the reaction mixture was filtered and dried under reduced pressure to afford the desired compound, 2-(6-(2-isopropyl-3-oxo-6-((1,2,3,4-tetrahydroisoquinolin-7-yl)amino)-2,3-dihydro-1H-pyrazolo[3,4-d]pyrimidin-1-yl)pyridin-2-yl)-2-methylpropanenitrile dihydrochloride (30 mg, 66.66%) as light yellow solid.

LCMS: 469.5 [M+1]⁺; UPLC @ 254 nm=95.20% and @ 220 nm=96.27%.

¹H NMR (400 MHz, DMSO-d₆): δ 10.28 (br. s., 1H), 9.17 (br. s., 1H), 8.87 (s, 1H) 8.18 (t, J=5.26 Hz, 1H) 8.0 (d, 1H) 7.70 (br. s., 1H) 7.58 (d, J=4.82 Hz, 1H) 7.48 (d, 1H) 7.19 (d, J=8.33 Hz, 1H) 4.22 (br. s., 2H) 3.94-3.99 (m, 1H) 3.35 (t, 2H) 2.95 (t, 2H) 1.70 (s, 6H) 1.37 (d, J=7.02 Hz, 6H).

Example S108. Synthesis of 2-(6-(2-isopropyl-3-oxo-6-((1,2,3,4-tetrahydroisoquinolin-6-yl)amino)-2,3-dihydro-1H-pyrazolo[3,4-d]pyrimidin-1-yl)pyridin-2-yl)-2-methylpropanenitrile dihydrochloride (Compound No. 3.036)

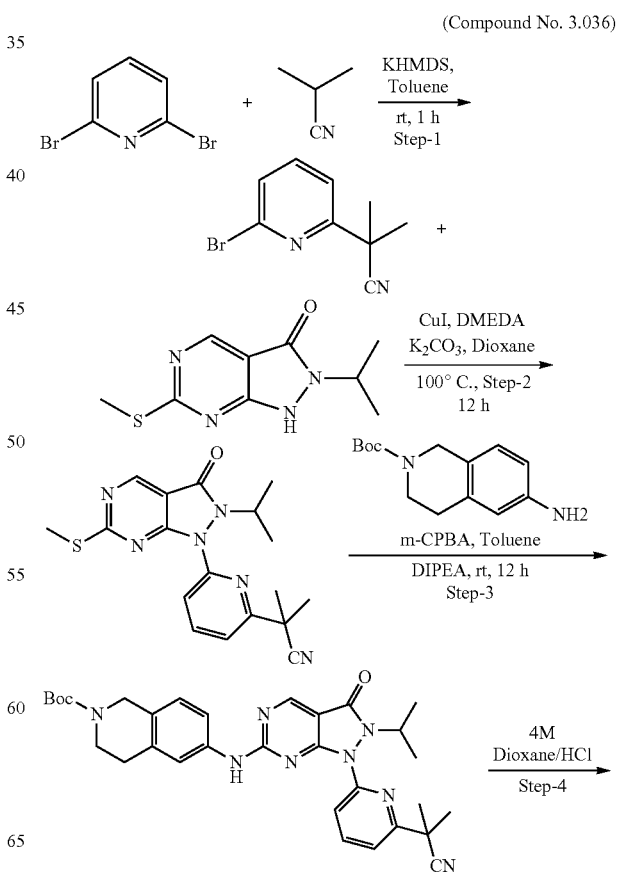

-continued

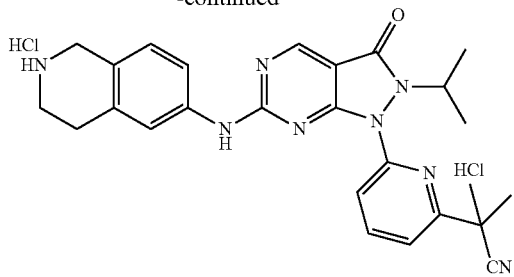

Step-1: Synthesis of 2-(6-bromopyridin-2-yl)-2-cyanopropan-1-ylium

To a stirred solution of isobutyronitrile (1 g, 14.46 mmol, 1 eq), in toluene (10 mL) was added KHMDS (32 ml, 15.91 mmol, 1.1 eq), at 0° C. & the reaction mixture was stirred for 1 h. 2,6-dibromopyridine (already dissolving in toluene 5 ml), (3.42 g, 14.46 mmol, 1.0 eq) was added dropwise & stirred for 18 h. After completion of reaction, the reaction mixture was diluted with saturated NH$_4$Cl solution and extracted with diethyl ether (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound 2-(6-bromopyridin-2-yl)-2-cyanopropan-1-ylium (600 mg, 18.52%) as colorless liquid.

LCMS: 224.9 [M+1]$^+$

Step-2: Synthesis of 2-(6-(2-isopropyl-6-(methylthio)-3-oxo-2,3-dihydro-1H-pyrazolo[3,4-d]pyrimidin-1-yl)pyridin-2-yl)-2-methylpropanenitrile To a stirred solution of 2-isopropyl-6-(methylthio)-1,2-dihydro-3H-pyrazolo[3,4-d]pyrimidin-3-one (126 mg, 0.5582 mmol, 1.0 eq) and 2-(6-bromopyridin-2-yl)-2-cyanopropan-1-ylium (150 mg, 0.6696 mmol, 1.2 eq) in (10 mL) of dioxane were added Potassium carbonate (154 mg, 1.116 mmol, 2 eq) and the resulting mixture was purged with nitrogen for 10 min followed by addition of copper iodide (22 mg, 0.11 mmol, 0.2 eq), and N,N'-dimethylethylenediamine (DMEDA) (100 mg, 0.22 mmol, 0.4 eq) and again purged with nitrogen for 10 min, stirred at 90° C. for overnight. After completion of reaction, the reaction mixture was diluted with water and extracted with EtOAc (50 mL×2). Combined organic layer was washed with water (50 mL) brine solution (50 mL), dried over anhydrous sodium sulphate and concentrated under reduced pressure to afford crude product, which was purified by flash chromatography to afford the desired compound 2-(6-(2-isopropyl-6-(methylthio)-3-oxo-2,3-dihydro-1H-pyrazolo[3,4-d]pyrimidin-1-yl)pyridin-2-yl)-2-methylpropanenitrile (200 mg 80.97%) as an off white solid.

LCMS: 369.2 [M+1]$^+$

Step-3: Synthesis of tert-butyl 6-((1-(6-(2-cyanopropan-2-yl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate To a stirred solution of 2-(6-(2-isopropyl-6-(methylthio)-3-oxo-2,3-dihydro-1H-pyrazolo[3,4-d]pyrimidin-1-yl)pyridin-2-yl)-2-methylpropanenitrile (125 mg, 0.339 mmol, 1.0 eq) in (3.0 mL) of toluene was added m-CPBA (117 mg, 0.6792 mmol, 2.0 eq) and allowed to stir at rt for 1 h. tert-butyl 6-amino-3,4-dihydroisoquinoline-2(1H)-carboxylate (101 mg, 0.4076 mmol, 1.2 eq) and DIPEA (0.25 mL, 1.3584 mmol, 4.0 eq) were added and allowed to stir at rt for overnight. After completion of reaction, the reaction mixture was diluted with water and extracted with EtOAc (50 mL×2). The combined organic layer was washed with water (50 mL), brine solution (50 mL), dried over anhydrous sodium sulfate and concentrated under reduced pressure to afford crude product, which was purified by flash chromatography [silica gel 100-200 mesh; elution 0-50% EtOAc in hexane] to afford the desired compound, tert-butyl 6-((1-(6-(2-cyanopropan-2-yl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (80 mg, 41.45%) as an off white solid.

LCMS: 569.4 [M+1]$^+$

Step-4: Synthesis of 2-(6-(2-isopropyl-3-oxo-6-((1,2,3,4-tetrahydroisoquinolin-6-yl)amino)-2,3-dihydro-1H-pyrazolo[3,4-d]pyrimidin-1-yl)pyridin-2-yl)-2-methylpropanenitrile dihydrochloride tert-butyl 6-((1-(6-(2-cyanopropan-2-yl)pyridin-2-yl)-2-isopropyl-3-oxo-2,3-dihydro-1H-pyrazolo[3,4-d]pyrimidin-6-yl)amino)-3,4-dihydroisoquinoline-2(1H)-carboxylate (80 mg, 0.140 mmol, 1.0 eq) was dissolved in dioxane (1 mL), followed by dropwise addition of 4.0M-HCl (2 mL) and allowed to stir at rt for 1 h. After completion of reaction, the reaction mixture was filtered and dried under reduced pressure to afford the desired compound, 2-(6-(2-isopropyl-3-oxo-6-((1,2,3,4-tetrahydroisoquinolin-6-yl)amino)-2,3-dihydro-1H-pyrazolo[3,4-d]pyrimidin-1-yl)pyridin-2-yl)-2-methylpropanenitrile dihydrochloride (50 mg, 75.75%) as light yellow solid.

LCMS: 469.5 [M+1]$^+$; UPLC @ 254 nm=95.81% and @ 220 nm=96.05%.

$^1$H NMR (400 MHz, DMSO-d$_6$): δ 10.28 (br. s., 1H), 9.17 (br. s., 1H), 8.87 (s, 1H) 8.18 (t, J=5.26 Hz, 1H) 8.0 (d, 1H) 7.70 (br. s., 1H) 7.58 (d, J=4.82 Hz, 1H) 7.48 (d, 1H) 7.19 (d, J=8.33 Hz, 1H) 4.22 (br. s., 2H) 3.94-3.99 (m, 1H) 3.35 (t, 2H) 2.95 (t, 2H) 1.70 (s, 6H) 1.37 (d, J=7.02 Hz, 6H).

Example S109. Synthesis of 1-(2-(tert-butyl)pyridin-4-yl)-2-isopropyl-6-((1,2,3,4-tetrahydroisoquinolin-7-yl)amino)-1,2-dihydro-3H-pyrazolo[4,3-c]pyridin-3-one trihydrochloride (Compound No. 2.744)

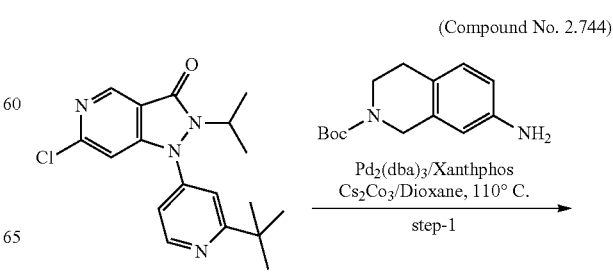

Pd$_2$(dba)$_3$/Xanthphos
Cs$_2$Co$_3$/Dioxane, 110° C.
→
step-1

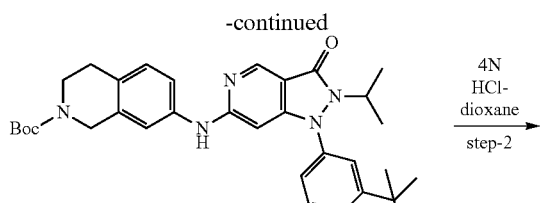

Step-1: Synthesis of tert-butyl 7-((1-(2-(tert-butyl)pyridin-4-yl)-2-isopropyl-3-oxo-2,3-dihydro-1H-pyrazolo[4,3-c]pyridin-6-yl)amino)-3,4-dihydroisoquinoline-2(1H)-carboxylate To a stirring solution of 1-(2-(tert-butyl)pyridin-4-yl)-6-chloro-2-isopropyl-1,2-dihydro-3H-pyrazolo[4,3-c]pyridin-3-one (200 mg, 0.579 mmol, 1 eq) in dioxane (20 mL), tert-butyl 7-amino-3,4-dihydroisoquinoline-2(1H)-carboxylate (173 mg, 0.695 mmol, 1.2 eq) and Cs$_2$CO$_3$ (377 mg, 1.158 mmol, 2 eq) were added. The mixture was degassed for 10-15 min followed addition of Pd$_2$(dba)$_3$ (64 mg, 0.069 mmol, 0.12 eq) and xantphos (50 mg, 0.086 mmol, 1.5 eq). The reaction was heated at 110° C. for 1 h under microwave irradiation. After completion, the reaction mixture was filtered through celite using EtOAc. The combined organic layer was dried, concentrated and purified by flash chromatography (EtOAc-Hexane 0-70%) to give tert-butyl 7-((1-(2-(tert-butyl)pyridin-4-yl)-2-isopropyl-3-oxo-2,3-dihydro-1H-pyrazolo[4,3-c]pyridin-6-yl)amino)-3,4-dihydroisoquinoline-2(1H)-carboxylate (60 mg, 18.58%) as yellow solid.)

LCMS: 557.3 [M+1]$^+$

Step-2: Synthesis of 1-(2-(tert-butyl)pyridin-4-yl)-2-isopropyl-6-((1,2,3,4-tetrahydroisoquinolin-7-yl)amino)-1,2-dihydro-3H-pyrazolo[4,3-c]pyridin-3-one trihydrochloride tert-butyl 7-((1-(2-(tert-butyl)pyridin-4-yl)-2-isopropyl-3-oxo-2,3-dihydro-1H-pyrazolo[4,3-c]pyridin-6-yl)amino)-3,4-dihydroisoquinoline-2(1H)-carboxylate (60 mg, 0.107 mmol, 1.0 eq) was dissolved in dioxane (1 mL), followed by dropwise addition of 4.0M-HCl (1 mL) and allowed to stir at rt for 1 h. After completion of reaction, the reaction mixture was filtered and dried under reduced pressure to afford the desired compound, 1-(2-(tert-butyl)pyridin-4-yl)-2-isopropyl-6-((1,2,3,4-tetrahydroisoquinolin-7-yl)amino)-1,2-dihydro-3H-pyrazolo[4,3-c]pyridin-3-one trihydrochloride (27 mg, 44.26%) as light yellow solid.

LCMS: 457.5 [M+1]$^+$; UPLC @ 254 nm=96.96% and @ 220 nm=98.33%.

$^1$H NMR (400 MHz, DMSO-d$_6$): δ 10.03 (br. s., 1H) 9.54 (br. s., 2H) 8.79 (d, J=6.36 Hz, 1H) 8.63 (s, 1H) 7.72 (br. s., 2H) 7.44-7.50 (m, 2H) 7.15 (d, J=8.80 Hz, 1H) 6.92 (s, 1H) 4.23 (br. s., 2H) 3.93-3.99 (m, 1H) 3.33 (br. s., 2H) 2.95 (t, J=5.87 Hz, 2H) 1.49 (s, 9H) 1.36 (s, 6H)

Example S110. Synthesis of 1-(2-(tert-butyl)pyridin-4-yl)-6-((1,1-dimethyl-1,2,3,4-tetrahydroisoquinolin-6-yl)amino)-2-isopropyl-1,2-dihydro-3H-pyrazolo[4,3-c]pyridin-3-one trihydrochloride (Compound No. 2.792)

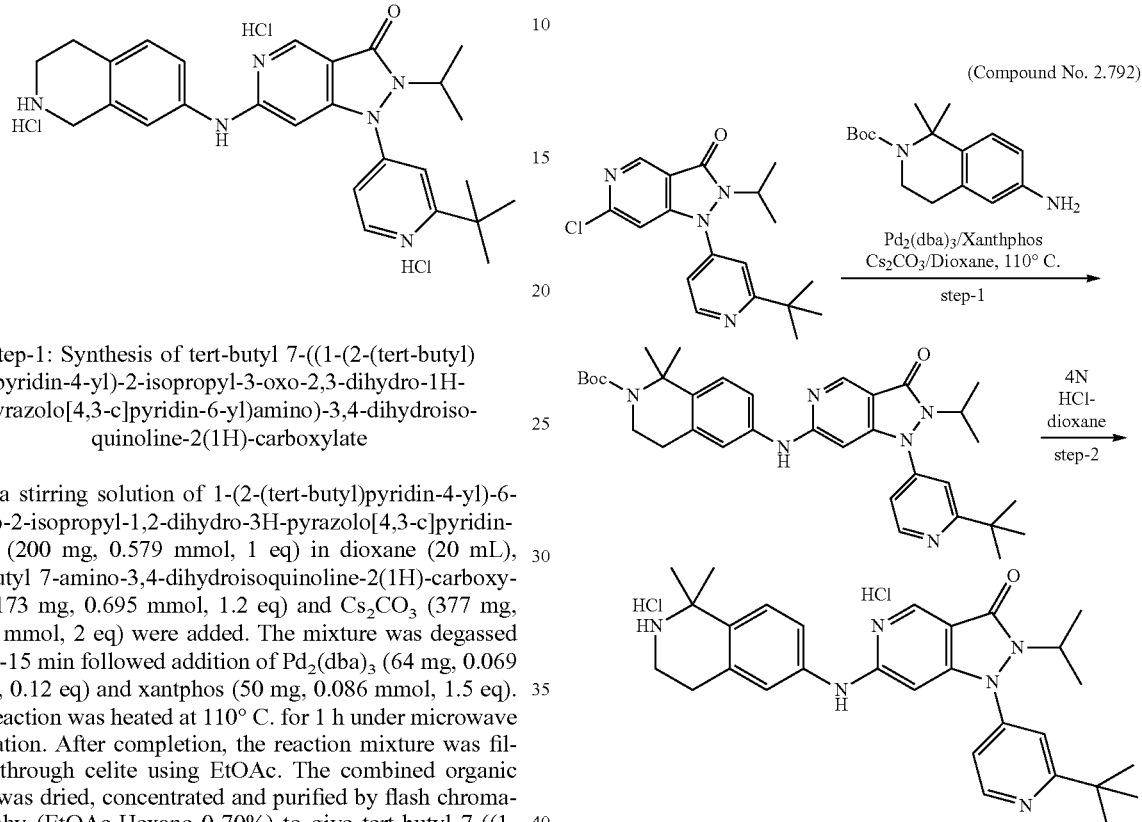

Step-1: Synthesis of tert-butyl 6-((1-(2-(tert-butyl)pyridin-4-yl)-2-isopropyl-3-oxo-2,3-dihydro-1H-pyrazolo[4,3-c]pyridin-6-yl)amino)-1,1-dimethyl-3,4-dihydroisoquinoline-2(1H)-carboxylate To a stirring solution of 1-(2-(tert-butyl)pyridin-4-yl)-6-chloro-2-isopropyl-1,2-dihydro-3H-pyrazolo[4,3-c]pyridin-3-one (200 mg, 0.579 mmol, 1 eq) in dioxane (20 mL), tert-butyl 6-amino-1,1-dimethyl-3,4-dihydroisoquinoline-2(1H)-carboxylate (160 mg, 0.695 mmol, 1.2 eq) and Cs$_2$CO$_3$ (377 mg, 1.158 mmol, 2 eq) were added. The mixture was degassed for 10-15 min followed addition of Pd$_2$(dba)$_3$ (64 mg, 0.069 mmol, 0.12 eq) and xantphos (50 mg, 0.086 mmol, 1.5 eq). The reaction was heated at 110° C. for 1 h under microwave irradiation. After completion, the reaction mixture was filtered through celite using EtOAc. The combined organic layer was dried, concentrated and purified by flash chromatography (EtOAc-Hexane 0-70%) to give tert-butyl 6-((1-(2-(tert-butyl)pyridin-4-yl)-2-isopropyl-3-oxo-2,3-dihydro-1H-pyrazolo[4,3-c]pyridin-6-yl)amino)-1,1-dimethyl-3,4-dihydroisoquinoline-2(1H)-carboxylate (60 mg, 23.58%) as yellow solid.)

LCMS: 557.3 [M+1]$^+$

Step-2: Synthesis of 1-(2-(tert-butyl)pyridin-4-yl)-6-((1,1-dimethyl-1,2,3,4-tetrahydroisoquinolin-6-yl)amino)-2-isopropyl-1,2-dihydro-3H-pyrazolo[4,3-c]pyridin-3-one trihydrochloride tert-butyl 6-((1-(2-(tert-butyl)pyridin-4-yl)-2-isopropyl-3-oxo-2,3-dihydro-1H-pyrazolo[4,3-c]pyridin-6-yl)amino)-1,1-dimethyl-3,4-dihydroisoquinoline-2(1H)-carboxylate (60 mg, 0.107 mmol, 1.0 eq) was dissolved in dioxane (1 mL), followed by dropwise addition of 4.0M-HCl (1 mL) and allowed to stir at rt for 1 h. After completion of reaction, the reaction mixture was filtered and dried under reduced pressure to afford the desired compound, 1-(2-(tert-butyl)pyridin-4-yl)-6-((1,1-dimethyl-1,2,3,4-tetrahydroisoquinolin-6-yl)amino)-2-isopropyl-1,2-dihydro-3H-pyrazolo[4,3-c]pyridin-3-one trihydrochloride (12 mg, 19.68%) as light yellow solid.

LCMS: 485.6 [M+1]$^+$; UPLC @ 254 nm=97.88% and @ 220 nm=97.77%.

$^1$H NMR (400 MHz, DMSO-d$_6$): δ 10.01 (br. s., 1H) 9.70 (br. s., 2H) 8.78 (d, J=5.87 Hz, 1H) 8.64 (s, 1H) 7.66-7.80 (m, 2H) 7.51 (d, J=8.80 Hz, 1H) 7.42 (s, 1H) 7.31 (d, J=8.80 Hz, 1H) 6.91 (s, 1H) 3.89-3.96 (m, 1H) 3.35 (br. s., 2H) 3.02 (t, J=5.38 Hz, 2H) 1.65 (s, 6H) 1.49 (s, 9H) 1.36 (s, 6H).

Example S111. Synthesis of 1-(2-(tert-butyl)pyridin-4-yl)-6-((4,4-dimethyl-1,2,3,4-tetrahydroisoquinolin-7-yl)amino)-2-isopropyl-1,2-dihydro-3H-pyrazolo[4,3-c]pyridin-3-one trihydrochloride (Compound No. 2.797)

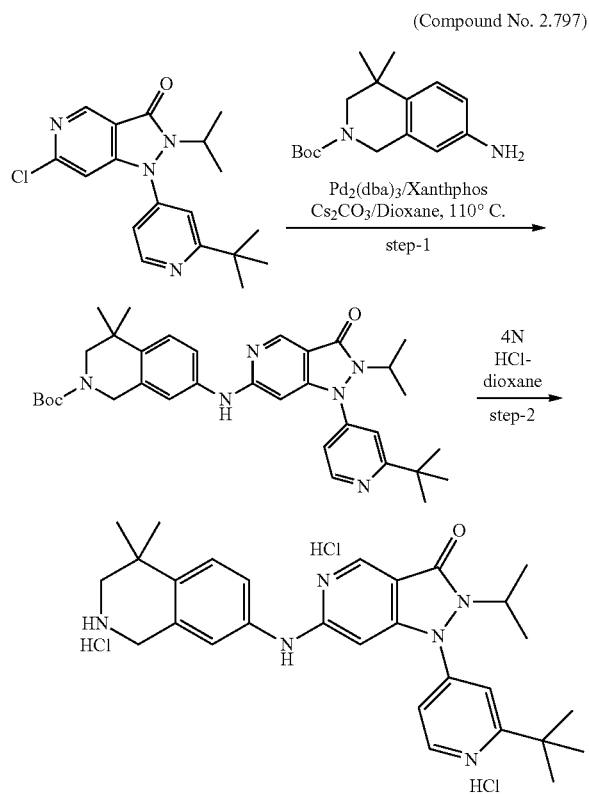

Step-1: Synthesis of tert-butyl 7-((1-(2-(tert-butyl)pyridin-4-yl)-2-isopropyl-3-oxo-2,3-dihydro-1H-pyrazolo[4,3-c]pyridin-6-yl)amino)-4,4-dimethyl-3,4-dihydroisoquinoline-2(1H)-carboxylate To a stirring solution of 1-(2-(tert-butyl)pyridin-4-yl)-6-chloro-2-isopropyl-2,3-dihydro-1H-pyrazolo[4,3-c]pyridin-3-one (200 mg, 0.579 mmol, 1 eq) in dioxane (20 mL), tert-butyl 7-amino-4,4-dimethyl-3,4-dihydroisoquinoline-2(1H)-carboxylate (160 mg, 0.695 mmol, 1.2 eq) and Cs$_2$CO$_3$ (377 mg, 1.158 mmol, 2 eq) were added. The mixture was degassed for 10-15 min followed addition of Pd$_2$(dba)$_3$ (64 mg, 0.069 mmol, 0.12 eq) and xantphos (50 mg, 0.086 mmol, 1.5 eq). The reaction was heated at 110° C. for 1 h under microwave irradiation. After completion, the reaction mixture was filtered through celite using EtOAc. The combined organic layer was dried, concentrated and purified by flash chromatography (EtOAc-Hexane 0-70%) to give tert-butyl 7-((1-(2-(tert-butyl)pyridin-4-yl)-2-isopropyl-3-oxo-2,3-dihydro-1H-pyrazolo[4,3-c]pyridin-6-yl)amino)-4,4-dimethyl-3,4-dihydroisoquinoline-2(1H)-carboxylate (60 mg, 23.58%) as yellow solid.)

LCMS: 557.3 [M+1]$^+$

Step-2: Synthesis of 1-(2-(tert-butyl)pyridin-4-yl)-6-((4,4-dimethyl-1,2,3,4-tetrahydroisoquinolin-7-yl)amino)-2-isopropyl-1,2-dihydro-3H-pyrazolo[4,3-c]pyridin-3-one trihydrochloride tert-butyl 7-((1-(2-(tert-butyl)pyridin-4-yl)-2-isopropyl-3-oxo-2,3-dihydro-1H-pyrazolo[4,3-c]pyridin-6-yl)amino)-4,4-dimethyl-3,4-dihydroisoquinoline-2(1H)-carboxylate (60 mg, 0.107 mmol, 1.0 eq) was dissolved in dioxane (1 mL), followed by dropwise addition of 4.0M-HCl (1 mL) and allowed to stir at rt for 1 h. After completion of reaction, the reaction mixture was filtered and dried under reduced pressure to afford the desired compound, 1-(2-(tert-butyl)pyridin-4-yl)-6-((4,4-dimethyl-1,2,3,4-tetrahydroisoquinolin-7-yl)amino)-2-isopropyl-1,2-dihydro-3H-pyrazolo[4,3-c]pyridin-3-one trihydrochloride (21 mg, 34.45%) as light yellow solid.

LCMS: 485.6 [M+1]$^+$; UPLC @ 254 nm=98.86% and @ 220 nm=98.90%.

$^1$H NMR (400 MHz, DMSO-d$_6$): δ 9.97 (br. s., 1H) 9.57 (br. s., 2H) 8.79 (d, J=5.87 Hz, 1H) 8.62 (s, 1H) 7.64-7.76 (m, 2H) 7.52 (d, J=8.31 Hz, 1H) 7.30-7.47 (m, 2H) 6.88 (br. s., 1H) 4.20-4.30 (S, 4H) 3.90-3.99 (m, 1H) 3.17 (br. s., 2H) 1.48 (s, 9H) 1.24-1.39 (m, 12H).

Compounds 1.19-1.68 and 1.70-1.125 can be prepared according to the experimental details exemplified in Examples S1-S21 and Scheme 1, using the appropriate starting materials and reagents.

Other compounds can be prepared according to the experimental details exemplified in Examples S1-S111 and Scheme 1 to Scheme 13, using the appropriate starting materials and reagents.

BIOLOGICAL EXAMPLES

Example B1. WEE1 IC$_{50}$ Determination

IC$_{50}$ values of compounds against WEE1 kinase enzyme were determined by LanthaScreen™ Terbium Labeled TR-FRET assay. Kinase assays were performed in 1× kinase buffer (#PV6135, Invitrogen, Life Technologies Grand Island, N.Y.) where total reaction volume was 10 μL in low-volume 384-well plates (#4511, Corning). Serially diluted compounds (3-fold) were incubated with WEE1 Enzyme (1 nM) (#PR7373A, Invitrogen, Life Technologies Grand Island, N.Y.) for 10 min, following which a mixture of ATP (10 μM) (#A1852, Sigma, St-Louis, Mo.) and fluorescent-PolyGT substrate (200 nM) (#PV3610, Invitrogen, Life Technologies Grand Island, N.Y.) was added and incubated in dark at room temperature for 1 h. After 1 h, 10 L stop solution containing Terbium labeled antibody (4 nM) (#PV3529, Invitrogen, Life Technologies Grand Island, N.Y.) and EDTA (#E5134, Sigma, St-Louis, Mo.) (20 mM) in TR-FRET dilution buffer (#PV3574, Invitrogen, Life Technologies Grand Island, N.Y.) was added. Readings were taken in a Synergy Neo Plate reader (BioTek, Winooski) at single excitation of 340 nm and Dual emission at 495 nm and 520 nm respectively.

The % activity of test samples was calculated as (Sample−Min)*100/(Max−Min). [Max: DMSO control, complete reaction with enzyme & DMSO and Min: No enzyme & DMSO]. Percent inhibition (100-% activity) was fitted to the "four-parameter logistic model" in XLfit for determination of $IC_{50}$ values. The results are shown in Table 2.

TABLE 2

| Synthesis Example No | Compound No. | Enzyme Activity Wee1 $IC_{50}$ (uM) |
|---|---|---|
| S-1 | 1.1 | 0.0024 |
| S-2 | 1.2 | 0.004 |
| S-3 | 1.3 | <0.002 |
| S-4 | 1.4 | 0.0016 |
| S-5 | 1.5 | 0.0031 |
| S-6 | 1.6 | 0.0031 |
| S-7 | 1.7 | 0.003 |
| S-8 | 1.8 | 0.001 |
| S-9 | 1.9 | 0.001 |
| S-10 | 1.10 | 0.002 |
| S-11 | 1.11 | 0.002 |
| S-12 | 1.12 | 0.004 |
| S-13 | 1.13 | 0.0015 |
| S-14 | 1.14 | 0.001 |
| S-15 | 1.15 | 0.0015 |
| S-16 | 1.16 | 0.0045 |
| S-17 | 1.17 | 0.0095 |
| S-18 | 1.18 | 0.025 |
| S-19 | 1.23 | 0.040 |
| S-20 | 1.69 | 0.011 |
| S-21 | 1.70 | 0.015 |
| S-22 | 1.125 | >5.00 |
| S-23 | 1.24 | 0.023 |
| S-24 | 1.31 | 0.005 |
| S-25 | 1.27 | 0.010 |
| S-26 | 1.25 | 0.099 |
| S-27 | 1.127 | 0.058 |
| S-28 | 1.126 | <0.001 |
| S-29 | 1.47 | 0.005 |
| S-30 | 1.128 | 0.006 |
| S-31 | 1.129 | 0.006 |
| S-32 | 1.130 | 0.018 |
| S-33 | 1.131 | 0.0006 |
| S-34 | 1.132 | 0.004 |
| S-35 | 1.41 | 0.044 |
| S-36 | 1.133 | 0.006 |
| S-37 | 1.134 | 0.009 |
| S-38 | 1.135 | 0.020 |
| S-39 | 1.136 | 0.007 |
| S-40 | 1.137 | 0.004 |
| S-41 | 1.138 | 0.006 |
| S-42 | 1.139 | 0.004 |
| S-43 | 1.140 | 0.005 |
| S-44 | 1.141 | 0.024 |
| S-45 | 1.142 | 0.004 |
| S-46 | 1.143 | 0.003 |
| S-47 | 1.144 | 0.0006 |
| S-48 | 1.145 | 0.003 |
| S-49 | 1.146 | 0.009 |
| S-50 | 1.147 | 0.007 |
| S-51 | 1.148 | 0.002 |
| S-52 | 1.149 | 0.003 |
| S-53 | 1.150 | 0.013 |
| S-54 | 1.151 | 2.540 |
| S-55 | 1.152 | <0.001 |
| S-56 | 1.153 | 0.016 |
| S-57 | 1.154 | 0.008 |
| S-58 | 1.155 | 0.002 |
| S-59 | 1.156 | 0.001 |
| S-60 | 1.157 | 0.005 |
| S-61 | 1.158 | 0.004 |
| S-62 | 1.159 | 0.030 |
| S-63 | 1.160 | 0.030 |
| S-64 | 2.287 | 0.120 |
| S-65 | 2.288 | 0.217 |
| S-66 | 1.161 | 0.004 |
| S-67 | 1.162 | 0.011 |
| S-68 | 1.163 | 0.015 |
| S-69 | 1.164 | 0.008 |
| S-70 | 1.165 | 0.014 |
| S-71 | 1.166 | 0.029 |
| S-72 | 1.167 | 0.041 |
| S-73 | 1.168 | 4.150 |
| S-74 | 1.169 | 0.016 |
| S-75a | 1.170 | 0.012 |
| S-75b | 1.171 | 0.006 |
| S-76 | 1.172 | 0.012 |
| S-77 | 1.173 | 0.343 |
| S-78 | 1.174 | 0.108 |
| S-79 | 1.175 | 0.156 |
| S-80 | 1.176 | 0.008 |
| S-81 | 1.177 | 0.012 |
| S-82 | 1.178 | 0.014 |
| S-83 | 2.182 | 0.062 |
| S-84 | 2.183 | 0.004 |
| S-85 | 2.184 | 0.002 |
| S-86 | 2.185 | 0.034 |
| S-87 | 2.186 | 0.024 |
| S-88 | 2.187 | 0.012 |
| S-89 | 2.188 | 0.053 |
| S-90 | 2.189 | 0.043 |
| S-91 | 2.289 | 0.049 |
| S-92 | 2.290 | 0.090 |
| S-93 | 2.291 | 0.046 |
| S-94 | 2.292 | 0.043 |
| S-95 | 2.293 | >3.65 |
| S-96 | 2.642 | 0.006 |
| S-97 | 2.643 | 0.026 |
| S-98 | 2.644 | 0.005 |
| S-99 | 2.645 | 0.005 |
| S-100 | 2.646 | 0.015 |
| S-101 | 2.647 | 0.010 |
| S-102 | 2.454 | 0.048 |
| S-103 | 2.600 | 0.025 |
| S-104 | 2.732 | 0.179 |
| S-105 | 2.555 | 0.153 |
| S-106 | 2.605 | 0.123 |
| S-107 | 3.035 | 0.002 |
| S-108 | 3.036 | 0.005 |
| S-109 | 2.744 | ND |
| S-110 | 2.792 | ND |
| S-111 | 2.797 | ND |

ND: Not Determined

Example B2. Determination of Potency of Compounds in Cytotoxicity Assay in A427, A549, As-Pc-1, Panc 10.05 and A172 Cell Lines A549 (CCL-185; ATCC) and A427 (HTB-53; ATCC), both lung epithelial cell lines were seeded in their respective medium (DMEM/MEM, 10569044/41090101; Gibco) at a cell count of 1500 cells per 100 μL per well in a 96 well edge plate (167425; ThermoFisher). Cells were allowed to grow at 37° C. for 24 hr in 5% $CO_2$ environment (culture conditions) in a Nuaire incubator (humidified). Serially diluted test compounds (100 μL) within the desired testing concentration ranges were added to the culture plate were further incubated in culture conditions for 72 hr and 96 hr for A427 and A549 respectively. The experiment was terminated at the designated incubation time by replacing the medium with 100 μL of 1 mM of resazurin (R7017; Sigma) prepared in respective culture medium, and the plates were further incubated in culture conditions for 4-6 hr. Fluorescence was recorded using a multimodal plate reader (Biotek Synergy Neo) at an excitation wavelength of 535 nm and emission wavelength of 590 nm to obtain relative fluorescence units. Data analysis was done by subtracting the background fluorescence (only medium blank) value from each reading and then normalizing with the vehicle control (DMSO treated cells) to obtain percent survival/proliferation. Percent survival was then subtracted by 100 to get the percent inhibition of proliferation which was used to calculate $IC_{50}$ values. Potency of compounds in other cell lines (As-Pc-1, Panc 10.05, A172) was determined in an analogous manner. The results are shown in Table 3.

TABLE 3

| Synthesis Example No | Compound No. | Cell Viability $IC_{50}$ A427 (μM) | Cell Viability $IC_{50}$ A549 (μM) | Cell Viability $IC_{50}$ As-Pc-1 (μM) | Cell Viability $IC_{50}$ Panc 10.05 (μM) | Cell Viability $IC_{50}$ A172 (μM) |
|---|---|---|---|---|---|---|
| S-1 | 1.1 | 0.095 | 0.46 | ND | ND | ND |
| S-2 | 1.2 | 0.33 | 0.842 | ND | ND | ND |
| S-3 | 1.3 | 0.62 | 1.22 | ND | ND | ND |
| S-4 | 1.4 | 0.065 | 0.272 | ND | ND | ND |
| S-5 | 1.5 | 0.12 | 0.585 | ND | ND | ND |
| S-6 | 1.6 | 0.355 | 0.972 | ND | ND | ND |
| S-7 | 1.7 | 0.8 | 0.66 | ND | ND | ND |
| S-8 | 1.8 | ND | 0.545 | ND | ND | ND |
| S-9 | 1.9 | ND | 0.52 | ND | ND | ND |
| S-10 | 1.10 | 0.34 | 0.51 | ND | ND | ND |
| S-11 | 1.11 | 0.43 | 1.18 | ND | ND | ND |
| S-12 | 1.12 | 1.715 | 1.055 | ND | ND | ND |
| S-13 | 1.13 | 1 | 0.895 | ND | ND | ND |
| S-14 | 1.14 | ND | 1.62 | ND | ND | ND |
| S-15 | 1.15 | 0.56 | 1.195 | ND | ND | ND |
| S-16 | 1.16 | 1.42 | 1.55 | ND | ND | ND |
| S-17 | 1.17 | 2.323 | 9.065 | ND | ND | ND |
| S-18 | 1.18 | 7.06 | ND | ND | ND | ND |
| S-19 | 1.23 | 3.21 | ND | ND | ND | ND |
| S-20 | 1.69 | 0.485 | ND | ND | ND | ND |
| S-21 | 1.70 | 0.640 | ND | ND | ND | ND |
| S-22 | 1.125 | >30 | ND | ND | ND | ND |
| S-23 | 1.24 | 6.03 | ND | ND | ND | ND |
| S-24 | 1.31 | 1.32 | ND | ND | ND | ND |
| S-25 | 1.27 | 4.14 | ND | ND | ND | ND |
| S-26 | 1.25 | >30 | ND | ND | ND | ND |
| S-27 | 1.127 | >23 | ND | ND | ND | ND |
| S-28 | 1.126 | 0.275 | ND | ND | ND | ND |
| S-29 | 1.47 | 3.02 | ND | ND | ND | ND |
| S-30 | 1.128 | 1.55 | ND | ND | ND | ND |
| S-31 | 1.129 | 0.865 | ND | ND | ND | ND |
| S-32 | 1.130 | 9.07 | ND | ND | ND | ND |
| S-33 | 1.131 | 0.285 | ND | ND | ND | ND |
| S-34 | 1.132 | 1.68 | ND | ND | ND | ND |
| S-35 | 1.41 | 5.12 | ND | ND | ND | ND |
| S-36 | 1.133 | 0.583 | ND | ND | ND | ND |
| S-37 | 1.134 | 0.820 | ND | ND | ND | ND |
| S-38 | 1.135 | 0.440 | ND | ND | ND | ND |
| S-39 | 1.136 | 1.086 | ND | ND | ND | ND |
| S-40 | 1.137 | 0.415 | ND | ND | ND | ND |
| S-41 | 1.138 | 0.993 | 2.42 | 0.20 | 2.82 | 4.09 |
| S-42 | 1.139 | 0.355 | ND | ND | ND | ND |
| S-43 | 1.140 | 0.555 | ND | ND | 1.52 | ND |
| S-44 | 1.141 | 2.97 | ND | ND | ND | ND |
| S-45 | 1.142 | 0.390 | ND | ND | ND | ND |
| S-46 | 1.143 | 0.470 | 2.85 | 0.27 | 1.85 | 3.625 |
| S-47 | 1.144 | 0.260 | ND | ND | ND | ND |
| S-48 | 1.145 | 0.255 | ND | ND | ND | ND |
| S-49 | 1.146 | 0.965 | 6.685 | 0.92 | 5.695 | 6.815 |
| S-50 | 1.147 | 0.370 | ND | ND | ND | ND |
| S-51 | 1.148 | 1.085 | ND | ND | ND | ND |
| S-52 | 1.149 | 1.130 | ND | ND | ND | ND |
| S-53 | 1.150 | 3.0 | ND | ND | ND | ND |
| S-54 | 1.151 | 3.38 | ND | ND | ND | ND |
| S-55 | 1.152 | 1.02 | ND | ND | ND | ND |
| S-56 | 1.153 | 2.54 | ND | ND | ND | ND |
| S-57 | 1.154 | 2.37 | ND | ND | ND | ND |
| S-58 | 1.155 | 1.98 | ND | ND | ND | ND |

TABLE 3-continued

| Synthesis Example No | Compound No. | Cell Viability IC$_{50}$ A427 (μM) | Cell Viability IC$_{50}$ A549 (μM) | Cell Viability IC$_{50}$ As-Pc-1 (μM) | Cell Viability IC$_{50}$ Panc 10.05 (μM) | Cell Viability IC$_{50}$ A172 (μM) |
|---|---|---|---|---|---|---|
| S-59 | 1.156 | 1.77 | ND | ND | ND | ND |
| S-60 | 1.157 | 0.460 | ND | ND | ND | ND |
| S-61 | 1.158 | 0.200 | ND | ND | ND | ND |
| S-62 | 1.159 | 3.32 | ND | ND | ND | ND |
| S-63 | 1.160 | 3.98 | ND | ND | ND | ND |
| S-64 | 2.287 | 1.96 | ND | ND | ND | ND |
| S-65 | 2.288 | 2.58 | ND | ND | ND | ND |
| S-66 | 1.161 | 0.240 | ND | ND | ND | ND |
| S-67 | 1.162 | 0.385 | ND | ND | ND | ND |
| S-68 | 1.163 | 0.720 | ND | ND | ND | ND |
| S-69 | 1.164 | 0.485 | ND | ND | ND | ND |
| S-70 | 1.165 | 1.57 | ND | ND | ND | ND |
| S-71 | 1.166 | 4.13 | ND | ND | ND | ND |
| S-72 | 1.167 | 2.06 | ND | ND | ND | ND |
| S-73 | 1.168 | 4.0 | ND | ND | ND | ND |
| S-74 | 1.169 | 2.74 | ND | ND | ND | ND |
| S-75a | 1.170 | 0.775 | ND | ND | ND | ND |
| S-75b | 1.171 | 0.735 | ND | ND | ND | ND |
| S-76 | 1.172 | 1.35 | ND | ND | ND | ND |
| S-77 | 1.173 | 2.33 | ND | ND | ND | ND |
| S-78 | 1.174 | 4.0 | ND | ND | ND | ND |
| S-79 | 1.175 | 1.16 | ND | ND | ND | ND |
| S-80 | 1.176 | 0.595 | ND | ND | ND | ND |
| S-81 | 1.177 | 1.97 | ND | ND | ND | ND |
| S-82 | 1.178 | 6.20 | ND | ND | ND | ND |
| S-83 | 2.182 | 0.720 | 7.75 | 1.74 | 8.6 | 10.64 |
| S-84 | 2.183 | 0.135 | 1.805 | 0.095 | 0.805 | 1.635 |
| S-85 | 2.184 | 0.090 | 0.655 | 0.085 | 0.545 | 0.985 |
| S-86 | 2.185 | 1.54 | ND | ND | ND | ND |
| S-87 | 2.186 | 0.905 | ND | ND | ND | ND |
| S-88 | 2.187 | 0.435 | ND | ND | ND | ND |
| S-89 | 2.188 | 0.815 | 0.91 | 0.965 | 3.105 | 1.525 |
| S-90 | 2.189 | 1.99 | ND | ND | ND | ND |
| S-91 | 2.289 | 8.76 | ND | ND | ND | ND |
| S-92 | 2.290 | 3.37 | ND | ND | ND | ND |
| S-93 | 2.291 | 7.99 | ND | ND | ND | ND |
| S-94 | 2.292 | 13.30 | ND | ND | ND | ND |
| S-95 | 2.293 | >30 | ND | ND | ND | ND |
| S-96 | 2.642 | 2.46 | ND | ND | ND | ND |
| S-97 | 2.643 | 2.18 | ND | ND | ND | ND |
| S-98 | 2.644 | 2.33 | ND | ND | ND | ND |
| S-99 | 2.645 | 4.01 | ND | ND | ND | ND |
| S-100 | 2.646 | 4.37 | ND | ND | ND | ND |
| S-101 | 2.647 | 2.65 | ND | ND | ND | ND |
| S-102 | 2.454 | ND | ND | ND | ND | ND |
| S-103 | 2.600 | ND | ND | ND | ND | ND |
| S-104 | 2.732 | ND | ND | ND | ND | ND |
| S-105 | 2.555 | ND | ND | ND | ND | ND |
| S-106 | 2.605 | 5.96 | ND | ND | ND | ND |
| S-107 | 3.035 | 0.420 | ND | ND | ND | ND |
| S-108 | 3.036 | 0.250 | ND | ND | ND | ND |
| S-109 | 2.744 | 10.37 | ND | ND | ND | ND |
| S-110 | 2.792 | ND | ND | ND | ND | ND |
| S-111 | 2.797 | ND | ND | ND | ND | ND |

ND: Not Determined

Example B3. Determination of Potency of Compounds in Cell Proliferation Assay in Selected Cancer Cell Lines and Cellular PD Effects The effects of test compounds were studied in five cell lines with various histotypes. The cancer cells (Table 4) were harvested during the logarithmic growth period and counted. Adjust cell concentrations to the appropriated number with respective medium, and add 90 μL cell suspensions to 96-well plates. After cells were seeded, the plates were shaken gently to distribute cells evenly and incubated at 37° C., 5% CO$_2$ on day 1.

TABLE 4

Cell Culture Conditions

| No. | Cell Line | Histopathology | Medium |
|---|---|---|---|
| 1 | A427 | Lung adenocarcinoma | MEM + 10% FBS + NEAA + Sodium Pyruvate |
| 2 | LoVo | Colorectal adenocarcinoma | Ham's F12K + 10% FBS |
| 3 | NCI-H460 | Large-cell lung carcinoma | RPMI1640 + 10% FBS |
| 4 | HCT-116 | Colorectal carcinoma | McCoy's 5a + 10% FBS |
| 5 | A2780 | Ovarian cancer | RPMI1640 + 10% FBS |

Cells were treated with test compounds at 9 concentrations within a desired concentration range (e.g. 1.5 nM-10

μM) on day 2 by series diluting the test compound stock solution (10 mM in DMSO) with culture medium. Cell viability was assessed by Cell Titer-Glo® as recommended by Promega (Cat. No.: G7572, Promega) typically 72 h post-treatment.

Cell viability data were plotted using GraphPad Prism (version 5, GraphPad Software, Inc., San Diego, Calif.). In addition, a nonlinear regression model with a sigmoidal dose response and variable slope within GraphPad Prism was used to calculate the $IC_{50}$ value of individual test compounds.

TABLE 5

| | $IC_{50}$ (μM) | | | | |
|---|---|---|---|---|---|
| Compound No. | LOVO | HCT116 | NCI-H460 | A427 | A2780 |
| 1.1 | 0.258 | 1.040 | >10 | 0.064 | ND |
| 1.2 | ND | ND | ND | 0.269 | ND |
| 1.3 | ND | ND | ND | 0.483 | ND |
| 1.4 | ND | ND | ND | 0.044 | ND |
| 1.5 | ND | ND | ND | 0.070 | 0.140 |
| 1.6 | ND | ND | ND | 0.277 | ND |
| 1.7 | ND | ND | ND | ND | 1.096 |

ND: Not Determined

Additional test compounds will be studied in the same and/or other cancer cell lines with various sensitivities to reported Wee1 compounds using similar proliferation method with possible variables, such as cell seeding densities and/or incubation durations.

Example B4. Determination of Potency of Compounds by Assay of Cellular PD Effects pCDC2 and γ-H2AX are two clinical relevant biomarkers associated with Wee1 inhibition. CDC2Y15 phosphorylation in cells was reported to be abolished by Wee1 inhibitors (Gavory G et. al., Almac Discovery, AACR poster, 2016). γ-H2AX, a DNA double-strand break marker, was upregulated by Wee1 treatment in Wee1 sensitive cell lines (Guertin A D et al., Molecular Cancer Therapeutics, 2013). The effects of selected test compounds on pCDC2 and γ-H2AX will be assessed in selected cancer cell lines post 24 or 48 hr treatment using Western blotting methods with selective antibodies (Guertin A D et al., Molecular Cancer Therapeutics, 2013).

Changes in the levels of phospho-CDC2 following treatment of cells with test compounds are assessed by enzyme-linked immunosorbent assay (ELISA) or Western blotting. A427 cells (or other suitable cell line) are plated in 6-well plates and cultured for 24 hr to approximately 80-90% confluency. Medium is then replaced, and the cells are treated with test compound at several different concentrations as well as vehicle control. After incubation of treated cells in cell culture conditions for a specified time (e.g., 24 hr), cells are rinsed with ice-cold PBS and lysed in 1× cell lysis buffer containing protease inhibitors and phosphatase inhibitors. The cells are scraped from the plate with a cell scraper after a brief incubation on ice and transferred to a centrifuge tube, and then subjected to three freeze-thaw cycles in liquid nitrogen and a 37° C. water bath for further lysis. The lysates are centrifuged to pellet cell debris (using, for example, a 10 min centrifugation of 2000×g at 4° C.) and the supernatants transferred to fresh tubes on ice. The protein concentrations of the samples are estimated by the Bradford method or equivalent. The ELISA is carried out with the PathScan® Phospho-CDC2 (Tyr15) Sandwich ELISA Kit (Cat. #7176, Cell Signaling Technology, Danvers, Mass.) or similar product according to the manufacturer's instructions. Changes in the levels of phospho-CDC2 may alternatively or additionally be analyzed by Western blotting of the samples using a primary antibody to phospho-CDC2 such as phospho-CDC2 (Tyr15) (10A11) rabbit mAb (Cat. #4539, Cell Signaling Technology) or rabbit polyclonal anti-CDK1 (phospho Y15) antibody (Cat. #ab47594, Abcam, Cambridge, United Kingdom).

Example B5. Determination of Activity of Compounds in Cancer Cells in Combination with Various DNA-Damaging Agents The activity of test compounds in combination with cisplatin in A427 cells was determined. Cells were seeded in a 96 well plate at 2000 cells/well. The next day, cells were treated with 2.5 μM cisplatin or vehicle (1×PBS) and incubated in culture conditions (37° C., 5% $CO_2$) for 24 hr. Following the incubation, culture medium was replaced with medium containing test compound and cisplatin/vehicle, and cells were further incubated in culture conditions for another 72 hr. By this procedure, cisplatin was either continued or discontinued after an initial 24-hr incubation. Addition of test compound was in concentrations needed to obtain an 8-point dose response curve, with concentrations prepared by 3-fold dilution. The assay was terminated upon addition of resazurin, incubation for 4 hr in culture conditions and measurement of fluorescence at excitation and emission wavelengths of 535 and 590 nm, respectively. Assay results are shown in Table 6.

It was reported that MK-1775 (aka AZD-1775), a potent and selective small molecule inhibitor of Wee1, in combination with gemcitabine, carboplatin, or cisplatin abolished the phosphorylation of CDC2 at Tyr15 residue and abrogate the DNA demage checkpoint, leading to apoptosis (Hirai H et al. Mol Cancer Ther 2009; 8:2992-3000, Small-molecule inhibition of Wee1 kinase by MK-1775 selectively sensitizes p53-deficient tumor cells to DNA-damaging agents).

Various cancer cell lines with p53 mutation will be studied by co-incubation of test compound and one of the various DNA-damaging agents, such as pemetrexed, doxorubicin, camptothecin, mitomycin C, gemcitabine, and 5-FU, etc. The anti-proliferation effects of the DNA-damaging agents will be evaluated in the presence or absence of individual test compound using CTG assays described in Example B3. The concentrations of test compounds in the combination studies will be selected based on the anti-cell proliferation effects of test compounds in cancer cell lines as monotherapy using CTG assays. Incubation time will be optimized prior to the combination treatment for individual test compound. In vitro mechanism based studies using histology staining and/or flow cytometry methods as described by Hirai H. et al. (Hirai H 2010, MK-1775 enhances antitumor efficacy 5-FU) may be used.

In addition, the sensitization of test compounds in drug-induced resistance cell lines (e.g., A2780cis) will be studied in vitro as combination therapy (e.g., cisplatin+Wee1 inhibitor) with the anti-proliferation assays, histology staining and/or flow cytometry methods mentioned therebefore.

TABLE 6

Cell viability $IC_{50}$ (μM) in A427 cells with 2.5 μM cisplatin

| Compound No. | 24 hr cisplatin then compound | 24 hr cisplatin then compound + cisplatin |
|---|---|---|
| 1.4 | 0.04 | <0.014 |
| 1.5 | 0.05 | <0.014 |
| 1.12 | 0.12 | 0.07 |
| 1.16 | 0.1 | <0.014 |

Example B6. Determination of Synergistic Activity of Compounds Combined with Chemotherapeutics in Cancer Cells Determination of synergistic activity of compounds in combination with a chemotherapeutic drug on cell viability is determined by a combination matrix method. Chemotherapeutics that may be used in the combination include but are not limited to a platinum-based chemotherapeutic agent, a DNA alkylating agent, a topoisomerase inhibitor, an anthracycline, a histone deacetylase inhibitor, a bromodomain inhibitor, a kinase inhibitor, a mTOR inhibitor, a PARP inhibitor, an ATM inhibitor, an ATR inhibitor, a Wee1 inhibitor, a proteasome inhibitor, and a nucleotide analog or precursor analog. Cancer cell lines that may be used in the assay include but are not limited to lung cancer, leukemia, lymphoma, multiple myeloma, ovarian cancer, breast cancer, pancreatic cancer, stomach cancer, colon cancer, liver cancer, head and neck cancer, kidney cancer, skin cancer and brain cancer cell lines. Cells are seeded in a 96-well plate and incubated at 37° C. in cell culture conditions for 24 hr. Drugs are added and then the cells are incubated further at 37° C. in cell culture conditions for 72 hr. Cells are treated with single agents to obtain a dose response curve for each agent. Cells are also treated with combinations of the drugs, based on a matrix generated by combining the two drugs at all different combinations of the doses used in the dose response curves. The assay is terminated by addition of Resazurin, incubation for 4 hr at 37° C., 5% $CO_2$. Measurement of fluorescence at an excitation and emission wavelength of 535 and 590 nm respectively. Synergy is evaluated with the combination index (CI) value using the Chou-Talalay method in which additive effect (CI=1), synergism (CI<1), and antagonism (CI>1) in drug combinations is determined (Chou T C. Cancer Res 2010; 70:440-6.). A fixed drug ratio dilution method in which drugs are combined in a fixed ratio which is diluted to 5 or more dilutions, may also be used in place of the combination matrix method.

Example B7. Determination of Synergistic Activity of Compound 1.138 Combined with Gemcitabine in Pancreatic Cancer Cells An assay testing the combination of compound 1.138 with the chemotherapeutic drug gemcitabine was conducted according to the method of Example B6. The pancreatic cancer cell line Panc 10.05 was seeded in a 96-well plate at 2000 cells/well. In a separate experiment, the pancreatic cancer cell line AsPC-1 was seeded in a 96-well plate at 2000 cells/well. Drug concentrations ranged from about 14 nM to 30 mM for compound 1.138 and 0.4 nM to 300 nM for gemcitabine in the dose response curves for the single agents. Each dose used in the dose response curve for compound 1.138 was combined with each dose used in the dose response curve for gemcitabine to generate the matrix combinations, which included all possible combinations of the doses. Combination of compound 1.138 and gemcitabine in Panc 10.05 cells resulted in combination index values less than 1 at a fractional effect level of about 0.5, indicating synergistic effects of the drugs in reducing cell viability. Combination of compound 1.138 and gemcitabine in AsPC-1 cells also resulted in combination index values less than 1 at a fractional effect level of about 0.5, indicating synergistic effects of the drugs in reducing cell viability.

Although the foregoing invention has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the invention.

What is claimed is:

1. A compound of the Formula (Ia-9):

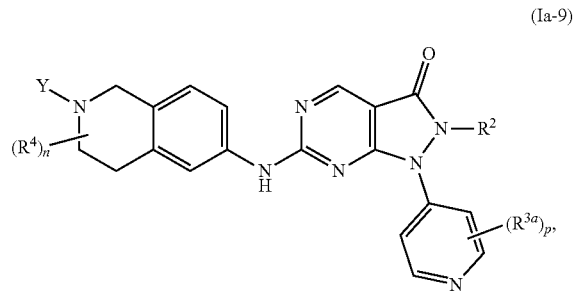

(Ia-9)

or a pharmaceutically acceptable salt thereof, wherein:
  $R^2$ is $C_1$-$C_6$ alkyl or $C_3$-$C_6$ cycloalkyl;
  Y is hydrogen or $R^4$;
  n and p are independently 0, 1, 2, 3, or 4;
  each $R^{3a}$ is independently $C_1$-$C_6$ alkyl optionally substituted by oxo, —OH or halogen;
  each $R^4$ is independently $C_1$-$C_6$ alkyl,
    or two $R^4$, when bound to the same carbon or two different carbon atoms, are taken together with the carbon or carbons to which they are attached to form a $C_3$-$C_6$ cycloalkyl.

2. The compound of claim 1, or a pharmaceutically acceptable salt thereof, wherein n is 0.

3. The compound of claim 1, or a pharmaceutically acceptable salt thereof, wherein n is 1.

4. The compound of claim 1, or a pharmaceutically acceptable salt thereof, wherein n is 2.

5. The compound of claim 1, or a pharmaceutically acceptable salt thereof, wherein Y is hydrogen.

6. The compound of claim 1, or a pharmaceutically acceptable salt thereof, wherein each $R^4$ is methyl.

7. The compound of claim 1, or a pharmaceutically acceptable salt thereof, wherein $R^2$ is $C_1$-$C_6$ alkyl.

8. The compound of claim 1, or a pharmaceutically acceptable salt thereof, wherein $R^2$ is isopropyl.

9. The compound of claim 1, or a pharmaceutically acceptable salt thereof, wherein $R^2$ is $C_3$-$C_6$ cycloalkyl.

10. The compound of claim 1, or a pharmaceutically acceptable salt thereof, wherein $R^2$ is cyclopropyl.

11. The compound of claim 1, or a pharmaceutically acceptable salt thereof, wherein $R^{3a}$ and the pyridin-4-yl are taken together to form a moiety selected from the group consisting of:

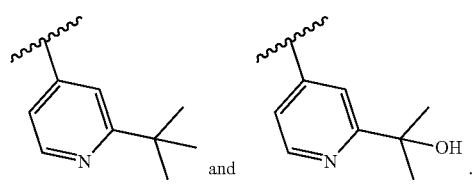 [SMILES: *c1ccnc(C(C)(C)C)c1 ; *c1ccnc(C(C)(C)O)c1] and
12. The compound of claim 1, or a pharmaceutically acceptable salt thereof, wherein p is 1.
13. The compound of claim 1, or a pharmaceutically acceptable salt thereof, wherein the compound is selected from the group consisting of
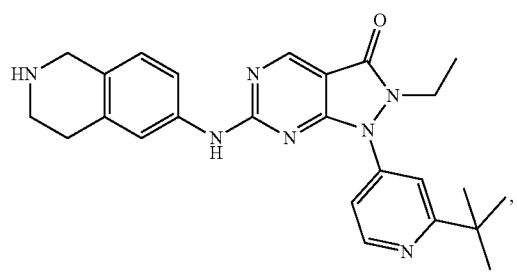
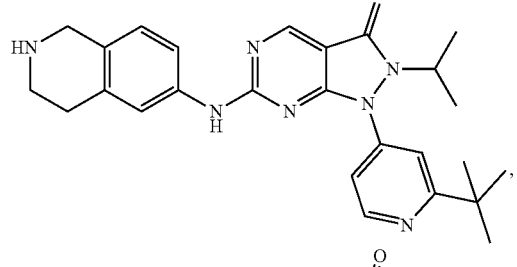
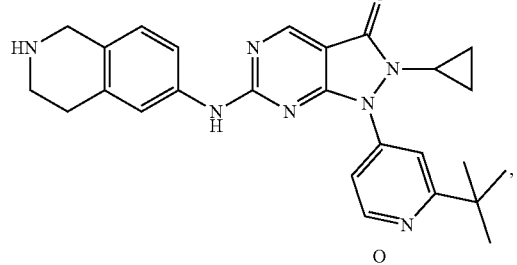
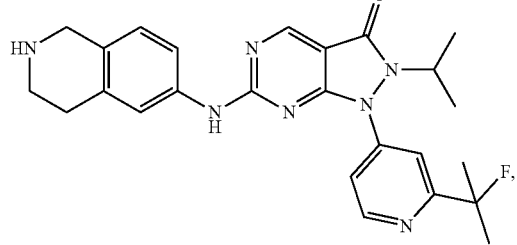
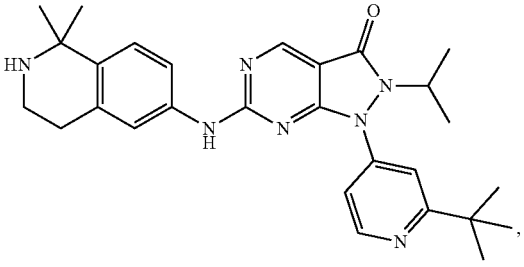
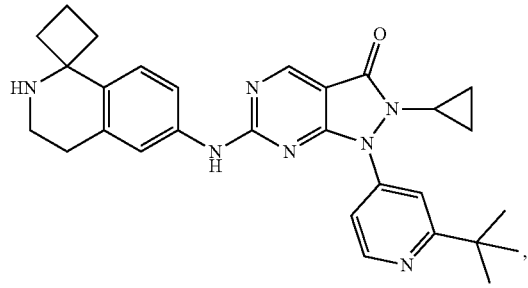
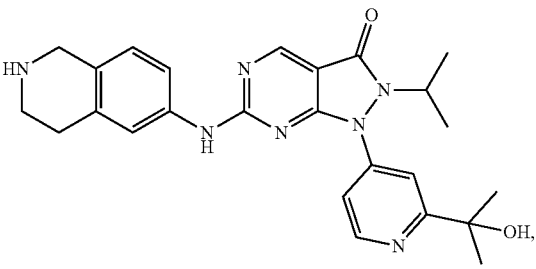 [SMILES: CC(C)n1c(=O)c2cnc(Nc3ccc4c(c3)CCNC4)nc2n1-c1ccnc(C(C)(C)O)c1]
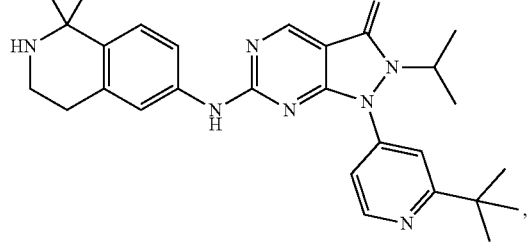
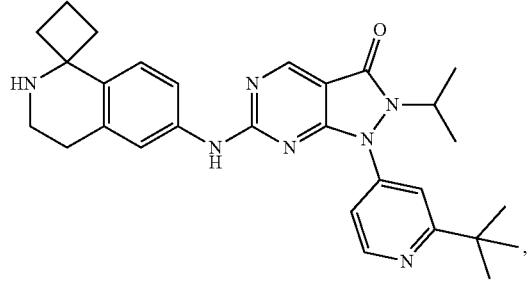
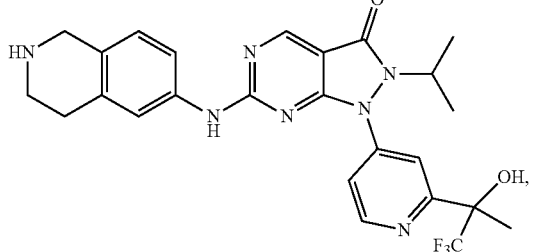
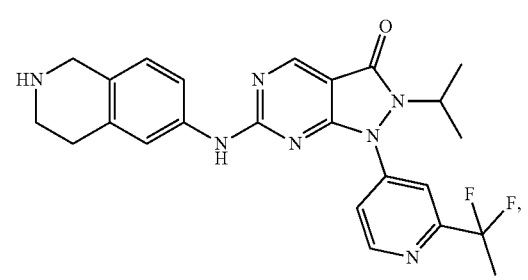

909
-continued
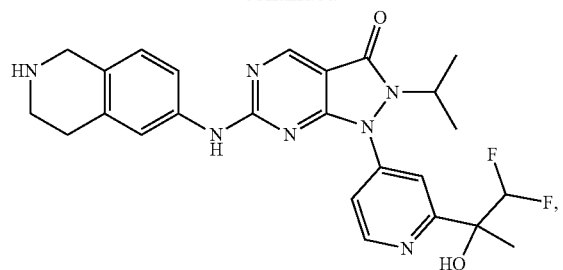
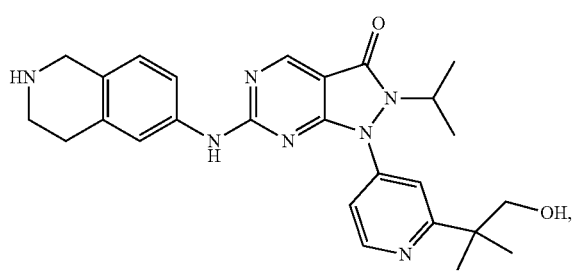
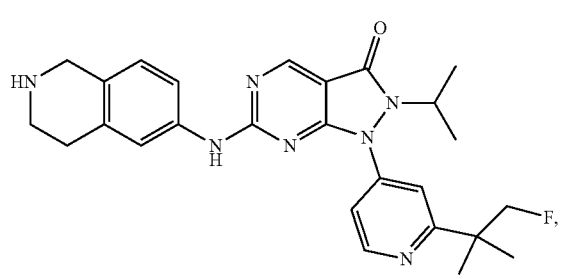
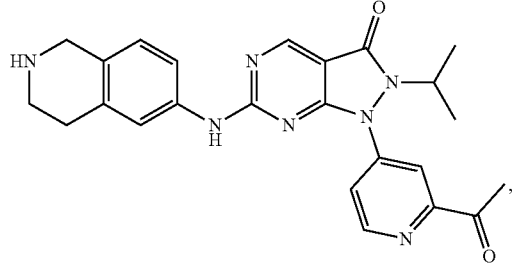
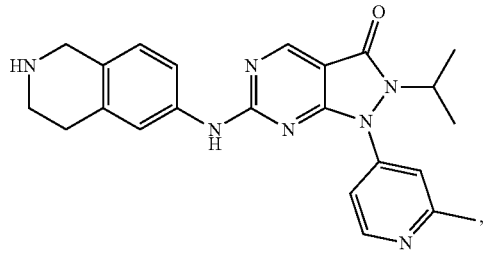
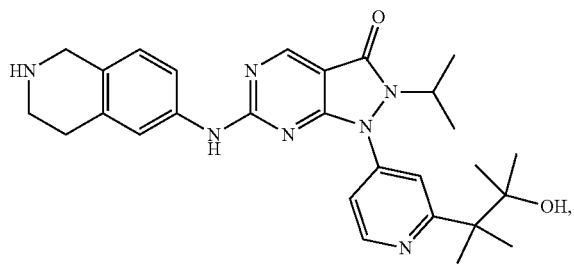
910
-continued
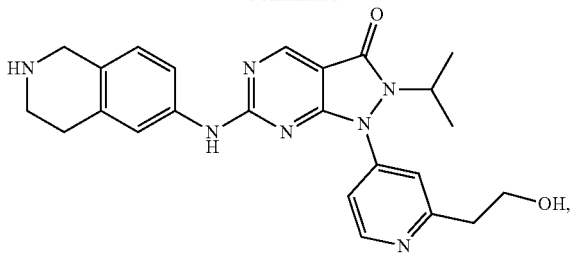
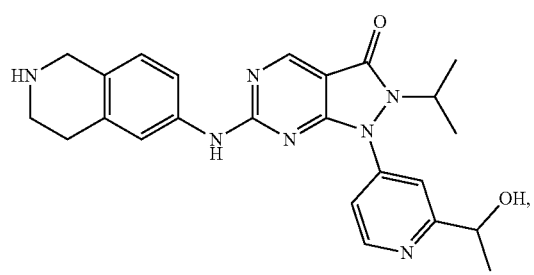
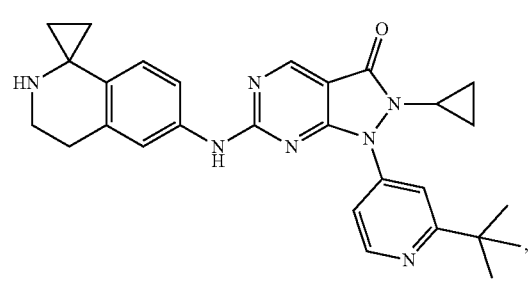
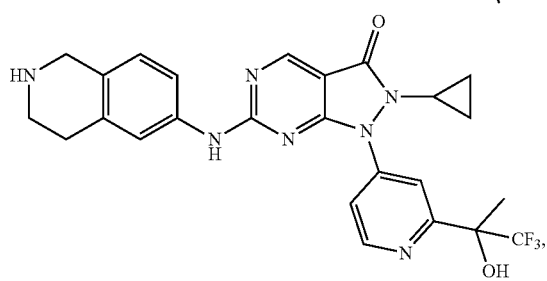
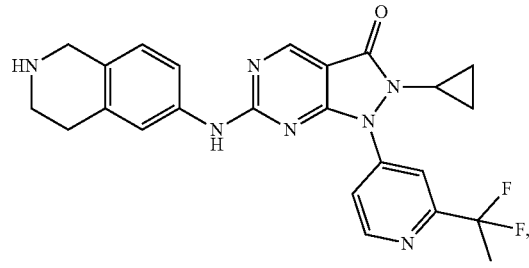
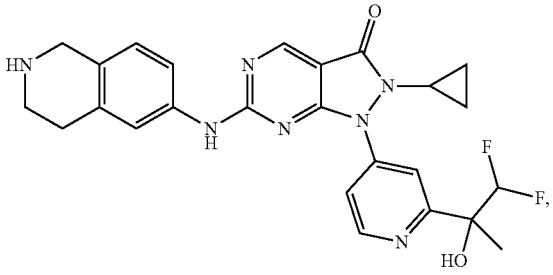

911
-continued
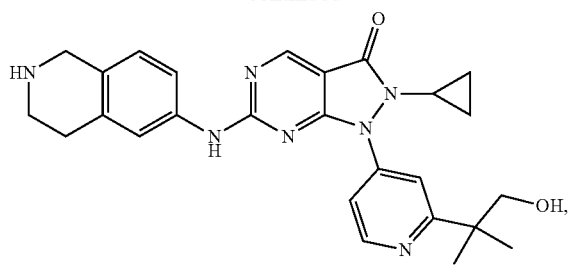
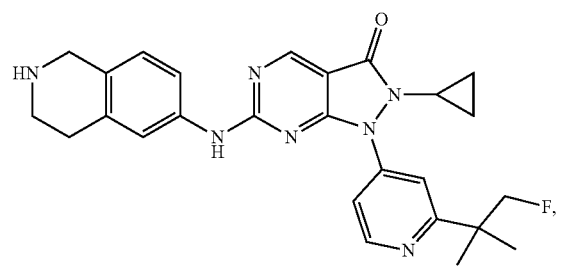
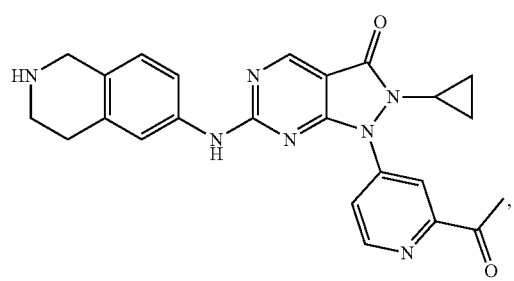
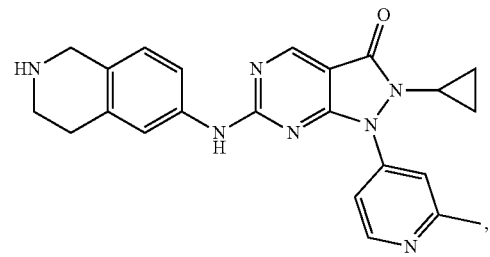
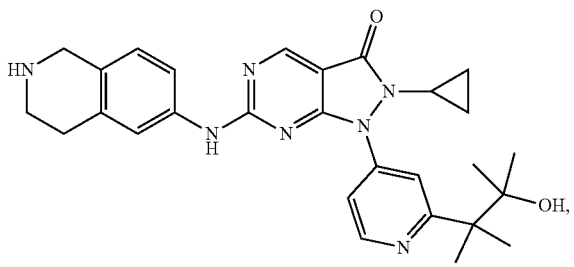
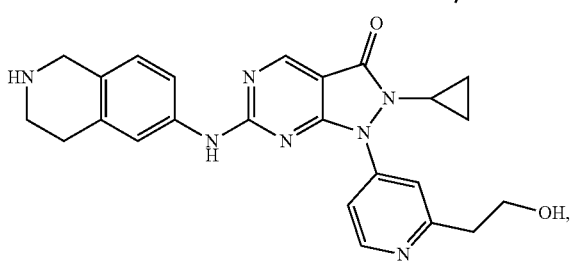
912
-continued
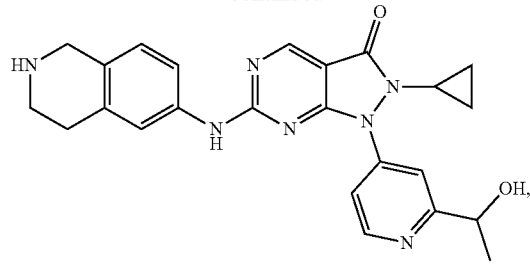
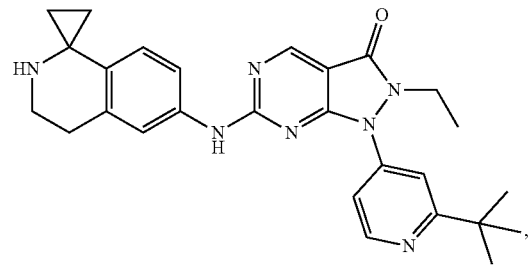
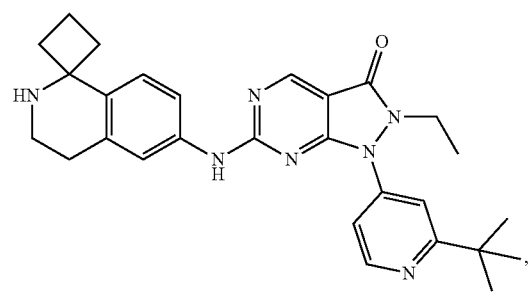
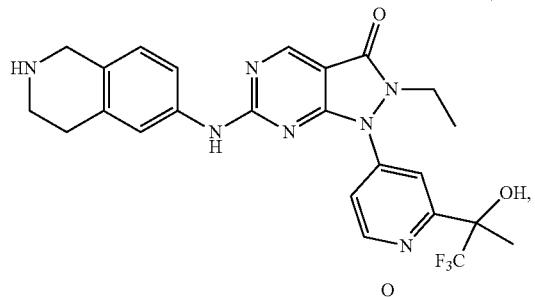
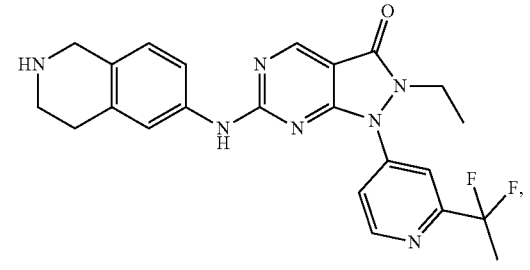
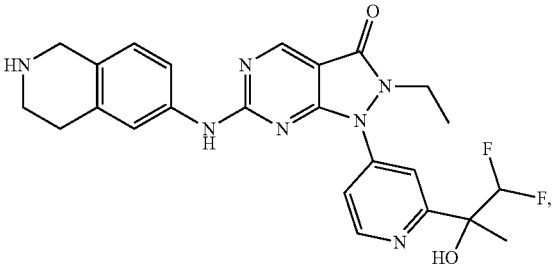

913
-continued
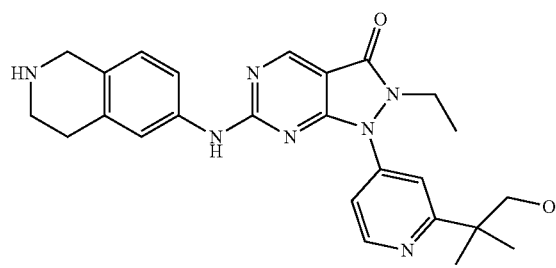
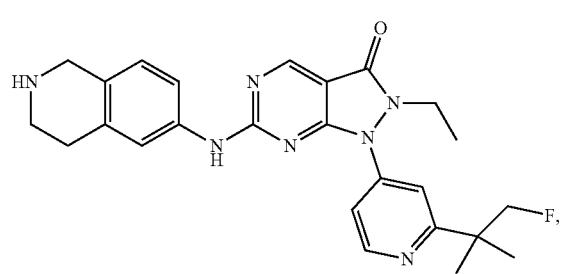
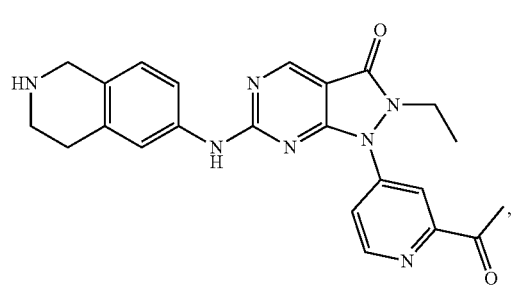
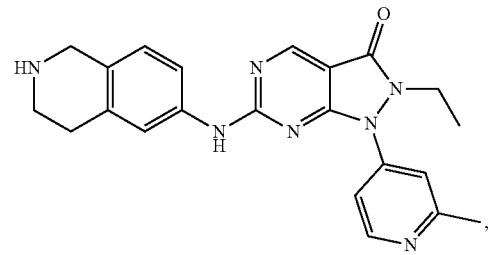
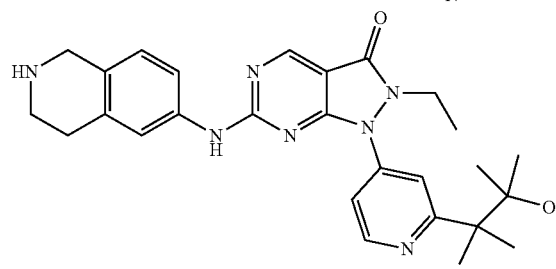
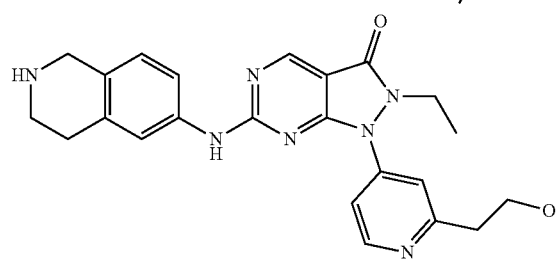
914
-continued
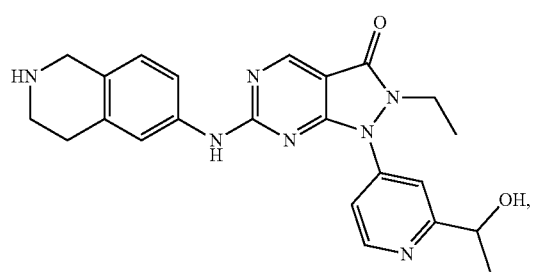
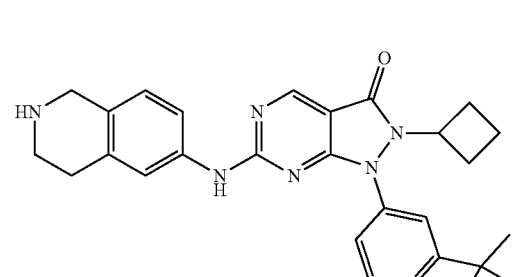
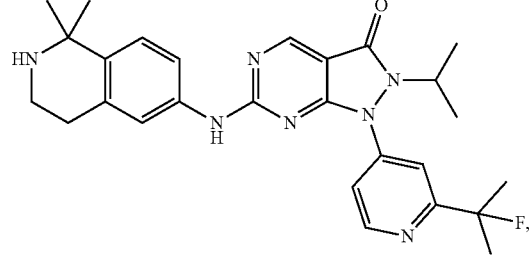
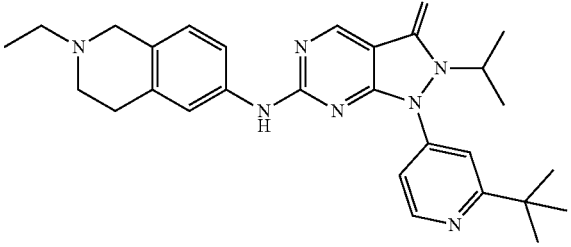
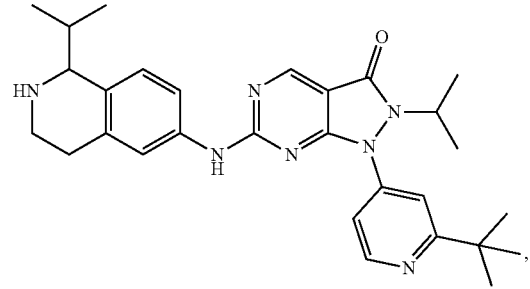
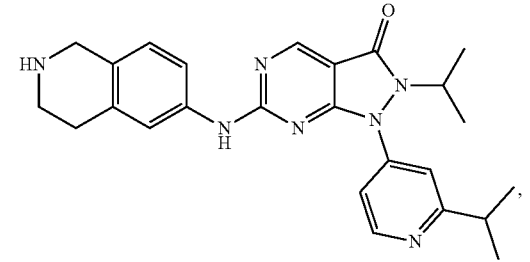

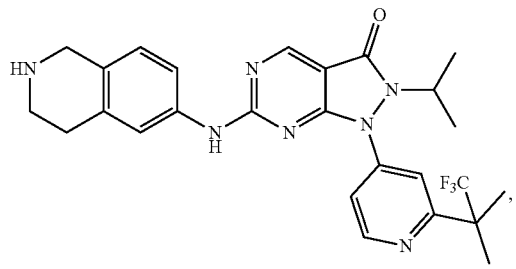
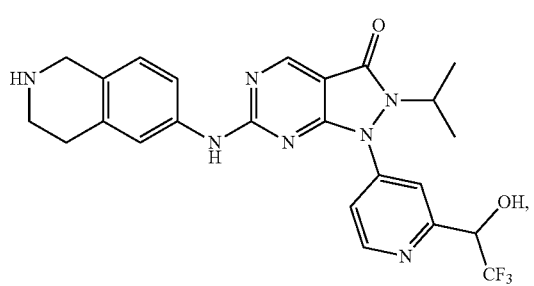
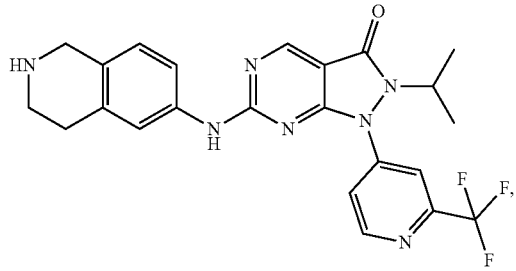
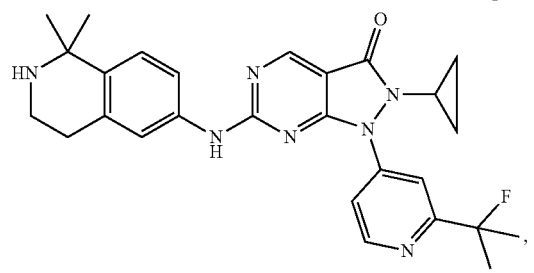
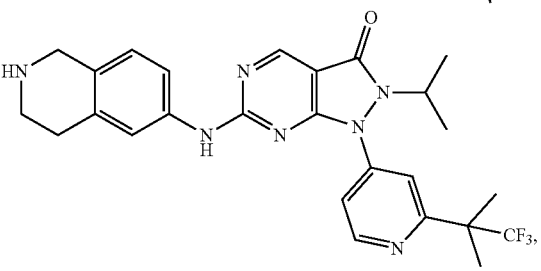
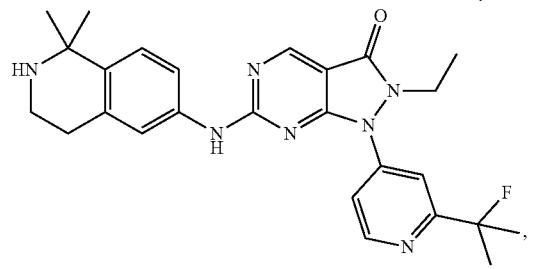
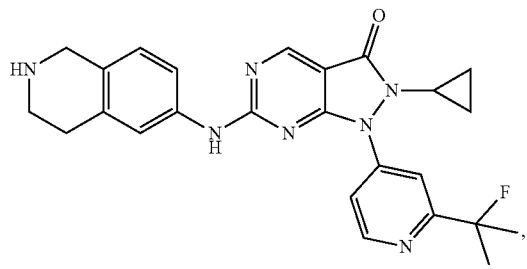
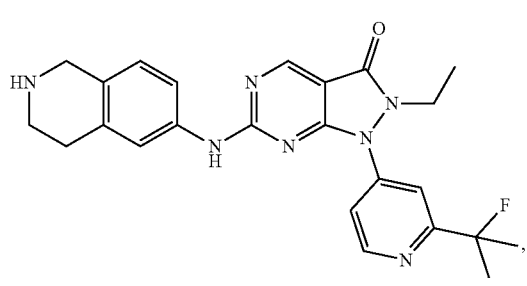
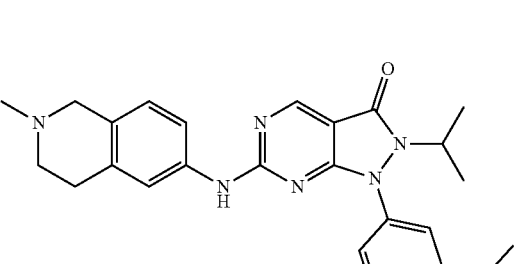
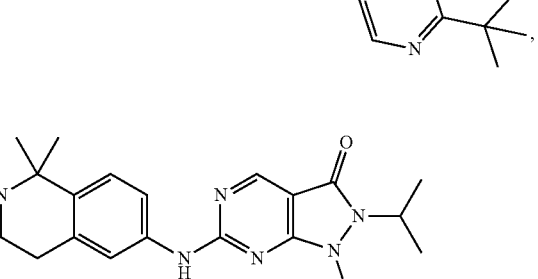
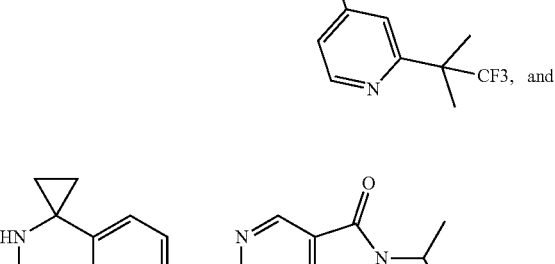
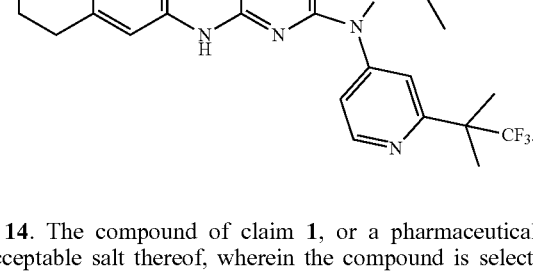
14. The compound of claim 1, or a pharmaceutically acceptable salt thereof, wherein the compound is selected from the group consisting of 917
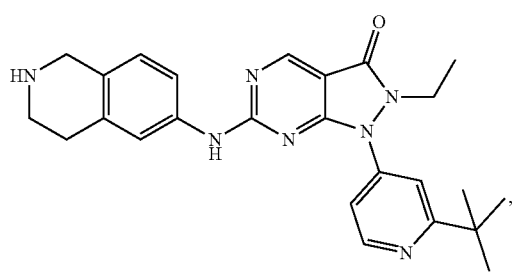
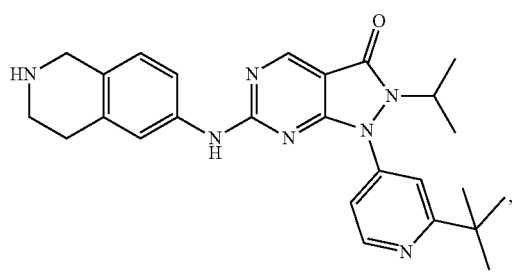
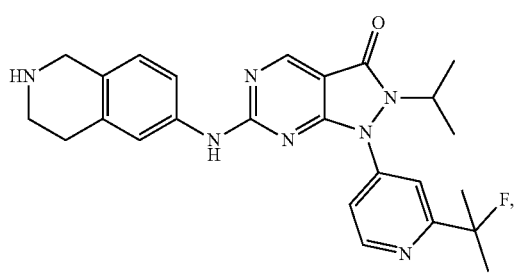 [SMILES: CCn1c(=O)c2cnc(Nc3ccc4c(c3)CCNC4)nc2n1-c1ccnc(C(C)(C)C)c1]
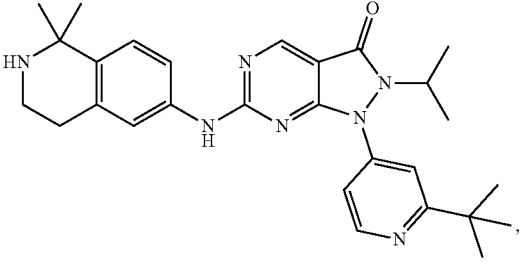
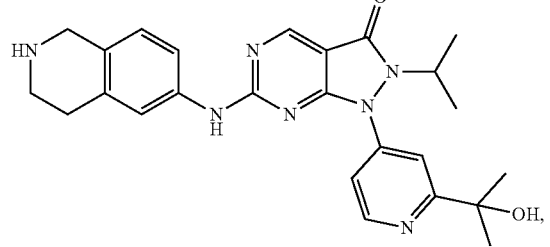
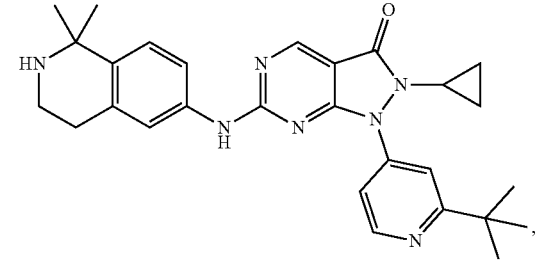
918
-continued
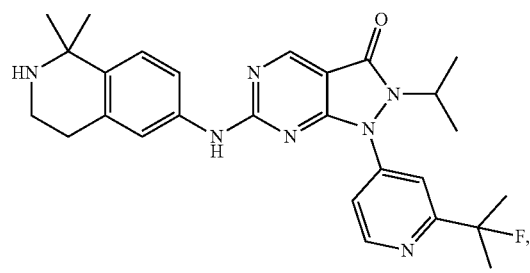
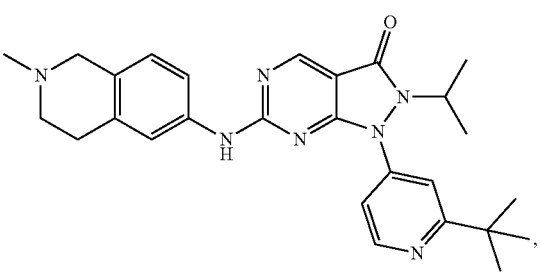
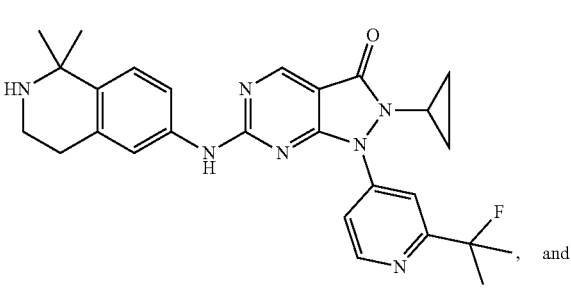
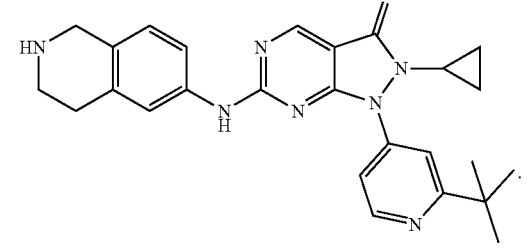
, and
15. The compound of claim 14, or a pharmaceutically acceptable salt thereof, wherein the compound is
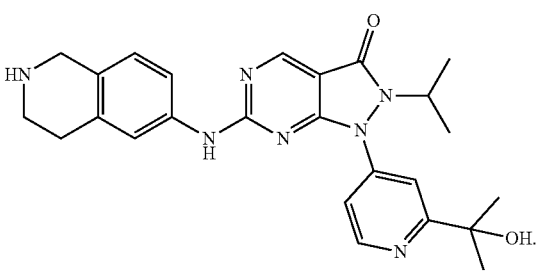
16. The compound of claim 14, or a pharmaceutically acceptable salt thereof, wherein the compound is 17. The compound of claim 14, or a pharmaceutically acceptable salt thereof, wherein the compound is

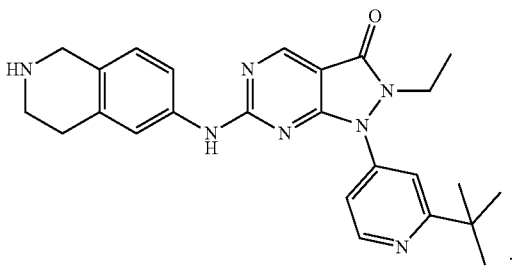

18. The compound of claim 14, or a pharmaceutically acceptable salt thereof, wherein the compound is

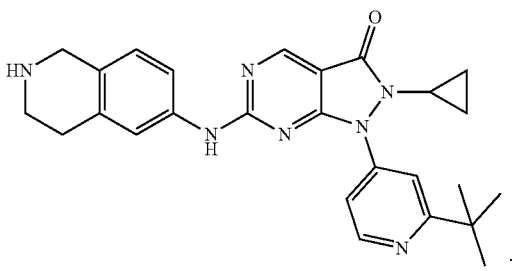 [SMILES: CC(C)(C)c1cc(-n2c3nc(Nc4ccc5c(c4)CCNC5)ncc3c(=O)n2C2CC2)ccn1]

19. A compound of the Formula (Ia-7):

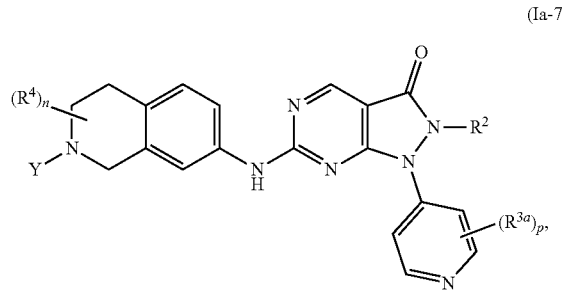

(Ia-7)

or a pharmaceutically acceptable salt thereof, wherein:
$R^2$ is isopropyl or $C_3$-$C_6$ cycloalkyl;
Y is hydrogen or $R^4$;
n and p are independently 0, 1, 2, 3, or 4;
each $R^{3a}$ is independently $C_1$-$C_6$ alkyl optionally substituted by oxo, —OH or halogen;
each $R^4$ is independently $C_1$-$C_6$ alkyl,
or two $R^4$, when bound to the same carbon or two different carbon atoms, are taken together with the carbon or carbons to which they are attached to form a $C_3$-$C_6$ cycloalkyl.

20. The compound of claim 19, or a pharmaceutically acceptable salt thereof, wherein n is 0.

21. The compound of claim 19, or a pharmaceutically acceptable salt thereof, wherein n is 1.

22. The compound of claim 19, or a pharmaceutically acceptable salt thereof, wherein n is 2.

23. The compound of claim 19, or a pharmaceutically acceptable salt thereof, wherein Y is hydrogen.

24. The compound of claim 19, or a pharmaceutically acceptable salt thereof, wherein each $R^4$ is methyl.

25. The compound of claim 19, or a pharmaceutically acceptable salt thereof, wherein $R^2$ is isopropyl.

26. The compound of claim 19, or a pharmaceutically acceptable salt thereof, wherein $R^2$ is $C_3$-$C_6$ cycloalkyl.

27. The compound of claim 19, or a pharmaceutically acceptable salt thereof, wherein $R^2$ is cyclopropyl.

28. The compound of claim 19, or a pharmaceutically acceptable salt thereof, wherein $R^{3a}$ and the pyridin-4-yl are taken together to form a moiety selected from the group consisting of:

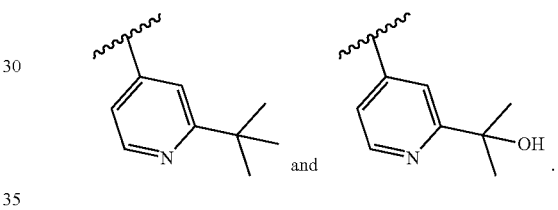

29. The compound of claim 19, or a pharmaceutically acceptable salt thereof, wherein p is 1.

30. A pharmaceutical composition comprising the compound of claim 19, or a pharmaceutically acceptable salt thereof, and a pharmaceutically acceptable carrier.

31. The compound of claim 19, or a pharmaceutically acceptable salt thereof, wherein the compound is selected from the group consisting of

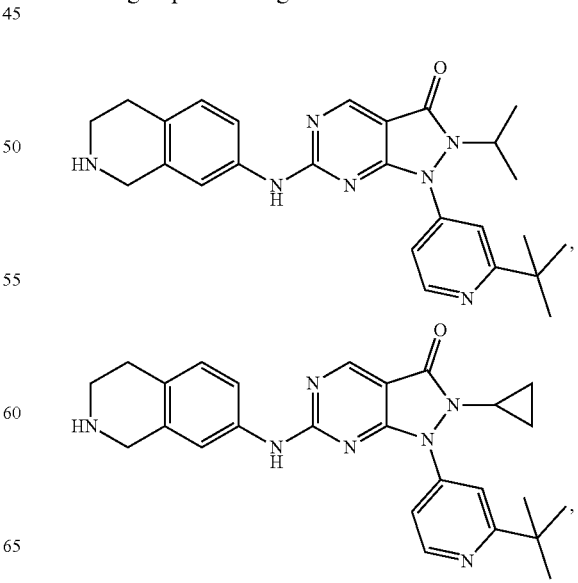

921
-continued
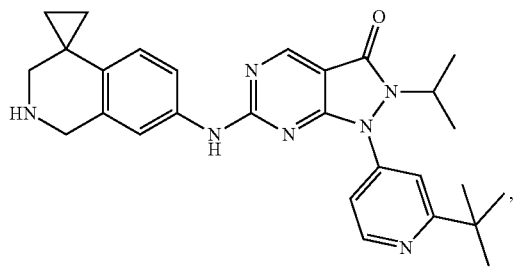
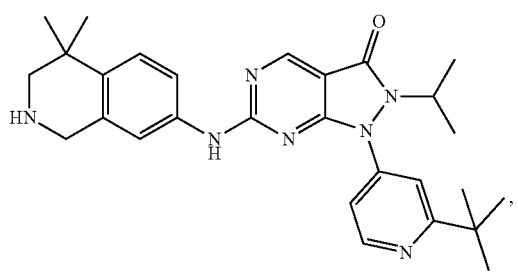 [SMILES: CC(C)n1c(=O)c2cnc(Nc3ccc4c(c3)CNCC4)nc2n1-c1ccnc(C(C)(C)C)c1]
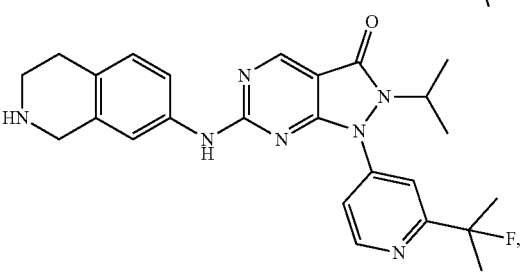
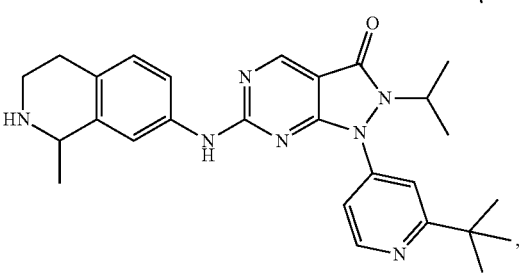
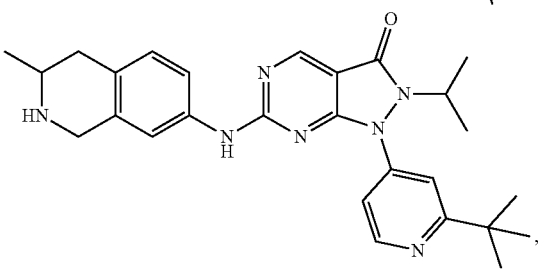
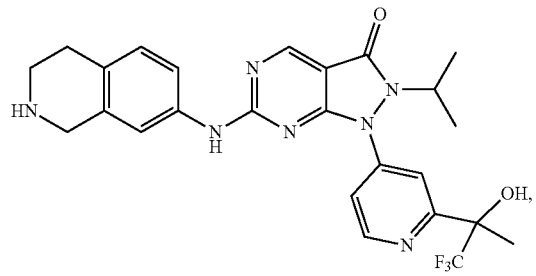
922
-continued
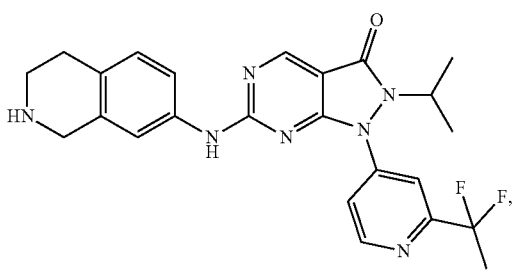
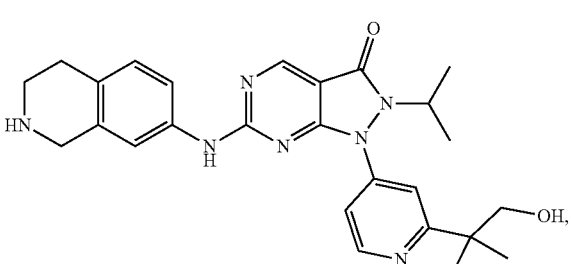
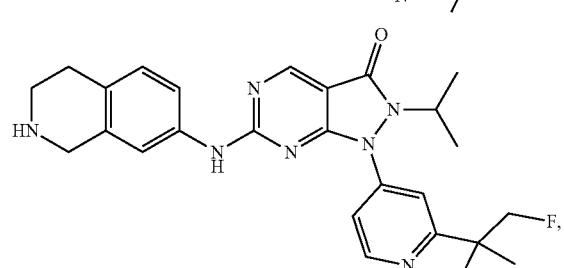
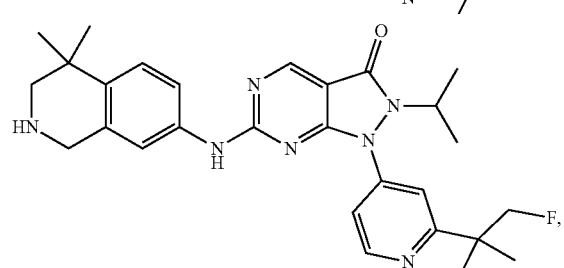
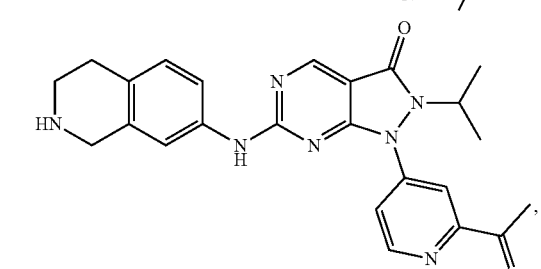
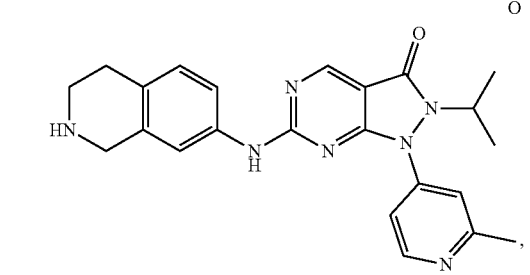

923
-continued
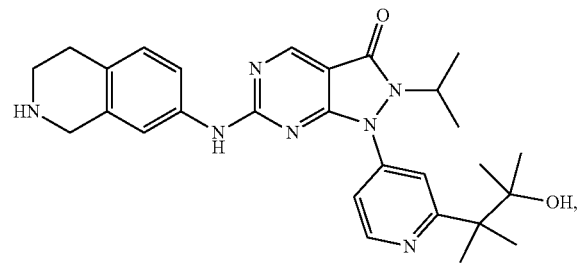
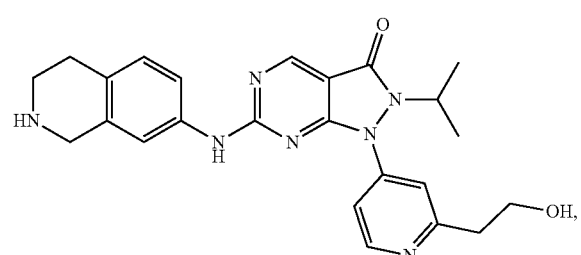
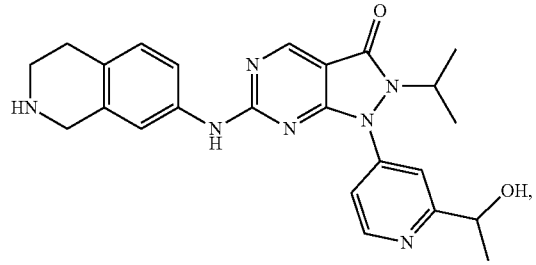
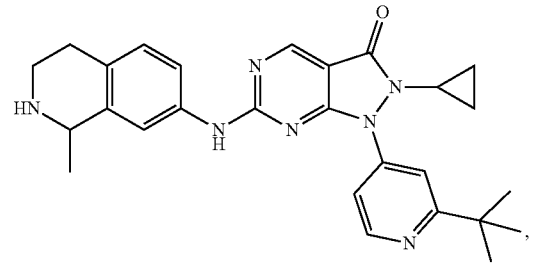
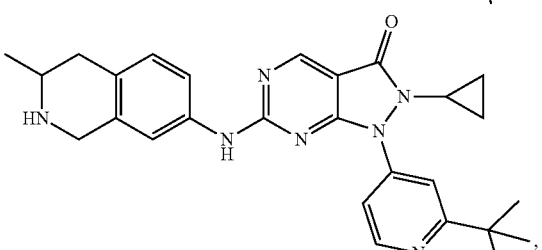
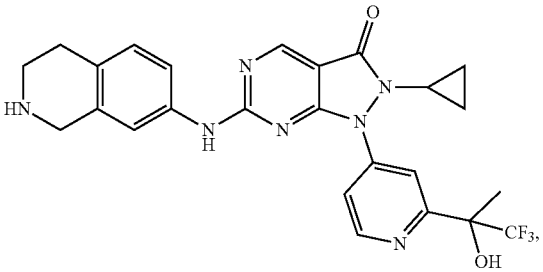
924
-continued
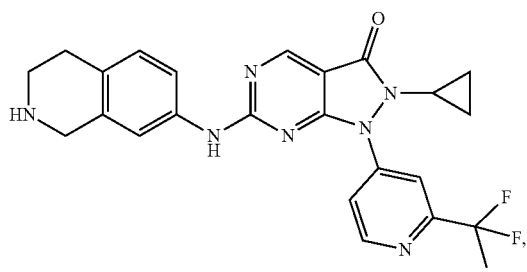
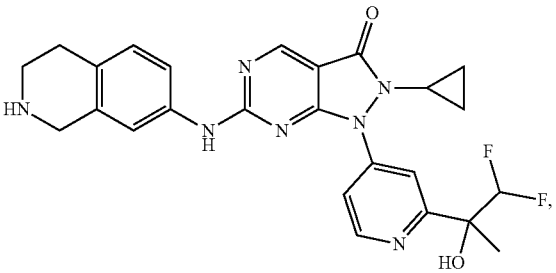
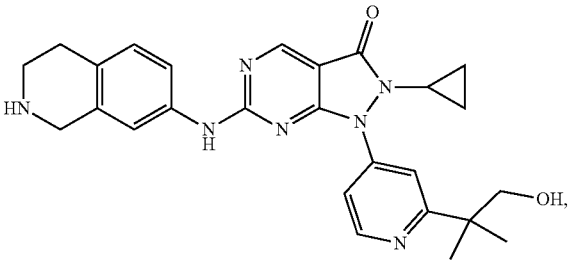
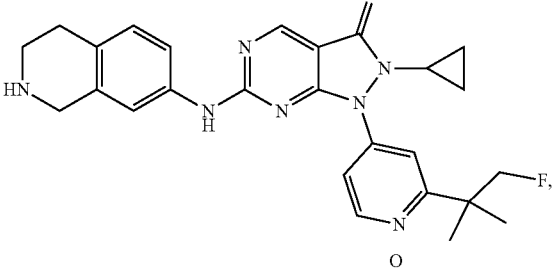
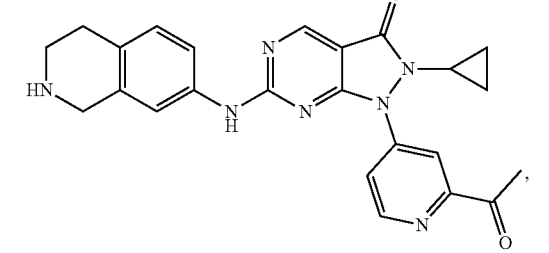
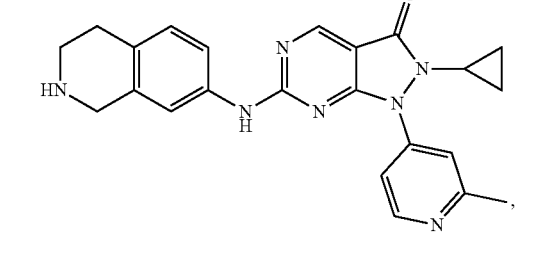

925
-continued
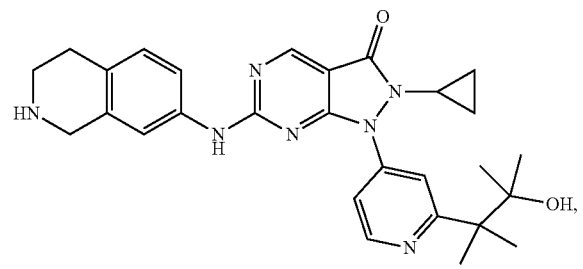
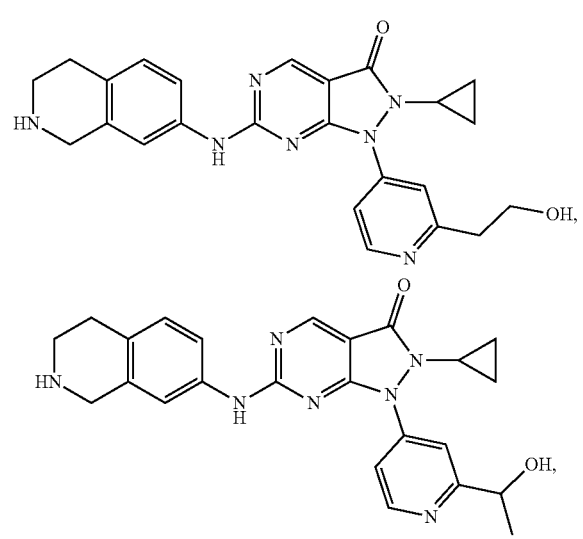
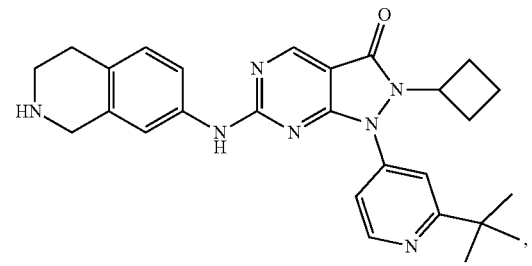
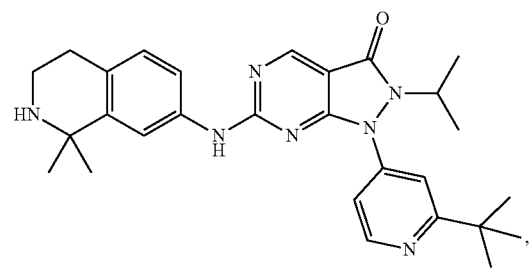
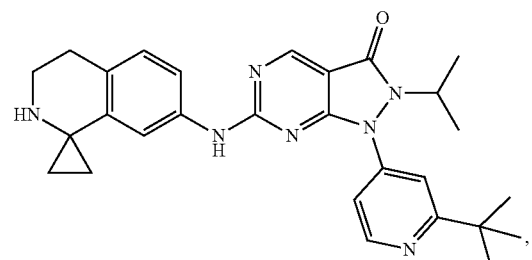
926
-continued
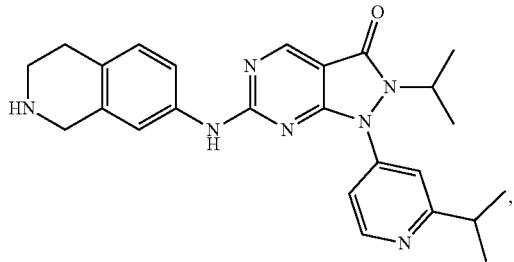
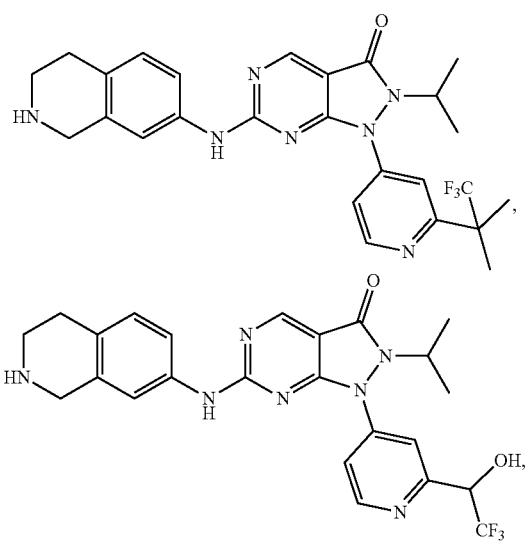
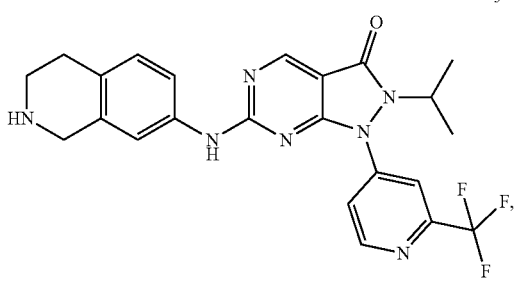
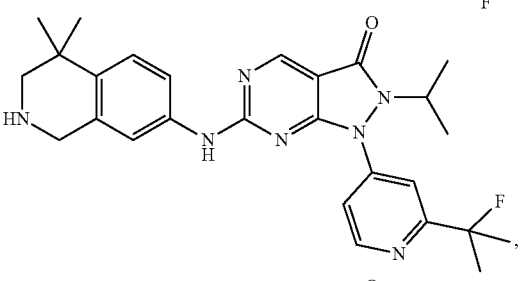
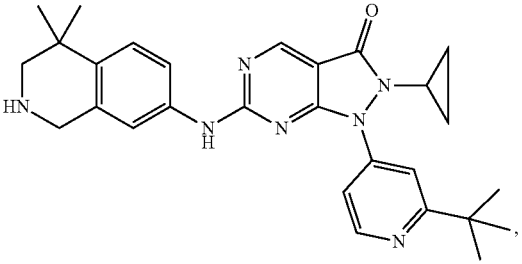

927
-continued
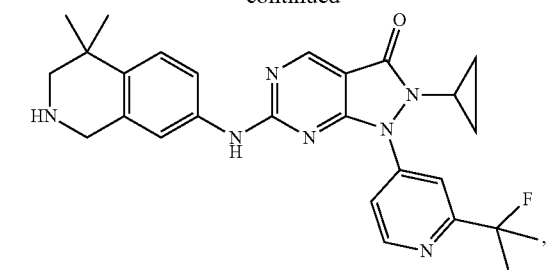
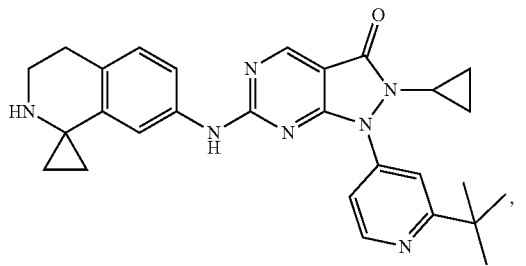
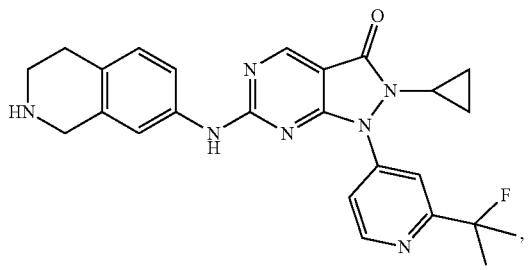
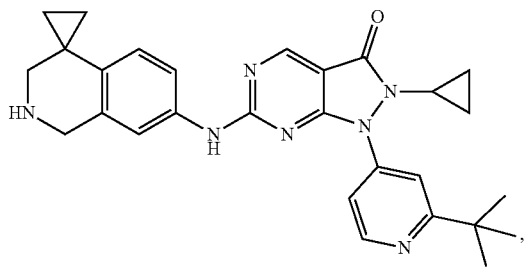
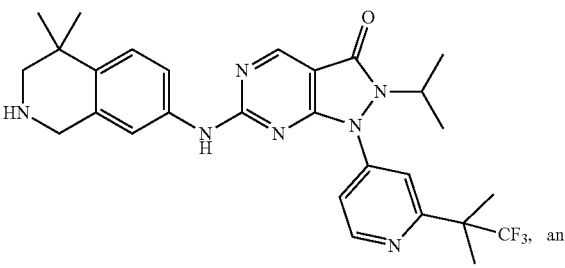
, and
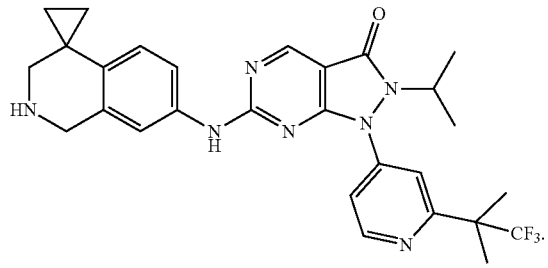
.
32. The compound of claim 19, or a pharmaceutically acceptable salt thereof, wherein the compound is selected from the group consisting of
928
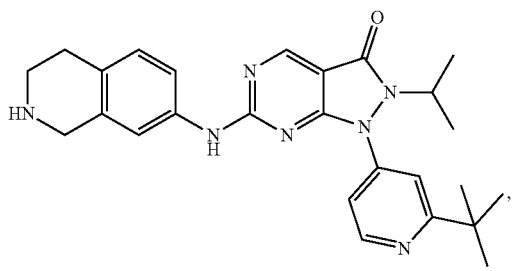
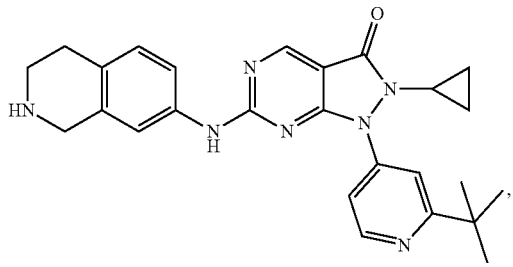 [SMILES: CC(C)(C)c1cc(-n2c3nc(Nc4ccc5c(c4)CNCC5)ncc3c(=O)n2C2CC2)ccn1]
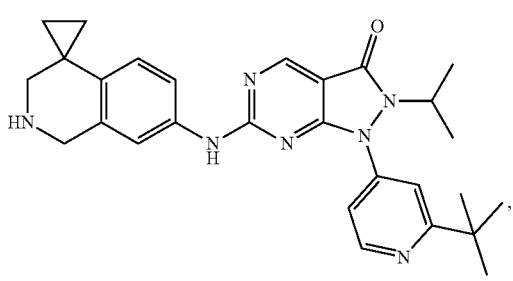
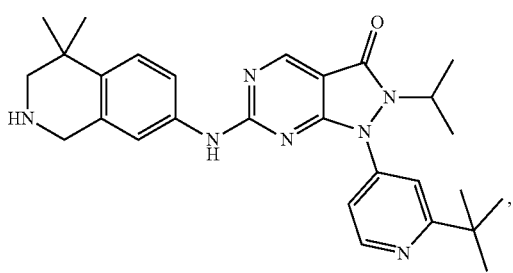
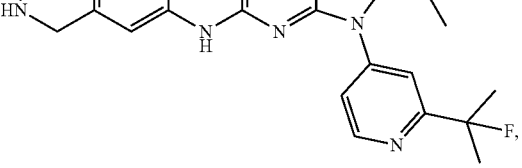

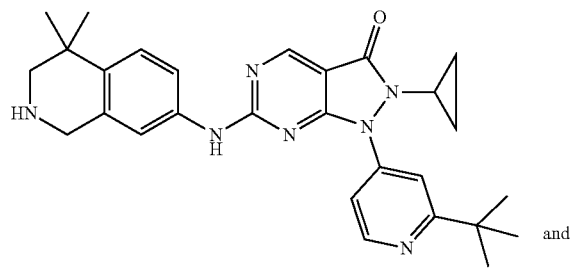
and
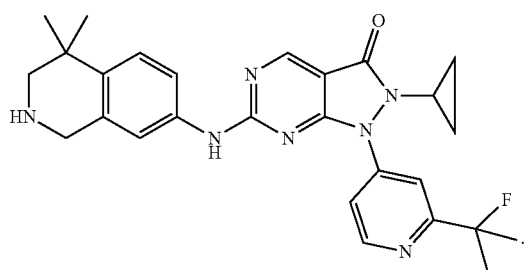
33. The compound of claim 32, or a pharmaceutically acceptable salt thereof, wherein the compound is
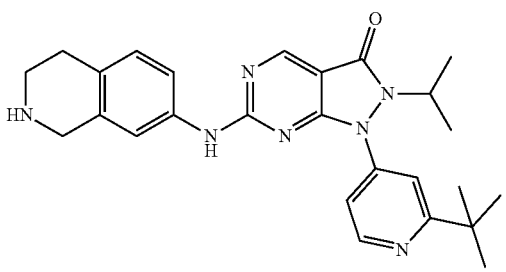
34. The compound of claim 32, or a pharmaceutically acceptable salt thereof, wherein the compound is
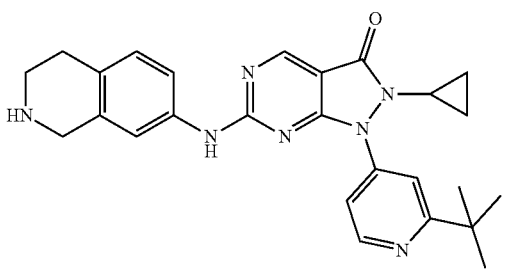
\* \* \* \* \*